US008173650B2

(12) United States Patent
Castanedo et al.

(10) Patent No.: US 8,173,650 B2
(45) Date of Patent: May 8, 2012

(54) BICYCLIC PYRIMIDINE PI3K INHIBITOR COMPOUNDS SELECTIVE FOR P110 DELTA, AND METHODS OF USE

(75) Inventors: Georgette Castanedo, Redwood City, CA (US); Bryan Chan, San Carlos, CA (US); David Goldstein, Nutley, NJ (US); Rama Kondru, Nutley, NJ (US); Matthew Lucas, Nutley, NJ (US); Wylie Palmer, Nutley, NJ (US); Stephen Price, Harlow (GB); Brian Safina, Redwood City, CA (US); Pascal Pierre Alexandre Savy, Harlow (GB); Eileen Mary Seward, Harlow (GB); Daniel P. Sutherlin, Burlingame, CA (US); Zachary K. Sweeney, Redwood City, CA (US)

(73) Assignee: Genentech, Inc., South San Francisco, CA (US)

(*) Notice: Subject to any disclaimer, the term of this patent is extended or adjusted under 35 U.S.C. 154(b) by 0 days.

(21) Appl. No.: 12/787,613

(22) Filed: May 26, 2010

(65) Prior Publication Data

US 2010/0305096 A1 Dec. 2, 2010

Related U.S. Application Data

(60) Provisional application No. 61/181,452, filed on May 27, 2009, provisional application No. 61/287,607, filed on Dec. 17, 2009.

(51) Int. Cl.
*A61K 31/535* (2006.01)
*C07D 413/14* (2006.01)

(52) U.S. Cl. ..................... 514/234.2; 544/118
(58) Field of Classification Search .................. 544/118; 514/234.2
See application file for complete search history.

(56) References Cited

U.S. PATENT DOCUMENTS

| 3,475,429 | A | 10/1969 | Woitun et al. |
| 3,661,908 | A | 5/1972 | Woitun et al. |
| 3,763,156 | A | 10/1973 | Woitun et al. |
| 3,838,121 | A | 9/1974 | Woitun et al. |
| 3,850,917 | A | 11/1974 | Mueller et al. |
| 3,888,851 | A | 6/1975 | Narr et al. |
| 4,007,187 | A | 2/1977 | Fauran et al. |
| 4,146,716 | A | 3/1979 | Cox et al. |
| 4,196,207 | A | 4/1980 | Webber et al. |
| 5,075,305 | A | 12/1991 | Hobbs et al. |
| 6,187,777 | B1 | 2/2001 | Norman et al. |
| 6,492,383 | B1 | 12/2002 | Munchhof et al. |
| 6,608,056 | B1 | 8/2003 | Hayakawa et al. |
| 7,750,002 | B2 | 7/2010 | Shuttleworth et al. |
| 7,776,856 | B2 | 8/2010 | Shuttleworth et al. |
| 7,781,433 | B2 | 8/2010 | Chuckowree et al. |
| 2006/0229306 | A1 | 10/2006 | Terricabras Belart et al. |
| 2007/0185139 | A1 | 8/2007 | Binnun et al. |
| 2007/0249587 | A1 | 10/2007 | Yonetoku et al. |
| 2008/0039459 | A1 | 2/2008 | Folkes et al. |
| 2008/0076758 | A1 | 3/2008 | Folkes et al. |
| 2008/0207609 | A1 | 8/2008 | Shuttleworth et al. |
| 2008/0242665 | A1 | 10/2008 | Bayliss et al. |
| 2008/0269210 | A1 | 10/2008 | Castanedo et al. |
| 2009/0118275 | A1 | 5/2009 | Castanedo et al. |
| 2009/0318411 | A1 | 12/2009 | Castanedo et al. |

FOREIGN PATENT DOCUMENTS

| WO | 2006/114606 | 11/2006 |
| WO | 2007/122410 | 11/2007 |
| WO | 2007/132171 | 11/2007 |
| WO | WO 2008/116129 A2 * | 9/2008 |
| WO | 2008/152390 | 12/2008 |
| WO | 2008/152394 | 12/2008 |
| WO | 2009/053715 | 4/2009 |
| WO | 2009/053716 | 4/2009 |

OTHER PUBLICATIONS

Cancer and Metastasis Reviews (1998), 17(1), 91-106.*
Science (1999), vol. 286, 531-537.*
Cecil Textbook of Medicine, 20th edition (1996), vol. 2, pp. 2050-2057.*
Cecil Textbook of Medicine, 20th edition (1996), vol. 2, pp. 1992-1996.*
FDA mulls drug to slow late-stage Alzheimer's [online], [retrieved on Sep. 23, 2003]. Retrieved from the Internet, URL;http://www.cnn.com/2003/HEALTH/conditions/09/24/alzheimers.drug.ap/index.html>.*
Huff, Joel R., "HIV Protease: A Novel Chemotherapeutic Target for AIDS," Journal of Medicinal Chemistry, vol. 34, No. 8, Aug. 1991, pp. 2305-2314.*
Bourguinon et al., "Synthesis of 2- and 4-substituted thieno[2,3-d]pyrimidines II" *Bulletin de la Societe Chimique de France* 11-12:2483-2487 (1975).
Bourguinon et al., "Synthesis of thieno[2,3-d]pyrimidines substituted at 2 and 4" *Bulletin de la Societe Chimique de France* 3-4(pt 2):815-819 (1975).
Briel et al., "Selective Nucleophilic Replacement of the Benzylsulfanyl Group in 2,4-Disulfanyl-substituted Thieno[2,3-d]pyrimidin-6-carboxylic Acid Derivatives by Secondary Amines" *Journal Heterocyclic Chem.* 42(5):841-846 (Jul.-Aug. 2005).

* cited by examiner

*Primary Examiner* — Rebecca Anderson
(74) *Attorney, Agent, or Firm* — Alex Andrus

(57) ABSTRACT

Formula I (Ia and Ib) compounds wherein (i) $X^1$ is N and $X^2$ is S, (ii) $X^1$ is $CR^7$ and $X^2$ is S, (iii) $X^1$ is N and $X^2$ is $NR^2$, or (iv) $X^1$ is $CR^7$ and $X^2$ is O, including stereoisomers, tautomers, metabolites and pharmaceutically acceptable salts thereof, are useful for inhibiting the delta isoform of PI3K, and for treating disorders mediated by lipid kinases such as inflammation, immunological, and cancer. Methods of using compounds of Formula I for in vitro, in situ, and in vivo diagnosis, prevention or treatment of such disorders in mammalian cells, or associated pathological conditions, are disclosed.

21 Claims, No Drawings

BICYCLIC PYRIMIDINE PI3K INHIBITOR COMPOUNDS SELECTIVE FOR P110 DELTA, AND METHODS OF USE

CROSS REFERENCE TO RELATED APPLICATIONS

This non-provisional application filed under 37 CFR §1.53(b), claims the benefit under 35 USC §119(e) of U.S. Provisional Applications Ser. No. 61/181,452 filed on 27 May 2009, and Ser. No. 61/287,607 filed on 17 Dec. 2009, which are incorporated by reference in there entireties.

FIELD OF THE INVENTION

The invention relates generally to compounds for treating disorders mediated by lipid kinases such as inflammation, immunological, and cancer, and more specifically to compounds which inhibit PI3 kinase activity. The invention also relates to methods of using the compounds for in vitro, in situ, and in vivo diagnosis or treatment of mammalian cells, or associated pathological conditions.

BACKGROUND OF THE INVENTION

Phosphatidylinositol (PI), a phospholipid found in cell membranes, plays an important role in intracellular signal transduction. Cell signaling via 3'-phosphorylated phosphoinositides has been implicated in a variety of cellular processes, e.g., malignant transformation, growth factor signaling, inflammation, and immunity (Rameh et al (1999) J. Biol Chem, 274:8347-8350). The enzyme responsible for generating these phosphorylated signaling products, phosphatidylinositol 3-kinase (also referred to as PI 3-kinase or PI3K), was originally identified as an activity associated with viral oncoproteins and growth factor receptor tyrosine kinases that phosphorylate phosphatidylinositol (PI) and its phosphorylated derivatives at the 3'-hydroxyl of the inositol ring (Panayotou et al (1992) Trends Cell Biol 2:358-60).

Phosphoinositide 3-kinases (PI3K) are lipid kinases that phosphorylate lipids at the 3-hydroxyl residue of the inositol ring of phosphoinositols (Whitman et al (1988) Nature, 332: 664). The 3'-phosphorylated phospholipids (PIP3s) generated by PI3-kinases act as second messengers recruiting kinases with lipid binding domains (including plekstrin homology (PH) regions), such as Akt and phosphoinositide-dependent kinase-1 (PDK1). Binding of Akt to membrane PIP3s causes the translocation of Akt to the plasma membrane, bringing Akt into contact with PDK1, which is responsible for activating Akt. The tumor-suppressor phosphatase, PTEN, dephosphorylates PIP3 and therefore acts as a negative regulator of Akt activation. The PI3-kinases Akt and PDK1 are important in the regulation of many cellular processes including cell cycle regulation, proliferation, survival, apoptosis and motility and are significant components of the molecular mechanisms of diseases such as cancer, diabetes and immune inflammation (Vivanco et al (2002) Nature Rev. Cancer 2:489; Phillips et al (1998) Cancer 83:41).

PI3 kinase is a heterodimer consisting of p85 and p110 subunits (Otsu et al (1991) Cell 65:91-104; Hiles et al (1992) Cell 70:419-29). Four distinct Class I PI3Ks have been identified, designated PI3K α (alpha), β (beta), δ (delta), and γ (gamma), each consisting of a distinct 110 kDa catalytic subunit and a regulatory subunit. More specifically, three of the catalytic subunits, i.e., p110 alpha, p110 beta and p110 delta, each interact with the same regulatory subunit, p85; whereas p110 gamma interacts with a distinct regulatory subunit, p101. The patterns of expression of each of these PI3Ks in human cells and tissues are also distinct.

The p110 delta isoform has been implicated in biological functions related to immune-inflammatory diseases, including signaling from the B-cell receptor, T cell receptor, FcR signaling of mast cells and monocyte/macrophage, and osteoclast function/RANKL signaling (Deane J and Fruman D A (2004) Annu Rev. Immunol. 2004. 22:563-98; Janas et al., The Journal of Immunology, 2008, 180: 739-746; Marone R et al., Biochim. Biophy. Acta 2007, 1784:159-185. Deletion of the PI3K delta gene or selective introduction of a catalytically inactive mutant of PI3K delta causes a nearly complete ablation of B cell proliferation and signaling, and impairment of signaling through T cells as well.

SUMMARY OF THE INVENTION

The invention relates generally to Formula I compounds with PI3 kinase inhibitory activity and selective binding to the p110 delta isoform relative to binding to the p110 alpha isoform. Formula I compounds at least 10 fold selective in binding to the p110 delta isoform relative to binding to the p110 alpha isoform.

Formula I compounds have the structures:

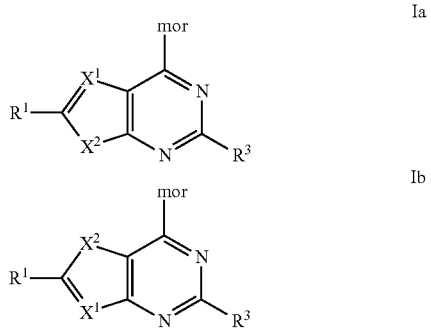

and stereoisomers, tautomers, or pharmaceutically acceptable salts thereof. The various substituents, including $X^1$, $X^2$, mor, $R^1$, $R^2$, $R^{2'}$, and $R^3$, are as defined herein.

Another aspect of the invention provides a pharmaceutical composition comprising a Formula I compound and a pharmaceutically acceptable carrier, glidant, diluent, or excipient.

Another aspect of the invention provides the use of a Formula I compound in the manufacture of a medicament for treating a disease or disorder selected from cancer, immune disorders, cardiovascular disease, viral infection, inflammation, metabolism/endocrine function disorders and neurological disorders, and mediated by the p110 delta isoform of PI3 kinase.

The invention also relates to methods of using the Formula I compounds for in vitro, in situ, and in vivo diagnosis or treatment of mammalian cells, organisms, or associated pathological conditions, such as cancer, systemic and local inflammation, immune-inflammatory diseases such as rheumatoid arthritis, immune suppression, organ transplant rejection, allergies, ulcerative colitis, Crohn's disease, dermatitis, asthma, systemic lupus erythematosus, Sjögren's Syndrome, multiple sclerosis, scleroderma/systemic sclerosis, idiopathic thrombocytopenic purpura (ITP), anti-neutrophil cytoplasmic antibodies (ANCA) vasculitis, chronic obstructive pulmonary disease (COPD), psoriasis, and for general joint protective effects.

Another aspect of the invention provides a method of treating a disease or disorder which method comprises administering a Formula I compound to a patient with a disease or disorder selected from cancer, immune disorders, cardiovascular disease, viral infection, inflammation, metabolism/endocrine function disorders and neurological disorders, and mediated by the p110 delta isoform of PI3 kinase. The method may further comprise administering an additional therapeutic agent selected from a chemotherapeutic agent, an anti-inflammatory agent, an immunomodulatory agent, a neurotropic factor, an agent for treating cardiovascular disease, an agent for treating liver disease, an anti-viral agent, an agent for treating blood disorders, an agent for treating diabetes, and an agent for treating immunodeficiency disorders.

Another aspect of the invention provides a kit for treating a condition mediated by the p110 delta isoform of PI3 kinase, comprising a first pharmaceutical composition comprising a Formula I compound; and instructions for use.

DETAILED DESCRIPTION OF EXEMPLARY EMBODIMENTS

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature, patents, and similar materials differs from or contradicts this application, including but not limited to defined terms, term usage, described techniques, or the like, this application controls.

Definitions

The term "alkyl" as used herein refers to a saturated linear or branched-chain monovalent hydrocarbon radical of one to twelve carbon atoms ($C_1$-$C_{12}$), wherein the alkyl radical may be optionally substituted independently with one or more substituents described below. In another embodiment, an alkyl radical is one to eight carbon atoms ($C_1$-$C_8$), or one to six carbon atoms ($C_1$-$C_6$). Examples of alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), 1-heptyl, 1-octyl, and the like.

The term "alkylene" as used herein refers to a saturated linear or branched-chain divalent hydrocarbon radical of one to twelve carbon atoms ($C_1$-$C_{12}$), wherein the alkylene radical may be optionally substituted independently with one or more substituents described below. In another embodiment, an alkylene radical is one to eight carbon atoms ($C_1$-$C_8$), or one to six carbon atoms ($C_1$-$C_6$). Examples of alkylene groups include, but are not limited to, methylene (—$CH_2$—), ethylene (—$CH_2CH_2$—), propylene (—$CH_2CH_2CH_2$—), and the like.

The term "alkenyl" refers to linear or branched-chain monovalent hydrocarbon radical of two to eight carbon atoms ($C_2$-$C_8$) with at least one site of unsaturation, i.e., a carbon-carbon, $sp^2$ double bond, wherein the alkenyl radical may be optionally substituted independently with one or more substituents described herein, and includes radicals having "cis" and "trans" orientations, or alternatively, "E" and "Z" orientations. Examples include, but are not limited to, ethylenyl or vinyl (—CH=$CH_2$), allyl (—$CH_2$CH=$CH_2$), and the like.

The term "alkenylene" refers to linear or branched-chain divalent hydrocarbon radical of two to eight carbon atoms ($C_2$-$C_8$) with at least one site of unsaturation, i.e., a carbon-carbon, $sp^2$ double bond, wherein the alkenyl radical may be optionally substituted, and includes radicals having "cis" and "trans" orientations, or alternatively, "E" and "Z" orientations. Examples include, but are not limited to, ethylenylene or vinylene (—CH=CH—), allyl (—$CH_2$CH=CH—), and the like.

The term "alkynyl" refers to a linear or branched monovalent hydrocarbon radical of two to eight carbon atoms ($C_2$-$C_8$) with at least one site of unsaturation, i.e., a carbon-carbon, sp triple bond, wherein the alkynyl radical may be optionally substituted independently with one or more substituents described herein. Examples include, but are not limited to, ethynyl (—C≡CH), propynyl (propargyl, —$CH_2$C≡CH), and the like.

The term "alkynylene" refers to a linear or branched divalent hydrocarbon radical of two to eight carbon atoms ($C_2$-$C_8$) with at least one site of unsaturation, i.e., a carbon-carbon, sp triple bond, wherein the alkynyl radical may be optionally. Examples include, but are not limited to, ethynylene (—C≡C—), propynylene (propargylene, —$CH_2$C≡C—), and the like.

The terms "carbocycle", "carbocyclyl", "carbocyclic ring" and "cycloalkyl" refer to a monovalent non-aromatic, saturated or partially unsaturated ring having 3 to 12 carbon atoms ($C_3$-$C_{12}$) as a monocyclic ring or 7 to 12 carbon atoms as a bicyclic ring. Bicyclic carbocycles having 7 to 12 atoms can be arranged, for example, as a bicyclo [4,5], [5,5], [5,6] or [6,6] system, and bicyclic carbocycles having 9 or 10 ring atoms can be arranged as a bicyclo [5,6] or [6,6] system, or as bridged systems such as bicyclo[2.2.1]heptane, bicyclo [2.2.2]octane and bicyclo[3.2.2]nonane. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, adamantanyl, and the like.

"Aryl" means a monovalent aromatic hydrocarbon radical of 6-20 carbon atoms ($C_6$-$C_{20}$) derived by the removal of one hydrogen atom from a single carbon atom of a parent aromatic ring system. Some aryl groups are represented in the exemplary structures as "Ar". Aryl includes bicyclic radicals comprising an aromatic ring fused to a saturated, partially unsaturated ring, or aromatic carbocyclic ring. Typical aryl groups include, but are not limited to, radicals derived from benzene (phenyl), substituted benzenes, naphthalene, anthracene, biphenyl, indenyl, indanyl, 1,2-dihydronaphthalene, 1,2,3,4-tetrahydronaphthyl, and the like. Aryl groups are optionally substituted independently with one or more substituents described herein.

"Arylene" means a divalent aromatic hydrocarbon radical of 6-20 carbon atoms ($C_6$-$C_{20}$) derived by the removal of two hydrogen atom from a two carbon atoms of a parent aromatic ring system. Some arylene groups are represented in the exemplary structures as "Ar". Arylene includes bicyclic radicals comprising an aromatic ring fused to a saturated, partially unsaturated ring, or aromatic carbocyclic ring. Typical arylene groups include, but are not limited to, radicals derived from benzene (phenylene), substituted benzenes, naphthalene, anthracene, biphenylene, indenylene, indanylene, 1,2-dihydronaphthalene, 1,2,3,4-tetrahydronaphthyl, and the like. Arylene groups are optionally substituted.

The terms "heterocycle," "heterocyclyl" and "heterocyclic ring" are used interchangeably herein and refer to a saturated or a partially unsaturated (i.e., having one or more double and/or triple bonds within the ring) carbocyclic radical of 3 to about 20 ring atoms in which at least one ring atom is a heteroatom selected from nitrogen, oxygen, phosphorus and sulfur, the remaining ring atoms being C, where one or more ring atoms is optionally substituted independently with one or more substituents described below. A heterocycle may be a monocycle having 3 to 7 ring members (2 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), for example: a bicyclo [4,5], [5,5], [5,6], or [6,6] system. Heterocycles are described in Paquette, Leo A.; "Principles of Modern Heterocyclic Chemistry" (W.A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. "Heterocyclyl" also includes radicals where heterocycle radicals are fused with a saturated, partially unsaturated ring, or aromatic carbocyclic or heterocyclic ring. Examples of heterocyclic rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, dihydroisoquinolinyl, tetrahydroisoquinolinyl, pyrazolidinylimidazolinyl, imidazolidinyl, 2-oxa-5-azabicyclo[2.2.2]octane, 3-oxa-8-azabicyclo[3.2.1]octane, 8-oxa-3-azabicyclo[3.2.1]octane, 6-oxa-3-azabicyclo[3.1.1] heptane, 2-oxa-5-azabicyclo[2.2.1]heptane, 3-azabicyco [3.1.0]hexanyl, 3-azabicyclo[4.1.0]heptanyl, azabicyclo [2.2.2]hexanyl, 3H-indolyl quinolizinyl and N-pyridyl ureas. Spiro moieties are also included within the scope of this definition. Examples of a heterocyclic group wherein 2 ring carbon atoms are substituted with oxo (=O) moieties are pyrimidinonyl and 1,1-dioxo-thiomorpholinyl. The heterocycle groups herein are optionally substituted independently with one or more substituents described herein.

The term "heteroaryl" refers to a monovalent aromatic radical of 5-, 6-, or 7-membered rings, and includes fused ring systems (at least one of which is aromatic) of 5-20 atoms, containing one or more heteroatoms independently selected from nitrogen, oxygen, and sulfur. Examples of heteroaryl groups are pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, tetrahydroisoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Heteroaryl groups are optionally substituted independently with one or more substituents described herein.

Examples of bicyclic heteroaryl groups include:

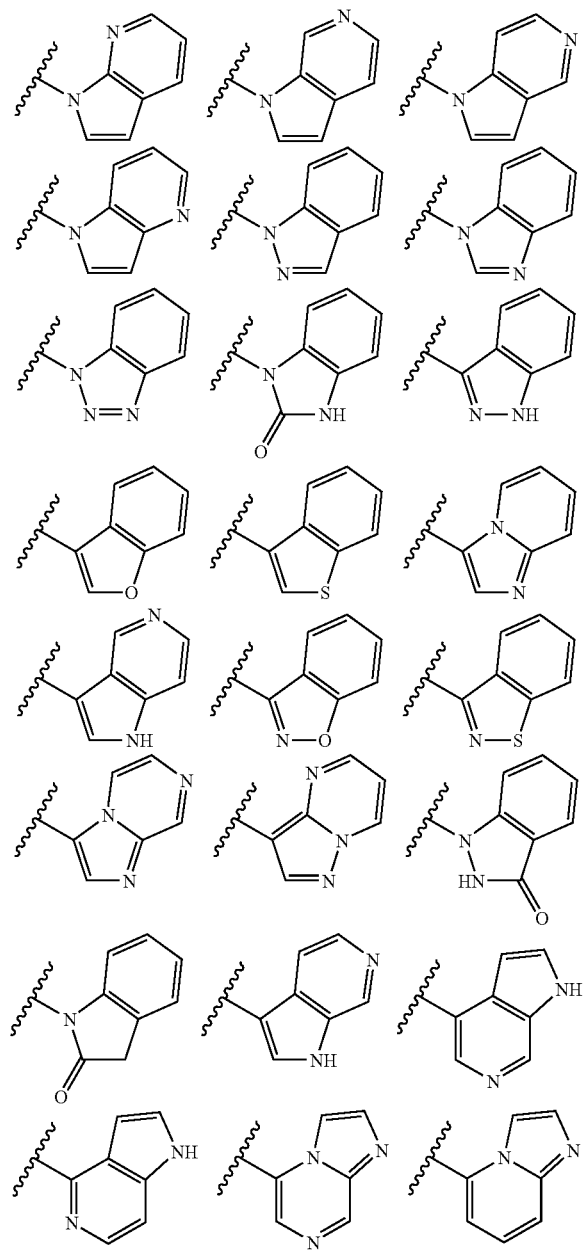

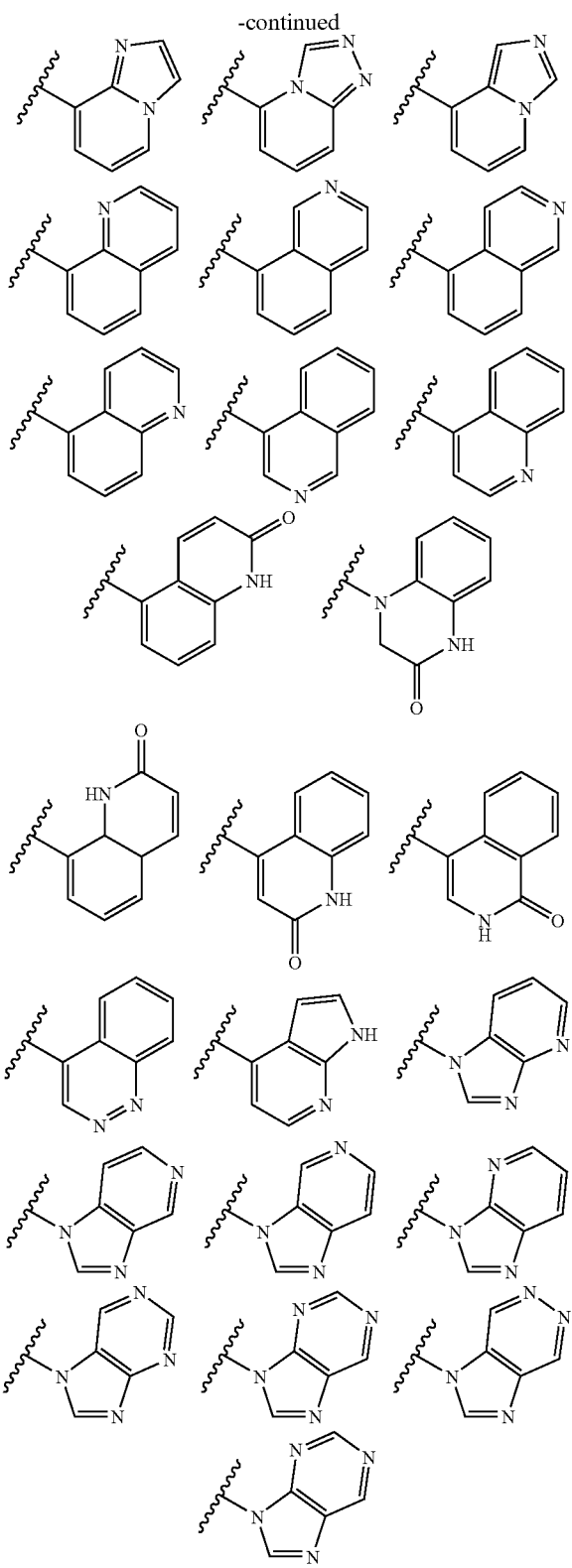

5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Ring nitrogen atoms of the heterocycle or heteroaryl groups may be bonded with oxygen to form N-oxides.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, benzimidazole, position 2 of a isoindole, or isoindoline, position 4 of a morpholine, and position 9 of a carbazole, or β-carboline.

The terms "treat" and "treatment" refer to both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

"Inflammatory disorder" as used herein can refer to any disease, disorder, or syndrome in which an excessive or unregulated inflammatory response leads to excessive inflammatory symptoms, host tissue damage, or loss of tissue function. "Inflammatory disorder" also refers to a pathological state mediated by influx of leukocytes and/or neutrophil chemotaxis.

"Inflammation" as used herein refers to a localized, protective response elicited by injury or destruction of tissues, which serves to destroy, dilute, or wall off (sequester) both the injurious agent and the injured tissue. Inflammation is notably associated with influx of leukocytes and/or neutrophil chemotaxis. Inflammation can result from infection with pathogenic organisms and viruses and from noninfectious The heterocycle or heteroaryl groups may be carbon (carbon-linked), or nitrogen (nitrogen-linked) bonded where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, means such as trauma or reperfusion following myocardial infarction or stroke, immune response to foreign antigen, and autoimmune responses. Accordingly, inflammatory disorders amenable to treatment with Formula I compounds encompass disorders associated with reactions of the specific defense system as well as with reactions of the nonspecific defense system.

"Specific defense system" refers to the component of the immune system that reacts to the presence of specific antigens. Examples of inflammation resulting from a response of the specific defense system include the classical response to foreign antigens, autoimmune diseases, and delayed type hypersensitivity response mediated by T-cells. Chronic inflammatory diseases, the rejection of solid transplanted tissue and organs, e.g., kidney and bone marrow transplants, and graft versus host disease (GVHD), are further examples of inflammatory reactions of the specific defense system.

The term "nonspecific defense system" as used herein refers to inflammatory disorders that are mediated by leukocytes that are incapable of immunological memory (e.g., granulocytes, and macrophages). Examples of inflammation that result, at least in part, from a reaction of the nonspecific defense system include inflammation associated with conditions such as adult (acute) respiratory distress syndrome (ARDS) or multiple organ injury syndromes; reperfusion injury; acute glomerulonephritis; reactive arthritis; dermatoses with acute inflammatory components; acute purulent meningitis or other central nervous system inflammatory disorders such as stroke; thermal injury; inflammatory bowel disease; granulocyte transfusion associated syndromes; and cytokine-induced toxicity.

"Autoimmune disease" as used herein refers to any group of disorders in which tissue injury is associated with humoral or cell-mediated responses to the body's own constituents.

"Allergic disease" as used herein refers to any symptoms, tissue damage, or loss of tissue function resulting from allergy. "Arthritic disease" as used herein refers to any disease that is characterized by inflammatory lesions of the joints attributable to a variety of etiologies. "Dermatitis" as used herein refers to any of a large family of diseases of the skin that are characterized by inflammation of the skin attributable to a variety of etiologies. "Transplant rejection" as used herein refers to any immune reaction directed against grafted tissue, such as organs or cells (e.g., bone marrow), characterized by a loss of function of the grafted and surrounding tissues, pain, swelling, leukocytosis, and thrombocytopenia. The therapeutic methods of the present invention include methods for the treatment of disorders associated with inflammatory cell activation.

"Inflammatory cell activation" refers to the induction by a stimulus (including, but not limited to, cytokines, antigens or auto-antibodies) of a proliferative cellular response, the production of soluble mediators (including but not limited to cytokines, oxygen radicals, enzymes, prostanoids, or vasoactive amines), or cell surface expression of new or increased numbers of mediators (including, but not limited to, major histocompatability antigens or cell adhesion molecules) in inflammatory cells (including but not limited to monocytes, macrophages, T lymphocytes, B lymphocytes, granulocytes (i.e., polymorphonuclear leukocytes such as neutrophils, basophils, and eosinophils), mast cells, dendritic cells, Langerhans cells, and endothelial cells). It will be appreciated by persons skilled in the art that the activation of one or a combination of these phenotypes in these cells can contribute to the initiation, perpetuation, or exacerbation of an inflammatory disorder.

The term "NSAID" is an acronym for "non-steroidal anti-inflammatory drug" and is a therapeutic agent with analgesic, antipyretic (lowering an elevated body temperature and relieving pain without impairing consciousness) and, in higher doses, with anti-inflammatory effects (reducing inflammation). The term "non-steroidal" is used to distinguish these drugs from steroids, which (among a broad range of other effects) have a similar eicosanoid-depressing, anti-inflammatory action. As analgesics, NSAIDs are unusual in that they are non-narcotic. NSAIDs include aspirin, ibuprofen, and naproxen. NSAIDs are usually indicated for the treatment of acute or chronic conditions where pain and inflammation are present. NSAIDs are generally indicated for the symptomatic relief of the following conditions: rheumatoid arthritis, osteoarthritis, inflammatory arthropathies (e.g. ankylosing spondylitis, psoriatic arthritis, Reiter's syndrome, acute gout, dysmenorrhoea, metastatic bone pain, headache and migraine, postoperative pain, mild-to-moderate pain due to inflammation and tissue injury, pyrexia, ileus, and renal colic. Most NSAIDs act as non-selective inhibitors of the enzyme cyclooxygenase, inhibiting both the cyclooxygenase-1 (COX-1) and cyclooxygenase-2 (COX-2) isoenzymes. Cyclooxygenase catalyzes the formation of prostaglandins and thromboxane from arachidonic acid (itself derived from the cellular phospholipid bilayer by phospholipase $A_2$). Prostaglandins act (among other things) as messenger molecules in the process of inflammation. COX-2 inhibitors include celecoxib, etoricoxib, lumiracoxib, parecoxib, rofecoxib, rofecoxib, and valdecoxib.

The terms "cancer" refers to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

A "chemotherapeutic agent" is a chemical compound useful in the treatment of cancer, regardless of mechanism of action. Classes of chemotherapeutic agents include, but are not limited to: alkylating agents, antimetabolites, spindle poison plant alkaloids, cytotoxic/antitumor antibiotics, topoisomerase inhibitors, antibodies, photosensitizers, and kinase inhibitors. Chemotherapeutic agents include compounds used in "targeted therapy" and conventional chemotherapy. Examples of chemotherapeutic agents include: erlotinib (TARCEVA®, Genentech/OSI Pharm.), docetaxel (TAXOTERE®, Sanofi-Aventis), 5-FU (fluorouracil, 5-fluorouracil, CAS No. 51-21-8), gemcitabine (GEMZAR®, Lilly), PD-0325901 (CAS No. 391210-10-9, Pfizer), cisplatin (cis-diamine, dichloroplatinum(II), CAS No. 15663-27-1), carboplatin (CAS No. 41575-94-4), paclitaxel (TAXOL®, Bristol-Myers Squibb Oncology, Princeton, N.J.), trastuzumab (HERCEPTIN®, Genentech), temozolomide (4-methyl-5-oxo-2,3,4,6,8-pentazabicyclo[4.3.0]nona-2,7,9-triene-9-carboxamide, CAS No. 85622-93-1, TEMODAR®, TEMODAL®, Schering Plough), tamoxifen ((Z)-2-[4-(1,2-diphenylbut-1-enyl)phenoxy]-N,N-dimethylethanamine, NOLVADEX®, ISTUBAL®, VALODEX®), and doxorubicin (ADRIAMYCINO), Akti-1/2, HPPD, and rapamycin.

More examples of chemotherapeutic agents include: oxaliplatin (ELOXATIN®, Sanofi), bortezomib (VELCADE®, Millennium Pharm.), sutent (SUNITINIB®, SU11248, Pfizer), letrozole (FEMARA®, Novartis), imatinib mesylate (GLEEVEC®, Novartis), XL-518 (Mek inhibitor, Exelixis, WO 2007/044515), ARRY-886 (Mek inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), PTK787/ZK 222584 (Novartis), fulvestrant (FASLODEX®, AstraZeneca), leucovorin (folinic acid), rapamycin (sirolimus, RAPAMUNE®, Wyeth), lapatinib (TYKERB®, GSK572016, Glaxo Smith Kline), lonafarnib (SARASAR™, SCH 66336, Schering Plough), sorafenib (NEXAVAR®, BAY43-9006, Bayer Labs), gefitinib (IRESSA®, AstraZeneca), irinotecan (CAMPTOSAR®, CPT-11, Pfizer), tipifarnib (ZARNESTRA™, Johnson & Johnson), ABRAXANE™ (Cremophor-free), albumin-engineered nanoparticle formulations of paclitaxel (American Pharmaceutical Partners, Schaumberg, Ill.), vandetanib (rINN, ZD6474, ZACTIMA®, AstraZeneca), chloranmbucil, AG1478, AG1571 (SU 5271; Sugen), temsirolimus (TORISEL®, Wyeth), pazopanib (GlaxoSmithKline), canfosfamide (TELCYTA®, Telik), thiotepa and cyclosphosphamide (CYTOXAN®, NEOSAR®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, calicheamicin gamma1I, calicheamicin omega1I (Angew Chem. Intl. Ed. Engl. (1994) 33:183-186); dynemicin, dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, morpholino-doxorubicin, cyanomorpholino-doxorubicin, 2-pyrrolino-doxorubicin and deoxydoxorubicin), epirubicin, esorubicin, idarubicin, nemorubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; 6-thioguanine; mercaptopurine; methotrexate; platinum analogs such as cisplatin and carboplatin; vinblastine; etoposide (VP-16); ifosfamide; mitoxantrone; vincristine; vinorelbine (NAVELBINE®); novantrone; teniposide; edatrexate; daunomycin; aminopterin; capecitabine (XELODA®, Roche); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors such as MEK inhibitors (WO 2007/044515); (v) lipid kinase inhibitors; (vi) antisense oligonucleotides, particularly those which inhibit expression of genes in signaling pathways implicated in aberrant cell proliferation, for example, PKC-alpha, Raf and H-Ras, such as oblimersen (GENASENSE®, Genta Inc.); (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; topoisomerase 1 inhibitors such as LURTOTECAN®; ABARELIX® rmRH; (ix) anti-angiogenic agents such as bevacizumab (AVASTIN®, Genentech); and pharmaceutically acceptable salts, acids and derivatives of any of the above.

Also included in the definition of "chemotherapeutic agent" are therapeutic antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG™, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth).

Humanized monoclonal antibodies with therapeutic potential as chemotherapeutic agents in combination with the PI3K inhibitors of the invention include: alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab, and visilizumab.

A "metabolite" is a product produced through metabolism in the body of a specified compound or salt thereof. Metabolites of a compound may be identified using routine techniques known in the art and their activities determined using tests such as those described herein. Such products may result for example from the oxidation, reduction, hydrolysis, amidation, deamidation, esterification, deesterification, enzymatic cleavage, and the like, of the administered compound. Accordingly, the invention includes metabolites of compounds of the invention, including compounds produced by a process comprising contacting a compound of this invention with a mammal for a period of time sufficient to yield a metabolic product thereof.

The term "package insert" is used to refer to instructions customarily included in commercial packages of therapeutic products, that contain information about the indications, usage, dosage, administration, contraindications and/or warnings concerning the use of such therapeutic products.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space. Stereoisomers include enantiomers and diastereomers.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography. Diastereomers include geometric isomers, cis/trans and E/Z isomers, and atropisomers.

"Enantiomers" refer to two stereoisomers of a compound which are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, and pamoate (i.e., 1,1'-methylene-bis(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, trifluoroacetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The phrase "pharmaceutically acceptable" indicates that the substance or composition must be compatible chemically and/or toxicologically, with the other ingredients comprising a formulation, and/or the mammal being treated therewith.

A "solvate" refers to an association or complex of one or more solvent molecules and a compound of the invention. Examples of solvents that form solvates include, but are not limited to, water, isopropanol, ethanol, methanol, DMSO, ethylacetate, acetic acid, and ethanolamine.

The terms "compound of this invention," and "compounds of the present invention" and "compounds of Formula I" include compounds of Formulas I and stereoisomers, tautomers, solvates, metabolites, and pharmaceutically acceptable salts and prodrugs thereof.

Any formula or structure given herein, including Formula I compounds, is also intended to represent hydrates, solvates, and polymorphs of such compounds, and mixtures thereof.

Any formula or structure given herein, including Formula I compounds, is also intended to represent isotopically labeled forms of the compounds as well as unlabeled forms. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as, but not limited to 2H (deuterium, D), 3H (tritium), 11C, 13C, 14C, 15N, 18F, 31P, 32P, 35S, 36Cl, and 125I. Various isotopically labeled compounds of the present invention, for example those into which radioactive isotopes such as 3H, 13C, and 14C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays, or in radioactive treatment of patients. Deuterium labelled or substituted therapeutic compounds of the invention may have improved DMPK (drug metabolism and pharmacokinetics) properties, relating to distribution, metabolism, and excretion (ADME). Substitution with heavier isotopes such as deuterium may afford certain therapeutic advantages resulting from greater metabolic stability, for example increased in vivo half-life or reduced dosage requirements. An 18F labeled compound may be useful for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., 2H or D) may afford certain therapeutic advantages resulting from greater metabolic stability, for example increased in vivo half-life or reduced dosage requirements or an improvement in therapeutic index. It is understood that deuterium in this context is regarded as a substituent in the compound of the formula (I). The concentration of such a heavier isotope, specifically deuterium, may be defined by an isotopic enrichment factor. In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this invention any atom specifically designated as a deuterium (D) is meant to represent deuterium.

Formula I Compounds of the Invention

Formula I compounds include compounds selected from Formulas Ia and Ib:

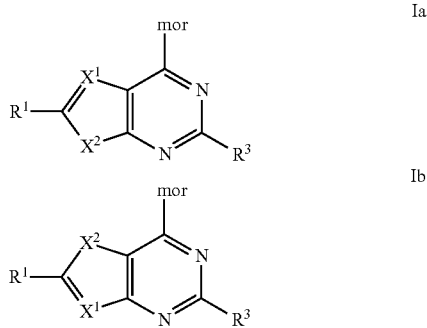

and stereoisomers, tautomers, or pharmaceutically acceptable salts thereof, wherein (i) $X^1$ is N and $X^2$ is S, (ii) $X^1$ is CR' and $X^2$ is S, (iii) $X^1$ is N and $X^2$ is $NR^2$, or (iv) $X^1$ is $CR^7$ and $X^2$ is O;

$R^1$ is selected from $C_1$-$C_{12}$ alkyl,
$C_2$-$C_8$ alkenyl,
$C_2$-$C_8$ alkynyl,
$C_6$-$C_{20}$ aryl,
$C_2$-$C_{20}$ heterocyclyl,
$C_3$-$C_{12}$ carbocyclyl,
$C_1$-$C_{20}$ heteroaryl,
—($C_1$-$C_{12}$ alkylene)-($C_3$-$C_{12}$ carbocyclyl),
—($C_1$-$C_{12}$ alkylene)-($C_2$-$C_{20}$ heterocyclyl),
—($C_1$-$C_{12}$ alkylene)-($C_2$-$C_{20}$ heterocyclyl)-($C_2$-$C_{20}$ heterocyclyl),
—($C_1$-$C_{12}$ alkylene)-($C_2$-$C_{20}$ heterocyclyl)-($C_3$-$C_{12}$ carbocyclyl),
—($C_1$-$C_{12}$ alkylene)-($C_2$-$C_{20}$ heterocyclyl)-C(=O)—($C_2$-$C_{20}$ heterocyclyl),
—($C_1$-$C_{12}$ alkylene)-($C_1$-$C_{20}$ heteroaryl),
—($C_1$-$C_{12}$ alkylene)-($C_2$-$C_{20}$ heterocyclyl)-($C_1$-$C_{12}$ alkyl),
—($C_1$-$C_{12}$ alkylene)-($C_6$-$C_{20}$ aryl)-($C_1$-$C_{12}$ alkyl),
—($C_1$-$C_{12}$ alkylene)-($C_1$-$C_{20}$ heteroaryl)-($C_1$-$C_{12}$ alkyl),
—($C_1$-$C_{12}$ alkylene)-C(=O)—($C_2$-$C_{20}$ heterocyclyl),
—($C_1$-$C_{12}$ alkylene)-$NHR^{2'}$,
—($C_1$-$C_{12}$ alkylene)-$NR^{2'}$—($C_1$-$C_{12}$ alkyl),
—($C_1$-$C_{12}$ alkylene)-$NR^{2'}$—($C_3$-$C_{12}$ carbocyclyl),
—($C_1$-$C_{12}$ alkylene)-$NR^{2'}$—($C_2$-$C_{20}$ heterocyclyl),
—($C_1$-$C_{12}$ alkylene)-$NR^{2'}$—($C_1$-$C_{20}$ heteroaryl),
—($C_1$-$C_{12}$ alkylene)-$NR^{2'}$—($C_6$-$C_{20}$ aryl),
—($C_1$-$C_{12}$ alkylene)-$NR^{2'}$—($C_1$-$C_{12}$ alkylene)-($C_3$-$C_{12}$ carbocyclyl),
—($C_1$-$C_{12}$ alkylene)-$NR^{2'}$—($C_1$-$C_{12}$ alkylene)-($C_1$-$C_{20}$ heteroaryl), —(C$_1$-C$_{12}$ alkylene)-NR$^{2'}$—(C$_1$-C$_{12}$ alkylene)-(C$_1$-C$_{20}$ heterocyclyl), —(C$_1$-C$_{12}$ alkylene)-NR$^{2'}$—(C$_1$-C$_{12}$ alkylene)-(C$_6$-C$_{20}$ aryl), —(C$_1$-C$_{12}$ alkylene)-NR$^{2'}$—(C$_1$-C$_{12}$ alkylene)-NHC(=O)—(C$_1$-C$_{20}$ heteroaryl), —(C$_1$-C$_{12}$ alkylene)-(C$_2$-C$_{20}$ heterocyclyl)-N(C$_1$-C$_{12}$ alkyl)R$^{2'}$, —(C$_1$-C$_{12}$ alkylene)-(C$_2$-C$_{20}$ heterocyclyl)-(C$_1$-C$_{12}$ alkyl)-N(C$_1$-C$_{12}$ alkyl)R$^{2'}$, —(C$_2$-C$_{12}$ alkenylene)-(C$_2$-C$_{20}$ heterocyclyl), —(C$_1$-C$_{20}$ heteroaryl)-(C$_2$-C$_{20}$ heterocyclyl), —(C$_1$-C$_{20}$ heteroaryl)-(C$_3$-C$_{12}$ carbocyclyl), —C(=O)—(C$_2$-C$_{20}$ heterocyclyl), —C(=O)—(C$_1$-C$_{20}$ heteroaryl), —C(=O)—(C$_2$-C$_{20}$ heterocyclyl)-(C$_2$-C$_{20}$ heterocyclyl), —C(=O)—(C$_2$-C$_{20}$ heterocyclyl)-(C$_1$-C$_{20}$ heteroaryl), —C(=O)—(C$_1$-C$_{12}$ alkyl), —C(=O)—NR$^{2'}$—(C$_1$-C$_{12}$ alkyl), and —CR$^4$=CR$^5$R$^6$ where R$^4$ is selected from H, F, Cl, Br, I, and C$_1$-C$_{12}$ alkyl, and R$^5$ and R$^6$ form C$_2$-C$_{20}$ heterocyclyl, C$_1$-C$_{20}$ heteroaryl, or C$_3$-C$_{12}$ carbocyclyl, where alkyl, alkenyl, alkynyl, alkylene, carbocyclyl, heterocyclyl, aryl, and heteroaryl are optionally substituted with one or more groups independently selected from F, Cl, Br, I, —CH$_3$, —CH$_2$CH$_3$, —CH$_2$CH(CH$_3$)$_2$, —CH$_2$NH$_2$, —CH$_2$N(CH$_3$)$_2$, —CH$_2$CH$_2$NH$_2$, —CH$_2$CH$_2$N(CH$_3$)$_2$, —CH$_2$OH, —CH$_2$OCH$_3$, —CH$_2$CH$_2$OH, —C(CH$_3$)$_2$OH, —CH$_2$C(CH$_3$)$_2$OH, —CH(OH)CH(CH$_3$)$_2$, —C(CH$_3$)$_2$CH$_2$OH, —CH$_2$CH$_2$SO$_2$CH$_3$, —CN, —CF$_3$, —CO$_2$H, —CHO, —COCH$_3$, —CO$_2$CH$_3$, —CO$_2$C(CH$_3$)$_3$, —COCH$_2$OH, —COC(OH)(CH$_3$)$_2$, —COCH(OH)CH$_3$, —CONH$_2$, —CONHCH$_3$, —CON(CH$_3$)$_2$, —CH$_2$CONH$_2$, —CH$_2$CON(CH$_3$)$_2$, —C(CH$_3$)$_2$CONH$_2$, —NO$_2$, —NH$_2$, —NHCH$_3$, —N(CH$_3$)$_2$, —NHCOCH$_3$, —N(CH$_3$)COCH$_3$, —NHS(O)$_2$CH$_3$, —N(CH$_3$)C(CH$_3$)$_2$CONH$_2$, —N(CH$_3$)CH$_2$CH$_2$S(O)$_2$CH$_3$, =O, —OH, —OCH$_3$, —S(O)$_2$N(CH$_3$)$_2$, —SCH$_3$, —CH$_2$OCH$_3$, —S(O)$_2$CH$_3$, —C(O)-cyclopropyl, cyclopropyl, cyclobutyl, oxetanyl, and morpholino;

R$^2$ and R$^{2'}$ are independently selected from H, C$_1$-C$_{12}$ alkyl, C$_2$-C$_8$ alkenyl, C$_2$-C$_8$ alkynyl, —(C$_1$-C$_{12}$ alkylene)-(C$_3$-C$_{12}$ carbocyclyl), —(C$_1$-C$_{12}$ alkylene)-(C$_2$-C$_{20}$ heterocyclyl), —(C$_1$-C$_{12}$ alkylene)-C(=O)—(C$_2$-C$_{20}$ heterocyclyl), —(C$_1$-C$_{12}$ alkylene)-(C$_6$-C$_{20}$ aryl), and —(C$_1$-C$_{12}$ alkylene)-(C$_1$-C$_{20}$ heteroaryl), where alkyl, alkenyl, alkynyl, alkylene, carbocyclyl, heterocyclyl, aryl, and heteroaryl are optionally substituted with one or more groups independently selected from F, Cl, Br, I, —CH$_3$, —CH$_2$OH, —CN, —CF$_3$, —CO$_2$H, —COCH$_3$, —CO$_2$CH$_3$, —CONH$_2$, —CONHCH$_3$, —CON(CH$_3$)$_2$, —NO$_2$, —NH$_2$, —NHCH$_3$, —NHCOCH$_3$, —NHS(O)$_2$CH$_3$, —OH, —OCH$_3$, —S(O)$_2$N(CH$_3$)$_2$, —SCH$_3$, —CH$_2$OCH$_3$, and —S(O)$_2$CH$_3$;

R$^3$ is a bicyclic heteroaryl group selected from:

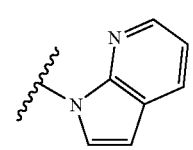 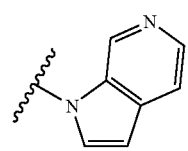 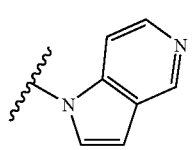

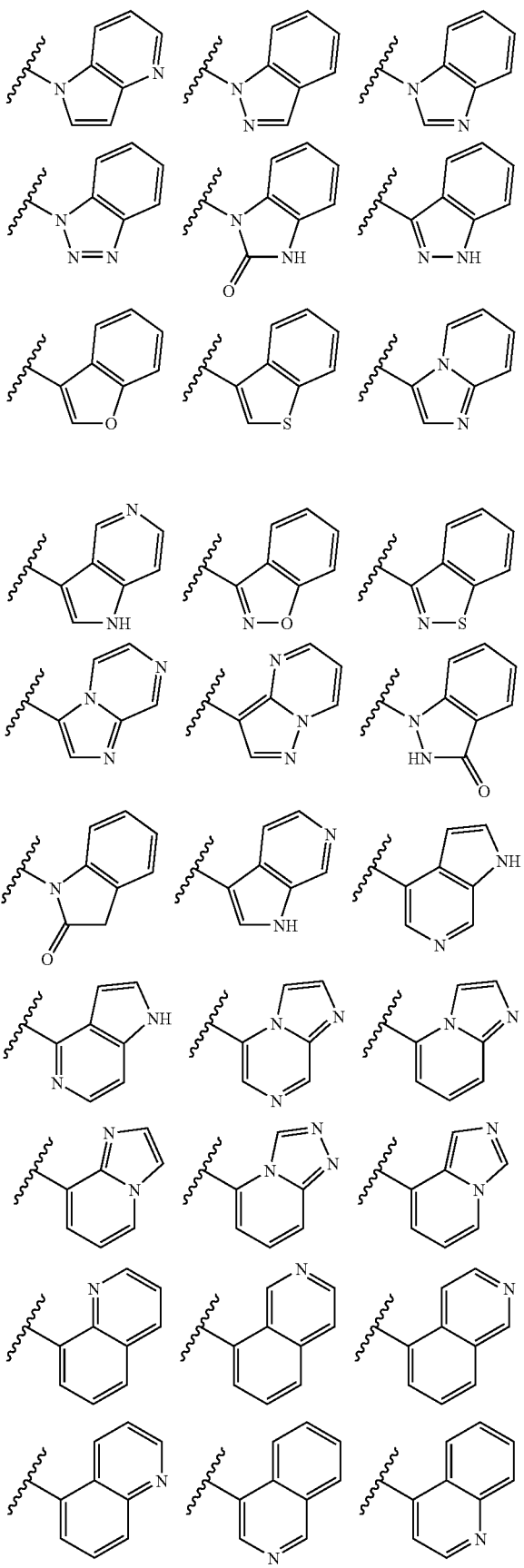

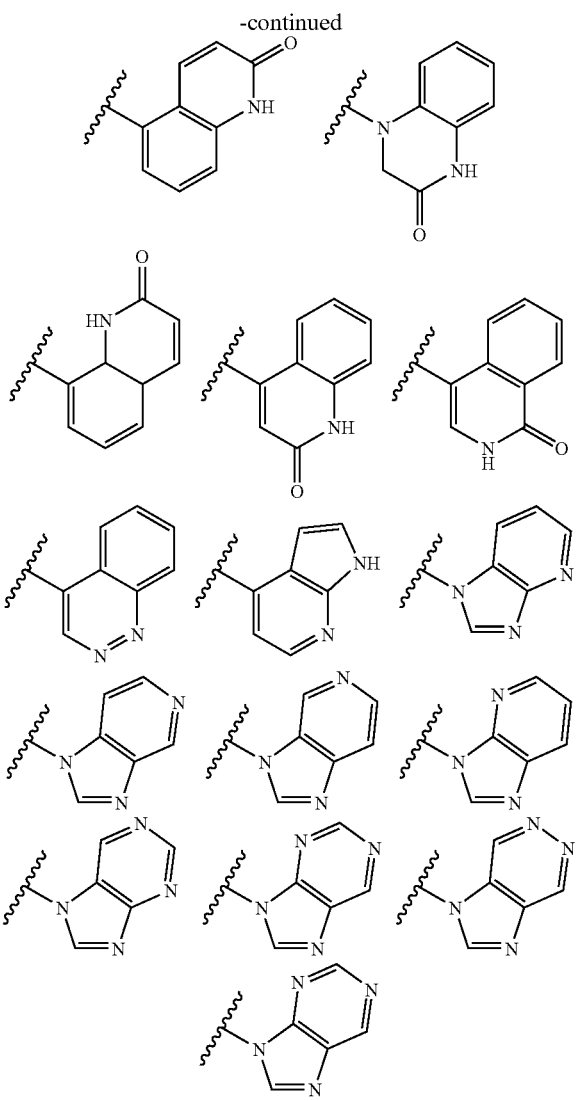

where the wavy line indicates the site of attachment;

optionally substituted with one or more groups independently selected from $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, $C_1$-$C_{20}$ heteroaryl, —($C_1$-$C_{12}$ alkylene)-($C_2$-$C_{20}$ heterocyclyl), —NH—($C_1$-$C_{12}$ alkylene)-($C_2$-$C_{20}$ heterocyclyl), —N($C_1$-$C_{12}$ alkyl)-($C_1$-$C_{12}$ alkylene)-($C_2$-$C_{20}$ heterocyclyl), —NH—($C_2$-$C_{20}$ heterocyclyl), —O—($C_2$-$C_{20}$ heterocyclyl), —NH—($C_3$-$C_{12}$ carbocyclyl), —O—($C_3$-$C_{12}$ carbocyclyl), F, Cl, Br, I, —CN, —$CO_2H$, —$CONH_2$, —CONH($C_1$-$C_{12}$ alkyl), —CON($C_1$-$C_{12}$ alkyl)$_2$, —CO($C_1$-$C_{12}$ alkyl), —$NO_2$, —$NH_2$, —NH($C_1$-$C_{12}$ alkyl), —N($C_1$-$C_{12}$ alkyl)$_2$, —NHCO ($C_1$-$C_{12}$ alkyl), —NHS(O)$_2$($C_1$-$C_{12}$ alkyl), —N($C_1$-$C_{12}$ alkyl)S(O)$_2$($C_1$-$C_{12}$ alkyl), —OH, —O($C_1$-$C_{12}$ alkyl), —NHC(=O)NH($C_1$-$C_{12}$ alkyl), —SH, —S($C_1$-$C_{12}$ alkyl), —S(O)($C_1$-$C_{12}$ alkyl), —S(O)$_2$($C_1$-$C_{12}$ alkyl), —S(O)$_2$NH$_2$, —S(O)$_2$NH($C_1$-$C_{12}$ alkyl), and —S(O)$_2$N($C_1$-$C_{12}$ alkyl)$_2$, where alkyl, alkenyl, alkynyl, alkylene, carbocyclyl, heterocyclyl, aryl, and heteroaryl are optionally substituted with one or more groups independently selected from F, Cl, Br, I, —CN, —$CF_3$, —$CO_2H$, —$COCH_3$, —$CO_2CH_3$, —$CONH_2$, —$CONHCH_3$, —$CON(CH_3)_2$, —$NO_2$, —$NH_2$, —$NHCH_3$, —$NHCOCH_3$, —NHS(O)$_2CH_3$, =O, —OH, —$OCH_3$, —S(O)$_2$N($CH_3$)$_2$, —SH, —$SCH_3$, —$CH_2OCH_3$, and —S(O)$_2$$CH_3$;

$R^7$ is selected from H, $C_1$-$C_{12}$ alkyl, $C_2$-$C_8$ alkenyl, $C_2$-$C_8$ alkynyl, —($C_1$-$C_{12}$ alkylene)-($C_3$-$C_{12}$ carbocyclyl), —($C_1$-$C_{12}$ alkylene)-($C_2$-$C_{20}$ heterocyclyl), —($C_1$-$C_{12}$ alkylene)-C(=O)—($C_2$-$C_{20}$ heterocyclyl), —($C_1$-$C_{12}$ alkylene)-($C_6$-$C_{20}$ aryl), and —($C_1$-$C_{12}$ alkylene)-($C_1$-$C_{20}$ heteroaryl), where alkyl, alkenyl, alkynyl, alkylene, carbocyclyl, heterocyclyl, aryl, and heteroaryl are optionally substituted with one or more groups independently selected from F, Cl, Br, I, —$CH_3$, —$CH_2OH$, —CN, —$CF_3$, —$CO_2H$, —$COCH_3$, —$CO_2CH_3$, —$CONH_2$, —$CONHCH_3$, —$CON(CH_3)_2$, —$NO_2$, —$NH_2$, —$NHCH_3$, —$NHCOCH_3$, —NHS(O)$_2CH_3$, =O, —OH, —$OCH_3$, —S(O)$_2$N($CH_3$)$_2$, —$SCH_3$, —$CH_2OCH_3$, and —S(O)$_2CH_3$;

mor is a morpholine group or a bicyclic structure selected from:

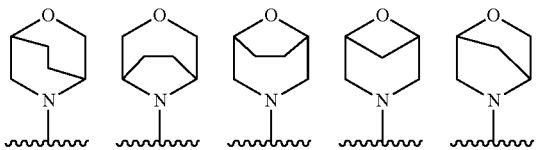

optionally substituted with one or more groups selected from F, Cl, Br, I, —$CH_3$, —$CH_2CH_3$, —$CH_2CH_2CH_3$, —CH($CH_3$)$_2$, —C($CH_3$)$_3$, —$CH_2OCH_3$, —$CHF_2$, —CN, —$CF_3$, —$CH_2OH$, —$CH_2OCH_3$, —$CH_2CH_2OH$, —$CH_2C(CH_3)_2$OH, —CH($CH_3$)OH, —CH($CH_2CH_3$)OH, —$CH_2$CH(OH)$CH_3$, —C($CH_3$)$_2$OH, —C($CH_3$)$_2OCH_3$, —CH($CH_3$)F, —C($CH_3$)$F_2$, —CH($CH_2CH_3$)F, —C($CH_2CH_3$)$_2$F, —$CO_2H$, —$CONH_2$, —CON($CH_2CH_3$)$_2$, —$COCH_3$, —$CON(CH_3)_2$, —$NO_2$, —$NH_2$, —$NHCH_3$, —N($CH_3$)$_2$, —$NHCH_2CH_3$, —NHCH($CH_3$)$_2$, —$NHCH_2CH_2OH$, —$NHCH_2CH_2OCH_3$, —$NHCOCH_3$, —$NHCOCH_2CH_3$, —$NHCOCH_2OH$, —NHS(O)$_2CH_3$, —N($CH_3$)S(O)$_2CH_3$, =O, —OH, —$OCH_3$, —$OCH_2CH_3$, —OCH($CH_3$)$_2$, —SH, —NHC(=O)$NHCH_3$, —NHC(=O)$NHCH_2CH_3$, —S(O)$CH_3$, —S(O)$CH_2CH_3$, —S(O)$_2CH_3$, —S(O)$_2NH_2$, —S(O)$_2$$NHCH_3$, —S(O)$_2$N($CH_3$)$_2$, —$CH_2$S(O)$_2CH_3$;

and wherein the IC50 binding activity to p110 delta is ten or more times lower than the binding activity to p110 alpha;

with the proviso that a Formula Ib compound wherein (ii) $X^1$ is $CR^7$ and $X^2$ is S, $R^1$ is —($C_1$-$C_{12}$ alkylene)-($C_2$-$C_{20}$ heterocyclyl), $R^3$ is optionally substituted benzo[d]imidazol-1-yl, and $R^7$ is H, excludes the $C_2$-$C_{20}$ heterocyclyl of $R^1$ substituted with —S(O)$_2CH_3$.

Exemplary Formula I compounds include where mor is an unsubstituted morpholine group, having the structures Ic and Id:

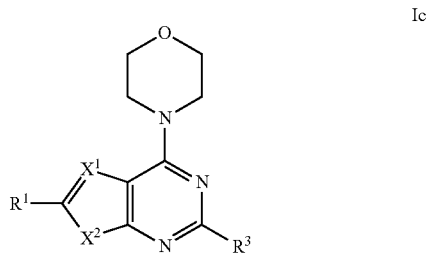

Ic

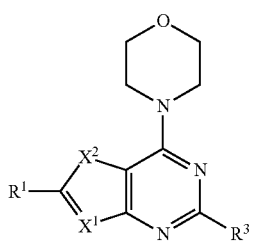

Exemplary Formula I compounds include thiazolopyrimidines where (i) $X^1$ is N and $X^2$ is S:

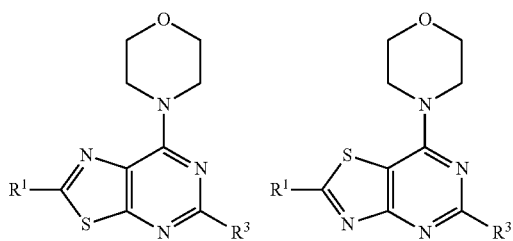

Exemplary Formula I compounds include thienopyrimidines where (ii) $X^1$ is $CR^7$ and $X^2$ is S:

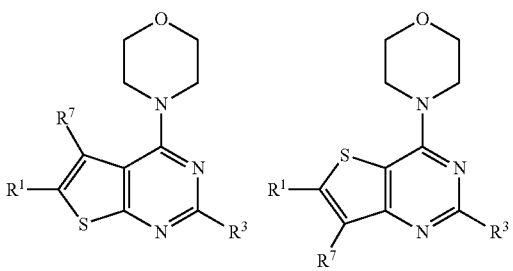

Exemplary Formula I compounds include purines where (iii) $X^1$ is N and $X^2$ is $NR^2$:

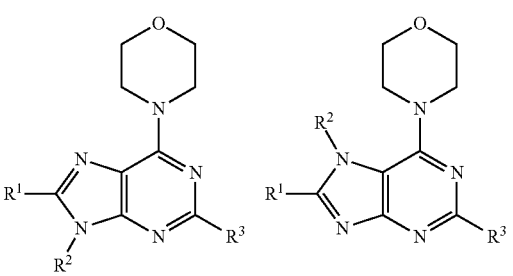

Exemplary Formula I compounds include furanopyrimidines where (iv) $X^1$ is $CR^7$ and $X^2$ is O:

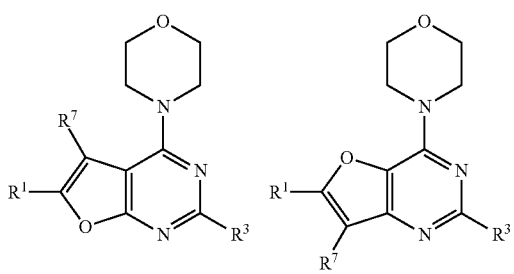

In additional exemplary embodiments, mor is selected from the structures:

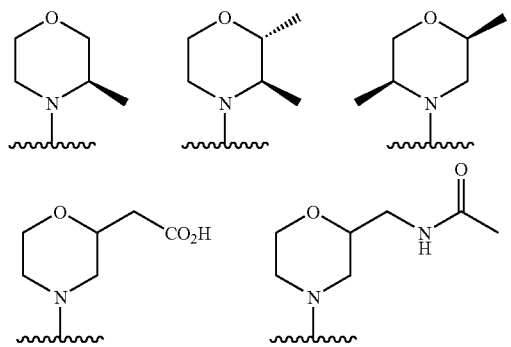

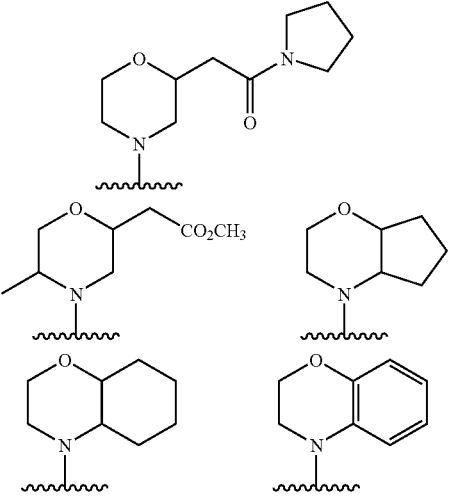

where the wavy line indicates the attachment to the 4-position of the pyrimidine ring.

Exemplary embodiments of $R^1$ include the groups:

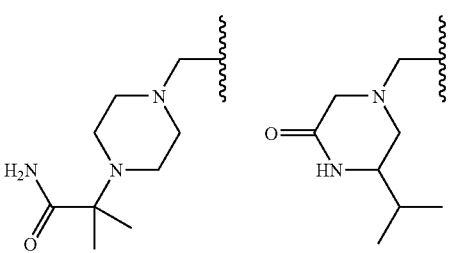

-continued
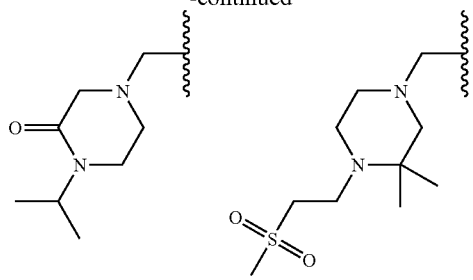 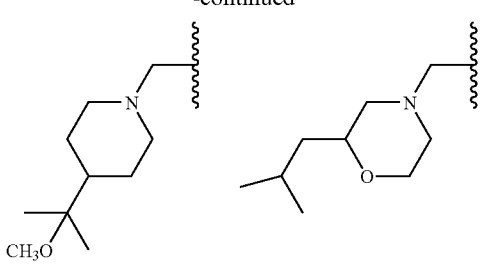
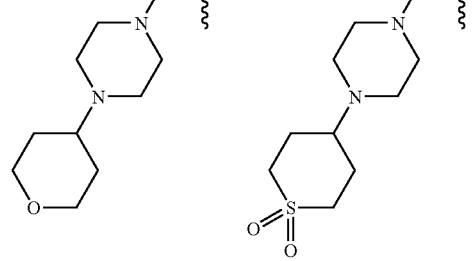
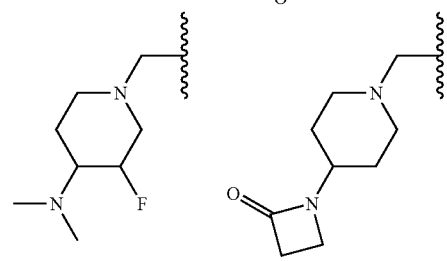
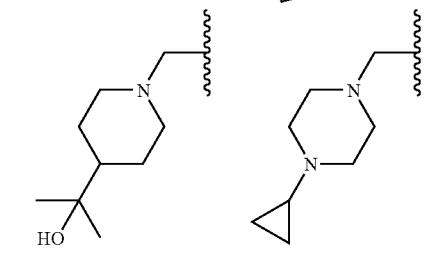
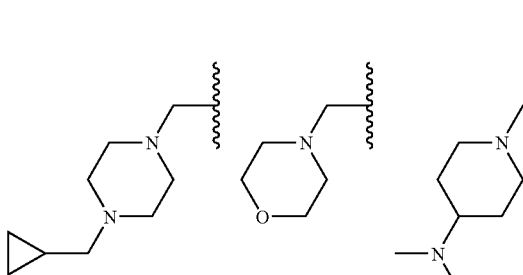
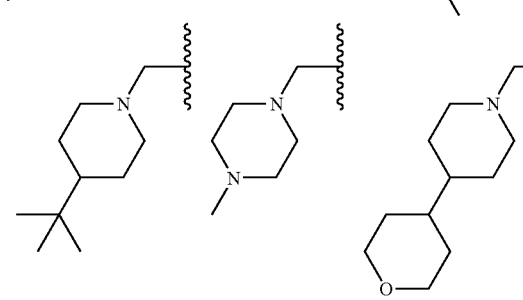
-continued
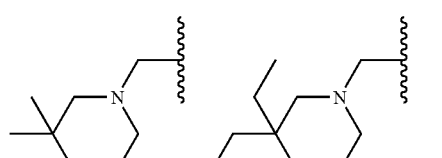
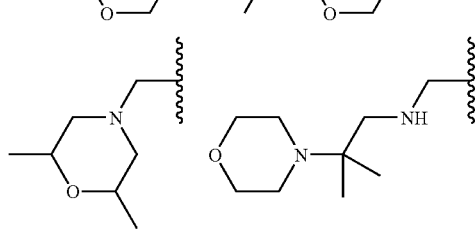
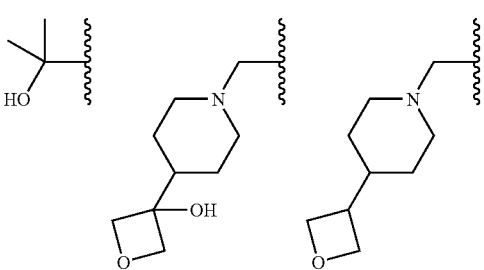
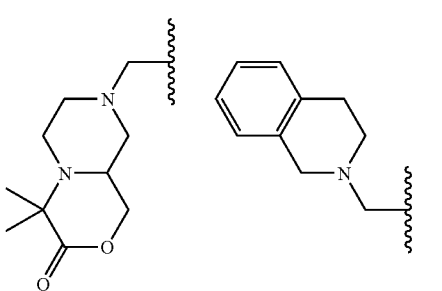
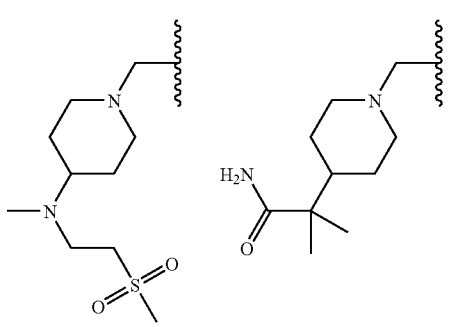

-continued
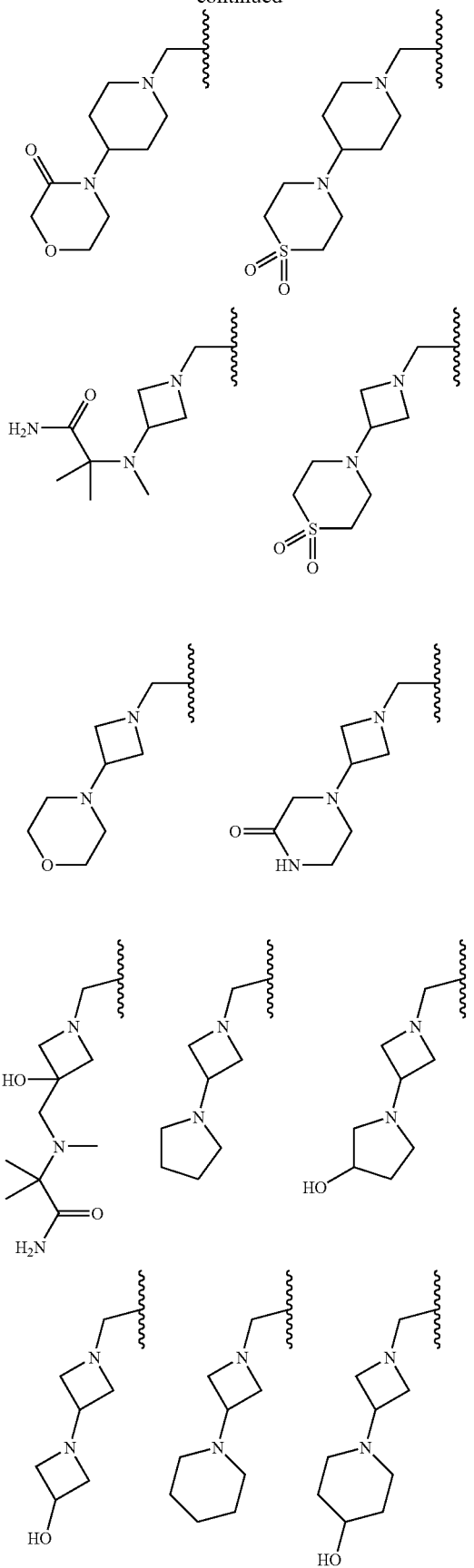
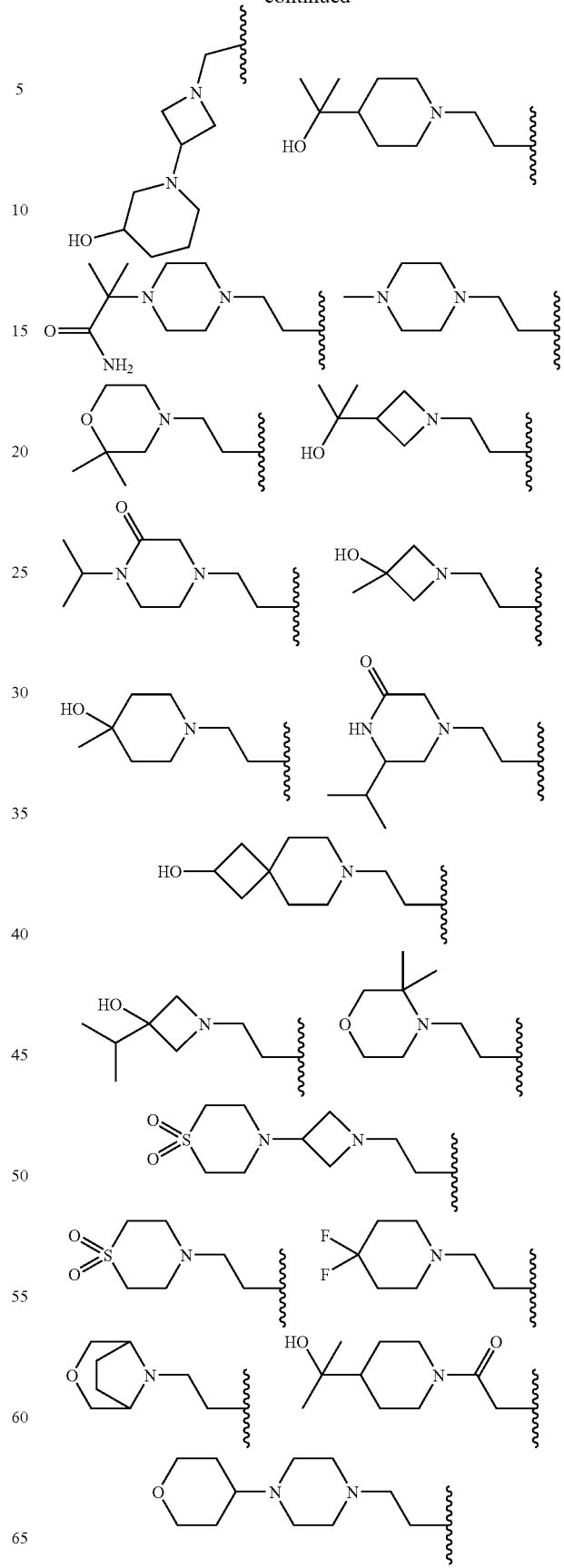

27
-continued
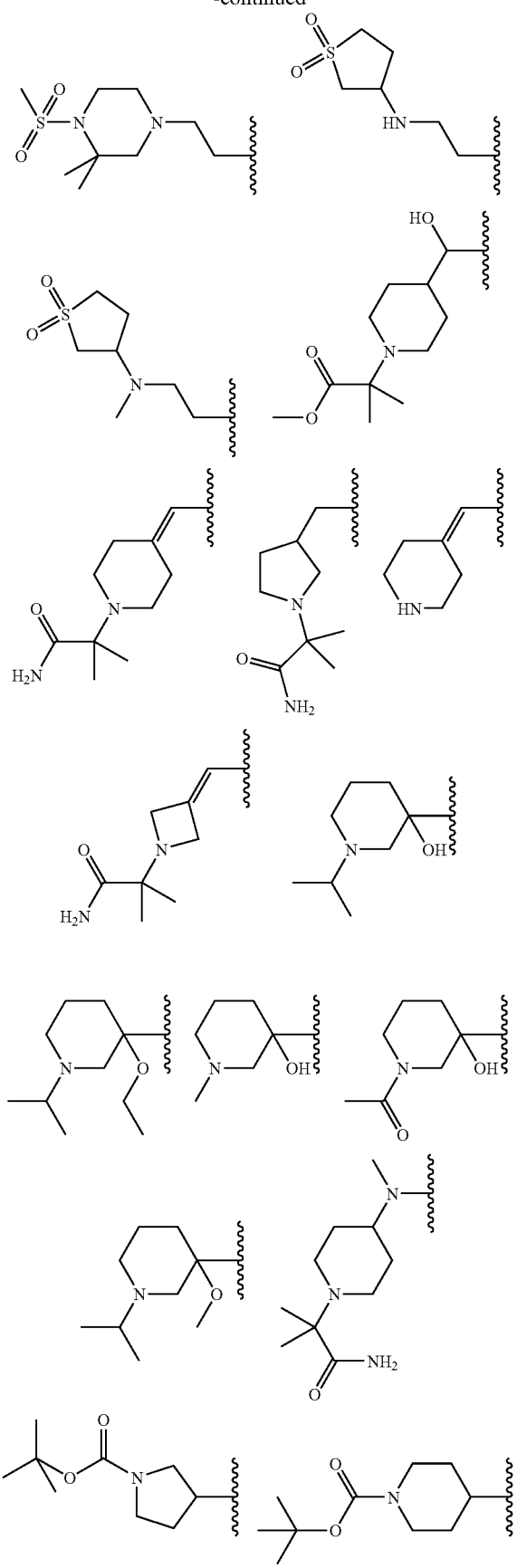
28
-continued
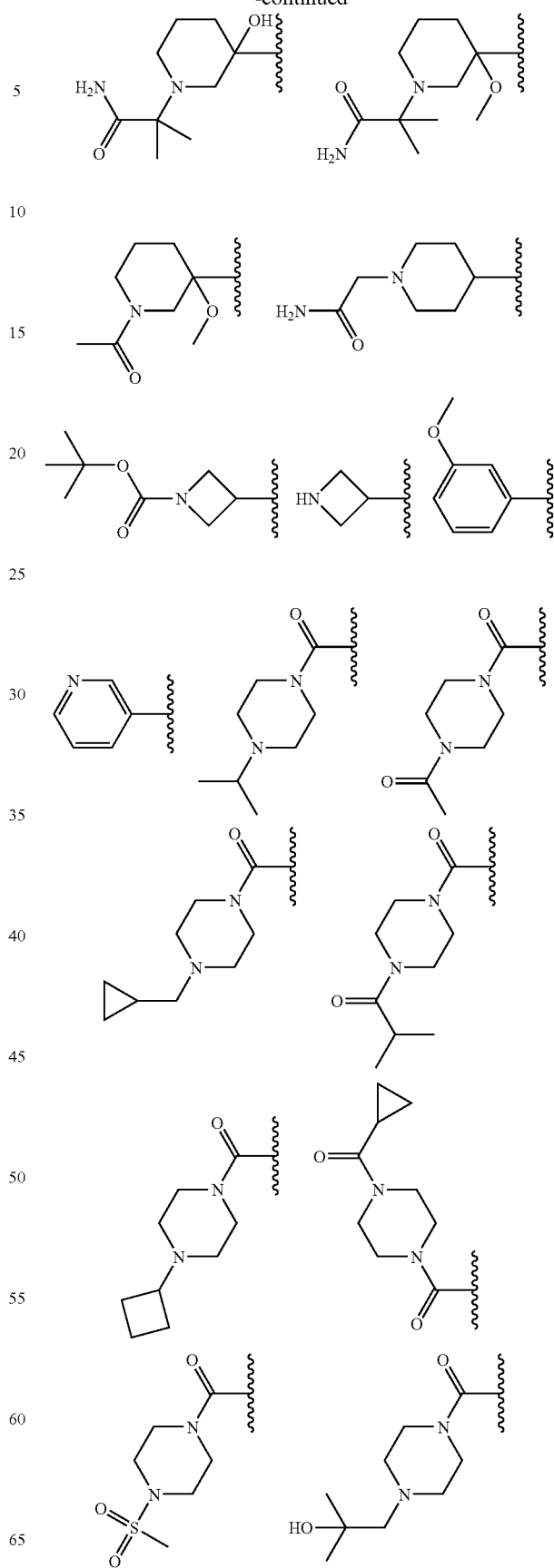

29
-continued
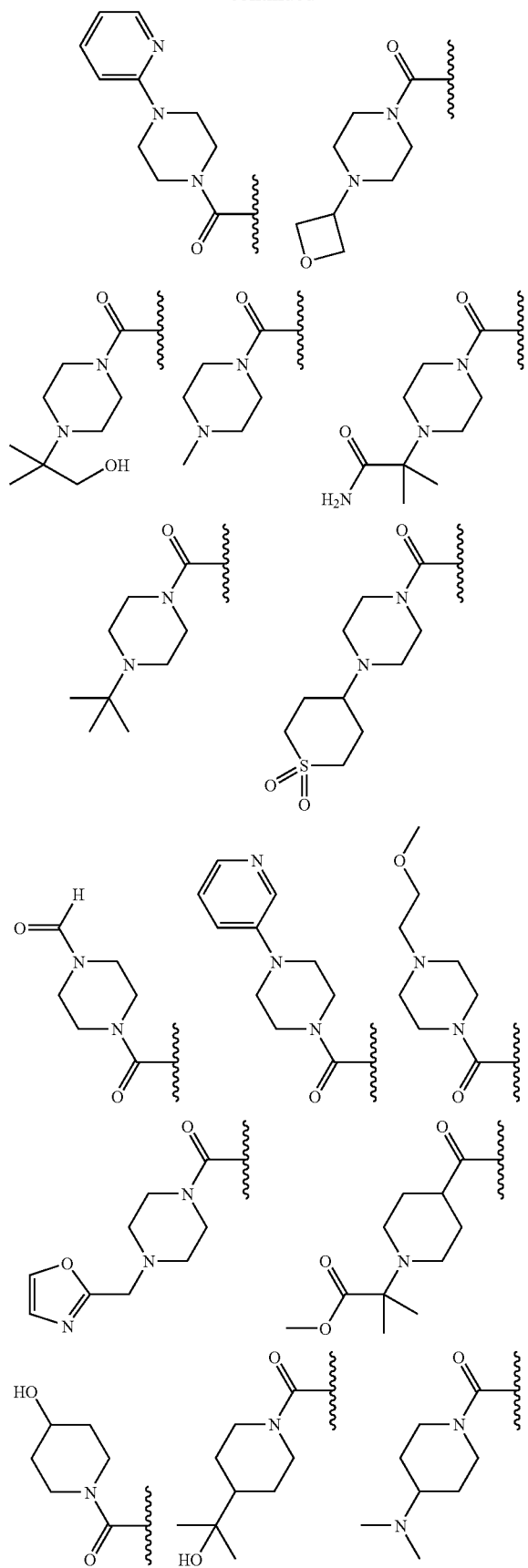
30
-continued
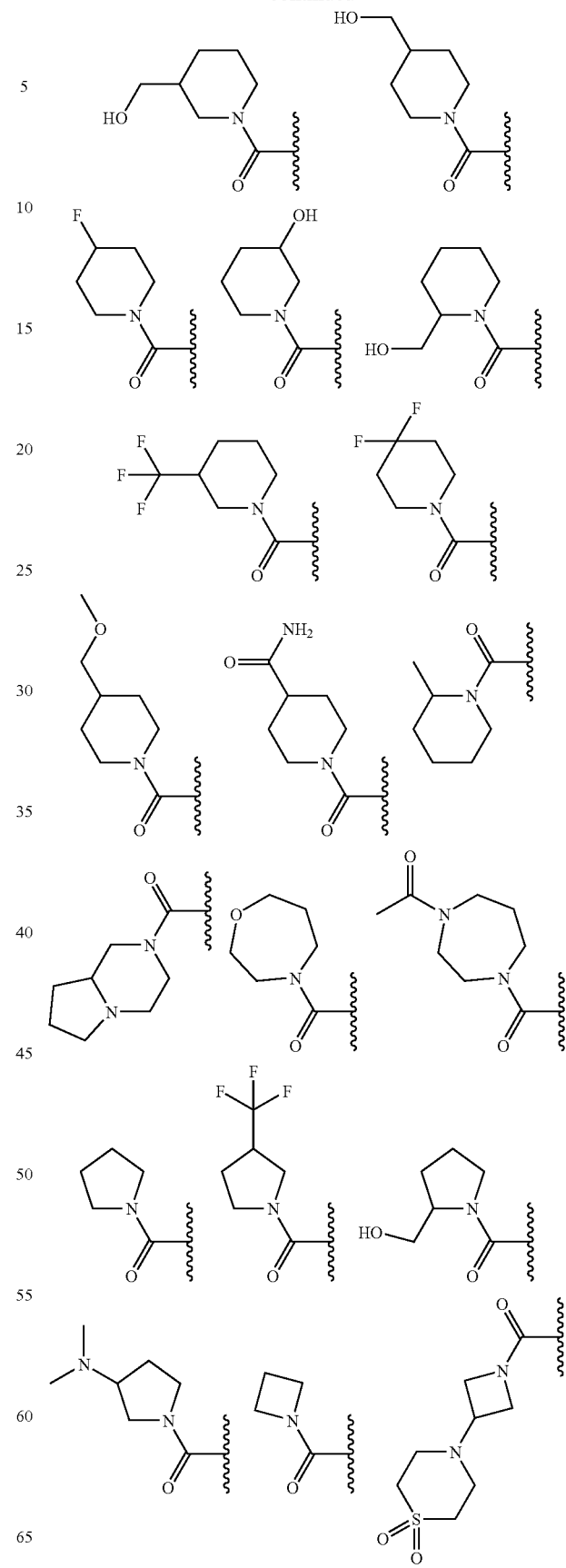

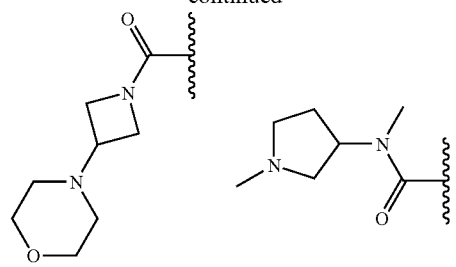
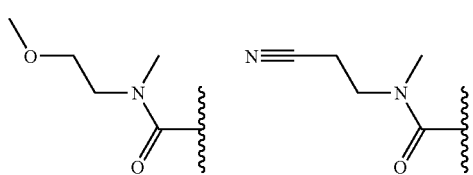
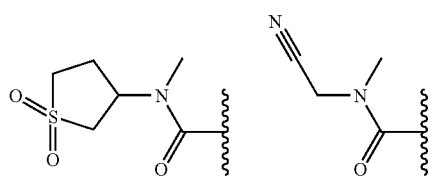
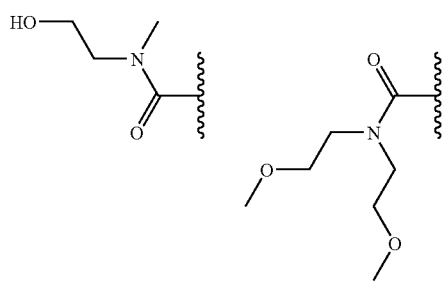
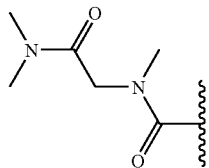
where the wavy line indicates the site of attachment to the Formula I structure.
Exemplary embodiments of $R^1$ also include the groups:
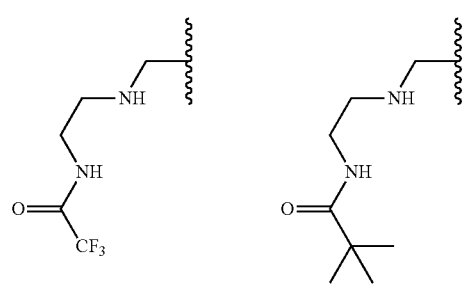
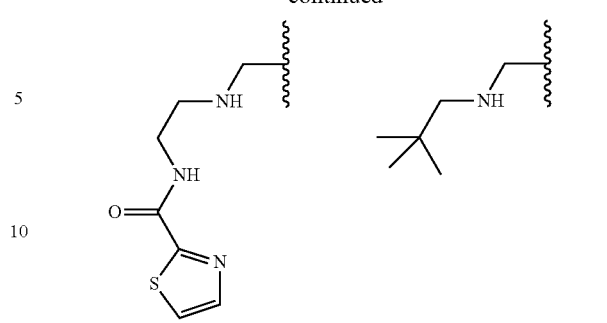
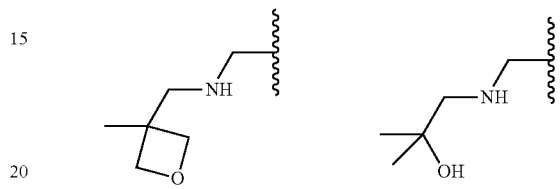
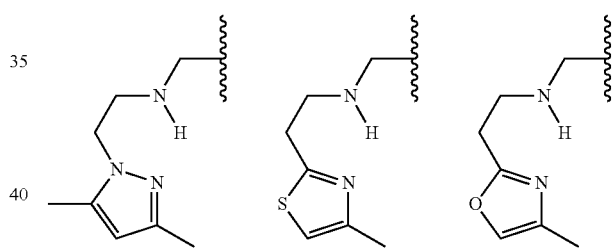
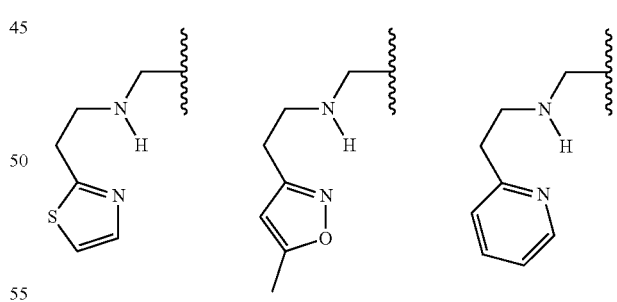
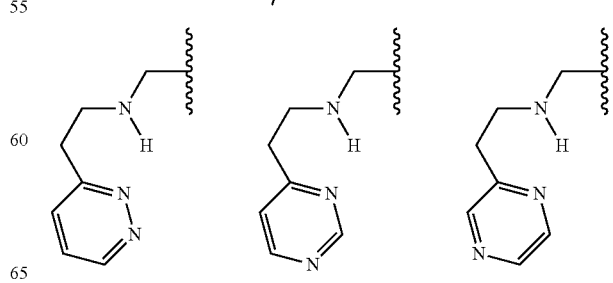

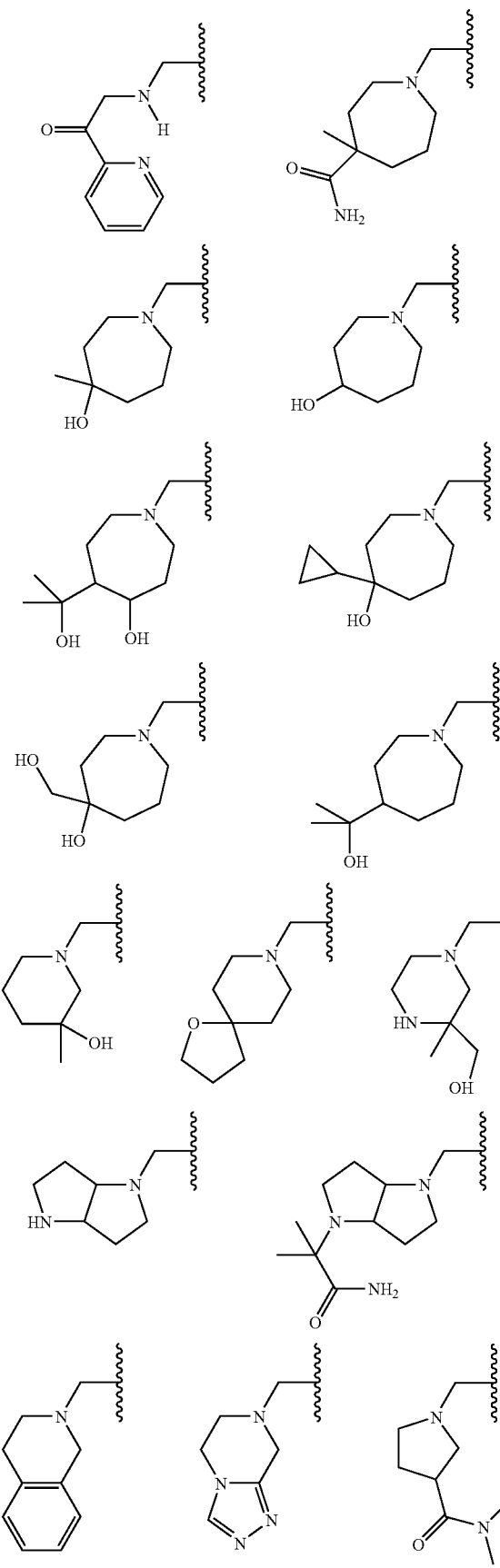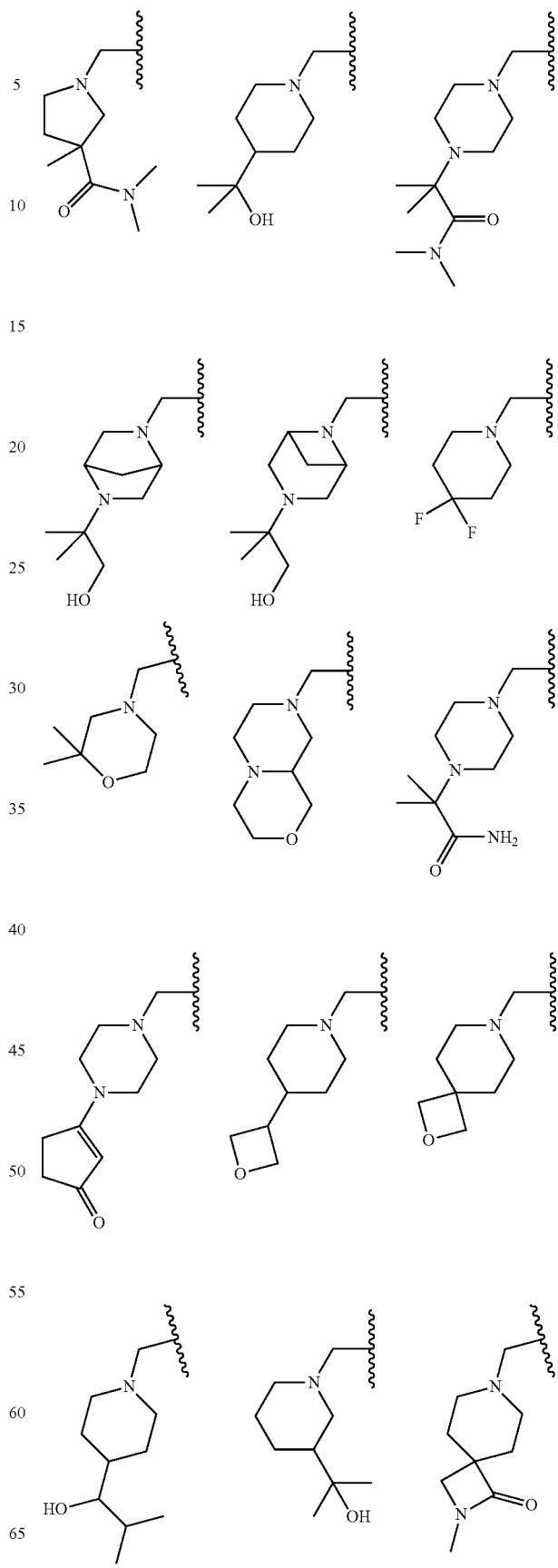

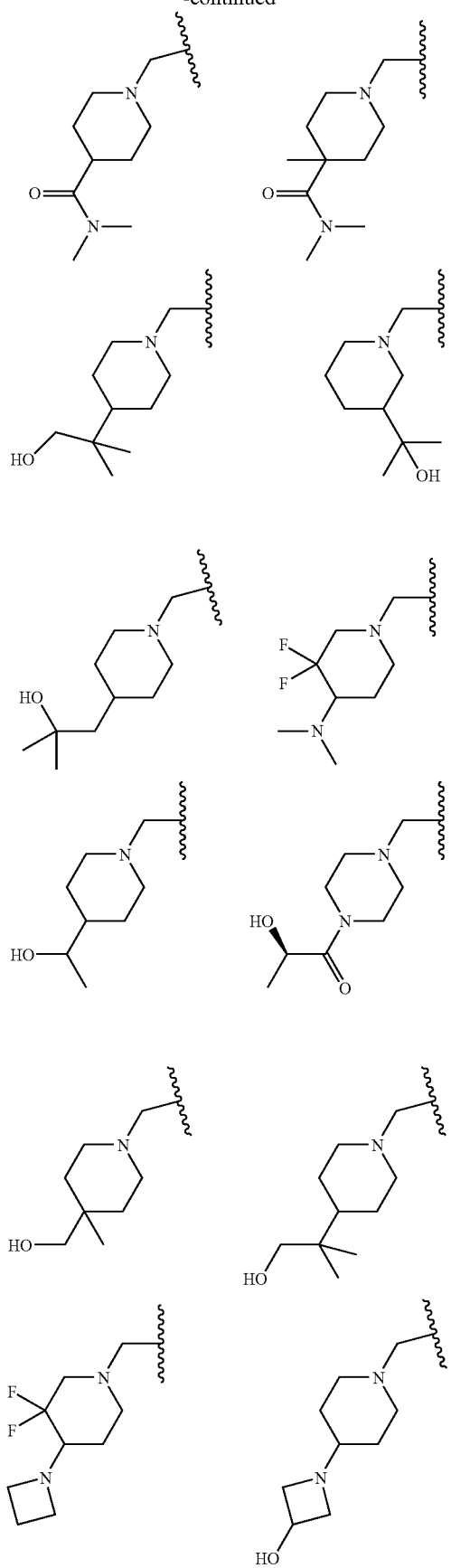
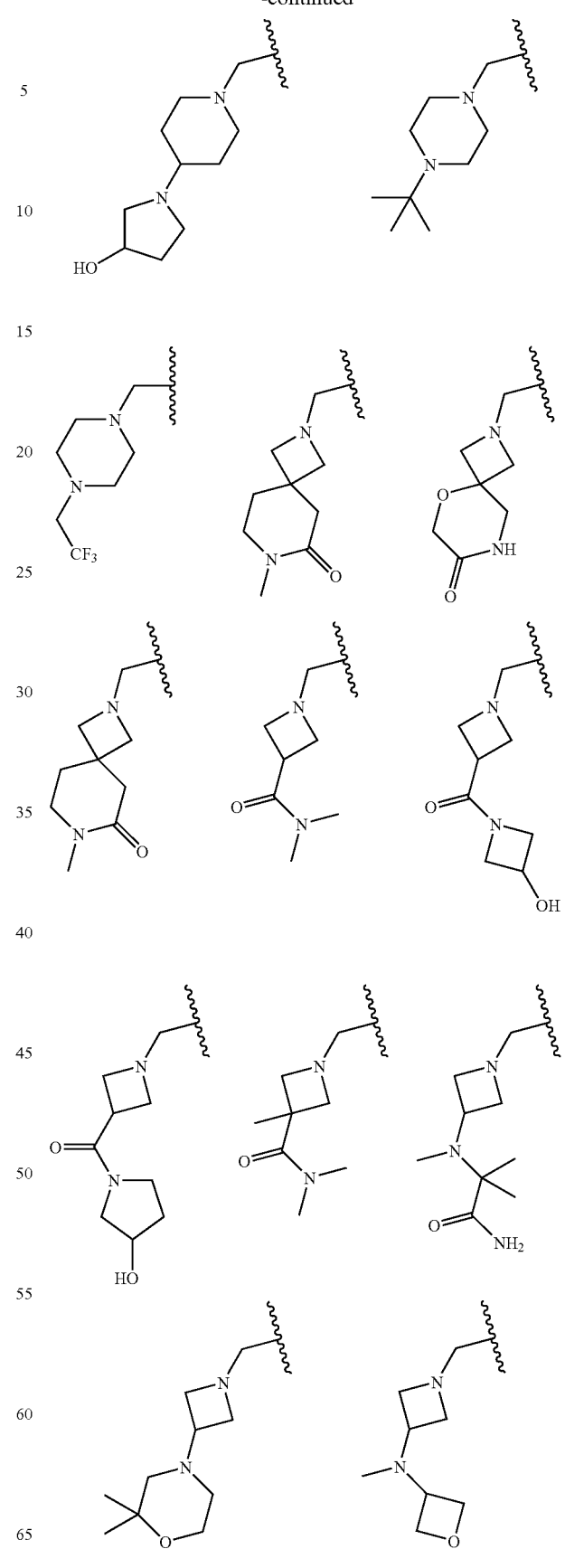

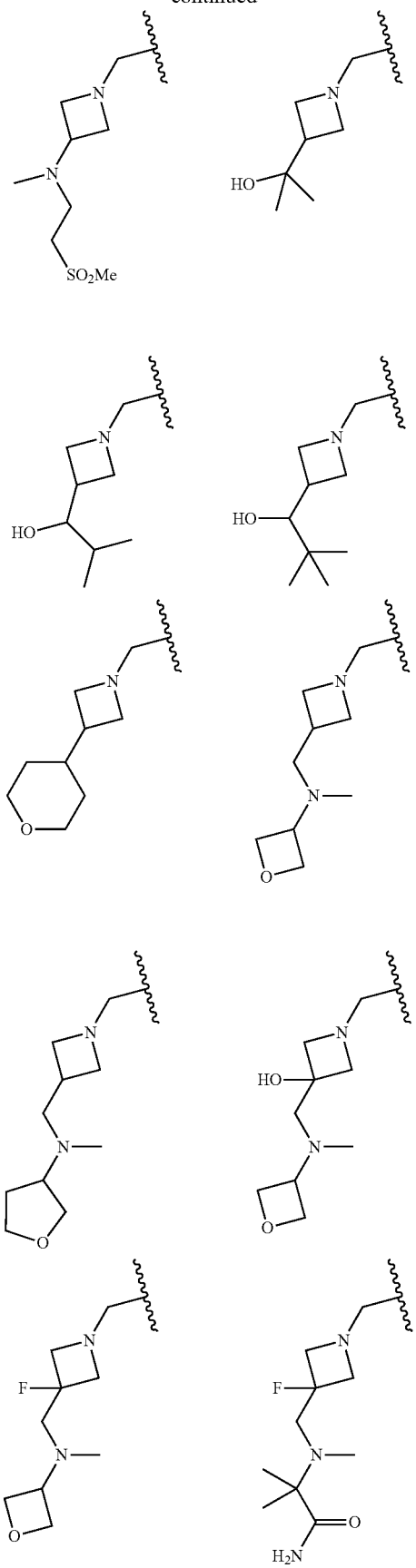
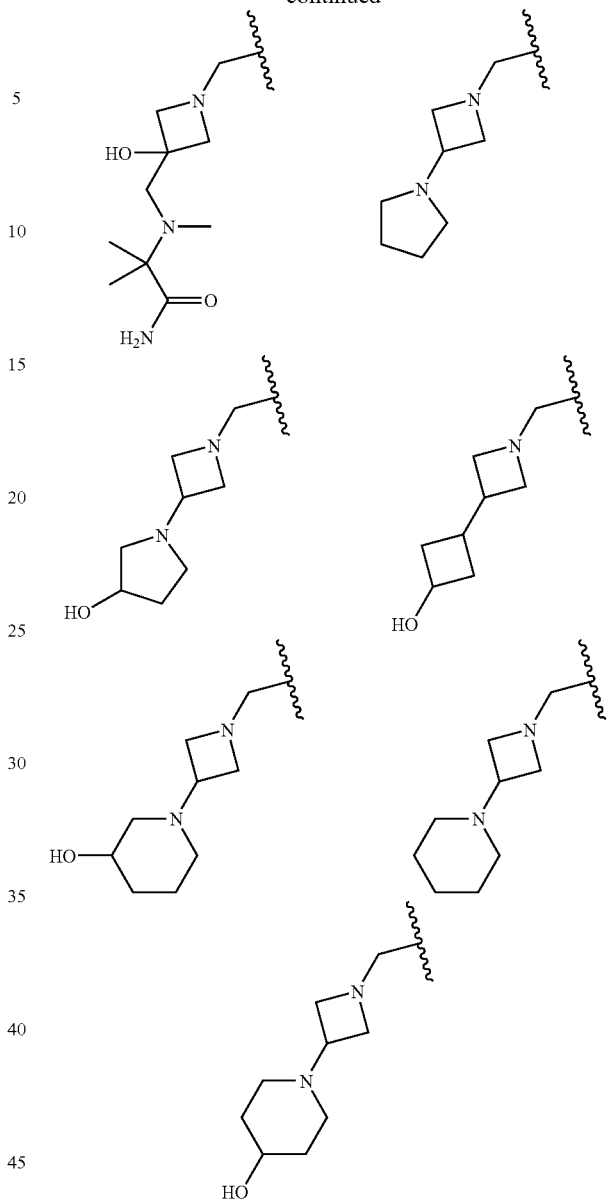

Exemplary embodiments include the $R^3$ bicyclic heteroaryl substituted with one or more groups independently selected from F, Cl, Br, I, —$CH_3$, —$CH_2CH_3$, —$CH_2CH_2CH_3$, —$CH(CH_3)_2$, —$C(CH_3)_3$, —$CH_2OCH_3$, —$CHF_2$, —$CH_2CN$, —CN, —$CF_3$, —$CH_2OH$, —$CH_2OCH_3$, —$CH_2CH_2OH$, —$CH_2CH_2CH_2OH$, —$CH_2C(CH_3)_2OH$, —$CH(CH_3)OH$, —$CH(CH_2CH_3)OH$, —$CH_2CH(OH)CH_3$, —$CH_2CH(OCH_3)CH_3$, —$C(CH_3)_2OH$, —$CH(CH_3)OCH_3$, —$C(CH_3)_2OCH_3$, —$CH(CH_3)F$, —$C(CH_3)F_2$, —$CH(CH_2CH_3)F$, —$C(CH_2CH_3)_2F$, —$C(CH_2CH_3)F_2$, —$CO_2H$, —$CONH_2$, —$CON(CH_2CH_3)_2$, —$COCH_3$, —$CON(CH_3)_2$, —$NO_2$, —$NH_2$, —$NHCH_3$, —$N(CH_3)_2$, —$NHCH_2CH_3$, —$NHCH(CH_3)_2$, —$NHCH_2CH_2OH$, —$NHCH_2CH_2OCH_3$, —$NHCOCH_3$, —$NHCOCH_2CH_3$, —$NHCOCH_2OH$, —$NHS(O)_2CH_3$, —$N(CH_3)S(O)_2CH_3$, —OH, —$OCH_3$, —$OCH_2CH_3$, —$OCH(CH_3)_2$, —SH, —$NHC(=O)NHCH_3$, —$NHC(=O)NHCH_2CH_3$, —$S(O)CH_3$, —$S(O)CH_2CH_3$, —$S(O)_2CH_3$, —$S(O)_2NH_2$, —$S(O)_2NHCH_3$, —$S(O)_2N(CH_3)_2$, $CH_2S(O)_2CH_3$, and a group selected from

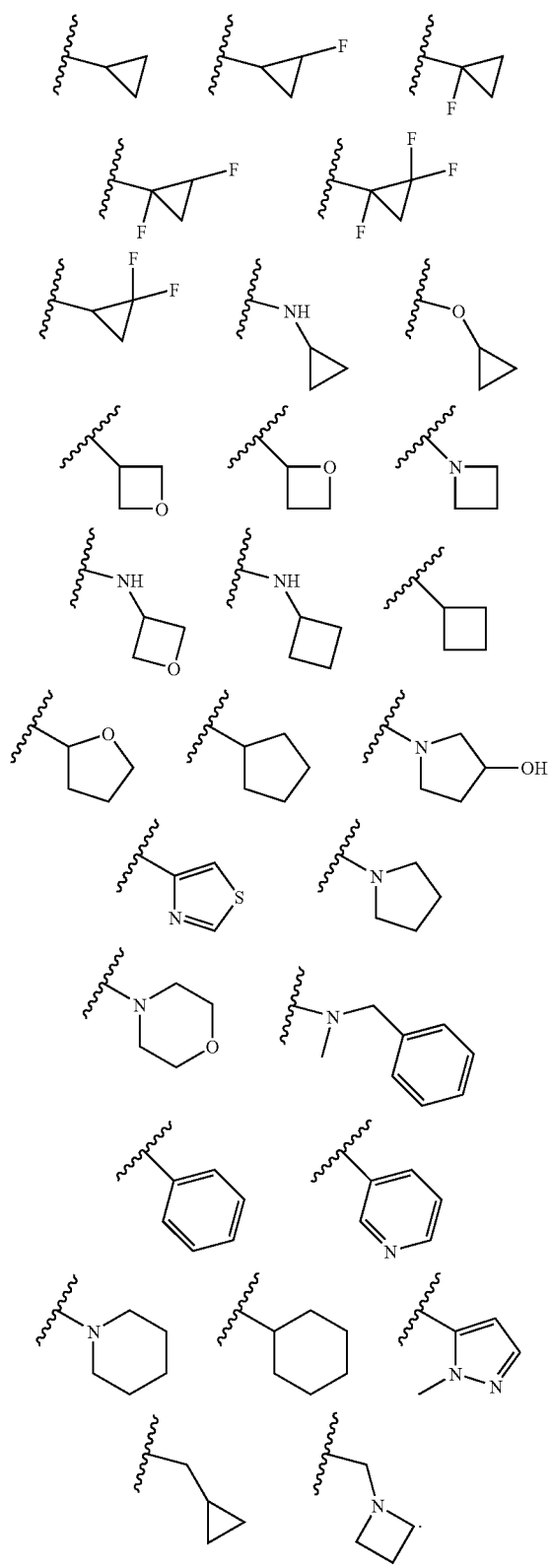

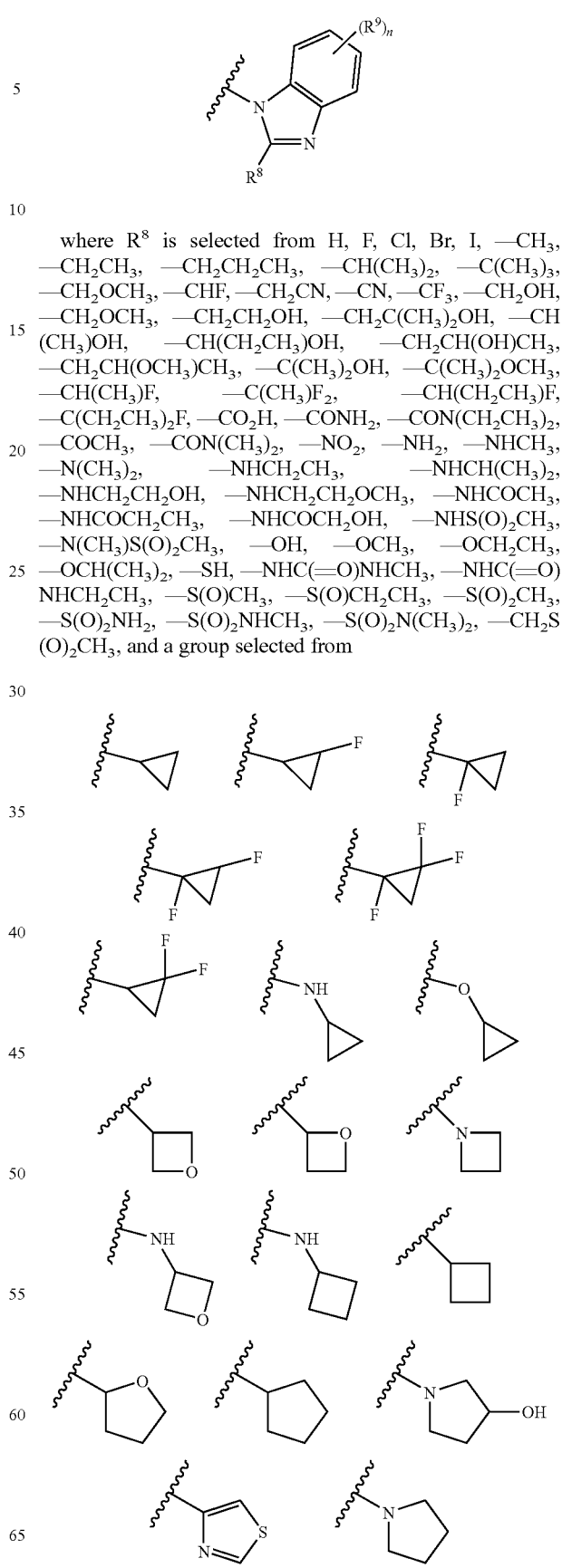

where $R^8$ is selected from H, F, Cl, Br, I, —$CH_3$, —$CH_2CH_3$, —$CH_2CH_2CH_3$, —$CH(CH_3)_2$, —$C(CH_3)_3$, —$CH_2OCH_3$, —CHF, —$CH_2CN$, —CN, —$CF_3$, —$CH_2OH$, —$CH_2OCH_3$, —$CH_2CH_2OH$, —$CH_2C(CH_3)_2OH$, —$CH(CH_3)OH$, —$CH(CH_2CH_3)OH$, —$CH_2CH(OH)CH_3$, —$CH_2CH(OCH_3)CH_3$, —$C(CH_3)_2OH$, —$C(CH_3)_2OCH_3$, —$CH(CH_3)F$, —$C(CH_3)F_2$, —$CH(CH_2CH_3)F$, —$C(CH_2CH_3)_2F$, —$CO_2H$, —$CONH_2$, —$CON(CH_2CH_3)_2$, —$COCH_3$, —$CON(CH_3)_2$, —$NO_2$, —$NH_2$, —$NHCH_3$, —$N(CH_3)_2$, —$NHCH_2CH_3$, —$NHCH(CH_3)_2$, —$NHCH_2CH_2OH$, —$NHCH_2CH_2OCH_3$, —$NHCOCH_3$, —$NHCOCH_2CH_3$, —$NHCOCH_2OH$, —$NHS(O)_2CH_3$, —$N(CH_3)S(O)_2CH_3$, —OH, —$OCH_3$, —$OCH_2CH_3$, —$OCH(CH_3)_2$, —SH, —$NHC(=O)NHCH_3$, —$NHC(=O)NHCH_2CH_3$, —$S(O)CH_3$, —$S(O)CH_2CH_3$, —$S(O)_2CH_3$, —$S(O)_2NH_2$, —$S(O)_2NHCH_3$, —$S(O)_2N(CH_3)_2$, —$CH_2S(O)_2CH_3$, and a group selected from Exemplary embodiments include where the $R^3$ bicyclic heteroaryl is a purine having the structure:

-continued

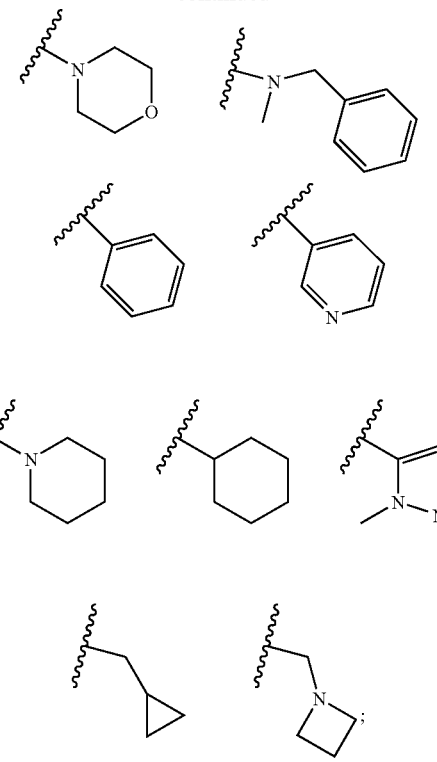

$R^9$ is independently selected from F, Cl, Br, I, —CH$_3$, —CH$_2$CH$_3$, —CH$_2$CH$_2$CH$_3$, —CH(CH$_3$)$_2$, —CH$_2$CH(CH$_3$)$_2$, —CH$_2$OH, —CH$_2$CH$_2$OH, —CN, —CF$_3$, —CO$_2$H, —COCH$_3$, —CO$_2$CH$_3$, —CONH$_2$, —CONHCH$_3$, —CON(CH$_3$)$_2$, —NO$_2$, —NH$_2$, —NHCH$_3$, —NHCOCH$_3$, —NHS(O)$_2$CH$_3$, —OH, —OCH$_3$, —S(O)$_2$N(CH$_3$)$_2$, —SCH$_3$, —CH$_2$OCH$_3$, and —S(O)$_2$CH$_3$; and n is 0, 1, 2, 3, or 4.

Exemplary Formula I compounds include the structures:

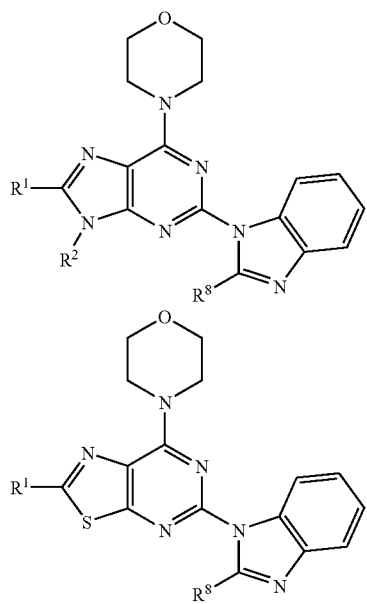

-continued

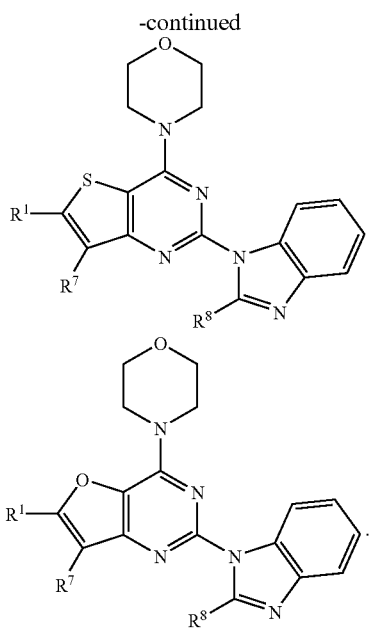

Exemplary Formula I compounds include compounds selected from Formulas Ie and If:

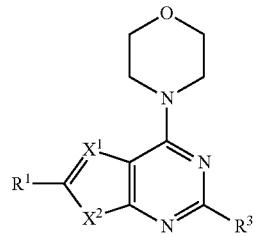

Ie

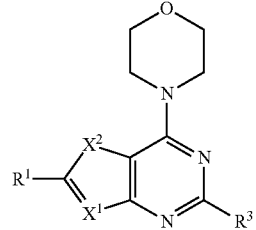

If and stereoisomers, geometric isomers, tautomers, or pharmaceutically acceptable salts thereof, wherein (i) $X^1$ is N and $X^2$ is S, (ii) $X^1$ is $CR^7$ and $X^2$ is S, (iii) $X^1$ is N and $X^2$ is $NR^2$, or (iv) $X^1$ is $CR^7$ and $X^2$ is O;

$R^1$ is selected from
$C_1$-$C_{12}$ alkyl,
$C_2$-$C_8$ alkenyl,
$C_2$-$C_8$ alkynyl,
$C_6$-$C_{20}$ aryl,
—($C_1$-$C_{12}$ alkylene)-($C_3$-$C_{12}$ carbocyclyl),
—($C_1$-$C_{12}$ alkylene)-($C_2$-$C_{20}$ heterocyclyl),
—($C_1$-$C_{12}$ alkylene)-($C_2$-$C_{20}$ heterocyclyl)-($C_2$-$C_{20}$ heterocyclyl),
—($C_1$-$C_{12}$ alkylene)-($C_2$-$C_{20}$ heterocyclyl)-($C_3$-$C_{12}$ carbocyclyl),
—($C_1$-$C_{12}$ alkylene)-($C_2$-$C_{20}$ heterocyclyl)-C(=O)—($C_2$-$C_{20}$ heterocyclyl), —(C$_1$-C$_{12}$ alkylene)-(C$_1$-C$_{20}$ heteroaryl),
—(C$_1$-C$_{12}$ alkylene)-(C$_2$-C$_{20}$ heterocyclyl)-(C$_1$-C$_{12}$ alkyl),
—(C$_1$-C$_{12}$ alkylene)-(C$_6$-C$_{20}$ aryl)-(C$_1$-C$_{12}$ alkyl),
—(C$_1$-C$_{12}$ alkylene)-(C$_1$-C$_{20}$ heteroaryl)-(C$_1$-C$_{12}$ alkyl),
—(C$_1$-C$_{12}$ alkylene)-C(=O)—(C$_2$-C$_{20}$ heterocyclyl),
—(C$_1$-C$_{12}$ alkylene)-NHR$^2$,
—(C$_1$-C$_{12}$ alkylene)-NR$^2$—(C$_1$-C$_{12}$ alkyl),
—(C$_1$-C$_{12}$ alkylene)-N(C$_1$-C$_{12}$ alkyl)(C$_2$-C$_{20}$ heterocyclyl),
—(C$_1$-C$_{12}$ alkylene)-NR$^2$—(C$_1$-C$_{12}$ alkylene)-(C$_1$-C$_{20}$ heteroaryl),
—(C$_1$-C$_{12}$ alkylene)-NR$^2$—(C$_1$-C$_{12}$ alkylene)-(C$_1$-C$_{20}$ heterocyclyl),
—(C$_1$-C$_{12}$ alkylene)-NR$^2$—(C$_1$-C$_{12}$ alkylene)-NHC(=O)—(C$_1$-C$_{20}$ heteroaryl),
—(C$_1$-C$_{12}$ alkylene)-(C$_2$-C$_{20}$ heterocyclyl)-N(C$_1$-C$_{12}$ alkyl)R$^2$,
—(C$_1$-C$_{12}$ alkylene)-(C$_2$-C$_{20}$ heterocyclyl)-(C$_1$-C$_{12}$ alkyl)-N(C$_1$-C$_{12}$ alkyl)R$^2$,
—(C$_1$-C$_{12}$ alkylene)-NR$^2$—(C$_2$-C$_{20}$ heterocyclyl),
—(C$_2$-C$_{12}$ alkenylene)-(C$_2$-C$_{20}$ heterocyclyl),
—NR$^2$—(C$_2$-C$_{20}$ heterocyclyl),
—C(=O)—(C$_2$-C$_{20}$ heterocyclyl), and
—C(=O)—(C$_1$-C$_{20}$ alkyl), where alkyl, alkenyl, alkynyl, alkylene, carbocyclyl, heterocyclyl, aryl, and heteroaryl are optionally substituted with one or more groups independently selected from F, Cl, Br, I, —CH$_3$, —CH$_2$CH$_3$, —CH$_2$CH(CH$_3$)$_2$, —CH$_2$OH, —CH$_2$CH$_2$OH, —C(CH$_3$)$_2$OH, —CH(OH)CH(CH$_3$)$_2$, —C(CH$_3$)$_2$CH$_2$OH, —CH$_2$CH$_2$SO$_2$CH$_3$, —CN, —CF$_3$, —CO$_2$H, —COCH$_3$, —CO$_2$CH$_3$, —CO$_2$C(CH$_3$)$_3$, —COCH(OH)CH$_3$, —CONH$_2$, —CONHCH$_3$, —CON(CH$_3$)$_2$, —C(CH$_3$)$_2$CONH$_2$, —NO$_2$, —NH$_2$, —NHCH$_3$, -N(CH$_3$)$_2$, —NHCOCH$_3$, —N(CH$_3$)COCH$_3$, —NHS(O)$_2$CH$_3$, —N(CH$_3$)C(CH$_3$)$_2$CONH$_2$, —N(CH$_3$)CH$_2$CH$_2$S(O)$_2$CH$_3$, =O, —OH, —OCH$_3$, —S(O)$_2$N(CH$_3$)$_2$, —SCH$_3$, —CH$_2$OCH$_3$, —S(O)$_2$CH$_3$, cyclopropyl, oxetanyl, and morpholino;

R$^2$ is selected from H, C$_1$-C$_{12}$ alkyl, C$_2$-C$_8$ alkenyl, C$_2$-C$_8$ alkynyl, —(C$_1$-C$_{12}$ alkylene)-(C$_3$-C$_{12}$ carbocyclyl), —(C$_1$-C$_{12}$ alkylene)-(C$_2$-C$_{20}$ heterocyclyl), —(C$_1$-C$_{12}$ alkylene)-C(=O)—(C$_2$-C$_{20}$ heterocyclyl), —(C$_1$-C$_{12}$ alkylene)-(C$_6$-C$_{20}$ aryl), and —(C$_1$-C$_{12}$ alkylene)-(C$_1$-C$_{20}$ heteroaryl), where alkyl, alkenyl, alkynyl, alkylene, carbocyclyl, heterocyclyl, aryl, and heteroaryl are optionally substituted with one or more groups independently selected from F, Cl, Br, I, —CH$_3$, —CH$_2$OH, —CN, —CF$_3$, —CO$_2$H, —COCH$_3$, —CO$_2$CH$_3$, —CONH$_2$, —CONHCH$_3$, —CON(CH$_3$)$_2$, —NO$_2$, —NH$_2$, —NHCH$_3$, —NHCOCH$_3$, —NHS(O)$_2$CH$_3$, —OH, —OCH$_3$, —S(O)$_2$N(CH$_3$)$_2$, —SCH$_3$, —CH$_2$OCH$_3$, and —S(O)$_2$CH$_3$;

R$^3$ is selected from:

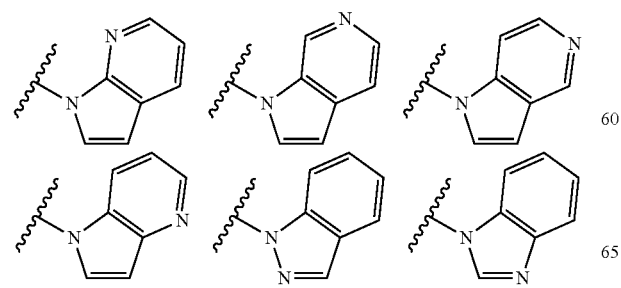

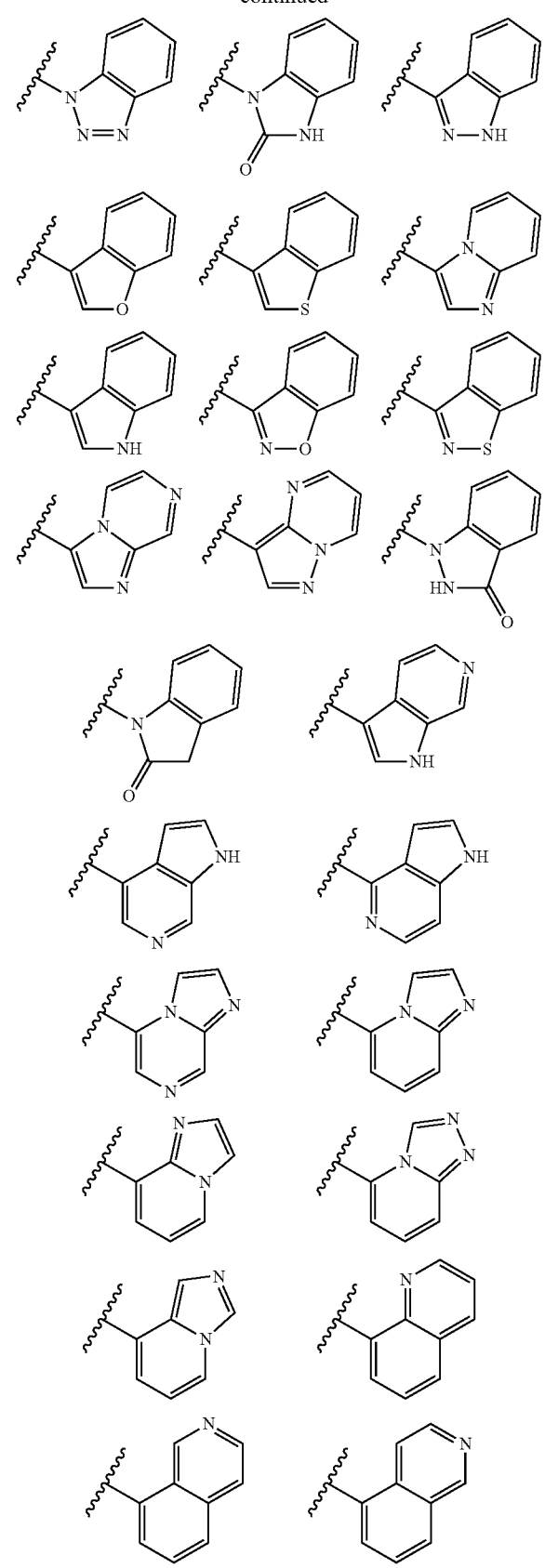

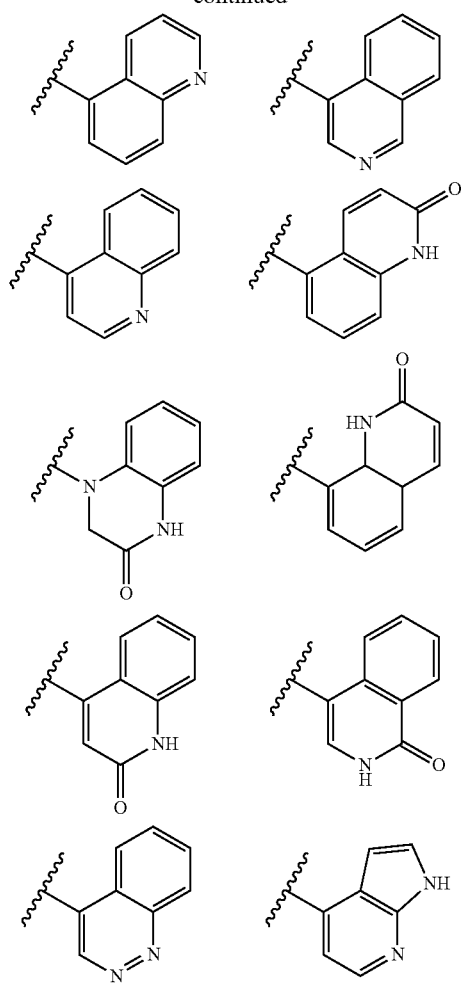

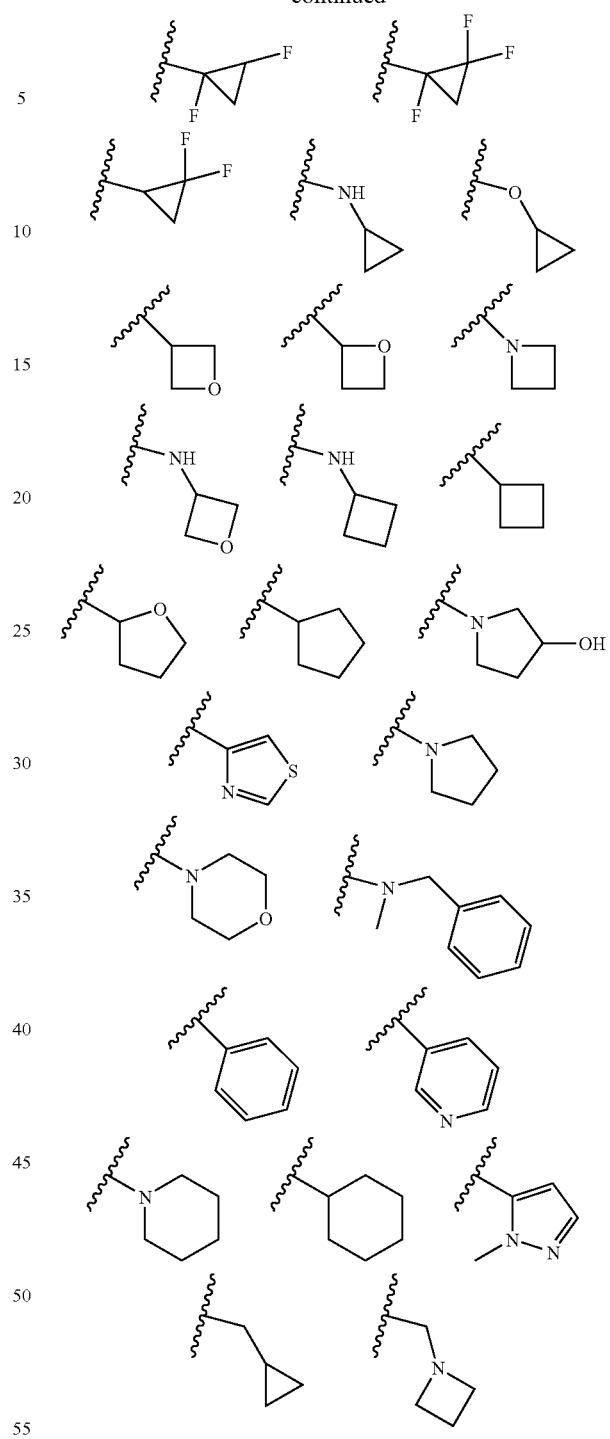

where the wavy line indicates the site of attachment;

each of which are optionally substituted with one or more groups independently selected from F, Cl, Br, I, —CH$_3$, —CH$_2$CH$_3$, —CH$_2$CH$_2$CH$_3$, —CH(CH$_3$)$_2$, —C(CH$_3$)$_3$, —CH$_2$OCH$_3$, —CHF, —CN, —CF$_3$, —CH$_2$OH, —CH$_2$OCH$_3$, —CH$_2$CH$_2$OH, —CH$_2$C(CH$_3$)$_2$OH, —CH(CH$_3$)OH, —CH(CH$_2$CH$_3$)OH, —CH$_2$CH(OH)CH$_3$, —CH$_2$CH(OCH$_3$)CH$_3$, —C(CH$_3$)$_2$OH, —C(CH$_3$)$_2$OCH$_3$, —CH(CH$_3$)F, —C(CH$_3$)F$_2$, —CH(CH$_2$CH$_3$)F, —C(CH$_2$CH$_3$)$_2$F, —CO$_2$H, —CONH$_2$, —CON(CH$_2$CH$_3$)$_2$, —COCH$_3$, —CON(CH$_3$)$_2$, —NO$_2$, —NH$_2$, —NHCH$_3$, —N(CH$_3$)$_2$, —NHCH$_2$CH$_3$, —NHCH(CH$_3$)$_2$, —NHCH$_2$CH$_2$OH, —NHCH$_2$CH$_2$OCH$_3$, —NHCOCH$_3$, —NHCOCH$_2$CH$_3$, —NHCOCH$_2$OH, —NHS(O)$_2$CH$_3$, —N(CH$_3$)S(O)$_2$CH$_3$, =O, —OH, —OCH$_3$, —OCH$_2$CH$_3$, —OCH(CH$_3$)$_2$, —SH, —NHC(=O)NHCH$_3$, —NHC(=O)NHCH$_2$CH$_3$, —S(O)CH$_3$, —S(O)CH$_2$CH$_3$, —S(O)$_2$CH$_3$, —S(O)$_2$NH$_2$, —S(O)$_2$NHCH$_3$, —S(O)$_2$N(CH$_3$)$_2$, —CH$_2$S(O)$_2$CH$_3$, and groups selected from

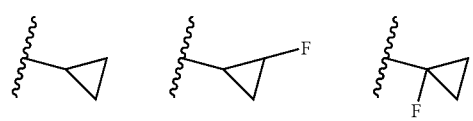

$R^7$ is selected from H, $C_1$-$C_{12}$ alkyl, $C_2$-$C_8$ alkenyl, $C_2$-$C_8$ alkynyl, —($C_1$-$C_{12}$ alkylene)-($C_3$-$C_{12}$ carbocyclyl), —($C_1$-$C_{12}$ alkylene)-($C_2$-$C_{20}$ heterocyclyl), —($C_1$-$C_{12}$ alkylene)-C(=O)—($C_2$-$C_{20}$ heterocyclyl), —($C_1$-$C_{12}$ alkylene)-($C_6$-$C_{20}$ aryl), and —($C_1$-$C_{12}$ alkylene)-($C_1$-$C_{20}$ heteroaryl), where alkyl, alkenyl, alkynyl, alkylene, carbocyclyl, heterocyclyl, aryl, and heteroaryl are optionally substituted with one or more groups independently selected from F, Cl, Br, I, —CH$_3$, —CH$_2$OH, —CN, —CF$_3$, —CO$_2$H, —COCH$_3$, —CO$_2$CH$_3$, —CONH$_2$, —CONHCH$_3$, —CON(CH$_3$)$_2$, —NO$_2$, —NH$_2$, —NHCH$_3$, —NHCOCH$_3$, —NHS(O)$_2$CH$_3$, —OH, —OCH$_3$, —S(O)$_2$N(CH$_3$)$_2$, —SCH$_3$, —CH$_2$OCH$_3$, and —S(O)$_2$CH$_3$;

and wherein the IC50 binding activity to p110 delta is ten or more times lower than the binding activity to p110 alpha; with the proviso that a Formula If compound wherein (ii) X$^1$ is CR$^7$ and X$^2$ is S, R$^1$ is —(C$_1$-C$_{12}$ alkylene)-(C$_2$-C$_{20}$ heterocyclyl), R$^3$ is optionally substituted benzo[d]imidazol-1-yl, and R$^7$ is H, excludes the C$_2$-C$_{20}$ heterocyclyl of R$^1$ substituted with —S(O)$_2$CH$_3$.

The Formula I compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention.

In addition, the present invention embraces all geometric and positional isomers. For example, if a Formula I compound incorporates a double bond or a fused ring, the cis- and trans-forms, as well as mixtures thereof, are embraced within the scope of the invention. Both the single positional isomers and mixture of positional isomers are also within the scope of the present invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

The compounds of the present invention may exist in unsolvated as well as solvated forms with pharmaceutically acceptable solvents such as water, ethanol, and the like, and it is intended that the invention embrace both solvated and unsolvated forms.

The compounds of the present invention may also exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The present invention also embraces isotopically-labeled compounds of the present invention which are identical to those recited herein, but for the fact that one or more atoms are replaced by an atom having an atomic mass or mass number different from the atomic mass or mass number usually found in nature. All isotopes of any particular atom or element as specified are contemplated within the scope of the compounds of the invention, and their uses. Exemplary isotopes that can be incorporated into compounds of the invention include isotopes of hydrogen, carbon, nitrogen, oxygen, phosphorus, sulfur, fluorine, chlorine and iodine, such as $^2$H, $^3$H, $^{11}$C, $^{13}$C, $^{14}$C, $^{13}$N, $^{15}$N, $^{15}$O, $^{17}$O, $^{18}$O, $^{32}$P, $^{33}$P, $^{35}$S, $^{18}$F, $^{36}$Cl, $^{123}$I and $^{125}$I. Certain isotopically-labeled compounds of the present invention (e.g., those labeled with $^3$H and $^{14}$C) are useful in compound and/or substrate tissue distribution assays. Tritiated ($^3$H) and carbon-14 ($^{14}$C) isotopes are useful for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Positron emitting isotopes such as $^{15}$O, $^{13}$N, $^{11}$C and $^{18}$F are useful for positron emission tomography (PET) studies to examine substrate receptor occupancy. Isotopically labeled compounds of the present invention can generally be prepared by following procedures analogous to those disclosed in the Schemes and/or in the Examples herein below, by substituting an isotopically labeled reagent for a non-isotopically labeled reagent.

Biological Evaluation

The relative efficacies of Formula I compounds as inhibitors of an enzyme activity (or other biological activity) can be established by determining the concentrations at which each compound inhibits the activity to a predefined extent and then comparing the results. Typically, the preferred determination is the concentration that inhibits 50% of the activity in a biochemical assay, i.e., the 50% inhibitory concentration or "IC$_{50}$". Determination of IC$_{50}$ values can be accomplished using conventional techniques known in the art. In general, an IC$_{50}$ can be determined by measuring the activity of a given enzyme in the presence of a range of concentrations of the inhibitor under study. The experimentally obtained values of enzyme activity then are plotted against the inhibitor concentrations used. The concentration of the inhibitor that shows 50% enzyme activity (as compared to the activity in the absence of any inhibitor) is taken as the IC$_{50}$ value. Analogously, other inhibitory concentrations can be defined through appropriate determinations of activity. For example, in some settings it can be desirable to establish a 90% inhibitory concentration, i.e., IC$_{90}$, etc.

Accordingly, a "selective PI3K delta inhibitor" can be understood to refer to a compound that exhibits a 50% inhibitory concentration (IC$_{50}$) with respect to PI3K delta that is at least at least 10-fold lower than the IC50 value with respect to any or all of the other Class I PI3K family members.

Determination of the activity of PI3 kinase activity of Formula I compounds is possible by a number of direct and indirect detection methods. Certain exemplary compounds described herein were assayed for their ability to inhibit PI3K alpha, beta, gamma, and delta isoforms (Example 901). The range of IC50 values for inhibition of PI3K delta was less than 1 nM (nanomolar) to about 10 μM (micromolar). Certain exemplary compounds of the invention had PI3K delta inhibitory IC$_{50}$ values less than 10 nM. The compounds are selective for the p110δ (delta) isoform, which is a class Ia PI3 kinase, over other class Ia PI3 kinases, and are thus selective for the p110δ isoform over both the p110α (alpha) isoform and the p110β (beta) isoform. In particular, they are selective for p110δ (delta) over p110α (alpha). The compounds are also selective for the p110δ isoform over p110γ (gamma), which is a class Ib kinase. The selectivity exhibited by Formula I compounds of the invention for p110δ (delta) over the p110α (alpha) isoform of PI3 kinase is at least 10 fold, as exemplified by the ratios of biochemical IC$_{50}$ values (Example 901).

Certain Formula I compounds may have antiproliferative activity to treat hyperproliferative disorders such as cancer. The Formula I compounds may inhibit tumor growth in mammals and may be useful for treating human cancer patients. Formula I compounds may be tested for in vitro cell proliferation activity and in vivo tumor growth inhibition according to the methods in WO 2006/046031; US 2008/0039459; US 2008/0076768; US 2008/0076758; WO 2008/070740; WO 2008/073785, which are incorporated by reference herein.

Evaluation of drug-induced immunosuppression by the compounds of the invention may be performed using in vivo functional tests, such as rodent models of induced arthritis and therapeutic or prophylactic treatment to assess disease score, T cell-dependent antibody response (TDAR), and delayed-type hypersensitivity (DTH). Other in vivo systems including murine models of host defense against infections or tumor resistance (Burleson G R, Dean J H, and Munson A E. *Methods in Immunotoxicology*, Vol. 1. Wiley-Liss, New York, 1995) may be considered to elucidate the nature or mechanisms of observed immunosuppression. The in vivo test systems can be complemented by well-established in vitro or ex vivo functional assays for the assessment of immune competence. These assays may comprise B or T cell proliferation in response to mitogens or specific antigens, measurement of signaling through the PI3K pathway in B or T cells or immortalized B or T cell lines, measurement of cell surface markers in response to B or T cell signaling, natural killer (NK) cell activity, mast cell activity, mast cell degranulation, macrophage phagocytosis or kill activity, and neutrophil oxidative burst and/or chemotaxis. In each of these tests determination of cytokine production by particular effector cells (e.g., lymphocytes, NK, monocytes/macrophages, neutrophils) may be included. The in vitro and ex vivo assays can be applied in both preclinical and clinical testing using lymphoid tissues and/or peripheral blood (House R V. "Theory and practice of cytokine assessment in immunotoxicology" (1999) Methods 19:17-27; Hubbard A K. "Effects of xenobiotics on macrophage function: evaluation in vitro" (1999) Methods; 19:8-16; Lebrec H, et al (2001) Toxicology 158:25-29).

Collagen-Induced Arthritis (CIA) 6-week detailed study using an autoimmune mechanism to mimic human arthritis; rat and mouse models (Example 902). Collagen-induced arthritis (CIA) is one of the most commonly used animal models of human rheumatoid arthritis (RA). Joint inflammation, which develops in animals with CIA, strongly resembles inflammation observed in patients with RA. Blocking tumor necrosis factor (TNF) is an efficacious treatment of CIA, just as it is a highly efficacious therapy in treatment of RA patients. CIA is mediated by both T-cells and antibodies (B-cells). Macrophages are believed to play an important role in mediating tissue damage during disease development, CIA is induced by immunizing animals with collagen emulsified in Complete Freund's Adjuvant (CFA). It is most commonly induced in the DBA/1 mouse strain, but the disease can also be induced in Lewis rats.

There is good evidence that B-cells play a key role in the pathogenesis of autoimmune and/or inflammatory disease. Protein-based therapeutics that deplete B cells such as Rituxan are effective against autoantibody-driven inflammatory diseases such as rheumatoid arthritis (Rastetter et al. (2004) Annu Rev Med 55:477). CD69 is the early activation marker in leukocytes including T cells, thymocytes, B cells, NK cells, neutrophils, and eosinophils. The CD69 human whole blood assay (Example 903) determines the ability of compounds to inhibit the production of CD69 by B lymphocytes in human whole blood activated by crosslinking surface IgM with goat F(ab')2 anti-human IgM.

The T-cell Dependent Antibody Response (TDAR) is a predictive assay for immune function testing when potential immunotoxic effects of compounds need to be studied. The IgM-Plaque Forming Cell (PFC) assay, using Sheep Red Blood Cells (SRBC) as the antigen, is currently a widely accepted and validated standard test. TDAR has proven to be a highly predictable assay for adult exposure immunotoxicity detection in mice based on the US National Toxicology Program (NTP) database (M. I. Luster et al (1992) Fundam. Appl. Toxicol. 18:200-210). The utility of this assay stems from the fact that it is a holistic measurement involving several important components of an immune response. A TDAR is dependent on functions of the following cellular compartments: (1) antigen-presenting cells, such as macrophages or dendritic cells; (2) T-helper cells, which are critical players in the genesis of the response, as well as in isotype switching; and (3) B-cells, which are the ultimate effector cells and are responsible for antibody production. Chemically-induced changes in any one compartment can cause significant changes in the overall TDAR (M. P. Holsapple In: G. R. Burleson, J. H. Dean and A. E. Munson, Editors, *Modern Methods in Immunotoxicology*, Volume 1, Wiley-Liss Publishers, New York, N.Y. (1995), pp. 71-108). Usually, this assay is performed either as an ELISA for measurement of soluble antibody (R. J. Smialowizc et al (2001) Toxicol. Sci. 61:164-175) or as a plaque (or antibody) forming cell assay (L. Guo et al (2002) Toxicol. Appl. Pharmacol. 181:219-227) to detect plasma cells secreting antigen specific antibodies. The antigen of choice is either whole cells (e.g. sheep erythrocytes) or soluble protein antigens (T. Miller et al (1998) Toxicol. Sci. 42:129-135).

Exemplary Formula I compounds in Tables 1-3 were made, characterized, and tested for inhibition of PI3K delta and selectivity according to the methods of this invention, and have the following structures and corresponding names (ChemDraw Ultra, Version 9.0.1, CambridgeSoft Corp., Cambridge Mass.).

TABLE 1

| No. | Structure | Name |
|---|---|---|
| 101 | 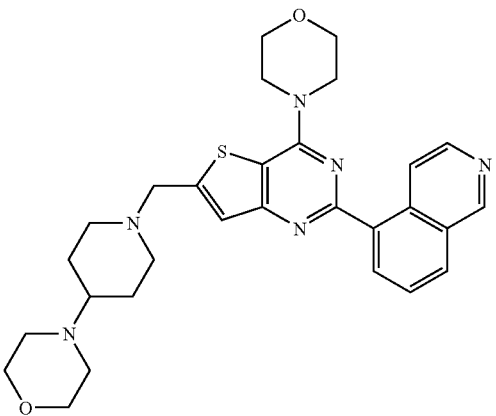 | 4-(1-((2-(isoquinolin-5-yl)-4-morpholinothieno[3,2-d]pyrimidin-6-yl)methyl)piperidin-4-yl)morpholine |

TABLE 1-continued

| No. | Structure | Name |
|---|---|---|
| 102 | 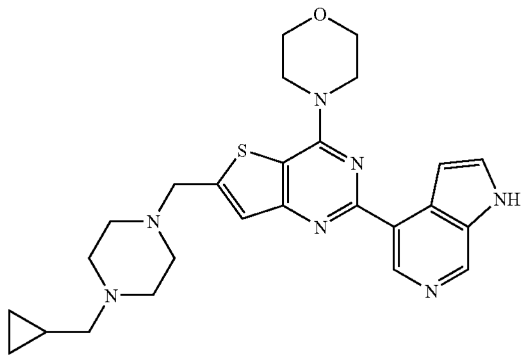 | 4-(6-((4-(cyclopropylmethyl)piperazin-1-yl)methyl)-2-(1H-pyrrolo[2,3-c]pyridin-4-yl)thieno[3,2-d]pyrimidin-4-yl)morpholine |
| 103 | 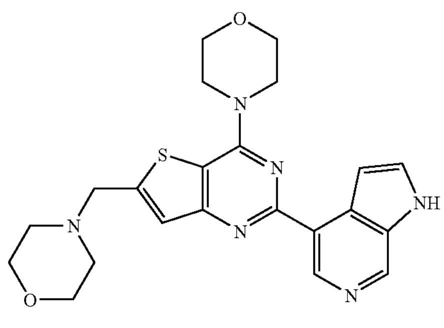 | 4-((4-morpholino-2-(1H-pyrrolo[2,3-c]pyridin-4-yl)thieno[3,2-d]pyrimidin-6-yl)methyl)morpholine |
| 104 | 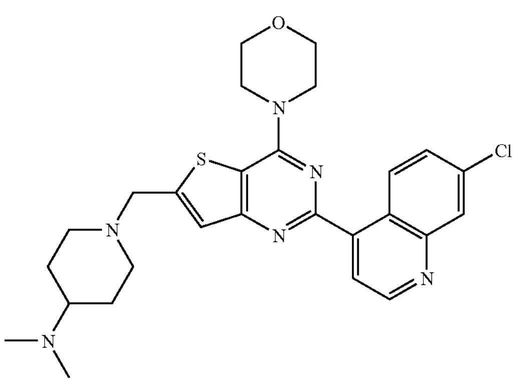 | 1-((2-(7-chloroquinolin-4-yl)-4-morpholinothieno[3,2-d]pyrimidin-6-yl)methyl)-N,N-dimethylpiperidin-4-amine |
| 105 | 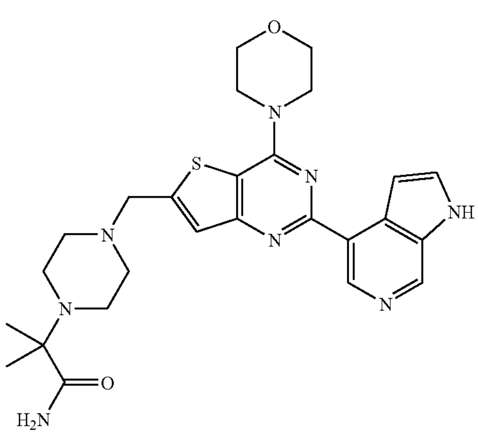 | 2-methyl-2-(4-((4-morpholino-2-(1H-pyrrolo[2,3-c]pyridin-4-yl)thieno[3,2-d]pyrimidin-6-yl)methyl)piperazin-1-yl)propanamide |

TABLE 1-continued

| No. | Structure | Name |
|---|---|---|
| 106 | 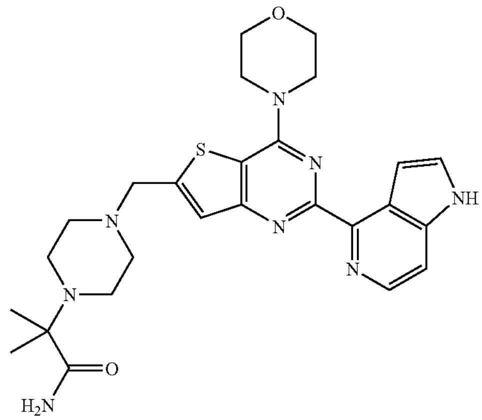 | 2-methyl-2-(4-((4-morpholino-2-(1H-pyrrolo[3,2-c]pyridin-4-yl)thieno[3,2-d]pyrimidin-6-yl)methyl)piperazin-1-yl)propanamide |
| 107 | 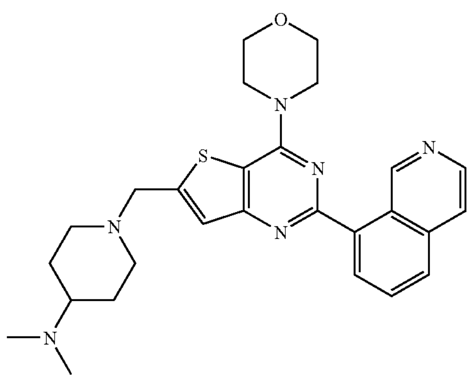 | 1-((2-(isoquinolin-8-yl)-4-morpholinothieno[3,2-d]pyrimidin-6-yl)methyl)-N,N-dimethylpiperidin-4-amine |
| 108 | 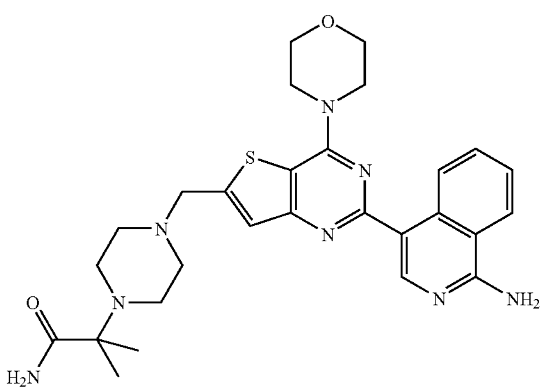 | 2-(4-((2-(1-aminoisoquinolin-4-yl)-4-morpholinothieno[3,2-d]pyrimidin-6-yl)methyl)-piperazin-1-yl)-2-methylpropanamide |
| 109 | 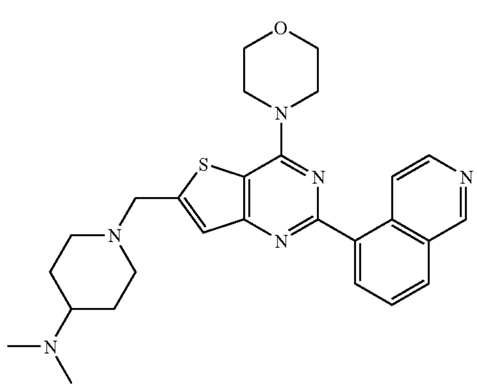 | 1-((2-(isoquinolin-5-yl)-4-morpholinothieno[3,2-d]pyrimidin-6-yl)methyl)-N,N-dimethylpiperidin-4-amine |

TABLE 1-continued

| No. | Structure | Name |
|---|---|---|
| 110 | 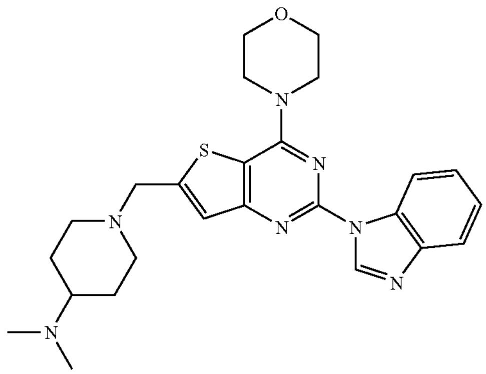 | 1-((2-(1H-benzo[d]imidazol-1-yl)-4-morpholinothieno[3,2-d]pyrimidin-6-yl)methyl)-N,N-dimethylpiperidin-4-amine |
| 111 | 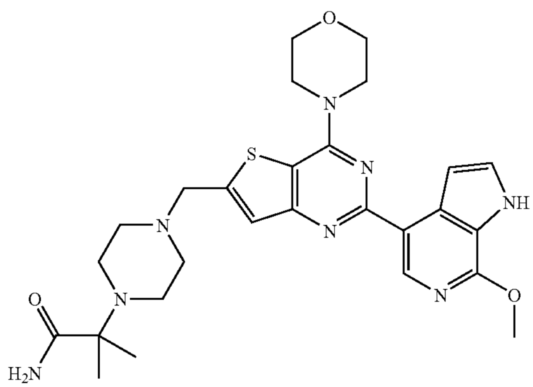 | 2-(4-((2-(7-methoxy-1H-pyrrolo[2,3-c]pyridin-4-yl)-4-morpholinothieno[3,2-d]pyrimidin-6-yl)methyl)piperazin-1-yl)-2-methylpropanamide |
| 112 | 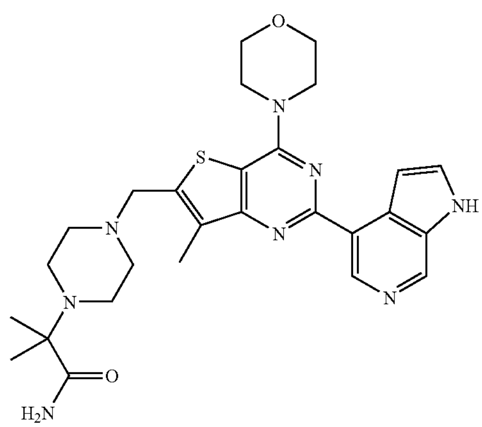 | 2-methyl-2-(4-((7-methyl-4-morpholino-2-(1H-pyrrolo[2,3-c]pyridin-4-yl)thieno[3,2-d]pyrimidin-6-yl)methyl)piperazin-1-yl)propanamide |
| 113 | 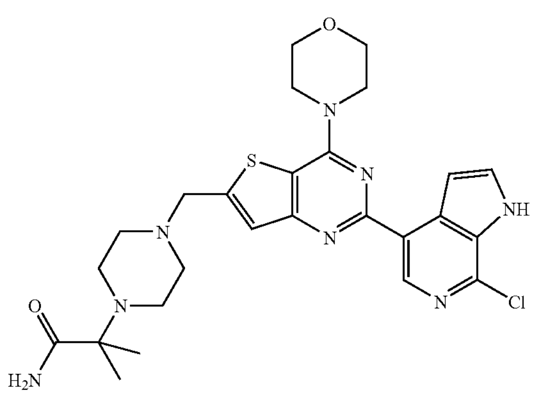 | 2-(4-((2-(7-chloro-1H-pyrrolo[2,3-c]pyridin-4-yl)-4-morpholinothieno[3,2-d]pyrimidin-6-yl)methyl)piperazin-1-yl)-2-methylpropanamide |

TABLE 1-continued

| No. | Structure | Name |
|---|---|---|
| 114 | 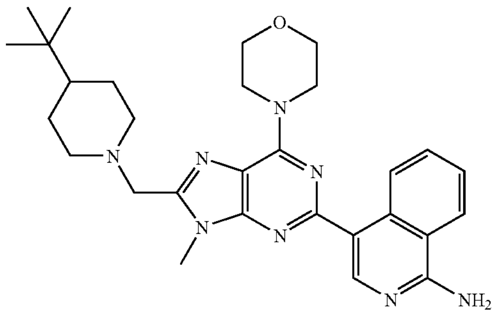 | 4-(8-((4-tert-butylpiperidin-1-yl)methyl)-9-methyl-6-morpholino-9H-purin-2-yl)isoquinolin-1-amine |
| 115 | 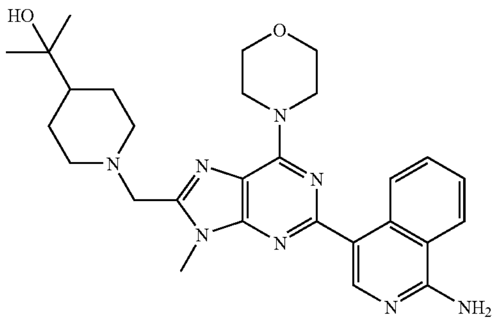 | 2-(1-((2-(1-aminoisoquinolin-4-yl)-9-methyl-6-morpholino-9H-purin-8-yl)methyl)piperidin-4-yl)propan-2-ol |
| 116 | 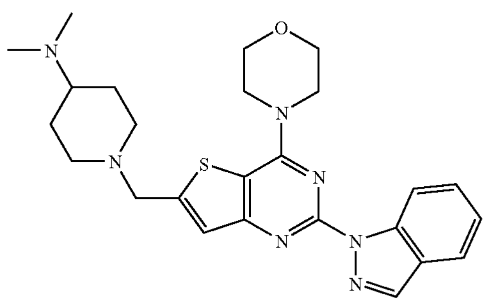 | 1-((2-(1H-indazol-1-yl)-4-morpholinothieno[3,2-d]pyrimidin-6-yl)methyl)-N,N-dimethylpiperidin-4-amine |
| 117 | 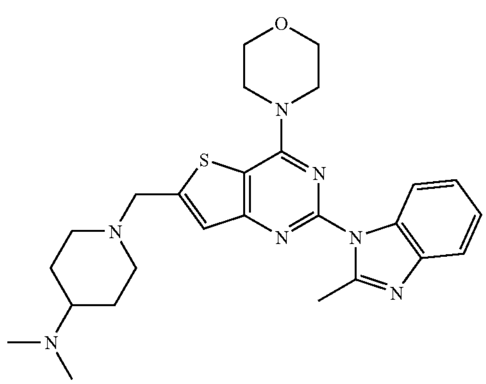 | N,N-dimethyl-1-((2-(2-methyl-1H-benzo[d]imidazol-1-yl)-4-morpholinothieno[3,2-d]pyrimidin-6-yl)methyl)piperidin-4-amine |

TABLE 1-continued

| No. | Structure | Name |
|---|---|---|
| 118 | 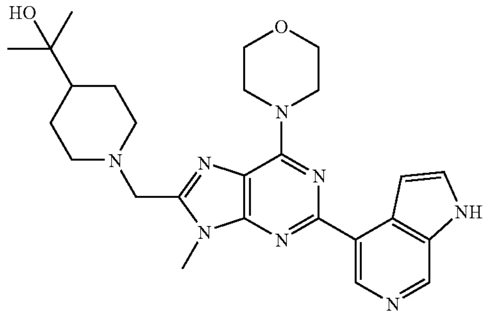 | 2-(1-((9-methyl-6-morpholino-2-(1H-pyrrolo[2,3-c]pyridin-4-yl)-9H-purin-8-yl)methyl)piperidin-4-yl)propan-2-ol |
| 119 | 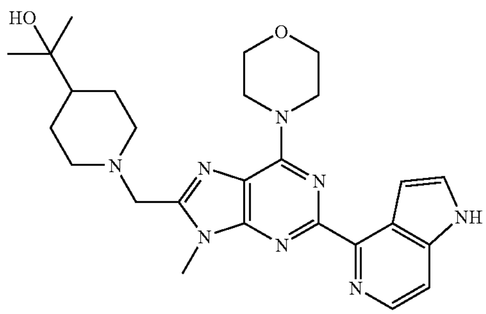 | 2-(1-((9-methyl-6-morpholino-2-(1H-pyrrolo[3,2-c]pyridin-4-yl)-9H-purin-8-yl)methyl)piperidin-4-yl)propan-2-ol |
| 120 | 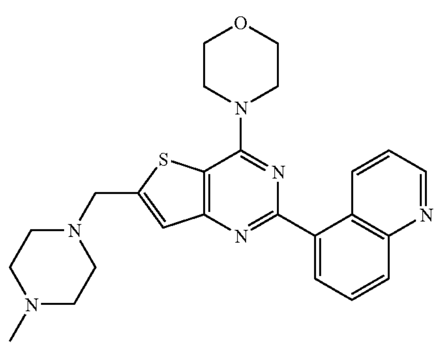 | 4-(6-((4-methylpiperazin-1-yl)methyl)-2-(quinolin-5-yl)thieno[3,2-d]pyrimidin-4-yl)morpholine |
| 121 | 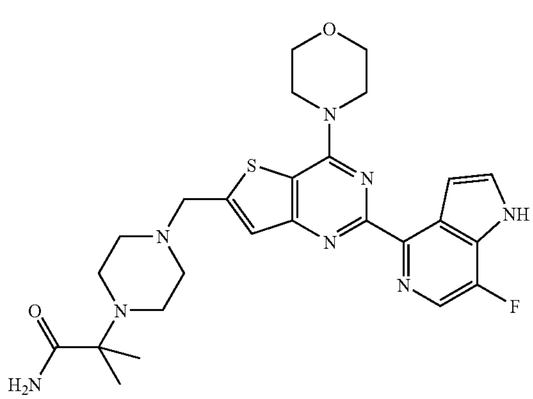 | 2-(4-((2-(7-fluoro-1H-pyrrolo[3,2-c]pyridin-4-yl)-4-morpholinothieno[3,2-d]pyrimidin-6-yl)methyl)piperazin-1-yl)-2-methylpropanamide |

TABLE 1-continued

| No. | Structure | Name |
|---|---|---|
| 122 | 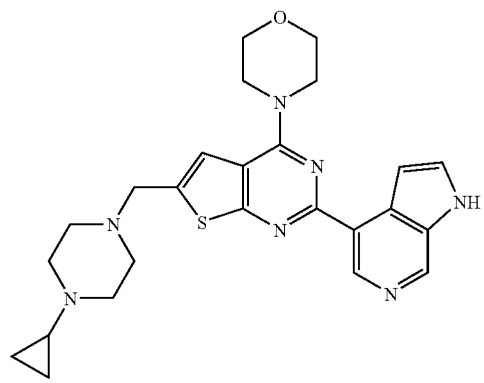 | 4-(6-((4-cyclopropylpiperazin-1-yl)methyl)-1-(1H-pyrrolo[2,3-c]pyridin-4-yl)thieno[2,3-d]pyrimidin-4-yl)morpholine |
| 123 | 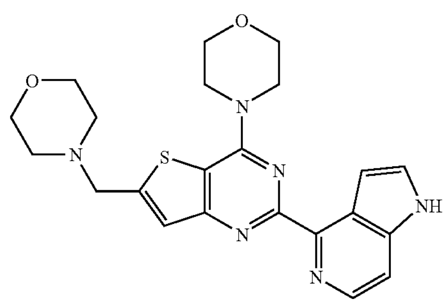 | 4-((4-morpholino-2-(1H-pyrrolo[3,2-c]pyridin-4-yl)thieno[3,2-d]pyrimidin-6-yl)methyl)morpholine |
| 124 | 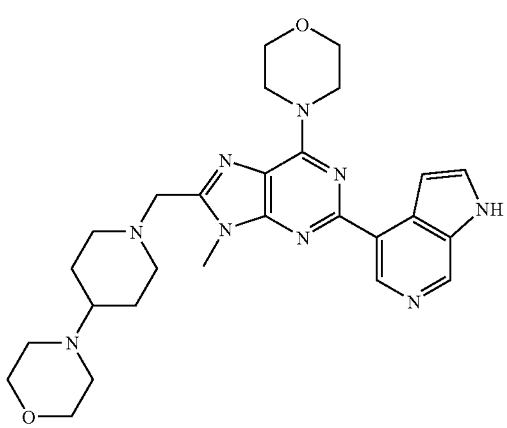 | 4-(1-((9-methyl-6-morpholino-2-(1H-pyrrolo[2,3-c]pyridin-4-yl)-9H-purin-8-yl)methyl)piperidin-4-yl)morpholine |
| 125 | 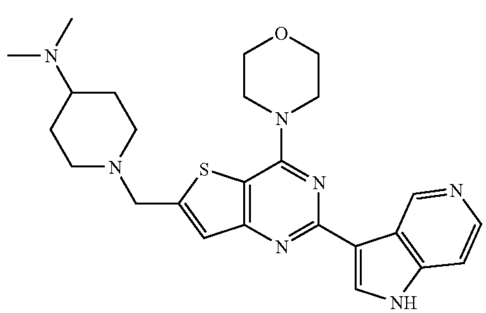 | N,N-dimethyl-1-((4-morpholino-2-(1H-pyrrolo[3,2-c]pyridin-3-yl)thieno[3,2-d]pyrimidin-6-yl)methyl)piperidin-4-amine |

| No. | Structure | Name |
|---|---|---|
| 126 | 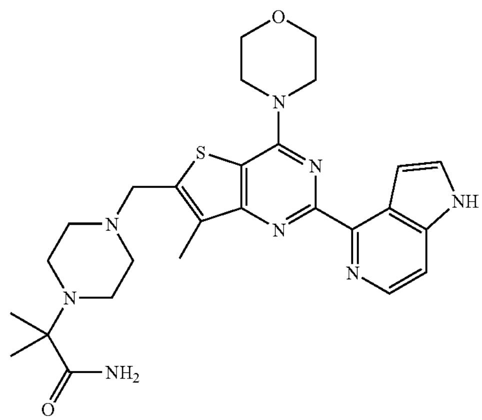 | 2-methyl-2-(4-((7-methyl-4-morpholino-2-(1H-pyrrolo[3,2-c]pyridin-4-yl)thieno[3,2-d]pyrimidin-6-yl)methyl)piperazin-1-yl)propanamide |
| 127 | 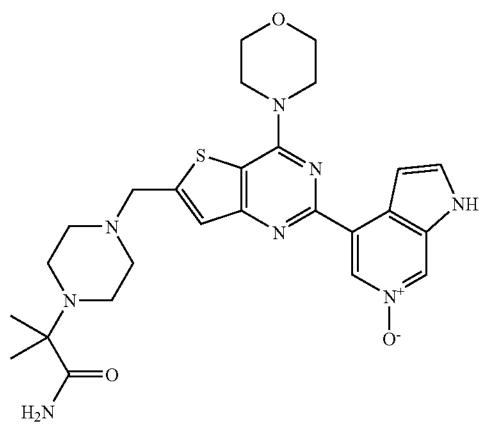 | 4-(6-((4-(1-amino-2-methyl-1-oxopropan-2-yl)piperazin-1-yl)methyl)-4-morpholinothieno[3,2-d]pyrimidin-2-yl)-1H-pyrrolo[2,3-c]pyridine 6-oxide |
| 128 | 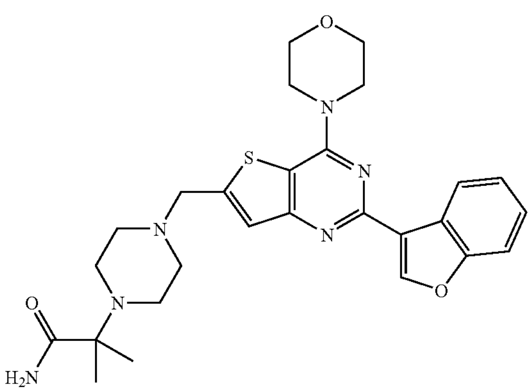 | 2-(4-((2-(benzofuran-3-yl)-4-morpholinothieno[3,2-d]pyrimidin-6-yl)methyl)piperazin-1-yl)-2-methylpropanamide |
| 129 | 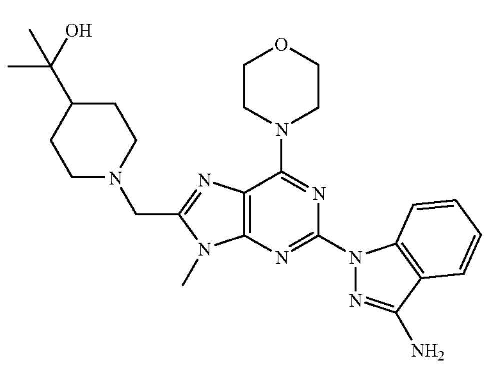 | 2-(1-((2-(3-amino-1H-indazol-1-yl)-9-methyl-6-morpholino-9H-purin-8-yl)methyl)piperidin-4-yl)propan-2-ol |

TABLE 1-continued

| No. | Structure | Name |
|---|---|---|
| 130 | 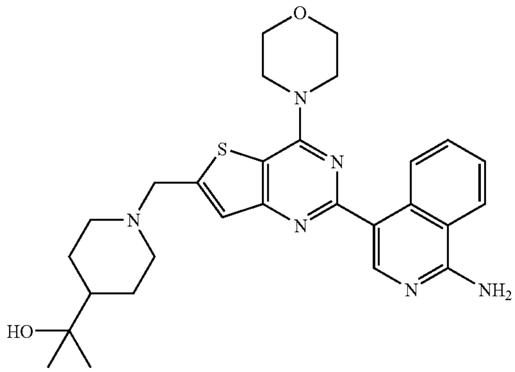 | 2-(1-((2-(1-aminoisoquinolin-4-yl)-4-morpholinothieno[3,2-d]pyrimidin-6-yl)methyl)piperidin-4-yl)propan-2-ol |
| 131 | 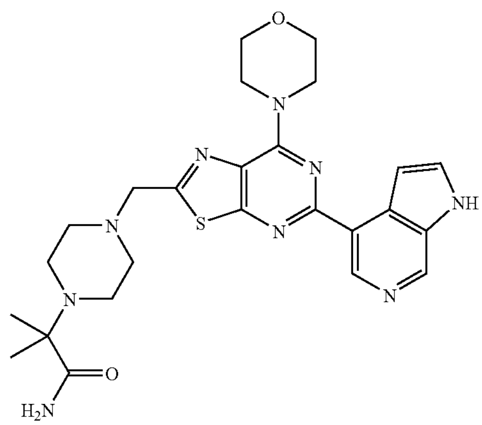 | 2-methyl-2-(4-((7-morpholino-5-(1H-pyrrolo[2,3-c]pyridin-4-yl)thiazolo[5,4-d]pyrimidin-2-yl)methyl)piperazin-1-yl)propanamide |
| 132 | 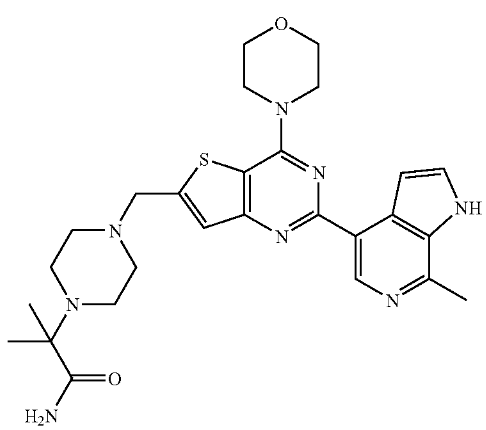 | 2-methyl-2-(4-((2-(7-methyl-1H-pyrrolo[2,3-c]pyridin-4-yl)-4-morpholinothieno[3,2-d]pyrimidin-6-yl)methyl)piperazin-1-yl)propanamide |

TABLE 1-continued

| No. | Structure | Name |
|---|---|---|
| 133 | 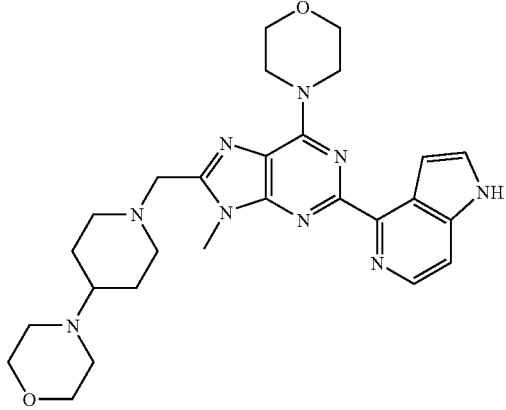 | 4-(1-((9-methyl-6-morpholino-2-(1H-pyrrolo[3,2-c]pyridin-4-yl)-9H-purin-8-yl)methyl)piperidin-4-yl)morpholine |
| 134 | 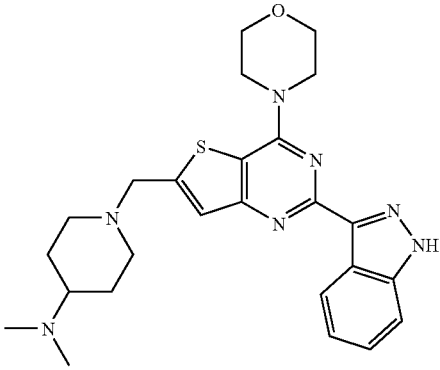 | 1-((2-(1H-indazol-3-yl)-4-morpholinothieno[3,2-d]pyrimidin-6-yl)methyl)-N,N-dimethylpiperidin-4-amine |
| 135 | 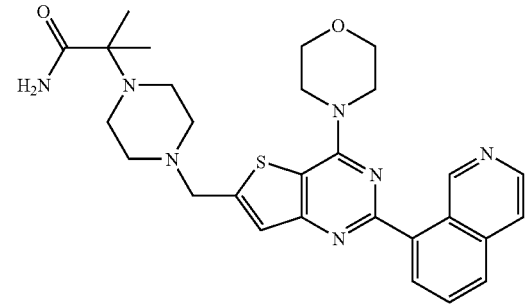 | 2-(4-((2-(isoquinolin-8-yl)-4-morpholinothieno[3,2-d]pyrimidin-6-yl)methyl)piperazin-1-yl)-2-methylpropanamide |
| 136 | 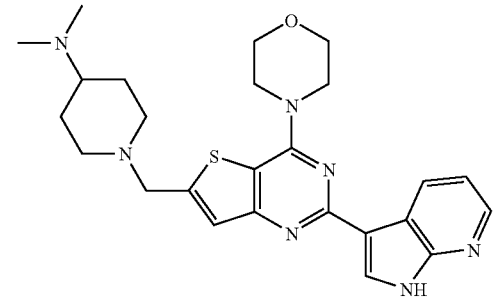 | N,N-dimethyl-1-((4-morpholino-2-(1H-pyrrolo[2,3-b]pyridin-3-yl)thieno[3,2-d]pyrimidin-6-yl)methyl)piperidin-4-amine |

TABLE 1-continued

| No. | Structure | Name |
|---|---|---|
| 137 | 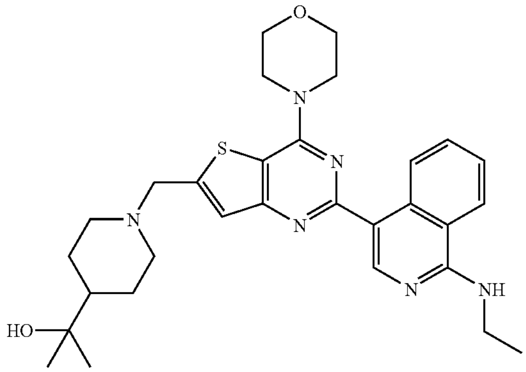 | 2-(1-((2-(1-(ethylamino)isoquinolin-4-yl)-4-morpholinothieno[3,2-d]pyrimidin-6-yl)methyl)piperidin-4-yl)propan-2-ol |
| 138 | 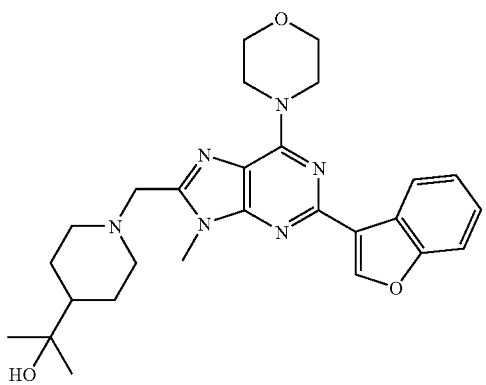 | 2-(1-((2-(benzofuran-3-yl)-9-methyl-6-morpholino-9H-purin-8-yl)methyl)piperidin-4-yl)propan-2-ol |
| 139 | 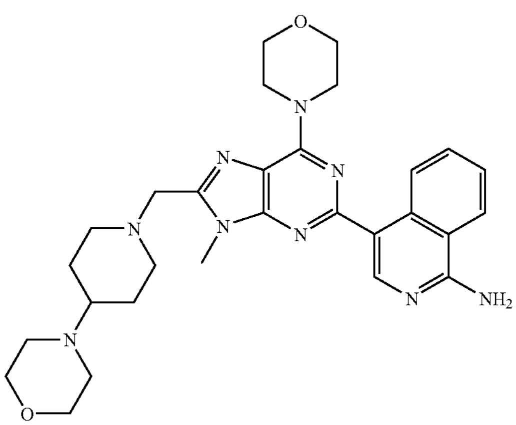 | 4-(9-methyl-6-morpholino-8-((4-morpholinopiperidin-1-yl)methyl)-9H-purin-2-yl)isoquinolin-1-amine |
| 140 | 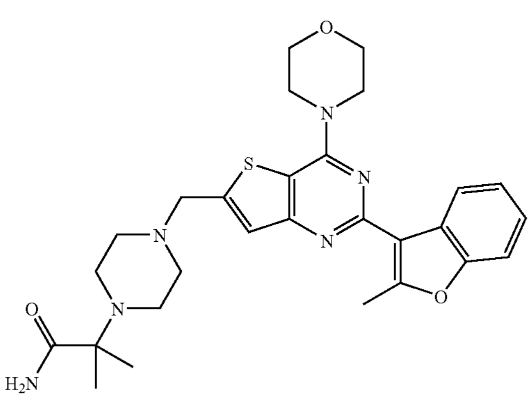 | 2-methyl-2-(4-((2-(2-methylbenzofuran-3-yl)-4-morpholinothieno[3,2-d]pyrimidin-6-yl)methyl)piperazin-1-yl)propanamide |

TABLE 1-continued

| No. | Structure | Name |
|---|---|---|
| 141 | 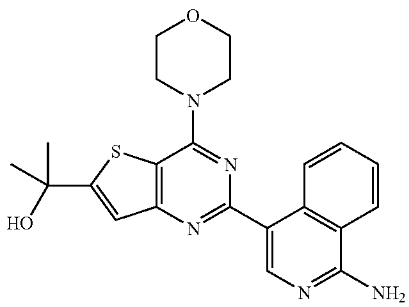 | 2-(2-(1-aminoisoquinolin-4-yl)-4-morpholinothieno[3,2-d]pyrimidin-6-yl)propan-2-ol |
| 142 | 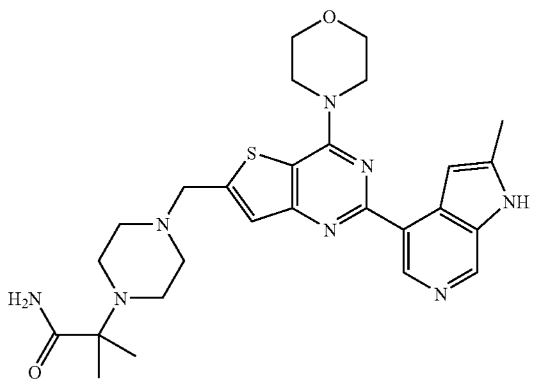 | 2-methyl-2-(4-((2-(2-methyl-1H-pyrrolo[2,3-c]pyridin-4-yl)-4-morpholinothieno[3,2-d]pyrimidin-6-yl)methyl)piperazin-1-yl)propanamide |
| 143 | 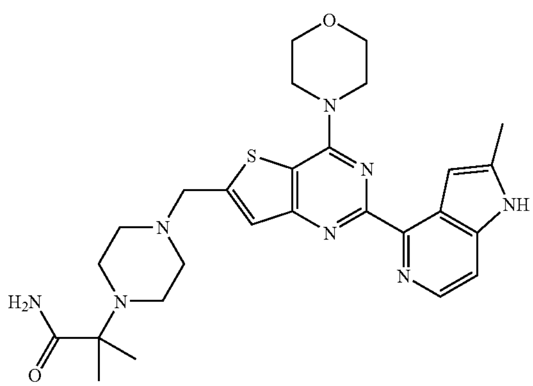 | 2-methyl-2-(4-((2-(2-methyl-1H-pyrrolo[3,2-c]pyridin-4-yl)-4-morpholinothieno[3,2-d]pyrimidin-6-yl)methyl)piperazin-1-yl)propanamide |
| 144 | 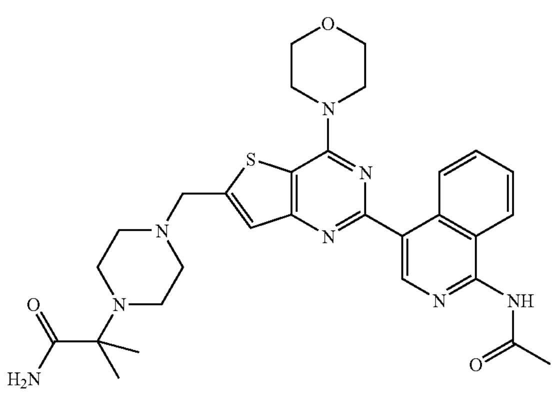 | 2-(4-((2-(1-acetamidoisoquinolin-4-yl)-4-morpholinothieno[3,2-d]pyrimidin-6-yl)methyl)piperazin-1-yl)-2-methylpropanamide |

TABLE 1-continued

| No. | Structure | Name |
|---|---|---|
| 145 | 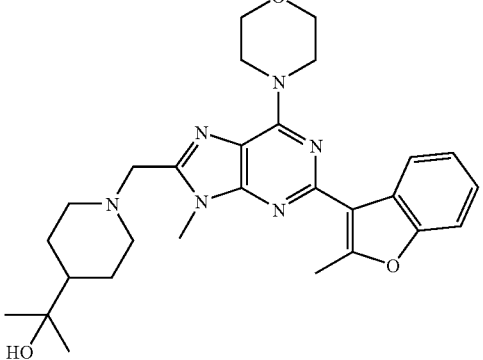 | 2-(1-((9-methyl-2-(2-methylbenzofuran-3-yl)-6-morpholino-9H-purin-8-yl)methyl)piperidin-4-yl)propan-2-ol |
| 146 | 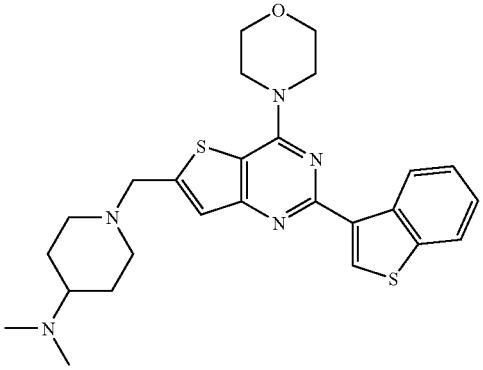 | 1-((2-(benzo[b]thiophen-3-yl)-4-morpholinothieno[3,2-d]pyrimidin-6-yl)methyl)-N,N-dimethylpiperidin-4-amine |
| 147 | 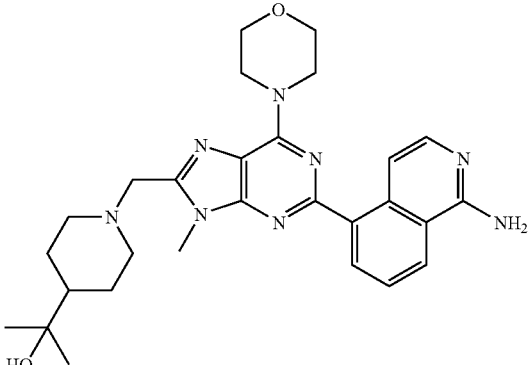 | 2-(1-((2-(1-aminoisoquinolin-5-yl)-9-methyl-6-morpholino-9H-purin-8-yl)methyl)pipern-4-yl)propan-2-ol |
| 148 | 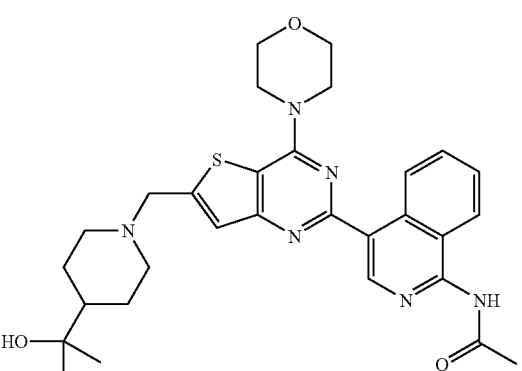 | N-(4-(6-((4-(2-hydroxypropan-2-yl)piperidin-1-yl)methyl)-4-morpholinothieno[3,2-d]pyrimidin-2-yl)isoquinolin-1-yl)acetamide |

TABLE 1-continued

| No. | Structure | Name |
|---|---|---|
| 149 | 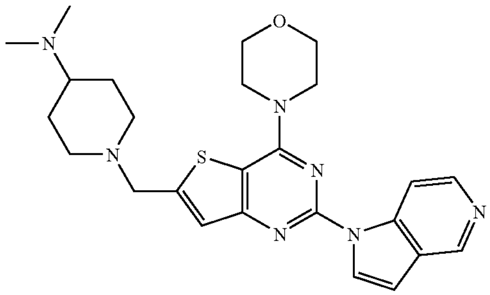 | N,N-dimethyl-1-((4-morpholino-2-(1H-pyrrolo[3,2-c]pyridin-1-yl)thieno[3,2-d]pyrimidin-6-yl)methyl)piperidin-4-amine |
| 150 | 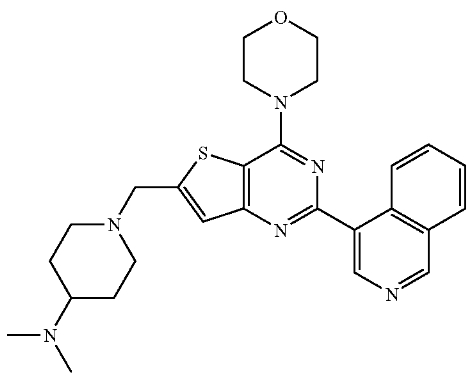 | 1-((2-(isoquinolin-4-yl)-4-morpholinothieno[3,2-d]pyrimidin-6-yl)methyl)-N,N-dimethylpiperidin-4-amine |
| 151 | 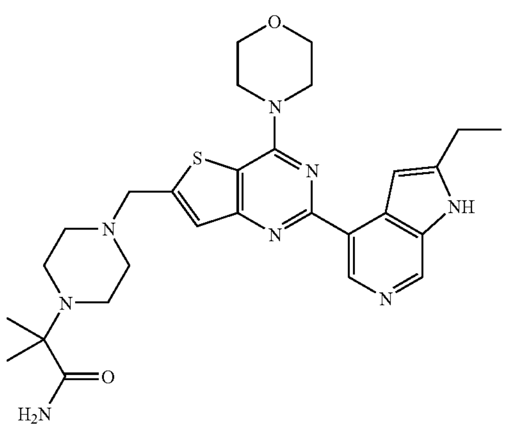 | 2-(4-((2-(2-ethyl-1H-pyrrolo[2,3-c]pyridin-4-yl)-4-morpholinothieno[3,2-d]pyrimidin-6-yl)methyl)piperazin-1-yl)-2-methylpropanamide |
| 152 | 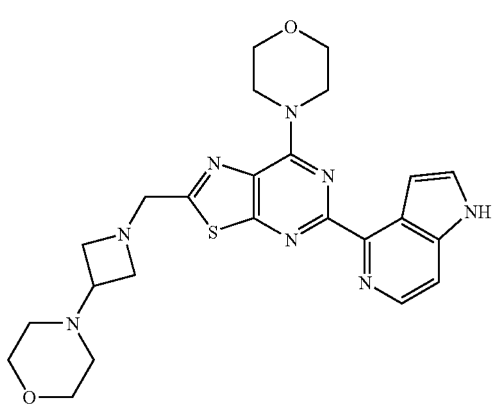 | 4-(1-((7-morpholino-5-(1H-pyrrolo[3,2-c]pyridin-4-yl)thiazolo[5,4-d]pyrimidin-2-yl)methyl)azetidin-3-yl)morpholine |

TABLE 1-continued

| No. | Structure | Name |
|---|---|---|
| 153 | 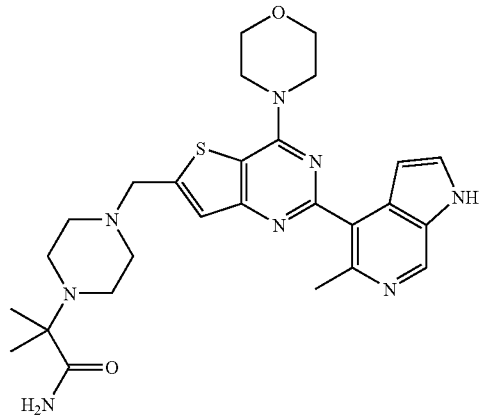 | 2-methyl-2-(4-((2-(5-methyl-1H-pyrrolo[2,3-c]pyridin-4-yl)-4-morpholinothieno[3,2-d]pyrimidin-6-yl)methyl)piperazin-1-yl)propanamide |
| 154 | 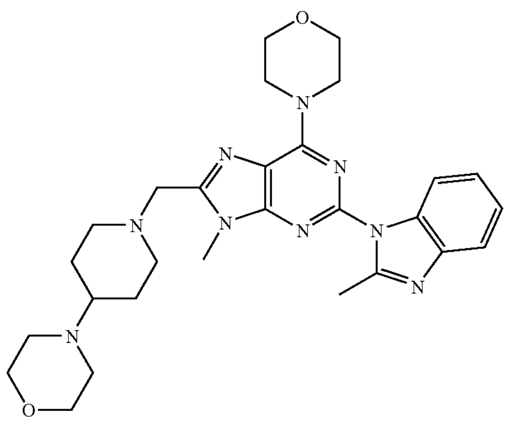 | 4-(1-((9-methyl-2-(2-methyl-1H-benzo[d]imidazol-1-yl)-6-morpholino-9H-purin-8-yl)methyl)piperidin-4-yl)morpholine |
| 155 | 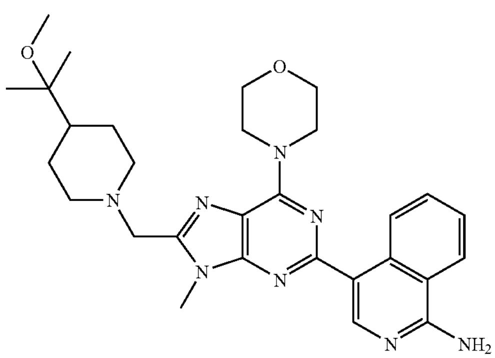 | 4-(8-((4-(2-methoxypropan-2-yl)piperidin-1-yl)methyl)-9-methyl-6-morpholino-9H-purin-2-yl)isoquinolin-1-amine |
| 156 | 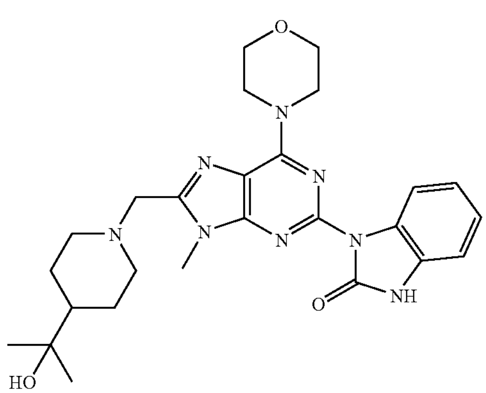 | 1-(8-((4-(2-hydroxypropan-2-yl)piperidin-1-yl)methyl)-9-methyl-6-morpholino-9H-purin-2-yl)-1H-benzo[d]imidazol-2(3H)-one |

TABLE 1-continued

| No. | Structure | Name |
|---|---|---|
| 157 | 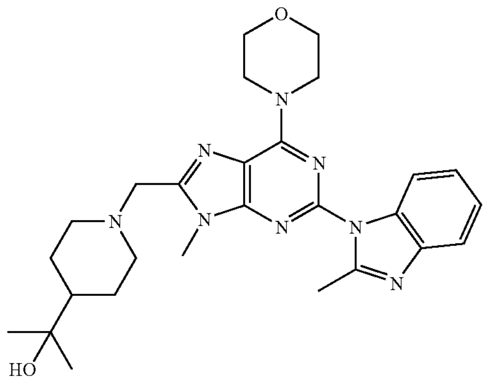 | 2-(1-((9-methyl-2-(2-methyl-1H-benzo[d]imidazol-1-yl)-6-morpholino-9H-purin-8-yl)methyl)piperidin-4-yl)propan-2-ol |
| 158 | 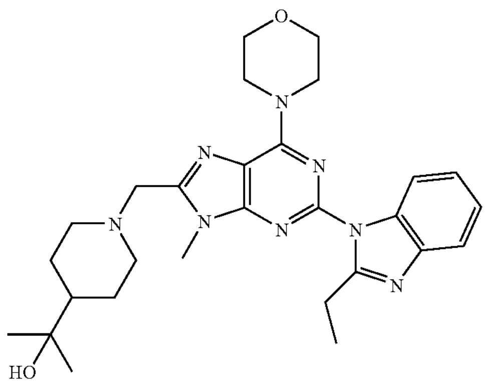 | 2-(1-((2-(2-ethyl-1H-benzo[d]imidazol-1-yl)-9-methyl-6-morpholino-9H-purin-8-yl)methyl)piperidin-4-yl)propan-2-ol |
| 159 | 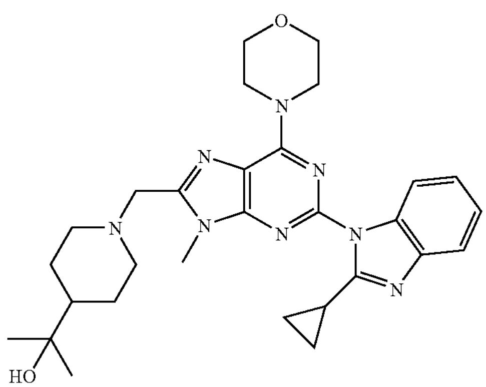 | 2-(1-((2-(2-cyclopropyl-1H-benzo[d]imidazol-1-yl)-9-methyl-6-morpholino-9H-purin-8-yl)methyl)piperidin-4-yl)propan-2-ol |
| 160 | 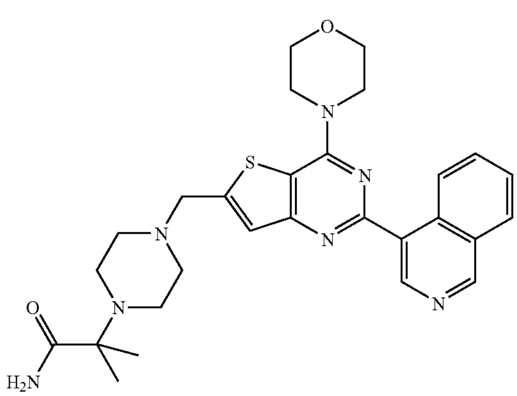 | 2-(4-((2-(isoquinolin-4-yl)-4-morpholinothieno[3,2-d]pyrimidin-6-yl)methyl)piperazin-1-yl)-2-methylpropanamide |

| No. | Structure | Name |
|---|---|---|
| 161 | 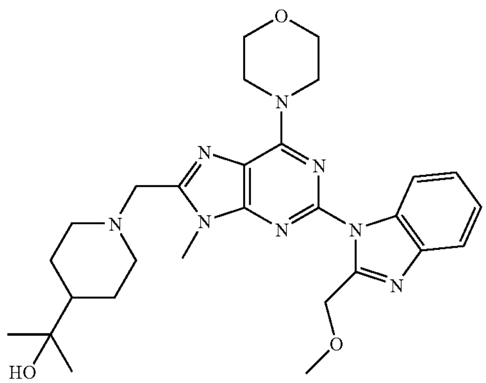 | 2-(1-((2-(2-(methoxymethyl)-1H-benzo[d]imidazol-1-yl)-9-methyl-6-morpholino-9H-purin-8-yl)methyl)piperidin-4-yl)propan-2-ol |
| 162 | 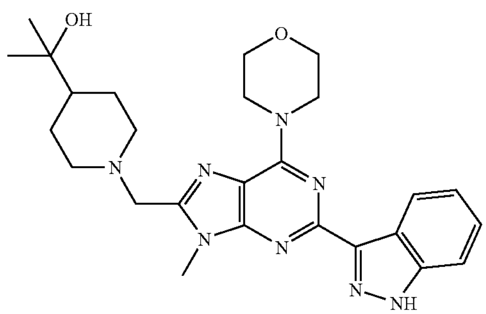 | 2-(1-((2-(1H-indazol-3-yl)-9-methyl-6-morpholino-9H-purin-8-yl)methyl)piperidin-4-yl)propan-2-ol |
| 163 | 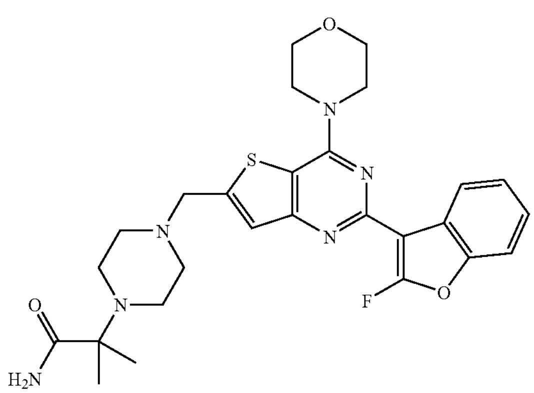 | 2-(4-((2-(2-fluorobenzofuran-3-yl)-4-morpholinothieno[3,2-d]pyrimidin-6-yl)methyl)piperazin-1-yl)-2-methylpropanamide |
| 164 | 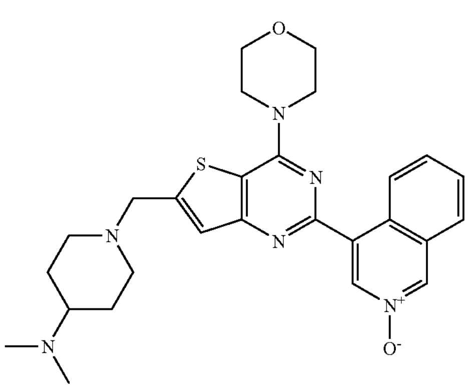 | 4-(6-((4-(dimethylamino)piperidin-1-yl)methyl)-4-morpholinothieno[3,2-d]pyrimidin-2-yl)isoquinoline 2-oxide |

TABLE 1-continued

| No. | Structure | Name |
|---|---|---|
| 165 | 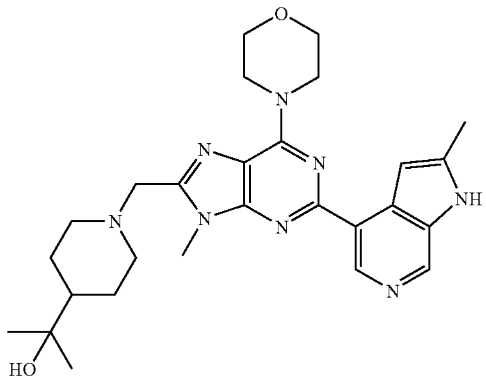 | 2-(1-((9-methyl-2-(2-methyl-1H-pyrrolo[2,3-c]pyridin-4-yl)-6-morpholino-9H-purin-8-yl)methyl)piperidin-4-yl)propan-2-ol |
| 166 | 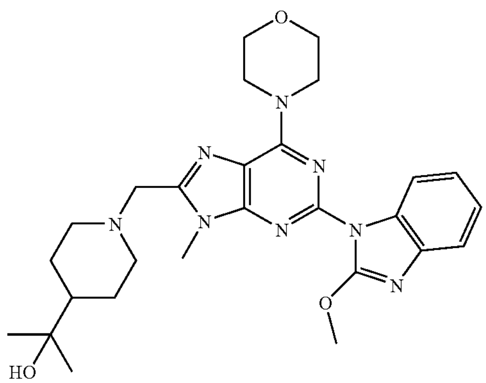 | 2-(1-((2-(2-methoxy-1H-benzo[d]imidazol-1-yl)-9-methyl-6-morpholino-9H-purin-8-yl)methyl)piperidin-4-yl)propan-2-ol |
| 167 | 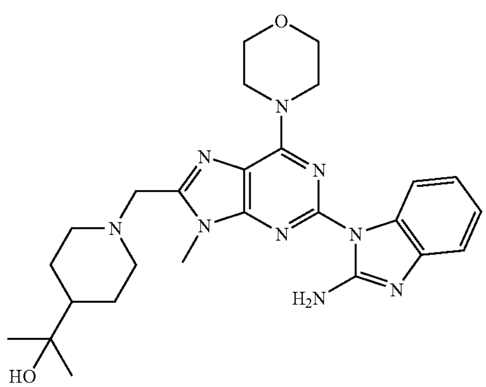 | 2-(1-((2-(2-amino-1H-benzo[d]imidazol-1-yl)-9-methyl-6-morpholino-9H-purin-8-yl)methyl)piperidin-4-yl)propan-2-ol |
| 168 | 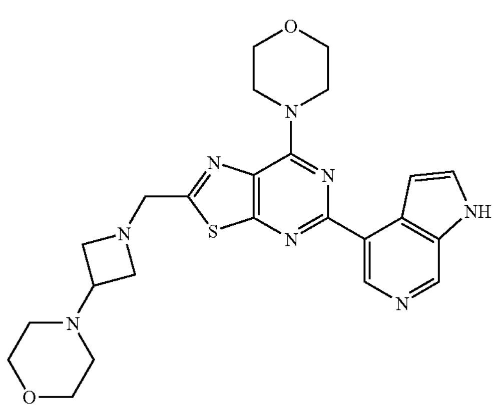 | 4-(1-((7-morpholino-5-(1H-pyrrolo[2,3-c]pyridin-4-yl)thiazolo[5,4-d]pyrimidin-2-yl)methyl)azetidin-3-yl)morpholine |

| No. | Structure | Name |
|---|---|---|
| 169 | 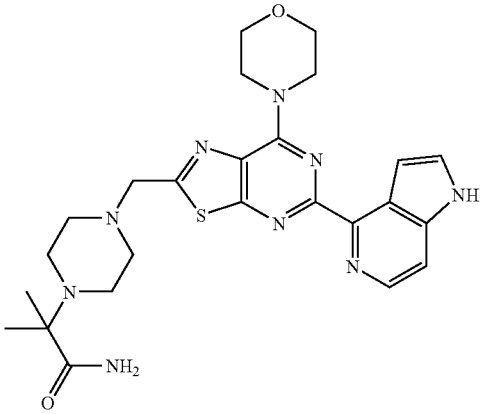 | 2-methyl-2-(4-((7-morpholino-5-(1H-pyrrolo[3,2-c]pyridin-4-yl)thiazolo[5,4-d]pyrimidin-2-yl)methyl)piperazin-1-yl)propanamide |
| 170 | 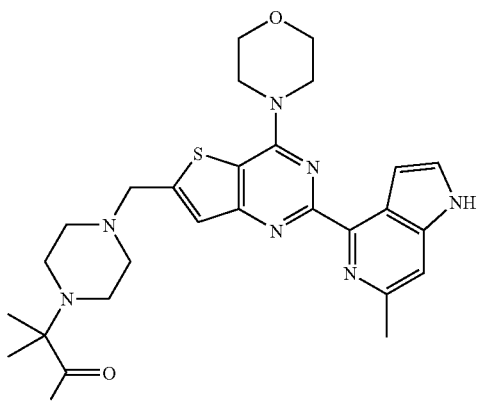 | 2-methyl-2-(4-((2-(6-methyl-1H-pyrrolo[3,2-c]pyridin-4-yl)-4-morpholinothieno[3,2-d]pyrimidin-6-yl)methyl)piperazin-1-yl)propanamide |
| 171 | 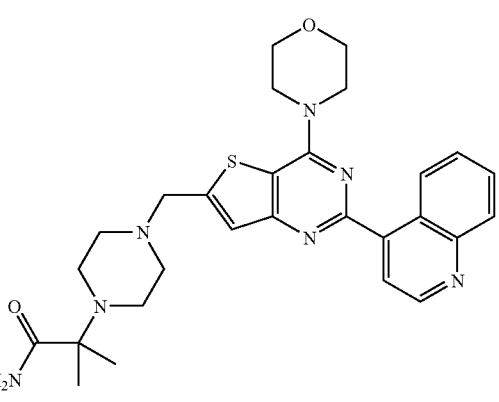 | 2-methyl-2-(4-((4-morpholino-2-(quinolin-4-yl)thieno[3,2-d]pyrimidin-6-yl)methyl)piperazin-1-yl)propanamide |

TABLE 1-continued

| No. | Structure | Name |
|---|---|---|
| 172 | 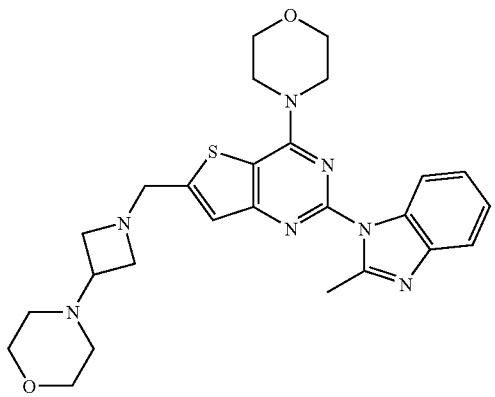 | 4-(1-((2-(2-methyl-1H-benzo[d]imidazol-1-yl)-4-morpholinothieno[3,2-d]pyrimidin-6-yl)methyl)azetidin-3-yl)morpholine |
| 173 | 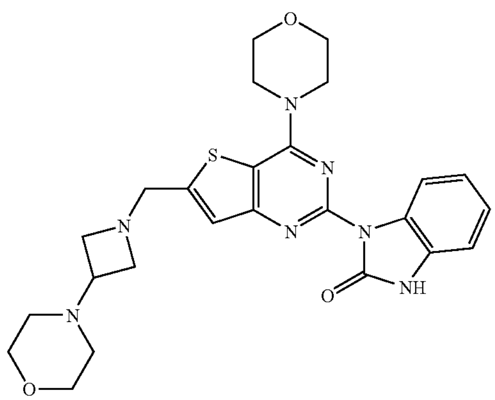 | 1-(4-morpholino-6-((3-morpholinoazetidin-1-yl)methyl)thieno[3,2-d]pyrimidin-2-yl)-1H-benzo[d]imidazol-2(3H)-one |
| 174 | 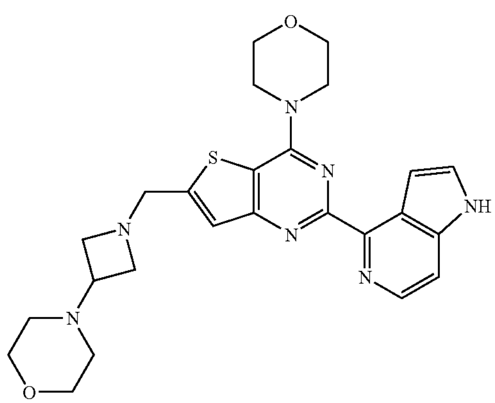 | 4-(1-((4-morpholino-2-(1H-pyrrolo[3,2-c]pyridin-4-yl)thieno[3,2-d]pyrimidin-6-yl)methyl)azetidin-3-yl)morpholine |
| 175 | 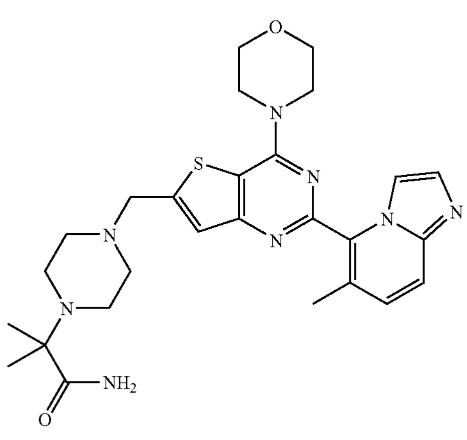 | 2-methyl-2-(4-((2-(6-methylimidazo[1,2-a]pyridin-5-yl)-4-morpholinothieno[3,2-d]pyrimidin-6-yl)methyl)piperazin-1-yl)propanamide |

TABLE 1-continued

| No. | Structure | Name |
| --- | --- | --- |
| 176 | 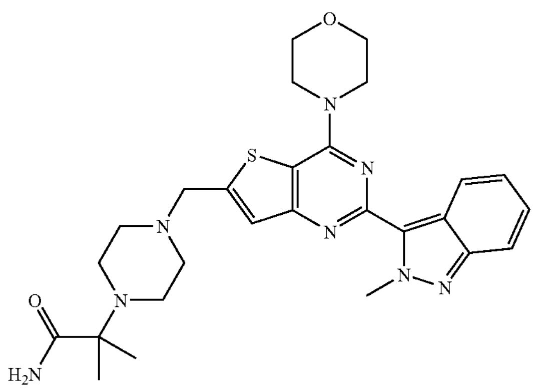 | 2-methyl-2-(4-((2-(2-methyl-2H-indazol-3-yl)-4-morpholinothieno[3,2-d]pyrimidin-6-yl)methyl)piperazin-1-yl)propanamide |
| 177 | 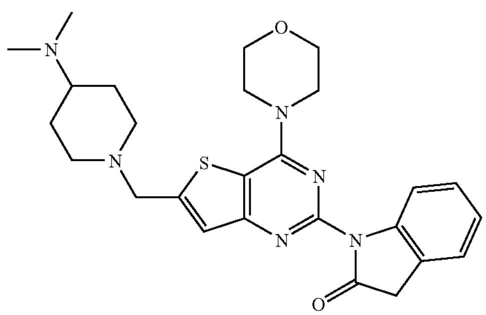 | 1-(6-((4-(dimethylamino)piperidin-1-yl)methyl)-4-morpholinothieno[3,2-d]pyrimidin-2-yl)indolin-2-one |
| 178 | 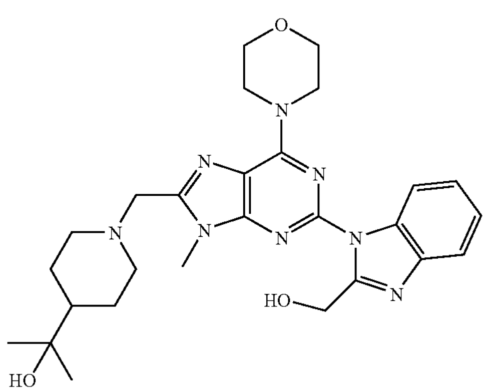 | 2-(1-((2-(2-(hydroxymethyl)-1H-benzo[d]imidazol-1-yl)-9-methyl-6-morpholino-9H-purin-8-yl)methyl)piperidin-4-yl)propan-2-ol |
| 179 | 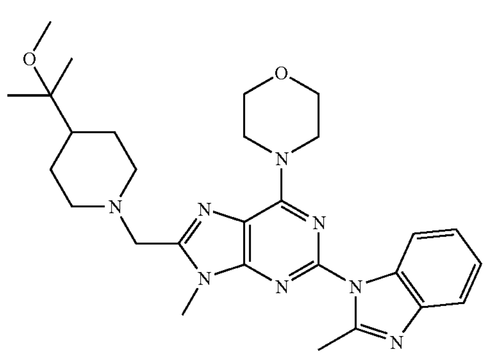 | 4-(8-((4-(2-methoxypropan-2-yl)piperidin-1-yl)methyl)-9-methyl-2-(2-methyl-1H-benzo[d]imidazol-1-yl)-9H-purin-6-yl)morpholine |

TABLE 1-continued

| No. | Structure | Name |
|---|---|---|
| 180 | 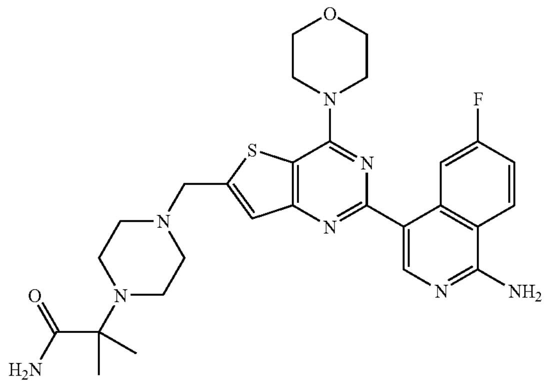 | 2-(4-((2-(1-amino-6-fluoroisoquinolin-4-yl)-4-morpholinothieno[3,2-d]pyrimidin-6-yl)methyl)piperazin-1-yl)-2-methylpropanamide |
| 181 | 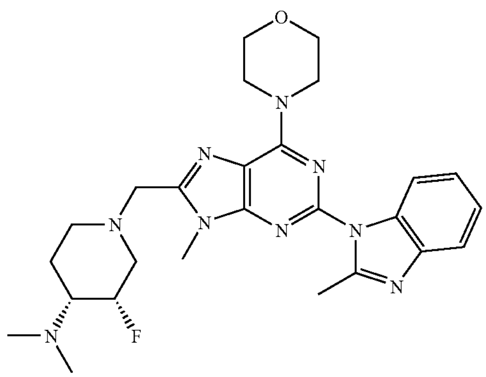 | (3S,4R)-3-fluoro-N,N-dimethyl-1-((9-methyl-2-(2-methyl-1H-benzo[d]imidazol-1-yl)-6-morpholino-9H-purin-8-yl)methyl)piperidin-4-amine |
| 182 | 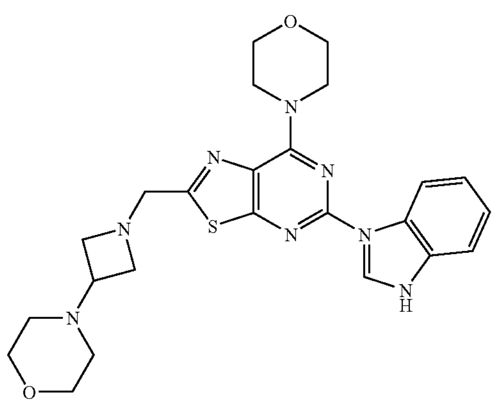 | 4-(5-(1H-indazol-3-yl)-2-((3-morpholinoazetidin-1-yl)methyl)thiazolo[5,4-d]pyrimidin-7-yl)morpholine |
| 183 | 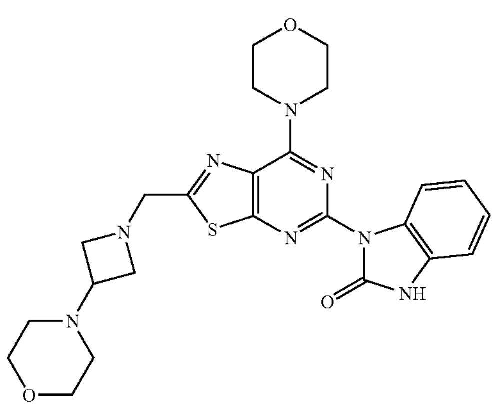 | 1-(7-morpholino-2-((3-morpholinoazetidin-1-yl)methyl)thiazolo[5,4-d]pyrimidin-5-yl)-1H-benzo[d]imidazol-2(3H)-one |

TABLE 1-continued

| No. | Structure | Name |
|---|---|---|
| 184 | 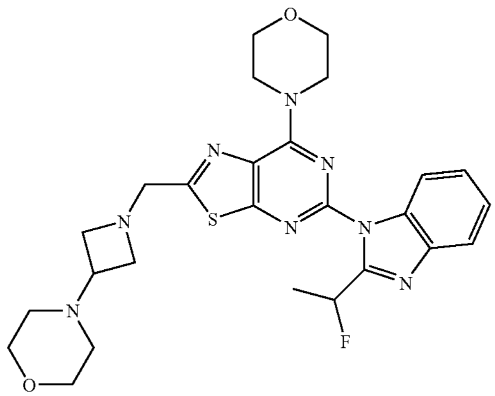 | 4-(5-(2-(difluoromethyl)-1H-benzo[d]imidazol-1-yl)-2-((3-morpholinoazetidin-1-yl)methyl)thiazolo[5,4-d]pyrimidin-7-yl)morpholine |
| 185 | 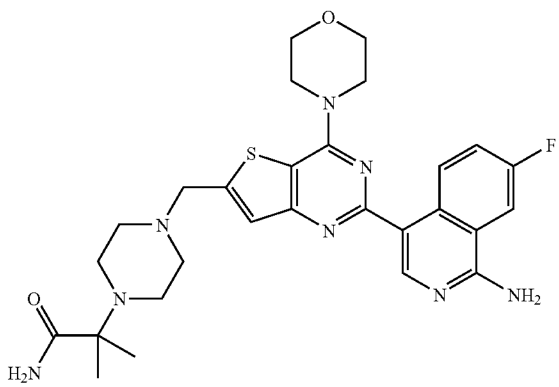 | 2-(4-((2-(1-amino-7-fluoroisoquinolin-4-yl)-4-morpholinothieno[3,2-d]pyrimidin-6-yl)methyl)piperazin-1-yl)-2-methylpropanamide |
| 186 | 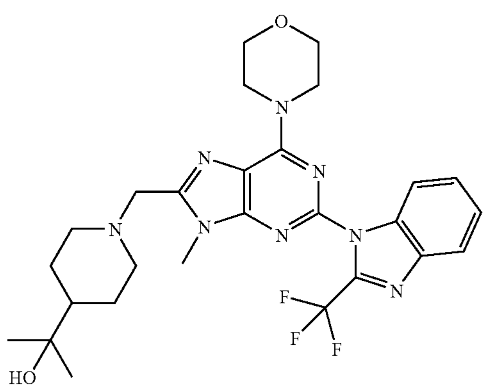 | 2-(1-((9-methyl-6-morpholino-2-(2-(trifluoromethyl)-1H-benzo[d]imidazol-1-yl)-9H-purin-8-yl)methyl)piperidin-4-yl)propan-2-ol |
| 187 | 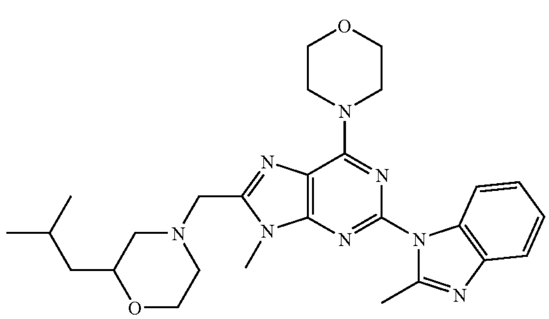 | 2-isobutyl-4-((9-methyl-2-(2-methyl-1H-benzo[d]imidazol-1-yl)-6-morpholino-9H-purin-8-yl)methyl)morpholine |

TABLE 1-continued

| No. | Structure | Name |
|---|---|---|
| 188 | 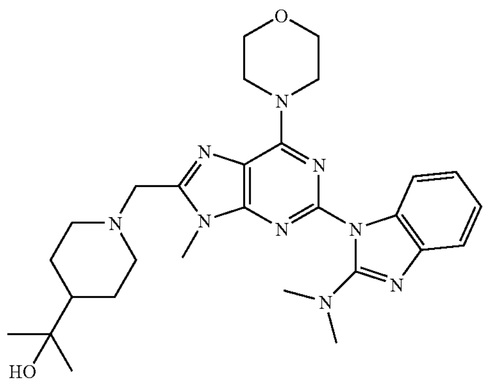 | 2-(1-((2-(2-(dimethylamino)-1H-benzo[d]imidazol-1-yl)-9-methyl-6-morpholino-9H-purin-8-yl)methyl)piperidin-4-yl)propan-2-ol |
| 189 | 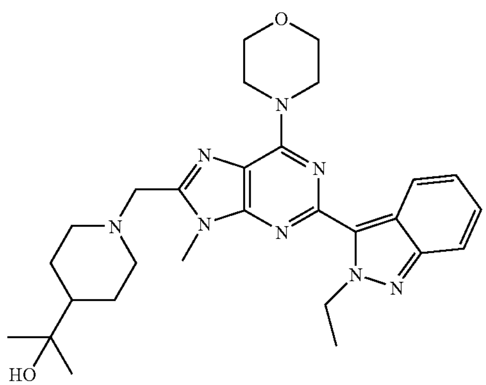 | 2-(1-((2-(2-ethyl-2H-indazol-3-yl)-9-methyl-6-morpholino-9H-purin-8-yl)methyl)piperidin-4-yl)propan-2-ol |
| 190 | 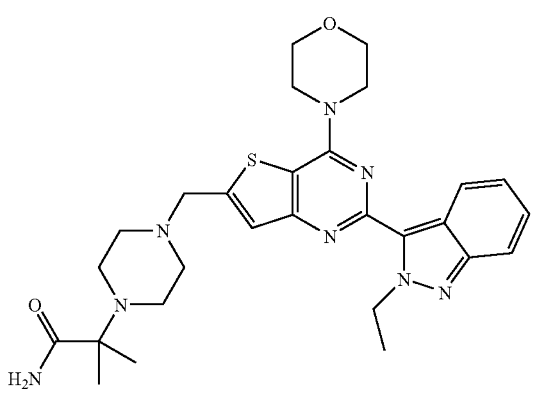 | 2-(4-((2-(2-ethyl-2H-indazol-3-yl)-4-morpholinothieno[3,2-d]pyrimidin-6-yl)methyl)piperazin-1-yl)-2-methylpropanamide |
| 191 | 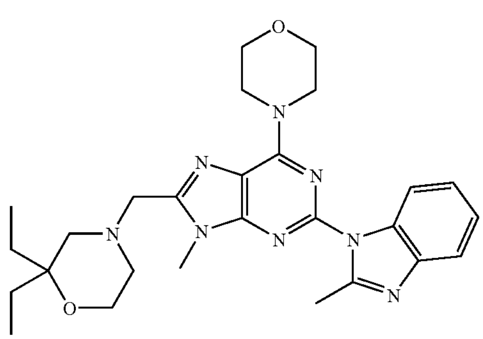 | 2,2-diethyl-4-((9-methyl-2-(2-methyl-1H-benzo[d]imidazol-1-yl)-6-morpholino-9H-purin-8-yl)methyl)morpholine |

TABLE 1-continued

| No. | Structure | Name |
|---|---|---|
| 192 | 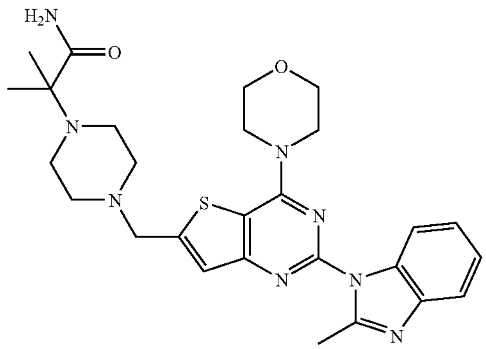 | 2-methyl-2-(4-((2-(2-methyl-1H-benzo[d]imidazol-1-yl)-4-morpholinothieno[3,2-d]pyrimidin-6-yl)methyl)piperazin-1-yl)propanamide |
| 193 | 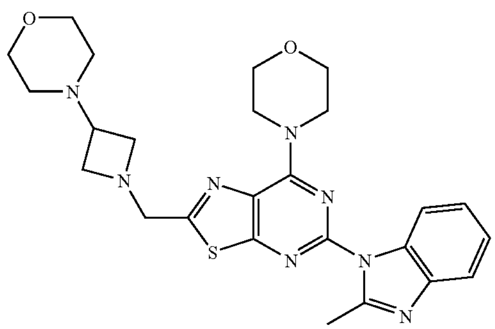 | 4-(5-(2-methyl-1H-benzo[d]imidazol-1-yl)-2-((3-morpholinoazetidin-1-yl)methyl)thiazolo[5,4-d]pyrimidin-7-yl)morpholine |
| 194 | 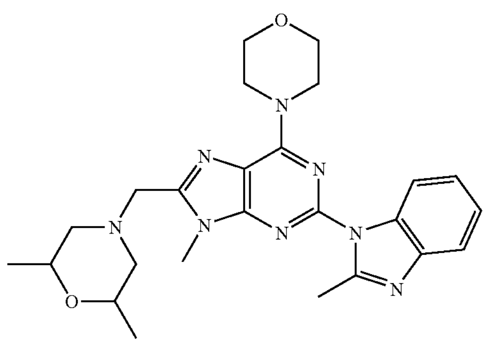 | 2,6-dimethyl-4-((9-methyl-2-(2-methyl-1H-benzo[d]imidazol-1-yl)-6-morpholino-9H-purin-8-yl)methyl)morpholine |
| 195 | 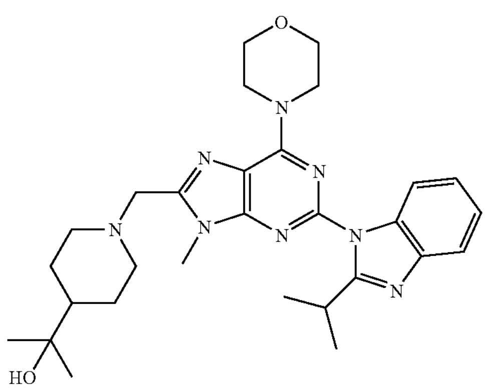 | 2-(1-((2-(2-isopropyl-1H-benzo[d]imidazol-1-yl)-9-methyl-6-morpholino-9H-purin-8-yl)methyl)piperidin-4-yl)propan-2-ol |

TABLE 1-continued

| No. | Structure | Name |
|---|---|---|
| 196 | 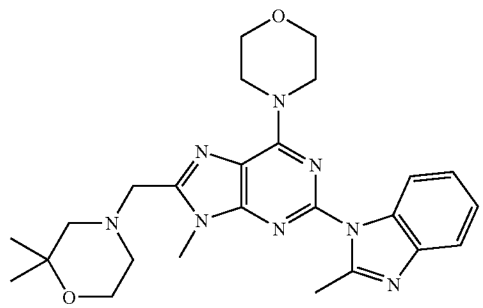 | 2,2-dimethyl-4-((9-methyl-2-(2-methyl-1H-benzo[d]imidazol-1-yl)-6-morpholino-9H-purin-8-yl)methyl)morpholine |
| 197 | 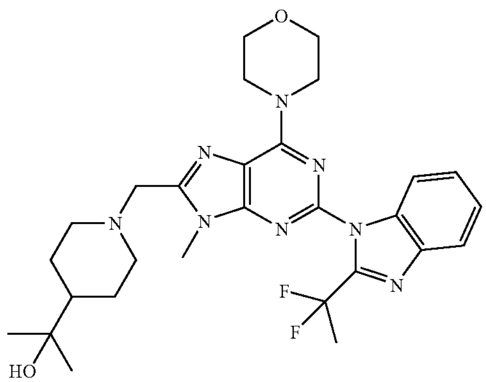 | 2-(1-((2-(2-(1,1-difluoroethyl)-1H-benzo[d]imidazol-1-yl)-9-methyl-6-morpholino-9H-purin-8-yl)methyl)piperidin-4-yl)propan-2-ol |
| 198 | 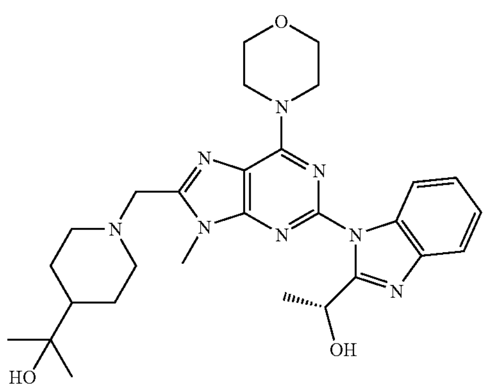 | (R)-2-(1-((2-(2-(1-hydroxyethyl)-1H-benzo[d]imidazol-1-yl)-9-methyl-6-morpholino-9H-purin-8-yl)methyl)piperidin-4-yl)propan-2-ol |
| 199 | 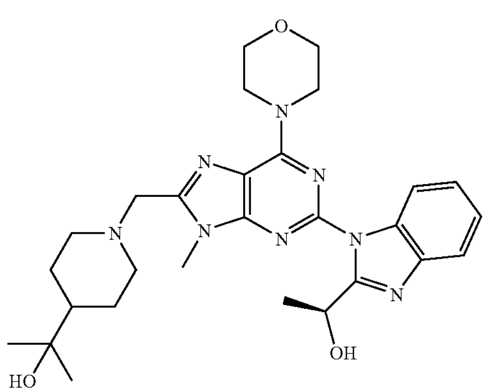 | (S)-2-(1-((2-(2-(1-hydroxyethyl)-1H-benzo[d]imidazol-1-yl)-9-methyl-6-morpholino-9H-purin-8-yl)methyl)piperidin-4-yl)propan-2-ol |

| No. | Structure | Name |
|---|---|---|
| 200 | 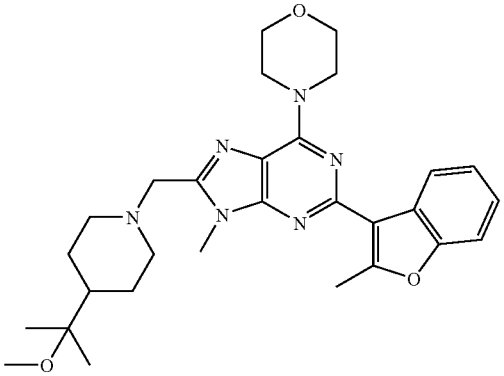 | 4-(8-((4-(2-methoxypropan-2-yl)piperidin-1-yl)methyl)-9-methyl-2-(2-methylbenzofuran-3-yl)-9H-purin-6-yl)morpholine |
| 201 | 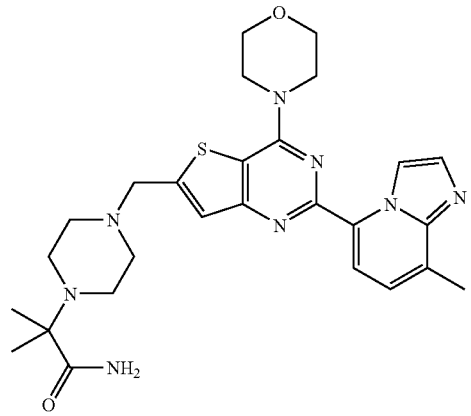 | 2-methyl-2-(4-((2-(8-methylimidazo[1,2-a]pyridin-5-yl)-4-morpholinothieno[3,2-d]pyrimidin-6-yl)methyl)piperazin-1-yl)propanamide |
| 202 | 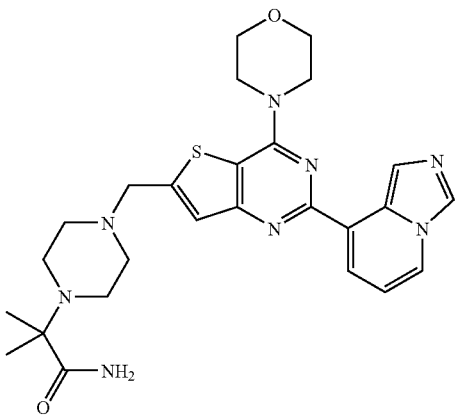 | 2-(4-((2-(imidazo[1,5-a]pyridin-8-yl)-4-morpholinothieno[3,2-d]pyrimidin-6-yl)methyl)piperazin-1-yl)-2-methylpropanamide |
| 203 | 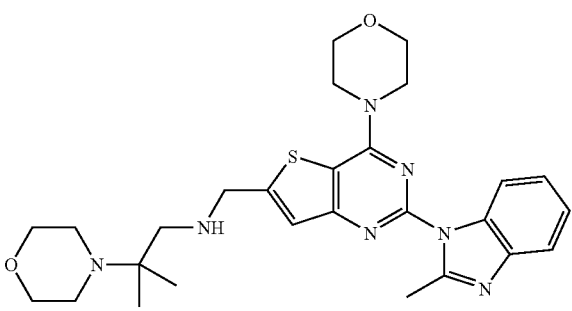 | 2-methyl-N-((2-(2-methyl-1H-benzo[d]imidazol-1-yl)-4-morpholinothieno[3,2-d]pyrimidin-6-yl)methyl)-2-morpholinopropan-1-amine |

TABLE 1-continued

| No. | Structure | Name |
|---|---|---|
| 204 | 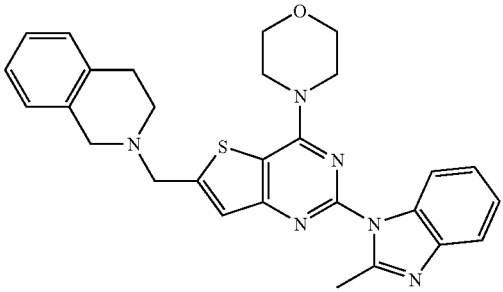 | 4-(6-((3,4-dihydroisoquinolin-2(1H)-yl)methyl)-2-(2-methyl-1H-benzo[d]imidazol-1-yl)thieno[3,2-d]pyrimidin-4-yl)morpholine |
| 205 | 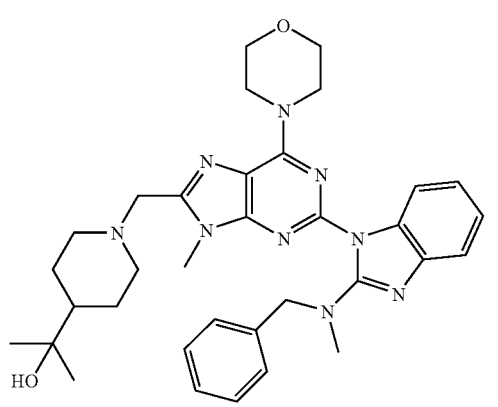 | 2-(1-((2-(2-(benzyl(methyl)amino)-1H-benzo[d]imidazol-1-yl)-9-methyl-6-morpholino-9H-purin-8-yl)methyl)piperidin-4-yl)propan-2-ol |
| 206 | 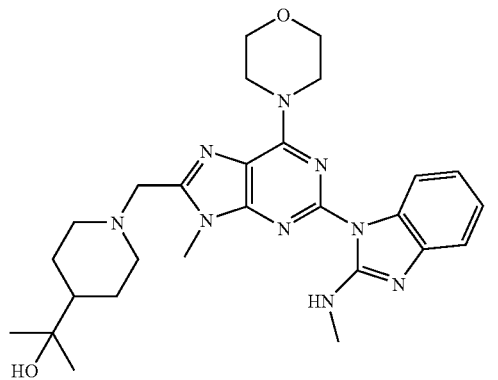 | 2-(1-((9-methyl-2-(2-(methylamino)-1H-benzo[d]imidazol-1-yl)-6-morpholino-9H-purin-8-yl)methyl)piperidin-4-yl)propan-2-ol |
| 207 | 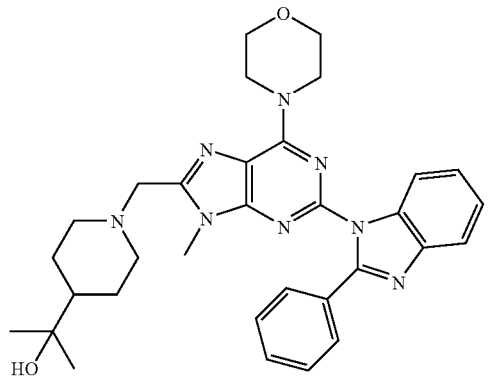 | 2-(1-((9-methyl-6-morpholino-2-(2-phenyl-1H-benzo[d]imidazol-1-yl)-9H-purin-8-yl)methyl)piperidin-4-yl)propan-2-ol |

TABLE 1-continued

| No. | Structure | Name |
|---|---|---|
| 208 | 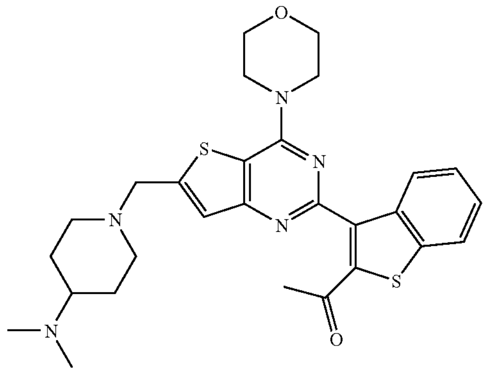 | 1-(3-(6-((4-dimethylamino)piperidin-1-yl)methyl)-4-morpholinothieno[3,2-d]pyrimidin-2-yl)benzo[b]thiophen-2-yl)ethanone |
| 209 | 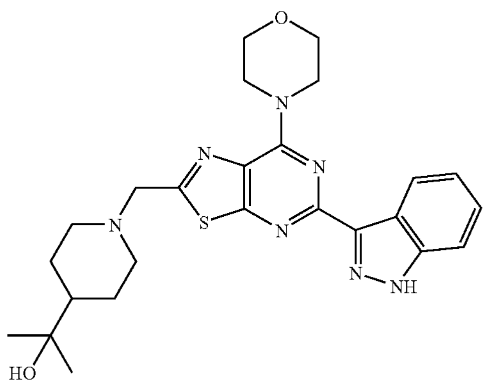 | 2-(1-((5-(1H-indazol-3-yl)-7-morpholinothiazolo[5,4-d]pyrimidin-2-yl)methyl)piperidin-4-yl)propan-2-ol |
| 210 | 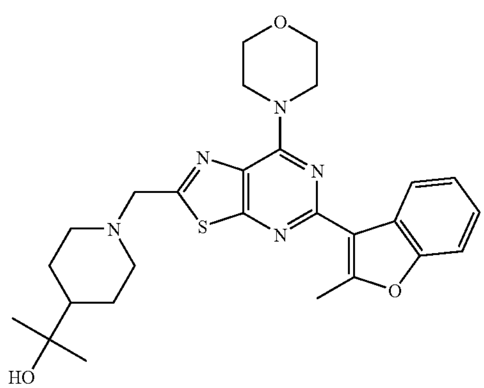 | 2-(1-5-(2-methylbenzofuran-3-yl)-7-morpholinothiazolo[5,4-d]pyrimidin-2-yl)methyl)piperidin-4-yl)propan-2-ol |
| 211 | 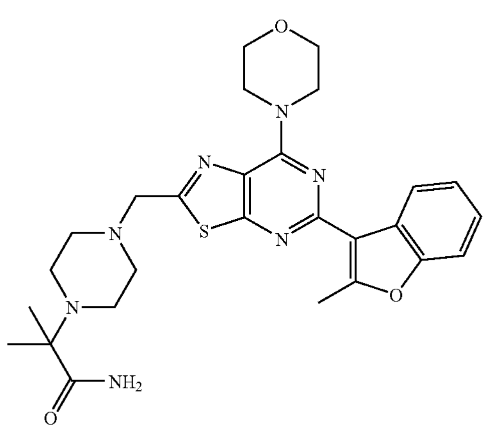 | 2-methyl-2-(4-((5-(2-methylbenzofuran-3-yl)-7-morpholinothiazolo[5,4-d]pyrimidin-2-yl)methyl)piperazin-1-yl)propanamide |

TABLE 1-continued

| No. | Structure | Name |
|---|---|---|
| 212 | 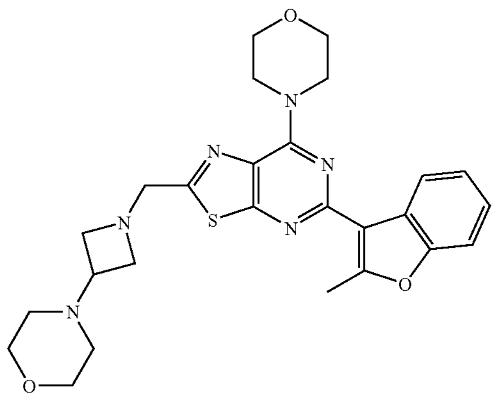 | 4-(5-(2-methylbenzofuran-3-yl)-2-((3-morpholinoazetidin-1-yl)methyl)thiazolo[5,4-d]pyrimidin-7-yl)morpholine |
| 213 | 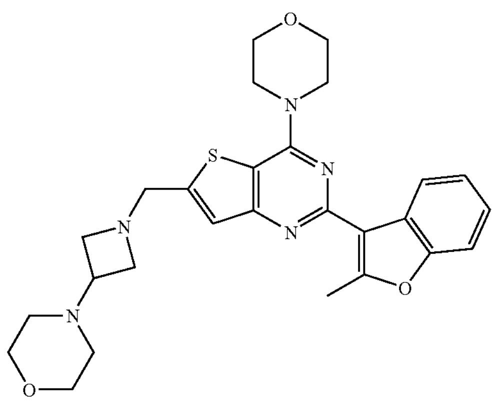 | 4-(1-((2-(2-methylbenzofuran-3-yl)-4-morpholinothieno[3,2-d]pyrimidin-6-yl)methyl)azetidin-3-yl)morpholine |
| 214 | 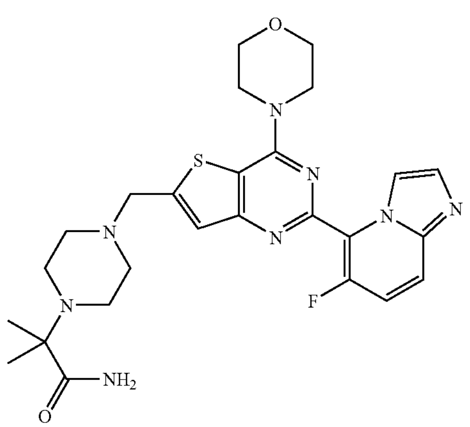 | 2-(4-((2-(6-fluoroimidazo[1,2-a]pyridin-5-yl)-4-morpholinothieno[3,2-d]pyrimidin-6-yl)methyl)piperazin-1-yl)-2-methylpropanamide |

| No. | Structure | Name |
|---|---|---|
| 215 | 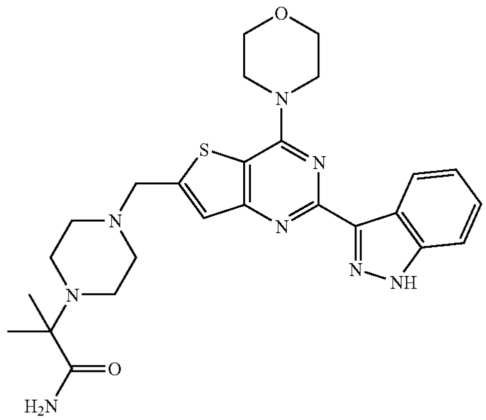 | 2-(4-((2-(1H-indazol-3-yl)-4-morpholinothieno[3,2-d]pyrimidin-6-yl)methyl)piperazin-1-yl)-2-methylpropanamide |
| 216 | 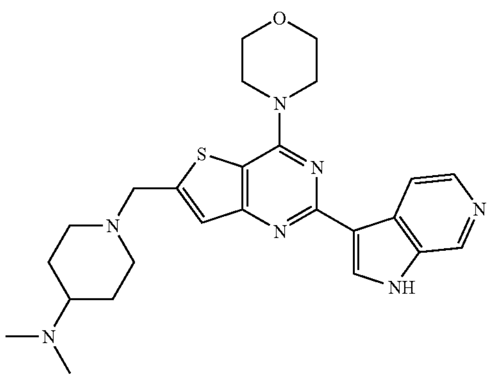 | N,N-dimethyl-1-((4-morpholino-2-(1H-pyrrolo[2,3-c]pyridin-3-yl)thieno[3,2-d]pyrimidin-6-yl)methyl)piperidin-4-amine |
| 217 | 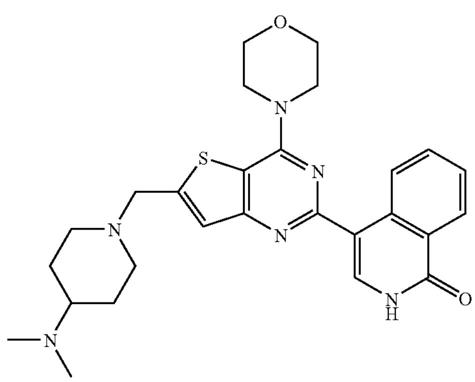 | 4-(6-((4-(dimethylamino)piperidin-1-yl)methyl)-4-morpholinothieno[3,2-d]pyrimidin-2-yl)isoquinolin-1(2H)-one |
| 218 | 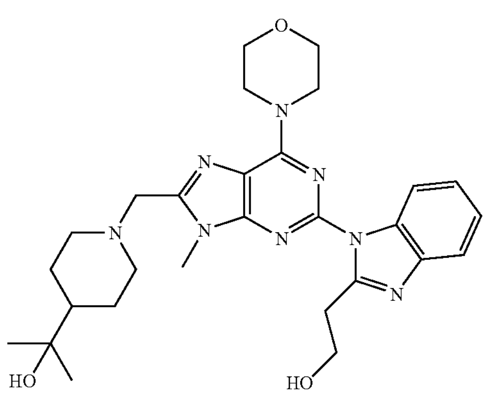 | 2-(1-((2-(2-(2-hydroxyethyl)-1H-benzo[d]imidazol-1-yl)-9-methyl-6-morpholino-9H-purin-8-yl)methyl)piperidin-4-yl)propan-2-ol |

| No. | Structure | Name |
| --- | --- | --- |
| 219 | 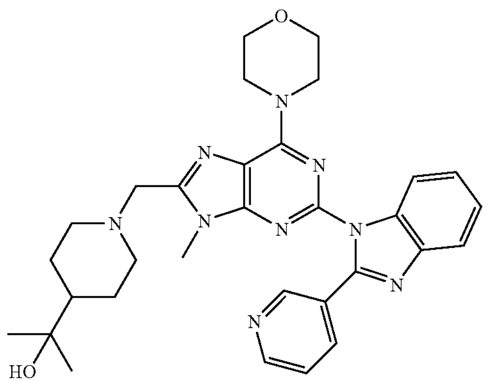 | 2-(1-((9-methyl-6-morpholino-2-(2-(pyridin-3-yl)-1H-benzo[d]imidazol-1-yl)-9H-purin-8-yl)methyl)piperidin-4-yl)propan-2-ol |
| 220 | 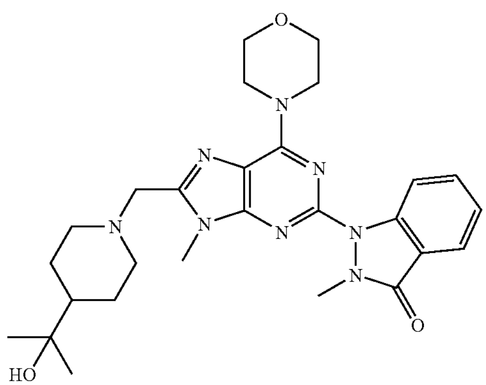 | 1-(8-((4-(2-hydroxypropan-2-yl)piperidin-1-yl)methyl)-9-methyl-6-morpholino-9H-purin-2-yl)-2-methyl-1H-indazol-3(2H)-one |
| 221 | 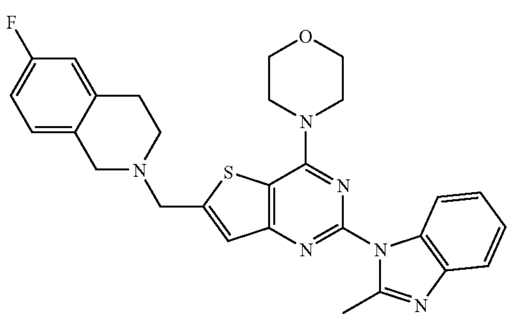 | 4-(6-((6-fluoro-3,4-dihydroisoquinolin-2(1H)-yl)methyl)-2-(2-methyl-1H-benzo[d]imidazol-1-yl)thieno[3,2-d]pyrimidin-4-yl)morpholine |
| 222 | 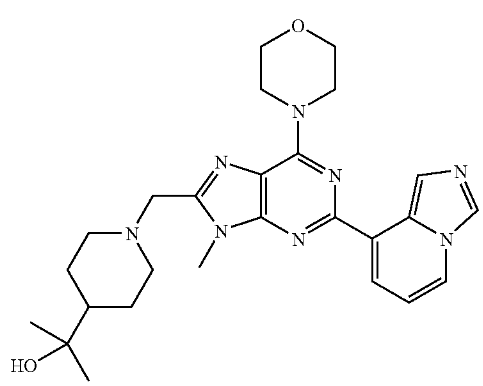 | 2-(1-((2-(imidazo[1,5-a]pyridin-8-yl)-9-methyl-6-morpholino-9H-purin-8-yl)methyl)piperidin-4-yl)propan-2-ol |

| No. | Structure | Name |
| --- | --- | --- |
| 223 | 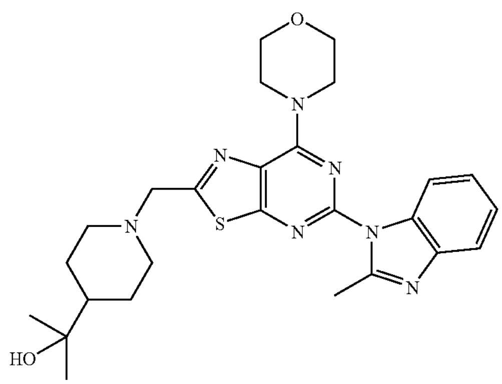 | 2-(1-((5-(2-methyl-1H-benzo[d]imidazol-1-yl)-7-morpholinothiazolo[5,4-d]pyrimidin-2-yl)methyl)piperidin-4-yl)propan-2-ol |
| 224 | 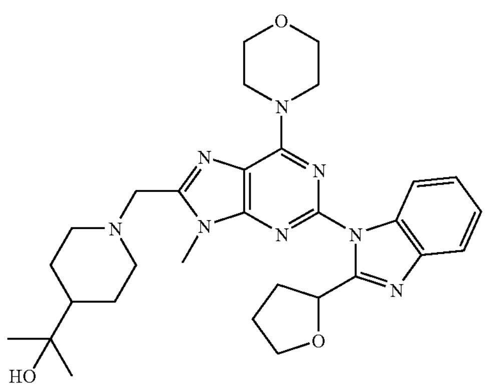 | 2-(1-((9-methyl-6-morpholino-2-(2-(tetrahydrofuran-2-yl)-1H-benzo[d]imidazol-1-yl)-9H-purin-8-yl)methyl)piperidin-4-yl)propan-2-ol |
| 225 | 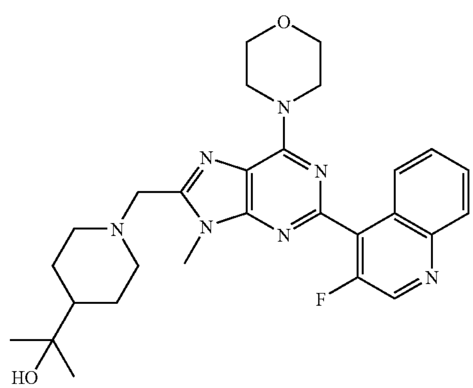 | 2-(1-((2-(3-fluoroquinolin-4-yl)-9-methyl-6-morpholino-9H-purin-8-yl)methyl)piperidin-4-yl)propan-2-ol |
| 226 | 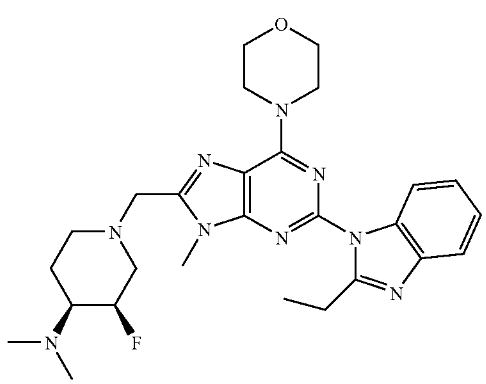 | (3R,4S)-1-((2-(2-ethyl-1H-benzo[d]imidazol-1-yl)-9-methyl-6-morpholino-9H-purin-8-yl)methyl)-3-fluoro-N,N-dimethylpiperidin-4-amine |

TABLE 1-continued

| No. | Structure | Name |
|---|---|---|
| 227 | 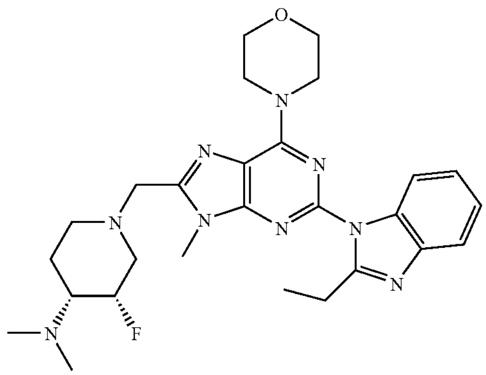 | (3R,4R)-1-((2-(2-ethyl-1H-benzo[d]imidazol-1-yl)-9-methyl-6-morpholino-9H-purin-8-yl)methyl)-3-fluoro-N,N-dimethylpiperidin-4-amine |
| 228 | 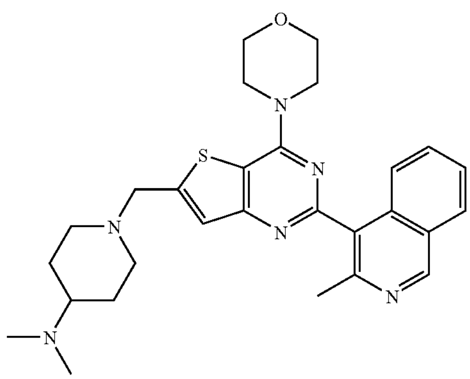 | N,N-dimethyl-1-((2-(3-methylisoquinolin-4-yl)-4-morpholinothieno[3,2-d]pyrimidin-6-yl)methyl)piperidin-4-amine |
| 229 | 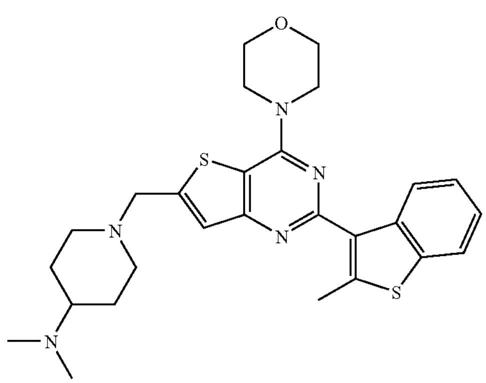 | N,N-dimethyl-1-((2-(2-methylbenzo[b]thiophen-3-yl)-4-morpholinothieno[3,2-d]pyrimidin-6-yl)methyl)piperidin-4-amine |
| 230 | 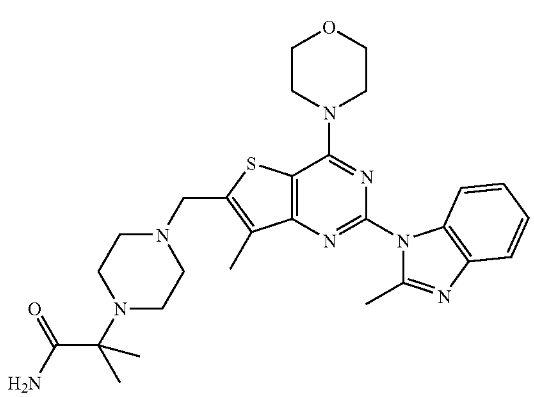 | 2-methyl-2-(4-((7-methyl-2-(2-methyl-1H-benzo[d]imidazol-1-yl)-4-morpholinothieno[3,2-d]pyrimidin-6-yl)methyl)piperazin-1-yl)propanamide |

TABLE 1-continued

| No. | Structure | Name |
|---|---|---|
| 231 | 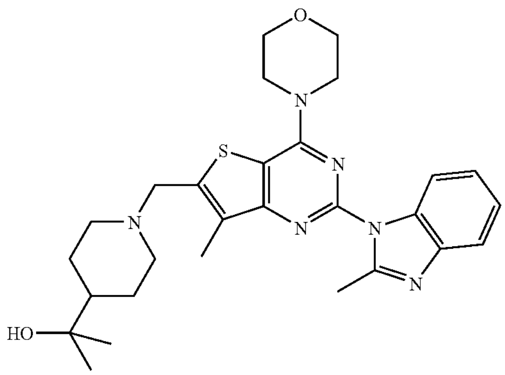 | 2-(1-((7-methyl-2-(2-methyl-1H-benzo[d]imidazol-1-yl)-4-morpholinothieno[3,2-d]pyrimidin-6-yl)methyl)piperidin-4-yl)propan-2-ol |
| 232 | 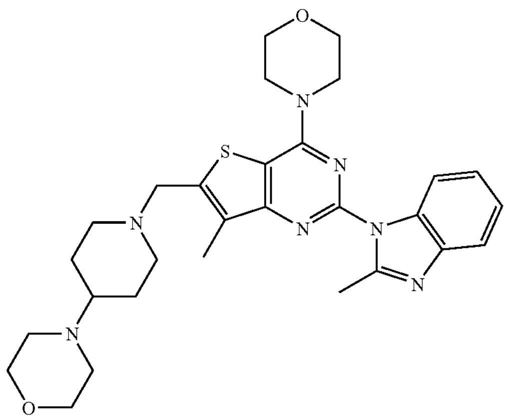 | 4-(1-((7-methyl-2-(2-methyl-1H-benzo[d]imidazol-1-yl)-4-morpholinothieno[3,2-d]pyrimidin-6-yl)methyl)piperidin-4-yl)morpholine |
| 233 | 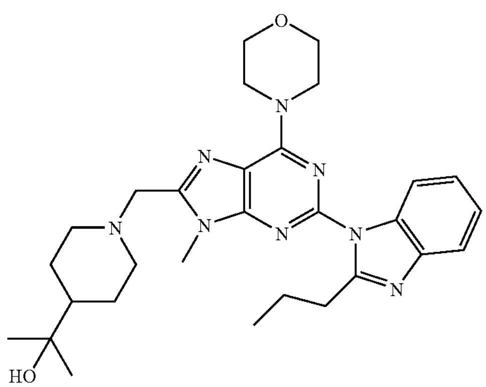 | 2-(1-((9-methyl-6-morpholino-2-(2-propyl-1H-benzo[d]imidazol-1-yl)-9H-purin-8-yl)methyl)piperidin-4-yl)propan-2-ol |
| 234 | 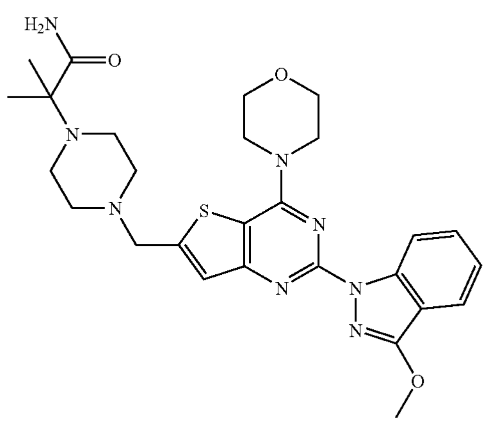 | 2-(4-((2-(3-methoxy-1H-indazol-1-yl)-4-morpholinothieno[3,2-d]pyrimidin-6-yl)methyl)piperazin-1-yl)-2-methylpropanamide |

TABLE 1-continued

| No. | Structure | Name |
|---|---|---|
| 235 | 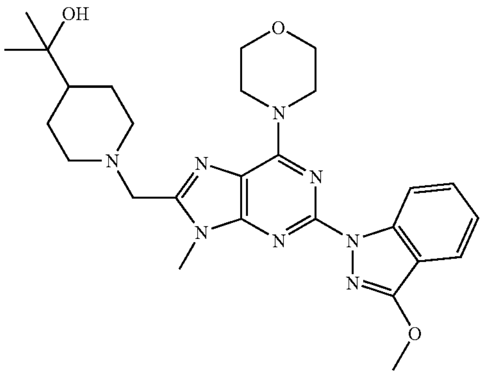 | 2-(1-((2-(3-methoxy-1H-indazol-1-yl)-9-methyl-6-morpholino-9H-purin-8-yl)methyl)piperidin-4-yl)propan-2-ol |
| 236 | 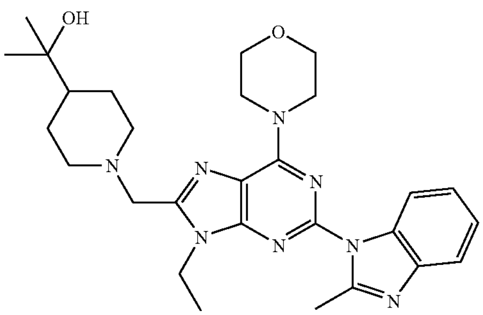 | 2-(1-((9-ethyl-2-(2-methyl-1H-benzo[d]imidazol-1-yl)-6-morpholino-9H-purin-8-yl)methyl)piperidin-4-yl)propan-2-ol |
| 237 | 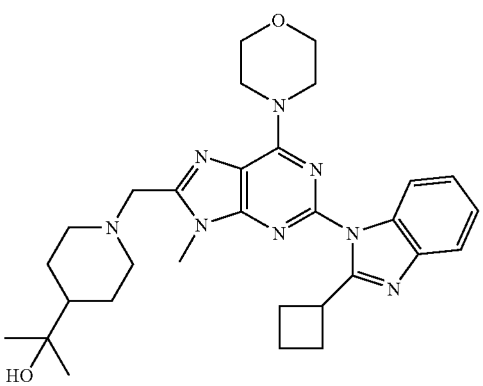 | 2-(1-((2-(2-cyclobutyl-1H-benzo[d]imidazol-1-yl)-9-methyl-6-morpholino-9H-purin-8-yl)methyl)piperidin-4-yl)propan-2-ol |
| 238 | 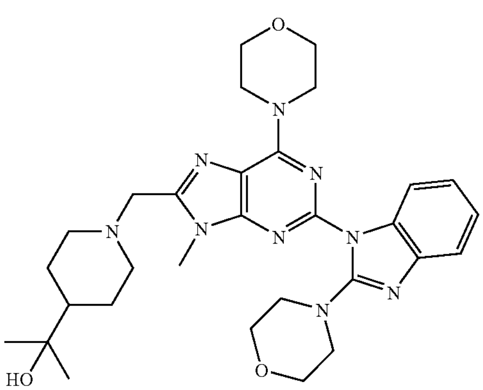 | 2-(1-((9-methyl-6-morpholino-2-(2-morpholino-1H-benzo[d]imidazol-1-yl)-9H-purin-8-yl)methyl)piperidin-4-yl)propan-2-ol |

TABLE 1-continued

| No. | Structure | Name |
|---|---|---|
| 240 | 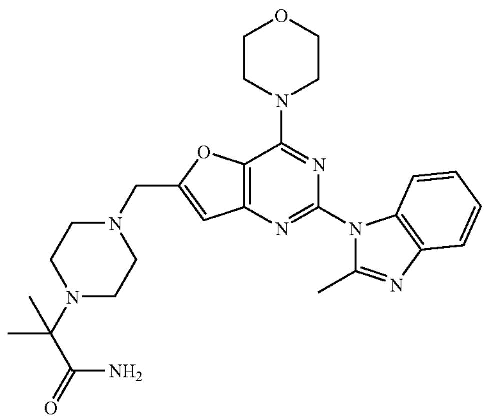 | 2-methyl-2-(4-((2-(2-methyl-1H-benzo[d]imidazol-1-yl)-4-morpholinofuro[3,2-d]pyrimidin-6-yl)methyl)piperazin-1-yl)propanamide |
| 241 | 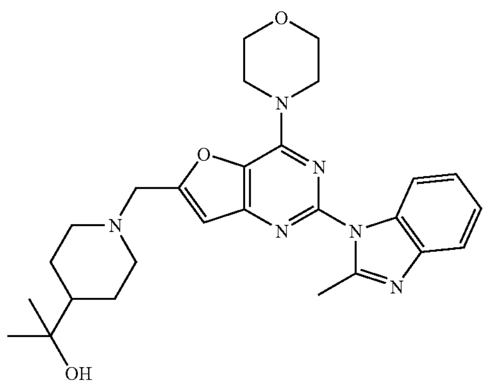 | 2-(1-((2-(2-methyl-1H-benzo[d]imidazol-1-yl)-4-morpholinofuro[3,2-d]pyrimidin-6-yl)methyl)piperidin-4-yl)propan-2-ol |
| 242 | 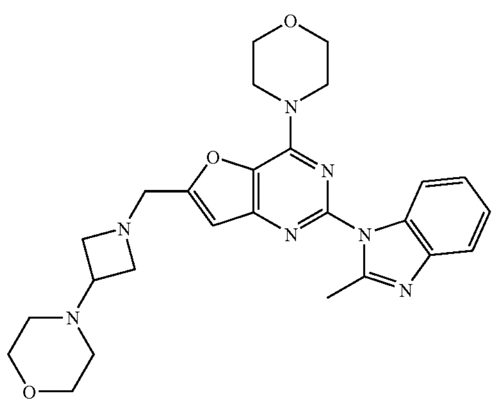 | 2-(2-methyl-1H-benzo[d]imidazol-1-yl)-4-morpholino-6-((3-morpholinoazetidin-1-yl)methyl)furo[3,2-d]pyrimidine |
| 243 | 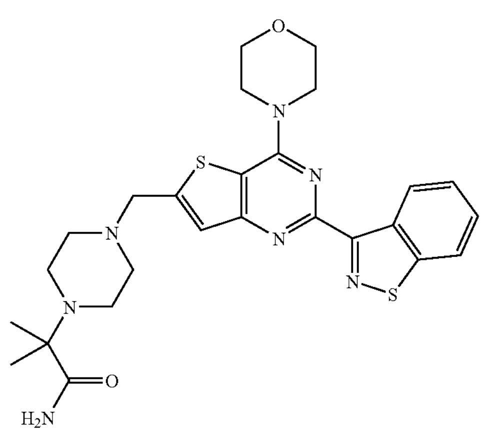 | 2-(4-((2-(benzo[d]isothiazol-3-yl)-4-morpholinothieno[3,2-d]pyrimidin-6-yl)methyl)piperazin-1-yl)-2-methylpropanamide |

| No. | Structure | Name |
|---|---|---|
| 244 | 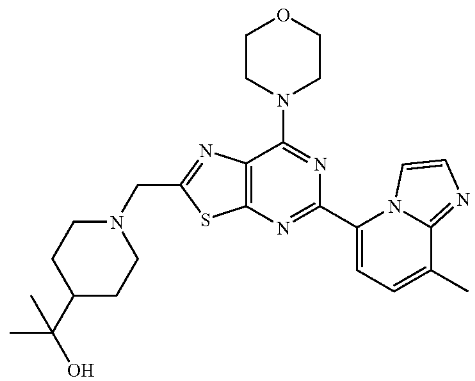 | 2-(1-((5-(8-methylimidazo[1,2-a]pyridin-5-yl)-7-morpholinothiazolo[5,4-d]pyrimidin-2-yl)methyl)piperidin-4-yl)propan-2-ol |
| 245 | 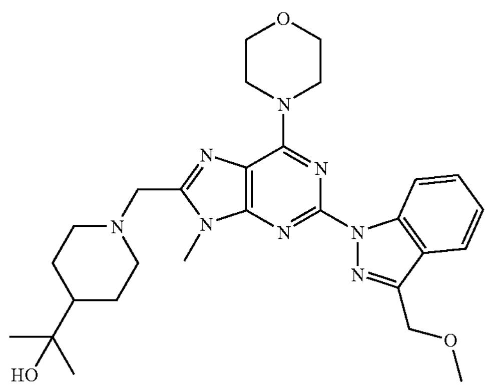 | 2-(1-((2-(3-ethoxy-1H-indazol-1-yl)-9-methyl-6-morpholino-9H-purin-8-yl)methyl)piperidin-4-yl)propan-2-ol |
| 246 | 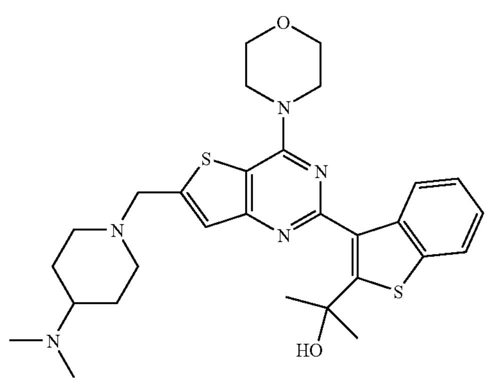 | 2-(3-(6-((4-(dimethylamino)piperidin-1-yl)methyl)-4-morpholinothieno[3,2-d]pyrimidin-2-yl)benzo[b]thiophen-2-yl)propan-2-ol |
| 247 | 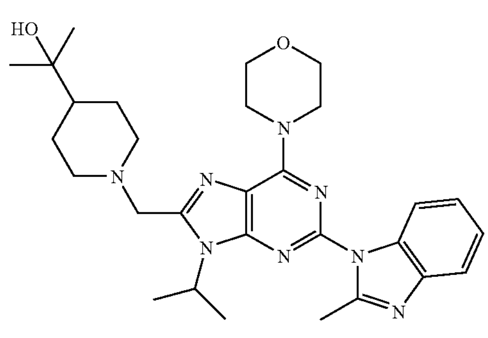 | 2-(1-((9-isopropyl-2-(2-methyl-1H-benzo[d]imidazol-1-yl)-6-morpholino-9H-purin-8-yl)methyl)piperidin-4-yl)propan-2-ol |

TABLE 1-continued

| No. | Structure | Name |
|---|---|---|
| 248 | 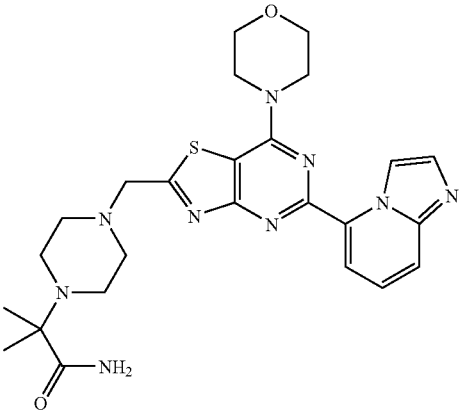 | 2-(4-((5-(imidazo[1,2-a]pyridin-5-yl)-7-morpholinothiazolo[4,5-d]pyrimidin-2-yl)methyl)piperazin-1-yl)-2-methylpropanamide |
| 249 | 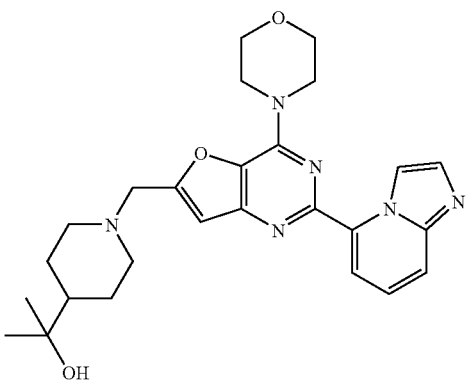 | 2-(1-((2-(imidazo[1,2-a]pyridin-5-yl)-4-morpholinofuro[3,2-d]pyrimidin-6-yl)methyl)piperazin-4-yl)-propan-2-ol |
| 250 | 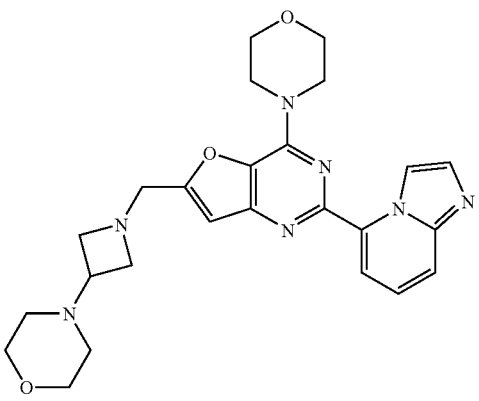 | 2-(imidazo[1,2-a]pyridin-5-yl)-4-morpholino-6-((3-morpholinoazetidin-1-yl)methyl)furo[3,2-d]pyrimidine |
| 251 | 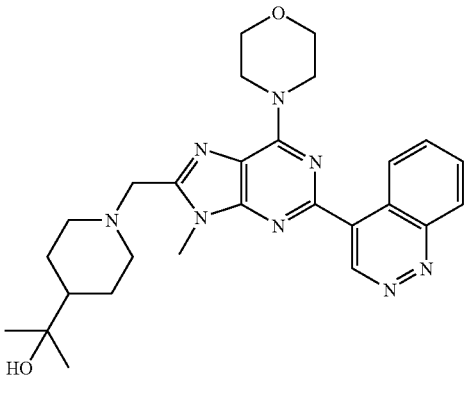 | 2-(1-((2-(cinnolin-4-yl)-9-methyl-6-morpholino-9H-purin-8-yl)methyl)piperidin-4-yl)propan-2-ol |

TABLE 1-continued

| No. | Structure | Name |
|---|---|---|
| 252 | 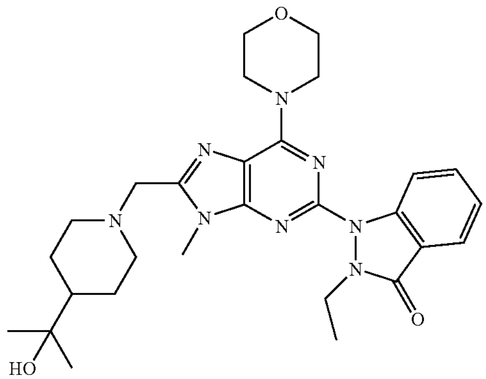 | 2-ethyl-1-(8-((4-(2-hydroxypropan-2-yl)piperidin-1-yl)methyl)-9-methyl-6-morpholino-9H-purin-2-yl)-1H-indazol-3(2H)-one |
| 253 | 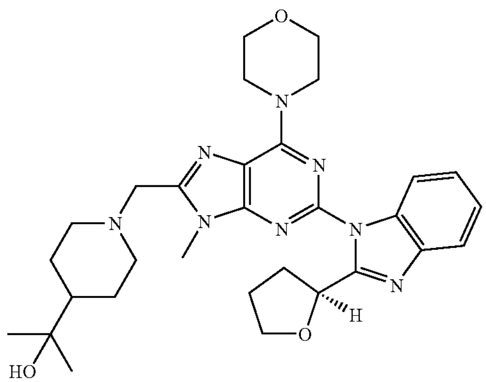 | (S)-2-(1-((9-methyl-6-morpholino-2-(2-(tetrahydrofuran-2-yl)-1H-benzo[d]imidazol-1-yl)-9H-purin-8-yl)methyl)piperidin-4-yl)propan-2-ol |
| 254 | 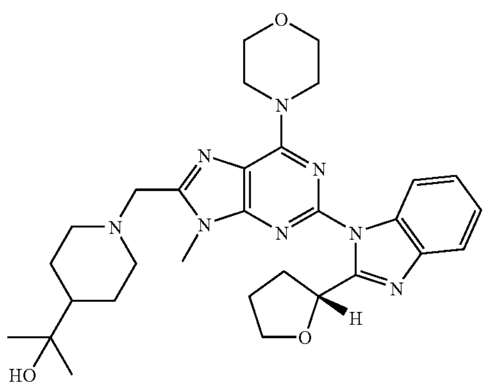 | (R)-2-(1-((9-methyl-6-morpholino-2-(2-(tetrahydrofuran-2-yl)-1H-benzo[d]imidazol-1-yl)-9H-purin-8-yl)methyl)piperidin-4-yl)propan-2-ol |
| 255 | 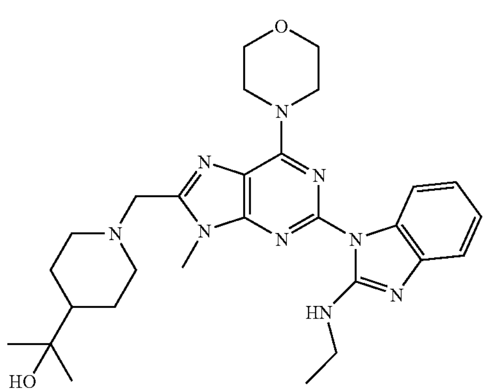 | 2-(1-((2-(2-(ethylamino)-1H-benzo[d]imidazol-1-yl)-9-methyl-6-morpholino-9H-purin-8-yl)methyl)piperidin-4-yl)propan-2-ol |

TABLE 1-continued

| No. | Structure | Name |
|---|---|---|
| 256 | 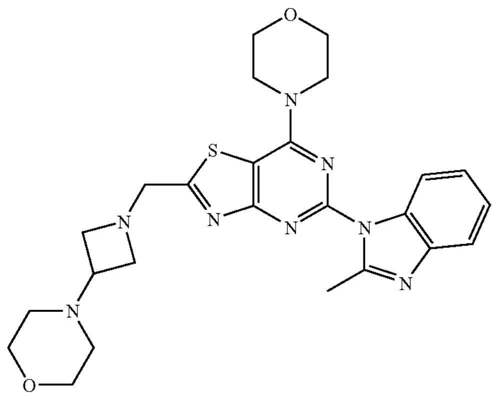 | 4-(5-(2-methyl-1H-benzo[d]imidazol-1-yl)-2-((3-morpholinoazetidin-1-yl)methyl)thiazolo[4,5-d]pyrimidin-7-yl)morpholine |
| 257 | 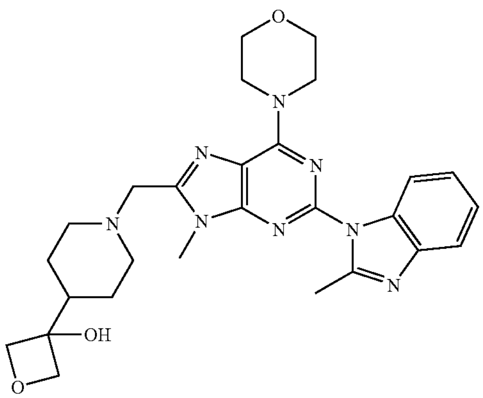 | 3-(1-((9-methyl-2-(2-methyl-1H-benzo[d]imidazol-1-yl)-6-morpholino-9H-purin-8-yl)methyl)piperidin-4-yl)oxetan-3-ol |

TABLE 2

| No. | Structure | Name |
|---|---|---|
| 258 | 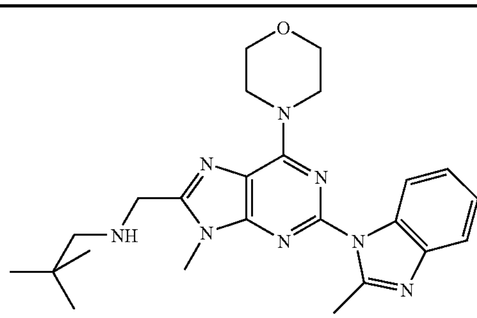 | 2,2-dimethyl-N-((9-methyl-2-(2-methyl-1H-benzo[d]imidazol-1-yl)-6-morpholino-9H-purin-8-yl)methyl)propan-1-amine |
| 259 | 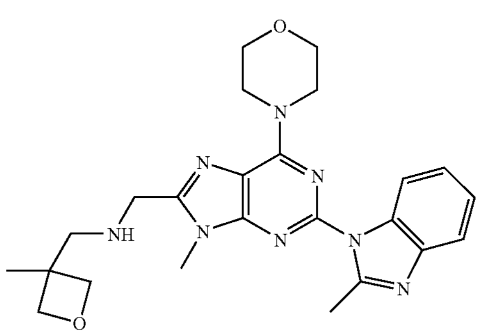 | 1-(9-methyl-2-(2-methyl-1H-benzo[d]imidazol-1-yl)-6-morpholino-9H-purin-8-yl)-N-((3-methyloxetan-3-yl)methyl)methanamine |

TABLE 2-continued

| No. | Structure | Name |
|---|---|---|
| 260 | 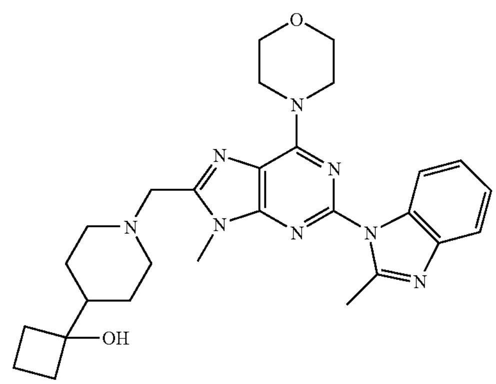 | 1-(1-((9-methyl-2-(2-methyl-1H-benzo[d]imidazol-1-yl)-6-morpholino-9H-purin-8-yl)methyl)piperidin-4-yl)cyclobutanol |
| 261 | 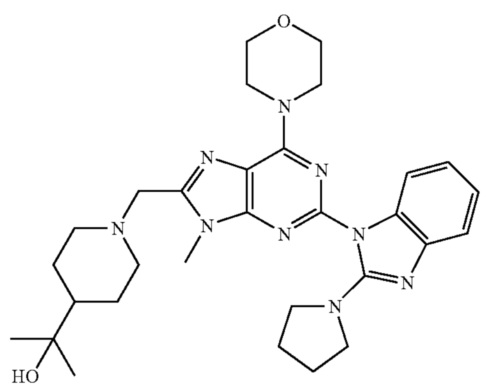 | 2-(1-((9-methyl-6-morpholino-2-(2-(pyrrolidin-1-yl)-1H-benzo[d]imidazol-1-yl)-9H-purin-8-yl)methyl)piperidin-4-yl)propan-2-ol |
| 262 | 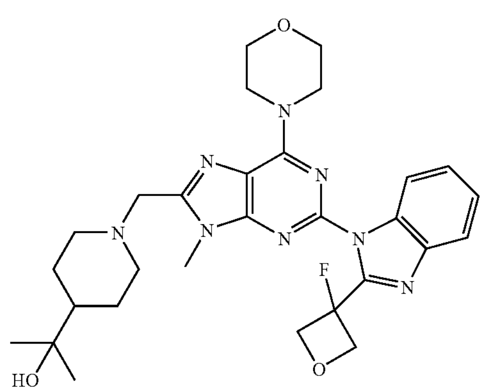 | 2-(1-((2-(2-(3-fluorooxetan-3-yl)-1H-benzo[d]imidazol-1-yl)-9-methyl-6-morpholino-9H-purin-8-yl)methyl)piperidin-4-yl)propan-2-ol |
| 263 | 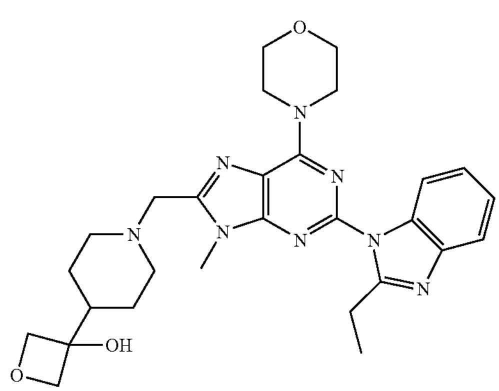 | 3-(1-((2-(2-ethyl-1H-benzo[d]imidazol-1-yl)-9-methyl-6-morpholino-9H-purin-8-yl)methyl)piperidin-4-yl)oxetan-3-ol |

TABLE 2-continued

| No. | Structure | Name |
|---|---|---|
| 264 | 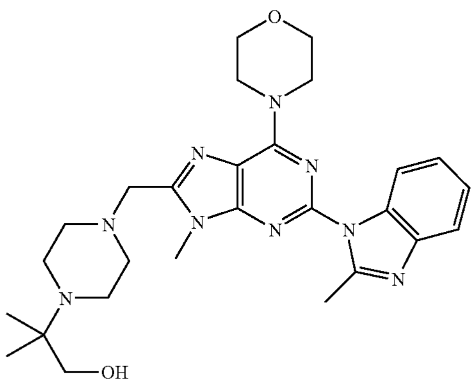 | 2-methyl-2-(4-((9-methyl-2-(2-methyl-1H-benzo[d]imidazol-1-yl)-6-morpholino-9H-purin-8-yl)methyl)piperazin-1-yl)propan-1-ol |
| 265 | 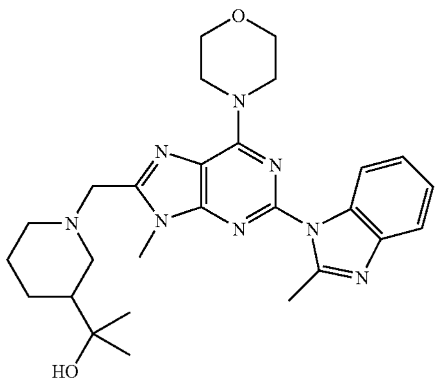 | 2-(1-((9-methyl-2-(2-methyl-1H-benzo[d]imidazol-1-yl)-6-morpholino-9H-purin-8-yl)methyl)piperidin-3-yl)propan-2-ol |
| 266 | 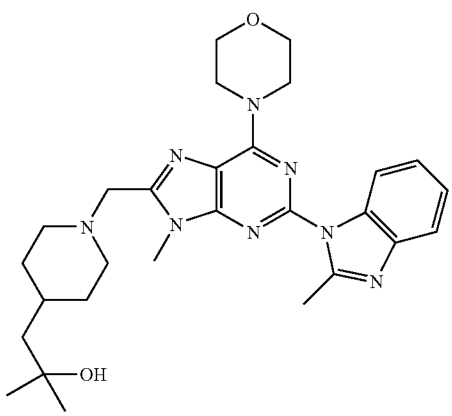 | 2-methyl-1-(1-((9-methyl-2-(2-methyl-1H-benzo[d]imidazol-1-yl)-6-morpholino-9H-purin-8-yl)methyl)piperidin-4-yl)propan-2-ol |
| 267 | 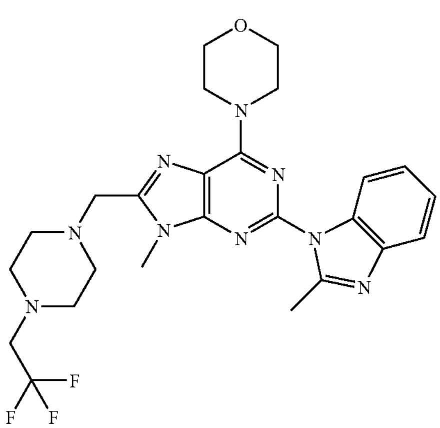 | 4-(9-methyl-2-(2-methyl-1H-benzo[d]imidazol-1-yl)-8-((4-(2,2,2-trifluoroethyl)piperazin-1-yl)methyl)-9H-purin-6-yl)morpholine |

TABLE 2-continued

| No. | Structure | Name |
|---|---|---|
| 268 | 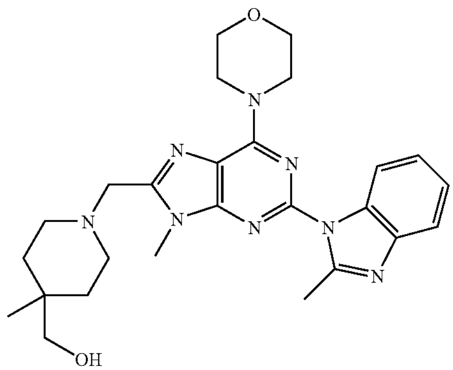 | (4-methyl-1-((9-methyl-2-(2-methyl-1H-benzo[d]imidazol-1-yl)-6-morpholino-9H-purin-8-yl)methyl)piperidin-4-yl)methanol |
| 269 | 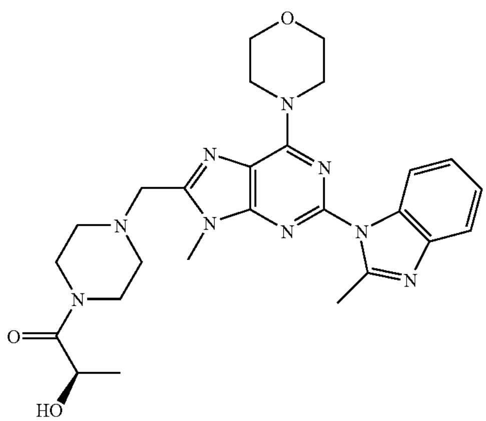 | (R)-2-hydroxy-1-(4-((9-methyl-2-(2-methyl-1H-benzo[d]imidazol-1-yl)-6-morpholino-9H-purin-8-yl)methyl)piperazin-1-yl)propan-1-one |
| 270 | 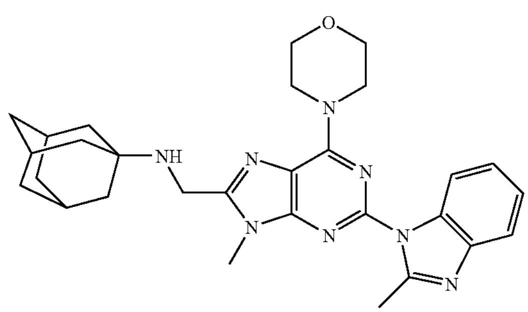 | adamantan-1-yl-[9-methyl-2-(2-methyl-benzoimidazol-1-yl)-6-morpholin-4-yl-9H-purin-8-ylmethyl]-amine |
| 271 | 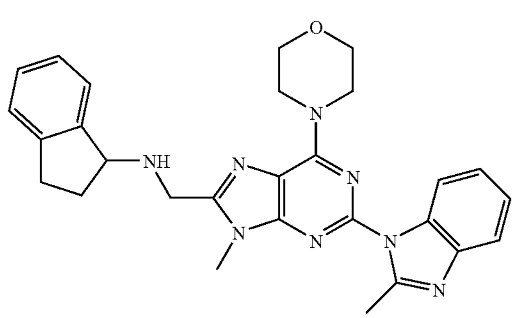 | N-((9-methyl-2-(2-methyl-1H-benzo[d]imidazol-1-yl)-6-morpholino-9H-purin-8-yl)methyl)-2,3-dihydro-1H-inden-1-amine |

TABLE 2-continued

| No. | Structure | Name |
|---|---|---|
| 272 | 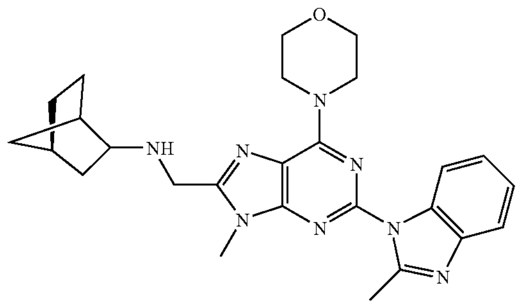 | (4R)-N-((9-methyl-2-(2-methyl-1H-benzo[d]imidazol-1-yl)-6-morpholino-9H-purin-8-yl)methyl)bicyclo[2.2.1]heptan-2-amine |
| 273 | 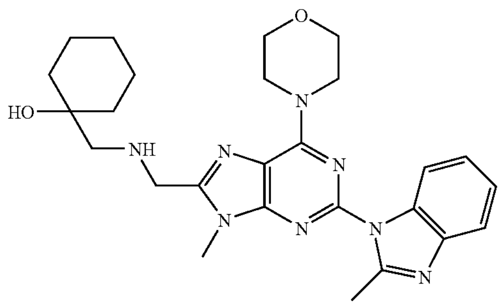 | 1-(((9-methyl-2-(2-methyl-1H-benzo[d]imidazol-1-yl)-6-morpholino-9H-purin-8-yl)methylamino)methyl)cyclohexanol |
| 274 | 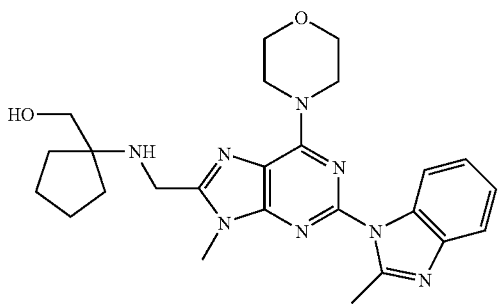 | (1-((9-methyl-2-(2-methyl-1H-benzo[d]imidazol-1-yl)-6-morpholino-9H-purin-8-yl)methylamino)cyclopentyl)methanol |
| 275 | 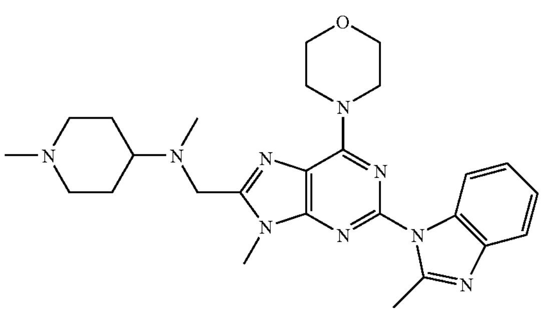 | N,1-dimethyl-N-((9-methyl-2-(2-methyl-1H-benzo[d]imidazol-1-yl)-6-morpholino-9H-purin-8-yl)methyl)piperidin-4-amine |
| 276 | 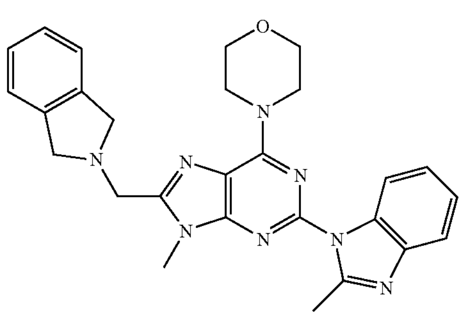 | 4-(8-(isoindolin-2-ylmethyl)-9-methyl-2-(2-methyl-1H-benzo[d]imidazol-1-yl)-9H-purin-6-yl)morpholine |

TABLE 2-continued

| No. | Structure | Name |
|---|---|---|
| 277 | 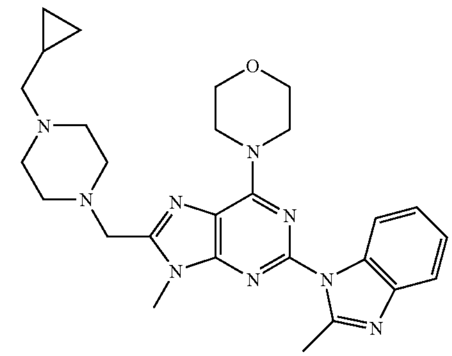 | 4-(8-((4-(cyclopropylmethyl)piperazin-1-yl)methyl)-9-methyl-2-(2-methyl-1H-benzo[d]imidazol-1-yl)-9H-purin-6-yl)morpholine |
| 278 | 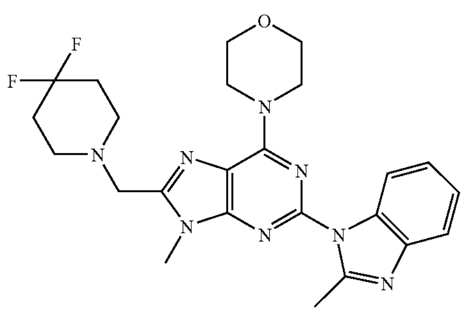 | 4-(8-((4,4-difluoropiperidin-1-yl)methyl)-9-methyl-2-(2-methyl-1H-benzo[d]imidazol-1-yl)-9H-purin-6-yl)morpholine |
| 279 | 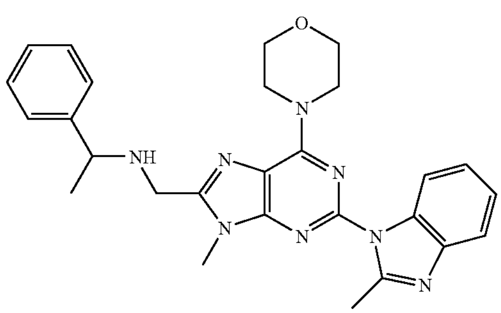 | N-((9-methyl-2-(2-methyl-1H-benzo[d]imidazol-1-yl)-6-morpholino-9H-purin-8-yl)methyl)-1-phenylethanamine |
| 280 | 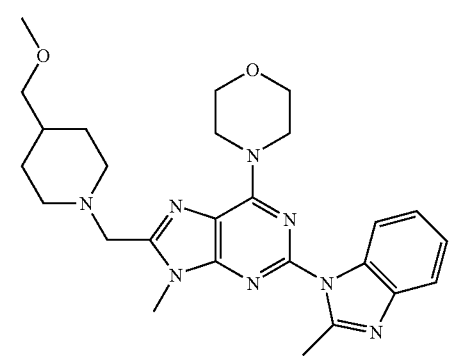 | 4-(8-((4-(methoxymethyl)piperidin-1-yl)methyl)-9-methyl-2-(2-methyl-1H-benzo[d]imidazol-1-yl)-9H-purin-6-yl)morpholine |

TABLE 2-continued

| No. | Structure | Name |
| --- | --- | --- |
| 281 | 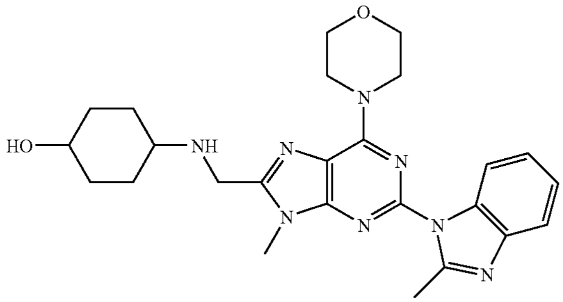 | 4-((9-methyl-2-(2-methyl-1H-benzo[d]imidazol-1-yl)-6-morpholino-9H-purin-8-yl)methylamino)cyclohexanol |
| 282 | 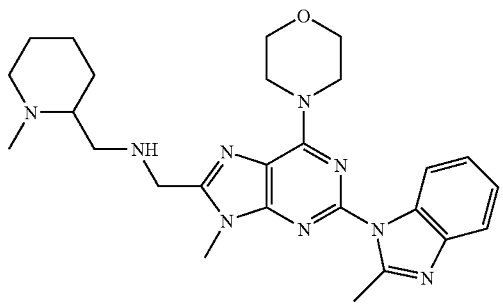 | 1-(9-methyl-2-(2-methyl-1H-benzo[d]imidazol-1-yl)-6-morpholino-9H-purin-8-yl)-N-((1-methylpiperidin-2-yl)methyl)methanamine |
| 283 | 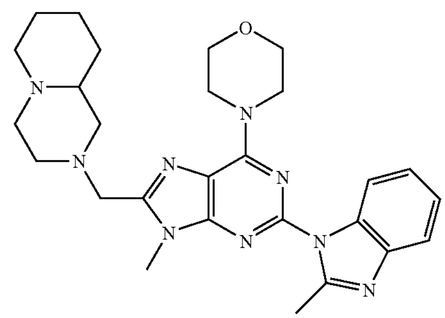 | 4-(8-((dihydro-1H-pyrido[1,2-a]pyrazin-2(6H,7H,8H,9H,9aH)-yl)methyl)-9-methyl-2-(2-methyl-1H-benzo[d]imidazol-1-yl)-9H-purin-6-yl)morpholine |
| 284 | 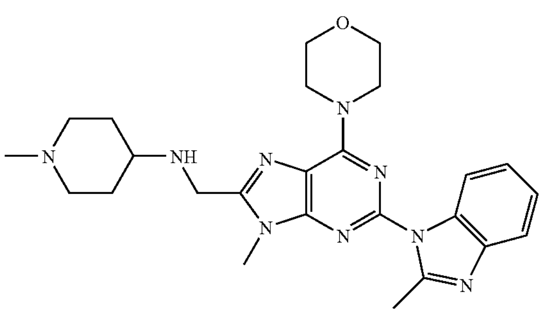 | 1-methyl-N-((9-methyl-2-(2-methyl-1H-benzo[d]imidazol-1-yl)-6-morpholino-9H-purin-8-yl)methyl)piperidin-4-amine |
| 285 | 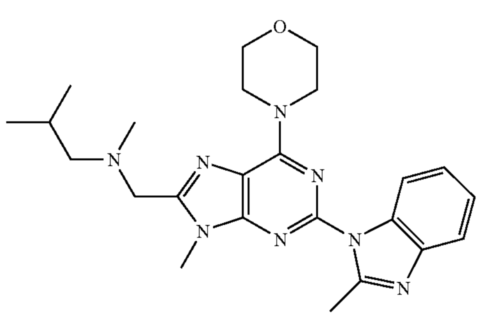 | N,2-dimethyl-N-((9-methyl-2-(2-methyl-1H-benzo[d]imidazol-1-yl)-6-morpholino-9H-purin-8-yl)methyl)propan-1-amine |

TABLE 2-continued

| No. | Structure | Name |
|---|---|---|
| 286 | 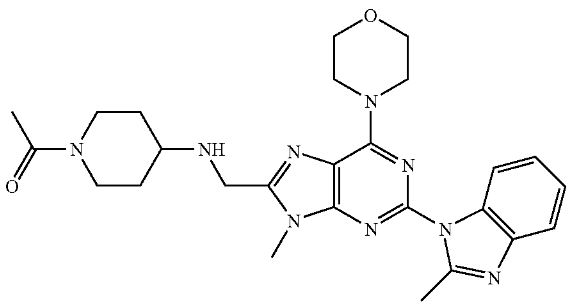 | 1-(4-((9-methyl-2-(2-methyl-1H-benzo[d]imidazol-1-yl)-6-morpholino-9H-purin-8-yl)methylamino)piperidin-1-yl)ethanone |
| 287 | 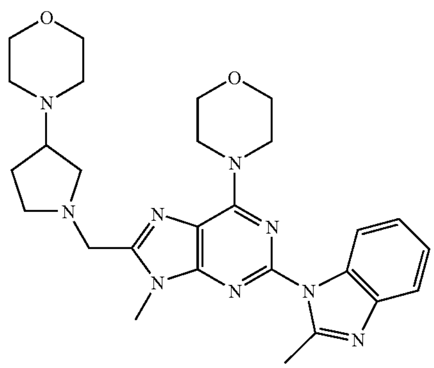 | 4-(1-((9-methyl-2-(2-methyl-1H-benzo[d]imidazol-1-yl)-6-morpholino-9H-purin-8-yl)methyl)pyrrolidin-3-yl)morpholine |
| 288 | 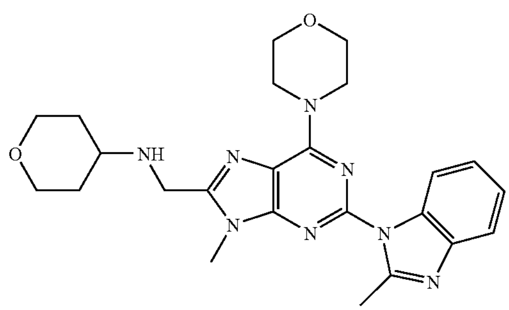 | N-((9-methyl-2-(2-methyl-1H-benzo[d]imidazol-1-yl)-6-morpholino-9H-purin-8-yl)methyl)tetrahydro-2H-pyran-4-amine |
| 289 | 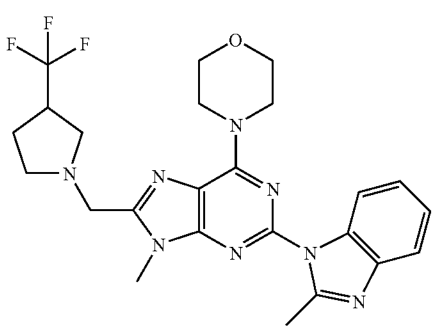 | 4-(9-methyl-2-(2-methyl-1H-benzo[d]imidazol-1-yl)-8-((3-(trifluoromethyl)pyrrolidin-1-yl)methyl)-9H-purin-6-yl)morpholine |
| 290 | 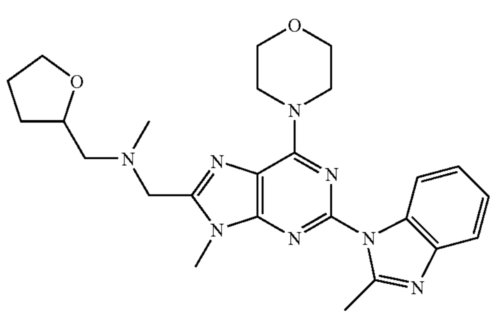 | N-methyl-1-(9-methyl-2-(2-methyl-1H-benzo[d]imidazol-1-yl)-6-morpholino-9H-purin-8-yl)-N-((tetrahydrofuran-2-yl)methyl)methanamine |

TABLE 2-continued

| No. | Structure | Name |
|---|---|---|
| 291 | 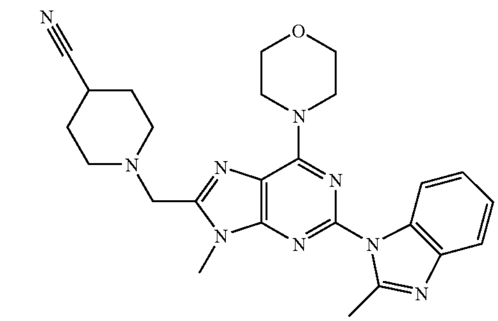 | 1-((9-methyl-2-(2-methyl-1H-benzo[d]imidazol-1-yl)-6-morpholino-9H-purin-8-yl)methyl)piperidine-4-carbonitrile |
| 292 | 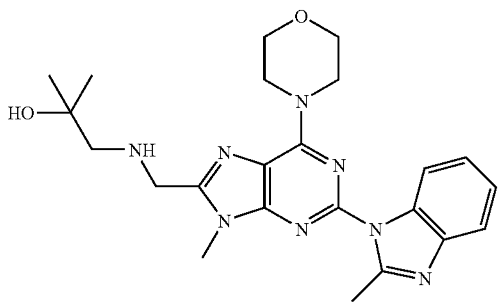 | 2-methyl-1-((9-methyl-2-(2-methyl-1H-benzo[d]imidazol-1-yl)-6-morpholino-9H-purin-8-yl)methylamino)propan-2-ol |
| 293 | 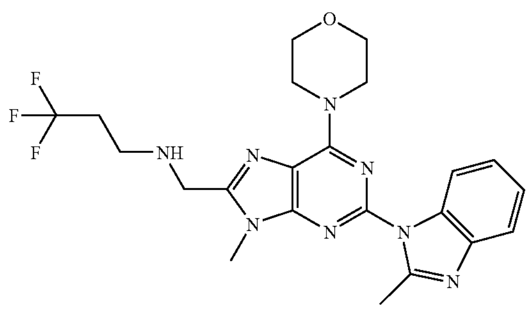 | 3,3,3-trifluoro-N-((9-methyl-2-(2-methyl-1H-benzo[d]imidazol-1-yl)-6-morpholino-9H-purin-8-yl)methyl)propan-1-amine |
| 294 | 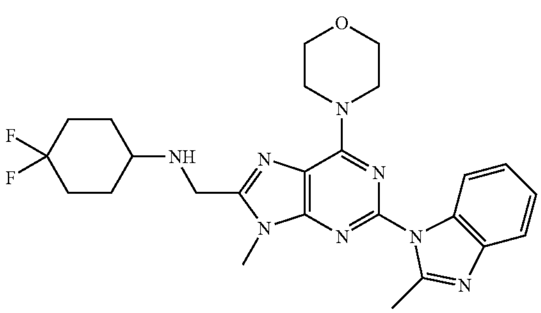 | 4,4-difluoro-N-((9-methyl-2-(2-methyl-1H-benzo[d]imidazol-1-yl)-6-morpholino-9H-purin-8-yl)methyl)cyclohexanamine |
| 295 | 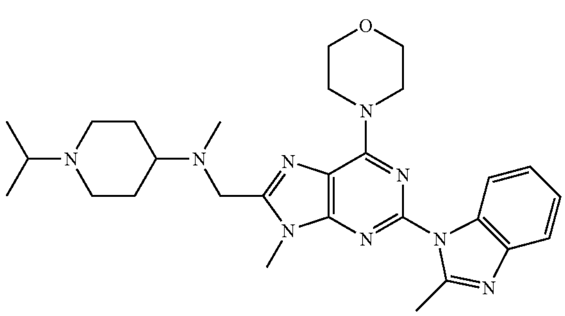 | 1-isopropyl-N-methyl-N-((9-methyl-2-(2-methyl-1H-benzo[d]imidazol-1-yl)-6-morpholino-9H-purin-8-yl)methyl)piperidin-4-amine |

TABLE 2-continued

| No. | Structure | Name |
|---|---|---|
| 296 | 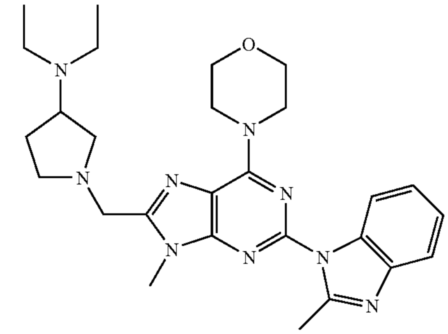 | N,N-diethyl-1-((9-methyl-2-(2-methyl-1H-benzo[d]imidazol-1-yl)-6-morpholino-9H-purin-8-yl)methyl)pyrrolidin-3-amine |
| 297 | 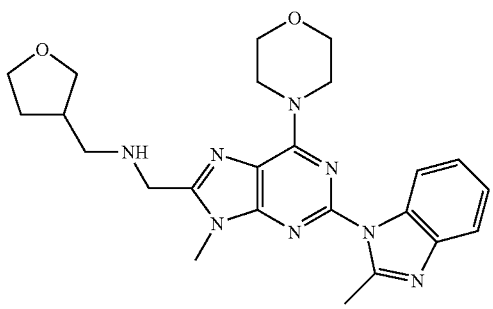 | 1-(9-methyl-2-(2-methyl-1H-benzo[d]imidazol-1-yl)-6-morpholino-9H-purin-8-yl)-N-((tetrahydrofuran-3-yl)methyl)methanamine |
| 298 | 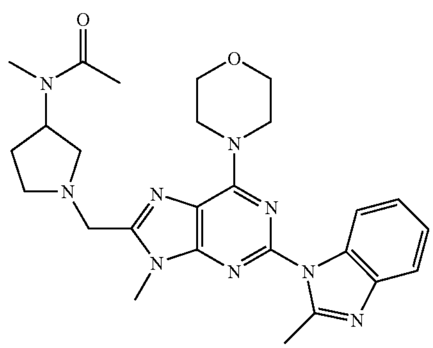 | N-methyl-N-(1-((9-methyl-2-(2-methyl-1H-benzo[d]imidazol-1-yl)-6-morpholino-9H-purin-8-yl)methyl)pyrrolidin-3-yl)acetamide |
| 299 | 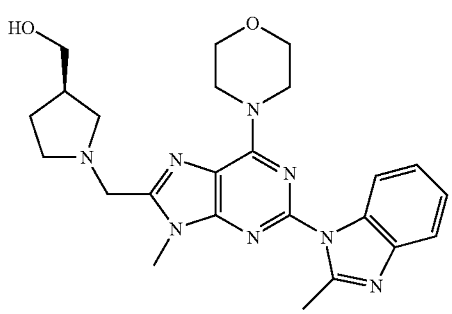 | (R)-(1-((9-methyl-2-(2-methyl-1H-benzo[d]imidazol-1-yl)-6-morpholino-9H-purin-8-yl)methyl)pyrrolidin-3-yl)methanol |
| 300 | 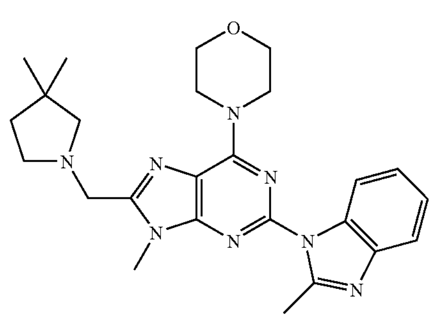 | 4-(8-((3,3-dimethylpyrrolidin-1-yl)methyl)-9-methyl-2-(2-methyl-1H-benzo[d]imidazol-1-yl)-9H-purin-6-yl)morpholine |

TABLE 2-continued

| No. | Structure | Name |
|---|---|---|
| 301 | 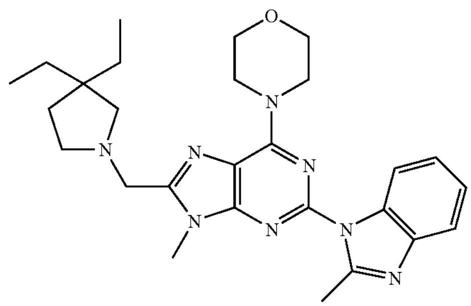 | 4-(8-((3,3-diethylpyrrolidin-1-yl)methyl)-9-methyl-2-(2-methyl-1H-benzo[d]imidazol-1-yl)-9H-purin-6-yl)morpholine |
| 302 | 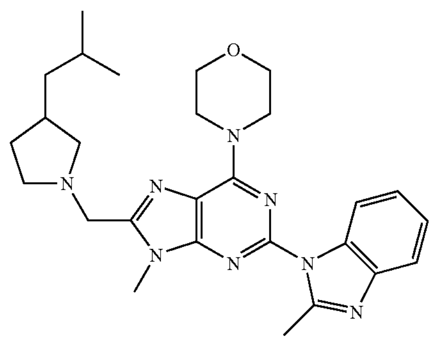 | 4-(8-((3-isobutylpyrrolidin-1-yl)methyl)-9-methyl-2-(2-methyl-1H-benzo[d]imidazol-1-yl)-9H-purin-6-yl)morpholine |
| 303 | 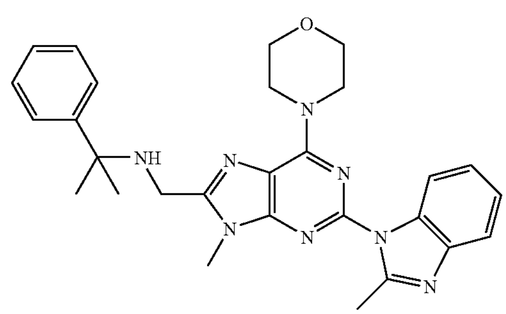 | N-((9-methyl-2-(2-methyl-1H-benzo[d]imidazol-1-yl)-6-morpholino-9H-purin-8-yl)methyl)-2-phenylpropan-2-amine |
| 304 | 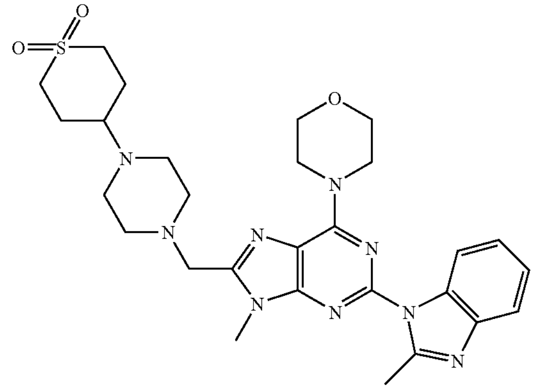 | 4-(9-methyl-2-(2-methyl-1H-benzo[d]imidazol-1-yl)-8-((1,1-dioxo-4-(tetrahydro-2H-thiopyran-4-yl)piperazin-1-yl)methyl)-9H-purin-6-yl)morpholine |

TABLE 2-continued

| No. | Structure | Name |
|---|---|---|
| 305 | 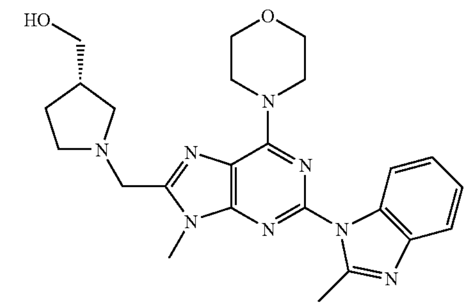 | (S)-(1-((9-methyl-2-(2-methyl-1H-benzo[d]imidazol-1-yl)-6-morpholino-9H-purin-8-yl)methyl)pyrrolidin-3-yl)methanol |
| 306 | 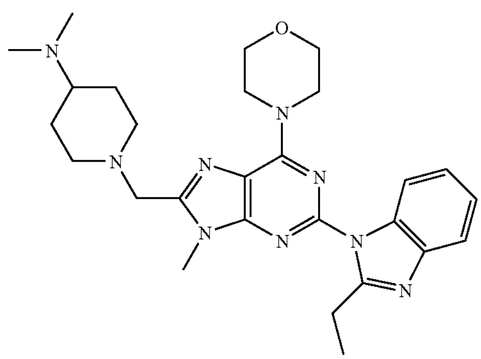 | 1-((2-(2-ethyl-1H-benzo[d]imidazol-1-yl)-9-methyl-6-morpholino-9H-purin-8-yl)methyl)-N,N-dimethylpiperidin-4-amine |
| 307 | 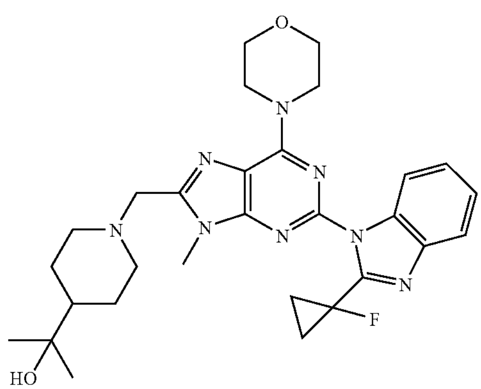 | 2-(1-((2-(2-(1-fluorocyclopropyl)-1H-benzo[d]imidazol-1-yl)-9-methyl-6-morpholino-9H-purin-8-yl)methyl)piperidin-4-yl)propan-2-ol |
| 308 | 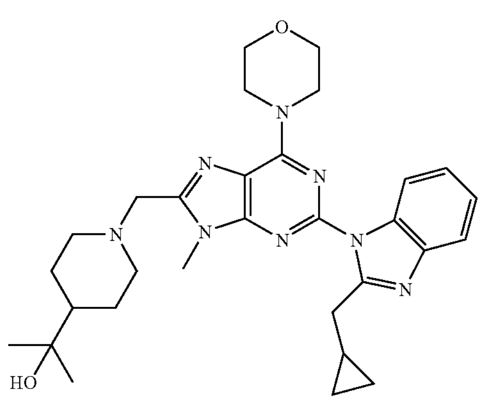 | 2-(1-((2-(2-(cyclopropylmethyl)-1H-benzo[d]imidazol-1-yl)-9-methyl-6-morpholino-9H-purin-8-yl)methyl)piperidin-4-yl)propan-2-ol |

TABLE 2-continued

| No. | Structure | Name |
|---|---|---|
| 309 | 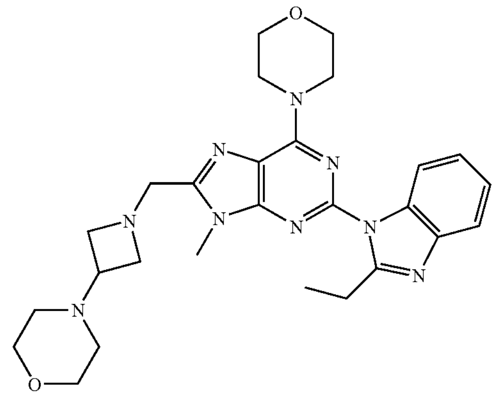 | 4-(1-((2-(2-ethyl-1H-benzo[d]imidazol-1-yl)-9-methyl-6-morpholino-9H-purin-8-yl)methyl)azetidin-3-yl)morpholine |
| 310 | 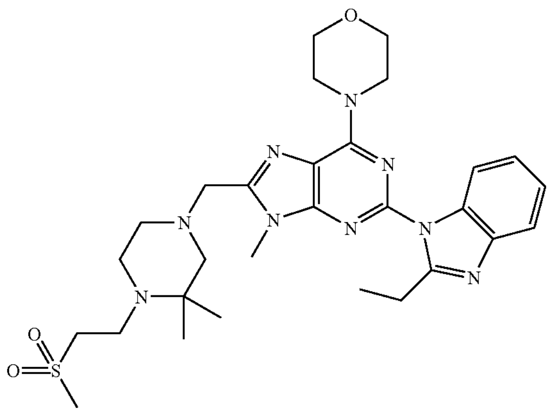 | 4-(8-((3,3-dimethyl-4-(2-(methylsulfonyl)ethyl)piperazin-1-yl)methyl)-2-(2-ethyl-1H-benzo[d]imidazol-1-yl)-9-methyl-9H-purin-6-yl)morpholine |
| 311 | 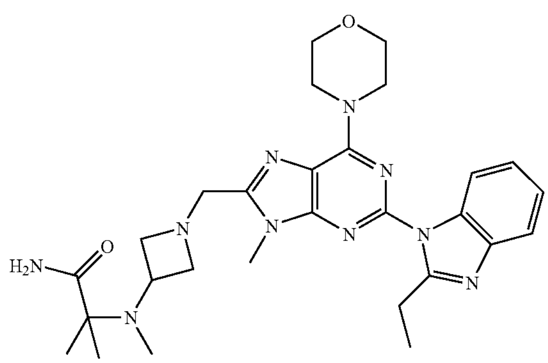 | 2-((1-((2-(2-ethyl-1H-benzo[d]imidazol-1-yl)-9-methyl-6-morpholino-9H-purin-8-yl)methyl)azetidin-3-yl)(methyl)amino)-2-methylpropanamide |
| 312 | 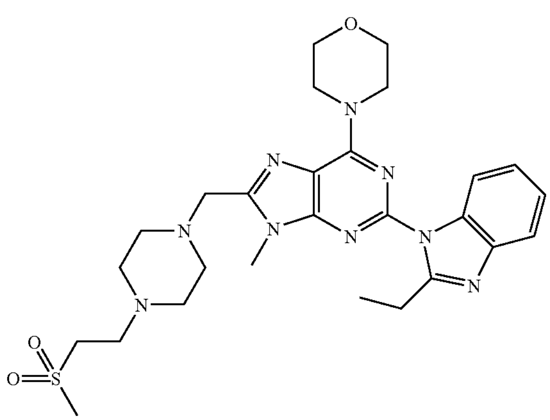 | 4-(2-(2-ethyl-1H-benzo[d]imidazol-1-yl)-9-methyl-8-((4-(2-(methylsulfonyl)ethyl)piperazin-1-yl)methyl)-9H-purin-6-yl)morpholine |

TABLE 2-continued

| No. | Structure | Name |
|---|---|---|
| 313 | 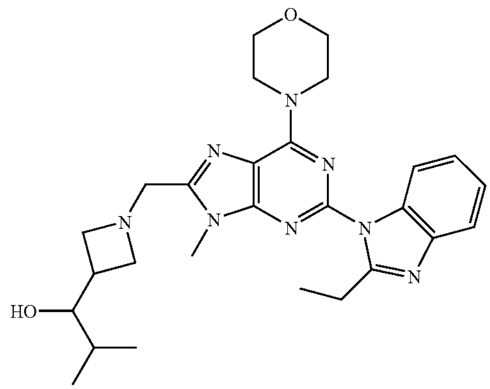 | 1-(1-((2-(2-ethyl-1H-benzo[d]imidazol-1-yl)-9-methyl-6-morpholino-9H-purin-8-yl)methyl)azetidin-3-yl)-2-methylpropan-1-ol |
| 314 | 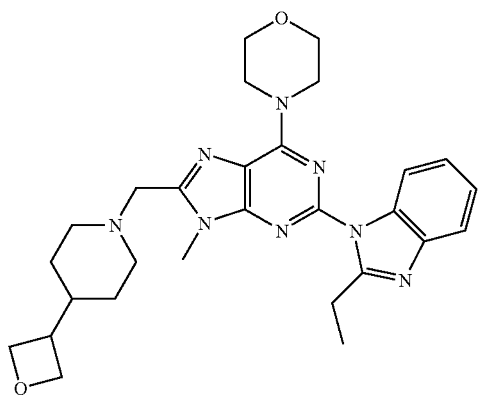 | 4-(2-(2-ethyl-1H-benzo[d]imidazole-yl)-9-methyl-8-((4-(oxetan-3-yl)piperidin-1-yl)methyl)-9H-purin-6-yl)morpholine |
| 315 | 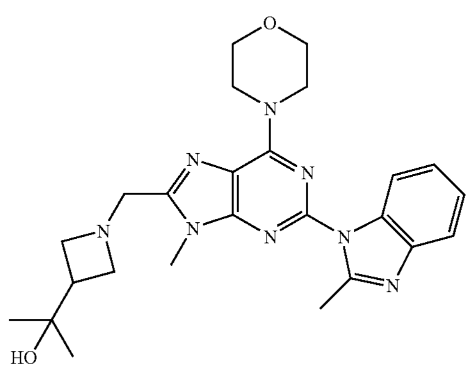 | 2-(1-((9-methyl-2-(2-methyl-1H-benzo[d]imidazol-1-yl)-6-morpholino-9H-purin-8-yl)methyl)azetidin-3-yl)propan-2-ol |
| 316 | 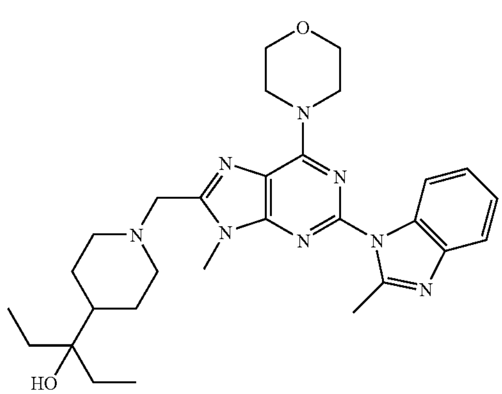 | 3-(1-((9-methyl-2-(2-methyl-1H-benzo[d]imidazol-1-yl)-6-morpholino-9H-purin-8-yl)methyl)piperidin-4-yl)pentan-3-ol |

TABLE 2-continued

| No. | Structure | Name |
|---|---|---|
| 317 | 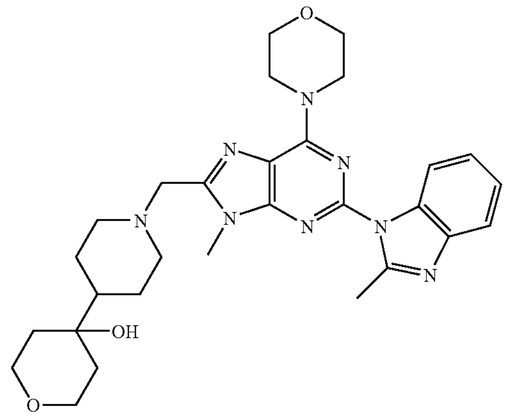 | 4-(1-((9-methyl-2-(2-methyl-1H-benzo[d]imidazol-1-yl)-6-morpholino-9H-purin-8-yl)methyl)piperidin-4-yl)tetrahydro-2H-pyran-4-ol |
| 318 | 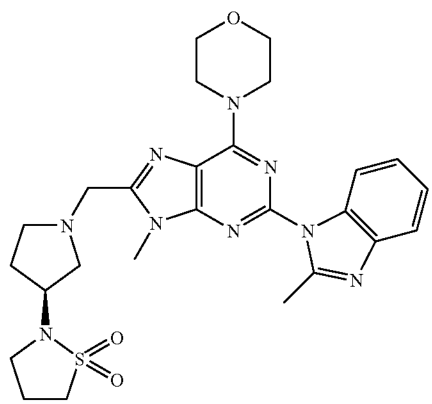 | (S)-4-(8-((3-(1,1-dioxo-isothiazolidin-2-yl)pyrrolidin-1-yl)methyl)-9-methyl-2-(2-methyl-1H-benzo[d]imidazol-1-yl)-9H-purin-6-yl)morpholine |
| 319 | 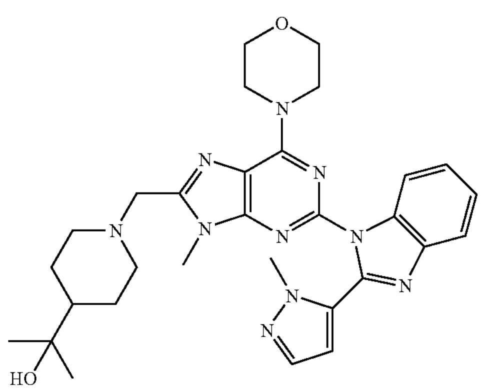 | 2-(1-((9-methyl-2-(2-(1-methyl-1H-pyrazol-5-yl)-1H-benzo[d]imidazol-1-yl)-6-morpholino-9H-purin-8-yl)methyl)piperidin-4-yl)propan-2-ol |
| 320 | 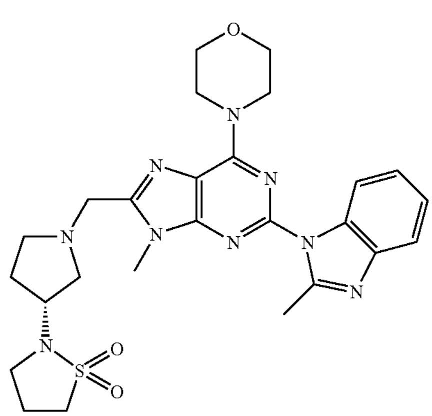 | (R)-4-(8-((3-(1,1-dioxo-isothiazolidin-2-yl)pyrrolidin-1-yl)methyl)-9-methyl-2-(2-methyl-1H-benzo[d]imidazol-1-yl)-9H-purin-6-yl)morpholine |

TABLE 2-continued

| No. | Structure | Name |
|---|---|---|
| 321 | 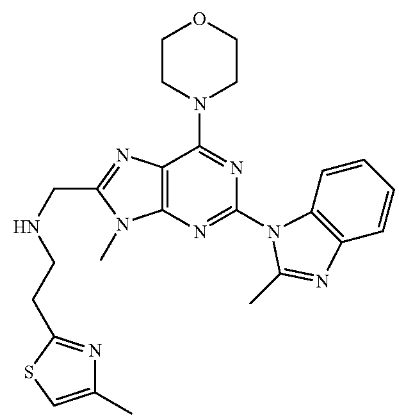 | N-((9-methyl-2-(2-methyl-1H-benzo[d]imidazol-1-yl)-6-morpholino-9H-purin-8-yl)methyl)-2-(4-methylthiazol-2-yl)ethanamine |
| 322 | 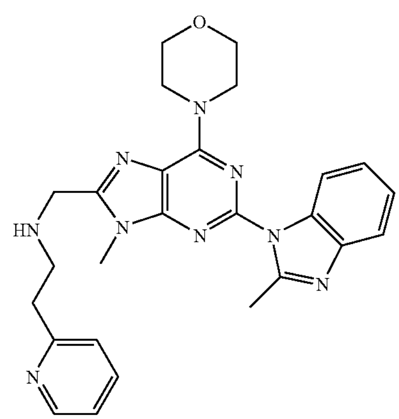 | N-((9-methyl-2-(2-methyl-1H-benzo[d]imidazol-1-yl)-6-morpholino-9H-purin-8-yl)methyl)-2-(pyridin-2-yl)ethanamine |
| 323 | 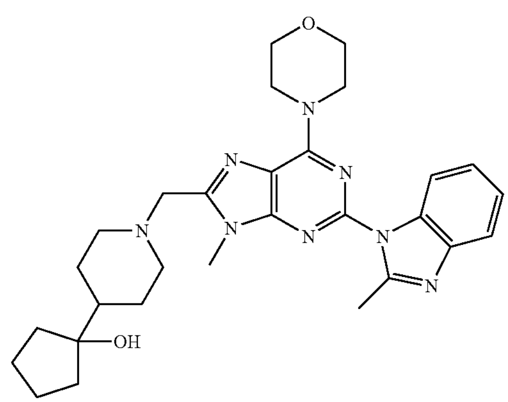 | 1-(1-((9-methyl-2-(2-methyl-1H-benzo[d]imidazol-1-yl)-6-morpholino-9H-purin-8-yl)methyl)piperidin-4-yl)cyclopentanol |
| 324 | 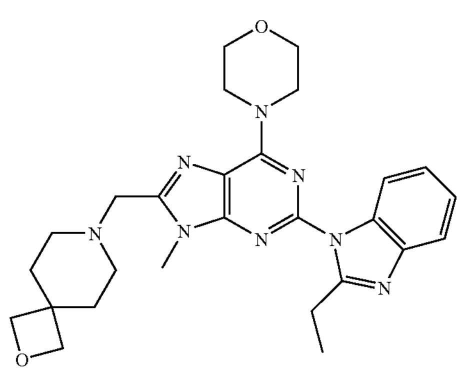 | 7-((2-(2-ethyl-1H-benzo[d]imidazol-1-yl)-9-methyl-6-morpholino-9H-purin-8-yl)methyl)-2-oxa-7-azaspiro[3.5]nonane |

| No. | Structure | Name |
|---|---|---|
| 325 | 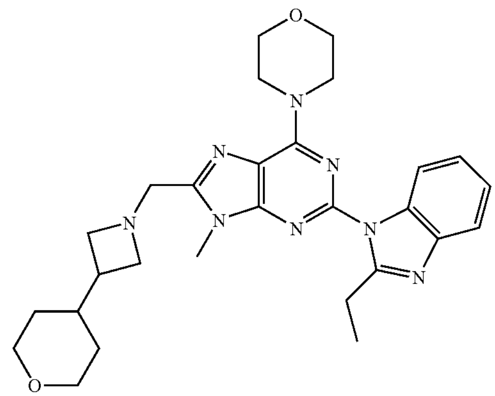 | 4-(2-(2-ethyl-1H-benzo[d]imidazol-1-yl)-9-methyl-8-((3-(tetrahydro-2H-pyran-4-yl)azetidin-1-yl)methyl)-9H-purin-6-yl)morpholine |
| 326 | 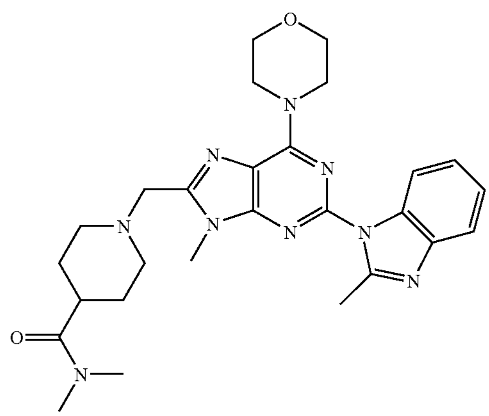 | N,N-dimethyl-1-((9-methyl-2-(2-methyl-1H-benzo[d]imidazol-1-yl)-6-morpholino-9H-purin-8-yl)methyl)piperidine-4-carboxamide |
| 327 | 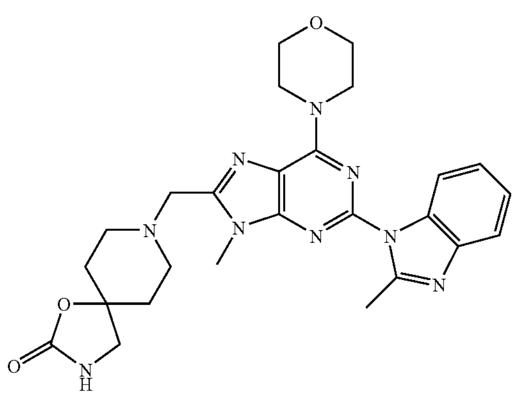 | 8-((9-methyl-2-(2-methyl-1H-benzo[d]imidazol-1-yl)-6-morpholino-9H-purin-8-yl)methyl)-1-oxa-3,8-diazaspiro[4.5]decan-2-one |
| 328 | 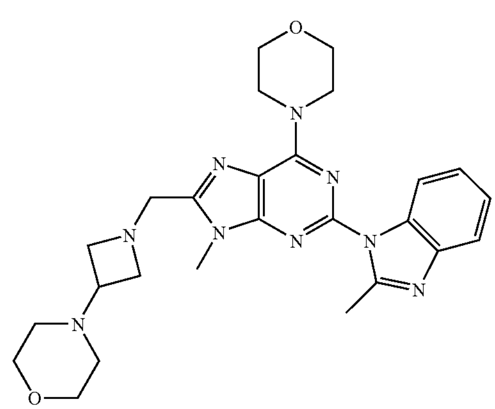 | 4-(1-((9-methyl-2-(2-methyl-1H-benzo[d]imidazol-1-yl)-6-morpholino-9H-purin-8-yl)methyl)azetidin-3-yl)morpholine |

TABLE 2-continued

| No. | Structure | Name |
|---|---|---|
| 329 | 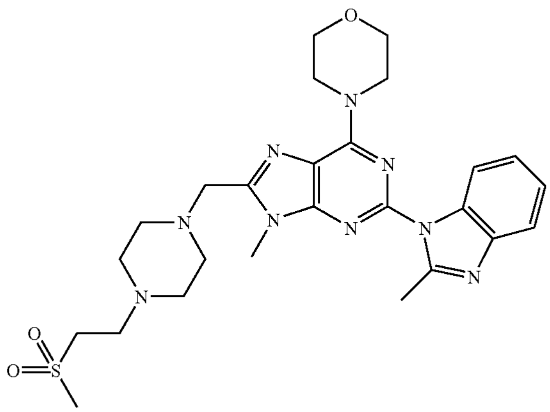 | 4-(9-methyl-2-(2-m ethyl-1H-benzo[d]imidazol-1-yl)-8-((4-(2-(methylsulfonyl)ethyl)piperazin-1-yl)methyl)-9H-purin-6-yl)morpholine |
| 330 | 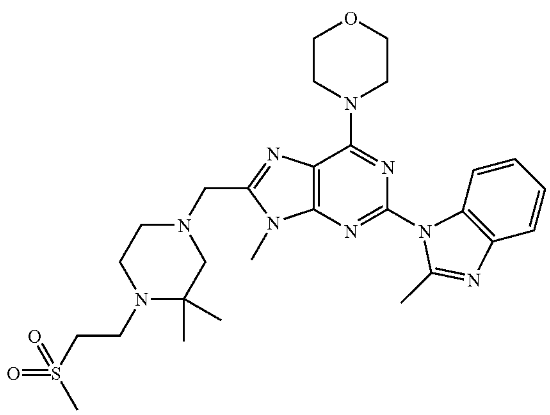 | 4-(8-((3,3-dimethyl-4-(2-(methylsulfonyl)ethyl)piperazin-1-yl)methyl)-9-methyl-2-(2-methyl-1H-benzo[d]imidazol-1-yl)-9H-purin-6-yl)morpholine |
| 331 | 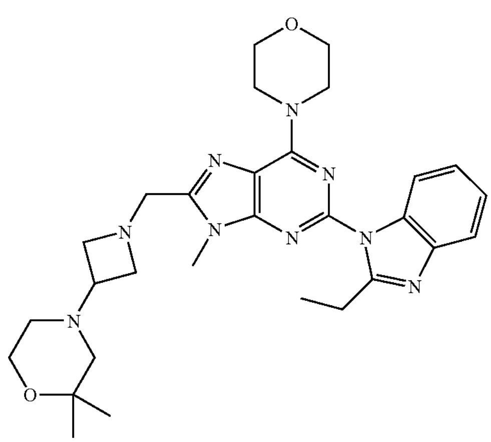 | 4-(1-((2-(2-ethyl-1H-benzo[d]imidazol-1-yl)-9-methyl-6-morpholino-9H-purin-8-yl)methyl)azetidin-3-yl)-2,2-dimethylmorpholine |

TABLE 2-continued

| No. | Structure | Name |
| --- | --- | --- |
| 332 | 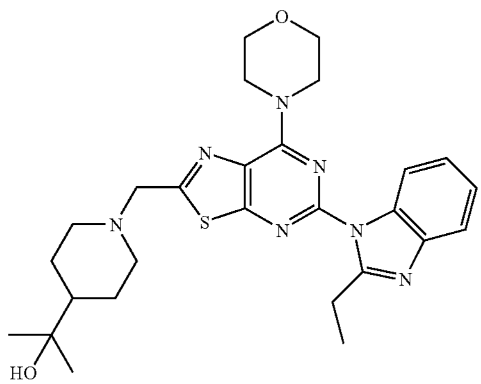 | 2-(1-((5-(2-ethyl-1H-benzo[d]imidazol-1-yl)-7-morpholinothiazolo[5,4-d]pyrimidin-2-yl)methyl)piperidin-4-yl)propan-2-ol |
| 333 | 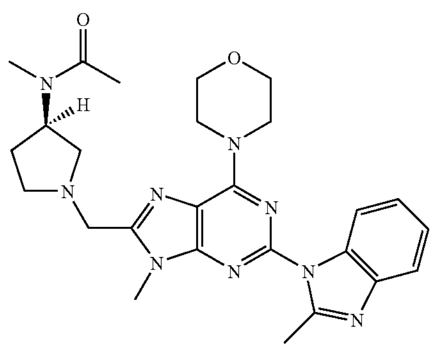 | (R)-N-methyl-N-(1-((9-methyl-2-(2-methyl-1H-benzo[d]imidazol-1-yl)-6-morpholino-9H-purin-8-yl)methyl)pyrrolidin-3-yl)acetamide |
| 334 | 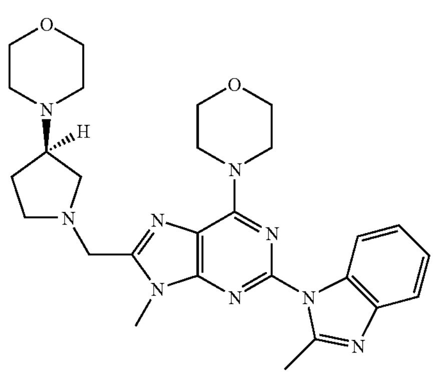 | (R)-4-(1-((9-methyl-2-(2-methyl-1H-benzo[d]imidazol-1-yl)-6-morpholino-9H-purin-8-yl)methyl)pyrrolidin-3-yl)morpholine |
| 335 | 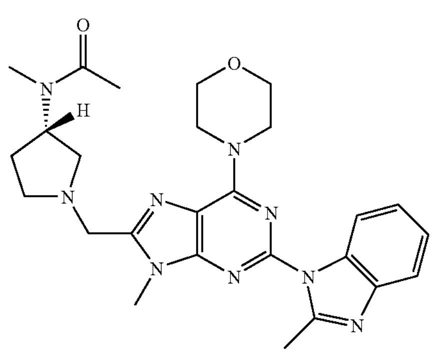 | (S)-N-methyl-N-(1-((9-methyl-2-(2-methyl-1H-benzo[d]imidazol-1-yl)-6-morpholino-9H-purin-8-yl)methyl)pyrrolidin-3-yl)acetamide |

TABLE 2-continued

| No. | Structure | Name |
|---|---|---|
| 336 | 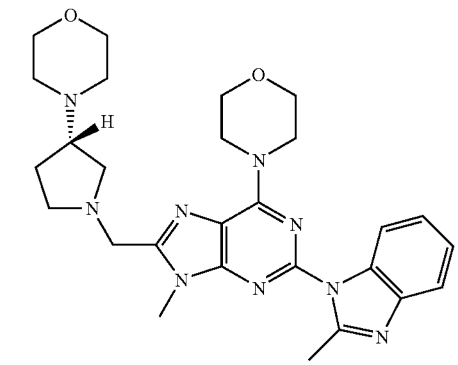 | (S)-4-(1-((9-methyl-2-(2-methyl-1H-benzo[d]imidazol-1-yl)-6-morpholino-9H-purin-8-yl)methyl)pyrrolidin-3-yl)morpholine |
| 337 | 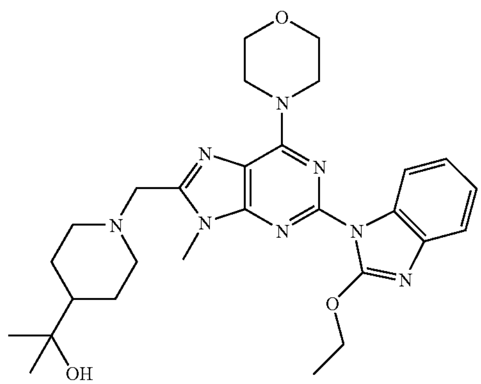 | 2-(1-((2-(2-ethoxy-1H-benzo[d]imidazol-1-yl)-9-methyl-6-morpholino-9H-purin-8-yl)methyl)piperidin-4-yl)propan-2-ol |
| 338 | 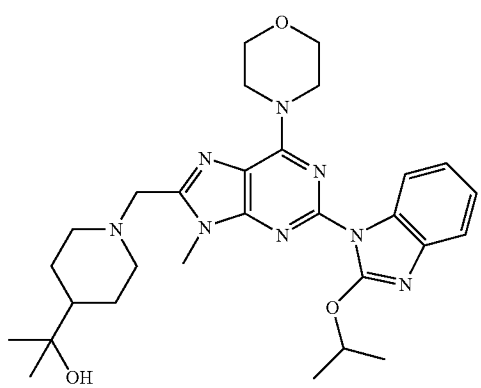 | 2-(1-((2-(2-isopropoxy-1H-benzo[d]imidazol-1-yl)-9-methyl-6-morpholino-9H-purin-8-yl)methyl)piperidin-4-yl)propan-2-ol |
| 339 | 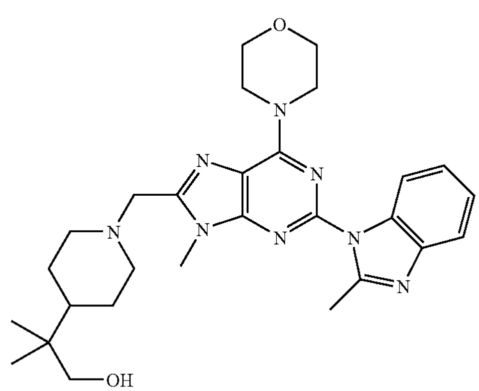 | 2-methyl-2-(1-((9-methyl-2-(2-methyl-1H-benzo[d]imidazol-1-yl)-6-morpholino-9H-purin-8-yl)methyl)piperidin-4-yl)propan-1-ol |

TABLE 2-continued

| No. | Structure | Name |
|---|---|---|
| 340 | 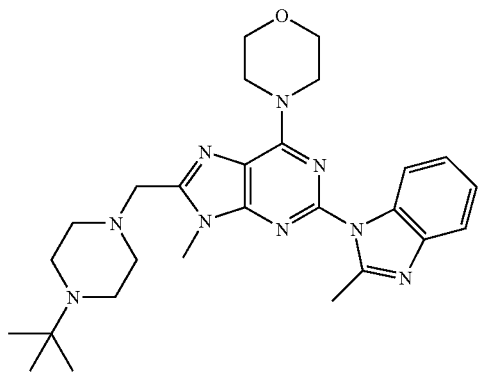 | 4-(8-((4-tert-butylpiperazin-1-yl)methyl)-9-methyl-2-(2-methyl-1H-benzo[d]imidazol-1-yl)-9H-purin-6-yl)morpholine |
| 341 | 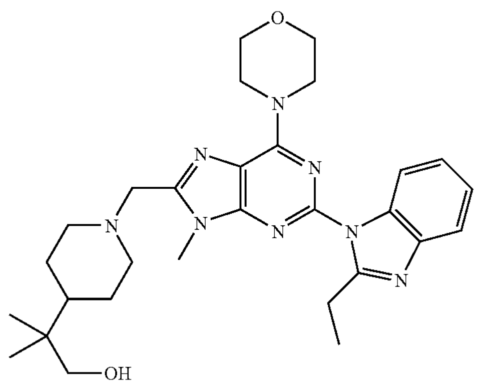 | 2-(1-((2-(2-ethyl-1H-benzo[d]imidazol-1-yl)-9-methyl-6-morpholino-9H-purin-8-yl)methyl)piperidin-4-yl)-2-methylpropan-1-ol |
| 342 | 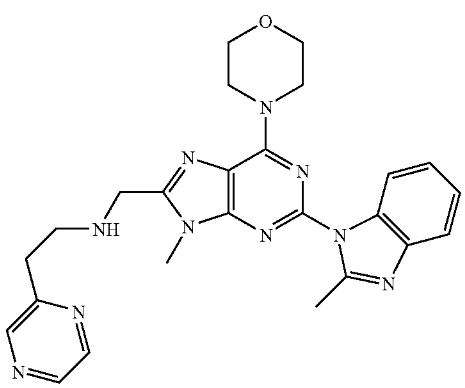 | N-((9-methyl-2-(2-methyl-1H-benzo[d]imidazol-1-yl)-6-morpholino-9H-purin-8-yl)methyl)-2-(pyrazin-2-yl)ethanamine |
| 343 | 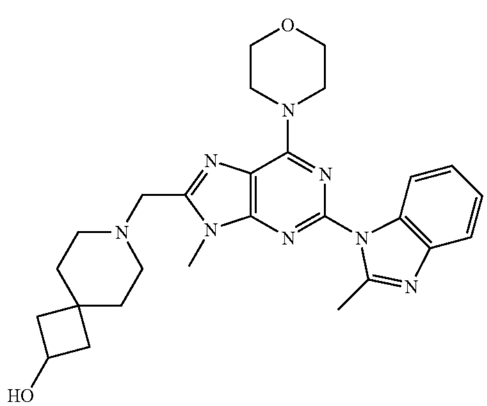 | 7-((9-methyl-2-(2-methyl-1H-benzo[d]imidazol-1-yl)-6-morpholino-9H-purin-8-yl)methyl)-7-azaspiro[3.5]nonan-2-ol |

TABLE 2-continued

| No. | Structure | Name |
|---|---|---|
| 344 | 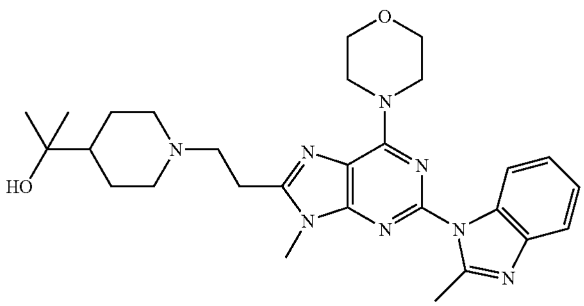 | 2-(1-(2-(9-methyl-2-(2-methyl-1H-benzo[d]imidazol-1-yl)-6-morpholino-9H-purin-8-yl)ethyl)piperidin-4-yl)propan-2-ol |
| 345 | 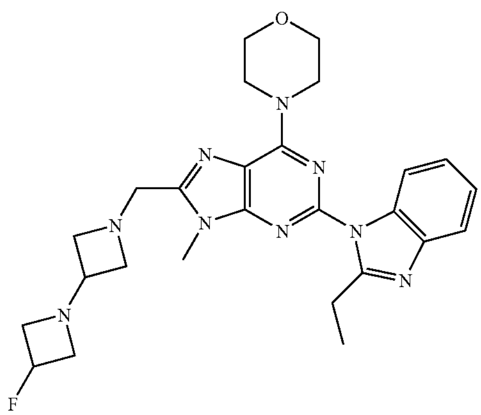 | 4-(2-(2-ethyl-1H-benzo[d]imidazol-1-yl)-8-((3-fluoro-1,3-biazetidin-1'-yl)methyl)-9-methyl-9H-purin-6-yl)morpholine |
| 346 | 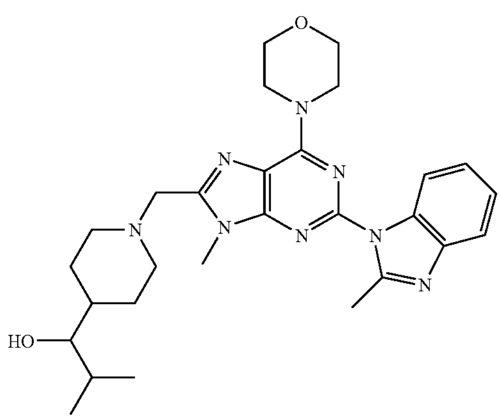 | 2-methyl-1-(1-((9-methyl-2-(2-methyl-1H-benzo[d]imidazol-1-yl)-6-morpholino-9H-purin-8-yl)methyl)piperidin-4-yl)propan-1-ol |
| 347 | 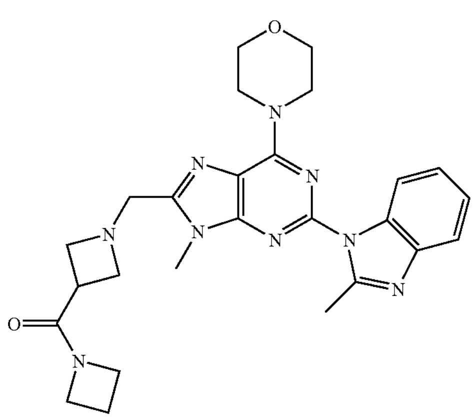 | azetidin-1-yl(1-((9-methyl-2-(2-methyl-1H-benzo[d]imidazol-1-yl)-6-morpholino-9H-purin-8-yl)methyl)azetidin-3-yl)methanone |

TABLE 2-continued

| No. | Structure | Name |
| --- | --- | --- |
| 348 | 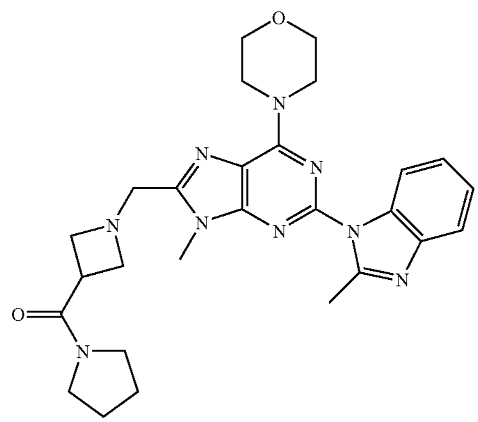 | (1-((9-methyl-2-(2-methyl-1H-benzo[d]imidazol-1-yl)-6-morpholino-9H-purin-8-yl)methyl)azetidin-3-yl)(pyrrolidin-1-yl)methanone |
| 349 | 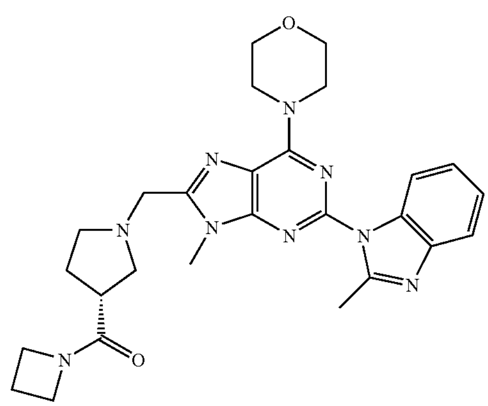 | (R)-azetidin-1-yl(1-((9-methyl-2-(2-methyl-1H-benzo[d]imidazol-1-yl)-6-morpholino-9H-purin-8-yl)methyl)pyrrolidin-3-yl)methanone |
| 350 | 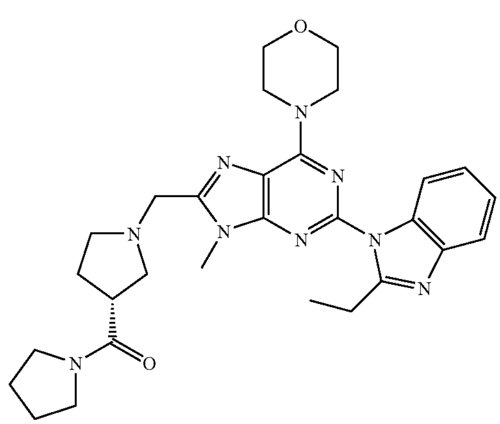 | (R)-(1-((2-(2-ethyl-1H-benzo[d]imidazol-1-yl)-9-methyl-6-morpholino-9H-purin-8-yl)methyl)pyrrolidin-3-yl)(pyrrolidin-1-yl)methanone |

TABLE 2-continued

| No. | Structure | Name |
| --- | --- | --- |
| 351 | 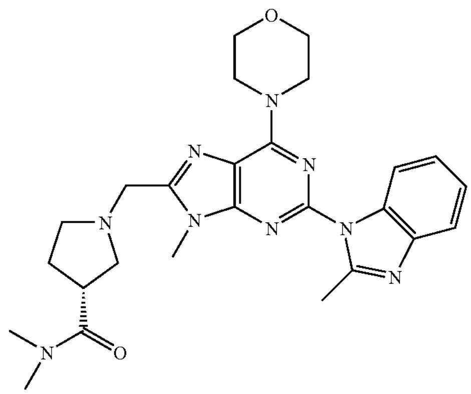 | (R)-N,N-dimethyl-1-((9-methyl-2-(2-methyl-1H-benzo[d]imidazol-1-yl)-6-morpholino-9H-purin-8-yl)methyl)pyrrolidine-3-carboxamide |
| 352 | 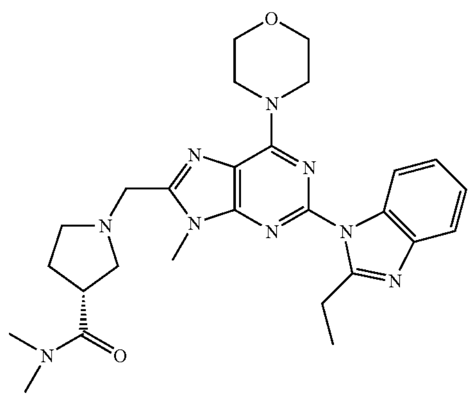 | (R)-1-((2-(2-ethyl-1H-benzo[d]imidazol-1-yl)-9-methyl-6-morpholino-9H-purin-8-yl)methyl)-N,N-dimethylpyrrolidine-3-carboxamide |
| 353 | 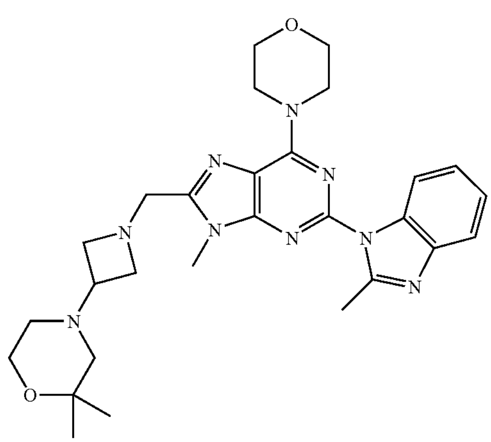 | 2,2-dimethyl-4-(1-((9-methyl-2-(2-methyl-1H-benzo[d]imidazol-1-yl)-6-morpholino-9H-purin-8-yl)methyl)azetidin-3-yl)morpholine |

TABLE 2-continued

| No. | Structure | Name |
|---|---|---|
| 354 | 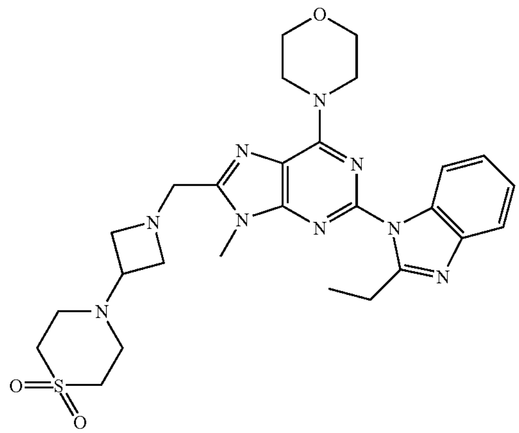 | 4-(2-(2-ethyl-1H-benzo[d]imidazol-1-yl)-9-methyl-8-((3-(1,1-dioxo-thiomorpholino)azetidin-1-yl)methyl)-9H-purin-6-yl)morpholine |
| 355 | 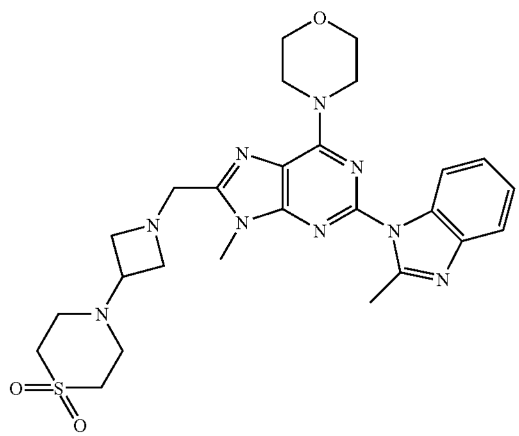 | 4-(2-(2-methyl-1H-benzo[d]imidazol-1-yl)-9-methyl-8-((3-(1,1-dioxo-thiomorpholino)azetidin-1-yl)methyl)-9H-purin-6-yl)morpholine |
| 356 | 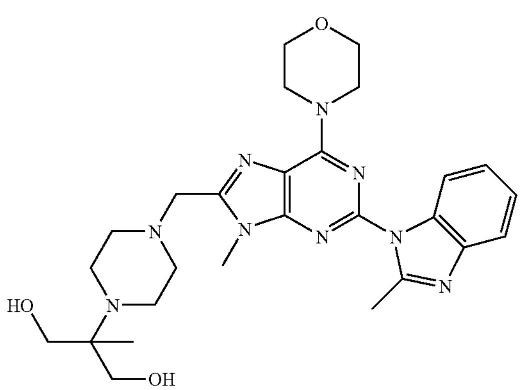 | 2-methyl-2-(4-((9-methyl-2-(2-methyl-1H-benzo[d]imidazol-1-yl)-6-morpholino-9H-purin-8-yl)methyl)piperazin-1-yl)propane-1,3-diol |

TABLE 2-continued

| No. | Structure | Name |
|---|---|---|
| 357 | 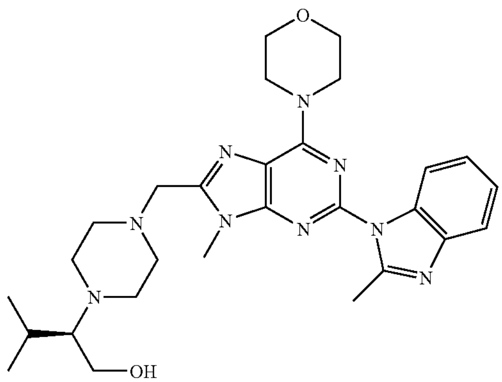 | (R)-3-methyl-2-(4-((9-methyl-2-(2-methyl-1H-benzo[d]imidazol-1-yl)-6-morpholino-9H-purin-8-yl)methyl)piperazin-1-yl)butan-1-ol |
| 358 | 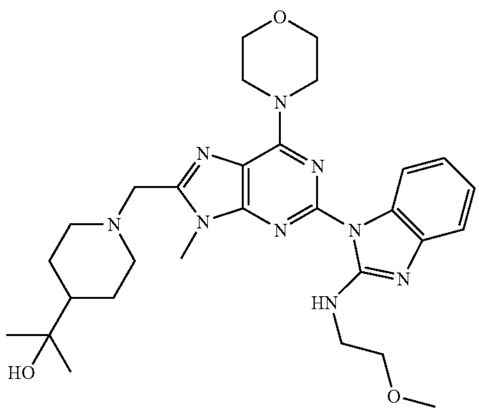 | 2-(1-((2-(2-(2-methoxyethylamino)-1H-benzo[d]imidazol-1-yl)-9-methyl-6-morpholino-9H-purin-8-yl)methyl)piperidin-4-yl)propan-2-ol |
| 359 | 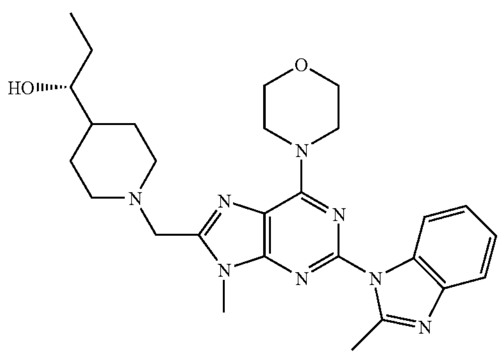 | (R)-1-(1-((9-methyl-2-(2-methyl-1H-benzo[d]imidazol-1-yl)-6-morpholino-9H-purin-8-yl)methyl)piperidin-4-yl)propan-1-ol |
| 360 | 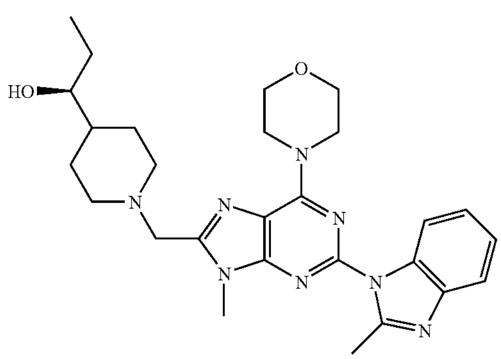 | (S)-1-(1-((9-methyl-2-(2-methyl-1H-benzo[d]imidazol-1-yl)-6-morpholino-9H-purin-8-yl)methyl)piperidin-4-yl)propan-1-ol |

| No. | Structure | Name |
|---|---|---|
| 361 | 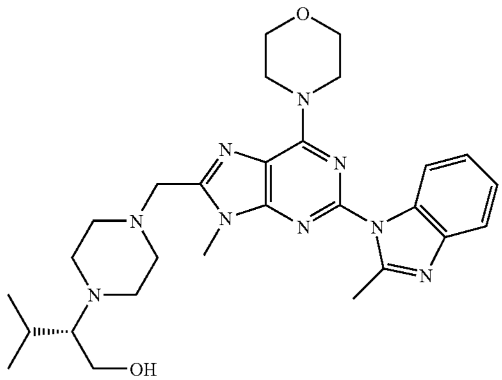 | (S)-3-methyl-2-(4-((9-methyl-2-(2-methyl-1H-benzo[d]imidazol-1-yl)-6-morpholino-9H-purin-8-yl)methyl)piperazin-1-yl)butan-1-ol |
| 362 | 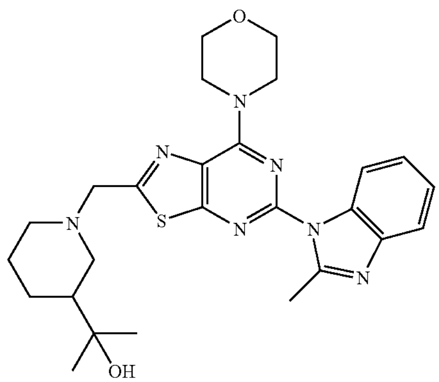 | 2-(1-((5-(2-methyl-1H-benzo[d]imidazol-1-yl)-7-morpholinothiazolo[5,4-d]pyrimidin-2-yl)methyl)piperidin-3-yl)propan-2-ol |
| 363 | 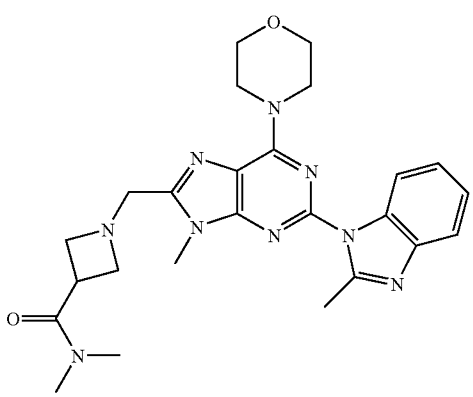 | N,N-dimethyl-1-((9-methyl-2-(2-methyl-1H-benzo[d]imidazol-1-yl)-6-morpholino-9H-purin-8-yl)methyl)azetidine-3-carboxamide |
| 364 | 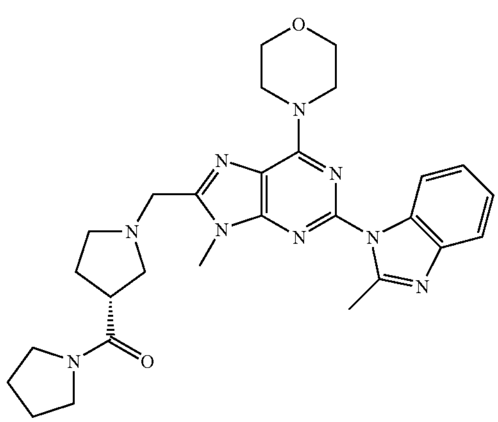 | (R)-(1-((9-methyl-2-(2-methyl-1H-benzo[d]imidazol-1-yl)-6-morpholino-9H-purin-8-yl)methyl)pyrrolidin-3-yl)(pyrrolidin-1-yl)methanone |

| No. | Structure | Name |
| --- | --- | --- |
| 365 | 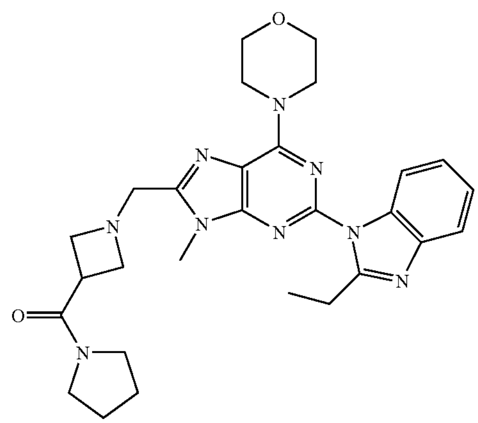 | (1-((2-(2-ethyl-1H-benzo[d]imidazol-1-yl)-9-methyl-6-morpholino-9H-purin-8-yl)methyl)azetidin-3-yl)(pyrrolidin-1-yl)methanone |
| 366 | 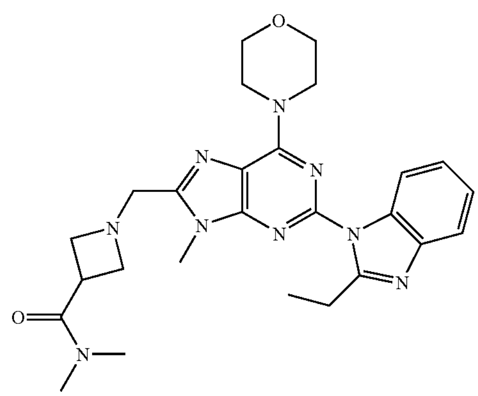 | 1-((2-(2-ethyl-1H-benzo[d]imidazol-1-yl)-9-methyl-6-morpholino-9H-purin-8-yl)methyl)-N,N-dimethylazetidine-3-carboxamide |
| 367 | 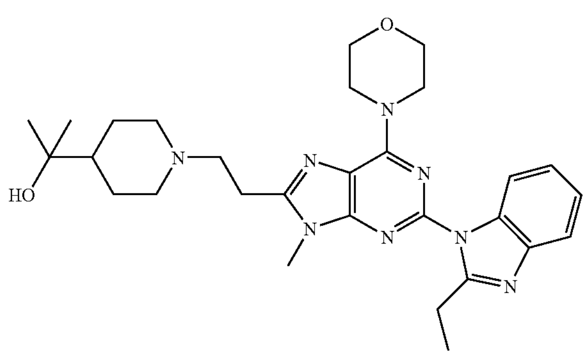 | 2-(1-(2-(2-(2-ethyl-1H-benzo[d]imidazol-1-yl)-9-methyl-6-morpholino-9H-purin-8-yl)ethyl)piperidin-4-yl)propan-2-ol |
| 368 | 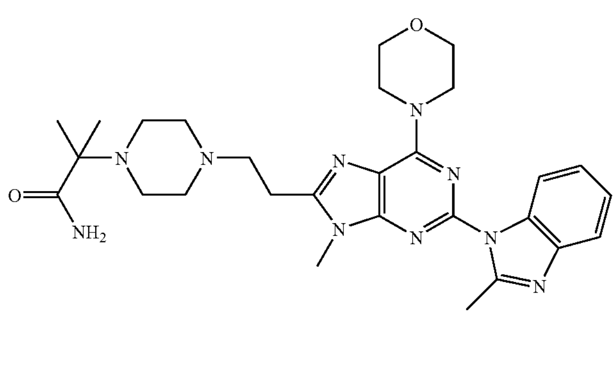 | 2-methyl-2-(4-(2-(9-methyl-2-(2-methyl-1H-benzo[d]imidazol-1-yl)-6-morpholino-9H-purin-8-yl)ethyl)piperazin-1-yl)propanamide |

TABLE 2-continued

| No. | Structure | Name |
|---|---|---|
| 369 | 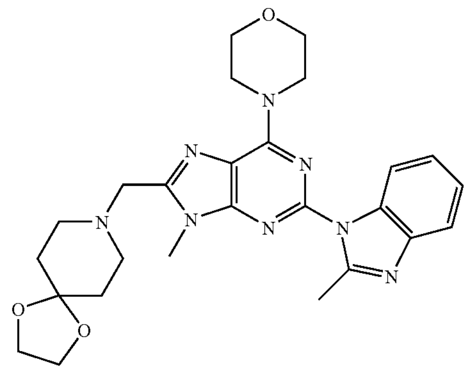 | 8-((9-methyl-2-(2-methyl-1H-benzo[d]imidazol-1-yl)-6-morpholino-9H-purin-8-yl)methyl)-1,4-dioxa-8-azaspiro[4.5]decane |
| 370 | 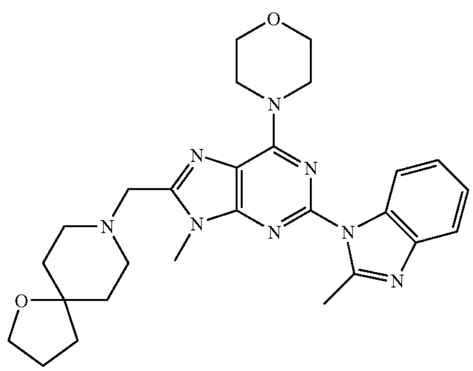 | 8-((9-methyl-2-(2-methyl-1H-benzo[d]imidazol-1-yl)-6-morpholino-9H-purin-8-yl)methyl)-1-oxa-8-azaspiro[4.5]decane |
| 371 | 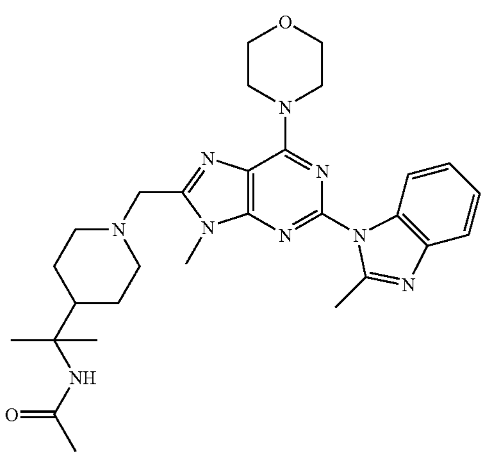 | N-(2-(1-((9-methyl-2-(2-methyl-1H-benzo[d]imidazol-1-yl)-6-morpholino-9H-purin-8-yl)methyl)piperidin-4-yl)propan-2-yl)acetamide |
| 372 | 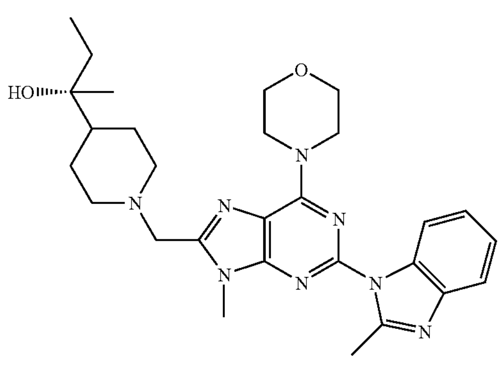 | (S)-2-(1-((9-methyl-2-(2-methyl-1H-benzo[d]imidazol-1-yl)-6-morpholino-9H-purin-8-yl)methyl)piperidin-4-yl)butan-2-ol |

TABLE 2-continued

| No. | Structure | Name |
|---|---|---|
| 373 | 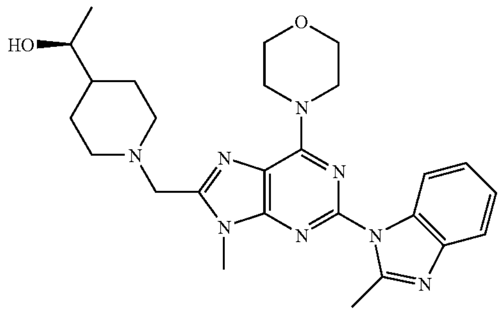 | (S)-1-(1-((9-methyl-2-(2-methyl-1H-benzo[d]imidazol-1-yl)-6-morpholino-9H-purin-8-yl)methyl)piperidin-4-yl)ethanol |
| 374 | 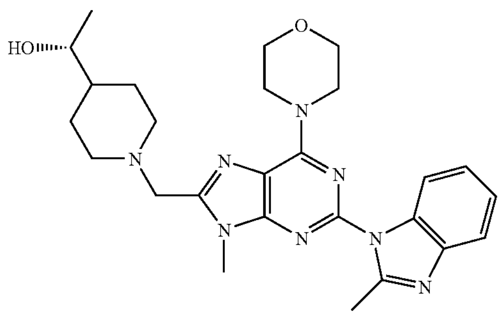 | (R)-1-(1-((9-methyl-2-(2-methyl-1H-benzo[d]imidazol-1-yl)-6-morpholino-9H-purin-8-yl)methyl)piperidin-4 -yl)ethanol |
| 375 | 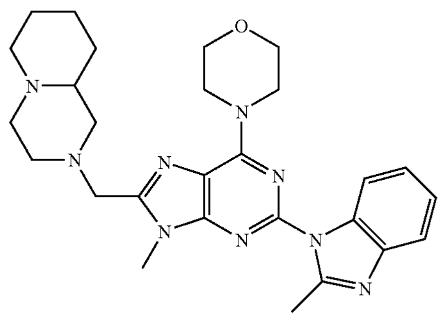 | 4-(8-((dihydro-1H-pyrido[1,2-a]pyrazin-2(6H,7H,8H,9H,9aH)-yl)methyl)-9-methyl-2-(2-methyl-1H-benzo[d]imidazol-1-yl)-9H-purin-6-yl)morpholine |
| 376 | 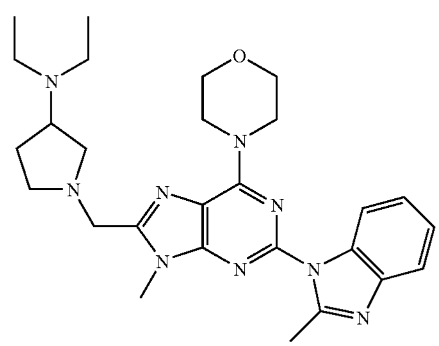 | N,N-diethyl-1-((9-methyl-2-(2-methyl-1H-benzo[d]imidazol-1-yl)-6-morpholino-9H-purin-8-yl)methyl)pyrrolidin-3-amine |
| 377 | 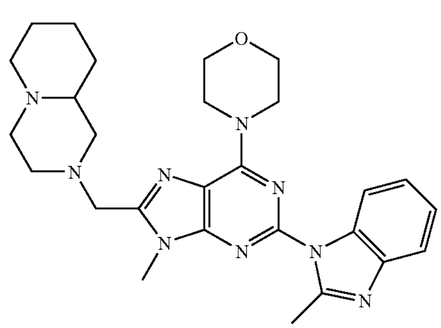 | 4-(8-((dihydro-1H-pyrido[1,2-a]pyrazin-2(6H,7H,8H,9H,9aH)-yl)methyl)-9-methyl-2-(2-methyl-1H-benzo[d]imidazol-1-yl)-9H-purin-6-yl)morpholine |

TABLE 2-continued

| No. | Structure | Name |
|---|---|---|
| 378 | 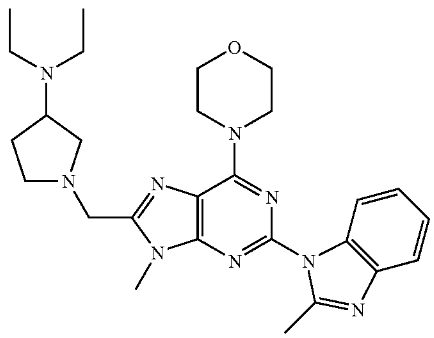 | N,N-diethyl-1-((9-methyl-2-(2-methyl-1H-benzo[d]imidazol-1-yl)-6-morpholino-9H-purin-8-yl)methyl)pyrrolidin-3-amine |
| 379 | 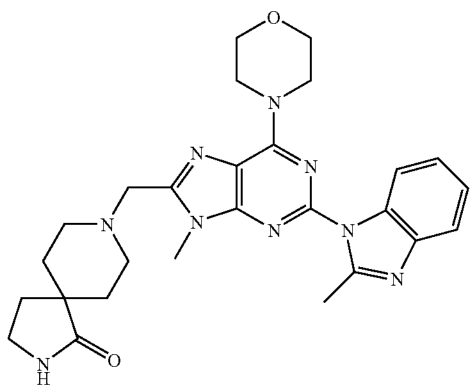 | 8-((9-methyl-2-(2-methyl-1H-benzo[d]imidazol-1-yl)-6-morpholino-9H-purin-8-yl)methyl)-2,8-diazaspiro[4.5]decan-1-one |
| 380 | 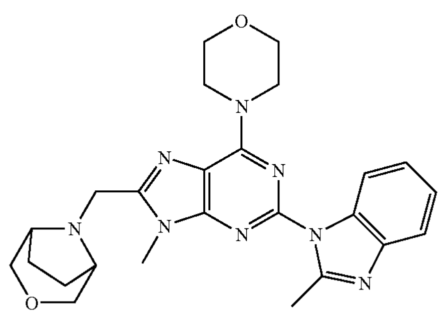 | 8-((9-methyl-2-(2-methyl-1H-benzo[d]imidazol-1-yl)-6-morpholino-9H-purin-8-yl)methyl)-3-oxa-8-azabicyclo[3.2.1]octane |
| 381 | 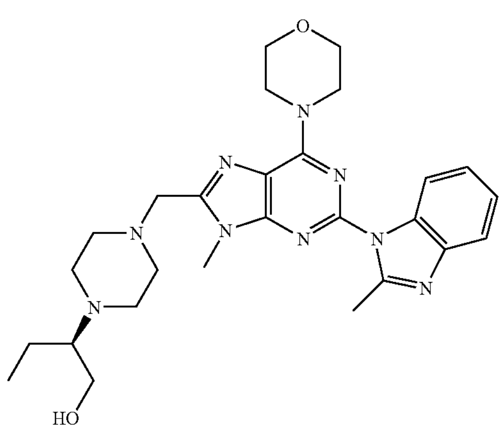 | (R)-2-(4-((9-methyl-2-(2-methyl-1H-benzo[d]imidazol-1-yl)-6-morpholino-9H-purin-8-yl)methyl)piperazin-1-yl)butan-1-ol |

TABLE 2-continued

| No. | Structure | Name |
|---|---|---|
| 382 | 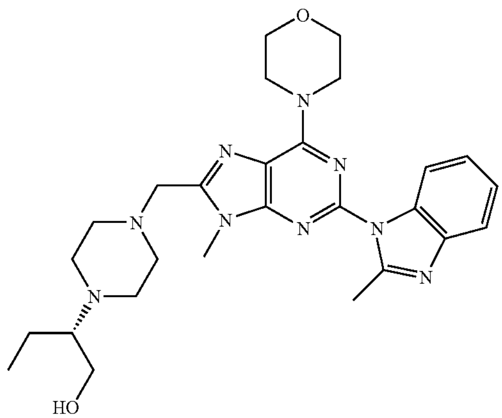 | (S)-2-(4-((9-methyl-2-(2-methyl-1H-benzo[d]imidazol-1-yl)-6-morpholino-9H-purin-8-yl)methyl)piperazin-1-yl)butan-1-ol |
| 383 | 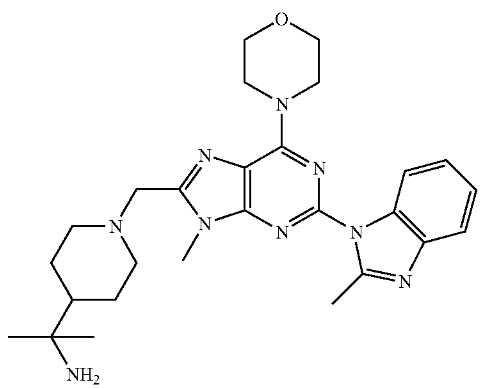 | 2-(1-((9-methyl-2-(2-methyl-1H-benzo[d]imidazol-1-yl)-6-morpholino-9H-purin-8-yl)methyl)piperidin-4-yl)propan-2-amine |
| 384 | 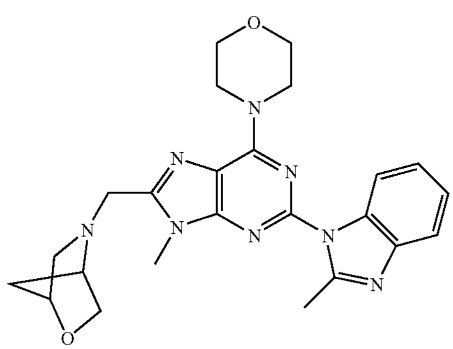 | 5-((9-methyl-2-(2-methyl-1H-benzo[d]imidazol-1-yl)-6-morpholino-9H-purin-8-yl)methyl)-2-oxa-5-azabicyclo[2.2.1]heptane |
| 385 | 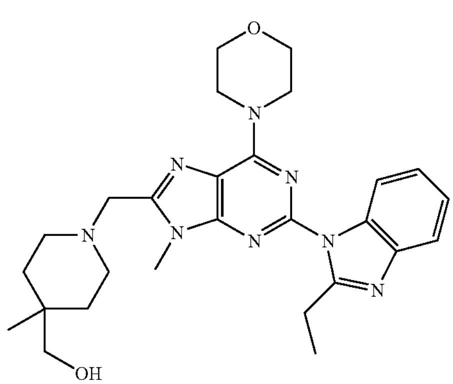 | (1-((2-(2-ethyl-1H-benzo[d]imidazol-1-yl)-9-methyl-6-morpholino-9H-purin-8-yl)methyl)-4-methylpiperidin-4-yl)methanol |

TABLE 2-continued

| No. | Structure | Name |
|---|---|---|
| 386 | 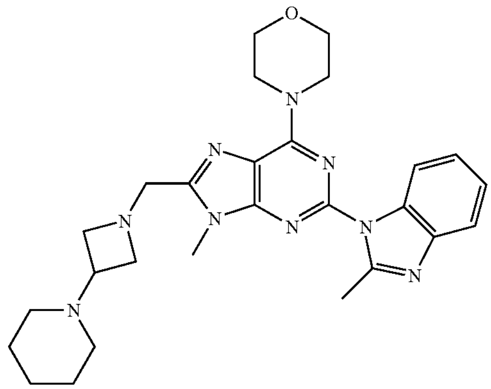 | 4-(9-methyl-2-(2-methyl-1H-benzo[d]imidazol-1-yl)-8-((3-(piperidin-1-yl)azetidin-1-yl)methyl)-9H-purin-6-yl)morpholine |
| 387 | 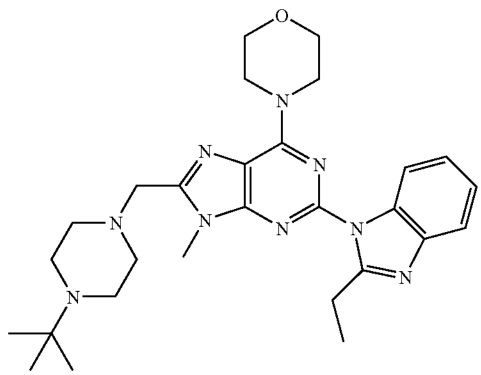 | 4-(8-((4-tert-butylpiperazin-1-yl)methyl)-2-(2-ethyl-1H-benzo[d]imidazol-1-yl)-9-methyl-9H-purin-6-yl)morpholine |
| 388 | 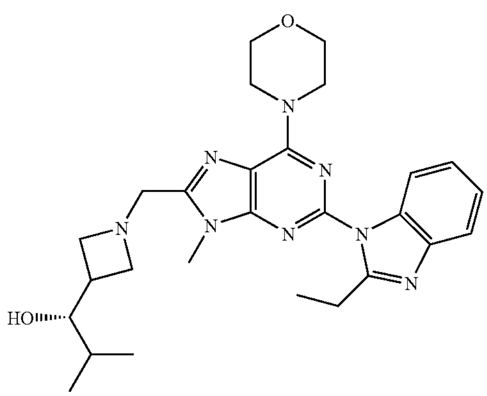 | (S)-1-(1-((2-(2-ethyl-1H-benzo[d]imidazol-1-yl)-9-methyl-6-morpholino-9H-purin-8-yl)methyl)azetidin-3-yl)-2-methylpropan-1-ol |
| 389 | 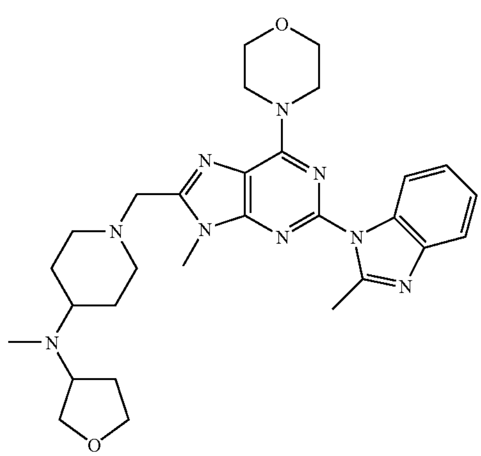 | N-methyl-1-((9-methyl-2-(2-methyl-1H-benzo[d]imidazol-1-yl)-6-morpholino-9H-purin-8-yl)methyl)-N-(tetrahydrofuran-3-yl)piperidin-4-amine |

TABLE 2-continued

| No. | Structure | Name |
|---|---|---|
| 390 | 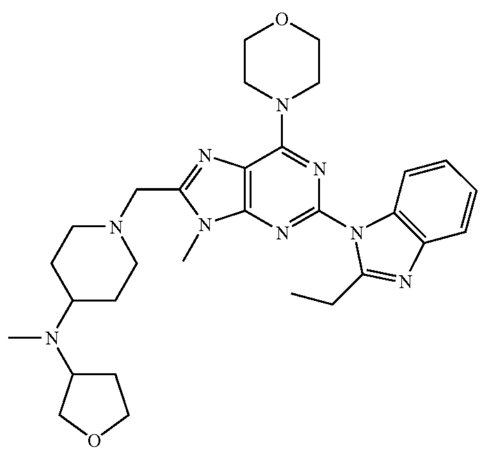 | 1-((2-(2-ethyl-1H-benzo[d]imidazol-1-yl)-9-methyl-6-morpholino-9H-purin-8-yl)methyl)-N-methyl-N-(tetrahydrofuran-3-yl)piperidin-4-amine |
| 391 | 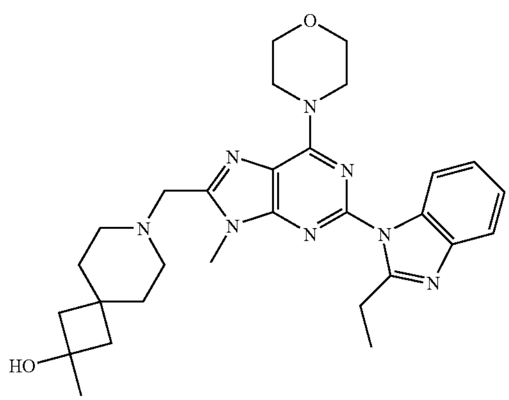 | 7-((2-(2-ethyl-1H-benzo[d]imidazol-1-yl)-9-methyl-6-morpholino-9H-purin-8-yl)methyl)-2-methyl-7-azaspiro[3.5]nonan-2-ol |
| 392 | 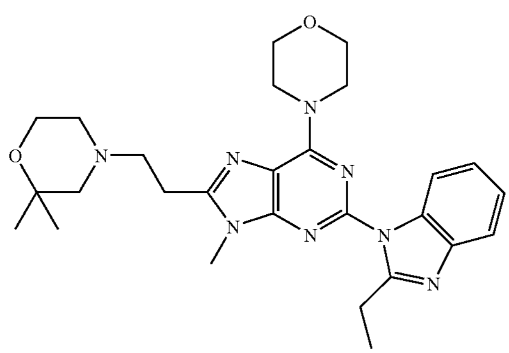 | 4-(2-(2-(2-ethyl-1H-benzo[d]imidazol-1-yl)-9-methyl-6-morpholino-9H-purin-8-yl)ethyl)-2,2-dimethylmorpholine |
| 393 | 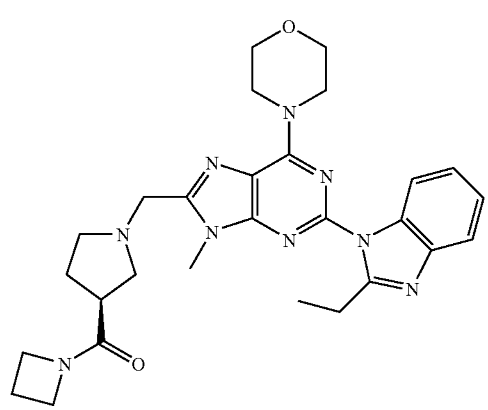 | (S)-azetidin-1-yl(1-((2-(2-ethyl-1H-benzo[d]imidazol-1-yl)-9-methyl-6-morpholino-9H-purin-8-yl)methyl)pyrrolidin-3-yl)methanone |

TABLE 2-continued

| No. | Structure | Name |
|---|---|---|
| 394 | 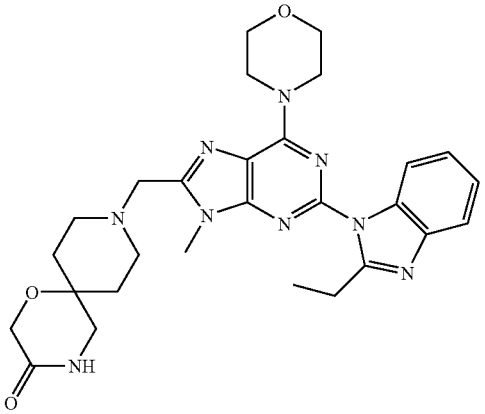 | 9-((2-(2-ethyl-1H-benzo[d]imidazol-1-yl)-9-methyl-6-morpholino-9H-purin-8-yl)methyl)-1-oxa-4,9-diazaspiro[5.5]undecan-3-one |
| 395 | 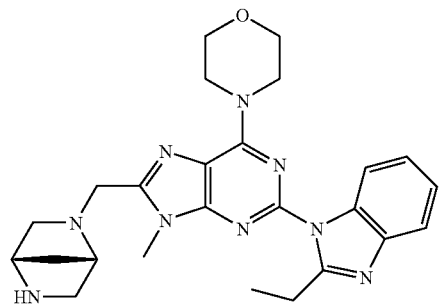 | 4-(8-((1S,4S)-2,5-diazabicyclo[2.2.1]heptan-2-ylmethyl)-2-(2-ethyl-1H-benzo[d]imidazol-1-yl)-9-methyl-9H-purin-6-yl)morpholine |
| 396 | 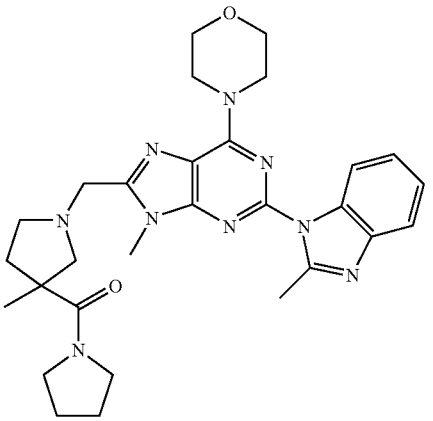 | (3-methyl-1-((9-methyl-2-(2-methyl-1H-benzo[d]imidazol-1-yl)-6-morpholino-9H-purin-8-yl)methyl)pyrrolidin-3-yl)(pyrrolidin-1-yl)methanone |
| 397 | 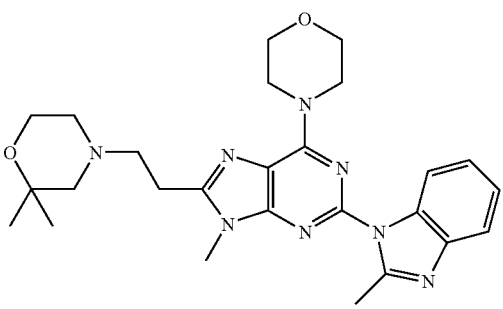 | 2,2-dimethyl-4-(2-(9-methyl-2-(2-methyl-1H-benzo[d]imidazol-1-yl)-6-morpholino-9H-purin-8-yl)ethyl)morpholine |

TABLE 2-continued

| No. | Structure | Name |
|---|---|---|
| 398 | 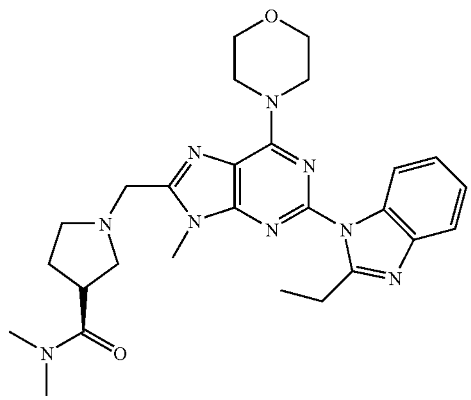 | (S)-1-((2-(2-ethyl-1H-benzo[d]imidazol-1-yl)-9-methyl-6-morpholino-9H-purin-8-yl)methyl)-N,N-dimethylpyrrolidine-3-carboxamide |
| 399 | 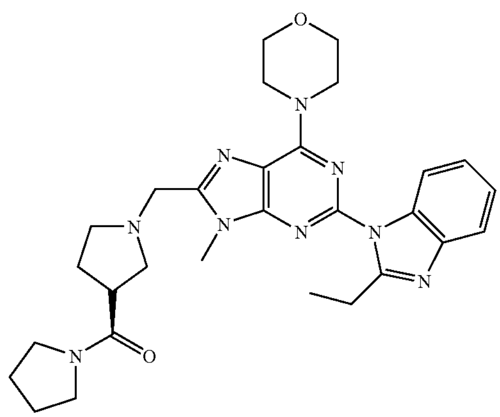 | (S)-(1-((2-(2-ethyl-1H-benzo[d]imidazol-1-yl)-9-methyl-6-morpholino-9H-purin-8-yl)methyl)pyrrolidin-3-yl)(pyrrolidin-1-yl)methanone |
| 400 | 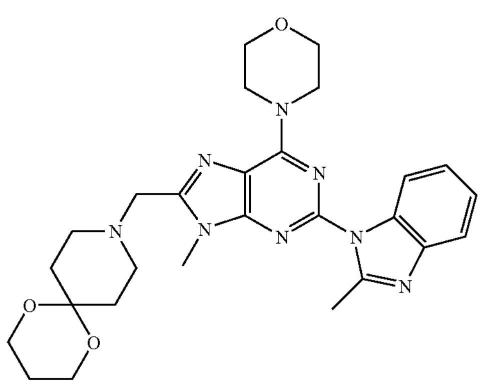 | 9-((9-methyl-2-(2-methyl-1H-benzo[d]imidazol-1-yl)-6-morpholino-9H-purin-8-yl)methyl)-1,5-dioxa-9-azaspiro[5.5]undecane |
| 401 | 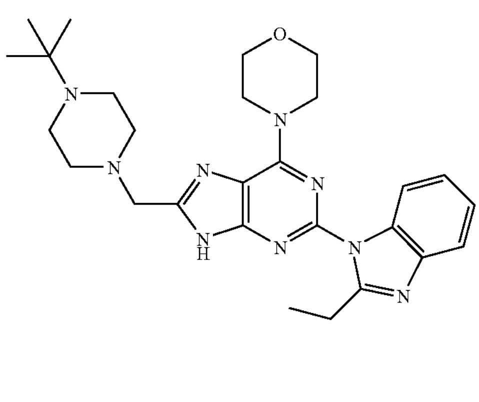 | 4-(8-((4-tert-butylpiperazin-1-yl)methyl)-2-(2-ethyl-1H-benzo[d]imidazol-1-yl)-9H-purin-6-yl)morpholine |

TABLE 2-continued

| No. | Structure | Name |
|---|---|---|
| 402 | 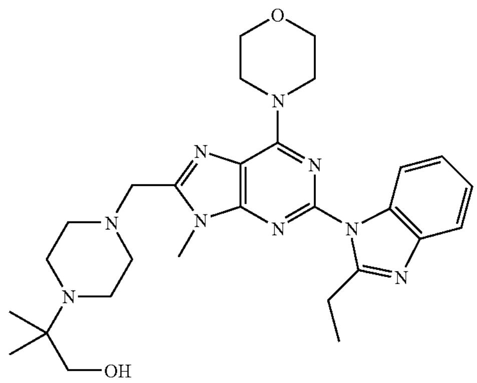 | 2-(4-((2-(2-ethyl-1H-benzo[d]imidazol-1-yl)-9-methyl-6-morpholino-9H-purin-8-yl)methyl)piperazin-1-yl)-2-methylpropan-1-ol |
| 403 | 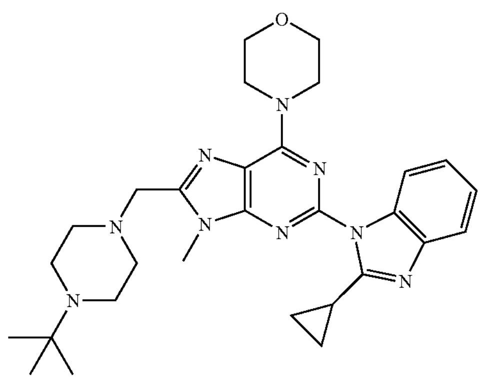 | 4-(8-((4-tert-butylpiperazin-1-yl)methyl)-2-(2-cyclopropyl-1H-benzo[d]imidazol-1-yl)-9-methyl-9H-purin-6-yl)morpholine |
| 404 | 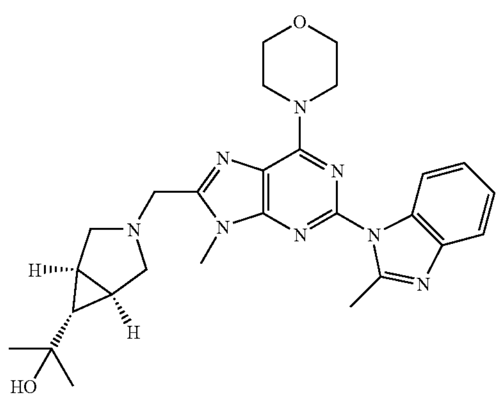 | 2-((1R,5S,6r)-3-((9-methyl-2-(2-methyl-1H-benzo[d]imidazol-1-yl)-6-morpholino-9H-purin-8-yl)methyl)-3-azabicyclo[3.1.0]hexan-6-yl)propan-2-ol |
| 405 | 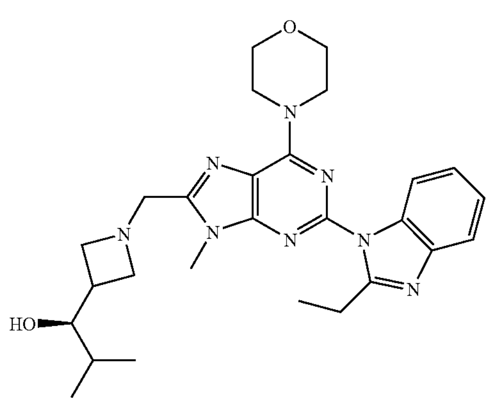 | (R)-1-(1-((2-(2-ethyl-1H-benzo[d]imidazol-1-yl)-9-methyl-6-morpholino-9H-purin-8-yl)methyl)azetidin-3-yl)-2-methylpropan-1-ol |

TABLE 2-continued

| No. | Structure | Name |
|---|---|---|
| 406 | 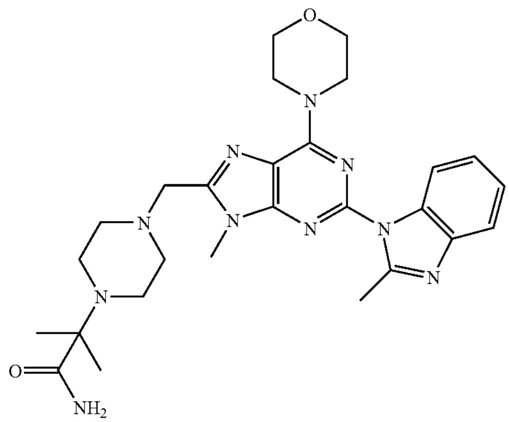 | 2-methyl-2-(4-((9-methyl-2-(2-methyl-1H-benzo[d]imidazol-1-yl)-6-morpholino-9H-purin-8-yl)methyl)piperazin-1-yl)propanamide |
| 407 | 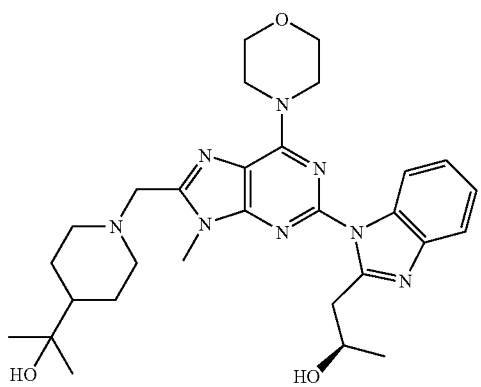 | (R)-1-(1-(8-((4-(2-hydroxypropan-2-yl)piperidin-1-yl)methyl)-9-methyl-6-morpholino-9H-purin-2-yl)-1H-benzo[d]imidazol-2-yl)propan-2-ol |
| 408 | 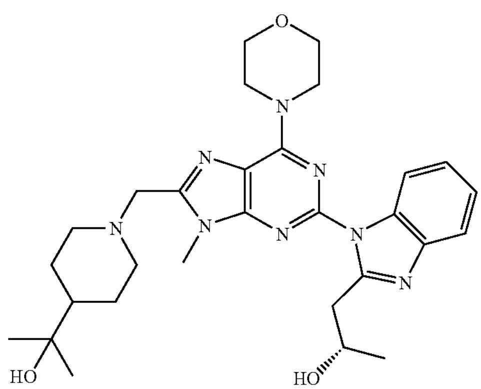 | (S)-1-(1-(8-((4-(2-hydroxypropan-2-yl)piperidin-1-yl)methyl)-9-methyl-6-morpholino-9H-purin-2-yl)-1H-benzo[d]imidazol-2-yl)propan-2-ol |
| 409 | 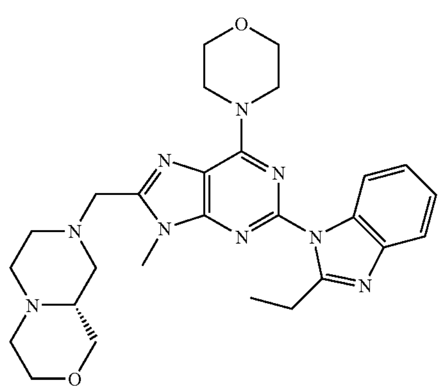 | (R)-8-((2-(2-ethyl-1H-benzo[d]imidazol-1-yl)-9-methyl-6-morpholino-9H-purin-8-yl)methyl)octahydropyrazino[2,1-c][1,4]oxazine |

TABLE 2-continued

| No. | Structure | Name |
|---|---|---|
| 410 | 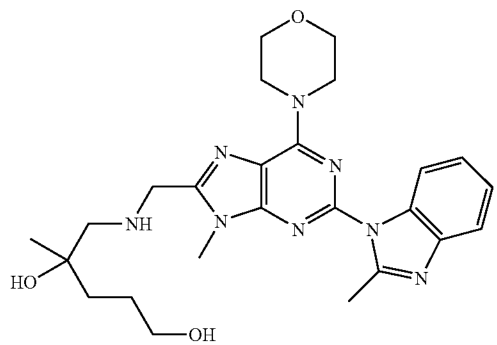 | 4-methyl-5-((9-methyl-2-(2-methyl-1H-benzo[d]imidazol-1-yl)-6-morpholino-9H-purin-8-yl)methylamino)pentane-1,4-diol |
| 411 | 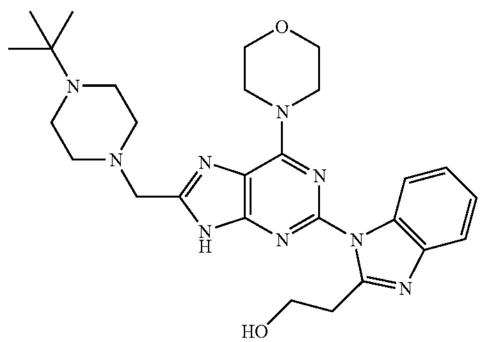 | 2-(1-(8-((4-tert-butylpiperazin-1-yl)methyl)-6-morpholino-9H-purin-2-yl)-1H-benzo[d]imidazol-2-yl)ethanol |
| 412 | 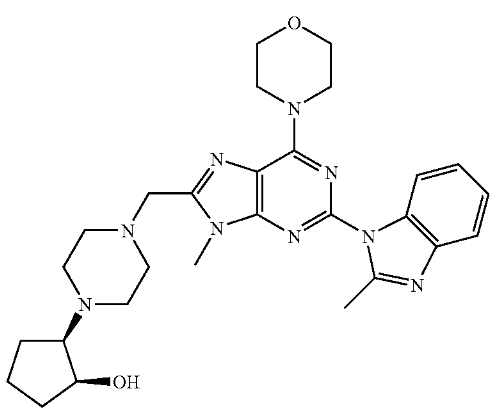 | (1S,2R)-2-(4-((9-methyl-2-(2-methyl-1H-benzo[d]imidazol-1-yl)-6-morpholino-9H-purin-8-yl)methyl)piperazin-1-yl)cyclopentanol |
| 413 | 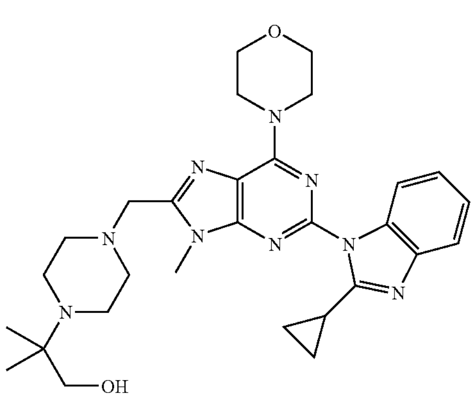 | 2-(4-((2-(2-cyclopropyl-1H-benzo[d]imidazol-1-yl)-9-methyl-6-morpholino-9H-purin-8-yl)methyl)piperazin-1-yl)-2-methylpropan-1-ol |

TABLE 2-continued

| No. | Structure | Name |
|---|---|---|
| 414 | 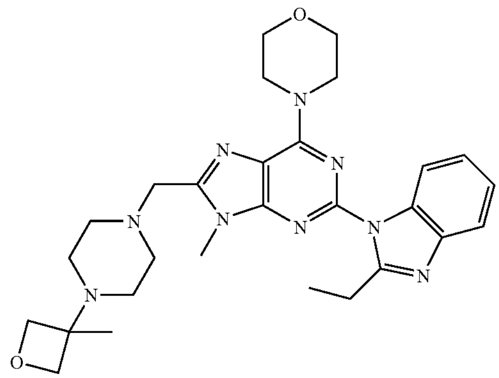 | 4-(2-(2-ethyl-1H-benzo[d]imidazol-1-yl)-9-methyl-8-((4-(3-methyloxetan-3-yl)piperazin-1-yl)methyl)-9H-purin-6-yl)morpholine |
| 415 | 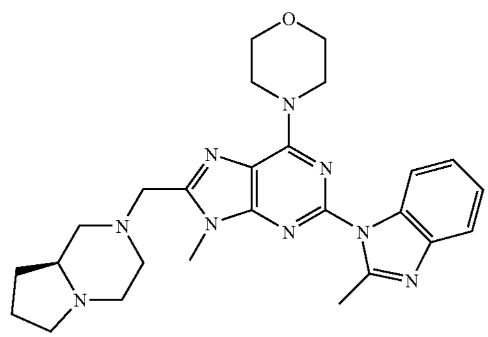 | (S)-4-(8-((hexahydropyrrolo[1,2-a]pyrazin-2(1H)-yl)methyl)-9-methyl-2-(2-methyl-1H-benzo[d]imidazol-1-yl)-9H-purin-6-yl)morpholine |
| 416 | 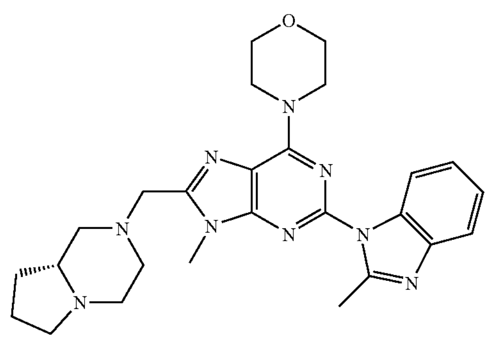 | (R)-4-(8-((hexahydropyrrolo[1,2-a]pyrazin-2(1H)-yl)methyl)-9-methyl-2-(2-methyl-1H-benzo[d]imidazol-1-yl)-9H-purin-6-yl)morpholine |
| 417 | 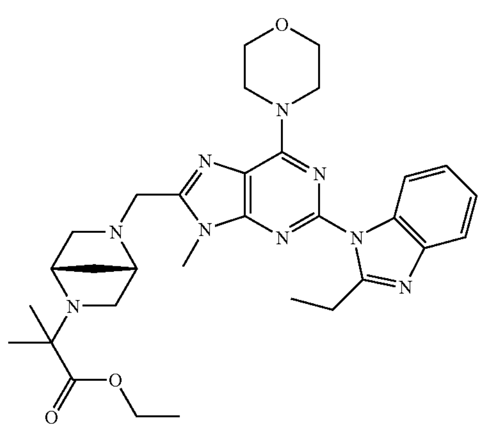 | ethyl 2-((1S,4S)-5-((2-(2-ethyl-1H-benzo[d]imidazol-1-yl)-9-methyl-6-morpholino-9H-purin-8-yl)methyl)-2,5-diazabicyclo[2.2.1]heptan-2-yl)-2-methylpropanoate |

TABLE 2-continued

| No. | Structure | Name |
|---|---|---|
| 418 | 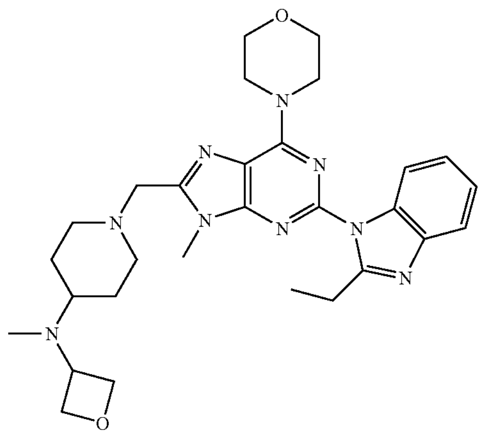 | 1-((2-(2-ethyl-1H-benzo[d]imidazol-1-yl)-9-methyl-6-morpholino-9H-purin-8-yl)methyl)-N-methyl-N-(oxetan-3-yl)piperidin-4-amine |
| 419 | 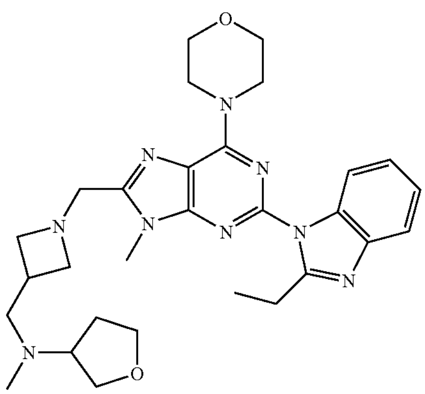 | N-((1-((2-(2-ethyl-1H-benzo[d]imidazol-1-yl)-9-methyl-6-morpholino-9H-purin-8-yl)methyl)azetidin-3-yl)methyl)-N-methyltetrahydrofuran-3-amine |
| 420 | 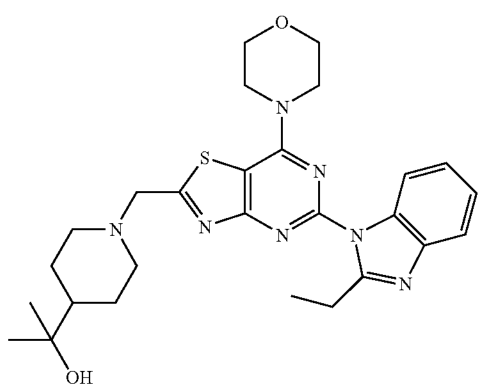 | 2-(1-((5-(2-ethyl-1H-benzo[d]imidazol-1-yl)-7-morpholinothiazolo[4,5-d]pyrimidin-2-yl)methyl)piperidin-4-yl)propan-2-ol |
| 421 | 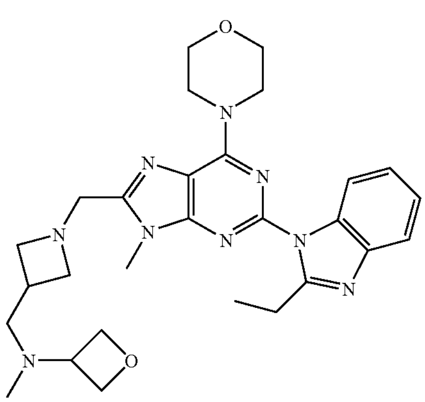 | N-((1-((2-(2-ethyl-1H-benzo[d]imidazol-1-yl)-9-methyl-6-morpholino-9H-purin-8-yl)methyl)azetidin-3-yl)methyl)-N-methyloxetan-3-amine |

TABLE 2-continued

| No. | Structure | Name |
|---|---|---|
| 422 | 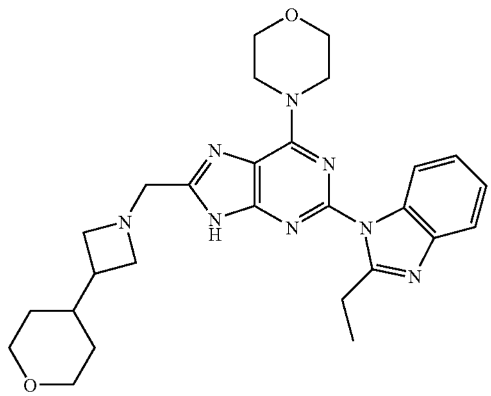 | 4-(2-(2-ethyl-1H-benzo[d]imidazol-1-yl)-8-((3-(tetrahydro-2H-pyran-4-yl)azetidin-1-yl)methyl)-9H-purin-6-yl)morpholine |
| 423 | 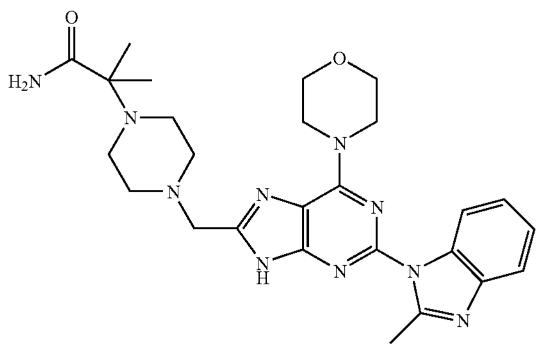 | 2-methyl-2-(4-((2-(2-methyl-1H-benzo[d]imidazol-1-yl)-6-morpholino-9H-purin-8-yl)methyl)piperazin-1-yl)propanamide |
| 424 | 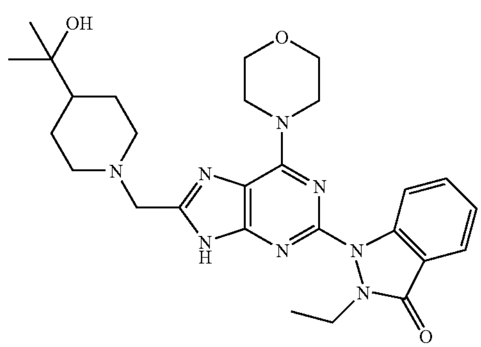 | 2-ethyl-1-(8-((4-(2-hydroxypropan-2-yl)piperidin-1-yl)methyl)-6-morpholino-9H-purin-2-yl)-1H-indazol-3(2H)-one |
| 425 | 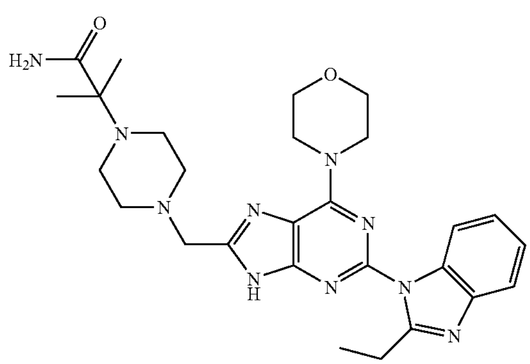 | 2-(4-((2-(2-ethyl-1H-benzo[d]imidazol-1-yl)-6-morpholino-9H-purin-8-yl)methyl)piperazin-1-yl)-2-methylpropanamide |

TABLE 2-continued

| No. | Structure | Name |
|---|---|---|
| 426 | 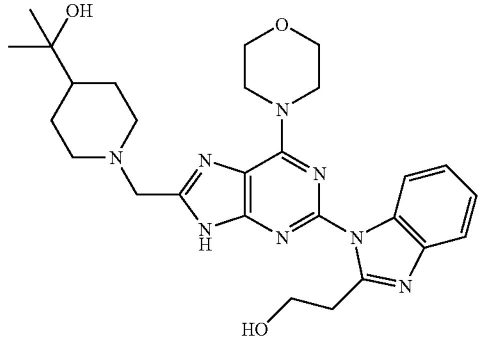 | 2-(1-((2-(2-(2-hydroxyethyl)-1H-benzo[d]imidazol-1-yl)-6-morpholino-9H-purin-8-yl)methyl)piperidin-4-yl)propan-2-ol |
| 427 | 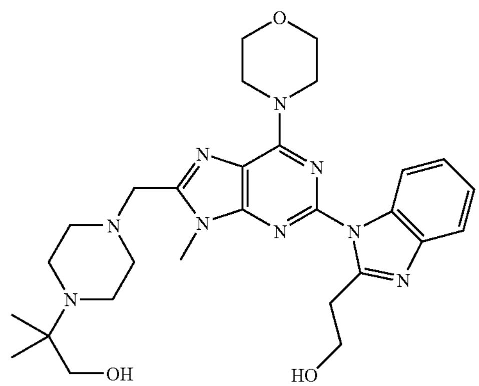 | 2-(4-((2-(2-(2-hydroxyethyl)-1H-benzo[d]imidazol-1-yl)-9-methyl-6-morpholino-9H-purin-8-yl)methyl)piperazin-1-yl)-2-methylpropan-1-ol |
| 428 | 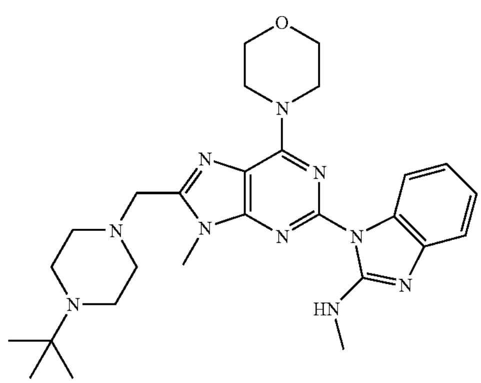 | 1-(8-((4-tert-butylpiperazin-1-yl)methyl)-9-methyl-6-morpholino-9H-purin-2-yl)-N-methyl-1H-benzo[d]imidazol-2-amine |
| 429 | 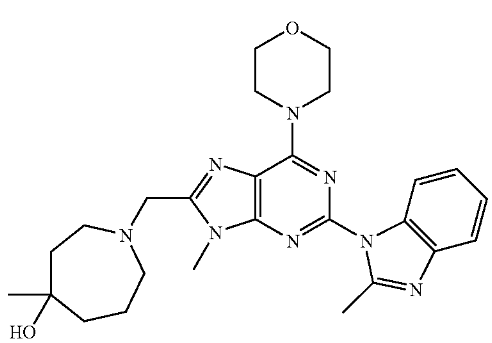 | 4-methyl-1-((9-methyl-2-(2-methyl-1H-benzo[d]imidazol-1-yl)-6-morpholino-9H-purin-8-yl)methyl)azepan-4-ol |

TABLE 2-continued

| No. | Structure | Name |
| --- | --- | --- |
| 430 | 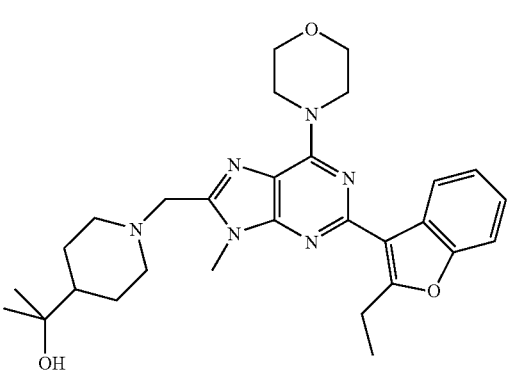 | 2-(1-((2-(2-ethylbenzofuran-3-yl)-9-methyl-6-morpholino-9H-purin-8-yl)methyl)piperidin-4-yl)propan-2-ol |
| 431 | 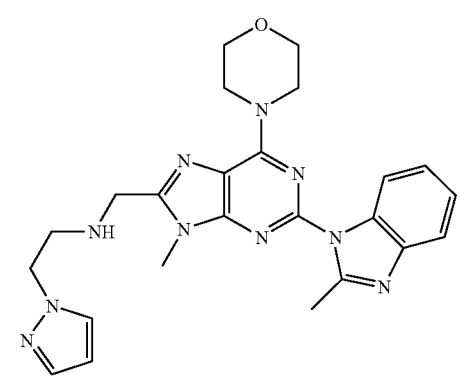 | N-((9-methyl-2-(2-methyl-1H-benzo[d]imidazol-1-yl)-6-morpholino-9H-purin-8-yl)methyl)-2-(1H-pyrazol-1-yl)ethanamine |
| 432 | 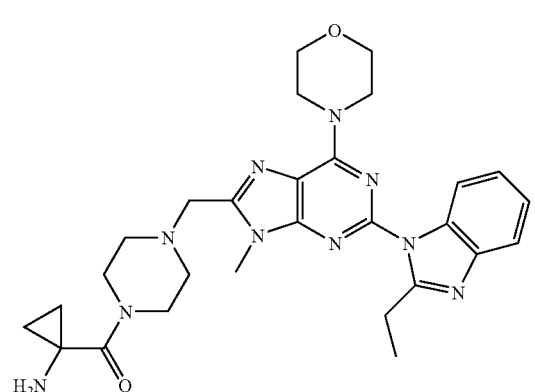 | (1-aminocyclopropyl)(4-((2-(2-ethyl-1H-benzo[d]imidazol-1-yl)-9-methyl-6-morpholino-9H-purin-8-yl)methyl)piperazin-1-yl)methanone |
| 433 | 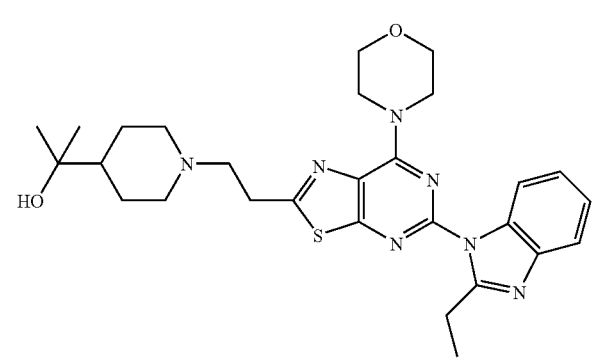 | 2-(1-(2-(5-(2-ethyl-1H-benzo[d]imidazol-1-yl)-7-morpholinothiazolo[5,4-d]pyrimidin-2-yl)ethyl)piperidin-4-yl)propan-2-ol |

| No. | Structure | Name |
| --- | --- | --- |
| 434 | 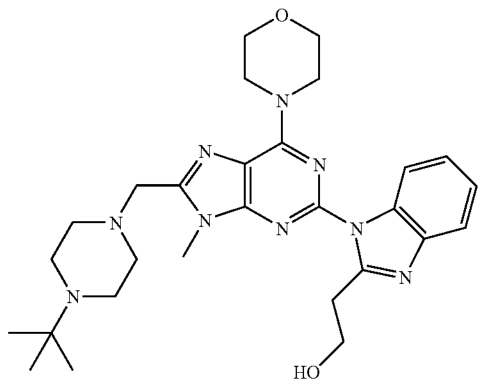 | 2-(1-(8-((4-tert-butylpiperazin-1-yl)methyl)-9-methyl-6-morpholino-9H-purin-2-yl)-1H-benzo[d]imidazol-2-yl)ethanol |
| 435 | 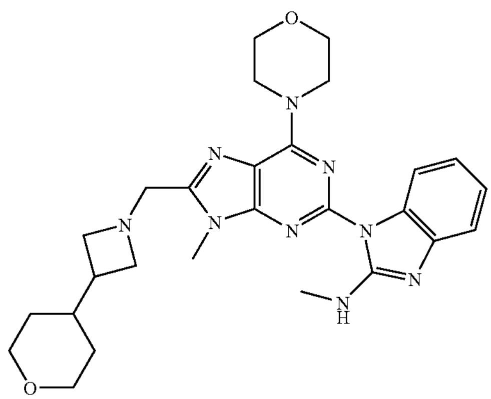 | N-methyl-1-(9-methyl-6-morpholino-8-((3-(tetrahydro-2H-pyran-4-yl)azetidin-1-yl)methyl)-9H-purin-2-yl)-1H-benzo[d]imidazol-2-amine |
| 436 | 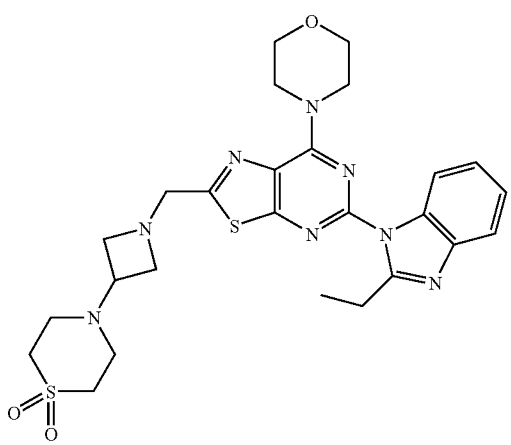 | 4-(5-(2-ethyl-1H-benzo[d]imidazol-1-yl)-2-((3-(1,1-dioxo-thiomorpholino)azetidin-1-yl)methyl)thiazolo[5,4-d]pyrimidin-7-yl)morpholine |
| 437 | 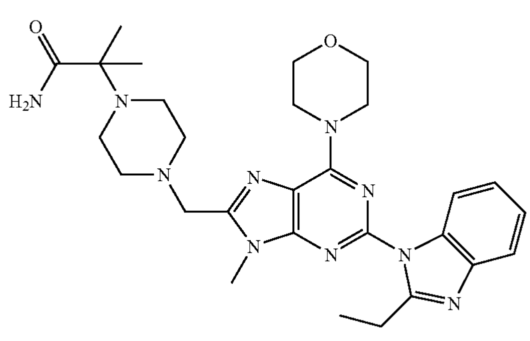 | 2-(4-((2-(2-ethyl-1H-benzo[d]imidazol-1-yl)-9-methyl-6-morpholino-9H-purin-8-yl)methyl)piperazin-1-yl)-2-methylpropanamide |

| No. | Structure | Name |
|---|---|---|
| 438 | 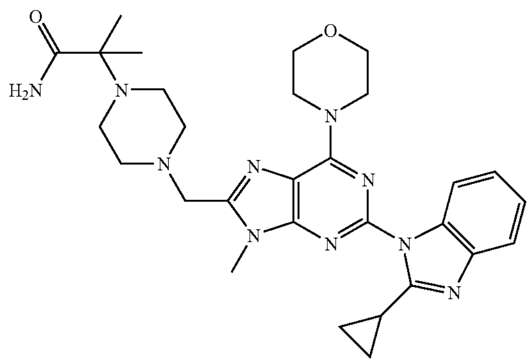 | 2-(4-((2-(2-cyclopropyl-1H-benzo[d]imidazol-1-yl)-9-methyl-6-morpholino-9H-purin-8-yl)methyl)piperazin-1-yl)-2-methylpropanamide |
| 439 | 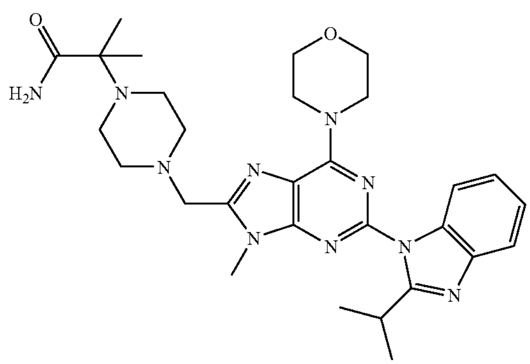 | 2-(4-((2-(2-isopropyl-1H-benzo[d]imidazol-1-yl)-9-methyl-6-morpholino-9H-purin-8-yl)methyl)piperazin-1-yl)-2-methylpropanamide |
| 440 | 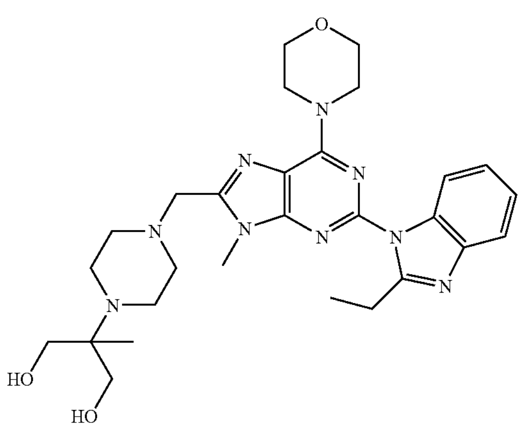 | 2-(4-((2-(2-ethyl-1H-benzo[d]imidazol-1-yl)-9-methyl-6-morpholino-9H-purin-8-yl)methyl)piperazin-1-yl)-2-methylpropane-1,3-diol |
| 441 | 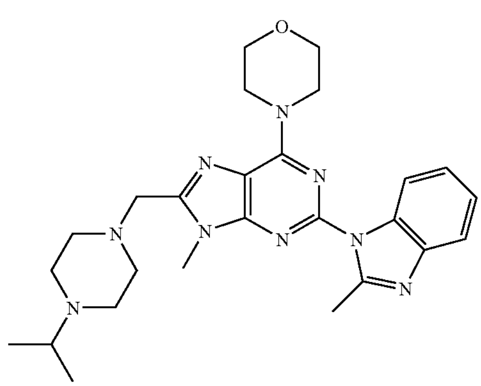 | 4-(8-((4-isopropylpiperazin-1-yl)methyl)-9-methyl-2-(2-methyl-1H-benzo[d]imidazol-1-yl)-9H-purin-6-yl)morpholine |

TABLE 2-continued

| No. | Structure | Name |
|---|---|---|
| 442 | 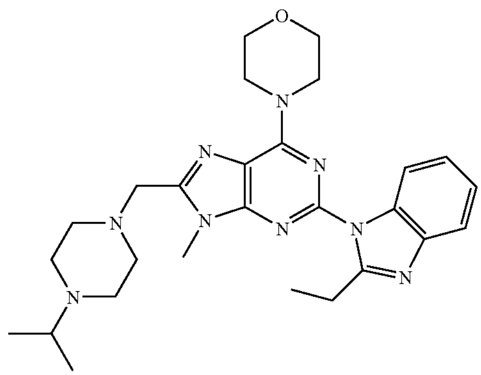 | 4-(2-(2-ethyl-1H-benzo[d]imidazol-1-yl)-8-((4-isopropylpiperazin-1-yl)methyl)-9-methyl-9H-purin-6-yl)morpholine |
| 443 | 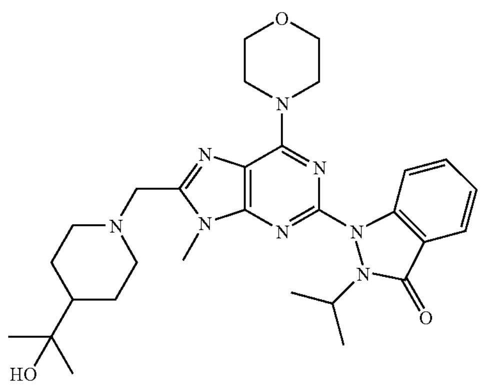 | 1-(8-((4-(2-hydroxypropan-2-yl)piperidin-1-yl)methyl)-9-methyl-6-morpholino-9H-purin-2-yl)-2-isopropyl-1H-indazol-3(2H)-one |
| 444 | 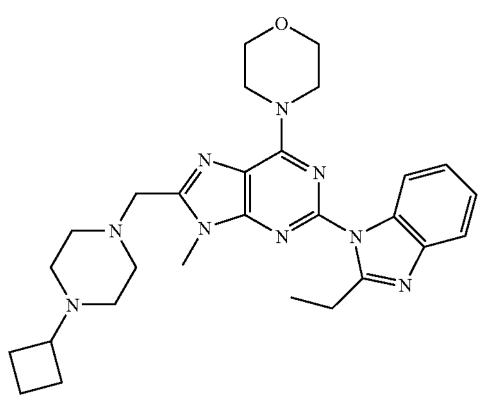 | 4-(8-((4-cyclobutylpiperazin-1-yl)methyl)-2-(2-ethyl-1H-benzo[d]imidazol-1-yl)-9-methyl-9H-purin-6-yl)morpholine |
| 445 | 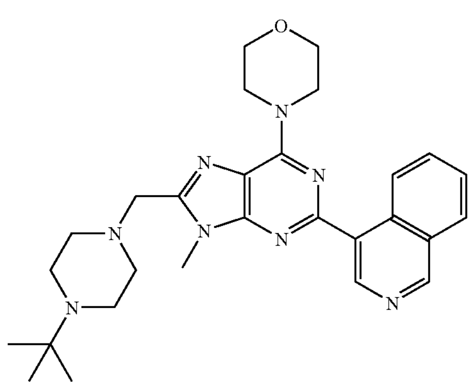 | 4-(8-((4-tert-butylpiperazin-1-yl)methyl)-2-(isoquinolin-4-yl)-9-methyl-9H-purin-6-yl)morpholine |

| No. | Structure | Name |
| --- | --- | --- |
| 446 | 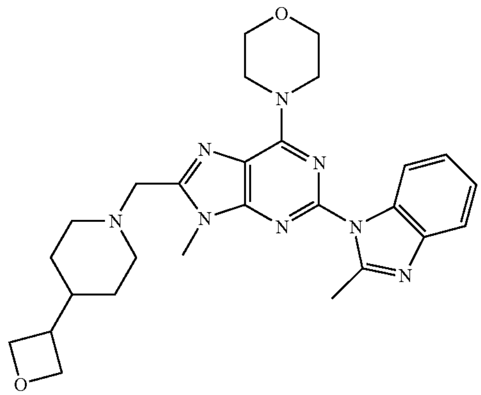 | 4-(9-methyl-2-(2-methyl-1H-benzo[d]imidazol-1-yl)-8-((4-(oxetan-3-yl)piperidin-1-yl)methyl)-9H-purin-6-yl)morpholine |
| 447 | 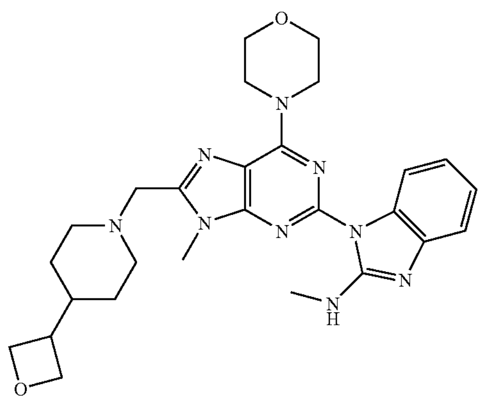 | N-methyl-1-(9-methyl-6-morpholino-8-((4-(oxetan-3-yl)piperidin-1-yl)methyl)-9H-purin-2-yl)-1H-benzo[d]imidazol-2-amine |
| 448 | 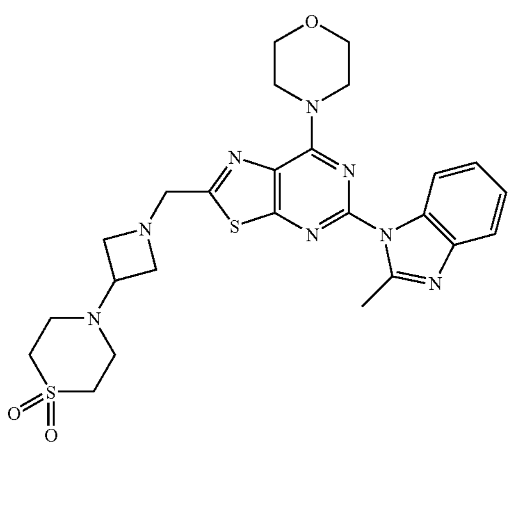 | 4-(5-(2-methyl-1H-benzo[d]imidazol-1-yl)-2-((3-(1,1-dioxo-thiomorpholino)azetidin-1-yl)methyl)thiazolo[5,4-d]pyrimidin-7-yl)morpholine |

TABLE 2-continued

| No. | Structure | Name |
|---|---|---|
| 449 | 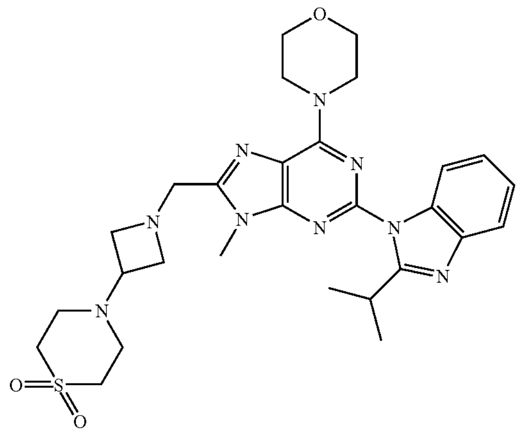 | 4-(2-(2-isopropyl-1H-benzo[d]imidazol-1-yl)-9-methyl-8-((3-(1,1-dioxo-thiomorpholino)azetidin-1-yl)methyl)-9H-purin-6-yl)morpholine |
| 450 | 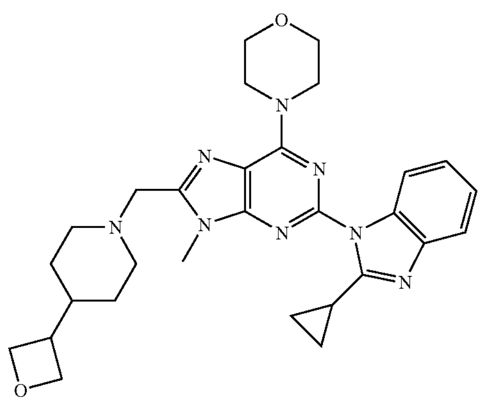 | 4-(2-(2-cyclopropyl-1H-benzo[d]imidazol-1-yl)-9-methyl-8-((4-(oxetan-3-yl)piperidin-1-yl)methyl)-9H-purin-6-yl)morpholine |
| 451 | 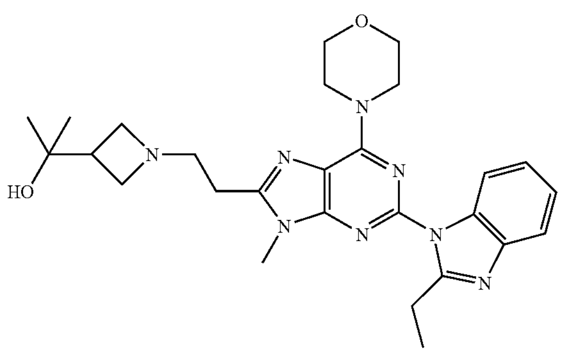 | 2-(1-(2-(2-(2-ethyl-1H-benzo[d]imidazol-1-yl)-9-methyl-6-morpholino-9H-purin-8-yl)ethyl)azetidin-3-yl)propan-2-ol |
| 452 | 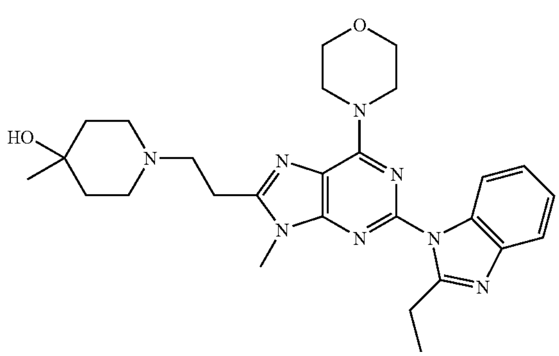 | 1-(2-(2-(2-ethyl-1H-benzo[d]imidazol-1-yl)-9-methyl-6-morpholino-9H-purin-8-yl)ethyl)-4-methylpiperidin-4-ol |

TABLE 2-continued

| No. | Structure | Name |
|---|---|---|
| 453 | 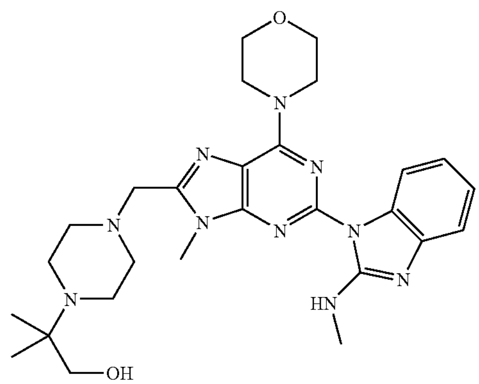 | 2-methyl-2-(4-((9-methyl-2-(2-(methylamino)-1H-benzo[d]imidazol-1-yl)-6-morpholino-9H-purin-8-yl)methyl)piperazin-1-yl)propan-1-ol |
| 454 | 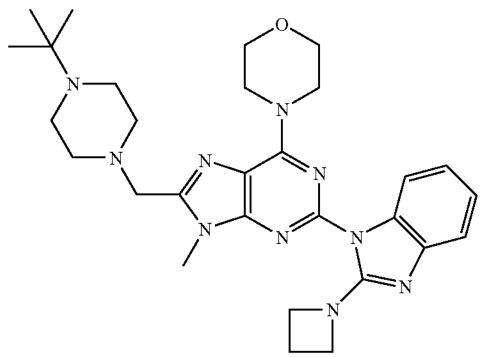 | 4-(2-(2-(azetidin-1-yl)-1H-benzo[d]imidazol-1-yl)-8-((4-tert-butylpiperazin-1-yl)methyl)-9-methyl-9H-purin-6-yl)morpholine |
| 455 | 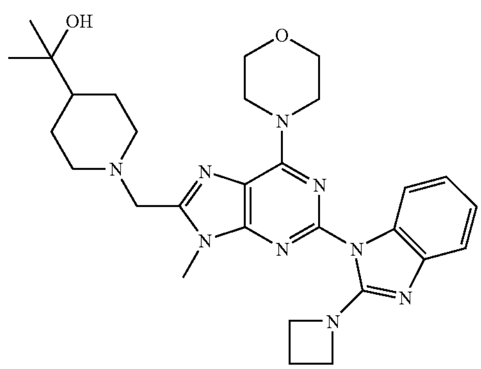 | 2-(1-((2-(2-(azetidin-1-yl)-1H-benzo[d]imidazol-1-yl)-9-methyl-6-morpholino-9H-purin-8-yl)methyl)piperidin-4-yl)propan-2-ol |
| 456 | 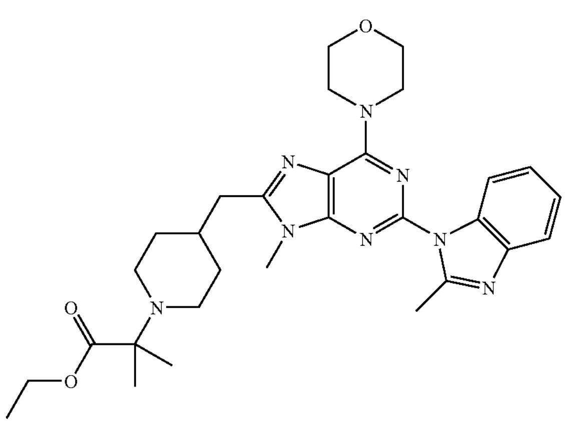 | ethyl 2-methyl-2-(4-((9-methyl-2-(2-methyl-1H-benzo[d]imidazol-1-yl)-6-morpholino-9H-purin-8-yl)methyl)piperidin-1-yl)propanoate |

TABLE 2-continued

| No. | Structure | Name |
|---|---|---|
| 457 | 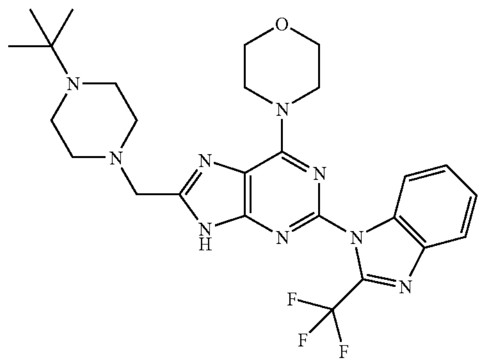 | 4-(8-((4-tert-butylpiperazin-1-yl)methyl)-2-(2-(1,1-difluoroethyl)-1H-benzo[d]imidazol-1-yl)-9H-purin-6-yl)morpholine |
| 458 | 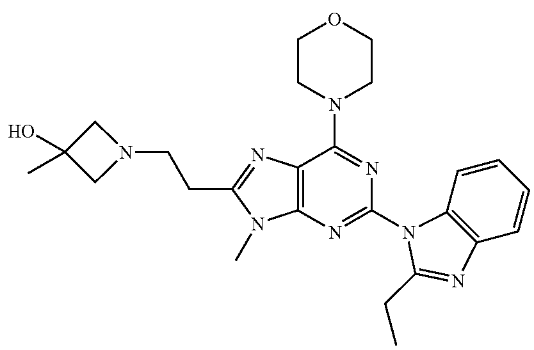 | 1-(2-(2-(2-ethyl-1H-benzo[d]imidazol-1-yl)-9-methyl-6-morpholino-9H-purin-8-yl)ethyl)-3-methylazetidin-3-ol |
| 459 | 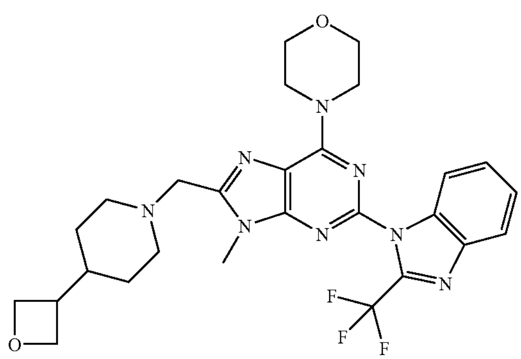 | 4-(2-(2-(1,1-difluoroethyl)-1H-benzo[d]imidazol-1-yl)-9-methyl-8-((4-(oxetan-3-yl)piperidin-1-yl)methyl)-9H-purin-6-yl)morpholine |
| 460 | 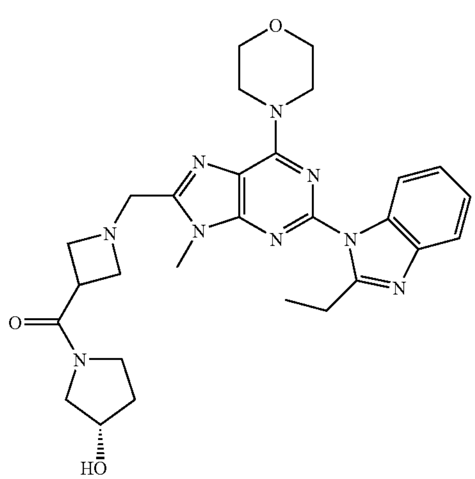 | (S)-(1-((2-(2-ethyl-1H-benzo[d]imidazol-1-yl)-9-methyl-6-morpholino-9H-purin-8-yl)methyl)azetidin-3-yl)(3-hydroxypyrrolidin-1-yl)methanone |

TABLE 2-continued

| No. | Structure | Name |
|---|---|---|
| 461 | 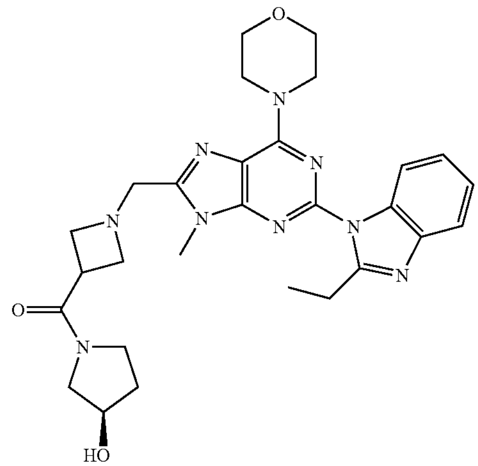 | (R)-(1-((2-(2-ethyl-1H-benzo[d]imidazol-1-yl)-9-methyl-6-morpholino-9H-purin-8-yl)methyl)azetidin-3-yl)(3-hydroxypyrrolidin-1-yl)methanone |
| 462 | 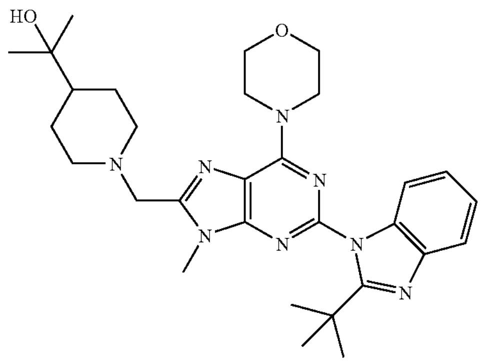 | 2-(1-((2-(2-tert-butyl-1H-benzo[d]imidazol-1-yl)-9-methyl-6-morpholino-9H-purin-8-yl)methyl)piperidin-4-yl)propan-2-ol |
| 463 | 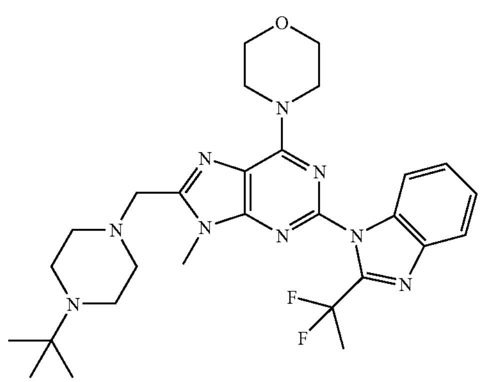 | 4-(8-((4-tert-butylpiperazin-1-yl)methyl)-2-(2-(1,1-difluoroethyl)-1H-benzo[d]imidazol-1-yl)-9-methyl-9H-purin-6-yl)morpholine |
| 464 | 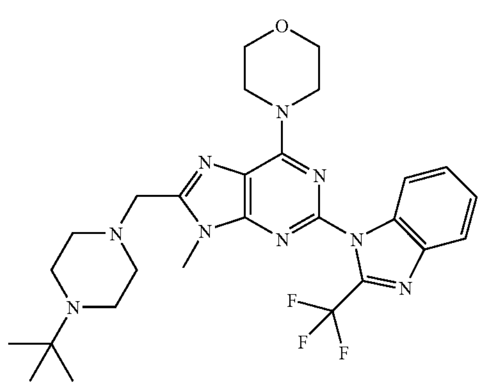 | 4-(8-((4-tert-butylpiperazin-1-yl)methyl)-9-methyl-2-(2-(trifluoromethyl)-1H-benzo[d]imidazol-1-yl)-9H-purin-6-yl)morpholine |

TABLE 2-continued

| No. | Structure | Name |
|---|---|---|
| 465 | 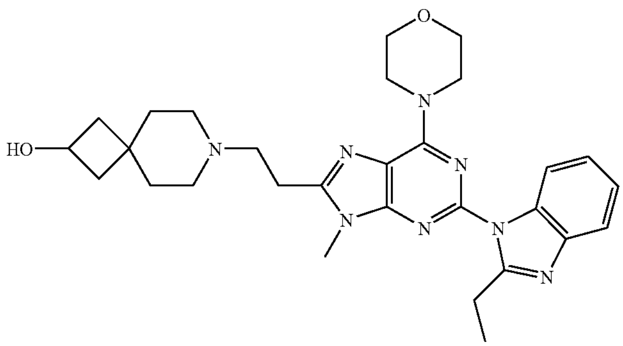 | 7-(2-(2-(2-ethyl-1H-benzo[d]imidazol-1-yl)-9-methyl-6-morpholino-9H-purin-8-yl)ethyl)-7-azaspiro[3.5]nonan-2-ol |
| 466 | 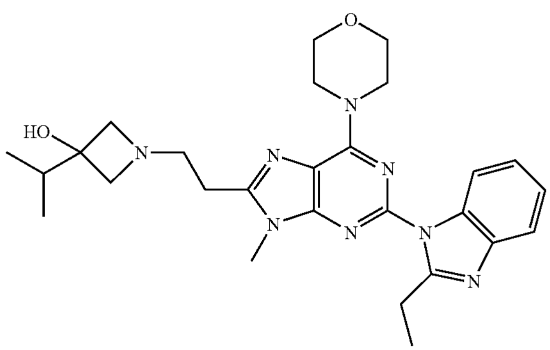 | 1-(2-(2-(2-ethyl-1H-benzo[d]imidazol-1-yl)-9-methyl-6-morpholino-9H-purin-8-yl)ethyl)-3-isopropylazetidin-3-ol |
| 467 | 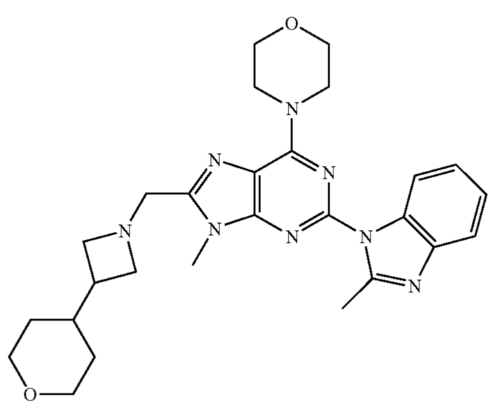 | 4-(9-methyl-2-(2-methyl-1H-benzo[d]imidazol-1-yl)-8-((3-(tetrahydro-2H-pyran-4-yl)azetidin-1-yl)methyl)-9H-purin-6-yl)morpholine |
| 468 | 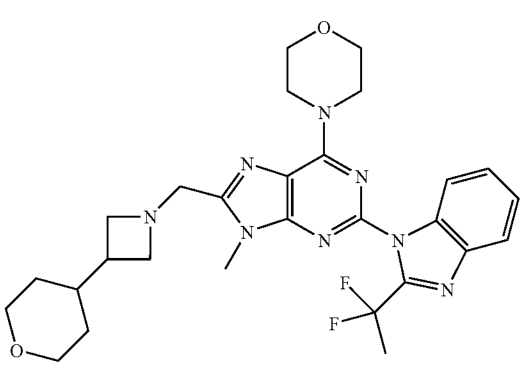 | 4-(2-(2-(1,1-difluoroethyl)-1H-benzo[d]imidazol-1-yl)-9-methyl-8-((3-(tetrahydro-2H-pyran-4-yl)azetidin-1-yl)methyl)-9H-purin-6-yl)morpholine |

TABLE 2-continued

| No. | Structure | Name |
|---|---|---|
| 469 | 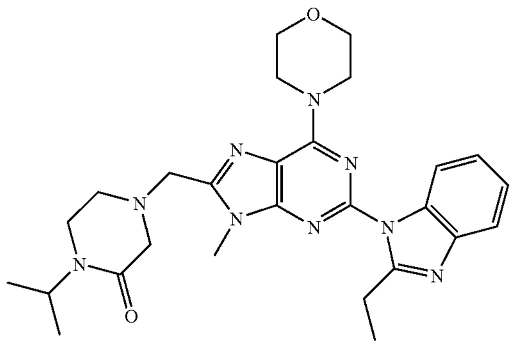 | 4-((2-(2-ethyl-1H-benzo[d]imidazol-1-yl)-9-methyl-6-morpholino-9H-purin-8-yl)methyl)-1-isopropylpiperazin-2-one |
| 470 | 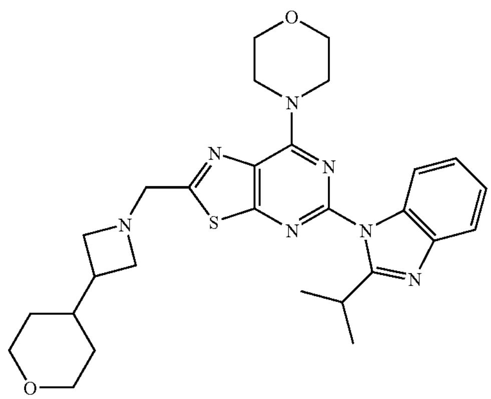 | 4-(5-(2-isopropyl-1H-benzo[d]imidazol-1-yl)-2-((3-(tetrahydro-2H-pyran-4-yl)azetidin-1-yl)methyl)thiazolo[5,4-d]pyrimidin-7-yl)morpholine |
| 471 | 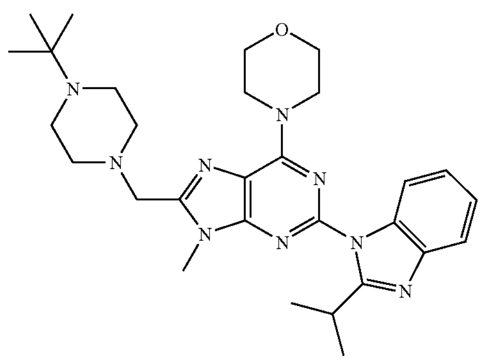 | 4-(8-((4-tert-butylpiperazin-1-yl)methyl)-2-(2-isopropyl-1H-benzo[d]imidazol-1-yl)-9-methyl-9H-purin-6-yl)morpholine |
| 472 | 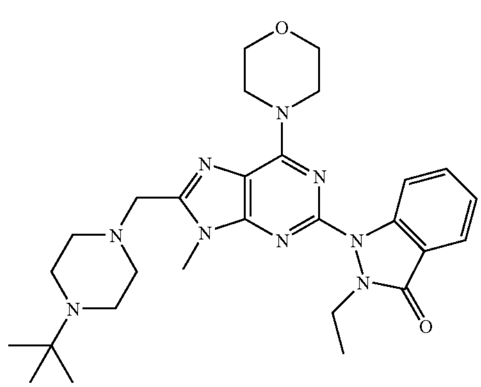 | 1-(8-((4-tert-butylpiperazin-1-yl)methyl)-9-methyl-6-morpholino-9H-purin-2-yl)-2-ethyl-1H-indazol-3(2H)-one |

TABLE 2-continued

| No. | Structure | Name |
|---|---|---|
| 473 | 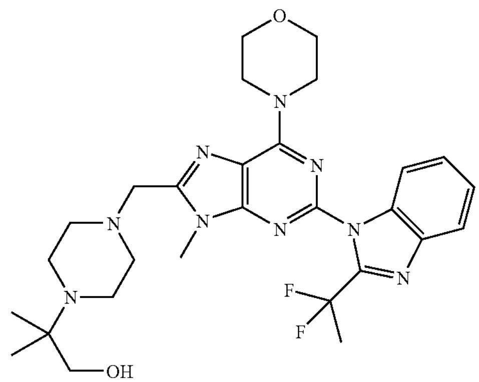 | 2-(4-((2-(2-(1,1-difluoroethyl)-1H-benzo[d]imidazol-1-yl)-9-methyl-6-morpholino-9H-purin-8-yl)methyl)piperazin-1-yl)-2-methylpropan-1-ol |
| 474 | 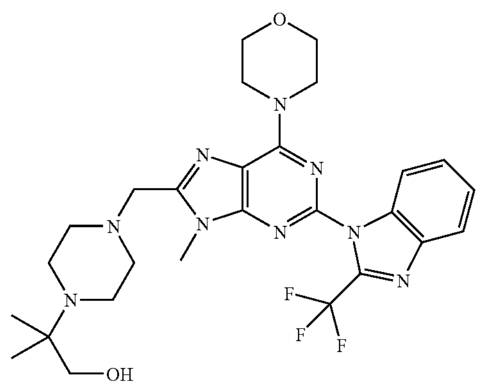 | 2-methyl-2-(4-((9-methyl-6-morpholino-2-(2-(trifluoromethyl)-1H-benzo[d]imidazol-1-yl)-9H-purin-8-yl)methyl)piperazin-1-yl)propan-1-ol |
| 475 | 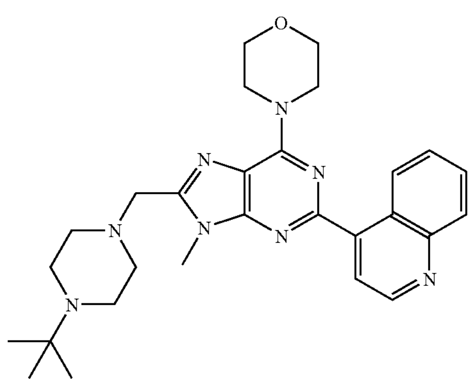 | 4-(8-((4-tert-butylpiperazin-1-yl)methyl)-9-methyl-2-(quinolin-4-yl)-9H-purin-6-yl)morpholine |
| 476 | 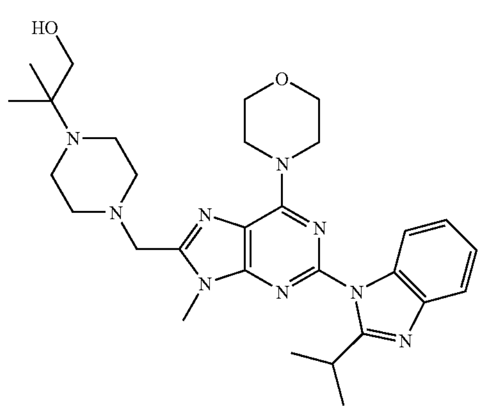 | 2-(4-((2-(2-isopropyl-1H-benzo[d]imidazol-1-yl)-9-methyl-6-morpholino-9H-purin-8-yl)methyl)piperazin-1-yl)-2-methylpropan-1-ol |

TABLE 2-continued

| No. | Structure | Name |
|-----|-----------|------|
| 477 | 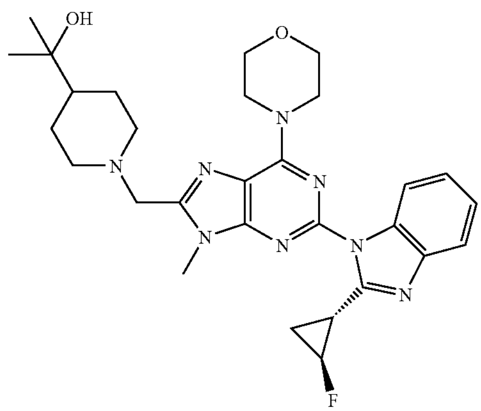 | 2-(1-((2-(2-((1R,2S)-2-fluorocyclopropyl)-1H-benzo[d]imidazol-1-yl)-9-methyl-6-morpholino-9H-purin-8-yl)methyl)piperidin-4-yl)propan-2-ol |
| 478 | 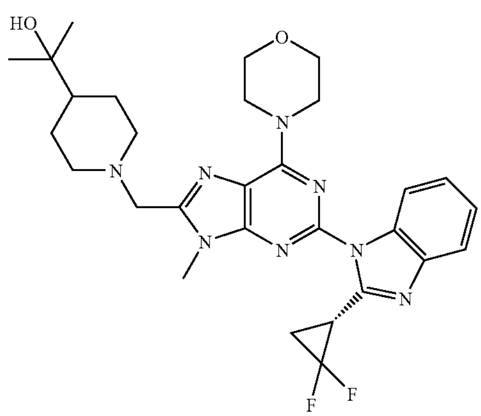 | (R)-2-(1-((2-(2-(2,2-difluorocyclopropyl)-1H-benzo[d]imidazol-1-yl)-9-methyl-6-morpholino-9H-purin-8-yl)methyl)piperidin-4-yl)propan-2-ol |
| 479 | 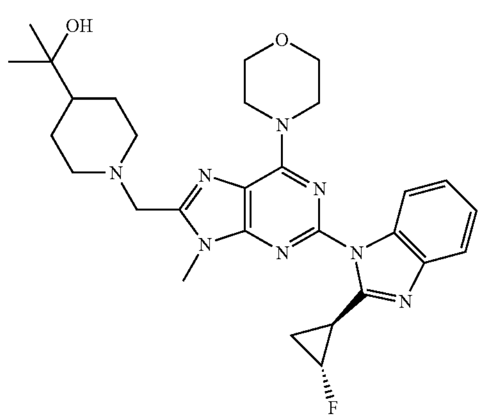 | 2-(1-((2-(2-((1S,2R)-2-fluorocyclopropyl)-1H-benzo[d]imidazol-1-yl)-9-methyl-6-morpholino-9H-purin-8-yl)methyl)piperidin-4-yl)propan-2-ol |

TABLE 2-continued

| No. | Structure | Name |
|---|---|---|
| 480 | 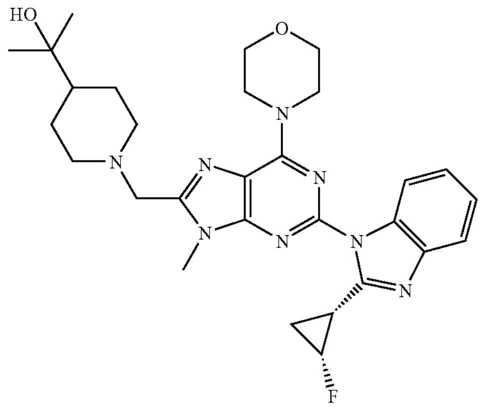 | 2-(1-((2-(2-((R,2R)-2-fluorocyclopropyl)-1H-benzo[d]imidazol-1-yl)-9-methyl-6-morpholino-9H-purin-8-yl)methyl)piperidin-4-yl)propan-2-ol |
| 481 | 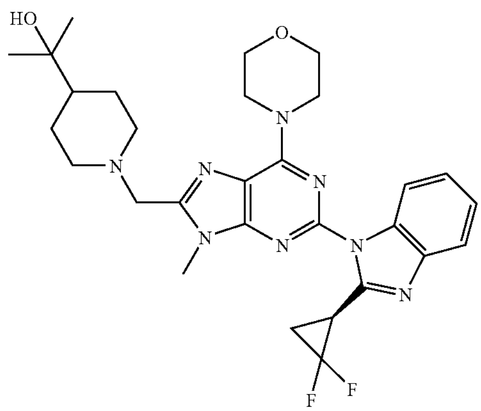 | (S)-2-(1-((2-(2-(2,2-difluorocyclopropyl)-1H-benzo[d]imidazol-1-yl)-9-methyl-6-morpholino-9H-purin-8-yl)methyl)piperidin-4-yl)propan-2-ol |
| 482 | 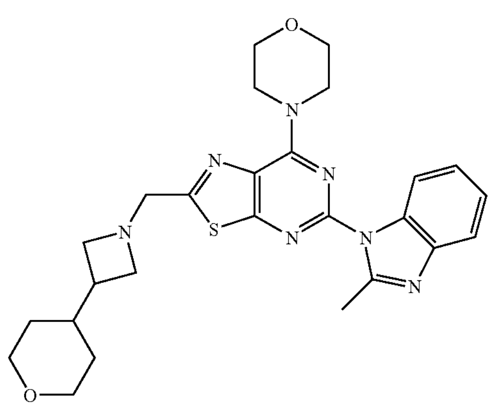 | 4-(5-(2-methyl-1H-benzo[d]imidazol-1-yl)-2-((3-(tetrahydro-2H-pyran-4-yl)azetidin-1-yl)methyl)thiazolo[5,4-d]pyrimidin-7-yl)morpholine |
| 483 | 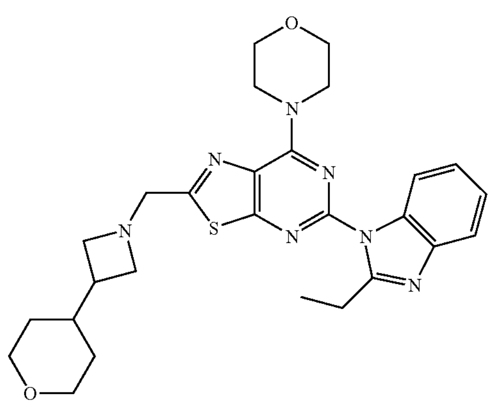 | 4-(5-(2-ethyl-1H-benzo[d]imidazol-1-yl)-2-((3-(tetrahydro-2H-pyran-4-yl)azetidin-1-yl)methyl)thiazolo[5,4-d]pyrimidin-7-yl)morpholine |

TABLE 2-continued

| No. | Structure | Name |
| --- | --- | --- |
| 484 | 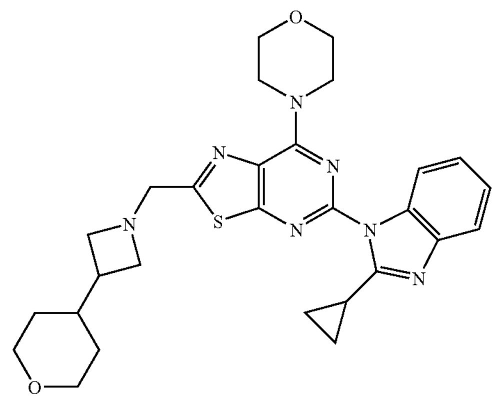 | 4-(5-(2-cyclopropyl-1H-benzo[d]imidazol-1-yl)-2-((3-(tetrahydro-2H-pyran-4-yl)azetidin-1-yl)methyl)thiazolo[5,4-d]pyrimidin-7-yl)morpholine |
| 485 | 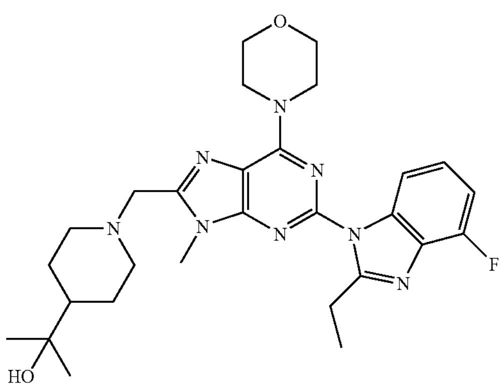 | 2-(1-((2-(2-ethyl-4-fluoro-1H-benzo[d]imidazol-1-yl)-9-methyl-6-morpholino-9H-purin-8-yl)methyl)piperidin-4-yl)propan-2-ol |
| 486 | 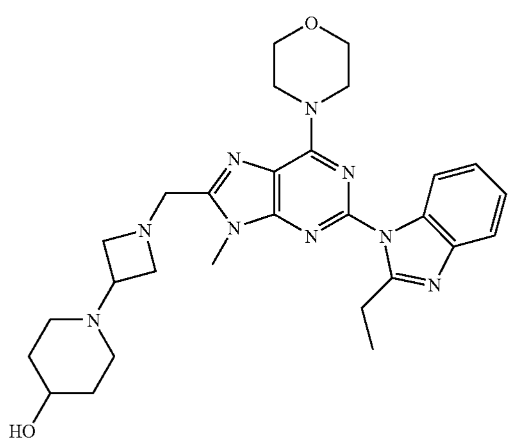 | 1-(1-((2-(2-ethyl-1H-benzo[d]imidazol-1-yl)-9-methyl-6-morpholino-9H-purin-8-yl)methyl)azetidin-3-yl)piperidin-4-ol |

TABLE 2-continued

| No. | Structure | Name |
|---|---|---|
| 487 | 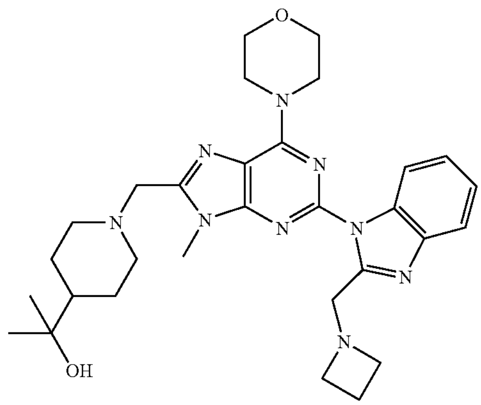 | 2-(1-((2-(2-(azetidin-1-ylmethyl)-1H-benzo[d]imidazol-1-yl)-9-methyl-6-morpholino-9H-purin-8-yl)methyl)piperidin-4-yl)propan-2-ol |
| 488 | 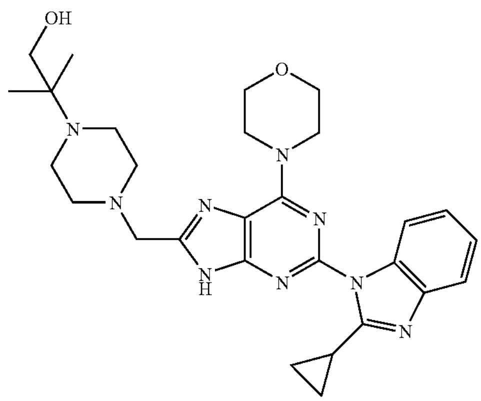 | 2-(4-((2-(2-cyclopropyl-1H-benzo[d]imidazol-1-yl)-6-morpholino-9H-purin-8-yl)methyl)piperazin-1-yl)-2-methylpropan-1-ol |
| 489 | 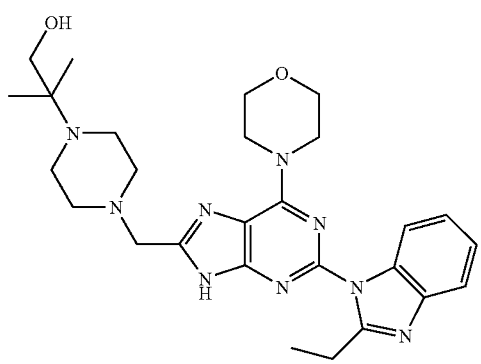 | 2-(4-((2-(2-ethyl-1H-benzo[d]imidazol-1-yl)-6-morpholino-9H-purin-8-yl)methyl)piperazin-1-yl)-2-methylpropan-1-ol |
| 490 | 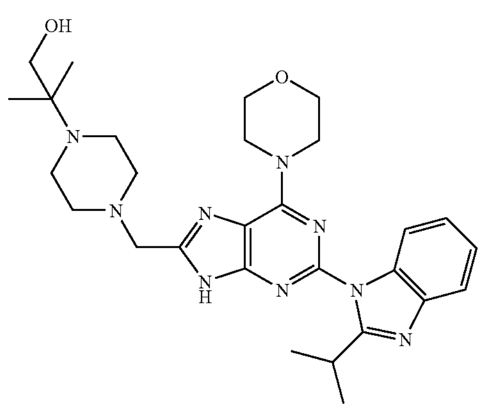 | 2-(4-((2-(2-isopropyl-1H-benzo[d]imidazol-1-yl)-6-morpholino-9H-purin-8-yl)methyl)piperazin-1-yl)-2-methylpropan-1-ol |

| No. | Structure | Name |
|---|---|---|
| 491 | 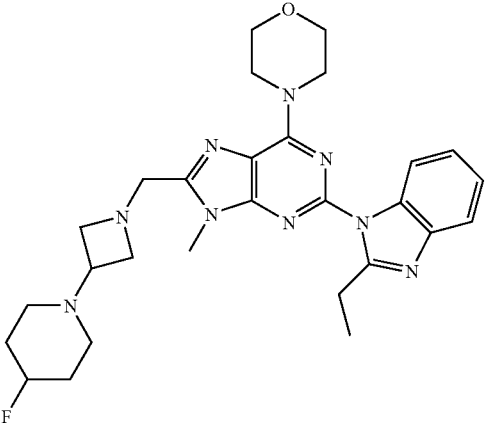 | 4-(2-(2-ethyl-1H-benzo[d]imidazol-1-yl)-8-((3-(4-fluoropiperidin-1-yl)azetidin-1-yl)methyl)-9-methyl-9H-purin-6-yl)morpholine |
| 492 | 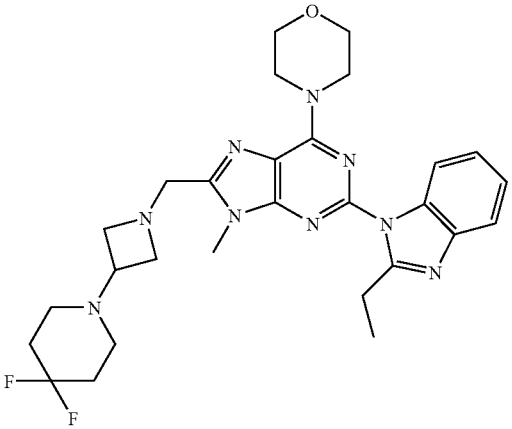 | 4-(8-((3-(4,4-difluoropiperidin-1-yl)azetidin-1-yl)methyl)-2-(2-ethyl-1H-benzo[d]imidazol-1-yl)-9-methyl-9H-purin-6-yl)morpholine |
| 493 | 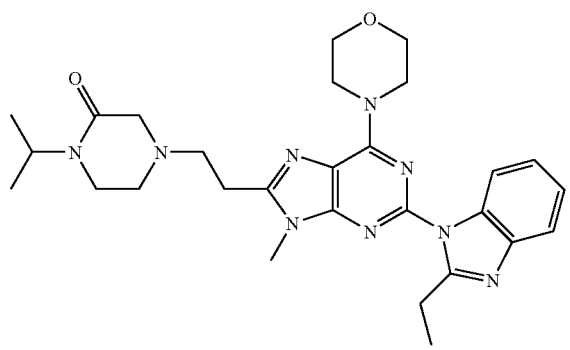 | 4-(2-(2-(2-ethyl-1H-benzo[d]imidazol-1-yl)-9-methyl-6-morpholino-9H-purin-8-yl)ethyl)-1-isopropylpiperazin-2-one |

TABLE 2-continued
| No. | Structure | Name |
|---|---|---|
| 494 | 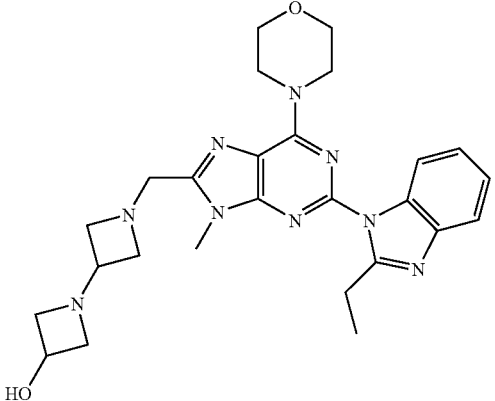 | 1'-((2-(2-ethyl-1H-benzo[d]imidazol-1-yl)-9-methyl-6-morpholino-9H-purin-8-yl)methyl)-1,3'-biazetidin-3-ol |
| 495 | 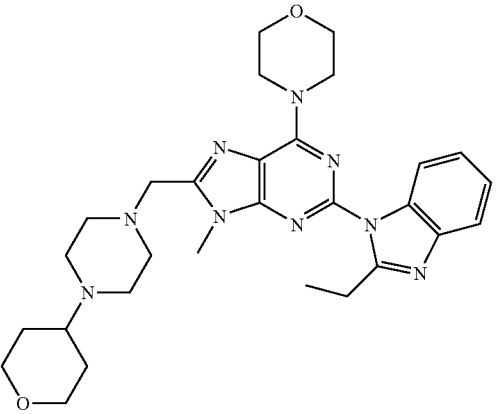 | 4-(2-(2-ethyl-1H-benzo[d]imidazol-1-yl)-9-methyl-8-((4-(tetrahydro-2H-pyran-4-yl)piperazin-1-yl)methyl)-9H-purin-6-yl)morpholine |
| 496 | 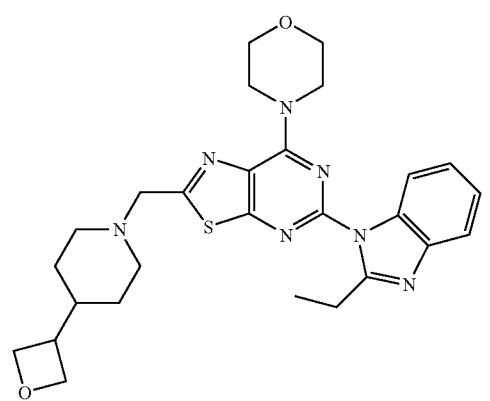 | 4-(5-(2-ethyl-1H-benzo[d]imidazol-1-yl)-2-((4-(oxetan-3-yl)piperidin-1-yl)methyl)thiazolo[5,4-d]pyrimidin-7-yl)morpholine |

TABLE 2-continued

| No. | Structure | Name |
|---|---|---|
| 497 | 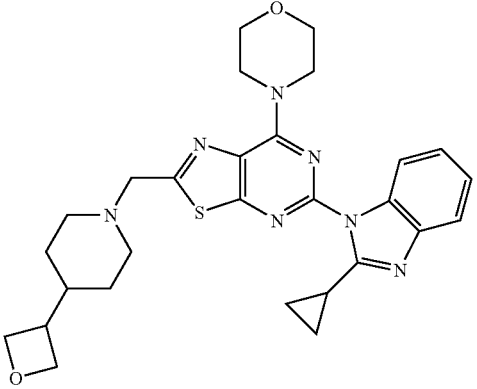 | 4-(5-(2-cyclopropyl-1H-benzo[d]imidazol-1-yl)-2-((4-(oxetan-3-yl)piperidin-1-yl)methyl)thiazolo[5,4-d]pyrimidin-7-yl)morpholine |
| 498 | 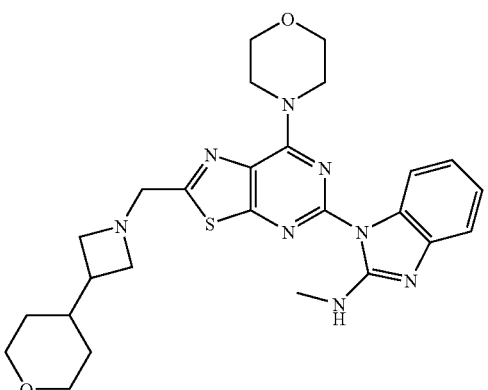 | N-methyl-1-(7-morpholino-2-((3-(tetrahydro-2H-pyran-4-yl)azetidin-1-yl)methyl)thiazolo[5,4-d]pyrimidin-5-yl)-1H-benzo[d]imidazol-2-amine |
| 499 | 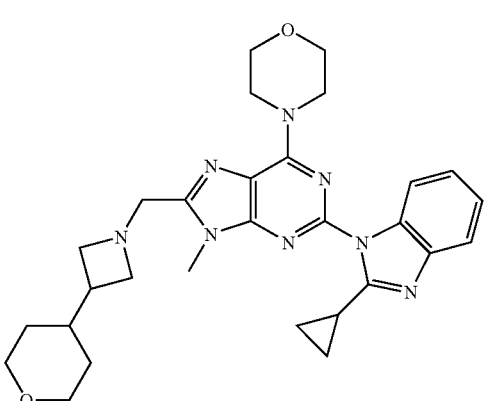 | 4-(2-(2-cyclopropyl-1H-benzo[d]imidazol-1-yl)-9-methyl-8-((3-(tetrahydro-2H-pyran-4-yl)azetidin-1-yl)methyl)-9H-purin-6-yl)morpholine |
| 500 | 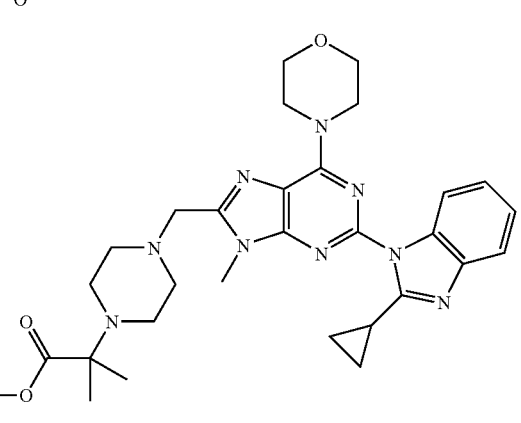 | ethyl 2-(4-((2-(2-cyclopropyl-1H-benzo[d]imidazol-1-yl)-9-methyl-6-morpholino-9H-purin-8-yl)methyl)piperazin-1-yl)-2-methylpropanoate |

TABLE 2-continued
| No. | Structure | Name |
|---|---|---|
| 501 | 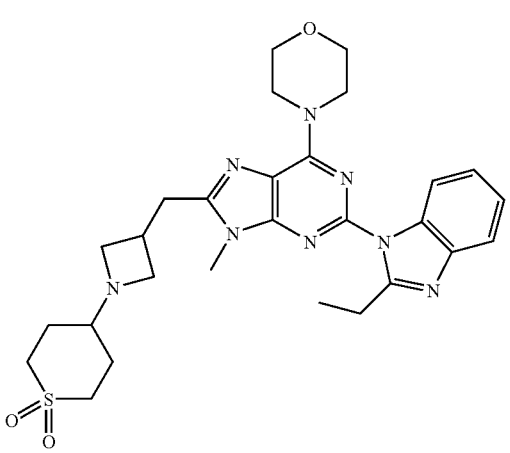 | 4-(2-(2-ethyl-1H-benzo[d]imidazol-1-yl)-9-methyl-8-((1-(tetrahydro-2H-(1,1-dioxo)-thiopyran-4-yl)azetidin-3-yl)methyl)-9H-purin-6-yl)morpholine |
| 502 | 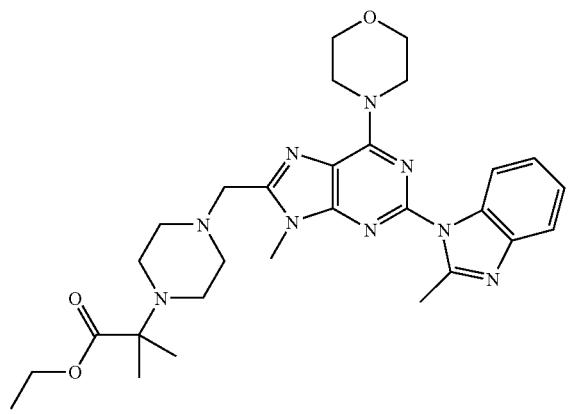 | ethyl 2-methyl-2-(4-((9-methyl-2-(2-methyl-1H-benzo[d]imidazol-1-yl)-6-morpholino-9H-purin-8-yl)methyl)piperazin-1-yl)propanoate |
| 503 | 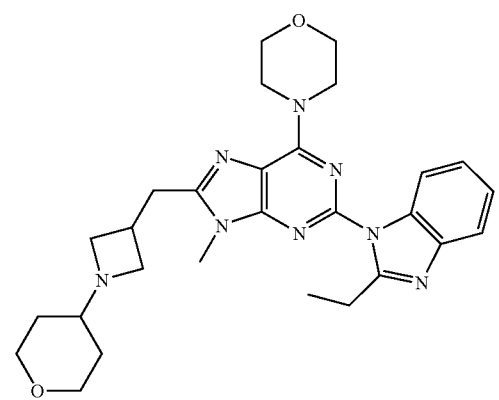 | 4-(2-(2-ethyl-1H-benzo[d]imidazol-1-yl)-9-methyl-8-((1-(tetrahydro-2H-pyran-4-yl)azetidin-3-yl)methyl)-9H-purin-6-yl)morpholine |

TABLE 2-continued

| No. | Structure | Name |
|---|---|---|
| 504 | 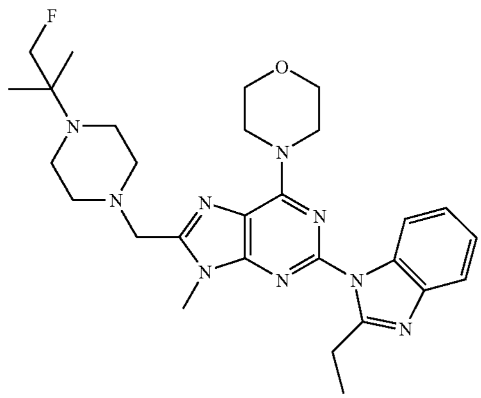 | 4-(2-(2-ethyl-1H-benzo[d]imidazol-1-yl)-8-((4-(1-fluoro-2-methylpropan-2-yl)piperazin-1-yl)methyl)-9-methyl-9H-purin-6-yl)morpholine |
| 505 | 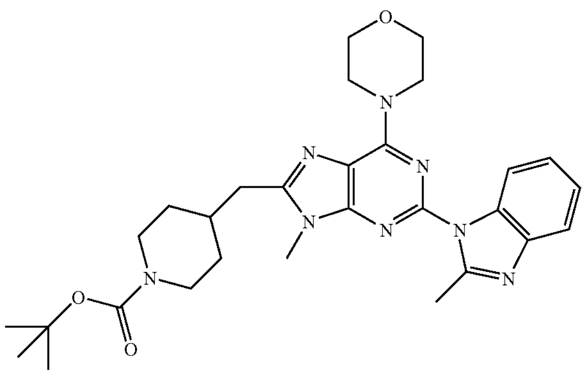 | tert-butyl 4-((9-methyl-2-(2-methyl-1H-benzo[d]imidazol-1-yl)-6-morpholino-9H-purin-8-yl)methyl)piperidine-1-carboxylate |
| 506 | 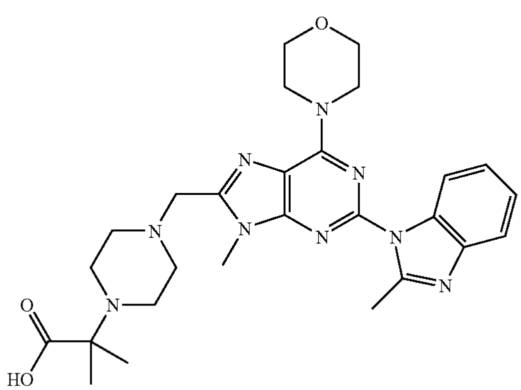 | 2-methyl-2-(4-((9-methyl-2-(2-methyl-1H-benzo[d]imidazol-1-yl)-6-morpholino-9H-purin-8-yl)methyl)piperazin-1-yl)propanoic acid |
| 507 | 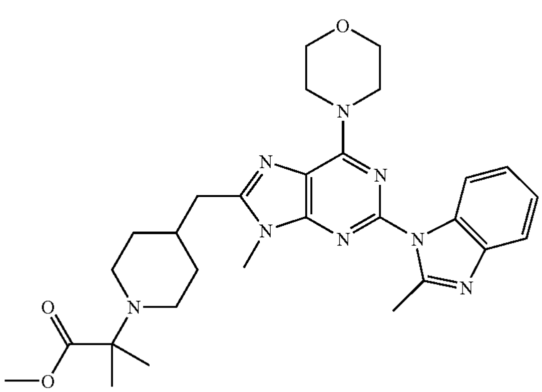 | methyl 2-methyl-2-(4-((9-methyl-2-(2-methyl-1H-benzo[d]imidazol-1-yl)-6-morpholino-9H-purin-8-yl)methyl)piperidin-1-yl)propanoate |

TABLE 2-continued

| No. | Structure | Name |
|---|---|---|
| 508 | 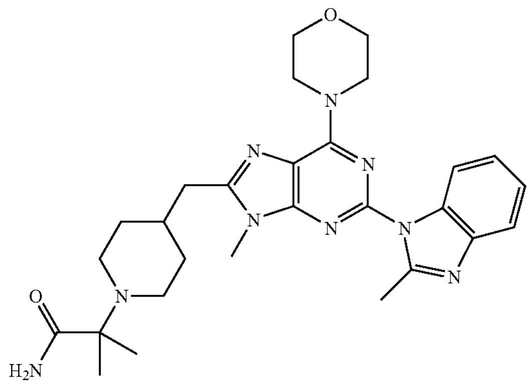 | 2-methyl-2-(4-((9-methyl-2-(2-methyl-1H-benzo[d]imidazol-1-yl)-6-morpholino-9H-purin-8-yl)methyl)piperidin-1-yl)propanamide |
| 509 | 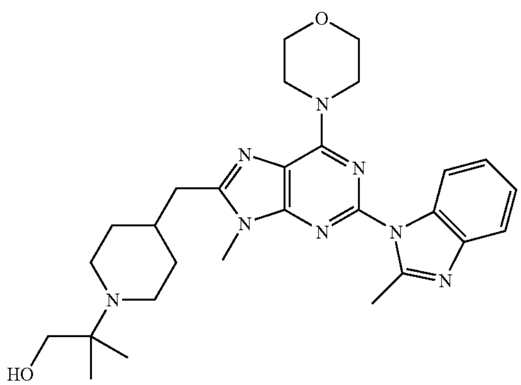 | 2-methyl-2-(4-((9-methyl-2-(2-methyl-1H-benzo[d]imidazol-1-yl)-6-morpholino-9H-purin-8-yl)methyl)piperidin-1-yl)propan-1-ol |
| 510 | 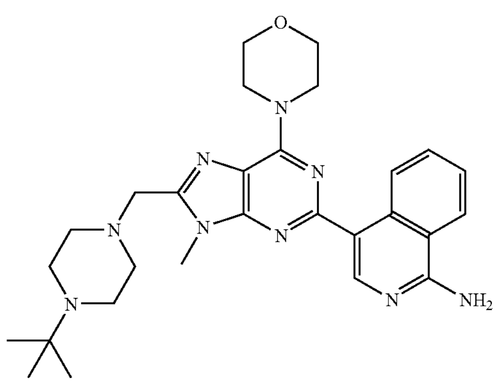 | 4-(8-((4-tert-butylpiperazin-1-yl)methyl)-9-methyl-6-morpholino-9H-purin-2-yl)isoquinolin-1-amine |
| 511 | 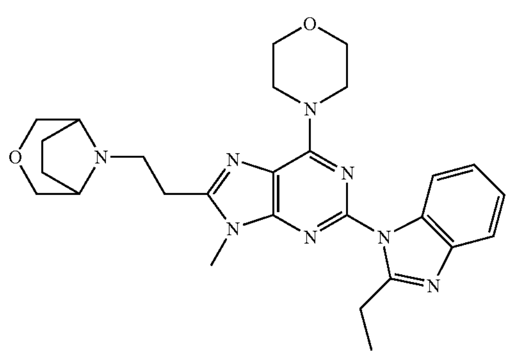 | 8-(2-(2-(2-ethyl-1H-benzo[d]imidazol-1-yl)-9-methyl-6-morpholino-9H-purin-8-yl)ethyl)-3-oxa-8-azabicyclo[3.2.1]octane |

TABLE 2-continued

| No. | Structure | Name |
| --- | --- | --- |
| 512 | 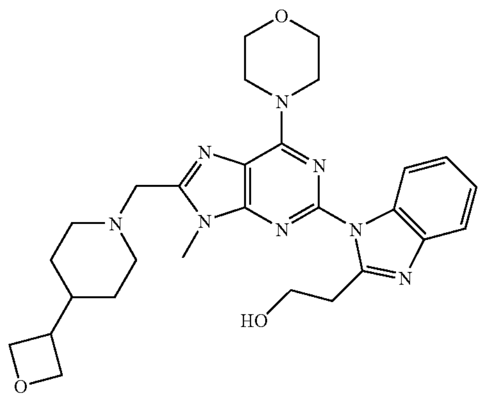 | 2-(1-(9-methyl-6-morpholino-8-((4-(oxetan-3-yl)piperidin-1-yl)methyl)-9H-purin-2-yl)-1H-benzo[d]imidazol-2-yl)ethanol |
| 513 | 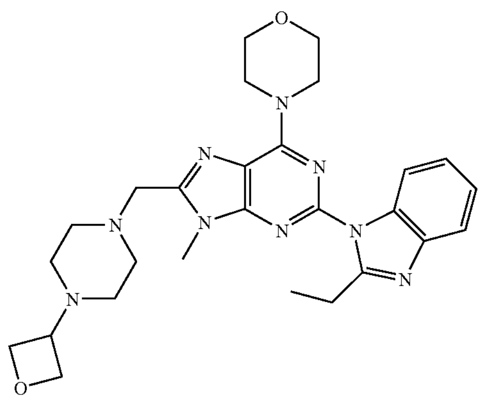 | 4-(2-(2-ethyl-1H-benzo[d]imidazol-1-yl)-9-methyl-8-((4-(oxetan-3-yl)piperazin-1-yl)methyl)-9H-purin-6-yl)morpholine |
| 514 | 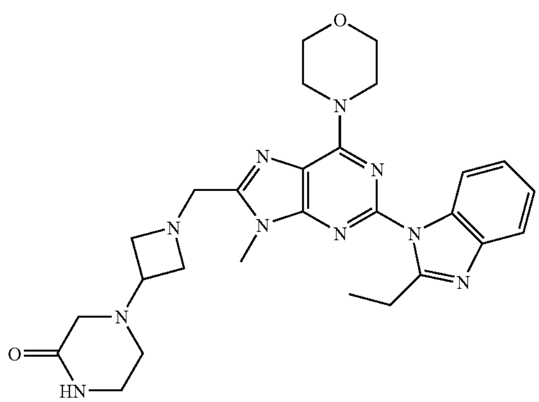 | 4-(1-((2-(2-ethyl-1H-benzo[d]imidazol-1-yl)-9-methyl-6-morpholino-9H-purin-8-yl)methyl)azetidin-3-yl)piperazin-2-one |
| 515 | 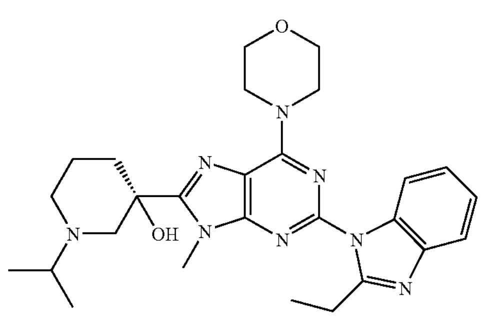 | (S)-3-(2-(2-ethyl-1H-benzo[d]imidazol-1-yl)-9-methyl-6-morpholino-9H-purin-8-yl)-1-isopropylpiperidin-3-ol |

| No. | Structure | Name |
|---|---|---|
| 516 | 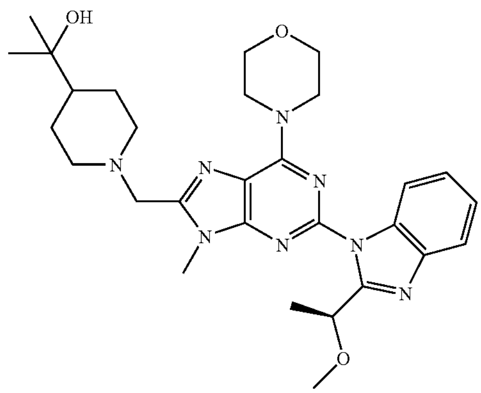 | (S)-2-(1-((2-(2-(1-methoxyethyl)-1H-benzo[d]imidazol-1-yl)-9-methyl-6-morpholino-9H-purin-8-yl)methyl)piperidin-4-yl)propan-2-ol |
| 517 | 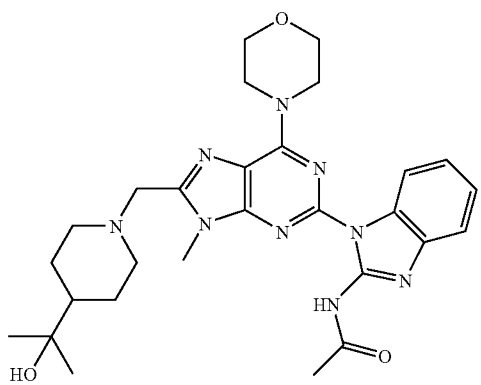 | N-(1-(8-((4-(2-hydroxypropan-2-yl)piperidin-1-yl)methyl)-9-methyl-6-morpholino-9H-purin-2-yl)-1H-benzo[d]imidazol-2-yl)acetamide |
| 518 | 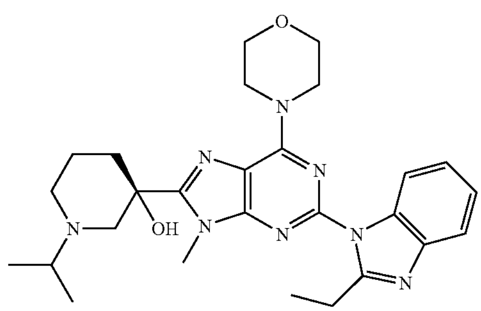 | (R)-3-(2-(2-ethyl-1H-benzo[d]imidazol-1-yl)-9-methyl-6-morpholino-9H-purin-8-yl)-1-isopropylpiperidin-3-ol |
| 519 | 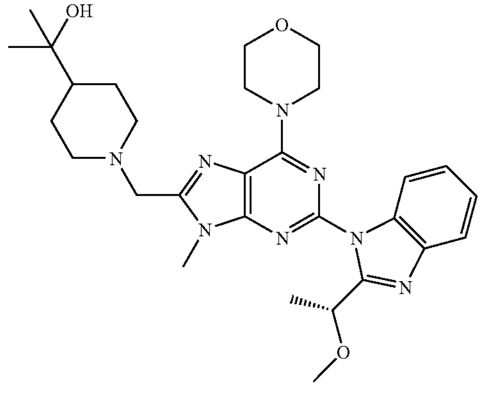 | (R)-2-(1-((2-(2-(1-methoxyethyl)-1H-benzo[d]imidazol-1-yl)-9-methyl-6-morpholino-9H-purin-8-yl)methyl)piperidin-4-yl)propan-2-ol |

TABLE 2-continued

| No. | Structure | Name |
|---|---|---|
| 520 | 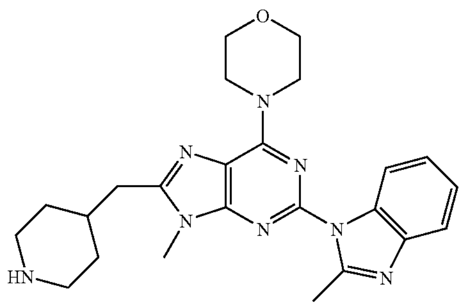 | 4-(9-methyl-2-(2-methyl-1H-benzo[d]imidazol-1-yl)-8-(piperidin-4-ylmethyl)-9H-purin-6-yl)morpholine |
| 521 | 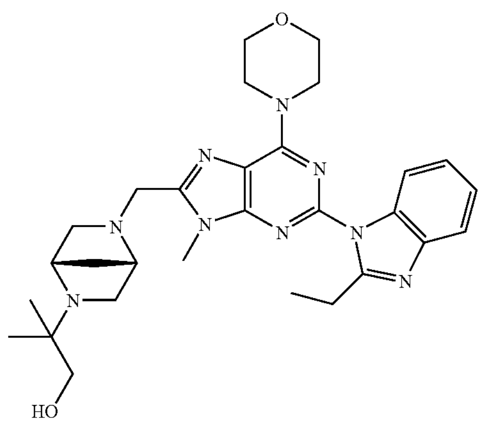 | 2-((1S,4S)-5-((2-(2-ethyl-1H-benzo[d]imidazol-1-yl)-9-methyl-6-morpholino-9H-purin-8-yl)methyl)-2,5-diazabicyclo[2.2.1]heptan-2-yl)-2-methylpropan-1-ol |
| 522 | 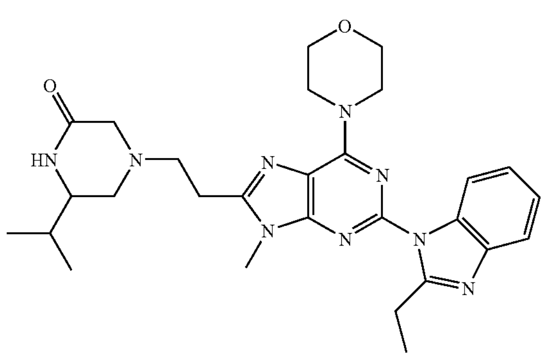 | 4-(2-(2-(2-ethyl-1H-benzo[d]imidazol-1-yl)-9-methyl-6-morpholino-9H-purin-8-yl)ethyl)-6-isopropylpiperazin-2-one |
| 523 | 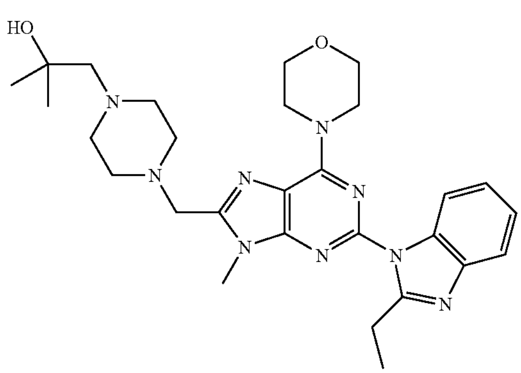 | 1(4-((2-(2-ethyl-1H-benzo[d]imidazol-1-yl)-9-methyl-6-morpholino-9H-purin-8-yl)methyl)piperazin-1-yl)-2-methylpropan-2-ol |

| No. | Structure | Name |
|---|---|---|
| 524 | 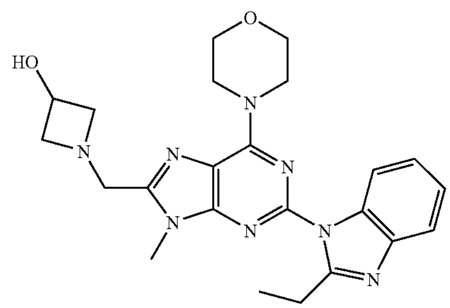 | 1-((2-(2-ethyl-1H-benzo[d]imidazol-1-yl)-9-methyl-6-morpholino-9H-purin-8-yl)methyl)azetidin-3-ol |
| 525 | 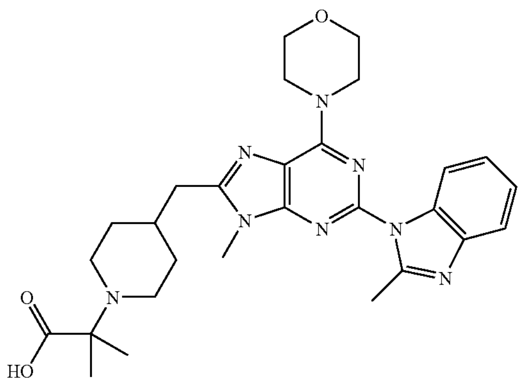 | 2-methyl-2-(4-((9-methyl-2-(2-methyl-1H-benzo[d]imidazol-1-yl)-6-morpholino-9H-purin-8-yl)methyl)piperidin-1-yl)propanoic acid |
| 526 | 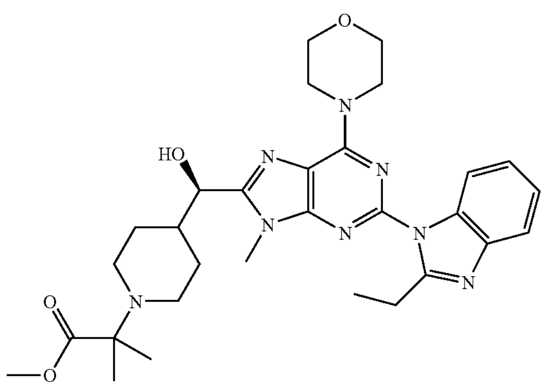 | (R)-methyl 2-(4-((2-(2-ethyl-1H-benzo[d]imidazol-1-yl)-9-methyl-6-morpholino-9H-purin-8-yl)(hydroxy)methyl)piperidin-1-yl)-2-methylpropanoate |
| 527 | 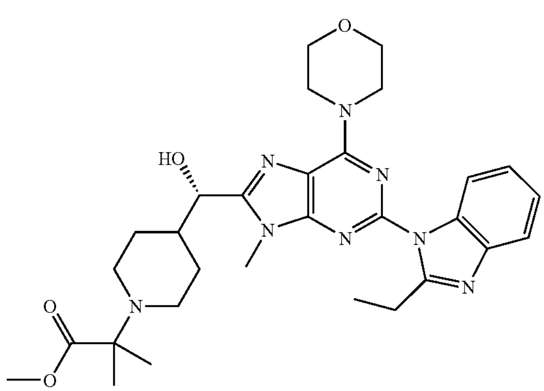 | (S)-methyl 2-(4-((2-(2-ethyl-1H-benzo[d]imidazol-1-yl)-9-methyl-6-morpholino-9H-purin-8-yl)(hydroxy)methyl)piperidin-1-yl)-2-methylpropanoate |

| No. | Structure | Name |
| --- | --- | --- |
| 528 | 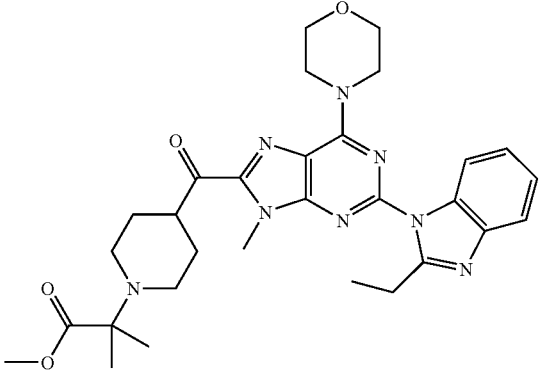 | methyl 2-(4-(2-(2-ethyl-1H-benzo[d]imidazol-1-yl)-9-methyl-6-morpholino-9H-purine-8-carbonyl)piperidin-1-yl)-2-methylpropanoate |
| 529 | 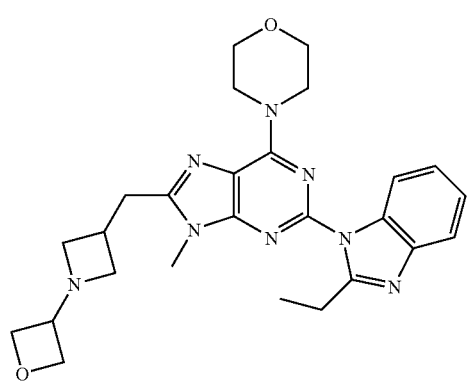 | 4-(2-(2-ethyl-1H-benzo[d]imidazol-1-yl)-9-methyl-8-((1-(oxetan-3-yl)azetidin-3-yl)methyl)-9H-purin-6-yl)morpholine |
| 530 | 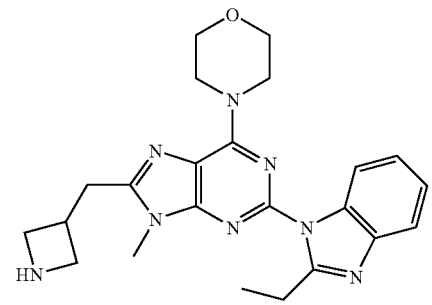 | 4-(8-(azetidin-3-ylmethyl)-2-(2-ethyl-1H-benzo[d]imidazol-1-yl)-9-methyl-9H-purin-6-yl)morpholine |
| 531 | 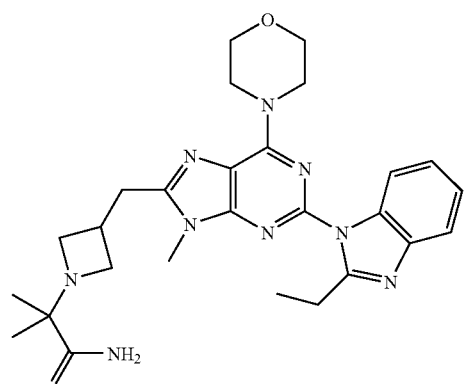 | 2-(3-((2-(2-ethyl-1H-benzo[d]imidazol-1-yl)-9-methyl-6-morpholino-9H-purin-8-yl)methyl)azetidin-1-yl)-2-methylpropanamide |

TABLE 2-continued

| No. | Structure | Name |
|---|---|---|
| 532 | 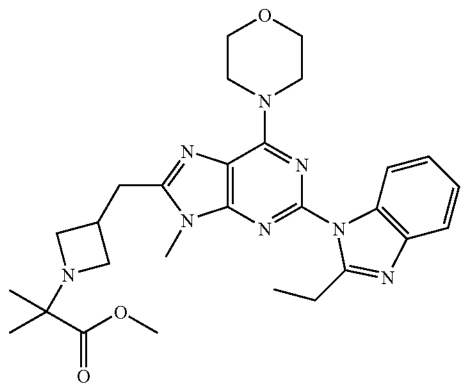 | methyl 2-(3-((2-(2-ethyl-1H-benzo[d]imidazol-1-yl)-9-methyl-6-morpholino-9H-purin-8-yl)methyl)azetidin-1-yl)-2-methylpropanoate |
| 533 | 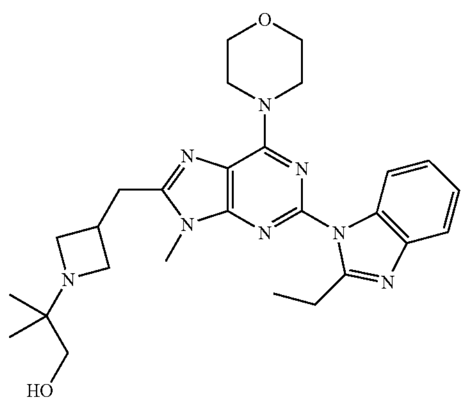 | 2-(3-((2-(2-ethyl-1H-benzo[d]imidazol-1-yl)-9-methyl-6-morpholino-9H-purin-8-yl)methyl)azetidin-1-yl)-2-methylpropan-1-ol |
| 534 | 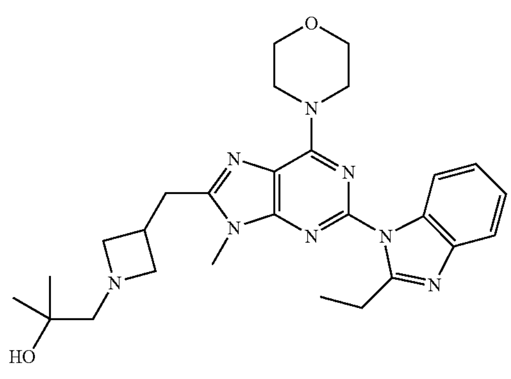 | 1-(3-((2-(2-ethyl-1H-benzo[d]imidazol-1-yl)-9-methyl-6-morpholino-9H-purin-8-yl)methyl)azetidin-1-yl)-2-methylpropan-2-ol |
| 535 | 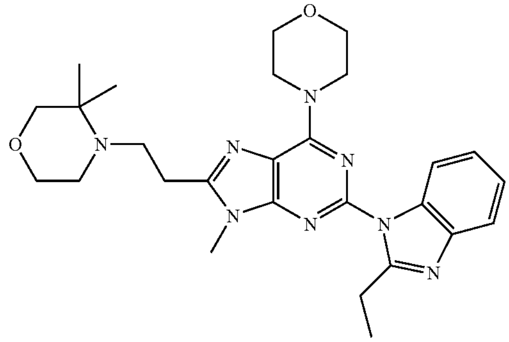 | 4-(2-(2-(2-ethyl-1H-benzo[d]imidazol-1-yl)-9-methyl-6-morpholino-9H-purin-8-yl)ethyl)-3,3-dimethylmorpholine |

TABLE 2-continued

| No. | Structure | Name |
|---|---|---|
| 536 | 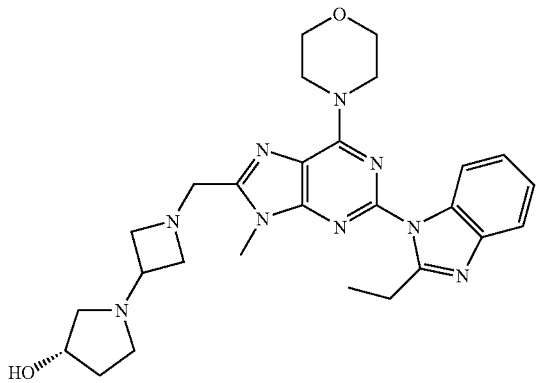 | (S)-1-(1-((2-(2-ethyl-1H-benzo[d]imidazol-1-yl)-9-methyl-6-morpholino-9H-purin-8-yl)methyl)azetidin-3-yl)pyrrolidin-3-ol |
| 537 | 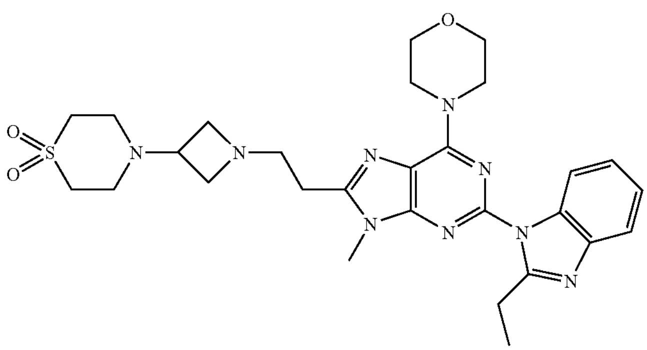 | 4-(2-(2-ethyl-1H-benzo[d]imidazol-1-yl)-9-methyl-8-(2-(3-(1,1-dioxo-thiomorpholino)azetidin-1-yl)ethyl)-9H-purin-6-yl)morpholine |
| 538 | 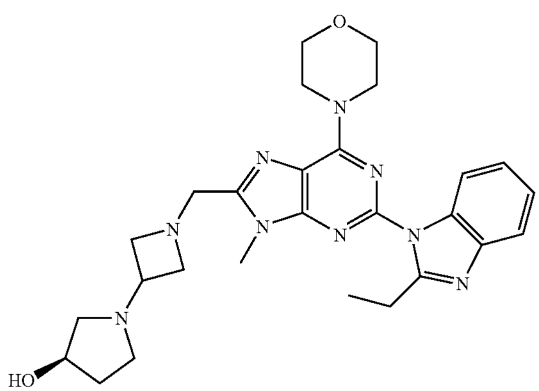 | (R)-1-(1-((2-(2-ethyl-1H-benzo[d]imidazol-1-yl)-9-methyl-6-morpholino-9H-purin-8-yl)methyl)azetidin-3-yl)pyrrolidin-3-ol |
| 539 | 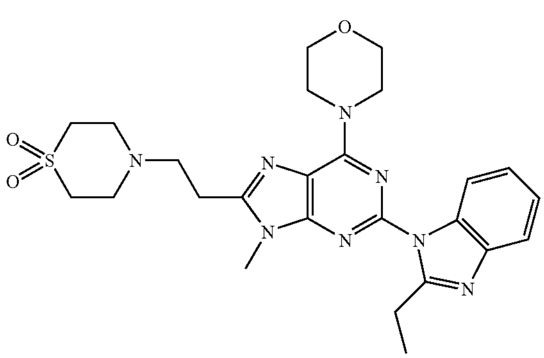 | 4-(2-(2-ethyl-1H-benzo[d]imidazol-1-yl)-9-methyl-8-(2-(1,1-dioxo-thiomorpholino)ethyl)-9H-purin-6-yl)morpholine |

TABLE 2-continued

| No. | Structure | Name |
|---|---|---|
| 540 | 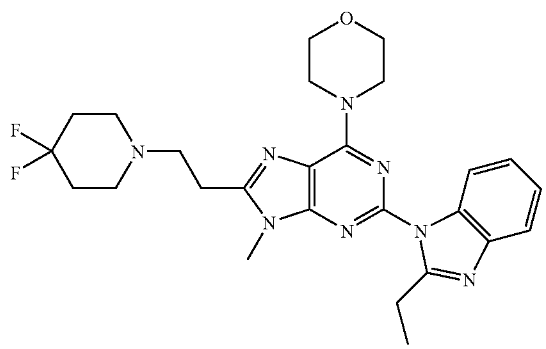 | 4-(8-(2-(4,4-difluoropiperidin-1-yl)ethyl)-2-(2-ethyl-1H-benzo[d]imidazol-1-yl)-9-methyl-9H-purin-6-yl)morpholine |
| 541 | 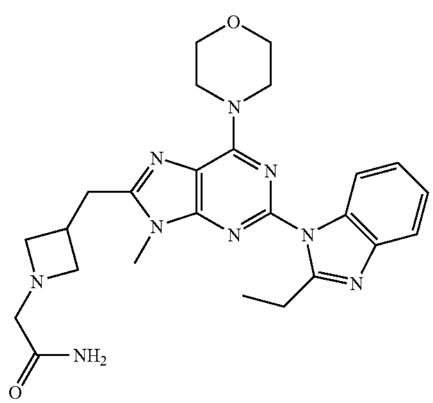 | 2-(3-((2-(2-ethyl-1H-benzo[d]imidazol-1-yl)-9-methyl-6-morpholino-9H-purin-8-yl)methyl)azetidin-1-yl)acetamide |
| 542 | 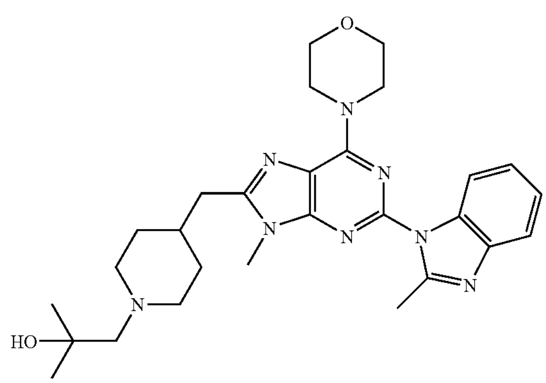 | 2-methyl-1-(4-((9-methyl-2-(2-methyl-1H-benzo[d]imidazol-1-yl)-6-morpholino-9H-purin-8-yl)methyl)piperidin-1-yl)propan-2-ol |
| 543 | 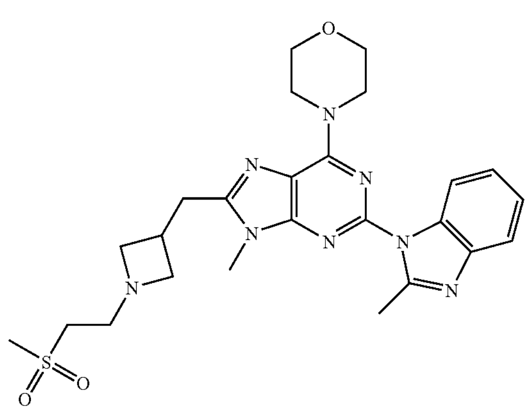 | 4-(9-methyl-2-(2-methyl-1H-benzo[d]imidazol-1-yl)-8-((1-(2-(methylsulfonyl)ethyl)azetidin-3-yl)methyl)-9H-purin-6-yl)morpholine |

TABLE 2-continued

| No. | Structure | Name |
|---|---|---|
| 544 | 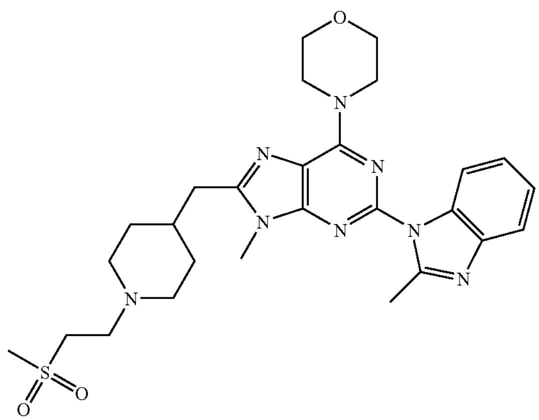 | 4-(9-methyl-2-(2-methyl-1H-benzo[d]imidazol-1-yl)-8-((1-(2-(methylsulfonyl)ethyl)piperidin-4-yl)methyl)-9H-purin-6-yl)morpholine |
| 545 | 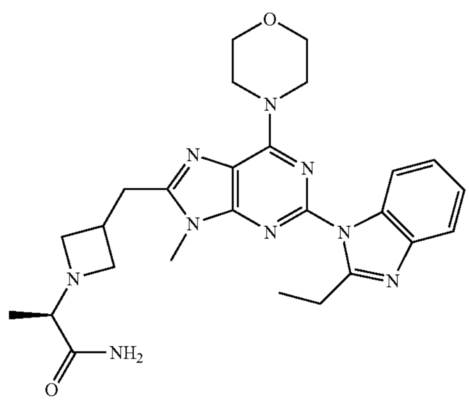 | (R)-2-(3-((2-(2-ethyl-1H-benzo[d]imidazol-1-yl)-9-methyl-6-morpholino-9H-purin-8-yl)methyl)azetidin-1-yl)propanamide |
| 546 | 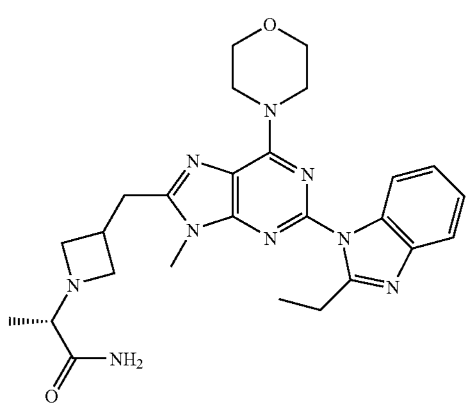 | (S)-2-(3-((2-(2-ethyl-1H-benzo[d]imidazol-1-yl)-9-methyl-6-morpholino-9H-purin-8-yl)methyl)azetidin-1-yl)propanamide |
| 547 | 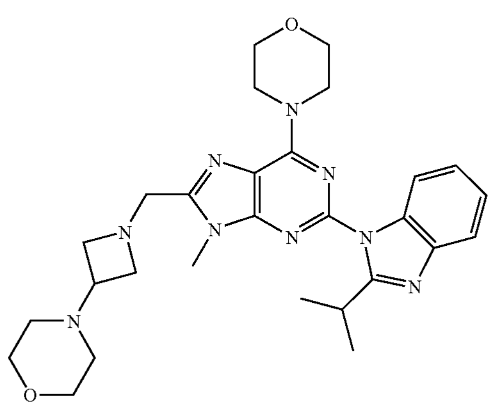 | 4-(1-((2-(2-isopropyl-1H-benzo[d]imidazol-1-yl)-9-methyl-6-morpholino-9H-purin-8-yl)methyl)azetidin-3-yl)morpholine |

TABLE 2-continued
| No. | Structure | Name |
|---|---|---|
| 548 | 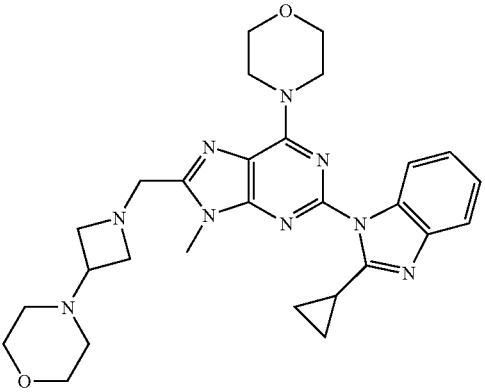 | 4-(1-((2-(2-cyclopropyl-1H-benzo[d]imidazol-1-yl)-9-methyl-6-morpholino-9H-purin-8-yl)methyl)azetidin-3-yl)morpholine |
| 549 | 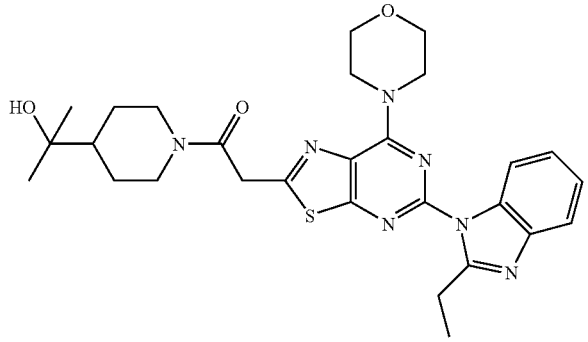 | 2-(5-(2-ethyl-1H-benzo[d]imidazol-1-yl)-7-morpholinothiazolo[5,4-d]pyrimidin-2-yl)-1-(4-(2-hydroxypropan-2-yl)piperidin-1-yl)ethanone |
| 550 | 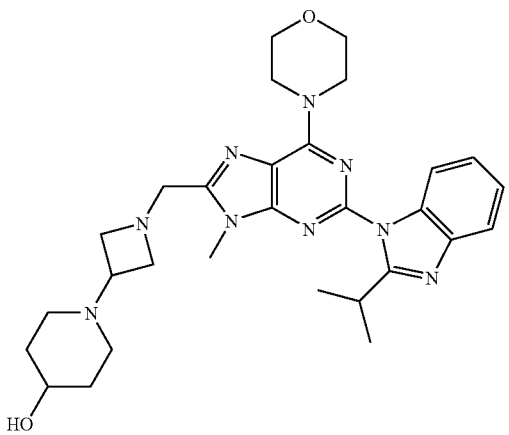 | 1-(1-((2-(2-isopropyl-1H-benzo[d]imidazol-1-yl)-9-methyl-6-morpholino-9H-purin-8-yl)methyl)azetidin-3-yl)piperidin-4-ol |

TABLE 2-continued

| No. | Structure | Name |
|---|---|---|
| 551 | 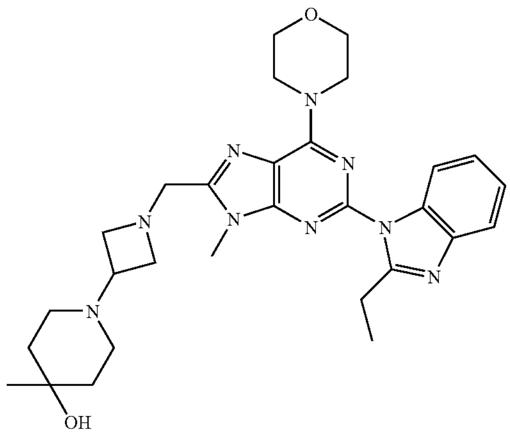 | 1-(1-((2-(2-ethyl-1H-benzo[d]imidazol-1-yl)-9-methyl-6-morpholino-9H-purin-8-yl)methyl)azetidin-3-yl)-4-methylpiperidin-4-ol |
| 552 | 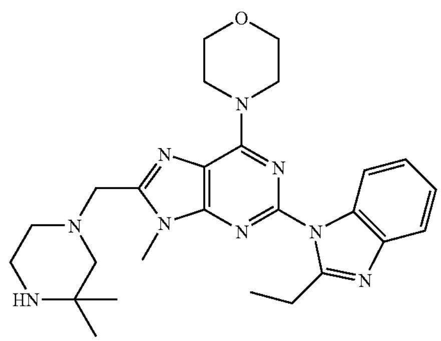 | 4-(8-((3,3-dimethylpiperazin-1-yl)methyl)-2-(2-ethyl-1H-benzo[d]imidazol-1-yl)-9-methyl-9H-purin-6-yl)morpholine |
| 553 | 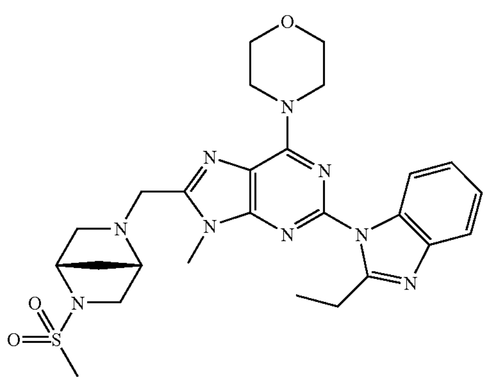 | 4-(2-(2-ethyl-1H-benzo[d]imidazol-1-yl)-9-methyl-8-(((1S,4S)-5-(methylsulfonyl)-2,5-diazabicyclo[2.2.1]heptan-2-yl)methyl)-9H-purin-6-yl)morpholine |
| 554 | 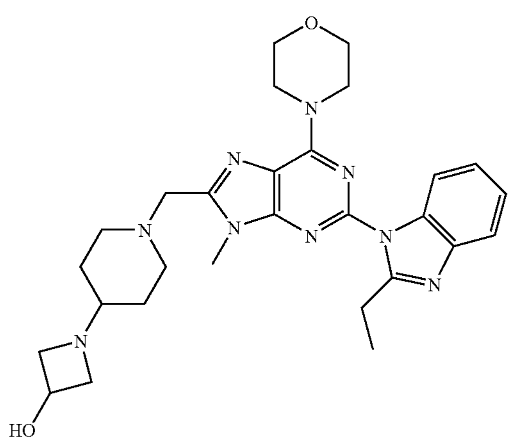 | 1-(1-((2-(2-ethyl-1H-benzo[d]imidazol-1-yl)-9-methyl-6-morpholino-9H-purin-8-yl)methyl)piperidin-4-yl)azetidin-3-ol |

TABLE 2-continued

| No. | Structure | Name |
|---|---|---|
| 555 | 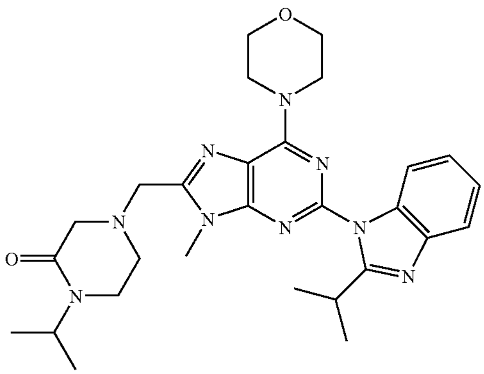 | 1-isopropyl-4-((2-(2-isopropyl-1H-benzo[d]imidazol-1-yl)-9-methyl-6-morpholino-9H-purin-8-yl)methyl)piperazin-2-one |
| 556 | 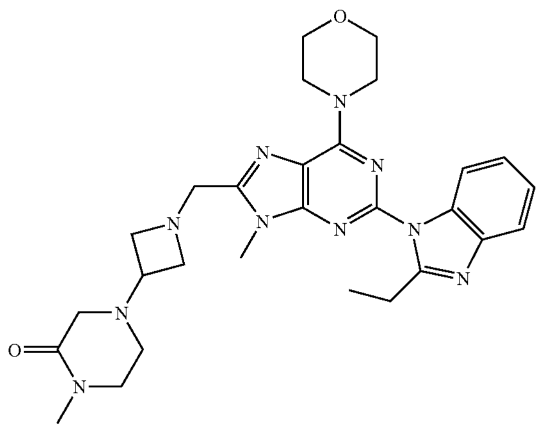 | 4-(1-((2-(2-ethyl-1H-benzo[d]imidazol-1-yl)-9-methyl-6-morpholino-9H-purin-8-yl)methyl)azetidin-3-yl)-1-methylpiperazin-2-one |
| 557 | 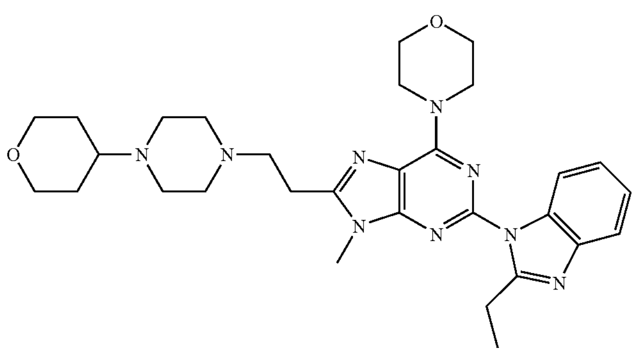 | 4-(2-(2-ethyl-1H-benzo[d]imidazol-1-yl)-9-methyl-8-(2-(4-(tetrahydro-2H-pyran-4-yl)piperazin-1-yl)ethyl)-9H-purin-6-yl)morpholine |
| 558 | 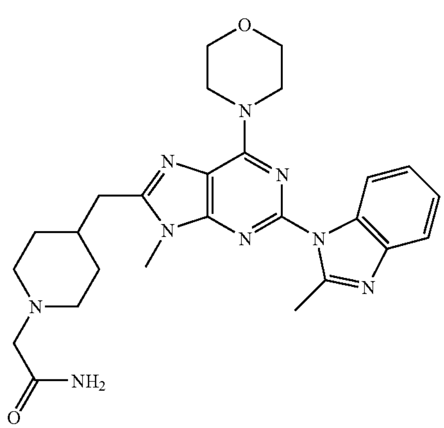 | 2-(4-((9-methyl-2-(2-methyl-1H-benzo[d]imidazol-1-yl)-6-morpholino-9H-purin-8-yl)methyl)piperidin-1-yl)acetamide |

| No. | Structure | Name |
| --- | --- | --- |
| 559 | 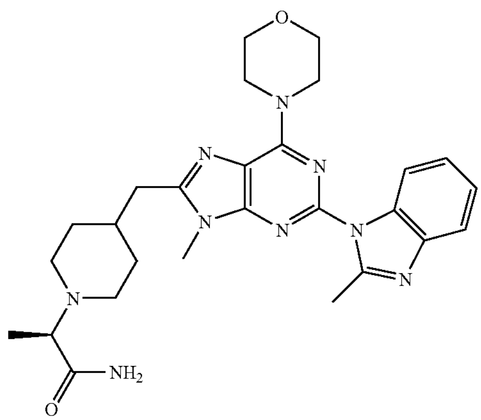 | (R)-2-(4-((9-methyl-2-(2-methyl-1H-benzo[d]imidazol-1-yl)-6-morpholino-9H-purin-8-yl)methyl)piperidin-1-yl)propanamide |
| 560 | 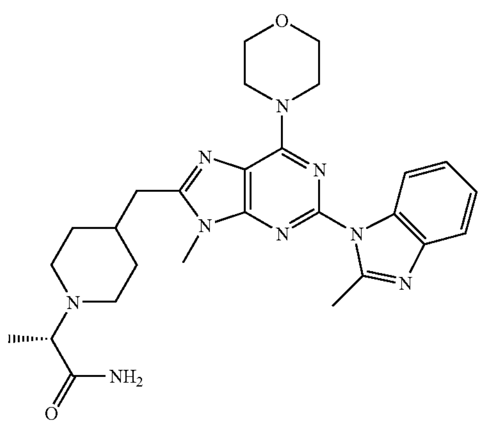 | (S)-2-(4-((9-methyl-2-(2-methyl-1H-benzo[d]imidazol-1-yl)-6-morpholino-9H-purin-8-yl)methyl)piperidin-1-yl)propanamide |
| 561 | 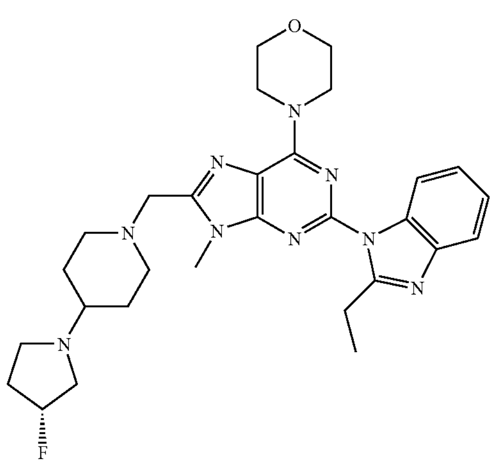 | (R)-4-(2-(2-ethyl-1H-benzo[d]imidazol-1-yl)-8-((4-(3-fluoropyrrolidin-1-yl)piperidin-1-yl)methyl)-9-methyl-9H-purin-6-yl)morpholine |

| No. | Structure | Name |
|-----|-----------|------|
| 562 | 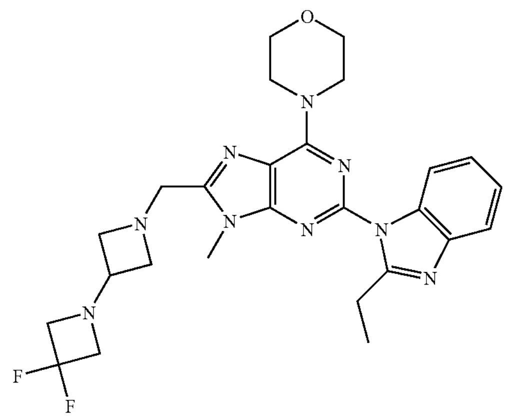 | 4-(8-((3,3-difluoro-1,3'-biazetidin-1'-yl)methyl)-2-(2-ethyl-1H-benzo[d]imidazol-1-yl)-9-methyl-9H-purin-6-yl)morpholine |
| 563 | 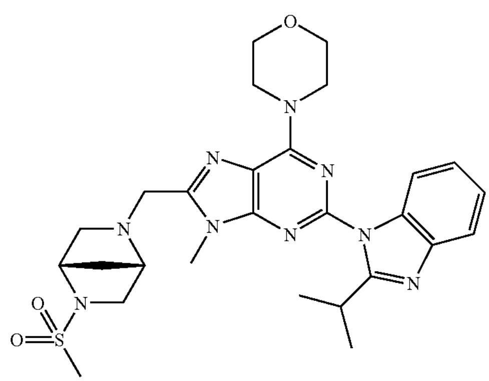 | 4-(2-(2-isopropyl-1H-benzo[d]imidazol-1-yl)-9-methyl-8-(((1S,4S)-5-(methylsulfonyl)-2,5-diazabicyclo[2.2.1]heptan-2-yl)methyl)-9H-purin-6-yl)morpholine |
| 564 | 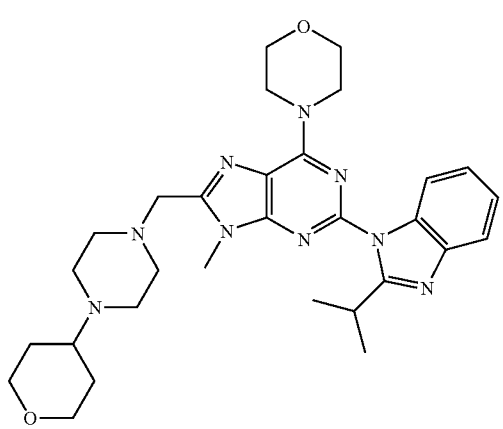 | 4-(2-(2-isopropyl-1H-benzo[d]imidazol-1-yl)-9-methyl-8-((4-(tetrahydro-2H-pyran-4-yl)piperazin-1-yl)methyl)-9H-purin-6-yl)morpholine |

TABLE 2-continued

| No. | Structure | Name |
|-----|-----------|------|
| 565 | 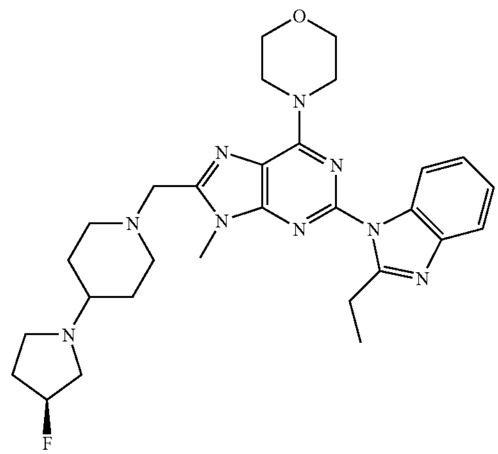 | (S)-4-(2-(2-ethyl-1H-benzo[d]imidazol-1-yl)-8-((4-(3-fluoropyrrolidin-1-yl)piperidin-1-yl)methyl)-9-methyl-9H-purin-6-yl)morpholine |
| 566 | 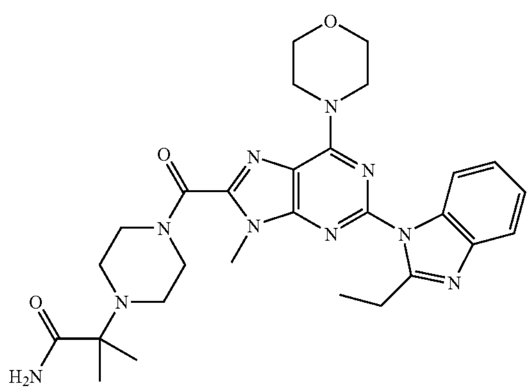 | 2-(4-(2-(2-ethyl-1H-benzo[d]imidazol-1-yl)-9-methyl-6-morpholino-9H-purine-8-carbonyl)piperazin-1-yl)-2-methylpropanamide |
| 567 | 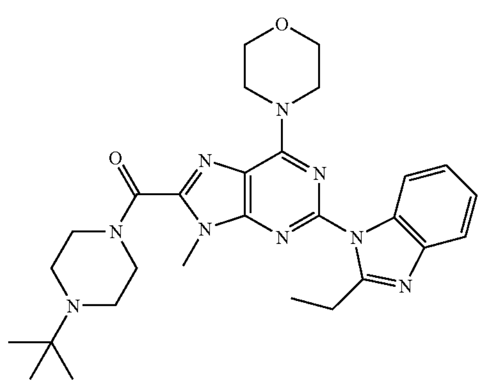 | (4-tert-butylpiperazin-1-yl)(2-(2-ethyl-1H-benzo[d]imidazol-1-yl)-9-methyl-6-morpholino-9H-purin-8-yl)methanone |

TABLE 2-continued

| No. | Structure | Name |
|---|---|---|
| 568 | 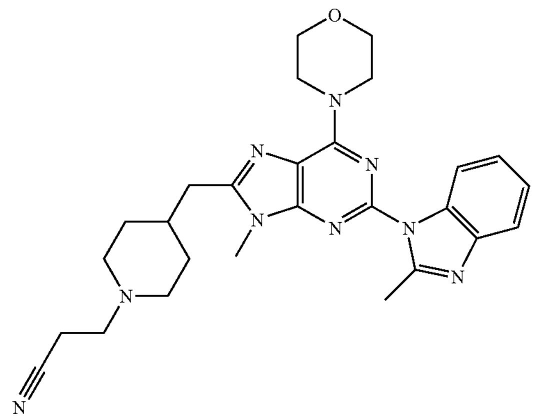 | 3-(4-((9-methyl-2-(2-methyl-1H-benzo[d]imidazol-1-yl)-6-morpholino-9H-purin-8-yl)methyl)piperidin-1-yl)propanenitrile |
| 569 | 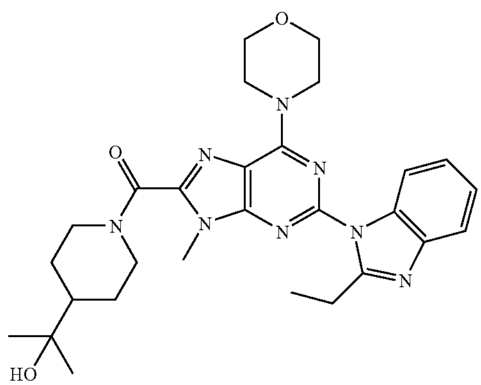 | (2-(2-ethyl-1H-benzo[d]imidazol-1-yl)-9-methyl-6-morpholino-9H-purin-8-yl)(4-(2-hydroxypropan-2-yl)piperidin-1-yl)methanone |
| 570 | 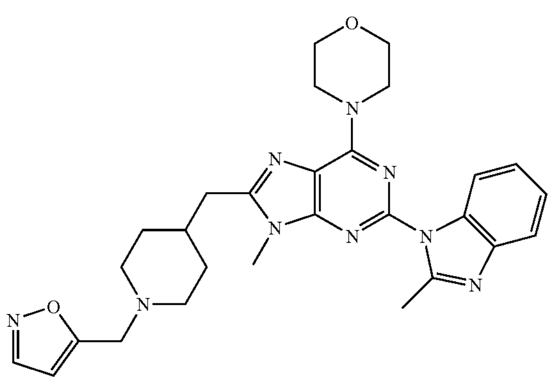 | 4-(8-((1-(isoxazol-5-ylmethyl)piperidin-4-yl)methyl)-9-methyl-2-(2-methyl-1H-benzo[d]imidazol-1-yl)-9H-purin-6-yl)morpholine |
| 571 | 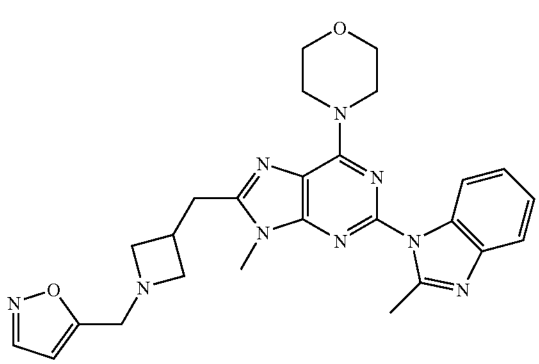 | 4-(8-((1-(isoxazol-5-ylmethyl)azetidin-3-yl)methyl)-9-methyl-2-(2-methyl-1H-benzo[d]imidazol-1-yl)-9H-purin-6-yl)morpholine |

TABLE 2-continued

| No. | Structure | Name |
|---|---|---|
| 572 | 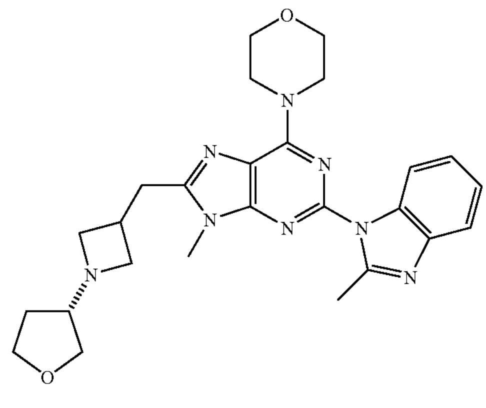 | (S)-4-(9-methyl-2-(2-methyl-1H-benzo[d]imidazol-1-yl)-8-((1-(tetrahydrofuran-3-yl)azetidin-3-yl)methyl)-9H-purin-6-yl)morpholine |
| 573 | 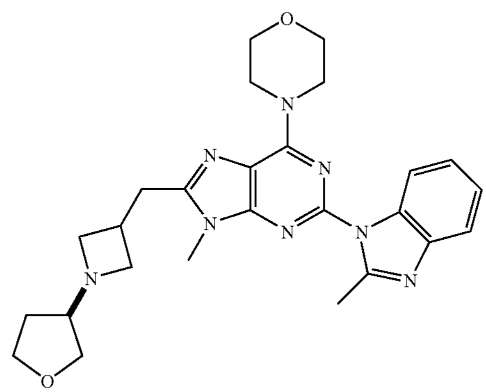 | (R)-4-(9-methyl-2-(2-methyl-1H-benzo[d]imidazol-1-yl)-8-((1-(tetrahydrofuran-3-yl)azetidin-3-yl)methyl)-9H-purin-6-yl)morpholine |
| 574 | 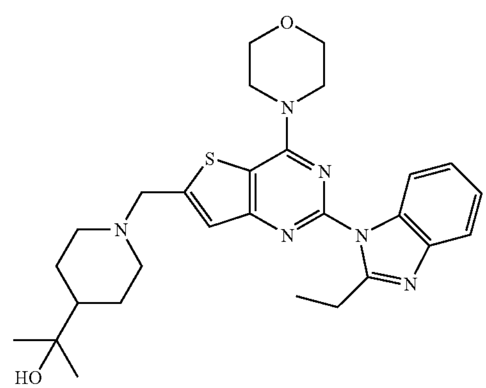 | 2-(1-((2-(2-ethyl-1H-benzo[d]imidazol-1-yl)-4-morpholinothieno[3,2-d]pyrimidin-6-yl)methyl)piperidin-4-yl)propan-2-ol |
| 575 | 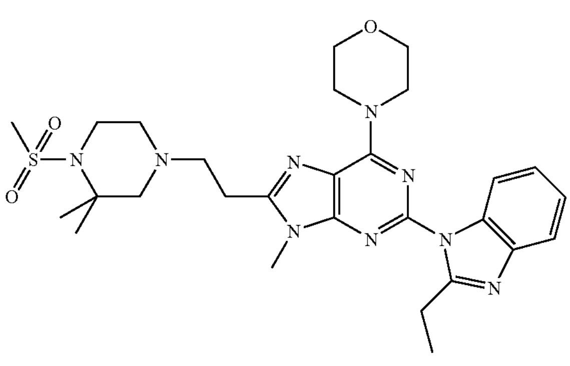 | 4-(8-(2-(3,3-dimethyl-4-(methylsulfonyl)piperazin-1-yl)ethyl)-2-(2-ethyl-1H-benzo[d]imidazol-1-yl)-9-methyl-9H-purin-6-yl)morpholine |

TABLE 2-continued

| No. | Structure | Name |
|---|---|---|
| 576 | 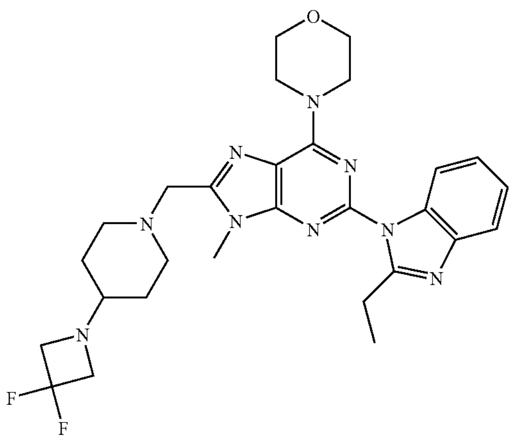 | 4-(8-((4-(3,3-difluoroazetidin-1-yl)piperidin-1-yl)methyl)-2-(2-ethyl-1H-benzo[d]imidazol-1-yl)-9-methyl-9H-purin-6-yl)morpholine |
| 577 | 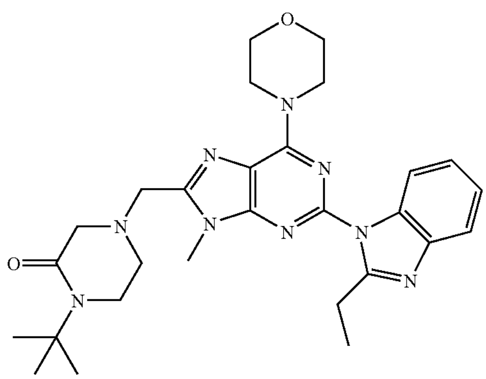 | 1-tert-butyl-4-((2-(2-ethyl-1H-benzo[d]imidazol-1-yl)-9-methyl-6-morpholino-9H-purin-8-yl)methyl)piperazin-2-one |
| 578 | | (S)-2-amino-1-(4-((9-methyl-2-(2-methyl-1H-benzo[d]imidazol-1-yl)-6-morpholino-9H-purin-8-yl)methyl)piperidin-1-yl)propan-1-one | ns

TABLE 2-continued

| No. | Structure | Name |
|---|---|---|
| 579 | 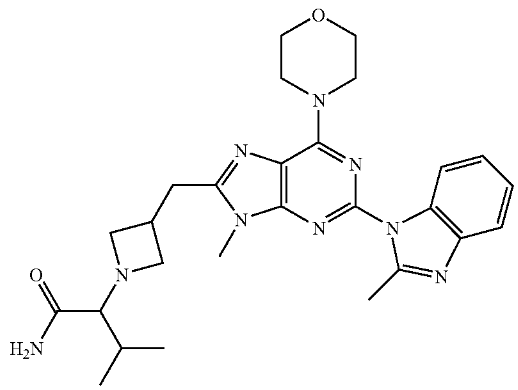 | 3-methyl-2-(3-((9-methyl-2-(2-methyl-1H-benzo[d]imidazol-1-yl)-6-morpholino-9H-purin-8-yl)methyl)azetidin-1-yl)butanamide |
| 580 | 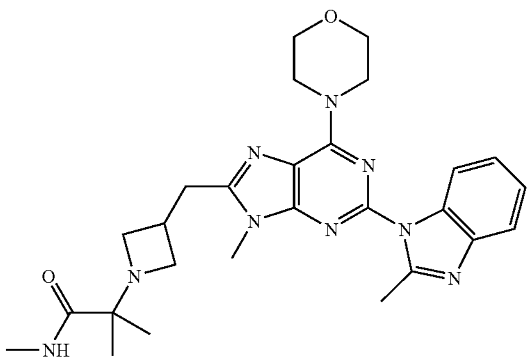 | N,2-dimethyl-2-(3-((9-methyl-2-(2-methyl-1H-benzo[d]imidazol-1-yl)-6-morpholino-9H-purin-8-yl)methyl)azetidin-1-yl)propanamide |
| 581 | 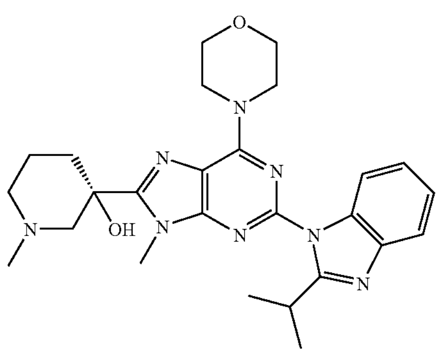 | (S)-3-(2-(2-isopropyl-1H-benzo[d]imidazol-1-yl)-9-methyl-6-morpholino-9H-purin-8-yl)-1-methylpiperidin-3-ol |
| 582 | 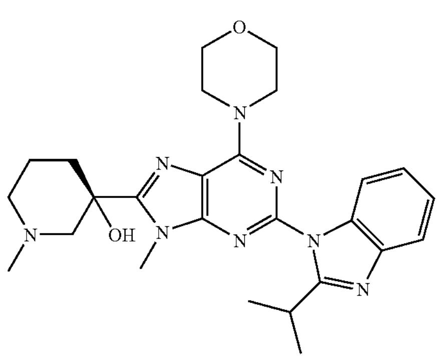 | (R)-3-(2-(2-isopropyl-1H-benzo[d]imidazol-1-yl)-9-methyl-6-morpholino-9H-purin-8-yl)-1-methylpiperidin-3-ol |

TABLE 2-continued

| No. | Structure | Name |
|---|---|---|
| 583 | 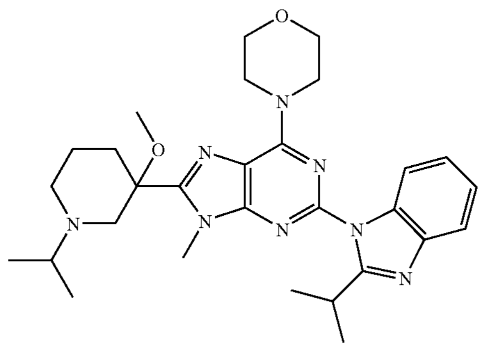 | 4-(2-(2-isopropyl-1H-benzo[d]imidazol-1-yl)-8-(1-isopropyl-3-methoxypiperidin-3-yl)-9-methyl-9H-purin-6-yl)morpholine |
| 584 | 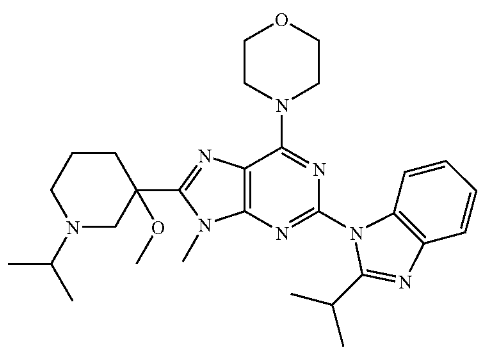 | 4-(2-(2-isopropyl-1H-benzo[d]imidazol-1-yl)-8-(1-isopropyl-3-methoxypiperidin-3-yl)-9-methyl-9H-purin-6-yl)morpholine |
| 585 | 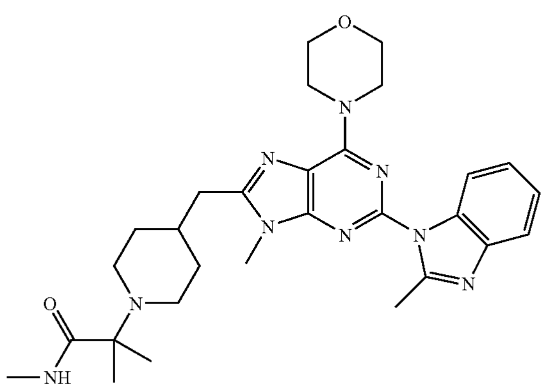 | N,2-dimethyl-2-(4-((9-methyl-2-(2-methyl-1H-benzo[d]imidazol-1-yl)-6-morpholino-9H-purin-8-yl)methyl)piperidin-1-yl)propanamide |
| 586 | 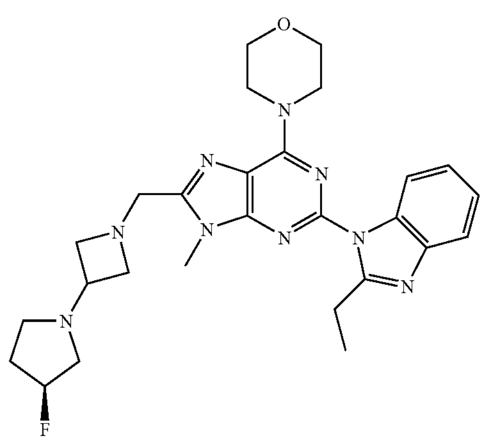 | (S)-4-(2-(2-ethyl-1H-benzo[d]imidazol-1-yl)-8-((3-(3-fluoropyrrolidin-1-yl)azetidin-1-yl)methyl)-9-methyl-9H-purin-6-yl)morpholine |

TABLE 2-continued

| No. | Structure | Name |
| --- | --- | --- |
| 587 | 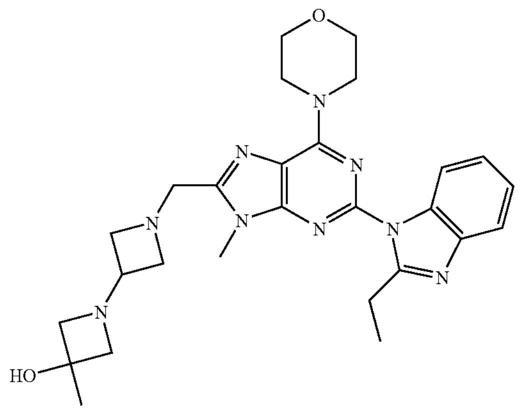 | 1'-((2-(2-ethyl-1H-benzo[d]imidazol-1-yl)-9-methyl-6-morpholino-9H-purin-8-yl)methyl)-3-methyl-1,3'-biazetidin-3-ol |
| 588 | 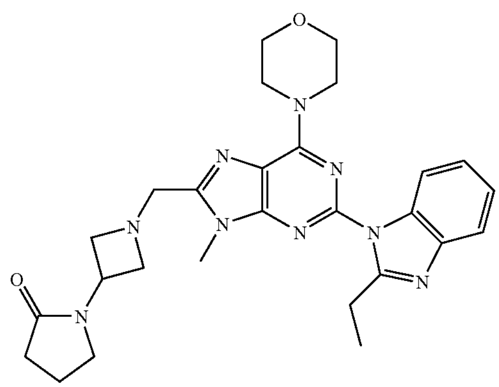 | 1-(1-((2-(2-ethyl-1H-benzo[d]imidazol-1-yl)-9-methyl-6-morpholino-9H-purin-8-yl)methyl)azetidin-3-yl)pyrrolidin-2-one |
| 589 | 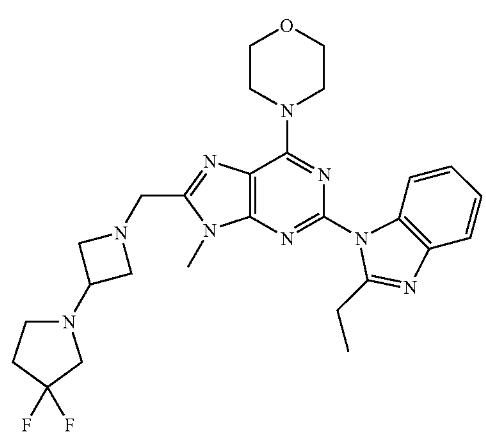 | 4-(8-((3-(3,3-difluoropyrrolidin-1-yl)azetidin-1-yl)methyl)-2-(2-ethyl-1H-benzo[d]imidazol-1-yl)-9-methyl-9H-purin-6-yl)morpholine |

TABLE 2-continued

| No. | Structure | Name |
|---|---|---|
| 590 | 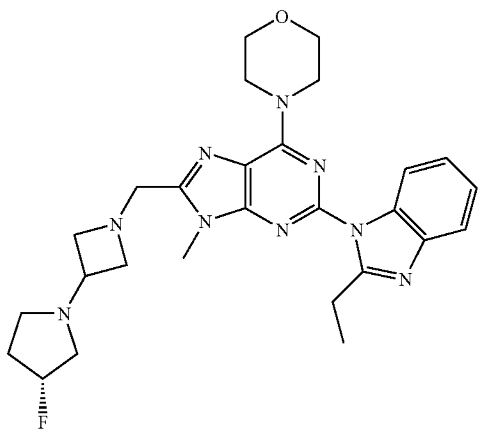 | (R)-4-(2-(2-ethyl-1H-benzo[d]imidazol-1-yl)-8-((3-(3-fluoropyrrolidin-1-yl)azetidin-1-yl)methyl)-9-methyl-9H-purin-6-yl)morpholine |
| 591 | 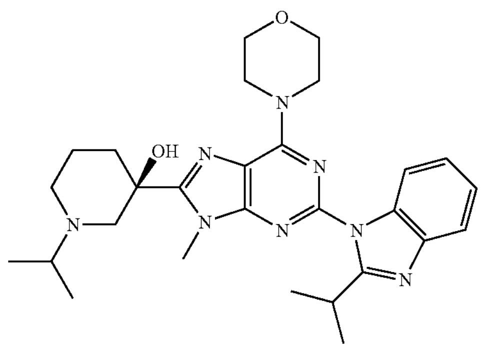 | (R)-1-isopropyl-3-(2-(2-isopropyl-1H-benzo[d]imidazol-1-yl)-9-methyl-6-morpholino-9H-purin-8-yl)piperidin-3-ol |
| 592 | 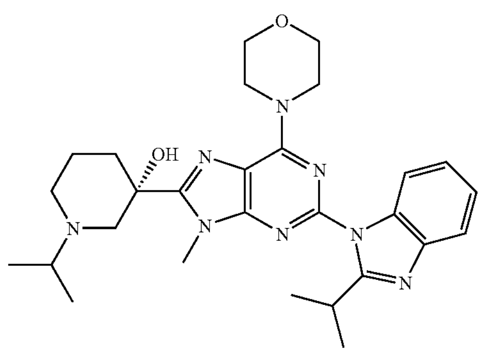 | (S)-1-isopropyl-3-(2-(2-isopropyl-1H-benzo[d]imidazol-1-yl)-9-methyl-6-morpholino-9H-purin-8-yl)piperidin-3-ol |
| 593 | 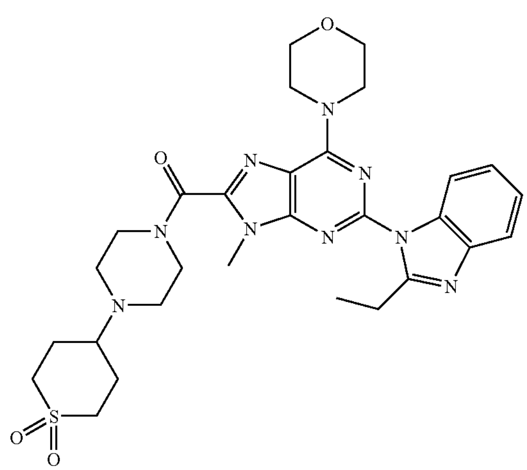 | (2-(2-ethyl-1H-benzo[d]imidazol-1-yl)-9-methyl-6-morpholino-9H-purin-8-yl)(4-(tetrahydro-2H-(1,1-dioxo)-thiopyran-4-yl)piperazin-1-yl)methanone |

TABLE 2-continued

| No. | Structure | Name |
|---|---|---|
| 594 | 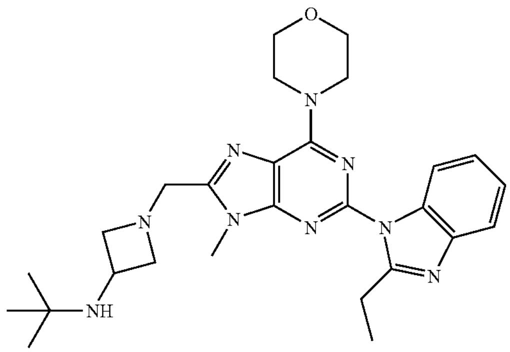 | N-tert-butyl-1-((2-(2-ethyl-1H-benzo[d]imidazol-1-yl)-9-methyl-6-morpholino-9H-purin-8-yl)methyl)azetidin-3-amine |
| 595 | 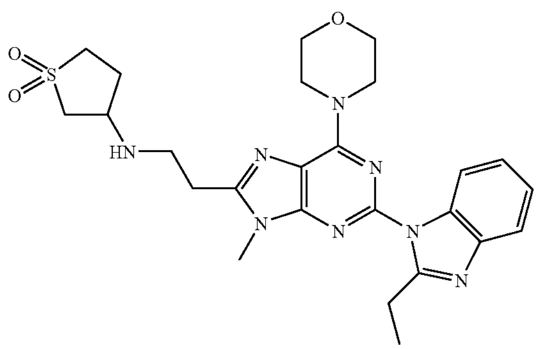 | N-(2-(2-(2-ethyl-1H-benzo[d]imidazol-1-yl)-9-methyl-6-morpholino-9H-purin-8-yl)ethyl)tetrahydro(1,1-dioxo)thiophen-3-amine |
| 596 | 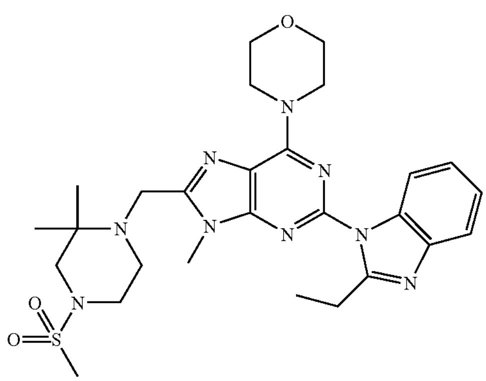 | 4-(8-((2,2-dimethyl-4-(methylsulfonyl)piperazin-1-yl)methyl)-2-(2-ethyl-1H-benzo[d]imidazol-1-yl)-9-methyl-9H-purin-6-yl)morpholine |
| 597 | 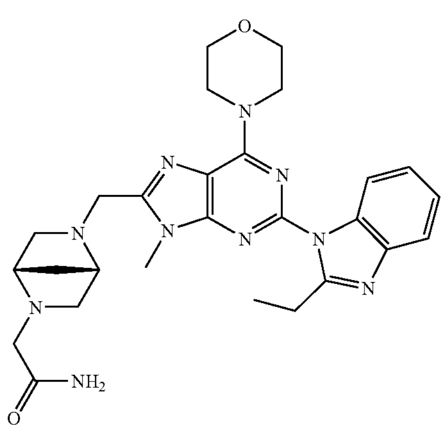 | 2-((1S,4S)-5-((2-(2-ethyl-1H-benzo[d]imidazol-1-yl)-9-methyl-6-morpholino-9H-purin-8-yl)methyl)-2,5-diazabicyclo[2.2.1]heptan-2-yl)acetamide |

TABLE 2-continued

| No. | Structure | Name |
|---|---|---|
| 598 | 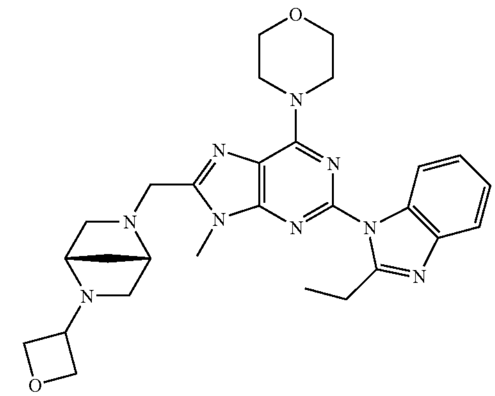 | 4-(2-(2-ethyl-1H-benzo[d]imidazol-1-yl)-9-methyl-8-(((1S,4S)-5-(oxetan-3-yl)-2,5-diazabicyclo[2.2.1]heptan-2-yl)methyl)-9H-purin-6-yl)morpholine |
| 599 | 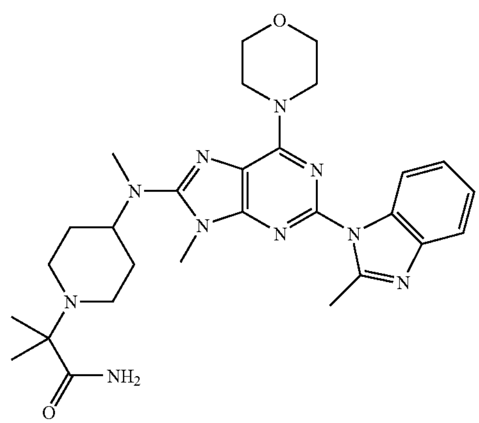 | 2-methyl-2-(4-(methyl(9-methyl-2-(2-methyl-1H-benzo[d]imidazol-1-yl)-6-morpholino-9H-purin-8-yl)amino)piperidin-1-yl)propanamide |
| 600 | 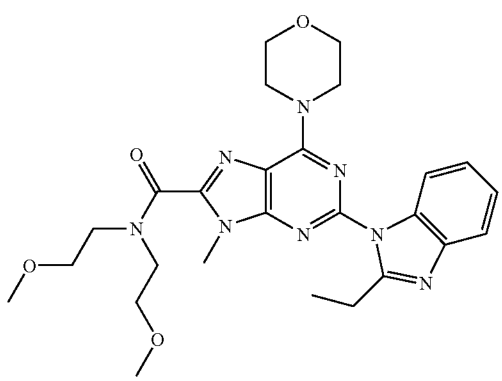 | 2-(2-ethyl-1H-benzo[d]imidazol-1-yl)-N,N-bis(2-methoxyethyl)-9-methyl-6-morpholino-9H-purine-8-carboxamide |
| 601 | 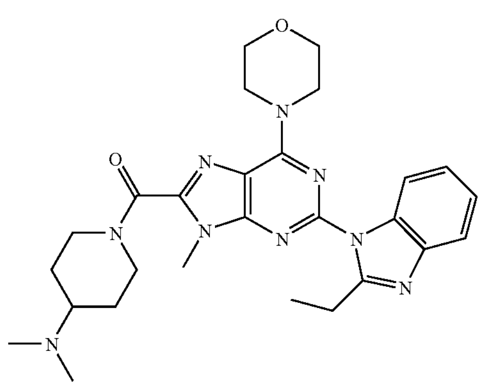 | (4-(dimethylamino)piperidin-1-yl)(2-(2-ethyl-1H-benzo[d]imidazol-1-yl)-9-methyl-6-morpholino-9H-purin-8-yl)methanone |

TABLE 2-continued

| No. | Structure | Name |
|---|---|---|
| 602 | 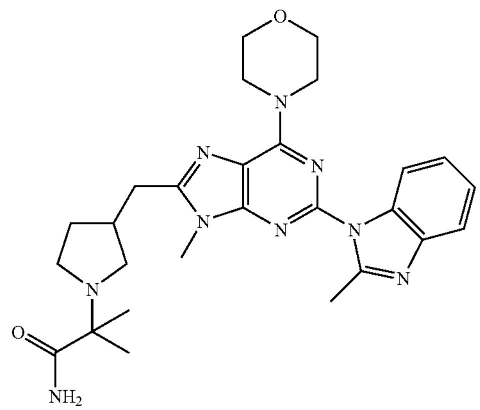 | 2-methyl-2-(3-((9-methyl-2-(2-methyl-1H-benzo[d]imidazol-1-yl)-6-morpholino-9H-purin-8-yl)methyl)pyrrolidin-1-yl)propanamide |
| 603 | 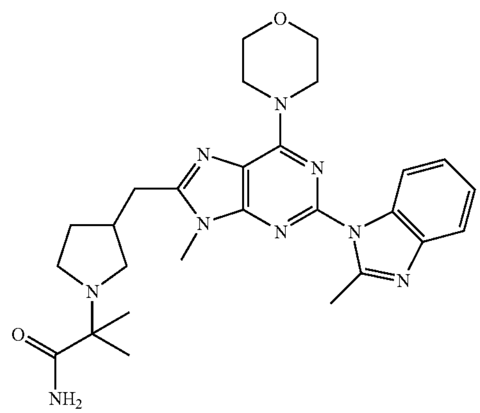 | 2-methyl-2-(3-((9-methyl-2-(2-methyl-1H-benzo[d]imidazol-1-yl)-6-morpholino-9H-purin-8-yl)methyl)pyrrolidin-1-yl)propanamide |
| 604 | 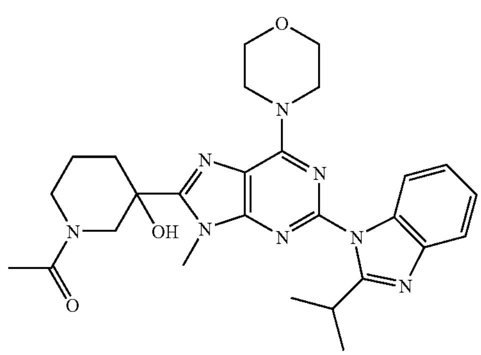 | 1-(3-hydroxy-3-(2-(2-isopropyl-1H-benzo[d]imidazol-1-yl)-9-methyl-6-morpholino-9H-purin-8-yl)piperidin-1-yl)ethanone |
| 605 | 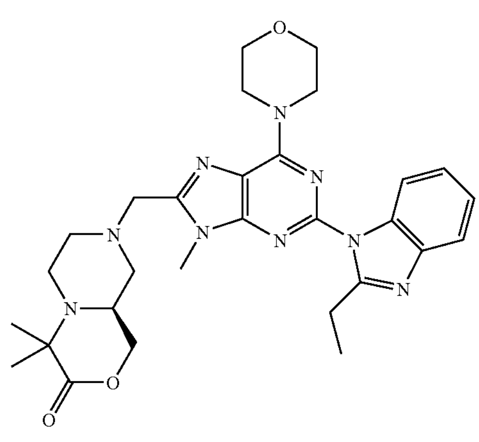 | (S)-8-((2-(2-ethyl-1H-benzo[d]imidazol-1-yl)-9-methyl-6-morpholino-9H-purin-8-yl)methyl)-4,4-dimethylhexahydropyrazino[2,1-c][1,4]oxazin-3(1H)-one |

TABLE 2-continued

| No. | Structure | Name |
|---|---|---|
| 606 | 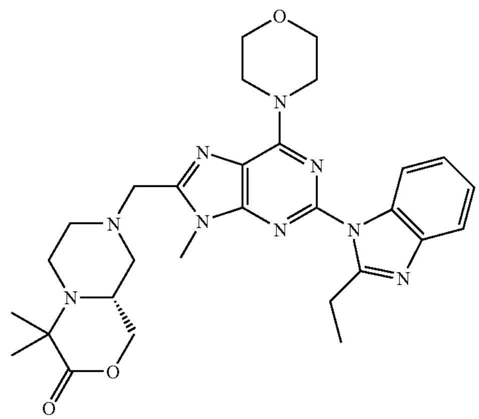 | (R)-8-((2-(2-ethyl-1H-benzo[d]imidazol-1-yl)-9-methyl-6-morpholino-9H-purin-8-yl)methyl)-4,4-dimethylhexahydropyrazino[2,1-c][1,4]oxazin-3(1H)-one |
| 607 | 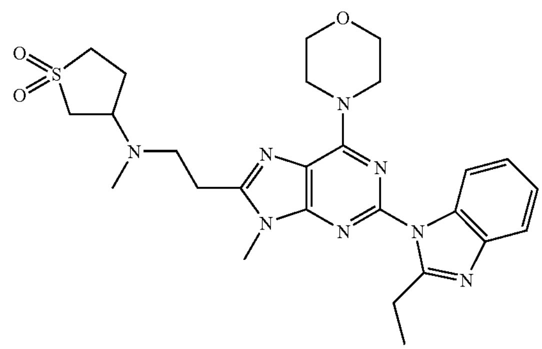 | N-(2-(2-(2-ethyl-1H-benzo[d]imidazol-1-yl)-9-methyl-6-morpholino-9H-purin-8-yl)ethyl)-N-methyl-1,1-dioxo-tetrahydrothiophen-3-amine |
| 608 | 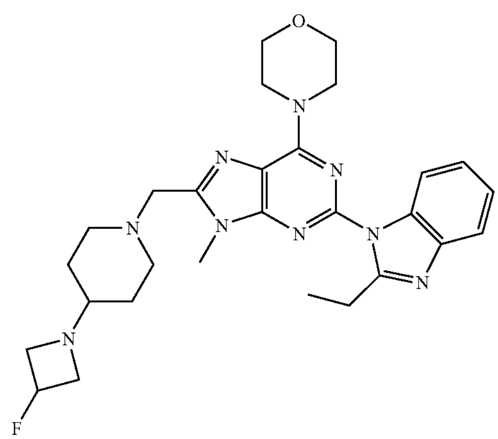 | 4-(2-(2-ethyl-1H-benzo[d]imidazol-1-yl)-8-((4-(3-fluoroazetidin-1-yl)piperidin-1-yl)methyl)-9-methyl-9H-purin-6-yl)morpholine |
| 609 | 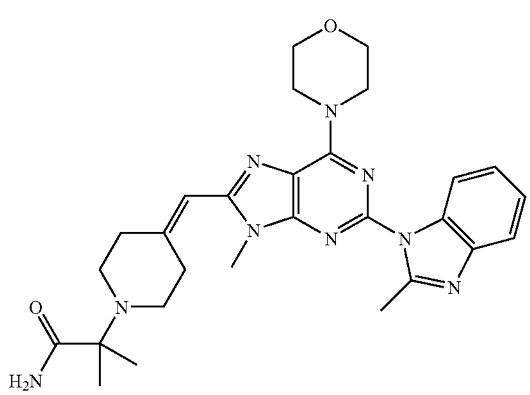 | 2-methyl-2-(4-((9-methyl-2-(2-methyl-1H-benzo[d]imidazol-1-yl)-6-morpholino-9H-purin-8-yl)methylene)piperidin-1-yl)propanamide |

| No. | Structure | Name |
|---|---|---|
| 610 | 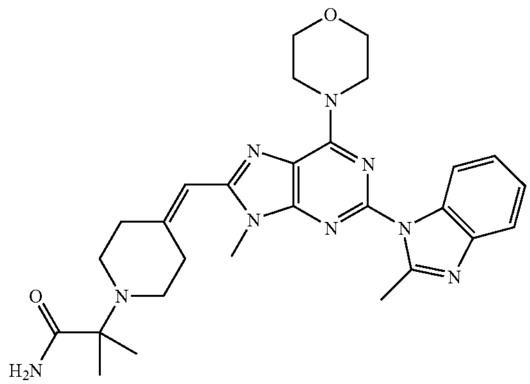 | 2-methyl-2-(4-((9-methyl-2-(2-methyl-1H-benzo[d]imidazol-1-yl)-6-morpholino-9H-purin-8-yl)methylene)piperidin-1-yl)propanamide |
| 611 | 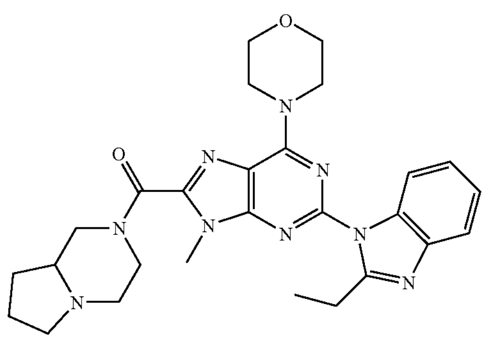 | (2-(2-ethyl-1H-benzo[d]imidazol-1-yl)-9-methyl-6-morpholino-9H-purin-8-yl)(hexahydropyrrolo[1,2-a]pyrazin-2(1H)-yl)methanone |
| 612 | 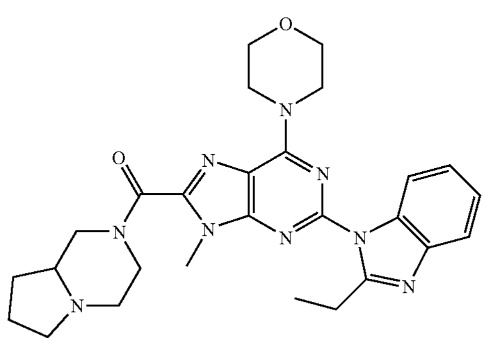 | (2-(2-ethyl-1H-benzo[d]imidazol-1-yl)-9-methyl-6-morpholino-9H-purin-8-yl)(hexahydropyrrolo[1,2-a]pyrazin-2(1H)-yl)methanone |
| 613 | 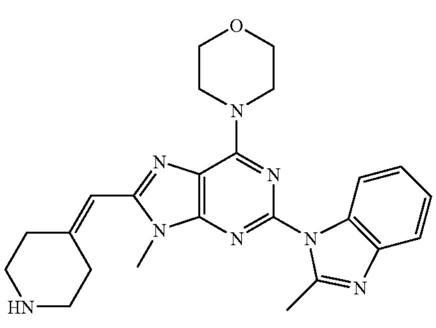 | 4-(9-methyl-2-(2-methyl-1H-benzo[d]imidazol-1-yl)-8-(piperidin-4-ylidenemethyl)-9H-purin-6-yl)morpholine |

TABLE 2-continued

| No. | Structure | Name |
| --- | --- | --- |
| 614 | 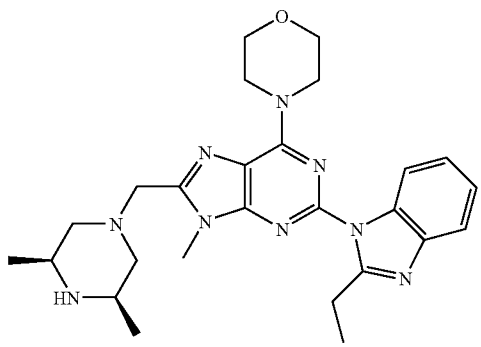 | 4-(8-(((3S,5R)-3,5-dimethylpiperazin-1-yl)methyl)-2-(2-ethyl-1H-benzo[d]imidazol-1-yl)-9-methyl-9H-purin-6-yl)morpholine |
| 615 | 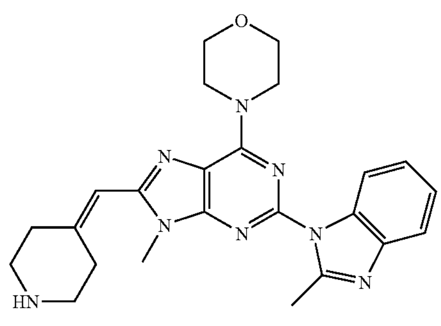 | 4-(9-methyl-2-(2-methyl-1H-benzo[d]imidazol-1-yl)-8-(piperidin-4-ylidenemethyl)-9H-purin-6-yl)morpholine |
| 616 | 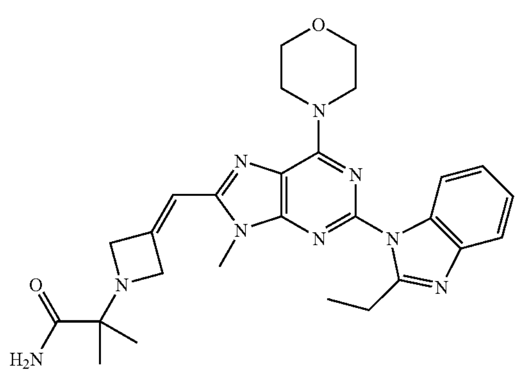 | 2-(3-((2-(2-ethyl-1H-benzo[d]imidazol-1-yl)-9-methyl-6-morpholino-9H-purin-8-yl)methylene)azetidin-1-yl)-2-methylpropanamide |
| 617 | 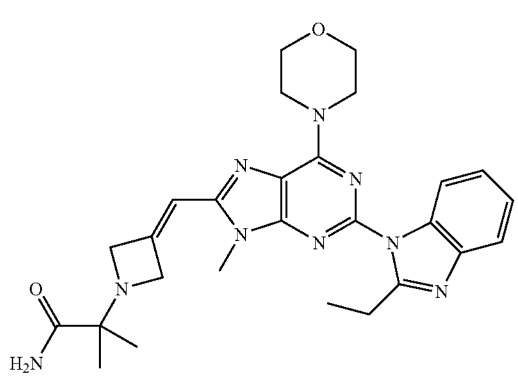 | 2-(3-((2-(2-ethyl-1H-benzo[d]imidazol-1-yl)-9-methyl-6-morpholino-9H-purin-8-yl)methylene)azetidin-1-yl)-2-methylpropanamide |

TABLE 2-continued

| No. | Structure | Name |
|---|---|---|
| 618 | 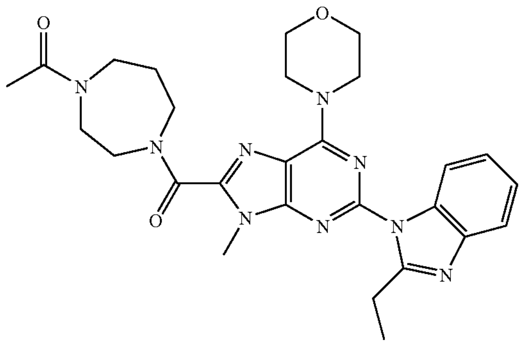 | 1-(4-(2-(2-ethyl-1H-benzo[d]imidazol-1-yl)-9-methyl-6-morpholino-9H-purine-8-carbonyl)-1,4-diazepan-1-yl)ethanone |
| 619 | 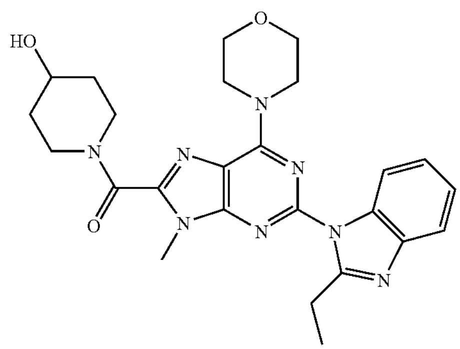 | (2-(2-ethyl-1H-benzo[d]imidazol-1-yl)-9-methyl-6-morpholino-9H-purin-8-yl)(4-hydroxypiperidin-1-yl)methanone |
| 620 | 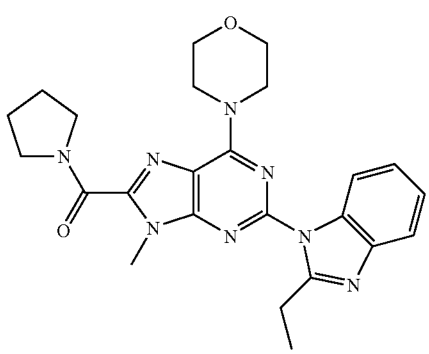 | (2-(2-ethyl-1H-benzo[d]imidazol-1-yl)-9-methyl-6-morpholino-9H-purin-8-yl)(pyrrolidin-1-yl)methanone |
| 621 | 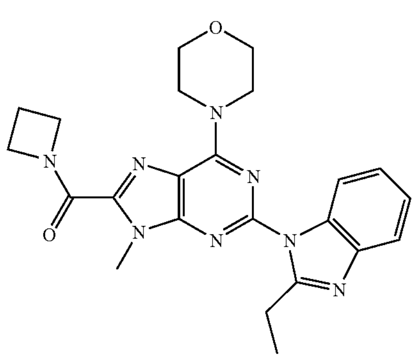 | azetidin-1-yl(2-(2-ethyl-1H-benzo[d]imidazol-1-yl)-9-methyl-6-morpholino-9H-purin-8-yl)methanone |

TABLE 2-continued

| No. | Structure | Name |
|---|---|---|
| 622 | 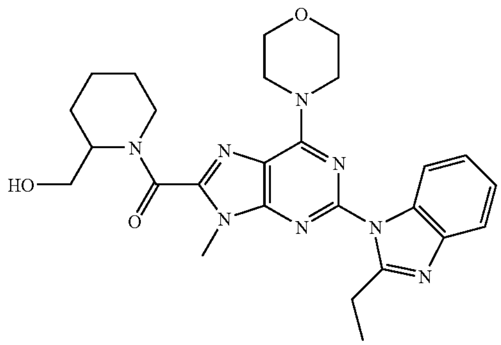 | (2-(2-ethyl-1H-benzo[d]imidazol-1-yl)-9-methyl-6-morpholino-9H-purin-8-yl)(2-(hydroxymethyl)piperidin-1-yl)methanone |
| 623 | 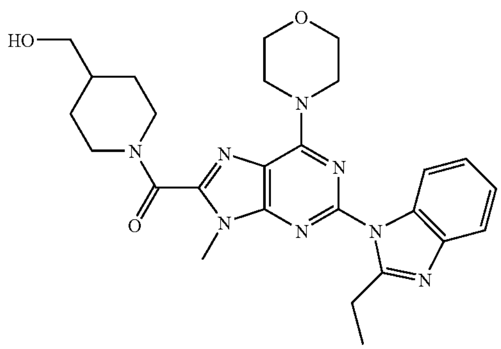 | (2-(2-ethyl-1H-benzo[d]imidazol-1-yl)-9-methyl-6-morpholino-9H-purin-8-yl)(4-(hydroxymethyl)piperidin-1-yl)methanone |
| 624 | 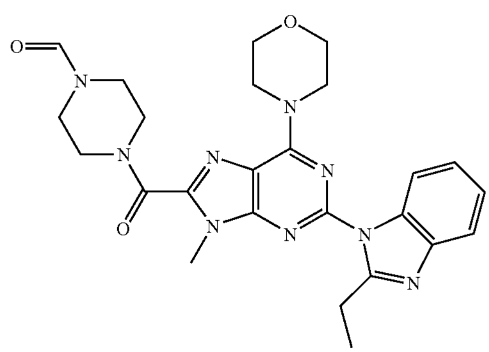 | 4-(2-(2-ethyl-1H-benzo[d]imidazole-yl)-9-methyl-6-morpholino-9H-purine-8-carbonyl)piperazine-1-carbaldehyde |
| 625 | 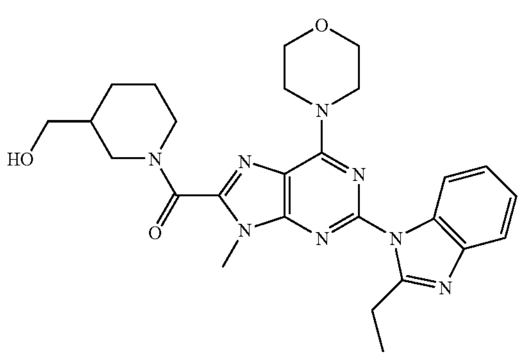 | (2-(2-ethyl-1H-benzo[d]imidazol-1-yl)-9-methyl-6-morpholino-9H-purin-8-yl)(3-(hydroxymethyl)piperidin-1-yl)methanone |

TABLE 2-continued

| No. | Structure | Name |
|---|---|---|
| 626 | 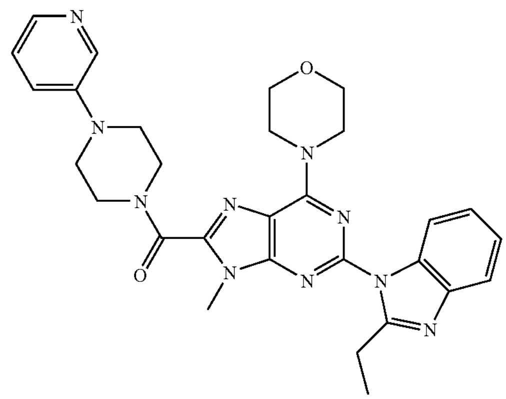 | (2-(2-ethyl-1H-benzo[d]imidazol-1-yl)-9-methyl-6-morpholino-9H-purin-8-yl)(4-(pyridin-3-yl)piperazin-1-yl)methanone |
| 627 | 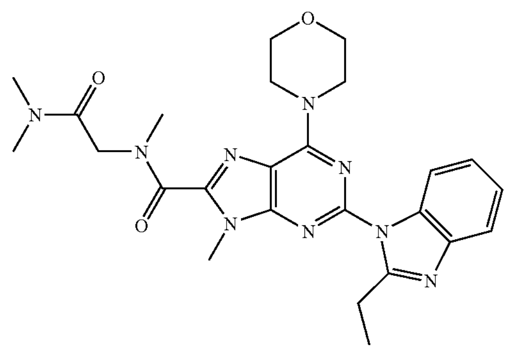 | N-(2-(dimethylamino)-2-oxoethyl)-2-(2-ethyl-1H-benzo[d]imidazol-1-yl)-N,9-dimethyl-6-morpholino-9H-purine-8-carboxamide |
| 628 | 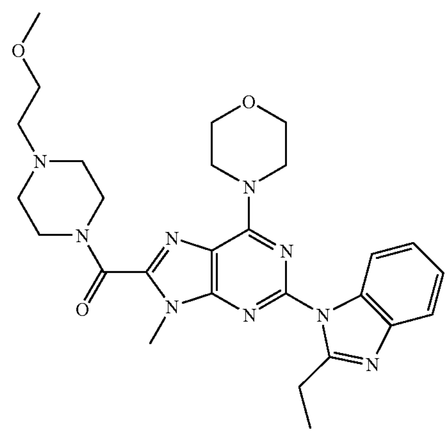 | (2-(2-ethyl-1H-benzo[d]imidazol-1-yl)-9-methyl-6-morpholino-9H-purin-8-yl)(4-(2-methoxyethyl)piperazin-1-yl)methanone |
| 629 | 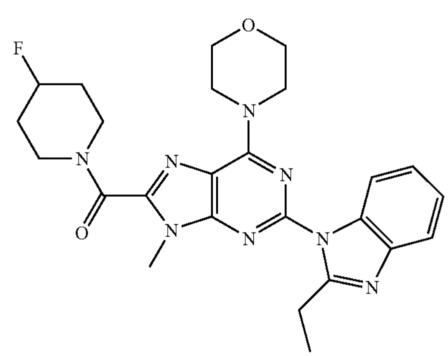 | (2-(2-ethyl-1H-benzo[d]imidazol-1-yl)-9-methyl-6-morpholino-9H-purin-8-yl)(4-fluoropiperidin-1-yl)methanone |

US 8,173,650 B2
321                                                                                                                              322
TABLE 2-continued

| No. | Structure | Name |
|---|---|---|
| 630 | 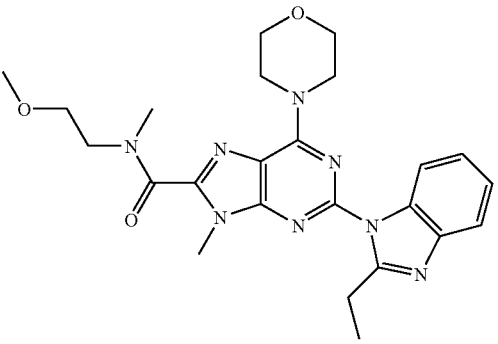 | 2-(2-ethyl-1H-benzo[d]imidazol-1-yl)-N-(2-methoxyethyl)-N,9-dimethyl-6-morpholino-9H-purine-8-carboxamide |
| 631 | 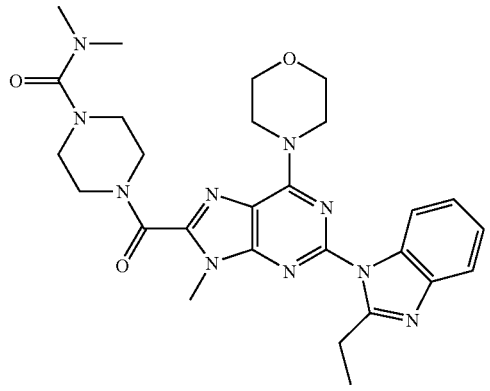 | 4-(2-(2-ethyl-1H-benzo[d]imidazol-1-yl)-9-methyl-6-morpholino-9H-purine-8-carbonyl)-N,N-dimethylpiperazine-1-carboxamide |
| 632 | 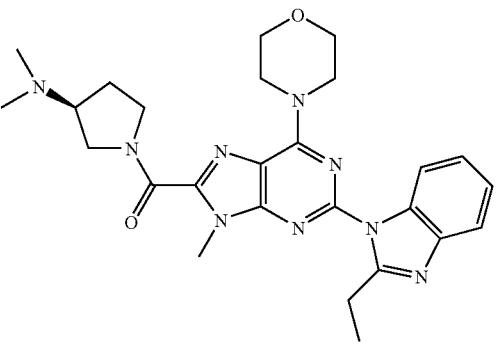 | (S)-(3-(dimethylamino)pyrrolidin-1-yl)(2-(2-ethyl-1H-benzo[d]imidazol-1-yl)-9-methyl-6-morpholino-9H-purin-8-yl)methanone |
| 633 | 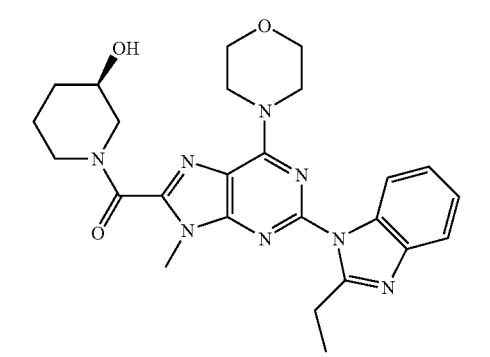 | (R)-(2-(2-ethyl-1H-benzo[d]imidazol-1-yl)-9-methyl-6-morpholino-9H-purin-8-yl)(3-hydroxypiperidin-1-yl)methanone |

TABLE 2-continued

| No. | Structure | Name |
|---|---|---|
| 634 | 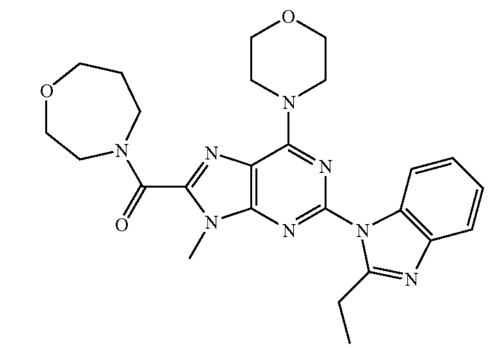 | (2-(2-ethyl-1H-benzo[d]imidazol-1-yl)-9-methyl-6-morpholino-9H-purin-8-yl)(1,4-oxazepan-4-yl)methanone |
| 635 | 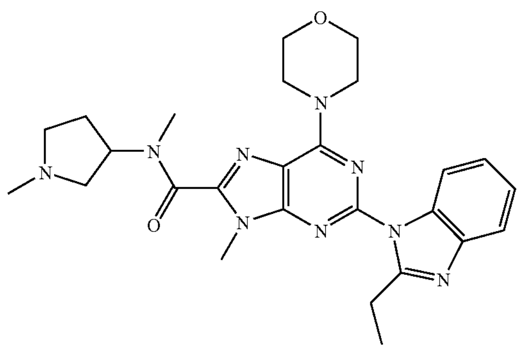 | 2-(2-ethyl-1H-benzo[d]imidazol-1-yl)-N,9-dimethyl-N-(1-methylpyrrolidin-3-yl)-6-morpholino-9H-purine-8-carboxamide |
| 636 | 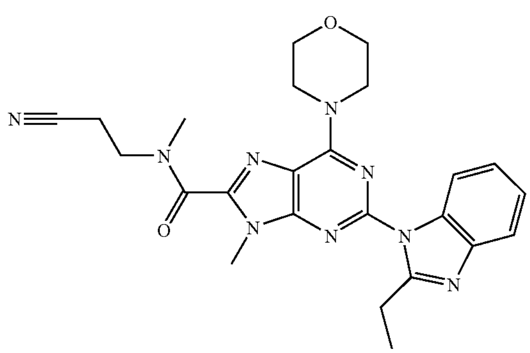 | N-(2-cyanoethyl)-2-(2-ethyl-1H-benzo[d]imidazol-1-yl)-N,9-dimethyl-6-morpholino-9H-purine-8-carboxamide |
| 637 | 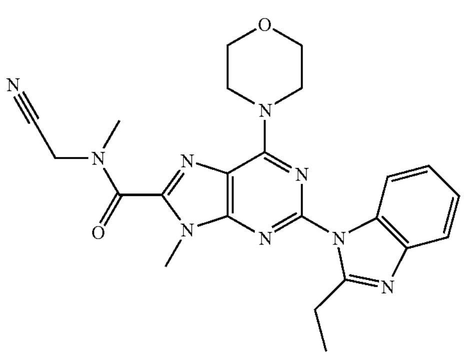 | N-(cyanomethyl)-2-(2-ethyl-1H-benzo[d]imidazol-1-yl)-N,9-dimethyl-6-morpholino-9H-purine-8-carboxamide |

TABLE 2-continued

| No. | Structure | Name |
|---|---|---|
| 638 | 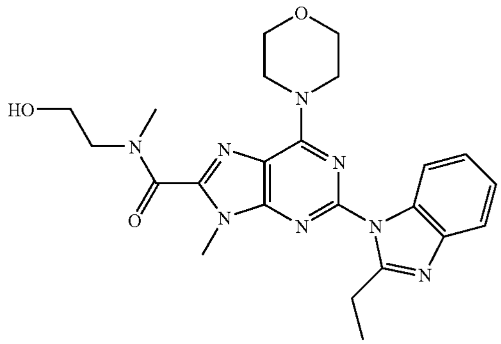 | 2-(2-ethyl-1H-benzo[d]imidazol-1-yl)-N-(2-hydroxyethyl)-N,9-dimethyl-6-morpholino-9H-purine-8-carboxamide |
| 639 | 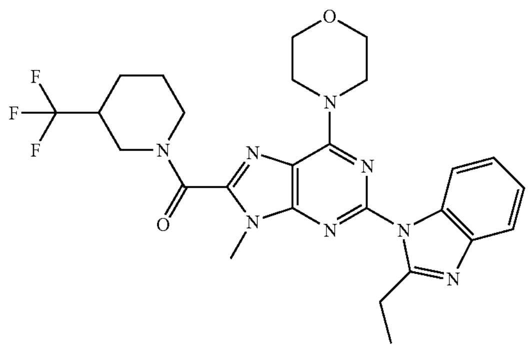 | (2-(2-ethyl-1H-benzo[d]imidazol-1-yl)-9-methyl-6-morpholino-9H-purin-8-yl)(3-(trifluoromethyl)piperidin-1-yl)methanone |
| 640 | 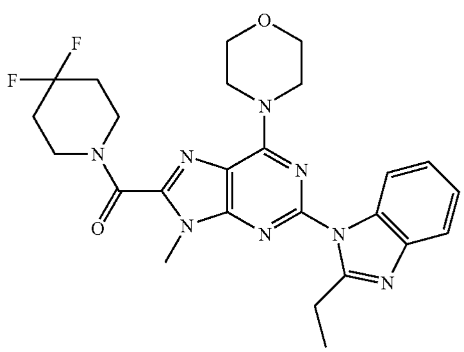 | (4,4-difluoropiperidin-1-yl)(2-(2-ethyl-1H-benzo[d]imidazol-1-yl)-9-methyl-6-morpholino-9H-purin-8-yl)methanone |
| 641 | 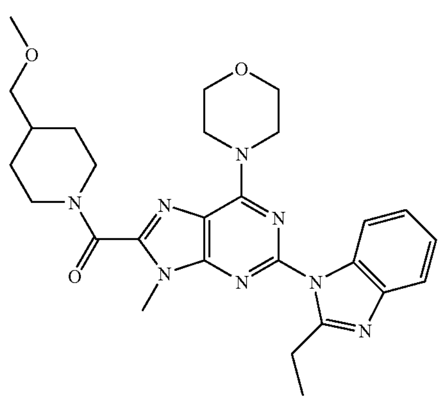 | (2-(2-ethyl-1H-benzo[d]imidazol-1-yl)-9-methyl-6-morpholino-9H-purin-8-yl)(4-(methoxymethyl)piperidin-1-yl)methanone |

TABLE 2-continued

| No. | Structure | Name |
|---|---|---|
| 642 | 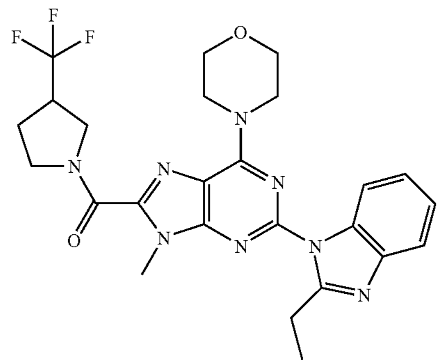 | (2-(2-ethyl-1H-benzo[d]imidazol-1-yl)-9-methyl-6-morpholino-9H-purin-8-yl)(3-(trifluoromethyl)pyrrolidin-1-yl)methanone |
| 643 | 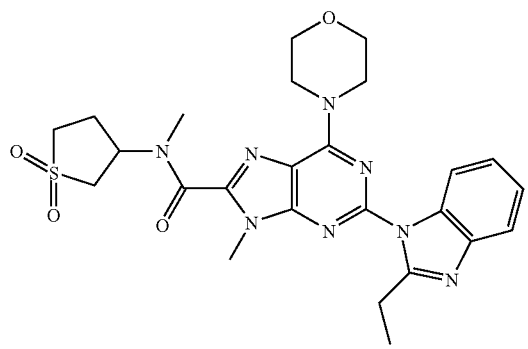 | 2-(2-ethyl-1H-benzo[d]imidazol-1-yl)-N,9-dimethyl-6-morpholino-N-(1,1-dioxo-tetrahydrothiophen-3-yl)-9H-purine-8-carboxamide |
| 644 | 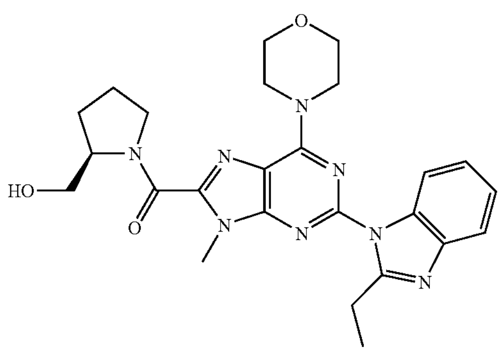 | (R)-(2-(2-ethyl-1H-benzo[d]imidazol-1-yl)-9-methyl-6-morpholino-9H-purin-8-yl)(2-(hydroxymethyl)pyrrolidin-1-yl)methanone |
| 645 | 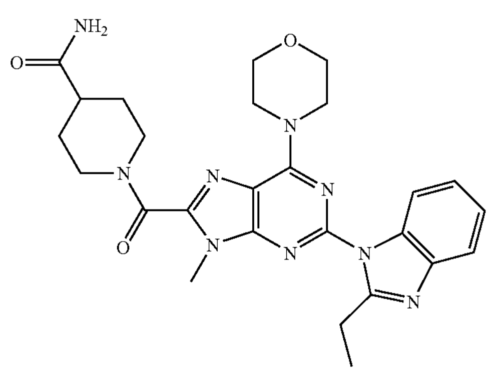 | 1-(2-(2-ethyl-1H-benzo[d]imidazol-1-yl)-9-methyl-6-morpholino-9H-purine-8-carbonyl)piperidine-4-carboxamide |

| No. | Structure | Name |
|---|---|---|
| 646 | 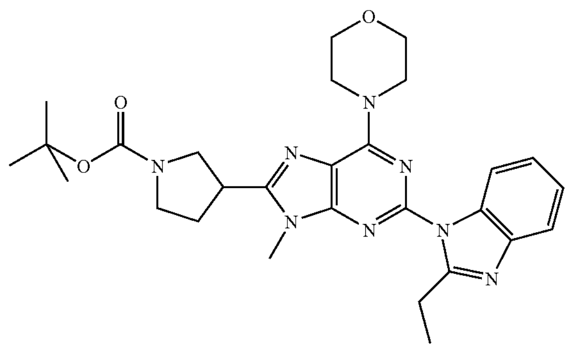 | tert-butyl 3-(2-(2-ethyl-1H-benzo[d]imidazol-1-yl)-9-methyl-6-morpholino-9H-purin-8-yl)pyrrolidine-1-carboxylate |
| 647 | 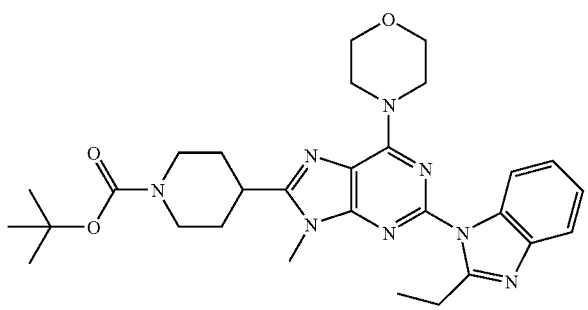 | tert-butyl 4-(2-(2-ethyl-1H-benzo[d]imidazol-1-yl)-9-methyl-6-morpholino-9H-purin-8-yl)piperidine-1-carboxylate |
| 648 | 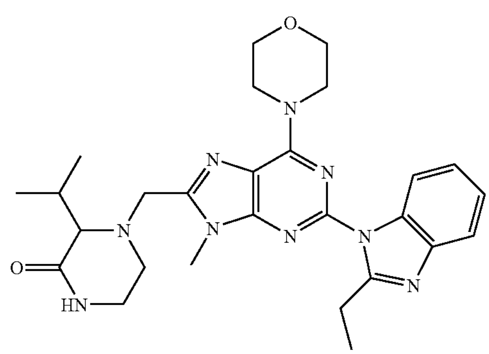 | 4-((2-(2-ethyl-1H-benzo[d]imidazole-yl)-9-methyl-6-morpholino-9H-purin-8-yl)methyl)-3-isopropylpiperazin-2-one |
| 649 | 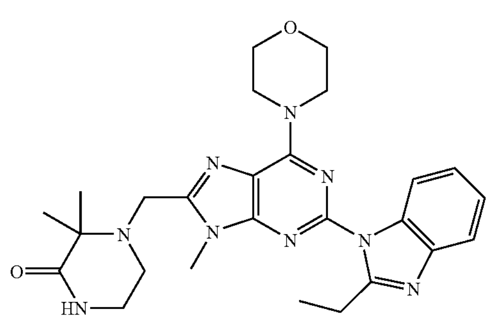 | 4-((2-(2-ethyl-1H-benzo[d]imidazol-1-yl)-9-methyl-6-morpholino-9H-purin-8-yl)methyl)-3,3-dimethylpiperazin-2-one |

TABLE 2-continued

| No. | Structure | Name |
|---|---|---|
| 650 | 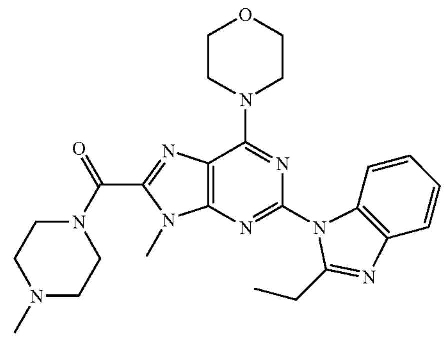 | (2-(2-ethyl-1H-benzo[d]imidazol-1-yl)-9-methyl-6-morpholino-9H-purin-8-yl)(4-methylpiperazin-1-yl)methanone |
| 651 | 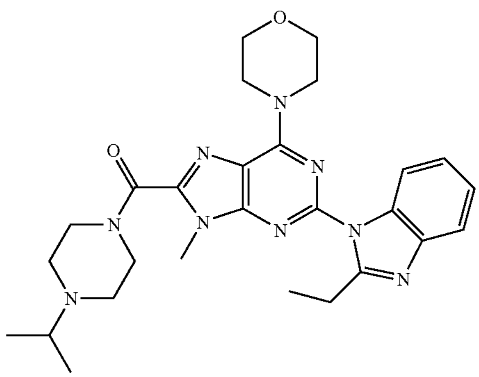 | (2-(2-ethyl-1H-benzo[d]imidazol-1-yl)-9-methyl-6-morpholino-9H-purin-8-yl)(4-isopropylpiperazin-1-yl)methanone |
| 652 | 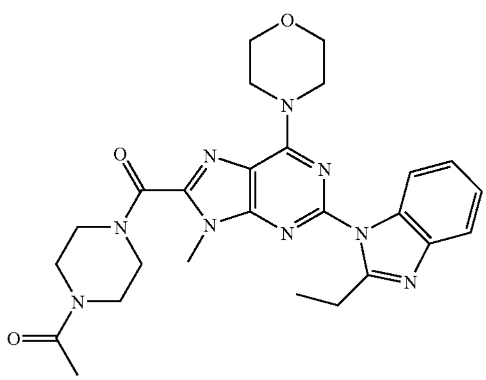 | l-(4-(2-(2-ethyl-1H-benzo[d]imidazol-1-yl)-9-methyl-6-morpholino-9H-purine-8-carbonyl)piperazin-1-yl)ethanone |
| 653 | 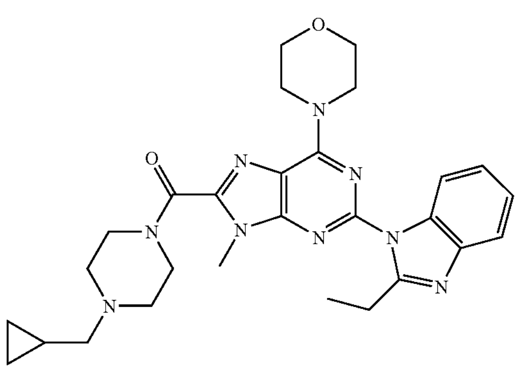 | (4-(cyclopropylmethyl)piperazin-1-yl)(2-(2-ethyl-1H-benzo[d]imidazol-1-yl)-9-methyl-6-morpholino-9H-purin-8-yl)methanone |

TABLE 2-continued

| No. | Structure | Name |
|---|---|---|
| 654 | 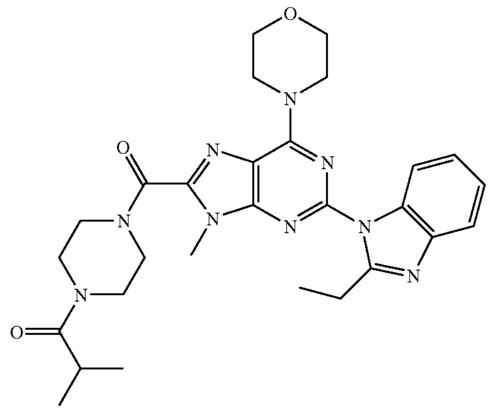 | 1-(4-(2-(2-ethyl-1H-benzo[d]imidazol-1-yl)-9-methyl-6-morpholino-9H-purine-8-carbonyl)piperazin-1-yl)-2-methylpropan-1-one |
| 655 | 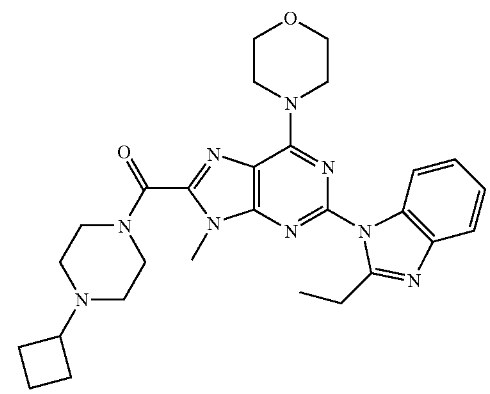 | (4-cyclobutylpiperazin-1-yl)(2-(2-ethyl-1H-benzo[d]imidazol-1-yl)-9-methyl-6-morpholino-9H-purin-8-yl)methanone |
| 656 | 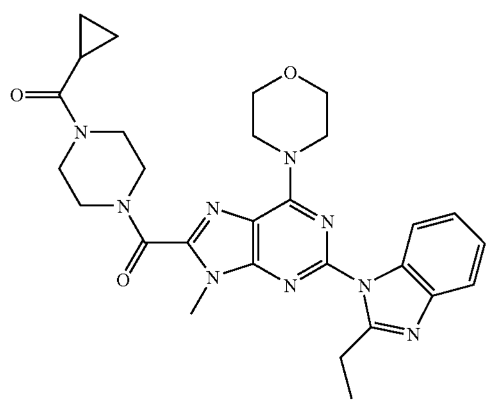 | (4-(cyclopropanecarbonyl)piperazin-1-yl)(2-(2-ethyl-1H-benzo[d]imidazol-1-yl)-9-methyl-6-morpholino-9H-purin-8-yl)methanone |
| 657 | 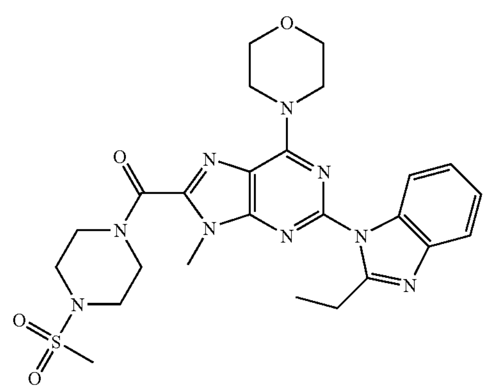 | (2-(2-ethyl-1H-benzo[d]imidazol-1-yl)-9-methyl-6-morpholino-9H-purin-8-yl)(4-(methylsulfonyl)piperazin-1-yl)methanone |

TABLE 2-continued

| No. | Structure | Name |
|---|---|---|
| 658 | 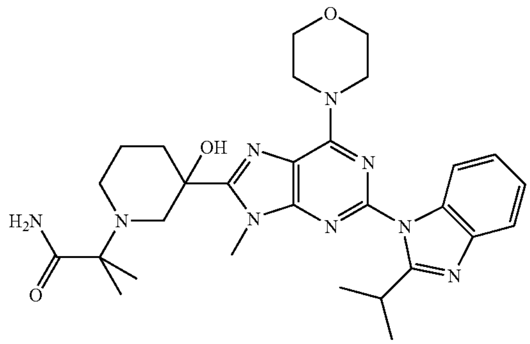 | 2-(3-hydroxy-3-(2-(2-isopropyl-1H-benzo[d]imidazol-1-yl)-9-methyl-6-morpholino-9H-purin-8-yl)piperidin-1-yl)-2-methylpropanamide |
| 659 | 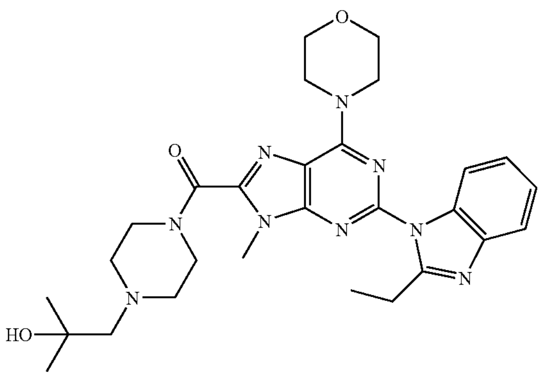 | (2-(2-ethyl-1H-benzo[d]imidazol-1-yl)-9-methyl-6-morpholino-9H-purin-8-yl)(4-(2-hydroxy-2-methylpropyl)piperazin-1-yl)methanone |
| 660 | 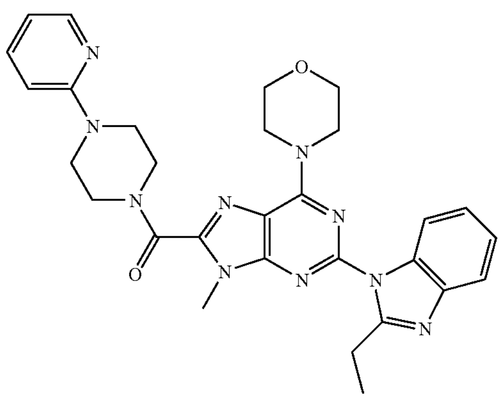 | (2-(2-ethyl-1H-benzo[d]imidazol-1-yl)-9-methyl-6-morpholino-9H-purin-8-yl)(4-(pyridin-2-yl)piperazin-1-yl)methanone |
| 661 | 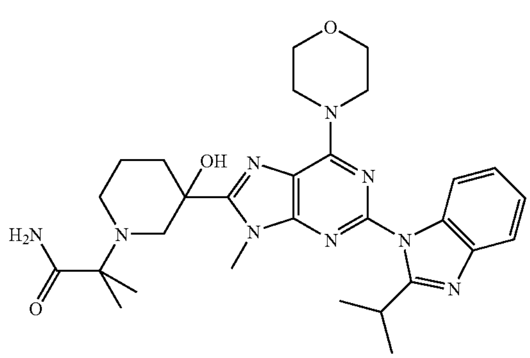 | 2-(3-hydroxy-3-(2-(2-isopropyl-1H-benzo[d]imidazol-1-yl)-9-methyl-6-morpholino-9H-purin-8-yl)piperidin-1-yl)-2-methylpropanamide |

TABLE 2-continued

| No. | Structure | Name |
|---|---|---|
| 662 | 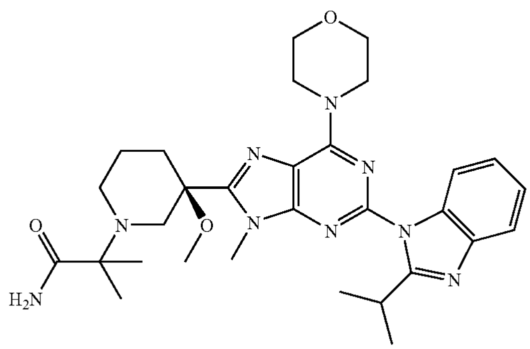 | (R)-2-(3-(2-(2-isopropyl-1H-benzo[d]imidazole-yl)-9-methyl-6-morpholino-9H-purin-8-yl)-3-methoxypiperidin-1-yl)-2-methylpropanamide |
| 663 | 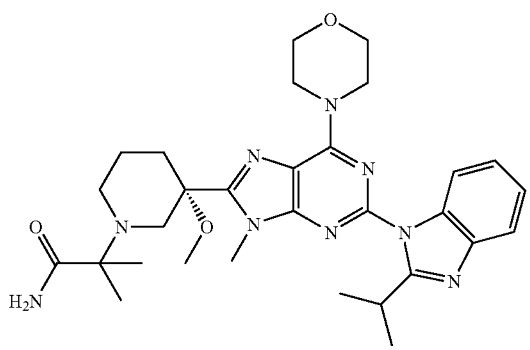 | (S)-2-(3-(2-(2-isopropyl-1H-benzo[d]imidazol-1-yl)-9-methyl-6-morpholino-9H-purin-8-yl)-3-methoxypiperidin-1-yl)-2-methylpropanamide |
| 664 | 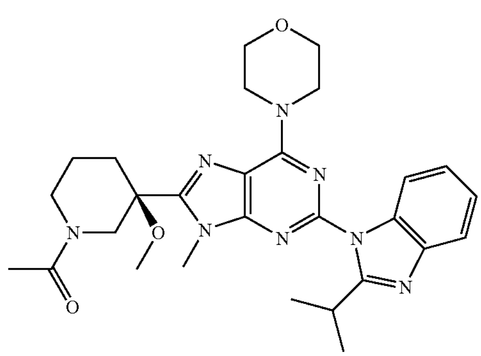 | (R)-1-(3-(2-(2-isopropyl-1H-benzo[d]imidazol-1-yl)-9-methyl-6-morpholino-9H-purin-8-yl)-3-methoxypiperidin-1-yl)ethanone |
| 665 | 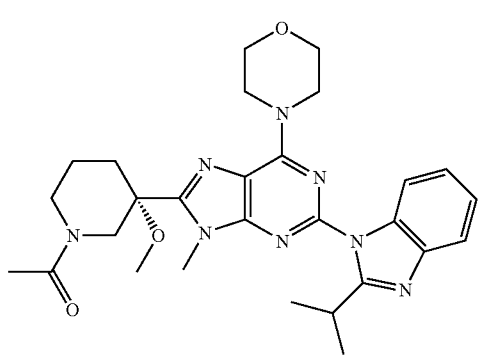 | (S)-1-(3-(2-(2-isopropyl-1H-benzo[d]imidazol-1-yl)-9-methyl-6-morpholino-9H-purin-8-yl)-3-methoxypiperidin-1-yl)ethanone |

TABLE 2-continued

| No. | Structure | Name |
|---|---|---|
| 666 | 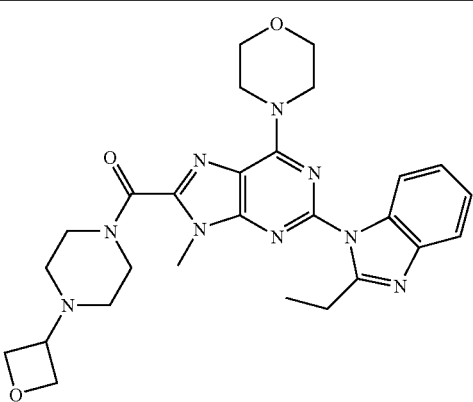 | (2-(2-ethyl-1H-benzo[d]imidazol-1-yl)-9-methyl-6-morpholino-9H-purin-8-yl)(4-(oxetan-3-yl)piperazin-1-yl)methanone |
| 667 | 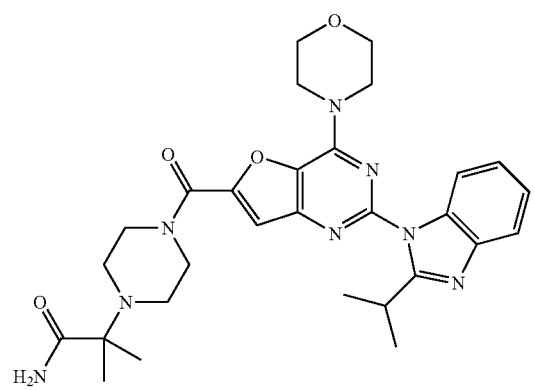 | 2-(4-(2-(2-isopropyl-1H-benzo[d]imidazol-1-yl)-4-morpholinofuro[3,2-d]pyrimidine-6-carbonyl)piperazin-1-yl)-2-methylpropanamide |
| 668 | 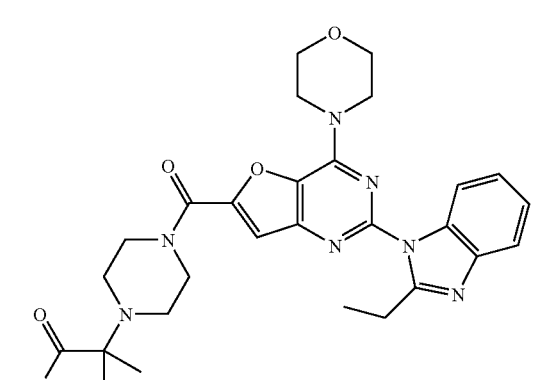 | 2-(4-(2-(2-ethyl-1H-benzo[d]imidazol-1-yl)-4-morpholinofuro[3,2-d]pyrimidine-6-carbonyl)piperazin-1-yl)-2-methylpropanamide |
| 669 | 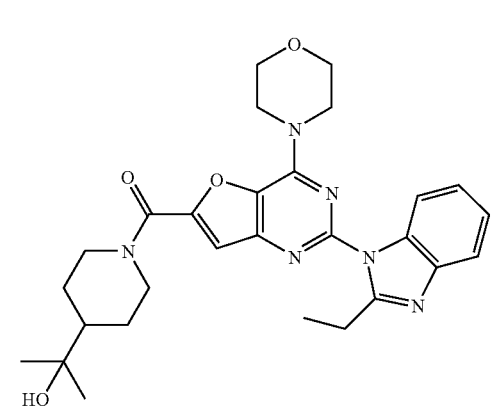 | (2-(2-ethyl-1H-benzo[d]imidazol-1-yl)-4-morpholinofuro[3,2-d]pyrimidin-6-yl)(4-(2-hydroxypropan-2-yl)piperidin-1-yl)methanone |

TABLE 2-continued

| No. | Structure | Name |
|---|---|---|
| 670 | 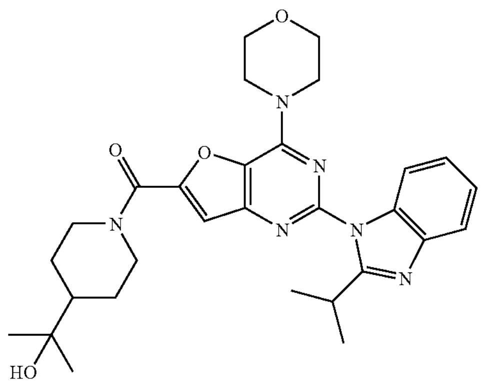 | (4-(2-hydroxypropan-2-yl)piperidin-1-yl)(2-(2-isopropyl-1H-benzo[d]imidazol-1-yl)-4-morpholinofuro[3,2-d]pyrimidin-6-yl)methanone |
| 671 | 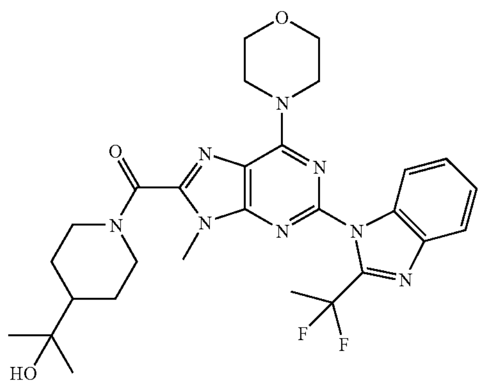 | (2-(2-(1,1-difluoroethyl)-1H-benzo[d]imidazol-1-yl)-9-methyl-6-morpholino-9H-purin-8-yl)(4-(2-hydroxypropan-2-yl)piperidin-1-yl)methanone |
| 672 | 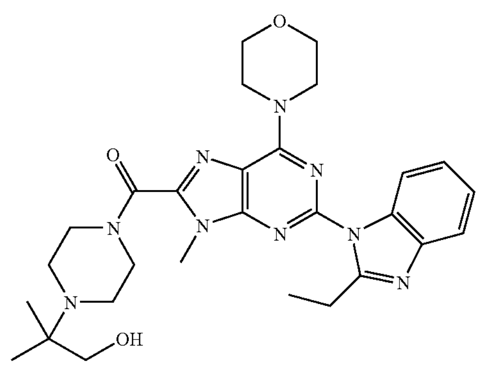 | (2-(2-ethyl-1H-benzo[d]imidazol-1-yl)-9-methyl-6-morpholino-9H-purin-8-yl)(4-(1-hydroxy-2-methylpropan-2-yl)piperazin-1-yl)methanone |
| 673 | 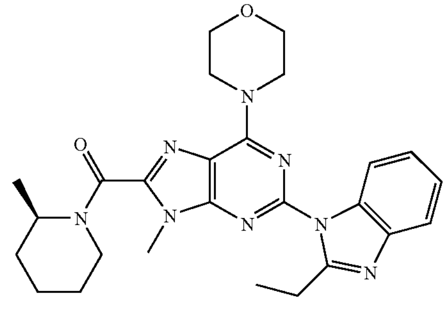 | (R)-(2-(2-ethyl-1H-benzo[d]imidazol-1-yl)-9-methyl-6-morpholino-9H-purin-8-yl)(2-methylpiperidin-1-yl)methanone |

TABLE 2-continued

| No. | Structure | Name |
| --- | --- | --- |
| 674 | 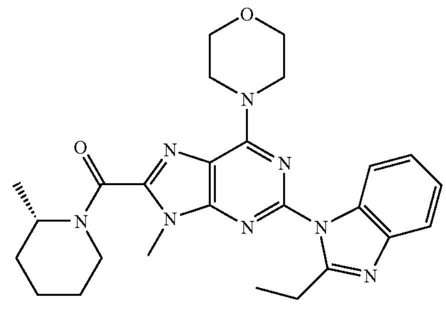 | (S)-(2-(2-ethyl-1H-benzo[d]imidazol-1-yl)-9-methyl-6-morpholino-9H-purin-8-yl)(2-methylpiperidin-1-yl)methanone |
| 675 | 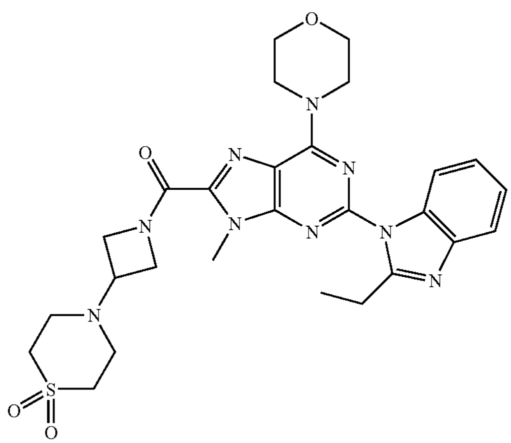 | (2-(2-ethyl-1H-benzo[d]imidazol-1-yl)-9-methyl-6-morpholino-9H-purin-8-yl)(3-(1,1-dioxo)thiomorpholinoazetidin-1-yl)methanone |
| 676 | 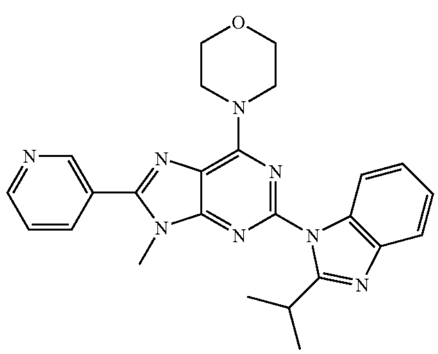 | 4-(2-(2-isopropyl-1H-benzo[d]imidazol-1-yl)-9-methyl-8-(pyridin-3-yl)-9H-purin-6-yl)morpholine |
| 677 | 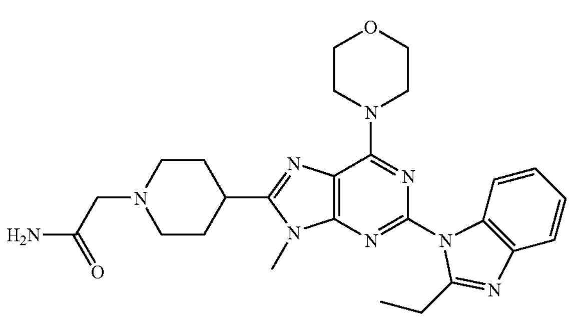 | 2-(4-(2-(2-ethyl-1H-benzo[d]imidazol-1-yl)-9-methyl-6-morpholino-9H-purin-8-yl)piperidin-1-yl)acetamide |

| No. | Structure | Name |
|---|---|---|
| 678 | 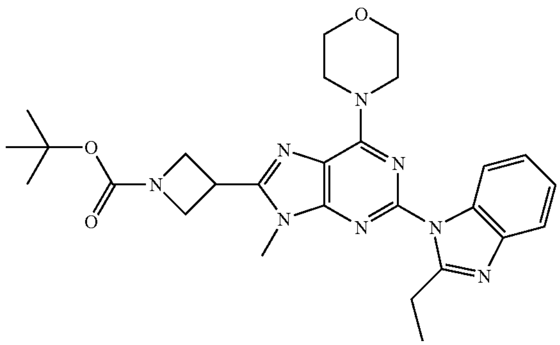 | tert-butyl 3-(2-(2-ethyl-1H-benzo[d]imidazol-1-yl)-9-methyl-6-morpholino-9H-purin-8-yl)azetidine-1-carboxylate |
| 679 | 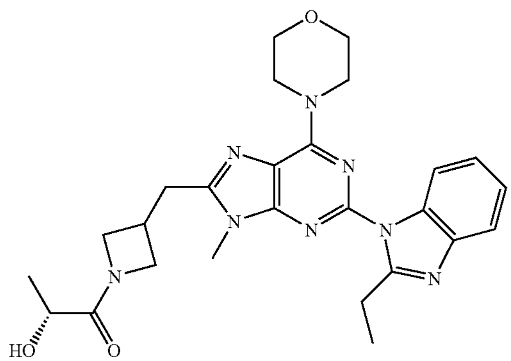 | (R)-1-(3-((2-(2-ethyl-1H-benzo[d]imidazol-1-yl)-9-methyl-6-morpholino-9H-purin-8-yl)methyl)azetidin-1-yl)-2-hydroxypropan-1-one |
| 680 | 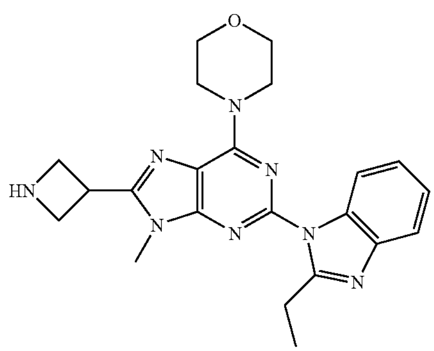 | 4-(8-(azetidin-3-yl)-2-(2-ethyl-1H-benzo[d]imidazol-1-yl)-9-methyl-9H-purin-6-yl)morpholine |
| 681 | 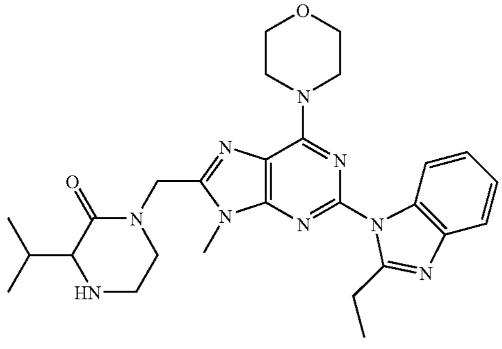 | 1-((2-(2-ethyl-1H-benzo[d]imidazol-1-yl)-9-methyl-6-morpholino-9H-purin-8-yl)methyl)-3-isopropylpiperazin-2-one |

TABLE 2-continued

| No. | Structure | Name |
|---|---|---|
| 682 | 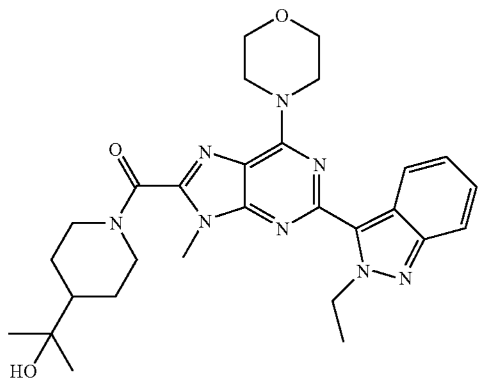 | (2-(2-ethyl-2H-indazol-3-yl)-9-methyl-6-morpholino-9H-purin-8-yl)(4-(2-hydroxypropan-2-yl)piperidin-1-yl)methanone |
| 683 | 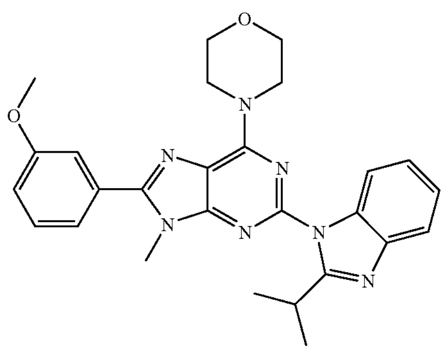 | 4-(2-(2-isopropyl-1H-benzo[d]imidazol-1-yl)-8-(3-methoxyphenyl)-9-methyl-9H-purin-6-yl)morpholine |
| 684 | 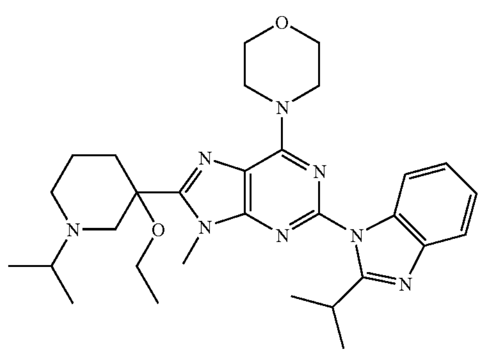 | 4-(8-(3-ethoxy-1-isopropylpiperidin-3-yl)-2-(2-isopropyl-1H-benzo[d]imidazol-1-yl)-9-methyl-9H-purin-6-yl)morpholine |
| 685 | 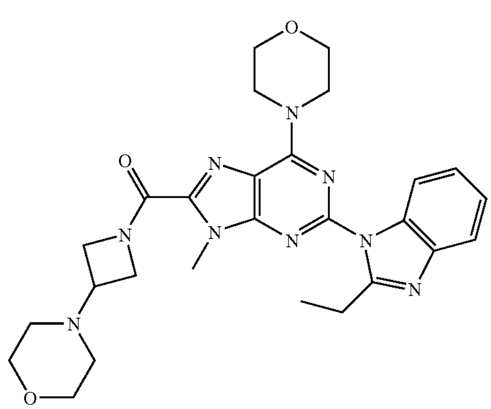 | (2-(2-ethyl-1H-benzo[d]imidazol-1-yl)-9-methyl-6-morpholino-9H-purin-8-yl)(3-morpholinoazetidin-1-yl)methanone |

TABLE 2-continued

| No. | Structure | Name |
|---|---|---|
| 686 | 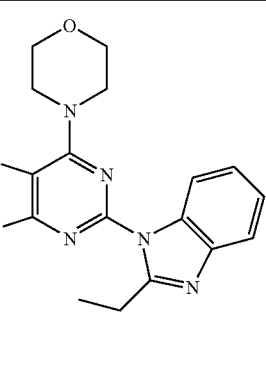 | (2-(2-ethyl-1H-benzo[d]imidazol-1-yl)-9-methyl-6-morpholino-9H-purin-8-yl)(4-(oxazol-2-ylmethyl)piperazin-1-yl)methanone |
| 687 | 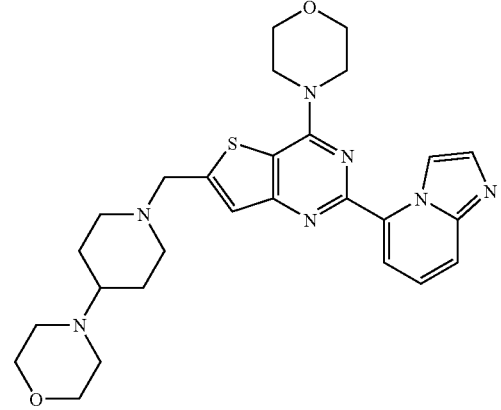 | 4-(1-((2-(imidazo[1,2-a]pyridin-5-yl)-4-morpholinothieno[3,2-d]pyrimidin-6-yl)methyl)piperidin-4-yl)morpholine |
| 688 | 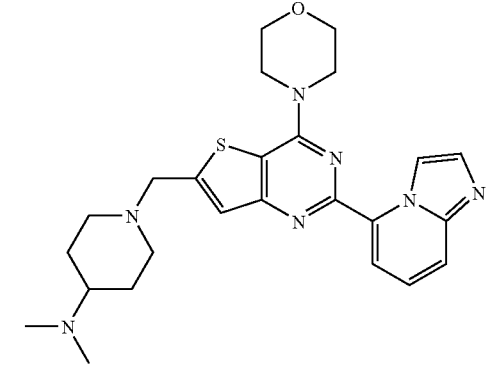 | 1-((2-(imidazo[1,2-a]pyridin-5-yl)-4-morpholinothieno[3,2-d]pyrimidin-6-yl)methyl)-N,N-dimethylpiperidin-4-amine |
| 689 | 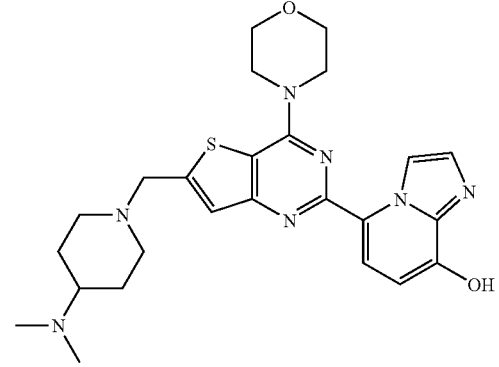 | 5-(6-((4-(dimethylamino)piperidin-1-yl)methyl)-4-morpholinothieno[3,2-d]pyrimidin-2-yl)imidazo[1,2-a]pyridin-8-ol |

TABLE 2-continued
| No. | Structure | Name |
|---|---|---|
| 690 | 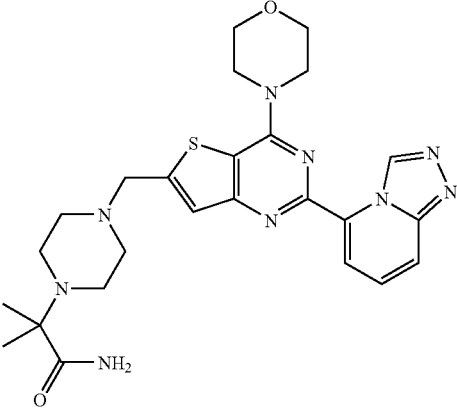 | 2-(4-((2-([1,2,4]triazolo[4,3-a]pyridin-5-yl)-4-morpholinothieno[3,2-d]pyrimidin-6-yl)methyl)piperazin-1-yl)-2-methylpropanamide |
| 691 | 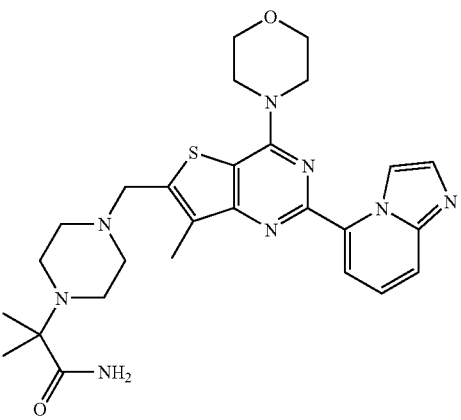 | 2-(4-((2-(imidazo[1,2-a]pyridin-5-yl)-7-methyl-4-morpholinothieno[3,2-d]pyrimidin-6-yl)methyl)piperazin-1-yl)-2-methylpropanamide |
| 692 | 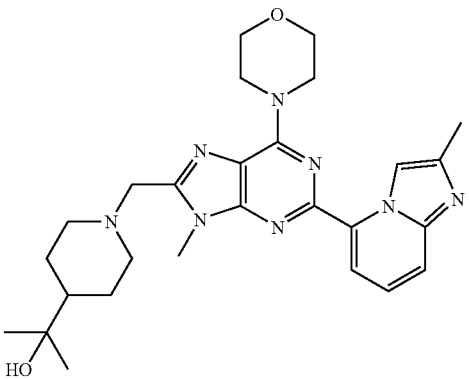 | 2-(1-((9-methyl-2-(2-methylimidazo[1,2-a]pyridin-5-yl)-6-morpholino-9H-purin-8-yl)methyl)piperidin-4-yl)propan-2-ol |

| No. | Structure | Name |
|---|---|---|
| 693 | 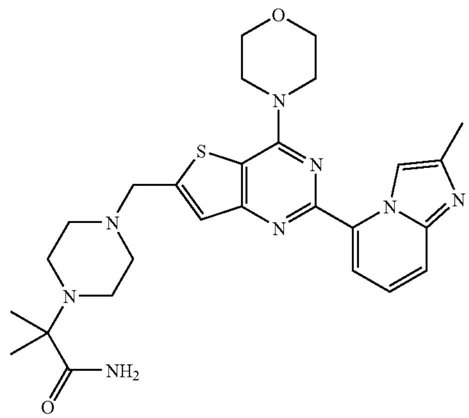 | 2-methyl-2-(4-((2-(2-methylimidazo[1,2-a]pyridin-5-yl)-4-morpholinothieno[3,2-d]pyrimidin-6-yl)methyl)piperazin-1-yl)propanamide |
| 694 | 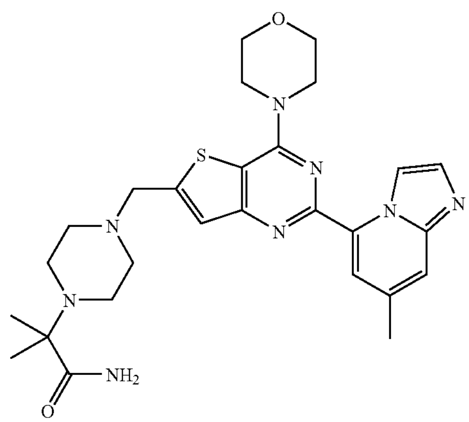 | 2-methyl-2-(4-((2-(7-methylimidazo[1,2-a]pyridin-5-yl)-4-morpholinothieno[3,2-d]pyrimidin-6-yl)methyl)piperazin-1-yl)propanamide |
| 695 | 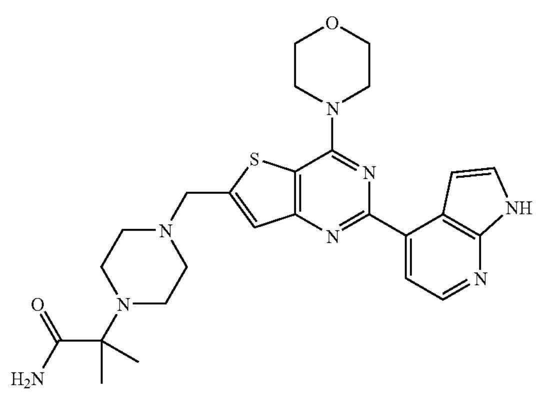 | 2-methyl-2-(4-((4-morpholino-2-(1H-pyrrolo[2,3-b]pyridin-4-yl)thieno[3,2-d]pyrimidin-6-yl)methyl)piperazin-1-yl)propanamide |
| 696 | 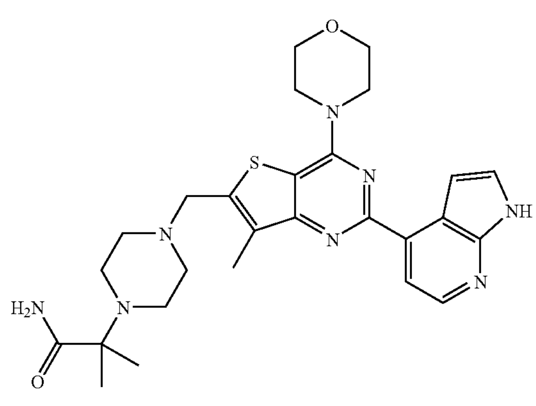 | 2-methyl-2-(4-((7-methyl-4-morpholino-2-(1H-pyrrolo[2,3-b]pyridin-4-yl)thieno[3,2-d]pyrimidin-6-yl)methyl)piperazin-1-yl)propanamide |

| No. | Structure | Name |
|---|---|---|
| 697 | 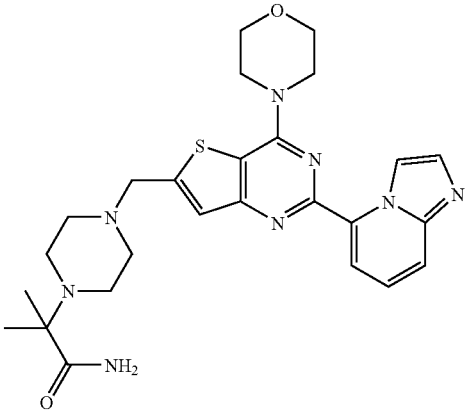 | 2-(4-((2-(imidazo[1,2-a]pyridin-5-yl)-4-morpholinothieno[3,2-d]pyrimidin-6-yl)methyl)piperazin-1-yl)-2-methylpropanamide |
| 698 | 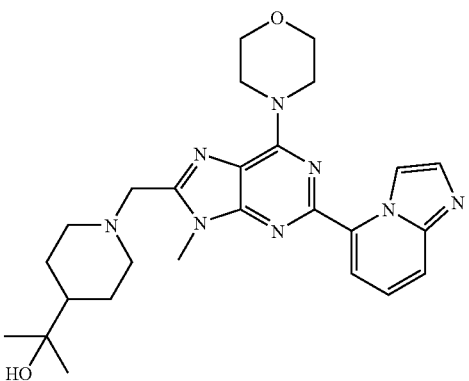 | 2-(1-((2-(imidazo[1,2-a]pyridin-5-yl)-9-methyl-6-morpholino-9H-purin-8-yl)methyl)piperidin-4-yl)propan-2-ol |
| 699 | 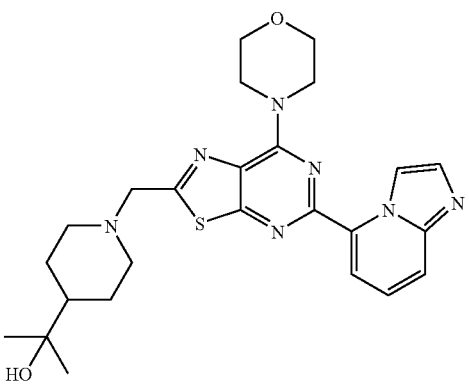 | 2-(1-((5-(imidazo[1,2-a]pyridin-5-yl)-7-morpholinothiazolo[5,4-d]pyrimidin-2-yl)methyl)piperidin-4-yl)propan-2-ol |
| 700 | 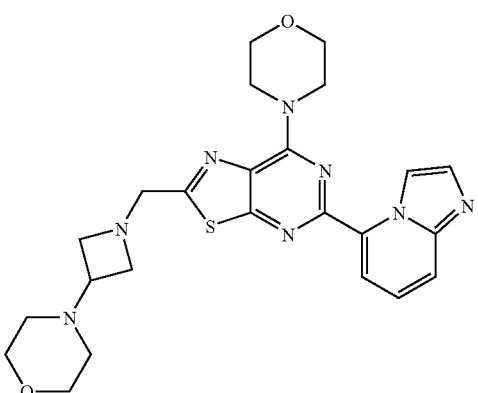 | 4-(5-(imidazo[1,2-a]pyridin-5-yl)-2-((3-morpholinoazetidin-1-yl)methyl)thiazolo[5,4-d]pyrimidin-7-yl)morpholine |

TABLE 2-continued

| No. | Structure | Name |
|---|---|---|
| 701 | 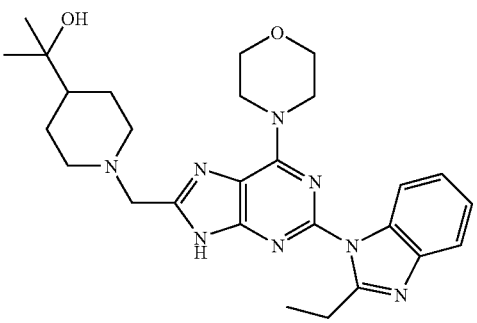 | 2-(1-((2-(2-ethyl-1H-benzo[d]imidazol-1-yl)-6-morpholino-9H-purin-8-yl)methyl)piperidin-4-yl)propan-2-ol |
| 702 | 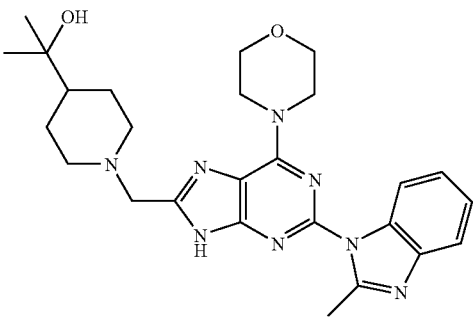 | 2-(1-((2-(2-methyl-1H-benzo[d]imidazol-1-yl)-6-morpholino-9H-purin-8-yl)methyl)piperidin-4-yl)propan-2-ol |

TABLE 3

| No. | Structure | Name |
|---|---|---|
| 703 | 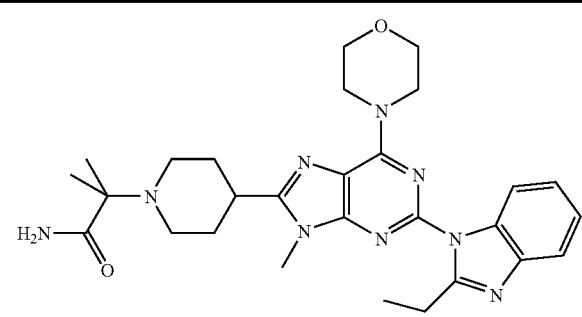 | 2-(4-(2-(2-ethyl-1H-benzo[d]imidazol-1-yl)-9-methyl-6-morpholino-9H-purin-8-yl)piperidin-1-yl)-2-methylpropanamide |
| 704 | 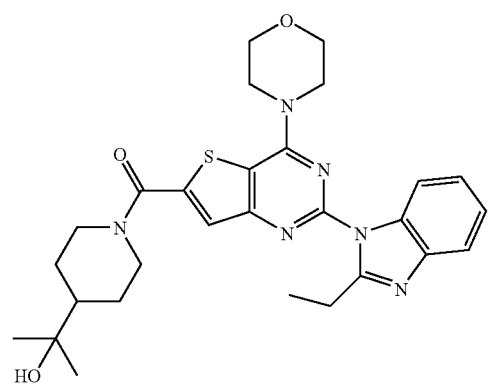 | (2-(2-ethyl-1H-benzo[d] imidazol-1-yl)-4-morpholinothieno[3,2-d]pyrimidin-6-yl)(4-(2-hydroxypropan-2-yl)piperidin-1-yl)methanone |

TABLE 3-continued

| No. | Structure | Name |
|---|---|---|
| 705 | 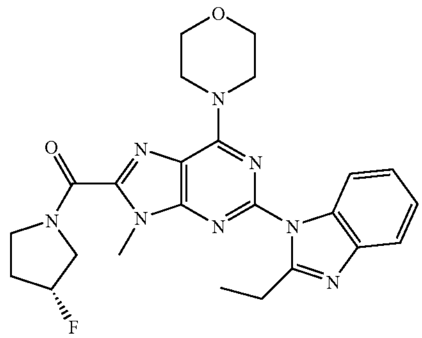 | (R)-(2-(2-ethyl-1H-benzo[d]imidazol-1-yl)-9-methyl-6-morpholino-9H-purin-8-yl)(3-fluoropyrrolidin-1-yl)methanone |
| 706 | 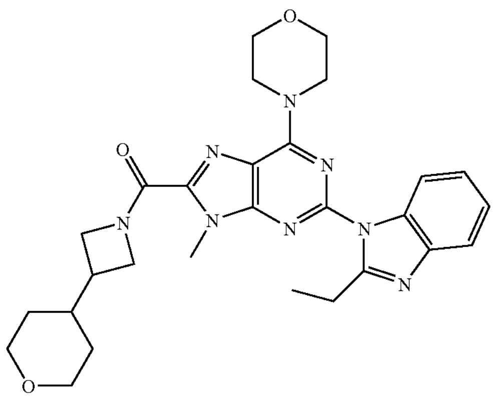 | (2-(2-ethyl-1H-benzo[d]imidazol-1-yl)-9-methyl-6-morpholino-9H-purin-8-yl)(3-(tetrahydro-2H-pyran-4-yl)azetidin-1-yl)methanone |
| 707 | 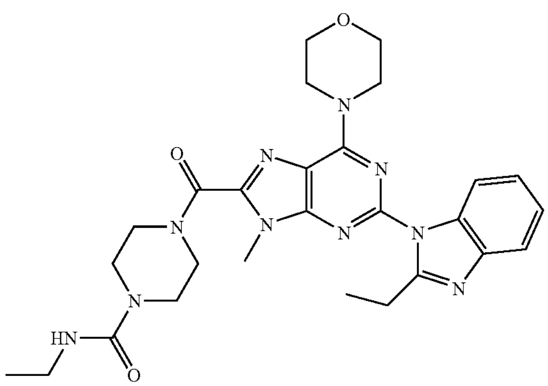 | N-ethyl-4-(2-(2-ethyl-1H-benzo[d]imidazol-1-yl)-9-methyl-6-morpholino-9H-purine-8-carbonyl)piperazine-1-carboxamide |
| 708 | 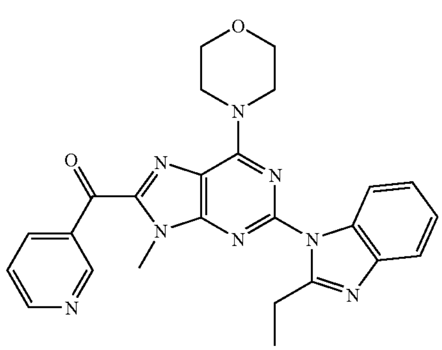 | (2-(2-ethyl-1H-benzo[d]imidazol-1-yl)-9-methyl-6-morpholino-9H-purin-8-yl)(pyridin-3-yl)methanone |

TABLE 3-continued

| No. | Structure | Name |
|---|---|---|
| 709 | 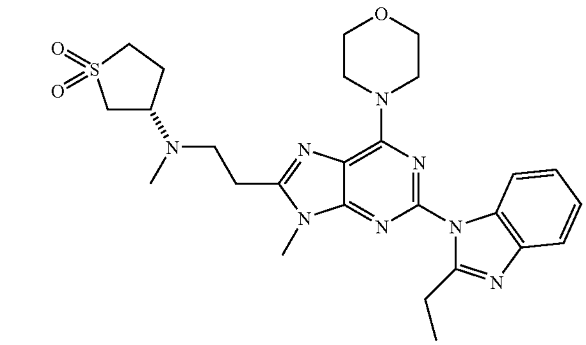 | (S)-N-(2-(2-(2-ethyl-1H-benzo[d]imidazol-1-yl)-9-methyl-6-morpholino-9H-purin-8-yl)ethyl)-N-methyl-(1,1-dioxo)-tetrahydrothiophen-3-amine |
| 710 | 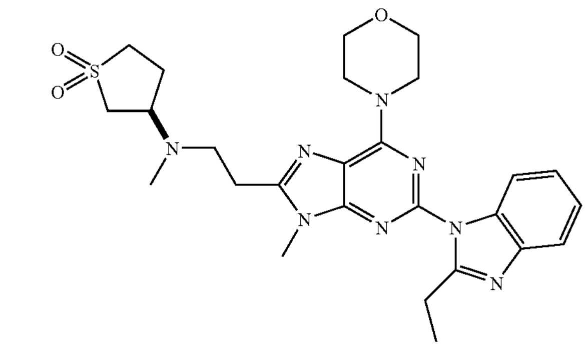 | (R)-N-(2-(2-(2-ethyl-1H-benzo[d]imidazol-1-yl)-9-methyl-6-morpholino-9H-purin-8-yl)ethyl)-N-methyl-(1,1-dioxo)-tetrahydrothiophen-3-amine |
| 711 | 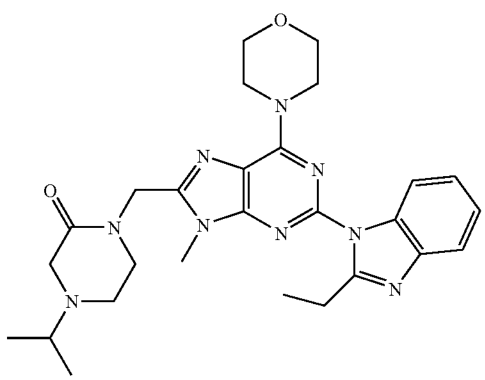 | 1-((2-(2-ethyl-1H-benzo[d]imidazol-1-yl)-9-methyl-6-morpholino-9H-purin-8-yl)methyl)-4-isopropylpiperazin-2-one |
| 712 | 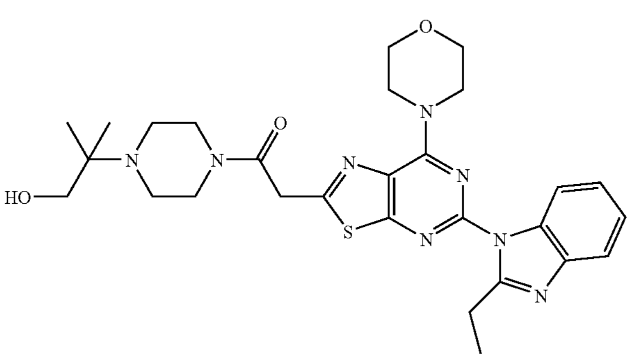 | 2-(5-(2-ethyl-1H-benzo[d]imidazol-1-yl)-7-morpholinothiazolo[5,4-d]pyrimidin-2-yl)-1-(4-(1-hydroxy-2-methylpropan-2-yl)piperazin-1-yl)ethanone |

| No. | Structure | Name |
|---|---|---|
| 713 | 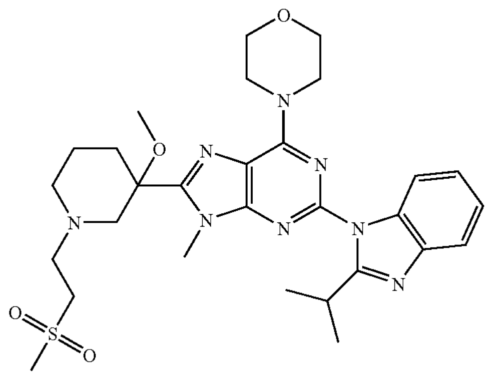 | 4-(2-(2-isopropyl-1H-benzo[d]imidazol-1-yl)-8-(3-methoxy-1-(2-(methylsulfonyl)ethyl)piperidin-3-yl)-9-methyl-9H-purin-6-yl)morpholine |
| 714 | 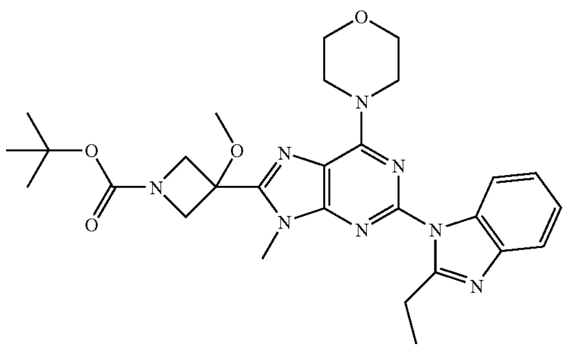 | tert-butyl 3-(2-(2-ethyl-1H-benzo[d]imidazol-1-yl)-9-methyl-6-morpholino-9H-purin-8-yl)-3-methoxyazetidine-1-carboxylate |
| 715 | 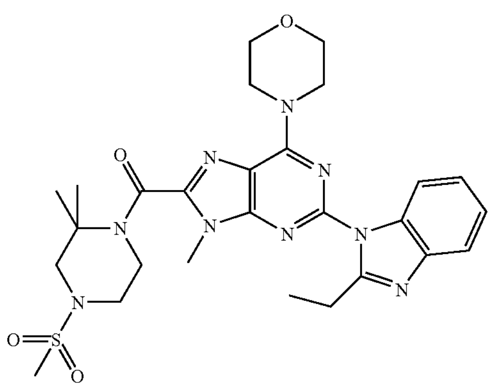 | (2,2-dimethyl-4-(methylsulfonyl)piperazin-1-yl)(2-(2-ethyl-1H-benzo[d]imidazol-1-yl)-9-methyl-6-morpholino-9H-purin-8-yl)methanone |
| 716 | 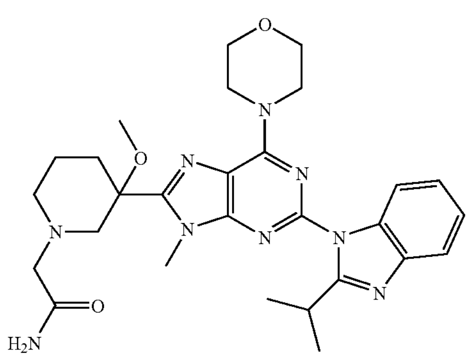 | 2-(3-(2-(2-isopropyl-1H-benzo[d]imidazol-1-yl)-9-methyl-6-morpholino-9H-purin-8-yl)-3-methoxypiperidin-1-yl)acetamide |

TABLE 3-continued

| No. | Structure | Name |
|---|---|---|
| 717 | 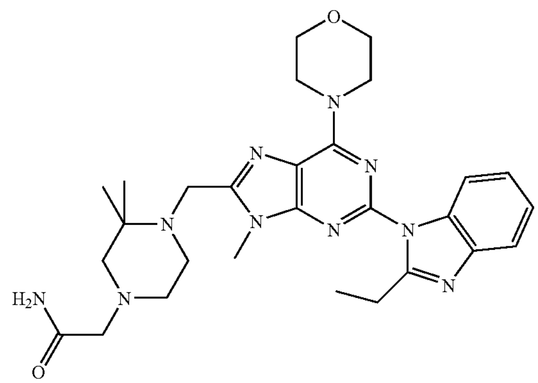 | 2-(4-((2-(2-ethyl-1H-benzo[d]imidazol-1-yl)-9-methyl-6-morpholino-9H-purin-8-yl)methyl)-3,3-dimethylpiperazin-1-yl)acetamide |
| 718 | 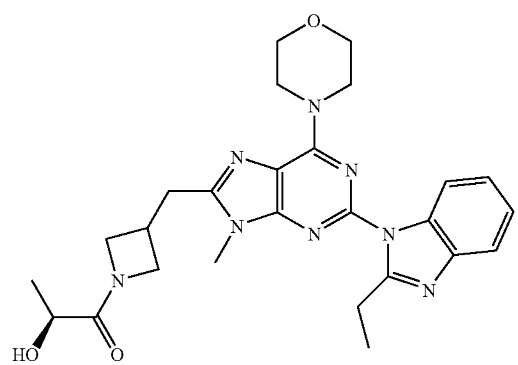 | (S)-1-(3-((2-(2-ethyl-1H-benzo[d]imidazol-1-yl)-9-methyl-6-morpholino-9H-purin-8-yl)methyl)azetidin-1-yl)-2-hydroxypropan-1-one |
| 719 | 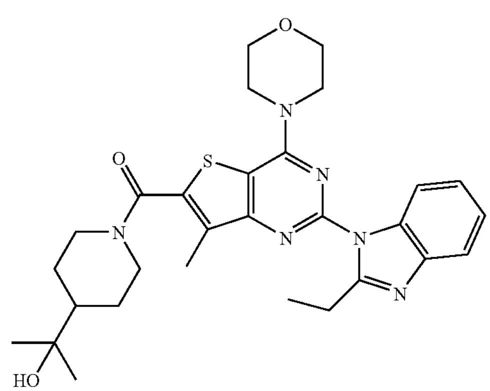 | (2-(2-ethyl-1H-benzo[d]imidazol-1-yl)-7-methyl-4-morpholinothieno[3,2-d]pyrimidin-6-yl)(4-(2-hydroxypropan-2-yl)piperidin-1-yl)methanone |
| 720 | 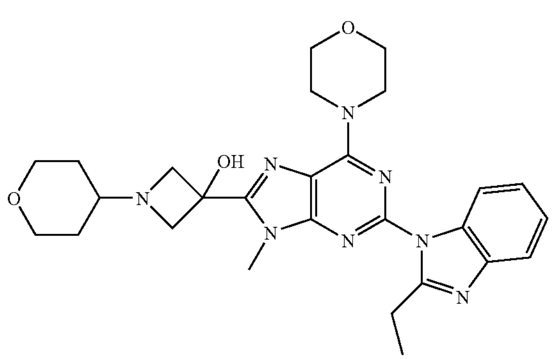 | 3-(2-(2-ethyl-1H-benzo[d]imidazol-1-yl)-9-methyl-6-morpholino-9H-purin-8-yl)-1-(tetrahydro-2H-pyran-4-yl)azetidin-3-ol |

TABLE 3-continued

| No. | Structure | Name |
|---|---|---|
| 721 | 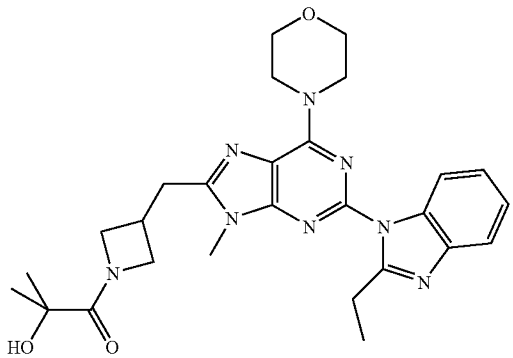 | 1-(3-((2-(2-ethyl-1H-benzo[d]imidazol-1-yl)-9-methyl-6-morpholino-9H-purin-8-yl)methyl)azetidin-1-yl)-2-hydroxy-2-methylpropan-1-one |
| 722 | 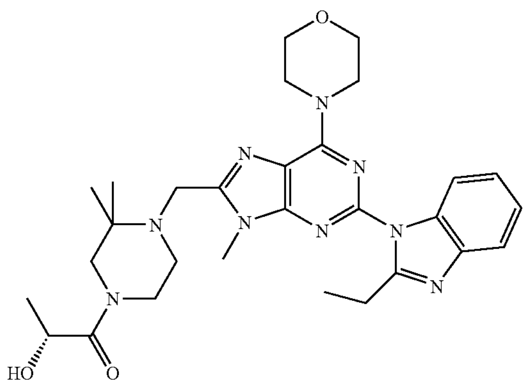 | (R)-1-(4-((2-(2-ethyl-1H-benzo[d]imidazol-1-yl)-9-methyl-6-morpholino-9H-purin-8-yl)methyl)-3,3-dimethylpiperazin-1-yl)-2-hydroxypropan-1-one |
| 723 | 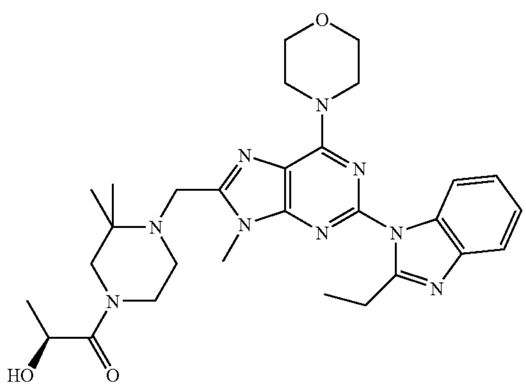 | (S)-1-(4-((2-(2-ethyl-1H-benzo[d]imidazol-1-yl)-9-methyl-6-morpholino-9H-purin-8-yl)methyl)-3,3-dimethylpiperazin-1-yl)-2-hydroxypropan-1-one |
| 724 | 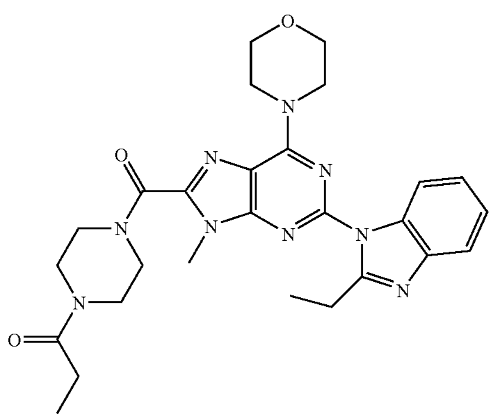 | 1-(4-(2-(2-ethyl-1H-benzo[d]imidazol-1-yl)-9-methyl-6-morpholino-9H-purine-8-carbonyl)piperazin-1-yl)propan-1-one |

| No. | Structure | Name |
|---|---|---|
| 725 | 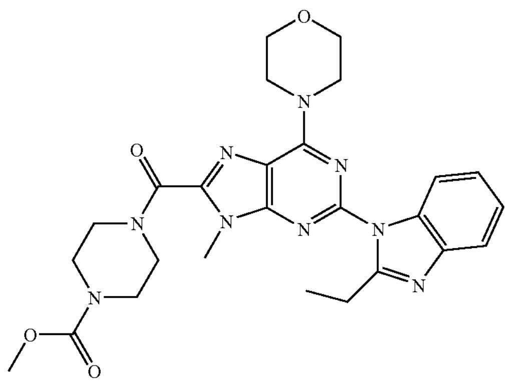 | methyl 4-(2-(2-ethyl-1H-benzo[d]imidazol-1-yl)-9-methyl-6-morpholino-9H-purine-8-carbonyl)piperazine-1-carboxylate |
| 726 | 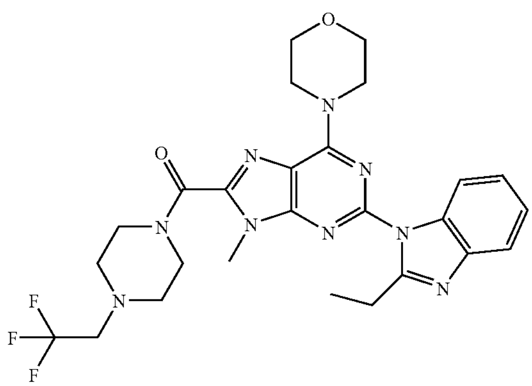 | (2-(2-ethyl-1H-benzo[d]imidazol-1-yl)-9-methyl-6-morpholino-9H-purin-8-yl)(4-(2,2,2-trifluoroethyl)piperazin-1-yl)methanone |
| 727 | 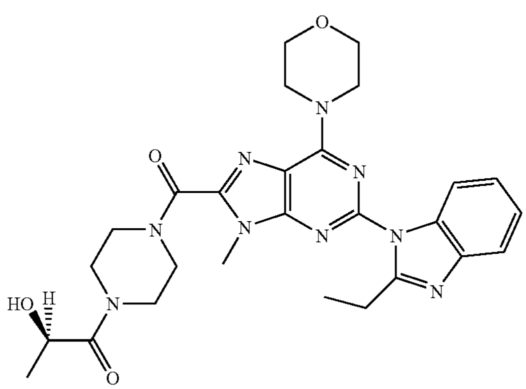 | (R)-1-(4-(2-(2-ethyl-1H-benzo[d]imidazol-1-yl)-9-methyl-6-morpholino-9H-purine-8-carbonyl)piperazin-1-yl)-2-hydroxypropan-1-one |
| 728 | 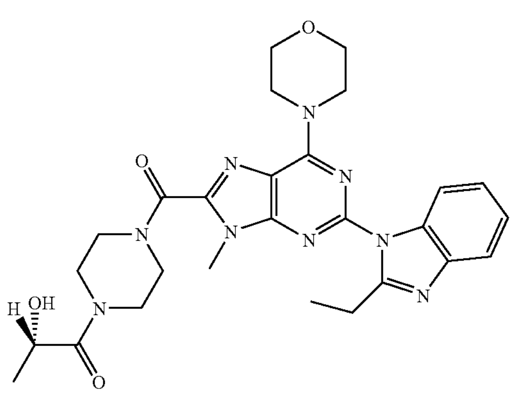 | (S)-1-(4-(2-(2-ethyl-1H-benzo[d]imidazol-1-yl)-9-methyl-6-morpholino-9H-purine-8-carbonyl)piperazin-1-yl)-2-hydroxypropan-1-one |

TABLE 3-continued

| No. | Structure | Name |
|---|---|---|
| 729 | 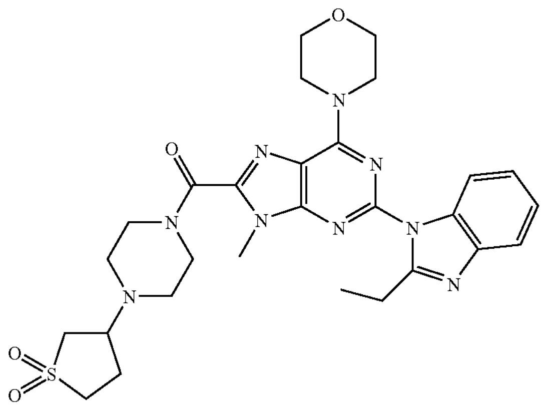 | (2-(2-ethyl-1H-benzo[d]imidazol-1-yl)-9-methyl-6-morpholino-9H-purin-8-yl)(4-(1,1-dioxotetrahydrothiophen-3-yl)piperazin-1-yl)methanone |
| 730 | 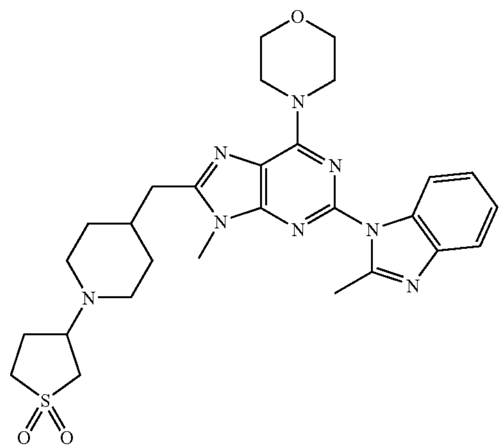 | 4-(9-methyl-2-(2-methyl-1H-benzo[d]imidazol-1-yl)-8-((1-(1,1-dioxo-tetrahydrothiophen-3-yl)piperidin-4-yl)methyl)-9H-purin-6-yl)morpholine |
| 731 | 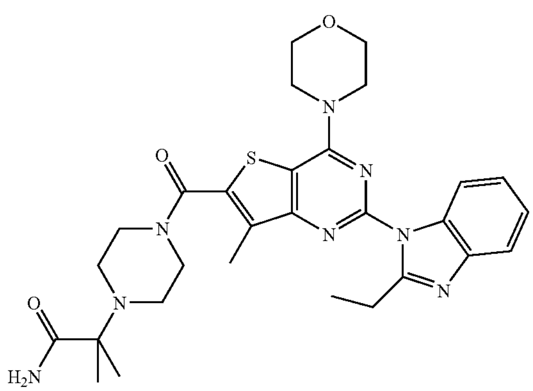 | 2-(4-(2-(2-ethyl-1H-benzo[d]imidazol-1-yl)-7-methyl-4-morpholinothieno[3,2-d]pyrimidine-6-carbonyl)piperazin-1-yl)-2-methylpropanamide |
| 732 | 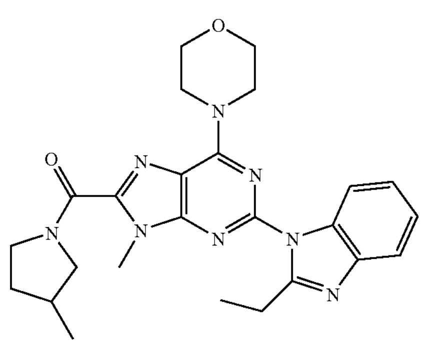 | (2-(2-ethyl-1H-benzo[d]imidazol-1-yl)-9-methyl-6-morpholino-9H-purin-8-yl)(3-methylpyrrolidin-1-yl)methanone |

TABLE 3-continued

| No. | Structure | Name |
|---|---|---|
| 733 | 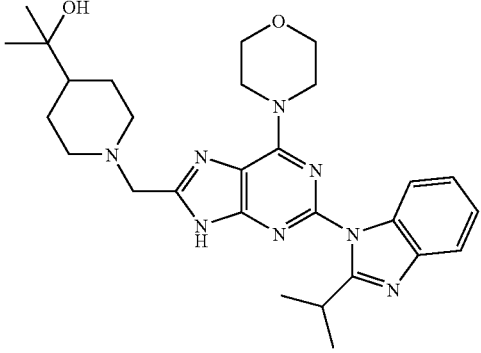 | 2-(1-((2-(2-isopropyl-1H-benzo[d]imidazol-1-yl)-6-morpholino-9H-purin-8-yl)methyl)piperidin-4-yl)propan-2-ol |
| 734 | 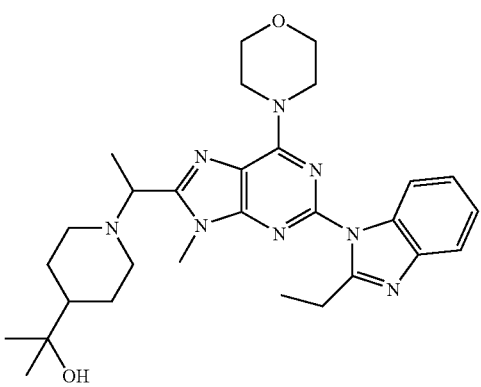 | 2-(1-(1-(2-(2-ethyl-1H-benzo[d]imidazol-1-yl)-9-methyl-6-morpholino-9H-purin-8-yl)ethyl)piperidin-4-yl)propan-2-ol |
| 735 | 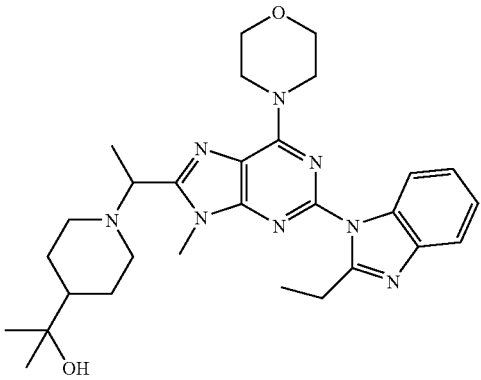 | 2-(1-(1-(2-(2-ethyl-1H-benzo[d]imidazol-1-yl)-9-methyl-6-morpholino-9H-purin-8-yl)ethyl)piperidin-4-yl)propan-2-ol |
| 736 | 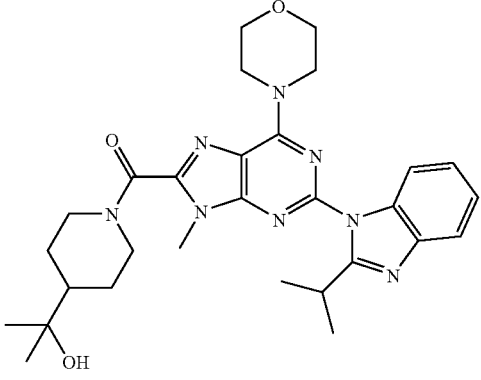 | (4-(2-hydroxypropan-2-yl)piperidin-1-yl)(2-(2-isopropyl-1H-benzo[d]imidazol-1-yl)-9-methyl-6-morpholino-9H-purin-8-yl)methanone |

TABLE 3-continued

| No. | Structure | Name |
|---|---|---|
| 737 | 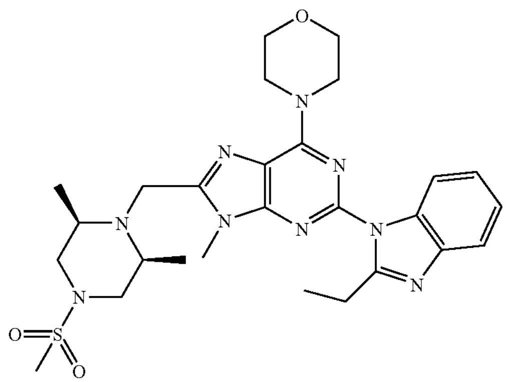 | 4-(8-(((2R,6S)-2,6-dimethyl-4-(methylsulfonyl)piperazin-1-yl)methyl)-2-(2-ethyl-1H-benzo[d]imidazol-1-yl)-9-methyl-9H-purin-6-yl)morpholine |
| 738 | 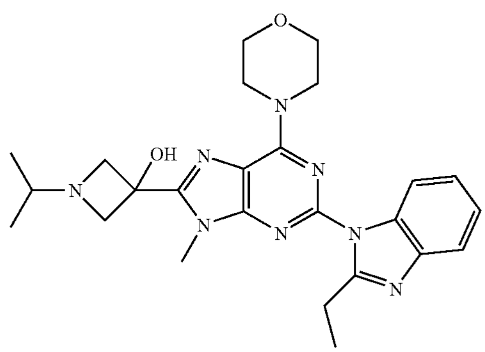 | 3-(2-(2-ethyl-1H-benzo[d]imidazol-1-yl)-9-methyl-6-morpholino-9H-purin-8-yl)-1-isopropylazetidin-3-ol |
| 739 | 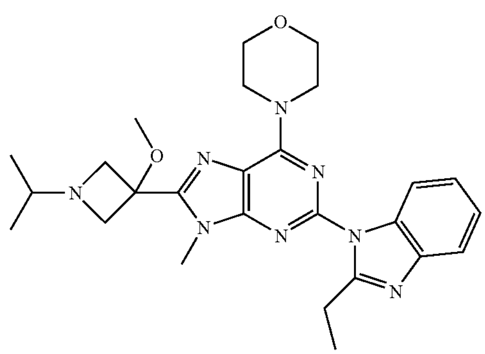 | 4-(2-(2-ethyl-1H-benzo[d]imidazol-1-yl)-8-(1-isopropyl-3-methoxyazetidin-3-yl)-9-methyl-9H-purin-6-yl)morpholine |
| 740 | 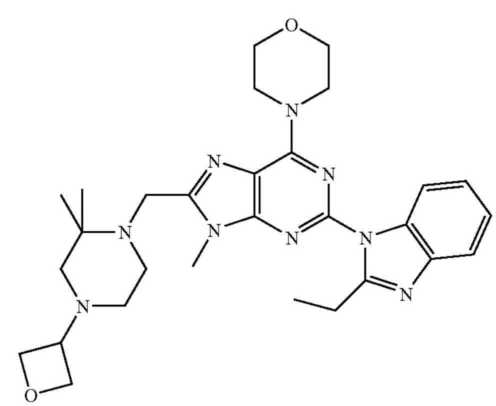 | 4-(8-((2,2-dimethyl-4-(oxetan-3-yl)piperazin-1-yl)methyl)-2-(2-ethyl-1H-benzo[d]imidazol-1-yl)-9-methyl-9H-purin-6-yl)morpholine |

TABLE 3-continued

| No. | Structure | Name |
|-----|-----------|------|
| 741 | 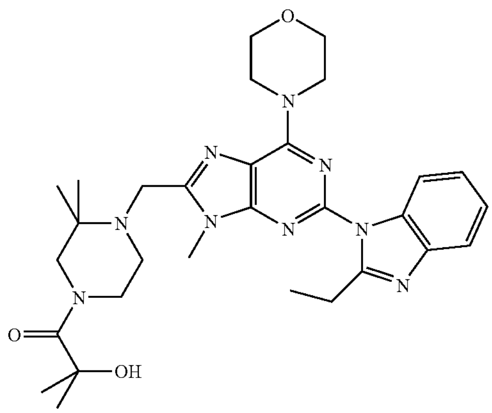 | 1-(4-((2-(2-ethyl-1H-benzo[d]imidazol-1-yl)-9-methyl-6-morpholino-9H-purin-8-yl)methyl)-3,3-dimethylpiperazin-1-yl)-2-hydroxy-2-methylpropan-1-one |
| 742 | 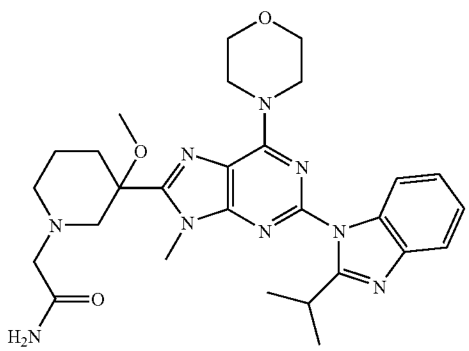 | 2-(3-(2-(2-isopropyl-1H-benzo[d]imidazol-1-yl)-9-methyl-6-morpholino-9H-purin-8-yl)-3-methoxypiperidin-1-yl)acetamide |
| 743 | 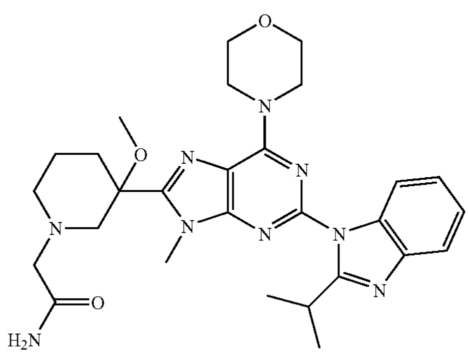 | 2-(3-(2-(2-isopropyl-1H-benzo[d]imidazol-1-yl)-9-methyl-6-morpholino-9H-purin-8-yl)-3-methoxypiperidin-1-yl)acetamide |
| 744 | 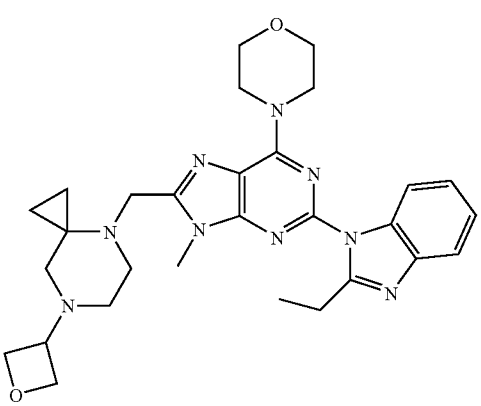 | 4-(2-(2-ethyl-1H-benzo[d]imidazol-1-yl)-9-methyl-8-((7-(oxetan-3-yl)-4,7-diazaspiro[2.5]octan-4-yl)methyl)-9H-purin-6-yl)morpholine |

TABLE 3-continued

| No. | Structure | Name |
|---|---|---|
| 745 | 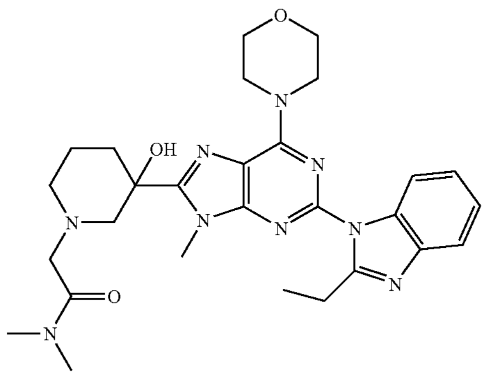 | 2-(3-(2-(2-ethyl-1H-benzo[d]imidazol-1-yl)-9-methyl-6-morpholino-9H-purin-8-yl)-3-hydroxypiperidin-1-yl)-N,N-dimethylacetamide |
| 746 | 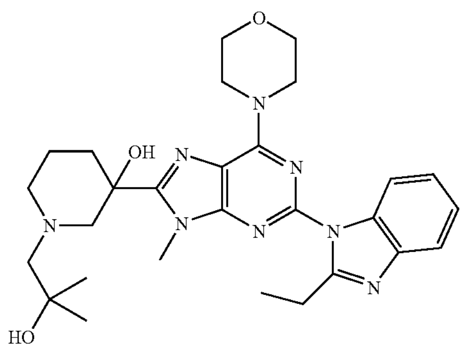 | 3-(2-(2-ethyl-1H-benzo[d]imidazol-1-yl)-9-methyl-6-morpholino-9H-purin-8-yl)-1-(2-hydroxy-2-methylpropyl)piperidin-3-ol |
| 747 | 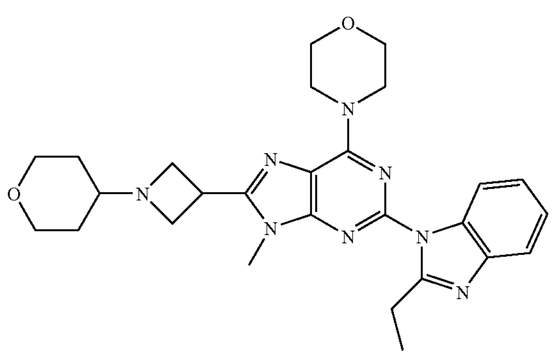 | 4-(2-(2-ethyl-1H-benzo[d]imidazol-1-yl)-9-methyl-8-(1-(tetrahydro-2H-pyran-4-yl)azetidin-3-yl)-9H-purin-6-yl)morpholine |
| 748 | 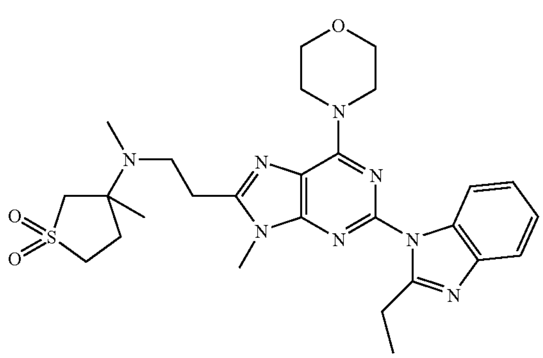 | N-(2-(2-(2-ethyl-1H-benzo[d]imidazol-1-yl)-9-methyl-6-morpholino-9H-purin-8-yl)ethyl)-N,3-dimethyl-1,1-dioxotetrahydrothiophen-3-amine |

TABLE 3-continued

| No. | Structure | Name |
|---|---|---|
| 749 | 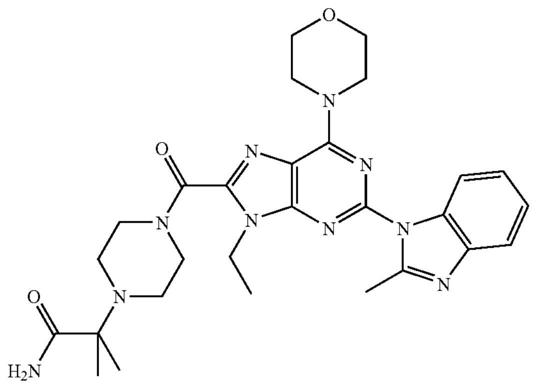 | 2-(4-(9-ethyl-2-(2-methyl-1H-benzo[d]imidazol-1-yl)-6-morpholino-9H-purine-8-carbonyl)piperazin-1-yl)-2-methylpropanamide |
| 750 | 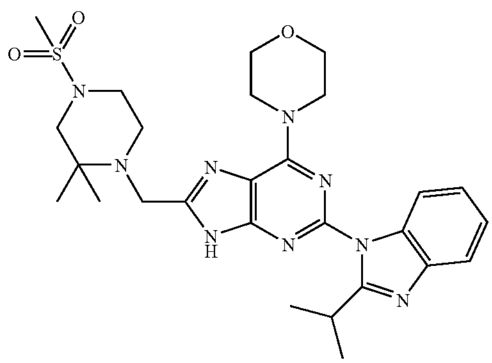 | 4-(8-((2,2-dimethyl-4-(methylsulfonyl)piperazin-1-yl)methyl)-2-(2-isopropyl-1H-benzo[d]imidazol-1-yl)-9H-purin-6-yl)morpholine |
| 751 | 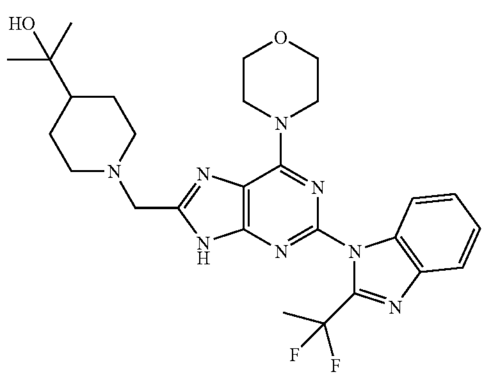 | 2-(1-((2-(2-(1,1-difluoroethyl)-1H-benzo[d]imidazol-1-yl)-6-morpholino-9H-purin-8-yl)methyl)piperidin-4-yl)propan-2-ol |
| 752 | 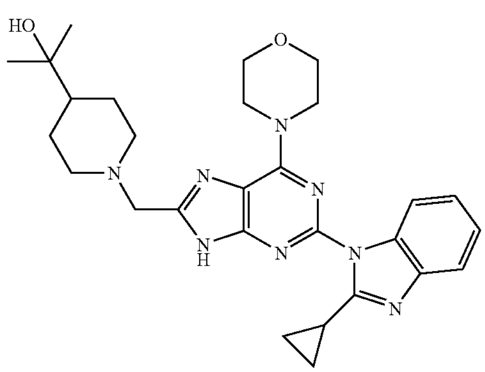 | 2-(1-((2-(2-cyclopropyl-1H-benzo[d]imidazol-1-yl)-6-morpholino-9H-purin-8-yl)methyl)piperidin-4-yl)propan-2-ol |

TABLE 3-continued

| No. | Structure | Name |
|---|---|---|
| 753 | 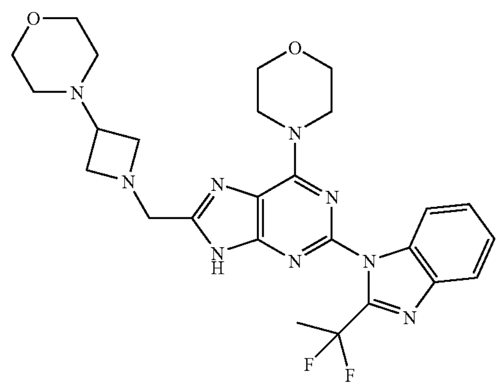 | 4-(1-((2-(2-(1,1-difluoroethyl)-1H-benzo[d]imidazol-1-yl)-6-morpholino-9H-purin-8-yl)methyl)azetidin-3-yl)morpholine |
| 754 | 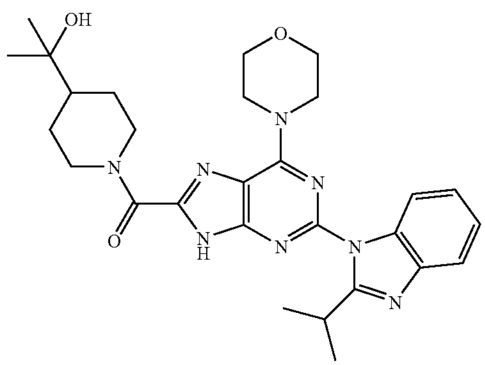 | (4-(2-hydroxypropan-2-yl)piperidin-1-yl)(2-(2-isopropyl-1H-benzo[d]imidazol-1-yl)-6-morpholino-9H-purin-8-yl)methanone |
| 755 | 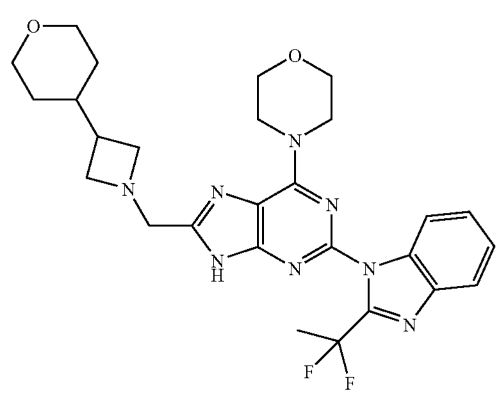 | 4-(2-(2-(1,1-difluoroethyl)-1H-benzo[d]imidazol-1-yl)-8-((3-(tetrahydro-2H-pyran-4-yl)azetidin-1-yl)methyl)-9H-purin-6-yl)morpholine |
| 756 | 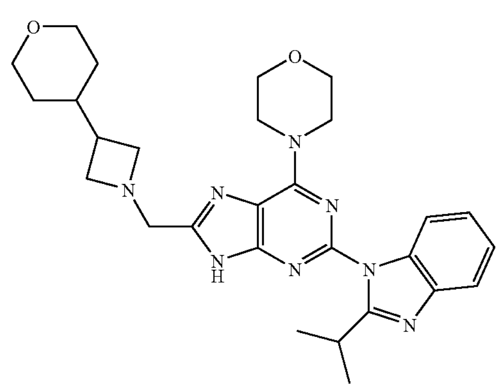 | 4-(2-(2-isopropyl-1H-benzo[d]imidazol-1-yl)-8-((3-(tetrahydro-2H-pyran-4-yl)azetidin-1-yl)methyl)-9H-purin-6-yl)morpholine |

TABLE 3-continued

| No. | Structure | Name |
|---|---|---|
| 757 | 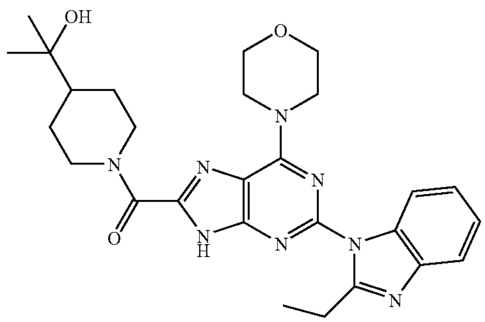 | (2-(2-ethyl-1H-benzo[d]imidazol-1-yl)-6-morpholino-9H-purin-8-yl)(4-(2-hydroxypropan-2-yl)piperidin-1-yl)methanone |
| 758 | 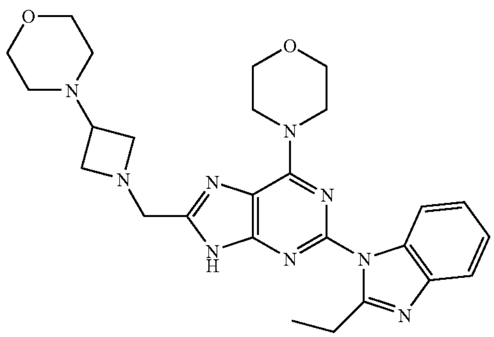 | 4-(1-((2-(2-ethyl-1H-benzo[d]imidazol-1-yl)-6-morpholino-9H-purin-8-yl)methyl)azetidin-3-yl)morpholine |
| 759 | 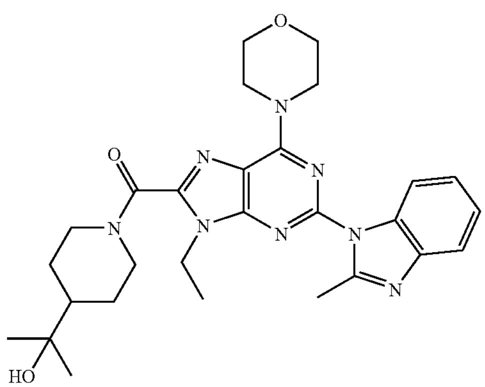 | (9-ethyl-2-(2-methyl-1H-benzo[d]imidazol-1-yl)-6-morpholino-9H-purin-8-yl)(4-(2-hydroxypropan-2-yl)piperidin-1-yl)methanone |
| 760 | 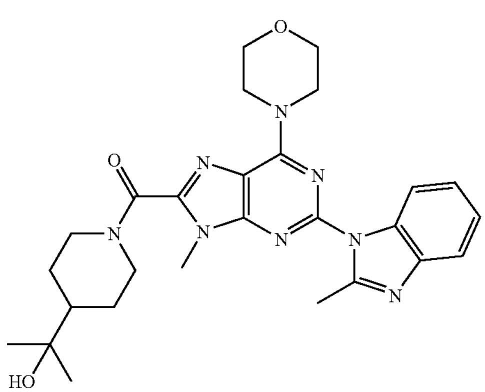 | (4-(2-hydroxypropan-2-yl)piperidin-1-yl)(9-methyl-2-(2-methyl-1H-benzo[d]imidazol-1-yl)-6-morpholino-9H-purin-8-yl)methanone |

TABLE 3-continued

| No. | Structure | Name |
|---|---|---|
| 761 | 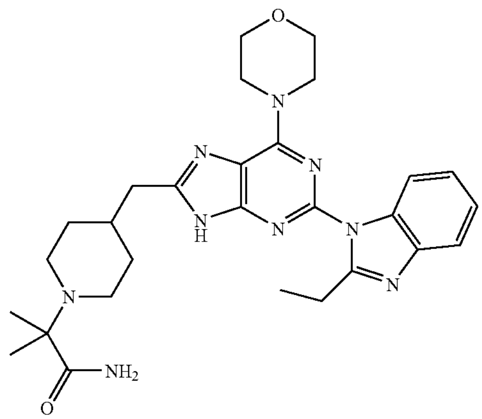 | 2-(4-((2-(2-ethyl-1H-benzo[d]imidazol-1-yl)-6-morpholino-9H-purin-8-yl)methyl)piperidin-1-yl)-2-methylpropanamide |
| 762 | 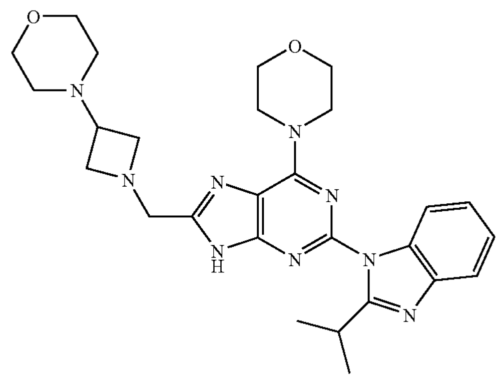 | 4-(1-((2-(2-isopropyl-1H-benzo[d]imidazol-1-yl)-6-morpholino-9H-purin-8-yl)methyl)azetidin-3-yl)morpholine |
| 763 | 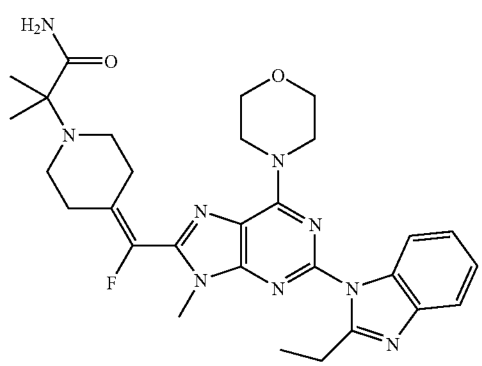 | 2-(4-((2-(2-ethyl-1H-benzo[d]imidazol-1-yl)-9-methyl-6-morpholino-9H-purin-8-yl)fluoromethylene)piperidin-1-yl)-2-methylpropanamide |
| 764 | 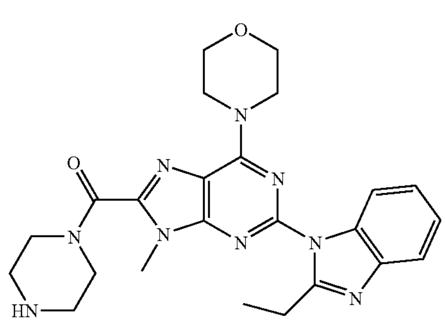 | (2-(2-ethyl-1H-benzo[d]imidazol-1-yl)-9-methyl-6-morpholino-9H-purin-8-yl)(piperazin-1-yl)methanone |

TABLE 3-continued

| No. | Structure | Name |
|---|---|---|
| 765 | 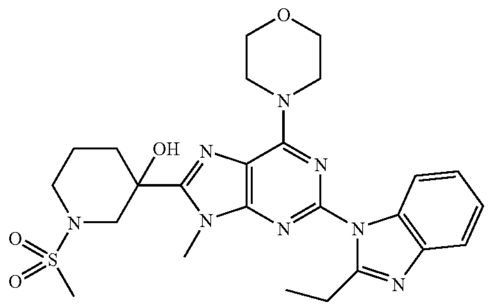 | 3-(2-(2-ethyl-1H-benzo[d]imidazol-1-yl)-9-methyl-6-morpholino-9H-purin-8-1)-1-(methylsulfonyl)piperidin-3-ol |
| 766 | 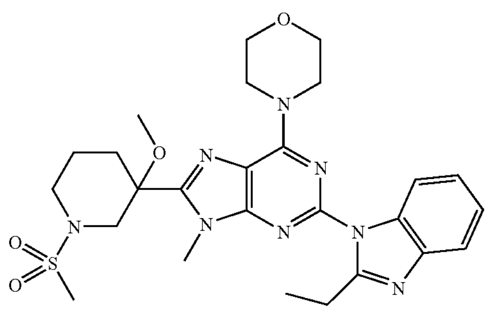 | 4-(2-(2-ethyl-1H-benzo[d]imidazol-1-yl)-8-(3-methoxy-1-(methylsulfonyl)piperidin-3-yl)-9-methyl-9H-purin-6-yl)morpholine |
| 767 | 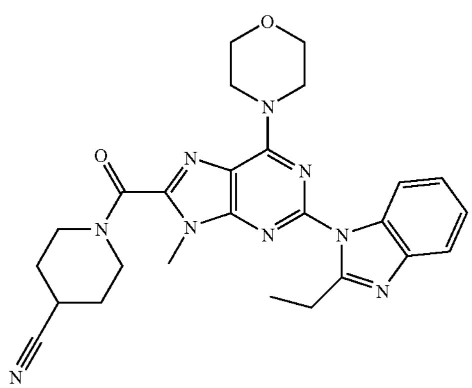 | 1-(2-(2-ethyl-1H-benzo[d]imidazol-1-yl)-9-methyl-6-morpholino-9H-purine-8-carbonyl)piperidine-4-carbonitrile |
| 768 | 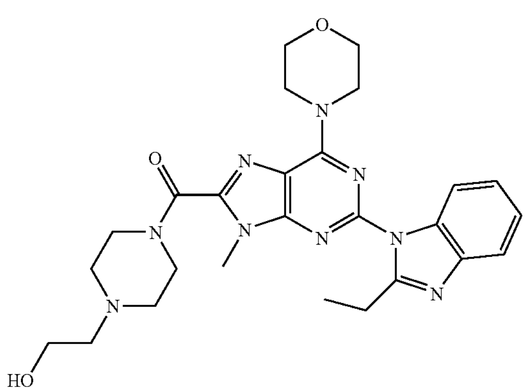 | (2-(2-ethyl-1H-benzo[d]imidazol-1-yl)-9-methyl-6-morpholino-9H-purin-8-yl)(4-(2-hydroxyethyl)piperazin-1-yl)methanone |

TABLE 3-continued

| No. | Structure | Name |
|---|---|---|
| 769 | 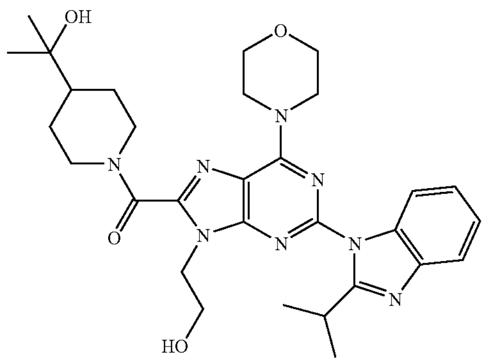 | (9-(2-hydroxyethyl)-2-(2-isopropyl-1H-benzo[d]imidazol-1-yl)-6-morpholino-9H-purin-8-yl)(4-(2-hydroxypropan-2-yl)piperidin-1-yl)methanone |
| 770 | 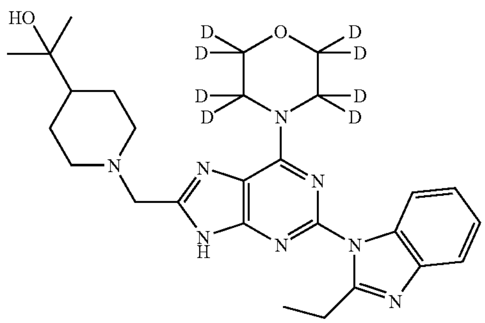 | 2-(1-((2-(2-ethyl-1H-benzo[d]imidazol-1-yl)-6-(octadeuterio)morpholino-9H-purin-8-yl)methyl)piperidin-4-yl)propan-2-ol |
| 771 | 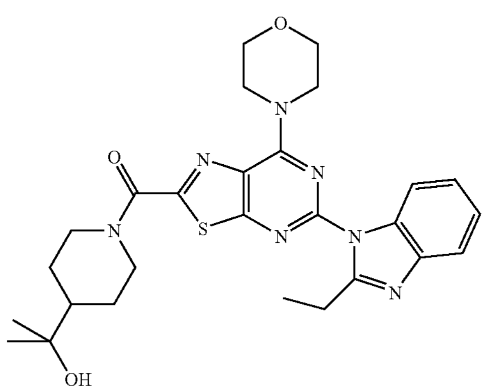 | (5-(2-ethyl-1H-benzo[d]imidazol-1-yl)-7-morpholinothiazolo[5,4-d]pyrimidin-2-yl)(4-(2-hydroxypropan-2-yl)piperidin-1-yl)methanone |
| 772 | 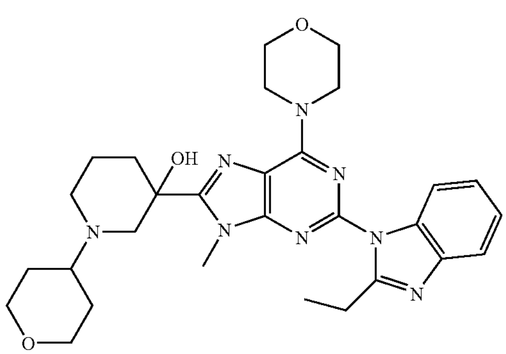 | 3-(2-(2-ethyl-1H-benzo[d]imidazol-1-yl)-9-methyl-6-morpholino-9H-purin-8-yl)-1-(tetrahydro-2H-pyran-4-yl)piperidin-3-ol |

| No. | Structure | Name |
|---|---|---|
| 773 | 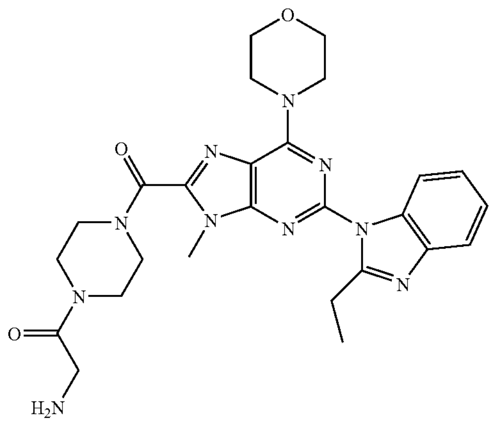 | 2-amino-1-(4-(2-(2-ethyl-1H-benzo[d]imidazol-1-yl)-9-methyl-6-morpholino-9H-purine-8-carbonyl)piperazin-1-yl)ethanone |
| 774 | 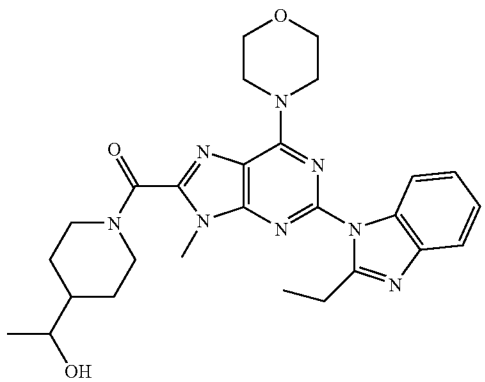 | (2-(2-ethyl-1H-benzo[d]imidazol-1-yl)-9-methyl-6-morpholino-9H-purin-8-yl)(4-(1-hydroxyethyl)piperidin-1-yl)methanone |
| 775 | 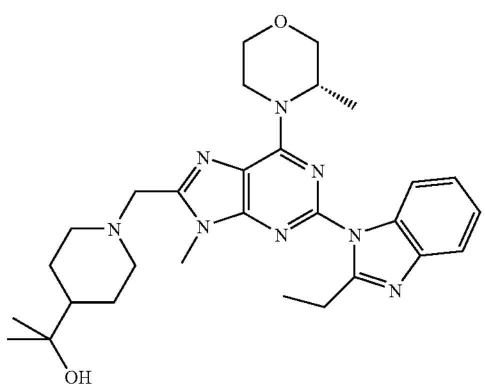 | (S)-2-(1-((2-(2-ethyl-1H-benzo[d]imidazol-1-yl)-9-methyl-6-(3-methylmorpholino)-9H-purin-8-yl)methyl)piperidin-4-yl)propan-2-ol |
| 776 | 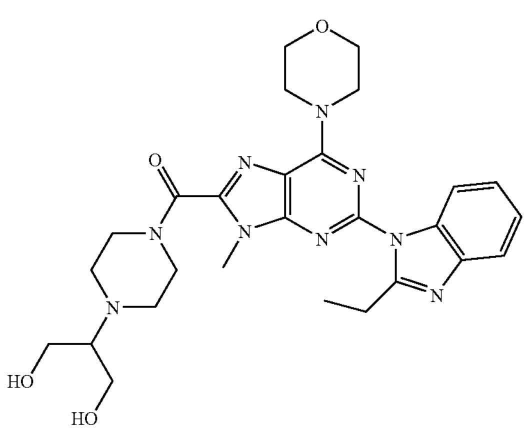 | (4-(1,3-dihydroxypropan-2-yl)piperazin-1-yl)(2-(2-ethyl-1H-benzo[d]imidazol-1-yl)-9-methyl-6-morpholino-9H-purin-8-yl)methanone |

| No. | Structure | Name |
|---|---|---|
| 777 | 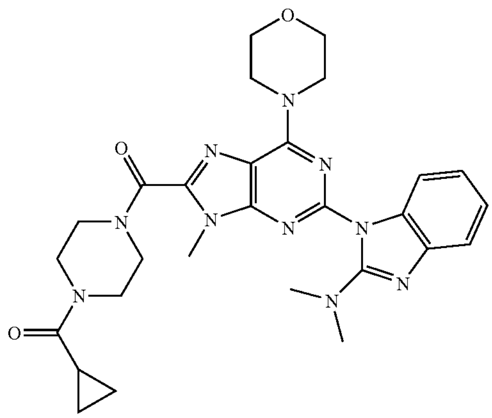 | (4-(cyclopropanecarbonyl)piperazin-1-yl)(2-(2-(dimethylamino)-1H-benzo[d]imidazol-1-yl)-9-methyl-6-morpholino-9H-purin-8-yl)methanone |
| 778 | 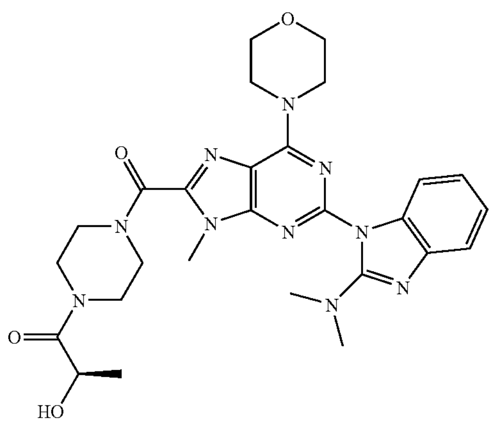 | (R)-1-(4-(2-(2-(dimethylamino)-1H-benzo[d]imidazol-1-yl)-9-methyl-6-morpholino-9H-purine-8-carbonyl)piperazin-1-yl)-2-hydroxypropan-1-one |
| 779 | 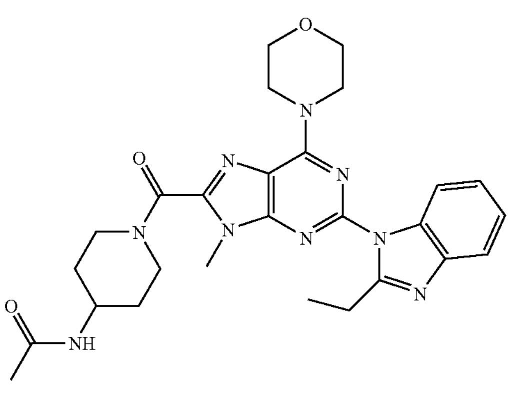 | N-(1-(2-(2-ethyl-1H-benzo[d]imidazol-1-yl)-9-methyl-6-morpholino-9H-purine-8-carbonyl)piperidin-4-yl)acetamide |

| No. | Structure | Name |
| --- | --- | --- |
| 780 | 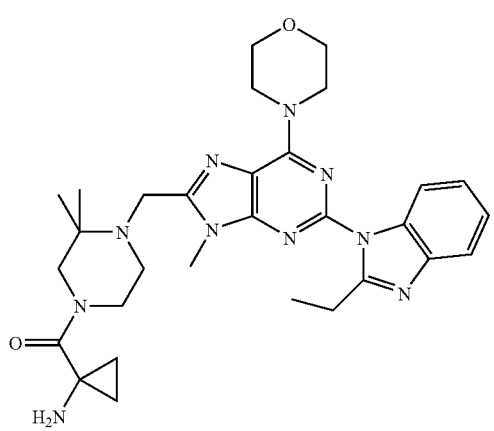 | (1-aminocyclopropyl)(4-((2-(2-ethyl-1H-benzo[d]imidazol-1-yl)-9-methyl-6-morpholino-9H-purin-8-yl)methyl)-3,3-dimethylpiperazin-1-yl)methanone |
| 781 | 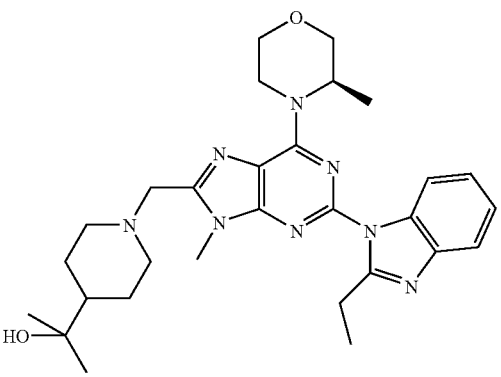 | (R)-2-(1-((2-(2-ethyl-1H-benzo[d]imidazol-1-yl)-9-methyl-6-(3-methylmorpholino)-9H-purin-8-yl)methyl)piperidin-4-yl)propan-2-ol |
| 782 | 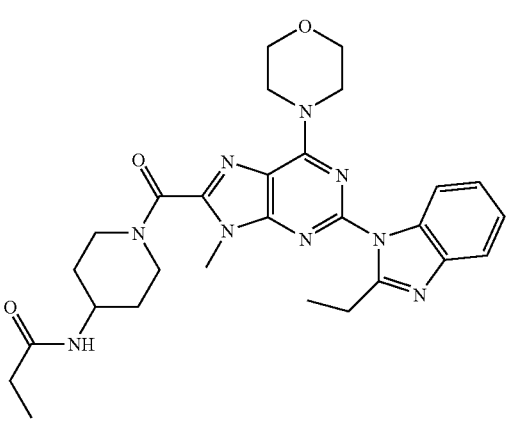 | N-(1-(2-(2-ethyl-1H-benzo[d]imidazol-1-yl)-9-methyl-6-morpholino-9H-purine-8-carbonyl)piperidin-4-yl)propionamide |

TABLE 3-continued

| No. | Structure | Name |
|---|---|---|
| 783 | 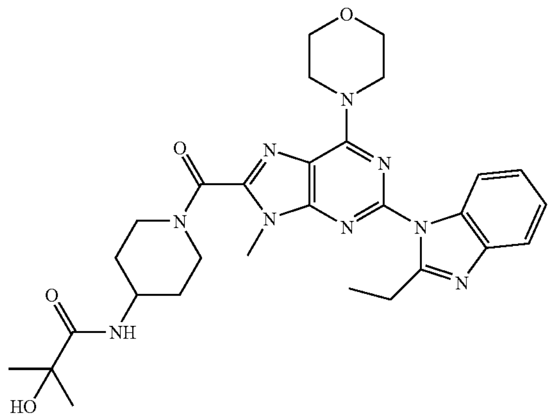 | N-(1-(2-(2-ethyl-1H-benzo[d]imidazol-1-yl)-9-methyl-6-morpholino-9H-purine-8-carbonyl)piperidin-4-yl)-2-hydroxy-2-methylpropanamide |
| 784 | 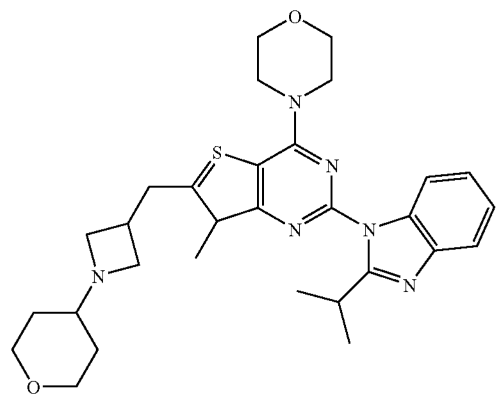 | 4-(2-(2-isopropyl-1H-benzo[d]imidazol-1-yl)-7-methyl-6-((1-(tetrahydro-2H-pyran-4-yl)azetidin-3-yl)methyl)thieno[3,2-d]pyrimidin-4-yl)morpholine |
| 785 | 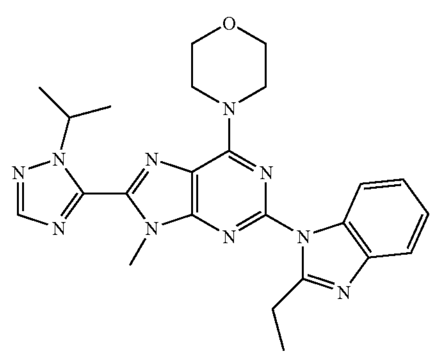 | 4-(2-(2-ethyl-1H-benzo[d]imidazol-1-yl)-8-(1-isopropyl-1H-1,2,4-triazol-5-yl)-9-methyl-9H-purin-6-yl)morpholine |
| 786 | 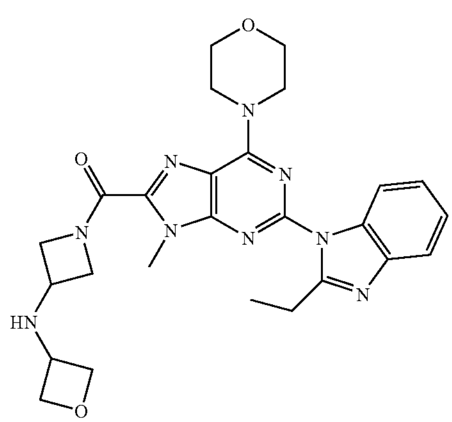 | (2-(2-ethyl-1H-benzo[d]imidazol-1-yl)-9-methyl-6-morpholino-9H-purin-8-yl)(3-(oxetan-3-ylamino)azetidin-1-yl)methanone |

TABLE 3-continued

| No. | Structure | Name |
|---|---|---|
| 787 | 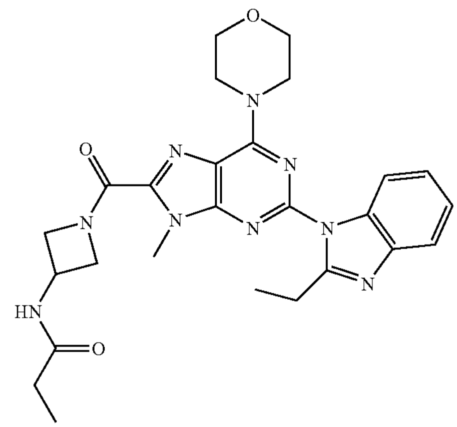 | N-(1-(2-(2-ethyl-1H-benzo[d]imidazol-1-yl)-9-methyl-6-morpholino-9H-purine-8-carbonyl)azetidin-3-yl)propionamide |
| 788 | 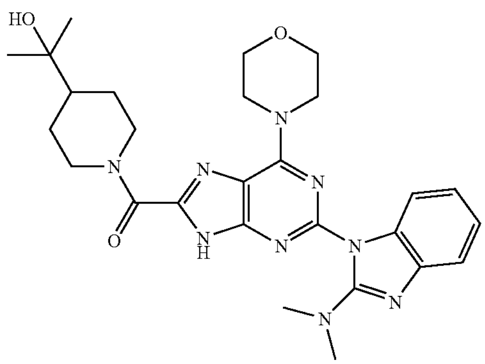 | (2-(2-(dimethylamino)-1H-benzo[d]imidazol-1-yl)-6-morpholino-9H-purin-8-yl)(4-(2-hydroxypropan-2-yl)piperidin-1-yl)methanone |
| 789 | 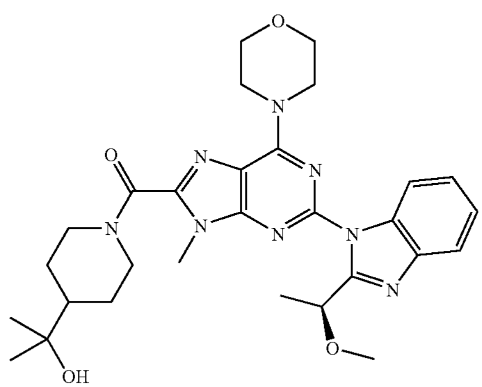 | (S)-(4-(2-hydroxypropan-2-yl)piperidin-1-yl)(2-(2-(1-methoxyethyl)-1H-benzo[d]imidazol-1-yl)-9-methyl-6-morpholino-9H-purin-8-yl)methanone |
| 790 | 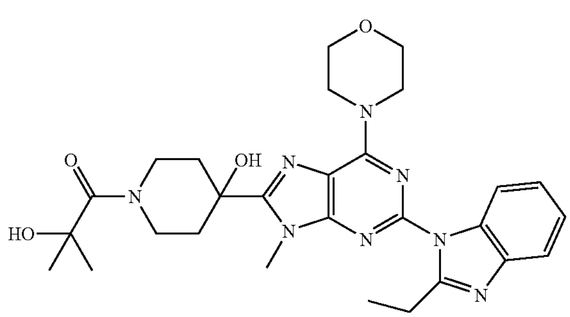 | 1-(4-(2-(2-ethyl-1H-benzo[d]imidazol-1-yl)-9-methyl-6-morpholino-9H-purin-8-yl)-4-hydroxypiperidin-1-yl)-2-hydroxy-2-methylpropan-1-one |

TABLE 3-continued

| No. | Structure | Name |
|---|---|---|
| 791 | 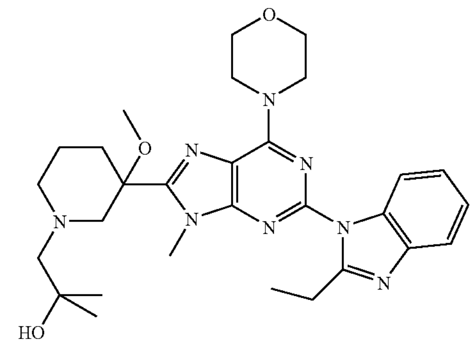 | 1-(3-(2-(2-ethyl-1H-benzo[d]imidazol-1-yl)-9-methyl-6-morpholino-9H-purin-8-yl)-3-methoxypiperidin-1-yl)-2-methylpropan-2-ol |
| 792 | 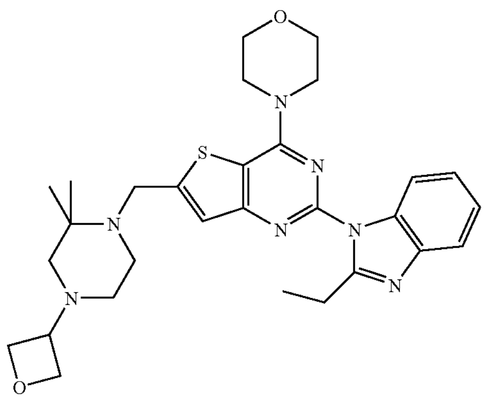 | 4-(6-((2,2-dimethyl-4-(oxetan-3-yl)piperazin-1-yl)methyl)-2-(2-ethyl-1H-benzo[d]imidazol-1-yl)thieno[3,2-d]pyrimidin-4-yl)morpholine |
| 793 | 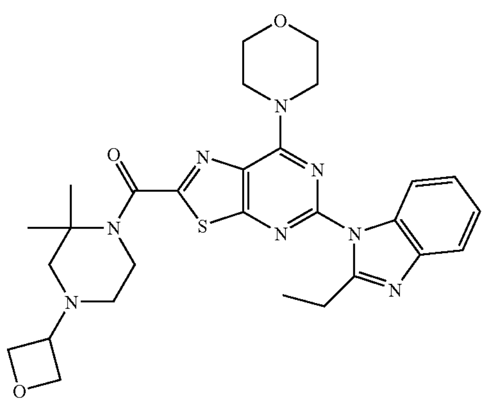 | (2,2-dimethyl-4-(oxetan-3-yl)piperazin-1-yl)(5-(2-ethyl-1H-benzo[d]imidazol-1-yl)-7-morpholinothiazolo[5,4-d]pyrimidin-2-yl)methanone |
| 794 | 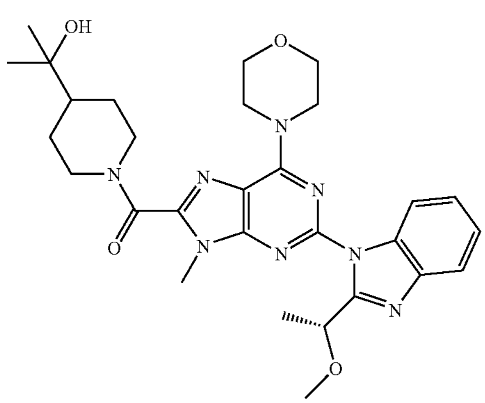 | (R)-(4-(2-hydroxypropan-2-yl)piperidin-1-yl)(2-(2-(1-methoxyethyl)-1H-benzo[d]imidazol-1-yl)-9-methyl-6-morpholino-9H-purin-8-yl)methanone |

TABLE 3-continued

| No. | Structure | Name |
|---|---|---|
| 795 | 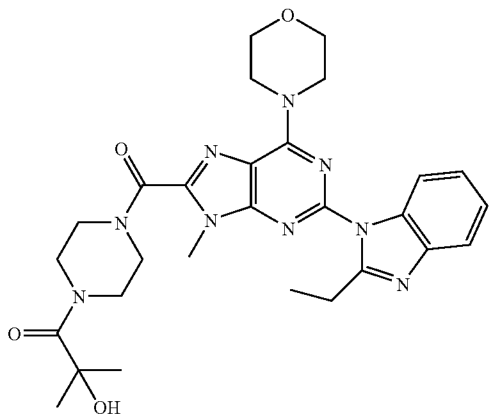 | 1-(4-(2-(2-ethyl-1H-benzo[d]imidazol-1-yl)-9-methyl-6-morpholino-9H-purine-8-carbonyl)piperazin-1-yl)-2-hydroxy-2-methylpropan-1-one |
| 796 | 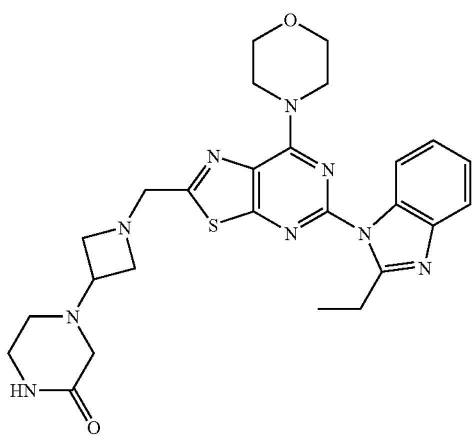 | 4-(1-((5-(2-ethyl-1H-benzo[d]imidazol-1-yl)-7-morpholinothiazolo[5,4-d]pyrimidin-2-yl)methyl)azetidin-3-yl)piperazin-2-one |
| 797 | 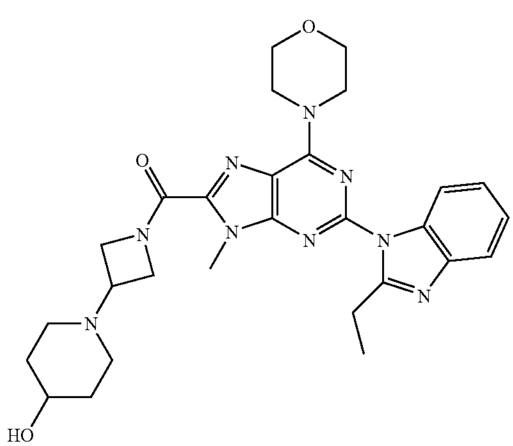 | (2-(2-ethyl-1H-benzo[d]imidazol-1-yl)-9-methyl-6-morpholino-9H-purin-8-yl)(3-(4-hydroxypiperidin-1-yl)azetidin-1-yl)methanone |

TABLE 3-continued

| No. | Structure | Name |
|---|---|---|
| 798 | 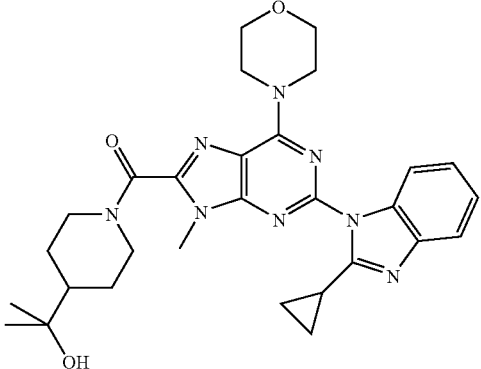 | (2-(2-cyclopropyl-1H-benzo[d]imidazol-1-yl)-9-methyl-6-morpholino-9H-purin-8-yl)(4-(2-hydroxypropan-2-yl)piperidin-1-yl)methanone |
| 799 | 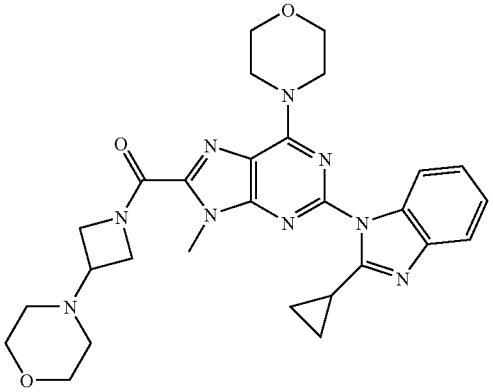 | (2-(2-cyclopropyl-1H-benzo[d]imidazol-1-yl)-9-methyl-6-morpholino-9H-purin-8-yl)(3-morpholinoazetidin-1-yl)methanone |
| 800 | 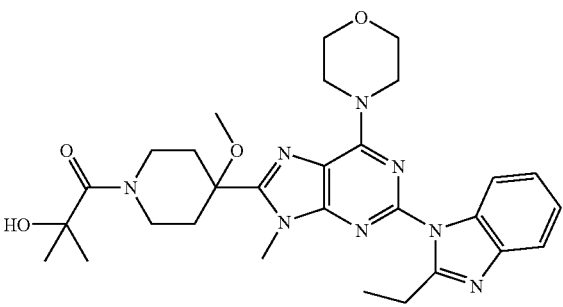 | 1-(4-(2-(2-ethyl-1H-benzo[d]imidazol-1-yl)-9-methyl-6-morpholino-9H-purin-8-yl)-4-methoxypiperidin-1-yl)-2-hydroxy-2-methylpropan-1-one |
| 801 | 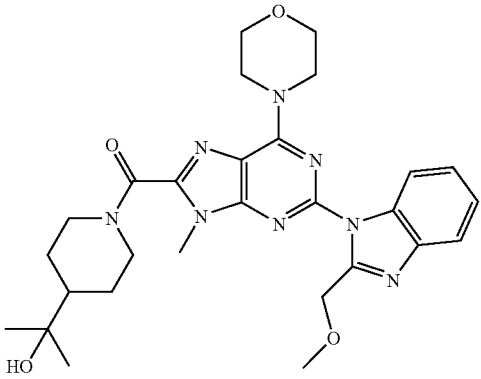 | (4-(2-hydroxypropan-2-yl)piperidin-1-yl)(2-(2-(methoxymethyl)-1H-benzo[d]imidazol-1-yl)-9-methyl-6-morpholino-9H-purin-8-yl)methanone |

| No. | Structure | Name |
| --- | --- | --- |
| 802 | 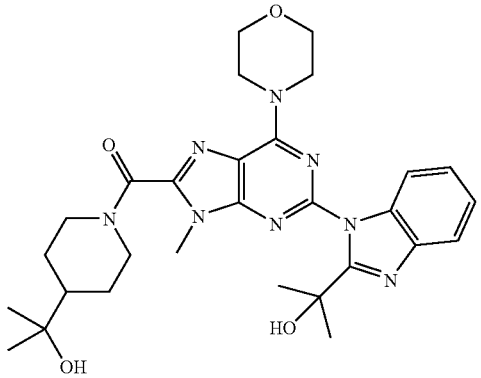 | (2-(2-(2-hydroxypropan-2-yl)-1H-benzo[d]imidazol-1-yl)-9-methyl-6-morpholino-9H-purin-8-yl)(4-(2-hydroxypropan-2-yl)piperidin-1-yl)methanone |
| 803 | 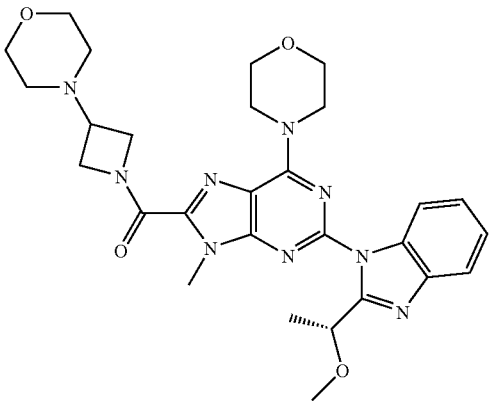 | (R)-(2-(2-(1-methoxyethyl)-1H-benzo[d]imidazol-1-yl)-9-methyl-6-morpholino-9H-purin-8-yl)(3-morpholinoazetidin-1-yl)methanone |
| 804 | 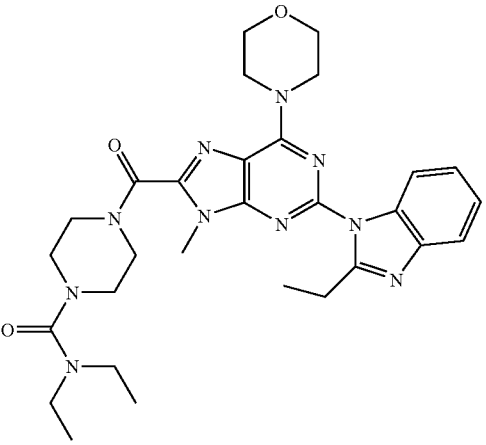 | N,N-diethyl-4-(2-(2-ethyl-1H-benzo[d]imidazol-1-yl)-9-methyl-6-morpholino-9H-purine-8-carbonyl)piperazine-1-carboxamide |

| No. | Structure | Name |
|---|---|---|
| 805 | 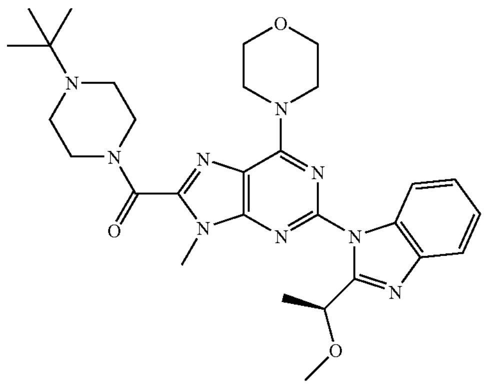 | (S)-(4-tert-butylpiperazin-1-yl)(2-(2-(1-methoxyethyl)-1H-benzo[d]imidazol-1-yl)-9-methyl-6-morpholino-9H-purin-8-yl)methanone |
| 806 | 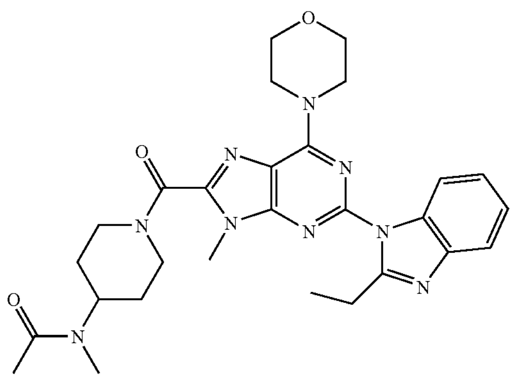 | N-(1-(2-(2-ethyl-1H-benzo[d]imidazol-1-yl)-9-methyl-6-morpholino-9H-purine-8-carbonyl)piperidin-4-yl)-N-methylacetamide |
| 807 | 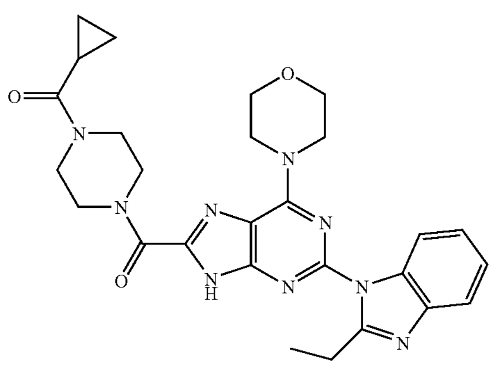 | (4-(cyclopropanecarbonyl)piperazin-1-yl)(2-(2-ethyl-1H-benzo[d]imidazol-1-yl)-6-morpholino-9H-purin-8-yl)methanone |
| 808 | 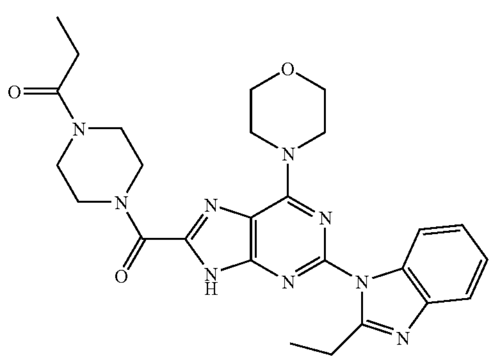 | 1-(4-(2-(2-ethyl-1H-benzo[d]imidazol-1-yl)-6-morpholino-9H-purine-8-carbonyl)piperazin-1-yl)propan-1-one |

| No. | Structure | Name |
| --- | --- | --- |
| 809 | 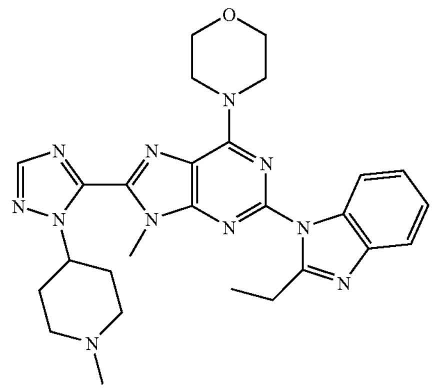 | 4-(2-(2-ethyl-1H-benzo[d]imidazol-1-yl)-9-methyl-8-(1-(1-methylpiperidin-4-yl)-1H-1,2,4-triazol-5-yl)-9H-purin-6-yl)morpholine |
| 810 | 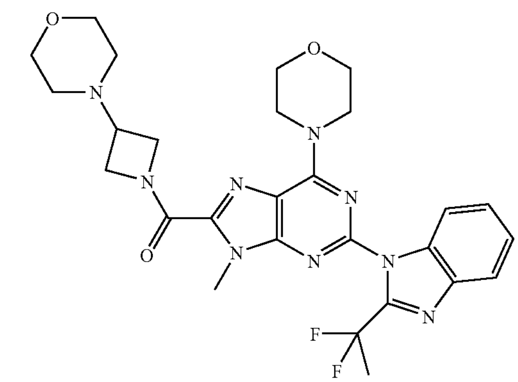 | (2-(2-(1,1-difluoroethyl)-1H-benzo[d]imidazol-1-yl)-9-methyl-6-morpholino-9H-purin-8-yl)(3-morpholinoazetidin-1-yl)methanone |
| 811 | 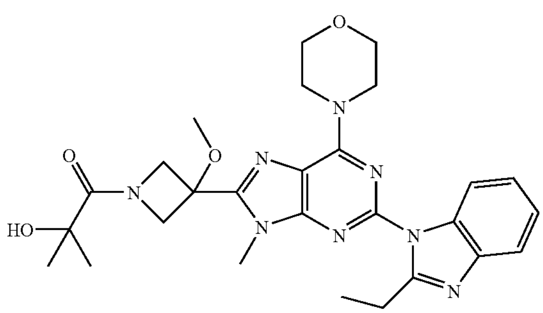 | 1-(3-(2-(2-ethyl-1H-benzo[d]imidazol-1-yl)-9-methyl-6-morpholino-9H-purin-8-yl)-3-methoxyazetidin-1-yl)-2-hydroxy-2-methylpropan-1-one |
| 812 | 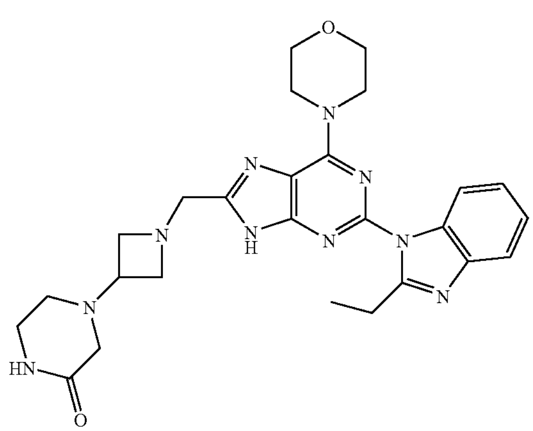 | 4-(1-((2-(2-ethyl-1H-benzo[d]imidazol-1-yl)-6-morpholino-9H-purin-8-yl)methyl)azetidin-3-yl)piperazin-2-one |

TABLE 3-continued

| No. | Structure | Name |
|---|---|---|
| 813 | 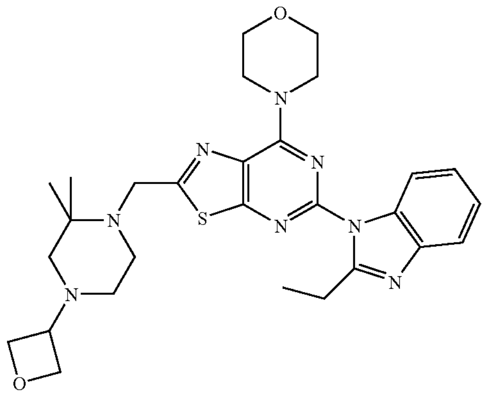 | 4-(2-((2,2-dimethyl-4-(oxetan-3-yl)piperazin-1-yl)methyl)-5-(2-ethyl-1H-benzo[d]imidazol-1-yl)thiazolo[5,4-d]pyrimidin-7-yl)morpholine |
| 814 | 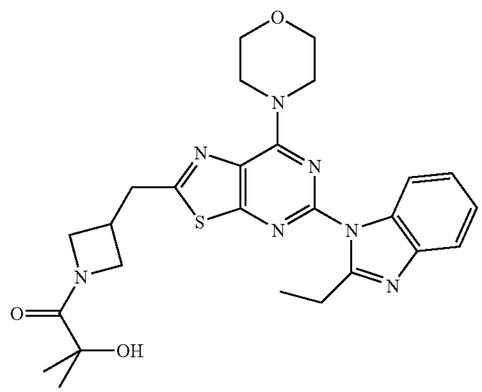 | 1-(3-((5-(2-ethyl-1H-benzo[d]imidazol-1-yl)-7-morpholinothiazolo[5,4-d]pyrimidin-2-yl)methyl)azetidin-1-yl)-2-hydroxy-2-methylpropan-1-one |
| 815 | 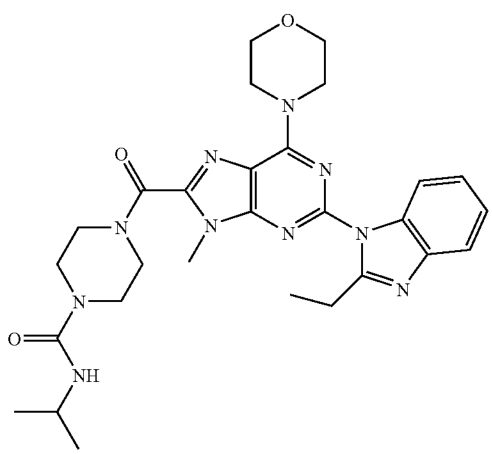 | 4-(2-(2-ethyl-1H-benzo[d]imidazol-1-yl)-9-methyl-6-morpholino-9H-purine-8-carbonyl)-N-isopropylpiperazine-1-carboxamide |
| 816 | 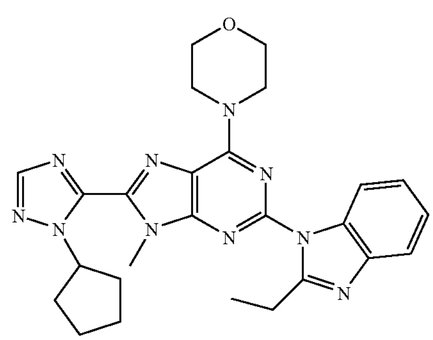 | 4-(8-(1-cyclopentyl-1H-1,2,4-triazol-5-yl)-2-(2-ethyl-1H-benzo[d]imidazol-1-yl)-9-methyl-9H-purin-6-yl)morpholine |

| No. | Structure | Name |
|---|---|---|
| 817 | 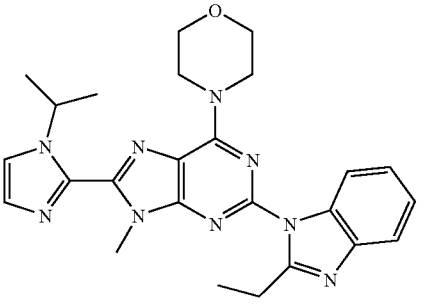 | 4-(2-(2-ethyl-1H-benzo[d]imidazol-1-yl)-8-(1-isopropyl-1H-imidazol-2-yl)-9-methyl-9H-purin-6-yl)morpholine |
| 818 | 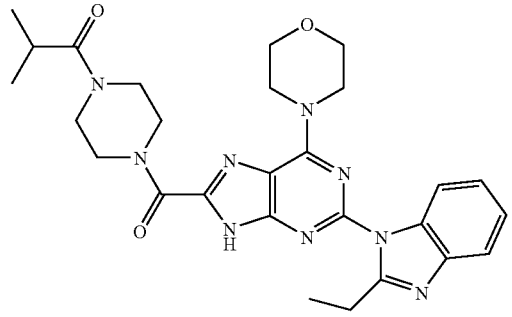 | 1-(4-(2-(2-ethyl-1H-benzo[d]imidazol-1-yl)-6-morpholino-9H-purine-8-carbonyl)piperazin-1-yl)-2-methylpropan-1-one |
| 819 | 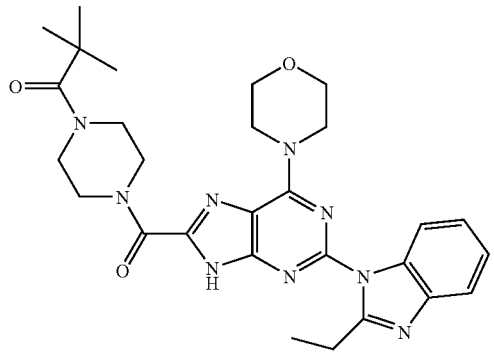 | 1-(4-(2-(2-ethyl-1H-benzo[d]imidazol-1-yl)-6-morpholino-9H-purine-8-carbonyl)piperazin-1-yl)-2,2-dimethylpropan-1-one |
| 820 | 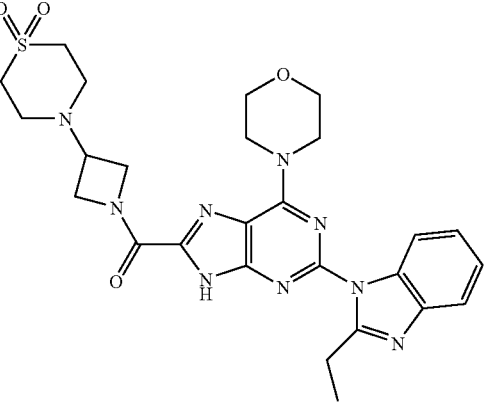 | (2-(2-ethyl-1H-benzo[d]imidazol-1-yl)-6-morpholino-9H-purin-8-yl)(3-(1,1-dioxo)-thiomorpholinoazetidin-1-yl)methanone |

| No. | Structure | Name |
| --- | --- | --- |
| 821 | 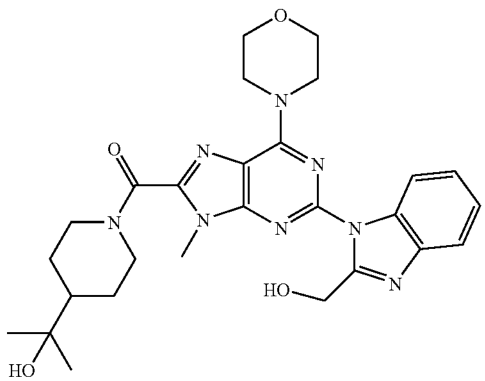 | (2-(2-(hydroxymethyl)-1H-benzo[d]imidazol-1-yl)-9-methyl-6-morpholino-9H-purin-8-yl)(4-(2-hydroxypropan-2-yl)piperidin-1-yl)methanone |
| 822 | 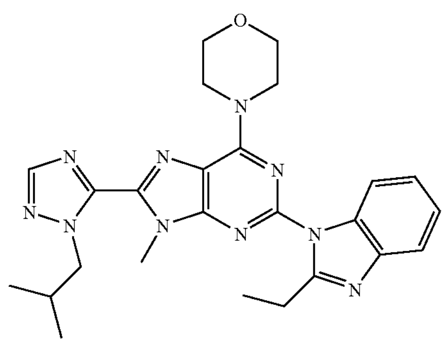 | 4-(2-(2-ethyl-1H-benzo[d]imidazol-1-yl)-8-(1-isobutyl-1H-1,2,4-triazol-5-yl)-9-methyl-9H-purin-6-yl)morpholine |
| 823 | 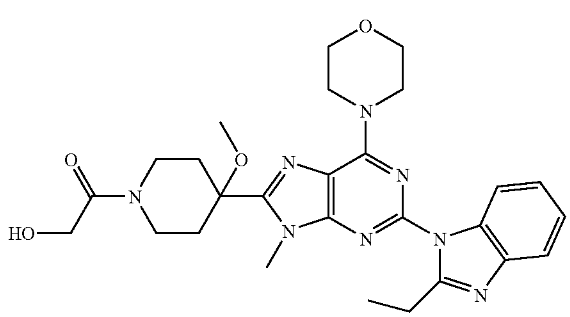 | 1-(4-(2-(2-ethyl-1H-benzo[d]imidazol-1-yl)-9-methyl-6-morpholino-9H-purin-8-yl)-4-methoxypiperidin-1-yl)-2-hydroxyethanone |
| 824 | 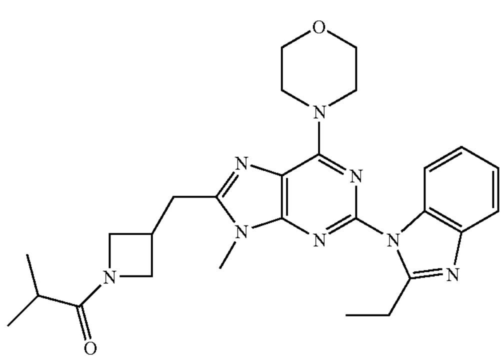 | 1-(3-((2-(2-ethyl-1H-benzo[d]imidazol-1-yl)-9-methyl-6-morpholino-9H-purin-8-yl)methyl)azetidin-1-yl)-2-methylpropan-1-one |

TABLE 3-continued

| No. | Structure | Name |
|---|---|---|
| 825 | 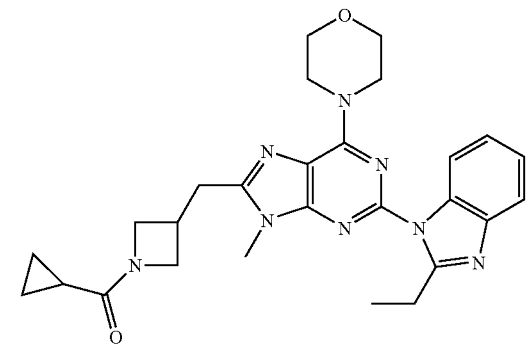 | cyclopropyl(3-((2-(2-ethyl-1H-benzo[d]imidazol-1-yl)-9-methyl-6-morpholino-9H-purin-8-yl)methyl)azetidin-1-yl)methanone |
| 826 | 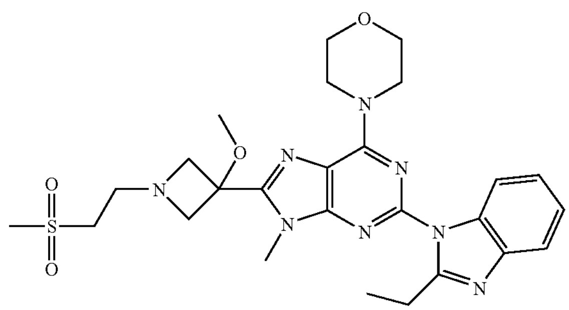 | 4-(2-(2-ethyl-1H-benzo[d]imidazol-1-yl)-8-(3-methoxy-1-(2-(methylsulfonyl)ethyl)azetidin-3-yl)-9-methyl-9H-purin-6-yl)morpholine |
| 827 | 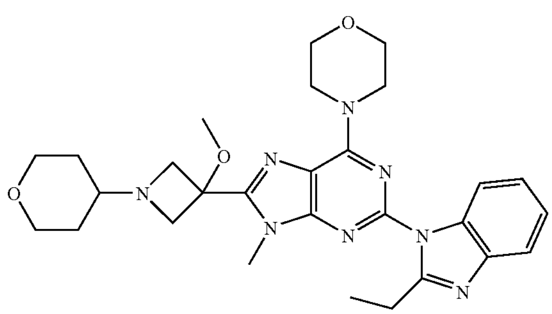 | 4-(2-(2-ethyl-1H-benzo[d]imidazol-1-yl)-8-(3-methoxy-1-(tetrahydro-2H-pyran-4-yl)azetidin-3-yl)-9-methyl-9H-purin-6-yl)morpholine |
| 828 | 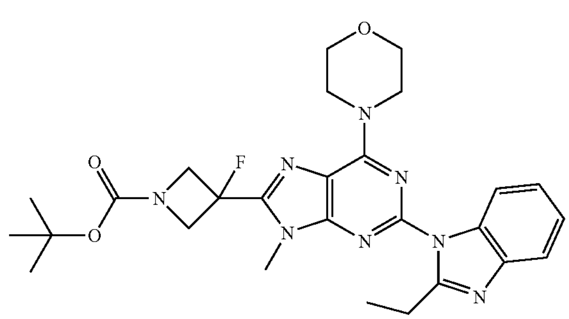 | tert-butyl 3-(2-(2-ethyl-1H-benzo[d]imidazol-1-yl)-9-methyl-6-morpholino-9H-purin-8-yl)-3-fluoroazetidine-1-carboxylate |

| No. | Structure | Name |
|---|---|---|
| 829 | 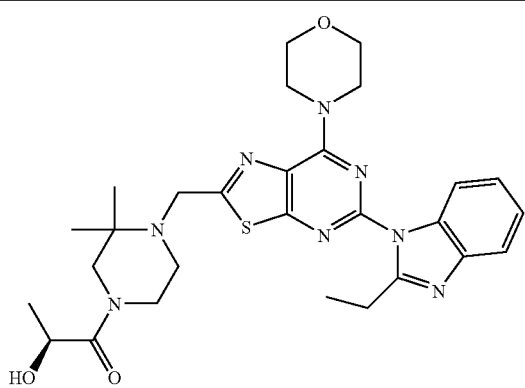 | (S)-1-(4-((5-(2-ethyl-1H-benzo[d]imidazol-1-yl)-7-morpholinothiazolo[5,4-d]pyrimidin-2-yl)methyl)-3,3-dimethylpiperazin-1-yl)-2-hydroxypropan-1-one |
| 830 | 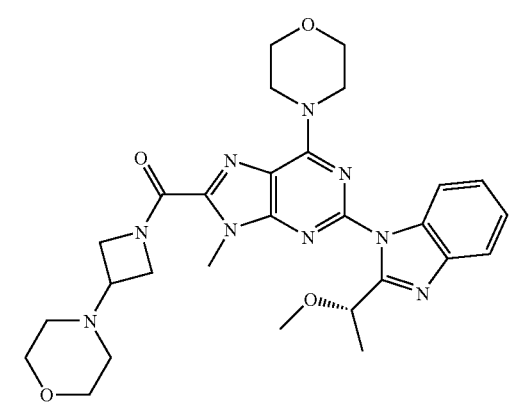 | (S)-(2-(2-(1-methoxyethyl)-1H-benzo[d]imidazol-1-yl)-9-methyl-6-morpholino-9H-purin-8-yl)(3-morpholinoazetidin-1-yl)methanone |
| 831 | 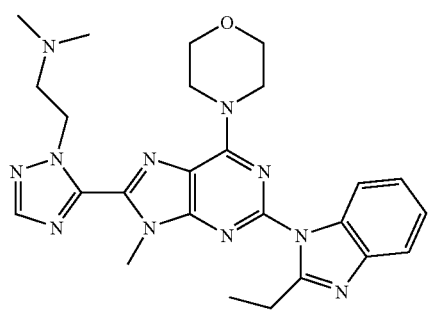 | 2-(5-(2-(2-ethyl-1H-benzo[d]imidazol-1-yl)-9-methyl-6-morpholino-9H-purin-8-yl)-1H-1,2,4-triazol-1-yl)-N,N-dimethylethanamine |
| 832 | 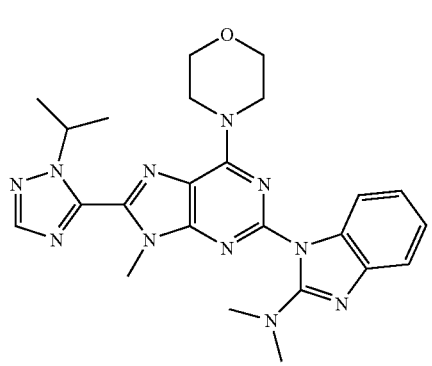 | 1-(8-(1-isopropyl-1H-1,2,4-triazol-5-yl)-9-methyl-6-morpholino-9H-purin-2-yl)-N,N-dimethyl-1H-benzo[d]imidazol-2-amine |

TABLE 3-continued

| No. | Structure | Name |
|---|---|---|
| 833 | 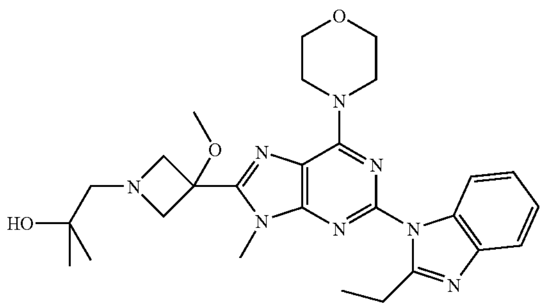 | 1-(3-(2-(2-ethyl-1H-benzo[d]imidazol-1-yl)-9-methyl-6-morpholino-9H-purin-8-yl)-3-methoxyazetidin-1-yl)-2-methylpropan-2-ol |
| 834 | 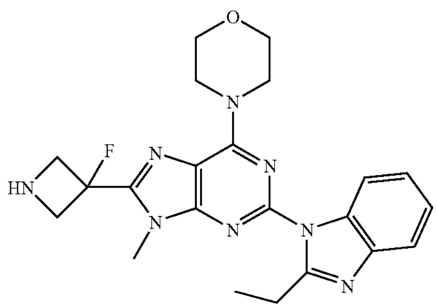 | 4-(2-(2-ethyl-1H-benzo[d]imidazol-1-yl)-8-(3-fluoroazetidin-3-yl)-9-methyl-9H-purin-6-yl)morpholine |
| 835 | 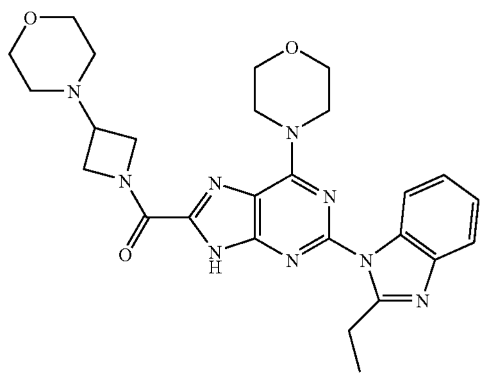 | (2-(2-ethyl-1H-benzo[d]imidazol-1-yl)-6-morpholino-9H-purin-8-yl)(3-morpholinoazetidin-1-yl)methanone |
| 836 | 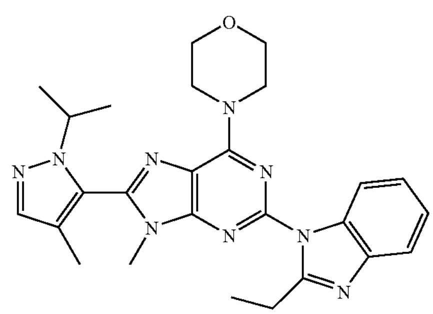 | 4-(2-(2-ethyl-1H-benzo[d]imidazol-1-yl)-8-(1-isopropyl-4-methyl-1H-pyrazol-5-yl)-9-methyl-9H-purin-6-yl)morpholine |
| 837 | 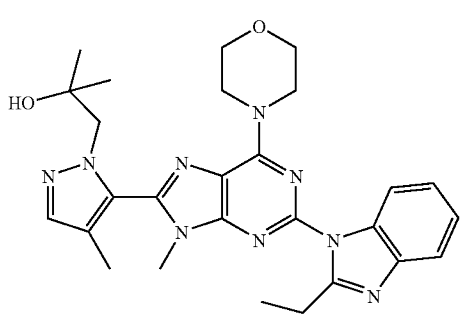 | 1-(5-(2-(2-ethyl-1H-benzo[d]imidazol-1-yl)-9-methyl-6-morpholino-9H-purin-8-yl)-4-methyl-1H-pyrazol-1-yl)-2-methylpropan-2-ol |

| No. | Structure | Name |
|---|---|---|
| 838 | 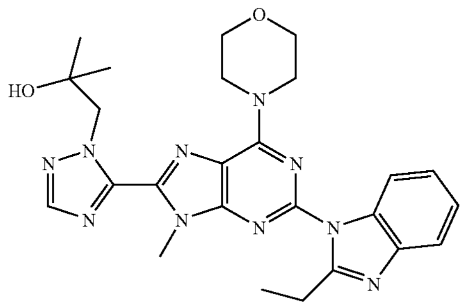 | 1-(5-(2-(2-ethyl-1H-benzo[d]imidazol-1-yl)-9-methyl-6-morpholino-9H-purin-8-yl)-1H-1,2,4-triazol-1-yl)-2-methylpropan-2-ol |
| 839 | 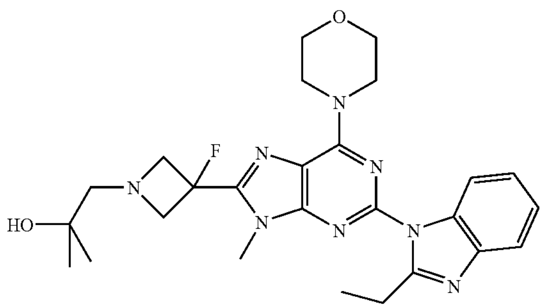 | 1-(3-(2-(2-ethyl-1H-benzo[d]imidazol-1-yl)-9-methyl-6-morpholino-9H-purin-8-yl)-3-fluoroazetidin-1-yl)-2-methylpropan-2-ol |
| 840 | 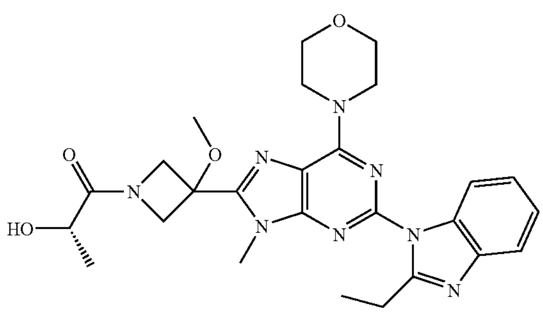 | (S)-1-(3-(2-(2-ethyl-1H-benzo[d]imidazol-1-yl)-9-methyl-6-morpholino-9H-purin-8-yl)-3-methoxyazetidin-1-yl)-2-hydroxypropan-1-one |
| 841 | 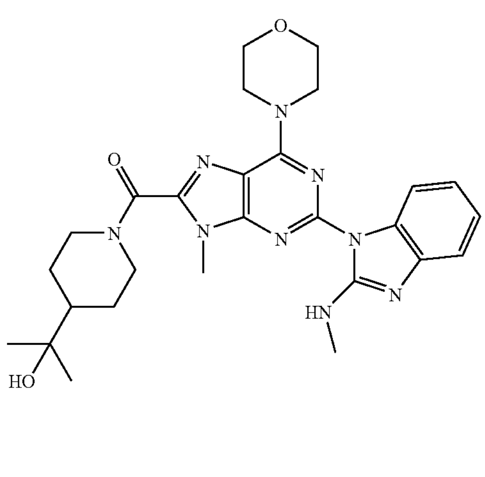 | (4-(2-hydroxypropan-2-yl)piperidin-1-yl)(9-methyl-2-(2-(methylamino)-1H-benzo[d]imidazol-1-yl)-6-morpholino-9H-purin-8-yl)methanone |

TABLE 3-continued

| No. | Structure | Name |
|---|---|---|
| 842 | 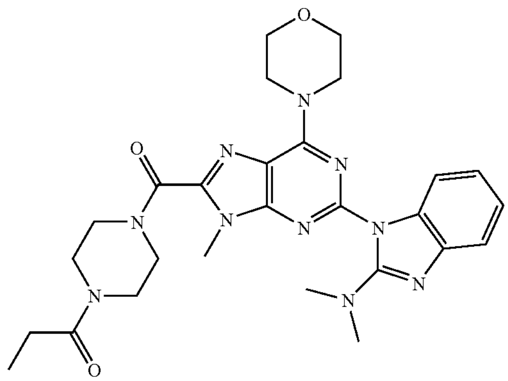 | 1-(4-(2-(2-(dimethylamino)-1H-benzo[d]imidazol-1-yl)-9-methyl-6-morpholino-9H-purine-8-carbonyl)piperazin-1-yl)propan-1-one |
| 843 | 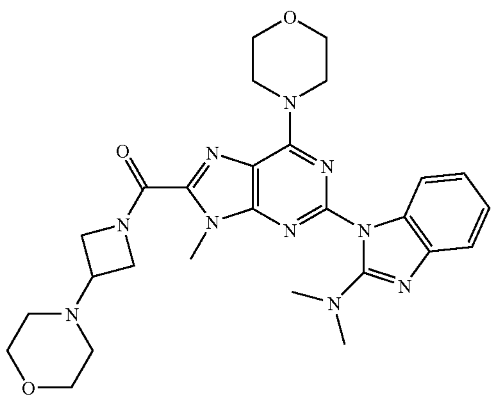 | (2-(2-(dimethylamino)-1H-benzo[d]imidazol-1-yl)-9-methyl-6-morpholino-9H-purin-8-yl)(3-morpholinoazetidin-1-yl)methanone |
| 844 | 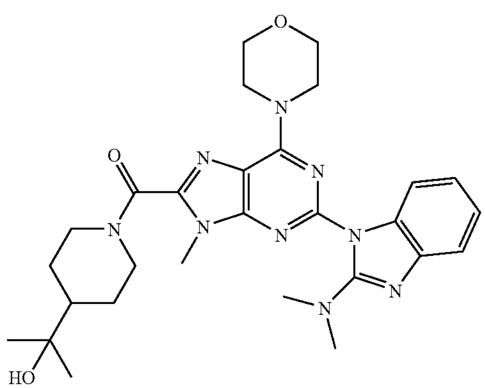 | (2-(2-(dimethylamino)-1H-benzo[d]imidazol-1-yl)-9-methyl-6-morpholino-9H-purin-8-yl)(4-(2-hydroxypropan-2-yl)piperidin-1-yl)methanone |
| 845 | 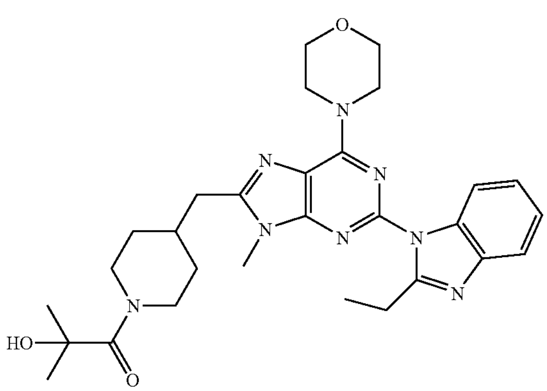 | 1-(4-((2-(2-ethyl-1H-benzo[d]imidazol-1-yl)-9-methyl-6-morpholino-9H-purin-8-yl)methyl)piperidin-1-yl)-2-hydroxy-2-methylpropan-1-one |

TABLE 3-continued

| No. | Structure | Name |
|---|---|---|
| 846 | 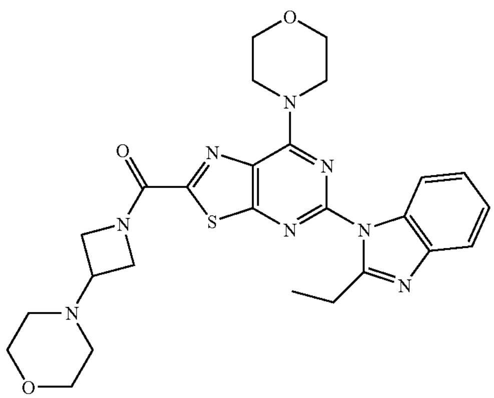 | (5-(2-ethyl-1H-benzo[d]imidazol-1-yl)-7-morpholinothiazolo[5,4-d]pyrimidin-2-yl)(3-morpholinoazetidin-1-yl)methanone |
| 847 | 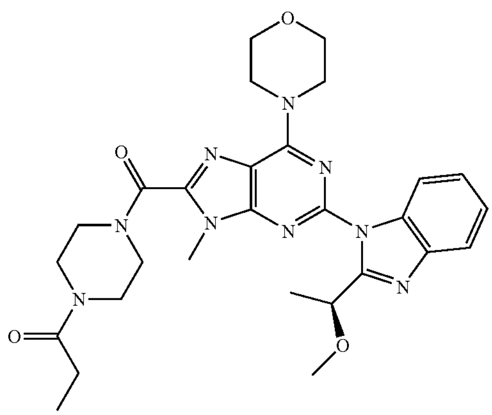 | (S)-1-(4-(2-(2-(1-methoxyethyl)-1H-benzo[d]imidazol-1-yl)-9-methyl-6-morpholino-9H-purine-8-carbonyl)piperazin-1-yl)propan-1-one |
| 848 | 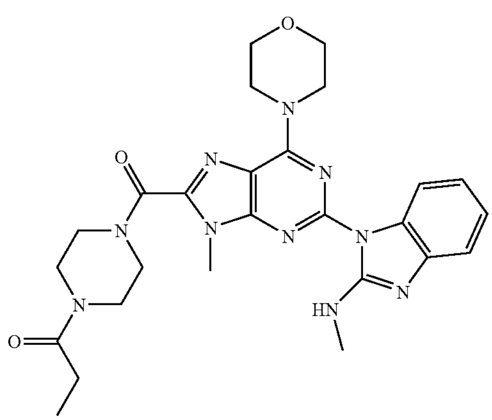 | 1-(4-(9-methyl-2-(2-(methylamino)-1H-benzo[d]imidazol-1-yl)-6-morpholino-9H-purine-8-carbonyl)piperazin-1-yl)propan-1-one |
| 849 | 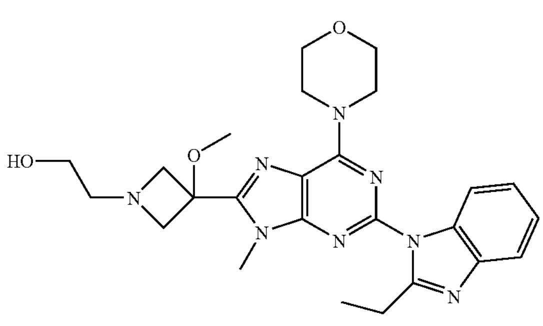 | 2-(3-(2-(2-ethyl-1H-benzo[d]imidazol-1-yl)-9-methyl-6-morpholino-9H-purin-8-yl)-3-methoxyazetidin-1-yl)ethanol |

| No. | Structure | Name |
|---|---|---|
| 850 | 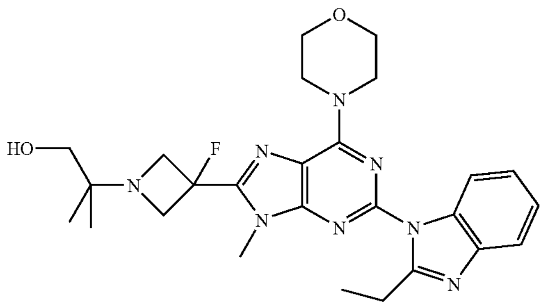 | 2-(3-(2-(2-ethyl-1H-benzo[d]imidazol-1-yl)-9-methyl-6-morpholino-9H-purin-8-yl)-3-fluoroazetidin-1-yl)-2-methylpropan-1-ol |
| 851 | 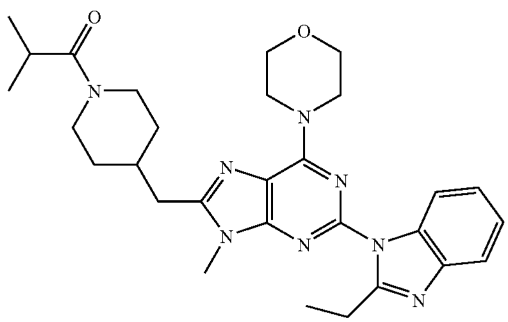 | 1-(4-((2-(2-ethyl-1H-benzo[d]imidazol-1-yl)-9-methyl-6-morpholino-9H-purin-8-yl)methyl)piperidin-1-yl)-2-methylpropan-1-one |
| 852 | 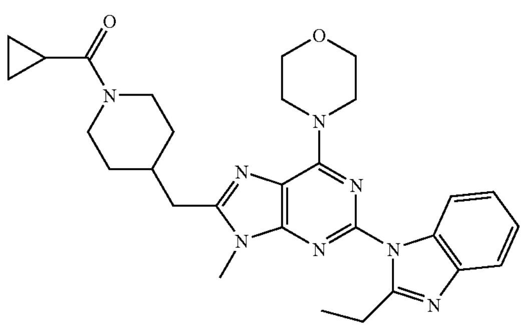 | cyclopropyl(4-((2-(2-ethyl-1H-benzo[d]imidazol-1-yl)-9-methyl-6-morpholino-9H-purin-8-yl)methyl)piperidin-1-yl)methanone |
| 853 | 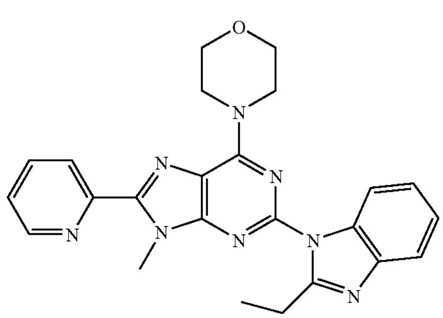 | 4-(2-(2-ethyl-1H-benzo[d]imidazol-1-yl)-9-methyl-8-(pyridin-2-yl)-9H-purin-6-yl)morpholine |

| No. | Structure | Name |
|---|---|---|
| 854 | 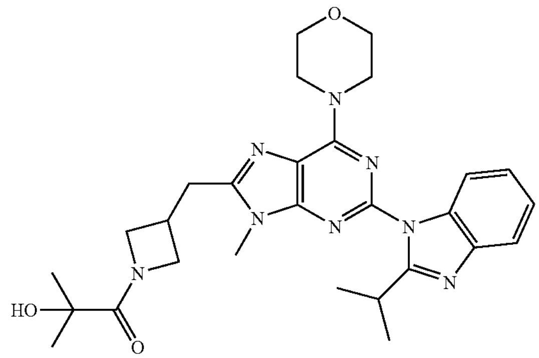 | 2-hydroxy-1-(3-((2-(2-isopropyl-1H-benzo[d]imidazol-1-yl)-9-methyl-6-morpholino-9H-purin-8-yl)methyl)azetidin-1-yl)-2-methylpropan-1-one |
| 855 | 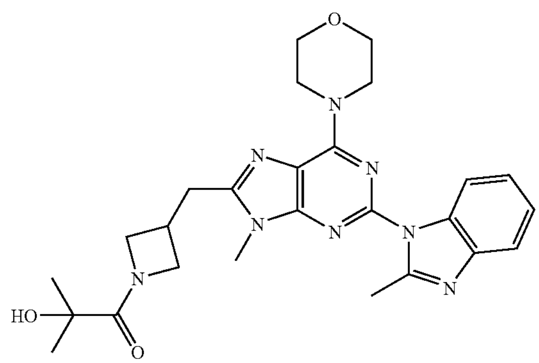 | 2-hydroxy-2-methyl-1-(3-((9-methyl-2-(2-methyl-1H-benzo[d]imidazol-1-yl)-6-morpholino-9H-purin-8-yl)methyl)azetidin-1-yl)propan-1-one |
| 856 | 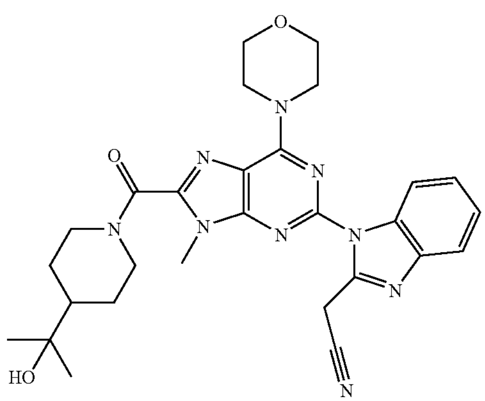 | 2-(1-(8-(4-(2-hydroxypropan-2-yl)piperidine-1-carbonyl)-9-methyl-6-morpholino-9H-purin-2-yl)-1H-benzo[d]imidazol-2-yl)acetonitrile |
| 857 | 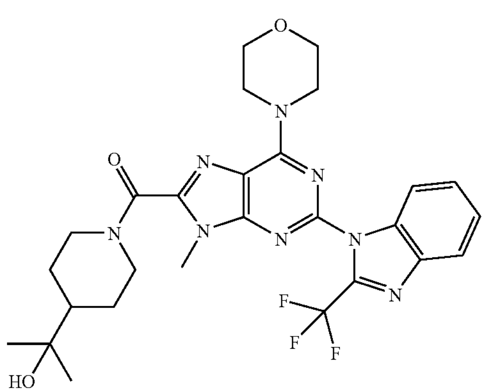 | (4-(2-hydroxypropan-2-yl)piperidin-1-yl)(9-methyl-6-morpholino-2-(2-(trifluoromethyl)-1H-benzo[d]imidazol-1-yl)-9H-purin-8-yl)methanone |

TABLE 3-continued

| No. | Structure | Name |
|---|---|---|
| 858 | 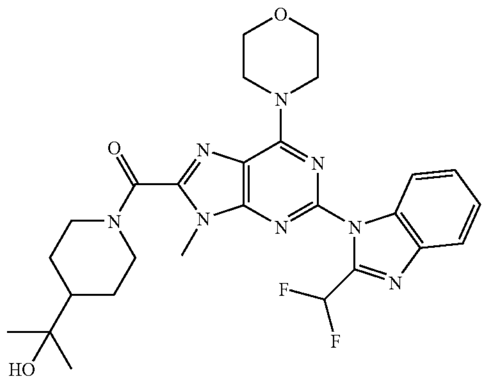 | (2-(2-(difluoromethyl)-1H-benzo[d]imidazol-1-yl)-9-methyl-6-morpholino-9H-purin-8-yl)(4-(2-hydroxypropan-2-yl)piperidin-1-yl)methanone |
| 859 | 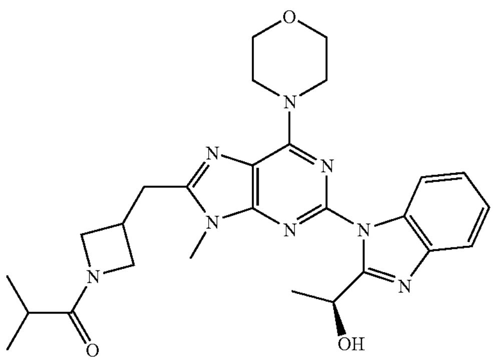 | (S)-1-(3-((2-(2-(1-hydroxyethyl)-1H-benzo[d]imidazol-1-yl)-9-methyl-6-morpholino-9H-purin-8-yl)methyl)azetidin-1-yl)-2-methylpropan-1-one |
| 860 | 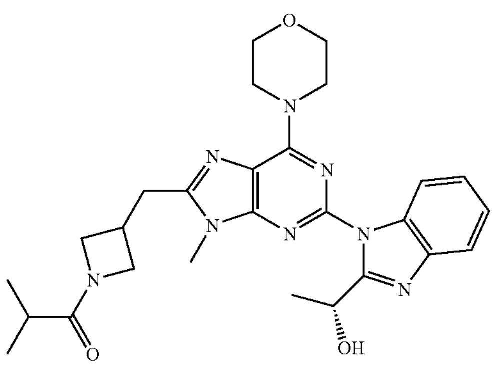 | (R)-1-(3-((2-(2-(1-hydroxyethyl)-1H-benzo[d]imidazol-1-yl)-9-methyl-6-morpholino-9H-purin-8-yl)methyl)azetidin-1-yl)-2-methylpropan-1-one |
| 861 | 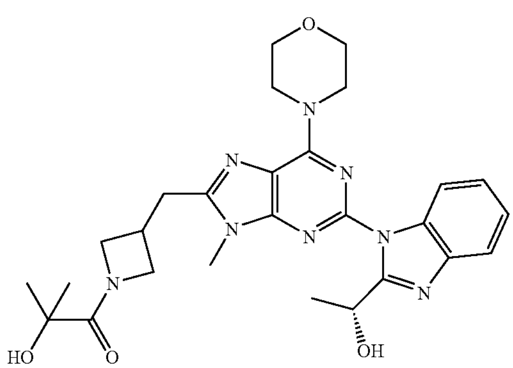 | (R)-2-hydroxy-1-(3-((2-(2-(1-hydroxyethyl)-1H-benzo[d]imidazol-1-yl)-9-methyl-6-morpholino-9H-purin-8-yl)methyl)azetidin-1-yl)-2-methylpropan-1-one |

TABLE 3-continued

| No. | Structure | Name |
|---|---|---|
| 862 | 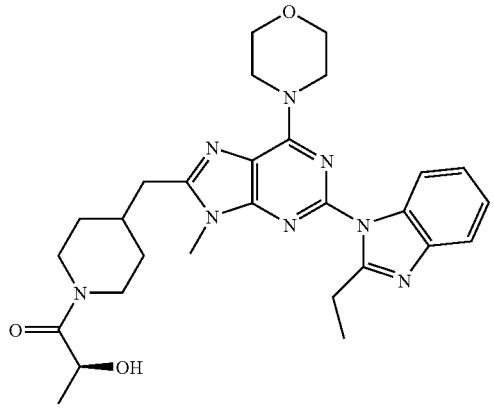 | (S)-1-(4-((2-(2-ethyl-1H-benzo[d]imidazol-1-yl)-9-methyl-6-morpholino-9H-purin-8-yl)methyl)piperidin-1-yl)-2-hydroxypropan-1-one |
| 863 | 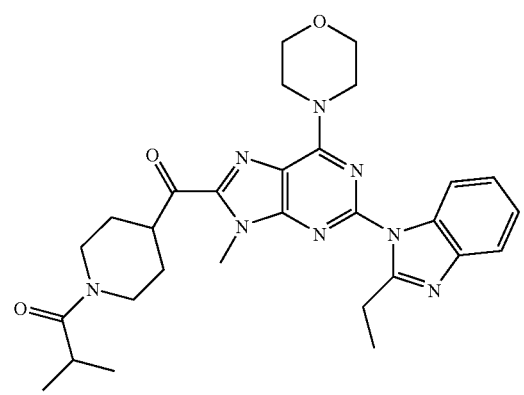 | 1-(4-(2-(2-ethyl-1H-benzo[d]imidazol-1-yl)-9-methyl-6-morpholino-9H-purine-8-carbonyl)piperidin-1-yl)-2-methylpropan-1-one |
| 864 | 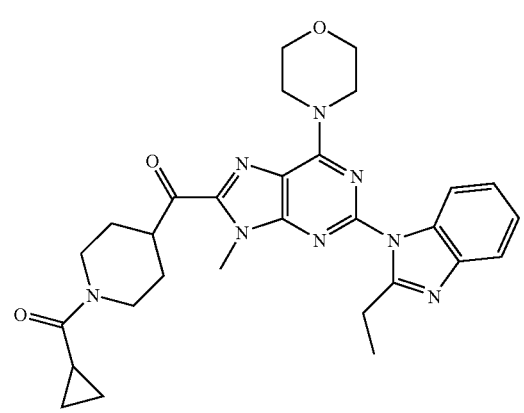 | (1-(cyclopropanecarbonyl)piperidin-4-yl)(2-(2-ethyl-1H-benzo[d]imidazol-1-yl)-9-methyl-6-morpholino-9H-purin-8-yl)methanone |
| 865 | 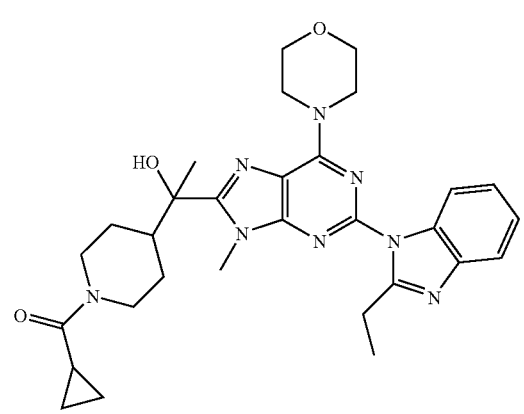 | cyclopropyl(4-(1-(2-(2-ethyl-1H-benzo[d]imidazol-1-yl)-9-methyl-6-morpholino-9H-purin-8-yl)-1-hydroxyethyl)piperidin-1-yl)methanone |

| No. | Structure | Name |
|---|---|---|
| 866 | 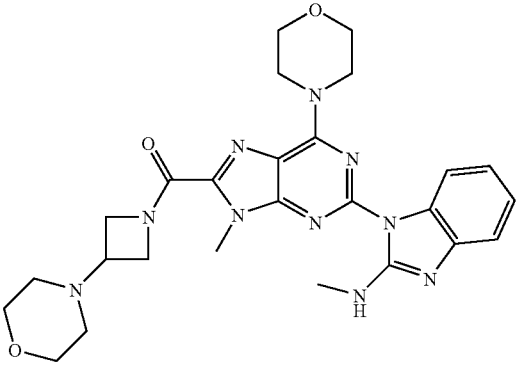 | (9-methyl-2-(2-(methylamino)-1H-benzo[d]imidazol-1-yl)-6-morpholino-9H-purin-8-yl)(3-morpholinoazetidin-1-yl)methanone |
| 867 | 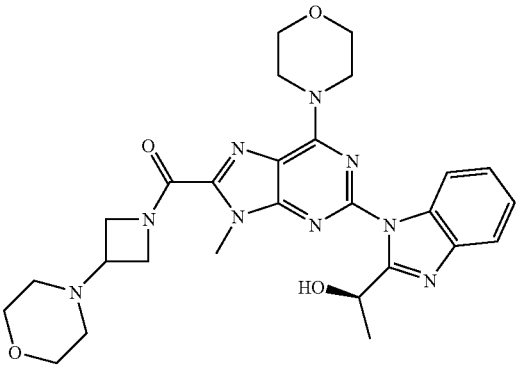 | (R)-(2-(2-(1-hydroxyethyl)-1H-benzo[d]imidazol-1-yl)-9-methyl-6-morpholino-9H-purin-8-yl)(3-morpholinoazetidin-1-yl)methanone |
| 868 | 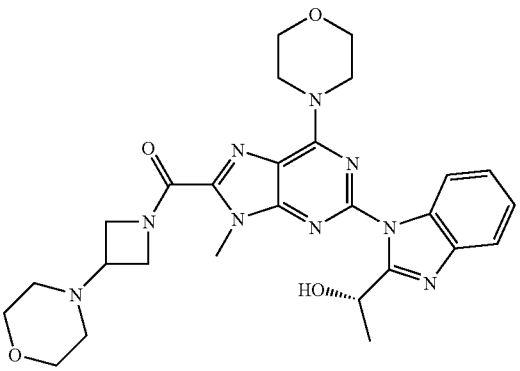 | (S)-(2-(2-(1-hydroxyethyl)-1H-benzo[d]imidazol-1-yl)-9-methyl-6-morpholino-9H-purin-8-yl)(3-morpholinoazetidin-1-yl)methanone |
| 869 | 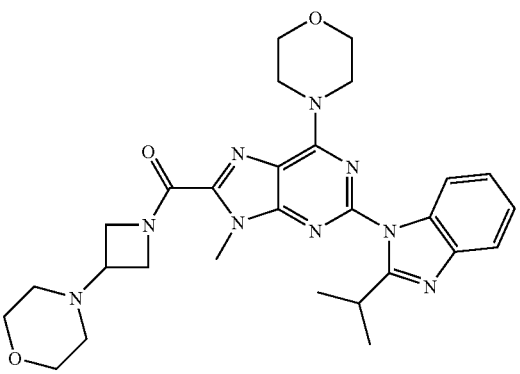 | (2-(2-isopropyl-1H-benzo[d]imidazol-1-yl)-9-methyl-6-morpholino-9H-purin-8-yl)(3-morpholinoazetidin-1-yl)methanone |

TABLE 3-continued

| No. | Structure | Name |
|---|---|---|
| 870 | 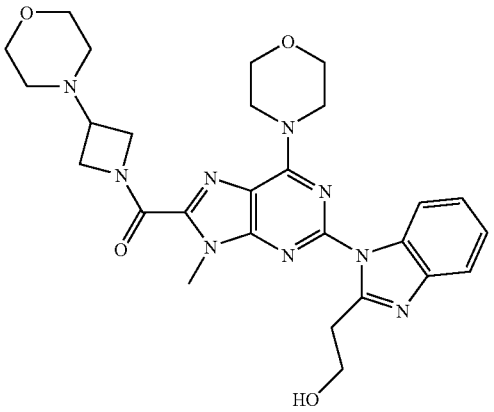 | (2-(2-(2-hydroxyethyl)-1H-benzo[d]imidazol-1-yl)-9-methyl-6-morpholino-9H-purin-8-yl)(3-morpholinoazetidin-1-yl)methanone |
| 871 | 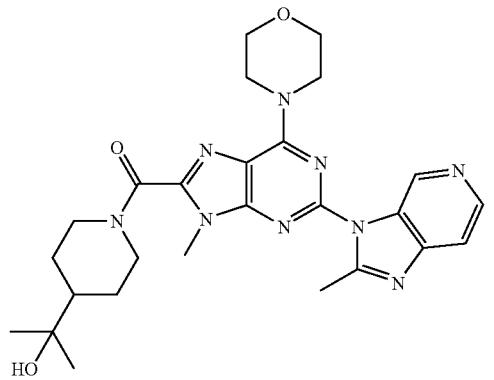 | (4-(2-hydroxypropan-2-yl)piperidin-1-yl)(9-methyl-2-(2-methyl-3H-imidazo[4,5-c]pyridin-3-yl)-6-morpholino-9H-purin-8-yl)methanone |
| 872 | 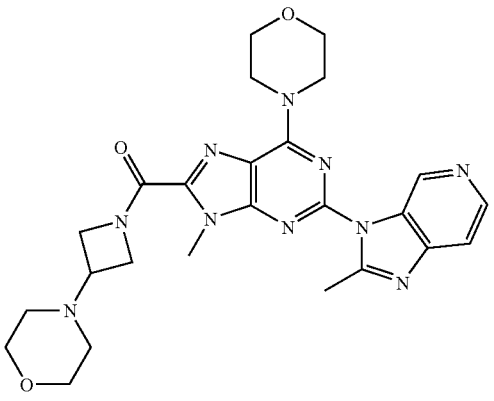 | (9-methyl-2-(2-methyl-3H-imidazo[4,5-c]pyridin-3-yl)-6-morpholino-9H-purin-8-yl)(3-morpholinoazetidin-1-yl)methanone |
| 873 | 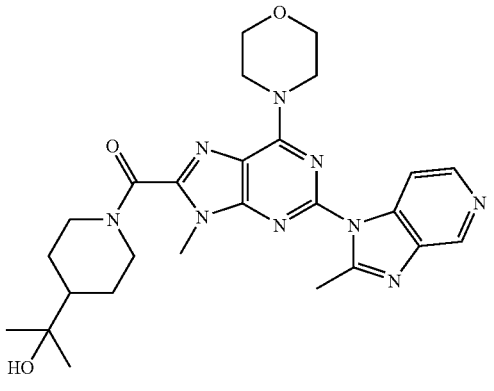 | (4-(2-hydroxypropan-2-yl)piperidin-1-yl)(9-methyl-2-(2-methyl-1H-imidazo[4,5-c]pyridin-1-yl)-6-morpholino-9H-purin-8-yl)methanone |

TABLE 3-continued

| No. | Structure | Name |
|---|---|---|
| 874 | 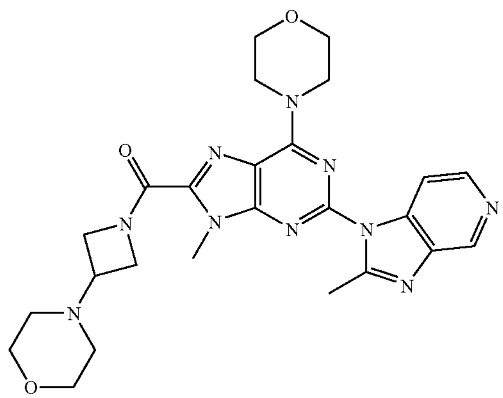 | (9-methyl-2-(2-methyl-1H-imidazo[4,5-c]pyridin-1-yl)-6-morpholino-9H-purin-8-yl)(3-morpholinoazetidin-1-yl)methanone |
| 875 | 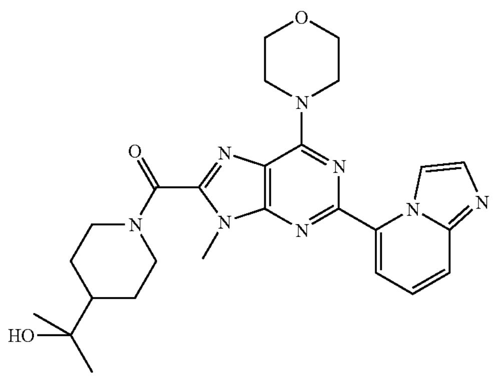 | (4-(2-hydroxypropan-2-yl)piperidin-1-yl)(2-(imidazo[1,2-a]pyridin-5-yl)-9-methyl-6-morpholino-9H-purin-8-yl)methanone |
| 876 | 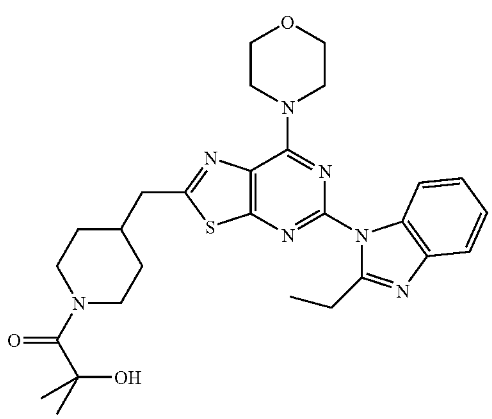 | 1-(4-((5-(2-ethyl-1H-benzo[d]imidazol-1-yl)-7-morpholinothiazolo[5,4-d]pyrimidin-2-yl)methyl)piperidin-1-yl)-2-hydroxy-2-methylpropan-1-one |
| 877 | 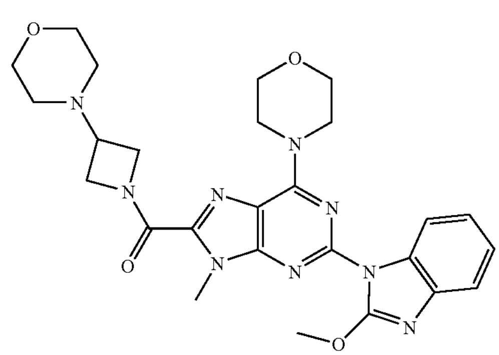 | (2-(2-methoxy-1H-benzo[d]imidazol-1-yl)-9-methyl-6-morpholino-9H-purin-8-yl)(3-morpholinoazetidin-1-yl)methanone |

TABLE 3-continued

| No. | Structure | Name |
|---|---|---|
| 878 | 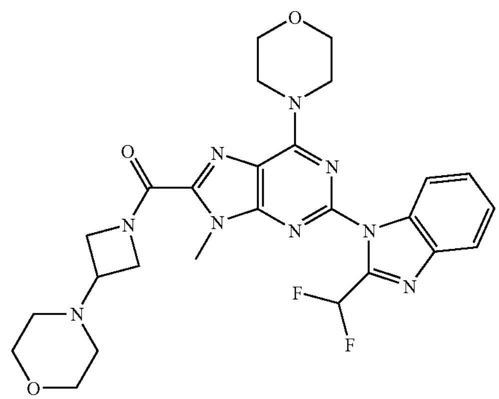 | (2-(2-(difluoromethyl)-1H-benzo[d]imidazol-1-yl)-9-methyl-6-morpholino-9H-purin-8-yl)(3-morpholinoazetidin-1-yl)methanone |
| 879 | 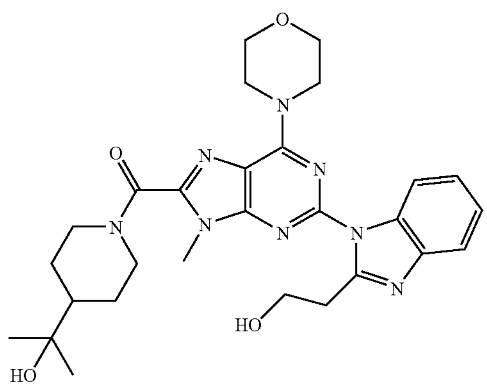 | (2-(2-(2-hydroxyethyl)-1H-benzo[d]imidazol-1-yl)-9-methyl-6-morpholino-9H-purin-8-yl)(4-(2-hydroxypropan-2-yl)piperidin-1-yl)methanone |
| 880 | 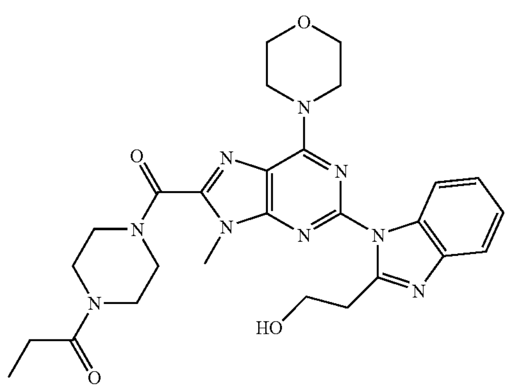 | 1-(4-(2-(2-(2-hydroxyethyl)-1H-benzo[d]imidazol-1-yl)-9-methyl-6-morpholino-9H-purine-8-carbonyl)piperazin-1-yl)propan-1-one |
| 881 | 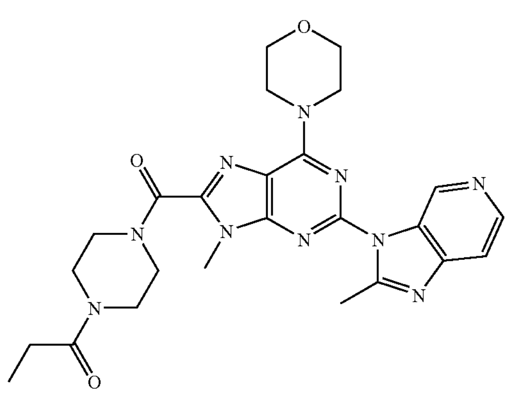 | 1-(4-(9-methyl-2-(2-methyl-3H-imidazo[4,5-c]pyridin-3-yl)-6-morpholino-9H-purine-8-carbonyl)piperazin-1-yl)propan-1-one |

| No. | Structure | Name |
|---|---|---|
| 882 | 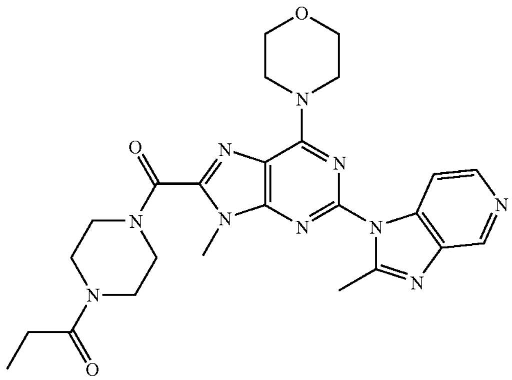 | 1-(4-(9-methyl-2-(2-methyl-1H-imidazo[4,5-c]pyridin-1-yl)-6-morpholino-9H-purine-8-carbonyl)piperazin-1-yl)propan-1-one |
| 883 | 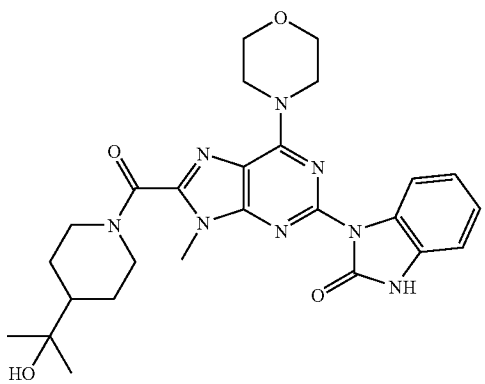 | 1-(8-(4-(2-hydroxypropan-2-yl)piperidine-1-carbonyl)-9-methyl-6-morpholino-9H-purin-2-yl)-1H-benzo[d]imidazol-2(3H)-one |
| 884 | 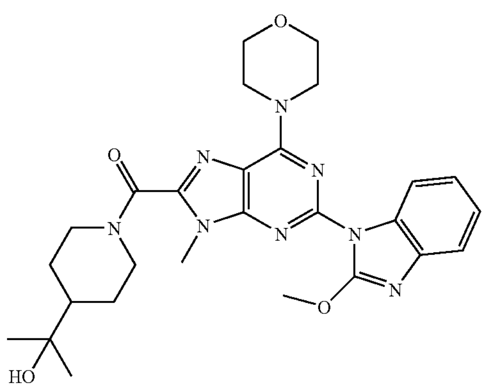 | (4-(2-hydroxypropan-2-yl)piperidin-1-yl)(2-(2-methoxy-1H-benzo[d]imidazol-1-yl)-9-methyl-6-morpholino-9H-purin-8-yl)methanone |
| 885 | 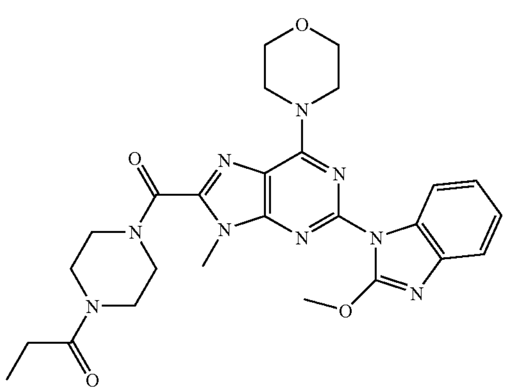 | 1-(4-(2-(2-methoxy-1H-benzo[d]imidazol-1-yl)-9-methyl-6-morpholino-9H-purine-8-carbonyl)piperazin-1-yl)propan-1-one |

Administration of Formula I Compounds

The Formula I compounds of the invention may be administered by a route appropriate to the condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary and intranasal. For local immunosuppressive treatment, the compounds may be administered by intralesional administration, including perfusing or otherwise contacting the graft with the inhibitor before transplantation. It will be appreciated that the preferred route may vary with for example the condition of the recipient. Where the compound is administered orally, it may be formulated as a pill, capsule, tablet, etc. with a pharmaceutically acceptable carrier or excipient. Where the compound is administered parenterally, it may be formulated with a pharmaceutically acceptable parenteral vehicle and in a unit dosage injectable form, as detailed below.

A dose to treat human patients may range from about 10 mg to about 1000 mg of Formula I compound. A typical dose may be about 100 mg to about 300 mg of the compound. A dose may be administered once a day (QID), twice per day (BID), or more frequently, depending on the pharmacokinetic and pharmacodynamic properties, including absorption, distribution, metabolism, and excretion of the particular compound. In addition, toxicity factors may influence the dosage and administration regimen. When administered orally, the pill, capsule, or tablet may be ingested daily or less frequently for a specified period of time. The regimen may be repeated for a number of cycles of therapy.

Methods of Treatment with Formula I Compounds

Formula I compounds of the present invention are useful for treating a human or animal patient suffering from a disease or disorder arising from abnormal cell growth, function or behavior associated with PI3 kinase, in particular with the p110δ (delta) isoform of PI3 kinase such as an immune disorder, cardiovascular disease, viral infection, inflammation, a metabolism/endocrine disorder or a neurological disorder, may thus be treated by a method comprising the administration thereto of a compound of the present invention as defined above. A human or animal patient suffering from cancer may also be treated by a method comprising the administration thereto of a compound of the present invention as defined above. The condition of the patient may thereby be improved or ameliorated.

Formula I compounds may be useful for in vitro, in situ, and in vivo diagnosis or treatment of mammalian cells, organisms, or associated pathological conditions, such as systemic and local inflammation, immune-inflammatory diseases such as rheumatoid arthritis, immune suppression, organ transplant rejection, allergies, ulcerative colitis, Crohn's disease, dermatitis, asthma, systemic lupus erythematosus, Sjögren's Syndrome, multiple sclerosis, scleroderma/systemic sclerosis, idiopathic thrombocytopenic purpura (ITP), anti-neutrophil cytoplasmic antibodies (ANCA) vasculitis, chronic obstructive pulmonary disease (COPD), psoriasis, and for general joint protective effects.

Methods of the invention also include treating such diseases as arthritic diseases, such as rheumatoid arthritis, monoarticular arthritis, osteoarthritis, gouty arthritis, spondylitis; Behcet disease; sepsis, septic shock, endotoxic shock, gram negative sepsis, gram positive sepsis, and toxic shock syndrome; multiple organ injury syndrome secondary to septicemia, trauma, or hemorrhage; ophthalmic disorders such as allergic conjunctivitis, vernal conjunctivitis, uveitis, and thyroid-associated ophthalmopathy; eosinophilic granuloma; pulmonary or respiratory disorders such as asthma, chronic bronchitis, allergic rhinitis, ARDS, chronic pulmonary inflammatory disease (e.g., chronic obstructive pulmonary disease), silicosis, pulmonary sarcoidosis, pleurisy, alveolitis, vasculitis, emphysema, pneumonia, bronchiectasis, and pulmonary oxygen toxicity; reperfusion injury of the myocardium, brain, or extremities; fibrosis such as cystic fibrosis; keloid formation or scar tissue formation; atherosclerosis; autoimmune diseases, such as systemic lupus erythematosus (SLE), autoimmune thyroiditis, multiple sclerosis, some forms of diabetes, and Reynaud's syndrome; and transplant rejection disorders such as GVHD and allograft rejection; chronic glomerulonephritis; inflammatory bowel diseases such as chronic inflammatory bowel disease (CIBD), Crohn's disease, ulcerative colitis, and necrotizing enterocolitis; inflammatory dermatoses such as contact dermatitis, atopic dermatitis, psoriasis, or urticaria; fever and myalgias due to infection; central or peripheral nervous system inflammatory disorders such as meningitis, encephalitis, and brain or spinal cord injury due to minor trauma; Sjogren's syndrome; diseases involving leukocyte diapedesis; alcoholic hepatitis; bacterial pneumonia; antigen-antibody complex mediated diseases; hypovolemic shock; Type I diabetes mellitus; acute and delayed hypersensitivity; disease states due to leukocyte dyscrasia and metastasis; thermal injury; granulocyte transfusion-associated syndromes; and cytokine-induced toxicity.

The methods of the invention can have utility in treating subjects who are or can be subject to reperfusion injury, i.e., injury resulting from situations in which a tissue or organ experiences a period of ischemia followed by reperfusion. The term "ischemia" refers to localized tissue anemia due to obstruction of the inflow of arterial blood. Transient ischemia followed by reperfusion characteristically results in neutrophil activation and transmigration through the endothelium of the blood vessels in the affected area. Accumulation of activated neutrophils in turn results in generation of reactive oxygen metabolites, which damage components of the involved tissue or organ. This phenomenon of "reperfusion injury" is commonly associated with conditions such as vascular stroke (including global and focal ischemia), hemorrhagic shock, myocardial ischemia or infarction, organ transplantation, and cerebral vasospasm. To illustrate, reperfusion injury occurs at the termination of cardiac bypass procedures or during cardiac arrest when the heart, once prevented from receiving blood, begins to reperfuse. It is expected that inhibition of PI3K delta activity may result in reduced amounts of reperfusion injury in such situations.

Pharmaceutical Formulations

In order to use a Formula I compound for the therapeutic treatment (including prophylactic treatment) of mammals including humans, it is normally formulated in accordance with standard pharmaceutical practice as a pharmaceutical composition. According to this aspect of the invention there is provided a pharmaceutical composition comprising a compound of this invention in association with a pharmaceutically acceptable diluent or carrier.

A typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which the compound of the present invention is being applied. Solvents are generally selected based on solvents recognized by persons skilled in the art as safe (GRAS) to be administered to a mammal In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent) is dissolved in a suitable solvent in the presence of one or more of the excipients described above. The compound of the present invention is typically formulated into pharmaceutical dosage forms to provide an easily controllable dosage of the drug and to enable patient compliance with the prescribed regimen.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Pharmaceutical formulations of the compounds of the present invention may be prepared for various routes and types of administration. For example, a compound of Formula I having the desired degree of purity may optionally be mixed with pharmaceutically acceptable diluents, carriers, excipients or stabilizers (Remington's Pharmaceutical Sciences (1980) 16$^{th}$ edition, Osol, A. Ed.), in the form of a lyophilized formulation, milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8. Formulation in an acetate buffer at pH 5 is a suitable embodiment.

The compound ordinarily can be stored as a solid composition, a lyophilized formulation or as an aqueous solution.

The pharmaceutical compositions of the invention will be formulated, dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations, and is the minimum amount necessary to prevent, ameliorate, or treat the hyperproliferative disorder.

As a general proposition, the initial pharmaceutically effective amount of the inhibitor administered parenterally per dose will be in the range of about 0.01-100 mg/kg, namely about 0.1 to 20 mg/kg of patient body weight per day, with the typical initial range of compound used being 0.3 to 15 mg/kg/day.

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16$^{th}$ edition, Osol, A. Ed. (1980).

Sustained-release preparations of compounds of Formula I may be prepared. Suitable examples of sustained-release preparations include semipermeable matrices of solid hydrophobic polymers containing a compound of Formula I, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid.

The formulations include those suitable for the administration routes detailed herein. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of a compound of Formula I suitable for oral administration may be prepared as discrete units such as pills, capsules, cachets or tablets each containing a predetermined amount of a compound of Formula I. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom. Tablets, troches, lozenges, aqueous or oil suspensions, dispersible powders or granules, emulsions, hard or soft capsules, e.g., gelatin capsules, syrups or elixirs may be prepared for oral use. Formulations of compounds of Formula I intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

For treatment of the eye or other external tissues, e.g., mouth and skin, the formulations may be applied as a topical ointment or cream containing the active ingredient(s) in an amount of, for example, 0.075 to 20% w/w. When formulated in an ointment, the active ingredients may be employed with either a paraffinic or a water-miscible ointment base. Alternatively, the active ingredients may be formulated in a cream with an oil-in-water cream base. If desired, the aqueous phase of the cream base may include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs. The oily phase of the emulsions of this invention may be constituted from known ingredients in a known manner, including a mixture of at least one emulsifier with a fat or an oil, or with both a fat and an oil. A hydrophilic emulsifier included together with a lipophilic emulsifier acts as a stabilizer. Together, the emulsifier(s) with or without stabilizer(s) make up the so-called emulsifying wax, and the wax together with the oil and fat make up the so-called emulsifying ointment base which forms the oily dispersed phase of the cream formulations. Emulsifiers and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

Aqueous suspensions of Formula I compounds contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

The pharmaceutical compositions of compounds of Formula I may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butanediol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 µg of the active ingredient per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, for example about 0.5 to 10% w/w, for example about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis disorders as described below.

Formulations suitable for vaginal administration may be presented as pessaries, tampons, creams, gels, pastes, foams or spray formulations containing in addition to the active ingredient such carriers as are known in the art to be appropriate.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Combination Therapy

The compounds of Formula I may be employed alone or in combination with other therapeutic agents for the treatment of a disease or disorder described herein, such as inflammation or a hyperproliferative disorder (e.g., cancer). In certain embodiments, a compound of Formula I is combined in a pharmaceutical combination formulation, or dosing regimen as combination therapy, with a second therapeutic compound that has anti-inflammatory or anti-hyperproliferative properties or that is useful for treating an inflammation, immune-response disorder, or hyperproliferative disorder (e.g., cancer). The second therapeutic agent may be an NSAID anti-inflammatory agent. The second therapeutic agent may be a chemotherapeutic agent. The second compound of the pharmaceutical combination formulation or dosing regimen preferably has complementary activities to the compound of Formula I such that they do not adversely affect each other. Such compounds are suitably present in combination in amounts that are effective for the purpose intended. In one embodiment, a composition of this invention comprises a compound of Formula I, or a stereoisomer, tautomer, or pharmaceutically acceptable salt or prodrug thereof, in combination with a therapeutic agent such as an NSAID.

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active agents simultaneously exert their biological activities.

Suitable dosages for any of the above coadministered agents are those presently used and may be lowered due to the combined action (synergy) of the newly identified agent and other therapeutic agents or treatments.

The combination therapy may provide "synergy" and prove "synergistic", i.e., the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g., by different injections in separate syringes, separate pills or capsules, or separate infusions. In general, during alternation therapy, an effective dosage of each active ingredient is administered sequentially, i.e., serially, whereas in combination therapy, effective dosages of two or more active ingredients are administered together.

In a particular embodiment of therapy, a compound of Formula I, or a stereoisomer, tautomer, or pharmaceutically acceptable salt or prodrug thereof, may be combined with other therapeutic, hormonal or antibody agents such as those described herein, as well as combined with surgical therapy and radiotherapy. Combination therapies according to the present invention thus comprise the administration of at least one compound of Formula I, or a stereoisomer, tautomer, or pharmaceutically acceptable salt or prodrug thereof, and the use of at least one other cancer treatment method. The amounts of the compound(s) of Formula I and the other pharmaceutically active chemotherapeutic agent(s) and the relative timings of administration will be selected in order to achieve the desired combined therapeutic effect.

Metaboliltes of Compounds of Formula I

Also falling within the scope of this invention are the in vivo metabolic products of Formula I described herein. Such products may result for example from the oxidation, reduction, hydrolysis, amidation, deamidation, esterification, deesterification, enzymatic cleavage, and the like, of the administered compound. Accordingly, the invention includes metabolites of compounds of Formula I, including compounds produced by a process comprising contacting a compound of this invention with a mammal for a period of time sufficient to yield a metabolic product thereof.

Metabolite products typically are identified by preparing a radiolabelled (e.g., $^{14}C$ or $^{3}H$) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

Articles of Manufacture

In another embodiment of the invention, an article of manufacture, or "kit", containing materials useful for the treatment of the diseases and disorders described above is provided. In one embodiment, the kit comprises a container comprising a compound of Formula I. The kit may further comprise a label or package insert, on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, etc. The container may be formed from a variety of materials such as glass or plastic.

The container may hold a compound of Formula I or a formulation thereof which is effective for treating the condition and may have a sterile access port (for example, the container may be an intravenous solution bag or a vial having a stopper pierceable by a hypodermic injection needle). At least one active agent in the composition is a compound of Formula I. The label or package insert indicates that the composition is used for treating the condition of choice, such as cancer. In addition, the label or package insert may indicate that the patient to be treated is one having a disorder such as a hyperproliferative disorder, neurodegeneration, cardiac hypertrophy, pain, migraine or a neurotraumatic disease or event. In one embodiment, the label or package inserts indicates that the composition comprising a compound of Formula I can be used to treat a disorder resulting from abnormal cell growth. The label or package insert may also indicate that the composition can be used to treat other disorders. Alternatively, or additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the compound of Formula I and, if present, the second pharmaceutical formulation. For example, if the kit comprises a first composition comprising a compound of Formula I and a second pharmaceutical formulation, the kit may further comprise directions for the simultaneous, sequential or separate administration of the first and second pharmaceutical compositions to a patient in need thereof.

In another embodiment, the kits are suitable for the delivery of solid oral forms of a compound of Formula I, such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to one embodiment, a kit may comprise (a) a first container with a compound of Formula I contained therein; and optionally (b) a second container with a second pharmaceutical formulation contained therein, wherein the second pharmaceutical formulation comprises a second compound with anti-hyperproliferative activity. Alternatively, or additionally, the kit may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In certain other embodiments wherein the kit comprises a composition of Formula I and a second therapeutic agent, the kit may comprise a container for containing the separate compositions such as a divided bottle or a divided foil packet, however, the separate compositions may also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

Preparation of Formula I Compounds

Compounds of Formula I may be synthesized by synthetic routes that include processes analogous to those well-known in the chemical arts, particularly in light of the description contained herein, and those for other heterocycles described in: Comprehensive Heterocyclic Chemistry II, Editors Katritzky and Rees, Elsevier, 1997, e.g. Volume 3; Liebigs Annalen der Chemie, (9):1910-16, (1985); Helvetica Chimica Acta, 41:1052-60, (1958); Arzneimittel-Forschung, 40(12):1328-31, (1990), each of which are expressly incorporated by reference. Starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-23, Wiley, N.Y. (1967-2006 ed.), or *Beilsteins Handbuch der organischen Chemie*, 4, Aufl. ed. Springer-Verlag, Berlin, including supplements (also available via the Beilstein online database).

In certain embodiments, thiazolopyrimidine compounds of Formula I ($X^1$ is N and $X^2$ is S) may be readily prepared using procedures well-known to prepare thiazoles, pyrimidines, and thiazolopyrimidines (U.S. Pat. No. 6,608,053; U.S. Pat. No. 6,492,383; U.S. Pat. No. 6,232,320; U.S. Pat. No. 6,187,777; U.S. Pat. No. 3,763,156; U.S. Pat. No. 3,661,908; U.S. Pat. No. 3,475,429; U.S. Pat. No. 5,075,305; US 2003/220365; GB 1390658; GB 1393161; WO 93/13664).

In certain embodiments, purine compounds of Formula I ($X^1$ is N and $X^2$ is $NR^2$) may be readily prepared using well-known procedures to prepare purines (Hammarstrom et al (2007) Tetrahedron Lett. 48(16):2823-2827; Cerna et al (2006) Organic Letters 8(23):5389-5392; Chang et al (2006) J. Med. Chem. 49(10):2861-2867; Yang et al (2005) J. Comb. Chem. 7:474-482; Liu et al (2005) J. Comb. Chem. 7:627-636; Hocek et al (2004) Synthesis 17:2869-2876; Hammarstrom et al (2003) Tetrahedron Lett. 44:8361-8363; Hammarstrom et al (2002) Tetrahedron Lett. 43:8071-8073; Booth et al (1987) J. Chem. Soc, Perkin Trans. 1: Organic and Bio-Organic Chem. 7:1521-1526; Booth et al (1981) J. Chem. Soc., Chemical Communications 15:788-789; Yoneda et al (1976) J. Chem. Soc., Perkin Trans. 1: Organic and Bio-Organic Chem. 14:1547-1550; Taylor et al (1971) J. Org. Chem. 36(21):3211-3217; Lister, J. H.; Fenn, M. D. The Purines, Supplementary 1, John Wiley & Sons, 1996, Volume 54; The Chemistry of Heterocyclic Compounds, Editors Weissberger, A.; Taylor E. C., Wiley Interscience, 1971, Volume 24; Legraverend, M.; Grierson, D. S. (2006) Bioorg. Med. Chem. 14:3987-4006; Hocek, M. (2003) Eur. J. Org. Chem. 245-254;U.S. Pat. No. 7,122,665; U.S. Pat. No. 6,743,919; U.S. Pat. No. 5,332,744; U.S. Pat. No. 4,728,644; U.S. Pat. No. 3,016,378; US 2008/0058297; US 2003/0139427; WO 2008/043031).

Synthetic chemistry transformations and protecting group methodologies (protection and deprotection) useful in synthesizing Formula I compounds and necessary reagents and intermediates are known in the art and include, for example, those described in R. Larock, Comprehensive Organic Transformations, VCH Publishers (1989); T. W. Greene and P. G. M. Wuts, Protective Groups in Organic Synthesis, 3$^{rd}$ Ed., John Wiley and Sons (1999); and L. Paquette, ed., Encyclopedia of Reagents for Organic Synthesis, John Wiley and Sons (1995) and subsequent editions thereof.

Compounds of Formula I may be prepared singly or as compound libraries comprising at least 2, for example 5 to 1,000 compounds, or 10 to 100 compounds. Libraries of compounds of Formula I may be prepared by a combinatorial 'split and mix' approach or by multiple parallel syntheses using either solution phase or solid phase chemistry, by procedures known to those skilled in the art. Thus according to a further aspect of the invention there is provided a compound library comprising at least 2 compounds, or pharmaceutically acceptable salts thereof.

A purine compound may be prepared by using 2,4,8-trichloropurine as a starting material. The three chloro groups can be displaced by various substituents. More specifically, the most reactive chloro group (i.e., chloro at position 4) is substituted with a morpholino group to form morpholinopurine.

For illustrative purposes, Scheme 1 shows a general method for preparing Formula I purine compounds, as well as key intermediates. For a more detailed description of the individual reaction steps, see the General Procedures and Examples sections. Those skilled in the art will appreciate that other synthetic routes may be used to synthesize the inventive compounds. Although specific starting materials and reagents are depicted and discussed in the General Procedures, Examples, Scheme 1, other starting materials and reagents can be easily substituted to provide a variety of derivatives and/or reaction conditions. In addition, many of the exemplary compounds prepared by the described methods can be further modified in light of this disclosure using conventional chemistry well known to those skilled in the art.

Scheme 1

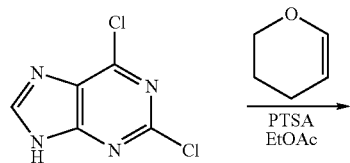

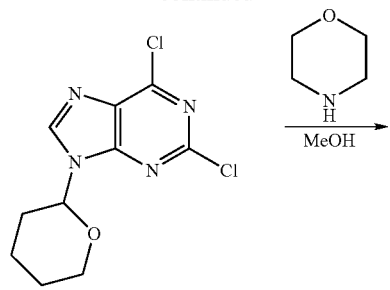

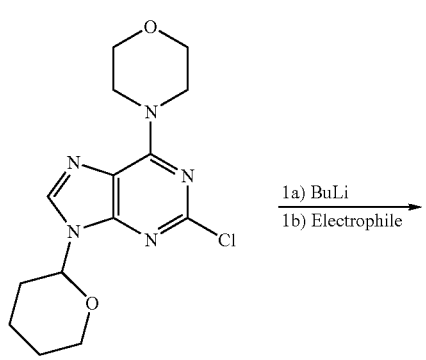

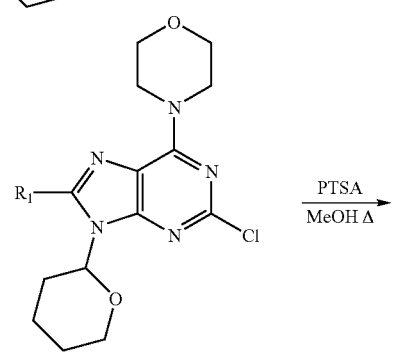

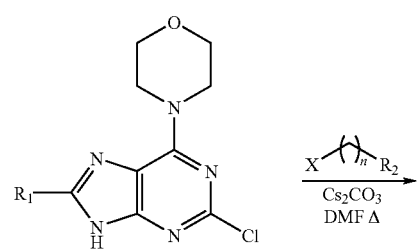

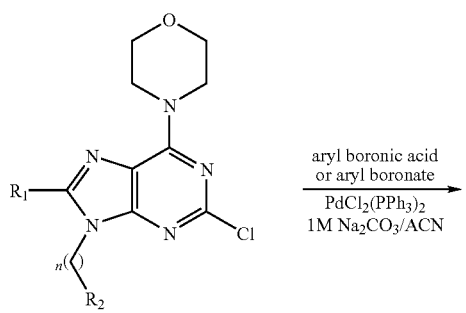

-continued

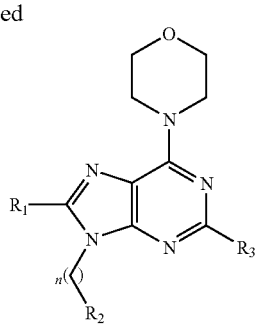

In preparing compounds of Formulas I, protection of remote functionality (e.g., primary or secondary amine) of intermediates may be necessary. The need for such protection will vary depending on the nature of the remote functionality and the conditions of the preparation methods. Suitable amino-protecting groups include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

Methods of Separation

In the methods of preparing Formula I compounds, it may be advantageous to separate reaction products from one another and/or from starting materials. The desired products of each step or series of steps is separated and/or purified to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like. Selection of appropriate methods of separation depends on the nature of the materials involved, such as, boiling point and molecular weight in distillation and sublimation, presence or absence of polar functional groups in chromatography, stability of materials in acidic and basic media in multiphase extraction, and the like.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column.

A single stereoisomer, e.g., an enantiomer, substantially free of its stereoisomer may be obtained by resolution of the racemic mixture using a method such as formation of diastereomers using optically active resolving agents (Eliel, E. and Wilen, S. "Stereochemistry of Organic Compounds," John Wiley & Sons, Inc., New York, 1994; Lochmuller, C. H., (1975) J. Chromatogr., 113(3):283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: "Drug Stereochemistry, Analytical Methods and Pharmacology," Irving W. Wainer, Ed., Marcel Dekker, Inc., New York (1993).

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (E. and Wilen, S. "Stereochemistry of Organic Compounds", John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob III. J. Org. Chem. (1982) 47:4165), of the racemic mixture, and analyzing the $^1$H NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111). By method (3), a racemic mixture of two enantiomers can be separated by chromatography using a chiral stationary phase ("Chiral Liquid Chromatography" (1989) W. J. Lough, Ed., Chapman and Hall, New York; Okamoto, J. Chromatogr., (1990) 513:375-378). Enriched or purified enantiomers can be distinguished by methods used to distinguish other chiral molecules with asymmetric carbon atoms, such as optical rotation and circular dichroism.

General Preparative Procedures
General Procedure A C-2 Suzuki Coupling

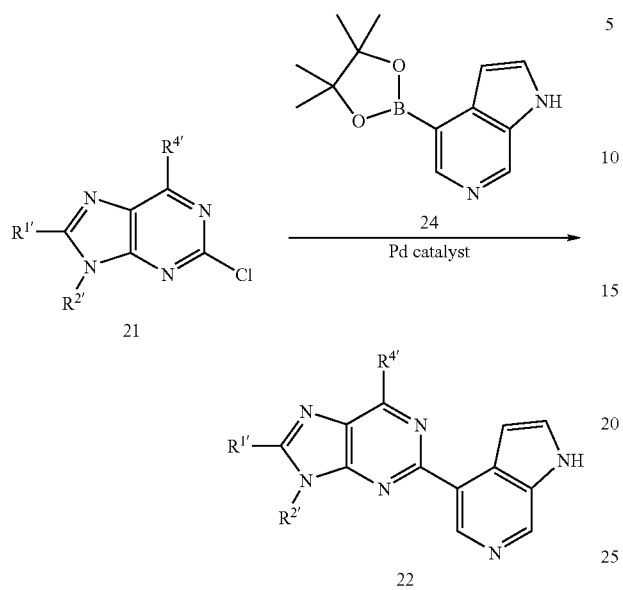

The Suzuki-type coupling reaction is useful to attach a fused bicyclic heterocycle or a fused bicyclic heteroaryl at the 2-position of the pyrimidine ring of a 2-chloro-purine 21. The Suzuki-type coupling reaction is useful to attach a fused bicyclic heterocycle or a fused bicyclic heteroaryl at the 2-position of the pyrimidine ring of thiazolopyrimidines (i), thienopyrimidines (ii), furanopyrimidines (iv), and pyrrolopyrimidines (v). For example, 21 may be combined with about 1.5 equivalents of 4-(4,4,5,5-tetramethyl-1,3,2-dioxaborolan-2-yl)-1H-pyrrolo[2,3-c]pyridine 24, and dissolved in 3 equivalents of sodium carbonate as a 1 molar solution in water and an equal volume of acetonitrile. A catalytic amount, or more, of a low valent palladium reagent, such as bis(triphenylphosphine)palladium(II) dichloride, is added. A variety of boronic acids or boronic esters can be used in place of the indazole boronic ester indicated. Also alternatively, a nitrogen of the fused bicyclic heterocycle or a fused bicyclic heteroaryl may be protected, for example as N-THP. In some cases potassium acetate was used in place of sodium carbonate to adjust the pH of the aqueous layer. The reaction is then heated to about 140-150° C. under pressure in a microwave reactor such as the Biotage Optimizer (Biotage, Inc.) for 10 to 30 minutes. The contents are extracted with ethyl acetate, or another organic solvent. After evaporation of the organic layer the Suzuki coupling products 22 may be purified on silica or by reverse phase HPLC. Substituents $R^{1'}$, $R^{2'}$, $R^{4'}$ may be $R^1$, $R^2$, $R^4$ as defined, or protected forms or precursors thereof.

A variety of palladium catalysts can be used during the Suzuki coupling step to form compounds, including exemplary embodiments 22. Suzuki coupling is a palladium mediated cross coupling reaction of a heteroarylhalide, such as 21, with a boronic acid such as 24. Low valent, Pd(II) and Pd(0) catalysts may be used in the Suzuki coupling reaction, including $PdCl_2(PPh_3)_2$, $Pd(t-Bu)_3$, $PdCl_2$ dppf $CH_2Cl_2$, $Pd(PPh_3)_4$, $Pd(Oac)/PPh_3$, $Cl_2Pd[(Pet_3)]_2$, $Pd(DIPHOS)_2$, $Cl_2Pd(Bipy)$, $[PdCl(Ph_2PCH_2PPh_2)]_2$, $Cl_2Pd[P(o-tol)_3]_2$, $Pd_2(dba)_3/P(o-tol)_3$, $Pd_2(dba)/P(furyl)_3$, $Cl_2Pd[P(furyl)_3]_2$, $Cl_2Pd(PmePh_2)_2$, $Cl_2Pd[P(4-F-Ph)_3]_2$, $Cl_2Pd[P(C_6F_6)_3]_2$, $Cl_2Pd[P(2-COOH-Ph)(Ph)_2]_2$, $Cl_2PD[P(4-COOH-Ph)(Ph)_2]_2$, and encapsulated catalysts Pd EnCat™ 30, Pd EnCat™ TPP30, and Pd(II)EnCat™ BINAP30 (US 2004/0254066).

General Procedure B C-6 Nitrogen Substitution

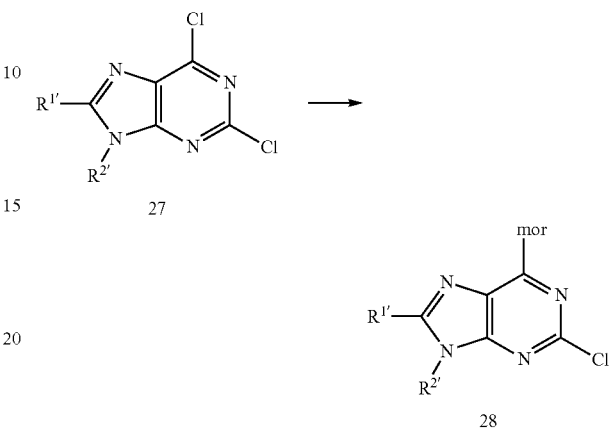

To a 2,6-dichloro purine intermediate 27 in a solvent such as ethanol is added a morpholine or a morpholine analog, and a non-nucleophilic base such as triethylamine (Net$_3$, 1.5 eq, 63 μl). Alternatively, acetonitrile may be used as the solvent and potassium carbonate may be used as the base. The reaction mixture is stirred at room temperature for about 1 hour or overnight, volatiles removed in vacuo and residue partitioned between DCM and brine. If the mixture is insoluble it may be sonicated and the solid product was collected by filtration. Drying with magnesium sulfate and evaporation of the solvent gives N'-(2-chloro purin-6-yl)-amine substituted intermediate 28, often as a crystalline solid, or by trituration. Substituents $R^{1'}$ and $R^{2'}$ may be $R^1$ and $R^2$ as defined, or protected forms or precursors thereof.

General Procedure C N-9 Nitrogen Alkylation

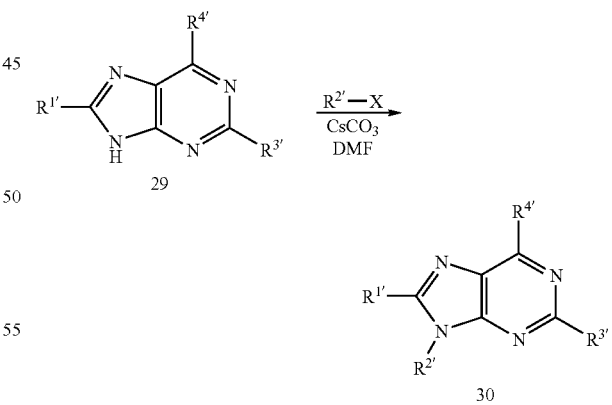

9-H Purine intermediate 29 is brought up into DMF and 2 equiv of cesium carbonate is added to the reaction mixture. The reaction is heated to 50° C. whereupon 1 to 3 equivalents of an alkyl halide $R^{2'}$-X are added to the reaction mixture. The reaction is monitored by TLC or LC/MS and stirred until completion, typically several hours. The reaction mixture is extracted with EtOAc and water, and the organic layer is dried, filtered and concentrated to get crude 9-alkylated purine 30 which is used directly in the next reaction or purified by reverse phase HPLC. Substituents $R^{1'}$, $R^{3'}$ and $R^{4'}$ may be $R^1$, $R^3$ and $R^4$ as defined, or protected forms or precursors thereof.

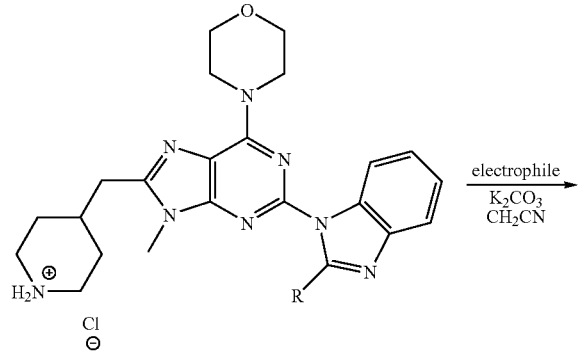

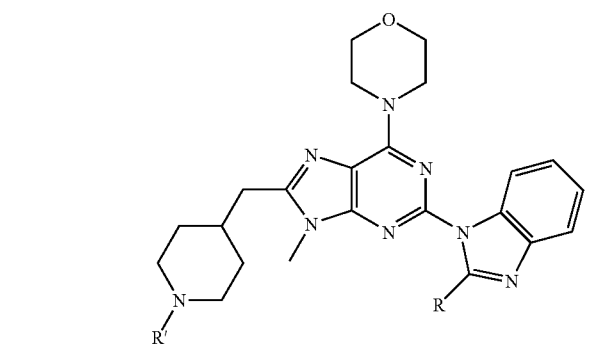

R = Me or Et

In an embodiment of N-alkylation of a piperidine group, to a suspension of 4-((9-methyl-2-(2-methyl-1H-benzo[d]imidazol-1-yl)-6-morpholino-9H-purin-8-yl)methyl)piperidinium chloride or 4-((2-(2-ethyl-1H-benzo[d]imidazol-1-yl)-9-methyl-6-morpholino-9H-purin-8-yl)methyl)piperidinium chloride (0.4 mmol), potassium carbonate (0.25 g, 1.8 mmol) in acetonitrile (2.0 mL) is added an electrophile (1.4 mmol). The resulting mixture is stirred in a pressure tube at about 95° C. for 5-18 hours. The reaction mixture is filtered, concentrated, and may be purified by RP-HPLC.

General Procedure D THP Deprotection

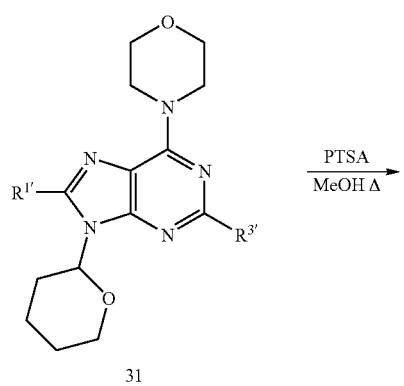

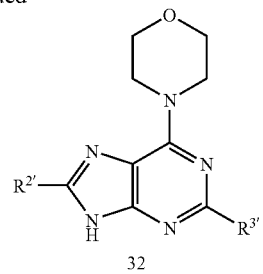

Generally, N-9-tetrahydropyranyl substituted 31 may be treated with catalytic amounts of para-toluenesulfonic acid (PTSA) in a solution of methanol and heated to about 50° C. until the tetrahydropyran (THP) group is removed to afford compound 32. The reaction may be monitored by LC-MS or TLC. Substituents $R^{1'}$ and $R^{3'}$ may be $R^1$ and $R^3$ as defined, or protected forms or precursors thereof.

General Procedure E Displacement of Alkyl Bromide with Amines:

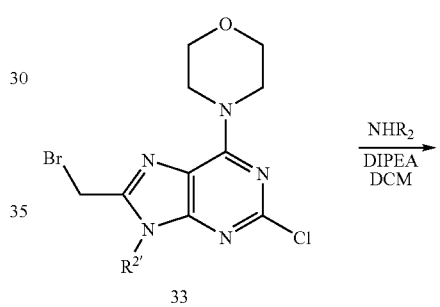

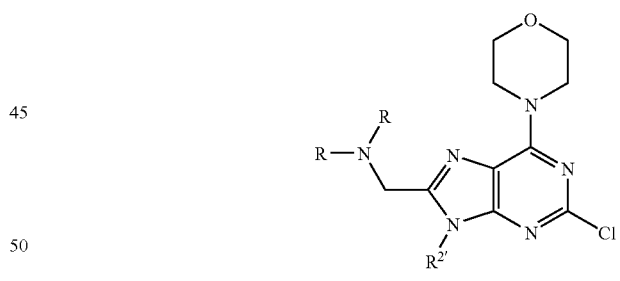

Generally, substituted 33 is suspended in dichloromethane whereupon 3 equivalents of Hunig's base (DIPEA) and 1.5 equivalents of an amine ($NHR_2$) are added to the reaction mixture. Other solvents such as tetrahydrofuran and methanol, or mixtures of solvents can be employed. The reaction is monitored by TLC or LC-MS until complete, usually within 30 minutes. The reaction mixture is extracted with water and the organic layer is dried, filtered and concentrated to dryness. The intermediate 34 can be taken as crude into subsequent reactions or in some cases is purified by column chromatography.

General Procedure F Amide Coupling

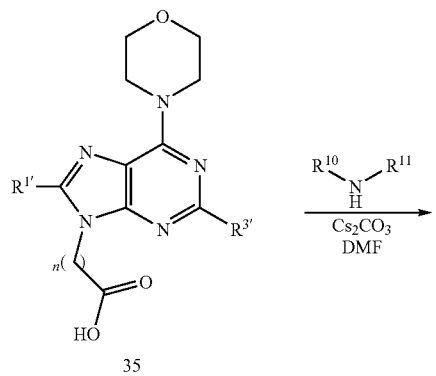

A 2,6,8 substituted, 9-alkylcarboxyl purine 35, where n is 1 to 12, is treated with 1.5 eq HATU (2-(7-aza-1H-benzotriazole-1-yl)-1,1,3,3-tetramethyluronium hexafluorophosphate), an excess (such as 3 eq) of an alkylamine ($HNR^{10}R^{11}$) and an excess (such as 3 eq) of cesium carbonate in dimethylformamide (DMF). Alternatively, other coupling reagents may be used. The reaction is stirred until complete and extracted in ethylacetate with saturated bicarbonate solution. The organic layer is dried, filtered and concentrated to yield the acylated, crude intermediate, which is purified via reverse phase HPLC to yield product 36. Substituents $R^{1'}$ and $R^{3'}$ may be $R^1$ and $R^3$ as defined, or protected forms or precursors thereof.

General Procedure G Stille Coupling

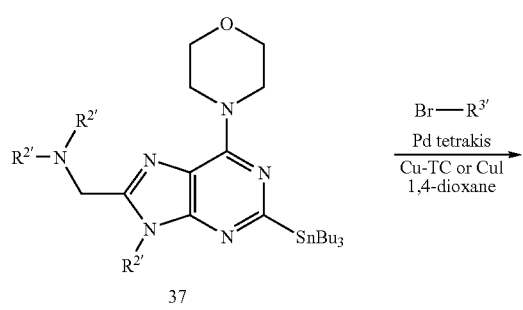

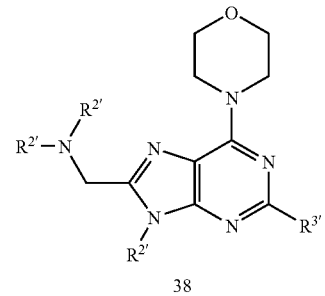

To intermediate 37 in a microwave vial is added 1.2 equivalents of an aryl bromide, 1 equivalent of copper (I) iodide or copper thiophene-carboxylate, and 1,4-dioxane as solvent. The reaction mixture is degassed under nitrogen for 5 minutes prior to addition of 0.12 equivalents of tetrakis(triphenylphosphine)palladium(0). The reaction is heated in a CEM or Biotage microwave for 20-30 minutes at 140° C. The crude reaction mixture is filtered and periodically passed through a Biotage Isolute scx-2 basic spe cartridge before being purified via normal or reverse phase chromatography to afford pure product 38. Substituents $R^{2'}$ and $R^{3'}$ may be $R^2$ and $R^3$ as defined, or protected forms or precursors thereof.

General Procedure H N-9 alkylation of purines

Scheme 1 shows a general method for preparation of polyfunctionalized purines begins with protection of the N-9 nitrogen of 2,6-dichloro-9H-purine as the tetrahydropyranyl group (THP). Displacement of the more reactive chloro group with morpholine gives 4-(2-chloro-9-(tetrahydro-2H-pyran-2-yl)-9H-purin-6-yl)morpholine. The C-8 proton is removed with strong base and reacted with various electrophiles ($R^1$). After deprotection with mild acid, N-9 is alkylated of N-9 with various electrophiles ($R^2$). Suzuki coupling at C-2 chloro by General Procedure A with various boronate reagents and palladium catalysts gives carbon-linked $C_2$-$C_{20}$ heterocyclyl and carbon-linked $C_1$-$C_{20}$ heteroaryl as $R^3$.

General Procedure I C-2 Halo Buchwald Coupling of amine-heteroaryls

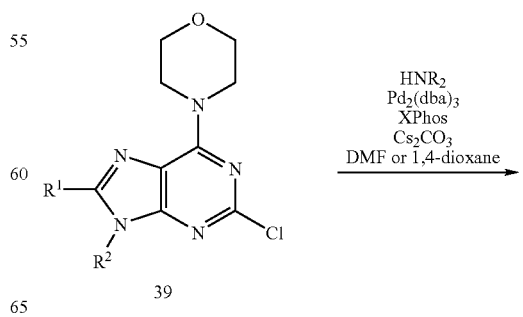

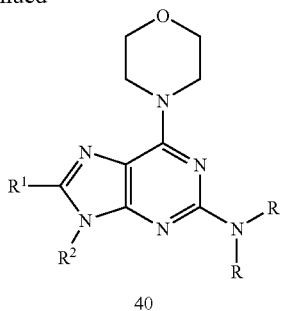

40

A microwave tube is charged with Xphos (2-Dicyclohexylphosphino-2',4',6'-triisopropylbiphenyl, CAS Reg. No. 564483-18-7, 0.1 equiv.), tris(dibenzylideneacetone)dipalladium(0) (0.05 equiv.), cesium carbonate (2 equiv.), the corresponding 2-chloropurine 39 (1 equiv.) and an amine (1.2 equiv.), such as a benzimidazole. The vessel is evacuated and refilled with nitrogen prior to the addition of DMF or 1,4-dioxane. The mixture is heated in a microwave device, such as Biotage at about 140° C. for about 25-35 minutes. The reaction mixture is cooled to room temperature, filtered and concentrated. Typically, the crude product 40 is purified by flash chromatography or RP-HPLC.

Alternatively, the reaction can be performed by a modified procedure: A microwave tube is charged with palladium acetate (0.10 equiv.), bis(tri-t-butylphosphine)palladium (0.10 equiv.), sodium t-butoxide (2 equiv.), the corresponding 2-chloropurine 39 (1 equiv.) and the amine (2 equiv.). The vessel is evacuated and refilled with nitrogen prior to the addition of toluene. The mixture is heated in a Biotage microwave at about 140° C. for about 25-35 minutes. The reaction mixture is cooled to room temperature, filtered and concentrated. Typically, the crude product 40 is purified by flash chromatography or RP-HPLC.

The Buchwald (and Suzuki) couplings may be conducted with a variety of palladium catalysts and ligands, including: Chloro {[t-butylXPhos][2-(2-aminoethylphenyl)palladium (II))/[t-butylXPhos] admixture (molar PdP/P=1:1), Chloro (2-di-t-butylphosphino-2',4',6'-tri-i-propyl-1,1'-biphenyl)[2-(2-aminoethyl)phenyl]palladium(II), Chloro(2-dicyclohexylphosphino-2',6'-dimethoxy-1,1'-biphenyl)[2-(2-aminoethylphenyl)]palladium(II) methyl-t-butylether adduct, Chloro[2-(dicyclohexylphosphino)-3,6-dimethoxy-2'-4'-6'-tri-i-propyl-1, 1'-biphenyl][2-(2-aminoethyl)phenyl] palladium(II), Chloro(2-dicyclohexylphosphino-2',6'-di-i-propoxy-1,1'-biphenyl)[2-(2-aminoethylphenyl)]palladium (II), methyl-t-butylether adduct, Chloro(2-dicyclohexylphosphino-2',4',6'-tri-i-propyl-1,1'-biphenyl) [2-(2-aminoethyl)phenyl]palladium(II) methyl-t-butylether adduct.

A variety of phosphorus ligands may also be employed in the Buchwald (and Suzuki) couplings, including: 2-Dicyclohexylphosphino-2',4',6'-triisopropylbiphenyl, Xphos (CAS Reg. No. 564483-18-7), racemic-2-Di-t-butylphosphino-1,1'-binaphthyl (CAS Reg. No. 255836-67-0), 2-(Di-t-butylphosphino)biphenyl, JohnPhos (CAS Reg. No. 224311-51-7), 2-Di-t-butylphosphino-2'-(N,N-dimethylamino) biphenyl (CAS Reg. No. 224311-49-3), 2-Di-t-butylphosphino-2'-methylbiphenyl (CAS Reg. No. 255837-19-5), 2-Di-t-butylphosphino-3,4,5,6-tetramethyl-2',4',6'-tri-i-propylbiphenyl (CAS Reg. No. 857356-94-6), 2-Di-t-butylphosphino-2',4',6'-tri-i-propyl-1,1'-biphenyl, t-butylXPhos (CAS Reg. No. 564483-19-8), 2-(Dicyclohexylphosphino)biphenyl (CAS Reg. No. 247940-06-3), 2-Dicyclohexylphosphino-2',6'-dimethoxy-1,1'-biphenyl, S-Phos (CAS Reg. No. 657408-07-6), 2'-Dicyclohexylphosphino-2,6-dimethoxy-3-sulfonato-1,1'-biphenyl hydrate sodium salt, 2-(Dicyclohexylphosphino)-3,6-dimethoxy-2'-4'-6'-tri-i-propyl-1,1'-biphenyl (BrettPhos), 2-(Dicyclohexylphosphino)-2'-(N,N-dimethylamino)biphenyl, DavePhos (CAS Reg. No. 213697-53-1), 2-Dicyclohexylphosphino-2',6'-di-i-propoxy-1,1'-biphenyl, RuPhos (CAS Reg. No. 787618-22-8), 2'-Dicyclohexylphosphino-2,6-di-i-propyl-4-sulfonato-1, 1'-biphenyl hydrate sodium salt (CAS Reg. No. 870245-84-4), 2-Dicyclohexylphosphino-2'-methylbiphenyl, MePhos (CAS Reg. No. 251320-86-2), 2-(Dicyclohexylphosphino)-2',4',6'-tri-i-propyl-1,1'-biphenyl, X-Phos (CAS Reg. No. 564483-18-7) 2-Diphenylphosphino-2'-(N,N-dimethylamino)biphenyl (CAS Reg. No. 240417-00-9). See: Mauger, C. C. and Mignani, G. A. *Aldrichimica Acta* (2006) 39:17; Schlummer, B. and Scholz, U. Adv. Synth. Catal. (2004) 346:1599 for reviews. Buchwald and Suzuki coupling reagents are available from commercial sources including Strem Chemicals, Inc., 7 Mulliken Way, Newburyport, Mass. 01950-4098 USA.

General Procedure J Multi-Step Benzimidazole Formation by Buchwald Coupling of amino-heteroaryls

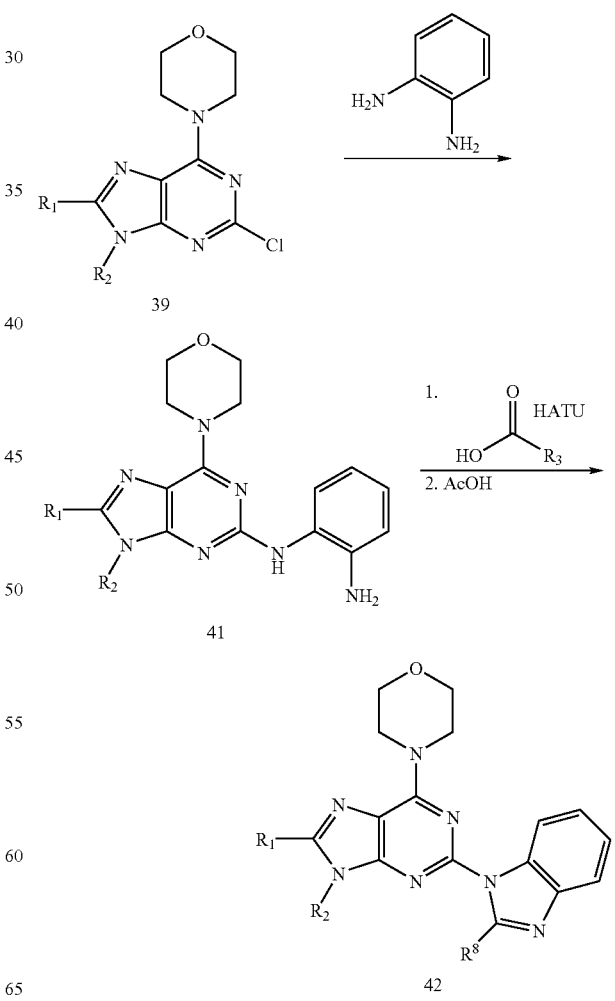

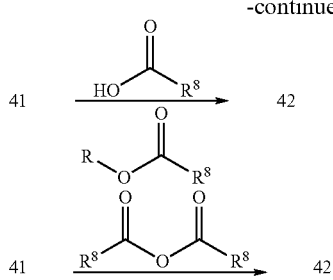

2-Chloropurine 39 is reacted with 1,2-diaminobenzene via General Procedure I for Buchwald Coupling to give 2-amino heteroaryl intermediate 41 which is subsequently transformed to 42 via one of two possible routes. In the top route; Intermediate 41 and acid with $R^8$ functional group (1.5 eq) and HATU (1.5 eq) are dissolved in DMF (100 eq) whereupon N,N-diisopropylethylamine (3-5 eq) is added. The reaction is stirred overnight at room temperature and then concentrated to dryness. The crude is dissolved in acetic acid (100 eq) and heated at 90° C. for 18 hours to cyclize to product 42. In the middle route, 41 is dissolved directly in either the acid (or ester) with $R^8$ functional group and refluxed overnight to cyclize to product 42. In the lower route, 41 is acylated with anhydride (1 to 1.5 equiv.) in the presence of a tertiary amine base such as $iPr_2Net$. Final products are purified via reverse phase HPLC and may be subsequently purified by chiral SFC (supercritical fluid chromatography) when enantiomers are present and require separation (Liu et al (2003) Chromatographia 58(11/12):775-779).

General Procedure K C2-carboxyl amide Formation

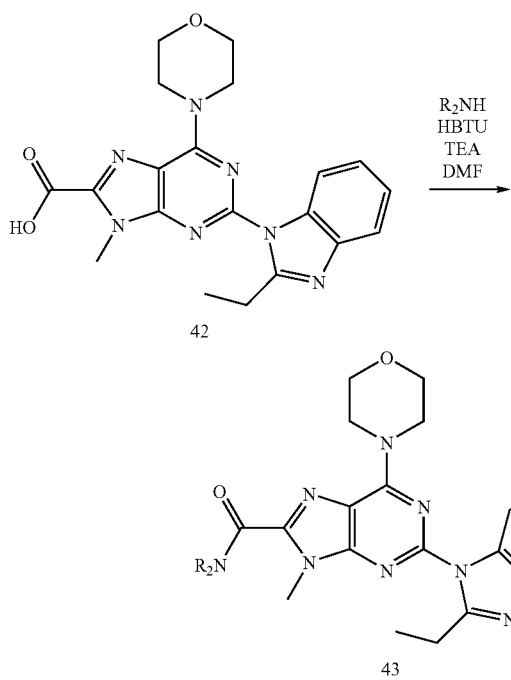

To a mixture of 2-(2-ethyl-1H-benzo[d]imidazol-1-yl)-9-methyl-6-morpholino-9H-purine-8-carboxylic acid 42 (1 equiv), HBTU (1.5 equiv.) in N,N-dimethylformamide is added triethylamine (TEA). The resulting mixture is stirred at room temperature for about 5 minutes before the addition of the amine ($R_2NH$, 1 equiv.). The reaction mixture is then stirred at room temperature for 2-18 hours. The reaction mixture is concentrated and purified by RP-HPLC to give the amide product 43. Other coupling agents, such as HATU, HCTU, TBTU, and PyBOP, can be used.

General Procedure L Reductive Amination

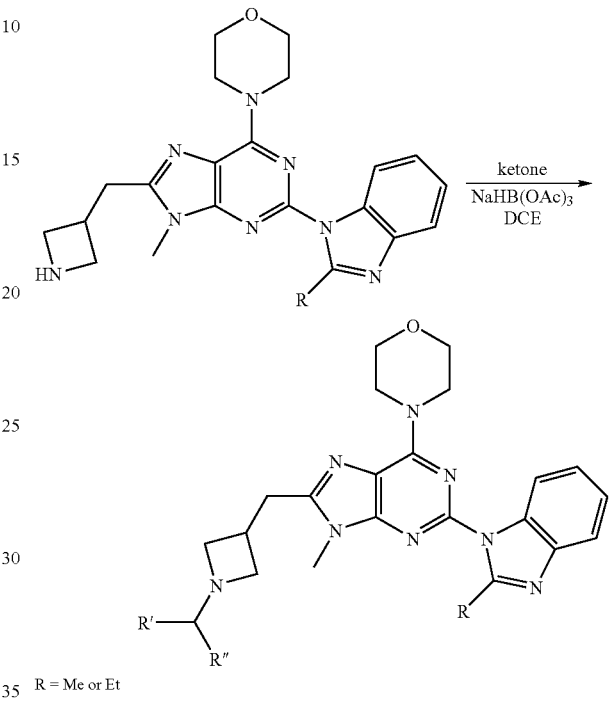

R = Me or Et

In an exemplary embodiment of the general procedure for reductive amination of amine groups, a suspension of 4-(8-(azetidin-3-ylmethyl)-2-(2-ethyl-1H-benzo[d]imidazol-1-yl)-9-methyl-9H-purin-6-yl)morpholine or 4-(8-(azetidin-3-ylmethyl)-2-(2-methyl-1H-benzo[d]imidazol-1-yl)-9-methyl-9H-purin-6-yl)morpholine (1 equiv.) in 1,2-dichloroethane is added a ketone (about 1.5-2.0 equiv.). The resulting mixture is stirred at room temperature for 15 minutes before the addition of sodium triacetoxyborohydride (about 1.5-2.0 equiv.). The reaction is then stirred at room temperature for about 18 hours. The reaction was then quenched by the addition of methanol. The mixture may be purified by chromatography, including RP-HPLC. Also, the mixture may be loaded onto an ISOLUTE SCX-2 column, washed with MeOH, and eluted with 2M $NH_3$ in MeOH to give the desired product.

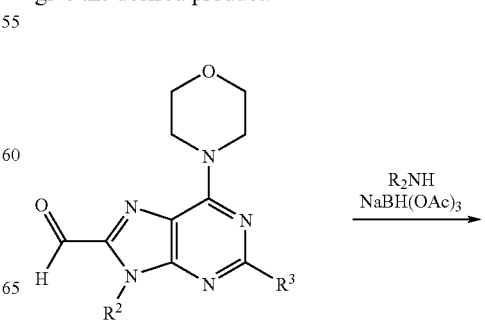

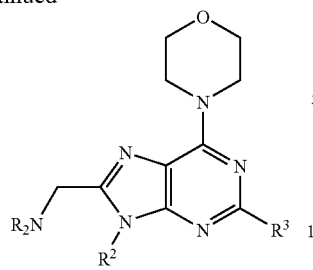

In an exemplary embodiment of reductive amination of a 2-carboxaldehyde purine interemediate, a mixture of 9-methyl-2-(2-methyl-benzoimidazol-1-yl)-6-morpholin-4-yl-9H-purine-8-carbaldehyde where $R^2$ is methyl and $R^3$ is 2-methyl-benzoimidazol-1-yl (0.1 g, 0.264 mmol), AcOH (0.03 mL, 0.53 mmol) and amine in CH2Cl2 (4 mL) was stirred at room temperature for 2 h. Sodium triacetoxyborohydride (78 mg, 0.37 mmol) was added and stirring continued for 18 h. Potassium carbonate (K2CO3) saturated solution was added and product extracted with CH2Cl2 (4×). Organics combined were dried (MgSO4) and concentrated. Flash chromatography with CH2Cl2:Methanol:Ammonium hydroxide (100:5:0.5) afforded the 2-aminomethyl product.

Alternatively, to a mixture of an aldehyde (1 mmol) and amine (1-1.2 mmol) in 1,2-dichloroethane (8-20 mL) was added acetic acid (2 mmol) and trimethoxymethane (10 mmol), or micronized 4 A (angstrom) molecular sieves. The mixture was stirred at room temperature for 0.5-4 hr. Sodium triacetoxyborohydride (1.1-1.5 mmol) was added. The resulting mixture was stirred at room temperature for 4-20 hr. The contents were partitioned between DCM and diluted NaOH. The organic layer was separated. The aqueous layer was extracted with DCM. The combined organic solutions were dried ($Na_2SO_4$). The crude was purified by chromatography or reverse phase HPLC, or used directly if pure enough for subsequent transformations.

EXAMPLES

The chemical reactions described in the Examples may be readily adapted to prepare a number of other PI3K inhibitors of the invention, and alternative methods for preparing the compounds of this invention are deemed to be within the scope of this invention. For example, the synthesis of non-exemplified compounds according to the invention may be successfully performed by modifications apparent to those skilled in the art, e.g., by appropriately protecting reactive functional groups, by utilizing other suitable reagents known in the art other than those described, and/or by making routine modifications of reaction conditions. Alternatively, other reactions disclosed herein or known in the art will be recognized as having applicability for preparing other compounds of the invention.

Chiral SFC (supercritical fluid chromatography) may be used to separate enantiomers (Liu et al (2003) Chromatographia 58(11/12):775-779)

$^1$H NMR spectra were recorded at ambient temperature using an NMR spectrometer, including a Varian Unity Inova (400 MHz) spectrometer with a triple resonance 5 mm probe. Chemical shifts are expressed in ppm relative to tetramethylsilane. The following abbreviations have been used: br=broad signal, s=singlet, d=doublet, dd=double doublet, t=triplet, q=quartet, m=multiplet.

High Pressure Liquid Chromatography—Mass Spectrometry (LCMS) experiments to determine retention times ($R_T$) and associated mass ions may be performed, for example by one of the following methods. The spectrometers have an electrospray source operating in positive and negative ion mode. Additional detection was achieved using a Sedex 85 evaporative light scattering detector.

Method A: Experiments performed on a Waters Platform LC quadrupole mass spectrometer linked to a Hewlett Packard HP1100 LC system, with diode array detector and a 100 position autosampler, using a Phenomenex Luna 3 μm $C_{18}$(2) 30×4.6 mm and a 2 mL/minute flow rate. The mobile phase consisted of formic acid 0.1% in water (solvent A) and formic acid 0.1% in methanol (solvent B). The initial solvent system was 95% solvent A and 5% solvent B for the first 0.5 minute followed by a gradient up to 5% solvent A and 95% solvent B over the next 4 minutes. The final solvent system was held constant for a further 1 minute.

Method B: Experiments performed on a Waters Platform LC quadrupole mass spectrometer linked to a Hewlett Packard HP1100 LC system, with diode array detector and a 100 position autosampler, using a using a Phenomenex Luna 3 μm $C_{18}$(2) 30×4.6 mm and a 2 mL/minute flow rate The mobile phase consisted of formic acid 0.1% in water (solvent A) and formic acid 0.1% in acetonitrile (solvent B). The initial solvent system was 95% solvent A and 5% solvent B for the first 0.50 minute followed by a gradient up to 5% solvent A and 95% solvent B over the next 4 minutes. The final solvent system was held constant for a further 1 minute.

Method C: Experiments performed on a Waters ZMD quadrupole mass spectrometer linked to a Waters 1525 LC system, with a Waters 996 diode array detector and a Waters 2700 autosampler, using a Phenomenex Luna 3 μm $C_{18}$(2) 30×4.6 mm and a 2 mL/minute flow rate. The mobile phase consisted of formic acid 0.1% in water (solvent A) and formic acid 0.1% in methanol (solvent B). The initial solvent system was 95% solvent A and 5% solvent B for the first 0.5 minute followed by a gradient up to 5% solvent A and 95% solvent B over the next 4 minutes. The final solvent system was held constant for a further 1 minute.

Method D: Experiments performed on a Waters ZMD quadrupole mass spectrometer linked to a Waters 1525 LC system, with a Waters 996 diode array detector and a Waters 2700 autosampler, using a Phenomenex Luna 3 μm $C_{18}$(2) 30×4.6 mm and a 2 mL/minute flow rate. The mobile phase consisted of formic acid 0.1% in water (solvent A) and formic acid 0.1% in acetonitrile (solvent B). The initial solvent system was 95% solvent A and 5% solvent B for the first 0.5 minute followed by a gradient up to 5% solvent A and 95% solvent B over the next 4 minutes. The final solvent system was held constant for a further 1 minute.

Method E: Experiments performed on a Waters Micromass ZQ2000 quadrupole mass spectrometer linked to a Hewlett Packard HP1100 LC system, with a DAD UV detector and a CTC HTS PAL autosampler, using a Higgins Clipeus 5 μm C18 100×3.0 mm column (at 40° C.) and a 1 mL/minute flow rate. The mobile phase consisted of formic acid 0.1% in water (solvent A) and formic acid 0.1% in methanol (solvent B). The initial solvent system was 85% solvent A and 15% solvent B for the first 1 minute followed by a gradient up to 5% solvent A and 95% solvent B over the next 12 minutes. The final solvent system was held constant for a further 7 minutes.

Method F: Experiments performed on a Waters Micromass ZQ2000 quadrupole mass spectrometer linked to a Hewlett Packard HP1100 LC system, with a DAD UV detector and a CTC HTS PAL autosampler, using a Higgins Clipeus 5 micron $C_{18}$ 100×3.0 mm column and a 1 mL/minute flow rate.

The mobile phase consisted of formic acid 0.1% in water (solvent A) and formic acid 0.1% in acetonitrile (solvent B). The initial solvent system was 85% solvent A and 15% solvent B for the first 1 minute followed by a gradient up to 5% solvent A and 95% solvent B over the next 14 minutes. The final solvent system was held constant for a further 5 minutes.

Microwave experiments were carried out using a CEM Explorer, Smith Synthesizer or a Biotage Initiator™, which uses a single-mode resonator and dynamic field tuning, both of which give reproducibility and control. Temperatures from 40-250° C. can be achieved and pressures up to 20 bar can be reached.

Unless otherwise stated, all reactions were performed under an inert, i.e. argon or nitrogen, atmosphere. F R$^1$ Reagents:

Example 1

3-(Tetrahydropyran-4-yl)azetidine-1-carboxylic acid tert-butyl ester

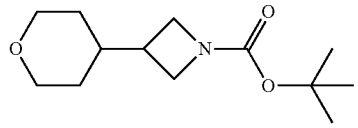

Step 1: Trifluoromethanesulfonic acid 3,6-dihydro-2H-pyran-4-yl ester

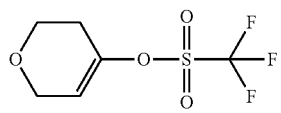

To a solution of diisopropylamine (35.2 mL, 0.25 mol) in anhydrous THF (200 mL) at −20° C. was added a 2.5M solution on n-buyllithium in hexanes (100 mL, 0.25 mol) over a 10 min period under an argon atmosphere. The reaction mixture was stirred at −20° C. for 15 min. A solution of tetrahydropyran-4-one (21.0 mL, 0.23 mol) in anhydrous THF (160 mL) was added dropwise over a 20 min period (internal temperature<−65° C.). The reaction mixture was stirred for 3 hours at −78° C. then a solution of N,N-bis (trifluoromethanesulfonyl)aniline (86.4 g, 0.24 mmol) in anhydrous THF (240 mL) was added dropwise over a 45 min period. The resulting mixture was stirred at −78° C. for 1.5 hours then allowed to reach room temperature and stirred for 18 hours. The solvents were removed in vacuo to give a residue which was partitioned between EtOAc (500 mL) and water (250 mL) The organic layer was separated and washed with water (250 mL), 2M NaOH in water (3×300 mL) and brine (2×200 mL), dried over Na$_2$SO$_4$, filtered and concentrated to give Trifluoromethanesulfonic acid 3,6-dihydro-2H-pyran-4-yl ester as a brown oil (43.7 g, 83%). $^1$H NMR (400 MHz, CHCl-d): δ 5.83-5.80 (m, 1H); 4.26 (dd, J=2.9, 0.4 Hz, 2H); 3.89 (t, J=5.5 Hz, 2H); 2.46 (ttd, J=5.5, 2.9, 1.4 Hz, 2H).

Step 2: 3-(3,6-Dihydro-2H-pyran-4-yl)azetidine-1-carboxylic acid tert-butyl ester

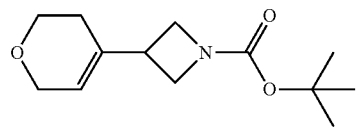

Zinc activation: To a suspension of zinc powder (20.3 g, 0.31 mol) and Celpure® P65 in anhydrous DMA (48 mL) was added a 7:5 (v:v) mixture of TMS-Cl:1,2-dibromoethane (6.2 mL) was added dropwise. The reaction mixture was stirred at room temperature for 45 min.

Zinc insertion: A solution of 3-iodoazetidine-1-carboxylic acid tert-butyl ester (72.9 g, 0.26 mol) in anhydrous DMA (120 mL) was added dropwise to the mixture described above over a 30 min period. The reaction mixture was stirred for 1 hour at room temperature.

Coupling reaction: A mixture of trifluoromethanesulfonic acid 3,6-dihydro-2H-pyran-4-yl ester (42.7 g, 0.18 mol), Pd(dppf)Cl$_2$.DCM (4.5 g, 5.5 mmol) and CuI (2.1 g, 11.0 mmol) was sonicated for 5 min. The vessel was then evacuated and back-filled with argon. The zincate mixture was quickly filtered through a grade-3 sintered funnel and added onto the palladium-containing mixture. The resulting reaction mixture was stirred at 85° C. for 18 hours then cooled to room temperature. EtOAc (1 L) and a 1M aqueous solution of ammonium chloride (0.5 L) were added and the mixture was stirred for 30 min. Water (0.5 L) was added to the reaction mixture and the organic layer was separated, was washed with water and brine, dried over Na$_2$SO$_4$, filtered and concentrated.

Purification: The residue was taken up in cyclohexane (ca 200 mL) and loaded onto a 600 g column of silica gel 60 pre-conditionned with cyclohexane. The product was eluted with a gradient of EtOAc in cyclohexane (0%-50%). The appropriate fractions were combined and concentrated to give the title compound as a dark-coloured oil (22.85 g, 52%). The mixed fractions were combined and concentrated to give a residue which was subjected to automated flash chromatography (Si—PPC, EtOAc:cyclohexane, gradient 5:95 to 50:50). The appropriate fractions were combined to give 3-(3, 6-Dihydro-2H-pyran-4-yl)azetidine-1-carboxylic acid tert-butyl ester as a dark-coloured oil (7.8 g, 18%). $^1$H NMR (400 MHz, CHCl-d): δ 5.56-5.53 (m, 1H); 4.17-4.13 (m, 2H); 4.02 (t, J=8.6 Hz, 2H); 3.85-3.78 (m, 4H); 3.20-3.09 (m, 1H); 2.11-2.06 (m, 2H); 1.44 (s, 9H).

Step 3: A mixture of 3-(3,6-dihydro-2H-pyran-4-yl)azetidine-1-carboxylic acid tert-butyl ester (28.6 g, 0.12 mol) and 10% palladium on charcoal (5.0 g) in IMS (500 mL) was stirred under hydrogen (4 bar) at room temperature for 36 hours. The reaction mixture was filtered through a bed of Celite® which was washed with IMS. The filtrates were combined and concentrated to give a residue which was reacted as above for 18 hours. The reaction mixture was worked up as above to give a residue which was dried under reduced pressure to give 3-(Tetrahydropyran-4-yl)azetidine-1-carboxylic acid tert-butyl ester as a beige solid (26.7 g, 92%). $^1$H NMR (300 MHz, CHCl-d): δ 4.03-3.90 (m, 4H);

3.63 (dd, J=8.6, 5.7 Hz, 2H); 3.37 (td, J=11.8, 2.0 Hz, 2H); 2.32-2.19 (m, 1H); 1.63-1.48 (m, 3H); 1.44 (s, 9H); 1.29-1.12 (m, 2H).

Example 2

(4-Methylpiperidin-4-yl)pyrrolidin-1-ylmethanone

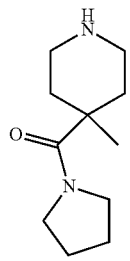

Step 1: 4-Methyl-4-(pyrrolidine-1-carbonyl)piperidine-1-carboxylic acid tert-butyl ester

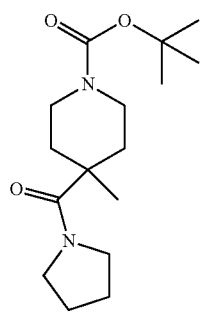

To a solution of 4-methylpiperidine-1,4-dicarboxylic acid mono-tert-butyl ester (229 mg, 0.94 mmol) in DMF (10 mL) were added DIPEA (0.493 mL, 2.83 mmol), pyrrolidine (0.118 mL, 1.41 mmol) and HATU (537 mg, 1.41 mmol). The reaction mixture was stirred at room temperature for 18 hours and then partitioned between water and EtOAc. The organic layer was separated and washed with a 0.1N aqueous HCl solution and brine, dried over $Na_2SO_4$, filtered and concentrated to give 4-Methyl-4-(pyrrolidine-1-carbonyl)piperidine-1-carboxylic acid tert-butyl ester as a white solid (279 mg, 100%). LCMS (Method H): $R_T$ 4.00 min; [M+Na]$^+$ 319

Step 2: A solution of 4-methyl-4-(pyrrolidine-1-carbonyl)piperidine-1-carboxylic acid tert-butyl ester (296 mg, 1.0 mmol) in TFA (5 mL), DCM (5 mL) and water (0.1 mL) was stirred at room temperature for 2 hours and then concentrated under reduced pressure. The residue was taken up in MeOH and and loaded onto an Isolute® SCX-2 cartridge (10 g). The cartridge was washed with MeOH and the desired product was eluted with 2M $NH_3$ in MeOH. The solvents were removed to give the desired product as a white solid (196 mg, 66%). LCMS (Method A): $R_T$ 0.31 min; [M+H]$^+$ 197

Example 3

(3-Methylpyrrolidin-3-yl)pyrrolidin-1-ylmethanone

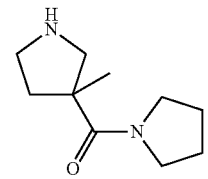

Step 1: 3-Methylpyrrolidine-1,3-dicarboxylic acid 1-tert-butyl ester

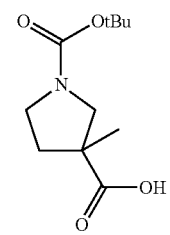

To a solution of 3-methylpyrrolidine-1,3-dicarboxylic acid 1-tert-butyl ester 3-methyl ester (370 mg, 1.52 mmol) in IMS (5 mL) was added a 1M aqueous solution of sodium hydroxide (2.0 mL, 2.0 mmol). The reaction mixture was stirred at room temperature for 2 hours, and then concentrated under reduced pressure. The residue was partitioned between EtOAc and a 0.1M aqueous solution of HCl. The organic layer was separated and washed with brine, dried over $Na_2SO_4$, filtered and concentrated to give the desired product as a white solid (348 mg, 100%). $^1$H NMR (400 MHz, CHCl$_3$-d): δ 3.85-3.75 (m, 1H); 3.52-3.41 (m, 2H); 3.27-3.15 (m, 1H); 2.39-2.30 (m, 1H); 1.83-1.74 (m, 1H); 1.51-1.40 (m, 9H); 1.38 (s, 3H).

Step 2: 3-Methyl-3-(pyrrolidine-1-carbonyl)pyrrolidine-1-carboxylic acid tert-butyl ester

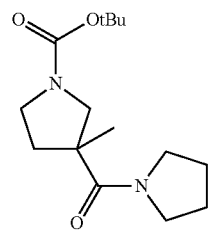

To a solution of 3-methylpyrrolidine-1,3-dicarboxylic acid 1-tert-butyl ester (348 mg, 1.52 mmol) in DMF (10 mL) were added DIPEA (0.53 mL, 3.04 mmol), pyrrolidine (0.25 mL, 3.04 mmol) and HATU (693 mg, 1.82 mmol). The reaction mixture was stirred at room temperature for 18 hours and then partitioned between water and EtOAc. The organic layer was separated and washed with a 0.1N aqueous HCl solution and brine, dried over $Na_2SO_4$, filtered and concentrated to give the desired product as a white solid (334 mg, 78%). $^1$H NMR (400 MHz, $CHCl_3$-d): δ 3.61-3.38 (m, 8H); 2.00-1.79 (m, 6H); 1.47-1.44 (m, 9H); 1.33 (s, 3H).

Step 3: A solution of 3-methyl-3-(pyrrolidine-1-carbonyl)pyrrolidine-1-carboxylic acid tert-butyl ester (330 mg, 1.17 mmol) in TFA (5 mL), DCM (5 mL) and water (0.1 mL) was stirred at room temperature for 2 hours and then concentrated under reduced pressure. The residue was taken up in MeOH and and loaded onto an Isolute® SCX-2 cartridge (10 g). The cartridge was washed with MeOH and the desired product was eluted with 2M $NH_3$ in MeOH. The solvents were removed to give (3-Methylpyrrolidin-3-yl)pyrrolidin-1-yl-methanone as a white solid (169 mg, 79%). $^1$H NMR (400 MHz, $CHCl_3$-d): δ 3.55-3.40 (m, 5H); 3.06-2.92 (m, 2H); 2.32-2.20 (m, 2H); 2.01-1.82 (m, 5H); 1.71 (m, 1H); 1.33 (s, 3H).

Example 4

1-(2-(Methanesulfonyl)ethyl)-2,2-dimethylpiperazine

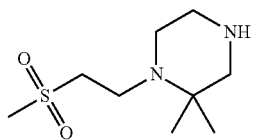

Step 1: 4-(2-(Methanesulfonyl)ethyl)-3,3-dimethylpiperazine-1-carboxylic acid tert-butyl ester

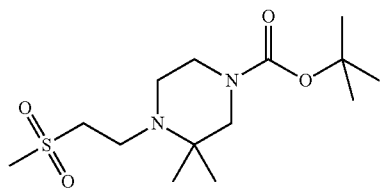

Step 2: A mixture of 3,3-dimethylpiperazine-1-carboxylic acid tert-butyl ester (500 mg, 2.33 mmol) and methyl vinyl sulfone (510 µL, 619 mg, 5.83 mmol) in MeOH (15 mL) was heated to 65° C. for 5.5 h then stirred at room temperature for 96 h. The reaction mixture was concentrated in vacuo. The resulting residue was purified by column chromatography (Si—PCC, MeOH:DCM, 0-3%) affording 1-(2-(Methanesulfonyl)ethyl)-2,2-dimethylpiperazine as a white waxy solid (550 mg, 74%). $^1$H NMR ($CDCl_3$, 300 MHz): δ 3.47-3.40 (m, 2H); 3.15 (s, 2H); 3.09 (t, J=6.4 Hz, 2H); 3.03 (s, 3H); 2.89 (t, J=6.4 Hz, 2H); 2.58-2.50 (m, 2H); 1.45 (s, 9H); 1.04 (s, 6H).

Step 3: A mixture of 4-(2-methanesulfonylethyl)-3,3-dimethylpiperazine-1-carboxylic acid tert-butyl ester (510 mg, 1.59 mmol) and TFA (5 mL) in DCM (10 mL) was stirred at room temperature for 2 h. The reaction mixture was loaded onto an Isolute® SCX-2 cartridge which was washed with MeOH/DCM and the product eluted with 2M $NH_3$/MeOH affording 1-(2-(Methanesulfonyl)ethyl)-2,2-dimethylpiperazine as a white solid (320 mg, 91%). $^1$H NMR ($CDCl_3$, 300 MHz): δ 3.49 (s, 1H); 3.12-3.03 (m, 5H); 2.92-2.84 (m, 4H); 2.60 (s, 2H); 2.53-2.47 (m, 2H); 1.06 (s, 6H).

Example 5

4-Azetidin-3-yl-2,2-dimethylmorpholine

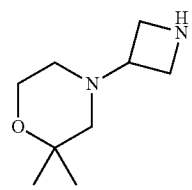

Step 1: 3-(2,2-Dimethylmorpholin-4-yl)azetidine-1-carboxylic acid tert-butyl ester

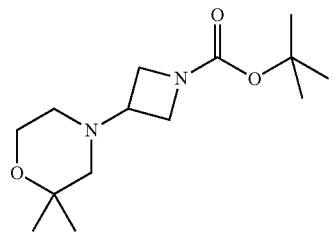

A mixture of 2,2-dimethylmorpholine (260 mg, 2.26 mmol) and 3-oxoazetidine-1-carboxylic acid tert-butyl ester (464 mg, 2.71 mmol) in DCE (15 mL) was stirred at room temperature for 2 h before the addition of sodium triacetoxyborohydride (957 mg, 4.52 mmol). The resulting mixture was stirred for 16 h, then diluted with DCM and washed with $H_2O$. The organic phase was dried (phase separator) and concentrated in vacuo. The resulting residue was purified by column chromatography (Si—PCC, EtOAc:cyclohexane, 0-40%) affording the title compound as an oil (492 mg, 81%). $^1$H NMR ($CDCl_3$, 300 MHz): δ 3.95-3.85 (m, 2H); 3.80-3.71 (m, 4H); 3.07-2.88 (m, 1H); 2.32-2.22 (m, 2H); 2.14-2.06 (m, 2H); 1.44 (s, 9H); 1.25 (s, 6H).

Step 2: A mixture of 3-(2,2-dimethylmorpholin-4-yl)azetidine-1-carboxylic acid tert-butyl ester (492 mg, 1.82 mmol) and TFA (5 mL) in DCM (10 mL) was stirred at room temperature for 2 h. The reaction mixture was loaded onto an Isolute® SCX-2 cartridge, washed with MeOH/DCM and eluted with 2M $NH_3$/MeOH affording 4-Azetidin-3-yl-2,2-dimethylmorpholine as a white solid (302 mg, 97%). $^1$H NMR ($CDCl_3$, 300 MHz): δ 3.73 (t, J=4.8 Hz, 2H); 3.64-3.51 (m, 4H); 3.18-3.11 (m, 1H); 2.23 (t, J=4.8 Hz, 2H); 2.23-2.07 (m, 1H); 2.06 (s, 2H); 1.25 (s, 6H).

Example 6

4-Azetidin-3-yl-thiomorpholine 1,1-dioxide

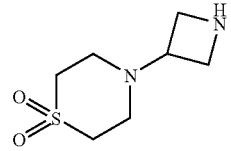

Step 1: 3-(1,1-Dioxo-1-thiomorpholin-4-yl)azetidine-1-carboxylic acid tert-butyl ester

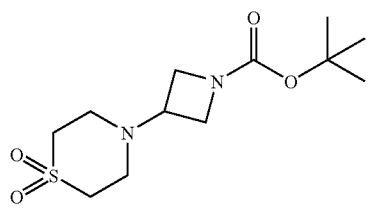

To a refluxing solution of 3-aminoazetidine-1-carboxylic acid tert-butyl ester (10.0 g, 58.1 mmol) in EtOH (50 mL) was added drop wise a solution of divinyl sulfone (5.9 mL, 6.86 g, 58.1 mmol) in EtOH (50 mL) The resulting mixture was stirred at reflux for 15.5 h, cooled to room temperature and concentrated in vacuo. The resulting beige solid was triturated with $Et_2O$, affording the title compound as a white solid (10.8 g, 64%). $^1$H NMR ($CDCl_3$, 300 MHz): δ 3.97 (dd, J=8.8, 7.1 Hz, 2H); 3.76 (dd, J=8.8, 7.1 Hz, 2H); 3.36-3.26 (m, 1H); 3.13-3.05 (m, 4H); 2.90-2.83 (m, 4H); 1.44 (s, 9H).

Step 2: A mixture of 3-(1,1-dioxo-1-thiomorpholin-4-yl)-azetidine-1-carboxylic acid tert-butyl ester (3.35 g, 11.5 mmol) and TFA (15 mL) in DCM (30 mL) was stirred at room temperature for 2 h. The reaction mixture was loaded onto an Isolute® SCX-2 cartridge which was washed with MeOH/DCM and the product eluted with 2M $NH_3$/MeOH affording 4-Azetidin-3-yl-thiomorpholine 1,1-dioxide as a white solid (2.0 g, 91%). $^1$H NMR ($CDCl_3$, 300 MHz): δ 3.64-3.53 (m, 4H); 3.49-3.39 (m, 1H); 3.08 (m, 4H); 2.86-2.79 (m, 4H); 1.83 (s, 1H).

Example 7

Methyl(piperidin-4-yl)(tetrahydro-furan-3-yl)amine

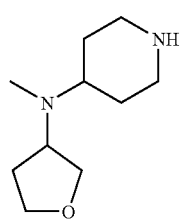

Step 1: 4-[Methyl(tetrahydrofuran-3-yl)amino]piperidine-1-carboxylic acid tert-butyl ester

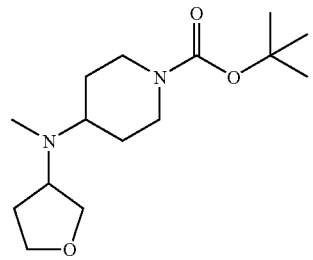

A mixture of 4-(methylamino)piperidine-1-carboxylic acid tert-butyl ester (200 mg, 0.93 mmol), dihydrofuran-3-one (145 μl, 161 mg, 1.87 mmol), 4 Å powdered molecular sieves (550 mg) and DIPEA (323 μl, 241 mg, 1.87 mmol) in DCM (10 mL) was stirred at room temperature for 30 min before the addition of sodium triacetoxyborohydride (396 mg, 1.87 mmol). The reaction mixture was stirred at room temperature for 16 h then diluted with DCM and washed with $H_2O$. The organic phase was dried ($Na_2SO_4$) and concentrated in vacuo. The resulting residue was purified by column chromatography (Si—PCC, MeOH:DCM, 0-10%) affording the title compound as an oil (132 mg, 50%). $^1$H NMR ($CDCl_3$, 300 MHz): δ 4.33-4.05 (m, 2H); 4.01-3.91 (m, 1H); 3.90-3.73 (m, 2H); 3.68-3.48 (m, 1H); 3.47-3.23 (m, 1H); 2.72-2.56 (m, 2H); 2.21 (s, 3H); 2.11-1.94 (m, 1H); 1.93-1.78 (m, 1H); 1.76-1.63 (m, 2H); 1.76-1.63 (m, 1H); 1.54-1.46 (m, 2H); 1.46 (s, 9H).

Step 2: A mixture of 4-[methyl(tetrahydrofuran-3-yl)amino]piperidine-1-carboxylic acid tert-butyl ester (132 mg, 0.46 mmol) and TFA (2 mL) in DCM (5 mL) was stirred at room temperature for 2 h. The reaction mixture was loaded onto an Isolute® SCX-2 cartridge which was washed with MeOH/DCM and the product eluted with 2M $NH_3$/MeOH affording Methyl(piperidin-4-yl)(tetrahydro-furan-3-yl)amine as a white solid (84 mg, quant.). $^1$H NMR ($CDCl_3$, 300 MHz): δ 3.98-3.91 (m, 1H); 3.88-3.83 (m, 1H); 3.80-3.73 (m, 1H); 3.61-3.53 (m, 1H); 3.42-3.35 (m, 1H); 3.26-3.14 (m, 2H); 2.71-2.53 (m, 2H); 2.57-2.46 (m, 1H); 2.23 (s, 3H); 2.05-1.97 (m, 1H); 1.93-1.77 (m, 1H); 1.78-1.72 (m, 2H); 1.64-1.49 (m, 2H).

Example 8

Methylpiperidin-4-yl(tetrahydropyran-4-yl)amine

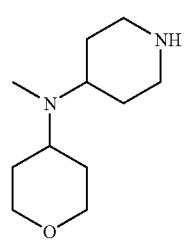

Step 1: 4-[Methyl(tetrahydropyran-4-yl)amino]piperidine-1-carboxylic acid tert-butyl ester

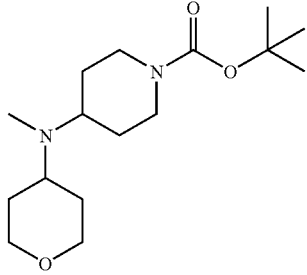

A mixture of 4-methylaminopiperidine-1-carboxylic acid tert-butyl ester (200 mg, 0.93 mmol), tetrahydropyran-3-one (187 mg, 1.87 mmol), 4 Å powdered molecular sieves (550 mg) and DIPEA (323 µl, 241 mg, 1.87 mmol) in DCM (10 mL) was stirred at room temperature for 30 min before the addition of sodium triacetoxyborohydride (396 mg, 1.87 mmol). The reaction mixture was stirred at room temperature for 16 h then diluted with DCM and washed with H$_2$O. The organic phase was dried (Na$_2$SO$_4$) and concentrated in vacuo. The resulting residue was purified by column chromatography (Si—PCC, MeOH:DCM, 0-10%) affording 4-[Methyl(tetrahydropyran-4-yl)amino]piperidine-1-carboxylic acid tert-butyl ester as an oil (101 mg, 36%). $^1$H NMR (CDCl$_3$, 300 MHz): δ 4.24-4.07 (m, 2H); 4.06-3.96 (m, 2H); 3.43-3.32 (m, 2H); 2.78-2.63 (m, 4H); 2.25 (s, 3H); 1.77-1.60 (m, 8H); 1.46 (s, 9H).

Step 2: A mixture of 4-[methyl(tetrahydropyran-4-yl)-amino]-piperidine-1-carboxylic acid tert-butyl ester (101 mg, 0.34 mmol) and TFA (2 mL) in DCM (5 mL) was stirred at room temperature for 2 h. The reaction mixture was loaded onto an Isolute® SCX-2 cartridge which was washed with MeOH/DCM and the product eluted with 2M NH$_3$/MeOH affording Methylpiperidin-4-yl(tetrahydropyran-4-yl)amine as a white solid (66 mg, 97%). $^1$H NMR (CDCl$_3$, 300 MHz): δ 4.05-3.97 (m, 2H); 3.38 (td, J=10.9, 3.8 Hz, 2H); 3.19 (d, J=12.1 Hz, 2H); 2.84-2.57 (m, 5H); 2.27 (s, 3H); 1.80-1.49 (m, 8H).

Step 1: 4-(Methyl(oxetan-3-yl)amino)piperidine-1-carboxylic acid tert-butyl ester

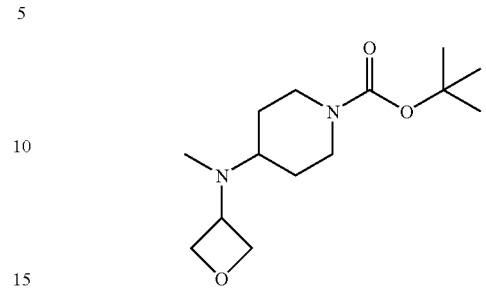

A mixture of 4-(methylamino)piperidine-1-carboxylic acid tert-butyl ester (200 mg, 0.93 mmol) and oxetan-3-one (56 mg, 0.78 mmol) in DCE (6 mL) was stirred at room temperature for 2 h before the addition of sodium triacetoxyborohydride (264 mg, 1.24 mmol). The resulting mixture was stirred for 16 h, then loaded onto an Isolute® SCX-2 cartridge which was washed with MeOH/DCM and the product eluted with 2M NH$_3$/MeOH. The resulting oil was purified by column chromatography (Si—PCC, MeOH/DCM, 0-20%) affording 4-(Methyl(oxetan-3-yl)amino)piperidine-1-carboxylic acid tert-butyl ester as an oil (40 mg, 16%). $^1$H NMR (CDCl$_3$, 300 MHz): δ 4.66 (t, J=6.6 Hz, 2H); 4.61 (t, J=6.6 Hz, 2H); 4.16 (s, 2H); 3.95 (p, J=6.6 Hz, 1H); 2.63 (t, J=12.5 Hz, 2H); 2.39 (tt, J=11.7, 3.7 Hz, 1H); 2.20 (s, 3H); 1.60 (d, J=12.5 Hz, 2H); 1.46 (s, 9H); 1.44-1.28 (m, 2H).

Step 2: A mixture of 4-(methyl(oxetan-3-yl)amino)piperidine-1-carboxylic acid tert-butyl ester (150 mg, 0.55 mmol) and TFA (4 mL) in DCM (10 mL) was stirred at room temperature for 2 h. The reaction mixture was loaded onto an Isolute® SCX-2 cartridge which was washed with MeOH/DCM and the product eluted with 2M NH$_3$/MeOH affording Methyl(oxetan-3-yl)piperidin-4-ylamine as a white solid (94 mg, quant.). $^1$H NMR (CDCl$_3$, 300 MHz): δ 4.67 (t, J=6.7 Hz, 2H); 4.61 (t, J=6.7 Hz, 2H); 3.97 (p, J=6.7 Hz, 1H); 3.14 (d, J=12.3 Hz, 2H); 2.56 (td, J=12.2, 4.0 Hz, 2H); 2.48-2.26 (m, 2H); 2.22 (s, 3H); 1.63 (d, J=12.3 Hz, 2H); 1.40 (qd, J=12.2, 4.0 Hz, 2H).

Example 9

Methyl(oxetan-3-yl)piperidin-4-ylamine

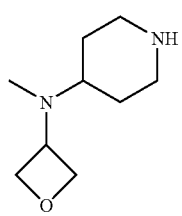

Example 10

4-Azetidin-3-ylpiperazin-2-one

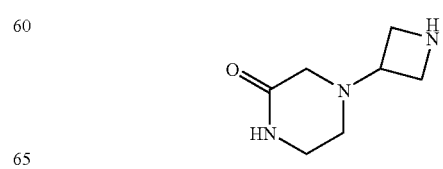

Step 1:
3-(3-Oxopiperazin-1-yl)azetidine-1-carboxylic acid tert-butyl ester

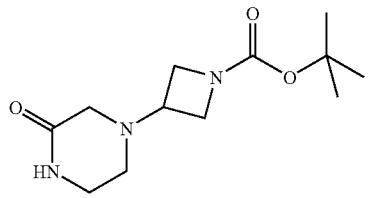

A mixture of piperazin-2-one (1.52 g, 15.1 mmol), 3-oxoazetidine-1-carboxylic acid tert-butyl ester (2.0 g, 11.6 mmol) and trimethyl orthoformate (12.8 mL, 12.4 g, 117 mmol) in AcOH (0.7 mL) and DCE (50 mL) was stirred for 5 h before the addition of triacetoxyborohydride (4.9 g, 23.2 mmol). The resulting mixture was stirred for 16 h then partitioned between DCM and H$_2$O. The organic layer was dried (Na$_2$SO$_4$) and concentrated in vacuo. The resulting oil was purified by column chromatography (Si—PCC, MeOH:DCM, 0-10%) affording the title compound as a foam (827 mg, 28%). $^1$H NMR (CDCl$_3$, 300 MHz): δ 6.24 (s, 1H); 3.97 (dd, J=8.9, 7.1 Hz, 2H); 3.82 (dd, J=5.2, 2.2 Hz, 2H); 3.40 (td, J=5.2, 2.2 Hz, 2H); 3.24-3.15 (m, 1H); 3.07 (s, 2H); 2.60 (t, J=5.4 Hz, 2H); 1.44 (s, 9H).

Step 2: A mixture of 3-(3-oxopiperazin-1-yl)azetidine-1-carboxylic acid tert-butyl ester (400 mg, 1.57 mmol) and TFA (3 mL) in DCM (6 mL) was stirred at room temperature for 2 h. The reaction mixture was loaded onto an Isolute® SCX-2 cartridge which was washed with MeOH/DCM and the product eluted with 2M NH$_3$/MeOH affording 4-Azetidin-3-ylpiperazin-2-one as a white solid (227 mg, 93%). $^1$H NMR (CDCl$_3$, 300 MHz): δ 6.08 (s, 1H); 3.63-3.56 (m, 3H); 3.42-3.35 (m, 3H); 3.31 (t, J=6.74 Hz, 1H); 3.03 (s, 2H); 2.59-2.51 (m, 2H).

Example 11

(S)-1-Azetidin-3-ylpyrrolidin-3-ol

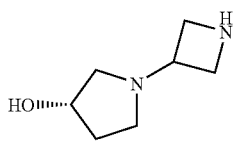

Step 1: 3-((S)-3-Hydroxypyrrolidin-1-yl)azetidine-1-carboxylic acid tert-butyl ester

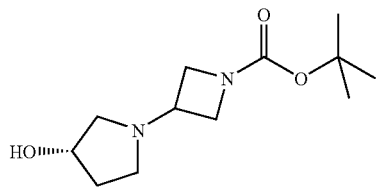

A mixture of (S)-pyrrolidin-3-ol (261 mg, 3.0 mmol), 3-oxoazetidine-1-carboxylic acid tert-butyl ester (513 mg, 3.0 mmol) and 4 Å powdered molecular sieves (1.0 g) in DCE (10 mL) was stirred at room temperature for 6 h before the addition of sodium triacetoxyborohydride (1.27 g, 6.0 mmol). The reaction mixture was filtered through celite, washing with DCM. The filtrate was concentrated in vacuo and the resulting residue was purified by column chromatography (Si—PCC, Acetone:DCM, 0-40%) affording 3-((S)-3-Hydroxypyrrolidin-1-yl)azetidine-1-carboxylic acid tert-butyl ester as a brown oil (390 mg, 54%). LCMS (Method A): R$_T$ 0.28 min [M+H]$^+$ 243.0

Step 2: A mixture of 3-((S)-3-hydroxypyrrolidin-1-yl)azetidine-1-carboxylic acid tert-butyl ester (390 mg, 1.61 mmol) and TFA (2 mL) in DCM (4 mL) was stirred at room temperature for 2 h. The reaction mixture was loaded onto an Isolute® SCX-2 cartridge which was washed with MeOH/DCM and the product eluted with 2M NH$_3$/MeOH affording the title compound as a white solid (244 mg, quant.). $^1$H NMR (CDCl$_3$, 300 MHz): δ 4.40-4.33 (m, 1H); 3.70-3.60 (m, 4H); 3.44-3.34 (m, 1H); 2.88-2.77 (m, 1H); 2.73-2.52 (m, 3H); 2.47 (dd, J=10.1, 5.2 Hz, 1H); 2.30-2.12 (m, 2H); 1.84-1.69 (m, 1H).

Example 12

(R)-1-Azetidin-3-ylpyrrolidin-3-ol

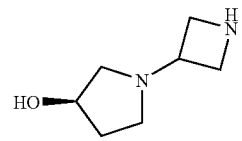

Step 1: 3-((R)-3-Hydroxypyrrolidin-1-yl)azetidine-1-carboxylic acid tert-butyl ester

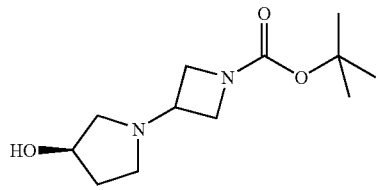

A mixture of I-pyrrolidin-3-ol (261 mg, 3.0 mmol), 3-oxoazetidine-1-carboxylic acid tert-butyl ester (513 mg, 3.0 mmol) and 4 Å powdered molecular sieves (1.0 g) in DCE (10 mL) was stirred at room temperature for 6 h before the addition of sodium triacetoxyborohydride (1.27 g, 6.0 mmol). The reaction mixture was filtered through celite, washing with DCM. The filtrate was concentrated in vacuo and the resulting residue was purified by column chromatography (Si—PCC, Acetone:DCM, 0-40%) affording 3-((R)-3-Hydroxypyrrolidin-1-yl)azetidine-1-carboxylic acid tert-butyl ester as a brown oil (479 mg, 66%). LCMS (Method A): R$_T$ 0.28 min [M+H]$^+$ 243.0

Step 2: A mixture of 3-(I-3-Hydroxypyrrolidin-1-yl)azetidine-1-carboxylic acid tert-butyl ester (479 mg, 1.98 mmol) and TFA (3 mL) in DCM (6 mL) was stirred at room temperature for 2 h. The reaction mixture was loaded onto an Isolute® SCX-2 cartridge, washed with MeOH/DCM and eluted with 2M NH$_3$/MeOH affording the title compound as a white solid (260 mg, 92%). $^1$H NMR (CDCl$_3$, 300 MHz): δ 4.41-4.33 (m, 1H); 3.69-3.58 (m, 4H); 3.45-3.32 (m, 1H); 2.88-2.79 (m, 1H); 2.65 (d, J=10.1 Hz, 1H); 2.55-2.41 (m, 3H); 2.30-2.12 (m, 2H); 1.83-1.70 (m, 1H).

Example 13

1-Methylpiperazin-2-one

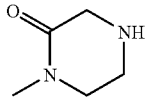

Step 1: 4-Methyl-3-oxopiperazine-1-carboxylic acid tert-butyl ester

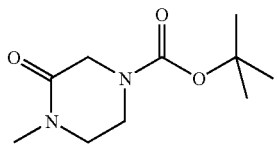

To a solution of 3-oxopiperazine-1-carboxylic acid tert-butyl ester (500 mg, 2.50 mmol) in DMF (20 mL) cooled on an ice-bath was added sodium hydride (120 mg, 3.00 mmol, 60% dispersion in mineral oil) and the resulting mixture stirred for 10 min. Methyl iodide (233 µL, 532 mg, 3.75 mmol) was added and the resulting mixture stirred at room temperature for 18 h. The reaction mixture was quenched with H$_2$O and extracted with EtOAc. The combined organics were dried (Na$_2$SO$_4$) and concentrated in vacuo affording 4-Methyl-3-oxopiperazine-1-carboxylic acid tert-butyl ester as a yellow oil (300 mg, 56%). $^1$H NMR (CDCl$_3$, 300 MHz): δ 4.08 (s, 2H); 3.65 (t, J=5.4 Hz, 2H); 3.35 (t, J=5.4 Hz, 2H); 3.00 (s, 3H); 1.47 (s, 9H).

Step 2: A mixture of 4-methyl-3-oxopiperazine-1-carboxylic acid tert-butyl ester (300 mg, 1.40 mmol) and TFA (1 mL) in DCM (2 mL) was stirred at room temperature for 2 h. The reaction mixture was loaded onto an Isolute® SCX-2 cartridge, washed with MeOH/DCM and eluted with 2M NH$_3$/MeOH affording 1-Methylpiperazin-2-one as a white solid (128 mg, 80%). $^1$H NMR (CDCl$_3$, 300 MHz): δ 3.52 (s, 2H); 3.32 (t, J=5.5 Hz, 2H); 3.09 (t, J=5.5 Hz, 2H); 2.97 (s, 3H); 1.83 (s, 1H).

Example 14

4-Azetidin-3-yl-1-methylpiperazin-2-one

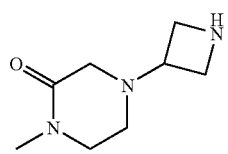

Step 1: 3-(4-Methyl-3-oxopiperazin-1-yl)azetidine-1-carboxylic acid tert-butyl ester

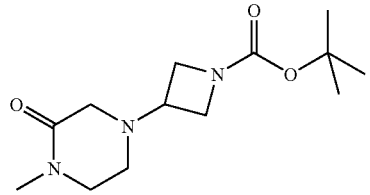

A mixture of 1-methylpiperazin-2-one (128 mg, 1.12 mmol), 3-oxoazetidine-1-carboxylic acid tert-butyl ester (231 mg, 1.35 mmol) and 4 Å powdered molecular sieves (150 mg) in DCE (4 mL) was stirred at room temperature for 1.5 h before the addition of sodium triacetoxyborohydride (475 mg, 2.24 mmol). The reaction mixture was filtered through celite, washing with DCM. The filtrate was concentrated in vacuo and the resulting residue was purified by column chromatography (Si—PCC, MeOH:EtOAc, 0-10%) affording 3-(4-Methyl-3-oxopiperazin-1-yl)azetidine-1-carboxylic acid tert-butyl ester as an oil (211 mg, 70%). $^1$H NMR (CDCl$_3$, 300 MHz): δ 3.99-3.92 (m, 2H); 3.81 (dd, J=8.8, 5.1 Hz, 2H); 3.36 (t, J=5.5 Hz, 2H); 3.20-3.14 (m, 1H); 3.08 (t, J=5.5 Hz, 2H); 2.97 (s, 3H); 2.70-2.56 (m, 2H); 1.44 (s, 9H).

Step 2: A mixture of 3-(4-methyl-3-oxopiperazin-1-yl)azetidine-1-carboxylic acid tert-butyl ester (211 mg, 0.78 mmol) and TFA (2 mL) in DCM (4 mL) was stirred at room temperature for 2 h. The reaction mixture was loaded onto an Isolute® SCX-2 cartridge which was washed with MeOH/DCM and the product eluted with 2M NH$_3$/MeOH affording 4-Azetidin-3-yl-1-methylpiperazin-2-one as a white solid (125 mg, 95%). $^1$H NMR (CDCl$_3$, 300 MHz): δ 3.63 (m, 4H); 3.37-3.27 (m, 3H); 3.03 (s, 2H); 2.96 (s, 3H); 2.58 (t, J=5.6 Hz, 2H); 2.13-1.97 (m, 1H).

Example 15

2-Azetidin-3-ylpropan-2-ol

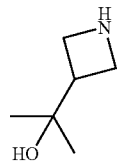

Step 1:
3-(1-Hydroxy-1-methylethyl)azetidine-1-carboxylic acid tert-butyl ester

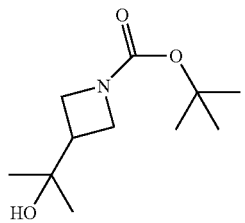

A 50 mL round-bottomed flask was charged with a solution of azetidine-1,3-dicarboxylic acid 1-tert-butyl ester 3-methyl ester (1 g, 4.65 mmol) in anhydrous THF (10 mL) at 4° C., under argon. A 3.0 M solution of methylmagnesium bromide in Et$_2$O (3.72 mL, 11.15 mmol) was added dropwise over 5 min and the reaction mixture was stirred for 5 h at room temperature. The reaction was quenched with a saturated aqueous solution of NH$_4$Cl (5 mL) and water (10 mL) The aqueous phase was extracted with EtOAc (20 mL). The organic layer was dried over sodium sulphate and concentrated in vacuo to give 3-(1-Hydroxy-1-methylethyl)azetidine-1-carboxylic acid tert-butyl ester as a colourless oil (0.8 g, 80%). $^1$H NMR (CDCl$_3$, 400 MHz) δ 3.95-3.75 (m, 4H); 2.60-2.50 (m, 1H); 1.43 (s, 9H); 1.17 (s, 6H).

Step 2: A 25 mL round-bottomed flask was charged with a solution of 3-(1-hydroxy-1-methylethyl)azetidine-1-carboxylic acid tert-butyl ester (0.8 g, 3.72 mmol) in DCM/TFA (3 mL/3 mL). The reaction mixture was stirred for 1 h at room temperature. The reaction mixture was loaded onto an Isolute® SCX-2 cartridge. The cartridge was washed with MeOH and the desired product was eluted using 2 M NH$_3$ in MeOH to give 2-Azetidin-3-ylpropan-2-ol as a white solid (0.36 g, 84%). $^1$H NMR (CDCl$_3$, 400 MHz) δ 3.55-3.62 (m, 4H); 2.75-2.65 (m, 1H); 1.15 (s, 6H).

Step 1: 3-Fluoro-[1,3']biazetidinyl-1'-carboxylic acid tert-butyl ester

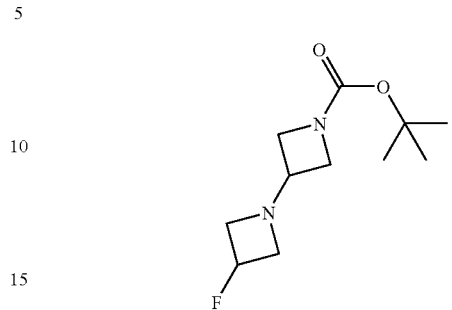

A 10 mL round-bottomed flask was charged with a solution of 3-oxoazetidine-1-carboxylic acid tert-butyl ester (0.14 g, 0.82 mmol), 3-fluoroazetidine hydrochloride (0.1 g, 0.9 mmol) in DCE (3 mL), trimethoxymethane (0.88 mL, 8.5 mmol) and acetic acid (0.046 mL, 0.81 mmol). The reaction mixture was stirred for 3 h at room temperature. Sodium triacetoxyborohydride (0.26 g, 1.22 mmol) was added and the reaction mixture was stirred for 18 h at room temperature. The reaction mixture was partitioned between DCM and water; the organic phase was washed with brine, dried over sodium sulphate and concentrated. The residue was purified by flash chromatography (Si—PPC, EtOAc:cyclohexane, gradient 40:60 to 100:0) to give 3-Fluoro-[1,31biazetidinyl-1'-carboxylic acid tert-butyl ester as a colourless oil (0.109 g, 59%). $^1$H NMR (CDCl$_3$, 400 MHz) δ 5.15 (dt, J=57.1, 5.3 Hz, 1H); 3.93 (dd, J=9.1, 7.0 Hz, 2H); 3.74-3.59 (m, 4H); 3.45-3.38 (m, 1H); 3.31-3.25 (m, 1H); 3.23-3.17 (m, 1H); 1.43 (s, 9H).

Step 2: A 25 mL round-bottomed flask was charged with a solution of 3-fluoro-[1,3']biazetidinyl-1'-carboxylic acid tert-butyl ester (0.109 g, 0.47 mmol) in DCM/TFA (2 mL/2 mL). The reaction mixture was stirred for 90 min at room temperature. The reaction mixture was loaded onto an Isolute® SCX-2 cartridge. The cartridge was washed with MeOH and the desired product was eluted using 2 M NH$_3$ in MeOH to give 3-Fluoro-[1,3']biazetidinyl as a colourless oil (0.058 g, 94%). $^1$H NMR (CDCl$_3$, 400 MHz) δ 5.14 (dp, J=57.2, 5.3 Hz, 1H); 3.75-3.46 (m, 8H); 3.34-3.24 (m, 1H); 3.27-3.10 (m, 1H).

Example 16

3-Fluoro-[1,3']biazetidinyl

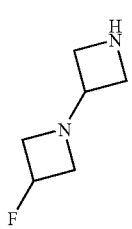

Example 17

1-Azetidin-3-ylpiperidin-4-ol

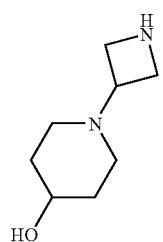

Step 1: 3-(4-Hydroxypiperidin-1-yl)azetidine-1-carboxylic acid tert-butyl ester

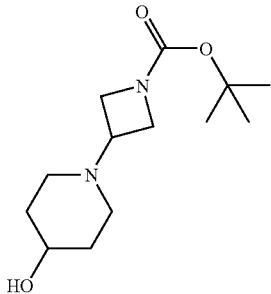

A 10 mL round-bottomed flask was charged with a solution of 3-oxoazetidine-1-carboxylic acid tert-butyl ester (1 g, 5.84 mmol), 4-hydroxypiperidine (0.65 g, 6.42 mmol) and 4 Å molecular sieves (10 g) in DCE (50 mL) The reaction mixture was stirred for 4 h at room temperature. Sodium triacetoxyborohydride (2.48 g, 11.68 mmol) was added and the reaction mixture was stirred for 18 h at room temperature. The suspension was filtered through Celite and the filtrate was concentrated in vacuo. The residue was purified by flash chromatography (Si—PPC, EtOAc:cyclohexane, gradient 0:100 to 100:0) to give 3-(4-Hydroxypiperidin-1-yl)azetidine-1-carboxylic acid tert-butyl ester as a colourless oil (0.34 g, 23%). $^1$H NMR (CDCl$_3$, 400 MHz) δ 3.92 (t, J=7.8 Hz, 2H); 3.87-3.72 (m, 3H);(m, 1H); 2.68-2.63 (m, 2H); 2.09-2.03 (m, 2H); 1.96-1.91 (m, 2H); 1.69-1.55 (m, 2H); 1.43 (s, 9H).

Step 2: A 25 mL round-bottomed flask was charged with a solution of 3-(4-hydroxypiperidin-1-yl)azetidine-1-carboxylic acid tert-butyl ester (0.34 g, 1.33 mmol) in DCM/TFA (4 mL/4 mL). The reaction mixture was stirred for 7 h at room temperature. The reaction mixture was loaded onto an Isolute® SCX-2 cartridge. The cartridge was washed with MeOH and the desired product was eluted using 2 M NH$_3$ in MeOH to give 1-Azetidin-3-ylpiperidin-4-ol as a colourless oil (0.194 g, 94%). $^1$H NMR (CDCl$_3$, 400 MHz) δ 3.75-3.68 (m, 1H); 3.67-3.51 (m, 4H); 3.25-3.17 (m, 1H); 2.66-2.56 (m, 3H); 2.03-1.84 (m, 5H); 1.65-1.53 (m, 2H).

Example 18

1-Azetidin-3-yl-4-fluoropiperidine

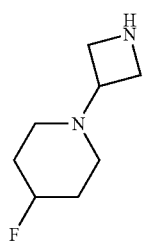

Step 1: 3-(4-Fluoropiperidin-1-yl)azetidine-1-carboxylic acid tert-butyl ester

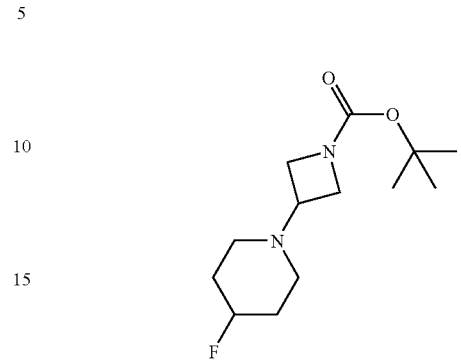

A 10 mL round-bottomed flask was charged with a solution of 3-oxoazetidine-1-carboxylic acid tert-butyl ester (1 g, 5.84 mmol), 4-fluoropiperidine hydrochloride (0.97 g, 6.42 mmol) and 4 Å molecular sieves (10 g) in DCE (50 mL). The reaction mixture was stirred for 4 h at room temperature. Sodium triacetoxyborohydride (2.48 g, 11.68 mmol) was added and the reaction mixture was stirred for 18 h at room temperature. The suspension was filtered through Celite and the filtrate was concentrated in vacuo. The residue was purified by flash chromatography (Si—PPC, EtOAc:cyclohexane, gradient 0:100 to 100:0) then (Si—PPC, MeOH: DCM, 0:100 to 5:95) to give 3-(4-Fluoropiperidin-1-yl)azetidine-1-carboxylic acid tert-butyl ester as a colourless oil (0.59 g, 39%). $^1$H NMR (CDCl$_3$, 400 MHz) δ 4.80-4.58 (m, 1H); 3.97-3.89 (m, 2H); 3.85-3.76 (m, 2H); 3.08 (t, J=6.4 Hz, 1H); 2.50-2.28 (m, 4H); 1.99-1.82 (m, 4H); 1.48-1.38 (m, 9H).

Step 2: A 25 mL round-bottomed flask was charged with a solution of 3-(4-fluoro-piperidin-1-yl)-azetidine-1-carboxylic acid tert-butyl ester (0.59 g, 2.26 mmol) in DCM/TFA (4 mL/4 mL). The reaction mixture was stirred for 6 h at room temperature. The reaction mixture was loaded onto an Isolute® SCX-2 cartridge. The cartridge was washed with MeOH and the desired product was eluted using 2 M NH$_3$ in MeOH to give 1-Azetidin-3-yl-4-fluoropiperidine as a pale yellow oil (0.263 g, 74%). $^1$H NMR (CDCl$_3$, 400 MHz) δ 4.60 (m, 1H); 3.64-3.52 (m, 4H); 3.26-3.18 (m, 1H); 2.45-2.38 (m, 2H); 2.28-2.17 (m, 2H); 1.96-1.81 (m, 4H)

Example 19

1-Azetidin-3-yl-4,4-difluoropiperidine

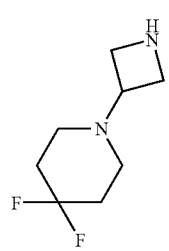

Step 1: 3-(4,4-Difluoropiperidin-1-yl)azetidine-1-carboxylic acid tert-butyl ester

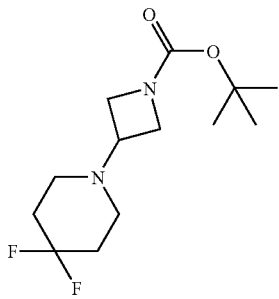

A 10 mL round-bottomed flask was charged with a solution of 3-oxoazetidine-1-carboxylic acid tert-butyl ester (0.51 g, 3 mmol), 4,4-difluoropiperidine hydrochloride (0.71 g, 4.5 mmol) and 4 Å molecular sieves (0.8 g) in DCE (8 mL). The reaction mixture was stirred for 7 h at room temperature. Sodium triacetoxyborohydride (1.27 g, 6 mmol) was added and the reaction mixture was stirred for 18 h at room temperature. The suspension was filtered through Celite and the filtrate was concentrated in vacuo. The residue was purified by flash chromatography (Si—PPC, EtOAc: cyclohexane, gradient 0:100 to 75:25) to give 3-(4,4-Difluoropiperidin-1-yl)azetidine-1-carboxylic acid tert-butyl ester as a yellow oil (0.69 g, 83%). $^1$H NMR (CDCl$_3$, 400 MHz) δ 3.94 (dd, J=8.7, 7.1 Hz, 2H); 3.78 (dd, J=8.7, 5.3 Hz, 2H); 3.17-3.10 (m, 1H); 2.45-2.41 (m, 4H); 2.10-1.94 (m, 4H); 1.43 (s, 9H).

Step 2: A 25 mL round-bottomed flask was charged with a solution of 3-(4,4-difluoropiperidin-1-yl)azetidine-1-carboxylic acid tert-butyl ester (0.684 g, 2.47 mmol) in DCM/TFA (4 mL/4 mL). The reaction mixture was stirred for 3 h at room temperature. The reaction mixture was loaded onto an Isolute® SCX-2 cartridge. The cartridge was washed with MeOH and the desired product was eluted using 2 M NH$_3$ in MeOH to give 1-Azetidin-3-yl-4,4-difluoropiperidine as a pale yellow oil (0.279 g, 64%). $^1$H NMR (CDCl$_3$, 400 MHz) δ 3.64-3.54 (m, 4H); 3.30-3.25 (m, 1H); 2.43-2.37 (m, 4H); 2.06-1.93 (m, 5H).

Step 1: 3-Hydroxy-[1,3']biazetidinyl-1'-carboxylic acid tert-butyl ester

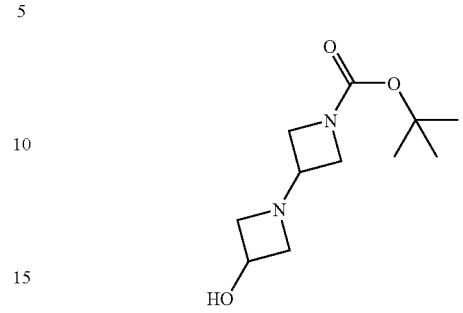

A 10 mL round-bottomed flask was charged with a solution of 3-oxoazetidine-1-carboxylic acid tert-butyl ester (0.52 g, 3.1 mmol), azetidin-3-ol hydrochloride (0.5 g, 4.6 mmol) and 4 Å molecular sieves (0.7 g) in DCE (8 mL). The reaction mixture was stirred for 7 h at room temperature. Sodium triacetoxyborohydride (1.3 g, 6.13 mmol) was added and the reaction mixture was stirred for 18 h at room temperature. The suspension was filtered through Celite and the filtrate was concentrated in vacuo. The residue was purified by flash chromatography (Si—PPC, MEOH:DCM, gradient 0:100 to 40:60) to give 3-Hydroxy-[1,3']biazetidinyl-1'-carboxylic acid tert-butyl ester as yellow oil (0.69 g, 99%). $^1$H NMR (CDCl$_3$, 400 MHz) δ 4.45-4.35 (m, 1H); 3.96 (dd, J=9.3, 6.7 Hz, 2H); 3.74 (dd, J=9.3, 4.5 Hz, 2H); 3.66 (td, J=8.8, 6.7 Hz, 2H); 3.40-3.37 (m, 1H); 3.20 (td, J=8.8, 4.5 Hz, 2H); 1.43 (s, 9H).

Step 2: A 25 mL round-bottomed flask was charged with a solution of 3-hydroxy-[1,3]biazetidinyl-1'-carboxylic acid tert-butyl ester (0.69 g, 3.05 mmol) in DCM/TFA (4 mL/4 mL). The reaction mixture was stirred for 30 min at room temperature. The reaction mixture was loaded onto an Isolute® SCX-2 cartridge. The cartridge was washed with MeOH and the desired product was eluted using 2 M NH$_3$ in MeOH to give [1,3']Biazetidinyl-3-ol as a colourless oil (0.225 g, 58%). LCMS (Method A): R$_T$=0.29 min, [M+H]$^+$ 288.9

Example 20

[1,3']Biazetidinyl-3-ol

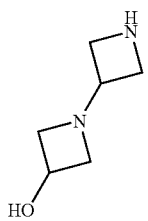

Example 21

1-Azetidin-3-yl-4-methylpiperidin-4-ol

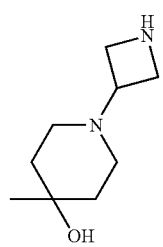

Step 1: 3-(4-Hydroxy-4-methylpiperidin-1-yl)azetidine-1-carboxylic acid tert-butyl ester

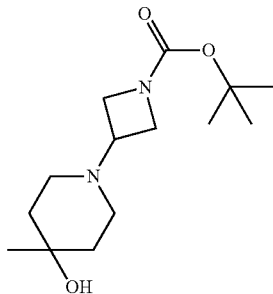

A 50 mL round-bottomed flask was charged with a solution of 3-oxoazetidine-1-carboxylic acid tert-butyl ester (0.57 g, 3.33 mmol), 4-methylpiperidin-4-ol (0.46 g, 3.99 mmol) and 4 Å molecular sieves (3.34 g) in DCE (20 mL) The reaction mixture was stirred for 6 h at room temperature. Sodium triacetoxyborohydride (1.41 g, 6.66 mmol) was added and the reaction mixture was stirred for 18 h at room temperature. The suspension was filtered through Celite and the solution was concentrated in vacuo. The residue was purified by flash chromatography (Si—PPC, EtOAc:cyclohexane, 0:100 to 100:0) to give 3-(4-Hydroxy-4-methylpiperidin-1-yl)azetidine-1-carboxylic acid tert-butyl ester as a colourless oil (0.49 g, 55%). $^1$H NMR (CDCl$_3$, 400 MHz) δ 3.93 (dd, J=8.7, 7.17 Hz, 2H); 3.82 (dd, J=8.7, 5.5 Hz, 2H); 3.15-3.07 (m, 1H); 2.58-2.44 (m, 2H); 2.27 (td, J=11.0, 3.5 Hz, 2H); 1.77-1.54 (m, 4H); 1.42 (s, 9H); 1.26 (t, J=6.7 Hz, 3H).

Step 2: A 25 mL round-bottomed flask was charged with a solution of 3-(4-hydroxy-4-methylpiperidin-1-yl)azetidine-1-carboxylic acid tert-butyl ester (0.2 g, 0.74 mmol) in DCM/TFA (3 mL/3 mL). The reaction mixture was stirred for 4 h at room temperature. The reaction mixture was loaded onto an Isolute® SCX-2 cartridge. The cartridge was washed with MeOH and the desired product was eluted using 2 M NH$_3$ in MeOH to give 1-Azetidin-3-yl-4-methylpiperidin-4-ol as a colourless oil (0.107 g, 85%). $^1$H NMR (CDCl$_3$, 400 MHz) δ 3.61 (t, J=7.3 Hz, 2H); 3.54 (t, J=7.3 Hz, 2H); 3.29-3.15 (m, 1H); 3.04 (s, 2H); 2.40 (d, J=10.8 Hz, 2H); 2.30-2.18 (m, 2H); 1.67-1.56 (m, 4H); 1.23 (s, 3H).

Example 22

4-Oxetan-3-ylpiperazine-1-carboxylic acid tert-butyl ester

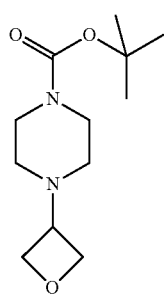

A solution of piperazine-1-carboxylic acid tert-butyl ester (1.56 g, 8.38 mmol) and oxetan-3-one (500 mg, 6.94 mmol) DCE (60 mL) was stirred at ambient temperature for 90 min. Sodium triacetoxyborohydride (2.34 g, 11.04 mmol) was added and the mixture stirred for 17 h, then loaded onto an Isolute® SCX-2 cartridge (25 g). The cartridge was then washed with methanol and the desired product was subsequently eluted using 2 M NH$_3$ in MeOH. The product was collected and concentrated in vacuo. The resultant residue was purified by flash chromatography (Si—PPC, DCM: MeOH; 100:0 to 99:1 to 98:2) to afford 4-Oxetan-3-ylpiperazine-1-carboxylic acid tert-butyl ester as a white solid (1.0 g, 59%). $^1$H NMR (CDCl$_3$, 400 MHz) δ 4.69-4.58 (m, 4H); 3.51-3.44 (m, 5H); 2.27 (m, 4H) and 1.46 (s, 9H).

Example 23

2-Hydroxy-2-methyl-7-azaspiro[3.5]nonane-7-carboxylic acid benzyl ester

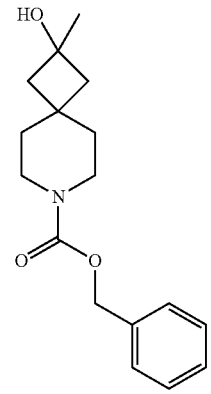

To a stirred solution of 2-oxo-7-azaspiro[3.5]nonane-7-carboxylic acid benzyl ester (164 mg, 0.60 mmol) in dry THF (2 mL) was added dropwise a 1.4 M solution of methylmagnesium bromide in toluene/THF (0.56 mL, 0.78 mmol) under an atmosphere of nitrogen, at −78° C. After 1 h the solution was quenched with saturated NH$_4$Cl$_{(aq)}$ and the resulting mixture partitioned between EtOAc and water. The organic layer was dried (Na$_2$SO$_4$) and evaporated to give a residue, which was purified by column chromatography (Si—PCC, 0-70% EtOAc in cyclohexane) to give 2-Hydroxy-2-methyl-7-azaspiro[3.5]nonane-7-carboxylic acid benzyl ester (96 mg, 55%) as a colourless oil. LCMS (Method H): R$_T$ 4.13 min, [M+H]$^+$ 290.4

Example 24

Azetidin-1-yl-I-pyrrolidin-3-ylmethanone

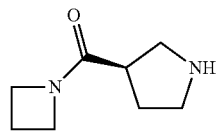

Azetidine hydrochloride (96 mg, 1.03 mmol) was added to a solution of I-pyrrolidine-1,3-dicarboxylic acid 1-tert-butyl ester (200 mg, 0.93 mmol), HATU (391 mg, 1.03 mmol) and DIPEA (410 µL, 2.35 mmol) in DMF (17 mL) and the resulting mixture stirred at ambient temperature for 1 h, then concentrated in vacuo. The resulting oil was partitioned between EtOAc and water. The organic layer was separated, washed with water and brine, then dried (MgSO₄) and concentrated in vacuo to give I-3-(azetidine-1-carbonyl)-pyrrolidine-1-carboxylic acid tert-butyl ester as a colourless oil. TFA (3 mL) was added to a solution of I-3-(azetidine-1-carbonyl)pyrrolidine-1-carboxylic acid tert-butyl ester in DCM (10 mL) and the mixture stirred at ambient temperature for 1 h, then loaded onto an Isolute® SCX-2 cartridge (10 g). The cartridge was then washed with methanol and the desired product was subsequently eluted using 2 M NH₃ in MeOH. The product was collected and concentrated in vacuo to afford Azetidin-1-yl-I-pyrrolidin-3-ylmethanone as a brown oil (77 mg, 54%). ¹H NMR (CDCl₃, 400 MHz) δ 4.18 (t, J=7.7 Hz, 2H); 4.01 (t, J=7.7 Hz, 2H); 3.18-3.04 (m, 3H); 2.96 (m, 1H); 2.88-2.71 (m, 2H); 2.35-2.23 (m, 2H) and 2.04-1.84 (m, 2H).

Example 25

Azetidin-1-yl-(S)-pyrrolidin-3-ylmethanone

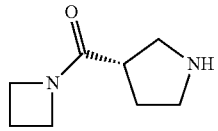

Azetidine hydrochloride (96 mg, 1.03 mmol) was added to a solution of I-pyrrolidine-1,3-dicarboxylic acid 1-tert-butyl ester (200 mg, 0.93 mmol), HATU (391 mg, 1.03 mmol) and DIPEA (410 µL, 2.35 mmol) in DMF (17 mL) and the resulting mixture stirred at ambient temperature for 1 h, then concentrated in vacuo. The resulting oil was partitioned between EtOAc and water. The organic layer was separated, washed with water and brine, then dried (MgSO₄) and concentrated in vacuo to give I-3-(azetidine-1-carbonyl)pyrrolidine-1-carboxylic acid tert-butyl ester as a colourless oil. TFA (3 mL) was added to a solution of I-3-(azetidine-1-carbonyl)pyrrolidine-1-carboxylic acid tert-butyl ester in DCM (10 mL) and the mixture stirred at ambient temperature for 1 h, then loaded onto an Isolute® SCX-2 cartridge (10 g). The cartridge was then washed with methanol and the desired product was subsequently eluted using 2 M NH₃ in MeOH. The product was collected and concentrated in vacuo to afford Azetidin-1-yl-(S)-pyrrolidin-3-ylmethanone as a brown oil (130 mg, 91%). ¹H NMR (CDCl₃, 400 MHz) δ 4.21-4.11 (m, 2H); 4.02 (t, J=7.7 Hz, 2H); 3.18-3.07 (m, 2H); 2.95 (dd, J=11.5, 7.7 Hz, 1H); 2.88-2.71 (m, 1H); 2.33-2.22 (m, 2H); 2.15 (m, 2H) and 2.05-1.82 (m, 2H).

Example 26

Pyrrolidin-1-yl-(R)-pyrrolidin-3-ylmethanone

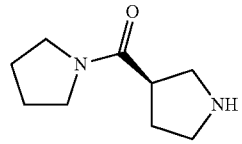

Pyrrolidine (51 µL, 1.03 mmol) was added to a solution of I-pyrrolidine-1,3-dicarboxylic acid 1-tert-butyl ester (200 mg, 0.93 mmol), HATU (391 mg, 1.03 mmol) and DIPEA (410 µL, 2.35 mmol) in DMF and the resulting mixture stirred at ambient temperature for 1 h, then concentrated in vacuo. The resulting oil was partitioned between EtOAc and water. The organic layer was separated, washed with water and brine, then dried (MgSO₄) and concentrated in vacuo to give I-3-(pyrrolidine-1-carbonyl)pyrrolidine-1-carboxylic acid tert-butyl ester as a colourless oil. TFA (3 mL) was added to a solution of I-3-(pyrrolidine-1-carbonyl)pyrrolidine-1-carboxylic acid tert-butyl ester in DCM (10 mL) and the mixture stirred at ambient temperature for 1 h, then loaded onto an Isolute® SCX-2 cartridge (10 g). The cartridge was then washed with methanol and the desired product was subsequently eluted using 2 M NH₃ in MeOH. The product was collected and concentrated in vacuo to afford Pyrrolidin-1-yl-(R)-pyrrolidin-3-ylmethanone as a yellow oil (121 mg, 77%). ¹H NMR (CDCl₃, 400 MHz) δ 3.50-3.42 (m, 3H); 3.19 (s, 1H); 3.14 (s, 1H); 3.00 (s, 2H); 2.96-2.59 (m, 3H); 2.04-1.92 (m, 3H) and 1.89-1.81 (m, 2H).

Example 27

Pyrrolidin-1-yl-(S)-pyrrolidin-3-ylmethanone

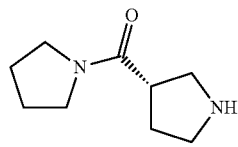

Pyrrolidine (51 µL, 1.03 mmol) was added to a solution of (S)-pyrrolidine-1,3-dicarboxylic acid 1-tert-butyl ester (200 mg, 0.93 mmol), HATU (391 mg, 1.03 mmol) and DIPEA (410 µL, 2.35 mmol) in DMF and the resulting mixture stirred at ambient temperature for 1 h, then concentrated in vacuo. The resulting oil was partitioned between EtOAc and water. The organic layer was separated, washed with water and brine, then dried (MgSO₄) and concentrated in vacuo to give (S)-3-(pyrrolidine-1-carbonyl)pyrrolidine-1-carboxylic acid tert-butyl ester as a colourless oil. TFA (3 mL) was added to a solution of (S)-3-(pyrrolidine-1-carbonyl)pyrrolidine-1-carboxylic acid tert-butyl ester in DCM (10 mL) and the mixture stirred at ambient temperature for 1 h, then loaded onto an Isolute® SCX-2 cartridge (10 g). The cartridge was then washed with methanol and the desired product was subsequently eluted using 2 M NH₃ in MeOH. The product was collected and concentrated in vacuo to afford the title compound as a pale brown oil (110 mg, 70%). ¹H NMR (CDCl₃, 400 MHz) δ 4.01 (m, 3H); 3.52-3.41 (m, 3H); 3.25-3.11 (m, 2H); 3.10-2.97 (m, 2H); 2.89 (dt, J=11.4, 7.5 Hz, 1H); 2.11-1.99 (m, 1H); 2.01-1.91 (m, 2H) and 1.93-1.82 (m, 2H).

Example 28

Azetidin-3-yl-azetidin-1-ylmethanone

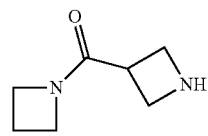

Azetidine hydrochloride salt (515 mg, 5.50 mmol) was added to a solution of azetidine-1,3-dicarboxylic acid mono-tert-butyl ester (1.0 g, 4.97 mmol), HATU (2.09 g, 5.50 mmol) and DIPEA (2.18 mL, 12.52 mmol) in DMF (100 mL) and the resulting mixture stirred at ambient temperature for 1 h, then concentrated in vacuo. The resulting oil was partitioned between EtOAc and water. The organic layer was separated, washed with water and brine, then dried (MgSO₄) and concentrated in vacuo to give 3-(azetidine-1-carbonyl)azetidine-1-carboxylic acid tert-butyl ester as a colourless oil. TFA (3 mL) was added to a solution of 3-(azetidine-1-carbonyl)-azetidine-1-carboxylic acid tert-butyl ester in DCM (15 mL) and the mixture stirred at ambient temperature for 1 h, then loaded onto an Isolute® SCX-2 cartridge (25 g). The cartridge was then washed with methanol and the desired product was subsequently eluted using 2 M NH$_3$ in MeOH. The product was collected and concentrated in vacuo to afford the title compound as a colourless oil (260 mg, 37%). $^1$H NMR (CD$_3$OD, 400 MHz) δ 4.19-4.08 (m, 2H); 4.07-3.92 (m, 2H); 3.91-3.78 (m, 2H); 3.72-3.52 (m, 3H) and 2.36-2.21 (m, 2H).

Example 29

Azetidin-3-yl-pyrrolidin-1-ylmethanone

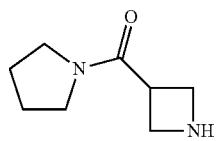

Pyrrolidine (271 μL, 5.50 mmol) was added to a solution of azetidine-1,3-dicarboxylic acid mono-tert-butyl ester (1.0 g, 4.97 mmol), HATU (2.09 g, 5.50 mmol) and DIPEA (2.18 mL, 12.52 mmol) in DMF (100 mL) and the resulting mixture stirred at ambient temperature for 1 h, then concentrated in vacuo. The resulting oil was partitioned between EtOAc and water. The organic layer was separated, washed with water and brine, then dried (MgSO$_4$) and concentrated in vacuo to give 3-(pyrrolidine-1-carbonyl)azetidine-1-carboxylic acid tert-butyl ester as a colourless oil. TFA (3 mL) was added to a solution of 3-(pyrrolidine-1-carbonyl)-azetidine-1-carboxylic acid tert-butyl ester in DCM (15 mL) and the mixture stirred at ambient temperature for 1 h, then loaded onto an Isolute® SCX-2 cartridge (25 g). The cartridge was then washed with methanol and the desired product was subsequently eluted using 2 M NH$_3$ in MeOH. The product was collected and concentrated in vacuo to afford the title compound as a colourless oil (550 mg, 72%). $^1$H NMR (CD$_3$OD, 400 MHz) δ 3.93-3.65 (m, 5H); 3.43-3.28 (m, 4H) and 2.00-1.81 (m, 4H).

Example 30

4-Oxetan-3-ylpiperidine

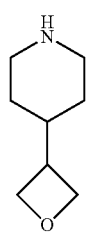

Step 1: 2-(1-(tert-Butoxycarbonyl)piperidin-4-ylidene)malonic acid diethyl ester

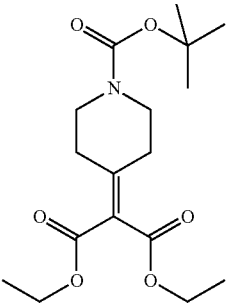

To anhydrous THF (50 mL) at 0° C. a solution of TiCl$_4$ (13.75 mL, 0.126 mol) in CCl$_4$ (10 mL) was added dropwise. To the resulting yellow suspension were a solution of 4-oxopiperidine-1-carboxylic acid tert-butyl ester (10 g, 0.05 mol) and diethylmalonate (6.85 mL, 0.05 mol) in anhydrous THF (50 mL) added, followed by addition of pyridine (26 mL) The dark yellow suspension was allowed to warm to ambient temperature and stirred at ambient temperature for 17 h, then partitioned between EtOAc and citric acid (10%, aq.). The organic layer was separated and washed with water and brine, then dried (MgSO$_4$) and concentrated in vacuo to afford 2-(1-(tert-Butoxycarbonyl)piperidin-4-ylidene)malonic acid diethyl ester as a brown oil (17 g, 100%). $^1$H NMR (CDCl$_3$, 400 MHz) δ 4.27-4.18 (m, 4H); 3.55-3.44 (m, 4H); 2.65 (m, 4H); 1.49 (s, 9H) and 1.32-1.26 (m, 6H).

Step 2:
2-(1-(tert-Butoxycarbonyl)piperidin-4-yl)malonic acid diethyl ester

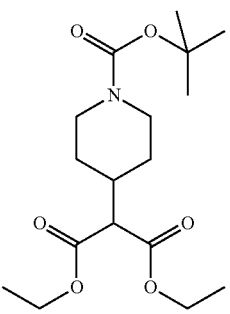

To IMS (200 mL) at 0° C., NaBH$_4$ (1.87 g, 0.047 mol) and a solution of 2-(1-(tert-butoxycarbonyl)piperidin-4-ylidene)malonic acid diethyl ester (17 g, 0.050 mol) in IMS (200 mL) were added. The resulting mixture was allowed to warm to ambient temperature and stirred for 1 h, then quenched with water and concentrated in vacuo. The resulting oil was then partitioned between EtOAc and water. The organic layer was separated and washed with brine, then dried (MgSO$_4$) and concentrated in vacuo to afford the title compound as a yellow oil (14.6 g, 85%). LCMS (Method H): $R_T$=3.90 min, [M+Na]$^+$ 366.

Step 3: 4-(2-Hydroxy-1-(hydroxymethyl)ethyl)piperidine-1-carboxylic acid tert-butyl ester

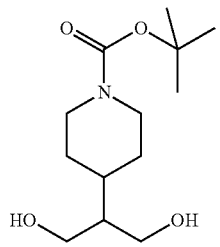

To a solution of 2-(1-(tert-butoxycarbonyl)piperidin-4-yl)malonic acid diethyl ester (14.6 g, 0.043 mol) in anhydrous THF (100 mL) and anhydrous toluene (100 mL), LiBH$_4$ (2.1 g. 0.96 mol) was added portion wise. The resulting mixture was heated at 60° C. for 17 h, then stirred at ambient temperature for 24 h. The reaction mixture was slowly added to aqueous HCl (0.1 M, 350 mL) and then extracted with EtOAc. The organic layer was separated and washed with brine, then dried (MgSO$_4$) and concentrated in vacuo. The resultant residue was purified by flash chromatography (Si—PPC, EtOAc:MeOH 100:0 to 98:2 to 95:5 to 90:10 to 80:20) to afford the title compound as a colourless oil (6.91 g, 63%). $^1$H NMR (CDCl$_3$, 400 MHz) δ 3.90-3.75 (m, 4H); 2.75-2.58 (m, 4H); 1.77-1.61 (m, 4H); 1.52 (m, 1H); 1.45 (s, 9H) and 1.26-1.13 (m, 1H).

Step 4: To a solution of 4-(2-hydroxy-1-(hydroxymethyl)ethyl)piperidine-1-carboxylic acid tert-butyl ester (7.62 g, 0.029 mol) in anhydrous THF (100 mL) at 0° C., a solution of n-BuLi (1.6 M in hexanes, 18.4 mL, 0.029 mol) was added dropwise. The resulting mixture was stirred at 0° C. for 30 min, then a solution of toluenesulfonyl chloride (5.26 g, 0.028 mol) in anhydrous THF (50 mL) was added by canula. The thick reaction mixture was allowed to warm to ambient temperature and stirred for 2 h. A solution of n-BuLi (1.6 M in hexanes, 18.4 mL, 0.029 mol) was added dropwise and the reaction mixture heated at 60° C. for 2 h, then concentrated in vacuo. The resulting oil was partitioned between EtOAc and water. The organic layer was separated and washed with brine, then dried (MgSO$_4$) and concentrated in vacuo. The resultant residue was purified by flash chromatography (Si—PPC, pentane:EtOAc; gradient from 100:0 to 20:80) to afford 4-oxetan-3-ylpiperidine-1-carboxylic acid tert-butyl ester as a white solid (5.33 g, 75%). TFA (10 mL) was added to a solution of 4-oxetan-3-yl-piperidine-1-carboxylic acid tert-butyl ester (7.1 g, 0.029 mol) in DCM (100 mL) and the mixture stirred at ambient temperature for 2 h. The reaction mixture was loaded onto an Isolute® SCX-2 cartridge (50 g), the cartridge was washed with MeOH before the desired product was eluted using 2 M NH$_3$ in MeOH. The product was collected and concentrated in vacuo. The resultant residue was purified by flash chromatography (Si—PPC, DCM: 2 M NH$_3$ in MeOH 100:0 to 98:2 to 95:5 to 90:10 to 85:15 to 80:20) to afford 4-Oxetan-3-ylpiperidine as a colourless oil which solidified on standing (2.05 g, 49%). $^1$H NMR (CDCl$_3$, 300 MHz) δ 4.75 (dd, J=7.9, 6.0 Hz, 2H); 4.52-4.42 (m, 2H); 3.14-3.04 (m, 2H); 2.81-2.67 (m, 1H); 2.61 (td, J=12.2, 2.6 Hz, 2H); 1.85-1.68 (m, 1H); 1.60 (m, 2H) and 1.02 (qd, J=12.2, 4.0 Hz, 2H).

Example 31

3-(Tetrahydropyran-4-yl)azetidine

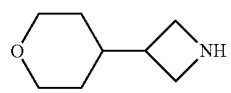

To a solution of 3-(tetrahydropyran-4-yl)azetidine-1-carboxylic acid tert-butyl ester (730 mg, 3.0 mmol) in DCM (10 mL) were added water (0.15 mL) and TFA (10 mL) The reaction mixture was stirred at room temperature for 4 hours and the concentrated under reduced pressure to give a residue that was taken up in MeOH. The resulting solution was loaded onto a SCX-2 cartridge (10 g) which was washed with MeOH. The desired product was eluted with a 2M solution of ammonia in MeOH. The appropriate fractions were combined and concentrated to give 3-(Tetrahydropyran-4-yl)azetidine as a yellow oil (393 mg, 92%). $^1$H NMR (300 MHz, CDCl$_3$): δ 3.96 (dd, J=11.0, 4.0, 2H); 3.65 (dd, J=8.0, 8.0 Hz, 2H); 3.44 (dd, J=7.6, 7.6 Hz, 2H); 3.37 (ddd, J=11.9, 11.9, 2.1, 2H); 2.50 (m, 1H); 1.75 (m, 1H); 1.53 (m, 2H); 1.18 (ddd, J=25.0, 11.9, 4.3, 2H).

Example 32

1-Azetidin-3-ylpyrrolidin-2-one

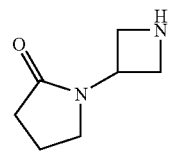

Step 1:
3-(4-Chlorobutyrylamino)azetidine-1-carboxylic acid tert-butyl ester

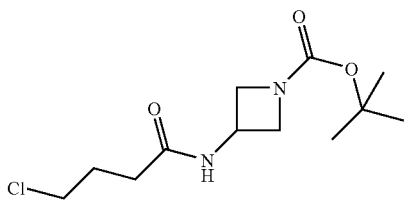

A mixture of 3-aminoazetidine-1-carboxylic acid tert-butyl ester (730 mg, 4.24 mmol) and triethylamine (1.74 mL, 1.29 g, 12.72 mmol) in DCM (10 mL) was cooled to 0° C. before the addition of 4-chlorobutyrylchloride (523 µL, 657 mg, 4.66 mmol). The resulting mixture was stirred for 16 h then quenched with H$_2$O and extracted with DCM. The combined organic extracts were washed with brine then dried (Na$_2$SO$_4$) and concentrated in vacuo. The resulting residue was purified by column chromatography (Si—PCC, EtOAc: cyclohexane, 30-70%) affording 3-(4-Chlorobutyrylamino) azetidine-1-carboxylic acid tert-butyl ester as a brown oil (1.04 g, 89%).

Step 2:
3-(2-Oxopyrrolidin-1-yl)azetidine-1-carboxylic acid tert-butyl ester

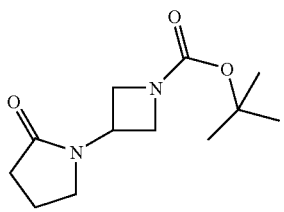

A solution of 3-(4-chlorobutyrylamino)azetidine-1-carboxylic acid tert-butyl ester (1.04 g, 3.76 mmol) in DMF (15 mL) was cooled to 0° C. before the addition of NaH (180 mg, 4.51 mmol). The resulting mixture was allowed to stir for 2 h then quenched with H₂O and extracted with EtOAc. The organic phase was washed with H₂O and brine, then dried (Na₂SO₄) and concentrated in vacuo. The resulting residue was purified by column chromatography (Si—PCC, EtOAc: cyclohexane, 20-100%) affording 3-(2-Oxopyrrolidin-1-yl) azetidine-1-carboxylic acid tert-butyl ester as a brown oil (320 mg, 35%). $^1$H NMR (CDCl₃, 300 MHz): δ 4.99 (m, 1H), 4.15 (m, 2H), 3.97 (m, 2H), 3.57 (t, J=7.0 Hz, 2H), 2.42 (t, J=8.1 Hz, 2H), 2.15-2.02 (m, 2H) and 1.45 (s, 9H)

A mixture of 3-(2-oxopyrrolidin-1-yl)azetidine-1-carboxylic acid tert-butyl ester (320 mg, 1.33 mmol) and TFA (1.5 mL) in DCM (3 mL) was stirred at room temperature for 4 h. The reaction mixture was loaded onto an Isolute® SCX-2 cartridge, washed with MeOH/DCM and eluted with 2M NH₃/MeOH affording 1-Azetidin-3-ylpyrrolidin-2-one as a white solid (174 mg, 93%). $^1$H NMR (CDCl₃, 300 MHz): γ 5.05 (m, 1H), 3.85-3.76 (m, 4H), 3.61 (m, 2H), 2.41 (m, 2H) and 2.07 (m, 2H)

Step 1: 3-(3,3-Difluoropyrrolidin-1-yl)azetidine-1-carboxylic acid tert-butyl ester

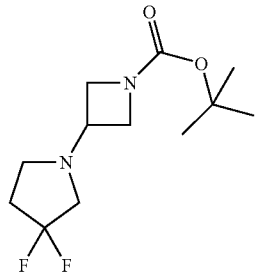

A mixture of 3,3-difluoropyrrolidine hydrochloride (200 mg, 1.17 mmol), 3-oxoazetidine-1-carboxylic acid tert-butyl ester (284 mg, 1.99 mmol) and triethylamine (295 µL, 221 mg, 2.18 mmol) in DCE (10 mL) was stirred at room temperature for 1 h before the addition of sodium triacetoxyborohydride (745 mg, 3.52 mmol). The resulting mixture was stirred for 72 h then diluted with DCM and washed with H₂O. The organic phase was dried (Na₂SO₄) and concentrated in vacuo. The resulting residue was purified by column chromatography (Si—PCC, EtOAc:cyclohexane, 0-50%) affording 3-(3,3-Difluoropyrrolidin-1-yl)azetidine-1-carboxylic acid tert-butyl ester as a colourless oil (193 mg, 63%). $^1$H NMR (CDCl₃, 300 MHz): δ 3.95 (m, 2H), 3.82 (dd, J=8.9, 4.9 Hz, 2H), 3.32 (m, 1H), 2.91 (m, 2H), 2.82-2.63 (m, 2H), 2.33-2.32 (m, 2H) and 1.43 (s, 9H).

A mixture of 3-(3,3-difluoropyrrolidin-1-yl)azetidine-1-carboxylic acid tert-butyl ester (193 mg, 0.74 mmol) and TFA (1 mL) in DCM (2 mL) was stirred at room temperature for 2 h. The reaction mixture was loaded onto an Isolute® SCX-2 cartridge, washed with MeOH/DCM and eluted with 2M NH₃/MeOH affording 1-Azetidin-3-yl-3,3-difluoropyrrolidine as a white solid (122 mg, quant.). $^1$H NMR (CDCl₃, 300 MHz): δ 3.63 (m, 4H), 3.48 (m, 1H), 2.87 (t, J=13.1 Hz, 2H), 2.70 (t, J=7.0 Hz, 2H) and 2.29 (m, 2H)

Example 33

1-Azetidin-3-yl-3,3-difluoropyrrolidine

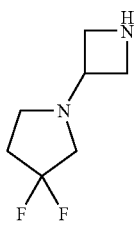

Example 34

3,3-Difluoro-[1,3']biazetidinyl

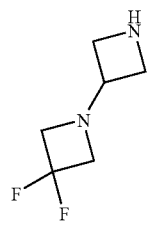

507

Step 1: 3,3-Difluoro-[1,3']biazetidinyl-1'-carboxylic acid tert-butyl ester

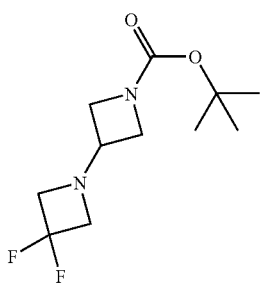

A 25 mL round-bottomed flask was charged with a solution of 3-oxoazetidine-1-carboxylic acid tert-butyl ester (0.4 g, 2.34 mmol), 3,3-difluoroazetidine hydrochloride (0.364 g, 2.80 mmol) and 4 Å molecular sieves (2.43 g) in DCE (10 mL). The reaction mixture was stirred for 3 h at room temperature. Sodium triacetoxyborohydride (0.99 g, 4.67 mmol) was added and the reaction mixture was stirred for 18 h at room temperature. The suspension was filtered through Celite and the filtrate was concentrated in vacuo. The residue was purified by flash chromatography (Si—PPC, MeOH:DCM, gradient 0:100 to 10:90) to give the title compound as a colourless oil (0.33 g, 57%). $^1$H NMR (300 MHz, CDCl$_3$): δ 4.02-3.69 (m, 4H), 3.65 (t, J=12.15 Hz, 4H), 3.55-3.48 (m, 1H), 1.43 (s, 9H).

Step 2: 3,3-Difluoro-[1,3']biazetidinyl

A 10 mL round-bottomed flask was charged with a solution of 3,3-difluoro-[1,3']biazetidinyl-1'-carboxylic acid tert-butyl ester (0.15 g, 0.61 mmol) in DCM/TFA (3 mL/3 mL) The reaction mixture was stirred for 3 h at room temperature. The reaction mixture was loaded onto an Isolute® SCX-2 cartridge. The cartridge was washed with MeOH and the desired product was eluted using 2 M NH$_3$ in MeOH to give 3,3-Difluoro-[1,3']biazetidinyl as a colourless oil (0.033 g, 37%). $^1$H NMR (300 MHz, CDCl$_3$): δ 3.73-3.55 (m, 8H), 3.57-3.43 (m, 1H), 2.77 (s, 1H)

Example 35

4-(3,3-Difluoroazetidin-1-yl)piperidine

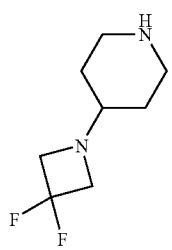

508

Step 1: 4-(3,3-Difluoroazetidin-1-yl)piperidine-1-carboxylic acid tert-butyl ester

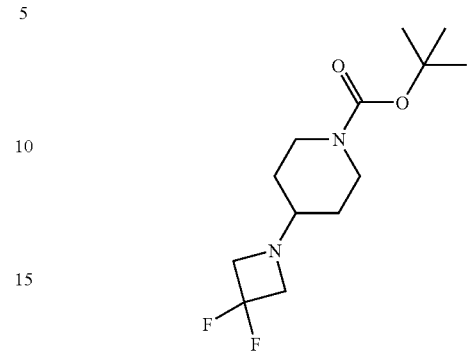

A 10 mL round-bottomed flask was charged with a solution of 4-oxopiperidine-1-carboxylic acid tert-butyl ester (0.4 g, 0.20 mmol), 3,3-difluoroazetidine hydrochloride (0.31 g, 0.24 mmol) and 4 Å molecular sieves (2.4 g) in DCE (10 mL). The reaction mixture was stirred for 3 h at room temperature. Sodium triacetoxyborohydride (0.85 g, 4.01 mmol) was added and the reaction mixture was stirred for 18 h at room temperature. The suspension was filtered through Celite and the filtrate was concentrated in vacuo to give 4-(3,3-Difluoroazetidin-1-yl)piperidine-1-carboxylic acid tert-butyl ester as a colourless oil (0.53 g, 96%). $^1$H NMR (300 MHz, CDCl$_3$): δ 3.94-3.90 (m, 2H), 3.57 (t, J=11.9 Hz, 4H), 2.96-2.81 (m, 2H), 2.34-2.23 (m, 1H), 1.71-1.58 (m, 2H), 1.45 (s, 9H), 1.35-1.21 (m, 2H).

Step 2: 4-(3,3-Difluoroazetidin-1-yl)piperidine

A 25 mL round-bottomed flask was charged with a solution of 4-(3,3-difluoroazetidin-1-yl)piperidine-1-carboxylic acid tert-butyl ester (0.265 g, 0.96 mmol) in DCM/TFA (3 mL/3 mL). The reaction mixture was stirred for 3 h at room temperature. The reaction mixture was loaded onto an Isolute® SCX-2 cartridge. The cartridge was washed with MeOH and the desired product was eluted using 2 M NH$_3$ in MeOH to give 4-(3,3-Difluoroazetidin-1-yl)piperidine as a white solid (0.154 g, 91%). $^1$H NMR (300 MHz, CDCl$_3$): δ 3.54 (t, J=11.9 Hz, 4H), 3.10 (dt, J=12.7, 3.9 Hz, 2H), 2.59 (td, J=11.9, 2.6 Hz, 2H), 2.24-2.13 (m, 1H), 1.76-1.65 (m, 2H), 1.30-1.15 (m, 2H).

Example 36

3-Methyl-[1,3']biazetidinyl-3-ol

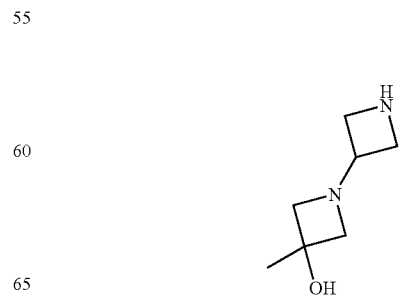

Step 1: 3-Hydroxy-3-methylazetidine-1-carboxylic acid benzyl ester

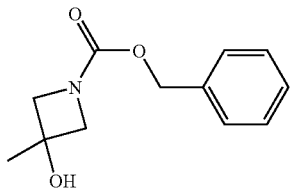

To a 3.0 M solution of methylmagnesium bromide in Et₂O (0.98 mL, 2.92 mmol), at 0° C., was added a solution of 3-oxoazetidine-1-carboxylic acid benzyl ester (0.5 g, 2.44 mmol) in anhydrous THF (5 mL) dropwise over 5 min under argon. The reaction mixture was stirred for 18 h at room temperature, and then quenched by addition of a saturated aqueous solution of NH₄Cl (2.5 mL) and water (5 mL). The aqueous phase was extracted with EtOAc (10 mL) The organic layer was separated, dried over sodium sulphate and concentrated in vacuo to give 3-Hydroxy-3-methylazetidine-1-carboxylic acid benzyl ester as a colourless oil (0.54 g, 99%). LCMS (Method A): R$_T$=3.60 min, [M+H]$^+$ 221.9

Step 2: 3-Methylazetidin-3-ol

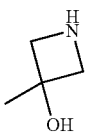

A 25 mL round-bottomed flask was charged with a solution of 3-hydroxy-3-methylazetidine-1-carboxylic acid benzyl ester (0.57 g, 2.58 mmol) in EtOH (5 mL) and acetic acid (0.25 mL). The reaction mixture was flushed with nitrogen and 10% Pd/C (67 mg, 0.29 mmol) was added. The reaction mixture was stirred under a hydrogen atmosphere for 36 h at room temperature. The reaction mixture was loaded onto an Isolute® SCX-2 cartridge. The cartridge was washed with MeOH and the desired product was eluted using 2 M NH₃ in MeOH to give the 3-Methylazetidin-3-ol as an orange oil (0.125 g, 56%). ¹H NMR (300 MHz, CDCl₃): δ 3.19-3.03 (m, 4H), 1.45 (s, 3H).

Step 3: 3-Hydroxy-3-methyl-[1,3']biazetidinyl-1'-carboxylic acid tert-butyl ester

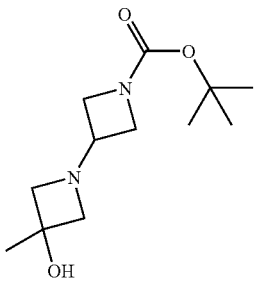

A 10 mL round-bottomed flask was charged with a solution of 3-oxoazetidine-1-carboxylic acid tert-butyl ester (0.21 g, 1.23 mmol), 3-methylazetidin-3-ol (0.13 g, 1.48 mmol) and 4 Å molecular sieves (1.2 g) in DCE (5 mL). The reaction mixture was stirred for 3 h at room temperature. Sodium triacetoxyborohydride (0.52 g, 2.47 mmol) was added and the reaction mixture was stirred for 18 h at room temperature. The suspension was filtered through Celite and the solution was concentrated in vacuo. The residue was purified by flash chromatography (Si—PPC, EtOAc:cyclohexane, 0:100 to 100:0) to give 3-Hydroxy-3-methyl-[1,3']biazetidinyl-1'-carboxylic acid tert-butyl ester as a colourless oil (0.09 g, 30%). ¹H NMR (300 MHz, CDCl₃): δ 3.93 (dd, J=9.2, 7.2 Hz, 2H), 3.82-3.70 (m, 2H), 3.50-3.40 (m, 1H), 3.32 (d, J=8.1 Hz, 2H), 3.21 (d, J=8.1 Hz, 2H), 1.51 (s, 3H), 1.43 (s, 9H).

Step 4: 3-Methyl-[1,3']biazetidinyl-3-ol

A 10 mL round-bottomed flask was charged with a solution of 3-hydroxy-3-methyl-[1,3']biazetidinyl-1'-carboxylic acid tert-butyl ester (0.09 g, 0.37 mmol) in DCM/TFA (2 mL/2 mL). The reaction mixture was stirred for 90 min at room temperature. The reaction mixture was loaded onto an Isolute® SCX-2 cartridge. The cartridge was washed with MeOH and the desired product was eluted using 2 M NH₃ in MeOH to give 3-Methyl-[1,3']biazetidinyl-3-ol as a colourless oil (0.04 g, 76%). ¹H NMR (300 MHz, CDCl₃): δ 3.68-3.51 (m, 6H), 3.25 (d, J=7.6 Hz, 2H), 3.15 (d, J=7.6 Hz, 2H), 1.49 (s, 3H).

Example 37

(R)-1-Azetidin-3-yl-3-fluoropyrrolidine

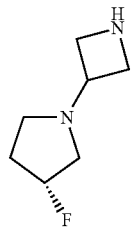

Step 1: 3-(I-3-Fluoropyrrolidin-1-yl)azetidine-1-carboxylic acid tert-butyl ester

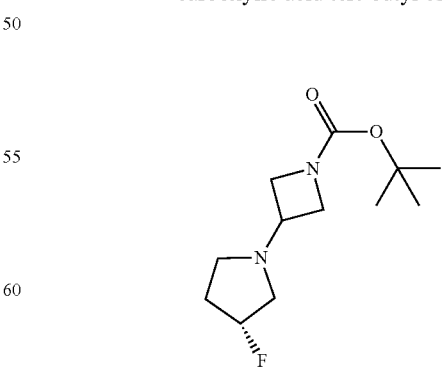

A 25 mL round-bottomed flask was charged with a solution of 3-oxoazetidine-1-carboxylic acid tert-butyl ester (0.4 g, 2.34 mmol), I-3-fluoropyrrolidine hydrochloride (0.35 g, 2.8 mmol) and 4 Å molecular sieves (2.43 g) in DCE (10 mL). The reaction mixture was stirred for 2.5 h at room temperature. Sodium triacetoxyborohydride (0.99 g, 4.68 mmol) was added and the reaction mixture was stirred for 18 h at room temperature. The suspension was filtered through Celite and the filtrate was concentrated in vacuo. The residue was purified by flash chromatography (Si—PPC, EtOAc:cyclohexane, gradient 30:70 to 100:0) to give 3-(I-3-Fluoropyrrolidin-1-yl)azetidine-1-carboxylic acid tert-butyl ester as a colourless oil (0.348 g, 61%). $^1$H NMR (300 MHz, CDCl$_3$): δ 5.30-5.20 (m, 3H), 4.01-3.92 (m, 2H), 3.91-3.82 (m, 2H), 2.87-2.78 (m, 2H), 2.17-2.11 (m, 3H), 1.43 (s, 9H).

Step 2: (R)-1-Azetidin-3-yl-3-fluoropyrrolidine

A 25 mL round-bottomed flask was charged with a solution of 3-(I-3-fluoropyrrolidin-1-yl)azetidine-1-carboxylic acid tert-butyl ester (0.175 g, 0.72 mmol) in DCM/TFA (5 mL/5 mL). The reaction mixture was stirred for 3 h at room temperature. The reaction mixture was loaded onto an Isolute® SCX-2 cartridge. The cartridge was washed with MeOH and (R)-1-Azetidin-3-yl-3-fluoropyrrolidine was eluted using 2 M NH$_3$ in MeOH to give the title compound as a colourless oil (0.088 g, 85%). $^1$H NMR (300 MHz, CDCl$_3$): δ 5.31-5.07 (m, 1H), 3.73-3.56 (m, 4H), 3.55-3.21 (m, 1H), 2.95-2.87 (m, 2H), 2.83-2.74 (m, 2H), 2.66 (m, 1H), 2.28-1.95 (m, 2H)

Example 38

(S)-1-Azetidin-3-yl-3-fluoropyrrolidine

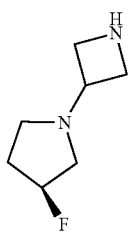

Step 1: 3-((S)-3-Fluoropyrrolidin-1-yl)azetidine-1-carboxylic acid tert-butyl ester

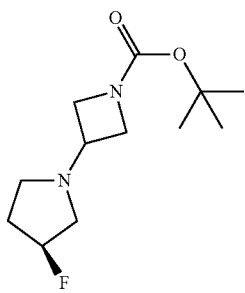

A 25 mL round-bottomed flask was charged with a solution of 3-oxoazetidine-1-carboxylic acid tert-butyl ester (0.4 g, 2.34 mmol), (S)-3-fluoropyrrolidine hydrochloride (0.35 g, 2.8 mmol) and 4 Å molecular sieves (2.43 g) in DCE (10 mL). The reaction mixture was stirred for 2.5 h at room temperature. Sodium triacetoxyborohydride (0.99 g, 4.68 mmol) was added and the reaction mixture was stirred for 18 h at room temperature. The suspension was filtered through Celite and the filtrate was concentrated in vacuo. The residue was purified by flash chromatography (Si—PPC, EtOAc:cyclohexane, gradient 30:70 to 100:0) to give 3-((S)-3-Fluoropyrrolidin-1-yl)azetidine-1-carboxylic acid tert-butyl ester as a colourless oil (0.342 g, 60%). $^1$H NMR (300 MHz, CDCl$_3$): δ 5.34-5.10 (m,1H), 4.01-3.93 (m, 2H), 3.91-3.81 (m, 2H), 3.41-3.31 (m, 1H), 2.94-2.67 (m, 3H), 2.56-2.46 (m, 1H), 2.24-2.06 (m, 2H), 1.43 (s, 9H).

Step 2: (S)-1-Azetidin-3-yl-3-fluoropyrrolidine

A 25 mL round-bottomed flask was charged with a solution of 3-(I-3-fluoropyrrolidin-1-yl)azetidine-1-carboxylic acid tert-butyl ester (0.228 g, 0.93 mmol) in DCM/TFA (6 mL/6 mL). The reaction mixture was stirred for 4 h at room temperature. The reaction mixture was loaded onto an Isolute® SCX-2 cartridge. The cartridge was washed with MeOH and: (S)-1-Azetidin-3-yl-3-fluoropyrrolidine was eluted using 2 M NH$_3$ in MeOH to give the title compound as a colourless oil (0.108 g, 75%). $^1$H NMR (300 MHz, CDCl$_3$): δ 5.46-4.86 (m, 1H), 4.05-3.79 (m, 4H), 3.78-3.20 (m, 1H), 2.95-2.80 (m, 2H), 2.70-2.62 (m, 2H), 2.46-2.37 (m, 1H), 2.29-1.97 (m, 2H)

Example 39

1-tert-Butylpiperazin-2-one

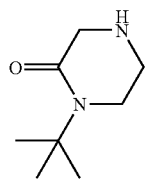

Step 1: 4-tert-Butyl-3-oxopiperazine-1-carboxylic acid benzyl ester

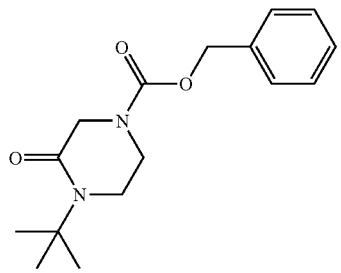

To a solution of (2-tert-butylaminoethyl)carbamic acid benzyl ester (1.44 g, 5.75 mmol) and triethylamine (2.4 mL, 17.26 mmol) in DCM (50 mL), at room temperature, was added dropwise chloroacetyl chloride (0.55 mL, 6.9 mmol) and the reaction mixture was stirred for 6 h at room temperature. The aqueous phase was extracted with EtOAc (10 mL) The reaction mixture was partitioned between DCM and a staturated aqueous solution of NaHCO$_3$. The organic layer was separated, dried over sodium sulphate and concentrated in vacuo. The brown residue was dissolved in dry THF (50 mL) and sodium hydride 60% in mineral oil (0.345 g, 8.63 mmol) was added and the reaction mixture was stirred at room temperature for 18 h. The reaction mixture was quenched with water and partitioned between EtOAc and water. The organic layer was washed with brine, separated, dried over sodium sulphate and concentrated in vacuo. The residue was dissolved in MeOH, loaded onto an Isolute® SCX-2 cartridge, and eluted using MeOH to give 4-tert-Butyl-3-oxopiperazine-1-carboxylic acid benzyl ester as yellow oil (1.57 g, 94%). LCMS (Method A): $R_T$=3.96 min, [M+H]$^+$ 291.2

Step 2: 1-tert-Butylpiperazin-2-one

A 10 mL round-bottomed flask was charged with a solution of 4-tert-butyl-3-oxopiperazine-1-carboxylic acid benzyl ester (0.75 g, 2.58 mmol) in EtOH (5 mL). The reaction mixture was flushed with nitrogen and 10% Pd/C (67 mg, 0.13 mmol) was added. The reaction mixture was stirred under a hydrogen atmosphere for 18 h. The reaction mixture was loaded onto an Isolute® SCX-2 cartridge. The cartridge was washed with MeOH and the desired product was eluted using 2 M $NH_3$ in MeOH to give 1-tert-Butylpiperazin-2-one as grey oil (0.276 g, 69%). $^1$H NMR (300 MHz, $CDCl_3$): δ 3.50 (s, 2H), 3.37 (t, J=5.5 Hz, 2H), 3.06 (t, J=5.5 Hz, 2H), 1.48-1.41 (m, 9H)

Example 40

(2-(1S,4S)-2,5-Diazabicyclo[2.2.1]hept-2-yl-2-methylpropan-1-ol

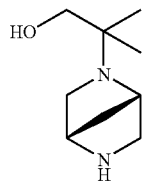

2-Bromo-2-methylpropionic acid ethyl ester (155 μL, 1.06 mmol) was added to a solution of potassium carbonate (145 mg, 1.05 mmol) and (1S,4S)-2,5-diazabicyclo[2.2.1]heptane-2-carboxylic acid tert-butyl ester (200 mg, 1.01 mmol) in anhydrous acetonitrile (1 mL) The resulting mixture was heated at 80° C. for 48 h, then cooled to ambient temperature and partitioned between EtOAc and water. The organic layer was separated, washed with brine, then dried ($MgSO_4$) and concentrated in vacuo. The resultant residue was purified by flash chromatography (Si—PPC, DCM:MeOH; 100:0 to 98:2) to give (1S,4S)-5-(1-ethoxycarbonyl-1-methylethyl)-2,5-diazabicyclo[2.2.1]heptane-2-carboxylic acid tert-butyl ester as a pale brown oil. To a solution of (1S,4S)-5-(1-ethoxycarbonyl-1-methylethyl)-2,5-diazabicyclo[2.2.1]-heptane-2-carboxylic acid tert-butyl ester (1 mmol) in anhydrous THF (5 mL) at 0° C., a solution of $LiAlH_4$ (1 M in THF, 3.2 mL, 3.2 mmol) was added dropwise. The reaction mixture was allowed to warm to ambient temperature and stirred for 1 h. The reaction mixture was loaded onto an Isolute® SCX-2 cartridge (10 g), washed with MeOH before the desired product was eluted using 2 M $NH_3$ in MeOH. The product was collected and concentrated in vacuo to afford the title compound as a brown oil (168 mg, 99%). $^1$H NMR ($CDCl_3$, 400 MHz) δ 3.37 (bs, 1H); 3.31 (d, J=10.2 Hz, 1H); 3.21 (d, J=10.2 Hz, 1H); 3.15-3.00 (m, 2H); 2.81-2.61 (m, 2H); 2.45 (s, 2H); 1.76 (d, J=10.0 Hz, 1H); 1.56 (d, J=10.0 Hz, 1H); 1.46 (t, J=5.02 Hz, 1H); 1.03 (s, 3H) and 1.00 (s, 2H).

Example 41

(1S,4S)-2-Methanesulfonyl-2,5-diazabicyclo[2.2.1]heptane

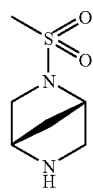

Methanesulfonyl chloride (120 μL, 1.55 mmol) and DIPEA (187 μL, 1.07 mmol) were added to a solution of (1S,4S)-2,5-diazabicyclo[2.2.1]heptane-2-carboxylic acid tert-butyl ester (200 mg, 1.01 mmol) in DCM (20 mL) and the reaction mixture stirred at ambient temperature for 17 h, then partitioned between EtOAc and water. The organic layer was separated and washed with brine, then dried ($MgSO_4$) and concentrated in vacuo to give (1S,4S)-5-methanesulfonyl-2,5-diazabicyclo[2.2.1]-heptane-2-carboxylic acid tert-butyl ester. TFA (3 mL) was added to a solution of (1S,4S)-5-methanesulfonyl-2,5-diazabicyclo[2.2.1]heptane-2-carboxylic acid tert-butyl ester in DCM (10 mL) and the mixture stirred at ambient temperature for 30 min. The reaction mixture was loaded onto an Isolute® SCX-2 cartridge (10 g); the cartridge was washed with MeOH before the desired product was eluted using 2 M $NH_3$ in MeOH. The product was collected and concentrated in vacuo to afford the title compound as a white solid (170 mg, 96%). $^1$H NMR ($CDCl_3$, 400 MHz) δ 4.37 (d, J=2.0 Hz, 1H); 3.83 (d, J=2.0 Hz, 1H); 3.41 (dd, J=9.2, 2.19 Hz, 1H); 3.25 (d, J=9.2 Hz, 1H); 3.20 (d, J=10.3 Hz, 1H); 3.01 (dd, J=10.3, 2.14 Hz, 1H); 2.89 (s, 3H); and 1.79 (bs, 2H)

Example 41a 3,3-dimethyl-1-(methylsulfonyl)piperazine

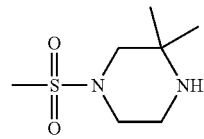

A mixture of 2,2-dimethylpiperazine-1-carboxylic acid tert-butyl ester (1.0 g, 4.60 mmol) and $NEt_3$ (1.3 mL, 9.34 mmol) in DCM (11 mL) was cooled to 0° C. before the drop wise addition of a solution of methanesulfonyl chloride (580 mg, 5.00 mmol) in DCM (2 mL). The resulting mixture was warmed to r.t. and allowed to stir for 30 min before $H_2O$ was added. The organic phase was dried (phase separator) and concentrated in vacuo. The resulting residue was dissolved in DCM (10 mL) and TFA (2 mL) was added. The resulting mixture was allowed to stir at r.t. for 30 min then concentrated in vacuo. The resulting residue was partitioned between DCM and sat. aq. $NaHCO_3$ and the aqueous phase was loaded onto an Isolute® SCX-2 cartridge which was washed with $H_2O$

Example 41b 4-(2-Hydroxy-1,1-dimethylethyl)piperazine-1-carboxylic acid tert-butyl ester

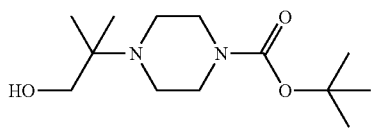

To a solution of 4-(1-ethoxycarbonyl-1-methylethyl)piperazine-1-carboxylic acid tert-butyl ester (500 mg, 1.67 mmol) in THF (5 mL) at 0° C. was added LiAlH$_4$ (3 mL, 1M in THF) drop wise. The resulting mixture was allowed to stir for 2.5 h then quenched with H$_2$O (0.1 mL), 20% aq. NaOH (0.1 mL) and H$_2$O (0.3 mL). The mixture was diluted with EtOAc and H$_2$O, filtered through Celite® then the organic layer separated, dried (Na$_2$SO$_4$) and concentrated in vacuo. The resulting residue was purified by column chromatography (Si—PCC, MeOH:DCM, 0-10%) affording the title compound as a colourless oil (217 mg, 50%). $^1$H NMR (CDCl$_3$, 400 MHz): δ 5.30 (1H, brd s), 3.42 (6H, m), 3.35 (4H, brd s), 2.51 (6H, brd s), 1.03 (9H, s)

Example 41c

2-Methyl-2-piperazin-1-ylpropan-1-ol

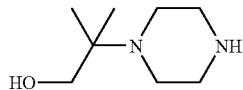

To a solution of 4-(2-hydroxy-1,1-dimethylethyl)piperazine-1-carboxylic acid tert-butyl ester (110 mg, 0.43 mmol) in DCM (3 mL) was added TFA (1 mL) and the resulting mixture stirred for 3 h. The reaction mixture was loaded onto an Isolute® SCX-2 cartridge which was washed with MeOH/DCM and the product eluted with 2M NH$_3$/MeOH affording the title compound as an off-white solid (62 mg, 91%). $^1$H NMR (CDCl$_3$, 400 MHz): δ 3.32 (2H, s), 2.90 (5H, t, J=4.78 Hz), 2.38-2.13 (4H, m), 1.03 (6H, s)

Example 41d

7-Oxetan-3-yl-4,7-diazaspiro[2.5]octane

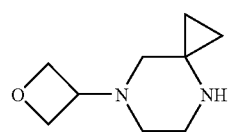

and MeOH. The product was eluted with 2M NH$_3$/MeOH affording the title compound (800 mg, 90%). LCMS (method A): R$_T$ 0.29 min [M+H]$^+$ 193.3

Step 1

7-Oxetan-3-yl-4,7-diazaspiro[2.5]octane-4-carboxylic acid benzyl ester

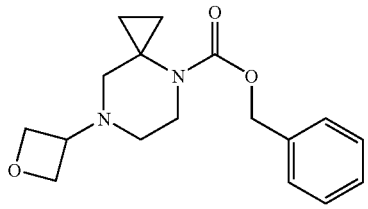

A mixture of 4,7-diazaspiro[2.5]octane-4-carboxylic acid benzyl ester oxalate (200 mg, 0.59 mmol), oxetan-3-one (50 mg, 0.69 mmol), NEt$_3$ (82 μL, 0.59 mmol) and 4 Å powdered molecular sieves (1.0 g) in DCE (10 mL) was stirred at r.t. for 2 h before the addition of sodium triacetoxyborohydride (164 mg, 0.78 mmol). The resulting mixture was stirred for 68 h then loaded onto an Isolute® SCX-2 cartridge which was washed with MeOH and the product eluted with 2M NH$_3$/MeOH affording the title compound. LCMS (method H): R$_T$ 2.01 min, [M+H]$^+$ 303.3

Step 2: 7-Oxetan-3-yl-4,7-diazaspiro[2.5]octane

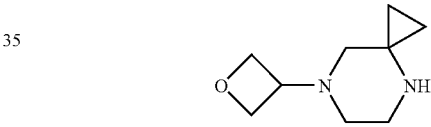

To a solution of 7-oxetan-3-yl-4,7-diazaspiro[2.5]octane-4-carboxylic acid benzyl ester in IMS (3 mL) was added 10% Pd/C (60 mg) and the resulting mixture stirred under an atmosphere of H$_2$ at r.t. for 20 h. The reaction mixture was filtered through Celite® and the filtrate loaded onto an Isolute® SCX-2 cartridge which was washed with MeOH and the product eluted with 2M NH$_3$/MeOH affording the title compound (90 mg, 90%). $^1$H NMR (CDCl$_3$, 400 MHz): δ 4.63-4.63 (2H, m), 3.50-3.42 (2H, m), 3.00-2.98 (2H, m), 2.35-2.25 (2H, m), 2.15 (2H, s), 2.05-2.03 (2H, m), 0.68-0.63 (2H, m), 0.52-0.51 (2H, m)

Example 41e

1-Azetidin-3-yl-2-methylpropan-1-ol

i) 3-(Methoxymethylcarbamoyl)azetidine-1-carboxylic acid tert-butyl ester

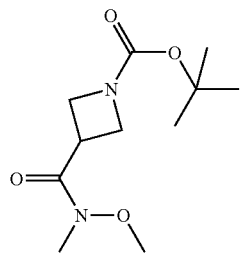

A mixture of N,O-dimethylhydroxylamine hydrochloride (773 mg, 7.93 mmol) and diisopropylethylamine (1.38 mL, 7.93 mmol) in dichloromethane (5 mL) was added to a mixture of azetidine-1,3-dicarboxylic acid mono-tert-butyl ester (1.0 g, 5.30 mmol) and N-(3-dimethylaminopropyl)-N'-ethylcarbodiimide hydrochloride (1.27 g, 6.63 mmol) in dichloromethane (10 mL) The resulting reaction mixture was stirred at RT under nitrogen atmosphere for 16 h. The organic phase was washed with water (1×25 mL), 10% aqueous citric acid solution (2×25 mL), brine (1×30 mL), and dried over sodium sulphate. The solvents were reduced in vacuo to afford the title compound as pale yellow oil (1.06 g, 82%). $^1$H NMR (400 MHz, CDCl$_3$): δ 4.14 (2H, m), 4.05 (2H, t, J=8.72 Hz), 3.66 (4H, s), 3.20 (3H, s), 1.43 (9H, s).

ii) 3-(Isobutyryl)azetidine-1-carboxylic acid tert-butyl ester

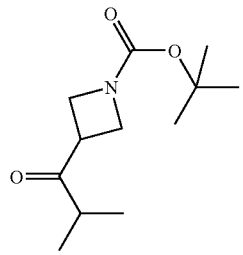

A solution of 3-(methoxymethylcarbamoyl)azetidine-1-carboxylic acid tert-butyl ester (1.06 g, 4.34 mmol) in anhydrous tetrahydrofuran (15 mL) was cooled to 4° C. under argon gas. 2M solution of isopropyl magnesium chloride (4.35 mL, 8.68 mmol) was added dropwise and the resulting reaction mixture was stirred at 4° C. for 5 min. The temperature was allowed to rise to RT and stirred for 1 h then the mixture was stirred at 40° C. for 1 h. The reaction mixture was quenched by addition of a saturated solution of ammonium chloride (5 mL) and water (10 mL). The aqueous phase was extracted with ethyl acetate (3×20 mL). The organic layer was dried over sodium sulfate, filtered and the solvents reduced in vacuo to afford the title compound as a pale yellow oil (950 mg, 96%) $^1$H NMR (400 MHz, CDCl$_3$): δ 4.03-4.01 (4H, m), 3.59-3.59 (1H, m), 2.61-2.61 (1H, m), 1.43 (9H), 1.11 (6H, d, J=6.94 Hz).

iii) 3-(1-Hydroxy-2-methylpropyl)azetidine-1-carboxylic acid tert-butyl ester

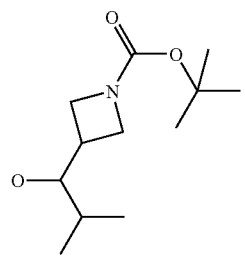

Sodium borohydride (237 mg, 6.26 mmol) was added to a solution of 3-(isobutyryl)azetidine-1-carboxylic acid tert-butyl ester (0.95 g, 4.18 mmol) in ethanol (7.5 mL). The resulting reaction mixture was stirred at RT for 2 h. Saturated hydrogen carbonate (25 mL) was added and the resulting mixture was stirred for further 15 min. The aqueous phase was extracted with dichloromethane (3×25 mL). The organic layer was dried over sodium sulfate and the solvents reduced in vacuo to give the crude product as yellow oil. The residue was purified by column chromatography (Si—PCC, ethyl acetate: cyclohexane: gradient 0:100 to 40:60). The solvents were reduced in vacuo to afford the title compound as colourless oil (840 mg, 88%). $^1$H NMR (400 MHz, CDCl$_3$): δ 3.91-3.90 (3H, m), 3.71 (1H, dd, J=8.54, 6.04 Hz), 3.51 (1H, dd, J=7.21, 4.97 Hz), 2.70-2.63 (1H, m), 1.65-1.63 (1H, m), 1.44 (9H, s), 0.90 (6H, t, J=6.59 Hz).

iv) Trifluoroacetic acid (3 mL) was added to a solution of 3-(1-hydroxy-2-methylpropyl)azetidine-1-carboxylic acid tert-butyl ester (0.84 g, 3.66 mmol) in dichloromethane (12 mL). The resulting reaction mixture was stirred at RT for 40 min. The solvents were reduced in vacuo. The resulting residue was loaded onto an Isolute® SCX-2 cartridge (5 g). The cartridge was washed with DCM/MeOH, the desired product was subsequently eluted using a mixture of 2M NH$_3$ in MeOH and DCM. The solvents were reduced in vacuo to afford 1-Azetidin-3-yl-2-methylpropan-1-ol as a white solid (0.42 g, 88%). $^1$H NMR (400 MHz, CDCl$_3$): δ 3.63-3.62 (3H, m), 3.53-3.51 (2H, m), 2.88-2.87 (1H, m), 1.62-1.62 (1H, m), 0.89 (6H, dd, J=6.84, 4.72 Hz)

Example 41f (Azetidin-3-ylmethyl)methyl(tetrahydrofuran-3-yl)amine

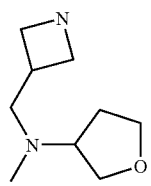

i) 3-{[Methyl(tetrahydrofuran-3-yl)-amino]methyl}azetidine-1-carboxylic acid tert-butyl ester

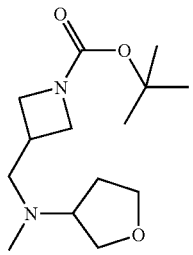

A mixture of 3-ethylaminomethyl-azetidine-1-carboxylic acid tert-butyl ester (200 mg, 1.0 mmol), dihydrofuran-3-one (0.155 mL, 2.0 mmol), diisopropylethylamine (0.347 mL, 2.0 mmol) and 4 Å molecular sieves (600 mg) in DCM (10 mL) was stirred at RT for 30 min. Sodium triacetoxyborohydride (424 mg, 2 mmol) was added and the resulting reaction mixture was stirred at RT under nitrogen atmosphere for 60 h. The suspension was filtered through Celite and the filtrate was concentrated in vacuo. The residue was purified by column chromatography (Si—PPC, MeOH:DCM, gradient 0:100 to 5:95) to afford the title compound as a colourless oil (257 mg, 95%). $^1$H NMR (400 MHz, CDCl$_3$): δ 4.04-3.92 (3H, m), 3.83 (1H, dd, J=8.89, 6.90 Hz), 3.75 (1H, q, J=8.07 Hz), 3.64 (1H, dd, J=8.87, 6.21 Hz), 3.56-3.55 (2H, m), 3.14 (1H, m), 2.67-2.66 (2H, m), 2.51 (1H, dd, J=12.33, 7.20 Hz), 2.17 (3H, s), 2.05 (1H, s), 1.89-1.79 (1H, m), 1.44 (9H, s).

ii) Trifluoroacetic acid (3 mL) was added to a solution of 3-{[methyl(tetrahydrofuran-3-yl)amino]methyl}azetidine-1-carboxylic acid tert-butyl ester (257 mg, 0.95 mmol) in dichloromethane (12 mL). The resulting reaction mixture was stirred at RT for 1.5 h. The solvents were reduced in vacuo. The resulting residue was loaded onto an Isolute® SCX-2 cartridge (5 g). The cartridge was washed with DCM/MeOH, the desired product was subsequently eluted using a mixture of 2M NH$_3$ in MeOH and DCM to afford (Azetidin-3-ylmethyl)methyl(tetrahydrofuran-3-yl)amine as colourless oil (140 mg, 86%). $^1$H NMR (400 MHz, CDCl$_3$): δ 3.94 (1H, td, J=8.62, 4.35 Hz), 3.84 (1H, dd, J=8.76, 6.50 Hz), 3.76-3.65 (3H, m), 3.62 (1H, dd, J=8.76, 6.50 Hz), 3.38 (2H, t, J=7.31 Hz), 3.09-3.07 (1H, m), 2.99-2.88 (1H, m), 2.64 (1H, dd, J=12.50, 7.22 Hz), 2.53 (1H, dd, J=12.50, 7.22 Hz), 2.15 (3H, s), 2.01 (1H, dtd, J=12.34, 7.72, 3.21 Hz), 1.83 (1H, dtd, J=12.35, 8.40, 6.96 Hz)

Example 41g (Azetidin-3-ylmethyl)methyloxetan-3-ylamine

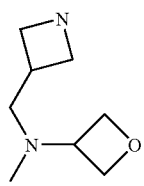

i) 3-[(Methyl(oxetan-3-yl)amino)methyl]azetidine-1-carboxylic acid tert-butyl ester

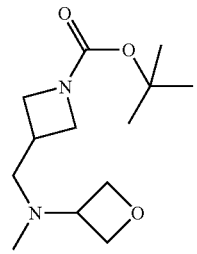

A mixture of 3-(methylamino)methylazetidine-1-carboxylic acid tert-butyl ester (450 mg, 2.25 mmol), oxetan-3-one (135 mg, 1.88 mmol), in dichloromethane (10 mL) was stirred at RT for 1.5 h. Sodium triacetoxyborohydride (797 mg, 3.76 mmol) was added and the resulting reaction mixture was stirred at RT under nitrogen atmosphere for 18 h. The mixture was diluted with water, the phases were separated and the aqueous phase was extracted with EtOAc (2×25 mL). The combined organic layers were dried over sodium sulfate, filtered and the solvents reduced in vacuo The residue was purified by column chromatography (Si—PPC, MeOH:DCM, gradient 0:100 to 5:95) to afford the title compound as a colourless oil (330 mg, 69%). $^1$H NMR (400 MHz, CDCl$_3$): δ 4.64 (2H, t, J=6.58 Hz), 4.57 (2H, t, J=6.26 Hz), 4.01 (2H, t, J=8.40 Hz), 3.57-3.55 (3H, m), 2.71-2.61 (1H, m), 2.41 (2H, d, J=7.57 Hz), 2.08 (3H, s), 1.44 (9H, s).

ii) Trifluoroacetic acid (3 mL) was added to a solution of 3-[(methyl(oxetan-3-yl)amino)methyl]azetidine-1-carboxylic acid tert-butyl ester (330 mg, 1.29 mmol) in dichloromethane (12 mL) The resulting reaction mixture was stirred at RT for 1.5 h. The solvents were reduced in vacuo. The resulting residue was loaded onto an Isolute® SCX-2 cartridge (5 g). The cartridge was washed with DCM/MeOH, the desired product was subsequently eluted using a mixture of 2M NH$_3$ in MeOH and DCM to afford (Azetidin-3-ylmethyl)methyl(oxetan-3-yl)amine as colourless oil (180 mg, 90%). $^1$H NMR (400 MHz, CDCl$_3$): δ 4.64 (2H, t, J=6.59 Hz), 4.57 (2H, t, J=6.31 Hz), 3.72 (2H, t, J=7.87 Hz), 3.58-3.49 (1H, m), 3.37 (2H, t, J=7.22 Hz), 2.92-2.82 (1H, m), 2.44 (3H, m), 2.06 (3H, s)

Example 41h

Azetidin-3-yl-((S)-3-hydroxypyrrolidin-1-yl)methanone

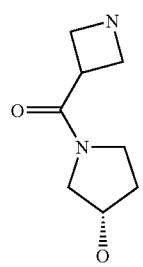

521 i) 3-((S)-3-Hydroxypyrrolidine-1-carbonyl)azetidine-1-carboxylic acid tert-butyl ester

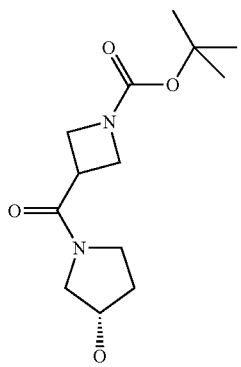

(S)-Pyrrolidin-3-ol (0.276 g, 3.17 mmol) was added to a mixture of azetidine-1,3-dicarboxylic acid mono-tert-butyl ester (0.4 g, 2.11 mmol) and N-(3-dimethylaminopropyl)-N'-ethylcarbodiimide hydrochloride (0.61 g, 3.17 mmol) in dichloromethane (7 mL). The resulting reaction mixture was stirred at RT under nitrogen atmosphere for 48 h. The mixture was diluted with DCM (10 mL) and washed with water (1×15 mL), 10% aqueous citric acid solution (2×15 mL) and brine (2×15 mL), and dried over sodium sulphate. The solvents were reduced in vacuo to afford the title compound as colourless oil (0.46 g, 81%). $^1$H NMR (400 MHz, CDCl$_3$): δ 4.55-4.48 (1 H, m), 4.17 (2 H, s), 4.05-4.04 (2 H, m), 3.50-3.47 (5 H, m), 2.01-2.00 (2 H, m), 1.43 (9 H, d, J=0.96 Hz).

ii) Trifluoroacetic acid (3 mL) was added to a solution of 3-((S)-3-hydroxypyrrolidine-1-carbonyl)azetidine-1-carboxylic acid tert-butyl ester (460 mg, 1.7 mmol) in dichloromethane (12 mL) The resulting reaction mixture was stirred at RT for 2 h. The solvents were reduced in vacuo. The resulting residue was loaded onto an Isolute® SCX-2 cartridge (10 g). The cartridge was washed with DCM/MeOH, the desired product was subsequently eluted using a mixture of 2M NH$_3$ in MeOH and DCM to afford Azetidin-3-yl-((S)-3-hydroxypyrrolidin-1-yl)methanone as colourless oil (243 mg, 84%). $^1$H NMR (400 MHz, DMSO, d$_6$): δ 4.28-4.18 (1 H, m), 3.72-3.17 (10 H, m), 2.11-2.10 (1 H, m), 1.81-1.80 (2 H, m)

Example 41i

Azetidin-3-yl-((R)-3-hydroxypyrrolidin-1-yl)methanone

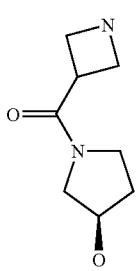

522 i) 3-((R)-3-Hydroxypyrrolidine-1-carbonyl)azetidine-1-carboxylic acid tert-butyl ester

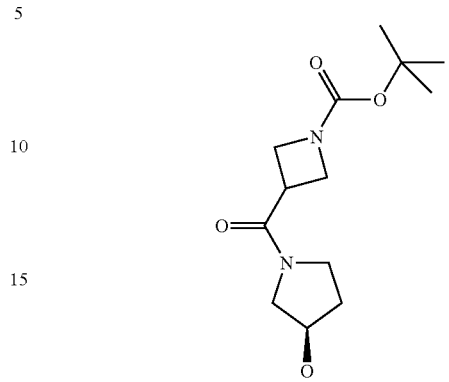

(R)-Pyrrolidin-3-ol (0.276 g, 3.17 mmol) was added to a mixture of azetidine-1,3-dicarboxylic acid mono-tert-butyl ester (0.4 g, 2.11 mmol) and N-(3-dimethylaminopropyl)-N'-ethylcarbodiimide hydrochloride (0.61 g, 3.17 mmol) in dichloromethane (7 mL). The resulting reaction mixture was stirred at RT under nitrogen atmosphere for 18 h. The mixture was diluted with DCM (10 mL) and washed with water (1×15 mL), 10% aqueous citric acid solution (2×15 mL) and brine (2×15 mL), and dried over sodium sulfate. The solvents were reduced in vacuo to afford the title compound as colourless oil (0.42 g, 74%). $^1$H NMR (400 MHz, CDCl$_3$): δ 4.54-4.52 (1 H, m), 4.11-4.09 (4 H, m), 3.50-3.48 (5 H, m), 2.01-2.00 (2 H, m), 1.43 (9 H, d, J=0.78 Hz)

ii) Trifluoroacetic acid (3 mL) was added to a solution of 3-((R)-3-hydroxypyrrolidine-1-carbonyl)azetidine-1-carboxylic acid tert-butyl ester (420 mg, 1.55 mmol) in dichloromethane (12 mL) The resulting reaction mixture was stirred at RT for 2 h. The solvents were reduced in vacuo. The resulting residue was loaded onto an Isolute® SCX-2 cartridge (10 g). The cartridge was washed with DCM/MeOH, the desired product was subsequently eluted using a mixture of 2M NH$_3$ in MeOH and DCM to afford Azetidin-3-yl-((R)-3-hydroxypyrrolidin-1-yl)methanone as colourless oil (225 mg, 85%). $^1$H NMR (400 MHz, DMSO, d$_6$): δ 4.26-4.22 (1 H, m), 3.47-3.44 (10 H, m), 2.13-2.09 (1 H, m), 1.81 (2 H, m)

R$^3$ Reagents:

Example 42

4-Bromo-1H-pyrrolo[2,3-c]pyridine-1-carboxylic acid tert-butyl ester

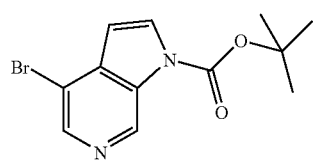

A mixture of 4-bromo-1H-pyrrolo[2,3-c]pyridine (248 mg, 1.26 mmol), di-tert-butyl dicarbonate (302 mg, 1.38 mmol), DMAP (31 mg, 0.25 mmol), triethylamine (140 mg, 1.38 mmol) and acetonitrile (8 mL) were stirred at room temperature for 2.5 h. The reaction mixture was evaporated and the residue was purified by column chromatography (Si—PPC, cyclohexane:EtOAc, gradient 0:100 to 50:50) to give the title compound (316 mg, 84%) as a colorless oil. LCMS (Method C): $R_T$=4.07 min, [M+H−$^t$Bu]$^+$ 241 ($^{79}$Br), 243 ($^{81}$Br)

Example 43

4-Bromo-6-oxypyrrolo[2,3-c]pyridine-1-carboxylic acid tert-butyl ester

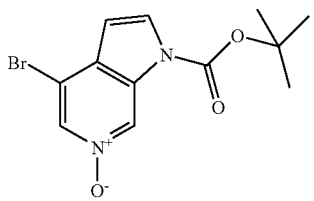

To a solution of 4-bromo-1H-pyrrolo[2,3-c]pyridine-1-carboxylic acid tert-butyl ester (316 mg, 1.06 mmol) in DCM (10 mL) was added a saturated aqueous solution of NaHCO$_3$ (10 mL) and the resulting mixture cooled to 0° C. 3-Chloroperbenzoic acid (70-75% in H$_2$O) (524 mg, 2.13 mmol) was added to the reaction mixture which was allowed to warm to room temperature and stirred for a further 20 h. The mixture was partitioned between water and DCM and the aqueous layer was extracted with DCM (2×10 mL). The combined organic extracts were dried (phase separator) and evaporated to give the title compound as an orange solid (317 mg, 95%). LCMS (Method C): $R_T$ 3.48 min, [M+H]$^+$ 313 ($^{79}$Br), 315 ($^{81}$Br)

Example 44

1-Benzenesulfonyl-4-bromo-2-methyl-1H-pyrrolo[3,2-c]pyridine

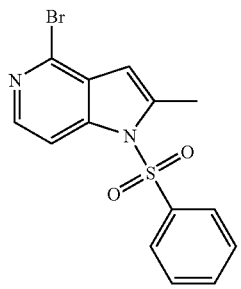

Step 1:
1-Benzenesulfonyl-1H-pyrrolo[3,2-c]pyridine

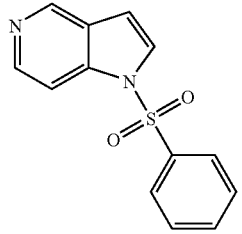

A 100 mL round-bottomed flask was charged with a solution of 1H-pyrrolo[3,2-c]pyridine (1.0 g, 8.4 mmol) in anhydrous THF (50 mL) NaH (60% in mineral oil, 0.41 g, 10.2 mmol) was added and the reaction mixture was stirred for 5 min at room temperature. To this solution was added dropwise, at 0° C., benzenesulfonyl chloride (1.35 mL, 10.2 mmol) and the resulting mixture was stirred at room temperature for 2 h. The reaction mixture was quenched with water (30 mL) and extracted with EtOAc (3×100 mL) The organic layers were combined, dried (Na$_2$SO$_4$) and concentrated in vacuo to give the title compound as a white solid (1.29 g, 55%). $^1$H NMR (DMSO, 300 MHz): δ 8.95 (s, 1 H); 8.49 (d, J=5.8 Hz, 1 H); 8.13-8.05 (m, 2 H); 8.02-7.94 (m, 2 H); 7.79-7.71 (m, 1 H); 7.69-7.59 (m, 2 H); 7.01 (dd, J=3.7, 0.9 Hz, 1 H).

Step 2:
1-Benzenesulfonyl-1H-pyrrolo[3,2-c]pyridine 5-oxide

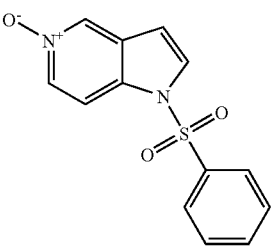

A 100 mL round-bottomed flask was charged with a solution of 1-benzenesulfonyl-1H-pyrrolo[3,2-c]pyridine (0.6 g, 2.3 mmol) in dioxane (20 mL). To the resultant solution was added mCPBA (0.6 g, 3.45 mmol) and the mixture was stirred at room temperature for 30 min. The reaction mixture was concentrated in vacuo then the residue was dissolved in DCM (50 mL), and washed successively with aqueous sodium sulfite solution, aqueous sodium bicarbonate solution and brine. The organic layer was isolated then dried (Na$_2$SO$_4$) and concentrated in vacuo to give the title compound as a white solid (0.6 g, 95%). $^1$HNMR (DMSO, 300 MHz): δ 8.61 (dd, J=1.8, 0.7 Hz, 1 H); 8.13 (dd, J=7.2, 1.8 Hz, 1 H); 8.09-8.04 (m, 2 H); 8.01 (d, J=3.7 Hz, 1 H); 7.92 (d, J=7.2 Hz, 1 H); 7.80-7.73 (m, 1 H); 7.69-7.61 (m, 2 H); 6.83 (dd, J=3.7, 0.8 Hz, 1 H).

Step 3: 1-Benzenesulfonyl-4-bromo-1H-pyrrolo[3,2-c]pyridine

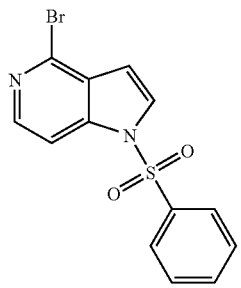

A 250 mL round-bottomed flask, under nitrogen, fitted with a thermometer probe and a condenser/inert gas bubbler (via a Claisen head), was charged with a solution of 1-benzenesulfonyl-1H-pyrrolo[3,2-c]pyridine 5-oxide (3.5 g, 12.8 mmol) in acetonitrile (50 mL) and dioxane (50 mL). To this solution was added dropwise phosphorus oxybromide (12 g, 40.9 mmol) and the resulting mixture was stirred at 70° C. for 18 h. The precipitate formed was removed by filtration and washed several times with dioxane. The solution was concentrated in vacuo and partitioned between DCM, water and brine. The organic layer was isolated then dried ($Na_2SO_4$) and concentrated in vacuo. The resultant residue was purified by flash chromatography (Si—PCC, 0-20% EtOAc in cyclohexane) to give the desired product (3.1 g, 72%). $^1$H NMR ($CDCl_3$, 300 MHz): δ 8.23 (d, J=5.7 Hz, 1 H); 7.94-7.85 (m, 3 H); 7.67-7.59 (m, 2 H); 7.55-7.48 (m, 2 H); 6.75 (dd, J=3.7, 0.8 Hz, 1 H).

Step 4: 1-Benzenesulfonyl-4-bromo-2-methyl-1H-pyrrolo[3,2-c]pyridine

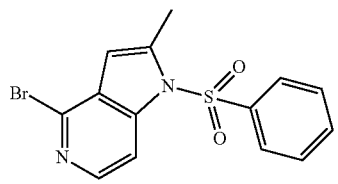

A 50 mL round-bottomed flask, under nitrogen, fitted with a thermometer probe and a condenser/inert gas bubbler (via a Claisen head) was charged with a solution of 1-benzenesulfonyl-4-bromo-1H-pyrrolo[3,2-c]pyridine (0.43 g, 1.27 mmol) in anhydrous THF (8 mL). To the resultant solution, at −35° C., was added dropwise a solution of lithium diisopropylamide (2.0M in heptane/THF/ethyl benzene, 1.27 mL, 2.54 mmol) and the mixture was stirred at −35° C. for 30 min. Methyl iodide (0.48 mL, 7.63 mmol) was added dropwise and solution was allowed to reach room temperature and stirred for 3 h. The reaction was quenched by addition of 1N HCl (3 mL). The solution was diluted with water (7 mL), extracted with EtOAc (2×50 mL). The organic extracts were pooled, was dried ($Na_2SO_4$) and concentrated in vacuo. The resultant residue was purified by flash chromatography (Si—PPC, 0-100% EtOAc:cyclohexane) to give the desired product (0.43 g, 96%) as a white powder. LCMS (Method A) $R_T$=4.67 min, [M+H]$^+$ 351 ($^{79}$Br), 353 ($^{8}$Br)

Example 45

1-Benzenesulfonyl-4-bromo-2-methyl-1H-pyrrolo[2,3-c]pyridine

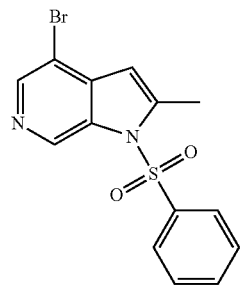

Step 1: 1-Benzenesulfonyl-4-bromo-1H-pyrrolo[2,3-c]pyridine

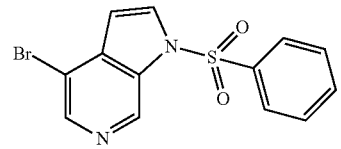

A 50 mL round-bottomed flask was charged with a solution of 4-bromo-1H-pyrrolo[2,3-c]pyridine (0.7 g, 3.55 mmol) in anhydrous DCM (20 mL). NaOH (0.43 g, 10.7 mmol) and benzenetriethylammonium chloride (0.016 g, 0.07 mmol) were added and the reaction mixture was stirred for 3 h at room temperature. The reaction mixture was filtered through Celite®, the Celite bed was washed with DCM and the resulting filtrate was concentrated in vacuo. The resultant solid residue was triturated with diethyl ether and the precipitate collected by filtration to give the title compound as an off-white solid (0.96 g, 80%). LCMS (Method A): $R_T$=4.29min, [M+H]$^+$ 337 ($^{79}$Br), 339 ($^{81}$Br)

Step 2: 1-Benzenesulfonyl-4-bromo-2-methyl-1H-pyrrolo[2,3-c]pyridine

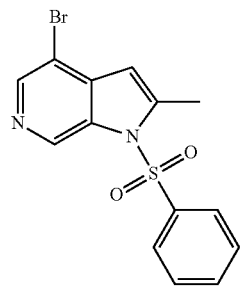

A 50 mL round-bottomed flask, under nitrogen fitted with a thermometer probe, and a condenser/inert gas bubbler (via a Claisen head), was charged with a solution of 1-benzenesulfonyl-4-bromo-1H-pyrrolo[2,3-c]pyridine (0.96 g, 2.84 mmol) in anhydrous THF (10 mL). To the resultant solution, at −35° C., was added dropwise a solution of lithium diisopropylamide (2.0M in heptane/THF/ethyl benzene, 2.84 mL, 5.68 mmol) and the mixture then stirred at −35° C. for 45 min. Methyl iodide (1.06 mL, 17.04 mmol) was added to the reaction mixture dropwise. The resulting solution was allowed to reach room temperature and was stirred for 3 h. The reaction was quenched by addition of a solution of 1N HCl (5 mL); the solution was diluted with water (15 mL) and extracted with EtOAc (2×75 mL). The organic layer was dried (Na$_2$SO$_4$) and concentrated in vacuo. The residue was purified by flash chromatography (Si—PPC, 0-100% DCM: cyclohexane). The residue was triturated with EtOAc (2 mL) and the precipitate was collected by filtration to give the title compound as a white solid (0.39 g, 39%). LCMS (Method A): R$_T$=4.47min, [M+H]$^+$ 351 ($^{79}$Br), 353 ($^{81}$Br)

Example 46

1-Benzenesulfonyl-4-tributylstannanyl-1H-pyrrolo[2,3-c]pyridine

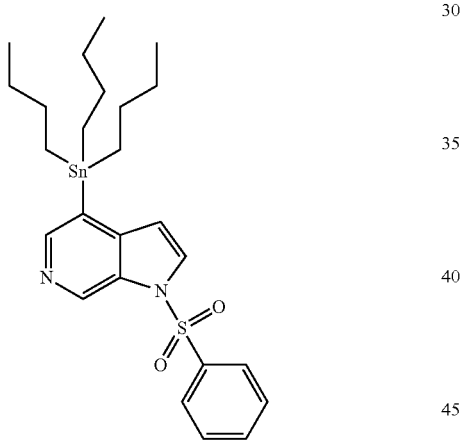

1-Benzenesulfonyl-4-bromo-1H-pyrrolo[2,3-c]pyridine (0.34 g, 1.0 mmol) was dissolved in THF (5 mL) and diethyl ether (5 mL) and the solution cooled to −78° C. n-Butyllithium (0.756 M in hexanes, 1.2 mL, 5.0 mmol) was added over 5 min then the mixture was stirred for 15 min before addition of tributyltin chloride (0.39 g, 1.2 mmol) over 10 min. The reaction mixture was stirred at −78° C. for 1 hour then allowed to warm to room temperature and diluted with cyclohexane (50 mL). The reaction mixture was washed with water (3×30 mL) followed by brine, before the organic phase was dried (MgSO$_4$) and evaporated. The crude residue was purified by chromatography on alumina using 30% EtOAc in cyclohexane. The material was further purified by flash chromatography (Si—PPC), eluting with 5-10% EtOAc in cyclohexane to yield the title product. $^1$H NMR (CDCl$_3$, 300 MHz): δ 9.23 (s, 1H), 8.36 (s, 1H), 7.91-8.00 (m, 2H), 7.71, d, J=1.1 Hz, 1H), 7.55-7.63 (m, 1H), 7.42-7.53 (m, 2H), 6.59 (d, J=1.1 Hz, 1H), 1.45-1.65 (m, 6H), 1.21-1.38 (m, 6H), 1.09-1.20 (m, 6H), 0.85 (t, J=7.5 Hz, 9H).

Example 47

4-Bromo-7-methyl-1H-pyrrolo[2,3-c]pyridine

5-Bromo-2-methyl-3-nitropyridine (217 mg, 1 mmol) was dissolved in THF (10 mL) and the solution was cooled to −50° C. under argon. Vinylmagnesium bromide (3 mL, 1M in THF) was added immediately in one portion, resulting in a bright orange solution. The orange solution was stirred at −40° C. for 30 min and the reaction was quenched by the addition of NH$_4$Cl (10 mL of saturated. aqueous solution). The mixture was diluted with water and extracted with EtOAc (2×10 mL). The combined organic extracts were dried (MgSO$_4$) and concentrated. The crude material was purified by chromatography on silica (Si—PPC) using EtOAc in cyclohexane (20-80%) as eluent to give the product as a pale yellow crystalline solid (63 mg, 30%). $^1$H NMR (CDCl$_3$) 8.23 (s, 1H), 7.41-7,45 (m, 1H), 6.62-6.65 (m, 1H), 2.73 (s, 3H)

Example 48

4-Bromo-6-methyl-1H-pyrrolo[3,2-c]pyridine

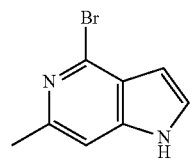

A mixture of 6-methyl-1H-pyrrolo[3,2-c]pyridin-4-ol (J. Het. Chem., 1996, 303) (161 mg, 1.09 mmol) and phosphorus oxybromide (1.87 g, excess) was heated in a sealed tube at 120° C. for 50 minutes. The reaction mixture was poured onto water (10 mL), basified with aqueous NaHCO$_3$ to pH 8 and the organic product extracted into DCM. The organic layer was dried (phase separator), evaporated and the residue purified by column chromatography (Si—PCC, cyclohexane: ethyl acetate, gradient 100:0 to 70:30) to give 4-bromo-6-methyl-1H-pyrrolo[3,2-c]pyridine (20 mg, 12%) as a white solid. LCMS R$_T$=2.00 min, [M+H]$^+$ 211

Example 49

4-Bromo-5-methyl-1H-pyrrolo[2,3-c]pyridine

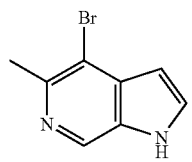

To a stirred suspension of vinylmagnesium bromide (1 M in THF, 37.5 mL, 37.50 mmol) was added dropwise a solution of 3-bromo-2-methyl-5-nitropyridine (2.50 g, 11.52 mmol) in THF, under an atmosphere of nitrogen, at 0° C. The resulting solution was allowed to warm to RT and stirred for 1 day then quenched with saturated $NH_4Cl_{(aq)}$. The resulting mixture was partitioned between EtOAc and water, the organic layer separated, dried ($MgSO_4$) and evaporated to give a red crude oil, which was purified by column chromatography (Si—PCC, 50-100% EtOAc in cyclohexane) followed by reverse phase HPLC (Phenomenex Gemini 5u C18, 0.1% formic acid in water on a gradient of methanol 5-75%). The relevant HPLC fractions were loaded onto an Isolute® SCX-2 cartridge, the cartridge was washed with MeOH and the desired product eluted with 2 M $NH_3$ in MeOH to give the title compound as a pale yellow solid (22 mg, 1%). LCMS (Method H): $R_T$ 2.23 min, $[M+H]^+$ 211.1 ($^{79}Br$), 213.1 ($^{81}Br$)

Example 50

1-Benzenesulfonyl-4-bromo-2-methyl-1H-pyrrolo[2,3-c]pyridine

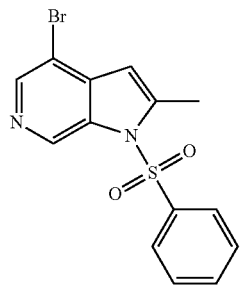

Step 1: 1-Benzenesulfonyl-4-bromo-1H-pyrrolo[2,3-c]pyridine

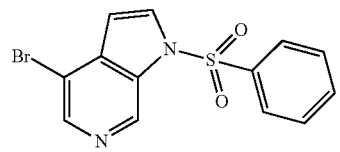

A 50 mL round-bottomed flask was charged with a solution of 4-bromo-1H-pyrrolo[2,3-c]pyridine (0.7 g, 3.55 mmol) in anhydrous DCM (20 mL). NaOH (0.43 g, 10.7 mmol) and benzenetriethylammonium chloride (0.016 g, 0.07 mmol) were added and the reaction mixture was stirred for 3 h at room temperature. The reaction mixture was filtered through Celite, the Celite bed was washed with DCM and the resulting filtrate was concentrated in vacuo. The resultant solid residue was triturated with diethyl ether and the precipitate collected by filtration to give the title compound as an off-white solid (0.96 g, 80%). LCMS (Method A): $R_T$=4.29min, $[M+H]^+$ 337 ($^{79}Br$), 339 ($^{81}Br$)

Step 2: 1-Benzenesulfonyl-4-bromo-2-methyl-1H-pyrrolo[2,3-c]pyridine

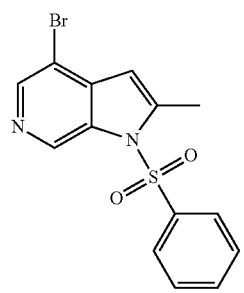

To a solution of 1-benzenesulfonyl-4-bromo-1H-pyrrolo[2,3-c]pyridine (0.96 g, 2.84 mmol) in anhydrous THF (10 mL), at −35° C., was added a solution of lithium diisopropylamide (2.0M in heptane/THF/ethyl benzene, 2.84 mL, 5.68 mmol) dropwise. The mixture was stirred at −35° C. for 45 min and then methyl iodide (1.06 mL, 17.04 mmol) was added dropwise. The resulting solution was allowed to reach room temperature and was stirred for 3 h. The reaction mixture was quenched by addition of an aqueous solution of 1N HCl (5 mL); the solution was diluted with water (15 mL) and extracted with EtOAc (2×75 mL). The organic extracts were combined, dried ($Na_2SO_4$) and concentrated in vacuo. The residue was purified by flash chromatography (Si—PPC, DCM:cyclohexane, gradient 0:100 to 100:0). The residue was triturated in EtOAc (2 mL) and collected by filtration to give the title compound as a white solid (0.39 g, 39%). LCMS (Method A): $R_T$=4.47min, $[M+H]^+$ 351 ($^{79}Br$), 353 ($^{81}Br$)

Example 51

1-Benzenesulfonyl-4-bromo-2-ethyl-1H-pyrrolo[2,3-c]pyridine

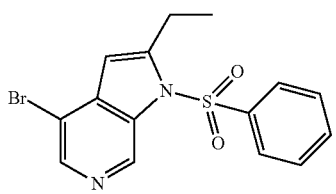

To a solution of 1-benzenesulfonyl-4-bromo-1H-pyrrolo[2,3-c]pyridine (0.63 g, 1.86 mmol) in anhydrous THF (10 mL), at −35° C., was added a solution of lithium diisopropylamide (2.0M in heptane/THF/ethyl benzene, 1.86 mL, 3.77 mmol) dropwise. The reaction mixture was stirred at −35° C. for 30 min and then ethyl iodide (0.90 mL, 11.18 mmol) was added dropwise. The resulting solution was allowed to reach room temperature and was stirred for 4 h. The reaction mixture was quenched by addition of a solution of 1N HCl (5 mL); the solution was diluted with water (15 mL) and extracted with EtOAc (2×75 mL) The organic extracts were combined, washed with brine, dried (Na$_2$SO$_4$) and concentrated in vacuo. The residue was purified by flash chromatography (Si—PPC, EtOAc:cyclohexane 0:100 to 70:30). The residue was triturated in EtOAc (2 mL) and collected by filtration to give the title compound as a white solid (0.27 g, 40%). LCMS (Method H): R$_T$=4.65 min, [M+H]$^+$ 367 ($^{79}$Br), 369 ($^{81}$Br)

Example 52

5-Bromo-8-methylimidazo[1,2-a]pyridine

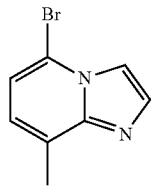

Step 1: 2-Bromo-5-methylpyridine 1-oxide

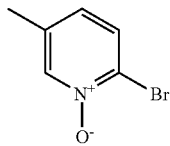

A mixture of 2-bromo-5-methylpyridine (2.0 g, 11.6 mmol) and 3-chloroperbenzoic acid (3.0 g, 14.8 mmol) in chloroform (7 mL) was stirred at 50° C. for 3 hours, cooled down to room temperature and filtered. The filtrate was concentrated under reduced pressure to give a residue that was purified by flash chromatography (Si—PPC, MeOH:EtOAc, gradient 0:100 to 10:90) to give 2-Bromo-5-methylpyridine 1-oxide as a white solid (2.0 g, 91%). $^1$H NMR (400 MHz, CHCl$_3$-d): δ 8.24 (s, 1 H); 7.52 (d, J=8.3 Hz, 1 H); 6.93 (d, J=8.33 Hz, 1 H); 2.29 (s, 3 H).

Step 2: (6-Bromo-3-methylpyridin-2-yl)-tert-butylamine

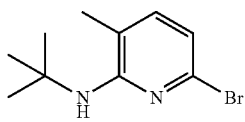

To a solution of 2-bromo-5-methylpyridine 1-oxide (2.0 g, 10.6 mmol) in DCM (40 mL) and trifluorobenzene (17 mL) at 0° C. were added tert-butylamine (8.0 mL, 76.7 mmol) and p-toluenesulfonic anhydride (11.4 g, 35.0 mmol) portionwise. The reaction mixture was stirred at 0° C. for 1.5 hours and then filtered. The filtrate was concentrated to give a residue that was purified by flash chromatography (Si—PPC, Et$_2$O:pentane, gradient 0:100 to 100:0) to give (6-Bromo-3-methylpyridin-2-yl)-tert-butylamine as a colourless oil (500 mg, 19%). $^1$H NMR (400 MHz, CHCl$_3$-d): δ 6.98 (d, J=7.5 Hz, 1 H); 6.59 (d, J=7.5 Hz, 1 H); 4.05 (s, 1 H); 1.96 (s, 3 H); 1.47 (s, 9 H).

Step 3: 6-Bromo-3-methylpyridin-2-ylamine

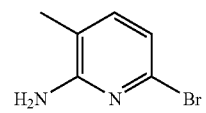

A solution of (6-bromo-3-methylpyridin-2-yl)-tert-butylamine (500 mg, 2.06 mmol) in DCE (2 mL) and TFA (2 mL) was heated at 120° C. for 10 min in a microwave reactor, and then concentrated under reduced pressure. The residue was taken up in MeOH and loaded onto an Isolute® SCX-2 cartridge (10 g). The cartridge was washed with MeOH then the desired product eluted with 2 M NH$_3$ in MeOH to give 6-Bromo-3-methylpyridin-2-ylamine as a white solid (359 mg, 93%). $^1$H NMR (400 MHz, CHCl$_3$-d): δ 7.11 (d, J=7.5 Hz, 1 H); 6.77 (d, J=7.5 Hz, 1 H); 4.50 (s, 2 H); 2.07 (s, 3 H).

Step 4: A mixture of 6-bromo-3-methylpyridin-2-ylamine (359 mg, 1.92 mmol) and chloroacetaldehyde (1 mL, 50 wt. % in water) in IMS (4 mL) was stirred at 100° C. in a sealed tube for 1.5 hours, then cooled to room temperature and loaded onto an Isolute® SCX-2 cartridge (10 g). The cartridge was washed with MeOH then eluted with 2 M NH$_3$ in MeOH to give 5-Bromo-8-methylimidazo[1,2-a]pyridine as a beige solid (387 mg, 95%). $^1$H NMR (400 MHz, CHCl$_3$-d): δ 7.79 (d, J=1.3 Hz, 1 H); 7.69 (d, J=1.3 Hz, 1 H); 6.96 (d, J=7.3 Hz, 1 H); 6.91 (dq, J=7.3, 1.1 Hz, 1 H); 2.61 (d, J=1.1 Hz, 3 H).

Example 53

5-Bromo-6-fluoroimidazo[1,2-a]pyridine

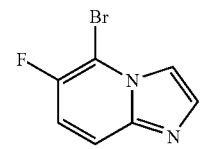

Step 1: 2-Bromo-3-fluoropyridine 1-oxide

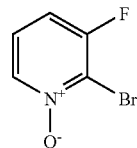

A mixture of 2-bromo-3-fluoropyridine (1.0 g, 5.7 mmol) and 3-chloroperbenzoic acid (1.5 g, 7.4 mmol) in chloroform (3.5 mL) was stirred at 50° C. for 18 hours, cooled down to room temperature and filtered. The filtrate was concentrated under reduced pressure to give a residue that was purified by flash chromatography (Si—PPC, MeOH:EtOAc, gradient 0:100 to 5:95) to give 2-Bromo-3-fluoropyridine 1-oxide as a white solid (878 mg, 80%). ¹H NMR (400 MHz, CHCl₃-d): δ 8.25 (dt, J=6.6, 1.3 Hz, 1H); 7.25-7.17 (m, 1 H); 7.06 (ddd, J=8.7, 6.6, 1.3 Hz, 1 H).

Step 2:
(6-Bromo-5-fluoropyridin-2-yl)-tert-butylamine

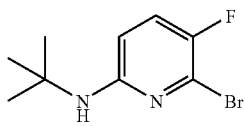

To a solution of 2-bromo-3-fluoropyridine 1-oxide (511 mg, 2.7 mmol) in DCM (10 mL) and trifluorobenzene (4 mL) at 50° C. were added tert-butylamine (2.5 mL, 23.9 mmol) and p-toluenesulfonic anhydride (3.7 g, 11.4 mmol) portionwise. The reaction mixture was stirred at 50° C. for 2 hours and then filtered. The filtrate was concentrated to give a residue that was purified by flash chromatography (Si—PPC, Et₂O:pentane, gradient 0:100 to 5:95) to give (6-Bromo-5-fluoropyridin-2-yl)-tert-butylamine as a colourless oil (30 mg, 5%). ¹H NMR (400 MHz, CHCl₃-d): δ 7.13 (dd, J=8.8, 7.3 Hz, 1 H); 6.29 (dd, J=8.8, 2.5 Hz, 1 H); 4.49 (s, 1 H); 1.40 (s, 9 H).

Step 3: 6-Bromo-5-fluoropyridin-2-ylamine

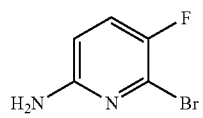

A solution of (6-bromo-5-fluoropyridin-2-yl)-tert-butylamine (46 mg, 0.19 mmol) in DCE (2 mL) and TFA (2 mL) was heated at 120° C. for 10 min in a microwave reactor, and then concentrated under reduced pressure. The residue was taken up in MeOH and loaded onto an Isolute® SCX-2 cartridge (5 g). The cartridge was washed with MeOH then the desired product eluted with 2 M NH₃ in MeOH to give 6-Bromo-5-fluoropyridin-2-ylamine as an off-white solid (25 mg, 71%). ¹H NMR (400 MHz, CHCl₃-d): δ 7.21 (dd, J=8.7, 7.2 Hz, 1 H); 6.39 (dd, J=8.7, 2.7 Hz, 1 H); 4.89-3.75 (s, 2 H).

Step 4: A mixture of 6-bromo-5-fluoropyridin-2-ylamine (25 mg, 0.13 mmol) and chloroacetaldehyde (0.1 mL, 50 wt. % in water) in IMS (2 mL) was stirred at 100° C. in a sealed tube for 18 hours, then cooled to room temperature and loaded onto an Isolute® SCX-2 cartridge (5 g). The desired product was washed with MeOH then eluted with 2 M NH₃ in MeOH to give 5-Bromo-6-fluoroimidazo[1,2-a]pyridine as a yellow oil (25 mg, 89%). ¹H NMR (400 MHz, CHCl₃-d): δ 7.84 (s, 1 H); 7.76 (m, 1 H); 7.61 (ddd, J=9.73, 4.67, 0.71 Hz, 1 H); 7.21-7.16 (m, 1 H).

Example 54

5-Bromo-7-methyl-imidazo[1,2-a]pyridine

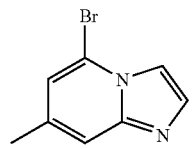

A mixture of 6-bromo-4-methyl-pyridin-2-ylamine (374 mg, 2.0 mmol) and chloroacetaldehyde (1 mL, 50 wt. % in water) in IMS (4 mL) was stirred at 100° C. in a sealed tube for 18 hours, then cooled to room temperature and loaded onto an Isolute® SCX-2 cartridge (10 g). The cartridge was washed with MeOH then the product was eluted with 2 M NH₃ in MeOH. After the solvents were removed, the residue was purified by flash chromatography (Si—PPC, MeOH:DCM, gradient 0:100 to 5:95) to give 5-Bromo-7-methyl-imidazo [1,2-a]pyridine as an orange solid (340 mg, 82%). ¹H NMR (400 MHz, CHCl₃-d): δ 7.72-7.70 (m, 1 H); 7.63-7.62 (m, 1 H); 7.38-7.37 (m, 1 H); 6.92-6.90 (m, 1 H); 2.40 (m, 3 H).

Example 55

5-Bromo-2-methylimidazo[1,2-a]pyridine

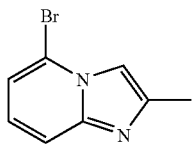

A mixture of 6-bromopyridin-2-ylamine (1.0 g, 5 6 mmol) and 1-chloropropan-2-one (0.5 mL, 6.3 mmol) in IMS (4 mL) was stirred at reflux for 36 hours, then cooled to room temperature and loaded onto an Isolute® SCX-2 cartridge (20 g). The cartridge was washed with MeOH then the desired product eluted with 2 M NH₃ in MeOH. After the solvents were removed, the residue was purified by flash chromatography (Si—PPC, MeOH:Et₂O, gradient 0:100 to 10:100) to give 5-Bromo-2-methylimidazo[1,2-a]pyridine as a yellow oil (547 mg, 45%). LCMS (Method H): R$_T$=0.31 min and 2.04 min, [M+H]⁺ 211(⁷⁹Br) and 213(⁸¹Br)

Example 56

5-bromo-[1,2,4]triazolo[4,3-a]pyridine

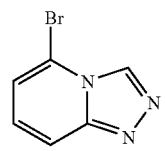

Step 1: (6-Bromopyridin-2-yl)hydrazine

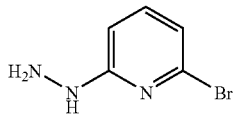

A mixture of 2,6-dibromopyridine (1.44 g, 6.1 mmol) and hydrazine (1.65 mL, 32.2 mmol) in butanol (100 mL) was stirred at reflux for 18 hours. The reaction mixture was cooled to room temperature and concentrated under reduced pressure. The residue was partitioned between an aqueous saturated solution of sodium bicarbonate and EtOAc. The organic layer was separated and washed with brine, dried over $Na_2SO_4$, filtered and concentrated to give (6-Bromopyridin-2-yl)hydrazine as a white solid (1.0 g, 92%). $^1$H NMR (400 MHz, CHCl$_3$-d): δ 7.36-7.28 (m, 1 H); 6.82 (d, J=7.70 Hz, 1 H); 6.67 (d, J=7.7 Hz, 1 H); 5.97 (s, 1 H); 3.80 (s, 2 H).

Step 2: A solution of (6-bromopyridin-2-yl)hydrazine (500 mg, 2.66 mmol) in diethoxymethyl acetate (2.5 mL) was stirred at room temperature for 18 hours. The reaction mixture was diluted with pentane and filtered. The precipitate was washed with pentane and dried at 50° C. under vacuum for 1 hour to give 5-bromo-[1,2,4]triazolo[4,3-a]pyridine as a beige solid (410 mg, 78%). $^1$H NMR (400 MHz, CHCl$_3$-d): δ 8.98 (s, 1 H); 7.83 (dt, J=9.2, 0.9 Hz, 1 H); 7.22 (dd, J=9.2, 7.0 Hz, 1 H); 7.09 (dd, J=7.0, 0.9 Hz, 1 H).

Example 57

8-Benzyloxy-5-bromo-imidazo[1,2-a]pyridine

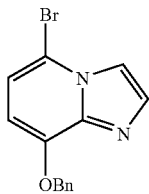

Step 1: 6-Bromo-2-nitropyridin-3-ol

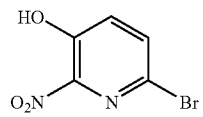

To a suspension of 6-bromopyridin-3-ol (2.5 g, 14.4 mmol) in acetic acid (20 mL) at 0° C. was added fuming nitric acid (0.9 mL, 22.4 mmol). The reaction mixture was stirred at room temperature for 1 hour and then at 60° C. for 1 hour. The reaction mixture was cooled to 0° C. and 10M aqueous hydroxide was added dropwise until pH 4-5 (ca 25 mL) The resulting mixture was diluted with water and partially concentrated under reduced pressure. The residue was extracted twice with EtOAc. The organic fractions were combined and washed with water and brine, dried over $Na_2SO_4$, filtered and concentrated. The residue was azeotroped with toluene to give 6-Bromo-2-nitropyridin-3-ol as an orange solid (2.2 g, 71%). $^1$H NMR (400 MHz, DMSO-d): δ 11.92 (s, 1 H); 7.86-7.83 (d, J=8.6 Hz, 1 H); 7.61 (d, J=8.6 Hz, 1 H).

Step 2: 3-Benzyloxy-6-bromo-2-nitropyridine

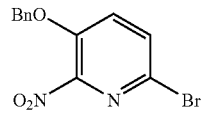

To a solution of 6-bromo-2-nitropyridin-3-ol (1.0 g, 4.6 mmol), in anhydrous DMF (15 mL) at 0° C. was added 60% sodium hydride in mineral oil (200 mg, 5.0 mmol). The reaction mixture was stirred at 0° C. for 5 min and at room temperature for 15 min. Benzyl bromide (0.6 mL, 5.0 mmol) was added dropwise and the resulting mixture was stirred at 60° C. for 1 hour, cooled to room temperature, diluted with water and extracted with EtOAc. The organic layer was separated and washed with water and brine, dried over $Na_2SO_4$, filtered and concentrated. The residue was purified by flash chromatography (Si—PPC, Et$_2$O:pentane, gradient 0:100 to 100:0) to give 3-Benzyloxy-6-bromo-2-nitropyridine as a yellow solid (956 mg, 67%). $^1$H NMR (400 MHz, CHCl$_3$-d): δ 7.60 (d, J=8.6 Hz, 1 H); 7.41-7.35 (m, 6 H); 5.25 (s, 2 H).

Step 3: 3-Benzyloxy-6-bromopyridin-2-ylamine

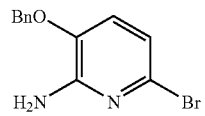

A mixture of 3-benzyloxy-6-bromo-2-nitropyridine (1.6 g, 5.2 mmol) and iron powder (2.9 g, 51.8 mmol) in acetic acid (25 mL) and IMS (25 mL) was stirred at reflux for 1 hour, then cooled to room temperature and filtered though a pad of celite. The filtrate was concentrated under reduced pressure to give a residue that was partitioned between an aqueous saturated solution of sodium bicarbonate and EtOAc. The organic layer was separated and washed with water and brine, dried over $Na_2SO_4$, filtered and concentrated. The residue was purified by flash chromatography (Si—PPC, EtOAc:cyclohexane, gradient 0:100 to 40:60) to give 3-Benzyloxy-6-bromopyridin-2-ylamine as a pale yellow solid (1.0 g, 71%). $^1$H NMR (400 MHz, CHCl$_3$-d): δ 7.41-7.34 (m, 5 H); 6.82 (d, J=8.1 Hz, 1 H); 6.71 (d, J=8.1 Hz, 1 H); 5.04 (s, 2 H); 4.80 (s, 2 H).

Step 4: A mixture of 3-benzyloxy-6-bromopyridin-2-ylamine (1.0 g, 3.6 mmol) and chloroacetaldehyde (1.2 mL, 50 wt. % in water) in IMS (12 mL) was stirred at reflux for 1 hour, then concentrated under reduced pressure. The residue was partitioned between an aqueous saturated solution of sodium bicarbonate and EtOAc. The organic layer was separated and washed with brine, dried over $Na_2SO_4$, filtered and concentrated. The residue was purified by flash chromatography (Si—PPC, MeOH:Et$_2$O, gradient 0:100 to 1:99) to give 8-Benzyloxy-5-bromo-imidazo[1,2-a]pyridine as an beige solid (960 mg, 88%). LCMS (Method H) R$_T$ 3.08 min; [M+H]$^+$ 303 ($^{79}$Br) and 305 ($^{81}$Br)

Example 58

3-Fluoro-2-nitrophenylamine

Step 1: 3-Fluoro-2-nitro-N-(triphenylphosphoranylidene)benzenamine

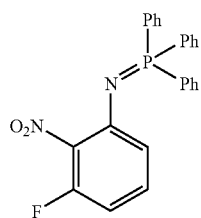

To a solution of 1-azido-3-fluoro-2-nitrobenzene (500 mg, 2.75 mmol) in THF (4 mL) and water (1 mL) was added triphenylphosphine (720 mg, 2.75 mmol). The reaction mixture was stirred at room temperature for 45 min then partitioned between water and EtOAc. The organic layer was separated and washed with brine, dried over Na$_2$SO$_4$, filtered and concentrated. The residue was subjected to flash chromatography (Si—PCC, Et$_2$O) to give the desired product as a yellow solid (844 mg, 73%). LCMS (Method A): R$_T$ 4.36 min; [M+H]$^+$ 417

Step 2: A 2-5 mL microwave vial equipped with a magnetic follower was charged with 3-fluoro-2-nitro-N-(triphenylphosphoranylidene)benzenamine (585 mg, 1.4 mmol), water (3 mL) and TFA (0.1 mL). The reaction mixture was irradiated at 160° C. for 15 min and then partitioned between water and EtOAc. The organic layer was separated and washed with an saturated aqueous solution of sodium bicarbonate and brine, dried over Na$_2$SO$_4$, filtered and concentrated. The residue was subjected to flash chromatography (Si—PCC, 0-100% Et$_2$O in pentane) to give 3-Fluoro-2-nitrophenylamine as an orange solid (218 mg, 100%). $^1$H NMR (CDCl$_3$, 400 MHz): δ 7.22 (ddd, J=8.2, 8.2, 5.5 Hz, 1 H); 6.57 (ddd, J=8.5, 1.4, 1.4 Hz, 1 H); 6.48 (ddd, J=11.3, 8.2, 1.4 Hz, 1 H.

Example 59

2-Methylaminobenzoimidazole-1-carboxylic acid tert-butyl ester

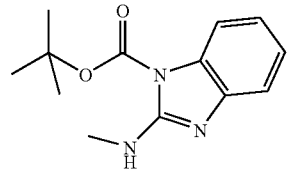

Di-tert-butyl dicarbonate (951 mg, 4.36 mmol) was added to a suspension of (1H-benzoimidazol-2-yl)methylamine (583 mg, 3.96 mmol) in water (5 mL) and the resulting reaction mixture was stirred at 35° C. for 2 h. The mixture was diluted with water and extracted with DCM (2×15 mL) and EtOAc (2×15 mL) The combined organic layers were dried over sodium sulfate, filtered and the solvents reduced in vacuo. The crude residue was purified by column chromatography (Si—PCC, EtOAc:cyclohexane, gradient 0:100 to 30:70) to afford the title compound as a pale-brown solid (720 mg, 74%). $^1$H NMR (400 MHz, CDCl$_3$): δ 7.55 (1 H, d, J=8.04 Hz), 7.38 (1 H, d, J=7.85 Hz), 7.16 (2 H, td, J=7.65, 1.27 Hz), 6.99 (1 H, td, J=7.75, 1.20 Hz), 3.14 (3 H, d, J=4.99 Hz), 1.67 (9 H, s)

Formula I(i) thiazole intermediates wherein (i) X$^1$ is N and X$^2$ is S

Example 65a 4-(5-chloro-2-((3-morpholinoazetidin-1-yl)methyl)thiazolo[5,4-d]pyrimidin-7-yl)morpholine

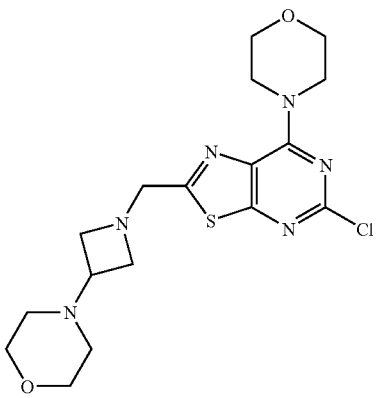

A solution of 5-chloro-7-morpholin-4-yl-thiazolo[5,4-d]pyrimidine-2-carbaldehyde (3.0 g, 10.54 mmol) and 4-azetidin-3-ylmorpholine (1.8 g, 12.66 mmol) in DCE (200 mL) was stirred at ambient temperature for 2 h. Sodium triacetoxyborohydride (3.5 g, 16.5 mmol) was added and the mixture stirred for 18 h, then loaded onto an Isolute® SCX-2 cartridge (50 g). The cartridge was then washed with MeOH and the desired product was subsequently eluted using 2 M NH$_3$ in MeOH. The eluent was collected and concentrated in vacuo. The resultant residue was purified by flash chromatography (Si—PPC, DCM:MeOH 100:0 to 99:1 to 98:2 to 95:5) to afford 4-(5-chloro-2-((3-morpholinoazetidin-1-yl)methyl)thiazolo[5,4-d]pyrimidin-7-yl)morpholine as a cream solid (2.66 g, 61%). LCMS (Method C): R$_T$=2.68 min, [M+H]$^+$ 411.3

Example 65b 2-methyl-2-(4-((7-morpholino-5-(tributylstannyl)thiazolo[5,4-d]pyrimidin-2-yl)methyl)piperazin-1-yl)propanamide

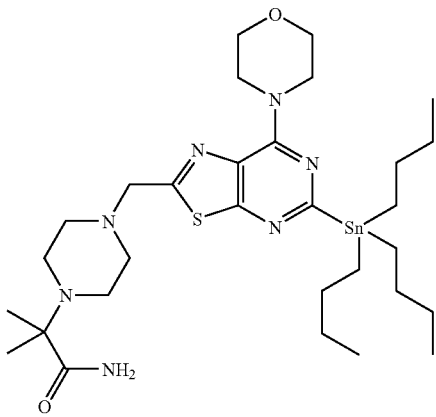

A mixture of 2-[4-(5-chloro-7-morpholin-4-yl-thiazolo[5,4-d]pyrimidin-2-ylmethyl)-piperazin-1-yl]-isobutyramide (1.0 g, 2.2 mmol), hexabutylditin (1.4 mL, 2.7 mmol), and PdCl$_2${P$^t$Bu$_2$(Ph-p-Nme$_2$)}$_2$ (161 mg, 0.2 mmol) in dioxane (10 mL) was degassed and then subjected to microwave irradiation at 150° C. for 30 min. The reaction mixture was diluted with MeOH and loaded onto an Isolute® SCX-2 cartridge (25 g). The cartridge was then washed with MeOH and the desired product was subsequently eluted using 2 M NH$_3$ in MeOH. Appropriate fractions were combined and concentrated to give a residue which was subjected to flash chromatography (Si—PPC, MeOH:DCM, gradient 0:100 to 10:90). Appropriate fractions were combined and concentrated to give 2-methyl-2-(4-((7-morpholino-5-(tributylstannyl)thiazolo[5,4-d]pyrimidin-2-yl)methyl)piperazin-1-yl)propanamide as a yellow oil (1.1 g, 67%). LCMS (Method C) R$_T$=4.83 min; [M+H]$^+$ 694.1 ($^{116}$Sn) 696.1 ($^{118}$Sn)

Example 65c

5-Chloro-7-morpholin-4-yl-thiazolo[5,4-a]pyrimidine-2-carbaldehyde

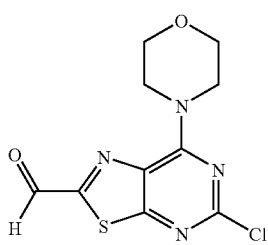

5-Chloro-7-morpholin-4-yl-thiazolo[5,4-d]pyrimidine (5.1 g, 0.02 mol) was suspended in THF (200 mL) and the resulting solution was cooled to −78° C. whereupon the starting material precipitated from solution. LiHMDS (1M in THF, 25 mL, 1.25 equiv) was added dropwise to the stirred suspension. After addition was complete, the mixture was stirred for 30 min, then DMF (9 mL, 6 equiv) was added and the resulting solution was stirred for 15 min at −78° C. and then warmed to 0° C. and stirred for 15 min. The solution was re-cooled to −78° C. and then cannulated (via a wide-bore double-ended needle) into a stirred solution of ~0.5M HCl (600 mL) The product precipitated from solution as a pale yellow powder. This was isolated by filtration through a sintered glass funnel, washed with water and dried in vacuo overnight to give 5 g of 5-Chloro-7-morpholin-4-yl-thiazolo[5,4-d]pyrimidine-2-carbaldehyde (87.7%). $^1$H NMR (400 MHz, CDCl$_3$): δ 3.83-3.88 (m, 4 H), 4.06-4.15 (m, 2 H), 4.72 (m, 2 H) and 9.95 (s, 1 H).

Example 65d

5-Chloro-2-[3-(1,1-Dioxo-1-thiomorpholin-4-yl)azetidin-1-ylmethyl]-7-morpholin-4-ylthiazolo[5,4-d]pyrimidine

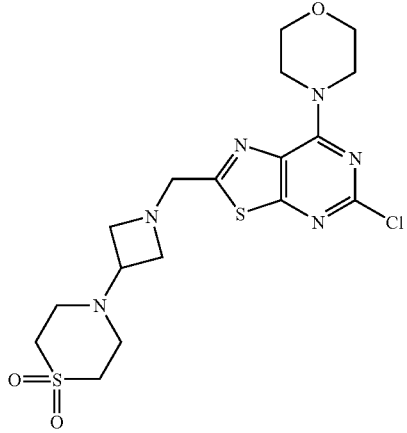

A mixture of 5-chloro-7-morpholin-4-yl-thiazolo[5,4-d]pyrimidine-2-carbaldehyde (400 mg, 1.40 mmol), 4-azetidin-3-ylthiomorpholine-1,1-dioxide (321 mg, 1.69 mmol) and 4 Å powdered molecular sieves (600 mg) in DCE (20 mL) was stirred at room temperature for 4 h before the addition of sodium triacetoxyborohydride (595 mg, 2.80 mmol). The reaction mixture was stirred for 65 h then filtered through celite, washing with DCM. The organic phase was washed with brine (×1) and concentrated in vacuo affording 5-Chloro-2-[3-(1,1-Dioxo-1-thiomorpholin-4-yl)azetidin-1-ylmethyl]-7-morpholin-4-ylthiazolo[5,4-d]pyrimidine as an orange powder (572 mg, 89%). LCMS (Method H): R$_T$ 2.43 min [M+H]$^+$ 459.2

Example 65e

5-Chloro-7-morpholin-4-yl-2-[3-(tetrahydropyran-4-yl)azetidin-1-ylmethyl]thiazolo[5,4-d]pyrimidine

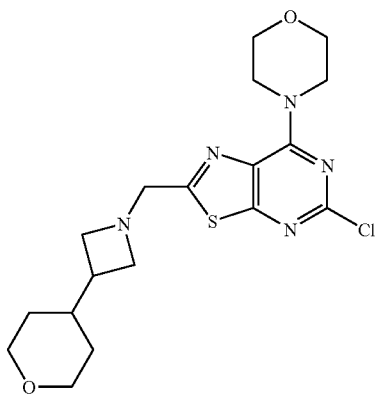

A mixture of 5-chloro-7-morpholin-4-yl-thiazolo[5,4-d]pyrimidine-2-carbaldehyde (650 mg, 2.28 mmol), 3-(tetrahydropyran-4-yl)azetidine (313 mg, 2.22 mmol) and 4 Å powdered molecular sieves (1.2 g) in DCE (40 mL) was stirred at room temperature for 4 h before the addition of sodium triacetoxyborohydride (941 mg, 4.44 mmol). The reaction mixture was stirred for 24 h then filtered through celite, washing with DCM. The organic phase was washed with brine (×1) and concentrated in vacuo. The residue was purified by column chromatography (Si—PCC, MeOH:EtOAc, 0-20%) affording 5-Chloro-7-morpholin-4-yl-2-[3-(tetrahydropyran-4-yl)azetidin-1-ylmethyl]thiazolo[5,4-a]pyrimidine as an orange powder (630 mg, 67%). LCMS (Method A): $R_T$ 2.54 min [M+H]$^+$ 410.2

Example 65f

2-[1-(5-Chloro-7-morpholin-4-ylthiazolo[5,4-d]pyrimidin-2-ylmethyl)piperidin-4-yl]propan-2-ol

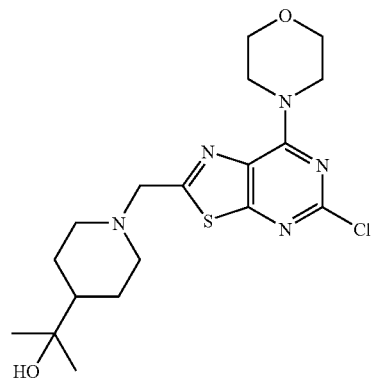

A mixture of 5-chloro-7-morpholin-4-yl-thiazolo[5,4-d]pyrimidine-2-carbaldehyde (5.11 g, 17.9 mmol), 2-piperidin-4-ylpropan-2-ol (3.08 g, 21.5 mmol) and 4 Å powdered molecular sieves (9 g) in DCE (85 mL) was stirred at room temperature for 1.5 h before the addition of sodium triacetoxyborohydride (7.61 g, 35.9 mmol). The reaction mixture was stirred for 90 h then filtered through celite, washing the celite bed with DCM. The organic phase was washed with brine and concentrated in vacuo. The resulting residue was purified by column chromatography (Si—PCC, EtOAc:DCM, 0-100%) affording 2-[1-(5-Chloro-7-morpholin-4-ylthiazolo[5,4-d]pyrimidin-2-ylmethyl)piperidin-4-yl]propan-2-ol as an orange solid (4.96 g, 67%). LCMS (Method A): $R_T$ 2.77 min [M+H]$^+$ 412.2

Example 65g

5-Chloro-2-((E)-2-methoxyvinyl)-7-morpholin-4-yl-thiazolo[5,4-d]pyrimidine

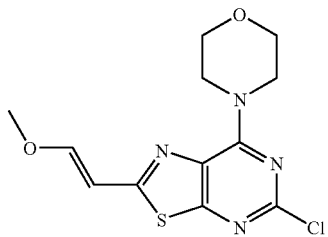

To a stirred suspension of (methoxymethyl)triphenylphosphonium chloride (3.37 g, 9.83 mmol) in dry THF (40 mL) was added dropwise a 1 M solution of LiHMDS in THF (9.8 mL, 9.8 mmol) under an atmosphere of nitrogen, at 0° C. After 15 min the solution was cooled to −78° C. and a suspension of 5-chloro-7-morpholin-4-yl-thiazolo[5,4-d]pyrimidine-2-carbaldehyde (2.0 g, 7.02 mmol) in dry THF (40 mL) was added. The mixture was allowed to warm to RT after 5 min, stirred for a further 1.5 h then quenched with H$_2$O. The resulting precipitate was filtered, washed with EtOAc and dried under vacuum to give 5-chloro-2-((E)-2-methoxyvinyl)-7-morpholin-4-yl-thiazolo[5,4-a]pyrimidine (730 mg, 33%) as a pale yellow solid. $^1$H NMR (CDCl$_3$, 300 MHz): δ 7.48 (d, J=12.8 Hz, 1 H), 6.01 (d, J=12.8 Hz, 1 H), 4.44-4.24 (br s, 4 H), 3.83 (m, 4 H), 3.79 (s, 3 H).

Example 65h

2-{1-[2-(5-Chloro-7-morpholin-4-yl-thiazolo[5,4-d]pyrimidin-2-yl)ethyl]piperidin-4-yl}propan-2-ol

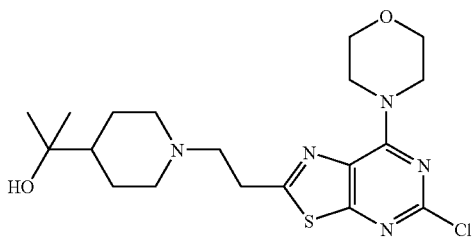

5-Chloro-2-((E)-2-methoxyvinyl)-7-morpholin-4-yl-thiazolo[5,4-d]pyrimidine (730 mg, 2.33 mmol) was stirred in 37 wt. % HCl$_{(aq)}$/THF (4:8 mL) at 50° C. for 2 h. The solution was allowed to cool, partitioned between EtOAc and saturated NaHCO$_3$ $_{(aq)}$, the organic layer separated and washed with brine. The organic layer was dried (Na$_2$SO$_4$) and concentrated in vacuo to give a residue (1.4 g), which was taken up in DCE (30 mL). 2-Piperidin-4-ylpropan-2-ol (300 mg, 2.10 mmol) and powdered 4 Å molecular sieves were then added. The reaction mixture was stirred at room temperature for 5 h, sodium triacetoxyborohydride (900 mg, 4.25 mmol) was added and the resulting mixture stirred for a further 18 h. The reaction mixture was loaded onto an Isolute® SCX-2 cartridge, washed with MeOH then the desired product eluted with 2 M NH$_3$ in MeOH. The resulting residue was purified by column chromatography (Si—PCC, 0-10% MeOH in DCM) to give the title compound as an orange solid (120 mg, 12% over 2 steps). LCMS (Method H): R$_T$=2.55 min, [M+H]$^+$ 426.5

Example 65j

N1-(7-morpholino-2-((3-morpholinoazetidin-1-yl)methyl)thiazolo[5,4-d]pyrimidin-5-yl)benzene-1,2-diamine

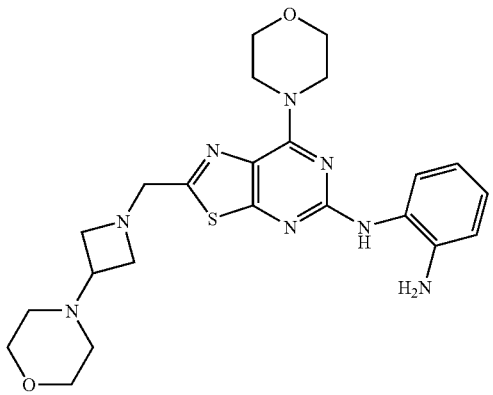

A mixture of 5-chloro-7-morpholin-4-yl-2-(3-morpholin-4-ylazetidin-1-ylmethyl)-thiazolo[5,4-d]pyrimidine (500 mg, 1.22 mmol), 1,2-diaminobenzene (300 mg, 2.77 mmol), palladium acetate (80 mg, 0.36 mmol), BINAP (110 mg, 0.18 mmol) and cesium carbonate (600 mg, 1.84 mmol) in 1,4-dioxane (5 mL)) was purged with argon gas then subjected to microwave irradiation at 150° C. for 30 min. The reaction mixture was loaded onto an Isolute® SCX-2 cartridge (25 g), washed with MeOH before the desired product was eluted using 2 M NH$_3$ in MeOH. The product was collected and concentrated in vacuo. The resultant residue was purified by flash chromatography (Si—PPC, DCM:2 M NH$_3$ in MeOH 100:0 to 99:1 to 98:2 to 97:3) to afford N1-(7-morpholino-2-((3-morpholinoazetidin-1-yl)methyl)thiazolo[5,4-d]pyrimidin-5-yl)benzene-1,2-diamine as a white solid (283 mg, 48%). LCMS (Method H): R$_T$=2.40 min, [M+H]$^+$ 483.

Example 65i 2-(5-Chloro-7-morpholin-4-yl-thiazolo[5,4-d]pyrimidin-2-yl)1-[4-(1-hydroxy-1-methylethyl)piperidin-1-yl]ethanone

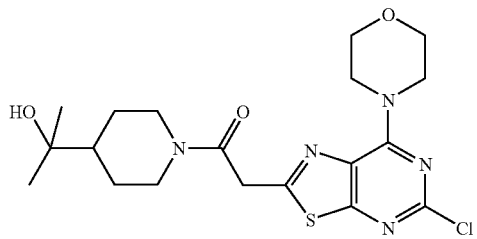

To a stirred solution of 5-chloro-2-methyl-7-morpholin-4-yl-thiazolo[5,4-d]pyrimidine (500 mg, 1.85 mmol) in THF (30 mL) was added dropwise a 1 M solution of LiHMDS in THF (2.80 mL, 2.80 mmol) under an atmosphere of nitrogen, at −78° C. After 2 h, the solution was poured onto a bed of CO$_{2(s)}$ and the resulting mixture allowed to warm to RT. The mixture was partitioned between DCM and 0.1 M HCl$_{(aq)}$, the organic layer separated, dried (phase separator) and concentrated in vacuo. The resultant crude was purified by flash chromatography (Si—PCC, 0-5% MeOH in DCM) to give a residue (200 mg), a portion of which (58 mg) was taken up in DMF (2 mL) and 2-piperidin-4-ylpropan-2-ol (32 mg, 0.22 mmol), HATU (84 mg, 0.22 mmol) and DIPEA (0.10 mL, 0.55 mmol) were added. The reaction mixture was stirred at RT for 18 h, the mixture was partitioned between EtOAc and water, the organic layer dried (MgSO$_4$) and evaporated to give a dark orange oil. Purification by column chromatography (Si—PCC, 0-10% MeOH in DCM) gave the title compound (40 mg, 49%) as a dark orange solid. LCMS (Method H): R$_T$ 3.96 min, [M+H]$^+$ 440.4

Example 65k

2-[1-(7-Morpholin-4-yl-5-(tributylstannanyl)thiazolo[5,4-d]pyrimidin-2-ylmethyl)piperidin-4-yl]propan-2-ol

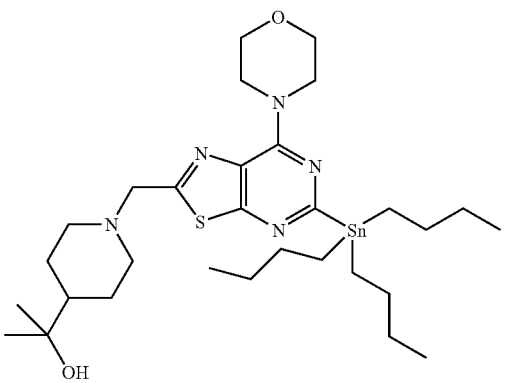

A mixture of 2-[1-(5-chloro-7-morpholin-4-ylthiazolo[5,4-d]pyrimidin-2-ylmethyl)piperidin-4-yl]propan-2-ol (500 mg, 1.21 mmol), hexabutylditin (910 μL, 1.81 mmol), and PdCl$_2${P$^t$Bu$_2$(Ph-p-Nme$_2$)}$_2$ (85 mg, 0.116 mmol) in 1,4-dioxane (5 mL) was purged with argon gas and then subjected to microwave irradiation at 150° C. for 30 min. The reaction mixture was diluted with MeOH and loaded onto an Isolute® SCX -2 cartridge (10 g). The cartridge was then washed with MeOH and the desired product was subsequently eluted using 2 M NH$_3$ in MeOH. The product was collected and concentrated in vacuo. The resultant residue was purified by flash chromatography (Si—PPC, DCM:MeOH; 100:0 to 98:2 to 95:5) to afford to afford the title compound as a yellow solid (681 mg, 84%). $^1$H NMR (CDCl$_3$, 400 MHz) δ 4.31 (m, 4 H); 3.82 (m, 6 H); 3.05 (m, 2 H); 2.16 (m, 2 H); 1.74 (m, 2 H); 1.65-1.54 (m, 7 H); 1.43-1.24 (m, 9 H); 1.19 (s, 6 H); 1.13 (m, 6 H); 0.88 (t, J=7.3 Hz, 9 H)

Example 65m 2-(5-Chloro-7-morpholin-4-ylthiazolo [5,4-d]pyrimidin-2-yl)-1-[4-(2-hydroxy-1,1-dimethylethyl)piperazin-1-yl]ethanone

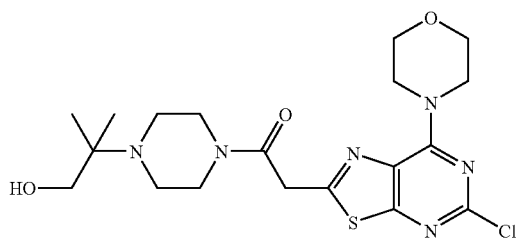

A mixture of (5-chloro-7-morpholin-4-ylthiazolo[5,4-d]pyrimidin-2-yl)acetic acid (80 mg, 0.25 mmol), 2-methyl-2-piperazin-1-ylpropan-1-ol (48 mg, 0.31 mmol), HATU (116 mg, 0.31 mmol) and DIPEA (133 μL, 0.76 mmol) in DMF (3 mL) was stirred at r.t. for 65 h then loaded onto an Isolute® SCX-2 cartridge which was washed with MeOH and the product eluted with 2M NH$_3$/MeOH/DCM. The resulting residue was purified by column chromatography (Si—PCC, MeOH:DCM, 0-10%) affording the title compound as an orange solid (65 mg, 56%). LCMS (method H): R$_T$ 2.02 min [M+H]$^+$ 455.3

Example 65l 4-(5-chloro-2-((4-(oxetan-3-yl)piperidin-1-yl)methyl)thiazolo[5,4-d]pyrimidin-7-yl)morpholine

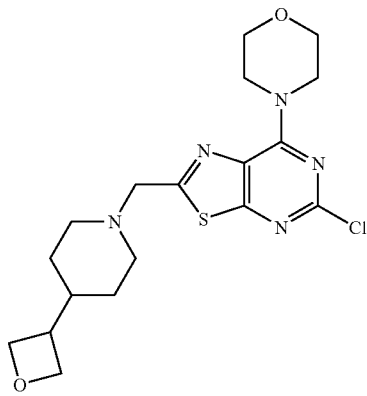

Example 65n 5-(2-Ethylbenzoimidazol-1-yl)-7-morpholin-4-ylthiazolo[5,4-d]pyrimidine

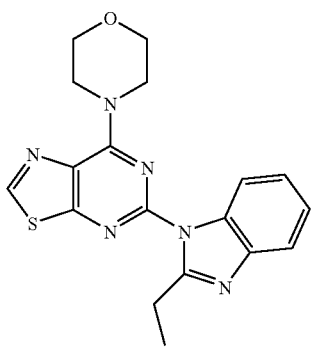

A solution of 5-chloro-7-morpholin-4-ylthiazolo [5,4-d]pyrimidine-2-carbaldehyde (1.0 g, 3.52 mmol), 4-oxetan-3-ylpiperidine (536 mg, 4.23 mmol) and molecular sieves (4 Å, powdered, 6.56 g) in DCE (30 mL) was stirred at ambient temperature for 4 h. Sodium triacetoxyborohydride (1.49 g, 7.05 mmol) was added and the mixture stirred for 6 h, then filtered through a pad of Celite® and the filtrate was concentrated in vacuo. The resultant residue was purified by flash chromatography (Si—PPC, DCM:MeOH; gradient from 100:0 to 97:3) to afford the title compound as a cream solid (334 mg, 41%). LCMS (Method A): R$_T$=2.48 min, M+H$^+$= 410

A mixture of 5-chloro-7-morpholin-4-ylthiazolo[5,4-d]pyrimidine (3.0 g, 11.7 mmol), 2-ethylbenzimidazole (1.88 g, 12.9 mmol), tris(dibenzylideneacetone)dipalladium (534 mg, 0.60 mmol), XPhos (1.11 g, 2.34 mmol) and Cs$_2$CO$_3$ (7.62 g, 23 4 mmol) in dioxane (60 mL) was purged with argon then heated at 120° C. for 16 h in a sealed tube. The reaction mixture was filtered through Celite®, and the filtrated partitioned between EtOAc and H$_2$O. The organic phase was washed with brine, then dried (Na$_2$SO$_4$) and concentrated in vacuo. The resulting residue was purified by column chromatography (Si—PCC, EtOAc:DCM, 0-90%)

followed by recrystallisation from ⁱPrOAc affording the title compound (3.17 g, 74%). LCMS (method A): R$_T$ 2.74 min [M+H]$^+$ 367.1

Example 65o 5-(2-Ethylbenzoimidazol-1-yl)-2-iodo-7-morpholin-4-ylthiazolo[5,4-d]pyrimidine

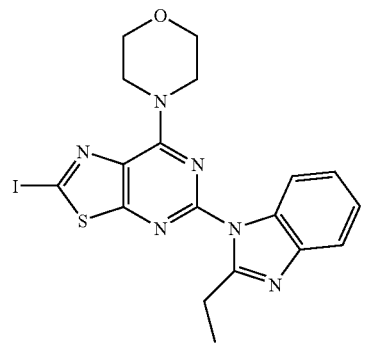

A solution of 5-(2-ethylbenzoimidazol-1-yl)-7-morpholin-4-ylthiazolo[5,4-d]pyrimidine (1.92 g, 5.23 mmol) in THF (60 mL) was cooled to −40° C. before the drop wise addition of LiHMDS (6.3 mL, 6.28 mmol, 1 M solution in THF). The resulting mixture was warmed to −5° C. over 30 min then mixture was cooled back to −30° C. before the addition of a solution of 1-chloro-2-iodoethane (2.0 g, 10.47 mmol) in THF (6 mL) The resulting mixture was allowed to warm to 0° C. then quenched with NH$_4$Cl and extracted with EtOAc. The combined organics were washed with brine then dried (Na$_2$SO$_4$) and concentrated in vacuo. The resulting residue was purified by column chromatography (Si—PCC, EtOAc:DCM, 50-80%) followed by recrystallisation from ⁱPrOAc affording the title compound as a yellow solid (1.58 g, 62%). LCMS (method A): R$_T$ 3.50 min [M+H]$^+$ 493.0

Example 65p (5-Chloro-7-morpholin-4-ylthiazolo[5,4-d]pyrimidin-2-yl)-[4-(1-hydroxy-1-methylethyl)piperidin-1-yl]methanone

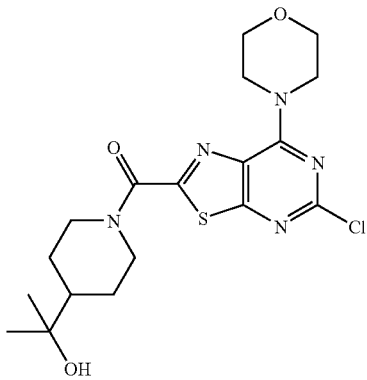

A mixture of 5-chloro-7-morpholin-4-ylthiazolo[5,4-d]pyrimidine-2-carboxylic acid (200 mg, 0.67 mmol), 2-piperidin-4-ylpropan-2-ol (105 mg, 0.73 mmol), HATU (278 mg, 0.73 mmol) and DIPEA (130 μL, 0.75 mmol) in DCM (7 mL) was allowed to stir at r.t. for 18 h. The reaction mixture was concentrated in vacuo and the resulting residue purified by column chromatography (Si—PCC, MeOH:DCM, 0-2%) affording the title compound as a white solid. $^1$H NMR (CDCl$_3$, 400 MHz): δ 5.15 (1 H, d, J=13.36 Hz), 4.79 (1 H, d, J=13.25 Hz), 4.35 (4 H, brd s), 3.85 (4 H, t, J=4.75 Hz), 3.16-3.13 (1 H, m), 1.92 (2 H, t, J=15.39 Hz), 1.75-1.60 (1 H, m), 1.49-1.38 (4 H, m), 1.22 (6 H, d, J=6.97 Hz).

Example 65q (5-Chloro-7-morpholin-4-ylthiazolo[5,4-d]pyrimidin-2-yl)-(2,2-dimethyl-4-oxetan-3-ylpiperazin-1-yl)methanone

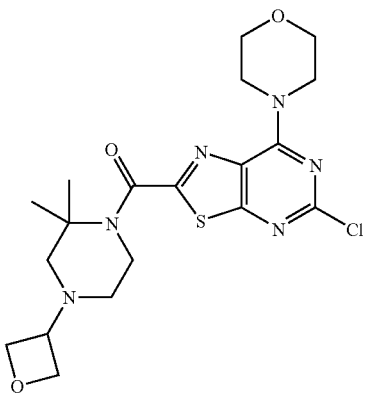

A mixture of 5-chloro-7-morpholin-4-ylthiazolo[5,4-d]pyrimidine-2-carboxylic acid (100 mg, 0.33 mmol), 3,3-dimethyl-1-oxetan-3-ylpiperazine (62 mg, 0.36 mmol), HATU (278 mg, 0.37 mmol) and DIPEA (65 μL, 0.37 mmol) in DCM (3 mL) was allowed to stir at r.t. for 18 h. The reaction mixture was concentrated in vacuo and the resulting residue purified by column chromatography (Si—PCC, MeOH:DCM, 0-2%) affording the title compound as a yellow solid. LCMS (method H): R$_T$ 2.67 min, [M+H]$^+$ 453.3

Example 65r 5-(2-Ethylbenzoimidazol-1-yl)-7-morpholin-4-ylthiazolo[5,4-d]pyrimidine-2-carbaldehyde

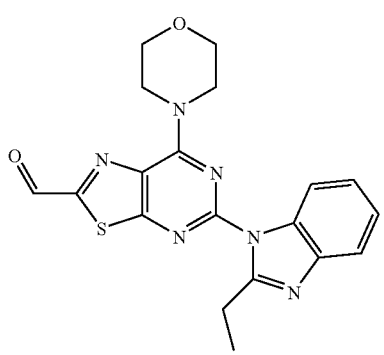

A mixture of 5-chloro-7-morpholin-4-ylthiazolo[5,4-d]pyrimidine-2-carbaldehyde (1.0 g, 3.51 mmol), 2-ethylbenzimidazole (512 mg, 3.71 mmol), tris(dibenzylideneacetone)dipalladium (90 mg, 2.5 mol %), XPhos (158 mg, 10 mol %) and Cs₂CO₃ (1.6 g, 4.91 mmol) in dioxane (30 mL) was purged with argon then heated at 115° C. for 17 h. The reaction mixture was filtered through Celite® which was washed with hot dioxane, and the filtrated concentrated in vacuo. The resulting residue was triturated with Et₂O and the resulting brown solid collected by filtration and dried in vacuo affording the title compound (1.23 g, 88%). ¹H NMR (CDCl₃, 400 MHz): δ 10.01 (1 H, s), 8.09-8.09 (1 H, m), 7.75-7.74 (1 H, m), 7.33-7.26 (2 H, m), 5.00-4.00 (4 H, brd s), 3.93 (4 H, t, J=4.72 Hz), 3.37 (2 H, q, J=7.45 Hz), 1.46 (3 H, t, J=7.45 Hz).

Example 65s

[5-(2-Ethylbenzoimidazol-1-yl)-7-morpholin-4-ylthiazolo[5,4-d]pyrimidin-2-yl]methanol

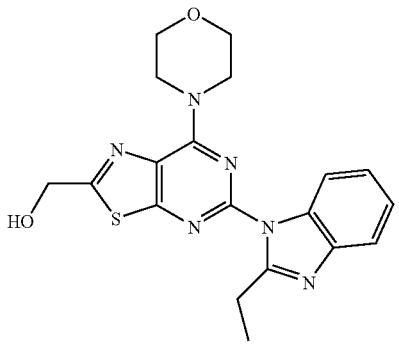

To a solution of 5-(2-ethylbenzoimidazol-1-yl)-7-morpholin-4-ylthiazolo[5,4-d]pyrimidine-2-carbaldehyde (1.2 g, 3.04 mmol) in DCE (30 mL) was added MeOH (3 mL) and NaBH₄ (119 mg, 3.15 mmol) and the resulting mixture stirred at r.t. for 4 h. The reaction mixture was concentrated in vacuo and the resulting residue triturated with H₂O. The resulting solid was collected by filtration and dried in vacuo affording the title compound (1.18 g, 98%). LCMS (method H): $R_T$ 2.42 min, [M+H]⁺ 397.4

Example 65t

2-Bromomethyl-5-(2-ethylbenzoimidazol-1-yl)-7-morpholin-4-ylthiazolo[5,4-d]pyrimidine

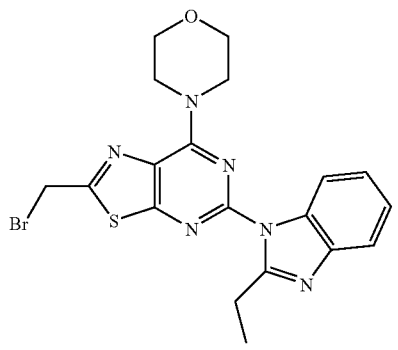

To a suspension of [5-(2-ethylbenzoimidazol-1-yl)-7-morpholin-4-ylthiazolo[5,4-d]pyrimidin-2-yl]methanol (1.18 g, 2.97 mmol) in DCM (60 mL) was added PBr₃ (3.36 mL, 3.36 mmol, 1M solution in DCM) and the resulting mixture allowed to stir at r.t. for 1 h. The reaction mixture was diluted with DCM and the organic phase washed with H₂O and brine, then dried (MgSO₄) and concentrated in vacuo affording the title compound as a yellow solid (673 mg, 49%). LCMS (method H): $R_T$ 3.24 min, [M+H]⁺ 459.1 and 461.1 (1:1)

Example 65u

[5-(2-Ethylbenzoimidazol-1-yl)-7-morpholin-4-ylthiazolo[5,4-d]pyrimidin-2-ylmethyl]phosphonic acid dimethyl ester

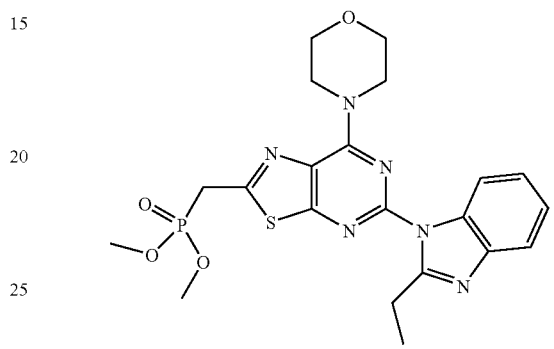

A mixture of 2-bromomethyl-5-(2-ethylbenzoimidazol-1-yl)-7-morpholin-4-ylthiazolo[5,4-d]pyrimidine (670 mg, 1.46 mmol) in trimethylphosphite (10 mL) was heated to reflux (120° C.) for 1 h then concentrated in vacuo. The resulting residue was purified by column chromatography (Si—PCC, MeOH:DCM, 0-2%) then (Si—PCC, MeOH:EtOAc, 0-5%) affording the title compound as a yellow solid (620 mg, 87%). LCMS (method H): $R_T$ 2.46 min, [M+H]⁺ 489.3

Example 65v

3-[5-(2-Ethylbenzoimidazol-1-yl)-7-morpholin-4-ylthiazolo[5,4-d]pyrimidin-2-ylmethylene]azetidine-1-carboxylic acid tert-butyl ester

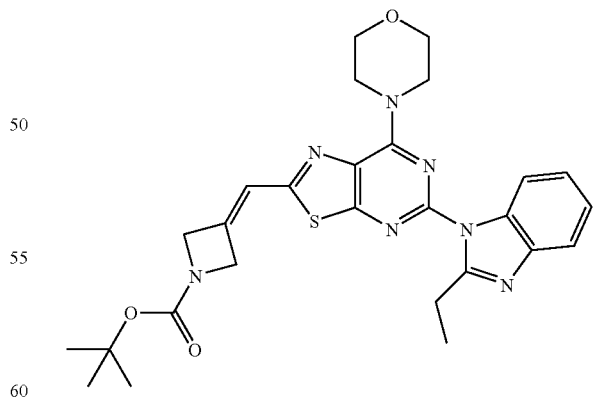

To a solution of diisopropylamine (200 μL, 1.42 mmol) in THF (0.5 mL) at −78° C. was added n-BuLi (556 μL, 1.42 mmol, 2.5 M in hexanes) and the resulting mixture stirred for 20 min. The resulting solution was added to a suspension of [5-(2-ethylbenzoimidazol-1-yl)-7-morpholin-4-ylthiazolo[5,4-d]pyrimidin-2-ylmethyl]phosphonic acid dimethyl ester (620 mg, 1.27 mmol) in THF (11 mL) at −78° C. The resulting mixture was warmed to r.t. before a solution of 3-oxo-azetidine-1-carboxylic acid tert-butyl ester (250 mg, 1.46 mmol) in THF (1.5 mL) was added. The resulting mixture was stirred at r.t. for 5 h then quenched with H$_2$O. The mixture was concentrated in vacuo and the residue was partitioned between DCM and brine. The organic phase was dried (MgSO$_4$) and concentrated in vacuo. The resulting residue was filtered through a pad of silica affording the title compound (493 mg, 73%). LCMS (method H): R$_T$ 3.72 min, [M+H]$^+$ 534.3

Example 65w

2-Azetidin-3-ylmethyl-5-(2-ethylbenzoimidazol-1-yl)-7-morpholin-4-ylthiazolo[5,4-d]pyrimidine

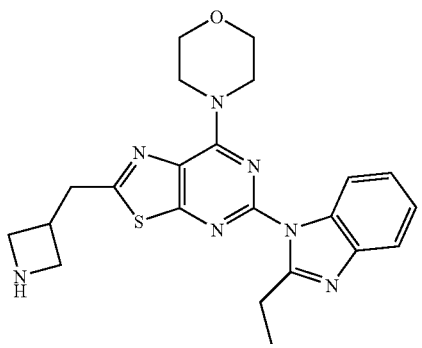

Step 1: 3-[5-(2-Ethylbenzoimidazol-1-yl)-7-morpholin-4-ylthiazolo[5,4-d]pyrimidin-2-ylmethyl]azetidine-1-carboxylic acid tert-butyl ester

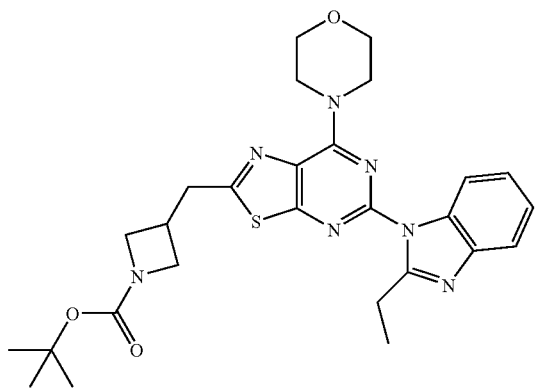

To a solution of 3-[5-(2-ethylbenzoimidazol-1-yl)-7-morpholin-4-ylthiazolo[5,4-c]pyrimidin-2-ylmethylene]azetidine-1-carboxylic acid tert-butyl ester (493 g, 0.92 mmol) in AcOH (20 mL) was added 10% Pd(OH)$_2$/C (200 mg) and the resulting mixture stirred under an atmosphere of H$_2$ for 2 h. The reaction mixture was filtered through Celite®, washing with EtOAc. The filtrate was loaded onto an Isolute® SCX-2 cartridge which was washed with MeOH and the product eluted with 2M NH$_3$/MeOH affording the title compound.

Step 2: To a solution of 3-[5-(2-ethylbenzoimidazol-1-yl)-7-morpholin-4-ylthiazolo[5,4-d]pyrimidin-2-ylmethyl]azetidine-1-carboxylic acid tert-butyl ester in DCM (10 mL) was added TFA (3 mL) and the resulting mixture allowed to stir at r.t. for 1 h. The reaction mixture was loaded onto an Isolute® SCX-2 cartridge which was washed with MeOH and the product eluted with 2M NH$_3$/MeOH affording 2-Azetidin-3-ylmethyl-5-(2-ethylbenzoimidazol-1-yl)-7-morpholin-4-ylthiazolo[5,4-d]pyrimidine as a yellow oil (209 mg, 52% over two steps). $^1$H NMR (CDCl$_3$, 400 MHz): δ 7.99-7.98 (1 H, m), 7.75-7.74 (1 H, m), 7.28-7.25 (2 H, m), 4.41 (4 H, brd s), 3.89-3.84 (5 H, m), 3.59 (2 H, t, J=7.25 Hz), 3.48 (2 H, s), 3.36-3.34 (5 H, m), 1.43 (3 H, t, J=7.47 Hz)

Example 65x

4-[1-(5-Chloro-7-morpholin-4-ylthiazolo[5,4-d]pyrimidin-2-ylmethyl)azetidin-3-yl]piperazin-2-one

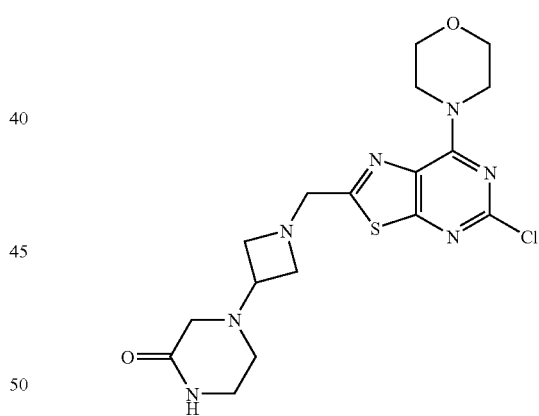

A mixture of 5-chloro-7-morpholin-4-ylthiazolo[5,4-d]pyrimidine-2-carbaldehyde (285 mg, 1.00 mmol), 4-azetidin-3-ylpiperazin-2-one (190 mg, 1.22 mmol) and 4 Å powdered molecular sieves (1.0 g) in DCE (10 mL) was allowed to stir at r.t. for 5 h before the addition of sodium triacetoxyborohydride (420 mg, 1.98 mmol). The resulting mixture was allowed to stir for 16 h then filtered through Celite® which was washed with DCM. The filtrate was concentrated in vacuo and the resulting residue purified by column chromatography (Si—PCC, MeOH:DCM, 2-10%) affording the title compound (321 mg, 75%). LCMS (method A): R$_T$ 1.96 and 0.33 min [M+H]$^+$ 424.3

Example 65y (5-Chloro-7-morpholin-4-ylthiazolo[5,4-d]pyrimidin-2-yl)-(3-morpholin-4-ylazetidin-1-yl)methanone

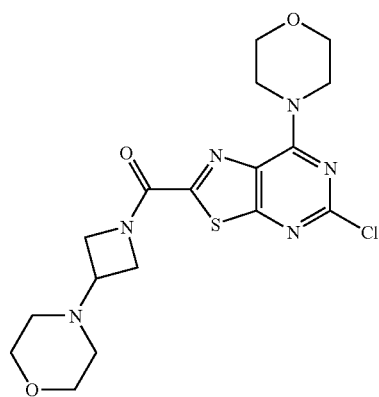

To a suspension of 5-chloro-7-morpholin-4-ylthiazolo[5,4-d]pyrimidine-2-carboxylic acid (301 mg, 1.0 mmol) in DCM (6 mL) was added oxalyl chloride (847 µL, 10.00 mmol) and the resulting mixture allowed to stir at r.t. for 1 h then concentrated in vacuo and azeotroped with toluene. The resulting yellow solid was suspended in a mixture of DCM (6 mL) and NEt$_3$ (418 µL, 3.00 mmol) at 0° C. before the addition of 4-azetidin-3-ylmorpholine (142 mg, 1.00 mmol). The resulting mixture was warmed to r.t. after 1 h then stirred for a further 30 min. The reaction mixture was partitioned between DCM and H$_2$O, the organic phase dried (Na$_2$SO$_4$) and concentrated in vacuo. The resulting residue was triturated with EtOAc and dried in vacuo affording the title compound as an off-white solid (269 mg, 63%). LCMS (method H): R$_T$ 2.19 min [M+H]$^+$ 425.3

Example 65z

5-Chloro-7-morpholin-4-yl-thiazolo[4,5-d]pyrimidine-2-carbaldehyde

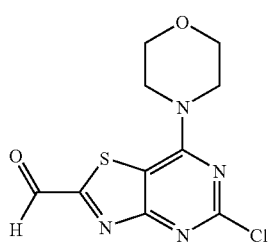

To a suspension of 5-chloro-7-morpholin-4-yl-thiazolo[4,5-d]pyrimidine (2 g, 7.79 mmol) in anhydrous tetrahydrofuran, cooled to −78° C. under nitrogen atmosphere, lithium bis(trimethylsilyl)amide (11.7 mL, 11.68 mmol) was added dropwise at −78° C. and the resulting reaction mixture stirred at −78° C. for 1 h. Subsequently DMF was slowly added and the mixture stirred for further 30 min. The temperature was allowed to rise to −5° C. over 10 min and then cooled again to −78° C. The resulting reaction mixture was transferred via cannula into ice-cold aqueous 1M HCl (400 mL) and stirred vigorously. The aqueous phase was extracted with ethyl acetate (2×150 mL). The organic layer was washed with water (1×125 mL), brine (2×125 mL), dried over Na$_2$SO$_4$ and filtered. The solvent was reduced in vacuo to afford the title compound as an orange-brown solid (1.82 g, 82%). $^1$H NMR (400 MHz, CDCl$_3$): δ 10.19 (1 H, s), 4.03 (4 H, t, J=4.90 Hz), 3.87 (4 H, t, J=4.90 Hz).

Example 66a

5-Chloro-7-morpholin-4-yl-2-(3-morpholin-4-yl-azetidin-1-ylmethyl)-thiazolo[4,5-d]pyrimidine

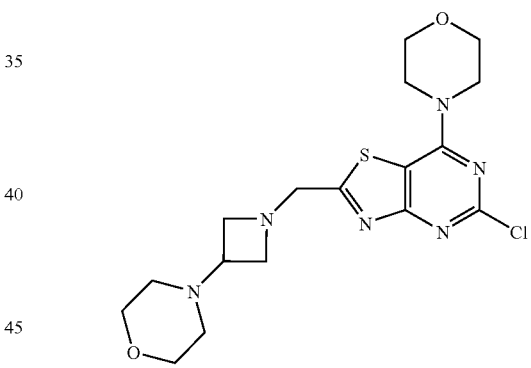

A mixture of 5-chloro-7-morpholin-4-yl-thiazolo[4,5-d]pyrimidine-2-carbaldehyde (250 mg, 0.88 mmol), 4-azetidin-3-yl-morpholine (150 mg, 1.05 mmol) and 4 Å molecular sieves (1.0 g) in 1,2-dichloroethane (15 mL) was stirred at RT under nitrogen atmosphere for 1.5 h. Sodium triacetoxyborohydride (280 mg, 1.32 mmol) was added and the resulting reaction mixture was stirred at RT for 16 h. The solvent was reduced in vacuo and the residue was loaded on an Isolute® SCX-2 cartridge (10 g). The cartridge was washed with DCM/MeOH, the desired product was subsequently eluted using a mixture of 2M NH$_3$ in MeOH and DCM. The resulting residue was further purified by column chromatography (Si—PCC, MeOH:DCM: 0:100 to 6:94 by volume). The solvents were reduced in vacuo to afford the title compound as a yellow solid (165 mg, 46%). LCMS (Method A): R$_T$ 2.31 min, [M+H]$^+$ 411. $^1$H NMR (400 MHz, CDCl$_3$): δ 4.11 (2 H, s), 3.95 (4 H, t, J=4.85 Hz), 3.83 (4 H, t, J=4.84 Hz), 3.74-3.67 (6 H, m), 3.22 (2 H, t, J=6.84 Hz), 3.12-3.11 (1 H, m), 2.34 (4 H, s)

Example 66b

2-[1-(5-Chloro-7-morpholin-4-yl-thiazolo[4,5-d]pyrimidin-2-ylmethyl)piperidin-4-yl]propan-2-ol

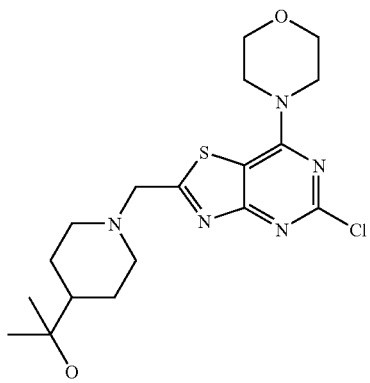

A mixture of 5-chloro-7-morpholin-4-yl-thiazolo[4,5-d]pyrimidine-2-carbaldehyde (400 mg, 1.4 mmol), 2-piperidin-4-yl-propan-2-ol (242 mg, 1 7 mmol), and 4 Å molecular sieves (1.5 g) in 1,2-dichloroethane (20 mL) was stirred at RT for 6 h. Sodium triacetoxyborohydride (593 mg, 2.8 mmol) was added and the resulting reaction mixture was stirred at RT under nitrogen atmosphere for 18 h. The suspension was filtered through Celite and the filtrate was concentrated in vacuo. The residue was purified by column chromatography (Si—PPC, (10% MeOH in EtOAc): EtOAc, gradient 0:100 to 20:80) to afford the title compound as an orange solid (344 mg, 60%). $^1$H NMR (400 MHz, CDCl$_3$): δ 3.98-3.93 (6 H, m), 3.85 (5 H, m), 3.08 (2 H, m), 2.28 (2 H, m), 1.79 (2 H, m), 1.48 (3 H, m), 1.23-1.21 (6 H, m).

Example 66c

2-[4-(5-Chloro-7-morpholin-4-yl-thiazolo[4,5-d]pyrimidin-2-ylmethyl)piperazin-1-yl]isobutyramide

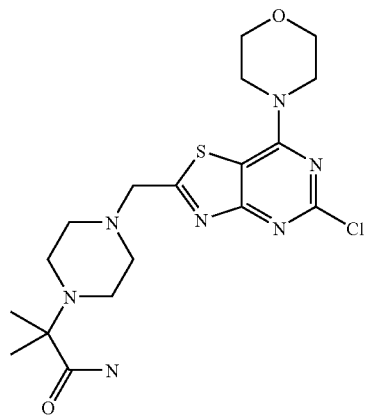

A mixture of 5-chloro-7-morpholin-4-yl-thiazolo[4,5-d]pyrimidine-2-carbaldehyde (250 mg, 0.88 mmol), 2-piperazin-1-yl-isobutyramide (173 mg, 1.01 mmol) and 4 Å molecular sieves (1.0 g) in 1,2-dichloroethane (15 mL) was stirred at RT under nitrogen atmosphere for 4 h. Sodium triacetoxyborohydride (280 mg, 1.32 mmol) was added and the resulting reaction mixture was stirred at RT for 16 h. The solvent was reduced in vacuo and the residue was loaded on an Isolute® SCX-2 cartridge (25 g). The cartridge was washed with DCM/MeOH and the desired product was subsequently eluted using a mixture of 2 M NH$_3$ in MeOH and DCM. The resulting residue was further purified by column chromatography (Si—PCC, MeOH:DCM: gradient 0:100 to 6:94). The solvents were reduced in vacuo to afford the title compound as a yellow solid (275 mg, 60%). LCMS (Method H): R$_T$ 2.41 min, [M+H]$^+$ 440. $^1$H NMR (400 MHz, CDCl$_3$): δ 7.04 (1 H, br s), 5.22 (1 H, br s), 3.97-3.95 (6 H, m), 3.85 (4 H, t, J=4.80 Hz), 2.67 (8 H, m), 1.25 (6 H, s)

Example 66d

2-[4-(7-Morpholin-4-yl-5-(tributylstannanyl)thiazolo[4,5-d]pyrimidin-2-ylmethyl)piperazin-1-yl]isobutyramide

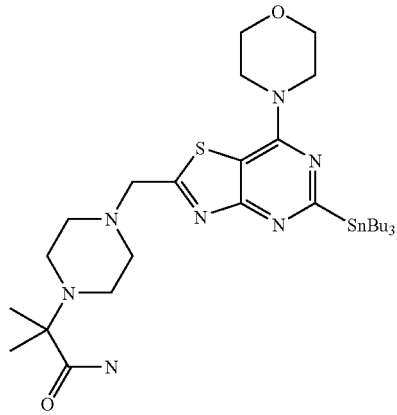

A mixture of 2-[4-(5-chloro-7-morpholin-4-yl-thiazolo[4,5-d]pyrimidin-2-ylmethyl)piperazin-1-yl]isobutyramide (120 mg, 0.27 mmol), PdCl$_2${P$^t$Bu$_2$(Ph-p-NMe$_2$)}$_2$ (19.5 mg, 0.027 mmol) and hexabutylditin (0.203 mL, 0.405 mmol) in 1,4-dioxane (1.2 mL) was purged with argon gas and then subjected to microwave irradiation at 150° C. for 30 min. The crude residue was loaded onto an Isolute® SCX-2 cartridge (20 g) and washed with DCM/MeOH, the desired product was subsequently eluted using a mixture of 2 M NH$_3$ in MeOH and DCM. The resulting residue was further purified by column chromatography (Si—PCC, cyclohexane:acetone, gradient 100:0 to 60:40). The solvents were reduced in vacuo to afford the title compound as a yellow gum (210 mg, 62%) LCMS (Method A): R$_T$ 4.26 min, [M+H]$^+$ 694 ($^{116}$Sn) 696 ($^{118}$Sn). $^1$H NMR (400 MHz, CDCl$_3$): δ 7.06 (1 H, s), 5.20 (1 H, s), 3.97 (2 H, s), 3.92 (4 H, t, J=4.60 Hz), 3.84 (4 H, t, J=4.60 Hz), 2.65 (8 H, m), 1.60-1.58 (6 H, m), 1.35-1.33 (6 H, m), 1.25 (6 H, s), 1.16-1.14 (6 H, m), 0.87 (9 H, t, J=7.32 Hz)

Example 66e

4-[5-(2-Ethylbenzoimidazol-1-yl)-7-morpholin-4-ylthiazolo[5,4-d]pyrimidin-2-ylmethylene]piperidine-1-carboxylic acid benzyl ester

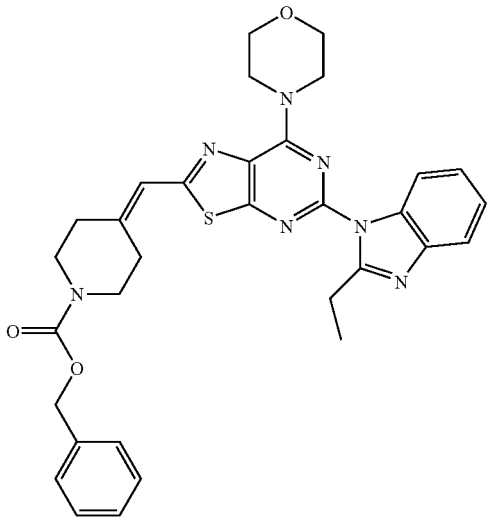

To a solution of diisopropylamine (121 μL, 0.86 mmol) in THF (0 5 mL) at −78° C. was added n-BuLi (336 μL, 0.86 mmol, 2.5 M in hexanes) and the resulting mixture stirred for 30 min. The resulting solution was added to a suspension of [5-(2-ethylbenzoimidazol-1-yl)-7-morpholin-4-ylthiazolo[5,4-c]pyrimidin-2-ylmethyl]phosphonic acid dimethyl ester (375 mg, 0.77 mmol) in THF (6 mL) at −78° C. The resulting mixture was warmed to r.t. before a solution of 4-oxopiperidine-1-carboxylic acid benzyl ester (206 mg, 0.88 mmol) in THF (1 mL) was added. The resulting mixture was stirred at r.t. for 3 h then quenched with $H_2O$. The mixture was concentrated in vacuo and the residue was partitioned between EtOAc and $H_2O$. The organic phase was dried ($MgSO_4$) and concentrated in vacuo. The resulting residue was purified by column chromatography (Si—PCC, EtOAc:pentane, 50-75%) affording 4-[5-(2-Ethylbenzoimidazol-1-yl)-7-morpholin-4-ylthiazolo[5,4-d]pyrimidin-2-ylmethylene]piperidine-1-carboxylic acid benzyl ester (300 mg, 66%). LCMS (method H): $R_T$ 3.98 min, [M+H]$^+$ 596.4

Example 66f 5-(2-Ethylbenzoimidazol-1-yl)-7-morpholin-4-yl-2-piperidin-4-ylmethylthiazolo[5,4-d]pyrimidine

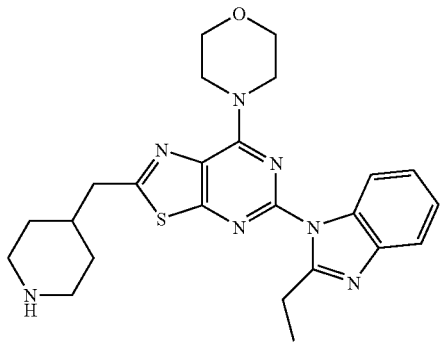

To a solution of 4-[5-(2-ethylbenzoimidazol-1-yl)-7-morpholin-4-ylthiazolo[5,4-d]pyrimidin-2-ylmethylene]piperidine-1-carboxylic acid benzyl ester (300 mg, 0.50 mmol) in AcOH (20 mL) was added 10% Pd(OH)$_2$/C (200 mg) and the resulting mixture stirred under an atmosphere of $H_2$ for 2 h. The reaction mixture was filtered through Celite®, washing with EtOAc. The filtrate was loaded onto an Isolute® SCX-2 cartridge which was washed with MeOH and the product eluted with 2M NH$_3$/MeOH. The resulting residue was purified by column chromatography (Si—PCC, 2M NH$_3$/MeOH:DCM, 0-10%) affording 5-(2-Ethylbenzoimidazol-1-yl)-7-morpholin-4-yl-2-piperidin-4-ylmethylthiazolo[5,4-d]pyrimidine (96 mg, 41%). $^1$H NMR (CDCl$_3$, 400 MHz): δ 7.99-7.98 (1 H, m), 7.74-7.73 (1 H, m), 7.30-7.26 (2 H, m), 4.43 (4 H, s), 3.88 (4 H, t, J=4.74 Hz), 3.33 (2 H, q, J=7.48 Hz), 3.12-3.08 (2 H, m), 2.99 (2 H, d, J=7.14 Hz), 2.63 (2 H, td, J=12.12, 2.54 Hz), 2.03-1.91 (1 H, m), 1.79 (2 H, brd d, J=13.18 Hz), 1.42 (3 H, t, J=7.48 Hz), 1.30-1.29 (2 H, m)

Example 66g

Acetic acid 2-{4-[5-(2-ethylbenzoimidazol-1-yl)-7-morpholin-4-ylthiazolo[5,4-d]pyrimidin-2-ylmethyl]piperidin-1-yl}-1,1-dimethyl-2-oxoethyl ester

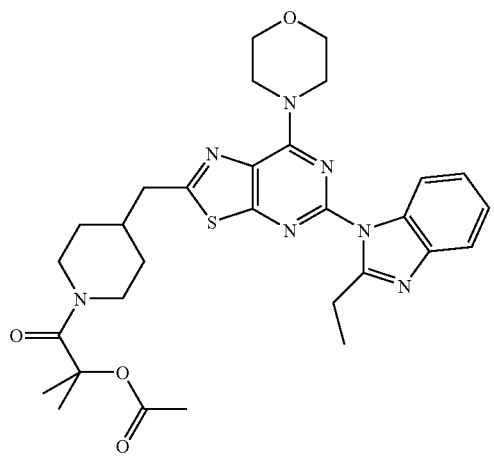

A mixture of 5-(2-ethylbenzoimidazol-1-yl)-7-morpholin-4-yl-2-piperidin-4-ylmethylthiazolo[5,4-d]pyrimidine (96 mg, 0.21 mmol), acetic acid 1-chlorocarbonyl-1-methylethyl ester (40 μL, 0.28 mmol) and NEt$_3$ (40 μL, 0.31 mmol) in DCM (1 mL) was allowed to stir at r.t. for 30 min then concentrated in vacuo. The resulting residue was loaded onto an Isolute® SCX-2 cartridge which was washed with MeOH and the product eluted with 2M NH$_3$/MeOH affording Acetic acid 2-{4-[5-(2-ethylbenzoimidazol-1-yl)-7-morpholin-4-ylthiazolo[5,4-d]pyrimidin-2-ylmethyl]piperidin-1-yl}-1,1-dimethyl-2-oxoethyl ester. LCMS (method A): $R_T$ 3.19 min [M+H]$^+$ 592.2

Formula I(ii) thiophenyl intermediates wherein (ii) $X^1$ is $CR^7$ and $X^2$ is S

Example 70a 9-(2-Chloro-4-morpholin-4-yl-thieno[3,2-d]pyrimidin-6-ylmethyl)-1-oxa-4,9-diazaspiro[5.5]undecan-3-one

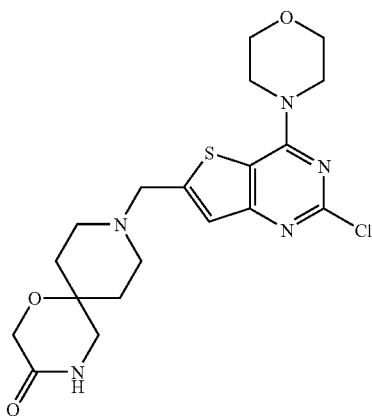

A solution of 6-bromomethyl-2-chloro-4-morpholin-4-yl-thieno[3,2-d]pyrimidine (500 mg, 1.43 mmol), 1-oxa-4,9-diaza-spiro[5.5]undecan-3-one (315 mg, 1.85 mmol) and potassium carbonate (450 mg, 3.26 mmol) in DMF (40 mL) was stirred at ambient temperature for 18 hours, then loaded onto an Isolute® SCX-2 cartridge (10 g). The cartridge was washed with MeOH and the desired product was subsequently eluted using 2 M $NH_3$ in MeOH. The eluent was collected and concentrated in vacuo. The resultant residue was purified by flash chromatography (Si—PPC, DCM: MeOH 100:0 to 98:2 to 95:5) to afford 9-(2-Chloro-4-morpholin-4-yl-thieno[3,2-d]pyrimidin-6-ylmethyl)-1-oxa-4,9-diazaspiro[5.5]undecan-3-one as a white solid (515 mg, 82%). LCMS (Method A): $R_T$=2.51 min, [M+H]$^+$ 438.1

Example 70b

2-[4-(4-Morpholin-4-yl-2-(tributylstannanyl)thieno[3,2-d]pyrimidin-6-ylmethyl)-piperazin-1-yl]isobutyramide

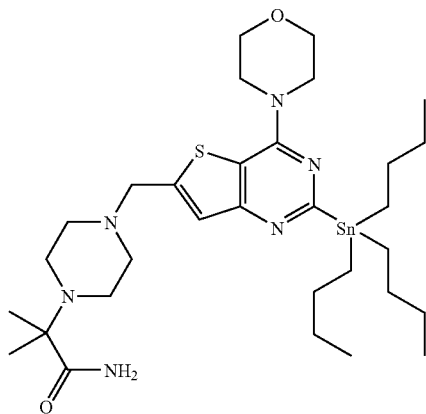

A mixture of 2-[4-(2-chloro-4-morpholin-4-yl-thieno[3,2-d]pyrimidin-6-ylmethyl)-piperazin-1-yl]isobutyramide (1.0 g, 2.3 mmol), hexabutylditin (1.4 mL, 2.7 mmol), and $PdCl_2\{P^tBu_2(Ph\text{-}p\text{-}Nme_2)\}_2$ (161 mg, 0.2 mmol) in dioxane (10 mL) was degassed and then subjected to microwave irradiation at 150° C. for 30 min. The reaction mixture was diluted with MeOH and loaded onto a Isolute® SCX-2 cartridge (25 g). The cartridge was then washed with MeOH and the desired product was subsequently eluted using 2 M $NH_3$ in MeOH. Appropriate fractions were combined and concentrated to give a residue which was subjected to flash chromatography (Si—PPC, MeOH:DCM, gradient 0:100 to 10:90). Appropriate fractions were combined and concentrated to give 2-[4-(4-Morpholin-4-yl-2-(tributylstannanyl)thieno[3,2-d]pyrimidin-6-ylmethyl)-piperazin-1-yl]isobutyramide as white foam (0.9 g, 56%). LCMS (Method C) $R_T$=3.88 min; [M +H]$^-$ 693.1 ($^{116}$Sn) 695.1 ($^{118}$Sn)

Example 70c

2-[4-(2-Chloro-7-methyl-4-morpholin-4-yl-thieno[3,2-d]pyrimidin-6-ylmethyl)piperazin-1-yl]isobutyramide

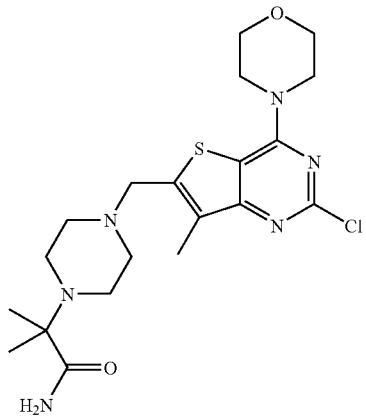

To a solution of 2-chloro-7-methyl-4-morpholin-4-yl-thieno[3,2-d]pyrimidine-6-carbaldehyde (1.00 g, 3.36 mmol) in DCE (50 mL) was added 2-(piperazin-1-yl)isobutyramide (630 mg, 3.69 mmol), trimethyl orthoformate (3.67 mL, 33.58 mmol) and acetic acid (0.19 mL, 3.36 mmol). After stirring at room temperature for 3 h sodium triacetoxyborohydride (1.10 g, 5.03 mmol) was added and the resulting mixture stirred for a further 17 h. The reaction mixture was loaded onto an Isolute® SCX-2 cartridge, washed with MeOH then eluted with 2 M $NH_3$ in MeOH/DCM. The resultant residue was triturated with MeOH to give 2-[4-(2-Chloro-7-methyl-4-morpholin-4-yl-thieno[3,2-d]pyrimidin-6-ylmethyl)piperazin-1-yl]isobutyramide as a white solid (1.12 g, 74%). LCMS (Method C): $R_T$=2.88 min, [M+H]$^+$ 453

Example 70d

2-[4-(7-Methyl-4-morpholin-4-yl-2-(tributylstannanyl)thieno[3,2-d]pyrimidin-6-ylmethyl)piperazin-1-yl]isobutyramide

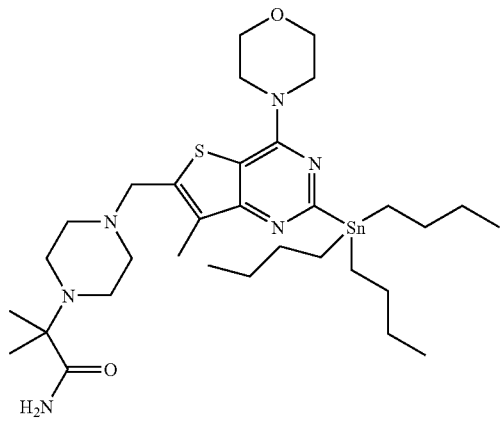

A mixture of 2-[4-(2-chloro-7-methyl-4-morpholin-4-yl-thieno[3,2-d]pyrimidin-6-ylmethyl)piperazin-1-yl]isobutyramide (194 mg, 0.43 mmol), hexabutylditin (373 mg, 0.64 mmol), PdCl$_2${P$^t$Bu$_2$(Ph-p-Nme$_2$)}$_2$ (30 mg, 10 mol %) in dioxane (2 mL) was purged with nitrogen gas then heated at 150° C., for 20 min, in a microwave reactor. The reaction mixture was loaded onto an Isolute® SCX-2 cartridge, washed with MeOH then eluted with 2M NH$_3$ in MeOH. The resulting residue was purified by column chromatography (Si—PPC, MeOH:DCM, gradient 0:100 to 05:95) to afford 2-[4-(7-Methyl-4-morpholin-4-yl-2-(tributylstannanyl)thieno[3,2-d]pyrimidin-6-ylmethyl)piperazin-1-yl]isobutyramide as a colorless oil (192 mg, 63%). LCMS (Method D): R$_T$ 2.92 min, [M+H]$^+$ 705 ($^{116}$Sn), 707 ($^{118}$Sn)

Example 70e

2-Chloro-4-morpholin-4-yl-6-(4-morpholin-4-yl-piperidin-1-ylmethyl)-thieno[3,2-d]pyrimidine

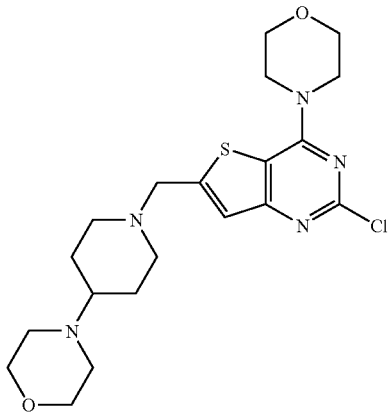

A mixture of 2-chloro-4-morpholin-4-yl-thieno[3,2-d]pyrimidine-6-carbaldehyde (2.0 g, 7.1 mmol) and 4-piperidin-4-yl-morpholine (1.4 g, 8 5 mmol) in DCE (40 mL) was stirred at room temperature for 1.5 hour then triacetoxyborohydride (2.2 g, 10.6 mmol) was added. The reaction mixture was stirred at room temperature for 18 hours then diluted with MeOH and loaded onto an Isolute® SCX-2 cartridge (70 g). The cartridge was washed with MeOH/DCM (1/1: v/v) and the desired product was eluted with (2M NH$_3$ in MeOH)/DCM (1/1: v/v). The solvents were removed and the residue was triturated in hot IMS, filtered and dried at 60° C. for 1 hour under vacuum to give 2-Chloro-4-morpholin-4-yl-6-(4-morpholin-4-yl-piperidin-1-ylmethyl)-thieno[3,2-d]pyrimidine as a white solid (2.6 g, 84%). LCMS (Method C): R$_T$ 0.34 min and 1.67 min; [M+H]$^+$ 438

Example 70f

4-Morpholin-4-yl-6-(4-morpholin-4-yl-piperidin-1-ylmethyl)-2-(tributylstannanyl)thieno[3,2-d]pyrimidine

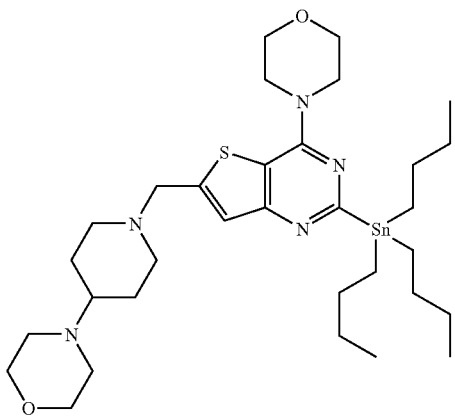

A mixture of 2-chloro-4-morpholin-4-yl-6-(4-morpholin-4-yl-piperidin-1-ylmethyl)thieno[3,2-d]pyrimidine (874 mg, 2.0 mmol), hexabutylditin (1.1 mL, 2.2 mmol), and PdCl$_2${P$^t$Bu$_2$(Ph-p-Nme$_2$)}$_2$ (71 mg, 0.1 mmol) in dioxane (10 mL) was then subjected to microwave irradiation at 150° C. for 20 min. The reaction mixture was diluted with MeOH and loaded onto a Isolute® SCX-2 cartridge (10 g). The cartridge was then washed with MeOH and the desired product was subsequently eluted using 2 M NH$_3$ in MeOH. Appropriate fractions were combined and concentrated to give a residue which was subjected to flash chromatography (Si—PPC, MeOH:EtOAc, gradient 0:100 to 40:60). Appropriate fractions were combined and concentrated to give 4-Morpholin-4-yl-6-(4-morpholin-4-yl-piperidin-1-ylmethyl)-2-(tributylstannanyl)thieno[3,2-d]pyrimidine as pale yellow oil (823 mg, 59%). LCMS (Method C): R$_T$=2.72 min; [M+H]$^+$ 692 ($^{116}$Sn) 694 ($^{118}$Sn)

Example 70g

[1-(2-Chloro-4-morpholin-4-yl-thieno[3,2-d]pyrimidin-6-ylmethyl)piperidin-4-yl]dimethylamine

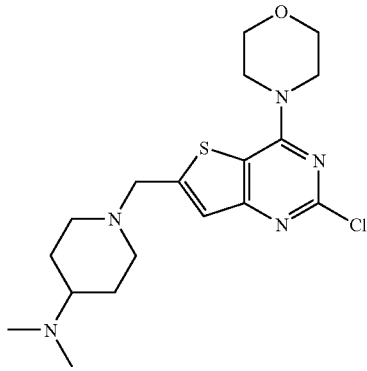

A mixture of 2-chloro-4-morpholin-4-ylthieno[3,2-d]pyrimidine-6-carbaldehyde (5.0 g, 17.7 mmol) and dimethylpiperidin-4-ylamine (2.7 g, 21.2 mmol) in DCE (100 mL) was stirred at room temperature for 4 hours then triacetoxyborohydride (5.6 g, 26.5 mmol) was added. The reaction mixture was stirred at room temperature for 18 hours then diluted with MeOH and loaded onto an Isolute® SCX-2 cartridge (2×70 g). The cartridge was washed with MeOH/DCM (1/1: v/v) and the desired product was eluted with (2M NH$_3$ in MeOH)/DCM (1/1: v/v). The solvents were removed and the residue was precipitated from IMS to give [1-(2-Chloro-4-morpholin-4-yl-thieno[3,2-d]pyrimidin-6-ylmethyl)piperidin-4-yl]dimethylamine as a white solid (4.45 g, 64%). LCMS (Method B): R$_T$ 0.37 min and 1.85 min; [M+H]$^+$ 396

Example 70h

Dimethyl-[1-(4-morpholin-4-yl-2-(tributylstannanyl)thieno[3,2-d]pyrimidin-6-ylmethyl)piperidin-4-yl]amine

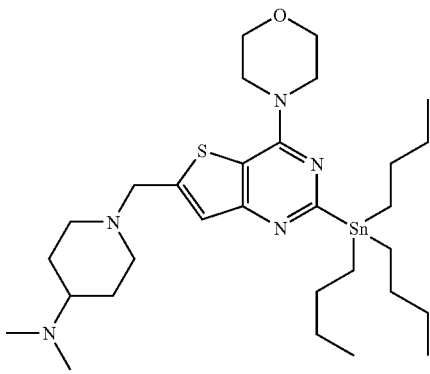

A mixture of [1-(2-chloro-4-morpholin-4-yl-thieno[3,2-d]pyrimidin-6-ylmethyl)piperidin-4-yl]dimethylamine (1.0 g, 2.5 mmol), hexabutylditin (1.5 mL, 3.0 mmol), and PdCl$_2${P$^t$Bu$_2$(Ph-p-Nme$_2$)}$_2$ (128 mg, 0.18 mmol) in dioxane (10 mL) was degassed and then subjected to microwave irradiation at 160° C. for 20 min. The reaction mixture was diluted with MeOH and loaded onto a Isolute® SCX-2 cartridge (25 g). The cartridge was then washed with MeOH and the desired product was subsequently eluted using 2 M NH$_3$ in MeOH. Appropriate fractions were combined and concentrated to give a residue which was subjected to flash chromatography (Si—PPC, MeOH:DCM, gradient 0:100 to 40:60). Appropriate fractions were combined and concentrated to give Dimethyl-[1-(4-morpholin-4-yl-2-(tributylstannanyl)thieno[3,2-d]pyrimidin-6-ylmethyl)piperidin-4-yl]amine as pale yellow oil (879 mg, 54%). LCMS (Method C): R$_T$=2.76 min; [M +H]$^+$ 650 ($^{116}$Sn) 652 ($^{118}$Sn)

Example 70i

1-[1-(2-Chloro-4-morpholin-4-ylthieno[3,2-d]pyrimidin-6-ylmethyl)azetidin-3-yl]piperidin-4-ol

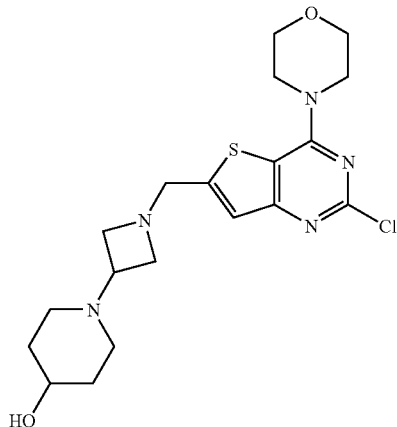

A mixture of 2-chloro-4-morpholin-4-ylthieno[3,2-d]pyrimidine-6-carbaldehyde (136 mg, 0.48 mmol), 1-azetidin-3-ylpiperidin-4-ol (90 mg, 0.58 mmol) and 4 Å powdered molecular sieves (260 mg) in DCE (15 mL) was stirred for 5 h before the addition of sodium triacetoxyborohydride (202 mg, 0.96 mmol). The resulting mixture was stirred for 18 h then filtered through Celite® and the filtrate loaded onto an Isolute® SCX-2 cartridge which was washed with MeOH and the product eluted with 2M NH$_3$/MeOH/DCM. The resulting residue was purified by column chromatography (Si—PCC, MeOH:DCM, 0-10%) affording the title compound as a pale yellow oil (153 mg, 75%). LCMS (method H): R$_T$ 1.88 min [M+H]$^+$ 424.3

Example 70j

2-Chloro-6-(2,2-dimethyl-4-oxetan-3-ylpiperazin-1-ylmethyl)-4-morpholin-4-yl-thieno[3,2-d]pyrimidine

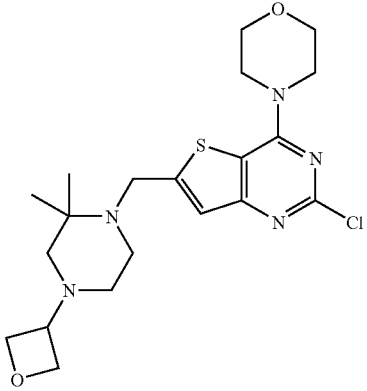

A mixture of 2-chloro-4-morpholin-4-ylthieno[3,2-d]pyrimidine-6-carbaldehyde (400 mg, 1.42 mmol), 3,3-dimethyl- 1-oxetan-3-ylpiperazine (290 mg, 1.71 mmol) and 4 Å powdered molecular sieves (500 mg) in DCE (20 mL) were allowed to stir at r.t. 3 h before the addition of sodium triacetoxyborohydride (420 mg, 1.98 mmol). The resulting mixture was allowed to stir for 18 h then filtered through Celite®. The filtrate was loaded onto an Isolute® SCX-2 cartridge which was washed with MeOH and the product eluted with 2M NH$_3$/MeOH. The resulting residue was purified by column chromatography (Si—PCC, MeOH:EtOAc, 0-10%) affording the title compound as a cream solid (305 mg, 49%). LCMS (method H): R$_T$ 2.12 min, [M+H]$^+$ 438.3

Example 70k 3-(2-Chloro-4-morpholin-4-ylthieno[3,2-d]pyrimidin-6-ylmethylene)azetidine-1-carboxylic acid tert-butyl ester

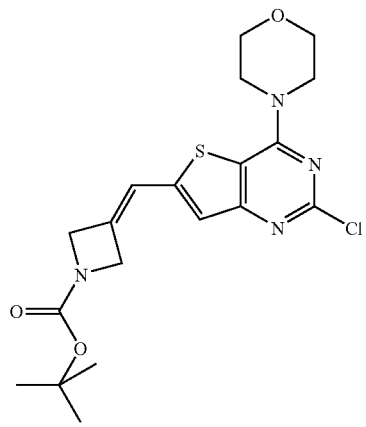

To a suspension of (2-chloro-4-morpholin-4-ylthieno[3,2-d]pyrimidin-6-ylmethyl)phosphonic acid dimethyl ester (3.0 g, 7.94 mmol) in THF (150 mL) at −78° C. was added LiHMDS (8.8 mL, 8.80 mmol, 1M solution in THF) and the resulting mixture stirred for 30 min then warmed to r.t. before the addition of a solution of 3-oxo-azetidine-1-carboxylic acid tert-butyl ester (1.51 g, 8.82 mmol) in THF (20 mL) The reaction mixture was stirred at r.t. for 16 h then quenched with H$_2$O and MeOH and concentrated in vacuo. The resulting residue was purified by column chromatography (Si—PCC, EtOAc:DCM, 5-100%) affording the title compound as a yellow solid (2.14 g, 63%). LCMS (method A): R$_T$ 3.97 min [M+H]$^+$ 423.3

Example 70l

3-[2-(2-Ethylbenzoimidazol-1-yl)-4-morpholin-4-ylthieno[3,2-d]pyrimidin-6-ylmethylene]azetidine-1-carboxylic acid tert-butyl ester

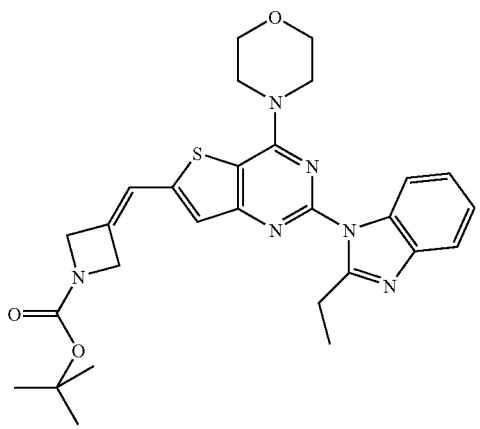

A mixture of 3-(2-chloro-4-morpholin-4-ylthieno[3,2-d]pyrimidin-6-ylmethylene)azetidine-1-carboxylic acid tert-butyl ester (1.1 g, 2.51 mmol), 2-ethylbenzimidazole (400 mg, 2.74 mmol), tris(dibenzylideneacetone)dipalladium (115 mg, 0.13 mmol), XPhos (240 mg, 0.50 mmol) and Cs$_2$CO$_3$ (1.25 g, 3.84 mmol) in dioxane (25 mL) was purged with argon then heated at 110° C. for 16 h. The reaction mixture was filtered through Celite®, washing with DCM, and the filtrate concentrated in vacuo. The resulting residue was purified by column chromatography (Si—PCC, MeOH:DCM, 0-10%) affording the title compound as an orange solid (1.5 g, quant.). LCMS (method A): R$_T$ 3.40 min [M+H]$^+$ 533.4

Example 70m

3-[2-(2-Ethylbenzoimidazol-1-yl)-4-morpholin-4-ylthieno[3,2-d]pyrimidin-6-ylmethyl]azetidine-1-carboxylic acid tert-butyl ester

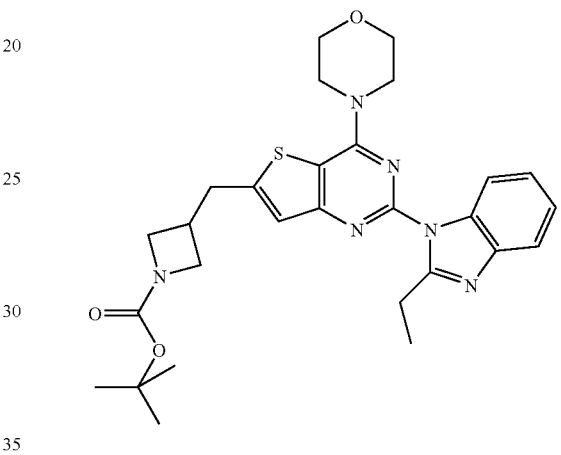

To a solution of 3-[2-(2-ethylbenzoimidazol-1-yl)-4-morpholin-4-ylthieno[3,2-d]pyrimidin-6-ylmethylene]azetidine-1-carboxylic acid tert-butyl ester (1.5 g, 2.51 mmol) in EtOH (30 mL) was added 10% Pd/C (275 mg) and the resulting mixture stirred under an atmosphere of H$_2$ for 65 h. The reaction mixture was filtered through Celite®, washing with EtOH, and the filtrate concentrated in vacuo. The resulting residue was purified by column chromatography (Si—PCC, MeOH:DCM, 0-10%) affording the title compound as an orange oil (0.71 g, 53%). LCMS (method A): R$_T$ 3.22 min [M+H]$^+$ 535.4

Example 70n

6-Azetidin-3-ylmethyl-2-(2-ethylbenzoimidazol-1-yl)-4-morpholin-4-ylthieno[3,2-d]pyrimidine

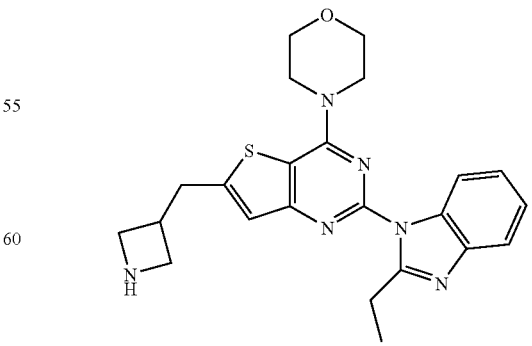

To a solution of 3-[2-(2-ethylbenzoimidazol-1-yl)-4-morpholin-4-ylthieno[3,2-c]pyrimidin-6-ylmethyl]azetidine-1- carboxylic acid tert-butyl ester (700 mg, 1.31 mmol) in DCM (3 mL) was added TFA (0.5 mL) and the resulting mixture stirred for 18 h at r.t. The reaction mixture was concentrated in vacuo and the resulting residue loaded onto an Isolute® SCX-2 cartridge which was washed with MeOH/DCM and the product eluted with 2M $NH_3$/MeOH affording the title compound as an orange gum (522 mg, 91%). LCMS (method A): $R_T$ 1.80 min $[M+H]^+$ 435.4

Formula I(iii) purine intermediates wherein (iii) $X^1$ is N and $X^2$ is $NR^2$ Example 75a 2,6-dichloro-9-methyl-9H-purine 4

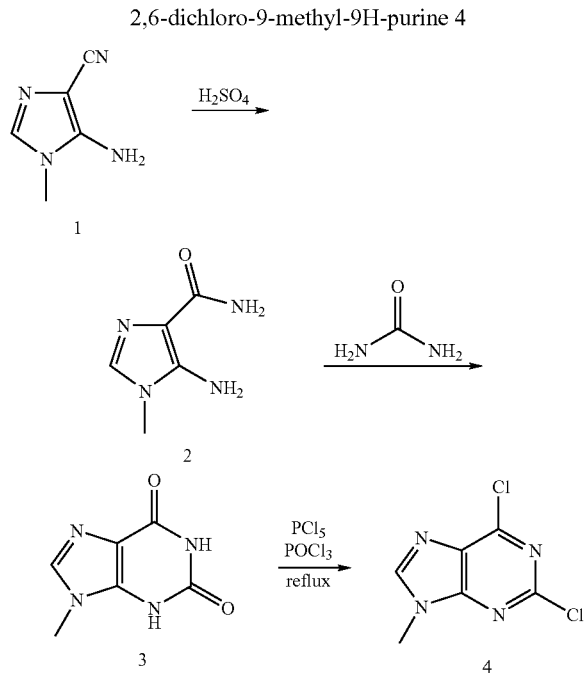

The cyano group of 5-amino-1-methyl-1H-imidazole-4-carbonitrile 1 is hydrolyzed with sulfuric acid to give 5-amino-1-methyl-1H-imidazole-4-carboxamide 2. Cyclization with urea gives 9-methyl-1H-purine-2,6(3H,9H)-dione 3. Chlorination with phosphorus pentachloride and phosphorusoxychloride gives 2,6-dichloro-9-methyl-9H-purine 4 (CAS Registry 2382-10-7).

Example 75b 2-(1-((2-chloro-9-methyl-6-morpholino-9H-purin-8-yl)methyl)piperidin-4-yl)propan-2-ol

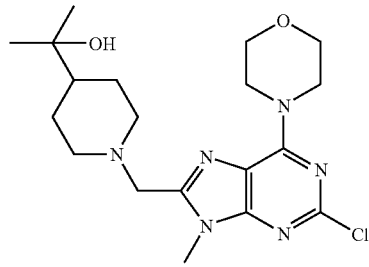

To 4-(2-chloro-9-(tetrahydro-2H-pyran-2-yl)-9H-purin-6-yl)morpholine (100 g) in methanol (500 mL) at 50° C. was added p-toluenesulfonic acid monohydrate (6 g). The reaction was stirred for 30 mins, whereupon white solid has crashed fully out of solution. The solid is filtered and collected thru Buchner funnel, rinsed with Methanol and dried under vacuum to get 4-(2-chloro-9H-purin-6-yl)morpholine. Cesium carbonate (200 g) and iodomethane (30 mL) were subsequently added to a stirring solution of 4-(2-chloro-9H-purin-6-yl)morpholine in DMF at 50° C. The reaction was monitored by lc-ms until complete, about 30 minutes, whereupon the solvent was concentrated to dryness. Subsequent suspension of the crude reaction in water precipitated 4-(2-chloro-9-methyl-9H-purin-6-yl)morpholine (72 g) as a white solid, which was filtered and dried under vacuum overnight.

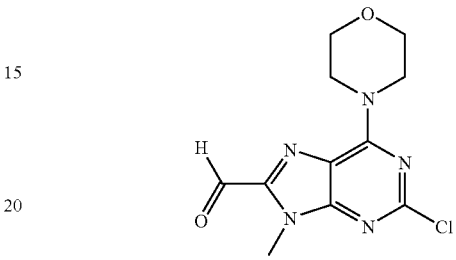

To stirred solution of 4-(2-chloro-9-methyl-9H-purin-6-yl)morpholine (10 g) and N,N,N',N'-tetramethylethylenediamine (9.0 mL) in tetrahydrofuran (200 mL) at −78° C. was added 2.5 M of n-butyllithium in tetrahydrofuran (35 mL). The solution was stirred at −40° C. for 30 minutes, and then re-cooled to −78° C., whereupon DMF (8 mL) was added and the reaction stirred for another hour. The reaction was quenched into cold 0.25N HCl solution via 10 mL serological pipet aliquots. Ice was added to keep quenching solution temperature below 5° C., to avoid formation of by-product during workup. 2-Chloro-9-methyl-6-morpholino-9H-purine-8-carbaldehyde (11g) precipitated as a light yellow solid which was filtered, rinsed with water and dried under vacuum.

A solution of 2-chloro-9-methyl-6-morpholino-9H-purine-8-carbaldehyde (17.2 g) in MeOH (800 mL) at 0° C. was treated portion wise with sodium borohydride (5 g). The reaction was warmed to room temperature and stirred 15 minutes. The reaction mixture was quenched with saturated solution of sodium bicarbonate. The aqueous layer was extracted twice with ethyl acetate. The combined organic layers were dried over magnesium sulfate and concentrated in vacuo to yield crude 2-chloro-9-methyl-6-morpholino-9H-purin-8-yl)methanol (16.9 g) as a white solid.

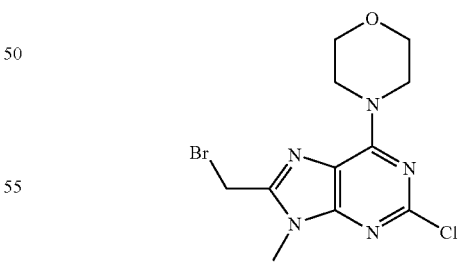

To a solution of crude 2-chloro-9-methyl-6-morpholino-9H-purin-8-yl)methanol (16.5 g) in a mixture of dichloroethane (600 mL) and THF (400 mL) at 0° C. was added phosphorus tribromide (11 mL) dropwise. The reaction was stirred for 1 h whereupon the solid that precipitated was filtered, rinsed with water, collected and dried to give 4-(8-(bromomethyl)-2-chloro-9-methyl-9H-purin-6-yl)morpholine (15.6 g) as a white solid.

2-(Piperidin-4-yl)propan-2-ol (0.73 g) was reacted with 4-(8-(bromomethyl)-2-chloro-9-methyl-9H-purin-6-yl)morpholine (1.6 g) via General Procedure C to yield 2-(1-((2-chloro-9-methyl-6-morpholino-9H-purin-8-yl)methyl)piperidin-4-yl)propan-2-ol (1.76 g) as a white solid.

Example 75c

9-Methyl-2-(2-methylbenzoimidazol-1-yl)-6-morpholin-4-yl-9H-purine-8-carbaldehyde

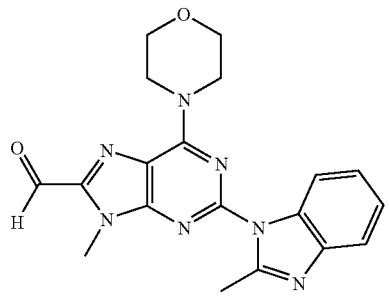

A mixture of Pd$_2$(dba)$_3$ (161 mg, 0.18 mmol), Xphos (CAS Reg. No. 564483-18-7, 336 mg, 0.72 mmol), 2-chloro-9-methyl-6-morpholin-4-yl-9H-purine-8-carbaldehyde (1.0 g, 3.52 mmol), 2-ethyl-1H-benzoimidazole (500 mg, 3.73 mmol), cesium carbonate (2.3 g, 7 mmol) in dioxane (15 mL) was degassed for 5 min and heated at 145° C. for 30 min under microwave irradiation. The reaction mixture was filtered while still hot through a pad of celite, and the pad was washed with hot dioxane. The product precipitated immediately as a pale yellow solid. The solid was filtered and dried at 50° C. under vacuum to give 9-Methyl-2-(2-methylbenzoimidazol-1-yl)-6-morpholin-4-yl-9H-purine-8-carbaldehyde (650 mg, 50%). Additional material could be recovered from the mother liquors. LCMS (Method H): R$_T$ 3.39 min; [M+MeOH]$^+$ 410

Example 75d 2-(2-Ethylbenzoimidazol-1-yl)-9-methyl-6-morpholin-4-yl-9H-purine-8-carbaldehyde

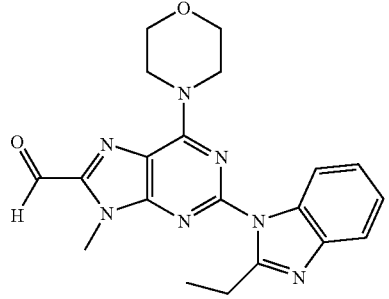

A mixture of Pd$_2$(dba)$_3$ (458 mg, 0.5 mmol), Xphos (954 mg, 2 0 mmol), 2-chloro-9-methyl-6-morpholin-4-yl-9H-purine-8-carbaldehyde (5.64 g, 20 0 mmol), 2-ethyl-1H-benzoimidazole (3.21 g, 22.0 mmol), cesium carbonate (9.78 g, 30.0 mmol) in dioxane (80 mL) was degassed for 5 min and heated at reflux for 18 h. The reaction mixture was filtered through a pad of celite while still hot, and the pad was washed with hot dioxane. The combined filtrate was concentrated under reduced pressure to give a residue which was triturated in Et$_2$O (ca 100 mL), filtered and dried at 50° C. under vacuum to give 2-(2-Ethylbenzoimidazol-1-yl)-9-methyl-6-morpholin-4-yl-9H-purine-8-carbaldehyde as a yellow solid (4.5 g). LCMS (Method H): R$_T$ 3.63 min; [M+MeOH]$^+$ 424

Example 75e 2-(2-Cyclopropylbenzoimidazol-1-yl)-9-methyl-6-morpholin-4-yl-9H-purine-8-carbaldehyde

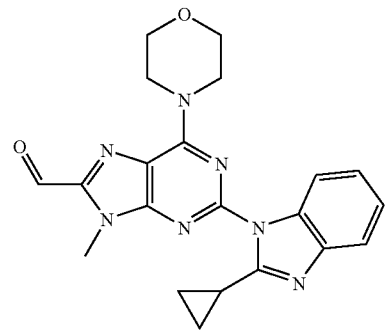

A mixture of 2-chloro-9-methyl-6-morpholin-4-yl-9H-purine-8-carbaldehyde (210 mg, 0.79 mmol), 2-cyclopropylbenzimidazole (150 mg, 0.95 mmol), tris(dibenzylideneacetone)dipalladium (44 mg, 0.05 mmol), Xphos (90 mg, 0.18 mmol) and Cs$_2$CO$_3$ (618 mg, 1.90 mmol) in dioxane (3 mL) and DMF (1 mL) was purged with argon then heated at 145° C. for 45 min in a microwave reactor. The reaction mixture was filtered through a pad of celite, washing with EtOAc. The filtrate was concentrated in vacuo and purified by column chromatography (Si—PCC, EtOAc:cyclohexane, 0-75%) affording 2-(2-Cyclopropylbenzoimidazol-1-yl)-9-methyl-6-morpholin-4-yl-9H-purine-8-carbaldehyde as an orange solid (282 mg, 89%). LCMS (Method H): R$_T$ 3.79 min, [M+H]$^+$ 436.4

Example 75f

2-[2-(2-Hydroxyethyl)benzoimidazol-1-yl]-9-methyl-6-morpholin-4-yl-9H-purine-8-carbaldehyde

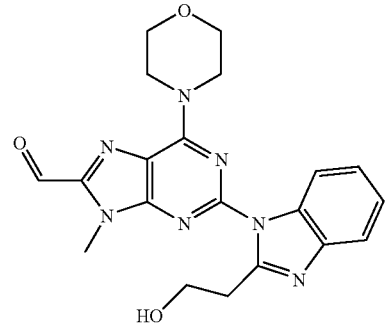

A mixture of 2-chloro-9-methyl-6-morpholin-4-yl-9H-purine-8-carbaldehyde (500 mg, 1.78 mmol), 2-(1H-benzoimidazol-2-yl)ethanol (335 mg, 2.06 mmol), Pd$_2$dba$_3$ (40 mg, 0.043 mmol), Xphos (85 mg, 0.18 mmol) and cesium carbonate (840 mg, 2.58 mmol) in 1,4-dioxane (10 mL) was purged with argon gas then subjected to microwave irradiation at 145° C. for 30 min. The reaction mixture was filtered through a pad of Celite® and the filtrate was concentrated in vacuo. The resultant residue was purified by flash chromatography (Si—PPC, EtOAc: MeOH; 100:0 to 98:2 to 95:5 to 90:10) to afford 2-[2-(2-Hydroxyethyl)benzoimidazol-1-yl]-9-methyl-6-morpholin-4-yl-9H-purine-8-carbaldehyde as a yellow solid (487 mg, 67%). $^1$H NMR (CDCl$_3$, 400MHz) δ 9.93 (s, 1 H); 8.16-8.12 (m, 1 H); 7.76-7.72 (m, 1 H); 7.35-7.29 (m, 2 H); 4.52 (m, 4 H); 4.20 (t, J=5.3 Hz, 2 H); 4.14 (s, 3 H); 3.91 (m, 5 H) and 3.57 (t, J=5.3 Hz, 2 H).

Example 75g

8-Chloromethyl-2-(2-ethylbenzoimidazol-1-yl)-9-methyl-6-morpholin-4-yl-9H-purine

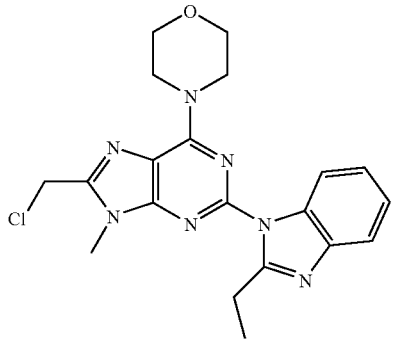

To a suspension of [2-(2-ethylbenzoimidazol-1-yl)-9-methyl-6-morpholin-4-yl-9H-purin-8-yl]methanol (200 mg, 0.51 mmol) in DCM (6 mL) and DMF (100 μL) was added oxalyl chloride (129 μL, 1.52 mmol) and the resulting solution was stirred at room temperature for 19 h. The reaction mixture was concentrated in vacuo to an oil which was purified by column chromatography (Si—PCC, MeOH:DCM, 0-10%) affording 8-Chloromethyl-2-(2-ethylbenzoimidazol-1-yl)-9-methyl-6-morpholin-4-yl-9H-purine as an impure mixture which was used directly in subsequent reactions.

Example 75h

2-Chloro-8-[3-(1,1-Dioxo-1-thiomorpholin-4-yl)azetidin-1-ylmethyl]-9-methyl-6-morpholin-4-yl-9H-purine

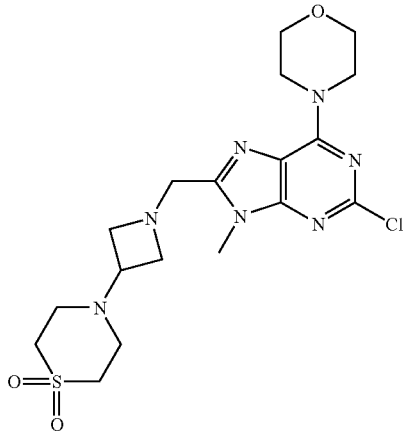

A mixture of 2-chloro-9-methyl-6-morpholin-4-yl-9H-purine-8-carbaldehyde (400 mg, 1.42 mmol), 4-azetidin-3-ylthiomorpholine-1,1-dioxide (324 mg, 1.70 mmol) and 4 Å powdered molecular sieves (900 mg) in DCE (20 mL) was stirred at room temperature for 4 h before the addition of sodium triacetoxyborohydride (602 mg, 2.84 mmol). The reaction mixture was stirred for 40 h then filtered through celite, washing with DCM. The organic phase was washed with brine (×1) and concentrated in vacuo. The resulting residue was purified by column chromatography (Si—PCC, MeOH:EtOAc, 0-15%) affording 2-Chloro-8-[3-(1,1-Dioxo-1-thiomorpholin-4-yl)azetidin-1-ylmethyl]-9-methyl-6-morpholin-4-yl-9H-purine as a cream solid (587 mg, 91%). LCMS (Method H): R$_T$ 2.25 min [M+H]$^+$ 456.3

Example 75i

2-Chloro-9-methyl-6-morpholin-4-yl-8-(3-morpholin-4-ylazetidin-1-ylmethyl)-9H-purine

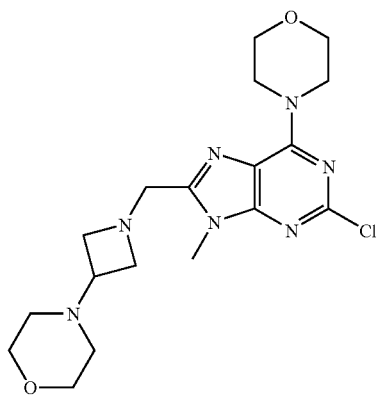

A mixture of 2-chloro-9-methyl-6-morpholin-4-yl-9H-purine-8-carbaldehyde (235 mg, 0.82 mmol), 4-azetidin-3-ylmorpholine (122 mg, 0.86 mmol) and 4 Å powdered molecular sieves (300 mg) in DCE (8 mL) was stirred at room temperature for 3 h before the addition of sodium triacetoxyborohydride (346 mg, 1.63 mmol). The reaction mixture was stirred for 65 h then filtered through celite, washing with DCM. The organic phase was washed with brine and concentrated in vacuo. The resulting residue was purified by column chromatography (Si—PCC, MeOH:EtOAc, 0-20%) affording 2-Chloro-9-methyl-6-morpholin-4-yl-8-(3-morpholin-4-ylazetidin-1-ylmethyl)-9H-purine as a cream solid (165 mg, 49%). LCMS (Method A): R$_T$ 2.22 min [M+H]$^+$ 408.2

Example 75j 2-(2-Ethylbenzoimidazol-1-yl)-6-morpholin-4-yl-9-(tetrahydropyran-2-yl)-8-[3-(tetrahydropyran-4-yl)azetidin-1-ylmethyl]-9H-purine

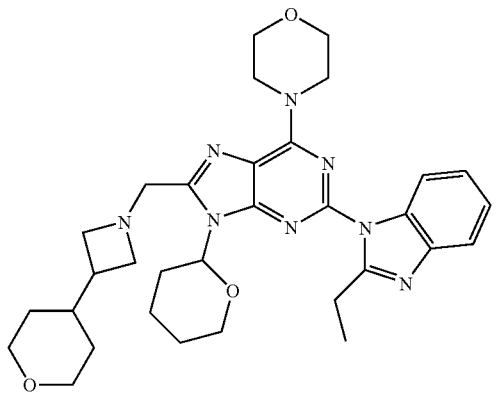

Step 1: 2-(2-Ethylbenzoimidazol-1-yl)-6-morpholin-4-yl-9-(tetrahydropyran-2-yl)-9H-purine-8-carbaldehyde

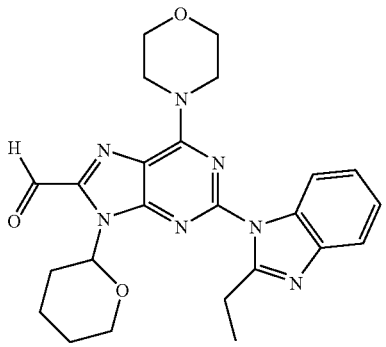

Step 1: A mixture of 2-chloro-6-morpholin-4-yl-9-(tetrahydropyran-2-yl)-9H-purine-8-carbaldehyde (0.8 g, 2.27 mmol), 2-ethyl-1H-benzoimidazole (0.4 g, 2.72 mmol), Xphos (0.216 g, 0.45 mmol), Pd$_2$(dba)$_3$ (0.104 g, 0.11 mmol) and Cs$_2$CO$_3$ (1.48 g, 4.54 mmol) in dioxane (10 mL) was subjected to microwave irradiation at 145° C. for 45 min. The suspension was filtered through Celite and the filtrate was concentrated in vacuo. The residue was purified by flash chromatography (Si—PPC, EtOAc:Cyclohexane, gradient 0:100 to 75:25) to give 2-(2-Ethylbenzoimidazol-1-yl)-6-morpholin-4-yl-9-(tetrahydropyran-2-yl)-8-[3-(tetrahydropyran-4-yl)azetidin-1-ylmethyl]-9H-purine as a yellow foam (0.444 g, 43%). LCMS (Method A): R$_T$=4.05 min, [M+H]$^+$ 494.4

Step 2: A 10 mL round-bottomed flask was charged with a solution of 2-(2-ethylbenzoimidazol-1-yl)-6-morpholin-4-yl-9-(tetrahydropyran-2-yl)-9H-purine-8-carbaldehyde (0.22 g, 0.48 mmol), 3-(tetrahydropyran-4-yl)azetidine hydrochloride (0.093 g, 0.53 mmol) in DCE (5 mL), trimethoxymethane (0.518 mL, 4.8 mmol) and acetic acid (0.03 mL, 0.48 mmol). The reaction mixture was stirred for 4 h at room temperature. Sodium triacetoxyborohydride (0.152 g, 0.72 mmol) was added and the reaction mixture was stirred for a further 72 h at room temperature. The suspension was partitioned between DCM and water; the organic layer was separated and washed with brine, dried with sodium sulphate and concentrated to give 2-(2-Ethylbenzoimidazol-1-yl)-6-morpholin-4-yl-9-(tetrahydropyran-2-yl)-8-[3-(tetrahydropyran-4-yl)azetidin-1-ylmethyl]-9H-purine as an orange oil (0.356 g, 99%). LCMS (Method A): R$_T$=2.97 min, [M+H]$^+$ 587.4

Example 75k

N-[9-Methyl-6-morpholin-4-yl-8-(4-oxetan-3-yl-piperidin-1-ylmethyl)-9H-purin-2-yl]benzene-1,2-diamine

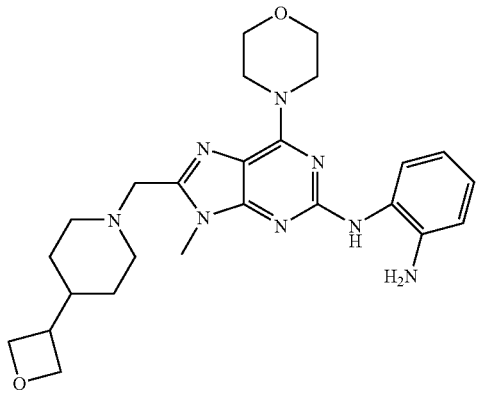

A mixture of 2-chloro-9-methyl-6-morpholin-4-yl-8-(4-oxetan-3-yl-piperidin-1-ylmethyl)-9H-purine (0.2 g, 0.49 mmol), benzene-1,2-diamine (0.106 g, 0.98 mmol), Xphos (0.047 g, 0.098 mmol), Pd$_2$(dba)$_3$ (0.022 g, 0.025 mmol) and Cs$_2$CO$_3$ (0.32 g, 0.98 mmol) in DMF (2 mL) was subjected to microwave irradiation at 150° C. for 30 min. The suspension was filtered through Celite and the solution was concentrated in vacuo. The residue was purified by flash chromatography (Si—PPC, MEOH:DCM, gradient 0:100 to 10:90) to give N-[9-Methyl-6-morpholin-4-yl-8-(4-oxetan-3-yl-piperidin-1-ylmethyl)-9H-purin-2-yl]benzene-1,2-diamine as yellow foam (0.117 g, 50%). LCMS (Method A): R$_T$=2.14 min, [M+H]$^+$ 479.2

Example 75l

2-Chloro-9-methyl-6-morpholin-4-yl-8-[3-(tetrahydropyran-4-yl)azetidin-1-ylmethyl]-9H-purine

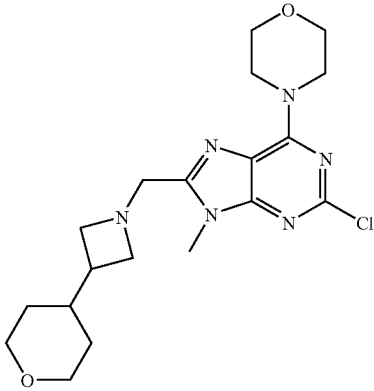

A 25 mL round-bottomed flask was charged with a solution of 2-chloro-9-methyl-6-morpholin-4-yl-9H-purine-8-carbaldehyde (0.173 g, 0.65 mmol), 3-(tetrahydropyran-4-yl)azetidine hydrochloride (0.138 g, 0.78 mmol) and 4 Å molecular sieves (0.9 g) in DCE (7 mL). The reaction mixture was stirred for 5 h at room temperature. Sodium triacetoxyborohydride (0.274 g, 1.29 mmol) was added and the reaction mixture was stirred for 18 h at room temperature. The suspension was filtered through Celite and the filtrate was concentrated in vacuo. The residue was purified by flash chromatography (Si—PPC, MeOH:EtOAc, gradient 0:100 to 10:90) to give 2-Chloro-9-methyl-6-morpholin-4-yl-8-[3-(tetrahydropyran-4-yl)azetidin-1-ylmethyl]-9H-purine as a white foam (0.117 g, 45%). LCMS (Method A): R$_T$=2.40 min, [M+H]$^+$ 407.2

Example 75m

N-{9-Methyl-6-morpholin-4-yl-8-[3-(tetrahydropyran-4-yl)azetidin-1-ylmethyl]-9H-purin-2-yl}benzene-1,2-diamine

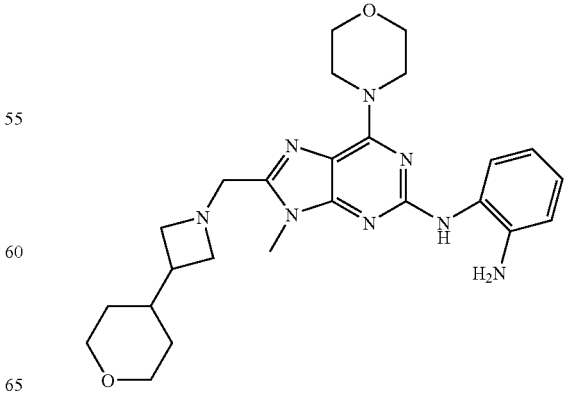

A mixture of 2-chloro-9-methyl-6-morpholin-4-yl-8-[3-(tetrahydropyran-4-yl)azetidin-1-ylmethyl]-9H-purine (0.25 g, 0.61 mmol), benzene-1,2-diamine (0.133 g, 1.23 mmol), Xphos (0.059g, 0.123 mmol), Pd$_2$(dba)$_3$ (0.028 g, 0.031 mmol) and Cs$_2$CO$_3$ (0.17 g, 1.23 mmol) in DMF (2.5 mL) was subjected to microwave irradiation at 150° C. for 30 min. The suspension was filtered through Celite and the filtrate was concentrated in vacuo. The residue was purified by flash chromatography (Si—PPC, MEOH:DCM, gradient 0:100 to 10:90) to give the title compound as a brown foam (0.234 g, 80%). LCMS (Method A): R$_T$=2.20 min, [M+H]$^+$ 479.4

Example 75n

2-[1-(9-Methyl-6-morpholin-4-yl-2-(tributylstanna-nyl)-9H-purin-8-ylmethyl)piperidin-4-yl]propan-2-ol

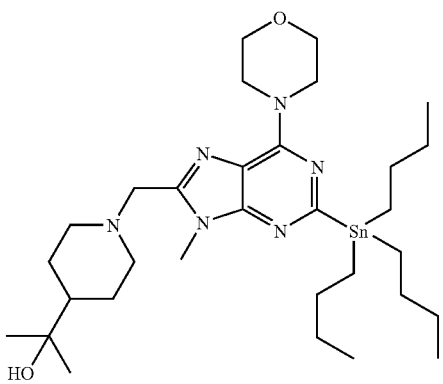

A mixture of 2-[1-(2-chloro-9-methyl-6-morpholin-4-yl-9H-purin-8-ylmethyl)-piperidin-4-yl]propan-2-ol (500 mg, 1.23 mmol), hexabutylditin (0.928 mL, 1.84 mmol), PdCl$_2${P$^t$Bu$_2$(Ph-p-Nme$_2$)}$_2$ (88 mg, 0.122 mmol) in dioxane (2.5 mL) and NMP (0.25 mL) was degassed and then subjected to microwave irradiation at 150° C. for 45 min. The reaction mixture was filtered through Celite and the filtrate was concentrated in vacuo. The residue was dissolved in DCM (10 mL), washed with water (10 mL) The organic layer was separated, dried with sodium sulphate and concentrated in vacuo. The residue was diluted with MeOH and loaded onto a Isolute® SCX-2 cartridge (10 g). The cartridge was then washed with MeOH and the desired product was subsequently eluted using 2 M NH$_3$ in MeOH. The solution was concentrated to give a residue which was subjected to flash chromatography (Si—PPC, MEOH:DCM, gradient 0:100 to 7.5:92.5) followed by (Si—PPC, EtOAc:cyclohexane, gradient 0:100 to 100:0). Appropriate fractions were combined and concentrated to give the title compound as pale yellow oil (236 mg, 29%). LCMS (Method A) R$_T$=4.58 min; [M+H]$^+$ 663.3 ($^{116}$Sn) 665.3 ($^{118}$Sn)

Example 75o (2-Chloro-9-methyl-6-morpholin-4-yl-9H-purin-8-yl)acetaldehyde

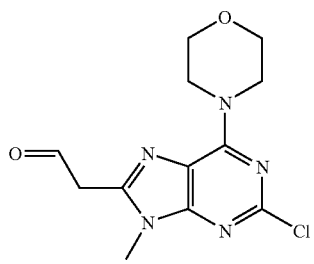

To a stirred suspension of (methoxymethyl)triphenylphosphonium chloride (1.49 g, 4.35 mmol) in dry THF (10 mL) was added dropwise a 1 M solution of LiHMDS in THF (4.35 mL, 4.35 mmol) under an atmosphere of nitrogen, at 0° C. After 15 min a suspension of 2-chloro-9-methyl-6-morpholin-4-yl-9H-purine-8-carbaldehyde (1.02 g, 3.62 mmol) in dry THF (10 mL) was added. The mixture was allowed to warm to RT after 30 min and stirred for a further 1 h then quenched with H$_2$O. The mixture was partitioned between EtOAc and 0.5 M HCl$_{(aq)}$, the organic layer separated and washed with water and then brine. The organic layer was dried (Na$_2$SO$_4$) and evaporated to give a residue (2.2 g), which was dissolved in MeOH, loaded onto an Isolute® SCX-2 cartridge, the cartridge was washed with MeOH then the desired product eluted with 2 M NH$_3$ in MeOH to give a residue (860 mg) which was taken up in 37 wt. % HCl$_{(aq)}$/THF (8:16 mL) The resulting mixture was stirred at 50° C. for 2 h then allowed to cool, partitioned between EtOAc and saturated NaHCO$_3$ $_{(aq)}$. The organic layer was separated and washed with brine then dried (Na$_2$SO$_4$) and concentrated in vacuo. The resultant residue was purified by flash chromatography (Si—PCC, 0-100% EtOAc in cyclohexane) to give the title compound (451 mg, 42% over 2 steps) as an orange solid. LCMS (Method H): R$_T$ 3.29 min, [M+H]$^+$ 296.2

Example 75p

2-{1-[2-(2-Chloro-9-methyl-6-morpholin-4-yl-9H-purin-8-yl)ethyl]piperidin-4-yl}propan-2-ol

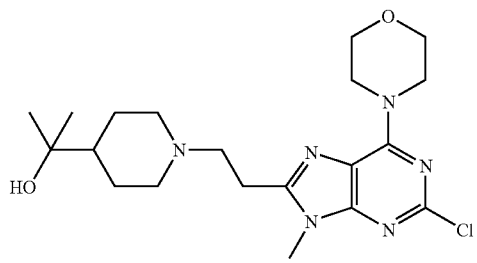

To a solution of (2-chloro-9-methyl-6-morpholin-4-yl-9H-purin-8-yl)acetaldehyde (150 mg, 0.51 mmol) in DCE (10 mL) was added 2-piperidin-4-ylpropan-2-ol (110 mg, 0.77 mmol), trimethyl orthoformate (0.55 mL, 5.02 mmol) and acetic acid (0.03 mL, 0.52 mmol). The reaction mixture was stirred at room temperature for 5 h, sodium triacetoxyborohydride (154 mg, 0.73 mmol) was added and the resulting mixture stirred for a further 2 h. The reaction mixture was loaded onto an Isolute® SCX-2 cartridge, the cartridge was washed with MeOH then the desired product eluted with 2 M NH$_3$ in MeOH. The resulting residue was purified by column chromatography (Si—PCC, 0-10% MeOH in DCM) to give the title compound as an off white solid (109 mg, 51%). LCMS (Method H): R$_T$=2.54 min, [M+H]$^+$ 423.5

Example 75q

2-{4-[2-(2-Chloro-9-methyl-6-morpholin-4-yl-9H-purin-8-yl)ethyl]piperazin-1-yl}isobutyramide

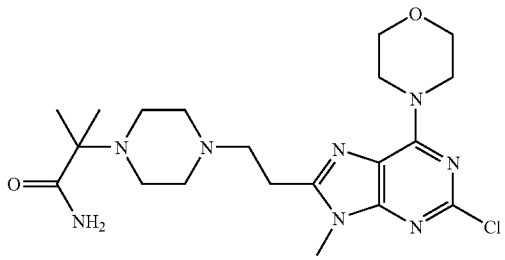

To a solution of (2-chloro-9-methyl-6-morpholin-4-yl-9H-purin-8-yl)acetaldehyde (110 mg, 0.37 mmol) in DCE (10 mL) was added 2-piperazin-1-ylisobutyramide (90 mg, 0.53 mmol), trimethyl orthoformate (0.20 mL, 1.86 mmol) and acetic acid (0.02 mL, 0.37 mmol). The reaction mixture was stirred at room temperature for 3 h, sodium triacetoxyborohydride (118 mg, 0.56 mmol) was added and the resulting mixture stirred for a further 2 days. The reaction mixture was loaded onto an Isolute® SCX-2 cartridge, the cartridge was washed with MeOH then the desired product eluted with 2 M NH$_3$ in MeOH. The resulting residue was purified by column chromatography (Si—PCC, 0-20% MeOH in EtOAc) to give the title compound as a pale yellow solid (71 mg, 42%). LCMS (Method H): R$_T$=2.40 min, [M+H]$^+$ 451.5

Example 75r

2-Chloro-8-[2-(2,2-dimethylmorpholin-4-yl)ethyl]-9-methyl-6-morpholin-4-yl-9H-purine

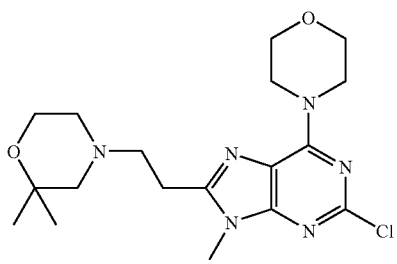

To a solution of (2-chloro-9-methyl-6-morpholin-4-yl-9H-purin-8-yl)acetaldehyde (116 mg, 0.39 mmol) in DCE (10 mL) was added 2,2-dimethylmorpholine (68 mg, 0.59 mmol), trimethyl orthoformate (0.22 mL, 1.96 mmol) and acetic acid (0.02 mL, 0.39 mmol). The reaction mixture was stirred at room temperature for 3 h, sodium triacetoxyborohydride (125 mg, 0.59 mmol) was added and the resulting mixture stirred for a further 18 h. The reaction mixture was loaded onto an Isolute® SCX-2 cartridge, he cartridge was washed with MeOH then the desired product eluted with 2 M NH$_3$ in MeOH. The resulting residue was purified by column chromatography (Si—PCC, 0-10% MeOH in EtOAc) to give the title compound as a pale yellow solid (100 mg, 65%). LCMS (Method H): R$_T$=2.51 min, [M+H]$^+$ 395.4

Example 75s

2-{1-[2-(2-Chloro-9-methyl-6-morpholin-4-yl-9H-purin-8-yl)ethyl]azetidin-3-yl}propan-2-ol

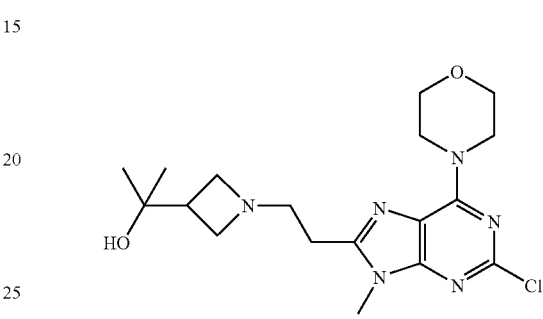

To a solution of (2-chloro-9-methyl-6-morpholin-4-yl-9H-purin-8-yl)acetaldehyde (300 mg, 1.01 mmol) in DCE (20 mL) was added 2-azetidin-3-ylpropan-2-ol (118 mg, 1.02 mmol), trimethyl orthoformate (1.11 mL, 10.14 mmol) and acetic acid (0.06 mL, 1.01 mmol). The reaction mixture was stirred at room temperature for 6 h, sodium triacetoxyborohydride (323 mg, 1.52 mmol) was added and the resulting mixture stirred for a further 18 h. The reaction mixture was loaded onto an Isolute® SCX-2 cartridge, the cartridge was washed with MeOH then the desired product eluted with 2 M NH$_3$ in MeOH. The resulting residue was purified by column chromatography (Si—PCC, 0-10% MeOH in DCM) to give the title compound as a pale yellow oil (90 mg, 23%). LCMS (Method A): R$_T$=2.37 min, [M+H]$^+$ 395.2

Example 75t

1-[2-(2-Chloro-9-methyl-6-morpholin-4-yl-9H-purin-8-yl)ethyl]-4-methylpiperidin-4-ol

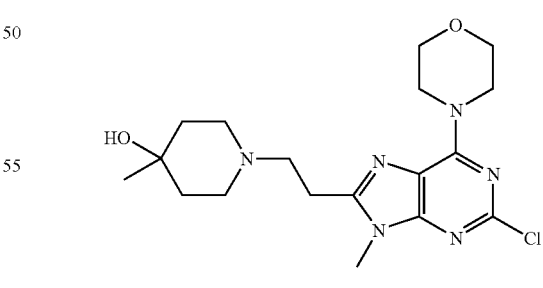

To a solution of (2-chloro-9-methyl-6-morpholin-4-yl-9H-purin-8-yl)acetaldehyde (200 mg, 0.68 mmol) in DCE (15 mL) was added 4-methylpiperidin-4-ol (117 mg, 1.01 mmol), trimethyl orthoformate (0.74 mL, 6.76 mmol) and acetic acid (0.04 mL, 0.68 mmol). The reaction mixture was stirred at room temperature for 1.5 h, sodium triacetoxyborohydride (187 mg, 1.35 mmol) was added and the resulting mixture stirred for a further 18 h. The reaction mixture was loaded onto an Isolute® SCX-2 cartridge, washed with MeOH then the desired product eluted with 2 M NH$_3$/MeOH in DCM. The resulting residue was purified by column chromatography (Si—PCC, 0-20% 2 M NH$_3$/MeOH in DCM) to give the title compound as a colourless oil (45 mg, 17%). LCMS (Method H): R$_T$=2.24 min, [M+H]$^+$ 395.5

Example 75u

1-[2-(2-Chloro-9-methyl-6-morpholin-4-yl-9H-purin-8-yl)ethyl]-3-methyl-azetidin-3-ol

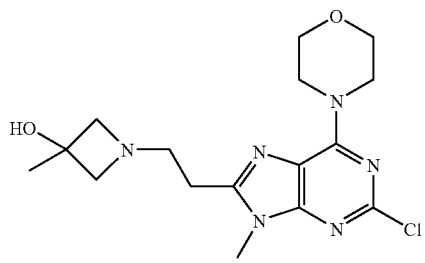

To a solution of (2-chloro-9-methyl-6-morpholin-4-yl-9H-purin-8-yl)acetaldehyde (150 mg, 0.51 mmol) in DCE (10 mL) was added 3-methyl-azetidin-3-ol (65 mg, 0.75 mmol) and powdered 4 Å molecular sieves. The reaction mixture was stirred at room temperature for 2 h, sodium triacetoxyborohydride (215 mg, 1.01 mmol) was added and the resulting mixture stirred for a further 17 h. The reaction mixture was loaded onto an Isolute® SCX-2 cartridge, washed with MeOH then the desired product eluted with 2 M NH$_3$ in MeOH. The resulting residue was purified by column chromatography (Si—PCC, 0-10% MeOH in DCM) to give the title compound as a pale yellow oil (83 mg, 45%). LCMS (Method H): R$_T$=2.29 min, [M+H]$^+$ 367.5

Example 75v

7-[2-(2-Chloro-9-methyl-6-morpholin-4-yl-9H-purin-8-yl)ethyl]-7-azaspiro[3.5]nonan-2-ol

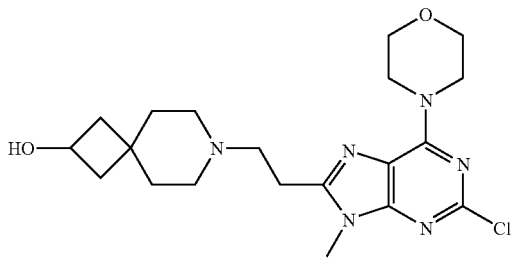

To a solution of (2-chloro-9-methyl-6-morpholin-4-yl-9H-purin-8-yl)acetaldehyde (157 mg, 0.53 mmol) in DCE (10 mL) was added 7-azaspiro[3.5]nonan-2-ol (109 mg, 0.77 mmol) and powdered 4 Å molecular sieves. The reaction mixture was stirred at room temperature for 4 h, sodium triacetoxyborohydride (225 mg, 1.06 mmol) was added and the resulting mixture stirred for a further 16 h. The reaction mixture was loaded onto an Isolute® SCX-2 cartridge, washed with MeOH then the desired product eluted with 2 M NH$_3$ in MeOH. The resulting residue was purified by column chromatography (Si—PCC, 0-10% 2 M NH$_3$/MeOH in DCM) to give the title compound as a colourless oil (155 mg, 69%). LCMS (Method H): R$_T$=2.41 min, [M+H]$^+$ 421.5

Example 75w

1-[2-(2-Chloro-9-methyl-6-morpholin-4-yl-9H-purin-8-yl)ethyl]-3-isopropyl-azetidin-3-ol

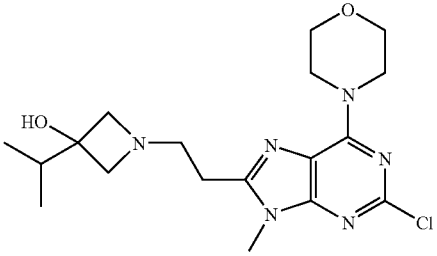

To a solution of (2-chloro-9-methyl-6-morpholin-4-yl-9H-purin-8-yl)acetaldehyde (69 mg, 0.23 mmol) in DCE (5 mL) was added 3-isopropyl-azetidin-3-ol (27 mg, 0.23 mmol) and powdered 4 Å molecular sieves. The reaction mixture was stirred at room temperature for 2 h, sodium triacetoxyborohydride (99 mg, 0.47 mmol) was added and the resulting mixture stirred for a further 2 days. The reaction mixture was loaded onto an Isolute® SCX-2 cartridge, washed with MeOH then the desired product eluted with 2 M NH$_3$ in MeOH. The resulting residue was purified by column chromatography (Si—PCC, 0-10% 2 M NH$_3$/MeOH in DCM) to give the title compound as a pale yellow oil (30 mg, 33%). LCMS (Method H): R$_T$=2.65 min, [M+H]$^+$ 395.5

Example 75x

4-[2-(2-Chloro-9-methyl-6-morpholin-4-yl-9H-purin-8-yl)ethyl]-1-isopropylpiperazin-2-one

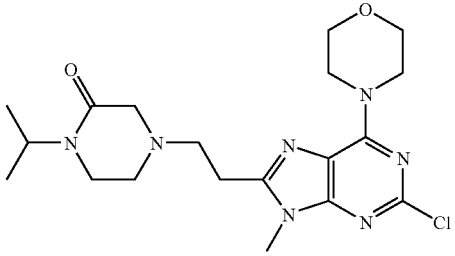

To a solution of (2-chloro-9-methyl-6-morpholin-4-yl-9H-purin-8-yl)acetaldehyde (167 mg, 0.57 mmol) in DCE (10 mL) was added 1-isopropylpiperazin-2-one (87 mg, 0.61 mmol) and powdered 4 Å molecular sieves. The reaction mixture was stirred at room temperature for 1 h, sodium triacetoxyborohydride (239 mg, 1.13 mmol) was added and the resulting mixture stirred for a further 16 h. The reaction mixture was filtered through Celite®, loaded onto an Isolute® SCX-2 cartridge, washed with MeOH then the desired product eluted with 2 M NH$_3$ in MeOH. The resulting residue was purified by column chromatography (Si—PCC, 0-10% 2

Example 75xx

2-Chloro-9-methyl-6-morpholin-4-yl-8-[2-(3-oxa-8-azabicyclo[3.2.1]oct-8-yl)ethyl]-9H-purine

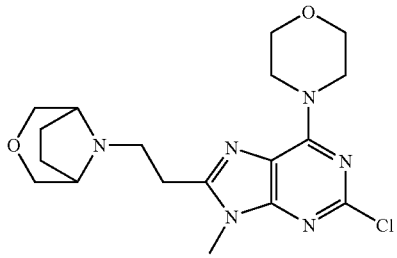

To a solution of (2-chloro-9-methyl-6-morpholin-4-yl-9H-purin-8-yl)acetaldehyde (117 mg, 0.40 mmol) in DCE (10 mL) was added 3-oxa-8-azabicyclo[3.2.1]octane (54 mg, 0.48 mmol) and powdered 4 Å molecular sieves. The reaction mixture was stirred at room temperature for 2 h, sodium triacetoxyborohydride (168 mg, 0.79 mmol) was added and the resulting mixture stirred for a further 16 h. The reaction mixture was filtered through Celite®, loaded onto an Isolute® SCX-2 cartridge, washed with MeOH then the desired product eluted with 2 M $NH_3$ in MeOH. The resulting residue was purified by column chromatography (Si—PCC, 0-10% MeOH in DCM) to give the title compound as a pale yellow oil (80 mg, 51%). LCMS (Method H): $R_T$=2.34 min, $[M+H]^+$ 393.5

Example 75y

4-[2-(2-Chloro-9-methyl-6-morpholin-4-yl-9H-purin-8-yl)ethyl]-6-isopropylpiperazin-2-one

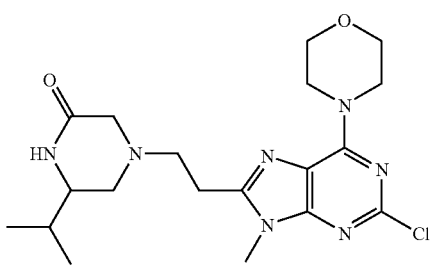

To a solution of (2-chloro-9-methyl-6-morpholin-4-yl-9H-purin-8-yl)acetaldehyde (184 mg, 0.62 mmol) in DCE (15 mL) was added 6-isopropylpiperazin-2-one (106 mg, 0.75 mmol) and powdered 4 Å molecular sieves. The reaction mixture was stirred at room temperature for 6 h, sodium triacetoxyborohydride (364 mg, 1.72 mmol) was added and the resulting mixture stirred for a further 18 h. The reaction mixture was filtered through Celite®, loaded onto an Isolute® SCX-2 cartridge, washed with MeOH then the desired product eluted with 2 M $NH_3$/MeOH in DCM. The resulting residue was purified by column chromatography (Si—PCC, 0-10% MeOH in DCM) to give the title compound as a pale yellow oil (51 mg, 33%). LCMS (Method H): $R_T$=3.31 min, $[M+H]^+$ 422.5

Example 75z

2-Chloro-8-[2-(3,3-dimethylmorpholin-4-yl)ethyl]-9-methyl-6-morpholin-4-yl-9H-purine

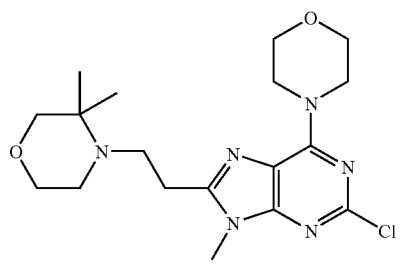

To a solution of (2-chloro-9-methyl-6-morpholin-4-yl-9H-purin-8-yl)acetaldehyde (119 mg, 0.40 mmol) in DCE (10 mL) was added 3,3-dimethylmorpholine.HCl (61 mg, 0.40mmol), triethylamine (0.06 mL, 0.40 mmol) and powdered 4 Å molecular sieves. After stirring at room temperature for 4 h, sodium triacetoxyborohydride (171 mg, 0.80 mmol) was added and the resulting mixture stirred for a further 16 h. The reaction mixture was filtered through Celite®, loaded onto an Isolute® SCX-2 cartridge, the cartridge was washed with MeOH then the desired product eluted with 2 M $NH_3$/MeOH in DCM. The resulting residue was purified by column chromatography (Si—PCC, 0-7% MeOH in DCM) to give the title compound as a pale yellow oil (44 mg, 28%). LCMS (Method H): $R_T$=2.45 min, $[M+H]^+$ 395.5

Example 75aa

2-Chloro-8-{2-[3-(1,1-dioxo-1-thiomorpholin-4-yl)azetidin-1-yl]-ethyl}-9-methyl-6-morpholin-4-yl-9H-purine

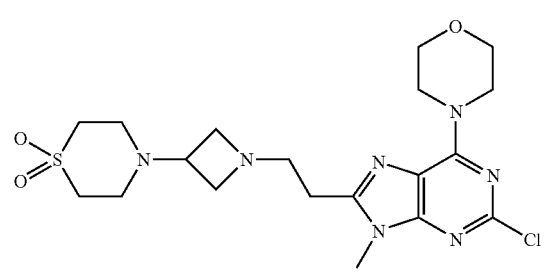

To a solution of (2-chloro-9-methyl-6-morpholin-4-yl-9H-purin-8-yl)acetaldehyde (115 mg, 0.39 mmol) in DCE (10 mL) was added 4-azetidin-3-yl-thiomorpholine,1-1-dioxide (74 mg, 0.39 mmol) and powdered 4 Å molecular sieves. The reaction mixture was stirred at room temperature for 4 h, sodium triacetoxyborohydride (165 mg, 0.78 mmol) was added and the resulting mixture stirred for a further 2 days. The reaction mixture was filtered through Celite®, loaded onto an Isolute® SCX-2 cartridge, washed with MeOH then the desired product eluted with 2 M $NH_3$/MeOH in DCM. The resulting residue was purified by column chromatography (Si—PCC, 0-10% 2 M NH$_3$/MeOH in DCM) to give the title compound as a pale yellow oil (93 mg, 51%). LCMS (Method H): R$_T$=2.25 min, [M+H]$^+$ 470.3

Example 75bb

2-Chloro-8-[2-(4,4-difluoropiperidin-1-yl)ethyl]-9-methyl-6-morpholin-4-yl-9H-purine

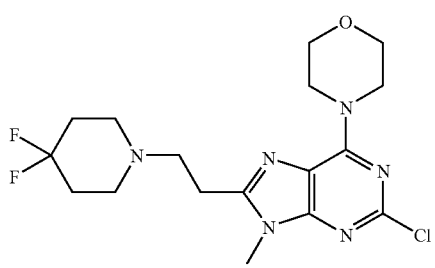

To a solution of (2-chloro-9-methyl-6-morpholin-4-yl-9H-purin-8-yl)acetaldehyde (60 mg, 0.20 mmol) in DCE (10 mL) was added 4,4-difluoropiperidine.HCl (42 mg, 0.26 mmol), triethylamine (0.04 mL, 0.26 mmol), powdered 4 Å molecular sieves and sodium triacetoxyborohydride (86 mg, 0.41 mmol). The reaction mixture was stirred at room temperature for 5 h, the reaction mixture was loaded onto an Isolute® SCX-2 cartridge, washed with MeOH then the desired product eluted with 2 M NH$_3$/MeOH in DCM. The resulting residue was purified by column chromatography (Si—PCC, 0-5% MeOH in DCM) to give the title compound as a pale yellow oil (30 mg, 37%). LCMS (Method H): R$_T$=2.61 min, [M+H]$^+$ 401.5

Example 75cc

2-Chloro-9-methyl-6-morpholin-4-yl-8-{2-[4-(tetrahydropyran-4-yl)piperazin-1-yl]ethyl}-9H-purine

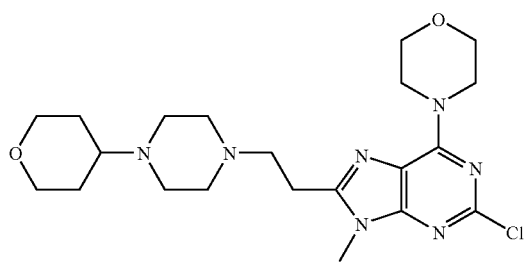

To a solution of (2-chloro-9-methyl-6-morpholin-4-yl-9H-purin-8-yl)acetaldehyde (72 mg, 0.24 mmol) in DCE (15 mL) was added 1-(tetrahydropyran-4-yl)piperazine (60 mg, 0.35 mmol), powdered 4 Å molecular sieves and sodium triacetoxyborohydride (103 mg, 0.49 mmol). The reaction mixture was stirred at room temperature for 17 h. The reaction mixture was loaded onto an Isolute® SCX-2 cartridge, the cartridge was washed with MeOH then the desired product eluted with 2 M NH$_3$/MeOH in DCM. The resulting residue was purified by column chromatography (Si—PCC, 0-10% MeOH in DCM) to give the title compound as a yellow solid (37 mg, 34%). LCMS (Method H): R$_T$=2.46 min, [M+H]$^+$ 450.5

Example 75dd

2-[(1S,4S)-5-(2-Chloro-9-methyl-6-morpholin-4-yl-9H-purin-8-ylmethyl)-2,5-diazabicyclo[2.2.1]hept-2-yl]-2-methylpropan-1-ol

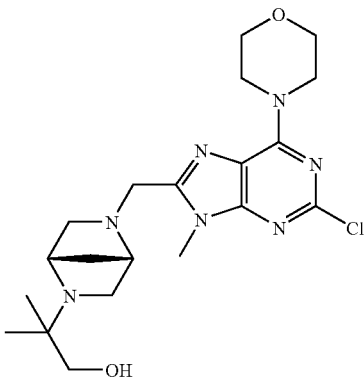

A solution of 2-chloro-9-methyl-6-morpholin-4-yl-9H-purine-8-carbaldehyde (235 mg, 0.83 mmol), (2-(1S,4S)-2,5-diazabicyclo[2.2.1]hept-2-yl-2-methylpropan-1-ol (168 mg, 0.99 mmol) and molecular sieves (4 Å, powdered, 1 g) in DCE (10 mL) was stirred at ambient temperature for 4 h. Sodium triacetoxyborohydride (265 mg, 1.25 mmol) was added and the mixture stirred for 18 h, then loaded onto an Isolute® SCX-2 cartridge (25 g). The cartridge was then washed with methanol and the desired product was subsequently eluted using 2 M NH$_3$ in MeOH. The product was collected and concentrated in vacuo. The resultant residue was purified by flash chromatography (Si—PPC, DCM:MeOH; 90:10) to afford the title compound as a tan solid (50 mg, 14%). LCMS (Method H): R$_T$=2.39 min, M+H$^+$=436.

Example 75ee

2-Chloro-8-((1S,4S)-5-methanesulfonyl-2,5-diazabicyclo[2.2.1]hept-2-ylmethyl)-9-methyl-6-morpholin-4-yl-9H-purine

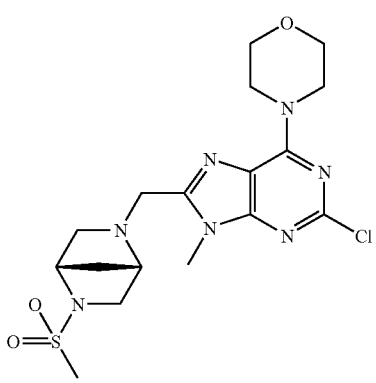

A solution of 2-chloro-9-methyl-6-morpholin-4-yl-9H-purine-8-carbaldehyde (227 mg, 0.81 mmol), (1S,4S)-2-methanesulfonyl-2,5-diazabicyclo[2.2.1]heptane (170 mg, 0.97 mmol) and molecular sieves (4 Å, powdered, 1 g) in DCE (12 mL) was stirred at ambient temperature for 3 h. Sodium triacetoxyborohydride (255 mg, 1.20 mmol) was added and the mixture stirred for 17 h, then loaded onto an Isolute® SCX-2 cartridge (25 g). The cartridge was then washed with methanol and the desired product was subsequently eluted using 2 M NH$_3$ in MeOH. The product was collected and concentrated in vacuo. The resultant residue was purified by flash chromatography (Si—PPC, DCM:MeOH; 98:2) to afford the title compound as a white solid (350 mg, 98%). LCMS (Method H): R$_T$=2.51 min, M+H$^+$=442.

Example 75ff

2-Chloro-9-methyl-6-morpholin-4-yl-8-(4-oxetan-3-ylpiperidin-1-ylmethyl)-9H-purine

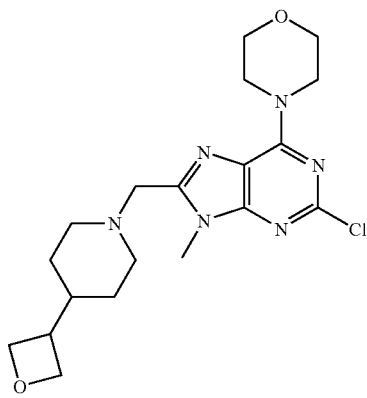

A solution of 2-chloro-9-methyl-6-morpholin-4-yl-9H-purine-8-carbaldehyde (1.0 g, 3.55 mmol), 4-oxetan-3-ylpiperidine (600 mg, 4.25 mmol) and molecular sieves (4 Å, powdered, 5 g) in anhydrous THF (25 mL) was stirred at ambient temperature for 5 h. Sodium triacetoxyborohydride (1.5 g, 7.08 mmol) was added and the mixture stirred for 18 h, then loaded onto an Isolute® SCX-2 cartridge (25 g). The cartridge was then washed with methanol and the desired product was subsequently eluted using 2 M NH$_3$ in MeOH. The product was collected and concentrated in vacuo. The resultant residue was purified by flash chromatography (Si—PPC, DCM:MeOH; 100:0 to 99:1 to 98:2 to 95:5 to 90:10) to afford the title compound as a white foam (0.82 g, 57%). LCMS (Method H): R$_T$=2.38 min, M+H$^+$=408.

Example 75gg

2-Chloro-8-[2-(4-methanesulfonyl-3,3-dimethylpiperazin-1-yl)-ethyl]-9-methyl-6-morpholin-4-yl-9H-purine

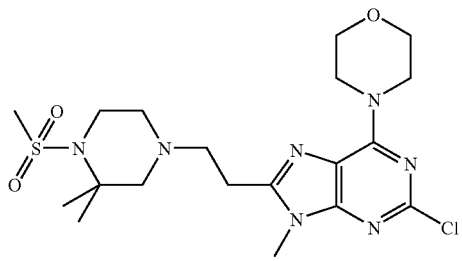

To a solution of (2-chloro-9-methyl-6-morpholin-4-yl-9H-purin-8-yl)acetaldehyde (137 mg, 0.46 mmol) in DCE (10 mL) was added 2,2-dimethylpiperazine-1-carboxylic acid tert-butyl ester (99 mg, 0.46 mmol), powdered 4 Å molecular sieves and sodium triacetoxyborohydride (146 mg, 0.69 mmol). After stirring at rt for 20 h, the reaction mixture was filtered through Celite®, loaded onto an Isolute® SCX-2 cartridge, washed with MeOH then the desired product eluted with 2 M NH$_3$/MeOH in DCM. The resulting residue was purified by column chromatography (Si—PCC, 0-10% MeOH in DCM) to give a residue, which was taken up in DCM (3 mL). TFA (1 mL) was then added and the reaction mixture stirred at RT for 2 h. The reaction mixture was loaded onto an Isolute® SCX-2 cartridge, washed with MeOH then the desired product eluted with 2 M NH$_3$ in MeOH. The resulting residue was purified by column chromatography (Si—PCC, 0-10% MeOH in DCM) to give a residue (28 mg), which was taken up in DCM (4 mL) The solution was cooled to 0° C. and Net$_3$ (0.03 mL, 0.21 mmol) and methanesulfonyl chloride (0.03 mL, 0.39 mmol) were added. After 10 min the reaction mixture was allowed to warm to RT then stirred for 60 h. The reaction mixture was partitioned between DCM and sat. NaHCO$_3$(aq), the organic layer separated and passed through a hydrophobic frit, then evaporated in vacuo. This residue was taken up in MeOH/DCM, loaded onto an Isolute® SCX-2 cartridge, washed with MeOH then eluted with 2 M NH$_3$/MeOH in DCM) to give 2-Chloro-8-[2-(4-methanesulfonyl-3,3-dimethylpiperazin-1-yl)-ethyl]-9-methyl-6-morpholin-4-yl-9H-purine (35 mg, 16% over 3 steps) as a yellow oil. LCMS (Method H): R$_T$=2.82 min, [M+H]$^+$ 472.4

Example 75hh

[2-(2-Chloro-9-methyl-6-morpholin-4-yl-9H-purin-8-yl)-ethyl]-(1,1-dioxo-tetrahydro-1-thiophen-3-yl)amine

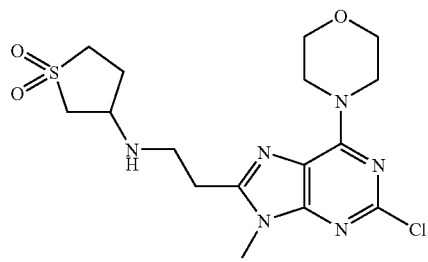

To a solution of (2-chloro-9-methyl-6-morpholin-4-yl-9H-purin-8-yl)acetaldehyde (118 mg, 0.40 mmol) in DCE (15 mL) was added 1,1-dioxo-tetrahydro-1-thiophen-3-ylamine (107 mg, 0.80 mmol) and powdered 4 Å molecular sieves. The reaction mixture was stirred at room temperature for 30 min, sodium triacetoxyborohydride (169 mg, 0.80 mmol) was added and the resulting mixture stirred for a further 18 h. The reaction mixture was filtered through Celite®, loaded onto an Isolute® SCX-2 cartridge, washed with MeOH then the desired product eluted with 2 M NH$_3$/MeOH in DCM. The resulting residue was purified by column chromatography (Si—PCC, 0-7% MeOH in DCM) to give [2-(2-Chloro-9-methyl-6-morpholin-4-yl-9H-purin-8-yl)-ethyl]-(1,1-dioxo-tetrahydro-1-thiophen-3-yl)amine as a yellow oil (45 mg, 27%). LCMS (Method H): R$_T$=2.38 min, [M+H]$^+$ 415.4

Example 75ii 3-(2-Chloro-9-methyl-6-morpholin-4-yl-9H-purin-8-yl)-pyrrolidine-1-carboxylic acid tert-butyl ester

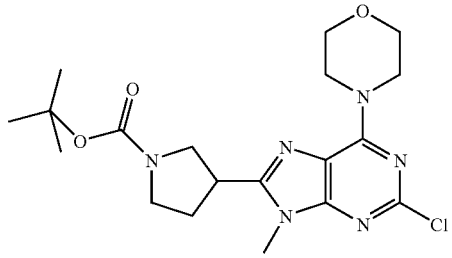

Zinc activation: To a suspension of zinc powder (128 mg, 0.99 mmol) and Celpure® P65 in anhydrous DMA (4 mL) was added a 7:5 (v:v) mixture of TMS-Cl:1,2-dibromoethane (25 µL). The reaction mixture was stirred at room temperature for 10 min.

Zinc insertion: A solution of 3-iodopyrrolidine-1-carboxylic acid tert-butyl ester (470 g, 1.58 mmol) in anhydrous DMA (2 mL) was added dropwise. The reaction mixture was stirred for 45 min at room temperature.

Coupling reaction: A mixture of 2-chloro-8-iodo-9-methyl-6-morpholin-4-yl-9H-purine (400 mg, 1.05 mmol), Pd(dppf)Cl$_2$.DCM (42 mg, 5 mol %) and CuI (20 mg, 10 mol %) in DMA (4 mL) was evacuated and back-filled with argon. The zincate mixture was quickly filtered (PTFE) and added onto the palladium-containing mixture. The resulting reaction mixture was stirred at 85° C. for 18 hours then cooled to room temperature. The mixture was partitioned between EtOAc and a 1M aqueous solution of ammonium chloride, the organic layer separated, washed with water, brine and dried (Na$_2$SO$_4$). The resulting residue was purified by column chromatography (Si—PCC, 0-100% EtOAc in cyclohexane) to give 3-(2-Chloro-9-methyl-6-morpholin-4-yl-9H-purin-8-yl)-pyrrolidine-1-carboxylic acid tert-butyl ester as an orange oil (79 mg, 18%). LCMS (Method H): R$_T$=4.48 min, [M+H]$^+$ 423.5

Example 75jj 4-(2-Chloro-9-methyl-6-morpholin-4-yl-9H-purin-8-ylmethyl)-3-isopropylpiperazin-2-one

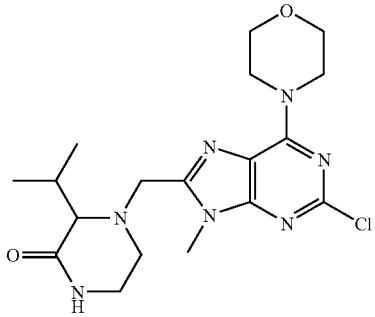

A mixture of 2-chloro-9-methyl-6-morpholin-4-yl-9H-purine-8-carbaldehyde (212 mg, 0.75 mmol), 3-isopropylpiperazin-2-one (128 mg, 0.90 mmol) and powdered 4 Å molecular sieves in DCE (18 mL) were stirred at RT. After 4 h, sodium triacetoxyborohydride (318 mg, 1.50 mmol) was added and the resulting mixture stirred for a further 17 h. The reaction mixture was filtered through Celite®, loaded onto an Isolute® SCX-2 cartridge, washed with MeOH then the desired product eluted with 2 M NH$_3$/MeOH in DCM. Trituration of the resulting residue with EtOAc gave 4-(2-Chloro-9-methyl-6-morpholin-4-yl-9H-purin-8-ylmethyl)-3-isopropylpiperazin-2-one as a yellow oil (198 mg, 65%). LCMS (Method H): R$_T$=2.82 min, [M+H]$^+$ 408.4

Example 75kk

2-Chloro-8-iodo-9-methyl-6-morpholin-4-yl-9H-purine

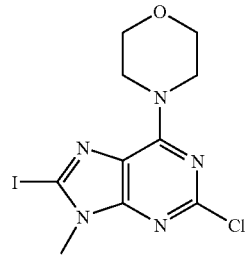

A suspension of 2-chloro-9-methyl-6-morpholin-4-yl-9H-purine (2.95 g, 11.7 mmol) and TMEDA (2.6 mL, 2.03 g, 17.5 mmol) in THF (80 mL) was cooled to −78° C. before the dropwise addition of n-BuLi (9.8 mL, 24.5 mmol, 2.5 M solution in hexanes). The resulting mixture was warmed to −40° C. and stirred for 40 mins. The mixture was cooled back to −78° C. before the addition of 1-chloro-2-iodoethane (3.7 mL, 7.8 g, 40.8 mmol). The resulting mixture was allowed to warm to r.t. over 2 h then quenched with NH$_4$Cl and extracted with EtOAc (×4). The combined organics were dried (Na$_2$SO$_4$) and concentrated in vacuo affording 2-Chloro-8-iodo-9-methyl-6-morpholin-4-yl-9H-purine as a yellow solid (4.02 g, 91%). LCMS (method H): R$_T$ 4.09 min [M+H]$^+$ 379.9

Example 75ll 2-(2-Ethylbenzoimidazol-1-yl)-9-methyl-6-morpholin-4-yl-9H-purine

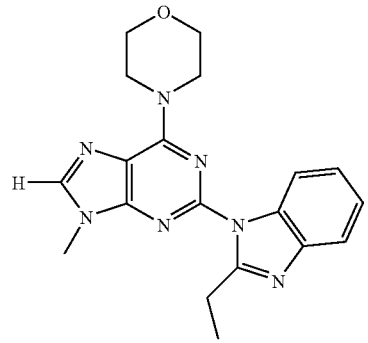

A mixture of 2-chloro-9-methyl-6-morpholin-4-yl-9H-purine (4.0 g, 15.8 mmol), 2-ethylbenzimidazole (2.8 g, 19.0 mmol), tris(dibenzylideneacetone)dipalladium (724 mg, 0.79 mmol), Xphos (1.5 g, 3.16 mmol) and Cs$_2$CO$_3$ (10.3 g, 31.6 mmol) in dioxane (90 mL) was purged with argon then heated at 120° C. for 16 h in a sealed reactor. The reaction mixture was filtered through a pad of celite, washing with EtOAc. The filtrate was concentrated in vacuo and purified by column chromatography (Si—PCC, MeOH:EtOAc, 0-10%) affording 2-(2-Ethylbenzoimidazol-1-yl)-9-methyl-6-morpholin-4-yl-9H-purine as an orange solid (3.49 g, 96%). LCMS (method H): R$_T$ 3.46 min, [M+H]$^+$ 364.5

Example 75mm 2-(2-Ethylbenzoimidazol-1-yl)-8-iodo-9-methyl-6-morpholin-4-yl-9H-purine

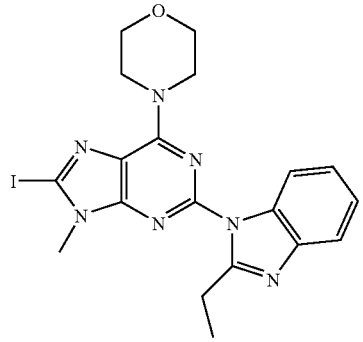

A suspension of 2-(2-ethylbenzoimidazol-1-yl)-9-methyl-6-morpholin-4-yl-9H-purine (1.67 g, 4.58 mmol) and TMEDA (1.0 mL, 799 mg, 6.88 mmol) in THF (25 mL) was cooled to −78° C. before the drop wise addition of n-BuLi (2.8 mL, 6.88 mmol, 2.5 M solution in hexanes). The resulting mixture was stirred for 40 mins before the addition of 1-chloro-2-iodoethane (629 μL, 1.3 g, 6.88 mmol). The resulting mixture was stirred at −78° C. for 1 h then quenched with H$_2$O and warmed to r.t. The pale yellow precipitate was collected by filtration washing with further H$_2$O and dried under vacuum at 50° C. 2-(2-Ethylbenzoimidazol-1-yl)-8-iodo-9-methyl-6-morpholin-4-yl-9H-purine was afforded as a pale yellow powder (2.0 g, 90%). LCMS (method H): R$_T$ 2.74 min [M+H]$^+$ 490.2

Example 75nn

2-Chloro-9-methyl-6-morpholin-4-yl-8-[4-(tetrahydropyran-4-yl)piperazin-1-ylmethyl]-9H-purine

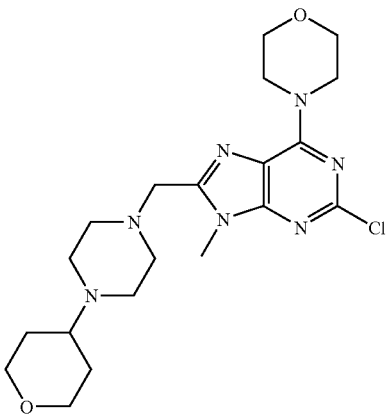

A mixture of 2-chloro-9-methyl-6-morpholin-4-yl-9H-purine-8-carbaldehyde (165 mg, 0.59 mmol), 1-(tetrahydropyran-4-yl)piperazine (110 mg, 0.65 mmol) and molecular sieves (4 Å, powdered, 750 mg) in DCE (10 mL) was stirred at ambient temperature for 4 h. Sodium triacetoxyborohydride (170 mg, 0.80 mmol) was added and the mixture stirred for 18 h, then loaded onto an Isolute® SCX-2 cartridge (10 g). The cartridge was then washed with methanol and the desired product was subsequently eluted using 2 M NH$_3$ in MeOH. The product was collected and concentrated in vacuo. The resultant residue was purified by flash chromatography (Si—PPC, DCM:MeOH, 100:0 to 98:2 to 95:5 to 90:10) to afford 2-Chloro-9-methyl-6-morpholin-4-yl-8-[4-(tetrahydropyran-4-yl)piperazin-1-ylmethyl]-9H-purine as a white solid (250 mg, 98%). $^1$H NMR (CDCl$_3$, 400MHz) δ 4.27 (m, 4 H), 4.01 (dd, J=11.5, 4.2 Hz, 2 H), 3.81 (m, 7 H), 3.69 (s, 2 H), 3.36 (dd, J=12.5, 10.9 Hz, 2 H), 2.55 (m, 8 H), 2.40 (m, 1 H), 1.75 (d, J=12.5 Hz, 2 H) and 1.56 (m, 2 H)

Example 76a (2-Chloro-9-methyl-6-morpholin-4-yl-9H-purin-8-ylmethyl)phosphonic acid dimethyl ester

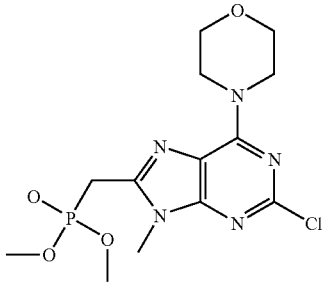

A mixture of 8-bromomethyl-2-chloro-9-methyl-6-morpholin-4-yl-9H-purine (3.92 g, 11 3 mmol) and trimethylphosphite (20 mL, mmol) was heated to reflux (120° C.) for 2 h. The reaction mixture was concentrated in vacuo to a fluorescent green solid which was triturated with H$_2$O. The resulting pale green solid was purified by column chromatography (Si—PCC, MeOH:EtOAc, 0-10%) affording the title compound as a green solid (3.36 g, 79%). LCMS (method A): R$_T$ 3.45 min [M+H]$^+$ 376.1

Example 76b 3-(2-Chloro-9-methyl-6-morpholin-4-yl-9H-purin-8-ylmethylene)azetidine-1-carboxylic acid tert-butyl ester

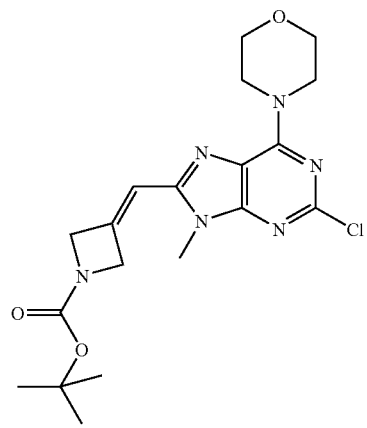

To a solution of diisopropylamine (1.4 mL, 9.8 mmol) in THF (3 mL) at −78° C. was added n-BuLi (3.9 mL, 9.8 mmol, 2.5 M in hexanes) and the resulting solution allowed to stir for 20 min. The resulting solution was added to a pale green solution of (2-chloro-9-methyl-6-morpholin-4-yl-9H-purin-8-ylmethyl)phosphonic acid dimethyl ester (3.36 g, 8.9 mmol) in THF (80 mL) at −78° C. The resulting mixture was warmed to r.t. before a solution of 3-oxo-azetidine-1-carboxylic acid tert-butyl ester (1.76 g, 10.2 mmol) in THF (10 mL) was added. The resulting pink mixture was stirred for 16 h then quenched with H$_2$O. The mixture was concentrated in vacuo and the residue was partitioned between DCM and brine. The organic phase was dried (Na$_2$SO$_4$) and concentrated in vacuo. The resulting residue was purified by column chromatography (Si—PCC, EtOAc:cyclohexane, 0-70%) affording the title compound as a green powder (3.46 g, 92%). ¹H NMR (CDCl₃, 400 MHz): δ 6.33-6.32 (1 H, m), 4.91-4.90 (2 H, m), 4.71-4.70 (2 H, m), 4.28 (4 H, brd s), 3.81 (4 H, t, J=4.74 Hz), 3.71 (3 H, s), 1.48 (9 H, s).

Example 76c

3-[2-(2-Ethylbenzoimidazol-1-yl)-9-methyl-6-morpholin-4-yl-9H-purin-8-ylmethylene]azetidine-1-carboxylic acid tert-butyl ester

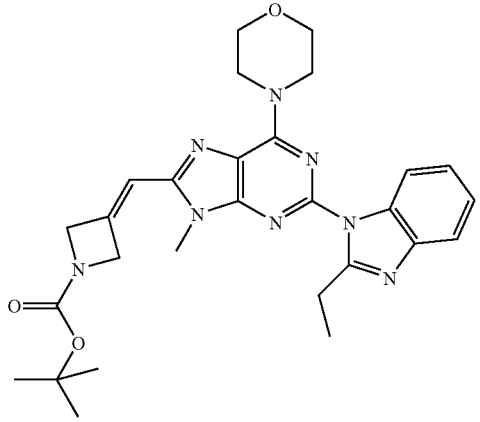

A mixture of 3-(2-chloro-9-methyl-6-morpholin-4-yl-9H-purin-8-ylmethylene)azetidine-1-carboxylic acid tert-butyl ester (1.4 g, 3.33 mmol), 2-ethylbenzimidazole (584 mg, 3.99 mmol), tris(dibenzylideneacetone)dipalladium (152 mg, 0.17 mmol), XPhos (317 mg, 0.66 mmol) and Cs₂CO₃ (2.17 g, 6.65 mmol) in dioxane (15 mL) was purged with argon then heated at 120° C. for 16 h in a sealed tube. The reaction mixture was filtered through Celite®, washing with EtOAc, and the filtrate concentrated in vacuo. The resulting residue was purified by column chromatography (Si—PCC, EtOAc:cyclohexane, 0-100%) affording the title compound as a cream solid (1.1 g, 62%). LCMS (method H): R$_T$ 3.20 min [M+H]⁺ 531.4

Example 76d

3-[2-(2-Ethylbenzoimidazol-1-yl)-9-methyl-6-morpholin-4-yl-9H-purin-8-ylmethyl]azetidine-1-carboxylic acid tert-butyl ester

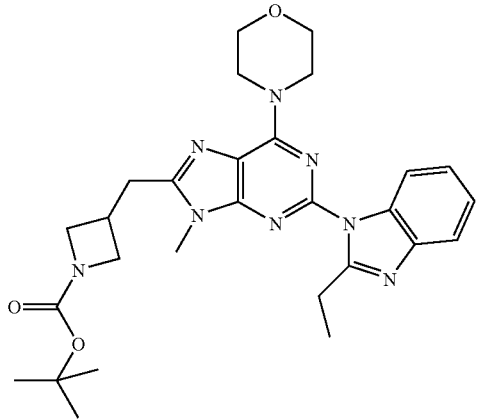

To a solution of 3-[2-(2-ethylbenzoimidazol-1-yl)-9-methyl-6-morpholin-4-yl-9H-purin-8-ylmethylene]azetidine-1-carboxylic acid tert-butyl ester (1.1 g, 2.07 mmol) in EtOH (40 mL) and AcOH (15 mL) was added 10% Pd/C (200 mg) and the resulting mixture stirred under an atmosphere of H₂ for 65 h. The reaction mixture was filtered through Celite®, washing with EtOAc, and the filtrate concentrated in vacuo. The resulting residue was purified by column chromatography (Si—PCC, EtOAc:cyclohexane, 70-100%) affording the title compound as an orange oil (0.92 g, 83%). LCMS (method H): R$_T$ 3.01 min [M+H]⁺ 533.4

Example 76e

8-Azetidin-3-ylmethyl-2-(2-ethylbenzoimidazol-1-yl)-9-methyl-6-morpholin-4-yl-9H-purine

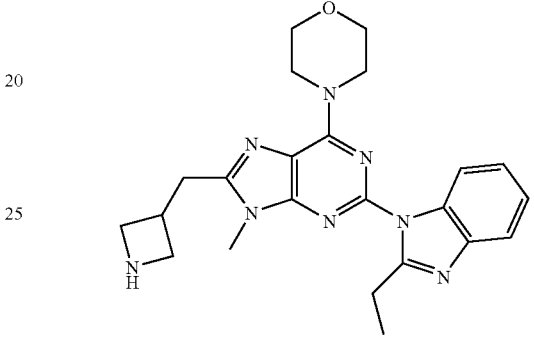

To a solution of 3-[2-(2-ethylbenzoimidazol-1-yl)-9-methyl-6-morpholin-4-yl-9H-purin-8-ylmethyl]azetidine-1-carboxylic acid tert-butyl ester (917 mg, 1.72 mmol) in DCM (6 mL) was added TFA (3 mL) and the resulting mixture stirred for 3 h at r.t. The reaction mixture was loaded onto an Isolute® SCX-2 cartridge which was washed with MeOH/DCM and the product eluted with 2M NH₃/MeOH affording the title compound as a colourless oil (647 mg, 87%). LCMS (method H): R$_T$ 1.83 min [M+H]⁺ 433.3

Example 76f

4-[2-(2-Ethylbenzoimidazol-1-yl)-9-methyl-6-morpholin-4-yl-9H-purin-8-ylmethyl]-2-isopropyl-3-oxopiperazine-1-carboxylic acid tert-butyl ester

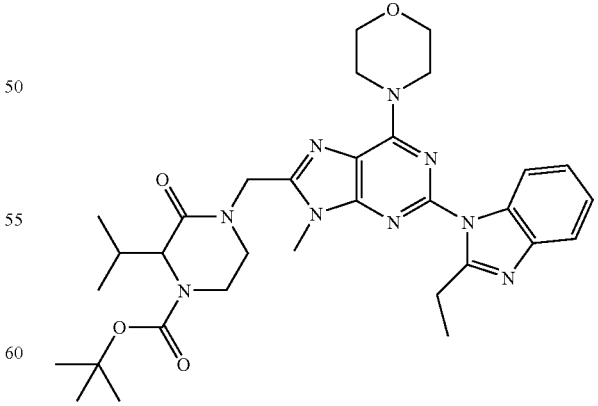

To a solution of 2-isopropyl-3-oxopiperazine-1-carboxylic acid tert-butyl ester (58 mg, 0.24 mmol) in DMF (1.5 mL) at 0° C. was added NaH (11 mg, 0.29 mmol, 60% dispersion in mineral oil) and the resulting mixture stirred at r.t. for 30 min before the addition of 8-bromomethyl-2-(2-ethylbenzoimidazol-1-yl)-9-methyl-6-morpholin-4-yl-9H-purine (100 mg, 0.22 mmol) in DMF (1.5 mL). The resulting mixture was allowed to stir for 19 h then partitioned between EtOAc and H₂O. The organic phase was dried (MgSO₄) and concentrated in vacuo. The resulting residue was purified by column chromatography (Si—PCC, MeOH:EtOAc, 0-10%) affording the title compound as a yellow oil (104 mg, 77%). LCMS (method H): R$_T$ 3.03 min [M+H]⁺ 618.4

Example 76g

[2-(2-Chloro-9-methyl-6-morpholin-4-yl-9H-purin-8-yl)ethyl]methyl-(3-methyl-1,1-dioxotetrahydrothiophen-3-yl)amine

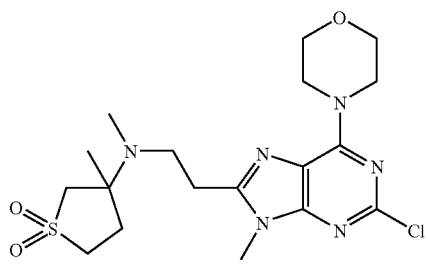

A mixture of (2-chloro-9-methyl-6-morpholin-4-yl-9H-purin-8-yl)acetaldehyde (210 mg, 0.71 mmol), methyl-(3-methyl-1,1-dioxotetrahydrothiophen-3-yl)amine (116 mg, 0.71 mmol), sodium triacetoxyborohydride (301 mg, 1.42 mmol) and 4 Å powdered molecular sieves (280 mg) in DCE (15 mL) was stirred for 23 h. The reaction mixture was filtered through Celite® and the filtrate loaded onto an Isolute® SCX-2 cartridge which was washed with MeOH and the product eluted with 2M NH₃/MeOH/DCM. The resulting residue was purified by column chromatography (Si—PCC, MeOH:EtOAc, 0-10%) affording the title compound as a pale yellow solid (87 mg, 28%). LCMS (method H): R$_T$ 2.01 min [M+H]⁺ 443.2

Example 76h 4-(2-Chloro-9-methyl-6-morpholin-4-yl-9H-purin-8-ylmethyl)-3,3-dimethyl-piperazine-1-carboxylic acid tert-butyl ester

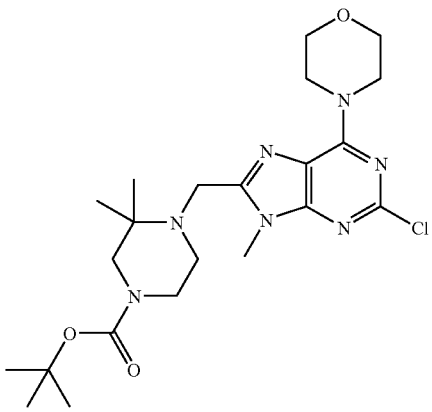

A mixture of 8-bromomethyl-2-chloro-9-methyl-6-morpholin-4-yl-9H-purine (400 mg, 1.16 mmol), 3,3-dimethylpiperazine-1-carboxylic acid tert-butyl ester (250 mg, 1.17 mmol) and K₂CO₃ (176 mg, 1.28 mmol) in DMF (20 mL) was allowed to stir at r.t. for 16 h. The reaction mixture was loaded onto an Isolute® SCX-2 cartridge which was washed with MeOH and the product eluted with 2M NH₃/MeOH. The resulting residue was purified by column chromatography (Si—PCC, MeOH:DCM, 0-10%) affording the title compound (150 mg, 27%). ¹H NMR (CDCl₃, 400 MHz): δ 4.26 (4 H, brd s), 3.82-3.80 (9 H, m), 3.33 (2 H, brd s), 3.22 (2 H, brd s), 2.42-2.35 (2 H, m), 1.45 (9 H, s), 1.15 (6 H, s).

Example 76i

2-Chloro-8-(2,2-dimethylpiperazin-1-ylmethyl)-9-methyl-6-morpholin-4-yl-9H-purine

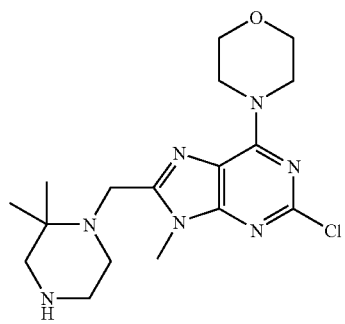

To a solution of 4-(2-chloro-9-methyl-6-morpholin-4-yl-9H-purin-8-ylmethyl)-3,3-dimethyl-piperazine-1-carboxylic acid tert-butyl ester (288 mg, 0.60 mmol) in DCM (30 mL) was added TFA (3 mL) and the mixture stirred at r.t for 1 h. The reaction mixture was loaded onto an Isolute® SCX-2 cartridge which was washed with MeOH and the product eluted with 2M NH₃/MeOH affording the title compound as a white solid (199 mg, 87%). ¹H NMR (CDCl₃, 400 MHz): δ 4.26 (4 H, brd s), 3.84-3.77 (9 H, m), 2.84 (2 H, t, J=4.87 Hz), 2.74 (2 H, s), 2.43 (2 H, t, J=4.89 Hz), 1.21 (6 H, s).

Example 76j

2-Chloro-8-(2,2-dimethyl-4-oxetan-3-ylpiperazin-1-ylmethyl)-9-methyl-6-morpholin-4-yl-9H-purine

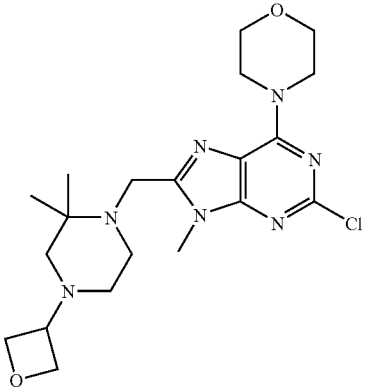

A mixture of 2-chloro-8-(2,2-dimethylpiperazin-1-ylmethyl)-9-methyl-6-morpholin-4-yl-9H-purine (198 mg, 0.52 mmol), oxetan-3-one (42 mg, 0.58 mmol) and 4 Å powdered molecular sieves in DCE (10 mL) was allowed to stir at r.t for 4 h before the addition of sodium triacetoxyborohydride (144 mg, 0.68 mmol). The resulting mixture was allowed to stir for 16 h then loaded onto an Isolute® SCX-2 cartridge which was washed with MeOH and the product eluted with 2M $NH_3$/MeOH affording the title compound (192 mg, 85%). $^1H$ NMR ($CDCl_3$, 400 MHz): δ 4.63 (2 H, t, J=6.48 Hz), 4.55 (2 H, t, J=6.08 Hz), 4.27 (4 H, brd s), 3.84-3.80 (7 H, m), 3.49 (2 H, s), 3.38-3.37 (1 H, m), 2.50-2.40 (2 H, m), 2.23-2.04 (4 H, m), 1.20 (6 H, s)

Example 76k (1-{4-[2-(2-Ethylbenzoimidazol-1-yl)-9-methyl-6-morpholin-4-yl-9H-purin-8-ylmethyl]-3,3-dimethylpiperazine-1-carbonyl}cyclopropyl)carbamic acid tert-butyl ester

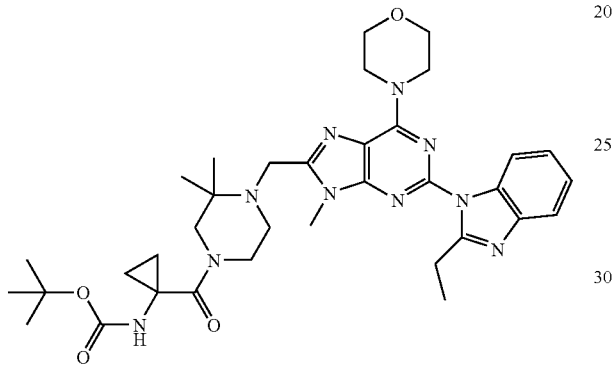

A mixture of 8-(2,2-dimethylpiperazin-1-ylmethyl)-2-(2-ethylbenzoimidazol-1-yl)-9-methyl-6-morpholin-4-yl-9H-purine (140 mg, 0.29 mmol), 1-aminocyclopropanecarboxylic acid (64 mg, 0.32 mmol), HATU (120 mg, 0.32 mmol) and DIPEA (56 μL, 0.32 mmol) in DCM (3 mL) was allowed to stir at r.t. for 60 h. The reaction mixture was loaded onto an Isolute® SCX-2 cartridge which was washed with MeOH and the product eluted with 2M $NH_3$/MeOH. The resulting residue was purified by column chromatography (Si—PCC, MeOH:DCM, 0-2%) affording the title compound. LCMS (method H): $R_T$ 2.56 min, [M+H]$^+$ 673.7

Example 76l 2-(2-Cyclopropylbenzoimidazol-1-yl)-9-methyl-6-morpholin-4-yl-9H-purine-8-carboxylic acid

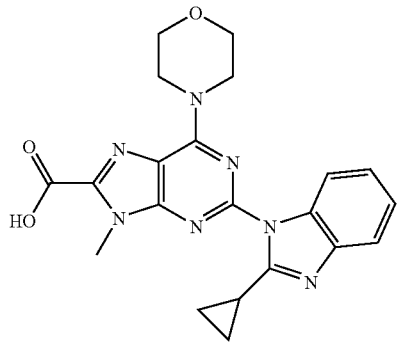

To a suspension of 2-(2-cyclopropylbenzoimidazol-1-yl)-9-methyl-6-morpholin-4-yl-9H-purine-8-carbaldehyde (500 mg, 1.24 mmol) in EtOH (16 mL) was added $AgNO_3$ (265 mg, 1.56 mmol) followed by a solution of NaOH (302 mg, 7.5 mmol) in $H_2O$ (5 mL). The resulting black suspension was allowed to stir at r.t. for 30 min then filtered through Celite® and the resulting filtrate concentrated in vacuo. The resulting residue was dissolved in $H_2O$ and basified by the addition of aq. NaOH. The aqueous phase was extracted with DCM then acidified to pH 2 with HCl. The aqueous phase was concentrated in vacuo to half volume then cooled on ice. The resulting precipitate was collected by filtration and dried in vacuo affording the title compound (280 mg, 55%). $^1H$ NMR (DMSO, 400 MHz): δ 8.12-8.11 (1 H, m), 7.72-7.68 (1 H, m), 7.44-7.43 (2 H, m), 4.60 (4 H, brd s), 4.04 (3 H, s), 3.90-3.70 (4 H, m), 3.06-3.00 (1 H, m), 1.33-1.31 (4 H, m)

Example 76m

4-{1-[2-Chloro-6-morpholin-4-yl-9-(tetrahydropyran-2-yl)-9H-purin-8-ylmethyl]azetidin-3-yl}piperazin-2-one

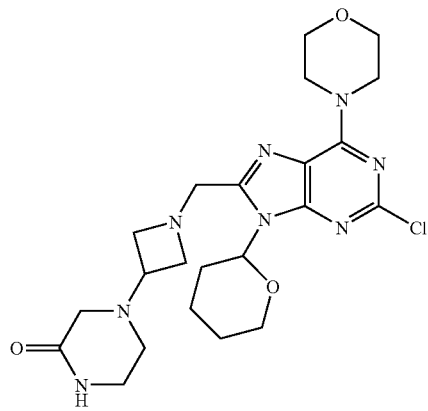

A mixture of 2-chloro-6-morpholin-4-yl-9-(tetrahydropyran-2-yl)-9H-purine-8-carbaldehyde (1.06 g, 3.01 mmol) and 4-azetidin-3-ylpiperazin-2-one (560 mg, 3.61 mmol) in DCE (60 mL) and DMF (20 mL) was allowed to stir at r.t. for 10 min before the addition of 4 Å powdered molecular sieves (3.0 g) followed by sodium triacetoxyborohydride (1.28 g, 6.04 mmol). The resulting mixture was allowed to stir for 64 h then filtered through Celite® which was washed with DCM. The filtrate was concentrated in vacuo and the resulting residue dissolved in EtOAc and washed with $NaHCO_3$, $H_2O$ and brine. The organic phase was dried ($Na_2SO_4$) and concentrated in vacuo affording the title compound as a yellow gum (997 mg, 67%). LCMS (method A): $R_T$ 2.19 and 2.11 min [M−$C_5H_9O$+H]$^+$ 407.3

Example 76n

4-{1-[2-(2-Ethylbenzoimidazol-1-yl)-6-morpholin-4-yl-9-(tetrahydropyran-2-yl)-9H-purin-8-ylmethyl]azetidin-3-yl}piperazin-2-one

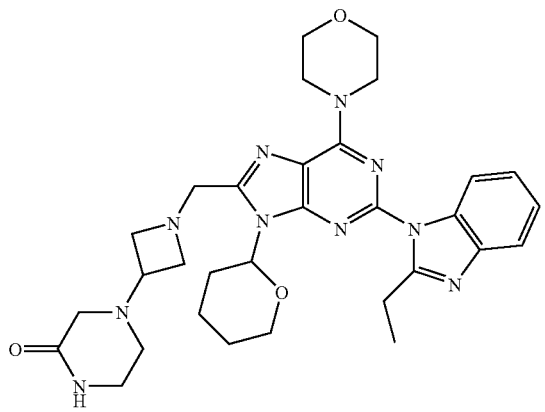

A mixture of 4-{1-[2-chloro-6-morpholin-4-yl-9-(tetrahydropyran-2-yl)-9H-purin-8-ylmethyl]azetidin-3-yl}piperazin-2-one (990 mg, 2.00 mmol), 2-ethylbenzimidazole (322 mg, 2.20 mmol), tris(dibenzylideneacetone)dipalladium (46 mg, 0.05 mmol), XPhos (95 mg, 0.20 mmol) and $Cs_2CO_3$ (980 mg, 3.01 mmol) in dioxane (30 mL) was purged with argon then heated at 115° C. for 6 h then stirred at r.t. for 16 h. The reaction mixture was filtered through Celite®, washing with dioxane, and the filtrate concentrated in vacuo. The resulting residue was purified by column chromatography (Si—PCC, MeOH:DCM, 0-10%) affording the title compound (470 mg, 39%). LCMS (method A): $R_T$ 2.01 and 1.92 min $[M+H]^+$ 601.6

Example 76o

2-Chloro-8-iodo-6-morpholin-4-yl-9-(tetrahydropyran-2-yl)-9H-purine

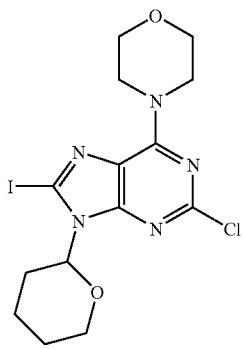

A solution of 2-chloro-6-morpholin-4-yl-9-(tetrahydropyran-2-yl)-9H-purine (1.50 g, 4.63 mmol) and TMEDA (1.72 mL, 6.94 mmol) in THF (30 mL) was cooled to −78° C. before the drop wise addition of n-BuLi (6.08 mL, 9.73 mmol, 1.6 M solution in hexanes). The resulting mixture was allowed to stir at −78° C. for 485 min before the addition of 1-chloro-2-iodoethane (902 μL, 16.22 mmol). The resulting mixture was allowed to warm to 0° C. over 2.5 h then quenched with $H_2O$ and extracted with DCM. The combined organics were washed with brine then dried ($Na_2SO_4$) and concentrated in vacuo. The residue was triturated with $^i$PrOAc and the resulting solid collected by filtration affording the title compound (1.80 g, 87%). LCMS (method A): $R_T$ 3.90 min $[M+H]^+$ 450.3

Example 76p

3-[2-(2-Methylbenzoimidazol-1-yl)-9-methyl-6-morpholin-4-yl-9H-purin-8-ylmethylene]azetidine-1-carboxylic acid tert-butyl ester

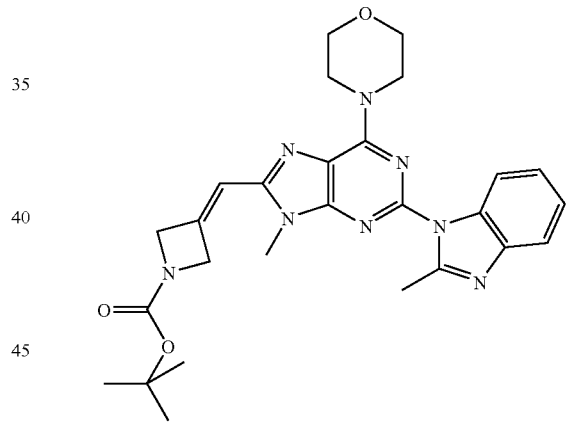

A mixture of 3-(2-chloro-9-methyl-6-morpholin-4-yl-9H-purin-8-ylmethylene)azetidine-1-carboxylic acid tert-butyl ester (200 mg, 0.48 mmol), 2-methylbenzimidazole (76 mg, 0.57 mmol), tris(dibenzylideneacetone)dipalladium (44 mg, 0.06 mmol), XPhos (58 mg, 0.10 mmol) and $Cs_2CO_3$ (320 mg, 0.95 mmol) in toluene (4 mL) was purged with argon then heated at 140° C. for 2 h in a microwave reactor. The reaction mixture was filtered through Celite®, washing with MeOH, and the filtrate concentrated in vacuo. The resulting residue was purified by column chromatography (Si—PCC, EtOAc:cyclohexane, 0-100%) affording the title compound as an off-white solid (156 mg, 64%). LCMS (method A): $R_T$ 3.11 min $[M+H]^+$ 517.3

Example 76q

3-[2-(2-Methylbenzoimidazol-1-yl)-9-methyl-6-morpholin-4-yl-9H-purin-8-ylmethyl]azetidine-1-carboxylic acid tert-butyl ester

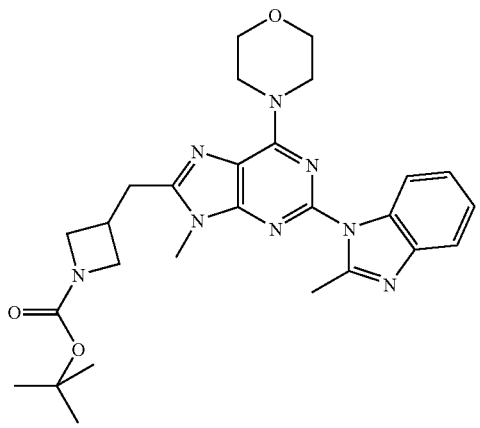

To a solution of 3-[2-(2-methylbenzoimidazol-1-yl)-9-methyl-6-morpholin-4-yl-9H-purin-8-ylmethylene]azetidine-1-carboxylic acid tert-butyl ester (205 mg, 0.40 mmol) in EtOH (10 mL) and AcOH (3 mL) was added 10% Pd/C (40 mg) and the resulting mixture stirred under an atmosphere of H$_2$ for 65 h. The reaction mixture was filtered through Celite®, washing with MeOH, and the filtrate concentrated in vacuo affording the title compound (207 mg, quant.). LCMS (method H): R$_T$ 2.92 min [M+H]$^+$ 519.4

Example 76r

8-Azetidin-3-ylmethyl-2-(2-methylbenzoimidazol-1-yl)-9-methyl-6-morpholin-4-yl-9H-purine

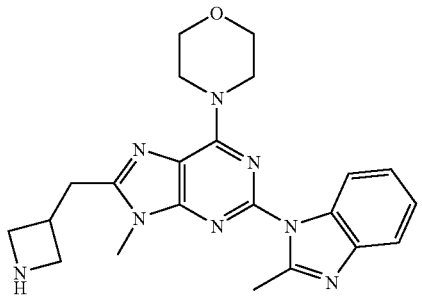

To a solution of 3-[2-(2-methylbenzoimidazol-1-yl)-9-methyl-6-morpholin-4-yl-9H-purin-8-ylmethyl]azetidine-1-carboxylic acid tert-butyl ester (207 mg, 0.40 mmol) in DCM (5 mL) was added TFA (5 mL) and the resulting mixture stirred for 2 h at r.t. The reaction mixture was loaded onto an Isolute® SCX-2 cartridge which was washed with MeOH/DCM and the product eluted with 2M NH$_3$/MeOH affording the title compound as a white foam (131 mg, 80%). LCMS (method H): R$_T$ 1.81 min [M+H]$^+$ 419.4

Example 76s

Acetic acid 1,1-dimethyl-2-{3-[9-methyl-2-(2-methylbenzoimidazol-1-yl)-6-morpholin-4-yl-9H-purin-8-ylmethyl]azetidin-1-yl}-2-oxoethyl ester

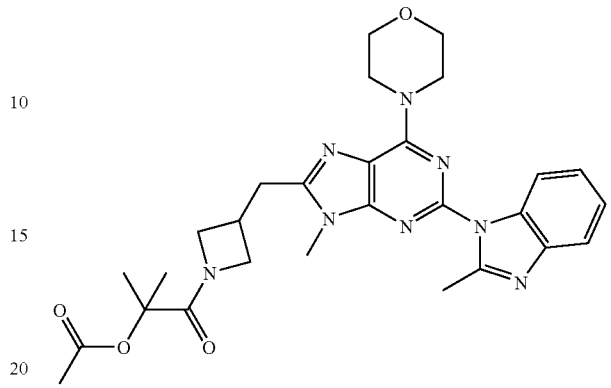

A mixture of 8-azetidin-3-ylmethyl-2-(2-methylbenzoimidazol-1-yl)-9-methyl-6-morpholin-4-yl-9H-purine (131 mg, 0.31 mmol), acetic acid 1-chlorocarbonyl-1-methylethyl ester (45 μL, 0.31 mmol) and NEt$_3$ (40 μL, 0.31 mmol) in THF (3 mL) was allowed to stir at r.t. for 16 h then concentrated in vacuo. The resulting residue was partitioned between DCM and H$_2$O, the organic phase dried (Na$_2$SO$_4$) and concentrated in vacuo. The residue was purified by column chromatography (Si—PCC, MeOH:EtOAc, 0-10%) affording the title compound as a white solid (125 mg, 73%). LCMS (method H): R$_T$ 2.50 min [M+H]$^+$ 547.5

Example 76t

3-[2-(2-Isopropylbenzoimidazol-1-yl)-9-methyl-6-morpholin-4-yl-9H-purin-8-ylmethylene]azetidine-1-carboxylic acid tert-butyl ester

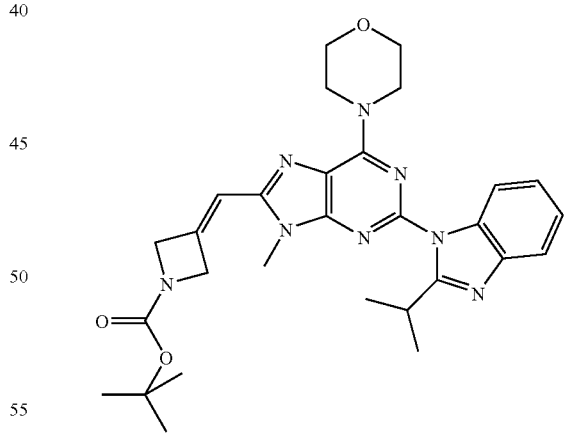

A mixture of 3-(2-chloro-9-methyl-6-morpholin-4-yl-9H-purin-8-ylmethylene)azetidine-1-carboxylic acid tert-butyl ester (200 mg, 0.48 mmol), 2-isopropylbenzimidazole (92 mg, 0.57 mmol), tris(dibenzylideneacetone)dipalladium (44 mg, 0.06 mmol), XPhos (58 mg, 0.10 mmol) and Cs$_2$CO$_3$ (310 mg, 0.95 mmol) in toluene (4 mL) was purged with argon then heated at 140° C. for 45 min in a microwave reactor. The reaction mixture was filtered through Celite®, washing with MeOH, and the filtrate concentrated in vacuo. The resulting residue was purified by column chromatography (Si—PCC, EtOAc:cyclohexane, 0-100%) affording the title compound as an off-white solid (255 mg, 99%). LCMS (method A): $R_T$ 3.40 min [M+H]$^+$ 545.3

Example 76u

3-[2-(2-Isopropylbenzoimidazol-1-yl)-9-methyl-6-morpholin-4-yl-9H-purin-8-ylmethyl]azetidine-1-carboxylic acid tert-butyl ester

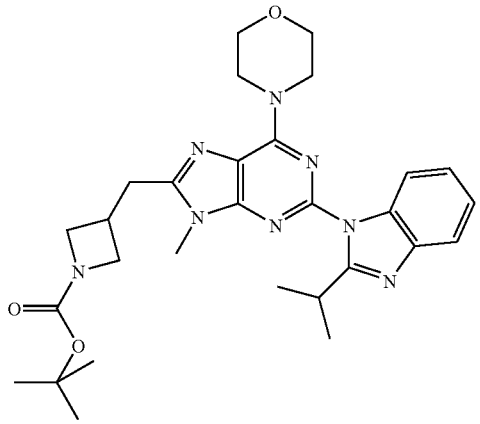

To a solution of 3-[2-(2-isopropylbenzoimidazol-1-yl)-9-methyl-6-morpholin-4-yl-9H-purin-8-ylmethylene]azetidine-1-carboxylic acid tert-butyl ester (255 mg, 0.47 mmol) in EtOH (15 mL) and AcOH (5 mL) was added 10% Pd/C (55 mg) and the resulting mixture stirred under an atmosphere of H$_2$ for 65 h. The reaction mixture was filtered through Celite®, washing with MeOH, and the filtrate concentrated in vacuo affording the title compound (256 mg, quant.). LCMS (method A): $R_T$ 3.16 min [M+H]$^+$ 547.4

Example 76v

8-Azetidin-3-ylmethyl-2-(2-isopropylbenzoimidazol-1-yl)-9-methyl-6-morpholin-4-yl-9H-purine

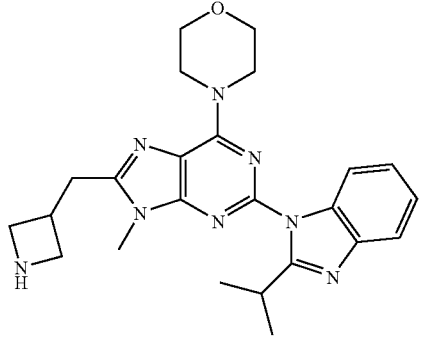

To a solution of 3-[2-(2-isopropylbenzoimidazol-1-yl)-9-methyl-6-morpholin-4-yl-9H-purin-8-ylmethyl]azetidine-1-carboxylic acid tert-butyl ester (256 mg, 0.47 mmol) in DCM (5 mL) was added TFA (5 mL) and the resulting mixture stirred for 2 h at r.t. The reaction mixture was loaded onto an Isolute® SCX-2 cartridge which was washed with MeOH/DCM and the product eluted with 2M NH$_3$/MeOH affording the title compound as an orange foam (205 mg, 97%). LCMS (method H): $R_T$ 1.91 min [M+H]$^+$ 447.4

Example 76w

Acetic acid 1,1-dimethyl-2-{3-[9-methyl-2-(2-methylbenzoimidazol-1-yl)-6-morpholin-4-yl-9H-purin-8-ylmethyl]azetidin-1-yl}-2-oxoethyl ester

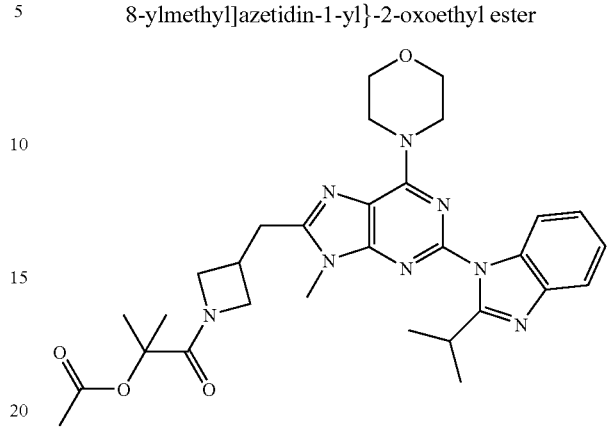

A mixture of 8-azetidin-3-ylmethyl-2-(2-isopropylbenzoimidazol-1-yl)-9-methyl-6-morpholin-4-yl-9H-purine (100 mg, 0.22 mmol), acetic acid 1-chlorocarbonyl-1-methylethyl ester (32 µL, 0.22 mmol) and NEt$_3$ (29 µL, 0.22 mmol) in THF (3 mL) was allowed to stir at r.t. for 16 h then concentrated in vacuo. The resulting residue was partitioned between DCM and H$_2$O, the organic phase dried (Na$_2$SO$_4$) and concentrated in vacuo. The residue was purified by column chromatography (Si—PCC, MeOH:EtOAc, 0-7%) affording the title compound as a white foam (97 mg, 75%). LCMS (method A): $R_T$ 2.65 min [M+H]$^+$ 575.3

Example 77a

4-[2-(2-Ethylbenzoimidazol-1-yl)-9-methyl-6-morpholin-4-yl-9H-purine-8-carbonyl]piperidine-1-carboxylic acid tert-butyl ester

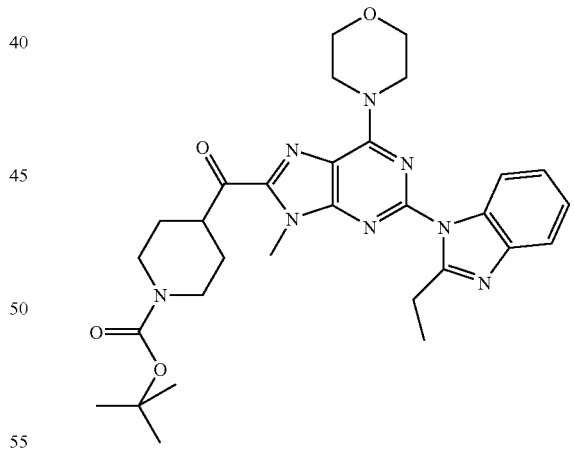

To a solution of 2-(2-ethylbenzoimidazol-1-yl)-9-methyl-6-morpholin-4-yl-9H-purine (500 mg, 1.38 mmol) and TMEDA (312 µL, 2.07 mmol) in THF (10 mL) at −78° C. was added n-BuLi (660 µL, 1.65 mmol, 2.5M solution in hexanes) and the resulting mixture stirred for 30 min before the addition of a solution of 4-(methoxymethylcarbamoyl)piperidine-1-carboxylic acid tert-butyl ester (564 mg, 2.07 mmol) in THF (5 mL) The resulting mixture was stirred for 2 h then quenched with H$_2$O and extracted with EtOAc. The combined organic phases were dried (MgSO$_4$) and concentrated in vacuo. The resulting residue was triturated with EtOAc:cyclohexane and the mother liquors concentrated in vacuo affording the title compound as an oil (760 mg, 96%). LCMS (method A): $R_T$ 3.67 min [M+H]$^+$ 557.3

Example 77b

4-{1-[2-(2-Ethylbenzoimidazol-1-yl)-9-methyl-6-morpholin-4-yl-9H-purin-8-yl]-1-hydroxyethyl}piperidine-1-carboxylic acid tert-butyl ester

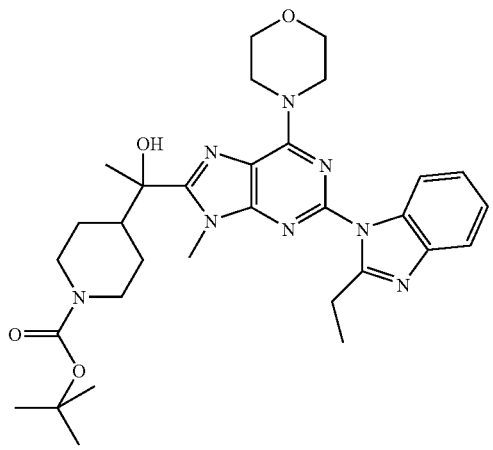

To a solution of 4-[2-(2-ethylbenzoimidazol-1-yl)-9-methyl-6-morpholin-4-yl-9H-purine-8-carbonyl]piperidine-1-carboxylic acid tert-butyl ester (177 mg, 0.31 mmol) in THF (3 mL) at 0° C. was added methylmagnesium bromide (130 μL, 0.37 mmol, 3M solution in Et$_2$O) and the resulting mixture stirred for 1 h before further methylmagnesium bromide (130 μL, 0.37 mmol) was added. The resulting mixture was warmed to r.t. and stirred for 16 h then concentrated in vacuo. The resulting residue was purified by column chromatography (Si—PCC, MeOH:EtOAc, 0-10%) affording the title compound as a clear oil (104 mg, 57%). LCMS (method A): $R_T$ 3.09 min [M+H]$^+$ 591.2

Example 77c

3-{2-[2-((R)-1-Hydroxyethyl)benzoimidazol-1-yl]-9-methyl-6-morpholin-4-yl-9H-purin-8-ylmethylene}azetidine-1-carboxylic acid tert-butyl ester

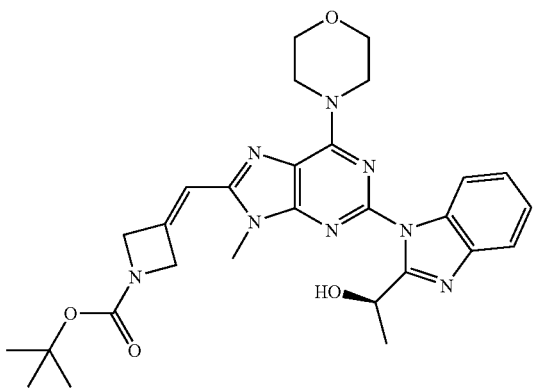

A mixture of 3-(2-chloro-9-methyl-6-morpholin-4-yl-9H-purin-8-ylmethylene)azetidine-1-carboxylic acid tert-butyl ester (180 mg, 0.43 mmol), (R)-1-(1H-benzoimidazol-2-yl)ethanol (84 mg, 0.52 mmol), tris(dibenzylideneacetone) dipalladium (40 mg, 0.04 mmol), XPhos (82 mg, 0.17 mmol) and Cs$_2$CO$_3$ (279 mg, 0.86 mmol) in toluene (3 mL) was purged with argon then heated at 140° C. for 1 h in a microwave reactor. The reaction mixture was filtered through Celite®, washing with EtOAc and the filtrate concentrated in vacuo. The resulting residue was purified by column chromatography (Si—PCC, MeOH:EtOAc, 0-15%) affording the title compound (167 mg, 72%). LCMS (method A): $R_T$ 3.24 min [M+H]$^+$ 547.4

Example 77d

3-{2-[2-((R)-1-Hydroxyethyl)benzoimidazol-1-yl]-9-methyl-6-morpholin-4-yl-9H-purin-8-ylmethyl}azetidine-1-carboxylic acid tert-butyl ester

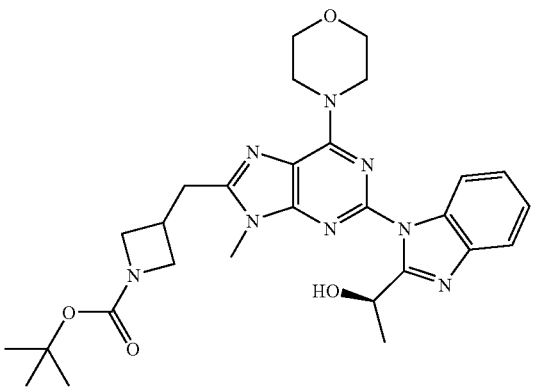

To a solution of 3-{2-[2-((R)-1-hydroxyethyl)benzoimidazol-1-yl]-9-methyl-6-morpholin-4-yl-9H-purin-8-ylmethylene}azetidine-1-carboxylic acid tert-butyl ester (167 mg, 0.31 mmol) in EtOAc (5 mL) and EtOH (5 mL) was added 20% Pd(OH)$_2$/C (160 mg) and the resulting mixture stirred under an atmosphere of H$_2$ for 16 h. The reaction mixture was filtered through Celite® and the filtrate concentrated in vacuo affording the title compound (156 mg, 93%). LCMS (method A): $R_T$ 3.07 min [M+H]$^+$ 549.4

Example 77e (R)-1-[1-(8-Azetidin-3-ylmethyl-9-methyl-6-morpholin-4-yl-9H-purin-2-yl)-1H-benzoimidazol-2-yl]ethanol

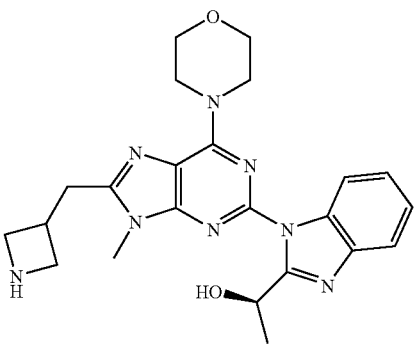

To a solution of 3-{2-[2-((R)-1-hydroxyethyl)benzoimidazol-1-yl]-9-methyl-6-morpholin-4-yl-9H-purin-8-ylmethyl}azetidine-1-carboxylic acid tert-butyl ester (156 mg, 0.28 mmol) in DCM (5 mL) was added TFA (2 mL) and the resulting mixture stirred at r.t. for 45 min. The reaction mixture was concentrated in vacuo and the resulting residue loaded onto an Isolute® SCX-2 cartridge which was washed with MeOH and the product eluted with 2M NH₃/MeOH affording the title compound (114 mg, 90%). LCMS (method A): $R_T$ 1.80 min [M+H]⁺ 449.4

Example 77f

3-{2-[2-((S)-1-Hydroxyethyl)benzoimidazol-1-yl]-9-methyl-6-morpholin-4-yl-9H-purin-8-ylmethylene}azetidine-1-carboxylic acid tert-butyl ester

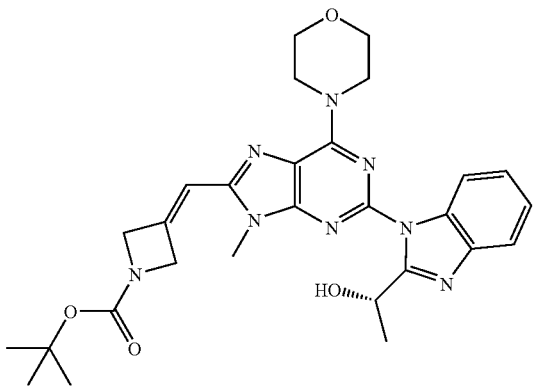

A mixture of 3-(2-chloro-9-methyl-6-morpholin-4-yl-9H-purin-8-ylmethylene)azetidine-1-carboxylic acid tert-butyl ester (180 mg, 0.43 mmol), (S)-1-(1H-benzoimidazol-2-yl)ethanol (84 mg, 0.52 mmol), tris(dibenzylideneacetone)dipalladium (40 mg, 0.04 mmol), XPhos (82 mg, 0.17 mmol) and Cs₂CO₃ (279 mg, 0.86 mmol) in toluene (3 mL) was purged with argon then heated at 140° C. for 1 h in a microwave reactor. Further tris(dibenzylideneacetone) dipalladium (40 mg, 0.04 mmol) and XPhos (82 mg, 0.17 mmol) were added and the mixture heated at 140° C. for a further 1 h. The reaction mixture was filtered through Celite®, washing with EtOAc and the filtrate concentrated in vacuo. The resulting residue was purified by column chromatography (Si—PCC, MeOH:EtOAc, 0-15%) affording the title compound (127 mg, 55%). LCMS (method A): $R_T$ 3.27 min [M+H]⁺ 547.4

Example 77g

3-{2-[2-((S)-1-Hydroxyethyl)benzoimidazol-1-yl]-9-methyl-6-morpholin-4-yl-9H-purin-8-ylmethyl}azetidine-1-carboxylic acid tert-butyl ester

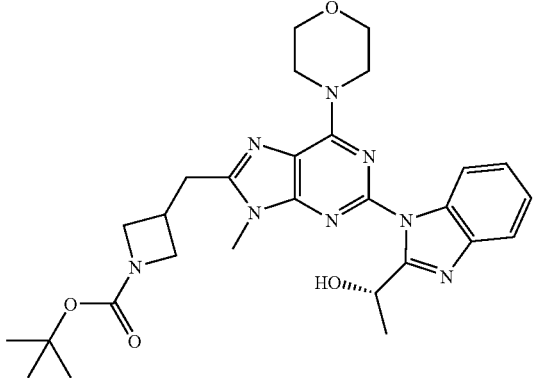

To a solution of 3-{2-[2-((S)-1-hydroxyethyl)benzoimidazol-1-yl]-9-methyl-6-morpholin-4-yl-9H-purin-8-ylmethylene}azetidine-1-carboxylic acid tert-butyl ester (127 mg, 0.23 mmol) in EtOAc (5 mL) and EtOH (5 mL) was added 20% Pd(OH)₂/C (130 mg) and the resulting mixture stirred under an atmosphere of H₂ for 18 h. The reaction mixture was filtered through Celite® and the filtrate concentrated in vacuo affording the title compound (109 mg, 86%). LCMS (method A): $R_T$ 3.06 min [M+H]⁺ 549.4

Example 77h (S)-1-[1-(8-Azetidin-3-ylmethyl-9-methyl-6-morpholin-4-yl-9H-purin-2-yl)-1H-benzoimidazol-2-yl]ethanol

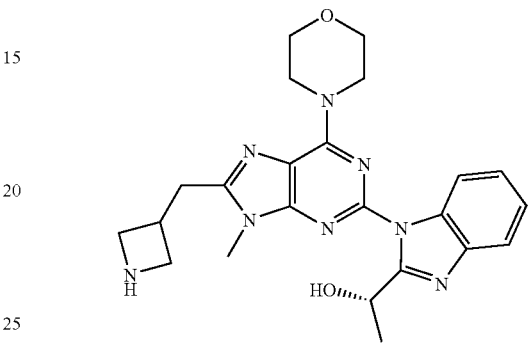

To a solution of 3-{2-[2-((S)-1-hydroxyethyl)benzoimidazol-1-yl]-9-methyl-6-morpholin-4-yl-9H-purin-8-ylmethyl}azetidine-1-carboxylic acid tert-butyl ester (109 mg, 0.20 mmol) in DCM (5 mL) was added TFA (2 mL) and the resulting mixture stirred at r.t. for 45 min. The reaction mixture was concentrated in vacuo and the resulting residue loaded onto an Isolute® SCX-2 cartridge which was washed with MeOH and the product eluted with 2M NH₃/MeOH affording the title compound (70 mg, 80%). LCMS (method A): $R_T$ 1.87 min [M+H]⁺ 449.4

Formula I(iv) furan intermediates wherein (iv) X¹ is CR⁷ and X² is O

Example 80a

2-[4-(2-Chloro-4-morpholin-4-ylfuro[3,2-d]pyrimidin-6-ylmethyl)piperazin-1-yl]-isobutyramide

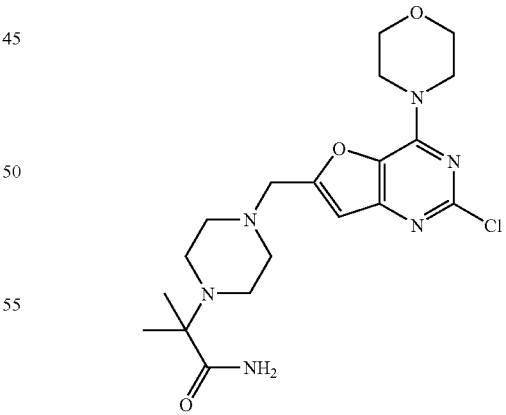

A solution of 2-chloro-4-morpholin-4-yl-furo[3,2-d]pyrimidine-6-carbaldehyde (300 mg, 1.12 mmol) and 2-piperazin-1-ylisobutyramide dihydrochloride (327 mg, 1.33 mmol) in DCE (12 mL) was stirred at ambient temperature for 1 h. Sodium triacetoxyborohydride (358 mg, 1.69 mmol) was added and the mixture stirred for 6 h, then loaded onto an Isolute® SCX-2 cartridge (25 g). The cartridge was then washed with methanol and the desired product was subsequently eluted using 2 M NH₃ in MeOH. The product was collected and concentrated in vacuo. The resultant residue was purified by flash chromatography (Si—PPC, DCM:MeOH; gradient from 100:0 to 90:10) to afford the title compound as a tan solid (390 mg, 82%). LCMS (Method H): R$_T$=2.39 min, M+H⁺=423

Example 80b

2-Chloro-4-morpholin-4-yl-6-(3-morpholin-4-ylazetidin-1-ylmethyl)furo[3,2-d]-pyrimidine

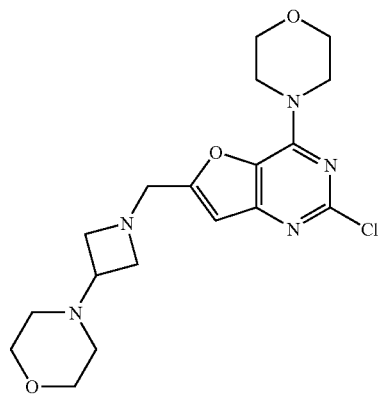

A solution of 2-chloro-4-morpholin-4-ylfuro[3,2-d]pyrimidine-6-carbaldehyde (300 mg, 1.12 mmol) and 4-azetidin-3-yl-morpholine (191 mg, 1.34 mmol) in DCE (12 mL) was stirred at ambient temperature for 1 h. Sodium triacetoxyborohydride (358 mg, 1.69 mmol) was added and the mixture stirred for 6 h, then loaded onto an Isolute® SCX-2 cartridge (10 g). The cartridge was then washed with methanol and the desired product was subsequently eluted using 2 M NH₃ in MeOH. The product was collected and concentrated in vacuo. The resultant residue was purified by flash chromatography (Si—PPC, DCM:MeOH; gradient from 100:0 to 90:10) to afford the title compound as a tan solid (357 mg, 81%). LCMS (Method H): R$_T$=2.26 min, M+H⁺=394

Example 80c

2-[1-(2-Chloro-4-morpholin-4-ylfuro[3,2-d]pyrimidin-6-ylmethyl)piperidin-4-yl]-propan-2-ol

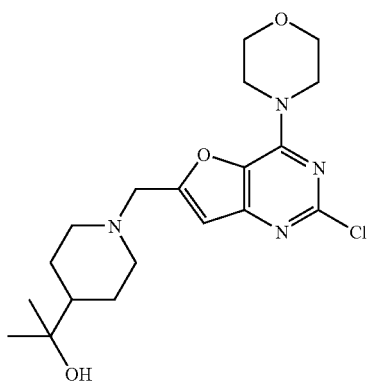

A solution of 2-chloro-4-morpholin-4-ylfuro[3,2-d]pyrimidine-6-carbaldehyde (78 mg, 0.29 mmol) and 2-piperidin-4-ylpropan-2-ol (50 mg, 0.35 mmol) in DCE (3 mL) was stirred at ambient temperature for 45 min. Sodium triacetoxyborohydride (93 mg, 0.44 mmol) was added and the mixture stirred for 2 h, then loaded onto an Isolute® SCX-2 cartridge (10 g). The cartridge was then washed with methanol and the desired product was subsequently eluted using 2 M NH₃ in MeOH. The product was collected and concentrated in vacuo. The resultant residue was purified by flash chromatography (Si—PPC, DCM:MeOH; 100:0 to 98:2 to 95:5) to afford the title compound as a tan solid (110 mg, 96%). LCMS (Method H): R$_T$=2.33 min, M+H⁺=395.

Example 80d

2-[1-(4-Morpholin-4-yl-2-(tributylstannanyl)furo[3,2-d]pyrimidin-6-ylmethyl)-piperidin-4-yl]-propan-2-ol

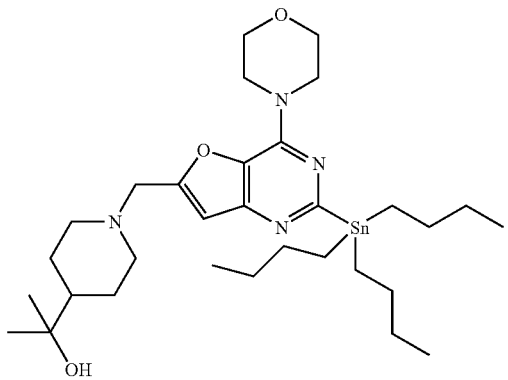

A mixture of 2-[1-(2-chloro-4-morpholin-4-ylfuro[3,2-d]pyrimidin-6-ylmethyl)piperidin-4-yl]propan-2-ol (140 mg, 0.36 mmol), hexabutylditin (266 µL, 0.53 mmol), and PdCl₂{P$^t$Bu₂(Ph-p-Nme₂)}₂ (25 mg, 0.034 mmol) in 1,4-dioxane purged with argon gas and then subjected to microwave irradiation at 150° C. for 30 min. The reaction mixture was diluted with MeOH and loaded onto an Isolute® SCX-2 cartridge (10 g). The cartridge was then washed with MeOH and the desired product was subsequently eluted using 2 M NH₃ in MeOH. The product was collected and concentrated in vacuo to afford the title compound which was used without

Example 80e

4-Morpholin-4-yl-6-(3-morpholin-4-yl-azetidin-1-ylmethyl)-2-(tributylstannanyl)furo[3,2-d]pyrimidine

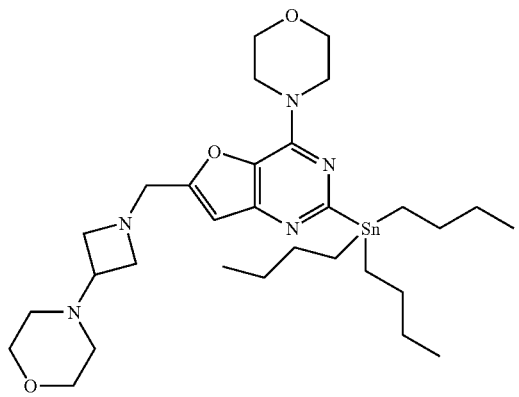

A mixture of 2-chloro-4-morpholin-4-yl-6-(3-morpholin-4-ylazetidin-1-ylmethyl)furo[3,2-d]pyrimidine (200 mg, 0.51 mmol), hexabutylditin (380 µL, 0.75 mmol), and PdCl$_2$ {P$^t$Bu$_2$(Ph-p-Nme$_2$)}$_2$ (36 mg, 0.051 mmol) in 1,4-dioxane (2.3 mL) was purged with argon gas and then subjected to microwave irradiation at 150° C. for 30 min. The reaction mixture was diluted with MeOH and loaded onto a Isolute® SCX-2 cartridge (10 g). The cartridge was then washed with MeOH and the desired product was subsequently eluted using 2 M NH$_3$ in MeOH. The product was collected and concentrated in vacuo. The resultant residue was purified by flash chromatography (Si—PPC, DCM:MeOH; 100:0 to 98:2 to 95:5) to afford to afford the title compound as a yellow oil (227 mg, 69%). LCMS (Method H) R$_T$=3.72 min; [M +H]$^+$ 648 ($^{116}$Sn) 650 ($^{118}$Sn)

Example 81a

2-Chloro-6-((R)-3-methylmorpholin-4-yl)-9H-purine

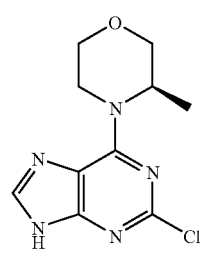

A mixture of 2,6-dichloro-9H-purine (2.18 g, 11.53 mmol), (R)-3-methylmorpholine (1.40 g, 13.84 mmol) and DIPEA (2.57 mL, 14.99 mmol) in IMS (50 mL) were heated at 80° C. for 8 h. The reaction mixture was concentrated in vacuo to a reduced volume and the residue partitioned between EtOAc and H$_2$O. The organic phase was dried (Na$_2$SO$_4$) and concentrated in vacuo. The resulting residue was purified by column chromatography (Si—PCC, MeOH: EtOAc, 0-10%) affording the title compound as an off-white solid (914 mg, 31%). LCMS (method H): R$_T$ 2.53 min [M+H]$^+$ 254.3

Example 81b

2-Chloro-9-methyl-6-((R)-3-methylmorpholin-4-yl)-9H-purine

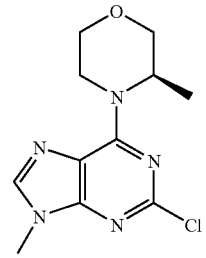

A mixture of 2-chloro-6-((R)-3-methylmorpholin-4-yl)-9H-purine (635 mg, 2.50 mmol), methyl iodide (187 µL, 3.00 mmol) and K$_2$CO$_3$ (484 mg, 3.50 mmol) in THF (15 mL) were stirred at r.t. for 18 h before further methyl iodide (187 µL, 3.00 mmol) was added. The resulting mixture was allowed to stir for 65 h then concentrated in vacuo. The resulting residue was partitioned between EtOAc and H$_2$O, the organic phase washed with brine, then dried (Na$_2$SO$_4$) and concentrated in vacuo affording the title compound as an off-white solid (552 mg, 83%). LCMS (method H): R$_T$ 2.76 min [M+H]$^+$ 268.3

Example 81c

2-Chloro-9-methyl-6-((R)-3 -methylmorpholin-4-yl)-9H-purine-8-carbaldehyde

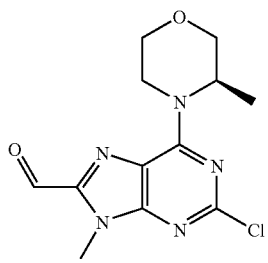

To a solution of 2-chloro-9-methyl-6-((R)-3-methylmorpholin-4-yl)-9H-purine (550 mg, 2.05 mmol) in THF (20 mL) at −78° C. was added LiHMDS (3.1 mL, 3.08 mmol, 1M solution in THF). The resulting mixture was allowed to stir for 45 min before the addition of DMF (800 µL, 10.33 mmol). The reaction mixture was warmed to r.t. over 1.5 h then poured onto 0.5M HCl. The resulting precipitate was collected by filtration and washed with H$_2$O then Et$_2$O affording the title compound as a yellow solid (406 mg, 67%). LCMS (method H): $R_T$ 3.35 min [M+H]$^+$ 296.3

Example 81d

2-{1-[2-Chloro-9-methyl-6-((R)-3-methylmorpholin-4-yl)-9H-purin-8-ylmethyl]piperidin-4-yl}propan-2-ol

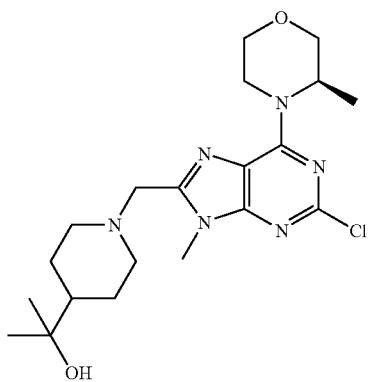

A mixture of 2-chloro-9-methyl-6-((R)-3-methylmorpholin-4-yl)-9H-purine-8-carbaldehyde (279 mg, 0.94 mmol), 2-piperidin-4-ylpropan-2-ol (149 mg, 1.04 mmol) and 4 Å powdered molecular sieves (700 mg) in DCE (15 mL) was stirred for 5.5 h before the addition of sodium triacetoxyborohydride (400 mg, 1.89 mmol). The resulting mixture was allowed to stir for 17 h then filtered through Celite®, washing with MeOH. The resulting filtrate was loaded onto an Isolute® SCX-2 cartridge which was washed with MeOH and the product eluted with 2M NH$_3$/MeOH/DCM. The resulting residue was purified by column chromatography (Si—PCC, MeOH:EtOAc, 0-15%) affording the title compound as a pale yellow solid (366 mg, 92%). LCMS (method H): $R_T$ 2.11 min [M+H]$^+$ 423.4

Example 82a

2-Chloro-6-(3-oxa-8-azabicyclo[3.2.1]oct-8-yl)-9H-purine

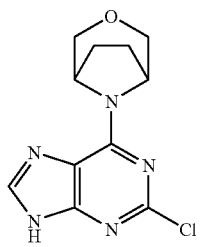

A mixture of 2,6-dichloro-9H-purine (527 Mg, 2.79 mmol), 3-Oxa-8-aza-bicyclo[3.2.1]octane hydrochloride (500 mg, 3.34 mmol) and DIPEA (1.2 mL, 6.98 mmol) in IMS (15 mL) were heated at 80° C. for 3 h then stirred at r.t. for 18 h. The resulting precipitate was collected by filtration and washed with further IMS. The resulting solid was dried in vacuo affording the title compound (663 mg, 90%). $^1$H NMR (CDCl$_3$, 400 MHz): δ 8.14 (1 H, s), 5.60 (1 H, brd s), 4.80 (1 H, brd s), 3.66 (4 H, brd s), 2.00 (4 H, s)

Example 82b

2-Chloro-9-methyl-6-(3-oxa-8-azabicyclo[3.2.1]oct-8-yl)-9H-purine

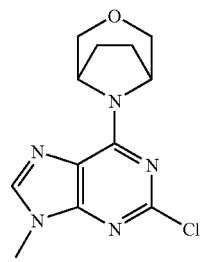

A mixture of 2-chloro-6-(3-oxa-8-azabicyclo[3.2.1]oct-8-yl)-9H-purine (650 mg, 2.45 mmol), methyl iodide (183 μL, 2.94 mmol) and K$_2$CO$_3$ (473 mg, 3.43 mmol) in THF (15 mL) was stirred at r.t. for 18 h before further methyl iodide (50 μL, 0.80 mmol) was added. The resulting mixture was allowed to stir for 65 h then concentrated in vacuo. The resulting residue was partitioned between EtOAc and H$_2$O, the organic phase washed with brine, then dried (Na$_2$SO$_4$) and concentrated in vacuo affording the title compound as an off-white solid (673 mg, 98%). LCMS (method H): $R_T$ 2.63 min [M+H]$^+$ 280.3

Example 82c

2-Chloro-9-methyl-6-(3-oxa-8-azabicyclo[3.2.1]oct-8-yl)-9H-purine-8-carbaldehyde

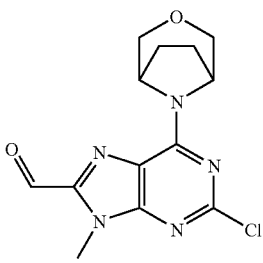

To a solution of 2-chloro-9-methyl-6-(3-oxa-8-azabicyclo[3.2.1]oct-8-yl)-9H-purine (620 mg, 2.22 mmol) and TMEDA (498 μL, 3.33 mmol) in THF (11 mL) at −78° C. was added n-BuLi (1.3 mL, 3.33 mmol, 2.5M solution in hexanes). The resulting mixture was warmed to −40° C. and allowed to stir for 30 min before cooling back to −78° C. DMF (517 μL, 6.65 mmol) was added and the resulting mixture was stirred at −78° C. for 30 min then poured onto 1M HCl. The aqueous layer was extracted with EtOAc and the organic phase washed with brine, then dried (Na$_2$SO$_4$) and concentrated in vacuo. The resulting residue was purified by column chromatography (Si—PCC, MeOH:DCM, 0-10%) affording the title compound as a pale yellow solid (500 mg, 73%). $^1$H NMR (CDCl₃, 400 MHz): δ 9.88 (1 H, s), 5.79 (1 H, d, J=6.14 Hz), 5.05 (1 H, d, J=6.84 Hz), 4.05 (3 H, s), 3.80-3.78 (4 H, m), 2.29-2.01 (4 H, m)

Example 82d

2-{1-[2-Chloro-9-methyl-6-(3-oxa-8-azabicyclo[3.2.1]oct-8-yl)-9H-purin-8-ylmethyl]piperidin-4-yl}propan-2-ol

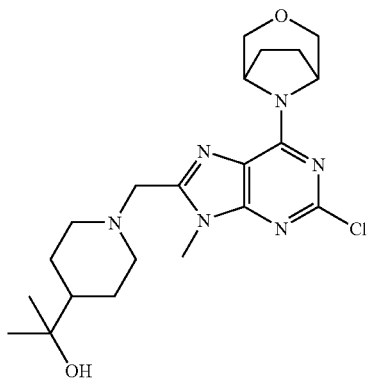

A mixture of 2-chloro-9-methyl-6-(3-oxa-8-azabicyclo[3.2.1]oct-8-yl)-9H-purine-8-carbaldehyde (500 mg, 1.63 mmol), 2-piperidin-4-ylpropan-2-ol (256 mg, 1.79 mmol) and 4 Å powdered molecular sieves (500 mg) in DCE (11 mL) was stirred for 4 h before the addition of sodium triacetoxyborohydride (690 mg, 3.26 mmol). The resulting mixture was allowed to stir for 17 h then filtered through Celite®, washing with MeOH. The resulting filtrate was loaded onto an Isolute® SCX-2 cartridge which was washed with MeOH and the product eluted with 2M NH₃/MeOH/DCM. The resulting residue was purified by column chromatography (Si—PCC, MeOH:DCM, 0-10%) affording the title compound as a pale yellow solid (577 mg, 82%). LCMS (method H): $R_T$ 0.30 and 2.00 min [M+H]⁺ 435.4

Example 83a

2-Chloro-6-((S)-3-methylmorpholin-4-yl)-9H-purine

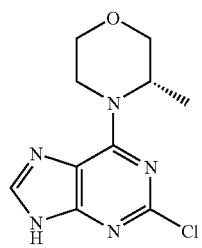

A mixture of 2,6-dichloro-9H-purine (5.2 g, 27.51 mmol), (S)-3-methylmorpholine (3.30 g, 32.62 mmol) and DIPEA (5.0 mL, 28.71 mmol) in IMS (130 mL) were heated at 80° C. for 3 h then stirred at r.t. for 17 h. The resulting white precipitate was collected by filtration and the filtrate concentrated in vacuo to a reduced volume and the resulting precipitate also collected by filtration. Both batches of solid were combined in DCM and the organic phase washed with H₂O and brine, then dried (MgSO₄) and concentrated in vacuo affording the title compound as a white powder (5.3 g, 76%). LCMS (method H): $R_T$ 2.54 min [M+H]⁺ 254.1

Example 83b

2-Chloro-9-methyl-6-((S)-3-methylmorpholin-4-yl)-9H-purine

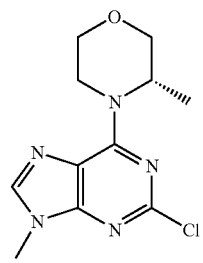

A mixture of 2-chloro-6-((S)-3-methylmorpholin-4-yl)-9H-purine (5.3 g, 20.89 mmol), methyl iodide (1.6 mL, 25.70 mmol) and K₂CO₃ (4.0 g, 28.94 mmol) in THF (100 mL) were stirred at r.t. for 18 h then concentrated in vacuo. The resulting residue was partitioned between EtOAc and H₂O, the organic phase washed with brine, then dried (Na₂SO₄) and concentrated in vacuo affording the title compound (4.84 g, 87%). LCMS (method H): $R_T$ 2.74 min [M+H]⁺ 268.2

Example 83c

2-Chloro-9-methyl-6-((S)-3-methylmorpholin-4-yl)-9H-purine-8-carbaldehyde

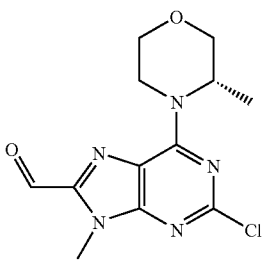

To a solution of 2-chloro-9-methyl-6-((S)-3-methylmorpholin-4-yl)-9H-purine (500 mg, 1.67 mmol) and TMEDA (419 µL, 2.80 mmol) in THF (10 mL) at −78° C. was added n-BuLi (1.12 mL, 2.80 mmol, 2.5M solution in hexanes). The resulting mixture was allowed to warm to −40° C. and stir for 30 min then cooled back to −78° C. before the addition of DMF (435 µL, 5.61 mmol). The reaction mixture was allowed to stir at −78° C. for 30 min then poured onto 1M HCl. The aqueous phase was extracted with EtOAc and the combined organic phases were washed with H₂O and brine, then dried (MgSO₄) and concentrated in vacuo. The resulting residue was purified by column chromatography (Si—PCC, EtOAc:

cyclohexane, 0-50%) affording the title compound as a white solid (450 mg, 81%). LCMS (method H): $R_T$ 3.28 min [M+H]$^+$ 296.3

Example 83d

2-{1-[2-Chloro-9-methyl-6-((S)-3-methylmorpholin-4-yl)-9H-purin-8-ylmethyl]piperidin-4-yl}propan-2-ol

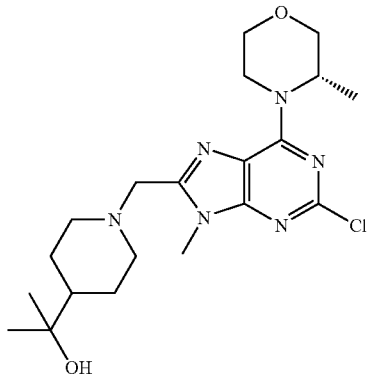

A mixture of 2-chloro-9-methyl-6-((S)-3-methylmorpholin-4-yl)-9H-purine-8-carbaldehyde (450 mg, 1.52 mmol), 2-piperidin-4-ylpropan-2-ol (239 mg, 1.67 mmol) and 4 Å powdered molecular sieves (450 mg) in DCE (10 mL) was stirred for 6 h before the addition of sodium triacetoxyborohydride (644 mg, 3.04 mmol). The resulting mixture was allowed to stir for 17 h then filtered through Celite®, washing with MeOH. The resulting filtrate was loaded onto an Isolute® SCX-2 cartridge which was washed with MeOH and the product eluted with 2M NH$_3$/MeOH/DCM. The resulting residue was purified by column chromatography (Si—PCC, MeOH:DCM, 0-4%) affording the title compound as a cream solid (538 mg, 84%). LCMS (method H): $R_T$ 2.02 min [M+H]$^+$ 423.3

Example 101

4-(1-((2-(isoquinolin-5-yl)-4-morpholinothieno[3,2-d]pyrimidin-6-yl)methyl)piperidin-4-yl)morpholine 101

A sealable tube was charged with 2-chloro-4-morpholin-4-yl-6-(4-morpholin-4-yl-piperidin-1-ylmethyl)-thieno[3,2-d]pyrimidine (0.100 g, 0.229 mmol), isoquinoline-5-boronic acid (0.048 g, 0.275 mmol), dichlorobis(triphenylphosphine)palladium(II) (0.008 g, 0.012 mmol), 1 N aqueous sodium carbonate solution (1 mL) and acetonitrile (3 mL). The vessel was evacuated and back-filled with argon three times then sealed and heated at 130° C. for 90 min. The reaction mixture was cooled, concentrated, redissolved in ethyl acetate and filtered through celite. The filtrates were concentrated then purified by chromatography (silica, 10 to 20% methanol in dichloromethane) to give 101 (0.033 g, 27%) as a yellow solid. MS m/e 531 [M+H]$^+$; $^1$H NMR (300 MHz, CDCl$_3$) δ ppm 1.54 - 1.71 (m, 2 H) 1.87 (d, J=11.3 Hz, 2 H), 2.09-2.30 (m, 3 H), 2.52-2.63 (m, 4 H) 3.01-3.11 (m, 2 H) 3.70-3.78 (m, 4 H) 3.85 (s, 2 H) 3.87-3.94 (m, 4 H) 4.03-4.12 (m, 4 H) 7.35 (s, 1 H), 7.67-7.75 (m, 1 H) 8.06 (d, J=8.3 Hz, 1 H) 8.31-8.37 (m, 1 H) 8.52-8.58 (m, 1 H) 8.61-8.67 (m, 1 H) 9.30 (s, 1 H)

Example 102

4-(6-((4-(cyclopropylmethyl)piperazin-1-yl)methyl)-2-(1H-pyrrolo[2,3-c]pyridin-4-yl)thieno[3,2-d]pyrimidin-4-yl)morpholine 102

Step 1: 6-(4-(Cyclopropylmethyl)piperazin-1-ylmethyl)-2-methylsulfanyl-4-morpholin-4-yl-thieno[3,2-d]pyrimidine

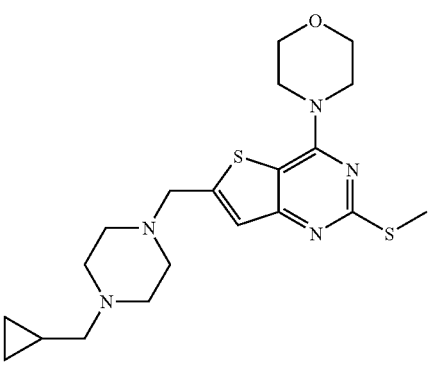

2-Chloro-6-(4-(cyclopropylmethyl)piperazin-1-ylmethyl)-4-morpholin-4-ylthieno[3,2-d]pyrimidine (0.2 g, 0.49 mmol) in DMF (3 mL) was treated with sodium thiomethoxide (0.12 g, 1.71 mmol) in a sealed tube and the reaction mixture heated at 100° C. with stirring. After 2 hours the contents of the tube were diluted with EtOAc then washed with saturated aqueous NaHCO$_3$ (×2) followed by brine and the organic phase was isolated, dried (Na$_2$SO$_4$), filtered and concentrated to afford 6-(4-(cyclopropylmethyl)piperazin-1-ylmethyl)-2-methylsulfanyl-4-morpholin-4-yl-thieno[3,2-d]pyrimidine as a pale yellow solid (0.2 g, 97%). LCMS (Method D): $R_T$=2.04 min, [M+H]$^+$ 419

Step 2: A solution of 6-(4-cyclopropylmethylpiperazin-1-ylmethyl)-2-methylsulfanyl-4-morpholin-4-yl-thieno[3,2-d]pyrimidine (46 mg, 0.11 mmol) and 1-benzenesulfonyl-4-tributylstannanyl-1H-pyrrolo[2,3-c]pyridine (129 mg, 0.24 mmol) in DME (2 mL) was treated with copper(I)bromide-dimethyl sulfide complex (50 mg, 2.43 mmol) in a sealed tube then the solution was degassed with argon for 5 min. Pd(PPh$_3$)$_4$ (20 mg, 0.016 mmol) was added and the reaction mixture heated at 100° C. for 3 hours. The mixture was filtered through Celite®, which was washed with DME and the combined filtrate was evaporated to give a yellow gum. The gum was purified by flash chromatography on silica, eluting with EtOAc to afford 2-(1-benzenesulfonyl-6-(4-cyclopropylmethylpiperazin-1-ylmethyl)-4-morpholin-4-yl-2-(1H-pyrrolo[2,3-c]pyridin-4-yl)thieno[3,2-d]pyrimidine (34 mg, 54%). This intermediate was dissolved in IMS (1 mL) and 1,4-dioxane (1 mL) and the stirring solution was treated with NaOH solution (0.1 mL from 2.5 g NaOH in 5 mL H$_2$O). After 10 min the reaction mixture was treated with HCl (10 N) until at pH 7. The reaction mixture was filtered to remove insoluble material. The solids were washed with 1,4-dioxane, and the filtrate was evaporated. The resulting residue was taken up in DCM and washed with brine; the isolated organic phase was dried (MgSO$_4$), filtered and evaporated. Purification was carried out by flash chromatography, eluting with 3-12% MeOH in DCM to afford 102 (22 mg, 41%). ¹H NMR (DMSO, 400 MHz): δ 11.76 (s, 1 H); 9.13 (s, 1 H); 8.81 (s, 1 H); 7.71 (d, J=2.71 Hz, 1 H); 7.45 (s, 1 H); 7.40-7.36 (m, 1 H); 3.99 (t, J=4.6 Hz, 4H); 3.87 (s, 2 H); 3.83 (t, J=4.65 Hz, 4 H); 3.30 (br s, 4H); 2.54 (br s, 4 H); 2.24 (br s, 2H); 0.89-0.77 (m, 1 H); 0.50-0.41 (m, 2 H); 0.12-0.04 (m, 2H). LCMS (Method F): R$_T$=4.63 min, [M+H]⁺ 490.1

Example 103

4-((4-morpholino-2-(1H-pyrrolo[2,3-c]pyridin-4-yl)thieno[3,2-d]pyrimidin-6-yl)methyl)morpholine 103

Step 1: 2-Methylsulfanyl-4-morpholin-4-yl-6-morpholin-4-ylmethyl-thieno[3,2-d]pyrimidine

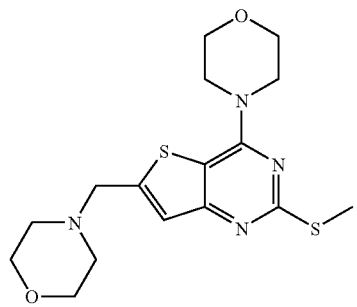

2-Chloro-4-morpholin-4-yl-6-morpholin-4-ylmethyl-thieno[3,2-d]pyrimidine (0.2 g, 0.56 mmol) in DMF (3 mL) was treated with sodium thiomethoxide (0.12 g, 1.71 mmol) in a sealed tube and the reaction mixture heated at 100° C. with stirring. After 2 h the contents of the tube were diluted with EtOAc, washed with saturated aqueous NaHCO₃ (×2) then brine, and the organic phase was isolated, dried (Na₂SO₄), filtered and concentrated to afford the title compound as a light brown solid (0.205 g, 100%). LCMS (Method D): R$_T$=1.80 min, [M+H]⁺ 366.

Step 2: A solution of 2-methylsulfanyl-4-morpholin-4-yl-6-morpholin-4-ylmethyl-thieno[3,2-d]pyrimidine (40 mg, 0.11 mmol) and 1-benzenesulfonyl-4-(tributylstannanyl)-1H-pyrrolo[2,3-c]pyridine (129 mg, 0.24 mmol) in DME (2 mL) was treated with copper(I)bromide-dimethyl sulfide complex (50 mg, 2.43 mmol) in a sealed tube and the solution was degassed with argon for 5 min. Pd(PPh₃)₄ (19 mg, 0.016 mmol) was added and the reaction mixture heated at 100° C. for 3 hours. The mixture was filtered through celite, which was washed with DME and the combined filtrate was evaporated to give a yellow gum. The gum was purified by flash chromatography on silica, eluting with EtOAc to afford 2-(1-benzenesulfonyl-1H-pyrrolo[2,3-c]pyridin-4-yl)-4-morpholin-4-yl-6-morpholin-4-ylmethyl-thieno[3,2-d]pyrimidine (34 mg, 54%). The sulfone intermediate was dissolved in IMS (1 mL) and 1,4-dioxane (1 mL) and the stirring solution was treated with NaOH solution (0.1 mL from 2.5 g NaOH in 5 mL H₂O). After 10 min the reaction mixture was treated with HCl (10 N) until at pH 7. The reaction mixture was filtered to remove insoluble material. The solids were washed with 1,4-dioxane, and the filtrate was evaporated. The resulting residue was taken up in DCM and washed with brine; the isolated organic phase was dried (MgSO₄), filtered and evaporated. The resultant crude residue was purified by flash chromatography, (Si—PPC) eluting with 2-8% MeOH in DCM to afford 103 as a white solid (14 mg, 29%). ¹H NMR (MeOD, 400 MHz): δ 8.99 (s, 1 H); 8.75 (s, 1 H); 7.66 (d, J=3.95 Hz, 1 H); 7.40-7.36 (m, 2 H); 4.14-4.05 (m, 4 H); 3.94-3.85 (m, 6 H); 3.73 (t, J=4.6 Hz, 4 H); 2.59 (t, J=4.35 Hz, 4 H). LCMS (Method F): R$_T$=4.59 min, [M+H]⁺ 437.2

Example 104

1-((2-(7-chloroquinolin-4-yl)-4-morpholinothieno[3,2-d]pyrimidin-6-yl)methyl)-N,N-dimethylpiperidin-4-amine 104

A sealable tube was charged with [1-(2-chloro-4-morpholin-4-yl-thieno[3,2-d]pyrimidin-6-ylmethyl)-piperidin-4-yl]-dimethyl-amine (0.150 g, 0.380 mmol), 7-chloroquinoline-4-boronic acid pinacol ester (0.132 g, 0.456 mmol), dichlorobis(triphenylphosphine)palladium(II) (0.013 g, 0.02 mmol), 1 N aqueous sodium carbonate solution (1 mL) and acetonitrile (3 mL). The vessel was evacuated and back-filled with argon three times then sealed and heated at 130° C. for 90 min. The reaction mixture was cooled, concentrated, redissolved in ethyl acetate and filtered through celite. The filtrates were concentrated then purified by chromatography (silica, 10 to 20% methanol in dichloromethane) to give 104 (0.085 g, 43%) as a yellow solid. MS m/e 531 [M+H]⁺; ¹H NMR (300 MHz, METHANOL-d₄) δ ppm 1.48-1.67 (m, 2 H) 1.82-1.96 (m, 2 H) 2.07-2.26 (m, 3 H) 2.30 (s, 6 H) 3.07 (d, J=11.7 Hz, 2 H) 3.82-3.91 (m, 6 H) 4.02-4.11 (m, 4 H) 7.36 (s, 1 H) 7.60 (dd, J=9.1, 2.3 Hz, 1 H) 7.95 (d, J=4.5 Hz, 1 H) 8.10 (d, J=2.3 Hz, 1 H) 8.67 (d, J=9.4 Hz, 1 H) 8.98 (d, J=4.9 Hz, 1 H)

Example 105

2-methyl-2-(4-((4-morpholino-2-(1H-pyrrolo[2,3-c]pyridin-4-yl)thieno[3,2-d]pyrimidin-6-yl)methyl)piperazin-1-yl)propanamide 105

A mixture of 2-[4-(4-morpholin-4-yl-2-(tributlystannanyl)thieno[3,2-d]pyrimidin-6-ylmethyl)piperazin-1-yl]isobutyramide (1.17 g, 1.69 mmol), 4-bromo-1H-pyrrolo[2,3-c]pyridine (432 mg, 2.19 mmol), tetrakis(triphenylphosphine)palladium (194 mg, 10 mol %) and CuI (385 mg, 2.02 mmol) in dioxane (20 mL) was purged with argon gas then heated at 140° C., for 20 min, in a microwave reactor. The reaction mixture was loaded onto an Isolute® SCX-2 cartridge, washed with MeOH/DCM then eluted with 2 M NH₃ in MeOH/DCM. The resulting residue was purified by column chromatography (Si—PPC, MeOH:DCM, gradient 0:100 to 20:80). The resulting solid was dissolved in MeOH, loaded onto an Isolute® SCX-2 cartridge, washed with MeOH then eluted with 2 M NH₃ in MeOH to afford 105 as a pale yellow solid (242 mg, 39%). LCMS (Method F): R$_T$ 4.51 min, [M+H]⁺ 521.2. ¹H NMR (DMSO, 400 MHz): δ 11.75 (s, 1H); 9.13 (s, 1 H); 8.81 (s, 1 H); 7.71 (t, J=2.7 Hz, 1 H); 7.45 (s, 1 H); 7.40-7.37 (m, 1 H); 7.07 (d, J=3.5 Hz, 1 H); 6.95 (d, J=3.5 Hz, 1 H); 4.01 (t, J=4.6 Hz, 4 H); 3.87 (s, 2 H); 3.83 (t, J=4.6 Hz, 4 H); 2.58 (s, 4 H); 2.49 (s, 4 H); 1.10 (s, 6 H)

Example 106

2-methyl-2-(4-((4-morpholino-2-(1H-pyrrolo[3,2-c]pyridin-4-yl)thieno[3,2-d]pyrimidin-6-yl)methyl)piperazin-1-yl)propanamide 106

A mixture of 2-((4-(4-morpholin-4-yl-2-(tributylstannanyl)thieno[3,2-d]pyrimidin-6-ylmethyl)piperazin-1-yl]isobutyramide (150 mg, 0.22 mmol), 1-benzenesulfonyl-4-bromo-1H-pyrrolo[3,2-c]pyridine (90 mg, 0.27 mmol), Pd(PPh$_3$)$_4$ (25 mg, 10 mol %) and CuI (50 mg, 0.25 mmol) in dioxane (2.5 mL) was purged with argon gas then heated at 140° C., for 20 min, in a microwave reactor. The reaction mixture was loaded onto an Isolute® SCX-2 cartridge, washed with MeOH/DCM then eluted with 2 M NH$_3$ in MeOH. The resulting residue was dissolved in IMS/dioxane (1:1 mL) and 12.5 M aqueous NaOH solution (0.1 mL) added. After stirring for 1 h the reaction mixture was loaded onto an Isolute® SCX-2 cartridge, washed with MeOH/DCM then eluted with 2 M NH$_3$ in MeOH/DCM. The resulting residue was purified by flash chromatography (Si—PPC, MeOH:DCM, gradient 0:100 to 05:95) to give 106 (28 mg, 24%) as a pale yellow solid. LCMS (Method F) R$_T$ 4.86 min; [M+H]$^+$ 521.3. $^1$H NMR (CDCl$_3$, 400 MHz): δ 9.11 (s, 1 H); 8.54 (d, J=5.6 Hz, 1 H); 7.45 (s, 1 H); 7.41 (dd, J=3.3, 0.9 Hz, 1 H); 7.38 (dd, J=5.6, 0.95 Hz, 1 H); 7.36 (d, J=3.3 Hz, 1 H); 7.10 (d, J=5.3 Hz, 1 H); 5.25 (d, J=5.2 Hz, 1 H); 4.10 (t, J=4.75 Hz, 4 H); 3.91 (t, J=4.7 Hz, 4 H); 3.85 (s, 2 H); 2.60 (s, 8 H); 1.25 (s, 6 H)

Example 107

1-((2-(isoquinolin-8-yl)-4-morpholinothieno[3,2-d]pyrimidin-6-yl)methyl)-N,N-dimethylpiperidin-4-amine 107

A microwave vessel was charged with dimethyl-[1-(4-morpholin-4-yl-2-tributylstannanyl-thieno[3,2-d]pyrimidin-6-methyl)-piperidin-4-yl]-amine (0.106 g, 0.163 mmol), 8-bromoisoquinoline (0.041 g, 0.196 mmol), copper(I)iodine (0.037 g, 0.196 mmol), palladium tetrakis(triphenylphosphine) (0.019 g, 0.016 mmol) and tetrahydrofuran (2 mL) The vessel was evacuated and back-filled with argon three times then sealed and heated at 140° C. under microwave irradiation for 20 min. The reaction mixture was cooled to room temperature and filtered through celite. The filtrates were concentrated then purified by chromatography (silica, 1 to 20% of a 49:1 MeOH:NH$_4$OH mixture in dichloromethane) to give a colorless residue. This residue was dissolved in dichloromethane (3 mL) then 1 N HCl in ether (0.2 mL) added dropwise. The resulting precipitate was collected by filtration to furnish 107 (0.028 g, 29%) as a pale yellow powder and as a tetrahydrochloride salt. MS m/e 489 [M+H]$^+$. $^1$H NMR (300 MHz, methanol-d$_4$) δ ppm 2.45 (br. s., 4 H) 2.94 (s, 6 H) 3.47 (br. s., 2 H) 3.64-4.09 (m, 7 H) 4.35 (br. s., 4 H) 4.98 (br. s., 2 H) 8.14 (br. s., 1 H) 8.45 (br. s., 1 H) 8.64 (d, J=7.9 Hz, 1 H) 8.70 (d, J=6.0 Hz, 1 H) 8.73-8.86 (m, 1 H) 10.37 (br. s., 1 H).

Example 108

2-(4-((2-(1-aminoisoquinolin-4-yl)-4-morpholinothieno[3,2-d]pyrimidin-6-yl)methyl)piperazin-1-yl)-2-methylpropanamide 108

Step 1: 4-bromoisoquinolin-1-amine

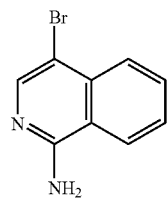

To a mixture of 4-bromoisoquinoline (1.102 g, 7.644 mmol), potassium bromide (0.9369 g, 7.873 mmol), and phosphomolybdic acid (70 mg) in acetic acid (23 mL) was added 30% of hydrogen peroxide in water (0.88 mL) over 5 min. The mixture formed a suspension and was stirred at room temperature for 2 h. Water (50 mL) was added. The suspension was extracted with EtOAc (2×100 mL) The combined EtOAc extracts were washed with water (2×50 mL), saturated NaHCO$_3$ (2×50 mL), and brine (20 mL), and dried (Na$_2$SO$_4$). The crude (1.322 g) was purified with flash chromatography to give the product as off-white powder (71 mg, 65%). LCMS: M+H$^+$=223.

Step 2: A mixture of 4-bromoisoquinolin-1-amine (126 mg, 0.565 mmol), bispinacol ester boronate (358 mg, 1.41 mmol), and potassium acetate (333 mg, 3.39 mmol) in 1,4-dioxane (4.6 mL) was sparged with N$_2$ for 10 min. [1,1'-bis(diphenylphosphino)ferrocene]dichloropalladium(II), complex with dichloromethane (1:1) (23.1 mg, 0.0282 mmol) was added. The mixture was sealed under N$_2$ and heated at 80° C. for 20 h, diluted with DCM, the contents were filtered, washed with DCM, and concentrated. The crude product was mixed with 2-(4-((2-chloro-4-morpholinothieno[3,2-d]pyrimidin-6-yl)methyl)piperazin-1-yl)-2-methylpropanamide (124 mg, 0.282 mmol), a 1 M solution of sodium carbonate (0.85 mL) and 1,4-dioxane (3.4 mL, 44 mmol). The mixture was sparged with N$_2$ for 10 min. Palladium acetate (6.342 mg, 0.02825 mmol) and a 1.0 M solution of tri-tert-butylphosphine in toluene (0.0565 mL) were added. The mixture was sealed under N$_2$ and heated at 85° C. for 6 h, diluted with DCM, the contents were filtered, and concentrated. The residue was purified with flash chromatography. The fractions containing the desired product were collected, concentrated, and purified with reverse-phase HPLC to give 108 (25 mg, 16%). LCMS: M+H$^+$=467. $^1$H NMR (400 MHz, CDCl$_3$) δ 8.91 (d, J=8.6, 1H), 8.67 (s, 1H), 7.85 (d, J=8.3, 1H), 7.71-7.64 (m, 1H), 7.53 (t, J=7.3, 1H), 7.34 (s, 1H), 7.10 (s, 1H), 5.29 (s, 2H), 5.20 (s, 1H), 4.10-3.99 (m, 4H), 3.87 (dd, J=9.1, 4.6, 6H), 2.61 (s, 8H), 1.24 (s, 6H)

Example 109

1-((2-(isoquinolin-5-yl)-4-morpholinothieno[3,2-d]pyrimidin-6-yl)methyl)-N,N-dimethylpiperidin-4-amine 109

A sealable tube was charged with [1-(2-chloro-4-morpholin-4-yl-thieno[3,2-d]pyrimidin-6-ylmethyl)-piperidin-4-yl]-dimethyl-amine (0.630 g, 1.59 mmol), isoquinoline-5-boronic acid (0.331 g, 1.91 mmol), dichlorobis(triphenylphosphine)palladium(II) (0.056 g, 0.08 mmol), 1 N aqueous sodium carbonate solution (2.5 mL) and acetonitrile (7.5 mL). The vessel was evacuated and back-filled with argon three times then sealed and heated at 130° C. for 90 min. The reaction mixture was cooled, concentrated, redissolved in methanol and filtered through celite. The filtrates were concentrated then purified by chromatography (C-18 reverse phase column, 5 to 95% acetonitrile in water containing 0.1% TFA). The fractions containing the desired product were concentrated then dissolved in MeOH/dichloromethane, basified with solid sodium carbonate then filtered and concentrated to furnish 109 (0.386 g, 50%) as a white foam. MS m/e 489 [M+H]; $^1$H NMR (300 MHz, MeOH-d$_4$) δ ppm 1.61-1.91 (m, 2 H) 1.99-2.15 (m, 2H) 2.17-2.36 (m, 2 H) 2.88 (s, 6 H) 3.04-3.28 (m, 3 H) 3.73-3.87 (m, 4 H) 3.91 (s, 2

H) 3.96-4.07 (m, 4 H) 7.33 (s, 1 H) 7.69-7.83 (m, 1 H) 8.18 (d, J=8.3 Hz, 1 H) 8.30 (d, J=7.2 Hz, 1 H) 8.43 (d, J=6.4 Hz, 1 H) 8.57 (d, J=6.0 Hz, 1 H) 9.28 (s, 1 H)

Example 110

1-((2-(1H-benzo[d]imidazol-1-yl)-4-morpholinothieno[3,2-d]pyrimidin-6-yl)methyl)-N,N-dimethylpiperidin-4-amine 110

A mixture of [1-(2-chloro-4-morpholin-4-yl-thieno[3,2-d]pyrimidin-6-ylmethyl)-piperidin-4-yl]dimethylamine (50 mg, 0.13 mmol), benzimidazole (32 mg, 0.27 mmol) and concentrated HCl (53 µL, 0.64 mmol) in 1,4-dioxane (1 mL) was subjected to microwave irradiation at 150° C. for 40 min. The reaction mixture was cooled to ambient temperature and loaded onto an Isolute® SCX-2 cartridge (2 g). The cartridge was then washed with MeOH and the desired product was subsequently eluted using 2 M $NH_3$ in MeOH. The eluent was collected and concentrated in vacuo. The resultant residue was purified by flash chromatography (Si—PPC, DCM:2 M $NH_3$ in MeOH 100:0 to 98:2 to 95:5 to 90:10) to afford 110 as a white solid (38 mg, 63%). LCMS (Method F): $R_T$=5.12 min, [M+H]$^+$ 478.2. $^1$H NMR (CDCl$_3$, 400 MHz): δ 9.04 (s, 1 H); 8.61-8.57 (m, 1 H); 7.86-7.82 (m, 1 H); 7.43-7.31 (m, 2 H); 7.27 (s, 1H); 4.07 (t, J=4.8 Hz, 4 H); 3.92 (t, J=4.8 Hz, 4 H); 3.82 (s, 2 H); 3.08-2.99 (m, 2 H); 2.30 (s, 6 H); 2.20-2.10 (m, 3 H); 1.88-1.78 (m, 2 H); 1.66-1.54 (m, 2 H)

Example 112

2-methyl-2-(4-((7-methyl-4-morpholino-2-(1H-pyrrolo[2,3-c]pyridin-4-yl)thieno[3,2-d]pyrimidin-6-yl)methyl)piperazin-1-yl)propanamide 112

A mixture of 2-[4-(7-methyl-4-morpholin-4-yl-2-(tributylstannanyl)thieno[3,2-c]pyrimidin-6-ylmethyl)piperazin-1-yl]isobutyramide (109 mg, 0.15 mmol), 4-bromo-1H-pyrrolo[2,3-c]pyridine (39 mg, 0.20 mmol), tetrakis(triphenylphosphine)palladium (18 mg, 10 mol %) and CuI (32 mg, 0.17 mmol) in toluene (2 mL) was purged with argon gas, then heated at 150° C. for 30 min in a microwave reactor. The reaction mixture was loaded onto an Isolute® SCX-2 cartridge, washed with MeOH then eluted with 2 M $NH_3$ in MeOH/DCM. The resulting residue was purified by column chromatography (Si—PPC, MeOH:DCM, gradient 0:100 to 05:95) followed by reverse phase HPLC (Phenomenex Gemini 5u C18, 20 mM triethylamine in water on a gradient of acetonitrile 80:20 to 2:98) to give 112 as an off-white solid (17 mg, 21%). LCMS (Method F): $R_T$ 4.93 min, [M+H]$^+$ 535.3. $^1$H NMR (MeOD plus CDCl$_3$, 400 MHz): δ 9.17 (s, 1 H); 8.75 (s, 1 H); 7.61 (d, J=3.0 Hz, 1 H); 7.56 (d, J=3.0 Hz, 1 H); 4.11 (t, J=4.7 Hz, 4 H); 3.94 (t, J=4.7 Hz, 4 H); 3.88 (s, 2 H); 2.74-2.56 (m, 8 H); 2.53 (s, 3 H); 1.24 (s, 6 H)

Example 114

4-(8-((4-tert-butylpiperidin-1-yl)methyl)-9-methyl-6-morpholino-9H-purin-2-yl)isoquinolin-1-amine 114

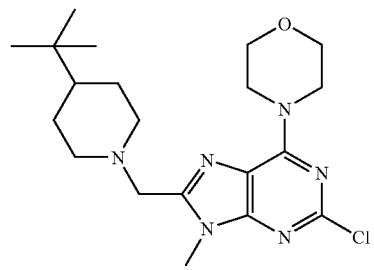

4-tert-butylpiperidine (0.45 g) was reacted with 4-(8-(bromomethyl)-2-chloro-9-methyl-9H-purin-6-yl)morpholine (1.0 g) via General Procedure C to yield 4-(8-((4-tert-butylpiperidin-1-yl)methyl)-2-chloro-9-methyl-9H-purin-6-yl)morpholine (0.80 g) as a white solid.

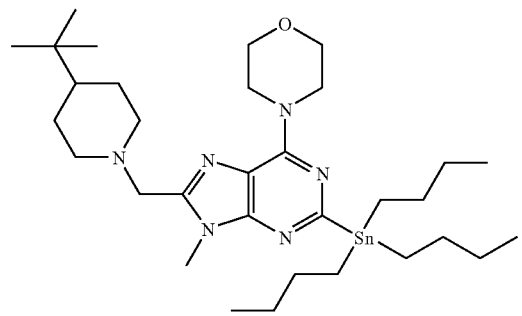

A mixture of 4-(8-((4-tert-butylpiperidin-1-yl)methyl)-2-chloro-9-methyl-9H-purin-6-yl)morpholine (697 mg), bis-tributyltin (1.71 mL) and PdCl$_2$[t-Bu$_2$P(Ph-p-Nme$_2$)$_2$] (190 mg, in 1,4-dioxane (8.5 mL) was heated in a CEM microwave at 140° C. for 40 minutes. The reaction mixture was then concentrated and the crude product was then purified by flash chromatography (0-30% hexanes/ethyl acetate over 15 minutes) to give intermediate 4-(8-((4-tert-butylpiperidin-1-yl)methyl)-9-methyl-2-(tributylstannyl)-9H-purin-6-yl)morpholine (627 mg).

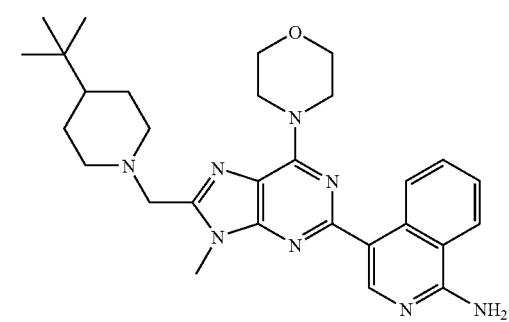

4-(8-((4-tert-butylpiperidin-1-yl)methyl)-9-methyl-2-(tributylstannyl)-9H-purin-6-yl)morpholine (0.1 g) was reacted with 4-bromoisoquinolin-1-amine via General Procedure D to afford 114 (10 mg) following reverse phase purification. MS (Q1) 515.3 (M)+. $^1$H NMR (500 MHz, CDCl$_3$) δ 9.02 (d, 1H), 7.94-7.45 (m, 6H), 4.35 (s, 4H), 4.02-3.61 (m, 9H), 2.97 (s, 2H), 2.13 (s, 2H), 1.92-1.52 (m, 5H), 1.52-0.68 (m, 26H)

Example 115

2-(1-((2-(1-aminoisoquinolin-4-yl)-9-methyl-6-morpholino-9H-purin-8-yl)methyl)piperidin-4-yl)propan-2-ol 115

2-(1-((9-Methyl-6-morpholino-2-(tributylstannyl)-9H-purin-8-yl)methyl)piperidin-4-yl)propan-2-ol (0.1 g) was reacted with 4-bromoisoquinolin-1-amine via General Procedure G to afford 115 following reverse phase purification. MS (Q1) 517.3 (M)+. $^1$H NMR (400 MHz, DMSO) δ 9.01 (d, 1H), 8.56 (s, 1H), 8.25 (d, 1H), 7.67 (t, 1H), 7.49 (t, 1H), 7.07 (s, 2H), 4.23 (s, 4H), 4.02 (s, 1H), 3.87-3.66 (m, 10H), 2.89 (d, 3H), 1.99 (t, 2H), 1.66 (d, 2H), 1.35-1.10 (m, 3H), 1.02 (s, 6H).

Example 116

1-((2-(1H-indazol-1-yl)-4-morpholinothieno[3,2-d]pyrimidin-6-yl)methyl)-N,N-dimethylpiperidin-4-amine 116

A solution of indazole (0.118 g) in DMF (8 mL) was cooled to 0° C. then sodium hydride (0.06 g) added. After 15 min, [1-(2-chloro-4-morpholin-4-yl-thieno[3,2-d]pyrimidin-6-ylmethyl)-piperidin-4-yl]-dimethyl-amine (0.395 g) was added and the reaction vessel sealed and heated at 150° C. After 1 h the reaction mixture was cooled to room temperature then diluted with water. The resulting precipitate was collected by filtration then purified by chromatography (silica, 0 to 20% of a 49:1 MeOH:NH$_4$OH mixture in dichloromethane) to furnish 116 (0.233 g, 49%) as a white solid after trituration with ethyl acetate. MS m/e 478 [M+H]$^-$; $^1$H NMR (300 MHz, DMSO-d$_6$) δ ppm 1.41 (dd, J=11.68, 3.39 Hz, 2 H) 1.73 (d, J=10.93 Hz, 2 H) 2.07 (t, J=10.74 Hz, 3 H) 2.17 (s, 6 H) 2.94 (d, J=11.68 Hz, 2 H) 3.75-3.90 (m, 6 H) 3.93-4.13 (m, 4 H) 7.31 (t, J=7.54 Hz, 1 H) 7.39 (s, 1 H) 7.56 (dd, J=7.91, 6.40 Hz, 1 H) 7.88 (d, J=7.91 Hz, 1 H) 8.39 (s, 1H) 8.68 (d, J=8.67 Hz, 1 H).

Example 117

N,N-dimethyl-1-((2-(2-methyl-1H-benzo[d]imidazol-1-yl)-4-morpholinothieno[3,2-d]pyrimidin-6-yl)methyl)piperidin-4-amine 117

A mixture of N-[6-(4-dimethylaminopiperidin-1-ylmethyl)-4-morpholin-4-yl-thieno[3,2-d]pyrimidin-2-yl]benzene-1,2-diamine (80 mg, 0.17 mmol) and triethyl orthoformate (1 mL, 6.0 mmol) in DMF (1 mL) was heated at 150° C. for 6 h. The reaction mixture was cooled to ambient temperature and loaded onto an Isolute® SCX-2 cartridge (10 g). The cartridge was then washed with MeOH and the desired product was subsequently eluted using 2 M NH$_3$ in MeOH. The eluent was collected and concentrated in vacuo. The resultant residue was purified by flash chromatography (Si—PPC, DCM:2 M NH$_3$ in MeOH 100:0 to 98:2 to 95:5) followed by reverse phase HPLC (Phenomenex Luna C$_{18}$, 20 mM Et$_3$N in water on a gradient of 20 mM Et$_3$N in acetonitrile 95:5 to 2:98) to afford 117 as a white solid (20 mg, 24%). LCMS (Method F): R$_T$=4.24 min, [M+H]$^+$ 492.3. $^1$H NMR (CDCl$_3$, 400 MHz): δ 8.09-8.04 (m, 1 H); 7.74-7.68 (m, 1 H); 7.29-7.24 (m, 3 H); 4.08-4.02 (m, 4 H); 3.91-3.86 (m, 4 H); 3.83 (s, 2 H); 3.08-3.00 (m, 2 H); 2.93 (s, 3 H); 2.30 (s, 6 H); 2.21-2.10 (m, 3 H); 1.88-1.79 (m, 2 H); 1.68-1.53 (m, 2 H)

Example 118

2-(1-((9-methyl-6-morpholino-2-(1H-pyrrolo[2,3-c]pyridin-4-yl)-9H-purin-8-yl)methyl)piperidin-4-yl)propan-2-ol 118

2-(1-((9-methyl-6-morpholino-2-(tributylstannyl)-9H-purin-8-yl)methyl)piperidin-4-yl)propan-2-ol (150 mg) was reacted with 4-bromo-6-azaindole via General Procedure G to afford 118 (31.8 mg) following reverse phase purification. MS (Q1) 491.2 (M)+. $^1$H NMR (400 MHz, DMSO) δ 11.70 (s, 1H), 9.14 (s, 1H), 8.79 (s, 1H), 7.70 (t, 1H), 7.43 (s, 1H), 4.30 (s, 4H), 4.02 (s, 1H), 3.89 (s, 3H), 3.83-3.76 (m, 4H), 3.73 (s, 2H), 2.92 (t, 2H), 1.97 (dd, 16.9, 2H), 1.69 (t, 2H), 1.40-1.09 (m, 3H), 1.02 (s, 6H)

Example 119

2-(1-((9-methyl-6-morpholino-2-(1H-pyrrolo[3,2-c]pyridin-4-yl)-9H-purin-8-yl)methyl)piperidin-4-yl)propan-2-ol 119

2-(1-((9-Methyl-6-morpholino-2-(tributylstannyl)-9H-purin-8-yl)methyl)piperidin-4-yl)propan-2-ol (150 mg) was reacted with 4-bromo-5-azaindole via General Procedure G to afford 119 (20 mg) following reverse phase purification. MS (Q1) 491.2 (M)+. $^1$H NMR (400 MHz, MeOD) δ 8.31 (d, 1H), 7.51 (d, 1H), 7.45 (d, 1H), 7.34 (d, 1H), 4.39 (s, 4H), 4.03-3.69 (m, 10H), 3.31 (d, 5H), 3.01 (d, 2H), 2.10 (t, 2H), 2.03 (s, 2H), 1.75 (d, 2H), 1.53-1.22 (m, 4H), 1.13 (s, 6H)

Example 120

4-(6-((4-methylpiperazin-1-yl)methyl)-2-(quinolin-5-yl)thieno[3,2-d]pyrimidin-4-yl)morpholine 120

Following General Procedure L for reductive amination, 4-morpholino-2-(quinolin-5-yl)thieno[3,2-d]pyrimidine-6-carbaldehyde and 1-methylpiperazine were reacted to give 120. LCMS m/z: 461.6 (MH+)

Example 121

2-(4-((2-(7-fluoro-1H-pyrrolo[3,2-c]pyridin-4-yl)-4-morpholinothieno[3,2-d]pyrimidin-6-yl)methyl)piperazin-1-yl)-2-methylpropanamide 121

Following the procedures for 142, 2-[4-(4-morpholin-4-yl-2-(tributylstannanyl)thieno[3,2-c]pyrimidin-6-ylmethyl)piperazin-1-yl]isobutyramide was converted to 121. LCMS m/z: 539.2 (MH+)

Example 123

4-((4-morpholino-2-(1H-pyrrolo[3,2-c]pyridin-4-yl)thieno[3,2-d]pyrimidin-6-yl)methyl)morpholine 123

Following General Procedure L for reductive amination, 4-morpholino-2-(1H-pyrrolo[3,2-c]pyridin-4-yl)thieno[3,2- d]pyrimidine-6-carbaldehyde and morpholine were reacted to give 123. LCMS: M+H ⁻=437.5

Example 124

4-(1-((9-methyl-6-morpholino-2-(1H-pyrrolo[2,3-c]pyridin-4-yl)-9H-purin-8-yl)methyl)piperidin-4-yl)morpholine 124

Step 1: 4-(1-((9-methyl-6-morpholino-2-(tributylstannyl)-9H-purin-8-yl)methyl)piperidin-4-yl)morpholine

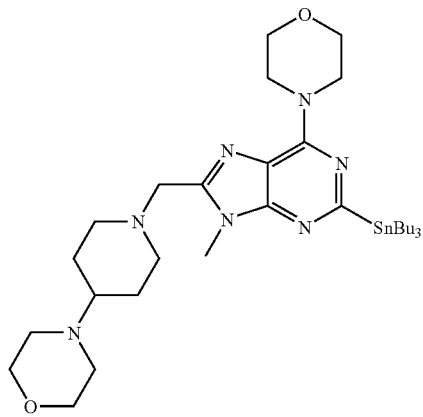

A mixture of 4-(1-((2-chloro-9-methyl-6-morpholino-9H-purin-8-yl)methyl)piperidin-4-yl)morpholine (593 mg, 1.36 mmol), bis(tributyltin) (1.36 mL, 2.72 mmol) and PdCl$_2$[t-Bu$_2$P(Ph-p-Nme$_2$)$_2$] (150 mg, 0.21 mmol) in 1,4-dioxane (5 mL) was heated in a microwave at 140° C. for 40 minutes. The reaction mixture was then concentrated. The crude product was then purified by flash chromatography (10% MeOH in DCM) to give the title compound (859 mg, 91.4%). LCMS: M+H $^+$=691.4.

Step 2: To a degassed mixture of 4-(1-((9-methyl-6-morpholino-2-(tributylstannyl)-9H-purin-8-yl)methyl)piperidin-4-yl)morpholine (859 mg, 1.24 mmol), 4-bromo-1-(phenylsulfonyl)-1H-pyrrolo[2,3-c]pyridine (385 mg, 1.14 mmol), copper(I)iodide (326 mg, 1.71 mmol) in 1,4-dioxane (10 mL) was added Pd(PPh$_3$)$_4$ (100 mg, 0.09 mmol). The reaction mixture was stirred at 110° C. for 18 hours. The reaction mixture was concentrated and then dissolved in DCM and filtered through a column of silica gel (20% MeOH in DCM). The elutant was concentrated to give a yellow paste which was taken up in ethanol (2 mL) and 1,4-dioxane (3 mL). A 12 M aqueous NaOH solution (0.5 mL) was then added and the resulting mixture was stirred at room temperature for 1 hour. The reaction mixture was then concentrated and the crude product was purified by flash chromatography using a Biotage KP-NH column (10% MeOH in DCM) followed by RP-HPLC to give 124. LCMS: M+H$^+$=518.3. $^1$H-NMR (400 MHz, DMSO-d$_6$): δ 11.70 (s, 1H), 9.14 (s, 1H), 8.79 (s, 1H), 7.70 (m, 1H), 7.43 (m, 1H), 4.30 (s, br, 4H), 3.88 (s, 3H), 3.78 (m, 4H), 3.70 (s, 2H), 3.54 (m, 4H), 2.86 (m, 2H), 2.43 (m, 4H), 2.09 (m, 2H), 1.75 (m, 2H), 1.36 (m, 3H).

Example 125

N,N-dimethyl-1-((4-morpholino-2-(1H-pyrrolo[3,2-c]pyridin-3-yl)thieno[3,2-d]pyrimidin-6-yl)methyl)piperidin-4-amine 125

A microwave vessel was charged with dimethyl-[1-(4-morpholin-4-yl-2-tributylstannanyl-thieno[3,2-d]pyrimidin-6-methyl)-piperidin-4-yl]-amine(0.4g) in dioxane (8 mL). The vessel was evacuated and back filled with argon. To this mixture was added 3-iodo-pyrrolo[3,2-c]pyridine-1-carboxylic acid tert-butyl ester (0.254 g), copper iodide (0.14 g) and tetrakistriphenylphosphine palladium (0.08 g). The vessel was evacuated and back filled with argon again, then the mixture was then irradiated with microwaves at 150° C. for 35 min. The reaction mixture was cooled to room temperature then filtered through HPLC filter. The filtrate was concentrated and the residue obtained was purified by chromatography (silica, 0 to 10% of a 49:1 MeOH:NH$_4$OH mixture in dichloromethane). The residue obtained was dissolved in anhydrous methanol (2 mL) and 4.0 N HCl in dioxane (6 mL) was added. The mixture was stirred at room temperature overnight. The precipitated solid was collected by filtration and the residue obtained was dried at 50° C. under vacuum overnight to furnish 125 (0.086g, 22%) as a white solid. MS m/e 478 [M+H]$^+$. $^1$H NMR (300 MHz, DMSO-d$_6$) δ ppm 2.19-2.34 (m, 4 H) 2.71 (s, 6 H) 3.06 (br. s., 2 H) 3.43 (br. s., 1 H) 3.50-3.47 (m, 2 H) 3.81-3.90 (m, 4 H) 4.01-4.11 (m, 4 H) 4.64 (s, 2 H) 7.93 (s, 1 H) 8.07 (d, J=6.78 Hz, 1 H) 8.50 (d, J=6.78 Hz, 1 H) 8.75 (s, 1 H) 9.76 (s, 1 H)

Example 126

2-methyl-2-(4-((7-methyl-4-morpholino-2-(1H-pyrrolo[3,2-c]pyridin-4-yl)thieno[3,2-d]pyrimidin-6-yl)methyl)piperazin-1-yl)propanamide 126

A degassed solution of 2-[4-(7-methyl-4-morpholin-4-yl-2-(tributylstannanyl)thieno[3,2-c]pyrimidin-6-ylmethyl)piperazin-1-yl]isobutyramide (100 mg, 0.14 mmol), 1-benzenesulfonyl-4-bromo-1H-pyrrolo[3,2-c]pyridine (60 mg, 0.18 mmol), Pd(PPh$_3$)$_4$ (16 mg, 0.014 mmol) and CuI (33 mg, 0.17 mmol) in 1,4-dioxane (1.5 mL) was subjected to microwave irradiation at 140° C. for 20 min. The reaction mixture was cooled to ambient temperature and loaded onto an Isolute® SCX-2 cartridge (10 g). The cartridge was then washed with MeOH and the desired product was subsequently eluted using 2 M NH$_3$ in MeOH. The eluent was collected and concentrated to give 2-{4-[2-(1-benzenesulfonyl-1H-pyrrolo[3,2-c]pyridin-4-yl)-7-methyl-4-morpholin-4-yl-thieno[3,2-d]pyrimidin-6-ylmethyl]-piperazin-1-yl}-isobutyramide as a crude oil. Aqueous NaOH (12.5 M, 0.2 mL) was added to a solution of this intermediate in 1,4-dioxane (2 mL) and IMS (2 mL). The reaction mixture was stirred at ambient temperature for 1 h, and then concentrated in vacuo. The residue was dissolved in MeOH then loaded onto an Isolute® SCX-2 cartridge (10 g). The cartridge was then washed with MeOH and the desired product was subsequently eluted using 2 M NH$_3$ in MeOH. The eluent was collected and concentrated to afford a crude solid. The solid was purified by flash chromatography (Si—PPC, DCM:2 M NH$_3$ in MeOH, 100:0 to 99:1 to 98:2 to 95:5 to 90:0) to afford 126 as a cream solid (36 mg, 48%). LCMS (Method F): R$_T$=5.04 min, [M+H]$^+$ 535.2. $^1$H NMR (CDCl$_3$, 400 MHz): δ 9.76 (s, 1 H); 8.46 (d, J=5.6 Hz, 1 H); 7.49 (dd, J=3.2, 1.0 Hz, 1 H); 7.34 (d, J=3.25 Hz, 1 H); 7.31 (dd, J=5.6, 1.0 Hz, 1 H); 7.12 (d, J=5.3 Hz, 1 H); 5.35 (d, J=5.25 Hz, 1 H); 4.08 (t, J=4.7 Hz, 4 H); 3.86 (t, J=4.7 Hz, 4 H); 3.82 (s, 2 H); 2.60 (s, 8 H); 2.58-2.45 (m, 3 H); 1.33-1.17 (m, 6 H)

Example 127

4-(6-((4-(1-amino-2-methyl-1-oxopropan-2-yl)piperazin-1-yl)methyl)-4-morpholinothieno[3,2-d]pyrimidin-2-yl)-1H-pyrrolo[2,3-c]pyridine 6-oxide 127

A mixture of 2-[4-(4-morpholin-4-yl-2-(tributylstannanyl)thieno[3,2-d]pyrimidin-6-ylmethyl)piperazin-1-yl]isobutyramide (170 mg, 0.25 mmol), 4-bromo-6-oxy-pyrrolo[2,3-c]pyridine-1-carboxylic acid tert-butyl ester (100 mg, 0.32 mmol), tetrakis(triphenylphosphine)palladium (28 mg, 10 mol %) and CuI (55 mg, 0.28 mmol) in dioxane (2.5 mL) was purged with argon gas then heated at 140° C., for 20 min, in a microwave reactor. The reaction mixture was loaded onto an Isolute® SCX-2 cartridge, washed with MeOH/DCM then eluted with 2 M NH$_3$ in MeOH/DCM. The resulting residue was dissolved in DCM (3 mL) and trifluoroacetic acid (0.4 mL) added. After stirring for 3 h the reaction mixture was loaded onto an Isolute® SCX-2 cartridge, washed with MeOH/DCM then eluted with 2 M NH$_3$ in MeOH/DCM. The resulting residue was purified by column chromatography (Si—PPC, MeOH:DCM, gradient 0:100 to 15:85) to give 127 (30 mg, 17%) as a pale yellow solid. LCMS (Method F): R$_T$ 4.95 min, [M+H]$^+$ 537.9. $^1$H NMR (CDCl$_3$, 400 MHz): δ 12.52 (s, 1 H); 9.07 (s, 1 H); 8.79 (s, 1 H); 7.65 (d, J=2.8 Hz, 1 H); 7.56 (d, J=2.8 Hz, 1 H); 7.34 (s, 1 H); 7.09 (d, J=5.3 Hz, 1 H); 5.38 (d, J=5.3 Hz, 1 H); 4.05 (t, J=4.6 Hz, 4 H); 3.89 (t, J=4.7 Hz, 4 H); 3.84 (s, 2 H); 2.60 (s, 8 H); 1.24 (m, 6 H)

Example 128

2-(4-((2-(benzofuran-3-yl)-4-morpholinothieno[3,2-d]pyrimidin-6-yl)methyl)piperazin-1-yl)-2-methylpropanamide 128

Following the procedures for 140, 2-(benzofuran-3-yl)-4,4,5,5-tetramethyl-1,3,2-dioxaborolane was converted to 128. LCMS: M+H$^+$=521.2. $^1$H-NMR (400 MHz, DMSO-d$_6$): δ 8.73 (s, 1H), 8.52 (m, 1H), 7.66 (m, 1H), 7.39 (m, 3H), 7.05 (s, 1H), 6.93 (s, 1H), 3.99 (m, 4H), 3.86 (s, 2H), 2.83 (m, 4H), 2.39-2.61 (m, 8H), 1.08 (s, 6H)

Example 129

2-(1-((2-(3-amino-1H-indazol-1-yl)-9-methyl-6-morpholino-9H-purin-8-yl)methyl)piperidin-4-yl)propan-2-ol 129

Sodium hydride (1.5 eq) was added to 3-iodoindazole (0.5 g) in DMF (5 mL) and the reaction was stirred for 30 minutes at 0° C. 2-(1-((2-Chloro-9-methyl-6-morpholino-9H-purin-8-yl)methyl)piperidin-4-yl)propan-2-ol was subsequently added to the reaction mixture and heated in a Biotage microwave for 10 minutes at 180° C. The reaction was purified by flash column chromatography to afford 2-(1-((2-(3-iodo-1H-indazol-1-yl)-9-methyl-6-morpholino-9H-purin-8-yl)methyl)piperidin-4-yl)propan-2-ol (0.4 g) as a brown solid.

To a solution of 2-(1-((2-(3-iodo-1H-indazol-1-yl)-9-methyl-6-morpholino-9H-purin-8-yl)methyl)piperidin-4-yl)propan-2-ol (0.1 g), tris(dibenzylideneacetone)dipalladium (0) (3 mg), 4,5-bis(diphenylphosphino)-9,9-dimethylxanthene (5.6 mg) and cesium carbonate (74 mg) in 1,4-dioxane (0.5 mL) was added benzophenone imine (40 µL). The reaction was heated at 120° C. until complete, about 90 minutes. The crude reaction mixture was loaded onto silica and purified by flash column chromatography to afford 2-(1-((2-(3-(diphenylmethyleneamino)-1H-indazol-1-yl)-9-methyl-6-morpholino-9H-purin-8-yl)methyl)piperidin-4-yl)propan-2-ol.

2-(1-((2-(3-(Diphenylmethyleneamino)-1H-indazol-1-yl)-9-methyl-6-morpholino-9H-purin-8-yl)methyl)piperidin-4-yl)propan-2-ol and hydroxylamine hydrochloride (12.4 mg) in MeOH (2 mL) were stirred overnight at room temperature. The crude was purified by reverse phase HPLC to give 129 as a white solid (32.6 mg). MS (Q1) 506.3 (M)+. $^1$H NMR (400 MHz, DMSO) δ 8.56 (d, 1H), 7.83 (d, 1H), 7.47 (t, 1H), 7.17 (t, 1H), 6.05 (s, 2H), 4.26 (s, 5H), 4.02 (s, 1H), 3.79 (s, 7H), 3.68 (s, 4H), 2.86 (t, 2H), 1.97 (t, J=2H), 1.66 (d, 2H), 1.33-1.11 (m, 4H), 1.02 (s, 6H).

Example 130

2-(1-((2-(1-aminoisoquinolin-4-yl)-4-morpholinothieno[3,2-d]pyrimidin-6-yl)methyl)piperidin-4-yl)propan-2-ol 130

Following the procedures for 108, 2-(1-((2-chloro-4-morpholinothieno[3,2-d]pyrimidin-6-yl)methyl)piperidin-4-yl)propan-2-ol and 4-bromoisoquinolin-1-amine were converted to 130. LCMS: M+H$^+$=519. $^1$H NMR (400 MHz, DMSO) δ 8.99 (d, J=8.5, 1H), 8.58 (s, 1H), 8.26 (d, J=8.5, 1H), 8.17 (s, 2H), 7.68 (t, J=7.6, 1H), 7.50 (t, J=7.5, 1H), 7.37 (s, 1H), 7.12 (s, 1H), 4.00-3.89 (m, 4H), 3.86-3.75 (m, 6H), 2.99 (d, J=11.0, 2H), 1.97 (t, J=11.2, 2H), 1.65 (t, J=15.4, 2H), 1.37-1.11 (m, 3H), 1.04 (s, 6H)

Example 131

2-methyl-2-(4-((7-morpholino-5-(1H-pyrrolo[2,3-c]pyridin-4-yl)thiazolo[5,4-d]pyrimidin-2-yl)methyl)piperazin-1-yl)propanamide 131

A mixture of 2-[4-(7-morpholin-4-yl-5-(tributylstannanyl)thiazolo[5,4-d]pyrimidin-2-ylmethyl)piperazin-1-yl]isobutyramide (167 mg, 0.24 mmol), 4-bromo-1H-pyrrolo[2,3-c]pyridine (62 mg, 0.31 mmol), tetrakis(triphenylphosphine)palladium (28 mg, 10 mol %) and CuI (55 mg, 0.28 mmol) in dioxane (2.5 mL) was purged with argon gas then heated at 140° C., for 20 min, in a microwave reactor. The reaction mixture was loaded onto an Isolute® SCX-2 cartridge, washed with MeOH/DCM then eluted with 2 M NH$_3$ in MeOH/DCM. The resulting residue was purified by column chromatography (Si—PPC, MeOH:DCM, gradient 0:100 to 15:85) to give 131 as an pale yellow solid (12 mg, 10%). LCMS (Method F): R$_T$ 4.70 min, [M+H]$^+$ 522.2. $^1$H NMR (DMSO, 400 MHz): δ 11.94 (s, 1H); 9.10 (s, 1 H); 8.88 (s, 1 H); 7.82 (s, 1 H); 7.35 (s, 1 H); 7.15 (s, 1 H); 7.04 (s, 1 H); 4.37 (s, 4 H); 3.95 (s, 2 H); 3.82 (t, J=4.6 Hz, 4 H); 2.68 (s, 4 H); 2.56 (s, 4 H); 1.13 (s, 6H)

Example 132

2-methyl-2-(4-((2-(7-methyl-1H-pyrrolo[2,3-c]pyridin-4-yl)-4-morpholinothieno[3,2-d]pyrimidin-6-yl)methyl)piperazin-1-yl)propanamide 132

A mixture of 2-[4-(4-morpholin-4-yl-2-(tributylstannanyl)thieno[3,2-d]pyrimidin-6-ylmethyl)-piperazin-1-yl]isobutyramide (197 mg, 0.28 mmol), 4-bromo-7-methyl-1H-pyrrolo[2,3-c]pyridine (60 mg, 0.28 mmol), copper(I)

2-thiophene carboxylate (11 mg, 0.056 mmol), and Pd(PPh$_3$)$_4$ (32 mg, 0.028 mmol) in dioxane (3 mL) was placed in a microwave tube which was sealed and evacuated. The reaction vessel was degassed and purged with argon (×3). The reaction mixture was irradiated at 140° C. for 20 min. The cooled mixture was then poured onto an Isolute® SCX-II cartridge and the cartridge was washed with MeOH (100 mL). The product was eluted with 2 M NH$_3$ in MeOH. The pooled fractions were evaporated and the product was further purified by chromatography on silica (Si—PPC), using MeOH in DCM (0-10%) as eluent. The pooled product-containing fractions were evaporated and the residue was crystallized from hot EtOAc to afford 132 as a white crystalline solid (70 mg, 46%). LCMS: (Method F): R$_T$ 5.02 min; [M+H]$^+$ 535.2. $^1$H NMR (DMSO, 400 MHz): δ 11.71 (s, 1 H); 9.02 (s, 1 H); 7.66 (t, J=2.7 Hz, 1 H); 7.44 (s, 1H); 7.38 (dd, J=2.9, 1.9 Hz, 1 H); 7.08 (d, J=3.5 Hz, 1 H); 6.95 (d, J=3.5 Hz, 1 H); 3.99 (t, J=4.6 Hz, 4 H); 3.86 (s, 2 H); 3.85-3.80 (m, 4 H); 2.73 (s, 3 H); 2.62-2.53 (m, 4 H); 2.47 (s, 4H); 1.08 (s, 6 H)

Example 133

4-(1-((9-methyl-6-morpholino-2-(1H-pyrrolo[3,2-c] pyridin-4-yl)-9H-purin-8-yl)methyl)piperidin-4-yl) morpholine 133

Following the procedures to prepare 124, 4-(1-((9-Methyl-6-morpholino-2-(tributylstannyl)-9H-purin-8-yl)methyl)piperidin-4-yl)morpholine and 4-bromo-1H-pyrrolo[3,2-c]pyridine were reacted to give 133. LCMS: M+H$^+$=518.3. $^1$H-NMR (400 MHz, DMSO-d$_6$): δ 11.55 (s, 1H), 8.30 (d, 1H), 7.51 (d, 1H), 7.48 (d, 1H), 7.20 (d, 1H), 4.30 (m, 4H), 3.80 (s, 3H), 3.78 (m, 6H), 3.55 (m, 4H), 2.88 (m, 2H), 2.44 (m, 4H), 2.09 (m, 2H), 1.77 (m, 2H), 1.40 (m, 3H)

Example 134

1-((2-(1H-indazol-3-yl)-4-morpholinothieno[3,2-d] pyrimidin-6-yl)methyl)-N,N-dimethylpiperidin-4-amine 134

A microwave vessel was charged with dimethyl-[1-(4-morpholin-4-yl-2-tributylstannanyl-thieno[3,2-d]pyrimidin-6-methyl)-piperidin-4-yl]-amine (0.400g, 0.615 mmol), 1-boc-3-bromo-1H-indazole (0.219 g, 0.737 mmol), tetrakis (triphenylpho'sphine)palladium (0.071 g, 0.061 mmol), copper iodide (0.140 g, 0.735 mmol), and THF (8 mL). The vessel was sealed, evacuated, and back filled with argon. Then the mixture was heated at 140° C. under microwave irradiation for 20 min. The reaction mixture was cooled to room temperature, ethyl acetate (30 mL) was added, and the mixture was filtered through celite. The filtrate was concentrated then purified by chromatography (silica, 0 to 20% of a 9:1 MeOH:NH$_4$OH mixture in dichloromethane) to yield a crude solid. This solid was dissolved in dichloromethane (10 mL) and methanol (0.5 mL) Then HCl (0.80 mL, 1 N in ether) was added dropwise. After stirring for 1 hr at room temperature, the mixture was concentrated then purified by chromatography (C18, 0 to 90% of a 0.1% aqueous TFA mixture in methanol). The fractions containing the title compound were combined and the volatile solvents were removed under reduced pressure. The remaining aqueous mixture was diluted with aqueous bicarbonate and extracted with ethyl acetate. The organic layer was dried on sodium sulfate, collected by filtration, and concentrated to give 134 (0.012 g, 9%) as a white solid. MS m/e 477 [M+H]$^+$. $^1$H NMR (300 MHz, DMSO-d$_6$) δ ppm 1.45 (dd, J=12, 23 Hz, 2 H), 1.77 (d, J=12 Hz, 2 H), 2.04-2.11 (m, 3H), 2.25 (s, 6H), 2.96 (d, J=12 Hz, 2 H), 3.81-3.85 (m, 6 H), 3.99-4.02 (m, 4 H), 7.24 (t, J=9 Hz, 1 H), 7.40 (t, J=9 Hz, 1 H), 7.42 (s, 1 H), 7.62 (d, J=9 Hz, 1 H), 8.54 (d, J=9 Hz, 1 H), 13.37 (s, 1 H)

Example 135

2-(4-((2-(isoquinolin-8-yl)-4-morpholinothieno[3,2-d]pyrimidin-6-yl)methyl)piperazin-1-yl)-2-methylpropanamide 135

A microwave vessel was charged with 2-[4-(4-morpholin-4-yl-2-tributylstannanyl-thieno[3,2-d]pyrimidin-6-ylmethyl)-piperazin-1-yl]-isobutyramide (0.200 g, 0.288 mmol), 5-bromoisoquinoline (0.072 g, 0.346 mmol), copper(I)iodine (0.066 g, 0.346 mmol), palladium tetrakis(triphenylphosphine) (0.033 g, 0.029 mmol) and dioxane (4 mL) The vessel was evacuated and back-filled with argon three times then sealed and heated at 140° C. under microwave irradiation for 20 min. The reaction mixture was cooled to room temperature and filtered through celite. The filtrates were concentrated then purified by chromatography (silica, 0 to 15% of a 9:1 MeOH:NH$_4$OH mixture in dichloromethane) to give a yellow residue. This residue was dissolved in dichloromethane then 1 N HCl in ether (0.2 mL) added dropwise. The resulting precipitate was collected by filtration to furnish 135 (0.012 g, 6%) as a pale yellow powder and as a tetrahydrochloride salt. MS m/e 532 [M+H]$^-$; $^1$H NMR (300 MHz, 360 K, DMSO-d$_6$) δ ppm 1.49 (s, 6 H) 2.96-3.33 (m, 8 H) 3.79-3.91 (m, 4 H) 3.97-4.09 (m, 4 H) 4.22 (br. s., 2 H) 6.00 (br. s., 2 H) 7.65 (s, 1 H) 8.06-8.18 (m, 1 H) 8.23-8.35 (m, 2 H) 8.54 (d, J=7.5 Hz, 1 H) 8.68 (br. s., 1 H) 10.57 (br. s., 1 H)

Example 136

N,N-dimethyl-1-((4-morpholino-2-(1H-pyrrolo[2,3-b]pyridin-3-yl)thieno[3,2-d]pyrimidin-6-yl)methyl) piperidin-4-amine 136

A microwave vessel was charged with dimethyl-[1-(4-morpholin-4-yl-2-tributylstannanyl-thieno[3,2-d]pyrimidin-6-methyl)-piperidin-4-yl]-amine (0.2 g) in dioxane (8 mL). The vessel was evacuated and back filled with argon. To this mixture was added 3-bromo-pyrrolo[2,3-b]pyridine-1-carboxylic acid tert-butyl ester (0.18 g), copper iodide (0.07 g) and tetrakistriphenylphosphine palladium (0.04 g). The vessel was evacuated and back filled with argon again, then the mixture was then irradiated with microwaves at 150° C. for 30 min. The reaction mixture was cooled to room temperature then filtered through HPLC filter. The filtrate was concentrated and the residue obtained was purified by chromatography (silica, 0 to 10% of a 49:1 MeOH:NH$_4$OH mixture in dichloromethane) to furnish 136 (0.026 g, 17%) as a light brown solid. MS m/e 478 [M+H]$^+$. $^1$H NMR (400 MHz, DMSO-d$_6$) δ ppm 1.41 (d, J=9.09 Hz, 2 H) 1.74 (d, J=11.12 Hz, 2 H) 2.06 (t, J=10.61 Hz, 3 H) 2.18 (s, 6H) 2.94 (d, J=11.12 Hz, 2 H) 3.75-3.88 (m, 6 H) 3.91-4.05 (m, 4 H) 7.21 (dd, J=8.08, 4.55 Hz, 1 H) 7.33 (s, 1 H) 8.12-8.35 (m, 2 H) 8.83 (dd, J=7.83, 1.77 Hz, 1 H) 12.09 (br. s., 1 H)

Example 137

2-(1-((2-(1-(ethylamino)isoquinolin-4-yl)-4-morpholinothieno[3,2-d]pyrimidin-6-yl)methyl)piperidin-4-yl)propan-2-ol 137

Step 1: 4-bromo-N-ethylisoquinolin-1-amine

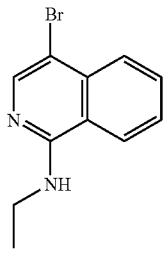

To a suspension of 4-bromo-1 chloroisoquinoline (0.831 g, 3.43 mmol) in MeOH (10.3 mL, 254 mmol) was added ethylamine (70% in water, 1.1 mL). The mixture was heated at 50° C. for 16 h. The mixture was concentrated. The residue was partitioned between water (20 mL) and DCM (20 mL). DCM layer was separated. The aqueous layer was extracted with DCM (10 mL) The combined DCM solutions were dried ($Na_2SO_4$). Filtration and concentration gave 4-bromo-N-ethylisoquinolin-1-amine (0.761 g, 88%). LCMS: M+H$^+$=251.

Step 2: Following the procedures for 108, 2-(1-((2-chloro-4-morpholinothieno[3,2-d]pyrimidin-6-yl)methyl)piperidin-4-yl)propan-2-ol and 4-bromo-N-ethylisoquinolin-1-amine were converted to 137. LCMS: M+H+=547. 1H NMR (400 MHz, DMSO) δ 9.03 (d, J=8.5, 1H), 8.67 (s, 1H), 8.28 (d, J=8.3, 1H), 7.68 (dd, J=16.9, 6.5, 2H), 7.51 (t, J=7.5, 1H), 7.37 (s, 1H), 4.04 (s, 1H), 3.93 (d, J=4.8, 4H), 3.80 (d, J=6.3, 6H), 3.65-3.54 (m, 2H), 2.99 (d, J=10.9, 2H), 2.07 (s, 1H), 1.97 (t, J=11.5, 2H), 1.67 (d, J=10.9, 2H), 1.36-1.12 (m, 6H), 1.04 (s, 6H)

Example 138

2-(1-((2-(benzofuran-3-yl)-9-methyl-6-morpholino-9H-purin-8-yl)methyl)piperidin-4-yl)propan-2-ol 138

Following the procedures for 140, 2-(1-((2-chloro-9-methyl-6-morpholino-9H-purin-8-yl)methyl)piperidin-4-yl)propan-2-ol and 2-(benzofuran-3-yl)-4,4,5,5-tetramethyl-1,3,2-dioxaborolane was converted to 138. LCMS: M+H$^+$=491.2. $^1$H-NMR (400 MHz, DMSO-d$_6$): δ 8.75 (s, 1H), 8.58 (m, 1H), 7.66 (m, 1H), 7.40 (m, 2H), 4.66 (s, 2H), 4.31 (m, 4H), 3.90 (s, 3H), 3.80 (m, 4H), 3.68 (s, br, 1H), 3.12 (m, 2H), 2.90 (m, 2H), 1.90 (m, 2H), 1.56 (m, 3H), 1.06 (s, 6H)

Example 139

4-(9-methyl-6-morpholino-8-((4-morpholinopiperidin-1-yl)methyl)-9H-purin-2-yl)isoquinolin-1-amine 139

To a degassed suspension of 4-(1-((2-chloro-9-methyl-6-morpholino-9H-purin-8-yl)methyl)piperidin-4-yl)morpholine (84 mg, 0.19 mmol), 4-(4,4,5,5-tetramethyl-1,3,2-dioxaborolan-2-yl)isoquinolin-1-amine (52 mg, 0.19 mmol), 2 M $Na_2CO_3$ aqueous solution (0.19 mL, 0.38 mmol) in toluene (3 mL) and ethanol (1 mL) was added Pd(PPh$_3$)$_4$ (11 mg, 0.010 mmol). The suspension was then stirred under nitrogen at 100° C. for 18 hours. The reaction mixture was then diluted with EtOAc and water. The aqueous layer was extracted three times with EtOAc. The combined organic extracts were washed with water, dried over $Na_2SO_4$, filtered and concentrated. The crude product was purified by flash chromatography (25% MeOH in DCM) to give 139 as a white solid (14.3 mg, 14%). LCMS: M+H$^+$=544.3. $^1$H-NMR (400 MHz, DMSO-d$_6$): δ 9.01 (d, 1H), 8.25 (d, 1H), 8.16 (s, 1H), 7.67 (t, 1H), 7.49 (t, 1H), 7.08 (s, 2H), 4.23 (s, br, 4H), 3.82 (s, 3H), 3.78 (m, 6H), 3.55 (m, 4H), 2.88 (m, 2H), 2.43 (m, 4H), 2.07 (m, 3H), 1.75 (m, 2H), 1.38 (m, 2H)

Example 140

2-methyl-2-(4-((2-(2-methylbenzofuran-3-yl)-4-morpholinothieno[3,2-d]pyrimidin-6-yl)methyl)piperazin-1-yl)propanamide 140

To a degassed suspension of 2-(4-((2-chloro-4-morpholinothieno[3,2-d]pyrimidin-6-yl)methyl)piperazin-1-yl)-2-methylpropanamide (90.0 mg 0.205 mmol), 4,4,5,5-tetramethyl-2-(2-methylbenzofuran-3-yl)-1,3,2-dioxaborolane (120 mg, 0.46 mmol) in acetonitrile (2 mL) was added 2 M aqueous solution of sodium carbonate (0.20 mL) and 1M aqueous solution of potassium acetate (0.2 mL). The mixture was then heated in a microwave at 140° C. for 30 minutes. The reaction mixture was diluted with water and EtOAc. The aqueous layer was extracted with EtOAc. The combined extracts were washed with brine, dried over $Na_2SO_4$, filtered and concentrated. The crude product was purified by RP-HPLC to give 140 (33.6 mg, 30.6%). LCMS: M+H$^+$=535.2. $^1$H-NMR (400 MHz, DMSO-d$_6$): δ 8.45 (m, 1H), 7.55 (m, 1H), 7.42 (s, 1H), 7.31 (m, 2H), 7.05 (s, 1H), 6.93 (s, 1H), 3.95 (m, 4H), 3.86 (s, 2H), 3.83 (m, 4H), 2.84 (s, 3H), 2.42-2.63 (m, 8H), 1.08 (s, 6H)

Example 141

2-(2-(1-aminoisoquinolin-4-yl)-4-morpholinothieno[3,2-d]pyrimidin-6-yl)propan-2-ol 141

To a solution of 2-(2-chloro-4-morpholinothieno[3,2-d]pyrimidin-6-yl)propan-2-ol (63 mg, 0.20 mmol) in acetonitrile (3.6 ml) in a microwave reaction vessel was added 4-(4,4,5,5-tetramethyl-1,3,2-dioxaborolan-2-yl)isoquinolin-1-amine (110 mg, 0.40 mmol), Bis(triphenylphosphine) palladium(II) chloride (7.02 mg, 0.010 mmol) and 1M sodium carbonate in water (0.60 ml). The reaction vessel was sealed and heated in the microwave at 140° C. for 20 minutes. LC-MS of the reaction mixture showed no more starting material. The solvent was evaporated and the resulting oil was purified on silica gel (0 to 20% of 2N NH$_3$ in MeOH/DCM). The resulting oil was further purified by reversed phase HPLC to give 141 as an off-white solid (4.7 mg, 6%) $^1$H NMR (DMSO d$_6$, 400 MHz) 9.02 (d, 1H, J=8.4 Hz), 8.26 (s, 1H), 8.26 (d, 1H, J=8.4 Hz), 7.67 (t, 1H, J=7.6 Hz), 7.50 (t, 1H, J=7.6)m 7.33 (s, 1H), 7.11 (s, 2H), 5.84 (s, 1H), 3.98-3.94 (m, 4H), 3.81-3.78 (m, 4H), 1.61 (m, 6H). LCMS m/z: 422 (MH$^+$)

Example 142

2-methyl-2-(4-((2-(2-methyl-1H-pyrrolo[2,3-c]pyridin-4-yl)-4-morpholinothieno[3,2-d]pyrimidin-6-yl)methyl)piperazin-1-yl)propanamide 142

Step 1: 2-{4-[2-(1-Benzenesulfonyl-2-methyl-1H-pyrrolo[2,3-c]pyridin-4-yl)-4-morpholin-4-yl-thieno[3,2-c]pyrimidin-6-ylmethyl]piperazine-1-yl}isobutyramide

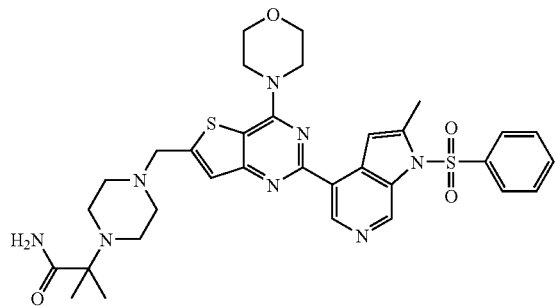

A 5 mL microwave vial was charged with a suspension of 2-[4-(4-morpholin-4-yl-2-(tributylstannanyl)thieno[3,2-c]pyrimidin-6-ylmethyl)piperazin-1-yl]isobutyramide (0.22 g, 0.31 mmol), 1-benzenesulfonyl-4-bromo-2-methyl-1H-pyrrolo[2,3-c]pyridine (0.13 g, 0.37 mmol), copper(I) 2-thiophene carboxylate (0.012 g, 0.062 mmol) and Pd(PPh$_3$)$_4$ (0.036 g, 0.031 mmol) in dioxane (3 mL) The reaction mixture was heated in a microwave for 20 min at 140° C. The crude reaction mixture was loaded onto a SCX-2 cartridge treated with MeOH. The cartridge was washed with MeOH (100 mL), then the product was recovered eluting with 2N ammonia in MeOH. The eluent was concentrated in vacuo, and the resultant residue was purified by flash chromatography (Si—PPC, 0% to 10% MeOH in DCM) to give the product as white foam (0.17 g, 82%). LCMS (Method C): R$_T$=3.36 min, [M+H]$^+$ 675.1

Step 2: 2-{4-[2-(2-Methyl-1H-pyrrolo[2,3-c]pyridin-4-yl)-4-morpholin-4-yl-thieno[3,2-c]pyrimidin-6-ylmethyl]piperazin-1-yl}isobutyramide

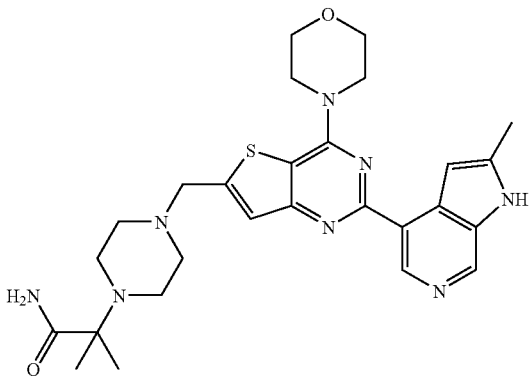

A 25 mL round-bottomed flask, under nitrogen, fitted with a condenser/inert gas bubbler (via a Claisen head), was charged with a solution of 2-{4-[2-(1-benzenesulfonyl-2-methyl-1H-pyrrolo[2,3-c]pyridin-4-yl)-4-morpholin-4-yl-thieno[3,2-c]pyrimidin-6-ylmethyl]piperazine-1-yl}isobutyramide (0.17 g, 0.25 mmol) in dioxane (4 mL), IMS (4 mL) and NaOH 12.5M (0.4 mL) The resulting mixture was stirred at room temperature for 2.5 h. The solution was concentrated in vacuo, the residue diluted with MeOH and loaded onto a Isolute® SCX-2 cartridge treated with MeOH. The cartridge was washed with MeOH (100 mL) and the product was recovered eluting with 2N NH$_3$ in MeOH, the eluent concentrated, suspended in dioxane/water and freeze-dried overnight. The resultant solid was dissolved in DMSO and purified by preparative HPLC (C18 column) gradient: (acetonitrile/20 mM triethylamine) 10% to 98% in (water/20 mM triethylamine) over 20 min (flow rate 18 ml/min). The product was freeze-dried overnight yielding 142 as a white powder (0.047 g, 35%). LCMS (Method E): R$_T$=5.27 min, [M+H]$^+$ 535.2. $^1$H NMR (DMSO, 400 MHz): δ 11.43 (s, 1 H); 8.22 (d, J=5.4 Hz, 1 H); 7.43 (s, 1 H); 7.33 (dd, J=6.3, 0.9 Hz, 1 H); 7.07 (d, J=3.5 Hz, 1 H); 6.95 (d, J=3.45 Hz, 1 H); 6.87 (s, 1 H); 3.98 (t, J=4.6 Hz, 4 H); 3.87 (s, 2 H); 3.81 (t, J=4.6 Hz, 4 H); 3.57 (s, 3 H); 2.61-2.53 (m, 2 H); 2.49-2.45 (m, 2H); 2.44 (s, 4H); 1.08 (s, 6 H)

Example 143

2-methyl-2-(4-((2-(2-methyl-1H-pyrrolo[3,2-c]pyridin-4-yl)-4-morpholinothieno[3,2-d]pyrimidin-6-yl)methyl)piperazin-1-yl)propanamide 143

Step 1: 2-{4-[2-(1-Benzenesulfonyl-2-methyl-1H-pyrrolo[3,2-c]pyridin-4-yl)-4-morpholin-4-yl-thieno[3,2-d]pyrimidin-6-ylmethyl]piperazine-1-yl}isobutyramide

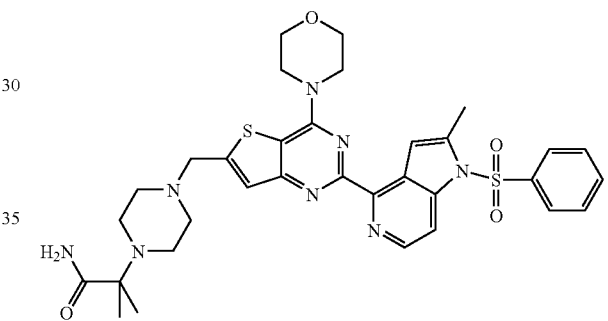

A 20 mL microwave vial was charged with a suspension of 2-[4-(4-morpholin-4-yl-2-(tributylstannanyl)thieno[3,2-c]pyrimidin-6-ylmethyl)piperazin-1-yl]isobutyramide (0.38 g, 0.54 mmol), 1-benzenesulfonyl-4-bromo-2-methyl-1H-pyrrolo[3,2-c]pyridine (0.21 g, 0.60 mmol), copper(I) 2-thiophene carboxylate (0.042 g, 0.22 mmol) and Pd(PPh$_3$)$_4$ (0.126 g, 0.108 mmol) in dioxane (8 mL) and NMP (2 mL). The reaction mixture was heated in a microwave for 100 min at 140° C. The crude reaction mixture was loaded onto a Isolute® SCX-2 cartridge treated with MeOH. The cartridge was washed with MeOH (100 mL), then the product was recovered eluting with 2N NH$_3$ in MeOH. The eluent was concentrated in vacuo and the resultant residue was purified by flash chromatography (Si—PPC, 0-10% MeOH in DCM) to give the product as yellow foam (0.24 g, 65%). LCMS (Method A): R$_T$=3.53min, [M+H]$^+$ 675.2

Step 2: A 25 mL round-bottomed flask, under nitrogen, fitted with a condenser and inert gas bubbler (via a Claisen head), was charged with a solution of 1-2-{4-[2-(1-benzenesulfonyl-2-methyl-1H-pyrrolo[3,2-c]pyridin-4-yl)-4-morpholin-4-yl-thieno[3,2-d]pyrimidin-6-ylmethyl]piperazine-1-yl}isobutyramide (0.24 g, 0.35 mmol) in dioxane (5 mL), IMS (5 mL) and NaOH 12.5M (0.5 mL) The resulting mixture was stirred at room temperature for 2 h and was then concentrated in vacuo. The resultant residue was diluted with MeOH and loaded onto a Isolute® SCX-2 cartridge pre-treated with MeOH. The cartridge was washed with MeOH (100 mL) and the product was recovered eluting with 2N ammonia in MeOH and concentrated in vacuo. The residue was purified by flash chromatography (Si—PPC, 0 to 100% EtOAc in cyclohexane) to give a yellow powder. The solid was dissolved in DMSO and purified by preparative HPLC (C 18 column, flow rate 18 ml/min)) gradient: (acetonitrile/20 mM triethylamine in water/20 mM triethylamine) 25-98% over 20 min. The product was freeze-dried overnight yielding 143 as a yellow powder (0.035 g, 21%). LCMS (Method E): $R_T$=5.60min, [M+H]$^+$ 535.2. $^1$H NMR (DMSO, 400 MHz): δ 11.43 (s, 1 H); 8.22 (d, J=5.4 Hz, 1 H); 7.43 (s, 1 H); 7.33 (dd, J=6.3, 0.9 Hz, 1H); 7.07 (d, J=3.5 Hz, 1 H); 6.95 (d, J=3.45 Hz, 1 H); 6.87 (s, 1 H); 3.98 (t, J=4.6 Hz, 4H); 3.87 (s, 2 H); 3.81 (t, J=4.6 Hz, 4 H); 3.57 (s, 3 H); 2.61-2.53 (m, 2 H); 2.49-2.45 (m, 2 H); 2.44 (s, 4 H); 1.08 (s, 6 H)

Example 144

2-(4-((2-(1-acetamidoisoquinolin-4-yl)-4-morpholinothieno[3,2-d]pyrimidin-6-yl)methyl)piperazin-1-yl)-2-methylpropanamide 144

Step 1: N-acetyl-N-(4-bromoisoquinolin-1-yl)acetamide

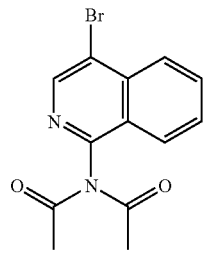

To a solution of 4-bromoisoquinolin-1-amine (403 mg, 1.81 mmol) in methylene chloride (11 mL) at 0° C. was added N,N-diisopropylethylamine (1.57 mL, 9.03 mmol), followed by acetyl chloride (0.321 mL, 4.52 mmol) dropwise. The mixture was stirred at 0° C. for 10 min then at room temperature for 2 h. The mixture was diluted with DCM (10 mL). Water (20 mL) was added. The organic layer was separated. The aqueous solution was extracted with DCM (10 mL). The combined DCM solutions were dried (Na$_2$SO$_4$). After filtration and concentration, the crude was purified with flash chromatography to give the desired product (470 mg, 85%). 1H NMR (400 MHz, DMSO) δ 8.79 (s, 1H), 8.23 (d, J=8.4, 1H), 8.13 (d, J=8.4, 1H), 8.05 (t, J=7.7, 1H), 7.87 (t, J=7.6, 1H), 2.23 (s, 6H).

Step 2: Following General Procedure B of Suzuki coupling, N-acetyl-N-(4-bromoisoquinolin-1-yl)acetamide (57 mg) was reacted with 2-(4-((2-chloro-4-morpholinothieno[3,2-d]pyrimidin-6-yl)methyl)piperazin-1-yl)-2-methylpropanamide (107 mg). After reaction completion, 1 M Na$_2$CO$_3$ (2 mL) and 1,4-dioxane (2 mL) were added to the mixture. The suspension was heated at 60° C. for 3 h. The reaction mixture was concentrated. Water (5 mL) was added. The contents were extracted with DCM (2×10 mL) The combined DCM solutions were dried (Na$_2$SO$_4$). The crude was purified with reverse-phase HPLC to give 144 (20 mg, 22%). LCMS: M+H+=589. 1H NMR (400 MHz, CDCl$_3$) δ 8.86 (2H), 8.07 (, s, br, 2H), 7.75 (t, J=7.7, 1H), 7.64 (t, J=7.6, 1H), 7.36 (s, 1H), 7.09 (s, 1H), 5.18 (s, 1H), 4.12-4.00 (m, 4H), 3.94-3.81 (m, 6H), 2.62 (s, 8H), 2.44 (s, 3H), 1.25 (s, 6H)

Example 145

2-(1-((9-methyl-2-(2-methylbenzofuran-3-yl)-6-morpholino-9H-purin-8-yl)methyl)piperidin-4-yl)propan-2-ol 145

Following the procedures for 140, 2-(1-((2-chloro-9-methyl-6-morpholino-9H-purin-8-yl)methyl)piperidin-4-yl) propan-2-ol was converted to 145. LCMS: M+H$^+$=505.3. $^1$H-NMR (400 MHz, DMSO-d$_6$): δ 8.49 (m, 1H), 7.54 (m, 1H), 7.31 (m, 2H), 4.26 (s, br, 4H), 4.05 (s, 1H), 3.86 (s, 3H), 3.77 (m, 4H), 3.68 (s, 2H), 2.94 (s, 3H), 2.90 (m, 2H), 2.01 (m, 2H), 1.66 (m, 2H), 1.21 (m, 3H), 0.94 (s, 6H).

Example 146

1-((2-(benzo[b]thiophen-3-yl)-4-morpholinothieno[3,2-d]pyrimidin-6-yl)methyl)-N,N-dimethylpiperidin-4-amine 146

A microwave vessel was charged with [1-(2-chloro-4-morpholin-4-yl-thieno[3,2-d]pyrimidin-6-ylmethyl)-piperidin-4-yl]-dimethyl-amine (0.400 g, 1.01 mmol), benzo[b]thien-3-ylboronic acid (197 mg, 1.11 mmol), 1 N sodium carbonate solution (2.5 mL), acetonitrile (7.5 mL) and Pd(dppf)Cl$_2$ (82.4 mg. 0.100 mmol), then the mixture was degassed, sealed, and heated at 140° C. under microwave irradiation for 20 min. The reaction mixture was diluted with dichloromethane (100 mL) and 1 N sodium carbonate solution (10 mL) then the phases were separated. The organic phase was washed with saturated aqueous sodium bicarbonate solution (15 mL) then dried (MgSO$_4$) and concentrated in vacuo. Purification by chromatography (silica, 0 to 15% of a 9.5:0.5 MeOH:NH$_4$OH solution in dichloromethane) to afford 146 (240 mg, 48.2%) as a light brown solid. MS m/e 494 [M+H]$^+$ $^1$H NMR (300 MHz, CHLOROFORM-d) δ ppm 1.47-1.68 (m, 2 H) 1.81 (d, J=12.43 Hz, 2 H) 2.03-2.20 (m, 3 H) 2.28 (s, 6 H) 3.02 (d, J=12.06 Hz, 2 H) 3.80 (s, 2 H) 3.85-3.95 (m, 4 H) 3.99-4.10 (m, 4 H) 7.32 (s, 1 H) 7.34-7.42 (m, 1 H) 7.43-7.53 (m, 1H) 7.89 (d, J=7.91 Hz, 1 H) 8.44 (s, 1 H) 9.00-9.15 (m, 1 H).

Example 147

2-(1-((2-(1-aminoisoquinolin-5-yl)-9-methyl-6-morpholino-9H-purin-8-yl)methyl)piperidin-4-yl)propan-2-ol 147

Step 1: 2-(1-((9-methyl-6-morpholino-2-(tributylstannyl)-9H-purin-8-yl)methyl)piperidin-4-yl)propan-2-ol

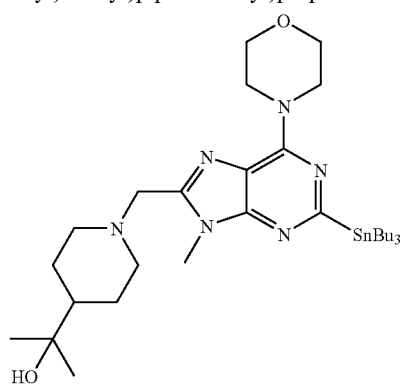

A mixture of 2-(1-((2-chloro-9-methyl-6-morpholino-9H-purin-8-yl)methyl)piperidin-4-yl)propan-2-ol (235 mg, 0.575 mmol), bis(tributyltin) (0.58 mL, 1.15 mmol) and PdCl$_2$[t-Bu$_2$P(Ph-p-Nme$_2$)$_2$] (41 mg, 0.057 mmol) in 1,4-dioxane (3 mL) was heated in a microwave at 140° C. for 40 minutes. The reaction mixture was then concentrated. The crude product was purified by flash chromatography (0-100% gradient EtOAc-Heptane) to give the title compound (256 mg, 67.1%). LCMS: M+H$^+$=663.2

Step 2: To a degassed mixture of 2-(1-((9-methyl-6-morpholino-2-(tributylstannyl)-9H-purin-8-yl)methyl)piperidin-4-yl)propan-2-ol (256 mg, 0.386 mmol), 5-bromoisoquinolin-1-amine (86 mg, 0.386 mmol), copper(I) thiophene-2-carboxylate (74 mg, 0.386 mmol) in 1,4-dioxane (4 mL) was added Pd(PPh$_3$)$_4$ (45 mg, 0.039 mmol). The reaction mixture was heated in the microwave at 140° C. for 35 minutes. The reaction mixture was then loaded onto a Biotage Isolute SPE SCX-2 column The column was first washed with MeOH. The product was eluted with 2 M NH$_3$ in MeOH and concentrated. The crude was further purified by RP-HPLC to give 147 (36.3 mg, 18.2%). LCMS: M+H$^+$=517.3. $^1$H-NMR (400 MHz, DMSO-d$_6$): δ 8.28 (d, 1H), 8.11 (d, 1H), 7.79 (d, 1H), 7.70 (d, 1H), 7.53 (t, 1H), 6.80 (s, 2H), 4.23 (s, br, 4H), 4.09 (s, 1H), 3.81 (s, 3H), 3.73 (m, 6H), 2.90 (m, 2H), 2.02 (m, 2H), 1.66 (m, 2H), 1.19 (m, 3H), 1.02 (s, 6H)

Example 149

N,N-dimethyl-1-((4-morpholino-2-(1H-pyrrolo[3,2-c]pyridin-1-yl)thieno[3,2-d]pyrimidin-6-yl)methyl)piperidin-4-amine 149

Following General Procedure I for Buchwald coupling, 1-((2-chloro-4-morpholinothieno[3,2-d]pyrimidin-6-yl)methyl)-N,N-dimethylpiperidin-4-amine and 1H-pyrrolo[3,2-c]pyridine were reacted to give 149. MS m/e 478.6 [M+H]$^+$

Example 150

1-((2-(isoquinolin-4-yl)-4-morpholinothieno[3,2-d]pyrimidin-6-yl)methyl)-N,N-dimethylpiperidin-4-amine 150

A microwave vessel was charged with 2-[4-(4-morpholin-4-yl-2-tributylstannanyl-thieno[3,2-d]pyrimidin-6-ylmethyl)-piperazin-1-yl]-isobutyramide (0.226 g, 0.347 mmol), 4-bromoisoquinoline (0.086 g, 0.416 mmol), copper(I) thiophene-2-carboxylate (Cu (TC)) (0.066 g, 0.347 mmol), palladium tetrakis(triphenylphosphine) (0.040 g, 0.034 mmol) and dioxane (2 mL) The vessel was degassed, sealed, and heated at 140° C. under microwave irradiation for 20 min. The reaction mixture was cooled to room temperature and filtered through celite. The filtrates were concentrated then purified twice by chromatography (silica, 0 to 15% of a 9:1 MeOH:NH$_4$OH mixture in dichloromethane) to furnish 150 (0.026 g, 15.38%) as an off-white foam. $^1$H NMR (400 MHz, CDCl$_3$-d) δ ppm 1.60 (qd, J=12.04, 3.79 Hz, 2 H) 1.83 (d, J=12.63 Hz, 2 H) 2.08-2.22 (m, 3 H) 2.30 (s, 6 H) 3.05 (d, J=12.13 Hz, 2 H) 3.84 (s, 2 H) 3.86-3.92 (m, 4 H) 4.03-4.11 (m, 4 H) 7.35 (s, 1H) 7.59-7.65 (m, 1 H) 7.69-7.77 (m, 1 H) 8.03 (d, J=8.59 Hz, 1 H) 8.82 (d, J=8.08 Hz, 1H) 9.11 (s, 1 H) 9.30 (s, 1 H). MS m/e 489 [M+H]$^+$

Example 151

2-(4-((2-(2-ethyl-1H-pyrrolo[2,3-c]pyridin-4-yl)-4-morpholinothieno[3,2-d]pyrimidin-6-yl)methyl)piperazin-1-yl)-2-methylpropanamide 151

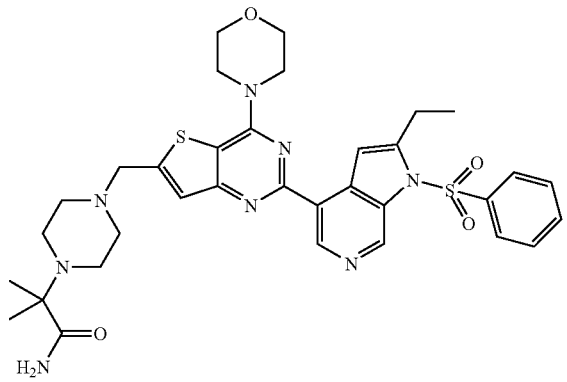

A mixture of 2-[4-(4-morpholin-4-yl-2-(tributylstannanyl)thieno[3,2-d]pyrimidin-6-ylmethyl)piperazin-1-yl]isobutyramide (0.241 g, 0.35 mmol), 1-benzenesulfonyl-4-bromo-2-ethyl-1H-pyrrolo[2,3-c]pyridine (0.14 g, 0.38 mmol), copper(I) 2-thiophene carboxylate (0.01 g, 0.069 mmol) and Pd(PPh$_3$)$_4$ (0.040 g, 0.035 mmol) in dioxane (3 mL) was subjected to microwave irradiation at 150° C. for 20 min. The reaction mixture was loaded onto an Isolute® SCX-2 cartridge. The cartridge was washed with MeOH and the desired product was eluted using 2 M NH$_3$ in MeOH. The eluent was concentrated in vacuo and the residue was purified by flash chromatography (Si—PPC, MEOH:DCM, gradient 0:100 to 20:80) to give 2-{4-[2-(1-benzenesulfonyl-2-ethyl-1H-pyrrolo[2,3-c]pyridin-4-yl)-4-morpholin-4-ylthieno[3,2-d]pyrimidin-6-ylmethyl]piperazin-1-yl}isobutyramide as a yellow foam (0.15 g, 64%). LCMS (Method A): R$_T$=3.53min, [M+H]$^+$ 689.2

A mixture of 2-{4-[2-(1-benzenesulfonyl-2-ethyl-1H-pyrrolo[2,3-c]pyridin-4-yl)-4-morpholin-4-ylthieno[3,2-c]pyrimidin-6-ylmethyl]piperazin-1-yl}isobutyramide (0.15 g, 0.22 mmol) in dioxane (3 mL), IMS (3 mL) and NaOH 12.5M (0.34 mL) was stirred at room temperature for 3 h and was then concentrated in vacuo. The residue was loaded onto an Isolute® SCX-2 cartridge. The cartridge was washed with MeOH and the desired product was eluted using 2 M NH$_3$ in MeOH. The residue was purified by reverse phase HPLC (Phenomenex Gemini 5u C18, 20 mM triethylamine in water on a gradient of acetonitrile 95:5 to 2:98) to give 151 as a white powder (0.034 g, 29%). LCMS (Method E): R$_T$=5.87 min, [M+H]$^+$ 549.2. $^1$H NMR (400 MHz, DMSO-d): δ 11.56 (s, 1 H); 9.09 (s, 1 H); 8.65 (s, 1 H); 7.45 (s, 1 H); 7.14 (s, 1 H); 7.07 (d, J=3.5 Hz, 1 H); 6.95 (d, J=3.5 Hz, 1 H); 3.99 (t, J=4.6 Hz, 4 H); 3.86 (s, 2 H); 3.82 (t, J=4.6 Hz, 4 H); 2.86 (q, J=7.6 Hz, 2 H); 2.56-2.53 (m, 4 H); 2.51-2.45 (m, 4 H); 1.34 (t, J=7.6 Hz, 3 H); 1.08 (s, 6 H)

Example 152

4-(1-((7-morpholino-5-(1H-pyrrolo[3,2-c]pyridin-4-yl)thiazolo[5,4-d]pyrimidin-2-yl)methyl)azetidin-3-yl)morpholine 152

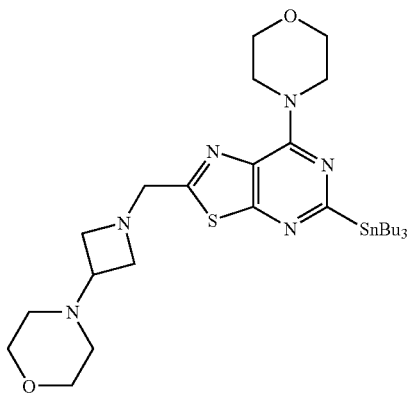

A degassed solution of 5-chloro-7-morpholin-4-yl-2-(3-morpholin-4-yl-azetidin-1-ylmethyl)thiazolo[5,4-d]pyrimidine (1.0 g, 2.43 mmol), PdCl$_2${P$^t$Bu$_2$(Ph-p-Nme$_2$)}$_2$ (170 mg, 0.24 mmol) and hexamethylditin (1.85 mL, 3.66 mmol) in 1,4-dioxane (10 mL) was subjected to microwave irradiation at 150° C. for 30 minutes. The reaction mixture was cooled to ambient temperature and loaded onto an Isolute® SCX-2 cartridge (25 g). The cartridge was then washed with MeOH and the desired product was subsequently eluted using 2 M NH$_3$ in MeOH. The product was collected and concentrated to give a yellow oil. The oil was purified by flash chromatography (Si—PPC, DCM:MeOH, 100:0 to 98:2 to 95:5) to afford 7-morpholin-4-yl-2-(3-morpholin-4-yl-azetidin-1-ylmethyl)-5-(tributylstannanyl)thiazolo[5,4-d]pyrimidine as a pale yellow oil (1.18 g, 73%). NMR (CDCl$_3$, 400 MHz) δ 4.31 (m, 4 H), 3.97 (s, 2 H), 3.82 (t, J=4.6 Hz, 4 H), 3.72 (m, 4 H), 3.65-3.59 (m, 2 H), 3.14-3.05 (m, 3 H), 2.34 (m, 4 H), 1.65-1.52 (m, 6 H), 1.39-1.26 (m, 6 H), 1.23-1.01 (m, 6 H), 0.93-0.84 (m, 9 H).

A degassed solution of 7-morpholin-4-yl-2-(3-morpholin-4-yl-azetidin-1-ylmethyl)-5-(tributylstannanyl)thiazolo[5,4-d]pyrimidine (200 mg, 0.30 mmol), 1-benzenesulfonyl-4-bromo-1H-pyrrolo[3,2-c]pyridine (132 mg, 0.39 mmol), PdCl$_2${P$^t$Bu$_2$(Ph-p-Nme$_2$)}$_2$ (22 mg, 0.03 mmol) and copper (I) thiophene-2-carboxylate (12 mg, 0.06 mmol) in 1,4-dioxane (4 mL) was subjected to microwave irradiation at 140° C. for 20 minutes. The reaction mixture was cooled to ambient temperature and loaded onto an Isolute® SCX-2 cartridge (10 g). The cartridge was then washed with MeOH and the desired product was subsequently eluted using 2 M NH$_3$ in MeOH. The product was collected and concentrated to give 5-(1-benzenesulfonyl-1H-pyrrolo[3,2-c]pyridin-4-yl)-7-morpholin-4-yl-2-(3-morpholin-4-yl-azetidin-1-ylmethyl)thioazolo[5,4-d]pyrimidine as a crude oil. Aqueous NaOH (12.5 M, 0.5 mL) was added to a solution of 5-(1-benzenesulfonyl-1H-pyrrolo[3,2-c]pyridin-4-yl)-7-morpholin-4-yl-2-(3-morpholin-4-yl-azetidin-1-ylmethyl)-thiozolo[5,4-d]pyrimidine in 1,4-dioxane (4 mL) and IMS (4 mL). The reaction mixture was stirred at ambient temperature for 45 min, then concentrated in vacuo. The residue was dissolved in MeOH then loaded onto an Isolute® SCX-2 cartridge (10 g). The cartridge was then washed with MeOH and the desired product was subsequently eluted using 2 M NH$_3$ in MeOH. The product was collected and concentrated to afford a solid. The solid was purified by flash chromatography (Si—PPC, DCM:MeOH, 100:0 to 98:2 to 96:4) to afford 152 as a yellow solid (56 mg, 38%). LCMS (Method E): R$_T$=4.34 min, M+H$^+$= 493.2. $^1$H NMR (CDCl$_3$, 400 MHz) δ 8.72 (bs, 1 H), 8.56 (d, J=5.7 Hz, 1 H), 7.41 (m, 2 H), 7.36 (d, J=3.2 Hz, 1 H), 4.49-4.44 (m, 4 H), 4.02 (s, 2 H), 3.90 (t, J=4.7 Hz, 4 H), 3.74-3.65 (m, 6 H), 3.16-3.07 (m, 3 H), 2.35 (m, 4 H)

Example 153

2-methyl-2-(4-((2-(5-methyl-1H-pyrrolo[2,3-c]pyridin-4-yl)-4-morpholinothieno[3,2-d]pyrimidin-6-yl)methyl)piperazin-1-yl)propanamide 153

A mixture of 2-[4-(4-morpholin-4-yl-2-(tributylstannanyl)thieno[3,2-d]pyrimidin-6-ylmethyl)piperazin-1-yl]isobutyramide (72 mg, 0.10 mmol), 4-bromo-5-methyl-1H-pyrrolo[2,3-c]pyridine (22 mg, 0.10 mmol), Pd(PPh$_3$)$_4$ (12 mg, 10 mol %) and copper(I)-thiophene-2-carboxylate (4 mg, 20 mol %) in dioxane (1 mL) was purged with argon gas then heated at 150° C., for 20 min, in a microwave reactor. The reaction mixture was loaded onto an Isolute® SCX-2 cartridge, the cartridge was washed with MeOH then the desired product eluted with 2 M NH$_3$ in MeOH. The resulting residue was purified by column chromatography (Si—PCC, 0-20% MeOH in DCM) to give 153 as a pale yellow solid (24 mg, 43%). LCMS (Method E): R$_T$=4.19 min, [M+H]$^+$ 535.2. $^1$H NMR (400 MHz, CHCl$_3$-d): δ 9.14 (s, 1 H), 8.73 (s, 1 H), 7.34-7.32 (m, 2 H), 7.11 (d, J=5.3 Hz, 1 H), 6.67-6.65 (m, 1H), 5.30 (d, J=4.7 Hz, 1 H), 4.04 (t, J=4.7 Hz, 4 H), 3.87 (d, J=4.7 Hz, 4 H), 3.85 (s, 2H), 2.76 (s, 3 H), 2.61 (m, 8 H), 1.28-1.22 (m, 6 H)

Example 154

4-(1-((9-methyl-2-(2-methyl-1H-benzo[d]imidazol-1-yl)-6-morpholino-9H-purin-8-yl)methyl)piperidin-4-yl)morpholine 154

Following the procedures for 178, 4-(1-((2-chloro-9-methyl-6-morpholino-9H-purin-8-yl)methyl)piperidin-4-yl)morpholine and acetic acid were converted to 154. LCMS: M+H$^+$=532.3. $^1$H-NMR (400 MHz, DMSO-d$_6$): δ 8.09 (m, 1H), 7.60 (m, 1H), 7.25 (m, 2H), 4.26 (s, br, 4H), 3.82 (s, 3H), 3.71 (m, 6H), 3.54 (m, 4H), 2.85 (m, 5), 2.43 (m, 4H), 2.08 (m, 3H), 1.76 (m, 2H), 1.39 (m, 2H).

Example 155

4-(8-((4-(2-methoxypropan-2-yl)piperidin-1-yl)methyl)-9-methyl-6-morpholino-9H-purin-2-yl)isoquinolin-1-amine 155

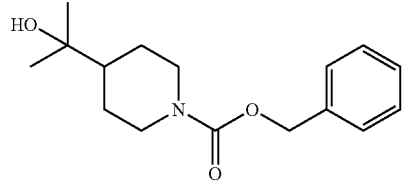

2-(Piperidin-4-yl)propan-2-ol (1 g) was reacted with 1.1 eq of benzyl chloroformate and 1.3 eq of triethylamine in 30 mL of chloroform. The reaction was halted after 2 days at room temperature and purified by isco (0-60% Hexanes/Ethyl Acetate over 20 minutes) to afford 1.49 g benzyl 4-(2-hydroxypropan-2-yl)piperidine-1-carboxylate.

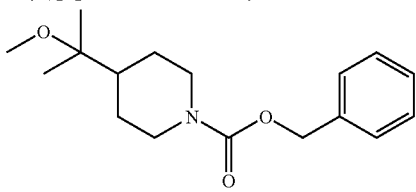

To a suspension of sodium hydride, 60% dispersion in mineral oil (0.322 g) and methyl iodide (1.00 mL) in 10 mL THF at room temp was carefully added portionwise benzyl 4-(2-hydroxypropan-2-yl)piperidine-1-carboxylate (1.49 g, 0.00537 mol) in 15 mL THF. The reaction was heated at 50° C. for 18 hours and then it was cooled down to 0° C. and carefully quenched by addition of sat NH4Cl solution, then extracted with EtOAc twice. The combined organics were washed with brine, dried over MgSO4 and concentrated in vacuo. The residue was purified by flash chrom to get 1.2 g benzyl 4-(2-methoxypropan-2-yl)piperidine-1-carboxylate as a colorless oil.

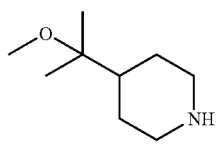

The cbz protecting group was hydrogenated off using the H-cube with palladium on carbon. The product in a solution of methanol was then concentrated and run through an isolute scx-2 spe cartridge to yield 0.44 g of 4-(2-methoxypropan-2-yl)piperidine as a colorless oil.

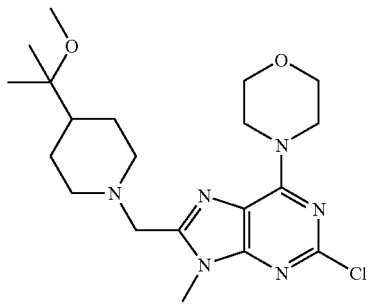

4-(2-methoxypropan-2-yl)piperidine (0.12 g) was reacted with 4-(8-(bromomethyl)-2-chloro-9-methyl-9H-purin-6-yl) morpholine (0.25 g) via General Procedure E to give 300 mg of crude 4-(2-chloro-8-((4-(2-methoxypropan-2-yl)piperidin-1-yl)methyl)-9-methyl-9H-purin-6-yl)morpholine, of which 0.78 g was reacted with 4-(4,4,5,5-tetramethyl-1,3,2-dioxaborolan-2-yl)isoquinolin-1-amine via General Procedure A to yield 12 mg of 155 as a white solid following reverse phase purification. MS (Q1) 531.3 (M)+

Example 156

1-(8-((4-(2-hydroxypropan-2-yl)piperidin-1-yl)methyl)-9-methyl-6-morpholino-9H-purin-2-yl)-1H-benzo[d]imidazol-2(3H)-one 156

A mixture of 2-(1-((2-(2-aminophenylamino)-9-methyl-6-morpholino-9H-purin-8-yl)methyl)piperidin-4-yl)propan-2-ol (40 mg, 0.083 mmol) and N,N-carbonyldiimidazole (17 mg, 0.108 mmol) in acetonitrile (2 mL) was stirred at reflux for 15 hours. The reaction mixture was then filtered through paper and purified by RP-HPLC to give 156 (6.7 mg, 16%). LCMS: M+H$^+$=507.2. $^1$H-NMR (400 MHz, DMSO-d$_6$): δ 11.0 (s, 1H), 7.55 (d, 1H), 7.04 (m, 3H), 4.21 (s, br, 4H), 4.02 (s, 1H), 3.78 (s, 3H), 3.74 (m, 6H), 2.88 (m, 2H), 2.00 (m, 2H), 1.66 (m, 2H), 1.20 (m, 3H), 1.02 (s, 6H)

Example 157

2-(1-((9-methyl-2-(2-methyl-1H-benzo[d]imidazol-1-yl)-6-morpholino-9H-purin-8-yl)methyl)piperidin-4-yl)propan-2-ol 157

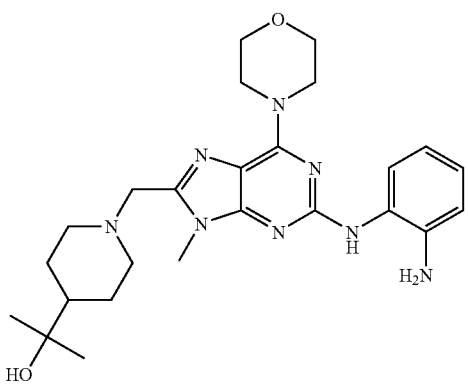

Step 1: A mixture of 2-(1-((2-chloro-9-methyl-6-morpholino-9H-purin-8-yl)methyl)piperidin-4-yl)propan-2-ol (1.21 g, 2.96 mmol), benzene-1,2-diamine (520 mg, 4.8 mmol), palladium acetate (66 mg, 0.29 mmol), bist(tri-t-butylphosphine)palladium (150 mg, 0.29 mmol) and sodium tert-butoxide (620 mg, 6 4 mmol) in toluene (30 mL) was stirred at 95° C. for 18 hours. The reaction mixture was then filtered through paper and then concentrated. The crude product was then purified by flash chromatography using a Biotage KP-NH column (0-10% gradient MeOH in DCM) to give 2-(1-((2-(2-aminophenylamino)-9-methyl-6-morpholino-9H-purin-8-yl)methyl)piperidin-4-yl)propan-2-ol (1.2 g, 84%). LCMS: M+H$^+$=481.2.

Step 2: A mixture of 2-(1-((2-(2-aminophenylamino)-9-methyl-6-morpholino-9H-purin-8-yl)methyl)piperidin-4-yl) propan-2-ol (177 mg, 0.368 mmol) in acetic acid (1.5 mL) was stirred at reflux for 5 hours. The reaction mixture was then concentrated and then purified first by flash chromatography (10% MeOH in DCM containing 1% 2 M ammonia in MeOH), followed by RP-HPLC to give 157 (0.0373 g, 21.1%). LCMS: M+H$^+$=505.3. $^1$H-NMR (400 MHz, DMSO-d$_6$): δ 8.09 (m, 1H), 7.60 (m, 1H), 7.25 (m, 2H), 4.26 (s, br, 4H), 4.02 (s, 1H), 3.83 (s, 3H), 3.78 (m, 4H), 3,73 (s, 2H), 2.90 (m, 2H), 2.84 (s, 3H), 1.99 (m, 2H), 1.66 (m, 2H), 1.21 (m, 3H), 1.02 (s, 6H).

Example 158

2-(1-((2-(2-ethyl-1H-benzo[d]imidazol-1-yl)-9-methyl-6-morpholino-9H-purin-8-yl)methyl)piperidin-4-yl)propan-2-ol 158

Following the procedures for 180, 2-(1-((2-(2-aminophenylamino)-9-methyl-6-morpholino-9H-purin-8-yl)methyl) piperidin-4-yl)propan-2-ol and propanoic acid were reacted to give 158. LCMS: M+H$^+$=519.3. $^1$H-NMR (400 MHz, DMSO-d$_6$): δ 8.02 (m, 1H), 7.63 (m, 1H), 7.26 (m, 2H), 4.24

(s, br, 4H), 4.02 (s, 1H), 3.82 (s, 3H), 3.77 (m, 4H), 3.73 (s, 2H), 3.28 (q, 2H), 2.90 (m, 2H), 2.00 (m, 2H), 1.66 (m, 2H), 1.34 (t, 3H), 1.22 (m, 3H), 1.02 (s, 6H)

Example 159

2-(1-((2-(2-cyclopropyl-1H-benzo[d]imidazol-1-yl)-9-methyl-6-morpholino-9H-purin-8-yl)methyl)piperidin-4-yl)propan-2-ol 159

Following the procedures for 178, 2-(1-((2-(2-aminophenylamino)-9-methyl-6-morpholino-9H-purin-8-yl)methyl)piperidin-4-yl)propan-2-ol and cyclopropanecarboxylic acid were reacted to give 159. LCMS: M+H+=531.3. ¹H-NMR (400 MHz, DMSO-d₆): δ 7.93 (m, 1H), 7.53 (m, 1H), 7.22 (m, 2H), 4.26 (s, br, 4H), 4.08 (m, 2H), 4.03 (s, 1H), 3.82 (s, 3H), 3.77 (m, 4H), 3.74 (s, 2H), 3.17 (d, 2H), 2.84-2.96 (m, 3H), 1.99 (m, 2H), 1.67 (m, 2H), 1.04-1.29 (m, 3H), 1.02 (s, 6H)

Example 160

2-(4-((2-(isoquinolin-4-yl)-4-morpholinothieno[3,2-d]pyrimidin-6-yl)methyl)piperazin-1-yl)-2-methylpropanamide 160

Following General Procedure A for Suzuki coupling, 2-(4-((2-chloro-4-morpholinothieno[3,2-d]pyrimidin-6-yl)methyl)piperazin-1-yl)-2-methylpropanamide and 4-(4,4,5,5-tetramethyl-1,3,2-dioxaborolan-2-yl)isoquinoline were reacted to give 160. LCMS: M+H+=532.2.

Example 161

2-(1-((2-(2-(methoxymethyl)-1H-benzo[d]imidazol-1-yl)-9-methyl-6-morpholino-9H-purin-8-yl)methyl)piperidin-4-yl)propan-2-ol 161

Following the procedures for 178, 2-(1-((2-(2-aminophenylamino)-9-methyl-6-morpholino-9H-purin-8-yl)methyl)piperidin-4-yl)propan-2-ol and methoxyacetic acid were reacted to give 161. LCMS: M+H⁻=535.3. ¹H-NMR (400 MHz, DMSO-d₆): δ 8.13 (d, 1H), 7.71 (d, 1H), 7.32 (m, 2H), 5.08 (s, 2H), 4.26 (s, br, 4H), 4.02 (s, 1H), 3.83 (s, 3H), 3.78 (m, 4H), 3.73 (s, 2H), 3.27 (s, 3H), 2.90 (m, 2H), 2.00 (m, 2H), 1.65 (m, 2H), 1.22 (m, 3H), 1.02 (s, 6H)

Example 162

2-(1-((2-(1H-indazol-3-yl)-9-methyl-6-morpholino-9H-purin-8-yl)methyl)piperidin-4-yl)propan-2-ol 162

2-(1-((9-Methyl-6-morpholino-2-(tributylstannyl)-9H-purin-8-yl)methyl)piperidin-4-yl)propan-2-ol (0.5 g) was reacted with 3-iodo-1H-indazole via General Procedure G to give 68.3 mg of 162 as a white solid following reverse phase purification. MS (Q1) 491.2 (M)+

Example 163

2-(4-((2-(2-fluorobenzofuran-3-yl)-4-morpholinothieno[3,2-d]pyrimidin-6-yl)methyl)piperazin-1-yl)-2-methylpropanamide 163

To a degassed mixture of 2-methyl-2-(4-((4-morpholino-2-(tributylstannyl)thieno[3,2-d]pyrimidin-6-yl)methyl)piperazin-1-yl)propanamide (150 mg, 0.22 mmol), 3-bromo-2-fluorobenzofuran (0.22 mmol), copper(I) thiophene-2-carboxylate (41 mg, 0.22 mmol) in dioxane (2 mL) was added Pd(PPh₃)₄ (12 mg, 0.011 mmol). The reaction mixture was reacted in the microwave at 140° C. for 35 min. The reaction mixture was filtered through paper and concentrated. The crude product was purified by flash chromatography (20% MeOH in DCM) to give a yellow paste which was dissolved in dioxane (5 mL) and ethanol (1 mL). A 12 M aqueous solution of NaOH was then added. The resulting mixture was then stirred at 65° C. for 15 hours. The reaction mixture was then loaded onto a Biotage Isolute SPE SCX-2 column. The column was washed with MeOH and the desired product was then eluted with 2 M NH₃ in MeOH and further purified by RP-HPLC to give 163. LCMS: M+H+=539.2. ¹H-NMR (400 MHz, DMSO-d₆): δ 8.46 (d, 1H), 7.63 (d, 1H), 7.41 (m, 3H), 7.05 (d, 1H), 6.93 (d, 1H), 3.97 (m, 4H), 3.86 (s, 2H), 3.82 (m, 4H), 2.31-2.62 (m, 8H), 1.08 (s, 6H)

Example 164

4-(6-((4-(dimethylamino)piperidin-1-yl)methyl)-4-morpholinothieno[3,2-d]pyrimidin-2-yl)isoquinoline 2-oxide 164

A microwave vessel was charged with 2-[4-(4-morpholin-4-yl-2-tributylstannanyl-thieno[3,2-d]pyrimidin-6-ylmethyl)-piperazin-1-yl]-isobutyramide (0.206 g, 0.316 mmol), 4-bromo-isoquinoline 2-oxide (0.085 g, 0.379 mmol), copper (I) thiophene-2-carboxylate (Cu (TC)) (0.060 g, 0.316 mmol), palladium tetrakis(triphenylphosphine) (0.036 g, 0.031 mmol) and dioxane (2 mL) The vessel was degassed, sealed, and heated at 140° C. under microwave irradiation for 20 min. The reaction mixture was cooled to room temperature and filtered through celite. The filtrates were concentrated then purified twice by chromatography (silica, 0 to 15% of a 9:1 MeOH:NH₄OH mixture in dichloromethane) to furnish 164 (0.017 g, 10.7%) as a light yellow foam. ¹H NMR (400 MHz, CDCl₃-d) δ ppm 1.54-1.68 (m, 3 H) 1.85 (d, J=12.13 Hz, 2 H) 1.97 (br. s., 2 H) 2.10-2.23 (m, 3 H) 2.31 (s, 6 H) 3.04 (d, J=11.62 Hz, 2 H) 3.85 (s, 2 H) 3.86-3.91 (m, 4 H) 4.04-4.09 (m, 4 H) 7.34 (s, 1 H) 7.59-7.66 (m, 2 H) 7.73-7.80 (m, 1 H) 8.78-8.82 (m, 2 H) 8.86-8.93 (m, 1 H). MS m/e 505 [M+H]+

Example 165

2-(1-((9-methyl-2-(2-methyl-1H-pyrrolo[2,3-c]pyridin-4-yl)-6-morpholino-9H-purin-8-yl)methyl)piperidin-4-yl)propan-2-ol 165

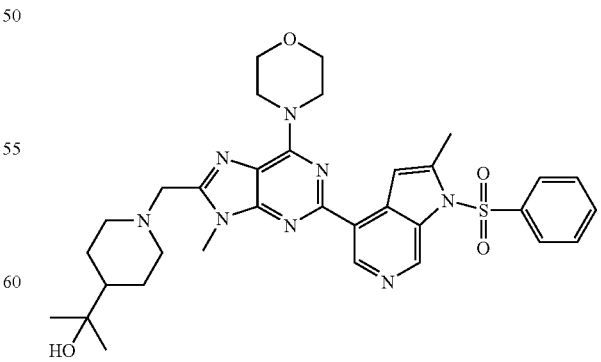

Step 1: A 20 mL microwave vial was charged with a suspension of 2-[1-(9-methyl-6-morpholin-4-yl-2-(tributylstannanyl)-9H-purin-8-ylmethyl)piperidin-4-yl]propan-2-ol (0.5 g, 0.75 mmol), 1-benzenesulfonyl-4-bromo-1H-pyrrolo[2,3-c]pyridine (0.29 g, 0.83 mmol), CuTC (0.029 g, 0.015 mmol) and Pd(PPh$_3$)$_4$ (0.087 g, 0.075 mmol) in dioxane (8 mL). The reaction mixture was heated in a microwave for 30 min at 150° C. The cooled reaction mixture was loaded onto an SCX-2 cartridge. The cartridge was washed with 3 volumes of MeOH, then the product was recovered eluting with 2N ammonia in MeOH. The solution was concentrated and the residue loaded onto a 40g SiO$_2$ column and purified by flash chromatography (Si—PCC; 40g SiO$_2$ column, 0% to 6% MeOH in DCM) to give 2-{1-[2-(1-Benzenesulfonyl-2-methyl-1H-pyrrolo[2,3-c]pyridin-4-yl)-9-methyl-6-morpholin-4-yl-9H-purin-8-ylmethyl]piperidin-4-yl}propan-2-ol as white foam (0.414 g, 86%). LCMS (Method A): R$_T$=3.24 min, [M+H]$^+$ 645.3

Step 2: A 50 mL round-bottomed flask, under nitrogen, fitted with a condenser/inert gas bubbler (via a Claisen head), was charged with a solution of 2-{1-[2-(1-benzenesulfonyl-2-methyl-1H-pyrrolo[2,3-c]pyridin-4-yl)-9-methyl-6-morpholin-4-yl-9H-purin-8-ylmethyl]piperidin-4-yl}propan-2-ol (0.41 g, 0.64 mmol) in dioxane (8 mL), IMS (8 mL) and NaOH 12.5M (0.8 mL). The resulting mixture was stirred at room temperature for 2 h. The solution was concentrated in vacuo, the residue was dissolved in DCM and a fine solid was removed by filtration through a Celite pad. The solution was purified by flash chromatography (Si—PCC; 25 g SiO$_2$ column, 0% to 20% MeOH in DCM). The residue was then purified further by preparative HPLC [(C18 column) gradient: (acetonitrile/20 mM triethylamine) 30% to 98% in (water/20 mM triethylamine) over 20 min (flow rate 18 ml/min)]. The product was freeze-dried overnight yielding 165 as a white powder (0.136 g, 43%). LCMS (method E): R$_T$=4.89 min, [M+H]$^+$ 505.24. $^1$H NMR (CDCl$_3$, 400 MHz) δ 9.28 (s, 1 H), 8.70 (s, 1 H), 8.30 (s, 1 H), 4.40 (m, 4 H), 3.96 (s, 3 H), 3.89 (m, 4 H), 3.74 (s, 2 H), 2.96 (m, 2 H), 2.58 (s, 3 H), 2.10 (m, 2 H), 1.75 (m, 2 H), 1.40-1.28 (m, 3 H), 1.18 (s, 6 H)

Example 166

2-(1-((2-(2-methoxy-1H-benzo[d]imidazol-1-yl)-9-methyl-6-morpholino-9H-purin-8-yl)methyl)piperidin-4-yl)propan-2-ol 166

Following the procedures for 179, 2-(1-((2-(2-aminophenylamino)-9-methyl-6-morpholino-9H-purin-8-yl)methyl)piperidin-4-yl)propan-2-ol, tetramethylorthocarbonate and acetic acid were reacted to give 166. LCMS: M+H$^+$=521.3. $^1$H-NMR (400 MHz, DMSO-d$_6$): δ 7.83 (m, 1H), 7.48 (m, 1H), 7.18 (m, 2H), 4.23 (s, br, 4H), 4.15 (s, 3H), 4.02 (s, 1H), 3.80 (s, 3H), 3.76 (m, 4H), 3.72 (s, 2H), 2.87 (m, 2H), 1.99 (m, 2H), 1.65 (m, 2H), 1.20 (m, 3H), 1.02 (s, 6H)

Example 167

2-(1-((2-(2-amino-1H-benzo[d]imidazol-1-yl)-9-methyl-6-morpholino-9H-purin-8-yl)methyl)piperidin-4-yl)propan-2-ol 167

A mixture of 2-(1-((2-(2-aminophenylamino)-9-methyl-6-morpholino-9H-purin-8-yl)methyl)piperidin-4-yl)propan-2-ol (220 mg, 0.46 mmol) and cyanogen bromide (150 mg, 1.4 mmol) in ethanol (2 mL) was stirred at 95° C. for 15 minutes. The reaction mixture was then loaded onto a Biotage Isolute SPE SCX-2 column. The column was washed with MeOH and the desired product was then eluted with 2 M NH$_3$ in MeOH and further purified by RP-HPLC to give 167 (18.1 mg, 7.8%). LCMS: M+H$^+$=506.3. $^1$H-NMR (400 MHz, DMSO-d$_6$): δ 8.17 (d, 1H), 7.70 (s, br, 2H), 7.24 (d, 1H), 7.12 (t, 1H), 7.03 (t, 1H), 4.26 (s, br, 4H), 4.10 (s, 1H), 3.84 (s, 3H), 3.80 (m, 4H), 1.73 (m, 2H), 1.27 (m, 3H), 1.03 (s, 6H)

Example 168

4-(1-((7-morpholino-5-(1H-pyrrolo[2,3-c]pyridin-4-yl)thiazolo[5,4-d]pyrimidin-2-yl)methyl)azetidin-3-yl)morpholine 168

A degassed solution of 7-morpholin-4-yl-2-(3-morpholin-4-yl-azetidin-1-ylmethyl)-5-(tributylstannanyl)thiazolo[5,4-d]pyrimidine (120 mg, 0.18 mmol), 4-bromo-1H-pyrrolo[2,3-c]pyridine (46 mg, 0.23 mmol), PdCl$_2${P$^t$Bu$_2$(Ph-p-Nme$_2$)}$_2$ (13 mg, 0.018 mmol) and copper(I) thiophene-2-carboxylate (7 mg, 0.036 mmol) in 1,4-dioxane (2.5 mL) was subjected to microwave irradiation at 140° C. for 20 minutes. The reaction mixture was cooled to ambient temperature and loaded onto an Isolute® SCX-2 cartridge (10 g). The cartridge was then washed with MeOH and the desired product was subsequently eluted using 2 M NH$_3$ in MeOH. The product was collected and concentrated to give a yellow oil. The oil was purified by chromatography (Si—PPC, DCM:MeOH, 100:0 to 98:2 to 95:5) to afford 168 as a yellow solid (12 mg, 14%). LCMS (Method E): R$_T$=4.15 min, [M+H]$^-$ 493.2. $^1$H NMR (CDCl$_3$, 400 MHz) δ 9.28 (bs, 1 H), 8.90 (s, 1 H), 7.53 (m, 2 H), 4.45 (m, 4 H), 4.02 (s, 2H), 3.90 (t, J=4.7 Hz, 4 H), 3.76-3.65 (m, 6 H), 3.19-3.09 (m, 3 H), 2.36 (d, J=4.76 Hz, 4H).

Example 169

2-methyl-2-(4-((7-morpholino-5-(1H-pyrrolo[3,2-c]pyridin-4-yl)thiazolo[5,4-d]pyrimidin-2-yl)methyl)piperazin-1-yl)propanamide 169

A degassed solution of 2-[4-(7-morpholin-4-yl-5-(tributylstannanyl)thiazolo[5,4-d]pyrimidin-2-ylmethyl)piperazin-1-yl]isobutyramide (250 mg, 0.36 mmol), 1-benzenesulfonyl-4-bromo-1H-pyrrolo[3,2-c]pyridine (130 mg, 0.39 mmol), PdCl$_2${P$^t$Bu$_2$(Ph-p-Nme$_2$)}$_2$ (26 mg, 0.036 mmol) and copper(I) thiophene-2-carboxylate (14 mg, 0.07 mmol) in 1,4-dioxane (4 mL) was subjected to microwave irradiation at 140° C. for 20 minutes. The reaction mixture was cooled to ambient temperature and loaded onto an Isolute® SCX-2 cartridge (10 g). The cartridge was then washed with MeOH and the desired product was subsequently eluted using 2 M NH$_3$ in MeOH. The product was collected and concentrated to give 2-{4-[5-(1-benzenesulfonyl-1H-pyrrolo[3,2-c]pyridin-4-yl)-7-morpholin-4-ylthiazolo[5,4-d]pyrimidin-2-ylmethyl]piperazin-1-yl}isobutyramide as a crude oil. Aqueous NaOH (12.5 M, 0 4 mL) was added to a solution of 2-{4-[5-(1-benzenesulfonyl-1H-pyrrolo[3,2-c]pyridin-4-yl)-7-morpholin-4-yl-thiazolo[5,4-d]pyrimidin-2-ylmethyl]-piperazin-1-yl}isobutyramide in 1,4-dioxane (4 mL) and IMS (4 mL). The reaction mixture was stirred at ambient temperature for 45 min, then concentrated in vacuo. The residue was dissolved in MeOH then loaded onto an Isolute® SCX-2 cartridge (10 g). The cartridge was then washed with MeOH and the desired product was subsequently eluted using 2 M NH$_3$ in MeOH. The product was collected and concentrated

Example 170

2-methyl-2-(4-((2-(6-methyl-1H-pyrrolo[3,2-c]pyridin-4-yl)-4-morpholinothieno[3,2-d]pyrimidin-6-yl)methyl)piperazin-1-yl)propanamide 170

A mixture of 2-[4-(4-morpholin-4-yl-2-(tributylstannanyl)thieno[3,2-d]pyrimidin-6-ylmethyl)-piperazin-1-yl]isobutyramide (100 mg, 0.14 mmol), 4-bromo-6-methyl-1H-pyrrolo[3,2-c]pyridine (20 mg, 0.09 mmol), tetrakis(triphenylphosphine)palladium (17 mg, 10 mol %) and copper(I)-thiophene-2-carboxylate (6 mg, 20 mol %) in dioxane (1.5 mL) was purged with argon gas then heated at 150° C., for 20 min, in a microwave reactor. The cooled reaction mixture was loaded onto an Isolute® SCX-2 cartridge, washed with MeOH/DCM then eluted with 2 M $NH_3$ in MeOH/DCM. The resulting residue was purified by column chromatography (Si—PPC, 2 M $NH_3$ in MeOH:DCM, gradient 0:100 to 10:90) followed by reverse phase HPLC (Phenomenex Gemini 5 μm C18, 20 mM triethylamine in water on a gradient of acetonitrile 90:10 to 02:98) to give 170 as an off-white solid (11 mg, 22%). LCMS $R_T$ 5.14 min, [M+H]$^+$ 535. $^1$H NMR (CDCl$_3$, 400 MHz) δ 7.41 (s, 1 H), 7.29-7.25 (m, 2 H), 7.14 (s, 1 H), 7.09 (d, J=5.3 Hz, 1 H), 5.36 (d, J=5.3 Hz, 1 H), 4.07 (t, J=4.6 Hz, 4 H), 3.88 (t, J=4.6 Hz, 4 H), 3.83 (s, 2 H), 2.70 (s, 3 H), 2.58 (m, 8 H), 1.23 (s, 6 H)

Example 171

2-methyl-2-(4-((4-morpholino-2-(quinolin-4-yl)thieno[3,2-d]pyrimidin-6-yl)methyl)piperazin-1-yl)propanamide 171

To a degassed mixture of 2-methyl-2-(4-((4-morpholino-2-(tributylstannyl)thieno[3,2-d]pyrimidin-6-yl)methyl)piperazin-1-yl)propanamide (235 mg, 0.339 mmol), 4-bromoquinoline (60 mg, 0.288 mmol), copper(I) thiophene-2-carboxylate (55 mg, 0.228 mmol) in dioxane (2 mL) was added Pd(PPh$_3$)$_4$ (17 mg, 0.014 mmol). The reaction mixture was reacted in the CEM microwave at 140° C. for 30 min. The reaction mixture was then loaded onto a Biotage Isolute SPE SCX-2 column. The column was washed with MeOH, eluted with 2 M $NH_3$ in MeOH and further purified by RP-HPLC to give 171 (44 mg, 29%). LCMS: M+H$^+$=532.2. $^1$H-NMR (400 MHz, DMSO-d$_6$): δ 9.39 (s, 1H), 9.04 (s, 1H), 8.86 (d, 1H), 8.22 (d, 1H), 7.84 (t, 1H), 7.73 (t, 1H), 7.47 (s, 1H), 7.06 (s, 1H), 6.94 (s, 1H), 3.97 (m, 4H), 3.88 (s, 2H), 3.68 (m, 4H), 2.54-2.67 (m, 8H), 1.09 (s, 6H)

Example 172

4-(1-((2-(2-methyl-1H-benzo[d]imidazol-1-yl)-4-morpholinothieno[3,2-d]pyrimidin-6-yl)methyl)azetidin-3-yl)morpholine 172

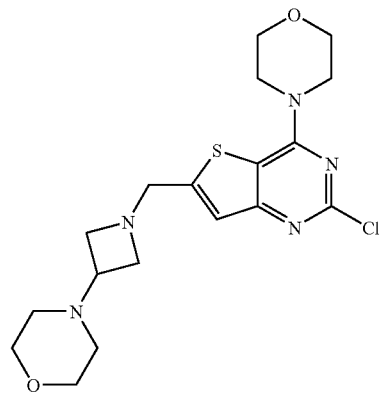

To a solution of 2-chloro-4-morpholin-4-yl-thieno[3,2-d]pyrimidine-6-carbaldehyde (953 mg, 3.36 mmol) in DCE (50 mL) was added 4-azetidin-3-ylmorpholine (525 mg, 3.69 mmol), trimethyl orthoformate (3.67 mL, 33.58 mmol) and acetic acid (0.19 mL, 3.36 mmol). After stirring at room temperature for 2 h sodium triacetoxyborohydride (1.10 g, 5.03 mmol) was added and the resulting mixture stirred for a further 2 h. The reaction mixture was loaded onto an Isolute® SCX-2 cartridge, washed with H$_2$O/MeOH then eluted with 2 M $NH_3$ in MeOH/DCM. The resulting residue was purified by column chromatography (Si—PCC, MeOH:EtOAc, gradient 0:100 to 20:80) to give 2-chloro-4-morpholin-4-yl-6-(3-morpholin-4-yl-azetidin-1-ylmethyl)thieno[3,2-d]pyrimidine as a pale yellow solid (856 mg, 62%). LCMS (Method C): $R_T$=2.77 min, [M+H]$^+$ 410

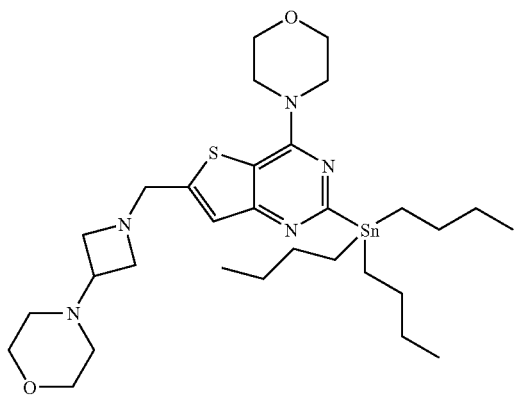

A mixture of 2-chloro-4-morpholin-4-yl-6-(3-morpholin-4-yl-azetidin-1-ylmethyl)thieno[3,2-d]pyrimidine (401 mg, 0.98 mmol), hexabutylditin (0.74 mL, 1.47 mmol), and PdCl$_2${P$^t$Bu$_2$(Ph-p-Nme$_2$)}$_2$ (69 mg, 10 mol %) in dioxane (4 mL) was purged with argon gas then heated at 150° C., for 25 min, in a microwave reactor. The reaction mixture was loaded onto a Isolute® SCX-2 cartridge cartridge, washed with MeOH then eluted with 2 M NH₃ in MeOH. The resulting residue was purified by column chromatography (Si—PCC, MeOH:EtOAc, gradient 0:100 to 20:80) to give 4-morpholin-4-yl-6-(3-morpholin-4-yl-azetidin-1-ylmethyl)-2-(tributylstannanyl)thieno[3,2-d]pyrimidine as a colorless oil (405 mg, 62%). LCMS (Method C) $R_T$ 3.87 min, [M+H]⁺ 664 (¹¹⁶Sn) 666 (¹¹⁸Sn).

A mixture of N-[4-morpholin-4-yl-6-(3-morpholin-4-yl-azetidin-1-ylmethyl)thieno[3,2-d]pyrimidin-2-yl]benzene-1,2-diamine (100 mg, 0.21 mmol) and glacial acetic acid (0.5 mL) was heated at 120° C. for 3 h. The reaction mixture was cooled to ambient temperature and loaded onto an Isolute® SCX-2 cartridge (10 g). The cartridge was then washed with MeOH and the desired product was subsequently eluted using 2 M NH₃ in MeOH. The product was collected and concentrated in vacuo. The resultant residue was purified by flash chromatography (Si—PPC, DCM: 2 M NH₃ in MeOH 100:0 to 98:2 to 95:5) followed by reversed phase HPLC (Phenomenex Luna C-18, 20 mM Et₃N in water on a gradient of 20 mM Et₃N in acetonitrile 95:5 to 2:98) to afford 172 as a white solid (45 mg, 43%). LCMS (method A): $R_T$=5.65 min, M+H⁻= 506.1. ¹H NMR (CDCl₃, 400 MHz) δ 8.08-8.03 (m, 1 H), 7.73-7.68 (m, 1 H), 7.30-7.26 (m, 3 H), 4.05 (t, J=4.8 Hz, 4 H), 3.99 (s, 2 H), 3.88 (t, J=4.8 Hz, 4 H), 3.73 (m, 4 H), 3.65 (s, 2 H), 3.18-2.99 (m, 3 H), 2.93 (s, 3 H), 2.34 (m, 4 H)

Alternatively, a mixture of 2-chloro-4-morpholin-4-yl-6-(3-morpholin-4-ylazetidin-1-ylmethyl)thieno[3,2-d]pyrimidine (100 mg, 0.24 mmol), 2-methylbenzimidazole (32 mg, 0.24 mmol), tris(dibenzylideneacetone)dipalladium (11 mg, 0.01 mmol), Xphos (12 mg, 0.02 mmol) and Cs₂CO₃ (158 mg, 0.48 mmol) in DMF (2 mL) was purged with argon then heated at 145° C. for 30 min in a microwave reactor. The reaction mixture was dissolved in EtOAc and washed with H₂O (×6) then brine (×2), then dried (Na₂SO₄) and concentrated in vacuo. The resulting residue was purified by column chromatography (Si—PCC, MeOH:DCM, 0-5%). The resulting oil was triturated with a mixture of Et₂O and pentane affording 172 as a pale yellow solid (33 mg, 27%)

Example 173

1-(4-morpholino-6-((3-morpholinoazetidin-1-yl) methyl)thieno[3,2-d]pyrimidin-2-yl)-1H-benzo[d] imidazol-2(3H)-one 173

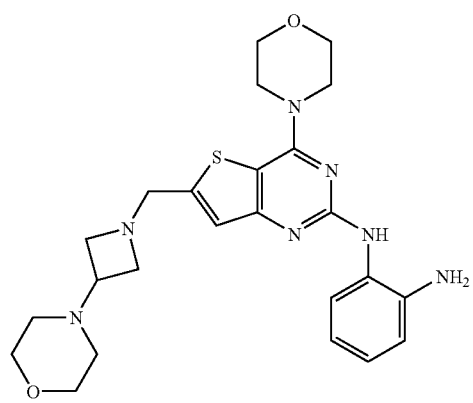

A degassed mixture of 2-chloro-4-morpholin-4-yl-6-(3-morpholin-4-yl-azetidin-1-ylmethyl)thieno[3,2-d]pyrimidine (400 mg, 0.98 mmol), 1,2-diaminobenzene (240 mg, 2.22 mmol), Pd(OAc)₂ (64 mg, 0.29 mmol), rac-BINAP (88 mg, 0.14 mmol) and Cs₂CO₃ (480 mg, 1.47 mmol) in 1,4-dioxane (4 mL)) was subjected to microwave irradiation at 150° C. for 30 minutes. The reaction mixture was cooled to ambient temperature and loaded onto an Isolute® SCX-2 cartridge (25 g). The cartridge was then washed with MeOH and the desired product was subsequently eluted using 2 M NH₃ in MeOH. The product was collected and concentrated in vacuo. The resultant residue was purified by flash chromatography (Si—PPC, DCM: 2 M NH₃ in MeOH 100:0 to 98:2 to 96:4) to afford N-[4-morpholin-4-yl-6-(3-morpholin-4-yl-azetidin-1-ylmethyl)thieno[3,2-d]pyrimidin-2-yl]benzene-1,2-diamine as a pale yellow oil (310 mg, 66%). LCMS (Method C): $R_T$=2.06 min, [M+H]⁻ 482.4

A mixture of N-[4-morpholin-4-yl-6-(3-morpholin-4-yl-azetidin-1-ylmethyl)-thieno[3,2-d]pyrimidin-2-yl]benzene-1,2-diamine (50 mg, 0.10 mmol) and N,N'-carbonyldiimidazole (50 mg, 0.31 mmol) in 1,4-dioxane (0 5 mL) was heated at 110° C. for 4 h. The reaction mixture was cooled to ambient temperature and loaded onto an Isolute® SCX-2 cartridge (10 g). The cartridge was then washed with MeOH and the desired product was subsequently eluted using 2 M NH₃ in MeOH. The product was collected and concentrated in vacuo. The resultant residue was purified by flash chromatography (Si—PPC, DCM: 2 M NH₃ in MeOH 100:0 to 98:2 to 96:4) to afford 173 as a tan solid (17 mg, 32%). LCMS (method E): $R_T$=6.42 min, [M+H]⁺=508.1. ¹H NMR (CDCl₃, 400 MHz) δ 8.50 (bs, 1 H), 7.76-7.72 (m, 1 H), 7.32 (s, 1 H), 7.13-7.04 (m, 3 H), 4.05 (t, J=4.7 Hz, 4 H), 3.97 (s, 2 H), 3.86 (t, J=4.7 Hz, 4 H), 3.73 (m, 4 H), 3.62 (m, 2 H), 3.06 (s, 3 H), 2.33 (m, 4 H)

Example 174

4-(1-((4-morpholino-2-(1H-pyrrolo[3,2-c]pyridin-4-yl)thieno[3,2-d]pyrimidin-6-yl)methyl)azetidin-3-yl) morpholine 174

A mixture of 4-morpholin-4-yl-6-(3-morpholin-4-yl-azetidin-1-ylmethyl)-2-(tributylstannanyl)thieno[3,2-d]pyrimidine (192 mg, 0.29 mmol), 1-benzenesulfonyl-4-bromo-1H-pyrrolo[3,2-c]pyridine (117 mg, 0.35 mmol), tetrakis (triphenylphosphine)palladium (34 mg, 10 mol %) and copper(I)-thiophene-2-carboxylate (11 mg, 20 mol %) in dioxane (2.0 mL) was purged with argon gas then heated at 150° C., for 20 min, in a microwave reactor. The reaction mixture was loaded onto an Isolute® SCX-2 cartridge, washed with MeOH/DCM then eluted with 2 M NH₃ in MeOH. The resulting residue was dissolved in IMS/dioxane (1:1 mL) and 12.5 M aqueous NaOH solution (0.1 mL) added. After stirring for 1 h the reaction mixture was loaded onto an Isolute® SCX-2 cartridge, washed with MeOH/DCM then eluted with 2 M NH₃ in MeOH/DCM. The resulting residue was purified by column chromatography (Si—PCC, 2 M NH₃ in MeOH:DCM, gradient 0:100 to 10:90) followed by trituration from diethyl ether to give 174 (38 mg, 27%) as a pale yellow solid. LCMS $R_T$ 4.52 min, [M+H]⁺ 492. ¹H NMR (CDCl₃, 400 MHz) δ 8.53 (m, 1 H), 7.45-7.35 (m, 4 H), 4.10 (t, J=4.7 Hz, 4 H), 3.97 (s, 2 H), 3.89 (t, J=4.7 Hz, 4 H), 3.72 (t, J=4.5 Hz, 4 H), 3.69-3.54 (m, 2 H), 3.08-3.01 (m, 3H), 2.33 (m, 4 H).

Example 176

2-methyl-2-(4-((2-(2-methyl-2H-indazol-3-yl)-4-morpholinothieno[3,2-d]pyrimidin-6-yl)methyl)piperazin-1-yl)propanamide 176

To a degassed mixture of 2-methyl-2-(4-((4-morpholino-2-(tributylstannyl)thieno[3,2-d]pyrimidin-6-yl)methyl)piperazin-1-yl)propanamide (270 mg, 0.389 mmol), 3-iodo-2-methyl-2H-indazole (95 mg, 0.368 mmol), copper(I) thiophene-2-carboxylate (70 mg, 0.368 mmol) in dioxane (2.3 mL) was added Pd(PPh$_3$)$_4$ (21 mg, 0.018 mmol). The reaction mixture was reacted in the CEM microwave at 140° C. for 30 min. The reaction mixture was then loaded onto a Biotage Isolute SPE SCX-2 column. The column was washed with MeOH and the desired product was then eluted with 2 M NH$_3$ in MeOH and further purified by RP-HPLC to give 176 (44 mg, 29%). LCMS: M+H$^+$=535.2. $^1$H-NMR (400 MHz, DMSO-d$_6$): δ 8.40 (d, 1H), 7.67 (d, 1H), 7.47 (s, 1H), 7.31 (t, 1H), 7.19 (t, 1H), 7.06 (s, 1H), 6.93 (s, 1H), 4.60 (s, 3H), 4.06 (m, 4H), 3.88 (s, 2H), 3.84 (m, 4H), 2.49-2.62 (m, 8H), 1.08 (s, 6H)

Example 177

1-(6-((4-(dimethylamino)piperidin-1-yl)methyl)-4-morpholinothieno[3,2-d]pyrimidin-2-yl)indolin-2-one 177

A microwave vessel was charged with [1-(2-chloro-4-morpholin-4-yl-thieno[3,2-d]pyrimidin-6-ylmethyl)-piperidin-4-yl]-dimethyl-amine (0.2 g) in dioxane (4 mL) The vessel was evacuated and back filled with argon. To this mixture was added 1,3-dihydro-indol-2-one (0.08 g), BINAP (0.015 g), cesium carbonate (0.2 g) and palladium acetate (0.009 g). The vessel was evacuated and back filled with argon again, and the mixture was irradiated with microwaves at 150° C. for 45 min. The reaction mixture was cooled to room temperature then filtered through HPLC filter. The filtrate was concentrated and the residue obtained was purified by chromatography (silica, 0 to 10% of a 49:1 MeOH:NH$_4$OH mixture in dichloromethane) to furnish 177 (0.022 g, 9%) as a light brown solid. MS m/e 493 [M+H]$^+$. $^1$H NMR (400 MHz, DMSO-d$_6$) δ ppm 1.44 (br. s., 2 H) 1.75 (d, J=11.12 Hz, 2 H) 2.03-2.13 (m, 3 H) 2.20 (s, 6 H) 2.95 (d, J=11.62 Hz, 2 H) 3.71-3.83 (m, 6 H) 3.85 (s, 2H) 3.89-3.98 (m, 4 H) 7.00-7.14 (m, 1 H) 7.24 (d, J=4.04 Hz, 2 H) 7.29-7.39 (m, 2 H)

Example 178

2-(1-((2-(2-(hydroxymethyl)-1H-benzo[d]imidazol-1-yl)-9-methyl-6-morpholino-9H-purin-8-yl)methyl)piperidin-4-yl)propan-2-ol 178

Following the procedures for synthesis of 157, 2-(1-(((2-(2-aminophenylamino)-9-methyl-6-morpholino-9H-purin-8-yl)methyl)piperidin-4-yl)propan-2-ol and glycolic acid were reacted to give 178. LCMS: M+H$^+$=521.3. $^1$H-NMR (400 MHz, DMSO-d$_6$): δ 8.17 (d, 1H), 7.68 (d, 1H), 7.31 (m, 2H), 5.28 (t, 1H), 5.08 (d, 2H), 4.27 (s, br, 4H), 4.02 (s, 1H), 3.82 (s, 3H), 3.78 (m, 4H), 3.73 (s, 2H), 2.90 (d, 2H), 2.01 (m, 2H), 1.66 (d, 2H), 1.21 (m, 3H), 1.02 (s, 6H).

Example 179

4-(8-((4-(2-methoxypropan-2-yl)piperidin-1-yl)methyl)-9-methyl-2-(2-methyl-1H-benzo[d]imidazol-1-yl)-9H-purin-6-yl)morpholine 179

Step 1: N1-(8-((4-(2-methoxypropan-2-yl)piperidin-1-yl)methyl)-9-methyl-6-morpholino-9H-purin-2-yl)benzene-1,2-diamine

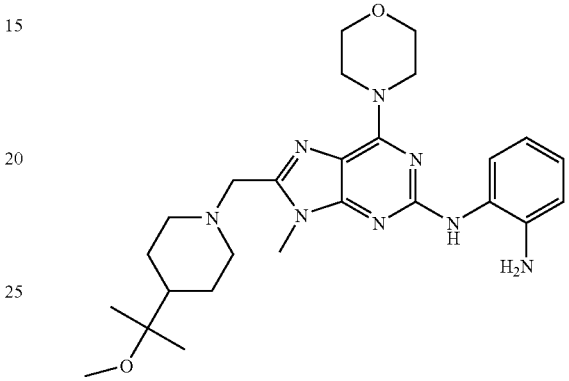

A mixture of 4-(2-chloro-8-((4-(2-methoxypropan-2-yl)piperidin-1-yl)methyl)-9-methyl-9H-purin-6-yl)morpholine (1.21 g, 2.96 mmol), benzene-1,2-diamine (520 mg, 4.8 mmol), palladium acetate (66 mg, 0.29 mmol), bis(tri-t-butylphosphine)palladium (150 mg, 0.29 mmol) and sodium t-butoxide (620 mg, 6.4 mmol) in toluene (30 mL) was stirred at 95° C. for 18 hours. The reaction mixture was then filtered through paper and then concentrated. The crude product was then purified by flash chromatography using a Biotage KP-NH column (0-10% gradient MeOH in DCM) to give N1-(8-((4-(2-methoxypropan-2-yl)piperidin-1-yl)methyl)-9-methyl-6-morpholino-9H-purin-2-yl)benzene-1,2-diamine (1.2 g, 84%). LCMS: M+H$^+$=481.2.

Step 2: A mixture of N1-(8-((4-(2-methoxypropan-2-yl)piperidin-1-yl)methyl)-9-methyl-6-morpholino-9H-purin-2-yl)benzene-1,2-diamine (177 mg, 0.368 mmol) in acetic acid (1.5 mL) was stirred at reflux for 5 hours. The reaction mixture was then concentrated and then purified first by flash chromatography (10% MeOH in DCM containing 1% 2 M ammonia in MeOH), followed by RP-HPLC to give 179 (0.0373 g, 21.1%). LCMS: M+H$^+$=519.1.

Alternatively, following General Procedure I, one-step Buchwald coupling, a microwave tube was charged with Xphos (0.1 equiv.), tris(dibenzylideneacetone)dipalladium (0) (0.05 equiv.), cesium carbonate (2 equiv.), 4-(2-chloro-8-((4-(2-methoxypropan-2-yl)piperidin-1-yl)methyl)-9-methyl-9H-purin-6-yl)morpholine (80 mg, 1 equiv.) and 2-methyl-1H-benzo[d]imidazole (1.2 equiv.). The vessel is evacuated and refilled with nitrogen prior to the addition of DMF or 1,4-dioxane. The mixture is heated in a microwave device, such as Biotage at about 140° C. for about 25-35 minutes. The reaction mixture is cooled to room temperature, filtered and concentrated, and purified by RP-HPLC to give 17.1 mg of 179. MS (Q1) 519.1 (M)+.

Example 180

2-(4-((2-(1-amino-6-fluoroisoquinolin-4-yl)-4-morpholinothieno[3,2-d]pyrimidin-6-yl)methyl)piperazin-1-yl)-2-methylpropanamide 180

Following General Procedure A for Suzuki coupling, 2-(4-((2-chloro-4-morpholinothieno[3,2-d]pyrimidin-6-yl)methyl)piperazin-1-yl)-2-methylpropanamide and 6-fluoro-4-(4,4,5,5-tetramethyl-1,3,2-dioxaborolan-2-yl)isoquinolin-1-amine were reacted to give 180. LCMS: M+H$^+$=565.3

Example 181

(3S,4R)-3-fluoro-N,N-dimethyl-1-((9-methyl-2-(2-methyl-1H-benzo[d]imidazol-1-yl)-6-morpholino-9H-purin-8-yl)methyl)piperidin-4-amine 181

Following General Procedure I for Buchwald coupling, (3S,4R)-1-((2-chloro-9-methyl-6-morpholino-9H-purin-8-yl)methyl)-3-fluoro-N,N-dimethylpiperidin-4-amine and 2-methyl-1H-benzo[d]imidazole were reacted to give 181. LCMS m/z: 508.3 (MH+)

Example 182

4-(5-(1H-indazol-3-yl)-2-((3-morpholinoazetidin-1-yl)methyl)thiazolo[5,4-d]pyrimidin-7-yl)morpholine 182

A mixture of 7-morpholin-4-yl-2-(3-morpholin-4-ylazetidin-1-ylmethyl)-5-(tributylstannanyl)thiazolo[5,4-d]pyrimidine (0.25 g, 0.37 mmol), 3-iodo-1H-indazole (0.2 g, 0.82 mmol), copper(I) 2-thiophene carboxylate (0.030 g, 0.150 mmol) and Pd(PPh$_3$)$_4$ (0.088 g, 0.075 mmol) in dioxane (3 mL) was subjected to microwave irradiation at 150° C. for 90 min. The reaction mixture was loaded onto an Isolute® SCX-2 cartridge. The cartridge was washed with MeOH and the desired product was eluted using 2 M NH$_3$ in MeOH. The eluent was concentrated in vacuo and the residue was purified by flash chromatography (Si—PPC, MEOH:DCM, gradient 0:100 to 20:80) followed by reverse phase HPLC (Phenomenex Gemini 5u C18, 20 mM triethylamine in water on a gradient of acetonitrile 95:5 to 2:98) to give 182 as an off-white solid (0.036 g, 20%). LCMS (Method G): R$_T$=7.40 min, [M+H]$^+$ 493.3. $^1$H NMR (CDCl$_3$, 400 MHz) δ 8.58 (d, J=8.2 Hz, 1 H); 7.55 (t, J=8.2 Hz, 1 H); 7.46-7.41 (m, 1 H); 7.34-7.29 (m, 1 H); 4.48-4.33 (m, 4 H); 4.02 (s, 2 H); 3.92 (t, J=4.6 Hz, 4 H); 3.73 (t, J=4.6 Hz, 4 H); 3.70-3.66 (m, 2 H); 3.18-3.09 (m, 3 H); 2.40-2.35 (m, 4H)

Example 183

1-(7-morpholino-2-((3-morpholinoazetidin-1-yl)methyl)thiazolo[5,4-d]pyrimidin-5-yl)-1H-benzo[d]imidazol-2(3H)-one 183

A mixture of N-[7-morpholin-4-yl-2-(3-morpholin-4-ylazetidin-1-ylmethyl)thiazolo[5,4-d]pyrimidin-5-yl]benzene-1,2-diamine (75 mg, 0.16 mmol) and 1,1'-carbonyldiimidazole (100 mg, 0.62 mmol) in 1,4-dioxane (1 mL) was heated at 110° C. for 3 h. After cooling to ambient temperature, the mixture was loaded onto an Isolute® SCX-2 cartridge (10 g). The cartridge was then washed with methanol and the desired product was subsequently eluted using 2 M NH$_3$ in MeOH. The product was collected and concentrated in vacuo. The resultant residue was purified by flash chromatography (Si—PPC, DCM: 2 M NH$_3$ in MeOH 100:0 to 99:1 to 98:2) to afford 183 as a cream solid (45 mg, 57%). LCMS (Method G): R$_T$=6.72 min, M+H$^+$=509. $^1$H NMR (CDCl$_3$, 400 MHz) δ 8.71 (s, 1 H); 7.77 (m, 1 H); 7.15-7.05 (m, 3 H); 4.42 (m, 4 H); 4.01 (s, 2 H); 3.86 (m, 4 H); 3.71 (m, 6 H); 3.15 (s, 3 H) and 2.36 (m, 4 H)

Example 184

4-(5-(2-(difluoromethyl)-1H-benzo[d]imidazol-1-yl)-2-((3-morpholinoazetidin-1-yl)methyl)thiazolo[5,4-d]pyrimidin-7-yl)morpholine 184

A mixture of N-[7-morpholin-4-yl-2-(3-morpholin-4-ylazetidin-1-ylmethyl)thiazolo[5,4-d]pyrimidin-5-yl]benzene-1,2-diamine (65 mg, 0.14 mmol) and ethyl difluoroacetate (0.3 mL, 2.8 mmol) in 1,4-dioxane (0.5 mL) was heated at 100° C. for 3 days. The reaction mixture was cooled to ambient temperature and loaded onto an Isolute® SCX-2 cartridge (10 g). The cartridge was then washed with MeOH and the desired product was subsequently eluted using 2 M NH$_3$ in MeOH. The product was collected and concentrated in vacuo. The resultant residue was purified by reversed phase HPLC (Phenomenex Luna C-18, 20 mM Et$_3$N in water on a gradient of 20 mM Et$_3$N in acetonitrile 30:70 to 2:98) to afford 184 as a white solid (26 mg, 35%). LCMS (Method G): R$_T$=8.03 min, M+H$^+$=543. $^1$H NMR (CDCl$_3$, 400 MHz) δ 8.29 (d, J=8.1 Hz, 1 H); 7.91 (d, J=7.8 Hz, 1 H); 7.60 (t, J=53.8 Hz, 1 H); 7.45-7.37 (m, 2 H); 4.43 (m, 4 H); 4.02 (s, 2 H); 3.89 (t, J=4.7 Hz, 4 H); 3.74 (t, J=4.5 Hz, 4 H); 3.69 (t, J=6.2 Hz, 2 H); 3.21-3.07 (m, 3 H) and 2.37 (m, 4 H)

Example 185

2-(4-((2-(1-amino-7-fluoroisoquinolin-4-yl)-4-morpholinothieno[3,2-d]pyrimidin-6-yl)methyl)piperazin-1-yl)-2-methylpropanamide 185

Following General Procedure A for Suzuki coupling, 2-(4-((2-chloro-4-morpholinothieno[3,2-d]pyrimidin-6-yl)methyl)piperazin-1-yl)-2-methylpropanamide and 7-fluoro-4-(4,4,5,5-tetramethyl-1,3,2-dioxaborolan-2-yl)isoquinolin-1-amine were reacted to give 185. LCMS: M+H$^+$=565.3

Example 186

2-(1-((9-methyl-6-morpholino-2-(2-(trifluoromethyl)-1H-benzo[d]imidazol-1-yl)-9H-purin-8-yl)methyl)piperidin-4-yl)propan-2-ol 186

Following the procedures for 157, 2-(1-((2-(2-aminophenylamino)-9-methyl-6-morpholino-9H-purin-8-yl)methyl)piperidin-4-yl)propan-2-ol and trifluoroacetic acid were reacted to give 186. LCMS m/z: 559.3 (MH+)

Example 187

2-isobutyl-4-((9-methyl-2-(2-methyl-1H-benzo[d]imidazol-1-yl)-6-morpholino-9H-purin-8-yl)methyl)morpholine 187

Following the procedures for 157, where in Step 1, 4-((2-chloro-9-methyl-6-morpholino-9H-purin-8-yl)methyl)-2-isobutylmorpholine was used to prepare 187. LCMS m/z: 505.3 (MH+)

Example 188

2-(1-((2-(2-(dimethylamino)-1H-benzo[d]imidazol-1-yl)-9-methyl-6-morpholino-9H-purin-8-yl)methyl)piperidin-4-yl)propan-2-ol 188

Following General Procedure I for Buchwald coupling, 2-(1-((2-chloro-9-methyl-6-morpholino-9H-purin-8-yl)methyl)piperidin-4-yl)propan-2-ol and N,N-dimethyl-1H-benzo[d]imidazol-2-amine were reacted to give 188. LCMS m/z: 534.3 (MH+)

Example 189

2-(1-((2-(2-ethyl-2H-indazol-3-yl)-9-methyl-6-morpholino-9H-purin-8-yl)methyl)piperidin-4-yl)propan-2-ol 189

Following the procedures for 165, 2-[1-(9-methyl-6-morpholin-4-yl-2-(tributylstannanyl)-9H-purin-8-ylmethyl)piperidin-4-yl]propan-2-ol and 2-ethyl-3-iodo-2H-indazole were reacted to give 189. LCMS m/z: 519.3 (MH+)

Example 190

2-(4-((2-(2-ethyl-2H-indazol-3-yl)-4-morpholinothieno[3,2-d]pyrimidin-6-yl)methyl)piperazin-1-yl)-2-methylpropanamide 190

Following the procedures for 143, 2-[4-(4-morpholin-4-yl-2-(tributylstannanyl)thieno[3,2-d]pyrimidin-6-ylmethyl)piperazin-1-yl]isobutyramide and 2-ethyl-3-iodo-2H-indazole were reacted to give 190. LCMS m/z: 549.3 (MH+)

Example 191

2,2-diethyl-4-((9-methyl-2-(2-methyl-1H-benzo[d]imidazol-1-yl)-6-morpholino-9H-purin-8-yl)methyl)morpholine 191

Following the procedures for 157 and General Procedure J, 4-((2-chloro-9-methyl-6-morpholino-9H-purin-8-yl)methyl)-2,2-diethylmorpholine and benzene-1,2-diamine were reacted, followed by condensation with acetic acid to give 191. LCMS m/z: 505.3 (MH+)

Example 192

2-methyl-2-(4-((2-(2-methyl-1H-benzo[d]imidazol-1-yl)-4-morpholinothieno[3,2-d]pyrimidin-6-yl)methyl)piperazin-1-yl)propanamide 192

2-(4-((2-Chloro-4-morpholinothieno[3,2-d]pyrimidin-6-yl)methyl)piperazin-1-yl)-2-methylpropanamide (0.15 g) was reacted with 2-methylbenzimidazole via General Procedure I for Buchwald coupling to give 29.3 mg 192 following reverse phase purification. MS (Q1) 535.2 (M)+.

Example 193

4-(5-(2-methyl-1H-benzo[d]imidazol-1-yl)-2-((3-morpholinoazetidin-1-yl)methyl)thiazolo[5,4-d]pyrimidin-7-yl)morpholine 193

4-(5-(2-Methyl-1H-benzo[d]imidazol-1-yl)-2-((3-morpholinoazetidin-1-yl)methyl)thiazolo[5,4-d]pyrimidin-7-yl)morpholine (75 mg) was reacted with 2-methylbenzimidazole via General Procedure I for Buchwald coupling to give 16.4 mg 193 following reverse phase purification. MS (Q1) 507.2 (M)+

Example 194

2,6-dimethyl-4-((9-methyl-2-(2-methyl-1H-benzo[d]imidazol-1-yl)-6-morpholino-9H-purin-8-yl)methyl)morpholine 194

Following the procedures for 157 and General Procedure J, where in Step 1, 4-((2-chloro-9-methyl-6-morpholino-9H-purin-8-yl)methyl)-2,6-dimethylmorpholine and benzene-1,2-diamine were reacted, followed by condensation with acetic acid to give 194. LCMS m/z: 477.2 (MH+)

Example 195

2-(1-((2-(2-isopropyl-1H-benzo[d]imidazol-1-yl)-9-methyl-6-morpholino-9H-purin-8-yl)methyl)piperidin-4-yl)propan-2-ol 195

Following General Procedure I for Buchwald coupling, 2-isopropylbenzimidazole and 2-(1-((2-chloro-9-methyl-6-morpholino-9H-purin-8-yl)methyl)piperidin-4-yl)propan-2-ol were reacted to give 195. LCMS m/z: 533.3 (MH+). 1H-NMR (DMSO-d6): 7.89 (m, 1H), 7.64 (m, 1H), 7.24 (m, 2H), 4.25 (s, br, 4H), 4.00 (s, 1H), 3.92 (m, 1H), 3.81 (s, 3H), 3.77 (t, 4H), 3.73 (s, 2H), 2.91 (d, 2H), 2.00 (t, 2H), 1.67 (t, 2H), 1.35 (d, 6H), 1.22 (m, 3H), 1.02 (s, 6H).

Example 196

2,2-dimethyl-4-((9-methyl-2-(2-methyl-1H-benzo[d]imidazol-1-yl)-6-morpholino-9H-purin-8-yl)methyl)morpholine 196

Following the procedures for 157 and General Procedure J, 4-((2-chloro-9-methyl-6-morpholino-9H-purin-8-yl)methyl)-2,2-dimethylmorpholine and benzene-1,2-diamine were reacted, followed by condensation with acetic acid to give 196. LCMS m/z: 477.2 (MH+)

Example 197

2-(1-((2-(2-(1,1-difluoroethyl)-1H-benzo[d]imidazol-1-yl)-9-methyl-6-morpholino-9H-purin-8-yl)methyl)piperidin-4-yl)propan-2-ol 197

Following the procedures for 157 and General Procedure J, 2-(1-((2-chloro-9-methyl-6-morpholino-9H-purin-8-yl)methyl)piperidin-4-yl)propan-2-ol (1.21 g, 2.96 mmol) and benzene-1,2-diamine were reacted followed by condensation with 2,2-difluoropropionic acid to give 197. LCMS m/z: 555.3 (MH+)

Example 198

I-2-(1-((2-(2-(1-hydroxyethyl)-1H-benzo[d]imidazol-1-yl)-9-methyl-6-morpholino-9H-purin-8-yl)methyl)piperidin-4-yl)propan-2-ol 198

Following the procedures for 157 and General Procedure J, 2-(1-((2-chloro-9-methyl-6-morpholino-9H-purin-8-yl)methyl)piperidin-4-yl)propan-2-ol (1.21 g, 2.96 mmol) and benzene-1,2-diamine were reacted followed by condensation with lactic acid to give a racemic mixture. The enantiomers were separated by SFC to give 198. LCMS m/z: 535.3 (MH+)

Example 199

(S)-2-(1-((2-(2-(1-hydroxyethyl)-1H-benzo[d]imidazol-1-yl)-9-methyl-6-morpholino-9H-purin-8-yl)methyl)piperidin-4-yl)propan-2-ol 199

Following the procedures for 157 and General Procedure J, 2-(1-((2-chloro-9-methyl-6-morpholino-9H-purin-8-yl)methyl)piperidin-4-yl)propan-2-ol (1.21 g, 2.96 mmol) and benzene-1,2-diamine were reacted followed by condensation with lactic acid to give a racemic mixture. The enantiomers were separated by SFC to give 199. LCMS m/z: 535.3 (MH+)

Example 201

2-methyl-2-(4-((2-(8-methylimidazo[1,2-a]pyridin-5-yl)-4-morpholinothieno[3,2-d]pyrimidin-6-yl)methyl)piperazin-1-yl)propanamide 201

A mixture of 2-[4-(4-morpholin-4-yl-2-(tributylstannanyl)-thieno[3,2-d]pyrimidin-6-ylmethyl)piperazin-1-yl]isobutyramide (205 mg, 0.30 mmol), 5-bromo-8-methylimidazo[1,2-a]pyridine (75 mg, 0.35 mmol), Pd(PPh$_3$)$_4$ (34 mg, 0.03 mmol) and copper(I) thiophene-2-carboxylate (11 mg, 0.06 mmol) in dioxane (3 mL) was purged with argon gas then heated at 150° C., for 20 min, in a microwave reactor. The reaction mixture was loaded onto an Isolute® SCX-2 cartridge (10 g). The cartridge was washed with MeOH then the desired product was eluted with 2 M NH$_3$ in MeOH. The resulting residue was purified by flash chromatography (Si—PPC, MeOH:DCM, gradient 0:100 to 10:90) to give a solid that was triturated in MeOH, filtered and dried at 60° C. under vacuum for 24 hours to give 201 as a white solid (97 mg, 62%). LCMS (Method G) R$_T$ 5.11 min; [M+H]$^+$ 535. $^1$H NMR (400 MHz, CHCl$_3$-d): δ 9.29 (s, 1 H); 7.93 (d, J=7.3 Hz, 1 H); 7.75 (s, 1 H); 7.37 (s, 1 H); 7.15 (d, J=7.3 Hz, 1 H); 7.13-6.96 (m, 1 H); 5.21 (s, 1 H); 4.06 (t, J=4.7 Hz, 4 H); 3.91 (t, J=4.7 Hz, 4 H); 3.86 (s, 2 H); 2.73 (s, 3 H); 2.62 (s, 8 H); 1.25 (s, 6 H)

Example 202

2-(4-((2-(imidazo[1,5-a]pyridin-8-yl)-4-morpholinothieno[3,2-d]pyrimidin-6-yl)methyl)piperazin-1-yl)-2-methylpropanamide 202

A mixture of 2-[4-(4-morpholin-4-yl-2-(tributylstannanyl)thieno[3,2-d]pyrimidin-6-ylmethyl)piperazin-1-yl]isobutyramide (132 mg, 0.19 mmol), 8-bromoimidazo[1,5-a]pyridine (45 mg, 0.23 mmol), Pd(PPh$_3$)$_4$ (22 mg, 0.02 mmol) and copper(I) thiophene-2-carboxylate (7 mg, 0.04 mmol) in dioxane (2 mL) was purged with argon gas then heated at 150° C., for 20 min, in a microwave reactor. The reaction mixture was loaded onto an Isolute® SCX-2 cartridge (10 g). The cartridge was washed with MeOH then the desired product eluted with 2 M NH$_3$ in MeOH. The resulting residue was purified by flash chromatography (Si—PPC, MeOH:DCM, gradient 0:100 to 10:90) to give 202 as a yellow solid (72 mg, 73%). LCMS (Method G): R$_T$ 5.12 min; [M+H]$^+$ 521. $^1$H NMR (400 MHz, CHCl$_3$-d): δ 8.33 (s, 1 H); 8.21 (s, 1 H); 8.04 (d, J=6.9 Hz, 1 H); 7.93 (d, J=6.9 Hz, 1 H); 7.36 (s, 1 H); 7.07 (m, 1 H); 6.74-6.69 (m, 1 H); 5.19 (s, 1 H); 4.07 (t, J=4.7 Hz, 4 H); 3.96-3.86 (m, 4 H); 3.88-3.83 (m, 2 H); 2.61 (s, 8 H); 1.25 (s, 6 H)

Example 203

2-methyl-N-((2-(2-methyl-1H-benzo[d]imidazol-1-yl)-4-morpholinothieno[3,2-d]pyrimidin-6-yl)methyl)-2-morpholinopropan-1-amine 203

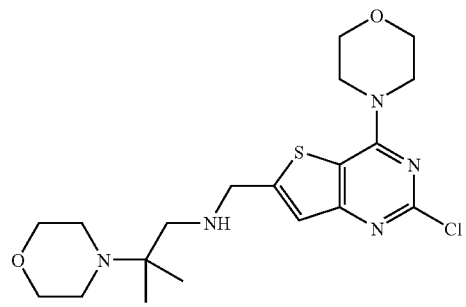

Following the procedures for 172, 2-chloro-4-morpholin-4-yl-thieno[3,2-d]pyrimidine-6-carbaldehyde and 2-methyl-2-morpholinopropan-1-amine were reacted by reductive amination to give N-((2-chloro-4-morpholinothieno[3,2-d]pyrimidin-6-yl)methyl)-2-methyl-2-morpholinopropan-1-amine, which was converted to the 2-tributylstannyl intermediate and reacted with 2-methyl-1H-benzo[d]imidazole to give 203. LCMS m/z: 522.2 (MH+)

Example 204

4-(6-((3,4-dihydroisoquinolin-2(1H)-yl)methyl)-2-(2-methyl-1H-benzo[d]imidazol-1-yl)thieno[3,2-d]pyrimidin-4-yl)morpholine 204

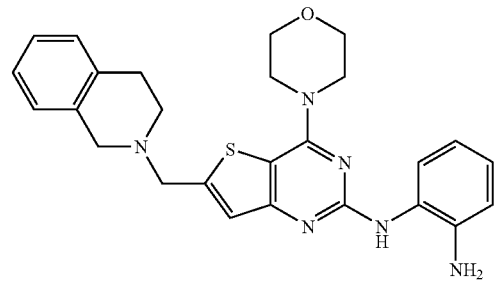

Following General Procedure J for Multi-Step Benzimidazole Formation by Buchwald coupling, 4-(2-chloro-6-((3,4-dihydroisoquinolin-2(1H)-yl)methyl)thieno[3,2-d]pyrimidin-4-yl)morpholine and 1,2-diaminobenzene were reacted to give N1-(6-((3,4-dihydroisoquinolin-2(1H)-yl)methyl)-4-morpholinothieno[3,2-d]pyrimidin-2-yl)benzene-1,2-diamine which was cyclized with acetic acid to give 204. LCMS m/z: 497.6 (MH+)

Example 205

2-(1-((2-(2-(benzyl(methyl)amino)-1H-benzo[d]imidazol-1-yl)-9-methyl-6-morpholino-9H-purin-8-yl)methyl)piperidin-4-yl)propan-2-ol 205

Following General Procedure I for Buchwald coupling, 2-(1-((2-chloro-9-methyl-6-morpholino-9H-purin-8-yl)methyl)piperidin-4-yl)propan-2-ol and 2-(benzylmethylamino)benzimidazole were reacted to give 205. LCMS m/z: 610.4 (MH+)

Example 206

2-(1-((9-methyl-2-(2-(methylamino)-1H-benzo[d]imidazol-1-yl)-6-morpholino-9H-purin-8-yl)methyl)piperidin-4-yl)propan-2-ol 206

A mixture of 2-(1-((2-(2-(benzyl(methyl)amino)-1H-benzo[d]imidazol-1-yl)-9-methyl-6-morpholino-9H-purin-8-yl)methyl)piperidin-4-yl)propan-2-ol 205 (0.2 g, 0.33 mmol) and palladium on carbon (10 wt %, 0.1 g) and acetic acid (0.1 mL) in ethanol (10 mL) was stirred under a hydrogen atmosphere at 60 degrees for 18 hours. The reaction mixture was then filtered though celite and concentrated. The crude product was purified by RP-HPLC to give 206 (28.5 mg, 17%). LCMS m/z: 520.3 (MH+)

Example 207

2-(1-((9-methyl-6-morpholino-2-(2-phenyl-1H-benzo[d]imidazol-1-yl)-9H-purin-8-yl)methyl)piperidin-4-yl)propan-2-ol 207

Following General Procedure I for Buchwald coupling, 2-(1-((2-chloro-9-methyl-6-morpholino-9H-purin-8-yl)methyl)piperidin-4-yl)propan-2-ol and 2-phenylbenzimidazole were reacted to give 207. LCMS m/z: 567.3 (MH+)

Example 208

1-(3-(6-((4-(dimethylamino)piperidin-1-yl)methyl)-4-morpholinothieno[3,2-d]pyrimidin-2-yl)benzo[b]thiophen-2-yl)ethanone 208

Following General Procedure G for Stille coupling, N,N-dimethyl-1-((4-morpholino-2-(tributylstannyl)thieno[3,2-d]pyrimidin-6-yl)methyl)piperidin-4-amine and 1-(3-bromobenzo[b]thiophen-2-yl)ethanone were reacted to give 208. LCMS m/z: 536.7 (MH+)

Example 209

2-(1-((5-(1H-indazol-3-yl)-7-morpholinothiazolo[5,4-d]pyrimidin-2-yl)methyl)piperidin-4-yl)propan-2-ol 209

A mixture of 2-(1-((7-morpholino-5-(tributylstannyl)thiazolo[5,4-d]pyrimidin-2-yl)methyl)piperidin-4-yl)propan-2-ol (0.211 g, 0.32 mmol), 3-iodo-1H-indazole (0.116 g, 0.48 mmol), copper(I) 2-thiophene carboxylate (0.012 g, 0.064 mmol) and Pd(PPh$_3$)$_4$ (0.037 g, 0.032 mmol) in dioxane (3 mL) was subjected to microwave irradiation at 150° C. for 90 min. The reaction mixture was loaded onto an Isolute® SCX-2 cartridge. The cartridge was washed with MeOH and the desired product was eluted using 2 M NH$_3$ in MeOH. The eluent was concentrated in vacuo and the resultant residue was purified by flash chromatography (Si—PPC, MEOH:DCM, gradient 0:100 to 10:90) to give 209 as a yellow solid (0.043 g, 28%). LCMS (Method G): R$_T$=7.71 min, [M+H]$^+$ 494.3. $^1$H NMR (400 MHz, DMSO-d): δ 13.45 (s, 1 H); 8.48 (d, J=8.3 Hz, 1 H); 7.61 (d, J=8.3 Hz, 1 H); 7.41 (t, J=7.6 Hz, 1 H); 7.26 (t, J=7.6 Hz, 1 H); 4.37 (m, 4 H); 3.88 (s, 2 H); 3.82 (t, J=4.6 Hz, 4 H); 3.02 (d, J=11.0 Hz, 2 H); 2.12 (t, J=11.0 Hz, 2 H); 1.74-1.69 (m, 2 H); 1.36-1.28 (m, 2 H); 1.26-1.23 (m, 2 H); 1.06 (s, 6 H)

Example 210

2-(1-((5-(2-methylbenzofuran-3-yl)-7-morpholinothiazolo[5,4-d]pyrimidin-2-yl)methyl)piperidin-4-yl)propan-2-ol 210

A mixture of 2-[1-(5-chloro-7-morpholin-4-ylthiazolo[5,4-d]pyrimidin-2-ylmethyl)-piperidin-4-yl]propan-2-ol (50 mg, 0.12 mmol), 2-methyl-3-(4,4,5,5-tetramethyl-[1,3,2]dioxaborolan-2-yl)benzofuran (47 mg, 0.18 mmol), tetrakis(triphenylphosphine) palladium (14 mg, 0.01 mmol) and Cs$_2$CO$_3$ (80 mg, 0.24 mmol) in dioxane (3 mL) and H$_2$O (1.5 mL) was purged with argon then heated at 140° C. for 30 min in a microwave reactor. The reaction mixture was loaded onto an Isolute® SCX-2 cartridge which was washed with DCM/MeOH and the product eluted with 2M NH$_3$/MeOH. The resulting residue was purified by column chromatography (Si—PCC, EtOAc:cyclohexane, 0-90%) to afford 210 as a white solid (29 mg, 48%). LCMS (Method G): R$_T$ 10.16 min, [M+H]$^+$ 508.4. $^1$H NMR (CDCl$_3$, 400 MHz): δ 8.40-8.37 (m, 1 H); 7.45-7.40 (m, 1 H); 7.32-7.24 (m, 2 H); 4.40 (m, 4 H); 3.94-3.84 (m, 6 H); 3.11 (m, 2 H); 2.92 (s, 3 H); 2.21 (m, 2 H); 1.78 (m, 2 H); 1.48 (m, 2 H) and 1.21 (m, 7 H)

Example 211

2-methyl-2-(4-((5-(2-methylbenzofuran-3-yl)-7-morpholinothiazolo[5,4-d]pyrimidin-2-yl)methyl)piperazin-1-yl)propanamide 211

A mixture of 1-amino-2-[4-(5-chloro-7-morpholin-4-ylthiazolo[5,4-d]pyrimidin-2-ylmethyl)piperazin-1-yl]-2-methylpropan-1-ol (100 mg, 0.23 mmol), 2-methyl-3-(4,4,5,5-tetramethyl-[1,3,2]dioxaborolan-2-yl)benzofuran (88 mg, 0.34 mmol), tetrakis(triphenylphosphine)palladium (26 mg, 0.02 mmol) and Cs$_2$CO$_3$ (148 mg, 0.45 mmol) in dioxane (6 mL) and H$_2$O (3 mL) was purged with argon then heated at 140° C. for 30 min in a microwave reactor. The reaction mixture was loaded onto an Isolute® SCX-2 cartridge which was washed with DCM/MeOH and the product eluted with 2M NH$_3$/MeOH. The resulting residue was purified by column chromatography (Si—PCC, EtOAc:cyclohexane, 50-100%) to afford 211 as a cream solid (75 mg, 61%). LCMS (Method G): R$_T$ 10.35 min, [M+H]$^+$ 536.4. $^1$H NMR (CDCl$_3$, 400 MHz): δ 8.40-8.37 (m, 1 H); 7.46-7.42 (m, 1 H); 7.32-7.23 (m, 2 H); 7.10 (d, J=5.3 Hz, 1 H); 5.22 (d, J=5.3 Hz, 1 H); 4.40 (m, 4 H); 3.93-3.87 (m, 6 H); 2.92 (s, 3 H); 2.69 (m, 4 H); 2.62 (m, 4 H) and 1.26 (s, 6 H)

Example 212

4-(5-(2-methylbenzofuran-3-yl)-2-((3-morpholinoazetidin-1-yl)methyl)thiazolo[5,4-d]pyrimidin-7-yl)morpholine 212

A mixture of 5-chloro-7-morpholin-4-yl-2-(3-morpholin-4-ylazetidin-1-ylmethyl)thiazolo[5,4-d]pyrimidine (100 mg, 0.24 mmol), 2-methyl-3-(4,4,5,5-tetramethyl-[1,3,2]dioxaborolan-2-yl)benzofuran (94 mg, 0.37 mmol), tetrakis(triphenylphosphine)palladium (28 mg, 0.02 mmol) and $Cs_2CO_3$ (159 mg, 0.48 mmol) in dioxane (6 mL) and $H_2O$ (3 mL) was purged with argon then heated at 140° C. for 30 min in a microwave reactor. The reaction mixture was loaded onto an Isolute® SCX-2 cartridge which was washed with DCM/MeOH and the product eluted with 2M $NH_3$/MeOH. The resulting residue was purified by column chromatography (Si—PCC, MeOH:EtOAc, 0-5%) to afford 212 as a cream solid (58 mg, 48%). LCMS (Method G): $R_T$ 9.83 min, $[M+H]^+$ 507.3. $^1H$ NMR ($CDCl_3$, 400 MHz): δ 8.39-8.36 (m, 1 H); 7.45-7.42 (m, 1 H); 7.32-7.24 (m, 2 H); 4.40 (m, 4 H); 4.01 (s, 2 H); 3.89 (m, 4 H); 3.70 (m, 6 H); 3.18-3.08 (m, 3 H); 2.92 (s, 3H) and 2.36 (m, 4 H)

Example 213

4-(1-((2-(2-methylbenzofuran-3-yl)-4-morpholinothieno[3,2-d]pyrimidin-6-yl)methyl)azetidin-3-yl)morpholine 213

A mixture of 2-chloro-4-morpholin-4-yl-6-(3-morpholin-4-ylazetidin-1-ylmethyl)thieno[3,2-d]pyrimidine (100 mg, 0.24 mmol), 2-methyl-3-(4,4,5,5-tetramethyl-[1,3,2]dioxaborolan-2-yl)benzofuran (94 mg, 0.36 mmol), tetrakis(triphenylphosphine)palladium (28 mg, 0.02 mmol) and $Cs_2CO_3$ (160 mg, 0.48 mmol) in dioxane (6 mL) and $H_2O$ (3 mL) was purged with argon then heated at 140° C. for 30 min in a microwave reactor. The reaction mixture was loaded onto an Isolute® SCX-2 cartridge, washed with DCM/MeOH then eluted with 2M $NH_3$/MeOH. The resulting residue was purified by column chromatography (Si—PCC, MeOH:DCM, 0-5%) to afford 213 as a white foam (98 mg, 81%). LCMS (Method G): $R_T$ 9.09 min, $[M+H]^-$ 506.3. $^1H$ NMR ($CDCl_3$, 400 MHz): δ 8.42-8.39 (m, 1 H); 7.46-7.42 (m, 1 H); 7.32-7.24 (m, 3 H); 4.02 (t, J=4.7 Hz, 4H); 3.97 (s, 2 H); 3.89 (t, J=4.7 Hz, 4 H); 3.73 (m, 4 H); 3.63 (s, 2 H); 3.06 (m, 3 H); 2.93 (s, 3 H) and 2.33 (m, 4 H)

Example 214

2-(4-((2-(6-fluoroimidazo[1,2-a]pyridin-5-yl)-4-morpholinothieno[3,2-d]pyrimidin-6-yl)methyl)piperazin-1-yl)-2-methylpropanamide 214

A mixture of 2-[4-(4-morpholin-4-yl-2-(tributylstannanyl)thieno[3,2-d]pyrimidin-6-ylmethyl)piperazin-1-yl]isobutyramide (69 mg, 0.10 mmol), 5-bromo-6-fluoro-imidazo[1,2-a]pyridine (25 mg, 0.12 mmol), $Pd(PPh_3)_4$ (12 mg, 0.01 mmol) and copper(I) thiophene-2-carboxylate (4 mg, 0.02 mmol) in dioxane (1 mL) was purged with argon gas then heated at 150° C., for 20 min, in a microwave reactor. The reaction mixture was loaded onto an Isolute® SCX-2 cartridge (10 g), washed with MeOH then eluted with 2 M $NH_3$ in MeOH. The resulting residue was purified by flash chromatography (Si—PPC, MeOH:DCM, gradient 0:100 to 10:90) followed by reverse phase HPLC (Phenomenex Gemini 5u C18, 20 mM triethylamine in water on a gradient of acetonitrile 95:5 to 2:98) to give 214 as a white solid (20 mg, 37%). LCMS (Method G) $R_T$ 4.52 min; $[M+H]^+$ 539. $^1H$ NMR (400 MHz, $CHCl_3$-d): 8.20 (s, 1 H); 7.71-7.62 (m, 2 H); 7.35 (s, 1 H); 7.25-7.16 (t, J=9.5 Hz, 1 H); 7.18-6.91 (m, 1 H); 5.22 (s, 1 H); 4.05 (t, J=4.7 Hz, 4 H); 3.87 (t+m, J=4.7 Hz, 6 H); 2.62 (s, 8 H); 1.25 (s, 6 H)

Example 215

2-(4-((2-(1H-indazol-3-yl)-4-morpholinothieno[3,2-d]pyrimidin-6-yl)methyl)piperazin-1-yl)-2-methylpropanamide 215

Following General Procedure G for Stille coupling, 2-methyl-2-(4-((4-morpholino-2-(tributylstannyl)thieno[3,2-d]pyrimidin-6-yl)methyl)piperazin-1-yl)propanamide and 3-bromo-1H-indazole were reacted to give 215. LCMS m/z: 521.6 (MH+)

Example 216

N,N-dimethyl-1-((4-morpholino-2-(1H-pyrrolo[2,3-c]pyridin-3-yl)thieno[3,2-d]pyrimidin-6-yl)methyl)piperidin-4-amine 216

Following General Procedure G for Stille coupling, N,N-dimethyl-1-((4-morpholino-2-(tributylstannyl)thieno[3,2-d]pyrimidin-6-yl)methyl)piperidin-4-amine and 3-bromo-1H-pyrrolo[2,3-c]pyridine were reacted to give 216. LCMS m/z: 478.6 (MH+)

Example 217

4-(6-((4-(dimethylamino)piperidin-1-yl)methyl)-4-morpholinothieno[3,2-d]pyrimidin-2-yl)isoquinolin-1(2H)-one 217

Following General Procedure G for Stille coupling, N,N-dimethyl-1-((4-morpholino-2-(tributylstannyl)thieno[3,2-d]pyrimidin-6-yl)methyl)piperidin-4-amine and 4-bromoisoquinolin-1(2H)-one were reacted to give 217. LCMS m/z: 505.7 (MH+)

Example 218

2-(1-((2-(2-(2-hydroxyethyl)-1H-benzo[d]imidazol-1-yl)-9-methyl-6-morpholino-9H-purin-8-yl)methyl)piperidin-4-yl)propan-2-ol 218

Following General Procedure I for Buchwald coupling, 2-(1-((2-chloro-9-methyl-6-morpholino-9H-purin-8-yl)methyl)piperidin-4-yl)propan-2-ol and 2-(1H-benzo[d]imidazol-2-yl)ethanol were reacted to give 218. LCMS m/z: 535.3 (MH+)

Example 219

2-(1-((9-methyl-6-morpholino-2-(2-(pyridin-3-yl)-1H-benzo[d]imidazol-1-yl)-9H-purin-8-yl)methyl)piperidin-4-yl)propan-2-ol 219

Following General Procedure I for Buchwald coupling, 2-(1-((2-chloro-9-methyl-6-morpholino-9H-purin-8-yl)methyl)piperidin-4-yl)propan-2-ol and 2-(pyridin-3-yl)-1H-benzo[d]imidazole were reacted to give 219. LCMS m/z: 568.3 (MH+)

Example 220

1-(8-((4-(2-hydroxypropan-2-yl)piperidin-1-yl)methyl)-9-methyl-6-morpholino-9H-purin-2-yl)-2-methyl-1H-indazol-3(2H)-one 220

Following General Procedure I for Buchwald coupling, 2-(1-((2-chloro-9-methyl-6-morpholino-9H-purin-8-yl)methyl)piperidin-4-yl)propan-2-ol and 2-methyl-1,2-dihydroindazol-3-one were reacted to give 220. LCMS m/z: 521.3 (MH+)

Example 221

4-(6-(((6-fluoro-3,4-dihydroisoquinolin-2(1H)-yl)methyl)-2-(2-methyl-1H-benzo[d]imidazol-1-yl)thieno[3,2-d]pyrimidin-4-yl)morpholine 221

Following General Procedure L for reductive amination, 2-(2-methyl-1H-benzo[d]imidazol-1-yl)-4-morpholinothieno[3,2-d]pyrimidine-6-carbaldehyde and 6-fluoro-1,2,3,4-tetrahydroisoquinoline were reacted to give 221. LCMS m/z: 515.6 (MH+)

Example 222

2-(1-((2-(imidazo[1,5-a]pyridin-8-yl)-9-methyl-6-morpholino-9H-purin-8-yl)methyl)piperidin-4-yl)propan-2-ol 222

A mixture of 2-[1-(9-methyl-6-morpholin-4-yl-2-(tributylstannanyl)-9H-purin-8-ylmethyl)piperidin-4-yl]propan-2-ol (135 mg, 0.20 mmol), 8-bromoimidazo[1,5-a]pyridine (44 mg, 0.22 mmol), Pd(PPh$_3$)$_4$ (24 mg, 10 mol %) and copper(I)-thiophene-2-carboxylate (8 mg, 20 mol %) in dioxane (2 mL) was purged with argon gas then heated at 150° C., for 20 min, in a microwave reactor. The reaction mixture was loaded onto an Isolute® SCX-2 cartridge, washed with MeOH then the desired product eluted with 2 M NH$_3$ in MeOH. The resulting residue was purified by column chromatography (Si—PCC, 0-10% MeOH in DCM) to give 222 as a yellow solid (58 mg, 58%). LCMS (Method G): R$_T$=4.86 min, [M+H]$^+$ 491.4. $^1$H NMR (400 MHz, CHCl$_3$-d): δ 8.42 (s, 1 H), 8.19 (s, 1 H), 8.02 (d, J=6.9 Hz, 1H), 7.95 (dd, J=6.9, 0.9 Hz, 1 H), 6.74-6.67 (m, 1 H), 4.38 (m, 4 H), 3.96 (s, 3 H), 3.91-3.87 (m, 4 H), 3.80-3.66 (m, 2 H), 2.97 (d, J=11.0 Hz, 2 H), 2.22-1.99 (m, 2 H), 1.75 (d, J=11.0 Hz, 2 H), 1.44-1.26 (m, 4 H), 1.20-1.17 (s, 6 H)

Example 223

2-(1-((5-(2-methyl-1H-benzo[d]imidazol-1-yl)-7-morpholinothiazolo[5,4-d]pyrimidin-2-yl)methyl)piperidin-4-yl)propan-2-ol 223

A 5-20 mL microwave vial equipped with a magnetic follower was charged with Pd$_2$(dba)$_3$ (28 mg, 0.03 mmol), Xphos (58 mg, 0.12 mmol), 2-[1-(5-chloro-7-morpholin-4-ylthiazolo[5,4-d]pyrimidin-2-ylmethyl)piperidin-4-yl]propan-2-ol (500 mg, 1.21 mmol), 2-methyl-1H-benzoimidazole (176 mg, 1.33 mmol), cesium carbonate (593 mg, 1.82 mmol) and dioxane (5 mL). The reaction mixture was degassed for 5 min and irradiated at 150° C. for 30 min. The reaction mixture was diluted with MeOH and loaded onto an Isolute® SCX-2 cartridge (25 g). The cartridge was washed with MeOH and the desired product was eluted with 2M NH$_3$ in MeOH. The solvents were removed and the residue was subjected to flash chromatography (Si—PCC, 0-10% (2M NH$_3$ in MeOH) in EtOAc) to give 223 as a red oil (290 mg, 47%). LCMS: (Method G): R$_T$ 6.76 min; [M+H]$^+$ 508.4. $^1$H NMR (400 MHz, CHCl$_3$-d): δ 8.10-8.05 (m, 1 H); 7.73-7.69 (m, 1 H); 7.32-7.26 (m, 2 H); 4.42 (m 4 H); 3.88 (t, J=4.6 Hz, 7 H); 3.11 (d, J=10.7 Hz, 2 H); 2.95 (s, 3 H); 2.31-2.19 (m, 2 H); 1.79 (d, J=12.7 Hz, 2 H); 1.50 (m, 2 H); 1.34 (m, 1 H); 1.22 (s, 6 H)

Example 224

2-(1-((9-methyl-6-morpholino-2-(2-(tetrahydrofuran-2-yl)-1H-benzo[d]imidazol-1-yl)-9H-purin-8-yl)methyl)piperidin-4-yl)propan-2-ol 224

Following General Procedure I for Buchwald coupling, 2-(1-((2-chloro-9-methyl-6-morpholino-9H-purin-8-yl)methyl)piperidin-4-yl)propan-2-ol and 2-(tetrahydrofuran-2-yl)-1H-benzimidazole were reacted to give 224. LCMS m/z: 561.3 (MH+)

Example 225

2-(1-((2-(3-fluoroquinolin-4-yl)-9-methyl-6-morpholino-9H-purin-8-yl)methyl)piperidin-4-yl)propan-2-ol 225

Following the procedure for 165, 2-[1-(9-methyl-6-morpholin-4-yl-2-(tributylstannanyl)-9H-purin-8-ylmethyl)piperidin-4-yl]propan-2-ol and 3-fluoro-4-iodoquinoline were reacted to give 225. LCMS m/z: 520.2 (MH+)

Example 226

(3R,4S)-1-((2-(2-ethyl-1H-benzo[d]imidazol-1-yl)-9-methyl-6-morpholino-9H-purin-8-yl)methyl)-3-fluoro-N,N-dimethylpiperidin-4-amine 226

Following General Procedure I for Buchwald coupling, racemic 1-((2-chloro-9-methyl-6-morpholino-9H-purin-8-yl)methyl)-3-fluoro-N,N-dimethylpiperidin-4-amine and 2-ethylbenzimidazole were reacted. The enantiomers were separated by SFC to give 226. LCMS m/z: 522.3 (MH+)

Example 227

(3S,4R)-1-((2-(2-ethyl-1H-benzo[d]imidazol-1-yl)-9-methyl-6-morpholino-9H-purin-8-yl)methyl)-3-fluoro-N,N-dimethylpiperidin-4-amine 227

Following General Procedure I for Buchwald coupling, racemic 1-((2-chloro-9-methyl-6-morpholino-9H-purin-8-yl)methyl)-3-fluoro-N,N-dimethylpiperidin-4-amine and 2-ethylbenzimidazole were reacted. The enantiomers were separated by SFC to give 227. LCMS m/z: 522.3 (MH+)

Example 228

N,N-dimethyl-1-((2-(3-methylisoquinolin-4-yl)-4-morpholinothieno[3,2-d]pyrimidin-6-yl)methyl)piperidin-4-amine 228

Following General Procedure G for Stille coupling, N,N-dimethyl-1-((4-morpholino-2-(tributylstannyl)thieno[3,2-d]pyrimidin-6-yl)methyl)piperidin-4-amine and 4-bromo-3-methylisoquinoline were reacted to give 228. LCMS m/z: 503.7 (MH+)

Example 229

N,N-dimethyl-1-((2-(2-methylbenzo[b]thiophen-3-yl)-4-morpholinothieno[3,2-d]pyrimidin-6-yl)methyl)piperidin-4-amine 229

Following General Procedure G for Stille coupling, N,N-dimethyl-1-((4-morpholino-2-(tributylstannyl)thieno[3,2-d]

pyrimidin-6-yl)methyl)piperidin-4-amine and 3-bromo-2-methylbenzo[b]thiophene were reacted to give 229. LCMS m/z: 508.7 (MH+)

Example 230

2-methyl-2-(4-((7-methyl-2-(2-methyl-1H-benzo[d]imidazol-1-yl)-4-morpholinothieno[3,2-d]pyrimidin-6-yl)methyl)piperazin-1-yl)propanamide 230

Following General Procedure I for Buchwald coupling, 2-(4-((2-chloro-7-methyl-4-morpholinothieno[3,2-d]pyrimidin-6-yl)methyl)piperazin-1-yl)-2-methylpropanamide and 2-methyl-1H-benzo[d]imidazole were reacted to give 230. LCMS: M+H$^+$=549.3

Example 231

2-(1-((7-methyl-2-(2-methyl-1H-benzo[d]imidazol-1-yl)-4-morpholinothieno[3,2-d]pyrimidin-6-yl)methyl)piperidin-4-yl)propan-2-ol 231

2-(4-((2-chloro-7-methyl-4-morpholinothieno[3,2-d]pyrimidin-6-yl)methyl)piperazin-1-yl)-2-methylpropanamide was reduced to give 2-(1-((2-chloro-7-methyl-4-morpholinothieno[3,2-d]pyrimidin-6-yl)methyl)piperidin-4-yl)propan-2-ol which was reacted with 2-methyl-1H-benzo[d]imidazole following General Procedure I for Buchwald coupling to give 231. LCMS: M+H$^+$=521.3

Example 232

4-(1-((7-methyl-2-(2-methyl-1H-benzo[d]imidazol-1-yl)-4-morpholinothieno[3,2-d]pyrimidin-6-yl)methyl)piperidin-4-yl)morpholine 232

Following General Procedure I for Buchwald coupling, 4-(1-((2-chloro-7-methyl-4-morpholinothieno[3,2-d]pyrimidin-6-yl)methyl)piperidin-4-yl)morpholine and 2-methyl-1H-benzo[d]imidazole were reacted to give 232. LCMS: M+H$^+$=548.3

Example 233

2-(1-((9-methyl-6-morpholino-2-(2-propyl-1H-benzo[d]imidazol-1-yl)-9H-purin-8-yl)methyl)piperidin-4-yl)propan-2-ol 233

Following General Procedure I for Buchwald coupling, 2-(1-((2-chloro-9-methyl-6-morpholino-9H-purin-8-yl)methyl)piperidin-4-yl)propan-2-ol and 2-propylbenzimidazole were reacted to give 233. LCMS m/z: 533.3 (MH+)

Example 234

2-(4-((2-(3-methoxy-1H-indazol-1-yl)-4-morpholinothieno[3,2-d]pyrimidin-6-yl)methyl)piperazin-1-yl)-2-methylpropanamide 234

2-(4-((2-Chloro-4-morpholinothieno[3,2-d]pyrimidin-6-yl)methyl)piperazin-1-yl)-2-methylpropanamide (0.1 g) was reacted with 3-methoxy-1H-indazole via General Procedure I for Buchwald coupling give 16.4 mg 234 following reverse phase purification. MS (Q1) 507.2 (M)+

Example 235

2-(1-((2-(3-methoxy-1H-indazol-1-yl)-9-methyl-6-morpholino-9H-purin-8-yl)methyl)piperidin-4-yl)propan-2-ol 235

2-(1-((2-Chloro-9-methyl-6-morpholino-9H-purin-8-yl)methyl)piperidin-4-yl)propan-2-ol (0.2 g) was reacted with 3-methoxy-1H-indazole via General Procedure I for Buchwald coupling to give 119.5 mg 235 following reverse phase purification. MS (Q1) 521.3 (M)+

Example 236

2-(1-((9-ethyl-2-(2-methyl-1H-benzo[d]imidazol-1-yl)-6-morpholino-9H-purin-8-yl)methyl)piperidin-4-yl)propan-2-ol 236

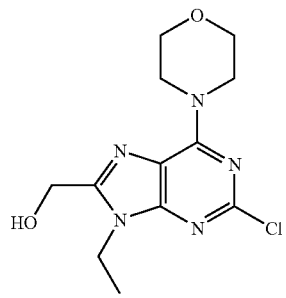

A solution of 2-chloro-9-ethyl-6-morpholino-9H-purine-8-carbaldehyde (2.4 g) in MeOH (200 mL) at 0° C. was treated portion wise with sodium borohydride (0.84 g). The reaction was warmed to room temperature and stirred 15 minutes. The reaction mixture was quenched with saturated solution of sodium bicarbonate. The aqueous layer was extracted twice with ethyl acetate. The combined organic layers were dried over magnesium sulfate and concentrated in vacuo to yield crude (2-chloro-9-ethyl-6-morpholino-9H-purin-8-yl)methanol (2.3 g) as a white solid.

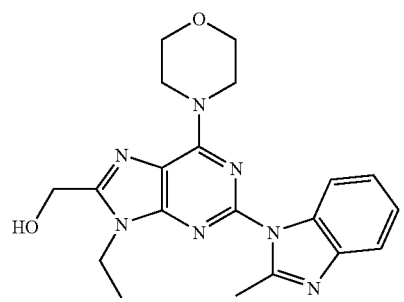

(2-chloro-9-ethyl-6-morpholino-9H-purin-8-yl)methanol (2.3 g) was reacted with 2-methylbenzimidazole via General Procedure I for Buchwald coupling. The crude product (9-ethyl-2-(2-methyl-1H-benzo[d]imidazol-1-yl)-6-morpholino-9H-purin-8-yl)methanol (3g) was obtained after concentration of the reaction mixture and filtration after addition of water.

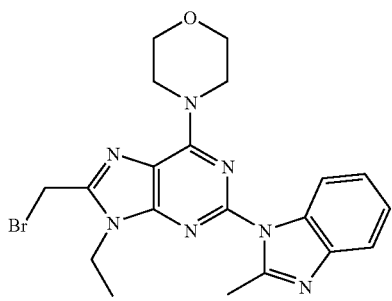

To a solution of (9-ethyl-2-(2-methyl-1H-benzo[d]imidazol-1-yl)-6-morpholino-9H-purin-8-yl)methanol (3 g, 7.65 mmol) in tetrahydrofuran (150 mL, 1800 mmol) was added phosphorus tribromide (1.44 mL, 15.3 mmol;) dropwise. The mixture was stirred for 2 hrs until LC/MS showed the reaction was complete. The reaction was quenched with MeOH and extracted with Ethyl acetate and water. The organic layer was collected, dried with Magnesium sulfate, filtered and concentrated to give a crude orange oil. The oil was purified by flash chromatography to give 2.6 g of 4-(8-(bromomethyl)-9-ethyl-2-(2-methyl-1H-benzo[d]imidazol-1-yl)-9H-purin-6-yl)morpholine as an orange solid, of which 50 mg was reacted with 2-(piperidin-4-yl)propan-2-ol via Gen Procedure E to give 34.6 mg 236 following reverse phase purification. MS (Q1) 519.3 (M)+

Example 237

2-(1-((2-(2-cyclobutyl-1H-benzo[d]imidazol-1-yl)-9-methyl-6-morpholino-9H-purin-8-yl)methyl)piperidin-4-yl)propan-2-ol 237

Following General Procedure I for Buchwald coupling, 2-(1-((2-chloro-9-methyl-6-morpholino-9H-purin-8-yl)methyl)piperidin-4-yl)propan-2-ol and 2-cyclobutylbenzimidazole were reacted to give 237. LCMS m/z: 545.3 (MH+)

Example 238

2-(1-((9-methyl-6-morpholino-2-(2-morpholino-1H-benzo[d]imidazol-1-yl)-9H-purin-8-yl)methyl)piperidin-4-yl)propan-2-ol 238

Following General Procedure I for Buchwald coupling, 2-(1-((2-chloro-9-methyl-6-morpholino-9H-purin-8-yl)methyl)piperidin-4-yl)propan-2-ol and 4-(1H-benzo[d]imidazol-2-yl)morpholine were reacted to give 238. LCMS m/z: 576.4 (MH+)

Example 240

2-methyl-2-(4-((2-(2-methyl-1H-benzo[d]imidazol-1-yl)-4-morpholinofuro[3,2-d]pyrimidin-6-yl)methyl)piperazin-1-yl)propanamide 240

A mixture of 2-[4-(2-chloro-4-morpholin-4-ylfuro[3,2-d]pyrimidin-6-ylmethyl)piperazin-1-yl]isobutyramide (500 mg, 1.18 mmol), 2-methyl-1H-benzoimidazole (180 mg, 1.36 mmol), Pd$_2$dba$_3$ (27 mg, 0.029 mmol), Xphos (57 mg, 0.12 mmol) and cesium carbonate (580 mg, 1.78 mmol) in 1,4-dioxane (10 mL) was heated at 110° C. for 18 h. The reaction mixture was cooled to ambient temperature, then loaded onto an Isolute® SCX-2 cartridge, which was washed with MeOH/DCM before the desired product was eluted with 2 M NH$_3$ in MeOH/DCM. The product was collected and concentrated in vacuo. The resultant residue was purified by flash chromatography (Si—PPC, EtOAc:MeOH; gradient from 100:0 to 70:30) followed by trituration from hot EtOAc to afford 240 as a white solid (408 mg, 67%). LCMS (Method G): R$_T$=5.23 min, M+H$^+$=519. $^1$H NMR (CDCl$_3$, 400 MHz) δ 8.03-7.98 (m, 1 H); 7.73-7.69 (m, 1 H); 7.28-7.23 (m, 2 H); 7.05 (bs, 1 H); 6.76 (s, 1 H); 5.27 (bs, 1 H); 4.08 (t, J=4.7 Hz, 4 H); 3.89 (t, J=4.7 Hz, 4 H); 3.76 (s, 2 H); 2.90 (s, 3 H); 2.62 (m, 8 H) and 1.24 (s, 6 H)

Example 241

2-(1-((2-(2-methyl-1H-benzo[d]imidazol-1-yl)-4-morpholinofuro[3,2-d]pyrimidin-6-yl)methyl)piperidin-4-yl)propan-2-ol 241

A mixture of 2-[1-(2-chloro-4-morpholin-4-ylfuro[3,2-d]pyrimidin-6-ylmethyl)piperidin-4-yl]propan-2-ol (110 mg, 0.28 mmol), 2-methyl-1H-benzoimidazole (42 mg, 0.32 mmol), Pd$_2$dba$_3$ (14 mg, 0.015 mmol), Xphos (15 mg, 0.031 mmol) and cesium carbonate (203 mg, 0.62 mmol) in DMF (2.5 mL) was purged with argon gas then subjected to microwave irradiation at 145° C. for 30 min. The reaction mixture was loaded onto an Isolute® SCX-2 cartridge, which was washed with MeOH/DCM before the desired product was eluted with 2 M NH$_3$ in MeOH/DCM. The product was collected and concentrated in vacuo. The resultant residue was purified by flash chromatography (Si—PPC, DCM:MeOH 100:0 to 97:3 to 95:5 to 90:10) to afford 241 as a tan solid (55 mg, 40%). LCMS (Method G): R$_T$=5.19 min, M+H$^+$=491. $^1$H NMR (CDCl$_3$, 400 MHz) δ 7.99 (m, 1 H); 7.71 (m, 1 H); 7.25 (m, 2 H); 6.77 (s, 1 H); 4.09 (t, J=4.7 Hz, 4 H); 3.89 (t, J=4.7 Hz, 4 H); 3.77 (s, 2H); 3.11 (m, 2 H); 2.90 (s, 3 H); 2.16 (m, 2 H); 1.80 (m, 2 H); 1.49 (m, 2 H); 1.33-1.22 (m, 2 H) and 1.20 (s, 6 H)

Example 242

2-(2-methyl-1H-benzo[d]imidazol-1-yl)-4-morpholino-6-((3-morpholinoazetidin-1-yl)methyl)furo[3,2-d]pyrimidine 242

A mixture of 2-chloro-4-morpholin-4-yl-6-(3-morpholin-4-ylazetidin-1-ylmethyl)furo[3,2-d]pyrimidine (100 mg, 0.25 mmol), 2-methyl-1H-benzoimidazole (38 mg, 0.29 mmol), Pd$_2$dba$_3$ (12 mg, 0.013 mmol), Xphos (13 mg, 0.027 mmol) and cesium carbonate (184 mg, 0.56 mmol) in DMF (2.2 mL) was purged with argon gas then subjected to microwave irradiation at 145° C. for 30 min. The reaction mixture was loaded onto an Isolute® SCX-2 cartridge (10 g), which was washed with MeOH/DCM before the desired product was eluted with 2 M NH$_3$ in MeOH/DCM. The product was collected and concentrated in vacuo. The resultant residue was purified by flash chromatography (Si—PPC, DCM:MeOH 100:0 to 97:3 to 95:5 to 90:10) to afford 242 as a tan solid (37 mg, 30%). LCMS (Method G): R$_T$=4.85 min, M+H$^+$= 490. $^1$H NMR (CDCl$_3$, 400 MHz) δ 7.99 (m, 1H); 7.70 (m, 1 H); 7.26 (m, 2 H); 6.72 (s, 1 H); 4.07 (t, J=4.7 Hz, 4 H); 3.90-3.79 (m, 6H); 3.75 (m, 4 H); 3.64 (m, 2 H); 3.17 (m, 1 H); 3.11 (m, 1 H); 2.89 (s, 3 H) and 2.37 (m, 5 H)

Example 244

2-(1-((5-(8-methylimidazo[1,2-a]pyridin-5-yl)-7-morpholinothiazolo[5,4-d]pyrimidin-2-yl)methyl)piperidin-4-yl)propan-2-ol 244

A mixture of 2-[1-(7-morpholin-4-yl-5-(tributylstannanyl)thiazolo[5,4-d]pyrimidin-2-ylmethyl)piperidin-4-yl]propan- 2-ol (118 mg, 0.18 mmol), 5-bromo-8-methylimidazo[1,2-a]pyridine (45 mg, 0.21 mmol), Pd(PPh$_3$)$_4$ (20 mg, 0.02 mmol) and copper(I) thiophene-2-carboxylate (7 mg, 0.035 mmol) in dioxane (2 mL) was purged with argon gas then heated at 150° C., for 20 min, in a microwave reactor. The reaction mixture was loaded onto an Isolute® SCX-2 cartridge (10 g). The cartridge was washed with MeOH then the desired product was eluted with 2 M NH$_3$ in MeOH. The resulting residue was purified by flash chromatography (Si—PPC, MeOH:DCM, gradient 0:100 to 10:90) to give 244 as an off-white solid (80 mg, 89%). LCMS (Method G) R$_T$ 5.09 min; [M+H]$^+$ 508. $^1$H NMR (400 MHz, CHCl$_3$-d): δ 9.22 (s, 1 H); 7.93 (d, J=7.4 Hz, 1 H); 7.75 (d, J=1.3 Hz, 1H); 7.14 (d, J=7.4 Hz, 1 H); 4.43 (m, 4 H); 3.90 (m, 4 H); 3.87 (s, 2 H); 3.10 (d, J=11.5 Hz, 2 H); 2.73 (s, 3 H); 2.23 (t, J=11.5 Hz, 2 H); 1.78 (m, 2 H); 1.55-1.41 (m, 2 H); 1.35 (m, 2 H); 1.22 (s, 6 H)

Example 246

2-(3-(6-((4-(dimethylamino)piperidin-1-yl)methyl)-4-morpholinothieno[3,2-d]pyrimidin-2-yl)benzo[b]thiophen-2-yl)propan-2-ol 246

To 1-(3-(6-((4-(dimethylamino)piperidin-1-yl)methyl)-4-morpholinothieno[3,2-d]pyrimidin-2-yl)benzo[b]thiophen-2-yl)ethanone 208 (64 mg, 0.119 mmol) in anhydrous THF (3 mL) was added dropwise with stirring a solution of methylmagnesium bromide 3M in ethyl ether (0.12 mL, 0.358 mmol) and mixture stirred at room temperature for 90 min. A saturated solution of NaHCO3 (5 mL) was added and product extracted with CH2Cl2 (3×15 mL) Organics combined were dried (MgSO4) and concentrated. Flash chromatography with CH2Cl2:Methanol:Ammonium hydroxide (100:5:0.5) afforded 15 mg (21.4%) of 246. [M+H]$^+$ 552

Example 247

2-(1-((9-isopropyl-2-(2-methyl-1H-benzo[d]imidazol-1-yl)-6-morpholino-9H-purin-8-yl)methyl)piperidin-4-yl)propan-2-ol 247

2-(1-((2-Chloro-6-morpholino-9H-purin-8-yl)methyl)piperidin-4-yl)propan-2-ol (0.1 g) was reacted with isopropyl iodide via General Procedure C to give 2-(1-((2-chloro-9-isopropyl-6-morpholino-9H-purin-8-yl)methyl)piperidin-4-yl)propan-2-ol which was subsequently reacted with 2-methylbenzimidazole via General Procedure I for Buchwald coupling to give 43.3 g 247 following reverse phase purification. MS (Q1) 533.3 (M)+

Example 249

2-(1-((2-(imidazo[1,2-a]pyridin-5-yl)-4-morpholino-furo[3,2-d]pyrimidin-6-yl)methyl)piperidin-4-yl)propan-2-ol 249

A mixture of 2-[1-(4-morpholin-4-yl-2-tributylstannanyl-furo[3,2-d]pyrimidin-6-ylmethyl)piperidin-4-yl]propan-2-ol (147 mg, 0.23 mmol), 5-bromoimidazo[1,2-a]pyridine (46 mg, 0.23 mmol), tetrakis(triphenylphosphine)palladium (22 mg, 8 mol %) and CuTC (9 mg, 20 mol %) in 1,4-dioxane (2.5 mL) was purged with argon gas then subjected to microwave irradiation at 140° C. for 30 min. The reaction mixture was loaded onto an Isolute® SCX-2 cartridge (10 g), which was washed with MeOH/DCM before the desired product was eluted with 2 M NH$_3$ in MeOH/DCM. The product was collected and concentrated in vacuo. The resultant residue was purified by flash chromatography (Si—PPC, DCM:NH$_3$/MeOH (2 M); gradient from 100:0 to 96:4)), followed by reverse phase HPLC (Phenomenex Gemini 5u C18, 20 mM triethylamine in water on a gradient of acetonitrile 95:5 to 2:98) to afford 249 as a white foam (46 mg, 42%). LCMS (Method G): R$_T$=3.47 min, M+H$^+$=477. $^1$H NMR (CDCl$_3$, 400 MHz) 9.14 (s, 1 H); 6 7.87 (dd, J=8.5, 1.19 Hz, 2H); 7.76 (d, J=8.9 Hz, 1 H); 7.73 (d, J=1.3 Hz, 1 H); 7.30 (m, 1 H); 6.79 (s, 1 H); 4.11 (t, J=4.7 Hz, 4 H); 3.90 (t, J=4.7 Hz, 4 H); 3.75 (s, 2 H); 3.08 (d, J=11.0 Hz, 2 H); 2.12 (t, J=11.0 Hz, 2 H); 1.78 (m, 2 H); 1.52-1.38 (m, 3 H); 1.31 (m, 1 H) and 1.19 (s, 6 H)

Example 250

2-(imidazo[1,2-a]pyridin-5-yl)-4-morpholino-6-((3-morpholinoazetidin-1-yl)methyl)furo[3,2-d]pyrimidine 250

A mixture of 4-morpholin-4-yl-6-(3-morpholin-4-yl-azetidin-1-ylmethyl)-2-tributylstannanylfuro[3,2-d]pyrimidine (227 mg, 0.35 mmol), 5-bromoimidazo[1,2-a]pyridine (84 mg, 0.43 mmol), tetrakis(triphenylphosphine)palladium (40 mg, 10 mol %) and CuTC (16 mg, 24 mol %) in 1,4-dioxane (4 mL) was purged with argon gas then subjected to microwave irradiation at 140° C. for 30 min. The reaction mixture was loaded onto an Isolute® SCX-2 cartridge (10 g); the cartridge was washed with MeOH/DCM before the desired product was eluted with 2 M NH$_3$ in MeOH/DCM. The product was collected and concentrated in vacuo. The resultant residue was purified by flash chromatography (Si—PPC, DCM:NH$_3$/MeOH (2 M); gradient from 100:0 to 96:4)), followed by reverse phase HPLC (Phenomenex Gemini 5u C18, 20 mM triethylamine in water on a gradient of acetonitrile 95:5 to 2:98) to afford 250 as a cream foam (79 mg, 47%). LCMS (Method G): R$_T$=3.22 min, M+H$^+$=476. $^1$H NMR (CDCl$_3$, 400 MHz) δ 9.14 (s, 1 H); 7.87 (dd, J=7.2, 1.2 Hz, 1H); 7.77 (d, J=8.9 Hz, 1 H); 7.74 (d, J=1.2 Hz, 1 H); 7.31 (dd, J=8.9, 7.2 Hz, 1 H); 6.76 (s, 1 H); 4.10 (t, J=4.7 Hz, 4 H); 3.89 (t, J=4.7 Hz, 4 H); 3.84 (s, 2 H); 3.74 (t, J=4.5 Hz, 4 H); 3.62 (t, J=6.2 Hz, 2 H); 3.15-3.02 (m, 3 H) and 2.35 (m, 4 H)

Example 252

2-ethyl-1-(8-((4-(2-hydroxypropan-2-yl)piperidin-1-yl)methyl)-9-methyl-6-morpholino-9H-purin-2-yl)-1H-indazol-3(2H)-one 252

Following General Procedure I for Buchwald coupling, 2-(1-((2-chloro-9-methyl-6-morpholino-9H-purin-8-yl)methyl)piperidin-4-yl)propan-2-ol and 2-ethyl-1,2-dihydroindazol-3-one were reacted to give 252. LCMS m/z: 535.3 (MH+)

Example 253

(S)-2-(1-((9-methyl-6-morpholino-2-(2-(tetrahydrofuran-2-yl)-1H-benzo[d]imidazol-1-yl)-9H-purin-8-yl)methyl)piperidin-4-yl)propan-2-ol 253

Following General Procedure I for Buchwald coupling, 2-(1-((2-chloro-9-methyl-6-morpholino-9H-purin-8-yl)methyl)piperidin-4-yl)propan-2-ol and racemic 2-(tetrahydrofuran-2-yl)-1H-benzimidazole were reacted to give a racemic mixture. The enantiomers were separated by SFC to give 253. LCMS m/z: 561.3 (MH+)

Example 254

1-2-(1-((9-methyl-6-morpholino-2-(2-(tetrahydrofuran-2-yl)-1H-benzo[d]imidazol-1-yl)-9H-purin-8-yl)methyl)piperidin-4-yl)propan-2-ol 254

Following General Procedure I for Buchwald coupling, 2-(1-((2-chloro-9-methyl-6-morpholino-9H-purin-8-yl)methyl)piperidin-4-yl)propan-2-ol and racemic 2-(tetrahydrofuran-2-yl)-1H-benzimidazole were reacted to give a racemic mixture. The enantiomers were separated by SFC to give 254. LCMS m/z: 561.3 (MH+)

Example 255

2-(1-((2-(2-(ethylamino)-1H-benzo[d]imidazol-1-yl)-9-methyl-6-morpholino-9H-purin-8-yl)methyl)piperidin-4-yl)propan-2-ol 255

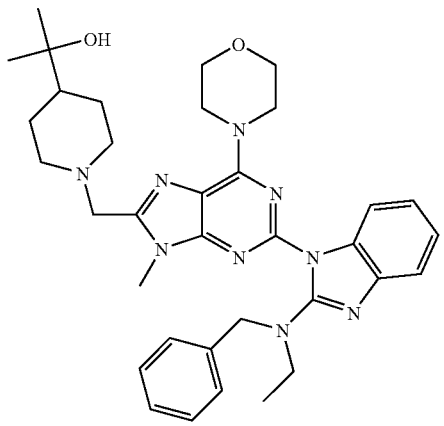

A mixture of 2-(1-((2-(2-(benzyl(ethyl)amino)-1H-benzo[d]imidazol-1-yl)-9-methyl-6-morpholino-9H-purin-8-yl)methyl)piperidin-4-yl)propan-2-ol (0.6 mmol) and palladium on carbon (10 wt %, 0.3 g) and acetic acid (0.1 mL) in ethanol (20 mL) was stirred under a hydrogen atmosphere at 65° C. for 18 hours. The reaction mixture was then filtered though celite and concentrated. The crude product was purified by RP-HPLC to give 255 (28.5 mg, 17%). LCMS m/z: 534.3 (MH+)

Example 256

4-(5-(2-methyl-1H-benzo[d]imidazol-1-yl)-2-((3-morpholinoazetidin-1-yl)methyl)thiazolo[4,5-d]pyrimidin-7-yl)morpholine 256

A mixture of 5-chloro-7-morpholin-4-yl-243-morpholin-4-yl-azetidin-1-ylmethyl)thiazolo[4,5-d]pyrimidine (50 mg, 0.12 mmol), 2-methyl-1H-benzoimidazole (18 mg, 0.13 mmol), Pd$_2$(dba)$_3$ (5.5 mg, 0.006 mmol), XPhos (5.7 mg, 0.02 mmol) and cesium carbonate (78 mg, 0.24 mmol) in 1,4-dioxane (1 5 mL) was purged with argon gas for 15 min. The resulting reaction mixture was irradiated with microwaves at 145° C. for 30 min. The crude residue was loaded on an Isolute® SCX-2 cartridge (5 g). The cartridge was washed with DCM/MeOH and the desired product was subsequently eluted using a mixture of 2M NH$_3$ in MeOH and DCM. The resulting residue was further purified by column chromatography (Si—PCC, 2 M NH$_3$ in MeOH:DCM: gradient 0:100 to 4:96). The solvents were reduced in vacuo to afford 256 as a brown solid (43 mg, 70%). LCMS (Method G): R$_T$ 5.52 min, [M+H]$^+$ 507. $^1$H NMR (400 MHz, CDCl$_3$): δ 8.22-8.21 (1 H, m), 7.71-7.70 (1 H, m), 7.30-7.27 (2 H, m), 4.18 (2 H, s), 4.03 (4 H, t, J=4.80 Hz), 3.89 (4 H, t, J=4.80 Hz), 3.76-3.72 (6 H, m), 3.27 (2 H, m), 3.15 (1 H, m), 3.00 (3 H, s), 2.37 (4 H, br s)

Example 257

3-(1-((9-methyl-2-(2-methyl-1H-benzo[d]imidazol-1-yl)-6-morpholino-9H-purin-8-yl)methyl)piperidin-4-yl)oxetan-3-ol 257

Following General Procedure I for Buchwald coupling, 2-methylbenzimidazole and 3-(1-((2-chloro-9-methyl-6-morpholino-9H-purin-8-yl)methyl)piperidin-4-yl)oxetan-3-ol were reacted to give 257. LCMS m/z: 519.3 (MH+)

Example 258

2,2-dimethyl-N-((9-methyl-242-methyl-1H-benzo[d]imidazol-1-yl)-6-morpholino-9H-purin-8-yl)methyl)propan-1-amine 258

Following General Procedure L for reductive amination, 9-methyl-2-(2-methyl-1H-benzo[d]imidazol-1-yl)-6-morpholino-9H-purine-8-carbaldehyde and 2,2-dimethylpropan-1-amine were reacted to give 258. [M+H]$^+$ 449.6.

Example 259

1-(9-methyl-2-(2-methyl-1H-benzo[d]imidazol-1-yl)-6-morpholino-9H-purin-8-yl)-N-((3-methyloxetan-3-yl)methyl)methanamine 259

Following General Procedure L for reductive amination, 9-methyl-2-(2-methyl-1H-benzo[d]imidazol-1-yl)-6-morpholino-9H-purine-8-carbaldehyde and (3-methyloxetan-3-yl)methanamine were reacted to give 259. [M+H]$^+$ 463.6.

Example 260

1-(1-((9-methyl-242-methyl-1H-benzo[d]imidazol-1-yl)-6-morpholino-9H-purin-8-yl)methyl)piperidin-4-yl)cyclobutanol 260

Following General Procedure I for Buchwald coupling, 2-methylbenzimidazole and 1-(1-((2-chloro-9-methyl-6-morpholino-9H-purin-8-yl)methyl)piperidin-4-yl)cyclobutanol were reacted to give 260. LCMS m/z: 517.3 (MH+)

Example 261

2-(1-((9-methyl-6-morpholino-2-(2-(pyrrolidin-1-yl)-1H-benzo[d]imidazol-1-yl)-9H-purin-8-yl)methyl)piperidin-4-yl)propan-2-ol 261

Following General Procedure I for Buchwald coupling, 2-(pyrrolidin-1-yl)-1H-benzo[d]imidazole and 2-(1-((2- chloro-9-methyl-6-morpholino-9H-purin-8-yl)methyl)piperidin-4-yl)propan-2-ol were reacted to give 261. LCMS m/z: 560.3 (MH+)

Example 262

2-(1-((2-(2-(3-fluorooxetan-3-yl)-1H-benzo[d]imidazol-1-yl)-9-methyl-6-morpholino-9H-purin-8-yl)methyl)piperidin-4-yl)propan-2-ol 262

Following General Procedure I for Buchwald coupling, 2-(3-fluorooxetan-3-yl)-1H-benzimidazole and 2-(1-((2-chloro-9-methyl-6-morpholino-9H-purin-8-yl)methyl)piperidin-4-yl)propan-2-ol were reacted to give 262. LCMS m/z: 565.3 (MH+)

Example 263

3-(1-((2-(2-ethyl-1H-benzo[d]imidazol-1-yl)-9-methyl-6-morpholino-9H-purin-8-yl)methyl)piperidin-4-yl)oxetan-3-ol 263

Following General Procedure I for Buchwald coupling, 2-ethylbenzimidazole and 3-(1-((2-chloro-9-methyl-6-morpholino-9H-purin-8-yl)methyl)piperidin-4-yl)oxetan-3-ol were reacted to give 263. LCMS m/z: 533.3 (MH+)

Example 264

2-methyl-2-(4-((9-methyl-2-(2-methyl-1H-benzo[d]imidazol-1-yl)-6-morpholino-9H-purin-8-yl)methyl)piperazin-1-yl)propan-1-ol 264

Following General Procedure I for Buchwald coupling, 2-(4-((2-chloro-9-methyl-6-morpholino-9H-purin-8-yl)methyl)piperazin-1-yl)-2-methylpropan-1-ol and 2-methyl-1H-benzo[d]imidazole were reacted to give 264. LCMS m/z: 520.3 (MH+)

Example 265

2-(1-((9-methyl-2-(2-methyl-1H-benzo[d]imidazol-1-yl)-6-morpholino-9H-purin-8-yl)methyl)piperidin-3-yl)propan-2-ol 265

Following General Procedure E of amine alkylation, 4-(8-(bromomethyl)-9-methyl-2-(2-methyl-1H-benzo[d]imidazol-1-yl)-9H-purin-6-yl)morpholine and 2-(piperidin-3-yl)propan-2-ol were reacted to give 265. M+H=505.3

Example 266

2-methyl-1-(1-((9-methyl-2-(2-methyl-1H-benzo[d]imidazol-1-yl)-6-morpholino-9H-purin-8-yl)methyl)piperidin-4-yl)propan-2-ol 266

Following General Procedure E of amine alkylation, 4-(8-(bromomethyl)-9-methyl-2-(2-methyl-1H-benzo[d]imidazol-1-yl)-9H-purin-6-yl)morpholine and 2-methyl-1-(piperidin-4-yl)propan-2-ol were reacted to give 266. LCMS: M+H$^+$=519.4

Example 267

4-(9-methyl-2-(2-methyl-1H-benzo[d]imidazol-1-yl)-8-((4-(2,2,2-trifluoroethyl)piperazin-1-yl)methyl)-9H-purin-6-yl)morpholine 267

Following General Procedure E of amine alkylation, 4-(8-(bromomethyl)-9-methyl-2-(2-methyl-1H-benzo[d]imida-zol-1-yl)-9H-purin-6-yl)morpholine and 1-(2,2,2-trifluoroethyl)piperazine were reacted to give 267. LCMS: M+H$^+$=530.2

Example 268

(4-methyl-1-((9-methyl-2-(2-methyl-1H-benzo[d]imidazol-1-yl)-6-morpholino-9H-purin-8-yl)methyl)piperidin-4-yl)methanol 268

Following General Procedure E of amine alkylation, 4-(8-(bromomethyl)-9-methyl-2-(2-methyl-1H-benzo[d]imidazol-1-yl)-9H-purin-6-yl)morpholine and (4-methylpiperidin-4-yl)methanol were reacted to give 268. LCMS: M+H$^+$=491.3

Example 269

I-2-hydroxy-1-(4-((9-methyl-2-(2-methyl-1H-benzo[d]imidazol-1-yl)-6-morpholino-9H-purin-8-yl)methyl)piperazin-1-yl)propan-1-one 269

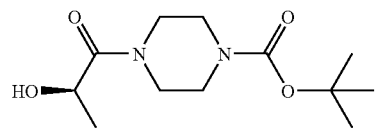

A mixture of tert-butyl piperazine-1-carboxylate (0.367 g), L-(+)-lactic acid (0.213 g), and HBTU (0.822 g) was stirred at rt overnight. Diluted with DCM, the mixture was washed with water (2×), brine, and dried (Na$_2$SO$_4$). Filtration and concentration gave I-tert-butyl 4-(2-hydroxypropanoyl)piperazine-1-carboxylate as viscous oil, which was treated with trifluoroacetic acid in dichloromethane. After concentration, the residue was reacted with 4-(8-(bromomethyl)-9-methyl-2-(2-methyl-1H-benzo[d]imidazol-1-yl)-9H-purin-6-yl)morpholine in the presence of diisopropylethylamine (10 eq) following General Procedure E of amine alkylation to give 269. LCMS: M+H$^+$=520.3

Example 270 adamantan-1-yl-[9-methyl-2-(2-methyl-benzoimidazol-1-yl)-6-morpholin-4-yl-9H-purin-8-ylmethyl]-amine 270

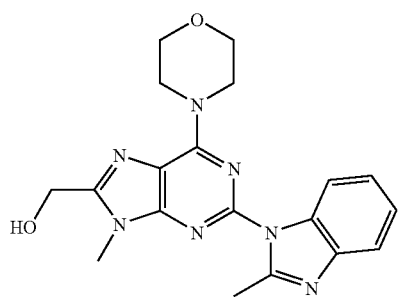

(2-Chloro-9-methyl-6-morpholino-9H-purin-8-yl)methanol (4.0 g) was reacted with 2-Methylbenzimidazole (1.96 g) via General Procedure I for Buchwald coupling. The solids were filtered from the reaction mixture while still warm. Water was added to the filtered reaction mixture (5 times the volume of DMF) to precipitate the product out of the reaction mixture. The precipitated orange solid was filtered and dried under vacuum for quantitative yield of (9-methyl-2-(2-methyl-1H-benzo[d]imidazol-1-yl)-6-morpholino-9H-purin-8-yl)methanol.

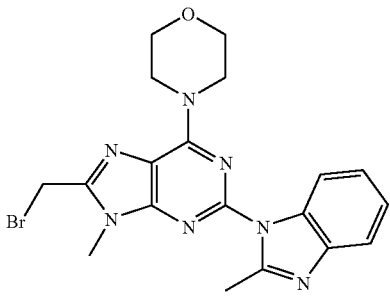

To crude (9-methyl-2-(2-methyl-1H-benzo[d]imidazol-1-yl)-6-morpholino-9H-purin-8-yl)methanol (6 g) in anhydrous THF (400 mL) was added phosphorus tribromide (2.7 mL). The reaction was monitored by LC/MS until complete. The heterogeneous reaction mixture was passed thru a Buchner funnel and the solid was collected and rinsed with thrice with water and twice with MeOH.to get 2 g of crude 4-(8-(bromomethyl)-9-methyl-2-(2-methyl-1H-benzo[d]imidazol-1-yl)-9H-purin-6-yl)morpholine of which 50 mg was reacted with bicyclo[2.2.2]octan-1-amine (1-adamantyl amine) via General Procedure E to give 5.7 mg of 270 following reverse phase purification. MS (Q1) 513.3 (M)+

Example 271

N-((9-methyl-2-(2-methyl-1H-benzo[d]imidazol-1-yl)-6-morpholino-9H-purin-8-yl)methyl)-2,3-dihydro-1H-inden-1-amine 271

4-(8-(Bromomethyl)-9-methyl-2-(2-methyl-1H-benzo[d]imidazol-1-yl)-9H-purin-6-yl)morpholine (25 mg) was reacted with 2,3-dihydro-1H-inden-1-amine via General Procedure E to give 10.6 mg of 271 following reverse phase purification. MS (Q1) 495.2 (M)+

Example 272

(4R)—N-((9-methyl-2-(2-methyl-1H-benzo[d]imidazol-1-yl)-6-morpholino-9H-purin-8-yl)methyl)bicyclo[2.2.1]heptan-2-amine 272

4-(8-(Bromomethyl)-9-methyl-2-(2-methyl-1H-benzo[d]imidazol-1-yl)-9H-purin-6-yl)morpholine (50 mg) was reacted with (1R,4S)-bicyclo[2.2.1]heptan-2-amine via General Procedure E to give 16 mg of 272 following reverse phase purification. MS (Q1) 473.3 (M)+

Example 273

1-(((9-methyl-2-(2-methyl-1H-benzo[d]imidazol-1-yl)-6-morpholino-9H-purin-8-yl)methylamino)methyl)cyclohexanol 273

4-(8-(Bromomethyl)-9-methyl-2-(2-methyl-1H-benzo[d]imidazol-1-yl)-9H-purin-6-yl)morpholine (50 mg) was reacted with 1-(aminomethyl)cyclohexanol via General Procedure E to give 22 mg of 273 following reverse phase purification. MS (Q1) 491.3 (M)+

Example 274

(1-((9-methyl-2-(2-methyl-1H-benzo[d]imidazol-1-yl)-6-morpholino-9H-purin-8-yl)methylamino)cyclopentyl)methanol 274

4-(8-(Bromomethyl)-9-methyl-2-(2-methyl-1H-benzo[d]imidazol-1-yl)-9H-purin-6-yl)morpholine (50 mg) was reacted with (1-aminocyclopentyl)methanol via General Procedure E to give 10.2 mg of 274 following reverse phase purification. MS (Q1) 477.2 (M)+

Example 275

N,1-dimethyl-N-((9-methyl-2-(2-methyl-1H-benzo[d]imidazol-1-yl)-6-morpholino-9H-purin-8-yl)methyl)piperidin-4-amine 275

4-(8-(Bromomethyl)-9-methyl-2-(2-methyl-1H-benzo[d]imidazol-1-yl)-9H-purin-6-yl)morpholine (50 mg) was reacted with N,1-dimethylpiperidin-4-amine via General Procedure E to give 5.2 mg of 275 following reverse phase purification. MS (Q1) 490.3 (M)+

Example 276

4-(8-(isoindolin-2-ylmethyl)-9-methyl-2-(2-methyl-1H-benzo[d]imidazol-1-yl)-9H-purin-6-yl)morpholine 276

4-(8-(Bromomethyl)-9-methyl-2-(2-methyl-1H-benzo[d]imidazol-1-yl)-9H-purin-6-yl)morpholine (50 mg) was reacted with isoindoline via General Procedure E to give 10.7 mg of 276 following reverse phase purification. MS (Q1) 481.2 (M)+

Example 277

4-(8-((4-(cyclopropylmethyl)piperazin-1-yl)methyl)-9-methyl-2-(2-methyl-1H-benzo[d]imidazol-1-yl)-9H-purin-6-yl)morpholine 277

4-(8-(bromomethyl)-9-methyl-2-(2-methyl-1H-benzo[d]imidazol-1-yl)-9H-purin-6-yl)morpholine (50 mg) was reacted with 1-(cyclopropylmethyl)piperazine via General Procedure E to give 23.5 mg of 277 following reverse phase purification. MS (Q1) 502.3 (M)+

Example 278

4-(8-((4,4-difluoropiperidin-1-yl)methyl)-9-methyl-2-(2-methyl-1H-benzo[d]imidazol-1-yl)-9H-purin-6-yl)morpholine 278

4-(8-(bromomethyl)-9-methyl-2-(2-methyl-1H-benzo[d]imidazol-1-yl)-9H-purin-6-yl)morpholine (50 mg) was reacted with 4,4-difluoropiperidine via General Procedure E to give 19.3 mg of 278 following reverse phase purification. MS (Q1) 483.2 (M)+

Example 279

N-((9-methyl-2-(2-methyl-1H-benzo[d]imidazol-1-yl)-6-morpholino-9H-purin-8-yl)methyl)-1-phenylethanamine 279

4-(8-(bromomethyl)-9-methyl-2-(2-methyl-1H-benzo[d]imidazol-1-yl)-9H-purin-6-yl)morpholine (50 mg) was reacted with 1-phenylethanamine via General Procedure E to give 10.8 mg of 279 following reverse phase purification. MS (Q1) 483.2 (M)+

Example 280

4-(8-((4-(methoxymethyl)piperidin-1-yl)methyl)-9-methyl-2-(2-methyl-1H-benzo[d]imidazol-1-yl)-9H-purin-6-yl)morpholine 280

4-(8-(bromomethyl)-9-methyl-2-(2-methyl-1H-benzo[d]imidazol-1-yl)-9H-purin-6-yl)morpholine (50 mg) was reacted with 4-(methoxymethyl)piperidine via General Procedure E to give 21.9 mg of 280 following reverse phase purification. MS (Q1) 491.3 (M)+

Example 281

4-((9-methyl-2-(2-methyl-1H-benzo[d]imidazol-1-yl)-6-morpholino-9H-purin-8-yl)methylamino)cyclohexanol 281

4-(8-(bromomethyl)-9-methyl-2-(2-methyl-1H-benzo[d]imidazol-1-yl)-9H-purin-6-yl)morpholine (50 mg) was reacted with 4-aminocyclohexanol via General Procedure E to give 11.1 mg of 281 following reverse phase purification. MS (Q1) 477.2 (M)+

Example 282

1-(9-methyl-2-(2-methyl-1H-benzo[d]imidazol-1-yl)-6-morpholino-9H-purin-8-yl)-N-((1-methylpiperidin-2-yl)methyl)methanamine 282

4-(8-(bromomethyl)-9-methyl-2-(2-methyl-1H-benzo[d]imidazol-1-yl)-9H-purin-6-yl)morpholine (50 mg) was reacted with (1-methylpiperidin-2-yl)methanamine via General Procedure E to give 4.1 mg of 282 following reverse phase purification. MS (Q1) 490.2 (M)+

Example 283

4-(8-((dihydro-1H-pyrido[1,2-a]pyrazin-2(6H,7H,8H,9H,9aH)-yl)methyl)-9-methyl-2-(2-methyl-1H-benzo[d]imidazol-1-yl)-9H-purin-6-yl)morpholine 283

4-(8-(Bromomethyl)-9-methyl-2-(2-methyl-1H-benzo[d]imidazol-1-yl)-9H-purin-6-yl)morpholine (50 mg) was reacted with octahydro-1H-pyrido[1,2-a]pyrazine via General Procedure E to give 24 mg of 284 following reverse phase purification. MS (Q1) 502.3 (M)+

Example 284

1-methyl-N-((9-methyl-2-(2-methyl-1H-benzo[d]imidazol-1-yl)-6-morpholino-9H-purin-8-yl)methyl)piperidin-4-amine 284

4-(8-(Bromomethyl)-9-methyl-2-(2-methyl-1H-benzo[d]imidazol-1-yl)-9H-purin-6-yl)morpholine (50 mg) was reacted with 1-methylpiperidin-4-amine via General Procedure E to give 4.6 mg of 284 following reverse phase purification. MS (Q1) 476.3 (M)+

Example 285

N,2-dimethyl-N-((9-methyl-2-(2-methyl-1H-benzo[d]imidazol-1-yl)-6-morpholino-9H-purin-8-yl)methyl)propan-1-amine 285

4-(8-(Bromomethyl)-9-methyl-2-(2-methyl-1H-benzo[d]imidazol-1-yl)-9H-purin-6-yl)morpholine (50 mg) was reacted with N,2-dimethylpropan-1-amine via General Procedure E to give 10.1 mg of 285 following reverse phase purification. MS (Q1) 449.2 (M)+

Example 286

1-(4-((9-methyl-2-(2-methyl-1H-benzo[d]imidazol-1-yl)-6-morpholino-9H-purin-8-yl)methylamino)piperidin-1-yl)ethanone 286

4-(8-(Bromomethyl)-9-methyl-2-(2-methyl-1H-benzo[d]imidazol-1-yl)-9H-purin-6-yl)morpholine (50 mg) was reacted with 1-(4-aminopiperidin-1-yl)ethanone via General Procedure E to give 19.6 mg of 286 following reverse phase purification. MS (Q1) 504.3 (M)+

Example 287

4-(1-((9-methyl-2-(2-methyl-1H-benzo[d]imidazol-1-yl)-6-morpholino-9H-purin-8-yl)methyl)pyrrolidin-3-yl)morpholine 287

4-(8-(Bromomethyl)-9-methyl-2-(2-methyl-1H-benzo[d]imidazol-1-yl)-9H-purin-6-yl)morpholine (50 mg) was reacted with 4-(pyrrolidin-3-yl)morpholine via General Procedure E to give 26.9 mg of 287 following reverse phase purification. MS (Q1) 518.2 (M)+

Example 288

N-((9-methyl-2-(2-methyl-1H-benzo[d]imidazol-1-yl)-6-morpholino-9H-purin-8-yl)methyl)tetrahydro-2H-pyran-4-amine 288

4-(8-(Bromomethyl)-9-methyl-2-(2-methyl-1H-benzo[d]imidazol-1-yl)-9H-purin-6-yl)morpholine (50 mg) was reacted with tetrahydro-2H-pyran-4-amine via General Procedure E to give 8.6 mg of 288 following reverse phase purification. MS (Q1) 463.2 (M)+

Example 289

4-(9-methyl-2-(2-methyl-1H-benzo[d]imidazol-1-yl)-8-((3-(trifluoromethyl)pyrrolidin-1-yl)methyl)-9H-purin-6-yl)morpholine 289

4-(8-(Bromomethyl)-9-methyl-2-(2-methyl-1H-benzo[d] imidazol-1-yl)-9H-purin-6-yl)morpholine (50 mg) was reacted with 3-(trifluoromethyl)pyrrolidine via General Procedure E to give 19.9 mg of 289 following reverse phase purification. MS (Q1) 501.2 (M)+

Example 290

N-methyl-1-(9-methyl-2-(2-methyl-1H-benzo[d] imidazol-1-yl)-6-morpholino-9H-purin-8-yl)-N-((tetrahydrofuran-2-yl)methyl)methanamine 290

4-(8-(Bromomethyl)-9-methyl-2-(2-methyl-1H-benzo[d] imidazol-1-yl)-9H-purin-6-yl)morpholine (50 mg) was reacted with N-methyl-1-(tetrahydrofuran-2-yl)methanamine via General Procedure E to give 10.7 mg of 290 following reverse phase purification. MS (Q1) 477.2 (M)+

Example 291

1-((9-methyl-2-(2-methyl-1H-benzo[d]imidazol-1-yl)-6-morpholino-9H-purin-8-yl)methyl)piperidine-4-carbonitrile 291

4-(8-(Bromomethyl)-9-methyl-2-(2-methyl-1H-benzo[d] imidazol-1-yl)-9H-purin-6-yl)morpholine (50 mg) was reacted with piperidine-4-carbonitrile via General Procedure E to give 21.9 mg of 291 following reverse phase purification. MS (Q1) 472.2 (M)+

Example 292

2-methyl-1-((9-methyl-2-(2-methyl-1H-benzo[d] imidazol-1-yl)-6-morpholino-9H-purin-8-yl)methylamino)propan-2-ol 292

4-(8-(Bromomethyl)-9-methyl-2-(2-methyl-1H-benzo[d] imidazol-1-yl)-9H-purin-6-yl)morpholine (50 mg) was reacted with 1-amino-2-methylpropan-2-ol via General Procedure E to give 8.1 mg of 292 following reverse phase purification. MS (Q1) 451.2 (M)+

Example 293

3,3,3-trifluoro-N-((9-methyl-2-(2-methyl-1H-benzo [d]imidazol-1-yl)-6-morpholino-9H-purin-8-yl)methyl)propan-1-amine 293

4-(8-(Bromomethyl)-9-methyl-2-(2-methyl-1H-benzo[d] imidazol-1-yl)-9H-purin-6-yl)morpholine (50 mg) was reacted with 3,3,3-trifluoropropan-1-amine via General Procedure E to give 8 mg of 293 following reverse phase purification. MS (Q1) 475.2 (M)+

Example 294

4,4-difluoro-N-((9-methyl-2-(2-methyl-1H-benzo[d] imidazol-1-yl)-6-morpholino-9H-purin-8-yl)methyl) cyclohexanamine 294

4-(8-(Bromomethyl)-9-methyl-2-(2-methyl-1H-benzo[d] imidazol-1-yl)-9H-purin-6-yl)morpholine (50 mg) was reacted with 4,4-difluorocyclohexanamine via General Procedure E to give 15.4 mg of 294 following reverse phase purification. MS (Q1) 497.2 (M)+

Example 295

1-isopropyl-N-methyl-N-((9-methyl-2-(2-methyl-1H-benzo[d]imidazol-1-yl)-6-morpholino-9H-purin-8-yl)methyl)piperidin-4-amine 295

4-(8-(Bromomethyl)-9-methyl-2-(2-methyl-1H-benzo[d] imidazol-1-yl)-9H-purin-6-yl)morpholine (50 mg) was reacted with 1-isopropyl-N-methylpiperidin-4-amine via General Procedure E to give 22.1 mg of 295 following reverse phase purification. MS (Q1) 518.3 (M)+

Example 296

N,N-diethyl-1-((9-methyl-2-(2-methyl-1H-benzo[d] imidazol-1-yl)-6-morpholino-9H-purin-8-yl)methyl) pyrrolidin-3-amine 296

4-(8-(Bromomethyl)-9-methyl-2-(2-methyl-1H-benzo[d] imidazol-1-yl)-9H-purin-6-yl)morpholine (50 mg) was reacted with N,N-diethylpyrrolidin-3-amine via General Procedure E to give 27.8 mg of 296 following reverse phase purification. MS (Q1) 504.3 (M)+

Example 297

1-(9-methyl-2-(2-methyl-1H-benzo[d]imidazol-1-yl)-6-morpholino-9H-purin-8-yl)-N-((tetrahydrofuran-3-yl)methyl)methanamine 297

4-(8-(Bromomethyl)-9-methyl-2-(2-methyl-1H-benzo[d] imidazol-1-yl)-9H-purin-6-yl)morpholine (50 mg) was reacted with (tetrahydrofuran-3-yl)methanamine via General Procedure E to give 6.9 mg of 297 following reverse phase purification. MS (Q1) 463.2 (M)+

Example 298

N-methyl-N-(1-((9-methyl-2-(2-methyl-1H-benzo[d] imidazol-1-yl)-6-morpholino-9H-purin-8-yl)methyl) pyrrolidin-3-yl)acetamide 298

4-(8-(Bromomethyl)-9-methyl-2-(2-methyl-1H-benzo[d] imidazol-1-yl)-9H-purin-6-yl)morpholine (50 mg) was reacted with N-methyl-N-(pyrrolidin-3-yl)acetamide via General Procedure E to give 25.5 mg of 298 following reverse phase purification. MS (Q1) 504.2 (M)+

Example 299

1-(1-((9-methyl-2-(2-methyl-1H-benzo[d]imidazol-1-yl)-6-morpholino-9H-purin-8-yl)methyl)pyrrolidin-3-yl)methanol 299

4-(8-(Bromomethyl)-9-methyl-2-(2-methyl-1H-benzo[d] imidazol-1-yl)-9H-purin-6-yl)morpholine (50 mg) was reacted with l-pyrrolidin-3-ylmethanol via General Procedure E to give 19.1 mg of 299 following reverse phase purification. MS (Q1) 463.2 (M)+

Example 300

4-(8-((3,3-dimethylpyrrolidin-1-yl)methyl)-9-methyl-2-(2-methyl-1H-benzo[d]imidazol-1-yl)-9H-purin-6-yl)morpholine 300

4-(8-(Bromomethyl)-9-methyl-2-(2-methyl-1H-benzo[d]imidazol-1-yl)-9H-purin-6-yl)morpholine (50 mg) was reacted with 3,3-dimethylpyrrolidine via General Procedure E to give 16.8 mg of 300 following reverse phase purification. MS (Q1) 461.2 (M)+

Example 301

4-(8-((3,3-diethylpyrrolidin-1-yl)methyl)-9-methyl-2-(2-methyl-1H-benzo[d]imidazol-1-yl)-9H-purin-6-yl)morpholine 301

4-(8-(Bromomethyl)-9-methyl-2-(2-methyl-1H-benzo[d]imidazol-1-yl)-9H-purin-6-yl)morpholine (50 mg) was reacted with 3,3-diethylpyrrolidine via General Procedure E to give 26.5 mg of 301 following reverse phase purification. MS (Q1) 4892 (M)+

Example 302

4-(8-((3-isobutylpyrrolidin-1-yl)methyl)-9-methyl-2-(2-methyl-1H-benzo[d]imidazol-1-yl)-9H-purin-6-yl)morpholine 302

4-(8-(Bromomethyl)-9-methyl-2-(2-methyl-1H-benzo[d]imidazol-1-yl)-9H-purin-6-yl)morpholine (50 mg) was reacted with 3-isobutylpyrrolidine via General Procedure E to give 27 mg of 302 following reverse phase purification. MS (Q1) 489.2 (M)+

Example 303

N-((9-methyl-2-(2-methyl-1H-benzo[d]imidazol-1-yl)-6-morpholino-9H-purin-8-yl)methyl)-2-phenylpropan-2-amine 303

4-(8-(Bromomethyl)-9-methyl-2-(2-methyl-1H-benzo[d]imidazol-1-yl)-9H-purin-6-yl)morpholine (50 mg) was reacted with 2-phenylpropan-2-amine via General Procedure E to give 7.4 mg of 303 following reverse phase purification. MS (Q1) 497.2 (M)+

Example 304

4-(9-methyl-2-(2-methyl-1H-benzo[d]imidazol-1-yl)-8-((1,1-dioxo-4-(tetrahydro-2H-thiopyran-4-yl)piperazin-1-yl)methyl)-9H-purin-6-yl)morpholine 304

4-(8-(Bromomethyl)-9-methyl-2-(2-methyl-1H-benzo[d]imidazol-1-yl)-9H-purin-6-yl)morpholine (50 mg) was reacted with amine via General Procedure E to give 1 mg of 304 following reverse phase purification. MS (Q1) 580.3 (M)+

Example 305

(S)-(1-((9-methyl-2-(2-methyl-1H-benzo[d]imidazol-1-yl)-6-morpholino-9H-purin-8-yl)methyl)pyrrolidin-3-yl)methanol 305

4-(8-(Bromomethyl)-9-methyl-2-(2-methyl-1H-benzo[d]imidazol-1-yl)-9H-purin-6-yl)morpholine (50 mg) was reacted with (S)-pyrrolidin-3-ylmethanol via General Procedure E to give 18.8 mg of 305 following reverse phase purification. MS (Q1) 463.2 (M)+

Example 306

1-((2-(2-ethyl-1H-benzo[d]imidazol-1-yl)-9-methyl-6-morpholino-9H-purin-8-yl)methyl)-N,N-dimethylpiperidin-4-amine 306

According to General Procedure I for Buchwald coupling, into a vial was added 1-((2-chloro-9-methyl-6-morpholino-8,9-dihydro-7H-purin-8-yl)methyl)-N,N-dimethylpiperidin-4-amine (0.044 g, 0.11 mmol), 2-ethyl-1H-benzo[d]imidazole (0.0171 g, 0.117 mmol), Xphos (0.00692 g, 0.0145 mmol), Tris(dibenzylideneacetone)dipalladium(0) (0.00696 g, 7.60E-6 mol), and Cesium Carbonate (0.0728 g, 0.223 mmol). The mixture was dissolved in N,N-Dimethylformamide (0.865 mL, 0.0112 mol). The reaction was heated at 145° C. under pressure for 30 minutes in a microwave reactor. The reaction mixture was filtered and concentrated. The crude was purified by reverse phase HPLC to give 306 (26.7 mg, 47%). [M+H]$^+$=536.3.

Example 307

2-(1-((2-(2-(1-fluorocyclopropyl)-1H-benzo[d]imidazol-1-yl)-9-methyl-6-morpholino-9H-purin-8-yl)methyl)piperidin-4-yl)propan-2-ol 307

Following General Procedure I for Buchwald coupling, 2-(1-((2-chloro-9-methyl-6-morpholino-9H-purin-8-yl)methyl)piperidin-4-yl)propan-2-ol and 2-(1-fluorocyclopropyl)-1H-benzimidazole were reacted to give 307. LCMS m/z: 549.3 (MH+)

Example 308

2-(1-((2-(2-(cyclopropylmethyl)-1H-benzo[d]imidazol-1-yl)-9-methyl-6-morpholino-9H-purin-8-yl)methyl)piperidin-4-yl)propan-2-ol 308

Following General Procedure I for Buchwald coupling, 2-(1-((2-chloro-9-methyl-6-morpholino-9H-purin-8-yl)methyl)piperidin-4-yl)propan-2-ol and 2-(cyclopropylmethyl)-benzimidazole were reacted to give 308. LCMS m/z: 545.3 (MH+)

Example 309

4-(1-((2-(2-ethyl-1H-benzo[d]imidazol-1-yl)-9-methyl-6-morpholino-9H-purin-8-yl)methyl)azetidin-3-yl)morpholine 309

To a solution of 8-chloromethyl-2-(2-ethylbenzoimidazol-1-yl)-9-methyl-6-morpholin-4-yl-9H-purine (107 mg, 0.26 mmol) and 4-azetidin-3-ylmorpholine (44 mg, 0.31 mmol) in DMF (3 mL) was added $K_2CO_3$ (106 mg, 0.77 mmol). The resulting mixture was allowed to stir at room temperature for 16 h. The reaction mixture was dissolved in EtOAc, washed with $H_2O$ (×4) then dried ($Na_2SO_4$) and concentrated in vacuo. The resulting residue was purified by column chromatography (Si—PCC, MeOH:DCM, 0-5%). The resulting residue was further purified by Isolute® SCX-2 cartridge which was washed with MeOH/DCM and the product eluted with 2M $NH_3$/MeOH, followed by reverse phase HPLC (Phenomenex Luna $C_{18}$, 20 mM $Et_3N$ in water on a gradient of 20 mM $Et_3N$ in acetonitrile 95:5 to 2:98) to afford 309 as a white solid (14 mg, 11%). LCMS (Method G): $R_T$ 5.74 min, $[M+H]^+$ 518.3. $^1H$ NMR ($CDCl_3$, 400 MHz): δ 8.02-7.98 (m, 1 H); 7.77-7.73 (m, 1 H); 7.27-7.23 (m, 2 H); 4.35 (m, 4 H); 3.89-3.82 (m, 6 H); 3.83 (s, 3 H); 3.72 (m, 4 H); 3.56 (m, 2H); 3.34 (q, J=7.5 Hz, 2 H); 3.15-3.03 (m, 3 H); 2.34 (m, 4 H) and 1.44 (t, J=7.5 Hz, 3 H)

Example 310

4-(8-((3,3-dimethyl-4-(2-(methylsulfonyl)ethyl)piperazin-1-yl)methyl)-2-(2-ethyl-1H-benzo[d]imidazol-1-yl)-9-methyl-9H-purin-6-yl)morpholine 310

To a solution of 8-chloromethyl-2-(2-ethylbenzoimidazol-1-yl)-9-methyl-6-morpholin-4-yl-9H-purine (107 mg, 0.26 mmol) and 1-(2-methanesulfonylethyl)-2,2-dimethylpiperazine (68 mg, 0.31 mmol) in DMF (3 mL) was added $K_2CO_3$ (106 mg, 0.77 mmol). The resulting mixture was allowed to stir at room temperature for 16 h. The reaction mixture was dissolved in EtOAc, washed with $H_2O$ (×4) then dried ($Na_2SO_4$) and concentrated in vacuo. The residue was purified by column chromatography (Si—PCC, MeOH:EtOAc, 0-20%) and (Si—PCC, MeOH:DCM 0-5%). The resulting residue was further purified by reverse phase HPLC (Phenomenex Luna $C_{18}$, 20 mM $Et_3N$ in water on a gradient of 20 mM $Et_3N$ in acetonitrile 95:5 to 5:95) to afford 310 as a white solid (40 mg, 26%). LCMS (Method G): $R_T$ 6.68 min, $[M+H]^+$ 596.3. $^1H$ NMR ($CDCl_3$, 400 MHz): δ 8.04-7.99 (m, 1 H); 7.77-7.72 (m, 1 H); 7.28-7.23 (m, 2 H); 4.35 (m, 4 H); 3.87 (m, 7 H); 3.69 (s, 2H); 3.36 (q, J=7.5 Hz, 2 H); 3.11-3.03 (m, 5 H); 2.92 (m, 2 H); 2.62 (m 2 H); 2.51 (m, 2H); 2.37-2.22 (m, 2 H); 1.45 (t, J=7.5 Hz, 3 H) and 1.09 (s, 6 H)

Example 311

2-((1-((2-(2-ethyl-1H-benzo[d]imidazol-1-yl)-9-methyl-6-morpholino-9H-purin-8-yl)methyl)azetidin-3-yl)(methyl)amino)-2-methylpropanamide 311

A mixture of 2-(2-ethylbenzoimidazol-1-yl)-9-methyl-6-morpholin-4-yl-9H-purine-8-carbaldehyde (0.106 g, 0.27 mmol), 2-(azetidin-3-ylmethylamino)-2-methylpropionamide (0.055 g, 0.32 mmol) in DCE (3 mL), trimethoxymethane (0.314 mL, 2.9 mmol) and acetic acid (0.017 mL, 0.29 mmol) was stirred for 30 min at room temperature. Sodium triacetoxyborohydride (0.101 g, 0.48 mmol) was added and the reaction mixture was stirred for 18 h at room temperature. The suspension was partitioned between DCM and water, the organic layer was separated, washed with brine, dried over sodium sulphate and concentrated. The residue was purified by flash chromatography (Si—PPC, MeOH:DCM gradient 0:100 to 7.5:92.5) to give 311 as a white solid (0.096 g, 65%). LCMS (Method G): $R_T$=5.87 min, $[M+H]^+$ 547.3. $^1H$ NMR ($CDCl_3$, 400 MHz) δ 8.02-7.98 (m, 1H); 7.79-7.75 (m, 1 H);); 7.25-7.50 (m, 2 H); 6.98 (s, 1 H); 5.23 (s, 1 H); 4.35 (m, 4 H); 3.89-3.82 (m, 7 H); 3.57-3.50 (m, 2 H); 3.36 (q, J=7.5 Hz, 2 H); 3.28-3.23 (m, 1 H); 2.27-2.22 (m, 2 H); 1.70-1.64 (m, 6 H); 1.44 (t, J=7.5 Hz, 2 H); 1.20 (s, 6 H)

Example 312

4-(2-(2-ethyl-1H-benzo[d]imidazol-1-yl)-9-methyl-8-((4-(2-(methylsulfonyl)ethyl)piperazin-1-yl)methyl)-9H-purin-6-yl)morpholine 312

A mixture of 2-(2-ethylbenzoimidazol-1-yl)-9-methyl-6-morpholin-4-yl-9H-purine-8-carbaldehyde (65 mg, 0.17 mmol) and 1-(2-methanesulfonylethyl)piperazine (38 mg, 0.20 mmol) in DCE (4 mL) was stirred at room temperature for 1.5 h before the addition of sodium triacetoxyborohydride (70 mg, 0.33 mmol). The reaction mixture was stirred for 16 h then partitioned between brine and DCM. The organic phase was dried ($Na_2SO_4$) and concentrated in vacuo. The resulting residue was purified by column chromatography (Si—PCC, MeOH:EtOAc, 0-20%). The resulting oil was loaded onto an Isolute® SCX-2 cartridge which was washed with MeOH/DCM and the product eluted with 2M $NH_3$/MeOH affording 312 as a cream solid (29 mg, 30%). LCMS (Method G): $R_T$ 5.97 min $[M+H]^+$ 568.3. $^1H$ NMR ($CDCl_3$, 400 MHz): δ 8.03-7.99 (m, 1 H); 7.78-7.73 (m, 1 H); 7.30-7.24 (m, 2 H); 4.35 (m, 4 H); 3.90-3.83 (m, 7 H); 3.77 (s, 2 H); 3.36 (q, J=7.5 Hz, 2 H); 3.22-3.11 (m, 2H); 3.04 (s, 3 H); 2.91 (t, J=6.4 Hz, 2 H); 2.59 (m, 8 H) and 1.45 (t, J=7.5 Hz, 3 H)

Example 313

1-(1-((2-(2-ethyl-1H-benzo[d]imidazol-1-yl)-9-methyl-6-morpholino-9H-purin-8-yl)methyl)azetidin-3-yl)-2-methylpropan-1-ol 313

A mixture of 242-ethylbenzoimidazol-1-yl)-9-methyl-6-morpholin-4-yl-9H-purine-8-carbaldehyde (125 mg, 0.32 mmol), 1-azetidin-3-yl-2-methylpropan-1-ol (50 mg, 0.38 mmol) and 4 Å molecular sieves (1.0 g) in 1,2-dichloroethane (5 mL) was stirred at RT under nitrogen atmosphere for 5 h. Sodium triacetoxyborohydride (102 mg, 0.48 mmol) was added and the resulting reaction mixture was stirred at RT for 16 h. The solvent was reduced in vacuo and the residue was loaded onto an Isolute® SCX-2 cartridge (10 g). The cartridge was washed with DCM/MeOH, the desired product was subsequently eluted using a mixture of 2M $NH_3$ in MeOH and DCM. The solvents were reduced in vacuo to afford 313 as an off-white foam (60 mg, 37%). LCMS (Method G): $R_T$ 6.95 min, $[M+H]^+$ 505. $^1H$ NMR (400 MHz, $CDCl_3$): δ 7.99-7.95 (1 H, m), 7.72-7.71 (1 H, m), 7.23 (2 H, m), 4.32 (4 H, br s), 3.85-3.78 (9 H, m), 3.47-3.45 (3 H, m), 3.32 (2 H, q, J=7.48 Hz), 3.25 (1 H, t, J=6.66 Hz), 3.13 (1 H, t, J=6.66 Hz), 2.66-2.65 (1 H, m), 1.62-1.60 (2 H, m), 1.41 (3 H, t, J=7.48 Hz), 0.87(6 H, dd, J=11.85, 6.78 Hz)

Example 314

4-(2-(2-ethyl-1H-benzo[d]imidazol-1-yl)-9-methyl-8-((4-(oxetan-3-yl)piperidin-1-yl)methyl)-9H-purin-6-yl)morpholine 314

A mixture of 2-(2-ethylbenzoimidazol-1-yl)-9-methyl-6-morpholin-4-yl-9H-purine-8-carbaldehyde (0.105 g, 0.27 mmol), 4-oxetan-3-ylpiperidine (0.045 g, 0.32 mmol) in DCE (2 mL), trimethoxymethane (0.314 mL, 2.9 mmol) and acetic acid (0.017 mL, 0.29 mmol) was stirred for 18 h at room temperature. Sodium triacetoxyborohydride (0.101 g, 0.48 mmol) was added and the reaction mixture was stirred for 5 h at room temperature. After adding sodium triacetoxyborohydride (0.101 g, 0.48 mmol) the reaction mixture was stirred for a further 2 h and the suspension was partitioned between DCM and water. The organic layer was separated, washed with brine, dried over sodium sulphate and concentrated. The residue was purified by flash chromatography (Si—PPC, MEOH:DCM gradient 0:100 to 5:95) then (Si—PPC, acetone:EtOAc, 0:100 to 70:30) followed by reverse phase HPLC (Phenomenex Gemini 5u C18, 20 mM triethylamine in water on a gradient of acetonitrile 95:5 to 2:98) to give 314 as an off-white solid (0.048 g, 35%). LCMS (Method G): $R_T$=5.92 min, [M+H]$^+$ 517.3. $^1$H NMR (CDCl$_3$, 400 MHz) δ 8.03-7.99 (m, 1 H); 7.78-7.74 (m, 1H); 7.29-7.25 (m, 2 H); 4.76 (dd, J=7.9, 6.2 Hz, 2 H); 4.46 (t, J=6.2 Hz, 2 H); 4.44-4.35 (m, 4 H); 3.90-3.84 (m, 7 H); 3.78-3.73 (m, 2 H); 3.36 (q, J=7.5 Hz, 2 H); 2.95-2.91 (m, 2H); 2.79-2.71 (m, 1 H); 2.21-2.17 (m, 2 H); 1.81-1.50 (m, 4 H); 1.49-1.41 (t, J=7.5 Hz, 3H); 1.21-1.15 (m, 1 H)

Example 315

2-(1-((9-methyl-2-(2-methyl-1H-benzo[d]imidazol-1-yl)-6-morpholino-9H-purin-8-yl)methyl)azetidin-3-yl)propan-2-ol 315

A mixture of 2-(2-methylbenzoimidazol-1-yl)-9-methyl-6-morpholin-4-yl-9H-purine-8-carbaldehyde (0.075 g, 0.20 mmol), 2-azetidin-3-ylpropan-2-ol (0.023 g, 0.20 mmol) in DCE (2 mL), trimethoxymethane (0.215 mL, 2 mmol) and acetic acid (0.012 mL, 0.2 mmol) was stirred for 1 h at room temperature. Sodium triacetoxyborohydride (0.042 g, 0.2 mmol) was added and the reaction mixture was stirred for 18 h at room temperature. The reaction mixture was partitioned between DCM and water, and the organic layer was separated, washed with brine, dried over sodium sulphate and concentrated. The residue was purified by flash chromatography (Si—PPC, MEOH:DCM, gradient 0:100 to 10:90) to give 315 as an off-white solid (0.020 g, 23%). LCMS (Method G): $R_T$=5.61 min, [M+H]$^+$ 477.2. $^1$H NMR (CDCl$_3$, 400 MHz) δ 8.11-8.07 (m, 1 H); 7.72-7.69 (m, 1 H); 7.35-7.26 (m, 2 H); 4.42-4.31 (m, 4 H); 3.89-3.82 (m, 11 H); 3.62-3.12 (m, 2 H); 2.94 (s, 3 H); 2.70-2.55 (m, 1H); 1.18 (s, 6 H)

Example 316

3-(1-((9-methyl-2-(2-methyl-1H-benzo[d]imidazol-1-yl)-6-morpholino-9H-purin-8-yl)methyl)piperidin-4-yl)pentan-3-ol 316

Following General Procedure I for Buchwald coupling, 2-methylbenzimidazole and 3-(1-((2-chloro-9-methyl-6-morpholino-9H-purin-8-yl)methyl)piperidin-4-yl)pentan-3-ol were reacted to give 316. LCMS m/z: 533.3 (MH+)

Example 317

4-(1-((9-methyl-2-(2-methyl-1H-benzo[d]imidazol-1-yl)-6-morpholino-9H-purin-8-yl)methyl)piperidin-4-yl)tetrahydro-2H-pyran-4-ol 317

Following General Procedure I for Buchwald coupling, 2-methylbenzimidazole and 4-(1-((2-chloro-9-methyl-6-morpholino-9H-purin-8-yl)methyl)piperidin-4-yl)-tetrahydro-2H-pyran-4-ol were reacted to give 317. LCMS m/z: 547.3 (MH+)

Example 318

(S)-4-(8-((3-(1,1-dioxo-isothiazolidin-2-yl)pyrrolidin-1-yl)methyl)-9-methyl-2-(2-methyl-1H-benzo[d]imidazol-1-yl)-9H-purin-6-yl)morpholine 318

Following General Procedure I for Buchwald coupling, 2-methylbenzimidazole and 4-(2-chloro-8-((3-(iso-dioxothiazolidin-2-yl)pyrrolidin-1-yl)methyl)-9-methyl-9H-purin-6-yl)morpholine were reacted to give 318. LCMS m/z: 552.2 (MH+)

Example 319

2-(1-((9-methyl-2-(2-(1-methyl-1H-pyrazol-5-yl)-1H-benzo[d]imidazol-1-yl)-6-morpholino-9H-purin-8-yl)methyl)piperidin-4-yl)propan-2-ol 319

Following General Procedure I for Buchwald coupling, 2-(1-methyl-1H-pyrazol-5-yl)-1H-benzo[d]imidazole and 2-(1-((2-chloro-9-methyl-6-morpholino-9H-purin-8-yl)methyl)piperidin-4-yl)propan-2-ol were reacted to give 319. LCMS m/z: 571.3 (MH+)

Example 320

I-4-(8-((3-(1,1-dioxo-isothiazolidin-2-yl)pyrrolidin-1-yl)methyl)-9-methyl-2-(2-methyl-1H-benzo[d]imidazol-1-yl)-9H-purin-6-yl)morpholine 320

Following General Procedure I for Buchwald coupling, 2-methylbenzimidazole and 4-(2-chloro-8-((3-(iso-dioxothiazolidin-2-yl)pyrrolidin-1-yl)methyl)-9-methyl-9H-purin-6-yl)morpholine were reacted to give 320. LCMS m/z: 552.2 (MH+)

Example 321

N-((9-methyl-2-(2-methyl-1H-benzo[d]imidazol-1-yl)-6-morpholino-9H-purin-8-yl)methyl)-2-(4-methylthiazol-2-yl)ethanamine 321

Following General Procedure L for reductive amination, 9-methyl-2-(2-methyl-1H-benzo[d]imidazol-1-yl)-6-morpholino-9H-purine-8-carbaldehyde and 2-(4-methylthiazol-2-yl)ethanamine were reacted to give 321. [M+H]$^+$ 504.6.

Example 322

N-((9-methyl-2-(2-methyl-1H-benzo[d]imidazol-1-yl)-6-morpholino-9H-purin-8-yl)methyl)-2-(pyridin-2-yl)ethanamine 322

Following General Procedure L for reductive amination, 9-methyl-2-(2-methyl-1H-benzo[d]imidazol-1-yl)-6-morpholino-9H-purine-8-carbaldehyde and 2-(pyridin-2-yl)ethanamine were reacted to give 322. [M+H]$^+$ 484.6.

Example 323

1-(1-((9-methyl-2-(2-methyl-1H-benzo[d]imidazol-1-yl)-6-morpholino-9H-purin-8-yl)methyl)piperidin-4-yl)cyclopentanol 323

Following General Procedure I for Buchwald coupling, 2-methylbenzimidazole and 1-(1-((2-chloro-9-methyl-6- morpholino-9H-purin-8-yl)methyl)piperidin-4-yl)cyclopentanol were reacted to give 323. LCMS m/z: 531.3 (MH+)

Example 324

7-((2-(2-ethyl-1H-benzo[d]imidazol-1-yl)-9-methyl-6-morpholino-9H-purin-8-yl)methyl)-2-oxa-7-azaspiro[3.5]nonane 324

A mixture of 2-(2-ethylbenzoimidazol-1-yl)-9-methyl-6-morpholin-4-yl-9H-purine-8-carbaldehyde (0.075 g, 0.19 mmol), 2-oxa-7-azaspiro[3.5]nonane trifluoroacetate (0.05 g, 0.20 mmol) in DCE (2 mL), trimethoxymethane (0.204 mL, 1.9 mmol) and acetic acid (0.011 mL, 0.2 mmol) was stirred for 2 h at room temperature. Sodium triacetoxyborohydride (0.061 g, 0.29 mmol) was added and the reaction mixture was stirred for 18 h at room temperature. The reaction mixture was partitioned between DCM and water, the organic layer was separated, washed with brine, dried over sodium sulphate and concentrated. The residue was purified by flash chromatography (Si—PPC, MEOH:DCM gradient 0:100 to 10:90) to give 324 as a white solid (0.066 g, 70%). LCMS (Method G): $R_T$=5.88 min, [M+H]$^+$ 503.2. $^1$H NMR (CDCl$_3$, 400 MHz) δ 8.03-7.99 (m, 1 H); 7.83-7.79 (m, 1 H); 7.33-7.29 (m, 2 H); 4.48-4.37 (m, 4 H); 4.34-4.30 (m, 4 H); 3.90-3.84 (m, 7 H); 3.76-3.72 (m, 2 H); 3.40 (d, J=8.3 Hz, 2 H); 2.49-2.44 (m, 4 H); 1.95-1.91 (m, 4 H); 1.48 (t, J=7.5 Hz, 3 H)

Example 325

4-(2-(2-ethyl-1H-benzo[d]imidazol-1-yl)-9-methyl-8-((3-(tetrahydro-2H-pyran-4-yl)azetidin-1-yl)methyl)-9H-purin-6-yl)morpholine 325

A mixture of 2-(2-ethylbenzoimidazol-1-yl)-9-methyl-6-morpholin-4-yl-9H-purine-8-carbaldehyde (0.10 g, 0.26 mmol), 3-(tetrahydropyran-4-yl)azetidine (0.050 g, 0.28 mmol) in DCE (2 mL), trimethoxymethane (0.277 mL, 2.6 mmol) and acetic acid (0.015 mL, 0.26 mmol) was stirred for 2 h at room temperature. Sodium triacetoxyborohydride (0.090 g, 0.43 mmol) was added and the reaction mixture was stirred for 18 h at room temperature. The reaction mixture was partitioned between DCM and water, the organic phase was separated, washed with brine, dried over sodium sulphate and concentrated. The residue was purified by flash chromatography (Si—PPC, MeOH:EtOAc gradient 0:100 to 10:90) to give 325 as a yellow solid (0.072 g, 56%). LCMS (Method G): $R_T$=6.14 min, [M+H]$^+$ 517.2. $^1$H NMR (CDCl$_3$, 400 MHz) δ 8.02-7.98 (m, 1 H); 7.78-7.73 (m, 1 H); 7.35-7.25 (m, 2 H); 4.40-4.32 (m, 4 H); 3.98 (dd, J=11.7, 4.3 Hz, 2 H); 3.89-3.86 (m, 9 H); 3.42-3.30 (m, 5 H); 1.67-1.64 (m, 4 H); 1.55 (d, J=11.7 Hz, 2 H); 1.48-1.39 (t, J=7.5 Hz, 3 H); 1.29-1.16 (m, 3 H)

Example 326

N,N-dimethyl-1-((9-methyl-2-(2-methyl-1H-benzo[d]imidazol-1-yl)-6-morpholino-9H-purin-8-yl)methyl)piperidine-4-carboxamide 326

A solution of 9-methyl-2-(2-methylbenzoimidazol-1-yl)-6-morpholin-4-yl-9H-purine-8-carbaldehyde (100 mg, 0.27 mmol) and piperidine-4-carboxylic acid dimethylamide (50 mg, 0.32 mmol) in DCE (3 mL) was stirred at ambient temperature for 90 min. Sodium triacetoxyborohydride (86 mg, 0.41 mmol) was added and the mixture stirred for 18 h, then loaded onto an Isolute® SCX-2 cartridge (10 g). The cartridge was then washed with methanol and the desired product was subsequently eluted using 2 M NH$_3$ in MeOH. The product was collected and concentrated in vacuo. The resultant residue was purified by flash chromatography (Si—PPC, DCM:MeOH; 100:0, 95:5, 90:10, to 85:15) to afford 326 as a white solid (69 mg, 51%). LCMS (Method G): $R_T$=5.48 min, M+H$^+$=518. $^1$H NMR (CDCl$_3$, 400 MHz) δ 8.19 (m, 1 H); 7.73-7.68 (m, 1 H); 7.29-7.25 (m, 2 H); 4.35 (m, 4 H); 3.91-3.83 (m, 7 H); 3.75 (s, 2 H); 3.06 (s, 3 H); 2.95 (s, 6 H); 2.54 (m, 1 H); 2.18 (m, 2 H); 1.92-1.79 (m, 2 H) and 1.71 (m, 4 H)

Example 327

8-((9-methyl-2-(2-methyl-1H-benzo[d]imidazol-1-yl)-6-morpholino-9H-purin-8-yl)methyl)-1-oxa-3,8-diazaspiro[4.5]decan-2-one 327

A solution of 9-methyl-2-(2-methylbenzoimidazol-1-yl)-6-morpholin-4-yl-9H-purine-8-carbaldehyde (100 mg, 0.27 mmol) and 1-oxa-3,8-diazaspiro[4.5]decan-2-one (50 mg, 0.32 mmol) in DCE (3 mL) was stirred at ambient temperature for 90 min. Sodium triacetoxyborohydride (86 mg, 0.41 mmol) was added and the mixture stirred for 18 h, then loaded onto an Isolute® SCX-2 cartridge (10 g). The cartridge was then washed with methanol and the desired product was subsequently eluted using 2 M NH$_3$ in MeOH. The product was collected and concentrated in vacuo. The resultant residue was purified by flash chromatography (Si—PPC, DCM:MeOH; 100:0 to 95:5 to 90:10 to 85:15) to afford 327 as a white solid (77 mg, 56%). LCMS (Method G): $R_T$=5.35 min, M+H$^+$=518. $^1$H NMR (CDCl$_3$, 400 MHz) δ 8.9 (m, 1 H); 7.72 (m, 1 H); 7.29 (m, 2 H); 4.99 (bs, 1 H); 4.35 (m, 4H); 3.90-3.83 (m, 7 H); 3.80 (s, 2 H); 3.36 (s, 2 H); 2.95 (s, 3 H); 2.76-2.65 (m, 4 H); 2.03 (m, 2 H) and 1.82 (m, 2 H)

Example 328

4-(1-((9-methyl-2-(2-methyl-1H-benzo[d]imidazol-1-yl)-6-morpholino-9H-purin-8-yl)methyl)azetidin-3-yl)morpholine 328

A mixture of 9-methyl-2-(2-methylbenzoimidazol-1-yl)-6-morpholin-4-yl-9H-purine-8-carbaldehyde (80 mg, 0.21 mmol), 4-azetidin-3-ylmorpholine (36 mg, 0.25 mmol) and 4 Å powdered molecular sieves (100 mg) in DCE (5 mL) was stirred at room temperature for 4 h before the addition of sodium triacetoxyborohydride (90 mg, 0.42 mmol). The reaction mixture was stirred for 64 h then filtered through celite, washing with DCM. The organic phase was washed with brine (×1) and concentrated in vacuo. The resulting residue was purified by column chromatography (Si—PCC, MeOH:EtOAc, 0-20%). The resulting oil was loaded onto an Isolute® SCX-2 cartridge which was washed with MeOH/DCM and the product eluted with 2M NH$_3$/MeOH affording 328 as a cream solid (71 mg, 67%). LCMS (Method G): $R_T$ 5.18 min [M+H]$^+$ 504.2. $^1$H NMR (CDCl$_3$, 400 MHz): δ 8.10-8.05 (m, 1 H); 7.73-7.69 (m, 1 H); 7.28-7.23 (m, 2 H); 4.35 (m, 4 H); 3.91-3.82 (m, 9 H); 3.73 (m, 4 H); 3.58 (m, 2 H); 3.18-3.04 (m, 3 H); 2.94 (s, 3 H) and 2.35 (m, 4 H)

Example 329

4-(9-methyl-2-(2-methyl-1H-benzo[d]imidazol-1-yl)-8-((4-(2-(methylsulfonyl)ethyl)piperazin-1-yl)methyl)-9H-purin-6-yl)morpholine 329

A mixture of 9-methyl-2-(2-methylbenzoimidazol-1-yl)-6-morpholin-4-yl-9H-purine-8-carbaldehyde (60 mg, 0.16 mmol), 1-(2-methanesulfonylethyl)piperazine (37 mg, 0.19 mmol) and 4 Å powdered molecular sieves (100 mg) in DCE (4 mL) was stirred at room temperature for 4 h before the addition of sodium triacetoxyborohydride (67 mg, 0.32 mmol). The reaction mixture was stirred for 64 h then filtered through celite, washing with DCM. The organic phase was washed with brine (×1) and concentrated in vacuo. The resulting residue was purified by column chromatography (Si—PCC, MeOH:EtOAc, 0-20%). The resulting oil was loaded onto an Isolute® SCX-2 cartridge which was washed with MeOH/DCM and the product eluted with 2M NH$_3$/MeOH affording 329 as a cream solid (55 mg, 62%). LCMS (Method G): R$_T$ 5.54 min [M+H]$^+$ 554.3. $^1$H NMR (CDCl$_3$, 400 MHz): δ 8.11-8.06 (m, 1 H); 7.74-7.70 (m, 1 H); 7.30-7.25 (m, 2 H); 4.35 (m, 4 H); 3.90-3.82 (m, 7H); 3.76 (s, 2 H); 3.15 (t, J=6.4 Hz, 2 H); 3.04 (s, 3 H); 2.95 (s, 3 H); 2.90 (t, J=6.4 Hz, 2 H) and 2.57 (m, 8 H)

Example 330

4-(8-((3,3-dimethyl-4-(2-(methylsulfonyl)ethyl)piperazin-1-yl)methyl)-9-methyl-2-(2-methyl-1H-benzo[d]imidazol-1-yl)-9H-purin-6-yl)morpholine 330

A mixture of 9-methyl-2-(2-methylbenzoimidazol-1-yl)-6-morpholin-4-yl-9H-purine-8-carbaldehyde (80 mg, 0.21 mmol), 1-(2-methanesulfonylethyl)-2,2-dimethylpiperazine (56 mg, 0.25 mmol) and 4 Å powdered molecular sieves (100 mg) in DCE (5 mL) was stirred at room temperature for 4 h before the addition of sodium triacetoxyborohydride (90 mg, 0.42 mmol). The reaction mixture was stirred for 64 h then filtered through celite, washing with DCM. The organic phase was washed with brine (×1) and concentrated in vacuo. The resulting residue was purified by column chromatography (Si—PCC, MeOH:EtOAc, 0-15%). The resulting oil was loaded onto an Isolute® SCX-2 cartridge which was washed with MeOH/DCM and the product eluted with 2M NH$_3$/MeOH affording 330 as a white solid (70 mg, 58%). LCMS (Method G): R$_T$ 6.62 min [M+H]$^+$ 582.3. $^1$H NMR (CDCl$_3$, 400 MHz): δ 8.12-8.07 (m, 1 H); 7.74-7.70 (m, 1 H); 7.29-7.25 (m, 2 H); 4.35 (m, 4 H); 3.91-3.83 (m, 7 H); 3.69 (s, 2 H); 3.11 (m, 2 H); 3.06 (s, 3 H); 2.95 (s, 3 H); 2.63 (m, 2 H); 2.54 (m, 2 H); 2.30 (s, 2 H); 1.78 (m, 2 H) and 1.10 (s, 6 H)

Example 331

4-(1-((2-(2-ethyl-1H-benzo[d]imidazol-1-yl)-9-methyl-6-morpholino-9H-purin-8-yl)methyl)azetidin-3-yl)-2,2-dimethylmorpholine 331

A mixture of 2-(2-ethylbenzoimidazol-1-yl)-9-methyl-6-morpholin-4-yl-9H-purine-8-carbaldehyde (112 mg, 0.29 mmol), 4-azetidin-3-yl-2,2-dimethylmorpholine (58 mg, 0.34 mmol) and 4 Å powdered molecular sieves (200 mg) in DCE (5 mL) was stirred at room temperature for 4 h before the addition of sodium triacetoxyborohydride (121 mg, 0.57 mmol). The reaction mixture was stirred for 40 h then filtered through celite, washing with DCM. The organic phase was washed with brine (x 1) and concentrated in vacuo. The organic phase was dried (Na$_2$SO$_4$) and concentrated in vacuo. The resulting residue was purified by column chromatography (Si—PCC, MeOH:EtOAc, 0-20%). The resulting oil was loaded onto an Isolute® SCX-2 cartridge which was washed with MeOH/DCM and the product eluted with 2M NH$_3$/MeOH affording 331 as a yellow solid (121 mg, 76%). LCMS (Method G): R$_T$ 6.85 min [M+H]$^+$ 546.3. $^1$H NMR (CDCl$_3$, 400 MHz): δ 8.02-7.97 (m, 1 H); 7.77-7.73 (m, 1 H); 7.29-7.22 (m, 2 H); 4.35 (m, 4 H); 3.91-3.82 (m, 9 H); 3.73 (m, 2 H); 3.57 (t, J=6.6 Hz, 2 H); 3.35 (q, J=7.5 Hz, 2 H); 3.10 (t, J=6.6 Hz, 2 H); 2.98 (p, J=6.6 Hz, 1 H); 2.24 (m, 2 H); 2.04 (s, 2 H); 1.44 (t, J=7.5 Hz, 3 H) and 1.25 (s, 6 H)

Example 332

2-(1-(((5-(2-ethyl-1H-benzo[d]imidazol-1-yl)-7-morpholinothiazolo[5,4-d]pyrimidin-2-yl)methyl)piperidin-4-yl)propan-2-ol 332

A mixture 2-[1-(5-chloro-7-morpholin-4-ylthiazolo[5,4-d]pyrimidin-2-ylmethyl)piperidin-4-yl]propan-2-ol (100 mg, 0.24 mmol), 2-ethyl-1H-benzoimidazole (42 mg, 0.29 mmol), copper(I) thiophene-2-carboxylate (9 mg, 0.048 mmol) and cesium carbonate (119 mg, 0.36 mmol) in NMP (0.5 mL) was stirred at 110° C. for 18 hours. The reaction mixture was diluted with MeOH and loaded onto an Isolute® SCX-2 cartridge (5 g). The cartridge was washed with MeOH and the desired product was eluted with 2M NH$_3$ in MeOH. The solvents were removed and the residue was subjected to flash chromatography (Si—PCC, 0-20% MeOH in EtOAc) followed by reverse phase HPLC (Phenomenex Gemini 5u C18, 20 mM triethylamine in water on a gradient of acetonitrile 95:5 to 2:98) to give 332 as a beige solid (45 mg, 36%). LCMS (Method G): R$_T$ 7.37 min; [M+H]$^+$ 522. $^1$H NMR (400 MHz, CHCl$_3$-d): δ 8.03-7.98 (m, 1 H); 7.77-7.73 (m, 1 H); 7.32-7.24 (m, 2 H); 4.41 (m, 4H); 3.90-3.85 (m, 6 H); 3.35 (q, J=7.5 Hz, 2 H); 3.11 (m, 2 H); 2.33-2.12 (m, 2 H); 1.79 (m, 2 H); 1.57 (m, 2 H); 1.44 (t, J=7.5 Hz, 3 H); 1.34 (m, 1 H); 1.22 (s, 6 H)

Example 337

2-(1-((2-(2-ethoxy-1H-benzo[d]imidazol-1-yl)-9-methyl-6-morpholino-9H-purin-8-yl)methyl)piperidin-4-yl)propan-2-ol 337

Following General Procedure I for Buchwald coupling, 2-(1-((2-chloro-9-methyl-6-morpholino-9H-purin-8-yl)methyl)piperidin-4-yl)propan-2-ol and 2-ethoxy-1H-benzo[d]imidazole were reacted to give 337. LCMS: M+H$^+$=535.3

Example 338

2-(1-((2-(2-isopropoxy-1H-benzo[d]imidazol-1-yl)-9-methyl-6-morpholino-9H-purin-8-yl)methyl)piperidin-4-yl)propan-2-ol 338

Following General Procedure I for Buchwald coupling, 2-(1-((2-chloro-9-methyl-6-morpholino-9H-purin-8-yl)methyl)piperidin-4-yl)propan-2-ol and 2-isopropoxy-1H-benzo[d]imidazole were reacted to give 338. LCMS: M+H$^+$=549.3

Example 339

2-methyl-2-(1-((9-methyl-2-(2-methyl-1H-benzo[d]imidazol-1-yl)-6-morpholino-9H-purin-8-yl)methyl)piperidin-4-yl)propan-1-ol 339

Following General Procedure E for amine alkylation, 4-(8-(bromomethyl)-9-methyl-2-(2-methyl-1H-benzo[d]imidazol-1-yl)-9H-purin-6-yl)morpholine and 2-methyl-2-(piperidin-4-yl)propan-1-ol were reacted to give 339. LCMS: M+H$^+$= 519.3

Example 341

2-(1-((2-(2-ethyl-1H-benzo[d]imidazol-1-yl)-9-methyl-6-morpholino-9H-purin-8-yl)methyl)piperidin-4-yl)-2-methylpropan-1-ol 341

Following General Procedure E for amine alkylation, 4-(8-(bromomethyl)-9-methyl-2-(2-ethyl-1H-benzo[d]imidazol-1-yl)-9H-purin-6-yl)morpholine and 2-methyl-2-(piperidin-4-yl)propan-1-ol were reacted to give 341. LCMS: M+H$^+$= 533.3

Example 342

N-((9-methyl-2-(2-methyl-1H-benzo[d]imidazol-1-yl)-6-morpholino-9H-purin-8-yl)methyl)-2-(pyrazin-2-yl)ethanamine 342

Following General Procedure L for reductive amination, 9-methyl-2-(2-methyl-1H-benzo[d]imidazol-1-yl)-6-morpholino-9H-purine-8-carbaldehyde and 2-(pyrazin-2-yl)ethanamine were reacted to give 342. [M+H]$^+$ 485.6.

Example 343

7-((9-methyl-2-(2-methyl-1H-benzo[d]imidazol-1-yl)-6-morpholino-9H-purin-8-yl)methyl)-7-azaspiro[3.5]nonan-2-ol 343

To a solution of 9-methyl-2-(2-methylbenzoimidazol-1-yl)-6-morpholin-4-yl-9H-purine-8-carbaldehyde (134 mg, 0.35 mmol) in DCE (5 mL) was added 7-azaspiro[3.5]nonan-2-ol (60 mg, 0.43 mmol), trimethyl orthoformate (0.19 mL, 1.77 mmol) and acetic acid (0.02 mL, 0.35 mmol). The reaction mixture was stirred at room temperature for 3 h, sodium triacetoxyborohydride (113 mg, 0.53 mmol) was added and the resulting mixture stirred for a further 2 h. The reaction mixture was loaded onto an Isolute® SCX-2 cartridge, washed with MeOH then the desired product eluted with 2 M NH$_3$ in MeOH. The resulting residue was purified by column chromatography (Si—PCC, 0-20% MeOH in EtOAc) to give 343 as a white solid (80 mg, 45%). LCMS (Method G): R$_T$=5.23 min, [M+H]$^+$ 503.2. $^1$H NMR (400 MHz, CHCl$_3$-d): δ 8.11-8.06 (m, 1 H), 7.73-7.68 (m, 1 H), 7.30-7.24 (m, 2 H), 4.37-4.24 (m, 4 H), 3.90-3.83 (m, 7 H), 3.72 (s, 2 H), 2.94 (s, 3 H), 2.58-2.31 (m, 4 H), 2.30-2.23 (m, 2 H), 1.75-1.55 (m, 8 H)

Example 344

2-(1-(2-(9-methyl-2-(2-methyl-1H-benzo[d]imidazol-1-yl)-6-morpholino-9H-purin-8-yl)ethyl)piperidin-4-yl)propan-2-ol 344

A mixture of 2-{1-[2-(2-chloro-9-methyl-6-morpholin-4-yl-9H-purin-8-yl)ethyl]-piperidin-4-yl}propan-2-ol (47 mg, 0.11 mmol), 2-methylbenzimidazole (16 mg, 0.12 mmol), Pd$_2$(dba)$_3$ (2.5 mg, 2.5 mol %), Xphos (5.0 mg, 10 mol %) and Cs$_2$CO$_3$ (54 mg, 0.17 mmol) in dioxane (1.0 mL) was purged with argon gas then heated at 150° C., for 30 min, in a microwave reactor. The reaction mixture was loaded onto an Isolute® SCX-2 cartridge, washed with MeOH then the desired product eluted with 2 M NH$_3$ in MeOH. The resulting residue was purified by flash chromatography (RediSep amine cartridge, 0-5% MeOH in DCM) followed by reverse phase HPLC (Phenomenex Gemini 5 µm C18, 20 mM triethylamine in water on a gradient of acetonitrile 30-50%) to give 344 (25 mg, 43%) as a white solid. LCMS: (Method G): R$_T$ 5.64 min; [M+H]$^+$ 519.3. $^1$H NMR (400 MHz, CHCl$_3$-d): δ 8.09-8.04 (m, 1 H), 7.73-7.69 (m, 1 H), 7.29-7.24 (m, 2 H), 4.48-4.16 (m, 4 H), 3.87 (t, J=4.7 Hz, 4 H), 3.79 (s, 3 H), 3.23-1.05 (m, 4 H), 2.93 (s, 3 H), 2.93-2.75 (m, 2 H), 2.11 (s, 3 H), 1.90-1.75 (m, 2 H), 1.55-1.25 (m, 3 H), 1.20 (s, 6 H)

Example 345

4-(2-(2-ethyl-1H-benzo[d]imidazol-1-yl)-8-((3-fluoro-1,3'-biazetidin-1'-yl)methyl)-9-methyl-9H-purin-6-yl)morpholine 345

A mixture of 2-(2-ethylbenzoimidazol-1-yl)-9-methyl-6-morpholin-4-yl-9H-purine-8-carbaldehyde (0.079 g, 0.20 mmol), 3-fluoro-[1,3']biazetidinyl (0.029 g, 0.22 mmol) in DCE (3 mL), trimethoxymethane (0.22 mL, 2 mmol) and acetic acid (0.012 mL, 0.2 mmol) was stirred for 5 h at room temperature. Sodium triacetoxyborohydride (0.065 g, 0.30 mmol) was added and the reaction mixture was stirred for 18 h at room temperature. The reaction mixture was partitioned between DCM and water. The organic layer was separated, washed with brine, dried over sodium sulphate and concentrated. The residue was purified by flash chromatography (Si—PPC, MeOH:EtOAc, gradient 0:100 to 16:84) followed by reverse phase HPLC (Phenomenex Gemini 5u C18, 20 mM triethylamine in water on a gradient of acetonitrile 95:5 to 5:95) to give 345 as an off-white solid (0.054 g, 53%). LCMS (Method G): R$_T$=5.78 min, [M+H]$^+$ 506.2. $^1$H NMR (CDCl$_3$, 400 MHz) δ 8.02-7.98 (m, 1 H); 7.77-7.73 (m, 1 H); 7.28-7.24 (m, 2 H); 5.15 (dt, J=57.3, 5.4 Hz, 1 H); 4.38-4.33 (m, 4 H); 3.90-3.85 (m, 6 H); 3.83 (s, 2 H); 3.72-3.62 (m, 3 H); 3.48-3.39 (m, 3 H); 3.35 (q, J=7.5 Hz, 2 H); 3.35-3.19 (m, 2 H); 3.17-3.15 (m, 2 H); 1.44 (t, J=7.5 Hz, 3 H)

Example 346

2-methyl-1-(1-((9-methyl-242-methyl-1H-benzo[d]imidazol-1-yl)-6-morpholino-9H-purin-8-yl)methyl)piperidin-4-yl)propan-1-ol 346

A mixture of 9-methyl-242-methylbenzoimidazol-1-yl)-6-morpholin-4-yl-9H-purine-8-carbaldehyde (200 mg, 0.53 mmol), 2-methyl-1-piperidin-4-yl-propan-1-ol (125 mg, 0.79 mmol) and 4 Å molecular sieves (1.0 g) in 1,2-dichloroethane (10 mL) was stirred at RT under nitrogen atmosphere for 1.5 h. Sodium triacetoxyborohydride (167 mg, 0.79 mmol) was added and the resulting reaction mixture was stirred at RT for 16 h. The solvent was reduced in vacuo and the residue was loaded onto an Isolute® SCX-2 cartridge (10 g). The cartridge was washed with DCM/MeOH, the desired product was subsequently eluted using a mixture of 2M NH$_3$ in MeOH and DCM. The residue was purified by column chromatography (Si—PCC, MeOH:DCM: gradient 0:100 to 5:95) followed by further purification (Si—PCC, acetone: cyclohexane: gradient 10:90 to 40:60). The solvents were reduced in vacuo to afford 346 as a white solid (114 mg, 41%). LCMS (Method G): R$_T$ 6.81 min, [M+H]$^+$ 519. $^1$H NMR (400 MHz, CH OH-d$_4$): δ 8.06-8.05 (1 H, m), 7.56-7.55 (1 H, m), 7.25-7.24 (2 H, m), 4.29 (4 H, br s), 3.84 (3 H, s), 3.81 (4 H, t, J=4.74 Hz), 3.74 (2 H, s), 2.98-2.95 (3 H, m), 2.86 (3 H, s), 2.11 (2 H, m), 1.84 (1 H, m), 1.72-1.71 (1 H, m), 1.57-1.20 (4 H, m), 0.87 (6 H, dd, J=15.35, 6.73 Hz)

Example 347 azetidin-1-yl(1-((9-methyl-2-(2-methyl-1H-benzo[d]imidazol-1-yl)-6-morpholino-9H-purin-8-yl)methyl)azetidin-3-yl)methanone 347

A solution of 9-methyl-2-(2-methylbenzoimidazol-1-yl)-6-morpholin-4-yl-9H-purine-8-carbaldehyde (100 mg, 0.27 mmol) and azetidin-3-ylazetidin-1-ylmethanone (45 mg, 0.31 mmol) in DCE (3 mL) was stirred at ambient temperature for 90 min. Sodium triacetoxyborohydride (86 mg, 0.41 mmol) was added and the mixture stirred for 18 h, then loaded onto an Isolute® SCX-2 cartridge (10 g). The cartridge was then washed with methanol and the desired product was subsequently eluted using 2 M $NH_3$ in MeOH. The product was collected and concentrated in vacuo. The resultant residue was purified by flash chromatography (Si—PPC, EtOAc:MeOH; 100:0 to 90:10 to 85:15) to afford 347 as a white solid (30 mg, 23%). LCMS (Method G): $R_T$=5.33 min, M+H$^+$=502. $^1$H NMR (CDCl$_3$, 400 MHz) δ 8.07 (m, 1 H); 7.69 (m, 1 H); 7.28 (m, 2 H); 4.35 (m, 4 H); 4.13-4.00 (m, 4 H); 3.87 (m, 6 H); 3.82 (s, 3 H); 3.68-3.58 (m, 2 H); 3.53-3.45 (m, 2 H); 3.34-3.26 (m, 1 H); 2.96 (s, 3 H) and 2.33-2.23 (m, 2 H)

Example 348

(1-((9-methyl-2-(2-methyl-1H-benzo[d]imidazol-1-yl)-6-morpholino-9H-purin-8-yl)methyl)azetidin-3-yl)(pyrrolidin-1-yl)methanone 348

A solution of 9-methyl-2-(2-methylbenzoimidazol-1-yl)-6-morpholin-4-yl-9H-purine-8-carbaldehyde (100 mg, 0.27 mmol) and azetidin-3-ylpyrrolidin-1-ylmethanone (50 mg, 0.32 mmol) in DCE (3 mL) was stirred at ambient temperature for 90 min. Sodium triacetoxyborohydride (86 mg, 0.41 mmol) was added and the mixture stirred for 18 h, then loaded onto an Isolute® SCX-2 cartridge (10 g). The cartridge was then washed with methanol and the desired product was subsequently eluted using 2 M $NH_3$ in MeOH. The product was collected and concentrated in vacuo. The resultant residue was purified by flash chromatography (Si—PPC, EtOAc:MeOH; gradient from 100:0 to 70:30) to afford 348 as a white foam (50 mg, 37%). LCMS (Method G): $R_T$=5.81 min, M+H$^+$= 516. $^1$H NMR (CDCl$_3$, 400 MHz) δ 8.08 (m, 1 H); 7.71 (m, 1 H); 7.26 (m, 2 H); 4.35 (m, 4 H); 3.89-3.83 (m, 9 H); 3.66 (m, 2 H); 3.55-3.43 (m, 5 H); 3.31 (m, 2 H); 2.94 (s, 3 H) and 1.98-1.81 (m, 4 H)

Example 349

I-azetidin-1-yl(1-((9-methyl-2-(2-methyl-1H-benzo[d]imidazol-1-yl)-6-morpholino-9H-purin-8-yl)methyl)pyrrolidin-3-yl)methanone 349

A solution of 9-methyl-2-(2-methylbenzoimidazol-1-yl)-6-morpholin-4-yl-9H-purine-8-carbaldehyde (141 mg, 0.37 mmol) and azetidin-1-yl-I-pyrrolidin-3-ylmethanone (77 mg, 0.50 mmol) in DCE (6 mL) was stirred at ambient temperature for 2 h. Sodium triacetoxyborohydride (134 mg, 0.63 mmol) was added and the mixture stirred for 18 h, then loaded onto an Isolute® SCX-2 cartridge (10 g). The cartridge was then washed with methanol and the desired product was subsequently eluted using 2 M $NH_3$ in MeOH. The product was collected and concentrated in vacuo. The resultant residue was purified by flash chromatography (Si—PPC, DCM:MeOH; gradient from 100:0 to 70:30) to afford 349 as a cream solid (157 mg, 81%). LCMS (Method G): $R_T$=5.52 min, M+H$^+$=516. $^1$H NMR (CDCl$_3$, 400 MHz) δ 8.09 (m, 1 H); 7.70 (m, 1 H); 7.28 (m, 2 H); 4.35 (m, 4 H); 4.18-4.08 (m, 2 H); 4.03 (m, 2 H); 3.92 (s, 2 H); 3.92-3.81 (m, 7 H); 3.08-2.71 (m, 7 H); 2.69 (m, 1H); 2.33-2.23 (m, 2 H) and 2.10-2.03 (m, 2 H)

Example 350

I-(1-((2-(2-ethyl-1H-benzo[d]imidazol-1-yl)-9-methyl-6-morpholino-9H-purin-8-yl)methyl)pyrrolidin-3-yl)(pyrrolidin-1-yl)methanone 350

A solution of 2-(2-ethylbenzoimidazol-1-yl)-9-methyl-6-morpholin-4-yl-9H-purine-8-carbaldehyde (110 mg, 0.28 mmol) and pyrrolidin-1-yl-I-pyrrolidin-3-ylmethanone (60 mg, 0.36 mmol) in DCE (6 mL) was stirred at ambient temperature for 2 h. Sodium triacetoxyborohydride (96 mg, 0.45 mmol) was added and the mixture stirred for 18 h, then loaded onto an Isolute® SCX-2 cartridge (10 g). The cartridge was then washed with methanol and the desired product was subsequently eluted using 2 M $NH_3$ in MeOH. The product was collected and concentrated in vacuo. The resultant residue was purified by flash chromatography (Si—PPC, DCM:MeOH; gradient from 100:0 to 70:30), followed by reverse phase HPLC (Phenomenex Gemini 5u C18, 20 mM triethylamine in water on a gradient of acetonitrile 80:20 to 2:98) to afford 350 as a white solid (61 mg, 37%). LCMS (Method G): $R_T$=6.55 min, M+H$^+$=544. $^1$H NMR (CDCl$_3$, 400 MHz) δ 8.00 (m, 1 H); 7.75 (m, 1 H); 7.26 (m, 2 H); 4.35 (m, 4 H); 3.96 (s, 2 H); 3.92-3.82 (m, 7 H); 3.49-3.40 (m, 4 H); 3.35 (q, J=7.5 Hz, 2 H); 3.25-2.70 (m, 5 H); 2.13 (m, 2 H); 2.01-1.91 (m, 2 H); 1.90-1.81 (m, 2H) and 1.47 (t, J=7.5 Hz, 3 H)

Example 351

I-N,N-dimethyl-1-((9-methyl-2-(2-methyl-1H-benzo[d]imidazol-1-yl)-6-morpholino-9H-purin-8-yl)methyl)pyrrolidine-3-carboxamide 351

A solution of 9-methyl-2-(2-methylbenzoimidazol-1-yl)-6-morpholin-4-yl-9H-purine-8-carbaldehyde (135 mg, 0.36 mmol) and I-pyrrolidine-3-carboxylic acid dimethylamide (65 mg, 0.46 mmol) in DCE (6 mL) was stirred at ambient temperature for 2 h. Sodium triacetoxyborohydride (123 mg, 0.58 mmol) was added and the mixture stirred for 18 h, then loaded onto an Isolute® SCX-2 cartridge (10 g). The cartridge was then washed with methanol and the desired product was subsequently eluted using 2 M $NH_3$ in MeOH. The product was collected and concentrated in vacuo. The resultant residue was purified by flash chromatography (Si—PPC, DCM:MeOH; gradient from 100:0 to 70:30) to afford 351 as a cream solid (144 mg, 80%). LCMS (Method G): $R_T$=5.48 min, M+H$^+$=504. $^1$H NMR (CDCl$_3$, 400 MHz) δ 8.09 (m, 1 H); 7.70 (m, 1 H); 7.28 (m, 2 H); 4.35 (m, 4 H); 3.93 (s, 2H); 3.87 (m, 7 H); 3.26 (m, 1 H); 3.03 (s, 3 H); 3.00-2.92 (m, 7 H); 2.86 (m, 2 H); 2.73-2.64 (m, 1 H) and 2.15-2.06 (m, 2 H)

Example 352

I-1-((2-(2-ethyl-1H-benzo[d]imidazol-1-yl)-9-methyl-6-morpholino-9H-purin-8-yl)methyl)-N,N-dimethylpyrrolidine-3-carboxamide 352

A solution of 2-(2-ethylbenzoimidazol-1-yl)-9-methyl-6-morpholin-4-yl-9H-purine-8-carbaldehyde (140 mg, 0.36 mmol) and I-pyrrolidine-3-carboxylic acid dimethylamide (65 mg, 0.46 mmol) in DCE (6 mL) was stirred at ambient temperature for 2 h. Sodium triacetoxyborohydride (123 mg, 0.58 mmol) was added and the mixture stirred for 18 h, then loaded onto an Isolute® SCX-2 cartridge (10 g). The cartridge was then washed with methanol and the desired product was subsequently eluted using 2 M NH₃ in MeOH. The product was collected and concentrated in vacuo. The resultant residue was purified by flash chromatography (Si—PPC, DCM:MeOH; gradient from 100:0 to 70:30) to afford 352 as a cream solid (136 mg, 74%). LCMS (Method G): $R_T$=5.90 min, M+H⁺=518. ¹H NMR (CDCl₃, 400 MHz) δ 8.02 (m, 1 H); 7.80 (m, 1 H); 7.28 (m, 2 H); 4.34 (m, 4 H); 3.93 (s, 2H); 3.90-3.84 (m, 7 H); 3.35 (q, J=7.5 Hz, 2 H); 3.26 (m, 1 H); 3.07-2.93 (m, 7 H); 2.87 (m, 2 H); 2.70 (m, 1 H); 2.16-2.06 (m, 2 H) and 1.45 (t, J=7.5 Hz, 3 H)

Example 353

2,2-dimethyl-4-(1-((9-methyl-2-(2-methyl-1H-benzo[d]imidazol-1-yl)-6-morpholino-9H-purin-8-yl)methyl)azetidin-3-yl)morpholine 353

A mixture of 9-methyl-2-(2-methylbenzoimidazol-1-yl)-6-morpholin-4-yl-9H-purine-8-carbaldehyde (100 mg, 0.26 mmol), 4-azetidin-3-yl-2,2-dimethylmorpholine (54 mg, 0.32 mmol) and 4A powdered molecular sieves (200 mg) in DCE (5 mL) was stirred at room temperature for 4 h before the addition of sodium triacetoxyborohydride (112 mg, 0.53 mmol). The reaction mixture was stirred for 16 h then filtered through celite, washing with DCM. The organic phase was washed with brine (×1) and concentrated in vacuo. The resulting residue was purified by column chromatography (Si—PCC, MeOH:EtOAc, 0-15%). The resulting oil was loaded onto an Isolute® SCX-2 cartridge which was washed with MeOH/DCM and the product eluted with 2M NH₃/MeOH affording 353 as a white solid (113 mg, 82%). LCMS (Method G): $R_T$ 6.47 min [M+H]⁺ 532.3. ¹H NMR (CDCl₃, 400 MHz): δ 8.10-8.05 (m, 1 H); 7.73-7.69 (m, 1 H); 7.29-7.24 (m, 2 H); 4.35 (m, 4 H); 3.89-3.83 (m, 9H); 3.73 (m, 2 H); 3.55 (t, J=6.5 Hz, 2 H); 3.08 (t, J=6.8 Hz, 2 H); 3.01-2.90 (m, 4 H); 2.24 (m, 2 H); 2.07 (s, 2 H) and 1.25 (s, 6 H)

Example 354

4-(2-(2-ethyl-1H-benzo[d]imidazol-1-yl)-9-methyl-8-((3-(1,1-dioxo-thiomorpholino)azetidin-1-yl)methyl)-9H-purin-6-yl)morpholine 354

A mixture of 2-(2-ethylbenzoimidazol-1-yl)-9-methyl-6-morpholin-4-yl-9H-purine-8-carbaldehyde (1.2 g, 3.07 mmol), 4-azetidin-3-ylthiomorpholine-1,1-dioxide (640 mg, 3.37 mmol) and 4 Å powdered molecular sieves (2.5 g) in DCE (65 mL) was stirred at room temperature for 6.5 h before the addition of sodium triacetoxyborohydride (1.3 g, 6.13 mmol). The reaction mixture was stirred for 18 h then filtered through celite, washing with DCM. The organic phase was washed with brine (x 1) and concentrated in vacuo. The organic phase was dried (Na₂SO₄) and concentrated in vacuo. The resulting residue was purified by column chromatography (Si—PCC, MeOH:EtOAc, 0-10%). A mixture of the resulting yellow powder and 3-mercaptopropyl ethyl sulphide silica (250 mg) was stirred in a mixture of EtOH and DCM at 50° C. for 3 h. The mixture was filtered and concentrated in vacuo. The resulting oil was loaded onto an Isolute® SCX-2 cartridge which was washed with EtOH and the product eluted with 2M NH₃/EtOH. The resulting oil was triturated with Et₂O and dried in vacuo at 60° C. affording 354 as a pale yellow solid (1.26 g, 73%). LCMS (Method I): $R_T$ 2.43 min [M+H]⁺ 566.3. ¹H NMR (CDCl₃, 400 MHz): δ 8.02-7.97 (m, 1 H); 7.77-7.73 (m, 1 H); 7.29-7.22 (m, 2 H); 4.34 (m, 4 H); 3.89-3.80 (m, 9 H); 3.59 (m, 2 H); 3.39-3.23 (m, 3 H); 3.12-3.04 (m, 6 H); 2.85 (m, 4 H) and 1.44 (t, J=7.5 Hz, 3 H)

Example 355

4-(2-(2-methyl-1H-benzo[d]imidazol-1-yl)-9-methyl-84(3-(1,1-dioxo-thiomorpholino)azetidin-1-yl)methyl)-9H-purin-6-yl)morpholine 355

A mixture of 2-chloro-8-[3-(1,1-Dioxo-1-thiomorpholin-4-yl)azetidin-1-ylmethyl]-9-methyl-6-morpholin-4-yl-9H-purine (125 mg, 0.27 mmol), 2-methylbenzimidazole (402 mg, 0.30 mmol), tris(dibenzylideneacetone)dipalladium (13 mg, 0.01 mmol), Xphos (13 mg, 0.02 mmol) and Cs₂CO₃ (179 mg, 0.55 mmol) in dioxane (4 mL) was purged with argon then heated at 145° C. for 30 min in a microwave reactor. The reaction mixture was loaded onto an Isolute® SCX-2 cartridge, washed with MeOH/DCM then eluted with 2M NH₃/MeOH. The resulting residue was purified by column chromatography (Si—PCC, MeOH:EtOAc, 0-15%) followed by an Isolute® SCX-2 cartridge which was washed with MeOH/DCM and the product eluted with 2M NH₃/MeOH to give 355 as a cream solid (125 mg, 84%). LCMS (Method G): $R_T$ 4.73 min, [M+H]⁺ 552.2. ¹H NMR (CDCl₃, 400 MHz): δ 8.10-8.05 (m, 1 H); 7.73-7.67 (m, 1 H); 7.29-7.24 (m, 2 H); 4.35 (m, 4 H); 3.90-3.82 (m, 9 H); 3.59 (m, 2 H); 3.28 (m, 1 H); 3.11-3.04 (m, 6 H); 2.94 (s, 3 H) and 2.87-2.82 (m, 4 H)

Example 356

2-methyl-2-(4-((9-methyl-2-(2-methyl-1H-benzo[d]imidazol-1-yl)-6-morpholino-9H-purin-8-yl)methyl)piperazin-1-yl)propane-1,3-diol 356

Following General Procedure I for Buchwald coupling, 2-methylbenzimidazole and 2-(4-((2-chloro-9-methyl-6-morpholino-9H-purin-8-yl)methyl)piperazin-1-yl)-2-methylpropane-1,3-diol were reacted to give 356. LCMS m/z: 536.3 (MH+)

Example 357

I-3-methyl-2-(4-((9-methyl-2-(2-methyl-1H-benzo[d]imidazol-1-yl)-6-morpholino-9H-purin-8-yl)methyl)piperazin-1-yl)butan-1-ol 357

Following General Procedure I for Buchwald coupling, 2-methylbenzimidazole and racemic 2-(4-((2-chloro-9-methyl-6-morpholino-9H-purin-8-yl)methyl)piperazin-1-yl)-3-methylbutan-1-ol were reacted. The enantiomers were separated by SFC to give 357. LCMS m/z: 534.3 (MH+)

Example 358

2-(1-((2-(2-(2-methoxyethylamino)-1H-benzo[d]imidazol-1-yl)-9-methyl-6-morpholino-9H-purin-8-yl)methyl)piperidin-4-yl)propan-2-ol 358

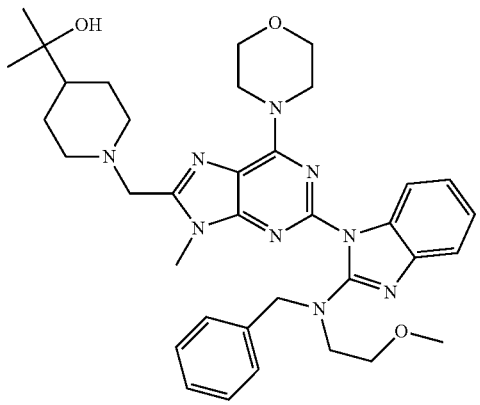

A mixture of 2-(1-((2-(2-(benzyl(methoxyethyl)amino)-1H-benzo[d]imidazol-1-yl)-9-methyl-6-morpholino-9H-purin-8-yl)methyl)piperidin-4-yl)propan-2-ol (0.22 g, 0.34 mmol) and palladium on carbon (10 wt %, 0.2 g) and acetic acid (0.15 mL) in ethanol (10 mL) was stirred under a hydrogen atmosphere at 70° C. for 18 hours. The reaction mixture was then filtered though celite and concentrated. The crude product was purified by RP-HPLC to give 358 (54 mg, 28%). LCMS m/z: 564.4 (MH+)

Example 361

(S)-3-methyl-2-(4-((9-methyl-2-(2-methyl-1H-benzo[d]imidazol-1-yl)-6-morpholino-9H-purin-8-yl)methyl)piperazin-1-yl)butan-1-ol 361

Following General Procedure I for Buchwald coupling, 2-methylbenzimidazole and racemic 2-(4-((2-chloro-9-methyl-6-morpholino-9H-purin-8-yl)methyl)piperazin-1-yl)-3-methylbutan-1-ol were reacted. The enantiomers were separated by SFC to give 361. LCMS m/z: 534.3 (MH+)

Example 362

2-(1-((5-(2-methyl-1H-benzo[d]imidazol-1-yl)-7-morpholinothiazolo[5,4-d]pyrimidin-2-yl)methyl)piperidin-3-yl)propan-2-ol 362

A mixture of 5-(2-methylbenzoimidazol-1-yl)-7-morpholin-4-yl-thiazolo[5,4-d]pyrimidine-2-carbaldehyde (78 mg, 0.2 mmol), 2-piperidin-3-yl-propan-2-ol (43 mg, 0.3 mmol) trimethyl orthoformate (0.109 mL, 1.0 mmol) and glacial acetic acid (0.017 mL, 0.3 mmol) in 1,2-dichloroethane (2 mL) was stirred at RT under nitrogen atmosphere for 1 h. Sodium triacetoxyborohydride (85 mg, 0 4 mmol) was added and the resulting reaction mixture was stirred at RT for 16 h. The solvent was reduced in vacuo and the residue was loaded onto an Isolute® SCX-2 cartridge (10g). The cartridge was washed with DCM/MeOH, the desired product was subsequently eluted using a mixture of 2M $NH_3$ in MeOH and DCM. The residue was purified by column chromatography (Si—PCC, acetone:cyclohexane: 10:90 to 35:65 by volume). Solvents were reduced in vacuo to afford the title compound as a white solid. The resulting solid was further purified by reverse phase HPLC (MeOH:$H_2O$+0.1% HCCOH, gradient 10:90 to 90:10 over 25 min). The solvent was reduced in vacuo and the aqueous residue freeze dried to afford 362 as a white solid (23 mg, 23%). LCMS (Method G): $R_T$ 6.73 min, [M+H]+ 508. $^1$H NMR (400 MHz, $CDCl_3$): δ 8.18 (1H, s), 8.04-8.03 (1 H, m), 7.70-7.69 (1 H, m), 7.27-7.26 (2 H, m), 4.38 (4 H, br s), 3.90 (2 H, s), 3.85 (4 H, t, J=4.74 Hz), 3.18 (2 H, m), 2.91 (5 H, m), 2.28-2.15 (2 H, m), 1.81 (2 H, m), 1.75-1.60 (2 H, m), 1.20 (3 H, s), 1.15 (3 H, s)

Example 363

N,N-dimethyl-1-((9-methyl-2-(2-methyl-1H-benzo[d]imidazol-1-yl)-6-morpholino-9H-purin-8-yl)methyl)azetidine-3-carboxamide 363

A solution of 9-methyl-2-(2-methylbenzoimidazol-1-yl)-6-morpholin-4-yl-9H-purine-8-carbaldehyde (100 mg, 0.27 mmol) and azetidine-3-carboxylic acid dimethylamide hydrochloride salt (53 mg, 0.32 mmol) in DCE (4 mL) was stirred at ambient temperature for 1 h. Sodium triacetoxyborohydride (86 mg, 0.41 mmol) was added and the mixture stirred for 18 h, then loaded onto an Isolute® SCX-2 cartridge (10 g). The cartridge was then washed with methanol and the desired product was subsequently eluted using 2 M $NH_3$ in MeOH. The product was collected and concentrated in vacuo. The resultant residue was purified by flash chromatography (Si—PPC, EtOAc:MeOH; gradient from 100:0 to 70:30) to afford 363 as a white solid (83 mg, 64%). LCMS (Method G): $R_T$=5.23 min, M+H+=490. $^1$H NMR ($CDCl_3$, 400 MHz) δ 8.08 (m, 1 H); 7.70 (m, 1 H); 7.28 (m, 2 H); 4.35 (m, 4 H); 3.89-3.82 (m, 9 H); 3.69-3.62 (m, 2 H); 3.57-3.46 (m, 3 H); 2.96 (s, 3 H); 2.93 (s, 3 H) and 2.90 (s, 3H)

Example 364

1-(1-((9-methyl-2-(2-methyl-1H-benzo[d]imidazol-1-yl)-6-morpholino-9H-purin-8-yl)methyl)pyrrolidin-3-yl)(pyrrolidin-1-yl)methanone 364

A solution of 9-methyl-2-(2-methylbenzoimidazol-1-yl)-6-morpholin-4-yl-9H-purine-8-carbaldehyde (105 mg, 0.28 mmol) and pyrrolidin-1-yl-1-pyrrolidin-3-ylmethanone (60 mg, 0.36 mmol) in DCE (6 mL) was stirred at ambient temperature for 2 h. Sodium triacetoxyborohydride (96 mg, 0.45 mmol) was added and the mixture stirred for 18 h, then loaded onto an Isolute® SCX-2 cartridge (10 g). The cartridge was then washed with methanol and the desired product was subsequently eluted using 2 M $NH_3$ in MeOH. The product was collected and concentrated in vacuo. The resultant residue was purified by flash chromatography (Si—PPC, DCM:MeOH; gradient from 100:0 to 70:30) to afford 364 as a white solid (110 mg, 74%). LCMS (Method G): $R_T$=6.10 min, M+H+=530. $^1$H NMR ($CDCl_3$, 400 MHz) δ 8.08 (m, 1 H); 7.70 (m, 1 H); 7.27 (m, 2 H); 4.35 (m, 4 H); 3.93 (s, 2H); 3.92-3.81 (m, 7 H); 3.50-3.38 (m, 4 H); 3.19-3.08 (m, 1 H); 2.99 (m, 1 H); 2.94 (s, 3H); 2.86 (m, 2 H); 2.70 (m, 1 H); 2.12 (m, 2 H); 2.02-1.90 (m, 2 H) and 1.91-1.81 (m, 2 H)

Example 365

(1-((2-(2-ethyl-1H-benzo[d]imidazol-1-yl)-9-methyl-6-morpholino-9H-purin-8-yl)methyl)azetidin-3-yl)(pyrrolidin-1-yl)methanone 365

A solution of 2-(2-ethylbenzoimidazol-1-yl)-9-methyl-6-morpholin-4-yl-9H-purine-8-carbaldehyde (100 mg, 0.27 mmol) and azetidin-3-ylpyrrolidin-1-ylmethanone (50 mg, 0.32 mmol) in DCE (3 mL) was stirred at ambient temperature for 90 min. Sodium triacetoxyborohydride (86 mg, 0.41 mmol) was added and the mixture stirred for 18 h, then loaded onto an Isolute® SCX-2 cartridge (10 g). The cartridge was then washed with methanol and the desired product was subsequently eluted using 2 M $NH_3$ in MeOH. The product was collected and concentrated in vacuo. The resultant residue was purified by flash chromatography (Si—PPC, EtOAc: MeOH; gradient from 100:0 to 70:30) followed by reverse phase HPLC (Phenomenex Gemini 5u C18, 20 mM triethylamine in water on a gradient of acetonitrile 80:20 to 2:98) to afford 365 as a white solid (65 mg, 48%). LCMS (Method G): $R_T$=6.26 min, M+H$^+$=530. $^1$H NMR (CDCl$_3$, 400 MHz) δ 8.01 (m, 1 H); 7.73 (m, 1 H); 7.27 (m, 2 H); 4.35 (m, 4 H); 3.86 (m, 6 H); 3.83 (s, 3 H); 3.69-3.63 (m, 2 H); 3.55-3.42 (m, 5 H); 3.39-3.27 (m, 4 H); 1.98-1.82 (m, 4 H) and 1.44 (t, J=7.5 Hz, 3 H)

Example 366

1-((2-(2-ethyl-1H-benzo[d]imidazol-1-yl)-9-methyl-6-morpholino-9H-purin-8-yl)methyl)-N,N-dimethylazetidine-3-carboxamide 366

A solution of 2-(2-ethylbenzoimidazol-1-yl)-9-methyl-6-morpholin-4-yl-9H-purine-8-carbaldehyde (100 mg, 0.27 mmol) and azetidine-3-carboxylic acid dimethylamide hydrochloride salt (53 mg, 0.32 mmol) in DCE (4 mL) was stirred at ambient temperature for 1 h. Sodium triacetoxyborohydride (86 mg, 0.41 mmol) was added and the mixture stirred for 3 h, then loaded onto an Isolute® SCX-2 cartridge (10 g). The cartridge was then washed with methanol and the desired product was subsequently eluted using 2 M $NH_3$ in MeOH. The product was collected and concentrated in vacuo. The resultant residue was purified by flash chromatography (Si—PPC, EtOAc:MeOH; gradient from 100:0 to 70:30) to afford 366 as a cream solid (107 mg, 83%). LCMS (Method G): $R_T$=5.51 min, M+H$^+$=504. $^1$H NMR (CDCl$_3$, 400 MHz) δ 8.00 (m, 1 H); 7.75 (m, 1 H); 7.28 (m, 2 H); 4.34 (m, 4 H); 3.89-3.83 (m, 6 H); 3.83 (s, 3 H); 3.70-3.62 (m, 2 H); 3.57-3.46 (m, 3 H); 3.34 (q, J=7.5 Hz, 2 H); 2.96 (s, 3 H); 2.90 (s, 3 H) and 1.44 (t, J=7.5 Hz, 3 H)

Example 367

2-(1-(2-(2-(2-ethyl-1H-benzo[d]imidazol-1-yl)-9-methyl-6-morpholino-9H-purin-8-yl)ethyl)piperidin-4-yl)propan-2-ol 367

A mixture of 2-{1-[2-(2-chloro-9-methyl-6-morpholin-4-yl-9H-purin-8-yl)ethyl]-piperidin-4-yl}propan-2-ol (71 mg, 0.17 mmol), 2-ethylbenzimidazole (27 mg, 0.19 mmol), Pd$_2$(dba)$_3$ (3.8 mg, 2.5 mol %), Xphos (8.0 mg, 10 mol %) and Cs$_2$CO$_3$ (82 mg, 0.25 mmol) in dioxane (1 0 mL) was purged with argon gas then heated at 120° C., for 19 h, in a sealed tube. The reaction mixture was loaded onto an Isolute® SCX-2 cartridge, washed with MeOH then the desired product eluted with 2 M $NH_3$ in MeOH. The resulting residue was purified by flash chromatography (Si—PCC, 0-10% MeOH in DCM) to give 367 (45 mg, 50%) as a yellow solid. LCMS: (Method G): $R_T$ 6.09 min; [M+H]$^+$ 533.3. $^1$H NMR (400 MHz, CHCl$_3$-d): δ 8.01-7.97 (m, 1 H), 7.77-7.72 (m, 1 H), 7.29-7.23 (m, 2 H), 4.49-4.15 (m, 4H), 3.88-3.83 (m, 4 H), 3.78 (s, 3 H), 3.34 (q, J=7.5, 2 H), 3.14 (m, 4 H), 2.93-2.75 (m, 2H), 2.20-2.08 (m, 2 H), 1.85-1.78 (m, 2 H), 1.44 (t, J=7.5 Hz, 3 H), 1.40-1.21 (m, 3 H), 1.24-1.18 (m, 6 H)

Example 368

2-methyl-2-(4-(2-(9-methyl-242-methyl-1H-benzo[d]imidazol-1-yl)-6-morpholino-9H-purin-8-yl)ethyl)piperazin-1-yl)propanamide 368

A mixture of 2-{4-[2-(2-chloro-9-methyl-6-morpholin-4-yl-9H-purin-8-yl)ethyl]piperazin-1-yl}isobutyramide (80 mg, 0.18 mmol), 2-methylbenzimidazole (26 mg, 0.20 mmol), Pd$_2$(dba)$_3$ (4 mg, 2.5 mol %), Xphos (8 mg, 10 mol %) and Cs$_2$CO$_3$ (87 mg, 0.27 mmol) in dioxane (1.0 mL) was purged with argon gas then heated at 120° C., for 19 h, in a sealed tube. The reaction mixture was loaded onto an Isolute® SCX-2 cartridge, washed with MeOH then the desired product eluted with 2 M $NH_3$ in MeOH. The resulting residue was purified by flash chromatography (Si—PCC, 0-10% MeOH in DCM) to give 368 (63 mg, 65%) as a pale yellow solid. LCMS: (Method G): $R_T$ 5.34 min; [M+H]$^+$ 547.3. $^1$H NMR (400 MHz, CHCl$_3$-d): δ 8.09-8.05 (m, 1 H), 7.73-7.69 (m, 1 H), 7.29-7.24 (m, 1 H), 7.06 (s, 1H), 5.23 (s, 1 H), 4.47-4.14 (m, 4 H), 3.87 (t, J=4.7 Hz, 4 H), 3.79 (s, 3 H), 3.49 (s, 1 H), 3.19-3.0 (m, 2 H), 2.94 (s, 3 H), 2.78-2.54 (m, 6 H), 1.78-1.48 (m, 4 H), 1.25 (s, 6 H)

Example 369

8-((9-methyl-2-(2-methyl-1H-benzo[d]imidazol-1-yl)-6-morpholino-9H-purin-8-yl)methyl)-1,4-dioxa-8-azaspiro[4.5]decane 369

Following General Procedure I for Buchwald coupling, 8-((2-chloro-9-methyl-6-morpholino-9H-purin-8-yl)methyl)-1,4-dioxa-8-azaspiro[4.5]decane and 2-methybenzimidazole were reacted to give 369. LCMS m/z: 505.2 (MH+)

Example 370

8-((9-methyl-2-(2-methyl-1H-benzo[d]imidazol-1-yl)-6-morpholino-9H-purin-8-yl)methyl)-1-oxa-8-azaspiro[4.5]decane 370

Following General Procedure I for Buchwald coupling, 8-((2-chloro-9-methyl-6-morpholino-9H-purin-8-yl)methyl)-1-oxa-8-azaspiro[4.5]decane and 2-methybenzimidazole were reacted to give 370. LCMS m/z: 503.2 (MH+)

Alternatively, following General Procedure E for Displacement of alkyl bromide with amines, 4-(8-(bromomethyl)-9-methyl-2-(2-methyl-1H-benzo[d]imidazol-1-yl)-9H-purin-6-yl)morpholine and 1-oxa-8-azaspiro[4.5]decane were reacted to give 370.

Example 379

8-((9-methyl-2-(2-methyl-1H-benzo[d]imidazol-1-yl)-6-morpholino-9H-purin-8-yl)methyl)-2,8-diazaspiro[4.5]decan-1-one 379

Following General Procedure I for Buchwald coupling, 2-methylbenzimidazole and 8-((2-chloro-9-methyl-6-morpholino-9H-purin-8-yl)methyl)-2,8-diazaspiro[4.5]decan-1-one were reacted to give 379. LCMS m/z 258.6 (2M+H+)

Example 380

8-((9-methyl-2-(2-methyl-1H-benzo[d]imidazol-1-yl)-6-morpholino-9H-purin-8-yl)methyl)-3-oxa-8-azabicyclo[3.2.1]octane 380

Following General Procedure I for Buchwald coupling, 2-methylbenzimidazole and 8-((2-chloro-9-methyl-6-morpholino-9H-purin-8-yl)methyl)-3-oxa-8-aza-bicyclo[3.2.1]octane were reacted to give 380. LCMS m/z: 475.2 (MH+)

Example 381

I-2-(4-((9-methyl-2-(2-methyl-1H-benzo[d]imidazol-1-yl)-6-morpholino-9H-purin-8-yl)methyl)piperazin-1-yl)butan-1-ol 381

Following General Procedure I for Buchwald coupling, 2-methylbenzimidazole and 2-(4-((2-chloro-9-methyl-6-morpholino-9H-purin-8-yl)methyl)piperazin-1-yl)butan-1-ol were reacted. The enantiomers were separated by SFC to give 381. LCMS m/z: 520.3 (MH+)

Example 382

(S)-2-(4-((9-methyl-2-(2-methyl-1H-benzo[d]imidazol-1-yl)-6-morpholino-9H-purin-8-yl)methyl)piperazin-1-yl)butan-1-ol 382

Following General Procedure I for Buchwald coupling, 2-methylbenzimidazole and 2-(4-((2-chloro-9-methyl-6-morpholino-9H-purin-8-yl)methyl)piperazin-1-yl)butan-1-ol were reacted. The enantiomers were separated by SFC to give 382. LCMS m/z: 520.3 (MH+)

Example 383

2-(1-((9-methyl-2-(2-methyl-1H-benzo[d]imidazol-1-yl)-6-morpholino-9H-purin-8-yl)methyl)piperidin-4-yl)propan-2-amine 383

According to General Procedure E, [(9H-fluoren-9-yl)methyl 2-(piperidin-4-yl)propan-2-ylcarbamate (0.0923 g, 0.253 mmol) and N,N-diisopropylethylamine (0.265 mL, 0.00152 mol) were mixed in THF (0.7 mL, 0.008 mol) and Methanol (0.7 mL, 0.02 mol) at room temperature, and 4-(8-(bromomethyl)-9-methyl-2-(2-methyl-1H-benzo[d]imidazol-1-yl)-9H-purin-6-yl)morpholine (0.112 g, 0.253 mmol) was added. The reaction was stirred overnight. The reaction mixture was concentrated to dryness. The crude residue was dissolved in N,N-Dimethylformamide (2.0 mL) and Piperidine (0.200 mL) was added. The mixture was stirred overnight at room temperature. The reaction mixture was concentrated. The crude was purified by reverse phase HPLC to give 383 (45.5 mg, 35.7%). [M+H]+=504.3.

Example 384

5-((9-methyl-2-(2-methyl-1H-benzo[d]imidazol-1-yl)-6-morpholino-9H-purin-8-yl)methyl)-2-oxa-5-azabicyclo[2.2.1]heptane 384

Following General Procedure I for Buchwald coupling, 2-methylbenzimidazole and 2-((2-chloro-9-methyl-6-morpholino-9H-purin-8-yl)methyl)-5-oxa-2-aza-bicyclo[2.2.1]heptane were reacted to give 384. LCMS m/z: 461.2 (MH+)

Example 385

(1-((2-(2-ethyl-1H-benzo[d]imidazol-1-yl)-9-methyl-6-morpholino-9H-purin-8-yl)methyl)-4-methylpiperidin-4-yl)methanol 385

Following General Procedure I for Buchwald coupling, (1-((2-chloro-9-methyl-6-morpholino-9H-purin-8-yl)methyl)-4-methylpiperidin-4-yl)methanol and 2-ethyl-1H-benzo[d]imidazole were reacted to give 385. LCMS m/z: 505.3 (MH+)

Example 386

4-(9-methyl-2-(2-methyl-1H-benzo[d]imidazol-1-yl)-8-((3-(piperidin-1-yl)azetidin-1-yl)methyl)-9H-purin-6-yl)morpholine 386

Following General Procedure E for amine alkylation, 4-(8-(bromomethyl)-9-methyl-2-(2-methyl-1H-benzo[d]imidazol-1-yl)-9H-purin-6-yl)morpholine and 1-(azetidin-3-yl)piperidine were reacted to give 386. LCMS m/z: 502.3 (MH+)

Example 387

4-(8-((4-tert-butylpiperazin-1-yl)methyl)-2-(2-ethyl-1H-benzo[d]imidazol-1-yl)-9-methyl-9H-purin-6-yl)morpholine 387

Following General Procedure I for Buchwald coupling, 4-(8-((4-tert-butylpiperazin-1-yl)methyl)-2-chloro-9-methyl-9H-purin-6-yl)morpholine and 2-ethyl-1H-benzo[d]imidazole were reacted to give 387. LCMS m/z: 518.3 (MH+)

Example 389

N-methyl-1-((9-methyl-2-(2-methyl-1H-benzo[d]imidazol-1-yl)-6-morpholino-9H-purin-8-yl)methyl)-N-(tetrahydrofuran-3-yl)piperidin-4-amine 389

A mixture of 9-methyl-2-(2-methylbenzoimidazol-1-yl)-6-morpholin-4-yl-9H-purine-8-carbaldehyde (72 mg, 0.19 mmol), methylpiperidin-4-yl(tetrahydrofuran-3-yl)amine (42 mg, 0.23 mmol) and 4 Å powdered molecular sieves (200 mg) in DCE (5 mL) was stirred at room temperature for 4 h before the addition of sodium triacetoxyborohydride (81 mg, 0.38 mmol). The reaction mixture was stirred for 16 h then filtered through celite, washing with DCM. The organic phase was washed with brine (×1) and concentrated in vacuo. The resulting residue was purified by column chromatography (Si—PCC, MeOH:DCM, 0-10%). The resulting oil was loaded onto an Isolute® SCX-2 cartridge which was washed with MeOH/DCM and the product eluted with 2M $NH_3$/MeOH affording 389 as a white solid (55 mg, 53%). LCMS (Method G): $R_T$ 4.96 min [M+H]$^+$ 546.3. $^1$H NMR (CDCl$_3$, 400 MHz): δ 8.11-8.07 (m, 1 H); 7.73-7.69 (m, 1 H); 7.29-7.24 (m, 1 H); 4.35 (m, 4 H); 3.96 (m, 1 H); 3.92-3.80 (m, 8 H); 3.83-3.71 (m, 4 H); 3.43 (m, 1 H); 3.02-2.90 (m, 4 H); 2.52 (m, 1 H); 2.26 (s, 3 H); 2.16 (m, 2 H); 2.03 (m, 1 H); 1.90 (m, 1 H); 1.77 (s, 3 H) and 1.59 (m, 2 H)

Example 390

1-((2-(2-ethyl-1H-benzo[d]imidazol-1-yl)-9-methyl-6-morpholino-9H-purin-8-yl)methyl)-N-methyl-N-(tetrahydrofuran-3-yl)piperidin-4-amine 390

A mixture of 2-(2-ethylbenzoimidazol-1-yl)-9-methyl-6-morpholin-4-yl-9H-purine-8-carbaldehyde (72 g, 0.19 mmol), methylpiperidin-4-yl(tetrahydrofuran-3-yl)amine (42 mg, 0.23 mmol) and 4 Å powdered molecular sieves (200 mg) in DCE (5 mL) was stirred at room temperature for 6.5 h before the addition of sodium triacetoxyborohydride (81 mg, 0.38 mmol). The reaction mixture was stirred for 16 h then filtered through celite, washing with DCM. The organic phase was washed with brine (x 1) and concentrated in vacuo. The organic phase was dried ($Na_2SO_4$) and concentrated in vacuo. The resulting residue was purified by column chromatography (Si—PCC, MeOH:EtOAc, 0-20%). The resulting oil was loaded onto an Isolute® SCX-2 cartridge which was washed with MeOH/DCM and the product eluted with 2M $NH_3$/MeOH affording 390 as a cream solid (55 mg, 53%). LCMS (Method G): $R_T$ 4.96 min [M+H]$^+$ 546.3. $^1$H NMR (CDCl$_3$, 400 MHz): δ 8.03-7.99 (m, 1 H); 7.77-7.73 (m, 1 H); 7.29-7.23 (m, 2 H); 4.34 (m, 4 H); 3.96 (m, 1 H); 3.91-3.69 (m, 12 H); 3.45-3.26 (m, 3 H); 2.97 (d, J=11.3 Hz, 2 H); 2.51 (m, 1 H); 2.26 (s, 3 H); 2.16 (t, J=11.3 Hz, 2 H); 2.03 (m, 1 H); 1.89 (m, 2 H); 1.76 (s, 2 H); 1.66 (m, 1 H) and 1.45 (t, J=7.5 Hz, 3 H)

Example 391

7-((2-(2-ethyl-1H-benzo[d]imidazol-1-yl)-9-methyl-6-morpholino-9H-purin-8-yl)methyl)-2-methyl-7-azaspiro[3.5]nonan-2-ol 391

To a solution of 2-hydroxy-2-methyl-7-azaspiro[3.5]nonane-7-carboxylic acid benzyl ester (96 mg, 0.33 mmol) in IMS (3 mL) was added palladium (10 wt. % on carbon, 10 mg). The vessel was evacuated and back-filled with hydrogen, and stirred at RT for 1 h under a hydrogen atmosphere. The reaction mixture was passed through a hydrophobic frit (PTFE) and the resulting filtrate evaporated to give a residue (70 mg) that was taken up in DCE (5 mL). To this solution was added 2-(2-ethylbenzoimidazol-1-yl)-9-methyl-6-morpholin-4-yl-9H-purine-8-carbaldehyde (150 mg, 0.38 mmol), trimethyl orthoformate (0.42 mL, 3.83 mmol) and acetic acid (0.02 mL, 0.38 mmol). The reaction mixture was stirred at room temperature for 2 h, sodium triacetoxyborohydride (122 mg, 0.57 mmol) was added and the resulting mixture stirred for a further 2 days. The reaction mixture was loaded onto an Isolute® SCX-2 cartridge, washed with MeOH then the desired product eluted with 2 M $NH_3$/MeOH in DCM. The resulting residue was purified by reverse phase HPLC (Phenomenex Gemini 5 μm C18, 20 mM triethylamine in water on a gradient of acetonitrile 15-98%) to give 391 as an off white solid (69 mg, 39% over 2 steps). LCMS (Method G): $R_T$=6.29 min, [M+H]$^+$ 531.3. $^1$H NMR (400 MHz, CHCl$_3$-d): δ 8.03-7.98 (m, 1 H), 7.77-7.72 (m, 1 H), 7.29-7.23 (m, 2 H), 4.50-4.32 (m, 4 H), 3.89-3.83 (m, 7 H), 3.85-3.63 (m, 2H), 3.35 (q, J=7.5 Hz, 2 H), 2.57-2.23 (m, 4 H), 2.00-1.85 (m, 4 H), 1.65 (m, 5 H), 1.45 (t, J=7.5 Hz, 3 H), 1.39 (s, 3 H)

Example 392

4-(2-(2-(2-ethyl-1H-benzo[d]imidazol-1-yl)-9-methyl-6-morpholino-9H-purin-8-yl)ethyl)-2,2-dimethylmorpholine 392

A mixture of 2-chloro-8-[2-(2,2-dimethylmorpholin-4-yl)ethyl]-9-methyl-6-morpholin-4-yl-9H-purine (57 mg, 0.14 mmol), 2-ethylbenzimidazole (23 mg, 0.16 mmol), Pd$_2$(dba)$_3$ (3.3 mg, 2.5 mol %), Xphos (6.9 mg, 10 mol %) and Cs$_2$CO$_3$ (71 mg, 0.27 mmol) in dioxane (1 0 mL) was purged with argon gas then heated at 120° C., for 16 h, in a sealed tube. The reaction mixture was loaded onto an Isolute® SCX-2 cartridge, washed with MeOH then the desired product eluted with 2 M $NH_3$ in MeOH. The resulting residue was purified by flash chromatography (Si—PCC, 0-5% MeOH in DCM) to give 392 (46 mg, 63%) as a pale yellow solid. LCMS: (Method G): $R_T$ 6.31 min; [M+H]$^+$ 505.3. $^1$H NMR (400 MHz, CHCl$_3$-d): δ 8.02-7.97 (m, 1 H), 7.78-7.72 (m, 1 H), 7.27-7.22 (m, 2 H), 4.48-4.20 (m, 4 H), 3.89-3.83 (m, 4 H), 3.79 (s, 3 H), 3.77-3.55 (m, 2 H), 3.35 (q, J=7.5 Hz, 2 H), 3.12-2.97 (m, 2 H), 2.91-2.76 (m, 2 H), 2.57-2.43 (m, 2 H), 2.42-2.29 (m, 2 H), 1.44 (t, J=7.5 Hz, 3 H), 1.26 (s, 6 H)

Example 393

(S)-azetidin-1-yl(1-((2-(2-ethyl-1H-benzo[d]imidazol-1-yl)-9-methyl-6-morpholino-9H-purin-8-yl)methyl)pyrrolidin-3-yl)methanone 393

A solution of 2-(2-ethylbenzoimidazol-1-yl)-9-methyl-6-morpholin-4-yl-9H-purine-8-carbaldehyde (100 mg, 0.26 mmol) and azetidin-1-yl-(S)-pyrrolidin-3-ylmethanone (47 mg, 0.31 mmol) in DCE (5 mL) was stirred at ambient temperature for 4 h. Sodium triacetoxyborohydride (81 mg, 0.38 mmol) was added and the mixture stirred for 18 h, then loaded onto an Isolute® SCX-2 cartridge (10 g). The cartridge was then washed with methanol and the desired product was subsequently eluted using 2 M $NH_3$ in MeOH. The product was collected and concentrated in vacuo. The resultant residue was purified by flash chromatography (Si—PPC, DCM: MeOH; gradient from 100:0 to 70:30) followed by reverse phase HPLC (Phenomenex Gemini 5u C18, 20 mM triethylamine in water on a gradient of acetonitrile 80:20 to 2:98) to afford 393 as a white solid (62 mg, 46%). LCMS (Method G): $R_T$=5.93 min, M+H$^+$=530. $^1$H NMR (CDCl$_3$, 400 MHz) δ 8.02 (m, 1 H); 7.75 (m, 1 H); 7.29-7.22 (m, 2 H); 4.35 (m, 4 H); 4.22-4.08 (m, 2 H); 4.02 (t, J=7.9 Hz, 2H); 3.94 (s, 2H); 3.90-3.83 (m, 7 H); 3.35 (q, J=7.5 Hz, 2 H); 3.09-2.57 (m, 5 H); 2.33-2.23 (m, 2 H); 2.09 (m, 2 H) and 1.45 (t, J=7.5 Hz, 3 H)

Example 394

9-((2-(2-ethyl-1H-benzo[d]imidazol-1-yl)-9-methyl-6-morpholino-9H-purin-8-yl)methyl)-1-oxa-4,9-diazaspiro[5.5]undecan-3-one 394

A mixture of 2-(2-ethylbenzoimidazol-1-yl)-9-methyl-6-morpholin-4-yl-9H-purine-8-carbaldehyde (100 mg, 0.26 mmol), 1-oxa-4,9-diazaspiro[5.5]undecan-3-one (61 mg, 0.36 mmol) and molecular sieves (4 Å, powdered, 255 mg) in DCE (5 mL) was stirred at ambient temperature for 1 h. Sodium triacetoxyborohydride (81 mg, 0.38 mmol) was added and the mixture stirred for 17 h, then loaded onto an Isolute® SCX-2 cartridge (10 g). The cartridge was then washed with methanol and the desired product was subsequently eluted using 2 M $NH_3$ in MeOH. The product was collected and concentrated in vacuo. The resultant residue was purified by flash chromatography (Si—PPC, EtOAc: MeOH; gradient from 100:0 to 70:30) to afford 394 as a cream solid (116 mg, 83%). LCMS (Method G): $R_T$=5.76 min, M+H$^+$=546. $^1$H NMR (CDCl$_3$, 400 MHz) δ 8.01 (m, 1 H); 7.77 (m, 1 H); 7.32-7.24 (m, 2 H); 5.93 (bs, 1 H); 4.35 (m, 4 H); 4.18 (s, 2 H); 3.90-3.84 (m, 7 H); 3.82 (bs, 2H); 3.37 (q, J=7.5 Hz, 2 H); 3.27 (m, 2 H); 2.72 (m, 2 H); 2.59 (m, 2 H); 2.05-1.93 (m, 2H); 1.68 (m, 2 H) and 1.46 (t, J=7.5 Hz, 3 H)

Example 395

4-(8-((1S,4S)-2,5-diazabicyclo[2.2.1]heptan-2-ylmethyl)-2-(2-ethyl-1H-benzo[d]imidazol-1-yl)-9-methyl-9H-purin-6-yl)morpholine 395

A mixture of 2-(2-ethylbenzoimidazol-1-yl)-9-methyl-6-morpholin-4-yl-9H-purine-8-carbaldehyde (200 mg, 0.51 mmol), (1S,4S)-2,5-diazabicyclo[2.2.1]heptane-2-carboxylic acid tert-butyl ester (122 mg, 0.62 mmol) and molecular sieves (4 Å, powdered, 520 mg) in DCE (10 mL) was stirred at ambient temperature for 3 h. Sodium triacetoxyborohydride (162 mg, 0.76 mmol) was added and the mixture stirred for 17 h, then loaded onto an Isolute® SCX-2 cartridge (25 g). The cartridge was then washed with methanol and the desired product was subsequently eluted using 2 M $NH_3$ in MeOH. The product was collected and concentrated in vacuo. The resultant residue was purified by flash chromatography (Si—PPC, EtOAc:MeOH; gradient from 100:0 to 85:15) to give (1S,4S)-5-[2-(2-ethylbenzoimidazol-1-yl)-9-methyl-6-morpholin-4-yl-9H-purin-8-ylmethyl]-2,5-diazabicyclo[2.2.1]heptane-2-carboxylic acid tert-butyl ester as a white solid. TFA (3 mL) was added to a solution of (1S,4S)-5-[2-(2-ethylbenzoimidazol-1-yl)-9-methyl-6-morpholin-4-yl-9H-purin-8-ylmethyl]-2,5-diazabicyclo[2.2.1]heptane-2-carboxylic acid tert-butyl ester in DCM (10 mL) and the mixture stirred at ambient temperature for 30 min, then loaded onto an Isolute® SCX-2 cartridge (25 g). The cartridge was then washed with methanol and the desired product was subsequently eluted using 2 M $NH_3$ in MeOH. The product was collected and concentrated in vacuo. The resultant residue was purified by flash chromatography (Si—PPC, DCM:MeOH; gradient from 100:0 to 85:15) to afford 395 as a white solid (153 mg, 63%). LCMS (Method G): $R_T$=5.78 min, M+H$^+$=474. $^1$H NMR (CDCl$_3$, 400 MHz) δ 8.01 (m, 1 H); 7.75 (m, 1 H); 7.26 (m, 2 H); 4.34 (m, 4 H); 4.00 (d, J=13.6 Hz, 1 H); 3.92-3.83 (m, 8 H); 3.70 (s, 1 H); 3.45 (s, 1 H); 3.35 (q, J=7.5 Hz, 2 H); 3.25 (d, J=10.2 Hz, 1 H); 2.97-2.91 (m, 2 H); 2.70 (d, J=10.2 Hz, 1 H); 1.85 (d, J=10.1 Hz, 1 H); 1.70 (d, J=10.1 Hz, 1 H) and 1.45 (t, J=7.5 Hz, 3 H)

Example 396

(3-methyl-1-((9-methyl-2-(2-methyl-1H-benzo[d]imidazol-1-yl)-6-morpholino-9H-purin-8-yl)methyl)pyrrolidin-3-yl)(pyrrolidin-1-yl)methanone 396

A mixture of 9-methyl-2-(2-methylbenzoimidazol-1-yl)-6-morpholin-4-yl-9H-purine-8-carbaldehyde (100 mg, 0.26 mmol), (3-methylpyrrolidin-3-yl)pyrrolidin-1-ylmethanone (58 mg, 0.32 mmol), trimethoxyorthoformate (0.29 mL, 2.65 mmol) and acetic acid (15 μL, 0.26 mmol) in DCE (5 mL) was stirred at room temperature for 1 hour then sodium triacetoxyborohydride (90 mg, 0.42 mmol) was added. The reaction mixture was stirred at room temperature for 18 hours then diluted with MeOH and loaded onto an Isolute® SCX-2 cartridge (10 g). The cartridge was washed with MeOH and the desired product was eluted with 2M $NH_3$ in MeOH. The solvents were removed and the residue was subjected to flash chromatography (Si—PCC, 0-20% MeOH in EtOAc) to give 396 as a white solid (107 mg, 76%). LCMS (Method G): $R_T$ 6.69 min; [M+H]$^+$ 544. $^1$H NMR (400 MHz, CHCl$_3$-d): δ 8.12-8.07 (m, 1 H); 7.74-7.70 (m, 1 H); 7.30-7.26 (m, 2 H); 4.35 (m, 4 H); 3.90 (s, 3 H); 3.87 (t, J=4.75 Hz, 5 H); 3.49 (m, 5 H); 2.96 (s, 3 H); 2.64 (s, 2 H); 2.46-2.37 (m, 2 H); 1.89 (m, 4 H); 1.81 (m, 2 H); 1.41 (s, 3 H).

Example 398

(S)-1-((2-(2-ethyl-1H-benzo[d]imidazol-1-yl)-9-methyl-6-morpholino-9H-purin-8-yl)methyl)-N,N-dimethylpyrrolidine-3-carboxamide 398

A solution of 2-(2-ethylbenzoimidazol-1-yl)-9-methyl-6-morpholin-4-yl-9H-purine-8-carbaldehyde (100 mg, 0.26 mmol) and (S)-pyrrolidine-3-carboxylic acid dimethylamide (44 mg, 0.31 mmol) in DCE (5 mL) was stirred at ambient temperature for 4 h. Sodium triacetoxyborohydride (81 mg, 0.38 mmol) was added and the mixture stirred for 18 h, then loaded onto an Isolute® SCX-2 cartridge (10 g). The cartridge was then washed with methanol and the desired product was subsequently eluted using 2 M $NH_3$ in MeOH. The product was collected and concentrated in vacuo. The resultant residue was purified by flash chromatography (Si—PPC, DCM:MeOH; gradient from 100:0 to 70:30) to afford 398 as a cream solid (50 mg, 38%). LCMS (Method G): $R_T$=5.90 min, M+H$^+$=518. $^1$H NMR (CDCl$_3$, 400 MHz) δ 8.01 (m, 1 H); 7.75 (m, 1 H); 7.28 (m, 2 H); 4.35 (m, 4 H); 3.98-3.80 (m, 9 H); 3.40-3.25 (m, 3 H); 3.20-2.78 (m, 10 H); 2.15-2.07 (m, 2 H) and 1.50-1.41 (m, 3H)

Example 399

(S)-(1-((2-(2-ethyl-1H-benzo[d]imidazol-1-yl)-9-methyl-6-morpholino-9H-purin-8-yl)methyl)pyrrolidin-3-yl)(pyrrolidin-1-yl)methanone 399

A solution of 2-(2-ethylbenzoimidazol-1-yl)-9-methyl-6-morpholin-4-yl-9H-purine-8-carbaldehyde (100 mg, 0.26 mmol) and pyrrolidin-1-yl-(S)-pyrrolidin-3-ylmethanone (51 mg, 0.30 mmol) in DCE (5 mL) was stirred at ambient temperature for 2 h. Sodium triacetoxyborohydride (96 mg, 0.45 mmol) was added and the mixture stirred for 18 h, then loaded onto an Isolute® SCX-2 cartridge (10 g). The cartridge was then washed with methanol and the desired product was subsequently eluted using 2 M $NH_3$ in MeOH. The product was collected and concentrated in vacuo. The resultant residue was purified by flash chromatography (Si—PPC, DCM:MeOH; gradient from 100:0 to 70:30) to afford 399 as a white solid (132 mg, 86%). LCMS (Method G): $R_T$=6.43 min, M+H$^+$=544. $^1$H NMR (CDCl$_3$, 400 MHz) δ 7.99 (m, 1 H); 7.75 (m, 1 H); 7.27 (m, 2 H); 4.35 (m, 4 H); 3.94 (s, 2H); 3.87 (m, 7 H); 3.50-3.38 (m, 4 H); 3.35 (q, J=7.5 Hz, 2 H); 3.20-3.10 (m, 1 H); 3.01 (m, 1 H); 2.87 (m, 2 H); 2.72 (m, 1 H); 2.16-2.07 (m, 2 H); 2.01-1.90 (m, 2 H); 1.91-1.81 (m, 2 H) and 1.45 (t, J=7.5 Hz, 3 H)

Example 400

9-((9-methyl-2-(2-methyl-1H-benzo[d]imidazol-1-yl)-6-morpholino-9H-purin-8-yl)methyl)-1,5-dioxa-9-azaspiro[5.5]undecane 400

Following General Procedure I for Buchwald coupling, 2-methylbenzimidazole and 9-((2-chloro-9-methyl-6-morpholino-9H-purin-8-yl)methyl)-1,5-dioxa-9-azaspiro[5.5]
undecane were reacted to give 400. LCMS m/z: 519.2 (MH+)

Example 401

4-(8-((4-tert-butylpiperazin-1-yl)methyl)-2-(2-ethyl-
1H-benzo[d]imidazol-1-yl)-9H-purin-6-yl)morpho-
line 401

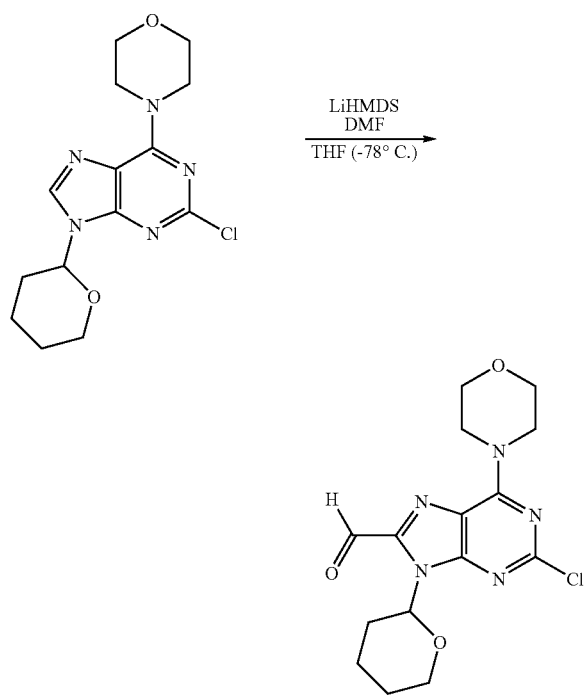

To stirred solution of 4-(2-chloro-9-(tetrahydro-2H-pyran-2-yl)-9H-purin-6-yl)morpholine (10.0 g, 0.0309 mol;) in THF (400 mL, 5 mol) at −78° C. was added 2.5 M of n-Butyllithium in hexane (18 mL). The solution was stirred at −78° C. for 30 minutes. N,N-Dimethylformamide (5.3 mL, 0.068 mol) was added and stirring continued at −78° C. for 1 hours. The reaction was slowly quenched using 0.1N HCl cold solution. The product was extracted with DCM. The organic extracts were combined, washed with brine, filtered, and concentrated to dryness to give 2-chloro-6-morpholino-9-(tetrahydro-2H-pyran-2-yl)-9H-purine-8-carbaldehyde (10.76 g, 99%) as a yellow solid. The crude was carried on without further purification.

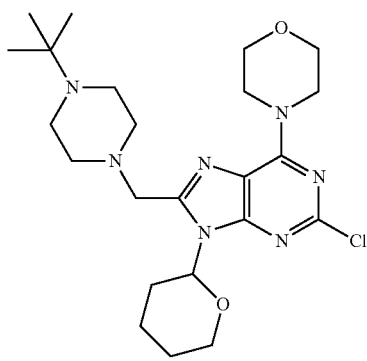

2-Chloro-6-morpholino-9-(tetrahydro-2H-pyran-2-yl)-
9H-purine-8-carbaldehyde (0.148 g, 0.422 mmol) was dissolved in 1,2-dichloroethane (3.7 mL, 0.047 mol) 1-tert-butylpiperazine (0.060 g, 0.42 mmol) was added followed by micronized 4 A molecular sieves (0.450 g). After 2 hours sodium triacetoxyborohydride (0.179 g, 0.844 mmol) was added and the reaction was stirred at room temperature overnight. The reaction mixture was filtered. The filter cake was washed with additional DCM and MeOH. The combined organics were concentrated to dryness. The crude was purified by flash column chromatography (Si—PPC; MeOH: DCM gradient 0:100 to 10:90) to give 4-(8-((4-tert-butylpiperazin-1-yl)methyl)-2-chloro-9-(tetrahydro-2H-pyran-2-yl)-9H-purin-6-yl)morpholine (126 mg, 62%). [M+H]$^+$=478.3

Into a vial was added 4-(8-((4-tert-butylpiperazin-1-yl)methyl)-2-chloro-9-(tetrahydro-2H-pyran-2-yl)-9H-purin-6-yl)morpholine (126 mg, 0.264 mmol), 2-ethyl-1H-benzo[d]imidazole (40.4 mg, 0.277 mmol), Xphos (16.3 mg, 0.0343 mmol), tris(dibenzylideneacetone)dipalladium(0) (16.4 mg, 0.0179 mmol), and cesium carbonate (172 mg, 0.527 mmol;). The mixture was dissolved in N,N-dimethylformamide (2.02 mL, 0.0261 mol) and heated at 145° C. under pressure for 30 minutes in a microwave reactor. The reaction mixture was filtered and concentrated. The crude residue was dissolved in MeOH (5.0 mL) and para-toluenesulfonic acid (90.8 mg, 0.527 mmol) was added. The reaction was heated overnight at 40° C. The reaction mixture was concentrated to dryness and purified by reverse phase HPLC to give 401 (50.9 mg, 38.3%). [M+H]$^+$=504.3

Example 404

2-((1R,5S,6r)-3-((9-methyl-2-(2-methyl-1H-benzo
[d]imidazol-1-yl)-6-morpholino-9H-purin-8-yl)me-
thyl)-3-azabicyclo[3.1.0]hexan-6-yl)propan-2-ol 404

Following General Procedure I for Buchwald coupling, 2-methylbenzimidazole and 2-((1R,5S,6r)-3-((2-chloro-9-methyl-6-morpholino-9H-purin-8-yl)methyl)-3-azabicyclo[3.1.0]hexan-6-yl)propan-2-ol were reacted to give 404. LCMS m/z: 503.3 (MH+)

Example 407

I-1-(1-(8-((4-(2-hydroxypropan-2-yl)piperidin-1-yl)
methyl)-9-methyl-6-morpholino-9H-purin-2-yl)-1H-
benzo[d]imidazol-2-yl)propan-2-ol 407

Following General Procedure I for Buchwald coupling, 1-(1H-benzmidazol-2-yl)propan-2-ol and racemic 2-(1-((2-chloro-9-methyl-6-morpholino-9H-purin-8-yl)methyl)piperidin-4-yl)propan-2-ol were reacted. The enantiomers were separated by SFC to give 407. LCMS m/z: 549.3 (MH+)

Example 408

(S)-1-(1-(8-((4-(2-hydroxypropan-2-yl)piperidin-1-
yl)methyl)-9-methyl-6-morpholino-9H-purin-2-yl)-
1H-benzo[d]imidazol-2-yl)propan-2-ol 408

Following General Procedure I for Buchwald coupling, 1-(1H-benzmidazol-2-yl)propan-2-ol and racemic 2-(1-((2-chloro-9-methyl-6-morpholino-9H-purin-8-yl)methyl)piperidin-4-yl)propan-2-ol were reacted. The enantiomers were separated by SFC to give 408. LCMS m/z: 549.3 (MH+)

Example 409

1-8-((2-(2-ethyl-1H-benzo[d]imidazol-1-yl)-9-methyl-6-morpholino-9H-purin-8-yl)methyl)octahydropyrazino[2,1-c][1,4]oxazine 409

A mixture of 2-(2-ethylbenzoimidazol-1-yl)-9-methyl-6-morpholin-4-yl-9H-purine-8-carbaldehyde (97 g, 0.25 mmol), (R)-octahydropyrazino[2,1-c][1,4]oxazine (42 mg, 0.30 mmol) and 4 Å powdered molecular sieves (200 mg) in DCE (6 mL) was stirred at room temperature for 5 h before the addition of sodium triacetoxyborohydride (106 mg, 0.50 mmol). The reaction mixture was stirred for 64 h then filtered through celite, washing with DCM. The organic phase was washed with brine (×1) and concentrated in vacuo. The organic phase was dried ($Na_2SO_4$) and concentrated in vacuo. The resulting residue was purified by column chromatography (Si—PCC, MeOH:DCM, 0-15%). The resulting oil was loaded onto an Isolute® SCX-2 cartridge which was washed with MeOH/DCM and the product eluted with 2M $NH_3$/MeOH affording 409 as a cream solid (31 mg, 24%). LCMS (Method I): $R_T$ 2.49 min [M+H]$^+$ 518.3. $^1$H NMR (CDCl$_3$, 400 MHz): δ 8.03-7.98 (m, 1 H); 7.78-7.74 (m, 1 H); 7.29-7.23 (m, 2 H); 4.34 (m, 4 H); 3.89-3.82 (m, 7 H); 3.84-3.70 (m, 2H); 3.70-3.63 (m, 1 H); 3.42-3.32 (m, 3 H); 2.85 (d, J=11.0 Hz, 2 H); 2.74 (m, 1 H); 2.63 (d, J=11.4 Hz, 2 H); 2.56 (m, 1 H); 2.43 (m, 3 H); 2.08 (m, 1 H) and 1.68 (s, 1 H); 1.50-1.42 (m, 3 H)

Example 410

4-methyl-5-((9-methyl-2-(2-methyl-1H-benzo[d]imidazol-1-yl)-6-morpholino-9H-purin-8-yl)methylamino)pentane-1,4-diol 410

Following General Procedure E for Displacement of alkyl bromide with amines, 4-(8-(bromomethyl)-9-methyl-2-(2-methyl-1H-benzo[d]imidazol-1-yl)-9H-purin-6-yl)morpholine and 5-amino-4-methylpentane-1,4-diol were reacted to give 410. [M+H]$^+$ 495.6

Example 413

2-(4-((2-(2-cyclopropyl-1H-benzo[d]imidazol-1-yl)-9-methyl-6-morpholino-9H-purin-8-yl)methyl)piperazin-1-yl)-2-methylpropan-1-ol 413

Following General Procedure I for Buchwald coupling, 4-(8-((4-tert-butylpiperazin-1-yl)methyl)-2-chloro-9-methyl-9H-purin-6-yl)morpholine and 2-cyclopropyl-1H-benzo[d]imidazole were reacted to give 413. LCMS: M+H$^+$= 546.3

Example 415

(S)-4-(8-((hexahydropyrrolo[1,2-a]pyrazin-2(1H)-yl)methyl)-9-methyl-2-(2-methyl-1H-benzo[d]imidazol-1-yl)-9H-purin-6-yl)morpholine 415

Following General Procedure I for Buchwald coupling, 2-methylbenzimidazole and racemic 4-(2-chloro-8-((hexahydropyrrolo[1,2-a]pyrazin-2(1H)-yl)methyl)-9-methyl-9H-purin-6-yl)morpholine were reacted. The enantiomers were separated by SFC to give 415. LCMS m/z: 488.2 (MH+)

Example 416

I-4-(8-((hexahydropyrrolo[1,2-a]pyrazin-2(1H)-yl)methyl)-9-methyl-2-(2-methyl-1H-benzo[d]imidazol-1-yl)-9H-purin-6-yl)morpholine 416

Following General Procedure I for Buchwald coupling, 2-methylbenzimidazole and racemic 4-(2-chloro-8-((hexahydropyrrolo[1,2-a]pyrazin-2(1H)-yl)methyl)-9-methyl-9H-purin-6-yl)morpholine were reacted. The enantiomers were separated by SFC to give 416. LCMS m/z: 488.2 (MH+)

Example 417 ethyl 2-((1S,4S)-5-((2-(2-ethyl-1H-benzo[d]imidazol-1-yl)-9-methyl-6-morpholino-9H-purin-8-yl)methyl)-2,5-diazabicyclo[2.2.1]heptan-2-yl)-2-methylpropanoate 417

2-Bromo-2-methylpropionic acid ethyl ester (90 μL, 0.61 mmol) was added to a solution of potassium carbonate (84 mg, 0.61 mmol) and 8-[(1S,4S)-1-(2,5-diazabicyclo[2.2.1]hept-2-yl)methyl]-2-(2-ethylbenzoimidazol-1-yl)-9-methyl-6-morpholin-4-yl-9H-purine (140 mg, 0.30 mmol) in anhydrous acetonitrile. The resulting mixture was heated at 80° C. for 48 h, then cooled to ambient temperature and partitioned between EtOAc and water. The organic layer was separated, washed with brine, then dried (MgSO$_4$) and concentrated in vacuo. The resultant residue was purified by flash chromatography (Si—PCC, DCM:MeOH; gradient from 100:0 to 85:15) to afford 417 as a cream solid (100 mg, 58%). LCMS (Method I): $R_T$=2.92 min, M+H$^+$=588. $^1$H NMR (CDCl$_3$, 400 MHz) δ 8.01 (m, 1 H); 7.75 (m, 1 H); 7.29-7.23 (m, 2 H); 4.34 (m, 4 H); 4.15 (m, 2 H); 3.93-3.82 (m, 9 H); 3.64 (m, 1 H); 3.35 (q, J=7.5 Hz, 2 H); 3.19 (m, 1 H); 2.81-2.63 (m, 3 H); 1.58 (m, 4 H); 1.45 (t, J=7.5 Hz, 3 H); 1.36 (m, 2 H) and 1.32-1.23 (m, 6 H)

Example 418

1-((2-(2-ethyl-1H-benzo[d]imidazol-1-yl)-9-methyl-6-morpholino-9H-purin-8-yl)methyl)-N-methyl-N-(oxetan-3-yl)piperidin-4-amine 418

A mixture of 2-(2-ethylbenzoimidazol-1-yl)-9-methyl-6-morpholin-4-yl-9H-purine-8-carbaldehyde (179 mg, 0.46 mmol), methyloxetan-3-ylpiperidin-4-ylamine (94 mg, 0.55 mmol) and 4 Å powdered molecular sieves (400 mg) in DCE (10 mL) was stirred at room temperature for 5 h before the addition of sodium triacetoxyborohydride (233 mg, 0.92 mmol). The reaction mixture was stirred for 16 h then filtered through celite, washing with DCM. The organic phase was washed with brine (×1) and concentrated in vacuo. The organic phase was dried (Na$_2$SO$_4$) and concentrated in vacuo. The resulting residue was purified by column chromatography (Si—PCC, MeOH:DCM, 0-15%) affording 418 as a cream solid (93 mg, 37%). LCMS (Method I): $R_T$ 2.31 min [M+H]$^+$546.4. $^1$H NMR (CDCl$_3$, 400 MHz): δ 8.03-7.99 (m, 1 H); 7.78-7.72 (m, 1 H); 7.29-7.22 (m, 2 H); 4.67 (t, J=6.5 Hz, 2 H); 4.60 (t, J=6.6 Hz, 2 H); 4.34 (m, 4 H); 3.98-3.88 (m, 1 H); 3.89-3.82 (m, 7 H); 3.72 (s, 2 H); 3.35 (q, J=7.5 Hz, 2 H); 2.94 (d, J=11.2 Hz, 2 H); 2.35-2.24 (m, 1 H); 2.21 (s, 3 H); 2.13 (t, J=11.2 Hz, 2 H); 1.64 (d, J=12.2 Hz, 2 H); 1.54 (m, 2 H) and 1.45 (t, J=7.5 Hz, 3 H)

Example 419

N-((1-((2-(2-ethyl-1H-benzo[d]imidazol-1-yl)-9-methyl-6-morpholino-9H-purin-8-yl)methyl)azetidin-3-yl)methyl)-N-methyltetrahydrofuran-3-amine 419

A mixture of 9-methyl-2-(2-methylbenzoimidazol-1-yl)-6-morpholin-4-yl-9H-purine-8-carbaldehyde (78 mg, 0.2 mmol), (azetidin-3-ylmethyl)methyl(tetrahydrofuran-3-yl) amine (51 mg, 0.3 mmol) and 4 Å molecular sieves (250 mg) in 1,2-dichloroethane (2 mL) was stirred at RT under nitrogen atmosphere for 6 h. Sodium triacetoxyborohydride (85 mg, 0.4 mmol) was added and the resulting reaction mixture was stirred at RT for 36 h. The solvent was reduced in vacuo and the residue was loaded onto an Isolute® SCX-2 cartridge (5 g). The cartridge was washed with DCM/MeOH, the desired product was subsequently eluted using a mixture of 2M $NH_3$ in MeOH and DCM. The residue was purified by column chromatography (Si—PCC, MeOH:DCM: gradient 0:100 to 10:90) to afford 419 as a white foam (80 mg, 73%). LCMS (Method I): $R_T$ 2.05 min, [M+H]$^+$ 546. $^1$H NMR (400 MHz, $CDCl_3$): δ 7.99-7.95 (1 H, m), 7.73-7.70 (1 H, m), 7.23 (2 H, m), 4.32 (4 H, s), 3.92 (1 H, m), 3.82-3.80 (7 H, m), 3.72 (1 H, q, J=8.06 Hz), 3.61 (1 H, m), 3.51 (2 H, t, J=7.19 Hz), 3.31 (2 H, q, J=7.48 Hz), 3.08 (1 H, m), 2.95 (2 H, t, J=6.81 Hz), 2.76-2.44 (2 H, m), 2.14 (3 H, s), 2.03-1.93 (1 H, m), 1.85-1.75 (1 H, m), 1.63 (4 H, br s), 1.41 (3 H, t, J=7.48 Hz)

Example 420

2-(1-((5-(2-ethyl-1H-benzo[d]imidazol-1-yl)-7-morpholinothiazolo[4,5-d]pyrimidin-2-yl)methyl)piperidin-4-yl)propan-2-ol 420

A mixture of 2-[1-(5-chloro-7-morpholin-4-yl-thiazolo[4,5-d]pyrimidin-2-ylmethyl)piperidin-4-yl]propan-2-ol (100 mg, 0.243 mmol), 2-ethyl-1H-benzoimidazole (39 mg, 0.267 mmol), $Pd_2(dba)_3$ (11 mg, 0.0122 mmol), XPhos (23 mg, 0.049 mmol) and cesium carbonate (158 mg, 0.486 mmol) in 1,4-dioxane (1.5 mL) was purged with argon gas for 15 min. The resulting reaction mixture was irradiated with microwaves at 150° C. for 30 min. The crude residue was loaded on an Isolute® SCX-2 cartridge (5 g). The cartridge was washed with DCM/MeOH and the desired product was subsequently eluted using a mixture of 2M $NH_3$ in MeOH and DCM. The resulting residue was further purified by column chromatography (Si—PCC, 2 M $NH_3$ in MeOH:DCM: gradient 0:100 to 5:95) to afford 420 as a brown solid (47 mg, 37%) LCMS (Method I): $R_T$ 2.53 min, [M+H]$^+$ 522. $^1$H NMR (400 MHz, $CDCl_3$): δ 8.11 (1 H, m), 7.77-7.70 (1 H, m), 7.23 (2 H, m), 4.01-3.99 (6 H, m), 3.87 (5H, m), 3.42-3.39 (2 H, m), 3.10 (2 H, m), 2.27 (2 H, m), 1.79 (2 H, m), 1.50 (2 H, d, m), 1.46-1.40 (3 H, m), 1.32 (1 H, m), 1.20 (6 H, s)

Example 421

N-((1-((2-(2-ethyl-1H-benzo[d]imidazol-1-yl)-9-methyl-6-morpholino-9H-purin-8-yl)methyl)azetidin-3-yl)methyl)-N-methyloxetan-3-amine 421

A mixture of 2-(2-ethylbenzoimidazol-1-yl)-9-methyl-6-morpholin-4-yl-9H-purine-8-carbaldehyde (78 mg, 0 2 mmol), (azetidin-3-ylmethyl)methyloxetan-3-yl-amine (47 mg, 0 3 mmol), and 4 Å molecular sieves (250 mg) in 1,2-dichloroethane (2 mL) was stirred at RT for 6 h. Sodium triacetoxyborohydride (85 mg, 0.4 mmol) was added and the resulting reaction mixture was stirred at RT under nitrogen atmosphere for 16 h. The suspension was filtered through Celite and the filtrate was concentrated in vacuo. The crude residue was loaded on an Isolute® SCX-2 cartridge (5 g). The cartridge was washed with DCM/MeOH and the desired product was subsequently eluted using a mixture of 2M $NH_3$ in MeOH and DCM. The residue was purified by column chromatography (Si—PPC, MeOH:DCM, gradient 0:100 to 8:92) to afford 421 as an off-white foam (63 mg, 59%). LCMS (Method I): $R_T$ 2.11 min, [M+H]$^+$ 532. $^1$H NMR (400 MHz, $CDCl_3$): δ 7.97-7.96 (1 H, m), 7.72-7.71 (1 H, m), 7.23 (2 H, t, J=3.78 Hz), 4.61 (2 H, t, J=6.53 Hz), 4.53 (2 H, t, J=6.23 Hz), 4.32 (4 H, s), 3.82-3.81 (9 H, m), 3.51-3.50 (3 H, m), 3.32 (2 H, q, J=7.48 Hz), 3.03-2.89 (2 H, m), 2.68-2.57 (1 H, m), 2.40 (2 H, d, J=7.26 Hz), 2.04 (3 H, s), 1.41 (3 H, t, J=7.47 Hz)

Example 422

4-(2-(2-ethyl-1H-benzo[d]imidazol-1-yl)-8-((3-(tetrahydro-2H-pyran-4-yl)azetidin-1-yl)methyl)-9H-purin-6-yl)morpholine 422

A mixture of 2-(2-ethylbenzoimidazol-1-yl)-6-morpholin-4-yl-9-(tetrahydropyran-2-yl)-8-[3-(tetrahydropyran-4-yl) azetidin-1-ylmethyl]-9H-purine (0.28 g, 0.48 mmol) in 1.25 M HCl (10 mL) was stirred for 48 h at room temperature. The reaction mixture was concentrated in vacuo. The residue was loaded in MeOH onto an Isolute® SCX-2 cartridge. The cartridge was washed with MeOH, then the desired product was eluted with DCM, 20-80% MeOH in DCM and 10-40% 2 M $NH_3$ in MeOH in DCM. The residue was purified by flash chromatography (Si—PPC, 2 M $NH_3$ in MEOH:DCM, gradient 0:100 to 4:96) followed by (Si—PPC, 2M $NH_3$ in MeOH:EtOAc, gradient 2.5:97.5 to 10:90 then 2 M $NH_3$ in MEOH:DCM, gradient 2:98 to 10:90) to give 422 as a white solid (0.14 g, 59%). LCMS (Method I): $R_T$=2.50 min, [M+H]$^+$ 503.4. $^1$H NMR (400 MHz, DMSO-d): δ 7.96-7.92 (m, 1 H); 7.64-7.60 (m, 1 H); 7.25-7.20 (m, 2 H); 4.28-4.19 (m, 4 H); 3.83 (dd, J=11.3, 4.3 Hz, 2 H); 3.77 (t, J=4.6 Hz, 2 H); 3.72 (s, 2 H); 3.43-3.38 (m, 7 H); 3.27-3.19 (q, J=7.4 Hz, 2 H); 2.96 (t, J=6.9 Hz, 2 H); 2.19-2.11 (m, 1 H); 1.69-1.57 (m, 1 H); 1.50 (d, J=13.0 Hz, 2 H); 1.31 (t, J=7.4 Hz, 3 H); 1.06 (td, J=12.2, 4.3 Hz, 2 H)

Example 427

2-(4-((2-(2-(2-hydroxyethyl)-1H-benzo[d]imidazol-1-yl)-9-methyl-6-morpholino-9H-purin-8-yl)methyl)piperazin-1-yl)-2-methylpropan-1-ol 427

Following General Procedure I for Buchwald coupling, 2-(4-((2-chloro-9-methyl-6-morpholino-9H-purin-8-yl)methyl)piperazin-1-yl)-2-methylpropan-1-ol and 2-(1H-benzo[d]imidazol-2-yl)ethanol were reacted to give 427. LCMS m/z: 550.3 (MH+)

Example 428

1-(8-((4-tert-butylpiperazin-1-yl)methyl)-9-methyl-6-morpholino-9H-purin-2-yl)-N-methyl-1H-benzo[d]imidazol-2-amine 428

Following General Procedure I for Buchwald coupling, 4-(8-((4-tert-butylpiperazin-1-yl)methyl)-2-chloro-9-methyl-9H-purin-6-yl)morpholine and N-methyl-1H-benzo[d]imidazol-2-amine were reacted to give 428. LCMS: M+H$^+$= 519.3

Example 429

4-methyl-1-((9-methyl-2-(2-methyl-1H-benzo[d]imidazol-1-yl)-6-morpholino-9H-purin-8-yl)methyl)azepan-4-ol 429

Following General Procedure E for Displacement of alkyl bromide with amines, 4-(8-(bromomethyl)-9-methyl-2-(2-methyl-1H-benzo[d]imidazol-1-yl)-9H-purin-6-yl)morpholine and 4-methylazepan-4-ol were reacted to give 429. [M+H]$^+$ 491.6

Example 430

2-(1-((2-(2-ethylbenzofuran-3-yl)-9-methyl-6-morpholino-9H-purin-8-yl)methyl)piperidin-4-yl)propan-2-ol 430

Following General Procedure L for reductive amination, 2-(2-ethylbenzofuran-3-yl)-9-methyl-6-morpholino-9H-purine-8-carbaldehyde and 2-(piperidin-4-yl)propan-2-ol were reacted to give 430. [M+H]$^+$ 519.6

Example 431

N-((9-methyl-2-(2-methyl-1H-benzo[d]imidazol-1-yl)-6-morpholino-9H-purin-8-yl)methyl)-2-(1H-pyrazol-1-yl)ethanamine 431

Following General Procedure L for reductive amination, 9-methyl-2-(2-methyl-1H-benzo[d]imidazol-1-yl)-6-morpholino-9H-purine-8-carbaldehyde and 2-(1H-pyrazol-1-yl)ethanamine were reacted to give 431. [M+H]$^+$ 473.3

Example 432

(1-aminocyclopropyl)(4-((2-(2-ethyl-1H-benzo[d]imidazol-1-yl)-9-methyl-6-morpholino-9H-purin-8-yl)methyl)piperazin-1-yl)methanone 432

A mixture of (1-{4-[2-(2-ethylbenzoimidazol-1-yl)-9-methyl-6-morpholin-4-yl-9H-purin-8-ylmethyl]piperazine-1-carbonyl}cyclopropyl)carbamic acid tert-butyl ester (0.123 g, 0.19 mmol) in DCM/TFA (5 mL/5 mL) was stirred for 4 h at room temperature. The reaction mixture was loaded onto an Isolute® SCX-2 cartridge. The cartridge was washed with MeOH and the desired product was eluted using 2 M NH$_3$ in MeOH. The eluent was concnentrated in vacuo and the residue was purified by flash chromatography (Si—PPC, MEOH:DCM, gradient 0:100 to 10:90) to give 432 as a white solid (0.066 g, 64%). LCMS (Method I): R$_T$=2.47 min, [M+H]$^+$ 462.3. $^1$H NMR (400 MHz, DMSO-d): δ 8.04-8.00 (m, 1 H); 7.66-7.61 (m, 1 H); 7.28-7.21 (m, 2 H); 4.18-4.22 (m, 4 H); 3.85 (s, 3 H); 3.82 (s, 2 H); 3.78 (t, J=4.6 Hz, 4 H); 3.58-3.53 (m, 4 H); 3.27 (q, J=7.4 Hz, 2 H); 2.55-2.45 (m, 4 H); 1.34 (t, J=7.4 Hz, 3 H); 0.92-0.87 (m, 2 H); 0.82-0.75 (m, 2 H)

Example 433

2-(1-(2-(5-(2-ethyl-1H-benzo[d]imidazol-1-yl)-7-morpholinothiazolo[5,4-d]pyrimidin-2-yl)ethyl)piperidin-4-yl)propan-2-ol 433

A mixture of 2-{1-[2-(5-chloro-7-morpholin-4-yl-thiazolo[5,4-d]pyrimidin-2-yl)ethyl]-piperidin-4-yl}propan-2-ol (56 mg, 0.13 mmol), 2-ethylbenzimidazole (21 mg, 0.15 mmol), Pd$_2$(dba)$_3$ (3.0 mg, 2.5 mol %), Xphos (6.3 mg, 10 mol %) and Cs$_2$CO$_3$ (64 mg, 0.20 mmol) in dioxane (1.0 mL) was purged with argon gas then heated at 120° C., for 18 h, in a sealed tube. The reaction mixture was loaded onto an Isolute® SCX-2 cartridge, washed with MeOH then the desired product eluted with 2 M NH$_3$ in MeOH. The resulting residue was purified by flash chromatography (Si—PCC, 0-10% MeOH in DCM) to give 433 (39 mg, 56%) as an orange solid. LCMS: (Method I): R$_T$ 2.71 min; [M+H]$^+$ 536.4. $^1$H NMR (400 MHz, CHCl$_3$-d): δ 8.01-7.97 (m, 1 H), 7.76-7.71 (m, 1 H), 7.29-7.24 (m, 2 H), 4.52-4.32 (m, 4H), 3.90-3.85 (m, 4 H), 3.34 (q, 7.5 Hz, 2 H), 3.35-3.23 (m, 2 H), 3.21-3.10 (m, 2 H), 2.87-2.83 (m, 2 H), 2.17-2.05 (m, 2 H), 1.86-1.75 (m, 2 H), 1.43 (t, J=7.5 Hz, 3 H), 1.38-1.23 (m, 3 H), 1.22 (s, 6 H)

Example 434

2-(1-(8-((4-tert-butylpiperazin-1-yl)methyl)-9-methyl-6-morpholino-9H-purin-2-yl)-1H-benzo[d]imidazol-2-yl)ethanol 434

A mixture of 9-methyl-2-(2-methylbenzoimidazol-1-yl)-6-morpholin-4-yl-9H-purine-8-carbaldehyde (100 mg, 0.26 mmol), (4-methylpiperidin-4-yl)pyrrolidin-1-ylmethanone (62 mg, 0.32 mmol), trimethoxyorthoformate (0.29 mL, 2.65 mmol) and acetic acid (40 μL, 0.70 mmol) in DCE (5 mL) was stirred at room temperature for 1 hour then sodium triacetoxyborohydride (90 mg, 0.42 mmol) was added. The reaction mixture was stirred at room temperature for 18 hours then diluted with MeOH and loaded onto an Isolute® SCX-2 cartridge (5 g). The cartridge was washed with MeOH and the desired product was eluted with 2M NH$_3$ in MeOH. The solvents were removed and the residue was subjected to flash chromatography (Si—PCC, 0-20% MeOH in EtOAc) to give 434 as a white solid (98 mg, 68%). LCMS (Method I): R$_T$ 2.64 min; [M+H]$^+$ 558. $^1$H NMR (400 MHz, CHCl$_3$-d): δ 8.11-8.07 (m, 1 H); 7.73-7.68 (m, 1 H); 7.31-7.26 (m, 2 H); 4.34 (m, 4 H); 3.90 (s, 3 H); 3.90-3.79 (m, 5 H); 3.76 (m, 2 H); 3.58-3.50 (m, 5 H); 2.95 (s, 3 H); 2.66 (m, 2 H); 2.49 (m, 2 H); 2.28 (m, 4 H); 1.87 (m, 2 H); 1.33 (s, 3 H)

Example 435

N-methyl-1-(9-methyl-6-morpholino-8-((3-(tetrahydro-2H-pyran-4-yl)azetidin-1-yl)methyl)-9H-purin-2-yl)-1H-benzo[d]imidazol-2-amine 435

A mixture of 2-chloro-9-methyl-6-morpholin-4-yl-8-[3-(tetrahydropyran-4-yl)azetidin-1-ylmethyl]-9H-purine (120 mg, 0.29 mmol), (1H-benzoimidazol-2-yl)methylamine (52 mg, 0.35 mmol), tris(dibenzylideneacetone)dipalladium (14 mg, 0.01 mmol), Xphos (28 mg, 0.06 mmol) and Cs$_2$CO$_3$ (192 mg, 0.59 mmol) in DMF (2.5 mL) was purged with argon then heated at 150° C. for 30 min in a microwave reactor. The reaction mixture was filtered through a pad of celite, washing with EtOAc. The filtrate was concentrated in vacuo and purified by column chromatography (Si—PCC, MeOH:EtOAc, 0-15%) affording 435 as a foam (104 mg, 69%). LCMS (Method I): R$_T$ 2.45 min, [M+H]$^+$ 518.4. $^1$H NMR (CDCl$_3$, 400 MHz): δ 8.48 (d, J=5.0 Hz, 1 H); 8.28 (d, J=8.0 Hz, 1 H); 7.49 (d, J=7.8 Hz, 1 H); 7.19 (m, 1 H); 7.10-7.04 (m, 1 H); 4.34 (m, 4 H); 3.97 (dd, J=11.5, 4.1 Hz, 2 H); 3.90 (t, J=4.7 Hz, 4 H); 3.85 (s, 3 H); 3.82 (s, 2 H); 3.51 (t, J=7.3 Hz, 2 H); 3.42-3.32 (m, 2 H); 3.26 (d, J=5.0 Hz, 3 H); 3.03 (t, J=7.0 Hz, 2 H); 2.34-2.25 (m, 1 H); 1.74-1.62 (m, 1 H); 1.54 (m, 2 H) and 1.27-1.13 (m, 2 H)

Example 436

4-(5-(2-ethyl-1H-benzo[d]imidazol-1-yl)-2-((3-(1,1-dioxo-thiomorpholino)azetidin-1-yl)methyl)thiazolo[5,4-d]pyrimidin-7-yl)morpholine 436

A mixture of 5-chloro-2-[3-(1,1-Dioxo-1-thiomorpholin-4-yl)azetidin-1-ylmethyl]-7-morpholin-4-ylthiazolo[5,4-d]pyrimidine (150 mg, 0.33 mmol), 2-ethylbenzimidazole (58 mg, 0.39 mmol), tris(dibenzylideneacetone)dipalladium (15 mg, 0.02 mmol), Xphos (31 mg, 0.07 mmol) and $Cs_2CO_3$ (213 mg, 0.65 mmol) in dioxane (3 mL) was purged with argon then heated at 145° C. for 45 min in a microwave reactor. The reaction mixture was filtered through a pad of celite, washing with EtOAc. The filtrate was concentrated in vacuo and purified by column chromatography (Si—PCC, MeOH:EtOAc, 0-10%) affording 436 as a foam (113 mg, 60%). LCMS (Method I): $R_T$ 2.59 min, $[M+H]^+$ 569.3. $^1H$ NMR ($CDCl_3$, 400 MHz): δ 8.02-7.97 (m, 1 H); 7.79-7.75 (m, 1 H); 7.33-7.27 (m, 2 H); 4.41 (m, 4 H); 4.02 (s, 2 H); 3.91-3.81 (m, 4 H); 3.72 (m, 2 H); 3.39-3.30 (m, 3 H); 3.16 (m, 2 H); 3.08 (m, 4 H); 2.90-2.85 (m, 4 H) and 1.44 (t, J=7.5 Hz, 3 H)

Example 437

2-(4-((2-(2-ethyl-1H-benzo[d]imidazol-1-yl)-9-methyl-6-morpholino-9H-purin-8-yl)methyl)piperazin-1-yl)-2-methylpropanamide 437

2-(4-((2-Chloro-9-methyl-6-morpholino-9H-purin-8-yl)methyl)piperazin-1-yl)-2-methylpropanamide (75 mg) was reacted with 2-methylbenzimidazole via General Procedure I for Buchwald coupling to give 39.9 mg 437 following reverse phase purification. MS (Q1) 547.1 (M)+

Example 438

2-(4-((2-(2-cyclopropyl-1H-benzo[d]imidazol-1-yl)-9-methyl-6-morpholino-9H-purin-8-yl)methyl)piperazin-1-yl)-2-methylpropanamide 438

2-(4-((2-Chloro-9-methyl-6-morpholino-9H-purin-8-yl)methyl)piperazin-1-yl)-2-methylpropanamide (75 mg) was reacted with 2-cyclopropylbenzimidazole via General Procedure I for Buchwald coupling to give 38.7 mg 438 following reverse phase purification. MS (Q1) 559.1 (M)+

Example 439

2-(4-((2-(2-isopropyl-1H-benzo[d]imidazol-1-yl)-9-methyl-6-morpholino-9H-purin-8-yl)methyl)piperazin-1-yl)-2-methylpropanamide 439

2-(4-((2-Chloro-9-methyl-6-morpholino-9H-purin-8-yl)methyl)piperazin-1-yl)-2-methylpropanamide (75 mg) was reacted with 2-isopropylbenzimidazole via General Procedure I for Buchwald coupling to give 24.9 mg 439 following reverse phase purification. MS (Q1) 561.7 (M)+

Example 440

2-(4-((2-(2-ethyl-1H-benzo[d]imidazol-1-yl)-9-methyl-6-morpholino-9H-purin-8-yl)methyl)piperazin-1-yl)-2-methylpropane-1,3-diol 440

Following General Procedure I for Buchwald coupling, 2-ethylbenzimidazole and 2-(4-((2-chloro-9-methyl-6-morpholino-9H-purin-8-yl)methyl)piperazin-1-yl)-2-methylpropane-1,3-diol were reacted to give 440. LCMS m/z: 550.3 (MH+)

Example 441

4-(8-((4-isopropylpiperazin-1-yl)methyl)-9-methyl-2-(2-methyl-1H-benzo[d]imidazol-1-yl)-9H-purin-6-yl)morpholine 441

Following General Procedure E for Displacement of alkyl bromide with amines, 4-(8-(bromomethyl)-9-methyl-2-(2-methyl-1H-benzo[d]imidazol-1-yl)-9H-purin-6-yl)morpholine and 1-isopropylpiperazine were reacted to give 441. LCMS m/z: 490.3 (MH+)

Example 443

1-(8-((4-(2-hydroxypropan-2-yl)piperidin-1-yl)methyl)-9-methyl-6-morpholino-9H-purin-2-yl)-2-isopropyl-1H-indazol-3(2H)-one 443

Following General Procedure I for Buchwald coupling, 2-isopropyl-1,2-dihydroindazol-3-one and 2-(1-((2-chloro-9-methyl-6-morpholino-9H-purin-8-yl)methyl)piperidin-4-yl)propan-2-ol were reacted to give 443. LCMS m/z: 549.3 (MH+)

Example 444

4-(8-((4-cyclobutylpiperazin-1-yl)methyl)-2-(2-ethyl-1H-benzo[d]imidazol-1-yl)-9-methyl-9H-purin-6-yl)morpholine 444

Following General Procedure I for Buchwald coupling, 2-ethylbenzimidazole and 4-(2-chloro-8-((4-cyclobutylpiperazin-1-yl)methyl)-9-methyl-9H-purin-6-yl)morpholine were reacted to give 444. LCMS m/z: 516.3 (MH+)

Example 445

4-(8-((4-tert-butylpiperazin-1-yl)methyl)-2-(isoquinolin-4-yl)-9-methyl-9H-purin-6-yl)morpholine 445

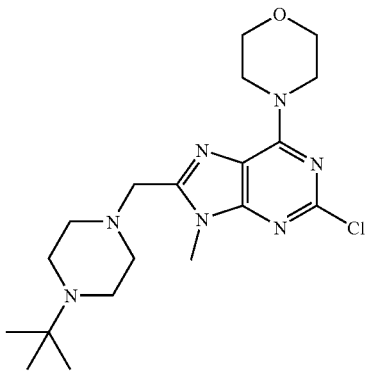

4-(8-((4-tert-butylpiperazin-1-yl)methyl)-2-chloro-9-methyl-9H-purin-6-yl)morpholine was prepared following General Procedure E of amine $SN_2$ alkylation. Following General Procedure A Suzuki coupling, 4-(8-((4-tert-butylpiperazin-1-yl)methyl)-2-chloro-9-methyl-9H-purin-6-yl)morpholine and 4-(4,4,5,5-tetramethyl-1,3,2-dioxaborolan-2-yl)isoquinoline were reacted to give 445. LCMS: M+H $^+$=501.3

Example 446

4-(9-methyl-2-(2-methyl-1H-benzo[d]imidazol-1-yl)-8-((4-(oxetan-3-yl)piperidin-1-yl)methyl)-9H-purin-6-yl)morpholine 446

A mixture of 2-chloro-9-methyl-6-morpholin-4-yl-8-(4-oxetan-3-yl-piperidin-1-ylmethyl)-9H-purine (100 mg, 0.25 mmol), 2-methyl-1H-benzoimidazole (38 mg, 0.29 mmol), Pd$_2$dba$_3$ (6 mg, 0.006 mmol), Xphos (12 mg, 0.025 mmol) and cesium carbonate (121 mg, 0.37 mmol) in DMF (2 mL) was purged with argon gas then subjected to microwave irradiation at 145° C. for 30 min. The reaction mixture was loaded onto an Isolute® SCX-2 cartridge (10 g), which was washed with MeOH/DCM before the desired product was eluted with 2 M NH$_3$ in MeOH/DCM. The product was collected and concentrated in vacuo. The resultant residue was purified by flash chromatography (Si—PPC, DCM:MeOH 100:0 to 99:1 to 98:2) to afford 446 as a white solid (29 mg, 23%). LCMS (Method I): R$_T$=2.37 min, M+H$^+$=503. $^1$H NMR (CDCl$_3$, 400 MHz) δ 8.09 (m, 1 H); 7.72 (m, 1 H); 7.39 (m, 2 H); 4.76 (dd, J=7.9, 6.0 Hz, 2 H); 4.46 (t, J=6.0 Hz, 2 H); 4.35 (m, 4 H); 3.90-3.84 (m, 7 H); 3.78 (s, 2 H); 2.96 (m, 5 H); 2.80-2.71 (m, 1 H); 2.22 (m, 2 H) and 1.69 (m, 5 H)

Example 447

N-methyl-1-(9-methyl-6-morpholino-8-((4-(oxetan-3-yl)piperidin-1-yl)methyl)-9H-purin-2-yl)-1H-benzo[d]imidazol-2-amine 447

A mixture of 2-chloro-9-methyl-6-morpholin-4-yl-8-(4-oxetan-3-yl-piperidin-1-ylmethyl)-9H-purine (100 mg, 0.25 mmol), (1H-benzoimidazol-2-yl)methyl-amine (43 mg, 0.29 mmol), Pd$_2$dba$_3$ (6 mg, 0.006 mmol), Xphos (12 mg, 0.025 mmol) and cesium carbonate (121 mg, 0.37 mmol) in DMF (2 mL) was purged with argon gas then subjected to microwave irradiation at 145° C. for 30 min. The reaction mixture was loaded onto an Isolute® SCX-2 cartridge (10 g), which was washed with MeOH/DCM before the desired product was eluted with 2 M NH$_3$ in MeOH/DCM. The product was collected and concentrated in vacuo. The resultant residue was purified by flash chromatography (Si—PPC, DCM:MeOH 100:0 to 99:1 to 98:2) to afford 447 as a cream foam (58 mg, 45%). LCMS (Method I): R$_T$=2.36 min, M+H$^+$=518. $^1$H NMR (CDCl$_3$, 400 MHz) δ 8.51 (bs, 1 H); 8.29 (d, J=7.9 Hz, 1 H); 7.51 (d, J=7.9 Hz, 1 H); 7.19 (t, J=7.8 Hz, 1 H); 7.08 (t, J=7.8 Hz, 1H); 4.75 (dd, J=7.9, 6.1 Hz, 2 H); 4.46 (t, J=6.1 Hz, 2 H); 4.33 (m, 4 H); 3.92-3.85 (m, 7H); 3.73 (s, 2 H); 3.26 (d, J=4.9 Hz, 3 H); 2.88 (m, 2 H); 2.78-2.69 (m, 1 H); 2.15 (m, 2H); 1.66 (m, 3 H) and 1.19-1.07 (m, 2 H)

Example 448

4-(5-(2-methyl-1H-benzo[d]imidazol-1-yl)-2-((3-(1,1-dioxo-thiomorpholino)azetidin-1-yl)methyl)thiazolo[5,4-d]pyrimidin-7-yl)morpholine 448

A mixture of 5-chloro-2-[3-(1,1-dioxo-1-thiomorpholin-4-yl)azetidin-1-ylmethyl]-7-morpholin-4-ylthiazolo[5,4-d]pyrimidine (150 mg, 0.33 mmol), 2-methylbenzimidazole (52 mg, 0.39 mmol), tris(dibenzylideneacetone)dipalladium (15 mg, 0.02 mmol), Xphos (31 mg, 0.07 mmol) and Cs$_2$CO$_3$ (213 mg, 0.65 mmol) in dioxane (3 mL) was purged with argon then heated at 145° C. for 45 min in a microwave reactor. The reaction mixture was filtered through a pad of celite, washing with EtOAc. The filtrate was concentrated in vacuo and purified by column chromatography (Si—PCC, MeOH:EtOAc, 0-5%) affording 448 as a foam (74 mg, 40%). LCMS (Method I): R$_T$ 2.45 min, [M+H]$^+$ 555.2. $^1$H NMR (CDCl$_3$, 400 MHz): δ 8.09-8.04 (m, 1 H); 7.74-7.69 (m, 1 H); 7.34-7.26 (m, 2 H); 4.41 (m, 4 H); 4.01 (s, 2 H); 3.88 (m, 4 H); 3.71 (t, J=6.7 Hz, 2 H); 3.37-3.30 (m, 1 H); 3.15 (t, J=6.7 Hz, 2 H); 3.09 (m, 4 H); 2.94 (s, 3 H) and 2.88 (m, 4 H)

Example 449

4-(2-(2-isopropyl-1H-benzo[d]imidazol-1-yl)-9-methyl-8-((3-(1,1-dioxo-thiomorpholino)azetidin-1-yl)methyl)-9H-purin-6-yl)morpholine 449

A mixture of 2-chloro-8-[3-(1,1-dioxo-1-thiomorpholin-4-yl)azetidin-1-ylmethyl]-9-methyl-6-morpholin-4-yl-9H-purine (0.162 g, 0.36 mmol), 2-isopropyl-1H-benzoimidazole (0.068 g, 0.43 mmol), Xphos (0.034 g, 0.071 mmol), Pd$_2$(dba)$_3$ (0.017 g, 0.018 mmol) and Cs$_2$CO$_3$ (0.231 g, 0.71 mmol) in dioxane (2 mL) was subjected to microwave irradiation at 145° C. for 45 min. The suspension was filtered through Celite and the filtrate was concentrated in vacuo. The residue was purified by flash chromatography (Si—PPC, MEOH:DCM gradient 0:100 to 7.5:92.5) to give 449 as a yellow solid (0.1 g, 49%). LCMS (Method I): R$_T$=2.56 min, [M+H]$^+$ 580.2. $^1$H NMR (400 MHz, DMSO-d): δ 7.91-7.86 (m, 1 H); 7.66-7.61 (m, 1 H); 7.26-7.21 (m, 2 H); 4.30-4.23 (m, 4 H); 3.97-3.86 (m, 1H); 3.87 (s, 2 H); 3.82-3.71 (m, 7 H); 3.46 (t, J=6.6 Hz, 2 H); 3.26-3.18 (m, 1 H); 3.12-3.08 (m, 4 H); 3.00 (t, J=6.8 Hz, 2 H); 2.74 (m, 4 H); 1.35 (d, J=6.8 Hz, 6 H)

Example 450

4-(2-(2-cyclopropyl-1H-benzo[d]imidazol-1-yl)-9-methyl-8-((4-(oxetan-3-yl)piperidin-1-yl)methyl)-9H-purin-6-yl)morpholine 450

A mixture of 2-chloro-9-methyl-6-morpholin-4-yl-8-(4-oxetan-3-ylpiperidin-1-ylmethyl)-9H-purine (100 mg, 0.25 mmol), 2-cyclopropyl-1H-benzoimidazole (47 mg, 0.30 mmol), Pd$_2$dba$_3$ (6 mg, 0.006 mmol), Xphos (12 mg, 0.025 mmol) and cesium carbonate (121 mg, 0.37 mmol) in DMF (2 mL) was purged with argon gas then subjected to microwave irradiation at 145° C. for 30 min. The reaction mixture was loaded onto an Isolute® SCX-2 cartridge (10 g), which was washed with MeOH/DCM before the desired product was eluted with 2 M NH$_3$ in MeOH/DCM. The product was collected and concentrated in vacuo. The resultant residue was purified by flash chromatography (Si—PPC, EtOAc:MeOH 100:0 to 99:1 to 98:2 to 95:5) to afford 450 as a pale purple foam (60 mg, 46%). LCMS (Method I): R$_T$=2.63 min, M+H$^+$= 529. $^1$H NMR (CDCl$_3$, 400 MHz) δ 7.94 (dd, J=7.1, 2.0 Hz, 1 H); 7.68 (d, J=7.4 Hz, 1 H); 7.27-7.19 (m, 2 H); 4.76 (dd, J=7.8, 6.1 Hz, 2 H); 4.46 (t, J=6.1 Hz, 2 H); 4.35 (m, 4 H); 3.89-3.82 (m, 7 H); 3.76 (s, 2 H); 2.91-2.81 (m, 3 H); 2.79-2.70 (m, 1 H); 2.18 (m, 2 H); 1.62 (m, 5 H); 1.36 (m, 2 H) and 1.08-1.01 (m, 2 H)

Example 451

2-(1-(2-(2-(2-ethyl-1H-benzo[d]imidazol-1-yl)-9-methyl-6-morpholino-9H-purin-8-yl)ethyl)azetidin-3-yl)propan-2-ol 451

A mixture of 2-{1-[2-(2-chloro-9-methyl-6-morpholin-4-yl-9H-purin-8-yl)ethyl]azetidin-3-yl}propan-2-ol (84 mg, 0.21 mmol), 2-ethylbenzimidazole (34 mg, 0.23 mmol), Pd$_2$(dba)$_3$ (4.9 mg, 2.5 mol %), Xphos (10.1 mg, 10 mol %) and Cs$_2$CO$_3$ (104 mg, 0.32 mmol) in dioxane (1.5 mL) was purged with argon gas then heated at 120° C., for 23 h, in a sealed tube. The reaction mixture was loaded onto an Isolute® SCX-2 cartridge, washed with MeOH then the desired product eluted with 2 M NH$_3$ in MeOH. The resulting residue was purified by flash chromatography (Si—PCC, 0-20% 2 M NH$_3$/MeOH in DCM) to give 451 (38 mg, 35%) as a yellow solid. LCMS: (Method I): R$_T$ 2.53 min; [M+H]$^+$ 505.3. $^1$H NMR (400 MHz, CHCl$_3$-d): δ 8.01-7.96 (m, 1 H), 7.77-7.73 (m, 1 H), 7.27-7.22 (m, 2 H), 4.49-4.24 (m, 4 H), 3.88-3.83 (m, 4 H), 3.76 (s, 3 H), 3.48-3.40 (m, 2 H), 3.38-3.27 (m, 4H), 3.15-2.95 (m, 2 H), 2.95-2.90 (m, 2 H), 2.55-2.47 (m, 1 H), 1.43 (t, J=7.48 Hz, 3 H), 1.17 (s, 6 H)

Example 452

1-(2-(2-(2-ethyl-1H-benzo[d]imidazol-1-yl)-9-methyl-6-morpholino-9H-purin-8-yl)ethyl)-4-methylpiperidin-4-ol 452

A mixture of 1-[2-(2-chloro-9-methyl-6-morpholin-4-yl-9H-purin-8-yl)ethyl]-4-methylpiperidin-4-ol (45 mg, 0.11 mmol), 2-ethylbenzimidazole (18 mg, 0.13 mmol), Pd$_2$(dba)$_3$ (2.6 mg, 2.5 mol %), Xphos (5.4 mg, 10 mol %) and Cs$_2$CO$_3$ (56 mg, 0.17 mmol) in dioxane (1 0 mL) was purged with argon gas then heated at 120° C., for 17 h, in a sealed tube. The reaction mixture was loaded onto an Isolute® SCX-2 cartridge, washed with MeOH then the desired product eluted with 2 M NH$_3$ in MeOH. The resulting residue was purified by flash chromatography (Si—PCC, 0-10% 2 M NH$_3$/MeOH in DCM) to give 452 (46 mg, 80%) as a pale orange solid. LCMS: (Method I): R$_T$ 2.46 min; [M+H]$^+$ 505.2. $^1$H NMR (400 MHz, CHCl$_3$-d): δ 8.01-7.96 (m, 1 H), 7.77-7.73 (m, 1 H), 7.28-7.22 (m, 2 H), 4.47-4.19 (m, 4 H), 3.88-3.83 (m, 4 H), 3.78 (s, 3 H), 3.34 (q, J=7.5 Hz, 2 H), 3.15-3.05 (m, 2H), 2.98-2.80 (m, 2 H), 2.78-2.73 (m, 2 H), 2.65-2.57 (m, 2 H), 1.69-1.65 (m, 4 H), 1.44 (t, J=7.5 Hz, 3 H), 1.33-1.27 (s, 3 H)

Example 453

2-methyl-2-(4-((9-methyl-2-(2-(methylamino)-1H-benzo[d]imidazol-1-yl)-6-morpholino-9H-purin-8-yl)methyl)piperazin-1-yl)propan-1-ol 453

Following General Procedure I for Buchwald coupling, 2-(4-((2-chloro-9-methyl-6-morpholino-9H-purin-8-yl)methyl)piperazin-1-yl)-2-methylpropan-1-ol and N-methyl-1H-benzo[d]imidazol-2-amine were reacted to give 453. LCMS m/z: 535.3 (MH+)

Example 454

4-(2-(2-(azetidin-1-yl)-1H-benzo[d]imidazol-1-yl)-8-((4-tert-butylpiperazin-1-yl)methyl)-9-methyl-9H-purin-6-yl)morpholine 454

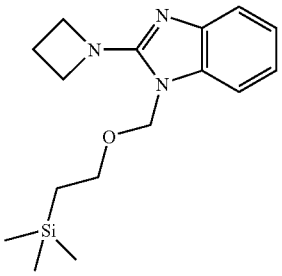

2-Chloro-1-((2-(trimethylsilyl)ethoxy)methyl)-1H-benzo[d]imidazole (0.5 g) was placed in a flask with azetidine (0.48 mL), Hunig's base (iPr2Net, 1.5 mL) in 1 mL of ethanol. The reaction was heated to 50° C. overnight and then concentrated to dryness to get 0.55 g of crude 2-(azetidin-1-yl)-1-((2-(trimethylsilyl)ethoxy)methyl)-1H-benzo[d]imidazole.

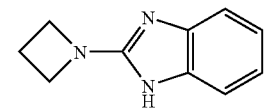

Into a sealed vessel was placed crude 2-(azetidin-1-yl)-1-((2-(trimethylsilyl)ethoxy)methyl)-1H benzo[d]imidazole (0.55 g) and sodium ethoxide (1.2 g) in DMF (14 mL). The reacted was heated for 30 mins at 150° C. in an oil bath. The reaction mixture was diluted with water and extracted with ethyl acetate. The organic layer was dried with magnesium sulfate, filtered and concentrated to give 310 mg of 2-(azetidin-1-yl)-1H-benzo[d]imidazole as yellow solid.

4-(8-((4-tert-butylpiperazin-1-yl)methyl)-2-chloro-9-methyl-9H-purin-6-yl)morpholine (75 mg) was reacted with 2-(azetidin-1-yl)-1H-benzo[d]imidazole (33 mg) via General Procedure for Buchwald coupling to give 36.1 mg 454 following reverse phase purification. MS (Q1) 545.4 (M)+

Example 455

2-(1-((2-(2-(azetidin-1-yl)-1H-benzo[d]imidazol-1-yl)-9-methyl-6-morpholino-9H-purin-8-yl)methyl)piperidin-4-yl)propan-2-ol 455

2-(1-((2-Chloro-9-methyl-6-morpholino-9H-purin-8-yl)methyl)piperidin-4-yl)propan-2-ol (75 mg) was reacted with 2-(azetidin-1-yl)-1H-benzo[d]imidazole (33 mg) via General Procedure I for Buchwald coupling to give 35.9 mg 455 following reverse phase purification. MS (Q1) 546.3 (M)+

Example 456 ethyl 2-methyl-2-(4-((9-methyl-2-(2-methyl-1H-benzo[d]imidazol-1-yl)-6-morpholino-9H-purin-8-yl)methyl)piperidin-1-yl)propanoate 456

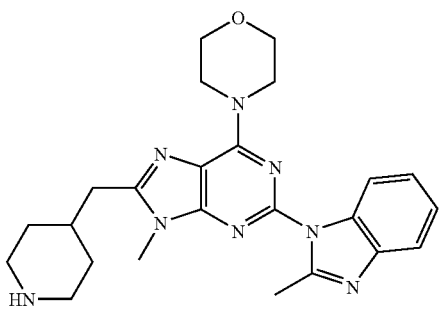

Following General Procedure C, 4-(9-methyl-2-(2-methyl-1H-benzo[d]imidazol-1-yl)-8-(piperidin-4-ylmethyl)-9H-purin-6-yl)morpholine was alkylated with 2-bromo-2-methyl-propanoic acid ethyl ester to give 456. LCMS m/z: 561.3 (MH+)

Example 457

4-(8-((4-tert-butylpiperazin-1-yl)methyl)-2-(2-(1,1-difluoroethyl)-1H-benzo[d]imidazol-1-yl)-9H-purin-6-yl)morpholine 457

N1-(8-((4-tert-butylpiperazin-1-yl)methyl)-6-morpholino-9-(tetrahydro-2H-pyran-2-yl)-9H-purin-2-yl)benzene-1,2-diamine (0.085 g, 0.15 mmol) and 2,2-difluoropropanoic acid (0.019 g, 0.17 mmol) were dissolved in N,N-dimethylformamide (2 mL, 0.02 mol). N,N-Diisopropylethylamine (0.054 mL, 0.31 mmol) was added. The resulting solution was cooled at 0° C. for 20 minutes. N,N,N',N'-Tetramethyl-O-(7-azabenzotriazol-1-yl)uronium hexafluorophosphate (0.070 g, 0.00018 mol) was added and the reaction stirred overnight at room temperature. The reaction mixture was concentrated to dryness. Acetic acid (3.0 mL, 0.053 mol) was added to the crude residue and the reaction mixture was heated at 90° C. for 18 hours. The reaction mixture was cooled, filtered and concentrated to dryness. The crude was purified by reverse phase HPLC to give 457 (15.3 mg, 18%). [M+H]$^+$=540.3

Example 458

1-(2-(2-(2-ethyl-1H-benzo[d]imidazol-1-yl)-9-methyl-6-morpholino-9H-purin-8-yl)ethyl)-3-methylazetidin-3-ol 458

A mixture of 1-[2-(2-chloro-9-methyl-6-morpholin-4-yl-9H-purin-8-yl)ethyl]-3-methylazetidin-3-ol (80 mg, 0.22 mmol), 2-ethylbenzimidazole (35 mg, 0.24 mmol), Pd$_2$(dba)$_3$ (5 mg, 2.5 mol %), Xphos (10.4 mg, 10 mol %) and Cs$_2$CO$_3$ (107 mg, 0.33 mmol) in dioxane (2.0 mL) was purged with argon gas then heated at 120° C., for 19 h, in a sealed tube. The reaction mixture was loaded onto an Isolute® SCX-2 cartridge, washed with MeOH then the desired product eluted with 2 M NH$_3$ in MeOH. The resulting residue was purified by flash chromatography (Si—PCC, 0-10% 2 M NH$_3$/MeOH in DCM) to give 458 (77 mg, 74%) as a pale beige solid. LCMS: (Method I): R$_T$ 2.39 min; [M+H]$^+$ 477.2. $^1$H NMR (400 MHz, CHCl$_3$-d): δ 8.01-7.96 (m, 1 H), 7.76-7.72 (m, 1 H), 7.26-7.22 (m, 2 H), 4.45-4.32 (m, 4 H), 3.86 (t, J=4.8 Hz, 4 H), 3.77 (s, 3 H), 3.40 (d, J=7.3 Hz, 2 H), 3.34 (q, J=7.5 Hz, 2 H), 3.14 (d, J=7.3 Hz, 2 H), 3.02 (t, J=7.3 Hz, 3 H), 2.92 (t, J=7.3 Hz, 2 H), 1.53 (s, 3 H), 1.44 (t, J=7.5 Hz, 3 H)

Example 459

4-(2-(2-(1,1-difluoroethyl)-1H-benzo[d]imidazol-1-yl)-9-methyl-8-((4-oxetan-3-yl)piperidin-1-yl)methyl)-9H-purin-6-yl)morpholine 459

To a mixture of N-[9-methyl-6-morpholin-4-yl-8-(4-oxetan-3-ylpiperidin-1-ylmethyl)-9H-purin-2-yl]benzene-1,2-diamine (0.115 g, 0.24 mmol) and 2,2-difluoropropionic acid (0.028 g, 0.25 mmol) and DIPEA (0.091 mL, 0.53 mL) in DMF (7 mL) was added HATU (0.11 g, 0.29 mmol). The reaction mixture was stirred at room temperature for 24 h, then at 90° C. for 24 h. The reaction mixture was concentrated in vacuo and the residue was loaded in MeOH onto an Isolute® SCX-2 cartridge. The cartrgidge was washed with MeOH and the desired product was eluted with 2 M NH$_3$ in MeOH. The solution was concentrated in vacuo, the residue was diluted in acetic acid (15 mL) and the reaction mixture was stirred at 90° C. for 7 h. The reaction mixture was concentrated in vacuo and the resultant residue was purified by flash chromatography (Si—PPC, MEOH:DCM, 0:100 to 10:90) followed by reverse phase HPLC (Phenomenex Gemini 5u C18, 20 mM triethylamine in water on a gradient of acetonitrile 95:5 to 2:98) to give 459 as a white solid (0.032 g, 27%). LCMS (Method I): R$_T$=3.30 min, [M+H]$^+$ 553.3. $^1$H NMR (400 MHz, DMSO-d): δ 7.84-7.81 (m, 1 H); 7.74-7.71 (m, 1 H); 7.43-7.35 (m, 2 H); 4.40-4.15 (m, 4 H); 3.84 (s, 2 H); 3.81 (d, J=4.3 Hz, 2 H); 3.78-3.71 (m, 7 H); 3.37 (t, J=6.9 Hz, 2 H); 3.30-3.18 (m, 2 H); 2.96 (t, J=6.9 Hz, 2 H); 2.34-2.21 (t, J=19.5 Hz, 3 H); 2.20-2.08 (m, 1 H); 1.64 (d, J=12.1 Hz, 1 H); 1.50 (d, J=13.0 Hz, 2 H); 1.06 (td, J=12.1, 4.3 Hz, 2 H)

Example 460

(S)-(1-((2-(2-ethyl-1H-benzo[d]imidazol-1-yl)-9-methyl-6-morpholino-9H-purin-8-yl)methyl)azetidin-3-yl)(3-hydroxypyrrolidin-1-yl)methanone 460

A mixture of 2-(2-ethylbenzoimidazol-1-yl)-9-methyl-6-morpholin-4-yl-9H-purine-8-carbaldehyde (75 mg, 0.19 mmol), azetidin-3-yl-((S)-3-hydroxypyrrolidin-1-yl)methanone (65 mg, 0.38 mmol), and 4 Å molecular sieves (250 mg) in 1,2-dichloroethane (2 mL) was stirred at RT for 4 h. Sodium triacetoxyborohydride (81 mg, 0.38 mmol) was added and the resulting reaction mixture was stirred at RT under nitrogen atmosphere for 60 h. The suspension was filtered through Celite and the filtrate was concentrated in vacuo. The crude residue was loaded on an Isolute® SCX-2 cartridge (5 g). The cartridge was washed with DCM/MeOH and the desired product was subsequently eluted using a mixture of 2M NH$_3$ in MeOH and DCM. The residue was purified by column chromatography (Si—PPC, MeOH:DCM, gradient 0:100 to 10:90) to afford 460 as an off-white solid (32 mg, 30%). LCMS (Method I): R$_T$ 2.33 min, [M+H]$^+$ 546. $^1$H NMR (400 MHz, CDCl$_3$): δ 7.98-7.93 (1h, m), 7.71-7.70 (1 H, m), 7.22 (2 H, s), 4.49 (2 H, s), 4.31 (4 H, s), 3.83-3.81 (8 H, m), 3.52-3.50 (9 H, m), 3.32-3.30 (2 H, m), 2.04-1.88 (3 H, m), 1.40 (3 H, t, J=7.47 Hz)

Example 461

(R)-(1-((2-(2-ethyl-1H-benzo[d]imidazol-1-yl)-9-methyl-6-morpholino-9H-purin-8-yl)methyl)azetidin-3-yl)(3-hydroxypyrrolidin-1-yl)methanone 461

A mixture of 2-(2-ethylbenzoimidazol-1-yl)-9-methyl-6-morpholin-4-yl-9H-purine-8-carbaldehyde (75 mg, 0.19 mmol), azetidin-3-yl-((R)-3-hydroxypyrrolidin-1-yl)methanone (65 mg, 0.38 mmol), and 4 Å molecular sieves (250 mg) in 1,2-dichloroethane (2 mL) was stirred at RT for 4 h. Sodium triacetoxyborohydride (81 mg, 0.38 mmol) was added and the resulting reaction mixture was stirred at RT under nitrogen atmosphere for 60 h. The suspension was filtered through Celite and the filtrate was concentrated in vacuo. The crude residue was loaded on an Isolute® SCX-2 cartridge (5 g). The cartridge was washed with DCM/MeOH and the desired product was subsequently eluted using a mixture of 2M $NH_3$ in MeOH and DCM. The residue was purified by column chromatography (Si—PPC, MeOH: DCM, gradient 0:100 to 10:90) to afford 461 as a white solid (17 mg, 16%). LCMS (Method I): $R_T$ 2.34 min, $[M+H]^+$ 546. $^1$H NMR (400 MHz, $CDCl_3$): δ 7.96-7.95 (1 H, m), 7.73-7.69 (1 H, m), 7.22 (2 H, s), 4.52-4.48 (2 H, m), 4.31 (4 H, s), 3.82-3.82 (8 H, m), 3.59-3.57 (9 H, m), 3.32-3.30 (2 H, m), 1.98-1.97 (2 H, m), 1.40 (3 H, t, J=7.48 Hz)

Example 462

2-(1-((2-(2-tert-butyl-1H-benzo[d]imidazol-1-yl)-9-methyl-6-morpholino-9H-purin-8-yl)methyl)piperidin-4-yl)propan-2-ol 462

2-(1-((2-Chloro-9-methyl-6-morpholino-9H-purin-8-yl)methyl)piperidin-4-yl)propan-2-ol (0.3 g) was reacted with tert-butylbenzimidazole via General Procedure I for Buchwald coupling to give 94.3 mg 462 following reverse phase purification. MS (Q1) 547.3 (M)+

Example 463

4-(8-((4-tert-butylpiperazin-1-yl)methyl)-2-(2-(1,1-difluoroethyl)-1H-benzo[d]imidazol-1-yl)-9-methyl-9H-purin-6-yl)morpholine 463

Following General Procedure J for Multi-Step Benzimidazole formation, 4-(8-((4-tert-butylpiperazin-1-yl)methyl)-2-chloro-9-methyl-9H-purin-6-yl)morpholine was converted to 463 with difluoroacetic acid. LCMS: $M+H^+$=554.3

Example 464

4-(8-((4-tert-butylpiperazin-1-yl)methyl)-9-methyl-2-(2-(trifluoromethyl)-1H-benzo[d]imidazol-1-yl)-9H-purin-6-yl)morpholine 464

Following General Procedure J for Multi-Step Benzimidazole formation, 4-(8-((4-tert-butylpiperazin-1-yl)methyl)-2-chloro-9-methyl-9H-purin-6-yl)morpholine was converted to 464 with trifluoroacetic acid. LCMS: $M+H^+$=558.3

Example 465

7-(2-(2-(2-ethyl-1H-benzo[d]imidazol-1-yl)-9-methyl-6-morpholino-9H-purin-8-yl)ethyl)-7-azaspiro[3.5]nonan-2-ol 465

A mixture of 7-[2-(2-chloro-9-methyl-6-morpholin-4-yl-9H-purin-8-yl)ethyl]-7-azaspiro[3.5]nonan-2-ol (75 mg, 0.18 mmol), 2-ethylbenzimidazole (29 mg, 0.20 mmol), $Pd_2(dba)_3$ (4.1 mg, 2.5 mol %), Xphos (8.5 mg, 10 mol %) and $Cs_2CO_3$ (87 mg, 0.27 mmol) in dioxane (2.0 mL) was purged with argon gas then heated at 120° C., for 18 h, in a sealed tube. The reaction mixture was loaded onto an Isolute® SCX-2 cartridge, washed with MeOH then the desired product eluted with 2 M $NH_3$ in MeOH. The resulting residue was purified by flash chromatography (Si—PCC, 0-10% 2 M $NH_3$/MeOH in DCM) followed by reverse phase HPLC (Phenomenex Gemini 5 μm C18, 20 mM triethylamine in water on a gradient of acetonitrile 20-98%) to give 465 (42 mg, 44%) as an off white solid. LCMS: (Method I): $R_T$ 2.47 min; $[M+H]^+$ 531.3. $^1$H NMR (400 MHz, $CHCl_3$-d): δ 8.01-7.96 (m, 1 H), 7.76-7.72 (m, 1 H), 7.28-7.22 (m, 2 H), 4.37-4.27 (m, 5 H), 3.86 (t, J=4.7 Hz, 4 H), 3.78 (s, 3 H), 3.34 (q, J=7.5 Hz, 2 H), 3.17-3.02 (m, 2 H), 2.99-2.81 (m, 2 H), 2.71-2.39 (m, 4 H), 2.31-2.24 (m, 2 H), 1.74-1.64 (m, 6 H), 1.44 (t, J=7.5 Hz, 3 H)

Example 466

1-(2-(2-(2-ethyl-1H-benzo[d]imidazol-1-yl)-9-methyl-6-morpholino-9H-purin-8-yl)ethyl)-3-isopropylazetidin-3-ol 466

A mixture of 1-[2-(2-chloro-9-methyl-6-morpholin-4-yl-9H-purin-8-yl)ethyl]-3-isopropyl-azetidin-3-ol (33 mg, 0.08 mmol), 2-ethylbenzimidazole (14 mg, 0.09 mmol), $Pd_2(dba)_3$ (1.9 mg, 2.5 mol %), Xphos (4.0 mg, 10 mol %) and $Cs_2CO_3$ (41 mg, 0.13 mmol) in dioxane (1.0 mL) was purged with argon gas then heated at 120° C., for 18 h, in a sealed tube. The reaction mixture was loaded onto an Isolute® SCX-2 cartridge, washed with MeOH then the desired product eluted with 2 M $NH_3$ in MeOH. The resulting residue was purified by flash chromatography (Si—PCC, 0-10% 2 M $NH_3$/MeOH in DCM) followed by reverse phase HPLC (Phenomenex Gemini 5 μm C18, 20 mM triethylamine in water on a gradient of acetonitrile 20-98%) to give 466 (18 mg, 42%) as an off white solid. LCMS: (Method I): $R_T$ 2.62 min; $[M+H]^+$ 505.3. $^1$H NMR (400 MHz, $CHCl_3$-d): δ 8.01-7.96 (m, 1H), 7.76-7.72 (m, 1 H), 7.28-7.22 (m, 2 H), 4.45-4.33 (m, 4 H), 3.86 (t, J=4.7 Hz, 4 H), 3.77 (s, 3 H), 3.41 (d, J=8.1 Hz, 2 H), 3.34 (q, J=7.5 Hz, 2 H), 3.18 (d, J=8.1 Hz, 2 H), 3.04 (t, J=7.2 Hz, 2 H), 2.93 (t, J=7.2 Hz, 2 H), 2.01-1.89 (m, 1 H), 1.44 (t, J=7.5 Hz, 3 H), 0.94 (d, J=6.8 Hz, 6 H)

Example 467

4-(9-methyl-2-(2-methyl-1H-benzo[d]imidazol-1-yl)-8-((3-(tetrahydro-2H-pyran-4-yl)azetidin-1-yl)methyl)-9H-purin-6-yl)morpholine 467

A mixture of 2-chloro-9-methyl-6-morpholin-4-yl-8-[3-(tetrahydropyran-4-yl)azetidin-1-ylmethyl]-9H-purine (112 mg, 0.28 mmol), 2-methylbenzimidazole (44 mg, 0.33 mmol), tris(dibenzylideneacetone)dipalladium (13 mg, 0.01 mmol), Xphos (26 mg, 0.06 mmol) and $Cs_2CO_3$ (179 mg, 0.55 mmol) in dioxane (3 mL) was purged with argon then heated at 150° C. for 30 min in a microwave reactor. The reaction mixture was filtered through a pad of celite, washing with EtOAc. The filtrate was concentrated in vacuo and purified by column chromatography (Si—PCC, MeOH:EtOAc, 0-20%) affording 467 as a cream solid (105 mg, 75%). LCMS (Method I): $R_T$ 2.46 min, $[M+H]^+$ 503.2. $^1$H NMR (CDCl$_3$, 400 MHz): δ 8.10-8.05 (m, 1 H); 7.73-7.67 (m, 1 H); 7.28-7.23 (m, 2 H); 4.35 (m, 4 H); 3.97 (dd, J=11.4, 4.1 Hz, 2 H); 3.89-3.82 (m, 9 H); 3.54 (m, 2 H); 3.37 (td, J=11.4, 2.0 Hz, 2 H); 3.06 (m, 2 H); 2.94 (s, 3 H); 2.38-2.27 (m, 1 H); 1.54 (m, 2 H) and 1.32-1.14 (m, 3 H)

Example 468

4-(2-(2-(1,1-difluoroethyl)-1H-benzo[d]imidazol-1-yl)-9-methyl-8-((3-(tetrahydro-2H-pyran-4-yl)azetidin-1-yl)methyl)-9H-purin-6-yl)morpholine 468

To a mixture of N-{9-methyl-6-morpholin-4-yl-8-[3-(tetrahydropyran-4-yl)azetidin-1-ylmethyl]-9H-purin-2-yl}benzene-1,2-diamine (0.234 g, 0.49 mmol) and 2,2-difluoropropionic acid (0.057 g, 0.51 mmol) and DIPEA (0.185 mL, 1.08 mL) in DMF (14 mL) was added HATU (0.223 g, 0.59 mmol) and the reaction mixture was stirred at room temperature for 24 h. The reaction mixture was concentrated in vacuo and the residue purified by flash chromatography (Si—PPC, MEOH:DCM, gradient 0:100 to 7.5:92.5). The solution was concentrated in vacuo, the residue was diluted in acetic acid (30 mL) and the reaction mixture was stirred at 90° C. for 18 h. The reaction mixture was concentrated in vacuo and the residue was purified by flash chromatography (Si—PPC, MEOH:DCM, 0:100 to 7.5:92.5) followed by reverse phase HPLC (Phenomenex Gemini 5u C18, 20 mM triethylamine in water on a gradient of acetonitrile 95:5 to 2:98) to give 468 as a white solid (0.063 g, 24%). LCMS (Method I): $R_T$=3.34 min, $[M+H]^+$ 553.3. $^1$H NMR (400 MHz, DMSO-d): δ 7.84-7.82 (m, 1 H); 7.75-7.72 (m, 1 H); 7.42-7.36 (m, 2 H); 4.58 (dd, J=7.85, 6.0 Hz, 2 H); 4.40-4.00 (m, 4 H); 4.32 (t, J=6.0 Hz, 2 H); 3.78 (s, 3 H); 3.77 (s, 2 H); 3.77-3.73 (m, 4 H); 2.85 (d, J=11.1 Hz, 2 H); 2.68-2.66 (m, 1 H); 2.26 (t, J=19.02 Hz, 3 H); 2.09 (t, J=11.1 Hz, 2 H); 1.57 (d, J=12.5 Hz, 3 H); 1.03 (d, J=12.5 Hz, 2 H)

Example 469

4-((2-(2-ethyl-1H-benzo[d]imidazol-1-yl)-9-methyl-6-morpholino-9H-purin-8-yl)methyl)-1-isopropylpiperazin-2-one 469

A mixture of 2-(2-ethylbenzoimidazol-1-yl)-9-methyl-6-morpholin-4-yl-9H-purine-8-carbaldehyde (0.15 g, 0.39 mmol), 1-isopropylpiperazin-2-one (0.082 g, 0.58 mmol) and 4 Å molecular sieves (0.718 g) in DCE (5 mL) and MeOH (1 mL) was stirred for 5 h at room temperature. Sodium triacetoxyborohydride (0.163 g, 0.77 mmol) was added and the reaction mixture was stirred for 72 h at room temperature. The reaction mixture was filtered through Celite and the filtrate was concentrated in vacuo. The residue was purified by flash chromatography (Si—PPC, MeOH:EtOAc, gradient 0:100 to 5:95) followed by reverse phase HPLC (Phenomenex Gemini 5u C18, 20 mM triethylamine in water on a gradient of acetonitrile 95:5 to 2:98) to give 469 as an off-white solid (0.044 g, 22%). LCMS (Method I): $R_T$=3.31 min, $[M+H]^+$ 518.3. $^1$H NMR (400 MHz, DMSO-d): δ 8.04-8.00 (m, 1 H); 7.65-7.61 (m, 1 H); 7.28-7.21 (m, 2 H); 4.64-4.58 (m, 1 H); 4.28-4.25 (m, 4 H); 3.86 (s, 2 H); 3.81 (s, 3 H); 3.80-3.77 (m, 4 H); 3.27 (q, 7.5 Hz, 2 H); 3.17 (t, J=5.3 Hz, 2 H); 3.13 (s, 2 H); 2.73 (t, J=5.3 Hz, 2 H); 1.34 (t, J=7.5 Hz, 3 H); 1.05 (d, J=6.8 Hz, 6 H)

Example 470

4-(5-(2-isopropyl-1H-benzo[d]imidazol-1-yl)-2-((3-(tetrahydro-2H-pyran-4-yl)azetidin-1-yl)methyl)thiazolo[5,4-d]pyrimidin-7-yl)morpholine 470

A mixture of 5-chloro-7-morpholin-4-yl-2-[3-(tetrahydropyran-4-yl)azetidin-1-ylmethyl]thiazolo[5,4-d]pyrimidine (0.1 g, 0.25 mmol), 2-isopropyl-1H-benzoimidazole 0.078 g, 0.49 mmol), Xphos (0.024g, 0.049 mmol), Pd$_2$(dba)$_3$ (0.012 g, 0.012 mmol) and Cs$_2$CO$_3$ (0.159 g, 0.49 mmol) in dioxane (1.5 mL) was subjected to microwave irradiation at 145° C. for 45 min. The reaction mixture was filtered through Celite and the filtrate was concentrated in vacuo. The residue was purified by flash chromatography (Si—PPC, MEOH:DCM, gradient 0:100 to 5:95) to give 470 as a yellow solid (0.044 g, 34%). LCMS (Method I): $R_T$=2.88 min, $[M+H]^+$ 534.2. $^1$H NMR (400 MHz, DMSO-d): δ 7.89-7.85 (m, 1 H); 7.66-7.61 (m, 1 H); 7.28-7.22 (m, 2 H); 4.36-4.30 (m, 4 H); 4.00 (s, 2 H); 3.97-3.89 (m, 1 H); 3.85 (dd, J=11.2, 4.0 Hz, 2 H); 3.79 (t, J=4.6 Hz, 4 H); 3.49 (t, J=7.3 Hz, 2 H); 3.39-3.35 (m, 2 H); 3.07 (t, J=6.8 Hz, 2 H); 2.27-2.21 (m, 1 H); 1.73-1.64 (m, 1 H); 1.52 (d, J=13.1 Hz, 2 H); 1.33 (dd, J=6.8, 4.0 Hz, 6 H); 1.10 (td, J=12.2, 4.6 Hz, 2 H)

Example 471

4-(8-((4-tert-butylpiperazin-1-yl)methyl)-2-(2-isopropyl-1H-benzo[d]imidazol-1-yl)-9-methyl-9H-purin-6-yl)morpholine 471

4-(8-((4-tert-Butylpiperazin-1-yl)methyl)-2-chloro-9-methyl-9H-purin-6-yl)morpholine (80 mg) was reacted with 2-isopropylbenzimidazole via General Procedure I for Buchwald coupling to give 31.4 mg 471 following reverse phase purification. MS (Q1) 532.4 (M)+

Example 472

1-(8-((4-tert-butylpiperazin-1-yl)methyl)-9-methyl-6-morpholino-9H-purin-2-yl)-2-ethyl-1H-indazol-3(2H)-one 472

Following General Procedure I for Buchwald coupling, 4-(8-((4-tert-butylpiperazin-1-yl)methyl)-2-chloro-9-methyl-9H-purin-6-yl)morpholine and 2-ethyl-1H-indazol-3(2H)-one were reacted to give 472. LCMS m/z: 534.3 (MH+)

Example 473

2-(4-((2-(2-(1,1-difluoroethyl)-1H-benzo[d]imidazol-1-yl)-9-methyl-6-morpholino-9H-purin-8-yl)methyl)piperazin-1-yl)-2-methylpropan-1-ol 473

Following General Procedure J for Multi-Step Benzimidazole formation, 2-(4-((2-chloro-9-methyl-6-morpholino-9H-purin-8-yl)methyl)piperazin-1-yl)-2-methylpropan-1-ol was converted to 473 with difluoroacetic acid. LCMS: $M+H^+$= 570.3

Example 474

2-methyl-2-(4-((9-methyl-6-morpholino-2-(2-(trifluoromethyl)-1H-benzo[d]imidazol-1-yl)-9H-purin-8-yl)methyl)piperazin-1-yl)propan-1-ol 474

Following General Procedure J for Multi-Step Benzimidazole formation, 2-(4-((2-chloro-9-methyl-6-morpholino-9H-purin-8-yl)methyl)piperazin-1-yl)-2-methylpropan-1-ol was converted to 474. LCMS: M+H$^+$=574.3

Example 475

4-(8-((4-tert-butylpiperazin-1-yl)methyl)-9-methyl-2-(quinolin-4-yl)-9H-purin-6-yl)morpholine 475

Following General Procedure A for Suzuki coupling, 4-(8-((4-tert-butylpiperazin-1-yl)methyl)-2-chloro-9-methyl-9H-purin-6-yl)morpholine and 4-(4,4,5,5-tetramethyl-1,3,2-dioxaborolan-2-yl)quinoline were reacted to give 475. LCMS: M+H$^+$=501.3

Example 476

2-(4-((2-(2-isopropyl-1H-benzo[d]imidazol-1-yl)-9-methyl-6-morpholino-9H-purin-8-yl)methyl)piperazin-1-yl)-2-methylpropan-1-ol 476

2-(4-((2-Chloro-9-methyl-6-morpholino-9H-purin-8-yl)methyl)piperazin-1-yl)-2-methylpropan-1-ol (70 mg) was reacted with 2-isopropylbenzimidazole via General Procedure I for Buchwald coupling to give 28 mg 476 following reverse phase purification. MS (Q1) 548.3 (M)+

Example 477

2-(1-((2-(2-((1R,2S)-2-fluorocyclopropyl)-1H-benzo[d]imidazol-1-yl)-9-methyl-6-morpholino-9H-purin-8-yl)methyl)piperidin-4-yl)propan-2-ol 477

2-(1-((2-chloro-9-methyl-6-morpholino-9H-purin-8-yl)methyl)piperidin-4-yl)propan-2-ol (75 mg) was reacted with trans-2-fluorocyclopropanecarboxylic acid via General Procedure J for two-step Buchwald coupling to give 16.3 mg of 477 following reverse phase purification and subsequent chiral separation from 479. MS (Q1) 549.3 (M)+

Example 478

I-2-(1-((2-(2-(2,2-difluorocyclopropyl)-1H-benzo[d]imidazol-1-yl)-9-methyl-6-morpholino-9H-purin-8-yl)methyl)piperidin-4-yl)propan-2-ol 478

2-(1-((2-Chloro-9-methyl-6-morpholino-9H-purin-8-yl)methyl)piperidin-4-yl)propan-2-ol (0.1 g) was reacted with 2,2-difluorocyclopropanecarboxylic acid via General Procedure J for two-step Buchwald coupling to give 8.8 mg of 478 [MS (Q1) 567.3 (M)+] following reverse phase purification and subsequent chiral separation from 8.8 mg of enantiomer 481. MS (Q1) 567.3 (M)+].

Example 479

2-(1-((2-(2-((1S,2R)-2-fluorocyclopropyl)-1H-benzo[d]imidazol-1-yl)-9-methyl-6-morpholino-9H-purin-8-yl)methyl)piperidin-4-yl)propan-2-ol 479

2-(1-((2-chloro-9-methyl-6-morpholino-9H-purin-8-yl)methyl)piperidin-4-yl)propan-2-ol (75 mg) was reacted with trans-2-fluorocyclopropanecarboxylic acid via General Procedure J for two-step Buchwald coupling to give 16.1 mg of 479 following reverse phase purification and subsequent chiral separation from 477. MS (Q1) 549.3 (M)+

Example 480

2-(1-((2-(2-((1R,2R)-2-fluorocyclopropyl)-1H-benzo[d]imidazol-1-yl)-9-methyl-6-morpholino-9H-purin-8-yl)methyl)piperidin-4-yl)propan-2-ol 480

2-(1-((2-Chloro-9-methyl-6-morpholino-9H-purin-8-yl)methyl)piperidin-4-yl)propan-2-ol (75 mg) was reacted with cis-2-fluorocyclopropanecarboxylic acid via General Procedure J for two-step Buchwald coupling to give 13 mg of 480. [MS (Q1) 549.3 (M)+] following reverse phase purification and subsequent chiral separation from 13.9 mg of the enantiomer, 2-(1-((2-(2-((1S,2S)-2-fluorocyclopropyl)-1H-benzo[d]imidazol-1-yl)-9-methyl-6-morpholino-9H-purin-8-yl)methyl)piperidin-4-yl)propan-2-ol. MS (Q1) 549.3 (M)+

Example 481

(S)-2-(1-((2-(2-(2,2-difluorocyclopropyl)-1H-benzo[d]imidazol-1-yl)-9-methyl-6-morpholino-9H-purin-8-yl)methyl)piperidin-4-yl)propan-2-ol 481

2-(1-((2-Chloro-9-methyl-6-morpholino-9H-purin-8-yl)methyl)piperidin-4-yl)propan-2-ol (0.1 g) was reacted with 2,2-difluorocyclopropanecarboxylic acid via General Procedure J for two-step Buchwald coupling to give 8.8 mg of 481 [MS (Q1) 567.3 (M)+] following reverse phase purification and subsequent chiral separation from 8.8 mg of enantiomer 478. MS (Q1) 567.3 (M)+

Example 482

4-(5-(2-methyl-1H-benzo[d]imidazol-1-yl)-2-((3-(tetrahydro-2H-pyran-4-yl)azetidin-1-yl)methyl)thiazolo[5,4-d]pyrimidin-7-yl)morpholine 482

A mixture of 5-chloro-7-morpholin-4-yl-2-(3-morpholin-4-yl-azetidin-1-ylmethyl)-thiazolo[5,4-d]pyrimidine (100 mg, 0.24 mmol), 2-methylbenzimidazole (32 mg, 0.24 mmol), tris(dibenzylideneacetone)dipalladium (11 mg, 0.01 mmol), Xphos (12 mg, 0.02 mmol) and Cs$_2$CO$_3$ (159 mg, 0.48 mmol) in DMF (2 mL) was purged with argon then heated at 145° C. for 30 min in a microwave reactor. The reaction mixture was dissolved in EtOAc and washed with H$_2$O (×6), then dried (Na$_2$SO$_4$) and concentrated in vacuo. The resulting residue was purified by column chromatography (Si—PCC, MeOH:DCM, 0-5%) to afford 482 as an orange solid (47 mg, 39%). LCMS (Method I): R$_T$ 2.59 min, [M+H]$^+$ 507.2. $^1$H NMR (CDCl$_3$, 400 MHz): δ 8.09-8.04 (m, 1 H); 7.73-7.68 (m, 1 H); 7.29-7.24 (m, 2 H); 4.41 (m, 4 H); 4.02 (s, 2 H); 3.88 (t, J=4.7 Hz, 4 H); 3.71 (m, 6 H); 3.17 (m, 3 H); 2.92 (s, 3 H) and 2.37 (m, 4 H)

Example 483

4-(5-(2-ethyl-1H-benzo[d]imidazol-1-yl)-2-((3-(tetrahydro-2H-pyran-4-yl)azetidin-1-yl)methyl)thiazolo[5,4-d]pyrimidin-7-yl)morpholine 483

A mixture of 5-chloro-7-morpholin-4-yl-2-[3-(tetrahydro-pyran-4-yl)azetidin-1-ylmethyl]thiazolo[5,4-d]pyrimidine (90 mg, 0.22 mmol), 2-ethylbenzimidazole (38 mg, 0.26 mmol), tris(dibenzylideneacetone)dipalladium (10 mg, 0.01 mmol), Xphos (21 mg, 0.04 mmol) and Cs$_2$CO$_3$ (143 mg, 0.44 mmol) in dioxane (2 5 mL) was purged with argon then heated at 145° C. for 30 min in a microwave reactor. The reaction mixture was filtered through a pad of celite, washing with EtOAc. The filtrate was concentrated in vacuo and purified by column chromatography (Si—PCC, MeOH:EtOAc, 0-7%). The resulting residue was loaded onto an Isolute® SCX-2 cartridge which was washed with MeOH/DCM and the product eluted with 2M NH$_3$/MeOH affording 483 as an orange solid (82 mg, 72%). LCMS (Method I): R$_T$ 2.70 min, [M+H]$^+$ 520.2. $^1$H NMR (CDCl$_3$, 400 MHz): δ 8.02-7.97 (m, 1 H); 7.76-7.71 (m, 1 H); 7.30-7.24 (m, 2 H); 4.41 (m, 4 H); 4.04-3.94 (m, 4 H); 3.91-3.82 (m, 4 H); 3.61 (m, 2 H); 3.44-3.30 (m, 4 H); 3.10 (m, 2 H); 2.40-2.30 (m, 1 H); 1.70 (m, 1 H); 1.55 (m, 2 H); 1.43 (t, J=7.5 Hz, 3 H) and 1.32-1.18 (m, 2 H)

Example 484

4-(5-(2-cyclopropyl-1H-benzo[d]imidazol-1-yl)-2-((3-(tetrahydro-2H-pyran-4-yl)azetidin-1-yl)methyl)thiazolo[5,4-d]pyrimidin-7-yl)morpholine 484

A mixture of 5-chloro-7-morpholin-4-yl-2-[3-(tetrahydropyran-4-yl)azetidin-1-ylmethyl]thiazolo[5,4-d]pyrimidine (90 mg, 0.22 mmol), 2-cyclopropylbenzimidazole (42 mg, 0.26 mmol), tris(dibenzylideneacetone)dipalladium (10 mg, 0.01 mmol), Xphos (21 mg, 0.04 mmol) and Cs$_2$CO$_3$ (143 mg, 0.44 mmol) in dioxane (2.5 mL) was purged with argon then heated at 145° C. for 30 min in a microwave reactor. The reaction mixture was filtered through a pad of celite, washing with EtOAc. The filtrate was concentrated in vacuo and purified by column chromatography (Si—PCC, MeOH:EtOAc, 0-7%). The resulting residue was loaded onto an Isolute® SCX-2 cartridge which was washed with MeOH/DCM and the product eluted with 2M NH$_3$/MeOH affording 484 as an orange solid (83 mg, 71%). LCMS (Method I): R$_T$ 2.89 min, [M+H]$^+$ 532.2. $^1$H NMR (CDCl$_3$, 400 MHz): δ 7.94-7.89 (m, 1 H); 7.69-7.65 (m, 1 H); 7.26-7.20 (m, 2 H); 4.43 (m, 4 H); 3.99 (m, 4 H); 3.87 (m, 4 H); 3.61 (m, 2 H); 3.38 (m, 2 H); 3.10 (m, 2 H); 2.89-2.82 (m, 1 H); 2.36 (m, 1 H); 1.71 (m, 1 H); 1.56 (m, 2 H); 1.37-1.31 (m, 2 H); 1.30-1.18 (m, 2 H) and 1.10-1.04 (m, 2 H)

Example 485

2-(1-((2-(2-ethyl-4-fluoro-1H-benzo[d]imidazol-1-yl)-9-methyl-6-morpholino-9H-purin-8-yl)methyl)piperidin-4-yl)propan-2-ol 485

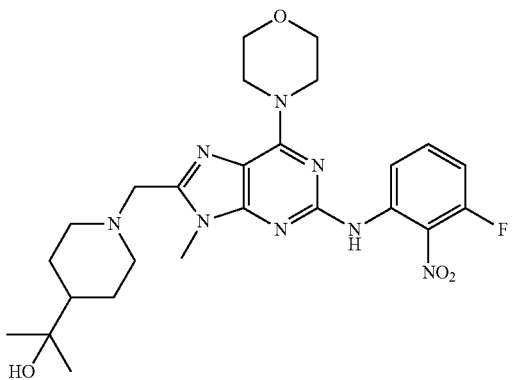

A microwave vial equipped with a magnetic follower was charged with Pd$_2$(dba)$_3$ (5.7 mg, 0.006 mmol), Xphos (11.9 mg, 0.025 mmol), 2-[1-(2-chloro-9-methyl-6-morpholin-4-yl-9H-purin-8-ylmethyl)-piperidin-4-yl]-propan-2-ol (102 mg, 0.25 mmol), 3-fluoro-2-nitro-phenylamine (47 mg, 0.30 mmol), cesium carbonate (114 mg, 0.35 mmol) and DMF (1 mL). The vial was capped, the reaction mixture was degassed for 5 min and irradiated at 150° C. for 30 min. The reaction mixture was diluted with MeOH and loaded onto an Isolute® SCX-2 cartridge (10 g). The cartridge was washed with MeOH and the desired product was eluted with 2M NH$_3$ in MeOH. The solvents were removed and the residue was subjected to flash chromatography (Si—PCC, 0-5% MeOH in EtOAc) to give 2-{1-[2-(3-fluoro-2-nitrophenylamino)-9-methyl-6-morpholin-4-yl-9H-purin-8-ylmethyl]piperidin-4-yl}propan-2-ol as a red oil (97 mg, 73%). LCMS (Method H): R$_T$ 0.27 min and 3.18 min; [M+H]$^+$ 529

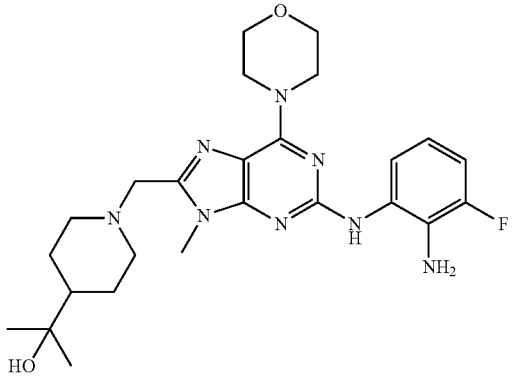

To a mixture of 2-{1-[2-(3-fluoro-2-nitrophenylamino)-9-methyl-6-morpholin-4-yl-9H-purin-8-ylmethyl]piperidin-4-yl}propan-2-ol (95 mg, 0.18 mmol) in IMS (5 mL) was added 10% Pd on charcoal (20 mg) under an argon atmosphere. The vessel was evacuated and backfilled with hydrogen (the process was repeated three times). The reaction mixture was stirred at room temperature for 18 hours then filtered through celite. The filtrate was concentrated under reduced pressure and the residue was subjected to flash chromatography (Si—PCC, 0-10% MeOH in EtOAc) to give 2-{1-[2-(2-Amino-3-fluoro-phenylamino)-9-methyl-6-morpholin-4-yl-9H-purin-8-ylmethyl]piperidin-4-yl}propan-2-ol as a red oil (65 mg, 72%). LCMS (Method H): R$_T$=0.28 min and 2.82 min, [M+H]$^-$ 499

To a solution of 2-{1-[2-(2-amino-3-fluorophenylamino)-9-methyl-6-morpholin-4-yl-9H-purin-8-ylmethyl]piperidin-4-yl}propan-2-ol (65 mg, 0.13 mmol), propionic acid (78 uL, 0.14 mmol) and DIPEA (49 uL, 0.29 mmol) in DMF (3 mL) was added HATU (59 mg, 0.16 mmol). The reaction mixture was stirred at room temperature for 18 hours. Propionic acid (78 uL, 0.14 mmol), DIPEA (49 uL, 0.29 mmol) and HATU (59 mg, 0.16 mmol) were added and the reaction mixture was stirred at room temperature for 2 days, then diluted with water and extracted with EtOAc. The organic layer was separated and washed with water, a saturated aqueous solution of sodium bicarbonate and brine, dried over $Na_2SO_4$, filtered and concentrated to give a red oil dissolved in acetic acid (2 mL) The mixture was stirred at 90° C. for 18 hours then concentrated under reduced pressure. The residue was azeotroped with toluene, then taken up in MeOH. The resulting solution was loaded onto an Isolute® SCX-2 cartridge (5 g). The cartridge was washed with MeOH and the desired product was eluted with 2M $NH_3$ in MeOH. The solvents were removed and the residue was subjected to flash chromatography (Si—PCC, 0-20% MeOH in EtOAc) to give 485 (36 mg, 52%). LCMS (Method I): $R_T$ 3.18 min; $[M+H]^+$ 537. $^1H$ NMR (400 MHz, $CHCl_3$-d): δ 7.78-7.75 (m, 1 H); 7.21-7.12 (m, 1 H); 6.97 (dd, J=10.3, 8.0 Hz, 1 H); 4.34 (m, 4 H); 3.90-3.84 (m, 7 H); 3.73 (s, 2 H); 3.35 (q, 7.5 Hz, 2 H); 2.97 (d, J=11.4 Hz, 2 H); 2.12 (m, 2 H); 1.77 (m, 2 H); 1.44 (t, J=7.5 Hz, 3 H); 1.44-1.28 (m, 4 H); 1.24-1.15 (m, 6 H)

Example 486

1-(1-((2-(2-ethyl-1H-benzo[d]imidazol-1-yl)-9-methyl-6-morpholino-9H-purin-8-yl)methyl)azetidin-3-yl)piperidin-4-ol 486

A mixture of 2-(2-ethylbenzoimidazol-1-yl)-9-methyl-6-morpholin-4-yl-9H-purine-8-carbaldehyde (0.167 g, 0.43 mmol), 1-azetidin-3-ylpiperidin-4-ol (0.1 g, 0.64 mmol) and 4 Å molecular sieves (0.8 g) in DCE (8 mL) was stirred for 6 h at room temperature. Sodium triacetoxyborohydride (0.272 g, 1.28 mmol) was added and the reaction mixture was stirred for 18 h at room temperature. The reaction mixture was filtered through Celite and the filtrate was concentrated in vacuo. The residue was purified by flash chromatography (Si—PPC, MEOH:DCM, gradient 0:100 to 5:95) to give 486 as a yellow solid (0.123 g, 55%). LCMS (Method I): $R_T$=2.31 min, $[M+H]^+$ 532.3. $^1H$ NMR (400 MHz, DMSO-d): δ 8.03-7.99 (m, 1 H); 7.65-7.61 (m, 1 H); 7.27-7.20 (m, 2 H); 4.54 (d, J=4.0 Hz, 1 H); 4.29-4.22 (m, 4 H); 3.86 (s, 2 H); 3.82-3.73 (m, 7 H); 3.42 (t, J=6.5 Hz, 2 H); 3.30-3.27 (m, 3 H); 3.27 (q, J=7.4 Hz, 2 H); 2.96 (t, J=6.5 Hz, 2 H); 2.89-2.86 (m, 1 H); 1.88-1.85 (m, 2 H); 1.71-1.68 (m, 2 H); 1.39-1.35 (m, 2 H); 1.33 (t, J=7.4 Hz, 3 H)

Example 491

4-(2-(2-ethyl-1H-benzo[d]imidazol-1-yl)-8-((3-(4-fluoropiperidin-1-yl)azetidin-1-yl)methyl)-9-methyl-9H-purin-6-yl)morpholine 491

A mixture of 2-(2-ethylbenzoimidazol-1-yl)-9-methyl-6-morpholin-4-yl-9H-purine-8-carbaldehyde (0.165 g, 0.42 mmol), 1-azetidin-3-yl-4-fluoropiperidine (0.1 g, 0.63 mmol) and 4 Å molecular sieves (0.8 g) in DCE (8 mL) was stirred for 18 h at room temperature. Sodium triacetoxyborohydride (0.179 g, 0.84 mmol) was added and the reaction mixture was stirred for 6 h at room temperature. The reaction mixture was filtered through Celite and the filtrate was concentrated in vacuo. The residue was purified by flash chromatography (Si—PPC, MEOH:DCM, gradient 0:100 to 10:90) to give 491 as a yellow solid (0.1 g, 45%). LCMS (Method I): $R_T$=2.52 min, $[M+H]^-$ 534.2. $^1H$ NMR (400 MHz, DMSO-d): δ 8.03-7.99 (m, 1 H); 7.64-7.61 (m, 1 H); 7.26-7.21 (m, 2 H); 4.81-4.52 (m, 1 H); 4.51-3.96 (m, 4 H); 3.86 (s, 2 H); 3.79-3.76 (m, 7 H); 3.43 (t, J=6.3 Hz, 2 H); 3.26 (q, J=7.4 Hz, 2 H); 2.97 (t, J=6.3 Hz, 2 H); 2.95-2.91 (m, 1 H); 2.37-2.33 (m, 2 H); 2.18-2.13 (m, 2 H); 1.90-1.75 (m, 2 H); 1.76-1.64 (m, 2 H); 1.33 (t, J=7.4 Hz, 3 H)

Example 492

4-(8-((3-(4,4-difluoropiperidin-1-yl)azetidin-1-yl)methyl)-2-(2-ethyl-1H-benzo[d]imidazol-1-yl)-9-methyl-9H-purin-6-yl)morpholine 492

A mixture of 2-(2-ethylbenzoimidazol-1-yl)-9-methyl-6-morpholin-4-yl-9H-purine-8-carbaldehyde (0.1 g, 0.26 mmol), 1-azetidin-3-yl-4,4-difluoropiperidine (0.087 g, 0.38 mmol) and 4A molecular sieves (0.6 g) in DCE (6 mL) was stirred for 18 h at room temperature. Sodium triacetoxyborohydride (0.109 g, 0.51 mmol) was added and the reaction mixture was stirred for 5 h at room temperature. The reaction mixture was filtered through Celite and the filtrate was concentrated in vacuo. The residue was purified by flash chromatography (Si—PPC, MEOH:DCM, gradient 0:100 to 3:97) to give 492 as a yellow solid (0.097 g, 69%). LCMS (Method I): $R_T$=2.82 min, $[M+H]^+$ 552.3. $^1H$ NMR (400 MHz, DMSO-d): δ 8.03-7.99 (m, 1 H); 7.65-7.61 (m, 1 H); 7.28-7.21 (m, 2 H); 4.30-4.23 (m, 4 H); 3.87 (s, 2 H); 3.80-3.75 (m, 7 H); 3.46-3.43 (m, 2 H); 3.25 (q, J=7.4 Hz, 2 H); 3.01-2.98 (m, 3 H); 2.37-2.33 (m, 4 H); 2.00-1.87 (m, 4 H); 1.33 (t, J=7.4 Hz, 3 H)

Example 493

4-(2-(2-(2-ethyl-1H-benzo[d]imidazol-1-yl)-9-methyl-6-morpholino-9H-purin-8-yl)ethyl)-1-isopropylpiperazin-2-one 493

A mixture of 4-[2-(2-chloro-9-methyl-6-morpholin-4-yl-9H-purin-8-yl)ethyl]-1-isopropylpiperazin-2-one (51 mg, 0.12 mmol), 2-ethylbenzimidazole (20 mg, 0.13 mmol), $Pd_2$(dba)$_3$ (2.8 mg, 2.5 mol %), Xphos (5.8 mg, 10 mol %) and $Cs_2CO_3$ (59 mg, 0.18 mmol) in dioxane (1 5 mL) was purged with argon gas then heated at 120° C., for 19 h, in a sealed tube. The reaction mixture was loaded onto an Isolute® SCX-2 cartridge, washed with MeOH then the desired product eluted with 2 M $NH_3$ in MeOH. The resulting residue was purified by flash chromatography (Si—PCC, 0-10% 2 M $NH_3$/MeOH in DCM) followed by reverse phase HPLC (Phenomenex Gemini 5 μm C18, 20 mM triethylamine in water on a gradient of acetonitrile 20-98%) to give 493 (28 mg, 44%) as an off white solid. LCMS: (Method I): $R_T$ 2.75 min; $[M+H]^+$ 532.3. $^1H$ NMR (400 MHz, $CHCl_3$-d): δ 8.01-7.96 (m, 1H), 7.80-7.76 (m, 1 H), 7.28 (m, 2 H), 4.91-4.82 (m, 1 H), 4.5-4.21 (m, 4 H), 3.87 (t, J=4.7 Hz, 4 H), 3.77 (s, 3 H), 3.37 (q, J=7.5 Hz, 2 H), 3.29 (s, 2 H), 3.26 (t, J=5.4 Hz, 2 H), 3.08-3.01 (m, 2 H), 3.00-2.93 (m, 2 H), 2.81 (t, J=5.4 Hz, 2 H), 1.45 (t, J=7.5 Hz, 3 H), 1.14 (d, J=6.9 Hz, 6 H)

Example 494

1'-((2-(2-ethyl-1H-benzo[d]imidazol-1-yl)-9-methyl-6-morpholino-9H-purin-8-yl)methyl)-1,3'-biazetidin-3-ol 494

A mixture of 2-(2-ethylbenzoimidazol-1-yl)-9-methyl-6-morpholin-4-yl-9H-purine-8-carbaldehyde (0.15 g, 0.38 mmol), [1,3']biazetidinyl-3-ol (0.098 g, 0.77 mmol) and 4 Å molecular sieves (0.8 g) in DCE (8 mL) was stirred for 4 h at room temperature. Sodium triacetoxyborohydride (0.162 g, 0.77 mmol) was added and the reaction mixture was stirred for 18 h at room temperature. The reaction mixture was filtered through Celite and the filtrate was concentrated in vacuo. The residue was purified by flash chromatography (Si—PPC, MEOH:DCM, gradient 0:100 to 20:80) to give 494 as an off-white solid (0.101 g, 53%). LCMS (Method I): $R_T$=2.31 min, [M+H]$^+$ 504.2. $^1$H NMR (400 MHz, DMSO-d): δ 8.03-7.98 (m, 1 H); 7.65-7.60 (m, 1 H); 7.28-7.22 (m, 2 H); 5.26 (d, J=6.8 Hz, 1 H); 4.28-4.21 (m, 4 H); 4.19-4.15 (m, 3 H); 3.83 (s, 2 H); 3.79-3.75 (m, 7 H); 3.47-3.35 (m, 2 H); 3.20 (q, J=7.4 Hz, 2 H); 3.02 (t, J=6.8 Hz, 2 H); 2.82 (t, J=6.8 Hz, 3 H); 1.36-1.29 (q, J=7.4 Hz, 3 H)

Example 495

4-(2-(2-ethyl-1H-benzo[d]imidazol-1-yl)-9-methyl-8-((4-(tetrahydro-2H-pyran-4-yl)piperazin-1-yl)methyl)-9H-purin-6-yl)morpholine 495

A solution of 2-(2-ethylbenzoimidazol-1-yl)-9-methyl-6-morpholin-4-yl-9H-purine-8-carbaldehyde (360 mg, 0.92 mmol), 1-(tetrahydropyran-4-yl)piperazine (250 mg, 1.47 mmol) and molecular sieves (4 Å, powdered, 1.5 g) in DCE (10 mL) was stirred at ambient temperature for 6 h. Sodium triacetoxyborohydride (530 mg, 2.50 mmol) was added and the mixture stirred for 18 h, then loaded onto an Isolute® SCX-2 cartridge (10 g). The cartridge was then washed with methanol and the desired product was subsequently eluted using 2 M NH$_3$ in MeOH. The product was collected and concentrated in vacuo. The resultant residue was purified by flash chromatography (Si—PPC, EtOAc: MeOH; gradient from 100:0 to 70:30) followed by reverse phase HPLC (Phenomenex Gemini 5u C18, 20 mM triethylamine in water on a gradient of acetonitrile 80:20 to 2:98) to afford 495 as a cream foam (439 mg, 87%). LCMS (Method I): $R_T$=2.50 min, M+H$^+$=546. $^1$H NMR (CDCl$_3$, 400 MHz) δ 8.01 (m, 1 H); 7.76 (m, 1 H); 7.27 (m, 2 H); 4.35 (m, 4 H); 4.03 (d, J=11.3 Hz, 2 H); 3.87 (m, 7 H); 3.78 (s, 2 H); 3.42-3.29 (m, 4 H); 2.64 (m, 8 H); 1.79 (m, 3 H); 1.62 (m, 2 H) and 1.45 (t, J=7.5 Hz, 3 H)

Example 496

4-(5-(2-ethyl-1H-benzo[d]imidazol-1-yl)-2-((4-(oxetan-3-yl)piperidin-1-yl)methyl)thiazole[5,4-d]pyrimidin-7-yl)morpholine 496

A mixture of 5-chloro-7-morpholin-4-yl-2-(4-oxetan-3-ylpiperidin-1-ylmethyl)thiazole[5,4-d]pyrimidine (200 mg, 0.49 mmol), 2-ethyl-1H-benzoimidazole (79 mg, 0.54 mmol), Pd$_2$dba$_3$ (12 mg, 0.013 mmol), Xphos (24 mg, 0.050 mmol) and cesium carbonate (240 mg, 0.74 mmol) in 1,4-dioxane (3 mL) was purged with argon gas then subjected to microwave irradiation at 145° C. for 30 min. The reaction mixture was loaded onto an Isolute® SCX-2 cartridge (10 g), which was washed with MeOH/DCM before the desired product was eluted with 2 M NH$_3$ in MeOH/DCM. The product was collected and concentrated in vacuo. The resultant residue was purified by flash chromatography (Si—PPC, DCM:MeOH 100:0 to 99:1 to 98:2) to afford 496 as a white solid (121 mg, 48%). LCMS (Method I): $R_T$=2.65 min, M+H$^+$= 520. $^1$H NMR (CDCl$_3$, 400 MHz) δ 8.02 (m, 1 H); 7.77 (m, 1 H); 7.30 (m, 2 H); 4.78 (dd, J=7.8, 6.1 Hz, 2 H); 4.47 (t, J=6.1 Hz, 2 H); 4.41 (m, 4H); 3.88 (m, 6 H); 3.36 (q, J=7.5 Hz, 2 H); 3.05 (m, 2 H); 2.84-2.76 (m, 1 H); 2.30 (m, 2H); 1.80-1.61 (m, 4 H); 1.44 (t, J=7.5 Hz, 3 H) and 1.28 (m, 1 H)

Example 497

4-(5-(2-cyclopropyl-1H-benzo[d]imidazol-1-yl)-2-((4-(oxetan-3-yl)piperidin-1-yl)methyl)thiazole[5,4-d]pyrimidin-7-yl)morpholine 497

A mixture of 5-chloro-7-morpholin-4-yl-2-(4-oxetan-3-ylpiperidin-1-ylmethyl)thiazole[5,4-d]pyrimidine (200 mg, 0.49 mmol), 2-cyclopropyl-1H-benzoimidazole (93 mg, 0.59 mmol), Pd$_2$dba$_3$ (12 mg, 0.013 mmol), Xphos (24 mg, 0.050 mmol) and cesium carbonate (240 mg, 0.74 mmol) in 1,4-dioxane (3 mL) was purged with argon gas then subjected to microwave irradiation at 145° C. for 30 min. The reaction mixture was loaded onto an Isolute® SCX-2 cartridge (10 g), washed with MeOH/DCM before the desired product was eluted with 2 M NH$_3$ in MeOH/DCM. The product was collected and concentrated in vacuo. The resultant residue was purified by flash chromatography (Si—PPC, DCM:MeOH 100:0 to 99:1) to afford 497 as a salmon coloured solid (118 mg, 45%). LCMS (Method I): $R_T$=2.83 min, M+H$^+$=532. $^1$H NMR (CDCl$_3$, 400 MHz) δ 7.92 (m, 1 H); 7.68 (m, 1 H); 7.27 (m, 2 H); 4.78 (dd, J=7.9, 6.0 Hz, 2 H); 4.52-4.39 (m, 6 H); 3.87 (m, 6 H); 3.04 (m, 2 H); 2.92-2.76 (m, 2 H); 2.29 (m, 2 H); 1.79-1.61 (m, 4 H); 1.43-1.18 (m, 3 H) and 1.11-1.05 (m, 2 H)

Example 498

N-methyl-1-(7-morpholino-2-((3-(tetrahydro-2H-pyran-4-yl)azetidin-1-yl)methyl)thiazolo[5,4-d]pyrimidin-5-yl)-1H-benzo[d]imidazol-2-amine 498

A mixture of 5-chloro-7-morpholin-4-yl-2-[3-(tetrahydro-pyran-4-yl)azetidin-1-ylmethyl]thiazole[5,4-d]pyrimidine (90 mg, 0.22 mmol), (1H-benzoimidazol-2-yl)methylamine (39 mg, 0.26 mmol), tris(dibenzylideneacetone)dipalladium (10 mg, 0.01 mmol), Xphos (21 mg, 0.04 mmol) and Cs$_2$CO$_3$ (143 mg, 0.44 mmol) in dioxane (2.5 mL) was purged with argon then heated at 145° C. for 30 min in a microwave reactor. The reaction mixture was filtered through a pad of celite, washing with EtOAc. The filtrate was concentrated in vacuo and purified by column chromatography (Si—PCC, MeOH:DCM, 0-10%). The resulting residue was loaded onto an Isolute® SCX-2 cartridge which was washed with MeOH/DCM and the product eluted with 2M NH$_3$/MeOH affording 498 as an orange solid (60 mg, 52%). LCMS (Method I): $R_T$ 2.43 min, [M+H]$^+$ 521.2. $^1$H NMR (CDCl$_3$, 400 MHz): δ 8.37 (d, J=5.0 Hz, 1 H); 8.19 (d, J=8.0 Hz, 1 H); 7.48 (d, J=7.8 Hz, 1 H); 7.19 (t, J=7.8 Hz, 1 H); 7.06 (t, J=8.0 Hz, 1 H); 4.41 (m, 4 H); 4.02-3.88 (m, 8 H); 3.58 (m, 2H); 3.38 (m, 2 H); 3.25 (d, J=5.0 Hz, 3 H); 3.09 (m, 2 H); 2.40-2.29 (m, 1 H); 1.71 (m, 1H); 1.56 (m, 2 H) and 1.30-1.17 (m, 2 H)

Example 499

4-(2-(2-cyclopropyl-1H-benzo[d]imidazol-1-yl)-9-methyl-8-((3-(tetrahydro-2H-pyran-4-yl)azetidin-1-yl)methyl)-9H-purin-6-yl)morpholine 499

A mixture of 2-(2-cyclopropylbenzoimidazol-1-yl)-9-methyl-6-morpholin-4-yl-9H-purine-8-carbaldehyde (100 mg, 0.25 mmol), 3-(tetrahydropyran-4-yl)azetidine (37 mg, 0.26 mmol) and 4 Å powdered molecular sieves (250 mg) in DCE (5 mL) was stirred at room temperature for 5 h before the addition of sodium triacetoxyborohydride (233 mg, 0.92 mmol). The reaction mixture was stirred for 16 h then filtered through celite, washing with DCM. The organic phase was washed with brine (×1) and concentrated in vacuo. The organic phase was dried ($Na_2SO_4$) and concentrated in vacuo. The resulting residue was purified by column chromatography (Si—PCC, MeOH:DCM, 0-10%). The resulting oil was loaded onto an Isolute® SCX-2 cartridge which was washed with MeOH/DCM and the product eluted with 2M $NH_3$/MeOH affording 499 as an orange solid (76 mg, 57%). LCMS (Method I): $R_T$ 2.72 min $[M+H]^+$ 529.3. $^1H$ NMR ($CDCl_3$, 400 MHz): δ 7.93 (d, J=7.6 Hz, 1H); 7.67 (d, J=7.4 Hz, 1 H); 7.27-7.18 (m, 2 H); 4.36 (m, 4 H); 4.00-3.93 (m, 2 H); 3.88-3.83 (m, 9 H); 3.55 (m, 2 H); 3.37 (m, 2 H); 3.06 (m, 2 H); 2.89-2.81 (m, 1 H); 2.34 (m, 1H); 1.71 (m, 1 H); 1.54 (m, 2 H); 1.38-1.32 (m, 2 H); 1.22 (m, 2 H) and 1.06 (m, 2 H)

Example 500 ethyl 2-(4-((2-(2-cyclopropyl-1H-benzo[d]imidazol-1-yl)-9-methyl-6-morpholino-9H-purin-8-yl)methyl)piperazin-1-yl)-2-methylpropanoate 500

Following General Procedure I for Buchwald coupling, 2-cyclopropylbenzimidazole and ethyl 2-(4-((2-chloro-9-methyl-6-morpholino-9H-purin-8-yl)methyl)piperazin-1-yl)-2-methylpropanoate were reacted to give 500. LCMS m/z: 588.4 (MH+)

Example 501

4-(2-(2-ethyl-1H-benzo[d]imidazol-1-yl)-9-methyl-8-((1-(tetrahydro-2H-(1,1-dioxo)-thiopyran-4-yl)azetidin-3-yl)methyl)-9H-purin-6-yl)morpholine 501

Following General Procedure L, 1,1-dioxo-tetrahydrothiopyran-4-one underwent reductive amination with 4-(8-(azetidin-3-ylmethyl)-2-(2-ethyl-1H-benzo[d]imidazol-1-yl)-9-methyl-9H-purin-6-yl)morpholine to give 501. LCMS m/z: 565.3 (MH+)

Example 502 ethyl 2-methyl-2-(4-((9-methyl-2-(2-methyl-1H-benzo[d]imidazol-1-yl)-6-morpholino-9H-purin-8-yl)methyl)piperazin-1-yl)propanoate 502

Following General Procedure C, 4-(9-methyl-2-(2-methyl-1H-benzo[d]imidazol-1-yl)-8-(piperazin-1-ylmethyl)-9H-purin-6-yl)morpholine was alkylated with ethyl 2-bromo-2-methyl-propionate to give 502. LCMS m/z: 281.7 (2M+H+)

Example 503

4-(2-(2-ethyl-1H-benzo[d]imidazol-1-yl)-9-methyl-8-((1-(tetrahydro-2H-pyran-4-yl)azetidin-3-yl)methyl)-9H-purin-6-yl)morpholine 503

Following General Procedure L, 2H-pyran-4(3H)-one underwent reductive amination with 4-(8-(azetidin-3-ylmethyl)-2-(2-ethyl-1H-benzo[d]imidazol-1-yl)-9-methyl-9H-purin-6-yl)morpholine to give 503. 517.3 (MH+)

Example 505 tert-butyl 4-((9-methyl-2-(2-methyl-1H-benzo[d]imidazol-1-yl)-6-morpholino-9H-purin-8-yl)methyl)piperidine-1-carboxylate 505

Following the procedures for 520, 505 was prepared. LCMS m/z: 547.3(MH+)

Example 506

2-methyl-2-(4-((9-methyl-2-(2-methyl-1H-benzo[d]imidazol-1-yl)-6-morpholino-9H-purin-8-yl)methyl)piperazin-1-yl)propanoic acid 506

A mixture of ethyl 2-methyl-2-(4-((9-methyl-2-(2-methyl-1H-benzo[d]imidazol-1-yl)-6-morpholino-9H-purin-8-yl)methyl)piperazin-1-yl)propanoate 507 (0.14 g, 0.25 mmol) in 2M LiOH (5.0 mL) and THF (8 mL) was stirred at reflux for 18 hours. The reaction was then cooled to room temperature and concentrated down to ⅓ of original volume. The residue was then loaded onto a SCX-2 column. The column was first washed with MeOH. The product was then eluted with 2M $NH_3$ in MeOH and then concentrated. The residue was purified by RP-HPLC to give 506. LCMS m/z: 534.3 (MH+)

Example 507 methyl 2-methyl-2-(4-((9-methyl-2-(2-methyl-1H-benzo[d]imidazol-1-yl)-6-morpholino-9H-purin-8-yl)methyl)piperidin-1-yl)propanoate 507

Following General Procedure C, 2-bromo-2-methyl-propionoic acid methyl ester and 4-(9-methyl-2-(2-methyl-1H-benzo[d]imidazol-1-yl)-8-(piperidin-4-ylmethyl)-9H-purin-6-yl)morpholine were reacted to give 507. LCMS m/z: 274.2 (2M+H)

Example 508

2-methyl-2-(4-((9-methyl-2-(2-methyl-1H-benzo[d]imidazol-1-yl)-6-morpholino-9H-purin-8-yl)methyl)piperidin-1-yl)propanamide 508

Following General Procedure C, 2-bromo-2-methyl-propionamide and 4-(9-methyl-2-(2-methyl-1H-benzo[d]imidazol-1-yl)-8-(piperidin-4-ylmethyl)-9H-purin-6-yl)morpholine were reacted to give 508. LCMS m/z: 532.2 (MH+)

Example 509

2-methyl-2-(4-((9-methyl-2-(2-methyl-1H-benzo[d]imidazol-1-yl)-6-morpholino-9H-purin-8-yl)methyl)piperidin-1-yl)propan-1-ol 509

To a solution of methyl 2-methyl-2-(4-((9-methyl-2-(2-methyl-1H-benzo[d]imidazol-1-yl)-6-morpholino-9H-purin-8-yl)methyl)piperidin-1-yl)propanoate 507 (0.10 g, 0.183 mmol) in THF (10 mL) was added a 1.0 M solution of lithium aluminum hydride in THF (0.18 mL, 0.18 mmol) at 0° C. The reaction was stirred at 0° C. for 1 hour. The reaction was then quenched by adding 2 mL of sat. NH$_4$Cl solution. The cloudy mixture was then loaded onto an ISOLUTE® SCX-2 column. The column was first washed with MeOH prior to eluting the product by adding 2M NH$_3$ in MeOH. The crude product was then concentrated and purified by RP-HPLC to give 509. LCMS m/z: 519.3 (MH+)

Example 510

4-(8-((4-tert-butylpiperazin-1-yl)methyl)-9-methyl-6-morpholino-9H-purin-2-yl)isoquinolin-1-amine 510

Following General Procedure A for Suzuki coupling, 4-(8-((4-tert-butylpiperazin-1-yl)methyl)-2-chloro-9-methyl-9H-purin-6-yl)morpholine and 4-(4,4,5,5-tetramethyl-1,3,2-dioxaborolan-2-yl)isoquinolin-1-amine were reacted to give 510. LCMS: M+H $^+$=519.3

Example 511

8-(2-(2-(2-ethyl-1H-benzo[d]imidazol-1-yl)-9-methyl-6-morpholino-9H-purin-8-yl)ethyl)-3-oxa-8-azabicyclo[3.2.1]octane 511

A mixture of 2-chloro-9-methyl-6-morpholin-4-yl-8-[2-(3-oxa-8-aza-bicyclo[3.2.1]oct-8-yl)ethyl]-9H-purine (75 mg, 0.19 mmol), 2-ethylbenzimidazole (31 mg, 0.21 mmol), Pd$_2$(dba)$_3$ (4.4 mg, 2.5 mol %), Xphos (9.1 mg, 10 mol %) and Cs$_2$CO$_3$ (93 mg, 0.29 mmol) in dioxane (2.0 mL) was purged with argon gas then heated at 120° C., for 18 h, in a sealed tube. The reaction mixture was loaded onto an Isolute® SCX-2 cartridge, washed with MeOH then the desired product eluted with 2 M NH$_3$/MeOH in DCM. The resulting residue was purified by reverse phase HPLC (Phenomenex Gemini 5 μm C18, 20 mM triethylamine in water on a gradient of acetonitrile 30-90%) to give 511 (50 mg, 52%) as an off white solid. LCMS: (Method I): R$_T$ 2.49 min; [M+H]$^+$ 503.2. $^1$H NMR (400 MHz, CHCl$_3$-d): δ 8.02-7.97 (m, 1 H), 7.77-7.73 (m, 1 H), 7.29-7.22 (m, 2 H), 4.52-4.20 (m, 4 H), 3.86 (t, J=4.7 Hz, 4 H), 3.82 (s, 3 H), 3.79-3.65 (m, 2 H), 3.58-3.50 (m, 2 H), 3.35 (q, J=7.5 Hz, 2 H), 3.18-3.09 (m, 2 H), 3.09-2.99 (m, 2 H), 2.90-2.76 (m, 2 H), 2.07-1.88 (m, 4 H), 1.44 (t, J=7.5 Hz, 3 H)

Example 512

2-(1-(9-methyl-6-morpholino-8-((4-(oxetan-3-yl)piperidin-1-yl)methyl)-9H-purin-2-yl)-1H-benzo[d]imidazol-2-yl)ethanol 512

A solution of 2-[2-(2-hydroxyethyl)benzoimidazol-1-yl]-9-methyl-6-morpholin-4-yl-9H-purine-8-carbaldehyde (200 mg, 0.49 mmol), 4-oxetan-3-ylpiperidine (83 mg, 0.59 mmol) and molecular sieves (4 Å, powdered, 1 g) in DCE (5 mL) was stirred at ambient temperature for 5 h. Sodium triacetoxyborohydride (156 mg, 0.74 mmol) was added and the mixture stirred for 18 h, then loaded onto an Isolute® SCX-2 cartridge (10 g). The cartridge was then washed with methanol and the desired product was subsequently eluted using 2 M NH$_3$ in MeOH. The product was collected and concentrated in vacuo. The resultant residue was purified by flash chromatography (Si—PPC, DCM:MeOH; 100:0 to 99:1 to 98:2 to 97:3 to 95:5) to afford 512 as a white solid (51 mg, 20%). LCMS (Method I): R$_T$=2.39 min, M+H$^+$=533. $^1$H NMR (CDCl$_3$, 400 MHz) δ 8.04 (m, 1 H); 7.75 (m, 1 H); 7.33 (m, 2 H); 4.76 (dd, J=7.8, 6.0 Hz, 2 H); 4.45 (t, J=6.0 Hz, 2 H); 4.35 (m, 4 H); 4.19 (t, J=5.5 Hz, 2 H); 3.94-3.80 (m, 9 H); 3.54 (t, J=5.5 Hz, 2 H); 3.02 (m, 2 H); 2.81-2.72 (m, 1 H); 2.29 (m, 2 H); 1.71 (m, 5 H) and 1.28 (m, 1 H)

Example 513

4-(2-(2-ethyl-1H-benzo[d]imidazol-1-yl)-9-methyl-8-((4-(oxetan-3-yl)piperazin-1-yl)methyl)-9H-purin-6-yl)morpholine 513

TFA (2 mL) was added to a solution of 4-oxetan-3-ylpiperazine-1-carboxylic acid tert-butyl ester (150 mg, 0.62 mmol) in DCM (10 mL) and the mixture was stirred at ambient temperature for 30 min, then loaded onto an Isolute® SCX-2 cartridge (10 g). The cartridge was then washed with methanol and the desired product was subsequently eluted using 2 M NH$_3$ in MeOH. The product was collected and concentrated in vacuo to give 1-oxetan-3-ylpiperazine as a colourless oil. A solution of 2-(2-ethylbenzoimidazol-1-yl)-9-methyl-6-morpholin-4-yl-9H-purine-8-carbaldehyde (200 mg, 0.51 mmol), 1-oxetan-3-ylpiperazine (88 mg, 0.62 mmol) and molecular sieves (4 Å, powdered, 1 g) in DCE (10 mL) was stirred at ambient temperature for 5 h. Sodium triacetoxyborohydride (162 mg, 0.76 mmol) was added and the mixture stirred for 18 h, then loaded onto an Isolute® SCX-2 cartridge (10 g). The cartridge was then washed with methanol and the desired product was subsequently eluted using 2 M NH$_3$ in MeOH. The product was collected and concentrated in vacuo. The resultant residue was purified by flash chromatography (Si—PPC, DCM:MeOH; 100:0 to 99:1 to 98:2 to 95:5) to afford 513 as a white solid (98 mg, 37%). LCMS (Method I): R$_T$=2.43 min, M+H$^+$=518. $^1$H NMR (CDCl$_3$, 400 MHz) δ 8.01 (dd, J=6.9, 2.4 Hz, 1 H); 7.78 (m, 1 H); 7.33-7.23 (m, 2 H); 4.70-4.60 (m, 4 H); 4.35 (m, 4 H); 3.97-3.75 (m, 7 H); 3.79 (s, 2 H); 3.57-3.49 (m, 1 H); 3.37 (q, J=7.5 Hz, 2 H); 2.66 (m, 4 H); 2.42 (m, 4 H); 1.46 (t, J=7.5 Hz, 3 H)

Example 514

4-(4-((2-(2-ethyl-1H-benzo[d]imidazol-1-yl)-9-methyl-6-morpholino-9H-purin-8-yl)methyl)azetidin-3-yl)piperazin-2-one 514

A mixture of 2-(2-ethylbenzoimidazol-1-yl)-9-methyl-6-morpholin-4-yl-9H-purine-8-carbaldehyde (100 mg, 0.26 mmol), 4-azetidin-3-ylpiperazin-2-one (44 mg, 0.28 mmol) and 4 Å powdered molecular sieves (250 mg) in MeOH (2 mL) and DCE (5 mL) was stirred at room temperature for 2 h before the addition of sodium triacetoxyborohydride (108 mg, 0.51 mmol). The reaction mixture was stirred for 16 h then filtered through celite, washing with DCM. The organic phase was washed with brine (×1) and concentrated in vacuo. The organic phase was dried (Na$_2$SO$_4$) and concentrated in vacuo. The resulting residue was purified by column chromatography (Si—PCC, MeOH:DCM, 0-7%). The resulting oil was loaded onto an Isolute® SCX-2 cartridge which was washed with MeOH/DCM and the product eluted with 2M NH$_3$/MeOH affording 514 as a yellow foam (42 mg, 31%). LCMS (Method I): R$_T$ 2.28 min [M+H]$^+$ 531.2. $^1$H NMR (CDCl$_3$, 400 MHz): δ 8.02-7.97 (m, 1 H); 7.79-7.74 (m, 1 H); 7.31-7.24 (m, 2 H); 5.93 (bs, 1 H); 4.35 (m, 4 H); 3.94 (s, 2 H);

3.94-3.80 (m, 7 H); 3.66 (bs, 2 H); 3.43-3.33 (m, 4 H); 3.21 (s, 3 H); 3.06 (s, 2 H); 2.58 (t, J=5.37 Hz, 2 H) and 1.45 (t, J=7.5 Hz, 3 H)

Example 515

(S)-3-(2-(2-ethyl-1H-benzo[d]imidazol-1-yl)-9-methyl-6-morpholino-9H-purin-8-yl)-1-isopropylpiperidin-3-ol 515

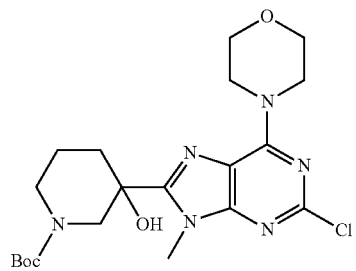

To a stirred solution of 4-(2-chloro-9-methyl-9H-purin-6-yl)morpholine (5.0 g) and N,N,N',N'-tetramethylethylenediamine (4.46 mL) in tetrahydrofuran (80 mL) at −78° C. was added 2.5 M of n-Butyllithium in THF (17 mL). The solution was stirred at −78° C. for 15 mins then the temp was raised to −40° C. until the solution became clear and dark red (indicating full lithiation). The solution was lowered back to −78° C. and tert-butyl 3-oxopiperidine-1-carboxylate (8.64 g) in 10 mL THF was added slowly over 5 minutes and stirred for 1.5 hrs then quenched with water. The reaction mixture was diluted with ethyl acetate and extracted with a saturated ammonium chloride solution. The organic layer was dried, filtered and concentrated. Any remaining starting material was removed by trituration with hot ether to afford the crude product tert-butyl 3-(2-chloro-9-methyl-6-morpholino-9H-purin-8-yl)-3-hydroxypiperidine-1-carboxylate as an orange oil in quantitative yield.

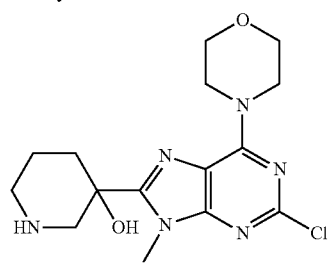

tert-Butyl 3-(2-chloro-9-methyl-6-morpholino-9H-purin-8-yl)-3-hydroxypiperidine-1-carboxylate (80 mg) was brought up into 1.25 M Hydrogen Chloride in ethanol and heated at 50° C. for several hours until reaction was complete. The reaction mixture was concentrated to dryness to afford 70 mg of the HCl salt of 3-(2-chloro-9-methyl-6-morpholino-9H-purin-8-yl)piperidin-3-ol.

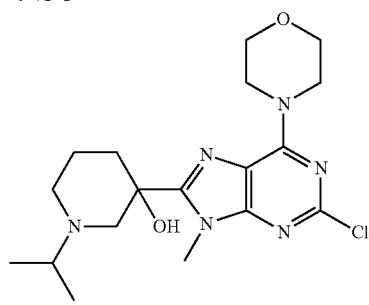

The HCl salt of 3-(2-chloro-9-methyl-6-morpholino-9H-purin-8-yl)piperidin-3-ol (70 mg) was reacted with isopropyl iodide (1.5 eq), cesium carbonate (2 eq) and DIPEA (3 eq) in DMF (1 mL). The reaction was heated at 50° C. for several hours until complete. The reaction mixture was diluted with Ethyl acetate and extracted with a saturated ammonium chloride solution. The organic layer was dried, filtered and concentrated to give 70 mg of crude 3-(2-chloro-9-methyl-6-morpholino-9H-purin-8-yl)-1-isopropylpiperidin-3-ol which was reacted with 2-ethyl benzimidazole via General Procedure I for Buchwald coupling to give 515 [7.6 mg; MS (Q1) 505.3 (M)+] and 518 [7.7 mg; MS (Q1) 505.2 (M)+] following reverse phase purification and subsequent chiral separation.

Example 516

(S)-2-(1-((2-(2-(1-methoxyethyl)-1H-benzo[d]imidazol-1-yl)-9-methyl-6-morpholino-9H-purin-8-yl)methyl)piperidin-4-yl)propan-2-ol 516

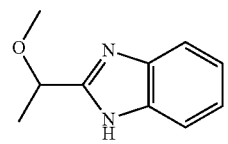

2-(1-chloroethyl)-1H-benzo[d]imidazole (0.39 g) and 25 wt % solution of Sodium Methoxide in Methanol (0.96 mL) in 10 mL of Methanol was heated for 20 minutes at 150° C. in a microwave synthesizer. The reaction mixture was extrated with EtOAc and sat NH4 chloride. The organic layer was dried, filtered and concentrated to afford crude 2-(1-methoxyethyl)-1H-benzo[d]imidazole in quantitative yield.

2-(1-((2-chloro-9-methyl-6-morpholino-9H-purin-8-yl)methyl)piperidin-4-yl)propan-2-ol (0.15 g) was reacted with 2-(1-methoxyethyl)-1H-benzo[d]imidazole (97 mg) via General Procedure I for Buchwald coupling to give 32.1 mg of 516 [MS (Q1) 549.4 (M)+] and 32.4 mg of 519 [MS (Q1) 549.3 (M)+] following reverse phase purification and subsequent chiral separation.

Example 517

N-(1-(8-((4-(2-hydroxypropan-2-yl)piperidin-1-yl)methyl)-9-methyl-6-morpholino-9H-purin-2-yl)-1H-benzo[d]imidazol-2-yl)acetamide 517

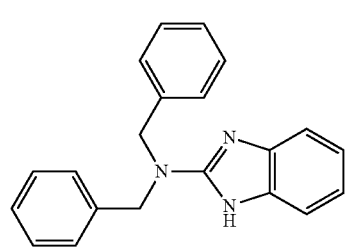

2-Chloro-1H-benzo[d]imidazole (1 g) was added to a neat solution of dibenzylamine (7 mL) and heated to 170° C. for 1.5 hours in a Biotage microwave synthesizer. The reaction mixture was concentrated to dryness and purified via flash column chromatography to afford 0.6 g of N,N-dibenzyl-1H-benzo[d]imidazol-2-amine.

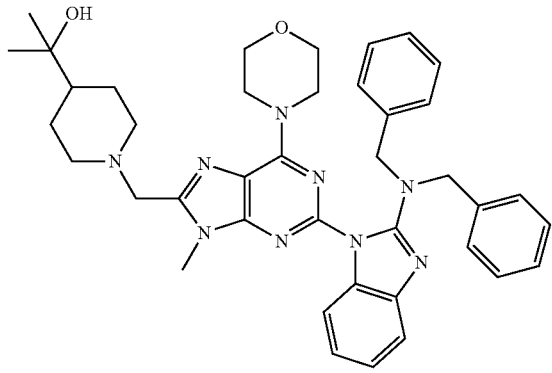

2-(1-((2-Chloro-9-methyl-6-morpholino-9H-purin-8-yl)methyl)piperidin-4-yl)propan-2-ol (0.35 g) was reacted with N,N-dibenzyl-1H-benzo[d]imidazol-2-amine.via General Procedure J for Buchwald coupling to give 255 mg of 2-(1-((2-(2-(dibenzylamino)-1H-benzo[d]imidazol-1-yl)-9-methyl-6-morpholino-9H-purin-8-yl)methyl)piperidin-4-yl)propan-2-ol following flash chromatography.

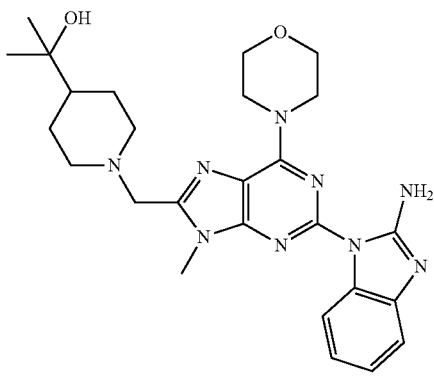

To a flask of 2-(1-((2-(2-(dibenzylamino)-1H-benzo[d]imidazol-1-yl)-9-methyl-6-morpholino-9H-purin-8-yl)methyl)piperidin-4-yl)propan-2-ol (125 mg) in Ethanol (5.4 mL) was added 10% Palladium on Carbon (0.2 g) and Acetic acid (83 uL). The flask was purged with a nitrogen balloon and then placed under a Hydrogen balloon. The reaction was heated at 70° C. for 48 hours. The reaction was filtered thru celite and the celite cake was rinsed with a mixture of 1% acetic acid in methanol several times. The solvent was concentrated to dryness to give 70 mg of crude 2-(1-((2-(2-amino-1H-benzo[d]imidazol-1-yl)-9-methyl-6-morpholino-9H-purin-8-yl)methyl)piperidin-4-yl)propan-2-ol, 70 mg of which was added to HATU (105 mg), DIPEA (0.12 mL) and acetic acid (24 uL) in DMF (0.8 mL). Upon completion, the reaction was diluted with Ethyl acetate and extracted with water. The organic layer was dried, filtered and concentrated to give crude product. The crude was purified via reverse phase HPLC to afford 11.5 mg of 517 as a white solid. MS (Q1) 548.3 (M)+

Example 518

I-3-(2-(2-ethyl-1H-benzo[d]imidazol-1-yl)-9-methyl-6-morpholino-9H-purin-8-yl)-1-isopropylpiperidin-3-ol 518

The HCl salt of 3-(2-chloro-9-methyl-6-morpholino-9H-purin-8-yl)piperidin-3-ol (70 mg) was reacted with isopropyl iodide (1.5 eq), cesium carbonate (2 eq) and DIPEA (3 eq) in DMF (1 mL). The reaction was heated at 50° C. for several hours until complete. The reaction mixture was diluted with Ethyl acetate and extracted with a saturated ammonium chloride solution. The organic layer was dried, filtered and concentrated to give 70 mg of crude 3-(2-chloro-9-methyl-6-morpholino-9H-purin-8-yl)-1-isopropylpiperidin-3-ol which was reacted with 2-ethyl benzimidazole via General Procedure I for Buchwald coupling to give 515 [7.6 mg; MS (Q1) 505.3 (M)+] and 518 [7.7 mg; MS (Q1) 505.2 (M)+] following reverse phase purification and subsequent chiral separation.

Example 519

I-2-(1-((2-(2-(1-methoxyethyl)-1H-benzo[d]imidazol-1-yl)-9-methyl-6-morpholino-9H-purin-8-yl)methyl)piperidin-4-yl)propan-2-ol 519

2-(1-((2-chloro-9-methyl-6-morpholino-9H-purin-8-yl)methyl)piperidin-4-yl)propan-2-ol (0.15 g) was reacted with 2-(1-methoxyethyl)-1H-benzo[d]imidazole (97 mg) via General Procedure I for Buchwald coupling to give 32.1 mg of 516 [MS (Q1) 549.4 (M)+] and 32.4 mg of 519 [MS (Q1) 549.3 (M)+] following reverse phase purification and subsequent chiral separation.

Example 520

4-(9-methyl-2-(2-methyl-1H-benzo[d]imidazol-1-yl)-8-(piperidin-4-ylmethyl)-9H-purin-6-yl)morpholine 520

Step 1 dimethyl (2-chloro-9-methyl-6-morpholino-9H-purin-8-yl)methylphosphonate

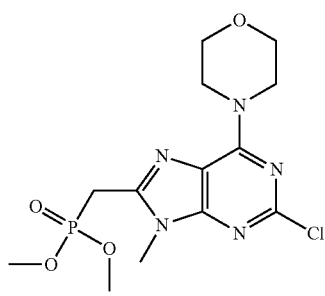

A mixture of 4-(8-(bromomethyl)-2-chloro-9-methyl-9H-purin-6-yl)morpholine (0.25 g, 0.72 mmol) and trimethylphosphite (4.0 mL, 34 mmol) was stirred at 120 degree for 1.25 hours. The resulting suspension was partitioned between water and dichloromethane. The aqueous layer was neutralized and extracted again with dichloromethane. The organic extracts were washed with water, dried over MgSO$_4$, filtered and concentrated. The crude product was purified by flash chromatography (0-5% methanol in DCM) to give the title compound (207 mg, 76%).

Step 2: tert-butyl 4-((2-chloro-9-methyl-6-morpholino-9H-purin-8-yl)methylene)piperidine-1-carboxylate

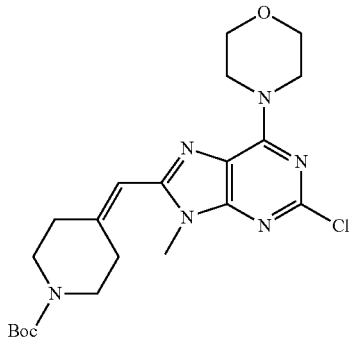

To a cold (−78° C.) suspension of dimethyl (2-chloro-9-methyl-6-morpholino-9H-purin-8-yl)methylphosphonate (0.35 g, 0.93 mmol) in THF (8.0 mL) was added a 2.0M solution of LDA in THF (0.49 mL) The resulting solution was allowed to warm to room temperature before the addition of a solution of 1-Boc-4-piperidone (0.19 g, 0.95 mmol) in THF (3 mL). The reaction mixture was then stirred at room temperature for 2 hours, and partitioned between brine and DCM. The organic layer was isolated, washed with brine, dried over $MgSO_4$ and concentrated. The crude residue was then purified by flash chromatrography (0-75% EtOAc in heptane) to give the title compound (0.38 g, 91%). LCMS m/z: 449.2 (MH+).

Step 3: tert-butyl 4-((9-methyl-2-(2-methyl-1H-benzo[d]imidazol-1-yl)-6-morpholino-9H-purin-8-yl)methylene)piperidine-1-carboxylate

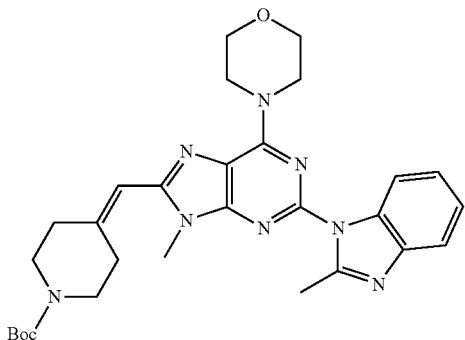

A mixture of tert-butyl 4-((2-chloro-9-methyl-6-morpholino-9H-purin-8-yl)methylene)piperidine-1-carboxylate (0.375 g, 0.835 mmol), 2-methylbenzimidazole (0.132 g, 1.0 mmol), Xphos (0.040 g, 0.084 mmol), $Pd_2(dba)_3$ (0.040 g, 0.042 mmol) and cesium carbonate (0.54 g, 1.67 mmol) in DMF (3 5 mL) was heated in a Biotage microwave at 140° C. for 30 minutes. The reaction mixture was then filtered through paper and then partitioned between brine and EtOAc. The combined extracts were washed with brine, dried over Na2SO4, filtered and concentrated. The crude product was purified by flash chromatography (0-10% MeOH in DCM) to give the title compound (0.39 g, 87%). LCMS m/z: 545.3 (MH+).

Step 4: tert-butyl 4-((9-methyl-2-(2-methyl-1H-benzo[d]imidazol-1-yl)-6-morpholino-9H-purin-8-yl)methyl)piperidine-1-carboxylate

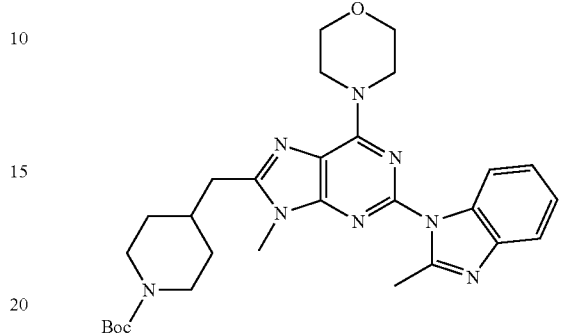

A suspension of tert-butyl 4-((9-methyl-2-(2-methyl-1H-benzo[d]imidazol-1-yl)-6-morpholino-9H-purin-8-yl)methylene)piperidine-1-carboxylate (0.39 g, 0.729 mmol) and Pd/C (10 wt %, 0.1 g) in ethanol (15 mL) was stirred under a hydrogen atmosphere (balloon) at room temperature for 18 hours. The reaction mixture was then filtered through celite and concentrated. The crude product was purified by flash chromatography (0-5% MeOH in DCM) to give the title compound (0.36 g, 90%). LCMS m/z: 547.2 (MH+)

Step 5: To a solution of tert-butyl 4-((9-methyl-2-(2-methyl-1H-benzo[d]imidazol-1-yl)-6-morpholino-9H-purin-8-yl)methyl)piperidine-1-carboxylate (0.36 g, 0.66 mmol) in 1,4-dioxane (10 mL) was added a 4M solution of hydrogen chloride in 1,4-dioxane. The reaction mixture was then stirred at room temperature for 1 hour. The resulting suspension was then filtered. The collected solid was washed 1,4-dioxane and dried under vacuum to give 520 (hydrochloride salt) as an off-white solid (0.34 g, quant.). LCMS m/z: 484.2 (MH+)

Example 521

2-((1S,4S)-5-((2-(2-ethyl-1H-benzo[d]imidazol-1-yl)-9-methyl-6-morpholino-9H-purin-8-yl)methyl)-2,5-diazabicyclo[2.2.1]heptan-2-yl)-2-methylpropan-1-ol 521

A mixture of 2-[(1S,4S)-5-(2-chloro-9-methyl-6-morpholin-4-yl-9H-purin-8-ylmethyl)-2,5-diazabicyclo[2.2.1]hept-2-yl]-2-methylpropan-1-ol (50 mg, 0.12 mmol), 2-ethyl-1H-benzoimidazole (20 mg, 0.14 mmol), $Pd_2dba_3$ (3 mg, 0.003 mmol), Xphos (6 mg, 0.012 mmol) and cesium carbonate (56 mg, 0.17 mmol) in DMF (1 mL) was purged with argon gas then subjected to microwave irradiation at 150° C. for 1 h. The reaction mixture was loaded onto an Isolute® SCX-2 cartridge (10 g), which was washed with MeOH/DCM before the desired product was eluted with 2 M $NH_3$ in MeOH/DCM. The product was collected and concentrated in vacuo. The resultant residue was purified by flash chromatography (Si—PPC, DCM:MeOH 100:0 to 95:5 to 90:10 to 80:20) to afford 521 as a tan solid (27 mg, 44%). LCMS (Method I): $R_T$=2.50 min, M+H+=546. $^1$H NMR ($CDCl_3$, 400 MHz) δ 8.01 (m, 1 H); 7.75 (m, 1 H); 7.28 (m, 2 H); 4.34 (m, 4 H); 4.02 (m, 2 H); 3.93-3.79 (m, 7 H); 3.49 (m, 2 H); 3.45-3.27 (m, 3 H); 2.89 (m, 2 H); 1.85 (s, 2 H); 1.64 (m, 3 H); 1.48-1.42 (m, 3 H) and 1.33-1.08 (m, 6 H)

Example 522

4-(2-(2-(2-ethyl-1H-benzo[d]imidazol-1-yl)-9-methyl-6-morpholino-9H-purin-8-yl)ethyl)-6-isopropylpiperazin-2-one 522

A mixture of 4-[2-(2-chloro-9-methyl-6-morpholin-4-yl-9H-purin-8-yl)ethyl]-6-isopropylpiperazin-2-one (90 mg, 0.21 mmol), 2-ethylbenzimidazole (35 mg, 0.24 mmol), Pd$_2$(dba)$_3$ (4.9 mg, 2.5 mol %), Xphos (10.2 mg, 10 mol %) and Cs$_2$CO$_3$ (104 mg, 0.32 mmol) in dioxane (2.0 mL) was purged with argon gas then heated at 120° C., for 19 h, in a sealed tube. The reaction mixture was loaded onto an Isolute® SCX-2 cartridge, washed with MeOH then the desired product eluted with 2 M NH$_3$/MeOH in DCM. The resulting residue was purified by reverse phase HPLC (Phenomenex Gemini 5 µm C18, 20 mM triethylamine in water on a gradient of acetonitrile 20-90%) to give 522 (50 mg, 44%) as a pale beige solid. LCMS: (Method I): R$_T$ 2.90 min; [M+H]$^+$ 532.3. $^1$H NMR (400 MHz, CHCl$_3$-d): δ 8.01-7.96 (m, 1 H), 7.84-7.78 (m, 1 H), 7.32-7.28 (m, 2 H), 5.82 (s, 1 H), 4.62-4.07 (m, 4 H), 3.86 (t, J=4.7 Hz, 4 H), 3.78 (s, 3 H), 3.47-3.23 (m, 4 H), 3.08-2.99 (m, 4 H), 3.01-2.93 (m, 2 H), 2.40 (dd, J=11.7, 8.9 Hz, 1 H), 1.79-1.67 (m, 1 H), 1.47 (t, J=7.5 Hz, 3 H), 0.98 (d, J=6.8 Hz, 3 H), 0.95 (d, J=6.88 Hz, 3 H)

Example 524

1-((2-(2-ethyl-1H-benzo[d]imidazol-1-yl)-9-methyl-6-morpholino-9H-purin-8-yl)methyl)azetidin-3-ol 524

Following General Procedure I for Buchwald coupling, 2-ethylbenzimidazole and 1-((2-chloro-9-methyl-6-morpholino-9H-purin-8-yl)methyl)azetidin-3-ol were reacted to give 524. LCMS m/z: 449.2 (MH+)

Example 525

2-methyl-2-(4-((9-methyl-2-(2-methyl-1H-benzo[d]imidazol-1-yl)-6-morpholino-9H-purin-8-yl)methyl)piperidin-1-yl)propanoic acid 525

Following the procedure for 506, the methyl ester of methyl 2-methyl-2-(4-((9-methyl-2-(2-methyl-1H-benzo[d]imidazol-1-yl)-6-morpholino-9H-purin-8-yl)methyl)piperidin-1-yl)propanoate 507 was hydrolyzed with lithium hydroxide to give 525. LCMS m/z: 267.2 (2M+H+)

Example 526

I-methyl 2-(4-((2-(2-ethyl-1H-benzo[d]imidazol-1-yl)-9-methyl-6-morpholino-9H-purin-8-yl)(hydroxy)methyl)piperidin-1-yl)-2-methylpropanoate 526

Step 1: tert-butyl 4-((2-chloro-9-methyl-6-morpholino-9H-purin-8-yl)(hydroxy)methyl)piperidine-1-carboxylate

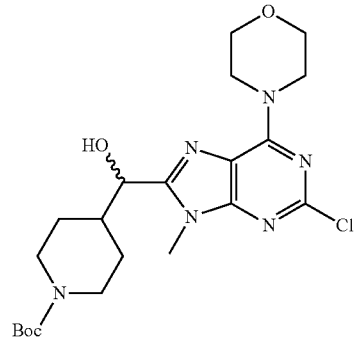

To a solution of 4-(2-chloro-9-methyl-9H-purin-6-yl)morpholine (750 mg, 3.0 mmol) and N,N,N',N'-Tetramethylethylenediamine (0.9816 mL, 6.504 mmol) in tetrahydrofuran (38 mL, 460 mmol) was added 1.6 M of n-butyllithium in hexane (4.065 mL) at −78° C. The resulting orange cloudy mixture was stirred at −78° C. for 45 minutes and at −40° C. for 5 minutes. Tert-butyl 4-formylpiperidine-1-carboxylate (1.261 g, 5.913 mmol) in 2 mL of THF was then added. The resulting yellow mixture was stirred at −78° C. for 1 hour. The reaction was then allowed to warm to room temperature. The reaction was then stirred at room temperature for 20 minutes. The reaction was then poured onto sat. NH$_4$Cl. the product was extracted with EtOAc. The combined extracts were washed with brine, dried over Na2SO4, filtered and concentrated. The crude product was purified by FCC (0-10% MeOH in DCM) to give the title compound as a white foam. LCMS m/z 467.3 (MH+).

Step 2: tert-butyl 4-((2-(2-ethyl-1H-benzo[d]imidazol-1-yl)-9-methyl-6-morpholino-9H-purin-8-yl)(hydroxy)methyl)piperidine-1-carboxylate

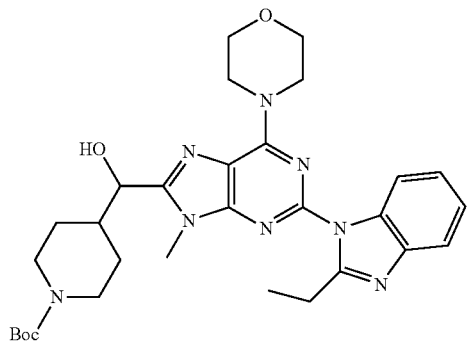

A mixture of tert-butyl 4-((2-chloro-9-methyl-6-morpholino-9H-purin-8-yl)(hydroxy)methyl)piperidine-1-carboxylate (0.375 g, 0.803 mmol), 2-ethylbenzimidazole (0.182 g, 1.23 mmol), Xphos (0.040 g, 0.084 mmol), Pd$_2$(dba)$_3$ (0.040 g, 0.042 mmol) and cesium carbonate (0.52 g, 1.67 mmol) in DMF (4.0 mL) was heated in a Biotage microwave at 140° C. for 30 minutes. The reaction mixture was then filtered through paper and then partitioned between brine and EtOAc. The combined extracts were washed with brine, dried over Na2SO4, filtered and concentrated. The crude product was purified by flash chromatography (0-5% MeOH in DCM) to give the title compound (0.32 g, 69%). LCMS m/z: 577.2 (MH+).

Step 3: (2-(2-ethyl-1H-benzo[d]imidazol-1-yl)-9-methyl-6-morpholino-9H-purin-8-yl)(piperidin-4-yl)methanol

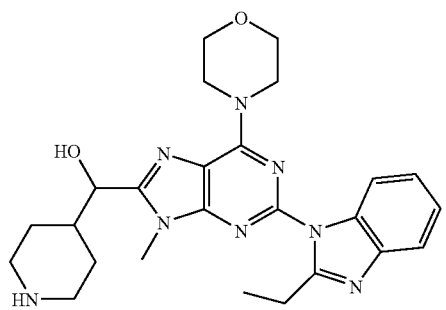

To a solution of tert-butyl 4-((2-(2-ethyl-1H-benzo[d]imidazol-1-yl)-9-methyl-6-morpholino-9H-purin-8-yl)(hydroxy)methyl)piperidine-1-carboxylate (0.320 g, 0.555 mmol) in Methylene chloride (10 mL, 200 mmol;) was added Trifluoroacetic Acid (0.50 mL, 6.5 mmol;). The reaction was stirred at room temperature for 1 hr. and the reaction mixture was evaporated to dryness. To the residue was added 2M NH3 in MeOH to neutralize any residual acid. The mixture was then evaporated to dryness. The crude was then purified by flash chromatography (0-15% MeOH in DCM) to give the desired product as pinkish paste (0.24 g, 91%). LCMS m/z 477.4 (MH+).

Step 4: I-methyl 2-(4-((2-(2-ethyl-1H-benzo[d]imidazol-1-yl)-9-methyl-6-morpholino-9H-purin-8-yl)(hydroxy)methyl)piperidin-1-yl)-2-methylpropanoate Following General Procedure C, (2-(2-ethyl-1H-benzo[d]imidazol-1-yl)-9-methyl-6-morpholino-9H-purin-8-yl)(piperidin-4-yl)methanol was alkylated with 2-bromo-2-methylpropionic acid methyl ester to give the racemate desired product (0.22 g, 83%). The enantiomers were separated by SFC to give 526. LCMS m/z: 289.2 (2M+H+)

Example 527

(S)-methyl 2-(4-((2-(2-ethyl-1H-benzo[d]imidazol-1-yl)-9-methyl-6-morpholino-9H-purin-8-yl)(hydroxy)methyl)piperidin-1-yl)-2-methylpropanoate The procedure to prepare (R) enantiomer 526 gave (S) enantiomer 527 after separation by SFC. LCMS m/z: 289.2 (2M+H+)

Example 528 methyl 2-(4-(2-(2-ethyl-1H-benzo[d]imidazol-1-yl)-9-methyl-6-morpholino-9H-purine-8-carbonyl)piperidin-1-yl)-2-methylpropanoate 528

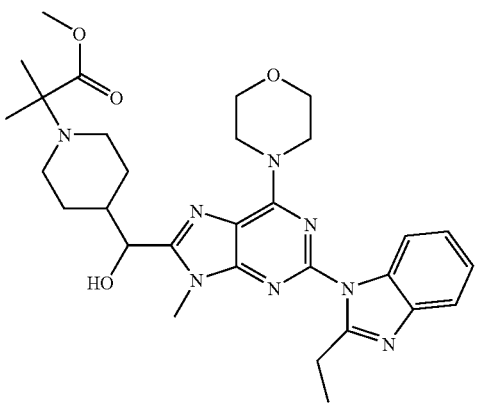

To a solution of racemic methyl 2-(4-((2-(2-ethyl-1H-benzo[d]imidazol-1-yl)-9-methyl-6-morpholino-9H-purin-8-yl)(hydroxy)methyl)piperidin-1-yl)-2-methylpropanoate, from the procedures for 526 and 527, (0.115 g, 0.199 mmol) in methylene chloride (5.0 mL, 78 mmol) was added Dess-Martin periodinane (0.0930 g, 0.219 mmol). The resulting mixture was then stirred at room temp. for 1 hour. The reaction mixture was filtered though paper to remove all solid precipitates and then concentrated. The residue was then purified by RP-HPLC to give 528 (52 mg, 64%). LCMS m/z: 288.3 (2M+H+)

Example 529

4-(2-(2-ethyl-1H-benzo[d]imidazol-1-yl)-9-methyl-8-((1-(oxetan-3-yl)azetidin-3-yl)methyl)-9H-purin-6-yl)morpholine 529

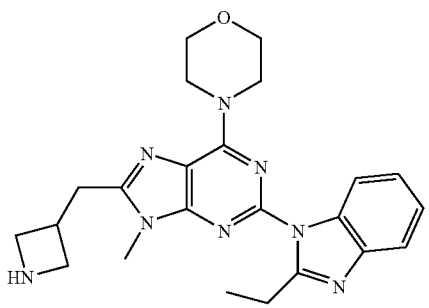

Following General Procedure L for reductive amination 4-(8-(azetidin-3-ylmethyl)-2-(2-ethyl-1H-benzo[d]imidazol-1-yl)-9-methyl-9H-purin-6-yl)morpholine 530 and 3-oxetanone were reacted to give 529. LCMS m/z: 489.2 (MH+)

Example 530

4-(8-(azetidin-3-ylmethyl)-2-(2-ethyl-1H-benzo[d]imidazol-1-yl)-9-methyl-9H-purin-6-yl)morpholine 530

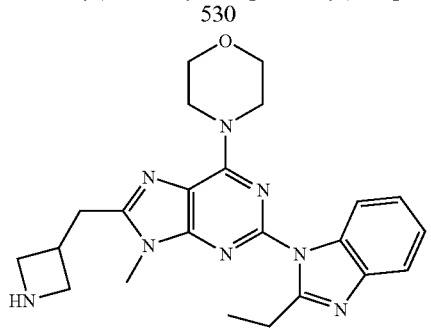

Step 1: tert-butyl 3-((2-chloro-9-methyl-6-morpholino-9H-purin-8-yl)methylene)azetidine-1-carboxylate

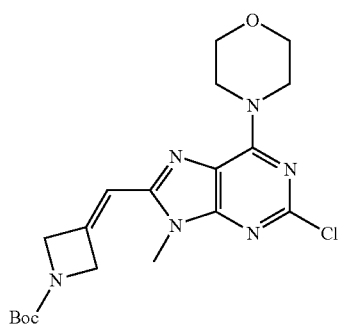

To a cold (−78° C.) suspension of dimethyl (2-chloro-9-methyl-6-morpholino-9H-purin-8-yl)methylphosphonate (1.1 g, 2.9 mmol) in THF (26 mL) was added a 2.0M solution of LDA in THF (1.6 mL) The resulting solution was allowed to warm to room temperature before the addition of a solution of 1-Boc-3-azetidinone (0.58 g, 3 4 mmol) in THF (12 mL). The reaction mixture was stirred at room temperature for 2 hours and partitioned between brine and DCM. The organic layer was isolated, washed with brine, dried over MgSO$_4$ and concentrated. The crude residue was then purified by flash chromatography (0-100% EtOAc in heptane) to give the title compound (1.15 g, 93%). LCMS m/z: 421.3 (MH+).

Step 2: tert-butyl 3-((9-methyl-2-(2-ethyl-1H-benzo[d]imidazol-1-yl)-6-morpholino-9H-purin-8-yl)methylene)azetidine-1-carboxylate

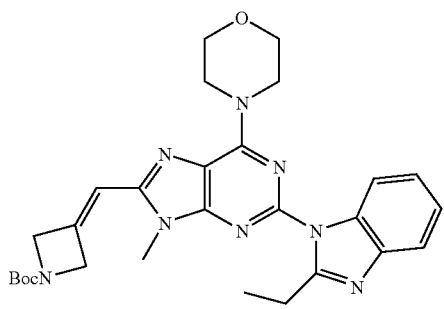

A mixture of tert-butyl 3-((2-chloro-9-methyl-6-morpholino-9H-purin-8-yl)methylene)azetidine-1-carboxylate (0.88 g, 2.9 mmol), 2-ethylbenzimidazole (0.40 g, 2.74 mmol), Xphos (0.10 g, 0.21 mmol), Pd$_2$(dba)$_3$ (0.10 g, 0.11 mmol) and cesium carbonate (1.4 g, 4.2 mmol) in DMF (4.0 mL) was heated in a Biotage microwave at 140° C. for 30 minutes. The reaction mixture was then filtered through paper and then partitioned between brine and EtOAc. The combined extracts were washed with brine, dried over Na$_2$SO$_4$, filtered and concentrated. The crude product was purified by flash chromatography (0-10% MeOH in DCM) to give the title compound (1.2 g, quant.). LCMS m/z: 531.2 (MH+).

Step 3: tert-butyl 3-((9-methyl-2-(2-ethyl-1H-benzo[d]imidazol-1-yl)-6-morpholino-9H-purin-8-yl)methyl)azetidine-1-carboxylate

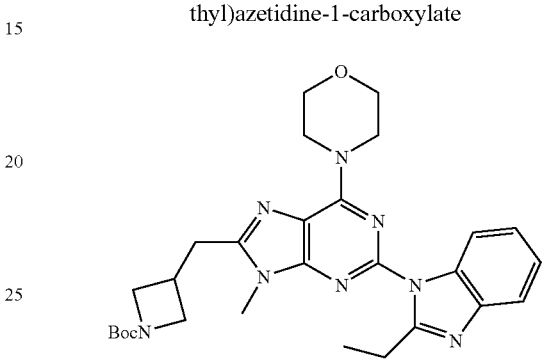

A suspension of tert-butyl 3-((9-methyl-2-(2-ethyl-1H-benzo[d]imidazol-1-yl)-6-morpholino-9H-purin-8-yl)methylene)azetidine-1-carboxylate (1.1 g, 2.1 mmol) and Pd/C (10 wt %, 0.4 g) in ethanol (25 mL) was stirred under a hydrogen atmosphere (balloon) at room temperature for 24 hours. The reaction mixture was then filtered through celite and concentrated. The crude product was purified by flash chromatography (0-5% MeOH in DCM) to give the title compound (0.64 g, 58%). LCMS m/z: 547.2 (MH+)

Step 4: 4-(8-(azetidin-3-ylmethyl)-9-methyl-2-(2-ethyl-1H-benzo[d]imidazol-1-yl)-9H-purin-6-yl)morpholine 530

To a solution of tert-butyl 3-((9-methyl-2-(2-ethyl-1H-benzo[d]imidazol-1-yl)-6-morpholino-9H-purin-8-yl)methyl)azetidine-1-carboxylate (0.64 g, 1.2 mmol) in DCM (10 mL) was added trifluoroacetic acid (1.0 mL, 13 mmol) The reaction mixture was then stirred at room temperature for 1 hour. The reaction mixture was then evaporated to dryness. The residue was then re-dissolved in MeOH and neutralized by adding a 2M NH3 in MeOH. The solution was then concentrated and purified by flash chromatography using a KP-NH2 column (0-10% MeOH in DCM) to give 530. LCMS m/z: 433.2 (MH+)

Example 531

2-(3-((2-(2-ethyl-1H-benzo[d]imidazol-1-yl)-9-methyl-6-morpholino-9H-purin-8-yl)methyl)azetidin-1-yl)-2-methylpropanamide 531

Following General Procedure C, 4-(8-(azetidin-3-ylmethyl)-2-(2-ethyl-1H-benzo[d]imidazol-1-yl)-9-methyl-9H-purin-6-yl)morpholine 530 was alkylated by 2-bromo-2-methyl-propionamide to give 531. LCMS m/z: 259.7 (2M+H+)

Example 532 methyl 2-(3-((2-(2-ethyl-1H-benzo[d]imidazol-1-yl)-9-methyl-6-morpholino-9H-purin-8-yl)methyl)azetidin-1-yl)-2-methylpropanoate 532

Following General Procedure C, 4-(8-(azetidin-3-ylmethyl)-2-(2-ethyl-1H-benzo[d]imidazol-1-yl)-9-methyl-9H-purin-6-yl)morpholine 530 was alkylated by 2-bromo-2-methyl-propionic acid methyl ester to give 532. LCMS m/z: 267.2 (2M+H+)

Example 533

2-(3-((2-(2-ethyl-1H-benzo[d]imidazol-1-yl)-9-methyl-6-morpholino-9H-purin-8-yl)methyl)azetidin-1-yl)-2-methylpropan-1-ol 533

Following the procedure for 509, methyl 2-(3-((2-(2-ethyl-1H-benzo[d]imidazol-1-yl)-9-methyl-6-morpholino-9H-purin-8-yl)methyl)azetidin-1-yl)-2-methylpropanoate was reduced with lithium aluminum hydride to give 533. LCMS m/z: 253.2 (2M+H+)

Example 534

1-(3-((2-(2-ethyl-1H-benzo[d]imidazol-1-yl)-9-methyl-6-morpholino-9H-purin-8-yl)methyl)azetidin-1-yl)-2-methylpropan-2-ol 534

Following General Procedure C, 4-(8-(azetidin-3-ylmethyl)-2-(2-ethyl-1H-benzo[d]imidazol-1-yl)-9-methyl-9H-purin-6-yl)morpholine and isobutylene oxide were reacted at room temperature to give 534. LCMS m/z: 253.2 (2M+H+)

Example 535

4-(2-(2-(2-ethyl-1H-benzo[d]imidazol-1-yl)-9-methyl-6-morpholino-9H-purin-8-yl)ethyl)-3,3-dimethylmorpholine 535

A mixture of 2-chloro-8-[2-(3,3-dimethylmorpholin-4-yl)ethyl]-9-methyl-6-morpholin-4-yl-9H-purine (44 mg, 0.11 mmol), 2-ethylbenzimidazole (18 mg, 0.12 mmol), Pd$_2$(dba)$_3$ (5.2 mg, 5 mol %), Xphos (5.3 mg, 10 mol %) and Cs$_2$CO$_3$ (54 mg, 0.17 mmol) in dioxane (1.5 mL) was purged with argon gas then heated at 120° C., for 24 h, in a sealed tube. The reaction mixture was loaded onto an Isolute® SCX-2 cartridge, washed with MeOH then the desired product eluted with 2 M NH$_3$/MeOH in DCM. The resulting residue was purified by reverse phase HPLC (Phenomenex Gemini 5 μm C18, 20 mM triethylamine in water on a gradient of acetonitrile 30-90%) to give 535 (33 mg, 59%) as a pale beige solid. LCMS: (Method I): R$_T$ 2.52 min; [M+H]$^+$ 505.2. $^1$H NMR (400 MHz, CHCl$_3$-d): δ 8.02-7.97 (m, 1H), 7.77-7.72 (m, 1 H), 7.29-7.22 (m, 2 H), 4.52-4.14 (m, 4 H), 3.86 (t, J=4.8 Hz, 4 H), 3.80 (s, 3 H), 3.79-3.67 (m, 2 H), 3.35 (q, J=7.5 Hz, 2 H), 3.34-3.23 (m, 2 H), 3.05-2.92 (m, 2 H), 2.92-2.80 (m, 2 H), 2.77-2.54 (m, 2 H), 1.44 (t, J=7.5 Hz, 3 H), 0.99 (s, 6 H)

Example 536

(S)-1-(1-((2-(2-ethyl-1H-benzo[d]imidazol-1-yl)-9-methyl-6-morpholino-9H-purin-8-yl)methyl)azetidin-3-yl)pyrrolidin-3-ol 536

A mixture of 2-(2-ethylbenzoimidazol-1-yl)-9-methyl-6-morpholin-4-yl-9H-purine-8-carbaldehyde (100 mg, 0.26 mmol), (S)-1-azetidin-3-ylpyrrolidin-3-ol (41 mg, 0.28 mmol) and 4 Å powdered molecular sieves (200 mg) in DCE (6 mL) was stirred at room temperature for 2 h before the addition of sodium triacetoxyborohydride (108 mg, 0.51 mmol). The reaction mixture was stirred for 65 h then filtered through celite, washing with DCM. The organic phase was washed with brine (×1) and concentrated in vacuo. The organic phase was dried (Na$_2$SO$_4$) and concentrated in vacuo. The resulting residue was purified by column chromatography (Si—PCC, MeOH:DCM, 0-15%) affording 536 as a yellow foam (71 mg, 53%). LCMS (Method I): R$_T$ 2.31 min [M+H]$^+$ 518.2. $^1$H NMR (CDCl$_3$, 400 MHz): δ 8.02-7.97 (m, 1 H); 7.76-7.71 (m, 1 H); 7.29-7.22 (m, 2 H); 4.53 (bs, 1 H); 4.35 (m, 4 H); 3.96 (s, 2 H); 3.90-3.82 (m, 7 H); 3.67 (bs, 2 H); 3.55 (m, 3 H); 3.34 (q, J=7.5 Hz, 2 H); 3.17 (m, 1 H); 2.99 (m, 1 H); 2.30 (m, 2 H); 2.02 (m, 2 H) and 1.44 (t, J=7.5 Hz, 3 H)

Example 537

4-(2-(2-ethyl-1H-benzo[d]imidazol-1-yl)-9-methyl-8-(2-(3-(1,1-dioxo-thiomorpholino)azetidin-1-yl)ethyl)-9H-purin-6-yl)morpholine 537

A mixture of 2-chloro-8-{2-[3-(1,1-dioxo-1-thiomorpholin-4-yl)azetidin-1-yl]-ethyl}-9-methyl-6-morpholin-4-yl-9H-purine (93 mg, 0.20 mmol), 2-ethylbenzimidazole (32 mg, 0.22 mmol), Pd$_2$(dba)$_3$ (4.5 mg, 2.5 mol %), Xphos (9.4 mg, 10 mol %) and Cs$_2$CO$_3$ (97 mg, 0.30 mmol) in dioxane (2.0 mL) was purged with argon gas then heated at 120° C., for 20 h, in a sealed tube. The reaction mixture was loaded onto an Isolute® SCX-2 cartridge, washed with MeOH then the desired product eluted with 2 M NH$_3$/MeOH in DCM. The resulting residue was purified by reverse phase HPLC (Phenomenex Gemini 5 μm C18, 20 mM triethylamine in water on a gradient of acetonitrile 20-90%) to give 537 (79 mg, 69%) as a beige solid. LCMS: (Method I): R$_T$ 2.42 min; [M+H]$^+$ 580.3. $^1$H NMR (400 MHz, CHCl$_3$-d): δ 8.01-7.96 (m, 1 H), 7.77-7.72 (m, 1 H), 7.29-7.22 (m, 2 H), 4.57-4.09 (m, 4H), 3.86 (t, J=4.8 Hz, 4 H), 3.77 (s, 3 H), 3.71-3.57 (m, 2 H), 3.34 (q, J=7.5 Hz, 2 H), 3.33-3.22 (m, 1 H), 3.07 (m, 8 H), 3.00-2.89 (m, 2 H), 2.85 (t, J=4.8 Hz, 4 H), 1.44 (t, J=7.5 Hz, 3 H)

Example 538

1-1-(1-((2-(2-ethyl-1H-benzo[d]imidazol-1-yl)-9-methyl-6-morpholino-9H-purin-8-yl)methyl)azetidin-3-yl)pyrrolidin-3-ol 538

A mixture of 2-(2-ethylbenzoimidazol-1-yl)-9-methyl-6-morpholin-4-yl-9H-purine-8-carbaldehyde (100 mg, 0.26 mmol), (R)-1-azetidin-3-ylpyrrolidin-3-ol (41 mg, 0.28 mmol) and 4 Å powdered molecular sieves (200 mg) in DCE (6 mL) was stirred at room temperature for 2 h before the addition of sodium triacetoxyborohydride (108 mg, 0.51 mmol). The reaction mixture was stirred for 65 h then filtered through celite, washing with DCM. The organic phase was washed with brine (×1) and concentrated in vacuo. The organic phase was dried (Na$_2$SO$_4$) and concentrated in vacuo. The resulting residue was purified by column chromatography (Si—PCC, MeOH:DCM, 0-15%) affording 538 as a yellow foam (49 mg, 36%). LCMS (Method I): R$_T$ 2.31 min [M+H]$^+$ 518.2. $^1$H NMR (CDCl$_3$, 400 MHz): δ 8.02-7.97 (m, 1 H); 7.76-7.71 (m, 1 H); 7.30-7.23 (m, 2 H); 4.60 (bs, 1 H); 4.35 (m, 4 H); 4.00 (s, 2 H); 3.89-3.81 (m, 7 H); 3.72 (m, 4 H);

3.34 (m, 3 H); 3.17 (m, 3 H); 2.39-2.29 (m, 2 H); 2.16-2.07 (m, 2 H) and 1.44 (t, J=7.5 Hz, 3 H)

Example 539

4-(2-(2-ethyl-1H-benzo[d]imidazol-1-yl)-9-methyl-8-(2-(1,1-dioxo-thiomorpholino)ethyl)-9H-purin-6-yl)morpholine 539

To a solution of (2-chloro-9-methyl-6-morpholin-4-yl-9H-purin-8-yl)acetaldehyde (120 mg, 0.24 mmol) in DCE (15 mL) was added thiomorpholine,1-1-dioxide (100 mg, 0.74 mmol), powdered 4 Å molecular sieves and sodium triacetoxyborohydride (314 mg, 1.48 mmol). The reaction mixture was stirred at room temperature for 6 h, the reaction mixture was loaded onto an Isolute® SCX-2 cartridge, washed with MeOH then the desired product eluted with 2 M NH$_3$/MeOH in DCM. The resulting residue was triturated with EtOAc, filtered and the mother liquor evaporated to give a yellow oil (97 mg). A mixture of this crude, 2-ethylbenzimidazole (38 mg, 0.26 mmol), Pd$_2$(dba)$_3$ (5.4 mg), Xphos (11.1 mg) and Cs$_2$CO$_3$ (114 mg, 0.35 mmol) in dioxane (2 mL) was purged with argon gas then heated at 120° C., for 20 h, in a sealed tube. The reaction mixture was loaded onto an Isolute® SCX-2 cartridge, washed with MeOH then the desired product eluted with 2 M NH$_3$/MeOH in DCM. The resulting residue was purified by reverse phase HPLC (Phenomenex Gemini 5 μm C18, 20 mM triethylamine in water on a gradient of acetonitrile 30-90%) to give 539 (11 mg, 5% over 2 steps) as a pale orange solid. LCMS: (Method I): R$_T$ 2.94 min; [M+H]$^+$ 525.2. $^1$H NMR (400 MHz, CHCl$_3$-d): δ 8.02-7.97 (m, 1H), 7.79 (d, J=7.17 Hz, 1 H), 7.32-7.26 (m, 2 H), 4.47-4.19 (m, 4 H), 3.89-3.83 (m, 4 H), 3.78 (s, 3 H), 3.38 (q, J=7.5 Hz, 2 H), 3.18-3.12 (m, 5 H), 3.12-3.01 (m, 7 H), 1.46 (t, J=7.5 Hz, 3 H)

Example 540

4-(8-(2-(4,4-difluoropiperidin-1-yl)ethyl)-2-(2-ethyl-1H-benzo[d]imidazol-1-yl)-9-methyl-9H-purin-6-yl)morpholine 540

A mixture of 2-chloro-8-[2-(4,4-difluoropiperidin-1-yl)ethyl]-9-methyl-6-morpholin-4-yl-9H-purine (30 mg, 0.08 mmol), 2-ethylbenzimidazole (12 mg, 0.08 mmol), Pd$_2$(dba)$_3$ (1.7 mg, 2.5 mol %), Xphos (3.6 mg, 10 mol %) and Cs$_2$CO$_3$ (37 mg, 0.11 mmol) in dioxane (1.0 mL) was purged with argon gas then heated at 120° C., for 20 h, in a sealed tube. The reaction mixture was loaded onto an Isolute® SCX-2 cartridge, washed with MeOH then the desired product eluted with 2 M NH$_3$/MeOH in DCM. The resulting residue was purified by reverse phase HPLC (Phenomenex Gemini 5 μm C18, 20 mM triethylamine in water on a gradient of acetonitrile 30-90%) to give 540 (25 mg, 64%) as a beige solid. LCMS: (Method I): R$_T$ 2.61 min; [M+H]$^+$ 511.2. $^1$H NMR (400 MHz, CHCl$_3$-d): δ 8.01-7.96 (m, 1 H), 7.78-7.74 (m, 1 H), 7.29-7.23 (m, 2 H), 4.68-4.02 (m, 4 H), 3.86 (t, J=4.8 Hz, 4 H), 3.78 (s, 3 H), 3.35 (q, J=7.5 Hz, 2 H), 3.12-2.99 (m, 4 H), 2.81-2.65 (m, 4 H), 2.15-1.99 (m, 4 H), 1.44 (t, J=7.5 Hz, 3 H)

Example 541

2-(3-((2-(2-ethyl-1H-benzo[d]imidazol-1-yl)-9-methyl-6-morpholino-9H-purin-8-yl)methyl)azetidin-1-yl)acetamide 541

Following General Procedure C, 4-(8-(azetidin-3-ylmethyl)-2-(2-ethyl-1H-benzo[d]imidazol-1-yl)-9-methyl-9H-purin-6-yl)morpholine and 2-bromoacetamide were reacted at room temperature to give 541. LCMS m/z: 490.3 (MH+)

Example 542

2-methyl-1-(4-((9-methyl-2-(2-methyl-1H-benzo[d]imidazol-1-yl)-6-morpholino-9H-purin-8-yl)methyl)piperidin-1-yl)propan-2-ol 542

Following General Procedure C, 4-(9-methyl-2-(2-methyl-1H-benzo[d]imidazol-1-yl)-8-(piperidin-4-ylmethyl)-9H-purin-6-yl)morpholine and isobutylene oxide were reacted to give 542. LCMS m/z: 519.3 (MH+)

Example 543

4-(9-methyl-2-(2-methyl-1H-benzo[d]imidazol-1-yl)-8-((1-(2-(methylsulfonyl)ethyl)azetidin-3-yl)methyl)-9H-purin-6-yl)morpholine 543

Following General Procedure C, 4-(8-(azetidin-3-ylmethyl)-9-methyl-2-(2-methyl-1H-benzo[d]imidazol-1-yl)-9H-purin-6-yl)morpholine and methylvinylsulfone were reacted to give 543. LCMS m/z: 525.3 (MH+)

Example 544

4-(9-methyl-2-(2-methyl-1H-benzo[d]imidazol-1-yl)-8-((1-(2-(methylsulfonyl)ethyl)piperidin-4-yl)methyl)-9H-purin-6-yl)morpholine 544

Following General Procedure C, 4-(9-methyl-2-(2-methyl-1H-benzo[d]imidazol-1-yl)-8-(piperidin-4-ylmethyl)-9H-purin-6-yl)morpholine and methylvinylsulfone were reacted to give 544. LCMS m/z: 553.3 (MH+)

Example 545

1-2-(3-((2-(2-ethyl-1H-benzo[d]imidazol-1-yl)-9-methyl-6-morpholino-9H-purin-8-yl)methyl)azetidin-1-yl)propanamide 545

Following General Procedure C, 4-(8-(azetidin-3-ylmethyl)-2-(2-ethyl-1H-benzo[d]imidazol-1-yl)-9-methyl-9H-purin-6-yl)morpholine and 2-bromopropionamide were reacted to give a racemic mixture. The enantiomers were separated by SFC to give 545. LCMS m/z: 252.7 (2M+H+)

Example 546

(S)-2-(3-((2-(2-ethyl-1H-benzo[d]imidazol-1-yl)-9-methyl-6-morpholino-9H-purin-8-yl)methyl)azetidin-1-yl)propanamide 546

Following General Procedure C, 4-(8-(azetidin-3-ylmethyl)-2-(2-ethyl-1H-benzo[d]imidazol-1-yl)-9-methyl-9H-purin-6-yl)morpholine and 2-bromopropionamide were reacted to give a racemic mixture. The enantiomers were separated by SFC to give 546. LCMS m/z: 252.7 (2M+H+)

Example 547

4-(1-((2-(2-isopropyl-1H-benzo[d]imidazol-1-yl)-9-methyl-6-morpholino-9H-purin-8-yl)methyl)azetidin-3-yl)morpholine 547

A mixture of 2-chloro-9-methyl-6-morpholin-4-yl-8-(3-morpholin-4-yl-azetidin-1-ylmethyl)-9H-purine (83 mg, 0.20 mmol), 2-isopropylbenzimidazole (39 mg, 0.24 mmol), tris(dibenzylideneacetone)dipalladium (9 mg, 0.01 mmol), Xphos (19 mg, 0.04 mmol) and $Cs_2CO_3$ (133 mg, 0.41 mmol) in dioxane (2 mL) was purged with argon then heated at 145° C. for 30 min in a microwave reactor. The reaction mixture was filtered through a pad of celite, washing with EtOAc. The filtrate was concentrated in vacuo and purified by column chromatography (Si—PCC, MeOH:DCM, 0-15%) affording 547 as a beige foam (72 mg, 68%). LCMS (Method I): $R_T$ 2.50 min, [M+H]$^+$ 532.3. $^1$H NMR (CDCl$_3$, 400 MHz): δ 7.89-7.84 (m, 1 H); 7.80-7.75 (m, 1 H); 7.29-7.21 (m, 2 H); 4.34 (m, 4 H); 4.00-3.92 (m, 3 H); 3.88-3.81 (m, 7 H); 3.76 (m, 4 H); 3.64 (m, 2 H); 3.24 (m, 2 H); 3.13 (m, 1 H); 2.40 (m, 4 H); 1.47 (s, 3 H) and 1.46 (s, 3 H)

Example 548

4-(1-((2-(2-cyclopropyl-1H-benzo[d]imidazol-1-yl)-9-methyl-6-morpholino-9H-purin-8-yl)methyl)azetidin-3-yl)morpholine 548

A mixture of 2-chloro-9-methyl-6-morpholin-4-yl-8-(3-morpholin-4-yl-azetidin-1-ylmethyl)-9H-purine (83 mg, 0.20 mmol), 2-cyclopropylbenzimidazole (39 mg, 0.24 mmol), tris(dibenzylideneacetone)dipalladium (9 mg, 0.01 mmol), Xphos (19 mg, 0.04 mmol) and $Cs_2CO_3$ (133 mg, 0.41 mmol) in dioxane (2 mL) was purged with argon then heated at 145° C. for 30 min in a microwave reactor. The reaction mixture was filtered through a pad of celite, washing with EtOAc. The filtrate was concentrated in vacuo and purified by column chromatography (Si—PCC, MeOH:DCM, 0-20%) affording 548 as a beige foam (92 mg, 87%). LCMS (Method I): $R_T$ 2.52 min, [M+H]$^+$ 530.3. $^1$H NMR (CDCl$_3$, 400 MHz): δ 7.95-7.91 (m, 1 H); 7.69-7.65 (m, 1 H); 7.27-7.18 (m, 2 H); 4.36 (m, 4 H); 3.93 (s, 2 H); 3.89-3.83 (m, 7 H); 3.75 (m, 4 H); 3.65 (m, 2 H); 3.24 (m, 2 H); 3.13 (m, 1 H); 2.89-2.81 (m, 1 H); 2.39 (m, 4 H); 1.37-1.32 (m, 2 H) and 1.08-1.02 (m, 2 H)

Example 549

2-(5-(2-ethyl-1H-benzo[d]imidazol-1-yl)-7-morpholinothiazolo[5,4-d]pyrimidin-2-yl)-1-(4-(2-hydroxypropan-2-yl)piperidin-1-yl)ethanone 549

A mixture of 2-(5-chloro-7-morpholin-4-yl-thiazolo[5,4-d]pyrimidin-2-yl)-1-[4-(1-hydroxy-1-methylethyl)piperidin-1-yl]ethanone (40 mg, 0.09 mmol), 2-ethylbenzimidazole (15 mg, 0.10 mmol), Pd$_2$(dba)$_3$ (2.1 mg, 2.5 mol %), Xphos (4.3 mg, 10 mol %) and $Cs_2CO_3$ (44 mg, 0.14 mmol) in dioxane (1.5 mL) was purged with argon gas then heated at 120° C., for 20 h, in a sealed tube. The reaction mixture diluted with EtOAc, filtered through Celite® and evaporated. The resulting residue was purified by column chromatography (Si—PCC, 0-10% MeOH in EtOAc) to give 549 as a pale beige solid (19 mg, 38%). LCMS (Method I): $R_T$=3.47 min, [M+H]$^+$ 550.2. $^1$H NMR (400 MHz, CHCl$_3$-d): δ 8.02-7.98 (m, 1 H), 7.81-7.76 (m, 1 H), 7.33-7.29 (m, 2 H), 4.81-4.75 (m, 1 H), 4.52-4.29 (m, 4 H), 4.19 (s, 2 H), 4.07 (m, 1 H), 3.89-3.84 (m, 4 H), 3.38 (q, J=7.5 Hz, 2 H), 3.15-3.06 (m, 1 H), 2.63-2.54 (m, 1 H), 1.90-1.92 (m, 2 H), 1.92-1.80 (m, 2 H), 1.61-1.50 (m, 1 H), 1.44 (t, J=7.5 Hz, 3 H), 1.36-1.23 (m, 1 H), 1.20 (d, J=11.0 Hz, 6 H)

Example 550

1-(1-((2-(2-isopropyl-1H-benzo[d]imidazol-1-yl)-9-methyl-6-morpholino-9H-purin-8-yl)methyl)azetidin-3-yl)piperidin-4-ol 550

A mixture of 2-(2-isopropylbenzoimidazol-1-yl)-9-methyl-6-morpholin-4-yl-9H-purine-8-carbaldehyde (0.150 g, 0.37 mmol), 1-azetidin-3-ylpiperidin-4-ol (0.069 g, 0.44 mmol) and 4 Å molecular sieves (0.37 g) in DCE (3 mL) was stirred for 2 h at room temperature. Sodium triacetoxyborohydride (0.157 g, 0.74 mmol) was added and the reaction mixture was stirred for 4 h at room temperature. The reaction mixture was filtered through Celite and the filtrate was concentrated in vacuo. The residue was purified by flash chromatography (Si—PPC, MEOH:DCM, gradient 0:100 to 20:80) to give 550 as a white solid (0.137 g, 68%). LCMS (Method I): $R_T$=2.41 min, [M+H]$^+$ 546.3. $^1$H NMR (400 MHz, DMSO-d): δ 7.90-7.85 (m, 1 H); 7.66-7.61 (m, 1 H); 7.25-7.21 (m, 2 H); 4.53 (d, J=4.1 Hz, 1 H); 4.28-4.23 (m, 4 H); 3.96-3.86 (m, 1 H); 3.86 (s, 2 H); 3.85-3.68 (m, 7 H); 3.48-3.43 (m, 1 H); 3.42 (t, J=6.5 Hz, 2 H); 2.95 (t, J=6.5 Hz, 2 H); 2.90-2.82 (m, 1 H); 2.45-2.55 (m, 2 H); 1.85 (t, J=10.6 Hz, 2 H); 1.71-1.68 (m, 2 H); 1.40-1.34 (m, 2 H); 1.35 (d, J=6.80 Hz, 6 H)

Example 551

1-(1-((2-(2-ethyl-1H-benzo[d]imidazol-1-yl)-9-methyl-6-morpholino-9H-purin-8-yl)methyl)azetidin-3-yl)-4-methylpiperidin-4-ol 551

A mixture of 2-(2-ethylbenzoimidazol-1-yl)-9-methyl-6-morpholin-4-yl-9H-purine-8-carbaldehyde (0.207 g, 0.53 mmol), 1-azetidin-3-yl-4-methylpiperidin-4-ol (0.108 g, 0.63 mmol) and 4 Å molecular sieves (0.5 g) in DCE (5 mL) was stirred for 3 h at room temperature. Sodium triacetoxyborohydride (0.224 g, 1.06 mmol) was added and the reaction mixture was stirred for 18 h at room temperature. The reaction mixture was filtered through Celite and the filtrate was concentrated in vacuo. The residue was purified by flash chromatography (Si—PPC, MeOH:EtOAc, gradient 0:100 to 30:70) to give 551 as a white solid (0.247 g, 86%). LCMS (Method I): $R_T$=2.35 min, [M+H]$^+$ 546.3. $^1$H NMR (400 MHz, DMSO-d): δ 8.04-7.98 (m, 1 H); 7.65-7.60 (m, 1 H); 7.27-7.20 (m, 2 H); 4.34-3.83 (m, 4 H); 3.85 (s, 2 H); 3.79-3.75 (m, 7 H); 3.43 (t, J=7.4 Hz, 2 H); 3.31-3.20 (q, J=7.4 Hz, 2 H); 2.96-2.93 (m, 2 H); 2.92-2.83 (m, 1 H); 2.27-2.23 (m, 2 H); 2.18-2.14 (m, 2 H); 1.48-1.36 (m, 4 H); 1.33 (t, J=7.4 Hz, 3 H); 1.12-1.06 (s, 3 H)

Example 552

4-(8-((3,3-dimethylpiperazin-1-yl)methyl)-2-(2-ethyl-1H-benzo[d]imidazol-1-yl)-9-methyl-9H-purin-6-yl)morpholine 552

A mixture of 2-(2-ethylbenzoimidazol-1-yl)-9-methyl-6-morpholin-4-yl-9H-purine-8-carbaldehyde (530 mg, 1.35 mmol), 2,2-dimethylpiperazine-1-carboxylic acid tert-butyl ester (350 mg, 1.63 mmol) and molecular sieves (4 Å, powdered, 2.5 g) in DCE (30 mL) was stirred at ambient temperature for 5 h. Sodium triacetoxyborohydride (427 mg, 2.02 mmol) was added and the mixture stirred for 17 h, then loaded onto an Isolute® SCX-2 cartridge (25 g). The cartridge was then washed with methanol and the desired product was subsequently eluted using 2 M NH$_3$ in MeOH. The product was collected and concentrated in vacuo. The resultant residue was purified by flash chromatography (Si—PPC, EtOAc: MeOH; 100:0 to 95:5 to 90:10) to give 4-[2-(2-ethylbenzoimidazol-1-yl)-9-methyl-6-morpholin-4-yl-9H-purin-8-ylmethyl]-2,2-dimethylpiperazine-1-carboxylic acid tert-butyl ester. TFA (3 mL) was added to a solution of 4-[2-(2-ethylbenzoimidazol-1-yl)-9-methyl-6-morpholin-4-yl-9H-purin-8-ylmethyl]-2,2-dimethylpiperazine-1-carboxylic acid tert-butyl ester in DCM (10 mL) and the mixture stirred at ambient temperature for 1 h. The reaction mixture was loaded onto an Isolute® SCX-2 cartridge (10 g), which was washed with MeOH before the desired product was subsequently eluted using 2 M $NH_3$ in MeOH. The product was collected and concentrated in vacuo. The resultant residue was purified by flash chromatography (Si—PPC, DCM:MeOH 100:0 to 98:2 to 95:5 to 90:10 to 80:20) to afford 552 as a cream solid (144 mg, 22%). LCMS (Method I): $R_T$=2.56 min, M+H$^+$=490. $^1$H NMR (CDCl$_3$, 400 MHz) δ 8.02 (m, 1 H); 7.75 (m, 1 H); 7.29 (m, 2 H); 4.35 (m, 4 H); 3.92-3.83 (m, 7 H); 3.70 (s, 2 H); 3.36 (q, J=7.5 Hz, 2 H); 2.97 (m, 2 H); 2.47 (m, 2 H); 2.28 (s, 2 H); 1.49-1.42 (m, 3 H) and 1.19 (s, 6 H)

Example 553

4-(2-(2-ethyl-1H-benzo[d]imidazol-1-yl)-9-methyl-8-(((1S,4S)-5-(methylsulfonyl)-2,5-diazabicyclo[2.2.1]heptan-2-yl)methyl)-9H-purin-6-yl)morpholine 553

A mixture of 2-chloro-8-((1S,4S)-5-methanesulfonyl-2,5-diazabicyclo[2.2.1]hept-2-ylmethyl)-9-methyl-6-morpholin-4-yl-9H-purine (150 mg, 0.34 mmol), 2-ethyl-1H-benzoimidazole (59 mg, 0.40 mmol), Pd$_2$dba$_3$ (9 mg, 0.009 mmol), Xphos (18 mg, 0.036 mmol) and cesium carbonate (165 mg, 0.51 mmol) in 1,4-dioxane (3 mL) was purged with argon gas then subjected to microwave irradiation at 150° C. for 30 min. The reaction mixture was loaded onto an Isolute® SCX-2 cartridge (10 g), which was washed with MeOH/DCM before the desired product was eluted with 2 M $NH_3$ in MeOH/DCM. The product was collected and concentrated in vacuo. The resultant residue was purified by flash chromatography (Si—PPC, EtOAc:MeOH 100:0 to 99:1 to 98:2) to afford 553 as a white solid (153 mg, 82%). LCMS (Method I): $R_T$=2.53 min, M+H$^+$=552. $^1$H NMR (CDC$_3$, 400 MHz) δ 8.01 (m, 1 H); 7.77 (m, 1 H); 7.28 (m, 2 H); 4.35 (m, 5 H); 4.06 (d, J=13.6 Hz, 1 H); 3.96 (d, J=13.6 Hz, 1 H); 3.87 (m, 7 H); 3.65 (d, J=9.5 Hz, 1 H); 3.61 (bs, 1 H); 3.37 (q, J=7.5 Hz, 2 H); 3.27 (dd, J=9.5, 2.3 Hz, 1 H); 3.02-2.93 (m, 2 H); 2.91 (s, 3 H); 1.99 (d, J=10.2 Hz, 1 H); 1.79 (d, J=10.2 Hz, 1 H) and 1.45 (t, J=7.5 Hz, 3 H)

Example 554

1-(1-((2-(2-ethyl-1H-benzo[d]imidazol-1-yl)-9-methyl-6-morpholino-9H-purin-8-yl)methyl)piperidin-4-yl)azetidin-3-ol 554

A mixture of 2-(2-ethylbenzoimidazol-1-yl)-9-methyl-6-morpholin-4-yl-9H-purine-8-carbaldehyde (0.157 g, 0.40 mmol), 1-piperidin-4-ylazetidin-3-ol (0.075 g, 0.48 mmol) and 4 Å molecular sieves (0.4 g) in DCE (5 mL) was stirred for 3 h at room temperature. Sodium triacetoxyborohydride (0.17 g, 0.80 mmol) was added and the reaction mixture was stirred for 18 h at room temperature. The reaction mixture was filtered through Celite and the filtrate was concentrated in vacuo. The residue was purified by flash chromatography (Si—PPC, MeOH:EtOAc, gradient 0:100 to 20:80) to give 554 as a white solid (0.145 g, 68%). LCMS (Method I): $R_T$=2.20 min, [M+H]$^+$ 532.3. $^1$H NMR (400 MHz, DMSO-d): δ 8.04-7.98 (m, 1 H); 7.65-7.60 (m, 1 H); 7.27-7.20 (m, 2 H); 4.27-4.19 (m, 4 H); 3.80 (s, 3 H); 3.77 (t, J=4.7 Hz, 4 H); 3.74 (s, 2 H); 3.44 (t, J=7.1 Hz, 3 H); 3.26 (q, J=7.4 Hz, 3 H); 2.78-2.70 (m, 2 H); 2.62 (t, J=7.1 Hz, 2 H); 2.12 (t, J=11.0 Hz, 2 H); 1.99-1.90 (m, 1 H); 1.60 (d, J=11.0 Hz, 2 H); 1.33 (t, J=7.4 Hz, 3 H); 1.21-1.10 (m, 2 H)

Example 555

1-isopropyl-4-((2-(2-isopropyl-1H-benzo[d]imidazol-1-yl)-9-methyl-6-morpholino-9H-purin-8-yl)methyl)piperazin-2-one 555

A mixture of 2-(2-isopropylbenzoimidazol-1-yl)-9-methyl-6-morpholin-4-yl-9H-purine-8-carbaldehyde (0.15 g, 0.37 mmol), 1-isopropylpiperazin-2-one (0.078 g, 0.44 mmol) and 4 Å molecular sieves (0.372 g) in DCE (3 mL) was stirred for 3 h at room temperature. Sodium triacetoxyborohydride (0.157 g, 0.74 mmol) was added and the reaction mixture was stirred for 18 h at room temperature. The reaction mixture was filtered through Celite and the filtrate was concentrated in vacuo. The residue was purified by flash chromatography (Si—PPC, MeOH:EtOAc, gradient 0:100 to 10:90) to give 555 as an off-white solid (0.168 g, 84%). LCMS (Method I): $R_T$=3.43 min, [M+H]$^+$ 532.3. $^1$H NMR (400 MHz, DMSO-d): δ 7.93-7.89 (m, 1 H); 7.68-7.63 (m, 1 H); 7.28-7.23 (m, 2 H); 4.64-4.58 (m, 1 H); 4.29-4.21 (m, 4 H); 3.97-3.90 (m, 1 H); 3.90 (d, J=4.6 Hz, 2 H); 3.80 (s, 3 H); 3.78 (t, J=4.6 Hz, 4 H); 3.21-3.15 (m, 4 H); 2.78-2.75 (m, 2 H); 1.36 (d, J=6.8 Hz, 6 H); 1.05 (d, J=6.8 Hz, 6 H)

Example 556

4-(1-((2-(2-ethyl-1H-benzo[d]imidazol-1-yl)-9-methyl-6-morpholino-9H-purin-8-yl)methyl)azetidin-3-yl)-1-methylpiperazin-2-one 556

A mixture of 2-(2-ethylbenzoimidazol-1-yl)-9-methyl-6-morpholin-4-yl-9H-purine-8-carbaldehyde (162 mg, 0.41 mmol), 4-azetidin-3-yl-1-methylpiperazin-2-one (77 mg, 0.46 mmol) and 4 Å powdered molecular sieves (250 mg) in DCE (10 mL) was stirred at room temperature for 2 h before the addition of sodium triacetoxyborohydride (175 mg, 0.83 mmol). The reaction mixture was stirred for 16 h then filtered through celite, washing with DCM. The organic phase was washed with brine (×1) and concentrated in vacuo. The organic phase was dried (Na$_2$SO$_4$) and concentrated in vacuo. The resulting residue was purified by column chromatography (Si—PCC, MeOH:EtOAc, 0-30%) affording 556 as a yellow foam (182 mg, 82%). LCMS (Method I): $R_T$ 2.34 min [M+H]$^+$ 545.3. $^1$H NMR (CDCl$_3$, 400 MHz): δ 8.02-7.97 (m, 1 H); 7.77-7.72 (m, 1 H); 7.29-7.22 (m, 2 H); 4.35 (m, 4 H); 3.89-3.84 (m, 6 H); 3.83 (s, 3 H); 3.59 (t, J=5.3 Hz, 2 H); 3.39-3.31 (m, 4 H); 3.18-3.10 (m, 3 H); 3.05 (m, 2 H); 2.96 (s, 3 H); 2.59 (t, J=5.3 Hz, 2 H) and 1.43 (t, J=7.5 Hz, 3 H)

Example 557

4-(2-(2-ethyl-1H-benzo[d]imidazol-1-yl)-9-methyl-8-(2-(4-(tetrahydro-2H-pyran-4-yl)piperazin-1-yl)ethyl)-9H-purin-6-yl)morpholine 557

A mixture of 2-chloro-9-methyl-6-morpholin-4-yl-8-{2-[4-(tetrahydropyran-4-yl)piperazin-1-yl]ethyl}-9H-purine (37 mg, 0.08 mmol), 2-ethylbenzimidazole (13 mg, 0.09 mmol), Pd$_2$(dba)$_3$ (1.9 mg, 2.5 mol %), Xphos (3.9 mg, 10 mol %) and Cs$_2$CO$_3$ (37 mg, 0.11 mmol) in dioxane (1.5 mL) was purged with argon gas then heated at 120° C., for 19 h, in a sealed tube. The reaction mixture was loaded onto an Isolute® SCX-2 cartridge, washed with MeOH then the desired product eluted with 2 M $NH_3$/MeOH in DCM. The resulting residue was purified by reverse phase HPLC (Phenomenex Gemini 5 μm C18, 20 mM triethylamine in water on a gradient of acetonitrile 30-90%) to give 557 (32 mg, 70%) as a pale beige solid. LCMS: (Method I): $R_T$ 2.42 min; [M+H]$^+$ 560.3. $^1$H NMR (400 MHz, CHCl$_3$-d): δ 8.01-7.97 (m, 1 H), 7.77-7.72 (m, 1 H), 7.29-7.22 (m, 2 H), 4.56-4.21 (m, 4 H), 4.04 (dd, J=11.4, 4.2 Hz, 2 H), 3.86 (t, J=4.7 Hz, 4 H), 3.77 (s, 3 H), 3.38-3.34 (m, 2 H), 3.34 (q, J=7.5 Hz, 2 H), 3.13-3.00 (m, 2 H), 3.00-2.87 (m, 2 H), 2.82-2.58 (m, 6 H), 2.57-2.42 (m, 1 H), 1.88-1.75 (m, 2 H), 1.71-1.55 (m, 4 H), 1.44 (t, J=7.5 Hz, 3 H)

Example 558

2-(4-((9-methyl-2-(2-methyl-1H-benzo[d]imidazol-1-yl)-6-morpholino-9H-purin-8-yl)methyl)piperidin-1-yl)acetamide 558

Following General Procedure C, 4-(9-methyl-2-(2-methyl-1H-benzo[d]imidazol-1-yl)-8-(piperidin-4-ylmethyl)-9H-purin-6-yl)morpholine and 2-bromoacetamide were reacted to give 558. LCMS m/z: 252.7 (2M+H+)

Example 559

I-2-(4-((9-methyl-2-(2-methyl-1H-benzo[d]imidazol-1-yl)-6-morpholino-9H-purin-8-yl)methyl)piperidin-1-yl)propanamide 559

Following General Procedure C, 4-(9-methyl-2-(2-methyl-1H-benzo[d]imidazol-1-yl)-8-(piperidin-4-ylmethyl)-9H-purin-6-yl)morpholine and 2-bromopropionamide were reacted to give the racemic mixture. The enantiomers were separated by SFC to give 559. LCMS m/z: 259.7 (2M+H+)

Example 560

(S)-2-(4-((9-methyl-2-(2-methyl-1H-benzo[d]imidazol-1-yl)-6-morpholino-9H-purin-8-yl)methyl)piperidin-1-yl)propanamide 560

Following General Procedure C, 4-(9-methyl-2-(2-methyl-1H-benzo[d]imidazol-1-yl)-8-(piperidin-4-ylmethyl)-9H-purin-6-yl)morpholine and 2-bromopropionamide were reacted to give the racemic mixture. The enantiomers were separated by SFC to give 560. LCMS m/z: 259.7 (2M+H+)

Example 561

I-4-(2-(2-ethyl-1H-benzo[d]imidazol-1-yl)-8-((4-(3-fluoropyrrolidin-1-yl)piperidin-1-yl)methyl)-9-methyl-9H-purin-6-yl)morpholine 561

A mixture of 2-(2-ethylbenzoimidazol-1-yl)-9-methyl-6-morpholin-4-yl-9H-purine-8-carbaldehyde (0.15 g, 0.383 mmol), 4-(I-3-fluoropyrrolidin-1-yl)piperidine (0.080 g, 0.46 mmol) and 4 Å molecular sieves (0.4 g) in DCE (5 mL) was stirred for 3 h at room temperature. Sodium triacetoxyborohydride (0.163 g, 0.77 mmol) was added and the reaction mixture was stirred for 18 h at room temperature. The reaction mixture was filtered through Celite and the filtrate was concentrated in vacuo. The residue was purified by flash chromatography (Si—PPC, MeOH:EtOAc, gradient 0:100 to 40:60) to give 561 as a white solid (0.14 g, 67%). LCMS (Method I): $R_T$=2.26 min, [M+H]$^+$ 548.2 $^1$H NMR (400 MHz, DMSO-d$_6$): δ 8.04-7.98 (m, 1 H), 7.65-7.60 (m, 1 H), 7.26-7.21 (m, 2 H), 5.16 (dt, J=55.97, 5.52 Hz, 1 H), 4.50-3.65 (m, 4 H), 3.82 (s, 3 H), 3.80-3.74 (m, 4 H), 3.75 (s, 2 H), 3.27 (q, J=7.4 Hz, 2 H), 2.89-2.74 (m, 4 H), 2.68-2.53 (m, 1 H), 2.37-2.28 (m, 1 H), 2.15-1.97 (m, 4 H), 1.94-1.76 (m, 3 H), 1.45-1.34 (m, 2 H), 1.34 (t, J=7.4 Hz, 3 H)

Example 562

4-(8-((3,3-difluoro-1,3'-biazetidin-1'-yl)methyl)-2-(2-ethyl-1H-benzo[d]imidazol-1-yl)-9-methyl-9H-purin-6-yl)morpholine 562

A mixture of 2-(2-ethylbenzoimidazol-1-yl)-9-methyl-6-morpholin-4-yl-9H-purine-8-carbaldehyde (0.0725 g, 0.18 mmol), 3,3-difluoro-[1,3']biazetidinyl (0.033 g, 0.22 mmol) and 4 Å molecular sieves (0.2 g) in DCE (5 mL). The reaction mixture was stirred for 7 h at room temperature. Sodium triacetoxyborohydride (0.079 g, 0.37 mmol) was added and the reaction mixture was stirred for 18 h at room temperature. The suspension was filtered through Celite and the filtrate was concentrated in vacuo. The residue was purified by flash chromatography (Si—PPC, MeOH:EtOAc, gradient 0:100 to 40:60) to give 562 as a yellow solid (0.075 g, 78%). LCMS (Method I): $R_T$=2.66 min, [M+H]$^+$ 524.2 $^1$H NMR (400 MHz, DMSO-d$_6$): δ 8.03-7.98 (m, 1 H), 7.65-7.60 (m, 1 H), 7.27-7.20 (m, 2 H), 4.50-3.96 (m, 4 H), 3.88 (s, 2 H), 3.86-3.67 (m, 7 H), 3.71-3.55 (m, 4 H), 3.48-3.39 (m, 1 H), 3.37-3.35 (m, 2 H), 3.26 (q, J=7.5 Hz, 2 H), 3.06 (dd, J=7.5, 5.3 Hz, 2 H), 1.33 (t, J=7.5 Hz, 3 H)

Example 564

4-(2-(2-isopropyl-1H-benzo[d]imidazol-1-yl)-9-methyl-8-((4-(tetrahydro-2H-pyran-4-yl)piperazin-1-yl)methyl)-9H-purin-6-yl)morpholine 564

A mixture of 2-chloro-9-methyl-6-morpholin-4-yl-8-[4-(tetrahydropyran-4-yl)piperazin-1-ylmethyl]-9H-purine (180 mg, 0.41 mmol), 2-isopropyl-1H-benzoimidazole (80 mg, 0.50 mmol), Pd$_2$dba$_3$ (11 mg, 0.012 mmol), Xphos (22 mg, 0.046 mmol) and cesium carbonate (201 mg, 0.62 mmol) in DMF (4 mL) was purged with argon gas then subjected to microwave irradiation at 145° C. for 30 min. The reaction mixture was loaded onto an Isolute® SCX-2 cartridge (10 g), which was washed with MeOH/DCM before the desired product was eluted with 2 M NH$_3$ in MeOH/DCM. The product was collected and concentrated in vacuo. The resultant residue was purified by flash chromatography (Si—PPC, DCM:MeOH 100:0 to 95:5) followed by reverse phase HPLC (Phenomenex Gemini 5u C18, 20 mM triethylamine in water on a gradient of acetonitrile 60:40 to 10:90) to afford 564 as a white solid (85 mg, 37%). LCMS (method I): $R_T$=2.61 min, M+H$^+$=560. $^1$H NMR (CDCl$_3$, 400 MHz) δ 7.89 (d, J=7.6 Hz, 1 H), 7.78 (d, J=7.5 Hz, 1 H), 7.26 (m, 2 H), 4.34 (m, 4 H), 4.03 (d, J=10.1 Hz, 2 H), 3.95 (m, 1 H), 3.86 (m, 7 H), 3.77 (s, 2 H), 3.38 (t, J=11.7 Hz, 2 H), 2.63 (m, 9 H), 1.79 (m, 2 H), 1.60 (m, 2 H), 1.48 (s, 3 H) and 1.46 (s, 3 H)

Example 565

(S)-4-(2-(2-ethyl-1H-benzo[d]imidazol-1-yl)-8-((4-(3-fluoropyrrolidin-1-yl)piperidin-1-yl)methyl)-9-methyl-9H-purin-6-yl)morpholine 565

A mixture of 2-(2-ethylbenzoimidazol-1-yl)-9-methyl-6-morpholin-4-yl-9H-purine-8-carbaldehyde (0.1 g, 0.255 mmol), 4-((S)-3-fluoropyrrolidin-1-yl)piperidine (0.053 g, 0.307 mmol) and 4 Å molecular sieves (0.25 g) in DCE (4 mL) was stirred for 3 h at room temperature. Sodium triacetoxyborohydride (0.109 g, 0.51 mmol) was added and the reaction mixture was stirred for 18 h at room temperature. The reaction mixture was filtered through Celite and the filtrate was concentrated in vacuo. The residue was purified by flash chromatography (Si—PPC, MeOH:EtOAc, gradient 0:100 to 40:60) to give 565 as a white solid (0.121 g, 87%). LCMS (Method I): $R_T$=2.26 min, [M+H]$^+$ 548.2 $^1$H NMR (400 MHz, DMSO-d$_6$): δ 8.04-8.00 (m, 1 H), 7.65-7.61 (m, 1 H), 7.26-7.21 (m, 2 H), 5.16 (dt, J=56.0, 5.5 Hz, 1 H), 4.50-3.96 (m, 4 H), 3.82 (s, 3 H), 3.79-3.74 (m, 4 H), 3.75 (s, 2 H), 3.32-3.19 (q, J=7.4 Hz, 2 H), 2.89-2.74 (m, 4 H), 2.69-2.55 (m, 1 H), 2.37-2.28 (m, 1 H), 2.15-1.97 (m, 4 H), 1.90-1.74 (m, 3 H), 1.45-1.34 (m, 2 H), 1.34 (t, J=7.4 Hz, 3 H)

Example 566

2-(4-(2-(2-ethyl-1H-benzo[d]imidazol-1-yl)-9-methyl-6-morpholino-9H-purine-8-carbonyl)piperazin-1-yl)-2-methylpropanamide 566

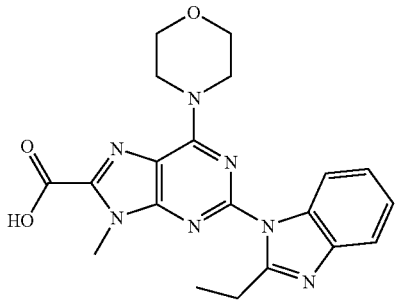

To a suspension of 2-(2-ethyl-1H-benzo[d]imidazol-1-yl)-9-methyl-6-morpholino-9H-purine-8-carbaldehyde (15 g, 38 mmol) in ethanol was added silver nitrate (8.1 g, 48 mmol) and a 1.5 M NaOH solution (150 mL). The resulting mixture was stirred at room temperature for 30 minutes prior to filtering through celite. The solution was then concentrated. To the residual solid was added water and made basic by adding 1M NaOH (cloudy mixture). The mixture was then washed with DCM. The aqueous layer was then made acidic (pH 2) by adding concentrated HCl. The acidic mixture was then concentrated under vacuum. A precipitate slowly formed during the concentration. After the volume was reduced by ⅓, the suspension was cooled in an ice-bath for 15 minutes before being filtered to collect the solid. The solid was then dried under vacuum to give 2-(2-ethyl-1H-benzo[d]imidazol-1-yl)-9-methyl-6-morpholino-9H-purine-8-carboxylic acid as a beige powder (15.2 g, 97%). LCMS m/z: 408.3 (MH+)

2-(2-Ethyl-1H-benzo[d]imidazol-1-yl)-9-methyl-6-morpholino-9H-purine-8-carboxylic acid was coupled with 2-methyl-2-(piperazin-1-yl)propanamide dihydrochloride according to General Procedure K to give 566. LCMS m/z: 281.3 (2M+H+)

Example 567

(4-tert-butylpiperazin-1-yl)(2-(2-ethyl-1H-benzo[d]imidazol-1-yl)-9-methyl-6-morpholino-9H-purin-8-yl)methanone 567

Following General Procedure K, 2-(2-Ethyl-1H-benzo[d]imidazol-1-yl)-9-methyl-6-morpholino-9H-purine-8-carboxylic acid was coupled with 1-tert-butylpiperazine according to General Procedure K to give 567. LCMS m/z: 266.7 (2M+H+)

Example 568

3-(4-((9-methyl-2-(2-methyl-1H-benzo[d]imidazol-1-yl)-6-morpholino-9H-purin-8-yl)methyl)piperidin-1-yl)propanenitrile 568

Following General Procedure C, 4-(9-methyl-2-(2-methyl-1H-benzo[d]imidazol-1-yl)-8-(piperidin-4-ylmethyl)-9H-purin-6-yl)morpholine and acrylonitrile were reacted to give 568. LCMS m/z: 250.7 (2M+H+)

Example 569

(2-(2-ethyl-1H-benzo[d]imidazol-1-yl)-9-methyl-6-morpholino-9H-purin-8-yl)(4-(2-hydroxypropan-2-yl)piperidin-1-yl)methanone 569

Following General Procedure K, 2-(2-ethyl-1H-benzo[d]imidazol-1-yl)-9-methyl-6-morpholino-9H-purine-8-carboxylic acid was coupled with 2-(piperidin-4-yl)propan-2-ol to give 569. LCMS m/z: 533.3 (M+H+)

Example 570

4-(8-((1-(isoxazol-5-ylmethyl)piperidin-4-yl)methyl)-9-methyl-2-(2-methyl-1H-benzo[d]imidazol-1-yl)-9H-purin-6-yl)morpholine 570

Following General Procedure C, 4-(9-methyl-2-(2-methyl-1H-benzo[d]imidazol-1-yl)-8-(piperidin-4-ylmethyl)-9H-purin-6-yl)morpholine and 5-(bromomethyl)isoxazole were reacted to give 570. LCMS m/z: 264.7 (2M+H+)

Example 571

4-(8-((1-(isoxazol-5-ylmethyl)azetidin-3-yl)methyl)-9-methyl-2-(2-methyl-1H-benzo[d]imidazol-1-yl)-9H-purin-6-yl)morpholine 571

Following General Procedure C, 4-(8-(azetidin-3-ylmethyl)-9-methyl-2-(2-methyl-1H-benzo[d]imidazol-1-yl)-9H-purin-6-yl)morpholine and 5-(bromomethyl)isoxazole were reacted to give 571. LCMS m/z: 250.7 (2M+H+)

Example 572

(S)-4-(9-methyl-2-(2-methyl-1H-benzo[d]imidazol-1-yl)-8-((1-(tetrahydrofuran-3-yl)azetidin-3-yl)methyl)-9H-purin-6-yl)morpholine 572

Following General Procedure L, 4-(8-(azetidin-3-ylmethyl)-9-methyl-2-(2-methyl-1H-benzo[d]imidazol-1-yl)-9H-purin-6-yl)morpholine and dihydrofuran-3(2H)-one were reacted to give the racemic mixture. The enantiomers were separated by SFC to give 572. LCMS m/z: 245.2 (2M+H+)

Example 573

(R)-4-(9-methyl-2-(2-methyl-1H-benzo[d]imidazol-1-yl)-8-((1-(tetrahydrofuran-3-yl)azetidin-3-yl)methyl)-9H-purin-6-yl)morpholine 573

Following General Procedure L, 4-(8-(azetidin-3-ylmethyl)-9-methyl-2-(2-methyl-1H-benzo[d]imidazol-1-yl)-

9H-purin-6-yl)morpholine and dihydrofuran-3(2H)-one were reacted to give the racemic mixture. The enantiomers were separated by SFC to give 573. LCMS m/z: 245.2 (2M+H+)

Example 575

4-(8-(2-(3,3-dimethyl-4-(methylsulfonyl)piperazin-1-yl)ethyl)-2-(2-ethyl-1H-benzo[d]imidazol-1-yl)-9-methyl-9H-purin-6-yl)morpholine 575

A mixture of 2-chloro-8-[2-(4-methanesulfonyl-3,3-dimethylpiperazin-1-yl)ethyl]-9-methyl-6-morpholin-4-yl-9H-purine (35 mg, 0.07 mmol), 2-ethylbenzimidazole (12 mg, 0.08 mmol), Pd$_2$(dba)$_3$ (1.7 mg, 2.5 mol %), Xphos (3.5 mg, 10 mol %) and Cs$_2$CO$_3$ (36 mg, 0.11 mmol) in dioxane (1.5 mL) was purged with argon gas then heated at 120° C., for 24 h, in a sealed tube. The reaction mixture was loaded onto an Isolute® SCX-2 cartridge, washed with MeOH then the desired product eluted with 2 M NH$_3$/MeOH in DCM. The resulting residue was purified by reverse phase HPLC (Phenomenex Gemini 5 µm C18, 20 mM triethylamine in water on a gradient of acetonitrile 30-90%) to give 575 (20 mg, 46%) as a pale beige solid. LCMS: (Method I): R$_T$ 2.74 min, [M+H]$^+$ 582.2 $^1$H NMR (400 MHz, CDCl$_3$d): δ 8.01-7.96 (m, 1 H), 7.79-7.75 (m, 1 H), 7.28-7.25 (m, 2 H), 4.50-3.96 (m, 4 H), 3.86 (t, J=4.7 Hz, 4 H), 3.78 (s, 3 H), 3.50-3.44 (m, 2 H), 3.36 (q, J=7.4 Hz, 2 H), 3.04 (t, J=7.4 Hz, 2 H), 2.94 (s, 3 H), 2.87 (t, J=7.4 Hz, 2 H), 2.64-2.58 (m, 2 H), 2.38 (s, 2 H), 1.50 (s, 6 H), 1.45 (t, J=7.4 Hz, 3 H)

Example 576

4-(8-((4-(3,3-difluoroazetidin-1-yl)piperidin-1-yl) methyl)-2-(2-ethyl-1H-benzo[d]imidazol-1-yl)-9-methyl-9H-purin-6-yl)morpholine 576

A mixture of 2-(2-ethylbenzoimidazol-1-yl)-9-methyl-6-morpholin-4-yl-9H-purine-8-carbaldehyde (0.139 g, 0.36 mmol), 4-(3,3-difluoroazetidin-1-yl)piperidine (0.075 g, 0.43 mmol) and 4 Å molecular sieves (0.4 g) in DCE (5 mL). The reaction mixture was stirred for 3 h at room temperature. Sodium triacetoxyborohydride (0.15 g, 0.71 mmol) was added and the reaction mixture was stirred for 72 h at room temperature. The suspension was filtered through Celite and the filtrate was concentrated in vacuo. The residue was purified by flash chromatography (Si—PPC, MeOH:DCM, gradient 0:100 to 12:88) followed by reverse phase HPLC (Phenomenex Gemini 5u C18, 20 mM triethylamine in water on a gradient of acetonitrile 95:5 to 2:98) to give 576 as an off-white solid (0.104 g, 53%). LCMS (Method I): R$_T$=2.61 min, [M+H]$^+$ 552.2 $^1$H NMR (400 MHz, DMSO-d$_6$): δ 8.03-7.99 (m, 1 H), 7.65-7.61 (m, 1 H), 7.27-7.20 (m, 2 H), 4.60-3.95 (s, 4 H), 3.81 (s, 3 H), 3.80-3.74 (m, 6 H), 3.52 (t, J=12.3 Hz, 4 H), 3.27 (q, J=7.4 Hz, 2 H), 2.79-2.70 (m, 2 H), 2.20-2.10 (m, 3 H), 1.68-1.59 (m, 2 H), 1.34 (t, J=7.4 Hz, 3 H), 1.30-1.17 (m, 2 H)

Example 577

1-tert-butyl-4-((2-(2-ethyl-1H-benzo[d]imidazol-1-yl)-9-methyl-6-morpholino-9H-purin-8-yl)methyl) piperazin-2-one 577

A mixture of 2-(2-ethylbenzoimidazol-1-yl)-9-methyl-6-morpholin-4-yl-9H-purine-8-carbaldehyde (0.15 g, 0.39 mmol), 1-tert-butylpiperazin-2-one (0.072 g, 0.46 mmol) and 4 Å molecular sieves (0.4 g) in DCE (5 mL) was stirred for 4 h at room temperature. Sodium triacetoxyborohydride (0.163 g, 0.77 mmol) was added and the reaction mixture was stirred for 18 h at room temperature. The reaction mixture was filtered through Celite and the filtrate was concentrated in vacuo. The residue was purified by flash chromatography (Si—PPC, MeOH:DCM, gradient 0:100 to 5:95) to give 577 as a white solid (0.178 g, 87%). LCMS (Method I): R$_T$=3.59 min, [M+H]$^+$ 532.2 $^1$H NMR (400 MHz, DMSO-d$_6$): δ 8.03-7.98 (m, 1 H), 7.65-7.60 (m, 1 H), 7.26-7.21 (m, 2 H), 4.50-3.95 (m, 5 H), 3.83-3.79 (m, 6 H), 3.78 (m, 4 H), 3.27 (q, J=7.4 Hz, 2 H), 3.08 (s, 2 H), 2.69-2.64 (m, 2 H), 1.36 (s, 9 H), 1.34 (t, J=7.4 Hz, 3 H)

Example 578

(S)-2-amino-1-(4-((9-methyl-2-(2-methyl-1H-benzo [d]imidazol-1-yl)-6-morpholino-9H-purin-8-yl)methyl)piperidin-1-yl)propan-1-one 578

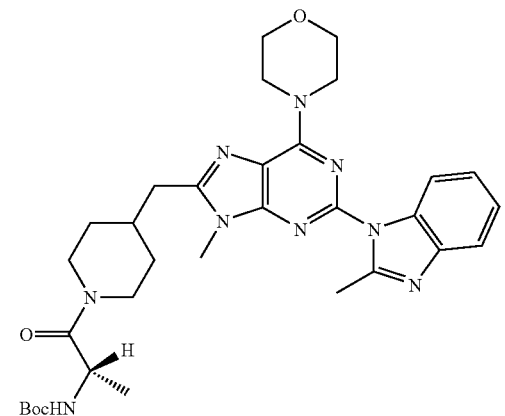

To a solution of N-(tert-Butoxycarbonyl)-L-alanine (80.0 mg, 0.423 mmol) in N,N-Dimethylformamide (5.0 mL, 0.064 mol) was added HATU (0.154 g, 0.404 mmol), 1-hydroxybenzotriazole (HOBt, 0.00839 g, 0.0621 mmol) and triethylamine (0.10 mL, 0.72 mmol). The resulting yellow solution was stirred at room temperature for 5 minutes before the addition of 4-(9-methyl-2-(2-methyl-1H-benzo[d]imidazol-1-yl)-8-(piperidin-4-ylmethyl)-9H-purin-6-yl)morpholine 520 (0.150 g, 0.310 mmol;). The reaction was stirred at room temperature for 2 hours. The reaction mixture was partitioned between brine and EtOAc. The organic extract was washed with brine, dried over Na$_2$SO$_4$, filtered and concentrated. The crude product was purified by flash chromatography (0-5% MeOH in DCM) to give tert-butyl 4-((9-methyl-2-(2-methyl-1H-benzo[d]imidazol-1-yl)-6-morpholino-9H-purin-8-yl) methyl)piperidine-1-carboxylate (0.15 g, 78%). LCMS m/z: 618.3 (MH+).

To a solution of tert-butyl 4-((9-methyl-2-(2-methyl-1H-benzo[d]imidazol-1-yl)-6-morpholino-9H-purin-8-yl)methyl)piperidine-1-carboxylate (0.18 g, 0.29 mmol) in dioxane (5 mL) was added a 2M HCl solution in ether (1 mL). The reaction was then stirred at room temperature for 1 hour before being concentrated. The crude was purified by RP-HPLC to give 578 (75 mg, 50%). LCMS m/z: 259.7 (2M+H+)

Example 579

3-methyl-2-(3-((9-methyl-2-(2-methyl-1H-benzo[d]imidazol-1-yl)-6-morpholino-9H-purin-8-yl)methyl)azetidin-1-yl)butanamide 579

Step 1: ethyl 3-methyl-2-(3-((9-methyl-2-(2-methyl-1H-benzo[d]imidazol-1-yl)-6-morpholino-9H-purin-8-yl)methyl)azetidin-1-yl)butanoate

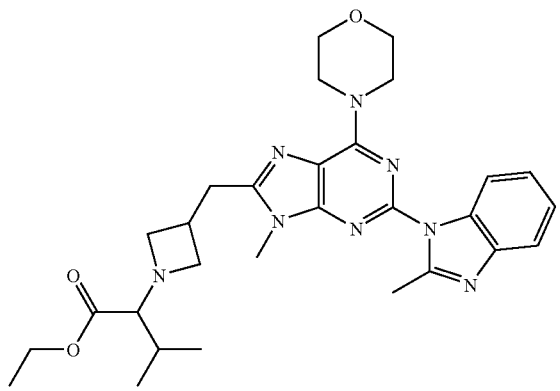

Ethyl 3-methyl-2-(3-((9-methyl-2-(2-methyl-1H-benzo[d]imidazol-1-yl)-6-morpholino-9H-purin-8-yl)methyl)azetidin-1-yl)butanoate was synthesized according to General Procedure C using ethyl 2-bromo-3-methylbutanoate as the electrophile.

Step 2: 3-methyl-2-(3-((9-methyl-2-(2-methyl-1H-benzo[d]imidazol-1-yl)-6-morpholino-9H-purin-8-yl)methyl)azetidin-1-yl)butanoic acid

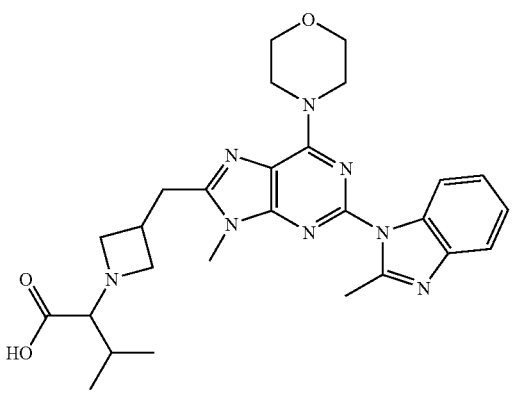

To a solution of ethyl 3-methyl-2-(3-((9-methyl-2-(2-methyl-1H-benzo[d]imidazol-1-yl)-6-morpholino-9H-purin-8-yl)methyl)azetidin-1-yl)butanoate (0.180 g, 0.329 mmol) in ethanol (1.0 mL, 17 mmol) was added 1.0 M of lithium hydroxide in water (2.0 mL). The resulting mixture was stirred at room temperature for 2 hours. The reaction mixture was neutralized with 1M HCl and concentrated. The residue was re-dissolved in MeOH and loaded onto a SCX-2 column. The column was first washed with MeOH. The product was then eluted with 2M NH$_3$ in MeOH and concentrated. LCMS m/z: 519.3 (MH+)

Step 3: 3-methyl-2-(3-((9-methyl-2-(2-methyl-1H-benzo[d]imidazol-1-yl)-6-morpholino-9H-purin-8-yl)methyl)azetidin-1-yl)butanamide 579

Following General Procedure K, 3-methyl-2-(3-((9-methyl-2-(2-methyl-1H-benzo[d]imidazol-1-yl)-6-morpholino-9H-purin-8-yl)methyl)azetidin-1-yl)butanoic acid and ammonium hydroxide were coupled to give 579. LCMS m/z: 259.7 (2M+H+)

Example 580

N,2-dimethyl-2-(3-((9-methyl-2-(2-methyl-1H-benzo[d]imidazol-1-yl)-6-morpholino-9H-purin-8-yl)methyl)azetidin-1-yl)propanamide 580

Following General Procedure C, 4-(8-(azetidin-3-ylmethyl)-9-methyl-2-(2-methyl-1H-benzo[d]imidazol-1-yl)-9H-purin-6-yl)morpholine and 2-bromo-N,2-dimethylpropanamide were reacted to give 580. LCMS m/z: 259.7 (2M+H+)

Example 581

(S)-3-(2-(2-isopropyl-1H-benzo[d]imidazol-1-yl)-9-methyl-6-morpholino-9H-purin-8-yl)-1-methylpiperidin-3-ol 581

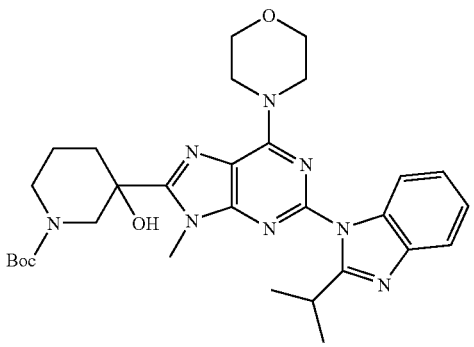

tert-Butyl 3-(2-chloro-9-methyl-6-morpholino-9H-purin-8-yl)-3-hydroxypiperidine-1-carboxylate (1 g) was reacted with 2-isopropylbenzimidazole via General Procedure I for Buchwald coupling to give 0.65 g of tert-butyl 3-hydroxy-3-(2-(2-isopropyl-1H-benzo[d]imidazol-1-yl)-9-methyl-6-morpholino-9H-purin-8-yl)piperidine-1-carboxylate following flash column chromatography.

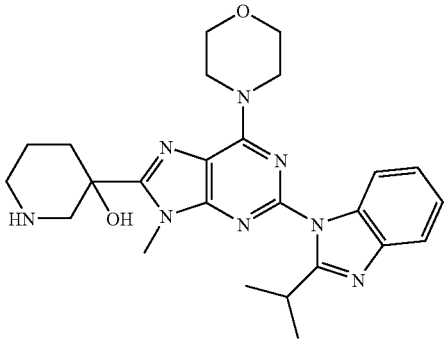

To a solution of tert-butyl 3-hydroxy-3-(2-(2-isopropyl-1H-benzo[d]imidazol-1-yl)-9-methyl-6-morpholino-9H-purin-8-yl)piperidine-1-carboxylate in DCM (7 mL) at ambient temperature was added 4 M Hydrogen Chloride in 1,4-Dioxane (2.8 mL) Upon completion the reaction mixture was concentrated to dryness to get the crude HCl salt of 3-(2-(2-isopropyl-1H-benzo[d]imidazol-1-yl)-9-methyl-6-morpholino-9H-purin-8-yl)piperidin-3-ol.

The HCl salt of 3-(2-(2-isopropyl-1H-benzo[d]imidazol-1-yl)-9-methyl-6-morpholino-9H-purin-8-yl)piperidin-3-ol (80 mg) was reacted with isopropyl iodide (1.5 eq) and potassium carbonate (5 eq) in a 1:1 mixture of DMF and Acetonitrile (2 mL). The reaction was heated at 75° C. for 18 hours until complete. The reaction mixture was diluted with Ethyl acetate and extracted with a saturated ammonium chloride solution. The organic layer was dried, filtered and concentrated to give 581 [4.6 mg; MS (Q1) 491.3 (M)+] and 582 [4.7 mg; MS (Q1) 491.3 (M)+] following reverse phase purification and subsequent chiral separation.

Example 582

I-3-(2-(2-isopropyl-1H-benzo[d]imidazol-1-yl)-9-methyl-6-morpholino-9H-purin-8-yl)-1-methylpiperidin-3-ol 582

The HCl salt of 3-(2-(2-isopropyl-1H-benzo[d]imidazol-1-yl)-9-methyl-6-morpholino-9H-purin-8-yl)piperidin-3-ol (80 mg) was reacted with isopropyl iodide (1.5 eq) and potassium carbonate (5 eq) in a 1:1 mixture of DMF and Acetonitrile (2 mL). The reaction was heated at 75° C. for 18 hours until complete. The reaction mixture was diluted with Ethyl acetate and extracted with a saturated ammonium chloride solution. The organic layer was dried, filtered and concentrated to give 581 [4.6 mg; MS (Q1) 491.3 (M)+] and 582 [4.7 mg; MS (Q1) 491.3 (M)+] following reverse phase purification and subsequent chiral separation.

Example 585

N,2-dimethyl-2-(4-((9-methyl-2-(2-methyl-1H-benzo[d]imidazol-1-yl)-6-morpholino-9H-purin-8-yl)methyl)piperidin-1-yl)propanamide 585

Following General Procedure C, 4-(9-methyl-2-(2-methyl-1H-benzo[d]imidazol-1-yl)-8-(piperidin-4-ylmethyl)-9H-purin-6-yl)morpholine and 2-bromo-N,2-dimethylpropanamide were reacted to give 585. LCMS m/z: 273.8 (2M+H+)

Example 586

(S)-4-(2-(2-ethyl-1H-benzo[d]imidazol-1-yl)-8-((3-(3-fluoropyrrolidin-1-yl)azetidin-1-yl)methyl)-9-methyl-9H-purin-6-yl)morpholine 586

A mixture of 2-(2-ethylbenzoimidazol-1-yl)-9-methyl-6-morpholin-4-yl-9H-purine-8-carbaldehyde (0.245 g, 0.627 mmol), (S)-1-azetidin-3-yl-3-fluoropyrrolidine (0.109 g, 0.752 mmol) and 4 Å molecular sieves (0.5 g) in DCE (5 mL). The reaction mixture was stirred for 90 min at room temperature. Sodium triacetoxyborohydride (0.266 g, 1.254 mmol) was added and the reaction mixture was stirred for 18 h at room temperature. The suspension was filtered through Celite and the filtrate was concentrated in vacuo. The residue was purified by flash chromatography (Si—PPC, MeOH:DCM, gradient 0:100 to 20:80) followed by reverse phase HPLC (Phenomenex Gemini 5u C18, 20 mM triethylamine in water on a gradient of acetonitrile 95:5 to 2:98) to give 586 as an off-white solid (0.204 g, 63%). LCMS (Method I): $R_T$=2.46 min, [M+H]$^+$ 520.2 $^1$H NMR (400 MHz, DMSO-$d_6$): δ 8.03-7.99 (m, 1 H), 7.65-7.61 (m, 1 H), 7.27-7.21 (m, 2 H), 5.19 (dt, J=55.8, 5.4 Hz, 1 H), 4.50-3.95 (m, 4 H), 3.87 (s, 2 H), 3.81-3.72 (m, 7 H), 3.40 (dd, J=7.1, 6.1 Hz, 2 H), 3.26 (q, J=7.4 Hz, 2 H), 3.21-3.12 (m, 1 H), 3.12-3.03 (m, 2 H), 2.79-2.65 (m, 2 H), 2.64-2.51 (m, 1 H), 2.34-2.25 (m, 1 H), 2.15-2.03 (m, 1 H), 1.76-1.95 (m, 1 H), 1.33 (t, J=7.4 Hz, 3 H)

Example 587

1'-((2-(2-ethyl-1H-benzo[d]imidazol-1-yl)-9-methyl-6-morpholino-9H-purin-8-yl)methyl)-3-methyl-1,3'-biazetidin-3-ol 587

A mixture of 2-(2-ethylbenzoimidazol-1-yl)-9-methyl-6-morpholin-4-yl-9H-purine-8-carbaldehyde (0.092 g, 0.234 mmol), 3-methyl-[1,3']biazetidinyl-3-ol (0.040 g, 0.28 mmol) and 4 Å molecular sieves (0.25 g) in DCE (3 mL). The reaction mixture was stirred for 90 min at room temperature. Sodium triacetoxyborohydride (0.099 g, 0.47 mmol) was added and the reaction mixture was stirred for 18 h at room temperature. The suspension was filtered through Celite and the filtrate was concentrated in vacuo. The residue was purified by flash chromatography (Si—PPC, MeOH:DCM, gradient 0:100 to 10:90) to give 587 as a white solid (0.107 g, 89%). LCMS (Method I): $R_T$=2.33 min, [M+H]$^+$ 518.2 $^1$H NMR (300 MHz, DMSO-$d_6$): δ 8.03-7.99 (m, 1 H), 7.65-7.61 (m, 1 H), 7.27-7.22 (m, 2 H), 4.49-3.95 (m, 4 H), 3.84 (s, 2 H), 3.80-3.74 (m, 4 H), 3.36-3.31 (s, 3 H), 3.31-3.20 (m, 6 H), 3.11-3.01 (m, 4 H), 2.98-2.93 (m, 2 H), 1.34 (m, 5 H)

Example 588

1-(1-((2-(2-ethyl-1H-benzo[d]imidazol-1-yl)-9-methyl-6-morpholino-9H-purin-8-yl)methyl)azetidin-3-yl)pyrrolidin-2-one 588

A mixture of 2-(2-ethylbenzoimidazol-1-yl)-9-methyl-6-morpholin-4-yl-9H-purine-8-carbaldehyde (165 mg, 0.42 mmol), 1-azetidin-3-ylpyrrolidin-2-one (65 mg, 0.46 mmol) and 4 Å powdered molecular sieves in DCE (4 mL) was stirred at room temperature for 2 h before the addition of sodium triacetoxyborohydride (180 mg, 0.84 mmol). The reaction mixture was stirred for 65 h then filtered through celite, washing with DCM. The organic phase was washed with brine and concentrated in vacuo. The organic phase was dried ($Na_2SO_4$) and concentrated in vacuo. The resulting residue was purified by column chromatography (Si—PCC, MeOH:EtOAc, 0-15%) affording 588 as an orange foam (138 mg, 64%). LCMS (method I): $R_T$ 2.42 min [M+H]$^+$ 516.2 $^1$H NMR (CDCl$_3$, 300 MHz): δ 8.00 (m, 1 H), 7.76 (m, 1 H), 7.27 (m, 2 H), 4.83 (t, J=6.9 Hz, 1 H), 4.35 (m, 4 H), 3.89-3.82 (m, 9 H), 3.67-3.54 (m, 4 H), 3.36 (m, 4 H), 2.42 (t, J=8.1 Hz, 2 H), 2.07 (m, 2 H) and 1.45 (t, J=7.5 Hz, 3 H)

Example 589

4-(8-((3-(3,3-difluoropyrrolidin-1-yl)azetidin-1-yl)methyl)-2-(2-ethyl-1H-benzo[d]imidazol-1-yl)-9-methyl-9H-purin-6-yl)morpholine 589

A mixture of 2-(2-ethylbenzoimidazol-1-yl)-9-methyl-6-morpholin-4-yl-9H-purine-8-carbaldehyde (100 mg, 0.26 mmol), 1-azetidin-3-yl-3,3-difluoropyrrolidine (46 mg, 0.28 mmol) and 4 Å powdered molecular sieves in DCE (6 mL) was stirred at room temperature for 2 h before the addition of sodium triacetoxyborohydride (108 mg, 0.52 mmol). The reaction mixture was stirred for 16 h then filtered through celite, washing with DCM. The organic phase was washed with brine and concentrated in vacuo. The organic phase was dried ($Na_2SO_4$) and concentrated in vacuo. The resulting residue was purified by column chromatography (Si—PCC, MeOH:EtOAc, 0-10%) affording 589 as an orange foam (97 mg, 69%). LCMS (method I): $R_T$ 2.74 min [M+H]$^+$ 538.2 $^1$H NMR (CDC$_3$, 300 MHz): δ 8.00 (m, 1 H), 7.75 (m, 1 H), 7.27 (m, 2 H), 4.42-4.27 (m, 4 H), 3.87-3.84 (m, 9 H), 3.54 (t, J=6.5 Hz, 2 H), 3.32-3.30 (m, 3 H), 3.19 (t, J=6.5 Hz, 2 H), 2.89 (t, J=13.1 Hz, 2 H), 2.70 (t, J=6.9 Hz, 2 H), 2.29-2.28 (m, 2 H) and 1.44 (t, J=7.5 Hz, 3 H)

Example 590

I-4-(2-(2-ethyl-1H-benzo[d]imidazol-1-yl)-8-((3-(3-fluoropyrrolidin-1-yl)azetidin-1-yl)methyl)-9-methyl-9H-purin-6-yl)morpholine 590

A mixture of 2-(2-ethylbenzoimidazol-1-yl)-9-methyl-6-morpholin-4-yl-9H-purine-8-carbaldehyde (0.188 g, 0.479 mmol), I-1-azetidin-3-yl-3-fluoropyrrolidine (0.083 g, 0.575 mmol) and 4 Å molecular sieves (0.4 g) in DCE (4 mL). The reaction mixture was stirred for 3 h at room temperature. Sodium triacetoxyborohydride (0.203 g, 0.959 mmol) was added and the reaction mixture was stirred for 72 h at room temperature. The suspension was filtered through Celite and the filtrate was concentrated in vacuo. The residue was purified by flash chromatography (Si—PPC, MeOH:EtOAc, gradient 0:100 to 40:60) to give 590 as a yellow solid (0.2 g, 81%). LCMS (Method I): $R_T$=2.46 min, [M+H]$^+$ 520.2 $^1$H NMR (400 MHz, DMSO-d$_6$): δ 8.03-7.99 (m, 1 H), 7.65-7.61 (m, 1 H), 7.27-7.21 (m, 2 H), 5.19 (dt, J=55.8, 5.4 Hz, 1 H), 4.50-3.95 (m, 4 H), 3.87 (s, 2 H), 3.82-3.72 (m, 7 H), 3.40 (dd, J=7.1, 6.1 Hz, 2 H), 3.26 (q, J=7.4 Hz, 2 H), 3.22-3.12 (m, 1 H), 3.10-2.95 (m, 2 H), 2.79-2.64 (m, 2 H), 2.64-2.50 (m, 1 H), 2.34-2.25 (m, 1 H), 2.18-2.02 (m, 1 H), 1.94-1.78 (m, 1 H), 1.33 (t, J=7.4 Hz, 3 H)

Example 595

N-(2-(2-(2-ethyl-1H-benzo[d]imidazol-1-yl)-9-methyl-6-morpholino-9H-purin-8-yl)ethyl)tetrahydro(1,1-dioxo)thiophen-3-amine 595

A mixture of [2-(2-chloro-9-methyl-6-morpholin-4-yl-9H-purin-8-yl)-ethyl]-(1,1-dioxo-tetrahydro-1-thiophen-3-yl)amine (45 mg, 0.11 mmol), 2-ethylbenzimidazole (18 mg, 0.12 mmol), Pd$_2$(dba)$_3$ (2.5 mg, 2.5 mol %), Xphos (5.2 mg, 10 mol %) and Cs$_2$CO$_3$ (53 mg, 0.16 mmol) in dioxane (1.5 mL) was purged with argon gas then heated at 120° C., for 4 h, in a sealed tube. The reaction mixture was loaded onto an Isolute® SCX-2 cartridge, washed with MeOH then the desired product eluted with 2 M NH$_3$/MeOH in DCM. The resulting residue was purified by column chromatography (Si—PCC, 0-10% MeOH in DCM) to give 595 (35 mg, 62%) as a pale yellow solid. LCMS: (Method I): $R_T$ 2.43 min, [M+H]$^+$ 525.2 $^1$H NMR (300 MHz, CDCl$_3$d): δ 8.02-7.98 (m, 1 H), 7.78-7.74 (m, 1 H), 7.31-7.23 (m, 2 H), 4.50-4.95 (m, 4 H), 3.87 (t, J=4.7 Hz, 4 H), 3.76 (s, 3 H), 3.73-3.67 (m, 1 H), 3.40-3.24 (m, 4 H), 3.23-3.14 (m, 2 H), 3.14-3.00 (m, 4 H), 2.94 (dd, J=13.2, 6.0 Hz, 1 H), 2.49-2.45 (m, 1 H), 2.15-2.05 (m, 1 H), 1.44 (t, J=7.5 Hz, 3 H)

Example 596

4-(8-((2,2-dimethyl-4-(methylsulfonyl)piperazin-1-yl)methyl)-2-(2-ethyl-1H-benzo[d]imidazol-1-yl)-9-methyl-9H-purin-6-yl)morpholine 596

A solution of 2-(2-ethylbenzoimidazol-1-yl)-9-methyl-6-morpholin-4-yl-9H-purine-8-carbaldehyde (167 mg, 0.43 mmol), 1-methanesulfonyl-3,3-dimethylpiperazine (100 mg, 0.52 mmol) and molecular sieves (4 Å, powdered, 830 mg) in DCE (10 mL) was stirred at ambient temperature for 5 h. Sodium triacetoxyborohydride (136 mg, 0.64 mmol) was added and the mixture stirred for 17 h, then loaded onto an Isolute® SCX-2 cartridge (10 g). The cartridge was then washed with methanol and the desired product was subsequently eluted using 2 M NH$_3$ in MeOH. The product was collected and concentrated in vacuo. The resultant residue was purified by flash chromatography (Si—PPC, DCM:MeOH, 100:0 to 99:1 to 98:2 to 95:5) followed by reverse phase HPLC (Phenomenex Gemini 5u C18, 20 mM triethylamine in water on a gradient of acetonitrile 51:49 to 49:51) to afford 596 as a cream foam (31 mg, 13%). LCMS (method I): $R_T$=3.42 min, M+H$^+$=568. $^1$H NMR (CDCl$_3$, 400 MHz) δ 8.01 (m, 1 H), 7.77 (m, 1 H), 7.26 (m, 2 H), 4.34 (m, 4 H), 3.87 (m, 9 H), 3.36 (q, J=7.5 Hz, 2 H), 3.16 (m, 2 H), 3.02 (s, 2 H), 2.77 (s, 3 H), 2.64 (m, 2 H), 1.46 (t, J=7.5 Hz, 3 H) and 1.29 (s, 6 H)

Example 597

2-((1S,4S)-5-((2-(2-ethyl-1H-benzo[d]imidazol-1-yl)-9-methyl-6-morpholino-9H-purin-8-yl)methyl)-2,5-diazabicyclo[2.2.1]heptan-2-yl)acetamide 597

Triethylamine (85 µL, 0.61 mmol) was added to a solution of 8-[(1S,4S)-1-(2,5-diazabicyclo[2.2.1]hept-2-yl)methyl]-2-(2-ethylbenzoimidazol-1-yl)-9-methyl-6-morpholin-4-yl-9H-purine (250 mg, 0.53 mmol) and 2-chloroacetamide (60 mg, 0.64 mmol) in DCM (10 mL) The mixture was stirred at ambient temperature for 24 h, then loaded onto an Isolute® SCX-2 cartridge (10 g). The cartridge was then washed with methanol and the desired product was subsequently eluted using 2 M NH$_3$ in MeOH. The product was collected and concentrated in vacuo. The resultant residue was purified by flash chromatography (Si—PPC, DCM:MeOH, 100:0 to 99:1 to 98:2) to afford 597 as a cream solid (175 mg, 62%). LCMS (method I): $R_T$=2.35 min, M+H$^+$=531. $^1$H NMR (CDCl$_3$, 400 MHz) δ 12.12 (bs, 1 H), 8.01 (m, 1 H), 7.77 (m, 1 H), 7.26 (m, 2 H), 5.62 (bs, 1 H), 4.34 (m, 4 H), 3.92-3.83 (m, 9 H), 3.54 (m, 2 H), 3.37 (q, J=7.4 Hz, 2 H), 3.09 (m, 4 H), 2.93 (m, 2 H), 2.00 (m, 2 H) and 1.42 (t, J=7.4 Hz, 3 H)

Example 598

4-(2-(2-ethyl-1H-benzo[d]imidazol-1-yl)-9-methyl-8-(((1S,4S)-5-(oxetan-3-yl)-2,5-diazabicyclo[2.2.1]heptan-2-yl)methyl)-9H-purin-6-yl)morpholine 598

A solution of of 8-[(1S,4S)-1-(2,5-diazabicyclo[2.2.1]hept-2-yl)methyl]-2-(2-ethyl-benzoimidazol-1-yl)-9-methyl-6-morpholin-4-yl-9H-purine (250 mg, 0.53 mmol), oxetan-3-one (40 mg, 0.31 mmol) and molecular sieves (4 Å, powdered, 200 mg) in DCE (7 mL) was stirred at ambient temperature for 4 h. Sodium triacetoxyborohydride (148 mg, 0.70 mmol) was added and the mixture stirred for 16 h, then loaded onto an Isolute® SCX-2 cartridge (10 g). The cartridge was then washed with methanol and the desired product was subsequently eluted using 2 M NH$_3$ in MeOH. The product was collected and concentrated in vacuo. The resultant residue was purified by flash chromatography (Si—PPC, DCM:MeOH, gradient from 100:0 to 90:0) to afford 598 as a white solid (125 mg, 45%). LCMS (method I): $R_T$=2.39 min, M+H$^+$=530. $^1$H NMR (CDCl$_3$, 400 MHz) δ 8.02 (m, 1 H), 7.76 (m, 1 H), 7.26 (m, 2 H), 4.72-4.65 (m, 4 H), 4.34 (m, 4 H), 4.01-3.86 (m, 10 H), 3.35 (m, 4 H), 2.99 (m, 1 H), 2.82 (m, 1 H), 2.76 (m, 2 H), 1.79 (m, 2 H) and 1.45 (t, J=7.5 Hz, 3 H)

Example 607

N-(2-(2-(2-ethyl-1H-benzo[d]imidazol-1-yl)-9-methyl-6-morpholino-9H-purin-8-yl)ethyl)-N-methyl-1,1-dioxo-tetrahydrothiophen-3-amine 607

To a solution of (1,1-dioxo-tetrahydro-1-thiophen-3-yl)-{2-[2-(2-ethylbenzoimidazol-1-yl)-9-methyl-6-morpholin-4-yl-9H-purin-8-yl]ethyl}amine (31 mg, 0.06 mmol) in DCE (5 mL) was added formaldehyde (37 wt. % in water, 50 µL, 0.67 mmol). The reaction mixture was stirred at room temperature for 5 h, sodium triacetoxyborohydride (25 mg, 0.12 mmol) was added and the resulting mixture stirred for a further 16 h. The reaction mixture was loaded onto an Isolute® SCX-2 cartridge, washed with MeOH then the desired product eluted with 2 M $NH_3$ in MeOH. The resulting residue was purified by column chromatography (Si—PCC, 0-10% MeOH in DCM) to give 607 as an off white solid (21 mg, 66%). LCMS (Method I): $R_T$=2.55 min, [M+H]$^+$ 539.14 $^1$H NMR (400 MHz, CDCl$_3$d): δ 8.02-7.97 (m, 1 H), 7.80-7.75 (m, 1 H), 7.34-7.24 (m, 2 H), 4.49-3.5 (m 4 H), 3.87 (t, J=4.7 Hz, 4 H), 3.77 (s, 3 H), 3.59-3.49 (m, 1 H), 3.37 (q, J=7.5 Hz, 2 H), 3.25 (dd, J=13.2 7.7 Hz, 2 H), 3.10-2.98 (m, 6 H), 2.42 (s, 3 H), 2.40-2.32 (m, 1 H), 2.21-2.11 (m, 1 H), 1.45 (t, J=7.5 Hz, 3 H)

Example 608

4-(2-(2-ethyl-1H-benzo[d]imidazol-1-yl)-8-((4-(3-fluoroazetidin-1-yl)piperidin-1-yl)methyl)-9-methyl-9H-purin-6-yl)morpholine 608

A mixture of 2-(2-ethylbenzoimidazol-1-yl)-9-methyl-6-morpholin-4-yl-9H-purine-8-carbaldehyde (0.155 g, 0.395 mmol), 4-(3-fluoroazetidin-1-yl)piperidine (0.075 g, 0.474 mmol) and 4 Å molecular sieves (0.5 g) in DCE (6 mL) was stirred for 3 h at room temperature. Sodium triacetoxyborohydride (0.168 g, 0.79 mmol) was added and the reaction mixture was stirred for 72 h at room temperature. The reaction mixture was filtered through Celite and the filtrate was concentrated in vacuo. The residue was purified by flash chromatography (Si—PPC, MeOH:DCM, gradient 0:100 to 15:85) to give 608 as a white solid (0.177 g, 84%). LCMS (Method I): $R_T$=2.25 min, [M+H]$^+$ 534.2 $^1$H NMR (400 MHz, DMSO-d$_6$): δ 8.03-7.98 (m, 1 H), 7.65-7.60 (m, 1 H), 7.27-7.21 (m, 2 H), 5.20-5.00 (m, 1 H), 4.50-3.96 (m, 4 H), 3.80 (s, 3 H), 3.80-3.74 (m, 4 H), 3.75 (s, 2 H), 3.56-3.45 (m, 2 H), 3.26 (q, J=7.4 Hz, 2 H), 3.06-2.94 (m, 2 H), 2.78-2.68 (m, 2 H), 2.19-2.09 (m, 2 H), 2.07 (s, 1 H), 1.66-1.57 (m, 2 H), 1.33 (t, J=7.4 Hz, 3 H), 1.25-1.12 (m, 2 H)

Example 646 tert-butyl 3-(2-(2-ethyl-1H-benzo[d]imidazol-1-yl)-9-methyl-6-morpholino-9H-purin-8-yl)pyrrolidine-1-carboxylate 646

A mixture of 3-(2-chloro-9-methyl-6-morpholin-4-yl-9H-purin-8-yl)-pyrrolidine-1-carboxylic acid tert-butyl ester (44 mg, 0.10 mmol), 2-ethylbenzimidazole (17 mg, 0.11 mmol), Pd$_2$(dba)$_3$ (2.4 mg, 2.5 mol %), Xphos (5.0 mg, 10 mol %) and Cs$_2$CO$_3$ (51 mg, 0.16 mmol) in dioxane (1.5 mL) was purged with argon gas then heated at 120° C., for 20 h, in a sealed tube. The reaction mixture was loaded onto an Isolute® SCX-2 cartridge, washed with MeOH then the desired product eluted with 2 M NH$_3$/MeOH in DCM. The resulting residue was purified by column chromatography (Si—PCC, 0-100% EtOAc in cyclohexane) to give 646 (37 mg, 67%) as a yellow solid. LCMS: (Method I): $R_T$ 4.34 min, [M+H]$^+$ 533.2 $^1$H NMR (400 MHz, CDCl$_3$d): δ 8.01-7.97 (m, 1 H), 7.78-7.73 (m, 1 H), 7.29-7.22 (m, 2 H), 4.55-4.10 (m, 4 H), 3.86 (t, J=4.67 Hz, 4 H), 3.80 (s, 3 H), 3.80-3.44 (m, 4 H), 3.35 (q, J=7.48 Hz, 2 H), 2.36 (s, 3 H), 1.49 (s, 9 H), 1.44 (t, J=7.48 Hz, 3 H)

Example 647 tert-butyl 4-(2-(2-ethyl-1H-benzo[d]imidazol-1-yl)-9-methyl-6-morpholino-9H-purin-8-yl)piperidine-1-carboxylate 647

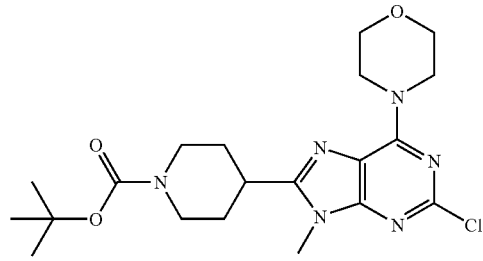

To a suspension of zinc powder (320 mg, 4.92 mmol) and Celpure P65 in anhydrous DMA (3 mL) was added a 7:5 (v:v) mixture of TMS-Cl:1,2-dibromoethane (65 µL) drop wise. The reaction mixture was stirred at room temperature for 15 min. A solution of 4-iodopiperidine-1-carboxylic acid tert-butyl ester (1.22 g, 3.95 mmol) in anhydrous DMA (2 mL) was added dropwise to the mixture described above and the reaction mixture was stirred for 30 minutes at room temperature. The zincate mixture was quickly filtered through a grade-3 sintered funnel and added onto a mixture of 2-Chloro-8-iodo-9-methyl-6-morpholin-4-yl-9H-purine (1.0 g, 2.63 mmol), Pd(dppf)Cl$_2$.DCM (107 mg, 0.13 mmol) and CuI (50 mg, 0.26 mmol). The vessel was then evacuated and back-filled with nitrogen. The resulting reaction mixture was stirred at 85° C. for 18 hours, after 3 hours additional Pd(dppf)Cl$_2$.DCM and CuI was added. The mixture was cooled to room temperature and partitioned between EtOAc and sat. aqueous solution of ammonium chloride. The organic layer was washed with water, brine, dried over Na$_2$SO$_4$, filtered and concentrated in vacuo. The residue was purified by column chromatography (cyclohexane:EtOAc, 20-70%) affording 4-(2-Chloro-9-methyl-6-morpholin-4-yl-9H-purin-8-yl)-piperidine-1-carboxylic acid tert-butyl ester as a solid (375 mg, 33%). LCMS (Method H): $R_T$ 4.57 min, [M+H]$^+$ 437.46 $^1$H NMR (400 MHz, CDCl$_3$): δ 4.40-4.15 (m, 6 H); 3.81 (t, J=12.1 Hz, 4 H); 3.71 (s, 3); 2.99-2.87 (m, 3 H); 1.94-1.85 (m, 4 H); 1.71-1.59 (m, 1 H); 1.48 (s, 9H).

A mixture of 4-(2-chloro-9-methyl-6-morpholin-4-yl-9H-purin-8-yl)piperidine-1-carboxylic acid tert-butyl ester (375 mg, 0.858 mmol), 2-ethylbenzimidazole (151 mg, 1.03 mmol), Xphos (43 mg, 0.09 mmol) and Cs$_2$CO$_3$ (421 mg, 1.29 mmol) in dioxane (5 mL) was degassed with nitrogen bubbling for 15 minutes. Tris(dibenzylideneacetone)dipalladium (20 mg, 0.022 mmol) was added and the mixture was heated to 120° C. for 20 hours. The reaction mixture was diluted with EtOAc, filtered, concentrated in vacuo and purified by column chromatography (Si—PCC, EtOAc:cyclohexane, 40-90%) affording 647 (390 mg, 83%). LCMS: $R_T$ 4.54 min, [M+H]⁺ 547.24 ¹H NMR (400 MHz, DMSO): δ 8.00-7.99 (m; 1 H); 7.68-7.60 (m; 1 H); 7.25-7.24 (m; 2 H); 4.45-4.12 (m; 4 H); 4.12-4.01 (d; J=13.26 Hz, 2 H); 3.85-3.70 (m; 6 H); 3.25-3.10 (m, 4 H); 3.04-2.82 (m, 2 H); 2.00-1.90 (d; J=13.26 Hz, 2 H); 1.76-1.59 (m, 2); 1.43 (s; 9 H); 1.35 (t, J=7.44 Hz, 3 H).

Example 648

4-((2-(2-ethyl-1H-benzo[d]imidazol-1-yl)-9-methyl-6-morpholino-9H-purin-8-yl)methyl)-3-isopropylpiperazin-2-one 648

A mixture of 4-(2-chloro-9-methyl-6-morpholin-4-yl-9H-purin-8-ylmethyl)-3-isopropylpiperazin-2-one (198 mg, 0.49 mmol), 2-ethylbenzimidazole (78 mg, 0.53 mmol), Pd₂(dba)₃ (11.1 mg, 2.5 mol %), Xphos (23.1 mg, 10 mol %) and Cs₂CO₃ (237 mg, 0.16 mmol) in dioxane (4 mL) was purged with argon gas then heated at 110° C., for 17 h, in a sealed tube. The reaction mixture was loaded onto an Isolute® SCX-2 cartridge, washed with MeOH then the desired product eluted with 2 M NH₃/MeOH in DCM. The resulting residue was purified by column chromatography (Si—PCC, 0-10% MeOH in EtOAc) to give 648 (196 mg, 78%) as a white solid. LCMS: (Method I): $R_T$ 3.37 min, [M+H]⁺ 518.2 ¹H NMR (400 MHz, CDCl₃d): δ 8.05-8.00 (m, 1 H), 7.79-7.75 (m, 1 H), 7.30-7.23 (m, 2 H), 6.02 (s, 1 H), 4.50-3.96 (m, 4 H), 4.09 (d, J=13.6 Hz, 1 H), 3.94 (d, J=13.6 Hz, 1 H), 3.89 (s, 3 H), 3.87 (t, J=4.80 Hz, 4 H), 3.63-3.54 (m, 1 H), 3.37 (q, J=7.5 Hz, 2 H), 3.34-3.28 (m, 1 H), 3.13-3.04 (m, 1 H), 3.03 (d, J=5.5 Hz, 1 H), 2.74-2.66 (m, 1 H), 2.25-2.14 (m, 1 H), 1.46 (t, J=7.5 Hz, 3 H), 1.11 (d, J=6.8 Hz, 3 H), 1.03 (d, J=6.8 Hz, 3 H)

Example 649

4-((2-(2-ethyl-1H-benzo[d]imidazol-1-yl)-9-methyl-6-morpholino-9H-purin-8-yl)methyl)-3,3-dimethylpiperazin-2-one 649

A solution of 2-(2-ethylbenzoimidazol-1-yl)-9-methyl-6-morpholin-4-yl-9H-purine-8-carbaldehyde (250 mg, 0.64 mmol), 3,3-dimethylpiperazin-2-one (100 mg, 0.78 mmol) and molecular sieves (4 Å, powdered, 1 g) in DCE (15 mL) was stirred at ambient temperature for 4 h. Sodium triacetoxyborohydride (204 mg, 0.96 mmol) was added and the mixture stirred for 16 h, then loaded onto an Isolute® SCX-2 cartridge (10 g). The cartridge was then washed with methanol and the desired product was subsequently eluted using 2 M NH₃ in MeOH. The product was collected and concentrated in vacuo. The resultant residue was purified by flash chromatography (Si—PPC, DCM:MeOH, 100:0 to 98:2 to 95:5) to afford 649 as a yellow solid (34 mg, 11%). LCMS (method I): $R_T$=3.12 min, M+H⁺=504. ¹H NMR (CDCl₃, 400 MHz) δ 8.02 (m, 1 H), 7.79 (m, 1 H), 7.30 (m, 2 H), 5.75 (bs, 1 H), 4.34 (m, 4 H), 3.94 (s, 2 H), 3.92 (s, 3 H), 3.87 (m, 4 H), 3.38 (q, J=7.4 Hz, 2), 3.23 (m, 2 H), 2.80 (m, 2 H), 1.54 (s, 6 H) and, 1.47 (t, J=7.4 Hz, 3 H)

Example 677

2-(4-(2-(2-ethyl-1H-benzo[d]imidazol-1-yl)-9-methyl-6-morpholino-9H-purin-8-yl)piperidin-1-yl)acetamide 677

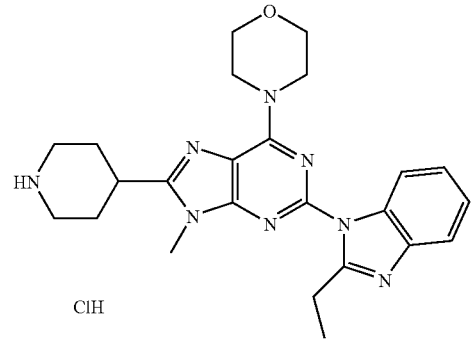

To a solution of 4-[2-(2-ethylbenzoimidazol-1-yl)-9-methyl-6-morpholin-4-yl-9H-purin-8-yl]piperidine-1-carboxylic acid tert-butyl ester (390 mg, 0.71 mmol) in DCM (20 mL) and MeOH (5 mL) was added 4M HCl in dioxane (20 mL). The resulting mixture was allowed to stir for 4 h at r.t. before Et₂O (80 mL) was added. The resulting precipitate was collected by filtration, washed with Et₂O and dried in vacuo affording 2-(2-Ethylbenzoimidazol-1-yl)-9-methyl-6-morpholin-4-yl-8-piperidin-4-yl-9H-purine hydrochloride (322 mg, 93%). LCMS (method I): $R_T$ 2.43 min [M+H]⁺ 447.2

A mixture of 2-(2-ethylbenzoimidazol-1-yl)-9-methyl-6-morpholin-4-yl-8-piperidin-4-yl-9H-purine hydrochloride (150 mg, 0.31 mmol), 2-bromoacetamide (45 mg, 0.33 mmol), sodium iodide (5 mg, 0.03 mmol) and K₂CO₃ (90 mg, 0.65 mmol) in MeCN (3 mL) was heated to 50° C. for 2 h in a sealed tube. The reaction mixture was diluted with EtOAc, filtered and concentrated in vacuo. The resulting residue was purified by column chromatography (Si—PCC, MeOH:EtOAc, 0-30%) affording 677 (119 mg, 76%). LCMS (method I): $R_T$ 2.40 min, [M+H]⁺ 504.2. ¹H NMR (DMSO, 400 MHz): δ 8.02-7.98 (1 H, m), 7.64-7.63 (1 H, m), 7.25-7.24 (4 H, m), 4.27 (4 H, brd s), 3.82-3.72 (7 H, m), 3.35-3.30 (2 H, m), 3.26 (2 H, q, J=7.45 Hz), 3.11-2.90 (4 H, m), 2.38-2.31 (1 H, m), 1.97 (4 H, s), 1.33 (3 H, t, J=7.44 Hz)

Example 678 tert-butyl 3-(2-(2-ethyl-1H-benzo[d]imidazol-1-yl)-9-methyl-6-morpholino-9H-purin-8-yl)azetidine-1-carboxylate 678

To a suspension of zinc powder (190 mg, 2.91 mmol) and Celpure® P65 (60 mg) in DMA (2 mL) was added a 7:5 (v:v) mixture of TMSCl:1,2-dibromoethane (38 μL) drop wise. The reaction mixture was stirred at room temperature for 15 min. A solution of 3-iodoazetidine-1-carboxylic acid tert-butyl ester from Example 1 (651 mg, 2.30 mmol) in DMA (2 mL) was added drop wise to the mixture described above. The resulting mixture was stirred for 1 hour at room temperature.

A mixture of 2-(2-ethylbenzoimidazol-1-yl)-8-iodo-9-methyl-6-morpholin-4-yl-9H-purine from Example 75mm (750 mg, 1.53 mmol), Pd(dppf)₂Cl₂.DCM (125 mg, 0.15 mmol)

and CuI (38 mg, 0.20 mmol) in DMA (9 mL) was purged with argon. The zincate mixture was added to the reaction mixture via a PTFE filter, and the resulting reaction mixture was stirred at 85° C. for 24 h. The reaction mixture was partitioned between EtOAc and H$_2$O. The organic phase was washed with H$_2$O (×3) and brine, then dried (Na$_2$SO$_4$) and concentrated in vacuo. The resulting residue was purified by column chromatography (Si—PCC, MeOH:DCM, 0-10% and MeOH:EtOAc, 0-5%) affording 678 as a solid (350 mg, 44%). LCMS (method I): R$_T$ 4.16 min, [M+H]$^+$ 519.2. $^1$H NMR (CDCl$_3$, 400 MHz): δ 8.0 (1 H, d, J=7.15 Hz), 7.76 (1 H, d, J=7.06 Hz), 7.32-7.23 (2 H, m), 4.57-4.24 (8 H, m), 4.00-3.99 (1 H, m), 3.88 (4 H, t, J=4.68 Hz), 3.69 (3 H, s), 3.35 (2 H, q, J=7.47 Hz), 1.48 (12 H, s).

Example 679

(R)-1-(3-((2-(2-ethyl-1H-benzo[d]imidazol-1-yl)-9-methyl-6-morpholino-9H-purin-8-yl)methyl)azetidin-1-yl)-2-hydroxypropan-1-one 679

To a mixture of 8-azetidin-3-ylmethyl-2-(2-ethylbenzoimidazol-1-yl)-9-methyl-6-morpholin-4-yl-9H-purine (57 mg, 0.13 mmol), D-lactic acid (14 mg, 0.16 mmol) and DIPEA (27 µL, 0.16 mmol) in DCM (2 mL) and DMF (1.5 mL) was added HATU (60 mg, 0.16 mmol). The resulting yellow mixture was stirred for 2 h at r.t. then partitioned between DCM and H$_2$O. The combined organic phases were dried (Na$_2$SO$_4$) and concentrated in vacuo. The resulting residue was purified by column chromatography (Si—PCC, MeOH:EtOAc, 0-10%) followed by Isolute® SCX-2 cartridge which was washed with MeOH/DCM and the product eluted with 2M NH$_3$/MeOH affording 679 as a cream foam (23 mg, 35%). LCMS: R$_T$ 2.92 min, [M+H]$^+$ 505.2. $^1$H NMR (CDCl$_3$, 400 MHz): δ 8.00-7.98 (1 H, m), 7.81-7.70 (1 H, m), 7.26 (2 H, s), 4.49-4.20 (7 H, m), 3.91 (1 H, dd, J=10.38, 5.67 Hz), 3.86 (5 H, t, J=4.71 Hz), 3.76-3.75 (3 H, m), 3.36-3.35 (4 H, m), 3.18-3.15 (2 H, m), 1.44 (3 H, t, J=7.46 Hz), 1.34 (3 H, dd, J=6.68, 4.79 Hz)

Example 680

4-(8-(azetidin-3-yl)-2-(2-ethyl-1H-benzo[d]imidazol-1-yl)-9-methyl-9H-purin-6-yl)morpholine 680

To a solution of 3-[2-(2-ethylbenzoimidazol-1-yl)-9-methyl-6-morpholin-4-yl-9H-purin-8-yl]azetidine-1-carboxylic acid tert-butyl ester 678 (325 mg, 0.63 mmol) in DCM (4 mL) was added TFA (2 mL) The resulting mixture was stirred for 2.5 h at r.t then loaded onto an Isolute® SCX-2 cartridge which was washed with MeOH/DCM and the product eluted with 2M NH$_3$/MeOH. The resulting residue was purified by column chromatography (Si—PCC, MeOH:DCM, 0-20%) affording 680 as a cream foam (224 mg, 85%). LCMS (method I): R$_T$ 2.30 min, [M+H]$^+$ 419.1. $^1$H NMR (CDCl$_3$, 400 MHz): δ 8.00-8.00 (1 H, m), 7.75-7.74 (1 H, m), 7.26 (2 H, s), 4.34-4.32 (7 H, m), 3.89-3.88 (6 H, m), 3.71-3.69 (3 H, m), 3.35-3.34 (2 H, m), 1.44-1.43 (3 H, m)

Example 681

1-((2-(2-ethyl-1H-benzo[d]imidazol-1-yl)-9-methyl-6-morpholino-9H-purin-8-yl)methyl)-3-isopropylpiperazin-2-one 681

To a solution of 4-[2-(2-ethylbenzoimidazol-1-yl)-9-methyl-6-morpholin-4-yl-9H-purin-8-ylmethyl]-2-isopropyl-3-oxopiperazine-1-carboxylic acid tert-butyl ester (104 mg, 0.17 mmol) in DCM (3 mL) was added TFA (1 mL) and the resulting mixture stirred for 2 h. The reaction mixture was loaded onto an Isolute® SCX-2 cartridge which was washed with MeOH/DCM and the product eluted with 2M NH$_3$/MeOH. The resulting residue was purified by column chromatography (Si—PCC, MeOH:DCM, 0-10%) affording 681 as an off-white solid (55 mg, 67%). LCMS (method I): R$_T$ 2.54 min, [M+H]$^+$ 518.2. $^1$H NMR (CDCl$_3$, 400 MHz): δ 8.00-8.00 (1 H, m), 7.76-7.76 (1 H, m), 7.32-7.22 (2 H, m), 4.95-4.79 (1 H, m), 4.35 (4 H, brd s), 3.90-3.82 (7 H, m), 3.47-3.45 (3 H, m), 3.35 (2 H, q, J=7.48 Hz), 3.23-3.22 (1 H, m), 3.02 (1 H, ddd, J=12.50, 11.03, 3.93 Hz), 2.57-2.56 (1 H, m), 1.44 (3 H, t, J=7.48 Hz), 1.21 (1 H, t, J=7.02 Hz), 1.04 (3 H, d, J=7.12 Hz), 0.93 (3 H, d, J=6.80 Hz)

Example 687

4-(1-((2-(imidazo[1,2-a]pyridin-5-yl)-4-morpholinothieno[3,2-d]pyrimidin-6-yl)methyl)piperidin-4-yl)morpholine 687

A mixture of 4-morpholin-4-yl-6-(4-morpholin-4-ylpiperidin-1-ylmethyl)-2-(tributylstannanyl)thieno[3,2-d]pyrimidine (69 mg, 0.10 mmol), 5-bromoimidazo[1,2-a]pyridine (24 mg, 0.12 mmol), Pd(PPh$_3$)$_4$ (11 mg, 0.01 mmol) and copper(I) iodide (23 mg, 0.12 mmol) in THF (1 mL) was purged with argon gas then heated at 140° C., for 20 min, in a microwave reactor. The reaction mixture was loaded onto an Isolute® SCX-2 cartridge (10 g). The cartridge was washed with MeOH then the product was eluted with 2 M NH$_3$ in MeOH. The appropriate fractions were evaporated and the resulting residue was purified by flash chromatography (Si—PPC, MeOH:DCM, gradient 0:100 to 3:97) followed by reverse phase HPLC (Phenomenex Gemini 5u C18, 20 mM triethylamine in water on a gradient of acetonitrile 70:30 to 2:98) to give 687 as a white solid (22 mg, 42%). LCMS (Method F): R$_T$ 3.90 min; [M+H]$^+$ 520. $^1$H NMR (400 MHz, CHCl$_3$-d): δ 9.23 (s, 1 H); 7.95 (dd, J=7.2, 1.2 Hz, 1 H); 7.77 (d, J=8.9 Hz, 1 H); 7.75 (d, J=1.2 Hz, 1 H); 7.35 (s, 1 H); 7.31 (dd, J=8.9, 7.2 Hz, 1 H); 4.07 (t, J=4.7 Hz, 4 H); 3.91 (t, J=4.7 Hz, 4 H); 3.84 (s, 2 H); 3.74 (t, J=4.4 Hz, 4 H); 3.05 (d, J=11.4 Hz, 2 H); 2.57 (t, J=4.4 Hz, 4 H); 2.29-2.19 (m,1 H); 2.15 (t, J=11.4 Hz, 2 H); 1.87 (d, J=12.5 Hz, 2 H); 1.65-1.59 (m, 2 H)

Example 688

1-((2-(imidazo[1,2-a]pyridin-5-yl)-4-morpholinothieno[3,2-d]pyrimidin-6-yl)methyl)-N,N-dimethylpiperidin-4-amine 688

A mixture of dimethyl-[1-(4-morpholin-4-yl-2-(tributylstannanyl)thieno[3,2-d]pyrimidin-6-ylmethyl)piperidin-4-yl]amine (156 mg, 0.24 mmol), 5-bromoimidazo[1,2-a]pyridine (56 mg, 0.29 mmol), Pd(PPh$_3$)$_4$ (28 mg, 0.02 mmol) and copper(I) iodide (55 mg, 0.29 mmol) in THF (2 5 mL) was purged with argon gas then heated at 140° C., for 20 min, in a microwave reactor. The reaction mixture was loaded onto an Isolute® SCX-2 cartridge (5 g), washed with MeOH then eluted with 2 M NH$_3$ in MeOH. The resulting residue was purified by flash chromatography (Si—PPC, MeOH:DCM, gradient 0:100 to 10:90) to give 688 as a white solid (72 mg, 63%). LCMS (Method F): R$_T$ 3.89 min; [M+H]$^+$ 478. $^1$H NMR (400 MHz, CHCl$_3$-d): δ 9.23 (s, 1 H); 7.95 (dd, J=8.6, 1.3 Hz, 1 H); 7.77 (d, J=8.6 Hz, 1 H); 7.75 (d, J=1.3 Hz, 1 H); 7.35 (s, 1 H); 7.32-7.29 (m, 1 H); 4.07 (t, J=4.8 Hz, 4 H); 3.91

(t, J=4.8 Hz, 4 H); 3.84 (s, 2 H); 3.04 (d, J=11.25 Hz, 2 H); 2.33-2.25 (m, 6 H); 2.21-2.10 (m, 3 H); 1.84 (d, J=12.5 Hz, 2 H); 1.61 (m, 2 H)

Example 689

5-(6-((4-(dimethylamino)piperidin-1-yl)methyl)-4-morpholinothieno[3,2-d]pyrimidin-2-yl)imidazo[1,2-a]pyridin-8-ol 689

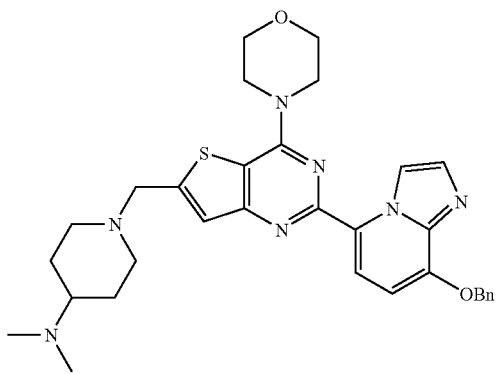

A mixture of dimethyl-[1-(4-morpholin-4-yl-2-(tributylstannanyl)thieno[3,2-d]pyrimidin-6-ylmethyl)piperidin-4-yl]amine (230 mg, 0.35 mmol), 8-benzyloxy-5-bromoimidazo[1,2-a]pyridine (127 mg, 0.42 mmol), Pd(PPh$_3$)$_4$ (40 mg, 0.035 mmol) and copper(I) iodide (66 mg, 0.35 mmol) in dioxane (3 mL) was purged with argon gas then heated at 140° C., for 20 min, in a microwave reactor. The reaction mixture was loaded onto an Isolute® SCX-2 cartridge (10 g). The cartridge was washed with MeOH then the desired product was eluted with 2 M NH$_3$ in MeOH. The appropriate fractions were combined and evaporated. The resulting residue was purified by flash chromatography (Si—PPC, MeOH:DCM, gradient 0:100 to 20:80) to give {1-[2-(8-Benzyloxyimidazo[1,2-a]pyridin-5-yl)-4-morpholin-4-yl-thieno[3,2-d]pyrimidin-6-ylmethyl]piperidin-4-yl}dimethylamine as a white solid (189 mg, 92%). LCMS (Method H): R$_T$ 3.07 min; [M+H]$^+$ 584

A mixture of {1-[2-(8-benzyloxyimidazo[1,2-a]pyridin-5-yl)-4-morpholin-4-yl-thieno[3,2-d]pyrimidin-6-ylmethyl]piperidin-4-yl}dimethylamine (381 mg, 0.65 mmol) in TFA was heated at 140° C., for 10 min, in a microwave reactor. The reaction mixture was loaded onto an Isolute® SCX-2 cartridge (10 g). The cartridge was washed with MeOH then the desired product was eluted with 2 M NH$_3$ in MeOH. The appropriate fractions were combined and evaporated. The resulting residue was purified by reverse phase HPLC (Phenomenex Gemini 5u C18, 20 mM triethylamine in water on a gradient of acetonitrile 95:5 to 2:98) to give 689 as a yellow solid (32 mg, 10%). LCMS (Method F) R$_T$ 3.98 min; [M+H]$^+$ 494. $^1$H NMR (400 MHz, CH$_3$OH-d): δ 9.43 (d, J=1.6 Hz, 1 H); 8.04 (d, J=8.2 Hz, 1 H); 7.65 (d, J=1.6 Hz, 1 H); 7.34 (s, 1 H); 6.71 (d, J=8.2 Hz, 1 H); 4.03 (t, J=4.7 Hz, 4 H); 3.87 (m, 7 H); 3.07 (d, J=11.5 Hz, 2 H); 2.37 (s, 6 H); 2.34 (m, 1 H); 2.16 (t, J=11.5 Hz, 2 H); 1.91 (d, J=12.3 Hz, 2 H); 1.66-1.54 (m, 2 H)

Example 690

2-(4-((2-([1,2,4]triazolo[4,3-a]pyridin-5-yl)-4-morpholinothieno[3,2-d]pyrimidin-6-yl)methyl)piperazin-1-yl)-2-methylpropanamide 690

A mixture of 2-[4-(4-morpholin-4-yl-2-(tributylstannanyl)thieno[3,2-d]pyrimidin-6-ylmethyl)piperazin-1-yl]isobutyramide (150 mg, 0.22 mmol), 5-bromo-[1,2,4]triazolo[4,3-a]pyridine (51 mg, 0.26 mmol), bis[di-tert-butyl(4-dimethylaminophenyl)phosphine]dichloropalladium (II) (15 mg, 0.02 mmol) and copper(I) iodide (41 mg, 0.22 mmol) in dioxane (2.5 mL) was purged with argon gas then heated at 150° C., for 20 min, in a microwave reactor. The reaction mixture was loaded onto an Isolute® SCX-2 cartridge (10 g). The cartridge was washed with MeOH then the desired product was eluted with 2 M NH$_3$ in MeOH. The appropriate fractions were combined and evaporated. The resulting residue was purified by flash chromatography (Si—PPC, MeOH: DCM, gradient 0:100 to 10:90) followed by reverse phase HPLC (Phenomenex Gemini 5u C18, 20 mM triethylamine in water on a gradient of acetonitrile 95:5 to 2:98) to give 690 as a white solid (14 mg, 12%). LCMS (Method F) R$_T$ 5.50 min; [M+H]$^+$ 522. $^1$H NMR (400 MHz, CHCl$_3$-d): δ 10.53 (d, J=0.9 Hz, 1 H); 8.08 (dd, J=7.0, 0.9 Hz, 1 H); 7.93 (d, J=9.1 Hz, 1 H); 7.41 (dd, J=9.1, 7.0 Hz, 1 H); 7.38 (s, 1 H); 7.08 (d, J=5.3 Hz, 1 H); 5.20 (d, J=5.3 Hz, 1 H); 4.07 (t, J=4.8 Hz, 4 H); 3.92 (t, J=4.8 Hz, 4 H); 3.88 (s, 2 H); 2.62 (m, 8 H);1.25 (s, 6 H)

Example 691

2-(4-((2-(imidazo[1,2-a]pyridin-5-yl)-7-methyl-4-morpholinothieno[3,2-d]pyrimidin-6-yl)methyl)piperazin-1-yl)-2-methylpropanamide 691

A mixture of 2-[4-(7-methyl-4-morpholin-4-yl-2-(tributylstannanyl)thieno[3,2-c]pyrimidin-6-ylmethyl)piperazin-1-yl]isobutyramide (150 mg, 0.21 mmol), 5-bromoimidazo[1,2-a]pyridine (50 mg, 0.25 mmol), Pd(PPh$_3$)$_4$ (24 mg, 0.02 mmol) and copper(I) thiophene-2-carboxylate (8 mg, 0.04 mmol) in dioxane (2 mL) was purged with argon gas then heated at 150° C., for 20 min, in a microwave reactor. The reaction mixture was loaded onto an Isolute® SCX-2 cartridge (10 g), washed with MeOH then eluted with 2 M NH$_3$ in MeOH. The resulting residue was purified by flash chromatography (Si—PPC, MeOH:DCM, gradient 0:100 to 100:0) followed by reverse phase HPLC (Phenomenex Gemini 5u C18, 20 mM triethylamine in water on a gradient of acetonitrile 95:5 to 2:98) to give 691 as a white solid (30 mg, 26%). LCMS (Method E) R$_T$ 5.27 min; [M+H]$^+$ 535. $^1$H NMR (400 MHz, CHCl$_3$-d): δ 9.45 (s, 1 H); 8.09-8.05 (m, 1 H); 7.80-7.76 (m, 2 H); 7.32 (dd, J=8.9, 7.19 Hz, 1 H); 7.10 (d, J=5.3 Hz, 1 H); 5.20 (d, J=5.3 Hz, 1 H); 4.07 (t, J=4.7 Hz, 4 H); 3.91 (t, J=4.7 Hz, 4 H); 3.84 (s, 2 H); 2.61 (m, 8 H); 2.51 (s, 3 H); 1.25 (s, 6 H)

Example 692

2-(1-((9-methyl-2-(2-methylimidazo[1,2-a]pyridin-5-yl)-6-morpholino-9H-purin-8-yl)methyl)piperidin-4-yl)propan-2-ol 692

A mixture of 2-[1-(9-methyl-6-morpholin-4-yl-2-(tributylstannanyl)-9H-purin-8-ylmethyl)-piperidin-4-yl]propan-2-ol (127 mg, 0.19 mmol), 5-bromo-2-methyl-imidazo[1,2-a]pyridine (48 mg, 0.23 mmol), Pd(PPh$_3$)$_4$(22 mg, 0.02 mmol) and copper(I) thiophene-2-carboxylate (7 mg, 0.04 mmol) in dioxane (2 mL) was purged with argon gas then heated at 150° C., for 20 min, in a microwave reactor. The reaction mixture was loaded onto an Isolute® SCX-2 cartridge (10 g). The cartridge was washed with MeOH then the desired product eluted with 2 M $NH_3$ in MeOH. The resulting residue was purified by flash chromatography (Si—PPC, MeOH:DCM, gradient 0:100 to 0:100) followed by reverse phase HPLC (Phenomenex Gemini 5u C18, 20 mM triethylamine in water on a gradient of acetonitrile 95:5 to 2:98) to give 692 as a pale yellow solid (30 mg, 31%). LCMS (Method E) $R_T$ 4.77 min; [M+H]$^+$ 505. $^1$H NMR (400 MHz, CHCl$_3$-d): δ 8.98 (s, 1 H); 7.91 (dd, J=7.2, 1.2 Hz, 1 H); 7.66 (d, J=8.8 Hz, 1 H); 7.30-7.25 (m, 1 H); 4.38 (s, 4 H); 3.96 (s, 3 H); 3.89 (t, J=4.7 Hz, 4 H); 3.75 (s, 2 H); 2.96 (d, J=11.0 Hz, 2 H); 2.54 (s, 3 H); 2.12 (t, J=11.0 Hz, 2 H); 1.81-1.71 (m, 1 H); 1.45-1.23 (m, 4 H); 1.19 (s, 6 H)

Example 693

2-methyl-2-(4-((2-(2-methylimidazo[1,2-a]pyridin-5-yl)-4-morpholinothieno[3,2-d]pyrimidin-6-yl)methyl)piperazin-1-yl)propanamide 693

A mixture of 2-[4-(4-morpholin-4-yl-2-(tributylstannanyl)thieno[3,2-d]pyrimidin-6-yl methyl)piperazin-1-yl]isobutyramide (150 mg, 0.21 mmol), 5-bromo-2-methyl-imidazo[1,2-a]pyridine (55 mg, 0.26 mmol), Pd(PPh$_3$)$_4$ (24 mg, 0.02 mmol) and copper(I) thiophene-2-carboxylate (8 mg, 0.04 mmol) in dioxane (2 mL) was purged with argon gas then heated at 150° C., for 20 min, in a microwave reactor. The reaction mixture was loaded onto an Isolute® SCX-2 cartridge (10 g). The cartridge was washed with MeOH then the desired product eluted with 2 M $NH_3$ in MeOH. The resulting residue was purified by flash chromatography (Si—PPC, MeOH:DCM, gradient 0:100 to 10:90) followed by reverse phase HPLC (Phenomenex Gemini 5u C18, 20 mM triethylamine in water on a gradient of acetonitrile 95:5 to 2:98) to give 693 as a white solid (55 mg, 47%). LCMS (Method E): $R_T$ 4.99 min; [M+H]$^+$ 535. $^1$H NMR (400 MHz, CHCl$_3$-d): δ 8.98 (s, 1 H); 7.92-7.89 (m, 1 H); 7.68 (d, J=8.8 Hz, 1 H); 7.39 (s, 1 H); 7.27-7.23 (m, 1 H); 7.09 (d, J=5.3 Hz, 1 H); 5.22 (d, J=5.3 Hz, 1 H); 4.09-4.04 (m, 4 H); 3.94-3.87 (m, 4 H); 3.87 (s, 2 H); 2.62 (m, 8 H); 2.54 (s, 3 H); 1.29-1.23 (m, 6 H)

Example 694

2-methyl-2-(4-((2-(7-methylimidazo[1,2-a]pyridin-5-yl)-4-morpholinothieno[3,2-d]pyrimidin-6-yl)methyl)piperazin-1-yl)propanamide 694

A mixture of 2-[4-(4-morpholin-4-yl-2-(tributylstannanyl)thieno[3,2-c]pyrimidin-6-ylmethyl)piperazin-1-yl]isobutyramide (150 mg, 0.22 mmol), 5-bromo-7-methyl-imidazo[1,2-a]pyridine (55 mg, 0.26 mmol), Pd(PPh$_3$)$_4$ (25 mg, 0.02 mmol) and copper(I) thiophene-2-carboxylate (8 mg, 0.04 mmol) in dioxane (2 mL) was purged with argon gas then heated at 150° C., for 20 min, in a microwave reactor. The reaction mixture was loaded onto an Isolute® SCX-2 cartridge (10 g). The cartridge was washed with MeOH then the desired product eluted with 2 M $NH_3$ in MeOH. The resulting residue was purified by flash chromatography (Si—PPC, MeOH:DCM, gradient 0:100 to 10:90) followed by reverse phase HPLC (Phenomenex Gemini 5u C18, 20 mM triethylamine in water on a gradient of acetonitrile 95:5 to 2:98) to give 694 as a white solid (38 mg, 32%). LCMS (Method E): $R_T$ 5.09 min; [M+H]$^+$ 535. $^1$H NMR (400 MHz, CHCl$_3$-d): δ 9.05 (s, 1 H); 7.76 (d, J=1.5 Hz, 1 H); 7.66 (d, J=1.5 Hz, 1 H); 7.55 (s, 1 H); 7.37 (s, 1 H); 7.09 (d, J=5.3 Hz, 1 H); 5.22 (d, J=5.3 Hz, 1 H); 4.10-4.04 (m, 4 H); 3.93-3.88 (m, 4 H); 3.87 (s, 2 H); 2.61 (m, 8 H); 2.50 (s, 3 H); 1.25 (s, 6 H)

Example 695

2-methyl-2-(4-((4-morpholino-2-(1H-pyrrolo[2,3-b]pyridin-4-yl)thieno[3,2-d]pyrimidin-6-yl)methyl)piperazin-1-yl)propanamide 695

A mixture of 2-[4-(4-morpholin-4-yl-2-(tributylstannanyl)thieno[3,2-d]pyrimidin-6-ylmethyl)piperazin-1-yl]isobutyramide (0.331 g, 0.48 mmol), 4-bromopyrrolo[2,3-b]pyridine-1-carboxylic acid tert-butylester (0.170 g, 0.573 mmol), Pd(Ph$_3$)$_4$ (55.1 mg, 0.048 mmol) and CuI (109 mg, 0.573 mmol) in toluene (8 mL) was purged with argon, then subjected to microwave irradiation at 140° C. for 20 min. The reaction mixture was loaded onto an Isolute® SCX-2 cartridge. The cartridge was washed with MeOH and the desired product was eluted using 2 M $NH_3$ in MeOH. The residue was then dissolved in DCM/TFA (8 mL/8 mL) and the resulting solution stirred for 2 h at room temperature. The reaction mixture was loaded onto an Isolute® SCX-2 cartridge. The cartridge was washed with MeOH and the desired product was eluted using 2 M $NH_3$ in MeOH. The residue was purified by column chromatography (Si—PPC, MEOH:DCM, gradient 0:100 to 5:95) followed by reverse phase HPLC (Phenomenex Gemini 5u C18, 20 mM triethylamine in water on a gradient of acetonitrile 70:30 to 40:60) to give 695 as a white powder (0.049 g, 20%). LCMS (Method F): $R_T$ 5.07 min, [M+H]$^+$ 521.3. $^1$H NMR (CDCl$_3$, 400 MHz) δ 8.93 (s, 1 H); 8.43 (d, J=5.2 Hz, 1 H); 8.08 (d, J=5.2 Hz, 1 H); 7.43 (d, J=2.2 Hz, 2 H); 7.38 (s, 1 H); 7.09 (d, J=5.2 Hz, 1 H); 5.24 (d, J=5.2 Hz, 1 H); 4.10 (t, J=4.7 Hz, 4 H); 3.92 (t, J=4.7 Hz, 4 H); 3.86 (s, 2 H); 2.65-2.58 (m, 4 H); 1.60-1.55 (m, 4 H); 1.24 (s, 6 H)

Example 696

2-methyl-2-(4-((7-methyl-4-morpholino-2-(1H-pyrrolo[2,3-b]pyridin-4-yl)thieno[3,2-d]pyrimidin-6-yl)methyl)piperazin-1-yl)propanamide 696

A mixture of 2-[4-(7-methyl-4-morpholin-4-yl-2-(tributylstannanyl)thieno[3,2-d]pyrimidin-6-ylmethyl)piperazin-1-yl]isobutyramide (200 mg, 0.28 mmol), 4-bromo-pyrrolo[2,3-b]pyridine-1-carboxylic acid tert-butylester (100 mg, 0.34 mmol), Pd(Ph$_3$)$_4$ (33 mg, 0.028 mmol) and CuI (65 mg, 0.34 mmol) in toluene (5 mL) was purged with argon, then subjected to microwave irradiation at 140° C. for 30 min. The reaction mixture was loaded onto an Isolute® SCX-2 cartridge. The cartridge was washed with MeOH and the desired product was eluted using 2 M $NH_3$ in MeOH. The residue was then dissolved in DCM/TFA (8 mL/8 mL) and stirred for 2 h at room temperature. The reaction mixture was loaded onto an Isolute® SCX-2 cartridge. The cartridge was washed with MeOH and the desired product was eluted using 2 M $NH_3$ in MeOH. The residue was purified by column chromatography (Si—PPC, MeOH:DCM, gradient 0:100 to 05:95) to give 696 as a white powder (0.036 g, 24%). LCMS (Method F): $R_T$ 5.68 min, [M+H]$^+$ 535.2. $^1$H NMR (CDCl$_3$, 400 MHz) δ 9.42-8.74 (m, 1 H); 8.59-7.95 (m, 1 H); 7.92-7.49 (m, 1 H); 7.46-7.35 (m, 2 H); 7.14-7.06 (m, 1 H); 5.27 (s, 1 H); 4.09 (t, J=4.2 Hz, 4); 3.92 (t, J=4.2 Hz, 4 H); 3.85 (s, 2 H); 2.66-2.61 (m, 4 H); 2.53 (s, 3 H); 1.63-1.58 (m, 4 H); 1.26 (s, 6 H)

Example 697

2-(4-((2-(imidazo[1,2-a]pyridin-5-yl)-4-morpholinothieno[3,2-d]pyrimidin-6-yl)methyl)piperazin-1-yl)-2-methylpropanamide 697

A mixture of 2-[4-(4-morpholin-4-yl-2-(tributylstannanyl)thieno[3,2-d]pyrimidin-6-ylmethyl)piperazin-1-yl]isobutyramide (0.35 g, 0.51 mmol), 5-bromoimidazo[1,2-a]pyridine (0.11 g, 0.56 mmol), copper(I) 2-thiophene carboxylate (0.019 g, 0.1 mmol) and Pd(PPh$_3$)$_4$ (0.059 g, 0.05 mmol) in dioxane (5 mL) was subjected to microwave irradiation at 140° C. for 20 min. The reaction mixture was loaded onto an Isolute® SCX-2 cartridge. The cartridge was washed with MeOH and the desired product was eluted using 2 M NH$_3$ in MeOH. The eluent was concentrated in vacuo and the residue was purified by flash chromatography (Si—PPC, MEOH:DCM, gradient 0:100 to 10:90). The residue was loaded onto an Isolute® SCX-2 cartridge. The cartridge was washed with MeOH and the desired product was eluted using 2 M NH$_3$ in MeOH. The solution was concentrated in vacuo and the residue was purified by reverse phase HPLC (Phenomenex Gemini 5u C18, 20 mM triethylamine in water on a gradient of acetonitrile 75:25 to 2:98) to give 697 as a white powder (0.117 g, 45%). LCMS: R$_T$=4.35 min, [M+H]$^+$ 521.2. $^1$H NMR (400 MHz, DMSO-d6): δ 9.33 (d, J=1.1 Hz, 1 H); 8.04 (dd, J=7.5, 1.2 Hz, 1 H); 7.78 (dd, J=8.9, 1.1 Hz, 1 H); 7.74 (d, J=1.2 Hz, 1 H); 7.54 (s, 1 H); 7.41 (dd, J=8.9, 7.5 Hz, 1 H); 7.07 (d, J=3.5 Hz, 1 H); 6.95 (d, J=3.5 Hz, 1 H); 4.00 (t, J=4.7 Hz, 4 H); 3.89 (s, 2 H); 3.82 (t, J=4.7 Hz, 4 H); 2.56-2.54 (m, 4 H); 2.49-2.44 (m, 4 H); 1.08 (s, 6 H)

Example 698

2-(1-((2-(imidazo[1,2-a]pyridin-5-yl)-9-methyl-6-morpholino-9H-purin-8-yl)methyl)piperidin-4-yl)propan-2-ol 698

A mixture of 2-[1-(9-methyl-6-morpholin-4-yl-2-(tributylstannanyl)-9H-purin-8-ylmethyl)piperidin-4-yl]propan-2-ol (0.2 g, 0.30 mmol), 5-bromoimidazo[1,2-a]pyridine (0.066 g, 0.33 mmol), copper(I) 2-thiophene carboxylate (0.018 g, 0.09 mmol) and Pd(PPh$_3$)$_4$ (0.052 g, 0.045 mmol) in dioxane (5 mL) was subjected to microwave irradiation at 150° C. for 60 min. The reaction mixture was loaded onto an Isolute® SCX-2 cartridge. The cartridge was washed with MeOH and the desired product was eluted using 2 M NH$_3$ in MeOH. The eluent was concentrated in vacuo and the resultant residue was purified by flash chromatography (Si—PPC, MEOH:DCM, gradient 0:100 to 94:6) followed by reverse phase HPLC (Phenomenex Gemini 5u C18, 20 mM triethylamine in water on a gradient of acetonitrile 95:5 to 2:98) to give 698 as a yellow powder (0.085 g, 58%). LCMS: R$_T$=4.17 min, [M+H]$^+$ 491.2. $^1$H NMR (CDCl$_3$, 400 MHz) δ 9.26 (d, J=1.2 Hz, 1 H); 7.96 (dd, J=8.2, 1.2 Hz, 1 H); 7.76-7.73 (m, 2 H); 7.31 (dd, J=8.2, 5.2 Hz, 1 H); 4.38 (t, J=4.6 Hz, 4 H); 3.96 (s, 3 H); 3.89 (t, J=4.6 Hz, 4 H); 3.75 (s, 2 H); 2.96 (d, J=11.0 Hz, 2 H); 2.11 (t, J=11.0 Hz, 2 H); 1.76 (d, J=11.0 Hz, 2 H); 1.44-1.29 (m, 3 H); 1.18 (s, 6 H)

Example 699

2-(1-((5-(imidazo[1,2-a]pyridin-5-yl)-7-morpholinothiazolo[5,4-d]pyrimidin-2-yl)methyl)piperidin-4-yl)propan-2-ol 699

A mixture of 2-[1-(5-imidazo[1,2-a]pyridin-5-yl-7-morpholin-4-ylthiazolo[5,4-d]pyrimidin-2-ylmethyl)piperidin-4-yl]propan-2-ol (0.25 g, 0.37 mmol), 5-bromoimidazo[1,2-a]pyridine (0.082 g, 0.41 mmol), copper(I) 2-thiophene carboxylate (0.015 g, 0.075 mmol) and Pd(PPh$_3$)$_4$ (0.044 g, 0.037 mmol) in dioxane (3 mL) was subjected to microwave irradiation at 150° C. for 60 min. The reaction mixture was loaded onto an Isolute® SCX-2 cartridge. The cartridge was washed with MeOH and the desired product was eluted using 2 M NH$_3$ in MeOH. The eluent was concentrated in vacuo and the residue was purified by flash chromatography (Si—PPC, MEOH:DCM, gradient 0:100 to 90:10) followed by reverse phase HPLC (Phenomenex Gemini 5u C18, 20 mM triethylamine in water on a gradient of acetonitrile 95:5 to 2:98) to give 699 as a yellow powder (0.052 g, 28%). LCMS (Method E): R$_T$=4.38 min, [M+H]$^+$ 494.2. $^1$H NMR (CDCl$_3$, 400 MHz) δ 9.19 (s, 1 H); 7.99 (dd, J=7.2, 1.3 Hz, 1 H); 7.81 (d, J=8.9 Hz, 1 H); 7.76 (d, J=1.3 Hz, 1 H); 7.33 (dd, J=8.9, 7.2 Hz, 1 H); 4.48-4.35 (m, 4 H); 3.92-3.85 (m, 7 H); 3.10 (d, J=11.2 Hz, 2 H); 2.23 (t, J=11.2 Hz, 2 H); 1.83-1.77 (m, 2 H); 1.54-1.41 (m, 2 H); 1.38-1.29 (m, 1 H); 1.22 (s, 6 H)

Example 700

4-(5-(imidazo[1,2-a]pyridin-5-yl)-2-((3-morpholinoazetidin-1-yl)methyl)thiazolo[5,4-d]pyrimidin-7-yl)morpholine 700

A mixture of 7-morpholin-4-yl-2-(3-morpholin-4-ylazetidin-1-ylmethyl)-5-(tributylstannanyl)thiazolo[5,4-d]pyrimidine (0.25 g, 0.37 mmol), 5-bromoimidazo[1,2-a]pyridine (0.082 g, 0.41 mmol), copper(I) 2-thiophene carboxylate (0.015 g, 0.075 mmol) and Pd(PPh$_3$)$_4$ (0.044 g, 0.037 mmol) in dioxane (3 mL) was subjected to microwave irradiation at 150° C. for 60 min. The reaction mixture was loaded onto an Isolute® SCX-2 cartridge. The cartridge was washed with MeOH and the desired product was eluted using 2 M NH$_3$ in MeOH. The eluent was concentrated in vacuo and the residue was purified by flash chromatography (Si—PPC, MEOH:DCM, 0:100 to 10:90) followed by reverse phase HPLC (Phenomenex Gemini 5u C18, 20 mM triethylamine in water on a gradient of acetonitrile 95:5 to 2:98) to give 700 as a yellow solid (0.101 g, 55%). LCMS (Method E): R$_T$=3.98 min, [M+H]$^+$ 493.15. $^1$H NMR (CDCl$_3$, 400 MHz) δ 9.16 (s, 1 H); 7.98 (dd, J=7.2, 1.2 Hz, 1 H); 7.81 (d, J=8.9 Hz, 1 H); 7.76 (d, J=1.2 Hz, 1 H); 7.33 (dd, J=8.9, 7.2 Hz, 1 H); 4.47-4.32 (m, 4 H); 4.04 (s, 2 H); 3.89 (t, J=4.6 Hz, 4 H); 3.74 (t, J=4.6 Hz, 4 H); 3.69 (t, J=6.4 Hz, 2 H); 3.23-3.15 (m, 2 H); 3.14 (t, J=6.4 Hz, 1 H); 2.40-2.36 (m, 4 H)

Example 703

2-(4-(2-(2-ethyl-1H-benzo[d]imidazol-1-yl)-9-methyl-6-morpholino-9H-purin-8-yl)piperidin-1-yl)-2-methylpropanamide 703

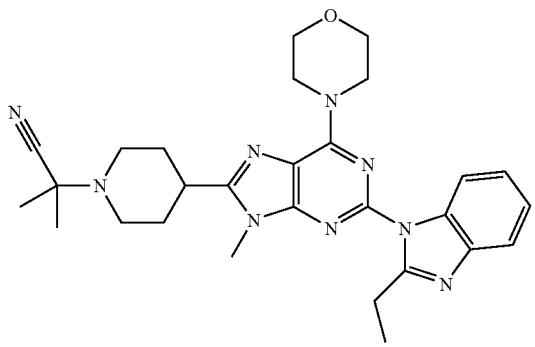

To a solution of 2-(2-ethylbenzoimidazol-1-yl)-9-methyl-6-morpholin-4-yl-8-piperidin-4-yl-9H-purine hydrochloride (396 mg, 0.89 mmol) in THF (3 mL) and H$_2$O (4 mL) was added 1M HCl to give pH 4 followed by NaCN (261 mg, 5.32 mmol) and propan-2-one (590 µL, 7.98 mmol). The resulting mixture was allowed to stir at r.t. for 16 h then partitioned between H$_2$O and DCM. The organic phase was dried (phase separator) and concentrated in vacuo. The resulting residue was triturated with Et$_2$O and the solid collected by filtration and dried in vacuo affording 2-{4-[2-(2-Ethylbenzoimidazol-1-yl)-9-methyl-6-morpholin-4-yl-9H-purin-8-yl]piperidin-1-yl}-2-methylpropionitrile (316 mg, 69%). LCMS (method H): R$_T$ 2.64 min, [M+H]$^+$ 514.4

2-{4-[2-(2-Ethylbenzoimidazol-1-yl)-9-methyl-6-morpholin-4-yl-9H-purin-8-yl]piperidin-1-yl}-2-methylpropionitrile (300 mg, 0.58 mmol) was added slowly to conc. H$_2$SO$_4$ (3.5 mL) The resulting mixture was allowed to stir at r.t. for 3 h then poured onto ice and basified with K$_2$CO$_3$. The resulting mixture was extracted with DCM and the combined organic phases dried (Na$_2$SO$_4$) and concentrated in vacuo. The resulting residue was purified by column chromatography (Si—PCC, MeOH:EtOAc, 0-20%) then loaded onto an Isolute® SCX-2 cartridge which was washed with MeOH and the product eluted with 2M NH$_3$/MeOH affording 703 (177 mg, 57%). LCMS (method I): R$_T$ 2.45 min, [M+H]$^+$ 532.3. $^1$H NMR (DMSO, 400 MHz): δ 8.01-7.97 (1 H, m), 7.63-7.62 (1 H, m), 7.23-7.22 (3 H, m), 6.93 (1 H, d, J=3.36 Hz), 4.26 (4 H, brd s), 3.79-3.74 (7 H, m), 3.26 (2 H, q, J=7.42 Hz), 3.07-2.97 (1 H, m), 2.88 (2 H, d, J=10.76 Hz), 2.32-2.21 (2 H, m), 1.93-1.91 (4 H, m), 1.33 (3 H, t, J=7.44 Hz), 1.12 (6 H, s)

Example 711

1-((2-(2-ethyl-1H-benzo[d]imidazol-1-yl)-9-methyl-6-morpholino-9H-purin-8-yl)methyl)-4-isopropylpiperazin-2-one 711

To a solution 4-isopropylpiperazin-2-one (56 mg, 0.35 mmol) in DMF (3 mL) at 0° C. was added sodium hydride (18 mg, 0.45 mmol, 60% dispersion in mineral oil) and the resulting mixture stirred for 30 min before the addition of a solution of 8-bromomethyl-2-(2-ethylbenzoimidazol-1-yl)-9-methyl-6-morpholin-4-yl-9H-purine (200 mg, 0.44 mmol) in DMF (2 mL). The resulting mixture was stirred at r.t. for 72 h, then partitioned between DCM and H$_2$O. The organic phase was dried (Na$_2$SO$_4$) and concentrated in vacuo. The resulting residue was purified by column chromatography (Si—PCC, MeOH:EtOAc, 0-20%) followed by reverse phase HPLC (Phenomenex Gemini 5 µm C18, 20 mM triethylamine in water on a gradient acetonitrile 30-70%) affording 711 as a white solid (22 mg, 15%). LCMS: R$_T$ 2.43 min, [M+H]$^+$ 518.2. $^1$H NMR (DMSO, 400 MHz): δ 8.01-8.01 (1 H, m), 7.63-7.62 (1 H, m), 7.25-7.24 (2 H, m), 4.83 (2 H, s), 4.26 (4 H, brd s), 3.77 (4 H, t, J=4.61 Hz), 3.74 (3 H, s), 3.31 (2 H, m), 3.26 (2 H, q, J=7.45 Hz), 3.15 (2 H, s), 2.69-2.68 (3 H, m), 1.33 (3 H, t, J=7.44 Hz), 0.98 (6 H, d, J=6.50 Hz)

Example 712

2-(5-(2-ethyl-1H-benzo[d]imidazol-1-yl)-7-morpholinothiazolo[5,4-d]pyrimidin-2-yl)-1-(4-(1-hydroxy-2-methylpropan-2-yl)piperazin-1-yl)ethanone 712

A mixture of 2-(5-chloro-7-morpholin-4-ylthiazolo[5,4-d]pyrimidin-2-yl)-1-[4-(2-hydroxy-1,1-dimethylethyl)piperazin-1-yl]ethanone (65 mg, 0.14 mmol), 2-ethylbenzimidazole (23 mg, 0.16 mmol), tris(dibenzylideneacetone)dipalladium (4 mg, 2.5 mol %), XPhos (7 mg, 10 mol %) and Cs$_2$CO$_3$ (70 mg, 0.21 mmol) in dioxane (2 mL) was purged with argon then heated at 110° C. for 24 h in a sealed tube. The reaction mixture was loaded onto an Isolute® SCX-2 cartridge which was washed with MeOH and the product eluted with 2M NH$_3$/MeOH/DCM. The resulting residue was purified by column chromatography (Si—PCC, MeOH:DCM, 0-10%) followed by reverse phase HPLC (Phenomenex Gemini 5 µm C18, 20 nM NEt$_3$ in water on a gradient acetonitrile 10-95%) affording 712 as a yellow solid (14 mg, 17%). LCMS (method I): R$_T$ 2.58 min, [M+H]$^+$ 565.2. $^1$H NMR (CDCl$_3$, 400 MHz): δ 8.01-7.98 (1 H, m), 7.76-7.75 (1 H, m), 7.29-7.29 (2 H, m), 4.41 (4 H, s), 4.18 (2 H, s), 3.93-3.75 (9 H, m), 3.56 (2 H, brd s), 3.34 (2 H, q, J=7.47 Hz), 2.90-2.70 (4 H, brd m), 1.43 (3 H, t, J=7.47 Hz), 1.23-1.21 (6 H, m)

Example 713

4-(2-(2-isopropyl-1H-benzo[d]imidazol-1-yl)-8-(3-methoxy-1-(2-(methylsulfonyl)ethyl)piperidin-3-yl)-9-methyl-9H-purin-6-yl)morpholine 713

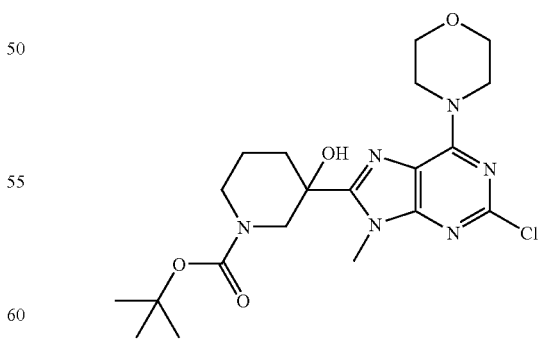

To a mixture of 2-chloro-9-methyl-6-morpholin-4-yl-9H-purine (3.5 g, 13.8 mmol) and TMEDA (3.1 mL, 20.7 mmol) in THF (100 mL) at −78° C. was added n-BuLi (8.3 mL, 2.5 M in hexanes, 20.7 mmol). The resulting mixture was allowed to warm to −30° C. over 45 min then cooled back to −78° C.

before the addition of a solution of 3-oxo-piperidine-1-carboxylic acid tert-butyl ester (4.1 g, 20.7 mmol) in THF (10 mL). The reaction mixture was warmed to r.t. and stirred for 2 h then quenched with H$_2$O and extracted with EtOAc. The combined organic phases were washed with brine, dried (Na$_2$SO$_4$) and concentrated in vacuo. The resulting residue was triturated with Et$_2$O and unreacted starting material removed by filtration. The resulting residue was purified by column chromatography (Si—PCC, EtOAc:cyclohexane, 30-80%) then triturated with cyclohexane affording 3-(2-Chloro-9-methyl-6-morpholin-4-yl-9H-purin-8-yl)-3-hydroxypiperidine-1-carboxylic acid tert-butyl ester (5.0 g, 81%). LCMS (method A): R$_T$ 3.50 min [M+H]$^+$ 453.3

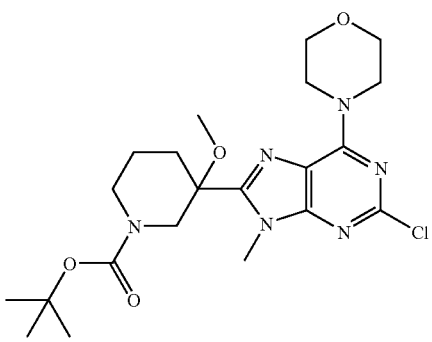

To a solution of 3-(2-chloro-9-methyl-6-morpholin-4-yl-9H-purin-8-yl)-3-hydroxypiperidine-1-carboxylic acid tert-butyl ester (4.54 g, 10.02 mmol) in THF (100 mL) was added NaH (481 mg, 12.02 mmol, 60% dispersion in mineral oil) and the mixture allowed to stir for 5 min before the addition of iodomethane (750 μL, 12.02 mmol) and 15-Crown-5 (10 drops). The resulting mixture was allowed to stir for 2.5 h then concentrated in vacuo. The resulting residue was partitioned between EtOAc and H$_2$O and the aqueous layer further extracted with 2-methyl THF. The combined organic phases were dried (Na$_2$SO$_4$) and concentrated in vacuo affording 3-(2-Chloro-9-methyl-6-morpholin-4-yl-9H-purin-8-yl)-3-methoxypiperidine-1-carboxylic acid tert-butyl ester (4.30 g, 92%). LCMS (method A): R$_T$ 4.05 min, [M+H]$^+$ 467.2

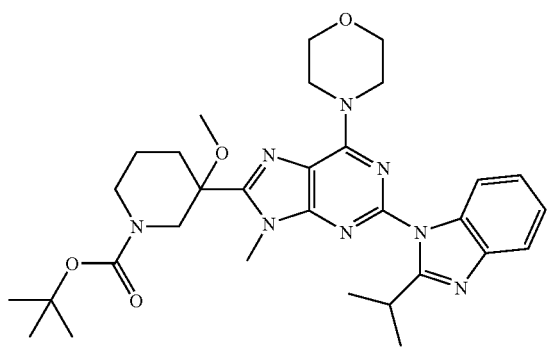

A mixture of 3-(2-chloro-9-methyl-6-morpholin-4-yl-9H-purin-8-yl)-3-methoxypiperidine-1-carboxylic acid tert-butyl ester (3.0 g, 6.42 mmol), 2-isopropylbenzimidazole (1.24 g, 7.71 mmol), tris(dibenzylideneacetone)dipalladium (150 mg, 0.16 mmol), XPhos (306 mg, 0.64 mmol) and Cs$_2$CO$_3$ (3.14 g, 9.64 mmol) in dioxane (50 mL) was purged with argon then heated at 110° C. for 16 h. The reaction mixture was partitioned between EtOAc and H$_2$O, the organic phase washed with brine then dried (Na$_2$SO$_4$) and concentrated in vacuo. The resulting residue was purified by column chromatography (Si—PCC, EtOAc:cyclohexane, 30-70%) affording 3-[2-(2-Isopropylbenzoimidazol-1-yl)-9-methyl-6-morpholin-4-yl-9H-purin-8-yl]-3-methoxypiperidine-1-carboxylic acid tert-butyl ester (2.47 g, 65%). LCMS (method A): R$_T$ 3.52 min, [M+H]$^+$ 591.5

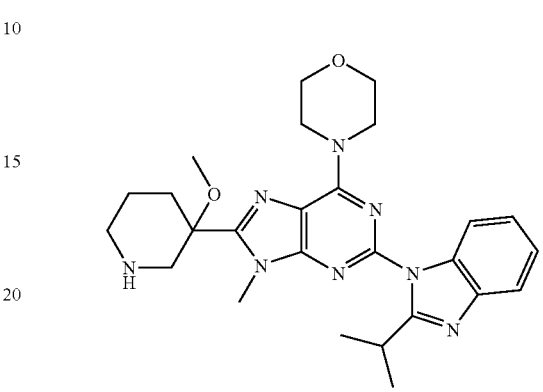

To a solution of 3-[2-(2-isopropylbenzoimidazol-1-yl)-9-methyl-6-morpholin-4-yl-9H-purin-8-yl]-3-methoxypiperidine-1-carboxylic acid tert-butyl ester (2.47 g, 4.18 mmol) in DCM (100 mL) was added 4M HCl in dioxane (10 mL). The resulting mixture was allowed to stir for 2 h at r.t. before further 1.25M HCl in MeOH (20 mL) was added. The resulting mixture was allowed to stir for 1.5 h then concentrated in vacuo. The resulting residue was loaded onto an Isolute® SCX-2 cartridge which was washed with MeOH and the product eluted with 2M NH$_3$/MeOH affording 2-(2-Isopropylbenzoimidazol-1-yl)-8-(3-methoxypiperidin-3-yl)-9-methyl-6-morpholin-4-yl-9H-purine (1.83 g, 89%). LCMS (method H): R$_T$ 2.12 min [M+H]$^+$ 491.4

A mixture of 2-(2-isopropylbenzoimidazol-1-yl)-8-(3-methoxypiperidin-3-yl)-9-methyl-6-morpholin-4-yl-9H-purine (150 mg, 0.31 mmol) and methanesulfonylethene (32 μL, 0.37 mmol) in IMS (5 mL) was allowed to stir for 4 h at room temp. before pouring the reaction mixture into H$_2$O. The resulting precipitate was collected by filtration and dried under vacuum affording 713 (141 mg, 77%). LCMS (method I): R$_T$ 2.82 min, [M+H]$^+$ 597.2. $^1$H NMR (DMSO, 400 MHz): δ 7.92-7.91 (1 H, m), 7.65-7.64 (1 H, m), 7.24-7.23 (2 H, m), 4.25 (4 H, brd s), 4.00-3.85 (4 H, m), 3.8-3.75 (4 H, m), 3.40-3.20 (2 H, m), 3.15-3.00 (4 H, m), 2.95 (3 H, s), 2.81-2.76 (4 H, m), 2.30-2.20 (1 H, m), 2.10-2.95 (2 H, m), 1.84-1.74 (2 H, m), 1.36 (6 H, dd, J=6.77, 2.96 Hz)

Example 714 tert-butyl 3-(2-(2-ethyl-1H-benzo[d]imidazol-1-yl)-9-methyl-6-morpholino-9H-purin-8-yl)-3-methoxyazetidine-1-carboxylate 714

To a solution of 3-[2-(2-ethylbenzoimidazol-1-yl)-9-methyl-6-morpholin-4-yl-9H-purin-8-yl]-3-hydroxyazetidine-1-carboxylic acid tert-butyl ester (208 mg, 0.39 mmol) in THF (3 mL) was added NaH (19 mg, 0.47 mmol, 60% dispersion in mineral oil) and the mixture allowed to stir for 5 min before the addition of iodomethane (29 μL, 66 mg, 0.47 mmol). The resulting mixture was allowed to stir for 3.5 h before further iodomethane (29 μL, 66 mg, 0.47 mmol) was added. The mixture was stirred for 16 h then concentrated in vacuo. The resulting residue was partitioned between EtOAc and H₂O. The organic phase was dried (Na₂SO₄) and concentrated in vacuo. The resulting residue was purified by column chromatography (Si—PCC, EtOAc:cyclohexane, 40-80%) affording 714 as an oil (123 mg, 57%). LCMS (method I): R$_T$ 4.49 min, [M+H]⁺ 549.2. ¹H NMR (CDCl₃, 400 MHz): δ 7.99-7.90 (1 H, m), 7.74-7.64 (1 H, m), 7.25-7.16 (2 H, m), 4.60-4.40 (4 H, brd m), 4.18 (2 H, d, J=9.17 Hz), 3.82-3.81 (6 H, m), 3.71 (3 H, s), 3.29 (2 H, t, J=7.54 Hz), 3.07 (3 H, s), 1.42-1.33 (12 H, m).

Example 715

(2,2-dimethyl-4-(methylsulfonyl)piperazin-1-yl)(2-(2-ethyl-1H-benzo[d]imidazol-1-yl)-9-methyl-6-morpholino-9H-purin-8-yl)methanone 715

To a mixture of 2-(2-ethylbenzoimidazol-1-yl)-9-methyl-6-morpholin-4-yl-9H-purine-8-carboxylic acid (117 mg, 0.26 mmol), 1-methanesulfonyl-3,3-dimethylpiperazine (51 mg, 0.26 mmol) and HATU (100 mg, 0.26 mmol) in DMF (1 mL) was added NEt₃ (720 µL, 5.18 mmol). The resulting mixture was allowed to stir at r.t. for 16 h then partitioned between EtOAc and H₂O. The organic phase was dried (MgSO₄) and concentrated in vacuo and the resulting residue was purified by column chromatography (Si—PCC, MeOH:EtOAc, 0-5%). The resulting solid was recrystallised from EtOAc and Et₂O affording 715 (50 mg, 33%). LCMS (method I): R$_T$ 3.68 min, [M+H]⁺ 582.2. ¹H NMR (CDCl₃, 400 MHz): δ 8.03-8.03 (1 H, m), 7.76-7.75 (1 H, m), 7.31-7.27 (2 H, m), 4.35 (4 H, brd s), 4.03 (2 H, t, J=5.39 Hz), 3.95 (3 H, s), 3.87 (4 H, t, J=4.70 Hz), 3.50 (2 H, t, J=5.40 Hz), 3.37 (2 H, q, J=7.47 Hz), 3.31 (2 H, s), 2.90 (3 H, s), 1.68 (6 H, s), 1.45 (3 H, t, J=7.47 Hz)

Example 716

2-(3-(2-(2-isopropyl-1H-benzo[d]imidazol-1-yl)-9-methyl-6-morpholino-9H-purin-8-yl)-3-methoxypiperidin-1-yl)acetamide 716

A mixture of 2-(2-isopropylbenzoimidazol-1-yl)-8-(3-methoxypiperidin-3-yl)-9-methyl-6-morpholin-4-yl-9H-purine from Example 713 (1.0 g, 2.10 mmol), 2-bromoacetamide (290 mg, 2.10 mmol), sodium iodide (32 mg, 0.21 mmol) and K₂CO₃ (610 mg, 4.41 mmol) in MeCN (20 mL) was stirred at r.t. for 66 h. The reaction mixture was diluted with EtOAc, filtered and concentrated in vacuo. The resulting residue was purified by column chromatography (Si—PCC, MeOH:EtOAc, 0-20%) then triturated with Et₂O affording 716 (675 mg, 59%). LCMS (method I): R$_T$ 2.66 min, [M+H]⁺ 548.2. ¹H NMR (DMSO, 400 MHz): δ 7.93-7.92 (1 H, m), 7.66-7.62 (1 H, m), 7.26-7.22 (2 H, m), 7.14 (1 H, s), 7.07 (1 H, s), 4.26 (4 H, brd s), 3.98-3.88 (4 H, m), 3.80-3.75 (4 H, m), 3.10-3.00 (4 H, m), 3.00-2.90 (3 H, m), 2.70-2.60 (1 H, m), 2.45-2.35 (1 H, m), 2.15-1.95 (2 H, m), 1.95-1.77 (1 H, m), 1.78-1.68 (1 H, m), 1.37-1.37 (6 H, m)

Example 717

2-(4-((2-(2-ethyl-1H-benzo[d]imidazol-1-yl)-9-methyl-6-morpholino-9H-purin-8-yl)methyl)-3,3-dimethylpiperazin-1-yl)acetamide 717

A mixture of 8-(2,2-dimethylpiperazin-1-ylmethyl)-2-(2-ethylbenzoimidazol-1-yl)-9-methyl-6-morpholin-4-yl-9H-purine (120 mg, 0.25 mmol), 2-chloroacetamide (50 mg, 0.54 mmol) and NEt₃ (50 µL, 0.36 mmol) in DCM (5 mL) was allowed to stir at r.t. for 5 h before further 2-chloroacetamide (100 mg, 1.07 mmol) and NEt₃ (100 µL, 0.72 mmol) was added. The resulting mixture was allowed to stir for 84 h then loaded onto an Isolute® SCX-2 cartridge which was washed with MeOH and the product eluted with 2M NH₃/MeOH. The resulting residue was purified by column chromatography (Si—PCC, MeOH:EtOAc, 0-5%) affording 717 (65 mg, 49%). LCMS (method I): R$_T$ 2.54 min, [M+H]⁺ 547.2. ¹H NMR (CDCl₃, 400 MHz): δ 8.02-7.99 (1 H, m), 7.77-7.74 (1 H, m), 7.32-7.22 (2 H, m), 6.95 (1 H, brd s), 5.43 (1 H, brd s), 4.34 (4 H, brd s), 3.90 (3 H, s), 3.86 (6 H, t, J=4.76 Hz), 3.35 (2 H, q, J=7.48 Hz), 2.96 (2 H, s), 2.62-2.45 (4 H, m), 2.38 (2 H, s), 1.45 (3 H, t, J=7.48 Hz), 1.25 (6 H, s)

Example 718

(S)-1-(3-((2-(2-ethyl-1H-benzo[d]imidazol-1-yl)-9-methyl-6-morpholino-9H-purin-8-yl)methyl)azetidin-1-yl)-2-hydroxypropan-1-one 718

To a mixture of 8-azetidin-3-ylmethyl-2-(2-ethylbenzoimidazol-1-yl)-9-methyl-6-morpholin-4-yl-9H-purine (100 mg, 0.23 mmol), L-lactic acid (23 mg, 0.25 mmol) and DIPEA (45 µL, 0.25 mmol) in DCM (2 mL) was added HATU (96 mg, 0.25 mmol). The resulting yellow mixture was stirred for 2.5 h at r.t. then partitioned between DCM and H₂O. The combined organic phases were dried (Na₂SO₄) and concentrated in vacuo. The resulting oil was loaded onto an Isolute® SCX-2 cartridge which was washed with MeOH/DCM and the product eluted with 2M NH₃/MeOH. The resulting residue was purified by column chromatography (Si—PCC, MeOH:EtOAc, 0-10%) followed by reverse phase HPLC (Phenomenex Gemini 5 µm C18, 0.1% HCO₂H in water on a gradient acetonitrile 20-35%) affording 718 as a white solid (19 mg, 16%). LCMS (method I): R$_T$ 2.92 min, [M+H]⁺ 505.2. ¹H NMR (CDCl₃, 400 MHz): δ 7.98-7.97 (1 H, m), 7.90-7.80 (1 H, m), 7.40-7.30 (2 H, m), 4.33-4.32 (7 H, m), 4.01-4.00 (1 H, m), 3.86-3.85 (5 H, m), 3.77 (3 H, d, J=1.96 Hz), 3.50-3.35 (4 H, m), 3.19-3.17 (2 H, m), 1.48 (3 H, t, J=7.42 Hz), 1.34 (3 H, dd, J=6.69, 4.73 Hz), Example 720

3-(2-(2-ethyl-1H-benzo[d]imidazol-1-yl)-9-methyl-6-morpholino-9H-purin-8-yl)-1-(tetrahydro-2H-pyran-4-yl)azetidin-3-ol 720

A mixture of 3-[2-(2-ethylbenzoimidazol-1-yl)-9-methyl-6-morpholin-4-yl-9H-purin-8-yl]-azetidin-3-ol (490 mg, 1.13 mmol), tetrahydropyran-4-one (158 mg, 1.58 mmol), AcOH (130 µL, 2.25 mmol) and 4 Å powdered molecular sieves (640 mg) in DCE (15 mL) was allowed to stir for 5 min before the addition of sodium triacetoxyborohydride (478 mg, 2.25 mmol) portion wise over 5 min. The resulting mixture was allowed to stir for 4 h at r.t before the addition of further tetrahydropyran-4-one (158 mg, 1.58 mmol) and sodium triacetoxyborohydride (478 mg, 2.25 mmol). The mixture was stirred for 2 h then diluted with DCM and washed with 1M NaOH. The organic phase was dried (phase separator) and concentrated in vacuo. The resulting oil was purified by column chromatography (Si—PCC, 2M NH₃/MeOH:DCM, 0-15%) then (C18, MeOH:H₂O, 7.5-25%). The resulting residue was loaded onto an Isolute® SCX-2 cartridge which was washed with DCM and MeOH and the product eluted with 2M NH₃/MeOH affording 720 as a white foam (309 mg, 53%). LCMS (method I): R$_T$ 2.40 min,

[M+H]+ 519.3. ¹H NMR (MeOD, 400 MHz): δ 8.01-8.00 (1 H, m), 7.66-7.61 (1 H, m), 7.28-7.27 (2 H, m), 4.38 (4 H, s), 4.24 (2 H, d, J=8.76 Hz), 3.97-3.94 (2 H, m), 3.85 (7 H, s), 3.56 (2 H, d, J=8.75 Hz), 3.31-3.31 (5 H, m), 2.54-2.52 (1 H, m), 1.83-1.73 (2 H, m), 1.38 (5 H, t, J=7.49 Hz)

Example 721

1-(3-((2-(2-ethyl-1H-benzo[d]imidazol-1-yl)-9-methyl-6-morpholino-9H-purin-8-yl)methyl)azetidin-1-yl)-2-hydroxy-2-methylpropan-1-one 721

To a mixture of 8-azetidin-3-ylmethyl-2-(2-ethylbenzoimidazol-1-yl)-9-methyl-6-morpholin-4-yl-9H-purine (60 mg, 0.14 mmol), 2-hydroxyisobutyric acid (17 mg, 0.17 mmol) and DIPEA (29 µL, 0.17 mmol) in DCM (1 mL) was added HATU (63 mg, 0.17 mmol). The resulting yellow mixture was stirred for 1.5 h at r.t. then the reaction mixture was loaded onto an Isolute® SCX-2 cartridge which was washed with DCM and MeOH and the product eluted with 2M NH₃/MeOH. The resulting residue was purified by column chromatography (Si—PCC, MeOH:EtOAc, 0-6%) affording 721 as a foam (41 mg, 56%). LCMS (method I): R$_T$ 3.00 min, [M+H]+ 519.2. ¹H NMR (CDCl₃, 400 MHz): δ 8.00-7.97 (1 H, m), 7.75-7.74 (1 H, m), 7.27-7.25 (2 H, m), 4.62 (1 H, s), 4.33 (5 H, s), 4.20 (1 H, s), 3.93 (1 H, s), 3.86 (4 H, t, J=4.72 Hz), 3.76 (3 H, s), 3.64 (1 H, s), 3.34 (3 H, q, J=7.44 Hz), 3.15-3.14 (2 H, m), 1.43-1.42 (9 H, m)

Example 722

(R)-1-(4-((2-(2-ethyl-1H-benzo[d]imidazol-1-yl)-9-methyl-6-morpholino-9H-purin-8-yl)methyl)-3,3-dimethylpiperazin-1-yl)-2-hydroxypropan-1-one 722

A mixture of 8-(2,2-dimethylpiperazin-1-ylmethyl)-2-(2-ethylbenzoimidazol-1-yl)-9-methyl-6-morpholin-4-yl-9H-purine (100 mg, 0.20 mmol), D-Lactic acid (20 mg, 0.22 mmol), HATU (85 mg, 0.22 mmol) and DIPEA (40 µL, 0.23 mmol) in DCM (2 mL) was allowed to stir at r.t. for 16 h. The reaction mixture was loaded onto an Isolute® SCX-2 cartridge which was washed with MeOH and the product eluted with 2M NH₃/MeOH. The resulting residue was purified by column chromatography (Si—PCC, MeOH:DCM, 2%) affording 722 as a white solid (37 mg, 33%). LCMS (method I): R$_T$ 2.90 min, [M+H]+ 562.2. ¹H NMR (CDCl₃, 400 MHz): δ 8.04-7.99 (1 H, m), 7.77-7.76 (1 H, m), 7.35-7.25 (2 H, m), 4.47-4.45 (1 H, m), 4.34 (4 H, brd s), 4.02-3.98 (1 H, m), 3.91 (3 H, s), 3.86 (4 H, t, J=4.67 Hz), 3.82-3.68 (2 H, m), 3.50-3.49 (1 H, m), 3.40-3.31 (3 H, m), 3.27-3.16 (1 H, m), 2.57-2.55 (2 H, m), 1.45 (3 H, t, J=7.47 Hz), 1.39-1.28 (4 H, m), 1.27-1.15 (5 H, m)

Example 723

(S)-1-(4-((2-(2-ethyl-1H-benzo[d]imidazol-1-yl)-9-methyl-6-morpholino-9H-purin-8-yl)methyl)-3,3-dimethylpiperazin-1-yl)-2-hydroxypropan-1-one 723

A mixture of 8-(2,2-dimethylpiperazin-1-ylmethyl)-2-(2-ethylbenzoimidazol-1-yl)-9-methyl-6-morpholin-4-yl-9H-purine (100 mg, 0.20 mmol), L-Lactic acid (17 µL, 0.22 mmol), HATU (85 mg, 0.22 mmol) and DIPEA (40 µL, 0.23 mmol) in DCM (2 mL) was allowed to stir at r.t. for 16 h. The reaction mixture was loaded onto an Isolute® SCX-2 cartridge which was washed with MeOH and the product eluted with 2M NH₃/MeOH. The resulting residue was purified by column chromatography (Si—PCC, MeOH:DCM, 2%) affording 723 as a white solid (27 mg, 29%). LCMS (method I): R$_T$ 2.90 min, [M+H]+ 562.3. ¹H NMR (CDCl₃, 400 MHz): δ 8.02-8.00 (1 H, m), 7.78-7.74 (1 H, m), 7.35-7.25 (2 H, s), 4.46-4.43 (1 H, m), 4.34 (4 H, brd s), 4.06-3.94 (1 H, m), 3.91 (3 H, s), 3.86 (4 H, t, J=4.68 Hz), 3.76-3.75 (2 H, m), 3.50-3.48 (1 H, m), 3.37-3.35 (3 H, m), 3.24-3.22 (1 H, m), 2.59-2.53 (2 H, m), 1.45 (3 H, t, J=7.48 Hz), 1.34-1.30 (4 H, m), 1.26-1.15 (5 H, m)

Example 737

4-(8-(((2R,6S)-2,6-dimethyl-4-(methylsulfonyl)piperazin-1-yl)methyl)-2-(2-ethyl-1H-benzo[d]imidazol-1-yl)-9-methyl-9H-purin-6-yl)morpholine 737

A mixture of 8-bromomethyl-2-(2-ethylbenzoimidazol-1-yl)-9-methyl-6-morpholin-4-yl-9H-purine hydrobromide (200 mg, 0.37 mmol), (3S,5R)-1-methanesulfonyl-3,5-dimethylpiperazine (88 mg, 0.46 mmol) and K₂CO₃ (150 mg, 1.09 mmol) in DMF (1 mL) was allowed to stir at r.t. for 24 h. The reaction mixture was partitioned between EtOAc and H₂O, the organic phase dried (MgSO₄) and concentrated in vacuo. The resulting residue was purified by column chromatography (Si-PCC, MeOH:EtOAc, 0-10%) followed by recrystallisation from EtOAc affording 737 (57 mg, 28%). LCMS (method I): R$_T$ 3.05 min, [M+H]+ 568.2. ¹H NMR (CDCl₃, 400 MHz): δ 8.02-7.98 (1 H, m), 7.76-7.75 (1 H, m), 7.26-7.25 (2 H, m), 4.34 (4 H, s), 4.18 (2 H, s), 3.87 (4 H, t, J=4.70 Hz), 3.84 (3 H, s), 3.54-3.51 (2 H, m), 3.35 (2 H, q, J=7.48 Hz), 3.29-3.23 (2 H, m), 2.80 (3 H, s), 2.68-2.66 (2 H, m), 1.45 (3 H, dd, J=7.69, 7.26 Hz), 1.17 (6 H, d, J=6.36 Hz)

Example 738

3-(2-(2-ethyl-1H-benzo[d]imidazol-1-yl)-9-methyl-6-morpholino-9H-purin-8-yl)-1-isopropylazetidin-3-ol 738

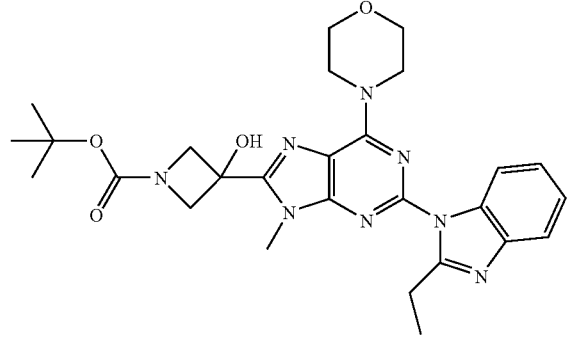

To a mixture of 2-(2-ethylbenzoimidazol-1-yl)-9-methyl-6-morpholin-4-yl-9H-purine (2.5 g, 6.88 mmol) and TMEDA (1.6 mL, 10.33 mmol) in THF (40 mL) at −78° C. was added n-BuLi (4.1 mL, 2.5 M in hexanes, 10.33 mmol). The resulting mixture was allowed to warm to −40° C. over 30 min then cooled back to −78° C. before the addition of a solution of 3-oxoazetidine-1-carboxylic acid tert-butyl ester (1.8 g, 10.33 mmol) in THF (10 mL). The reaction mixture was warmed to −10° C. over 2 h then quenched with sat. aq. NH₄Cl and extracted with EtOAc. The combined organic phases were washed with brine, dried (Na₂SO₄) and concentrated in vacuo. The resulting residue was purified by column chromatography (Si-PCC, MeOH:EtOAc, 0-5%) then recrystallised from ⁱPrOAc and pentane affording 3-[2-(2-Ethyl-benzoimidazol-1-yl)-9-methyl-6-morpholin-4-yl-9H-purin-8-yl]-3-hydroxy-azetidine-1-carboxylic acid tert-butyl ester as a cream solid (2.4 g, 64%). LCMS (method A): $R_T$ 2.83 min [M+H]⁺ 535.4

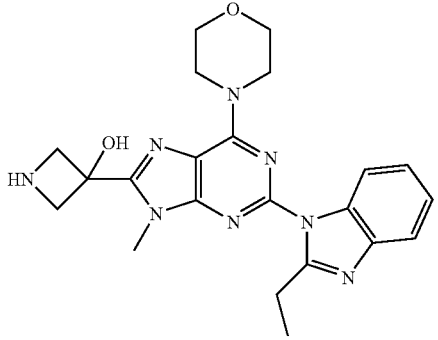

To a solution of 3-[2-(2-ethylbenzoimidazol-1-yl)-9-methyl-6-morpholin-4-yl-9H-purin-8-yl]-3-hydroxyazetidine-1-carboxylic acid tert-butyl ester (620 mg, 1.16 mmol) in DCM (5 mL) was added TFA (2 mL) and the resulting mixture allowed to stir for 1.5 h at r.t. The reaction mixture was loaded onto an Isolute® SCX-2 cartridge which was washed with DCM and MeOH and the product eluted with 2M NH₃/MeOH affording 3-[2-(2-Ethylbenzoimidazol-1-yl)-9-methyl-6-morpholin-4-yl-9H-purin-8-yl]azetidine-3-ol as a yellow oil (450 mg, 89%). LCMS: (method A): $R_T$ 1.84 min [M+H]⁺ 435.2

A mixture of 3-[2-(2-ethylbenzoimidazol-1-yl)-9-methyl-6-morpholin-4-yl-9H-purin-8-yl]-azetidin-3-ol (100 mg, 0.23 mmol), propan-2-one (34 µL, 27 mg, 0.46 mmol) and 4 Å powdered molecular sieves (150 mg) in DCE (3 mL) was stirred for 3 h before sodium triacetoxyborohydride (96 mg, 0.46 mmol) was added. The resulting mixture was stirred for 16 h at r.t., then filtered through Celite®, washing with DCM. The filtrate was washed with brine, dried (Na₂SO₄) and concentrated in vacuo. The resulting residue was purified by column chromatography (Si-PCC, MeOH:EtOAc, 0-20%) followed by reverse phase HPLC (Phenomenex Gemini 5 µm C18, 20 mM triethylamine in water on a gradient of acetonitrile 50-70%) affording 738 as a white solid (15 mg, 13%). LCMS (method I): $R_T$ 2.43 min, [M+H]⁺ 477.2. ¹H NMR (MeOD, 400 MHz): δ 8.01-8.01 (1 H, m), 7.64-7.61 (1 H, m), 7.29-7.28 (2 H, m), 4.39 (5 H, s), 4.19-4.17 (2 H, m), 3.85 (4 H, s), 3.46 (2 H, d, J=8.87 Hz), 3.31-3.30 (5 H, m), 2.56-2.54 (1 H, m), 1.39 (3 H, t, J=7.50 Hz), 1.01 (6 H, d, J=6.25 Hz)

Example 739

4-(2-(2-ethyl-1H-benzo[d]imidazol-1-yl)-8-(1-isopropyl-3-methoxyazetidin-3-yl)-9-methyl-9H-purin-6-yl)morpholine 739

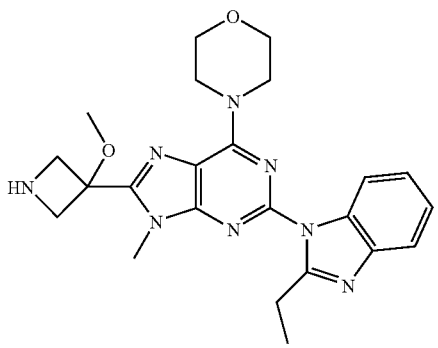

To a solution of 3-[2-(2-ethylbenzoimidazol-1-yl)-9-methyl-6-morpholin-4-yl-9H-purin-8-yl]-3-methoxyazetidine-1-carboxylic acid tert-butyl ester (109 mg, 0.20 mmol) in DCM (2 mL) was added TFA (1 mL) and the resulting mixture allowed to stir for 1.5 h at r.t. The reaction mixture was loaded onto an Isolute® SCX-2 cartridge which was washed with DCM and MeOH and the product eluted with 2M NH₃/MeOH affording 2-(2-Ethylbenzoimidazol-1-yl)-8-(3-methoxyazetidin-3-yl)-9-methyl-6-morpholin-4-yl-9H-purine as an oil (72 mg, 80%). LCMS: (method A): $R_T$ 1.86 min [M+H]⁺ 449.2

To a solution of 2-(2-ethylbenzoimidazol-1-yl)-8-(3-methoxyazetidin-3-yl)-9-methyl-6-morpholin-4-yl-9H-purine (553 mg, 1.23 mmol) and propan-2-one (1.0 mL) in MeOH (20 mL) was added 10% Pd/C (30 mg) as a slurry in MeOH (0.5 mL) and the resulting mixture stirred under an atmosphere of H₂ for 1.5 h at r.t. The reaction mixture was filtered through Celite®, washing with MeOH, and the filtrate concentrated in vacuo. The resulting residue was purified by column chromatography (Si-PCC, 2M NH₃/MeOH:EtOAc, 0-12%) then (C18, MeOH:H₂O, 5-25%). The resulting residue was loaded onto an Isolute® SCX-2 cartridge which was washed with DCM and MeOH and the product eluted with 2M NH₃/MeOH. The resulting colourless foam was recrystallised from ⁱPrOAc and pentane affording 739 as colourless crystals (166 mg, 28%). LCMS (method I): $R_T$ 2.48 min, [M+H]⁺ 491.3. ¹H NMR (CDCl₃, 400 MHz): δ 8.03-8.02 (1 H, m), 7.64-7.63 (1 H, m), 7.29-7.28 (2 H, m), 4.40 (4 H, s), 4.05 (2 H, d, J=8.89 Hz), 3.86 (4 H, s), 3.81 (3 H, s), 3.57-3.55 (2 H, m), 3.31-3.30 (2 H, m), 3.10 (3 H, s), 2.54-2.53 (1 H, m), 1.40 (3 H, t, J=7.50 Hz), 1.02 (6 H, d, J=6.24 Hz)

Example 740

4-(8-((2,2-dimethyl-4-(oxetan-3-yl)piperazin-1-yl)methyl)-2-(2-ethyl-1H-benzo[d]imidazol-1-yl)-9-methyl-9H-purin-6-yl)morpholine 740

A mixture of 2-chloro-8-(2,2-dimethyl-4-oxetan-3-ylpiperazin-1-ylmethyl)-9-methyl-6-morpholin-4-yl-9H-purine (90 mg, 0.21 mmol), 2-ethylbenzimidazole (32 mg, 0.22 mmol), tris(dibenzylideneacetone)dipalladium (5 mg, 2.5 mol %), XPhos (9 mg, 10 mol %) and Cs₂CO₃ (95 mg, 0.29 mmol) in dioxane (1 mL) was purged with argon then heated at 150° C. for 1 h in a microwave reactor. The reaction mixture was loaded onto an Isolute® SCX-2 cartridge which was washed with MeOH and the product eluted with 2M NH₃/MeOH. The resulting residue was purified by column chromatography (Si-PCC, MeOH:DCM, 1-3%) followed by reverse phase HPLC (Phenomenex Gemini 5 µm C18, 20 mM triethylamine in water on a gradient of acetonitrile 5-98%) affording 740 (54 mg, 48%). LCMS (method I): $R_T$ 2.62 min [M+H]⁺ 546.2. ¹H NMR (CDCl₃, 400 MHz): δ 8.01-8.01 (1 H, m), 7.75-7.74 (1 H, m), 7.31-7.22 (2 H, m), 4.64 (2 H, t, J=6.47 Hz), 4.57 (2 H, t, J=6.07 Hz), 4.34 (4 H, brd s), 3.90 (3 H, s), 3.86 (6 H, t, J=4.78 Hz), 3.36-3.35 (3 H, m), 2.52 (2 H, s), 2.24 (2 H, s), 2.11 (2 H, s), 1.45 (3 H, t, J=7.48 Hz), 1.24 (6 H, s)

Example 741

1-(4-((2-(2-ethyl-1H-benzo[d]imidazol-1-yl)-9-methyl-6-morpholino-9H-purin-8-yl)methyl)-3,3-dimethylpiperazin-1-yl)-2-hydroxy-2-methylpropan-1-one 741

A mixture of 8-(2,2-dimethylpiperazin-1-ylmethyl)-2-(2-ethylbenzoimidazol-1-yl)-9-methyl-6-morpholin-4-yl-9H- purine (100 mg, 0.20 mmol), 2-hydroxyisobutyric acid (24 mg, 0.23 mmol), HATU (85 mg, 0.22 mmol) and DIPEA (40 µL, 0.23 mmol) in DCM (2 mL) was allowed to stir at r.t. for 17 h. The reaction mixture was loaded onto an Isolute® SCX-2 cartridge which was washed with MeOH and the product eluted with 2M $NH_3$/MeOH. The resulting residue was purified by column chromatography (Si-PCC, MeOH: DCM, 0-3%) affording 741 as a white solid (55 mg, 46%). LCMS (method I): $R_T$ 2.89 min, $[M+H]^+$ 576.3. $^1$H NMR ($CDCl_3$, 400 MHz): δ 8.02-8.02 (1 H, m), 7.76-7.75 (1 H, m), 7.33-7.22 (2 H, m), 4.40-4.20 (5 H, m), 3.92 (3 H, s), 3.88-3.83 (5 H, m), 3.63 (2 H, s), 3.53 (2 H, s), 3.36 (2 H, q, J=7.48 Hz), 2.59-2.53 (2 H, m), 1.50 (6 H, s), 1.45 (3 H, t, J=7.48 Hz), 1.23 (6 H, s)

Example 7

4-(2-(2-ethyl-1H-benzo[d]imidazol-1-yl)-9-methyl-8-((7-(oxetan-3-yl)-4,7-diazaspiro[2.5]octan-4-yl)methyl)-9H-purin-6-yl)morpholine 744

A mixture of 2-(2-ethylbenzoimidazol-1-yl)-9-methyl-6-morpholin-4-yl-9H-purine-8-carbaldehyde (183 mg, 0.47 mmol), 7-oxetan-3-yl-4,7-diazaspiro[2.5]octane (90 mg, 0.54 mmol) and 4 Å powdered molecular sieves (1.0 g) in DCE (10 mL) was allowed to stir at r.t. for 6 h before the addition of sodium triacetoxyborohydride (144 mg, 0.68 mmol). The resulting mixture was allowed to stir for 16 h then loaded onto an Isolute® SCX-2 cartridge which was washed with MeOH and the product eluted with 2M $NH_3$/MeOH. The resulting residue was purified by column chromatography (Si-PCC, MeOH:EtOAc, 5% then MeOH:DCM, 1-5%) followed by recrystallisation from $Et_2O$ affording 744 (156 mg, 61%). LCMS (method I): $R_T$ 2.53 min $[M+H]^+$ 544.2. $^1$H NMR (DMSO, 400 MHz): δ 8.00-7.99 (1 H, m), 7.65-7.61 (1 H, m), 7.24-7.23 (2 H, m), 4.53 (2 H, t, J=6.46 Hz), 4.42 (2 H, t, J=6.05 Hz), 4.24 (4 H, brd s), 4.07 (2 H, s), 3.77 (4 H, t, J=4.61 Hz), 3.73 (3 H, s), 3.50-3.42 (1 H, m), 3.26 (2 H, q, J=7.44 Hz), 2.85-2.75 (2 H, m), 2.32 (2 H, t, J=4.72 Hz), 2.17 (2 H, brd s), 1.33 (3 H, t, J=7.44 Hz), 0.72-0.65 (2 H, m), 0.52-0.51 (2 H, m)

Example 746

3-(2-(2-ethyl-1H-benzo[d]imidazol-1-yl)-9-methyl-6-morpholino-9H-purin-8-yl)-1-(2-hydroxy-2-methylpropyl)piperidin-3-ol 746

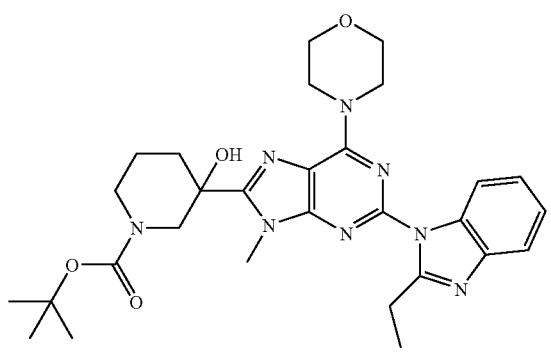

A mixture of 3-(2-chloro-9-methyl-6-morpholin-4-yl-9H-purin-8-yl)-3-hydroxypiperidine-1-carboxylic acid tert-butyl ester (3.0 g, 6.62 mmol), 2-ethylbenzimidazole (1.16 g, 7.94 mmol), tris(dibenzylideneacetone)dipalladium (152 mg, 0.17 mmol), XPhos (316 mg, 0.66 mmol) and $K_3PO_4$ (2.81 g, 13.24 mmol) in dioxane (80 mL) was purged with $N_2$ then heated at 90° C. for 22 h before further tris(dibenzylideneacetone)dipalladium (152 mg, 0.17 mmol) and XPhos (316 mg, 0.66 mmol) were added. The resulting mixture was heated at 100° C. for 65 h then diluted with 2-methyl THF and filtered through a silica plug. The filtrate was washed with $H_2O$ and brine, then dried ($Na_2SO_4$) and concentrated in vacuo. The resulting residue was purified by column chromatography (Si-PCC, EtOAc:cyclohexane, 20-85%) affording 3-[2-(2-Ethylbenzoimidazol-1-yl)-9-methyl-6-morpholin-4-yl-9H-purin-8-yl]-3-hydroxypiperidine-1-carboxylic acid tert-butyl ester (3.15 g, 85%). LCMS (method H): $R_T$ 2.87 min, $[M+H]^+$ 563.5

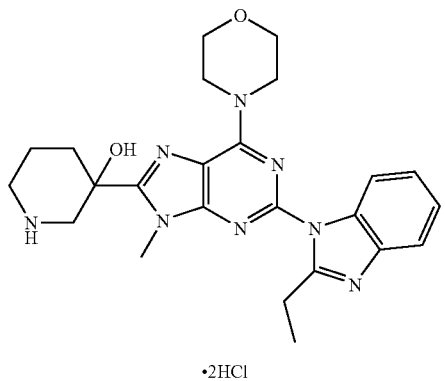

·2HCl

To a solution of 3-[2-(2-ethylbenzoimidazol-1-yl)-9-methyl-6-morpholin-4-yl-9H-purin-8-yl]-3-hydroxypiperidine-1-carboxylic acid tert-butyl ester (1.0 g, 1.78 mmol) in DCM (5 mL) and MeOH (1 mL) was added 4M HCl in dioxane (5 mL). The resulting mixture was allowed to stir for 2 h at r.t. before $Et_2O$ was added. The resulting precipitate was collected by filtration, washed with $Et_2O$ and dried in vacuo affording 3-[2-(2-Ethylbenzoimidazol-1-yl)-9-methyl-6-morpholin-4-yl-9H-purin-8-yl]piperidin-3-ol dihydrochloride (870 mg, 92%). LCMS (method H): $R_T$ 1.84 min $[M+H]^+$ 463.3

A mixture of 3-[2-(2-ethylbenzoimidazol-1-yl)-9-methyl-6-morpholin-4-yl-9H-purin-8-yl]piperidin-3-ol dihydrochloride (150 mg, 0.28 mmol), 2,2-dimethyloxirane (100 µL, 1.12 mmol) and DIPEA (192 µL, 1.12 mmol) in MeCN (4 mL) was stirred at r.t. for 20 h then heated at 70° C. for 24 h. The reaction mixture was concentrated in vacuo and the resulting residue purified by reverse phase HPLC (Phenomenex Gemini 5 µm C18, 0.1% $HCO_2H$ in water on a gradient acetonitrile 5-30%) affording 746 (35 mg, 23%). LCMS (method I): $R_T$ 2.57 min, $[M+H]^+$ 535.2. $^1$H NMR (DMSO, 400 MHz): δ 8.03-7.98 (1 H, m), 7.65-7.61 (1 H, m), 7.28-7.21 (2 H, m), 5.46 (1 H, s), 4.45-4.05 (5 H, m), 3.96 (3 H, s), 3.77-3.76 (4 H, m), 3.30-3.22 (2 H, m), 3.07-2.99 (1 H, m), 2.91-2.83 (1 H, m), 2.70-2.60 (1 H, m), 2.45-2.35 (1 H, m), 2.26 (2 H, s), 2.15-2.00 (1 H, m), 1.96-1.69 (3 H, m), 1.32 (3 H, t, J=7.43 Hz), 1.01 (6 H, d, J=15.78 Hz)

Example 747

4-(2-(2-ethyl-1H-benzo[d]imidazol-1-yl)-9-methyl-8-(1-(tetrahydro-2H-pyran-4-yl)azetidin-3-yl)-9H-purin-6-yl)morpholine 747

A mixture of 4-(8-(azetidin-3-yl)-2-(2-ethyl-1H-benzo[d] imidazol-1-yl)-9-methyl-9H-purin-6-yl)morpholine 680

(100 mg, 0.24 mmol), tetrahydropyran-4-one (34 mg, 0.33 mmol) and 4 Å powdered molecular sieves (130 mg) in DCE (3 mL) was stirred for 5.5 h before the addition of sodium triacetoxyborohydride (101 mg, 0.48 mmol). The resulting mixture was allowed to stir for 16 h at r.t, then filtered through Celite®, washing with DCM. The filtrate was washed with brine, dried ($Na_2SO_4$) and concentrated in vacuo. The resulting residue was purified by column chromatography (Si-PCC, MeOH:EtOAc, 0-30%) followed by Isolute® SCX-2 cartridge which was washed with MeOH/DCM and the product eluted with 2M $NH_3$/MeOH. The resulting solid was triturated with EtOAc affording 747 as a white powder (37 mg, 31%). LCMS (method I): $R_T$ 2.46 min, [M+H]$^+$ 503.1. $^1$H NMR ($CDCl_3$, 400 MHz): δ 8.01-7.97 (1 H, m), 7.75-7.74 (1 H, m), 7.26 (2 H, s), 4.37 (4 H, s), 4.02-3.80 (9 H, m), 3.70 (3 H, s), 3.51-3.37 (4 H, m), 3.34 (2 H, q, J=7.48 Hz), 2.41-2.33 (1 H, m), 1.77-1.66 (3 H, m), 1.43 (4 H, t, J=7.47 Hz)

Example 748

N-(2-(2-(2-ethyl-1H-benzo[d]imidazol-1-yl)-9-methyl-6-morpholino-9H-purin-8-yl)ethyl)-N,3-dimethyl-1,1-dioxotetrahydrothiophen-3-amine 748

A mixture of [2-(2-chloro-9-methyl-6-morpholin-4-yl-9H-purin-8-yl)ethyl]methyl-(3-methyl-1,1-dioxotetrahydrothiophen-3-yl)amine (87 mg, 0.20 mmol), 2-ethylbenzimidazole (32 mg, 0.22 mmol), tris(dibenzylideneacetone)dipalladium (5 mg, 2.5 mol %), XPhos (9 mg, 10 mol %) and $Cs_2CO_3$ (96 mg, 0.30 mmol) in dioxane (2 mL) was purged with argon then heated at 110° C. for 20 h in a sealed tube. The reaction mixture was loaded onto an Isolute® SCX-2 cartridge which was washed with MeOH and the product eluted with 2M $NH_3$/MeOH/DCM. The resulting residue was purified by column chromatography (Si-PCC, MeOH:DCM, 0-5%) affording 748 as an off-white solid (60 mg, 55%). LCMS (method I): $R_T$ 2.63 min, [M+H]$^+$ 553.1. $^1$H NMR ($CDCl_3$, 400 MHz): δ 8.01-7.98 (1 H, m), 7.75-7.74 (1 H, m), 7.30-7.23 (2 H, m), 4.34 (4 H, brd s), 3.87 (4 H, t, J=4.78 Hz), 3.78 (3 H, s), 3.37-3.30 (3 H, m), 3.01-3.00 (7 H, m), 2.40-2.30 (4 H, m), 2.08-2.08 (1 H, m), 1.44 (3 H, t, J=7.48 Hz), 1.29 (3 H, s)

Example 765

3-(2-(2-ethyl-1H-benzo[d]imidazol-1-yl)-9-methyl-6-morpholino-9H-purin-8-yl)-1-(methylsulfonyl)piperidin-3-ol 765

A mixture of 3-[2-(2-ethylbenzoimidazol-1-yl)-9-methyl-6-morpholin-4-yl-9H-purin-8-yl]piperidin-3-ol dihydrochloride from Example 746 (150 mg, 0.28 mmol) and DIPEA (192 μL, 1.12 mmol) in THF (3 mL) was stirred for 5 min before the addition of methanesulfonyl chloride (22 μL, 0.28 mmol). The resulting mixture was stirred at r.t. for 4 h then partitioned between $H_2O$ and DCM. The organic phase was washed with brine, then dried ($Na_2SO_4$) and concentrated in vacuo. The resulting residue was purified by column chromatography (Si-PCC, MeOH:EtOAc, 0-20%) affording 765 (67 mg, 44%). LCMS (method I): $R_T$ 3.30 min, [M+H]$^+$ 541.2. $^1$H NMR (DMSO, 400 MHz): δ 8.02-8.01 (1 H, m), 7.64-7.64 (1 H, m), 7.25-7.24 (2 H, m), 6.05 (1 H, s), 4.26 (4 H, brd s), 3.96 (3 H, s), 3.78 (4 H, t, J=4.60 Hz), 3.61 (2 H, s), 3.44-3.41 (1 H, m), 3.28-3.26 (2 H, m), 3.06-3.03 (1 H, m), 2.95 (3 H, s), 2.17-2.14 (1 H, m), 2.09-1.92 (2 H, m), 1.80-1.70 (1 H, m), 1.33 (3 H, t, J=7.43 Hz)

Example 766

4-(2-(2-ethyl-1H-benzo[d]imidazol-1-yl)-8-(3-methoxy-1-(methylsulfonyl)piperidin-3-yl)-9-methyl-9H-purin-6-yl)morpholine 766

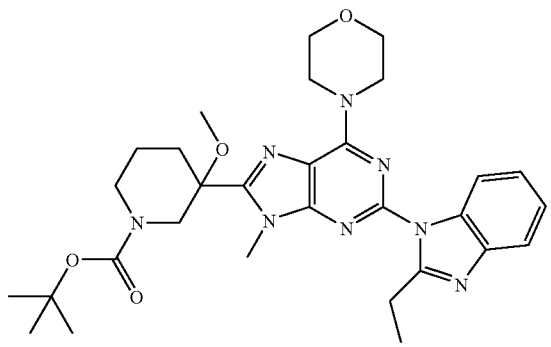

To a solution of 3-[2-(2-ethylbenzoimidazol-1-yl)-9-methyl-6-morpholin-4-yl-9H-purin-8-yl]-3-hydroxypiperidine-1-carboxylic acid tert-butyl ester (1.0 g, 1.78 mmol) in THF (20 mL) was added NaH (86 mg, 2.14 mmol, 60% dispersion in mineral oil) and the resulting mixture allowed to stir for 5 min before the addition of iodomethane (135 μL, 2.14 mmol) and 15-Crown-5 (4 drops). The resulting mixture was stirred for 3 h before further NaH (86 mg, 2.14 mmol) and iodomethane (135 μL, 2.14 mmol) were added. The resulting mixture was allowed to stir for 8 days then partitioned between 2-methyl THF and $H_2O$. The organic phase was washed with sat. aq. $NaHCO_3$ and brine, then dried ($Na_2SO_4$) and concentrated in vacuo affording 3-[2-(2-Ethylbenzoimidazol-1-yl)-9-methyl-6-morpholin-4-yl-9H-purin-8-yl]-3-methoxypiperidine-1-carboxylic acid tert-butyl ester. LCMS (method H): $R_T$ 3.28 min [M+H]$^+$ 577.5

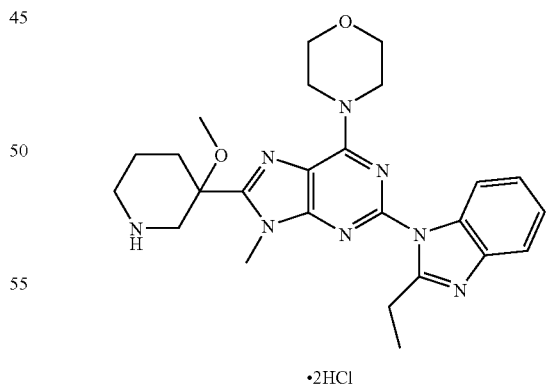

•2HCl

To a solution of 3-[2-(2-ethylbenzoimidazol-1-yl)-9-methyl-6-morpholin-4-yl-9H-purin-8-yl]-3-methoxypiperidine-1-carboxylic acid tert-butyl ester in DCM (10 mL) and MeOH (10 mL) was added 4M HCl in dioxane (10 mL). The resulting mixture was allowed to stir at r.t. for 16 h then concentrated in vacuo. The resulting residue was triturated with $Et_2O$, the solid collected by filtration and dried in vacuo affording 2-(2-Ethylbenzoimidazol-1-yl)-8-(3-methoxypiperidin-3-yl)-9-methyl-6-morpholin-4-yl-9H-purine dihydrochloride (1.0 g, quant.). LCMS (method H): $R_T$ 2.05 min [M+H]$^+$ 477.2

A mixture of 2-(2-ethylbenzoimidazol-1-yl)-8-(3-methoxypiperidin-3-yl)-9-methyl-6-morpholin-4-yl-9H-purine dihydrochloride (150 mg, 0.27 mmol) and DIPEA (190 μL, 1.09 mmol) in THF (3 mL) was stirred for 5 min before the addition of methanesulfonyl chloride (21 μL, 0.27 mmol). The resulting mixture was stirred at r.t. for 4 h then partitioned between H$_2$O and DCM. The organic phase was washed with brine, then dried (Na$_2$SO$_4$) and concentrated in vacuo. The resulting residue was purified by column chromatography (Si-PCC, EtOAc:TBME, 0-100%) affording 766 (39 mg, 26%). LCMS (method I): $R_T$ 3.74 min, [M+H]$^+$ 555.2. $^1$H NMR (DMSO, 400 MHz): δ 8.05-8.04 (1 H, m), 7.64-7.63 (1 H, m), 7.28-7.24 (2 H, m), 4.27 (4 H, brd s), 3.97 (1 H, d, J=13.24 Hz), 3.92 (3 H, s), 3.79 (4 H, t, J=4.61 Hz), 3.50-3.47 (2 H, m), 3.28-3.26 (2 H, m), 3.08 (3 H, s), 3.05-2.95 (4 H, m), 2.35-2.25 (1 H, m), 1.98-1.95 (2 H, m), 1.76-1.72 (1 H, m), 1.35 (3 H, t, J=7.43 Hz)

Example 771

(5-(2-ethyl-1H-benzo[d]imidazol-1-yl)-7-morpholinothiazolo[5,4-d]pyrimidin-2-yl)(4-(2-hydroxypropan-2-yl)piperidin-1-yl)methanone 771

A mixture of (5-chloro-7-morpholin-4-ylthiazolo[5,4-d]pyrimidin-2-yl)-[4-(1-hydroxy-1-methylethyl)piperidin-1-yl]methanone (250 mg, 0.59 mmol), 2-ethylbenzimidazole (90 mg, 0.62 mmol), tris(dibenzylideneacetone)dipalladium (15 mg, 2.5 mol %), XPhos (25 mg, 10 mol %) and Cs$_2$CO$_3$ (270 mg, 0.83 mmol) in DMF (6 mL) was purged with argon then heated at 150° C. for 30 min in a microwave reactor. The reaction mixture was purified by column chromatography (Si-PCC, MeOH:DCM, 1-5%) followed by recrystallisation from Et$_2$O and EtOAc affording 771 (109 mg, 35%). LCMS (method I): $R_T$ 3.96 min [M+H]$^+$ 536.3. $^1$H NMR (CDCl$_3$, 400 MHz): δ 8.06-8.05 (1 H, m), 7.76-7.75 (1 H, m), 7.32-7.28 (2 H, m), 5.22 (1 H, d, J=13.34 Hz), 4.84 (1 H, d, J=13.16 Hz), 4.41 (4 H, brd s), 3.89 (4 H, t, J=4.74 Hz), 3.37 (2 H, q, J=7.46 Hz), 3.17-3.15 (1 H, m), 2.84-2.82 (1 H, m), 1.94 (2 H, t, J=13.72 Hz), 1.72-1.62 (1 H, m), 1.49-1.40 (5 H, m), 1.23 (6 H, d, J=7.01 Hz)

Example 772

3-(2-(2-ethyl-1H-benzo[d]imidazol-1-yl)-9-methyl-6-morpholino-9H-purin-8-yl)-1-(tetrahydro-2H-pyran-4-yl)piperidin-3-ol 772

A mixture of 3-[2-(2-ethylbenzoimidazol-1-yl)-9-methyl-6-morpholin-4-yl-9H-purin-8-yl]piperidin-3-ol dihydrochloride from Example 746 (150 mg, 0.28 mmol), tetrahydropyran-2-one (39 μL, 0.42 mmol), NEt$_3$ (78 μL, 0.56 mmol) and 4 Å powdered molecular sieves (300 mg) in DCE (3 mL) was stirred for 2 h before the addition of sodium triacetoxyborohydride (119 mg, 0.56 mmol). The resulting mixture was allowed to stir at r.t for 20 h then diluted with DCM and filtered. The filtrate was concentrated in vacuo and the residue was purified by column chromatography (Si-PCC, MeOH:EtOAc, 0-20%). The resulting residue was dissolved in DCM and treated with 4M HCl in dioxane. The resulting solid was triturated with Et$_2$O and dried in vacuo affording 772 (124 mg, 72%). LCMS (method I): $R_T$ 2.52 min, [M+H]$^+$ 547.2. $^1$H NMR (DMSO, 400 MHz): δ 9.36 (1 H, s), 8.18-8.14 (1 H, m), 7.80-7.79 (1 H, m), 7.50-7.48 (2 H, m), 4.28 (4 H, brd s), 4.10-3.90 (6 H, m), 3.78-3.77 (5 H, m), 3.43-3.39 (7 H, m), 3.25-3.10 (1 H, m), 2.30-1.65 (7 H, m), 1.44-1.38 (3 H, m)

Example 775

(S)-2-(1-((2-(2-ethyl-1H-benzo[d]imidazol-1-yl)-9-methyl-6-(3-methylmorpholino)-9H-purin-8-yl)methyl)piperidin-4-yl)propan-2-ol 775

A mixture of 2-{1-[2-chloro-9-methyl-6-((S)-3-methylmorpholin-4-yl)-9H-purin-8-ylmethyl]piperidin-4-yl}propan-2-ol (200 mg, 0.47 mmol), 2-ethylbenzimidazole (73 mg, 0.50 mmol), tris(dibenzylideneacetone)dipalladium (12 mg, 2.5 mol %), XPhos (20 mg, 10 mol %) and Cs$_2$CO$_3$ (218 mg, 0.67 mmol) in DMF (6 mL) was purged with argon then heated at 150° C. for 1 h in a microwave reactor. The reaction mixture was loaded onto an Isolute® SCX-2 cartridge which was washed with MeOH and the product eluted with 2M NH$_3$/MeOH. The resulting residue was purified by column chromatography (Si-PCC, MeOH:DCM, 0-5%) then (Si-PCC, MeOH:DCM, 0-3%) affording 775 (95 mg, 38%). LCMS (method I): $R_T$ 2.65 min, [M+H]$^+$ 533.3. $^1$H NMR (CDCl$_3$, 400 MHz): δ 8.03-8.02 (1 H, m), 7.75-7.74 (1 H, m), 7.27-7.24 (2 H, m), 5.40 (2 H, brd s), 4.09-4.03 (1 H, m), 3.88 (3 H, s), 3.83 (2 H, s), 3.75-3.55 (4 H, m), 3.36 (2 H, q, J=7.48 Hz), 2.98-2.95 (2 H, m), 2.11 (2 H, t, J=10.92 Hz), 1.81-1.71 (2 H, m), 1.45-1.44 (6 H, m), 1.34-1.31 (4 H, m), 1.19 (6 H, s)

Example 780

(1-aminocyclopropyl)(4-((2-(2-ethyl-1H-benzo[d]imidazol-1-yl)-9-methyl-6-morpholino-9H-purin-8-yl)methyl)-3,3-dimethylpiperazin-1-yl)methanone 780

To a solution of (1-{4-[2-(2-ethylbenzoimidazol-1-yl)-9-methyl-6-morpholin-4-yl-9H-purin-8-ylmethyl]-3,3-dimethylpiperazine-1-carbonyl}cyclopropyl)carbamic acid tert-butyl ester in DCM (3 mL) was added TFA (2 mL) and the resulting mixture stirred at r.t. for 30 min then loaded onto an Isolute® SCX-2 cartridge which was washed with MeOH and the product eluted with 2M NH$_3$/MeOH. The resulting residue was purified by column chromatography (Si-PCC, MeOH:DCM, 0-10%) affording 780 as a white foam (99 mg, 60%). LCMS (method I): $R_T$ 2.67 min, [M+H]$^+$ 573.3. $^1$H NMR (CDCl$_3$, 400 MHz): δ 8.02-8.01 (1 H, m), 7.76-7.75 (1 H, m), 7.32-7.22 (2 H, m), 4.34 (4 H, s), 3.93 (3 H, s), 3.88-3.86 (6 H, m), 3.65 (2 H, s), 3.48 (2 H, s), 3.36 (2 H, q, J=7.48 Hz), 2.57 (2 H, t, J=5.16 Hz), 1.85-1.75 (2 H, brd s), 1.45 (3 H, t, J=7.46 Hz), 1.23 (6 H, s), 1.05-0.99 (2 H, m), 0.81-0.80 (2 H, m)

Example 781

(R)-2-(1-((2-(2-ethyl-1H-benzo[d]imidazol-1-yl)-9-methyl-6-(3-methylmorpholino)-9H-purin-8-yl)methyl)piperidin-4-yl)propan-2-ol 781

A mixture of 2-{1-[2-chloro-9-methyl-6-((R)-3-methylmorpholin-4-yl)-9H-purin-8-ylmethyl]piperidin-4-yl}propan-2-ol (120 mg, 0.28 mmol), 2-ethylbenzimidazole (46 mg, 0.31 mmol), tris(dibenzylideneacetone)dipalladium (7 mg, 2.5 mol %), XPhos (14 mg, 10 mol %) and Cs$_2$CO$_3$ (139 mg, 0.43 mmol) in dioxane (3 mL) was purged with argon then heated at 110° C. for 4 h in a sealed tube. The reaction mixture was loaded onto an Isolute® SCX-2 cartridge which was washed with MeOH and the product eluted with 2M NH₃/MeOH/DCM. The resulting residue was purified by column chromatography (Si-PCC, MeOH:EtOAc, 0-20%) followed by (Si-PCC, MeOH:DCM, 0-10%) affording 781 as a white solid (65 mg, 43%). LCMS (method I): R$_T$ 2.64 min, [M+H]⁺ 533.3. ¹H NMR (CDCl₃, 400 MHz): δ 8.03-8.02 (1 H, m), 7.76-7.75 (1 H, m), 7.30-7.25 (2 H, m), 4.06-4.05 (1 H, m), 3.88 (3 H, s), 3.83 (2 H, s), 3.73 (2 H, s), 3.70-3.55 (2 H, m), 3.36 (2 H, q, J=7.48 Hz), 2.99-2.96 (2 H, m), 2.16-2.06 (2 H, m), 1.81-1.71 (2 H, m), 1.58 (2 H, brd s), 1.48-1.42 (6 H, m), 1.43-1.27 (3 H, m), 1.19 (6 H, s)

Example 790

1-(4-(2-(2-ethyl-1H-benzo[d]imidazol-1-yl)-9-methyl-6-morpholino-9H-purin-8-yl)-4-hydroxypiperidin-1-yl)-2-hydroxy-2-methylpropan-1-one 790

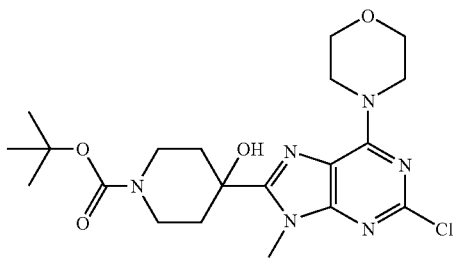

To a mixture of 2-chloro-9-methyl-6-morpholin-4-yl-9H-purine (2.5 g, 9.86 mmol) and TMEDA (2.1 mL, 14.8 mmol) in THF (80 mL) at −78° C. was added n-BuLi (6 mL, 2.5 M in hexanes, 14.8 mmol). The resulting mixture was allowed to warm to −30° C. for 30 min then cooled back to −78° C. before the addition of a solution of 4-oxo-piperidine-1-carboxylic acid tert-butyl ester (2.9 g, 14.8 mmol) in THF (20 mL). The reaction mixture was slowly warmed to r.t. and stirred for 16 h then quenched with H₂O and extracted with EtOAc. The combined organic phases were washed with brine, dried (Na₂SO₄) and concentrated in vacuo. The resulting residue was purified by column chromatography (Si-PCC, EtOAc:cyclohexane, 10-75%) affording 4-(2-Chloro-9-methyl-6-morpholin-4-yl-9H-purin-8-yl)-4-hydroxypiperidine-1-carboxylic acid tert-butyl ester (3.2 g, 71%). LCMS (method H): R$_T$ 3.52 min [M+H]⁺ 453.3

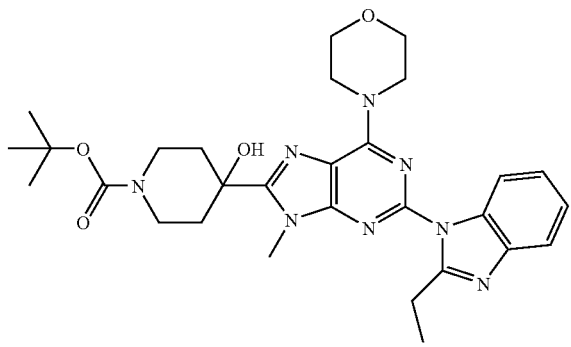

A mixture of 4-(2-chloro-9-methyl-6-morpholin-4-yl-9H-purin-8-yl)-4-hydroxypiperidine-1-carboxylic acid tert-butyl ester (2.5 g, 5.52 mmol), 2-ethylbenzimidazole (968 mg, 6.62 mmol), tris(dibenzylideneacetone)dipalladium (126 mg, 0.14 mmol), XPhos (263 mg, 0.55 mmol) and K₃PO₄ (2.34 g, 11.04 mmol) in dioxane (50 mL) was purged with N₂ then heated at 100° C. for 6 h before further tris(dibenzylideneacetone)dipalladium (126 mg, 0.14 mmol) and XPhos (263 mg, 0.55 mmol) were added. The resulting mixture was heated at 100° C. for 18 h then diluted with 2-methyl THF and filtered through Celite®. The filtrate was washed with H₂O and brine, then dried (Na₂SO₄) and concentrated in vacuo. The resulting residue was purified by column chromatography (Si-PCC, EtOAc:cyclohexane, 40-100%) affording 4-[2-(2-Ethylbenzoimidazol-1-yl)-9-methyl-6-morpholin-4-yl-9H-purin-8-yl]-4-hydroxypiperidine-1-carboxylic acid tert-butyl ester (2.6 g, 84%). LCMS (method H): R$_T$ 2.99 min, [M+H]⁺ 563.4

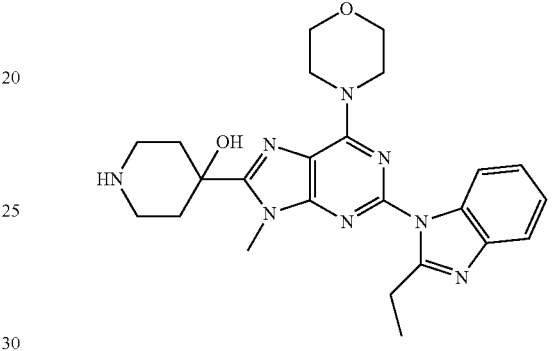

To a solution of 4-[2-(2-ethylbenzoimidazol-1-yl)-9-methyl-6-morpholin-4-yl-9H-purin-8-yl]-4-hydroxypiperidine-1-carboxylic acid tert-butyl ester (1.3 g, 2.31 mmol) in DCM (10 mL) was added TFA (2 mL) and the resulting mixture allowed to stir at r.t. for 3 h. The reaction mixture was concentrated in vacuo and the resulting residue loaded onto an Isolute® SCX-2 cartridge which was washed with MeOH and the product eluted with 2M NH₃/MeOH affording 4-[2-(2-Ethylbenzoimidazol-1-yl)-9-methyl-6-morpholin-4-yl-9H-purin-8-yl]piperidin-4-ol (1.1 g, quant.). LCMS (method H): R$_T$ 1.79 min, [M+H]⁺ 463.3

To a mixture of 4-[2-(2-ethylbenzoimidazol-1-yl)-9-methyl-6-morpholin-4-yl-9H-purin-8-yl]piperidin-4-ol (150 mg, 0.32 mmol), 2-hydroxyisobutyric acid (41 mg, 0.39 mmol) and DIPEA (68 μL, 0.39 mmol) in DCM (2 mL) was added HATU (149 mg, 0.39 mmol). The resulting mixture was allowed to stir at r.t. for 18 h then diluted with DCM and washed with sat. aq. NaHCO₃. The organic phase was dried (Na₂SO₄) and concentrated in vacuo. The resulting residue was purified by column chromatography (Si-PCC, MeOH:EtOAc, 0-20%) affording 790 (60 mg, 34%). LCMS (method I): R$_T$ 3.09 min, [M+H]⁺ 549.3. ¹H NMR (DMSO, 400 MHz): δ 8.02-8.01 (1 H, m), 7.64-7.63 (1 H, m), 7.27-7.23 (2 H, m), 5.84 (1 H, s), 5.42 (1 H, s), 4.25 (6 H, brd s), 3.98 (3 H, s), 3.77 (4 H, t, J=4.55 Hz), 3.60 (1 H, brd s), 3.2-3.24 (3 H, m), 2.11-2.10 (2 H, m), 2.06-1.94 (2 H, m), 1.38-1.30 (9 H, m)

Example 791

1-(3-(2-(2-ethyl-1H-benzo[d]imidazol-1-yl)-9-methyl-6-morpholino-9H-purin-8-yl)-3-methoxypiperidin-1-yl)-2-methylpropan-2-ol 791

A mixture of 2-(2-ethylbenzoimidazol-1-yl)-8-(3-methoxypiperidin-3-yl)-9-methyl-6-morpholin-4-yl-9H-purine dihydrochloride (150 mg, 0.27 mmol), 2,2-dimethyloxirane (242 μL, 2.73 mmol) and DIPEA (187 μL, 1.09 mmol) in MeCN (3 mL) was heated at 70° C. r.t. for 3 h before further 2,2-dimethyloxirane (242 μL, 2.73 mmol) was added and the mixture heated at 90° C. for 6 h. The reaction mixture was concentrated in vacuo and the resulting residue purified by column chromatography (Si-PCC, MeOH:EtOAc, 0-20%) affording 791 (51 mg, 34%). LCMS (method I): $R_T$ 2.72 min, [M+H]$^+$ 549.3. $^1$H NMR (DMSO, 400 MHz): δ 8.03-8.02 (1 H, m), 7.64-7.63 (1 H, m), 7.25-7.24 (2 H, m), 4.26 (4 H, brd s), 4.08 (1 H, s), 3.91 (3 H, s), 3.79 (4 H, t, J=4.72 Hz), 3.27-3.26 (2 H, m), 3.20-3.15 (1 H, m), 3.06 (3 H, s), 3.01-2.97 (1 H, m), 2.69-2.61 (1 H, m), 2.46-2.38 (1 H, m), 2.25 (2 H, s), 2.17-2.14 (1 H, m), 1.92-1.75 (3 H, m), 1.33 (3 H, t, J=7.43 Hz), 1.03 (3 H, s), 0.94 (3 H, s)

Example 792

4-(6-((2,2-dimethyl-4-(oxetan-3-yl)piperazin-1-yl) methyl)-2-(2-ethyl-1H-benzo[d]imidazol-1-yl)thieno [3,2-d]pyrimidin-4-yl)morpholine 792

A mixture of 2-chloro-6-(2,2-dimethyl-4-oxetan-3-ylpiperazin-1-ylmethyl)-4-morpholin-4-yl-thieno[3,2-d]pyrimidine (136 mg, 0.31 mmol), 2-ethylbenzimidazole (48 mg, 0.33 mmol), tris(dibenzylideneacetone)dipalladium (8 mg, 3 mol %), XPhos (14 mg, 9 mol %) and Cs$_2$CO$_3$ (143 mg, 0.44 mmol) in DMF (4 mL) was purged with argon then heated at 150° C. for 30 min in a microwave reactor. The reaction mixture was loaded onto an Isolute® SCX-2 cartridge which was washed with MeOH and the product eluted with 2M NH$_3$/MeOH. The resulting residue was purified by column chromatography (Si-PCC, MeOH:DCM, 0-5%) then (Si-PCC, 2M NH$_3$/MeOH:DCM, 0-2%) affording 792 as a cream solid (45 mg, 26%). LCMS (method I): $R_T$ 2.78 min [M+H]$^+$ 548.3. $^1$H NMR (CDCl$_3$, 400 MHz): δ 7.97-7.96 (1 H, m), 7.75-7.74 (1 H, m), 7.32-7.22 (3 H, m), 4.66 (2 H, t, J=6.47 Hz), 4.59 (2 H, t, J=6.08 Hz), 4.04 (4 H, t, J=4.72 Hz), 3.91-3.86 (6 H, m), 3.46-3.45 (1 H, m), 3.33 (2 H, q, J=7.48 Hz), 2.64 (2 H, t, J=4.98 Hz), 2.33 (2 H, s), 2.14 (2 H, s), 1.42 (3 H, t, J=7.47 Hz), 1.20 (6 H, s)

Example 793

(2,2-dimethyl-4-(oxetan-3-yl)piperazin-1-yl)(5-(2-ethyl-1H-benzo[d]imidazol-1-yl)-7-morpholinothiazolo[5,4-d]pyrimidin-2-yl)methanone 793

A mixture of (5-chloro-7-morpholin-4-ylthiazolo[5,4-d] pyrimidin-2-yl)-(2,2-dimethyl-4-oxetan-3-ylpiperazin-1-yl) methanone (137 mg, 0.30 mmol), 2-ethylbenzimidazole (47 mg, 0.32 mmol), tris(dibenzylideneacetone)dipalladium (8 mg, 2.5 mol %), XPhos (13 mg, 10 mol %) and Cs$_2$CO$_3$ (140 mg, 0.43 mmol) in DMF (4 mL) was purged with argon then heated at 150° C. for 30 min in a microwave reactor. The reaction mixture was loaded onto an Isolute® SCX-2 cartridge which was washed with MeOH and the product eluted with 2M NH$_3$/MeOH. The resulting residue was purified by column chromatography (Si-PCC, MeOH:DCM, 1-2%) followed by triturating with EtOAc affording 793 (22 mg, 13%). LCMS (method I): $R_T$ 3.79 min [M+H]$^+$ 563.3. $^1$H NMR (CDCl$_3$, 400 MHz): δ 8.07-8.03 (1 H, m), 7.76-7.75 (1 H, m), 7.30-7.29 (2 H, m), 4.72 (2 H, t, J=6.51 Hz), 4.62 (2 H, t, J=6.07 Hz), 4.40 (4 H, brd s), 4.07-4.06 (2 H, m), 3.89 (4 H, t, J=4.72 Hz), 3.53-3.52 (1 H, m), 3.36 (2 H, q, J=7.46 Hz), 2.47 (2 H, t, J=5.08 Hz), 2.25 (2 H, s), 1.56 (6 H, s), 1.44 (3 H, t, J=7.45 Hz)

Example 796

4-(1-((5-(2-ethyl-1H-benzo[d]imidazol-1-yl)-7-morpholinothiazolo[5,4-d]pyrimidin-2-yl)methyl)azetidin-3-yl)piperazin-2-one 796

A mixture of 4-[1-(5-chloro-7-morpholin-4-ylthiazolo[5, 4-d]pyrimidin-2-ylmethyl)azetidin-3-yl]piperazin-2-one (315 mg, 0.74 mmol), 2-ethylbenzimidazole (120 mg, 0.82 mmol), tris(dibenzylideneacetone)dipalladium (17 mg, 0.02 mmol), XPhos (35 mg, 0.07 mmol) and Cs$_2$CO$_3$ (365 mg, 1.12 mmol) in dioxane (10 mL) was purged with argon then heated at 115° C. for 4 h then stirred at r.t. for 16 h. The reaction mixture was filtered through Celite®, washing with dioxane, and the filtrate concentrated in vacuo. The resulting residue was purified by column chromatography (Si-PCC, MeOH:DCM, 1-10%) affording 796 (146 mg, 37%). LCMS (method G): $R_T$ 4.90 min, [M+H]$^+$ 534.3. $^1$H NMR (DMSO, 400 MHz): δ 7.99-7.99 (1 H, m), 7.75 (1 H, s), 7.64-7.63 (1 H, m), 7.26-7.25 (2 H, m), 4.32 (4 H, brd s), 4.04 (2 H, s), 3.79 (4 H, t, J=4.61 Hz), 3.57-3.52 (2 H, m), 3.31 (2 H, s), 3.25 (2 H, q, J=7.43 Hz), 3.18-3.14 (5 H, m), 2.87 (2 H, s), 1.32 (3 H, t, J=7.42 Hz)

Example 797

(2-(2-ethyl-1H-benzo[d]imidazol-1-yl)-9-methyl-6-morpholino-9H-purin-8-yl)(3-(4-hydroxypiperidin-1-yl)azetidin-1-yl)methanone 797

A mixture of 2-(2-ethylbenzoimidazol-1-yl)-9-methyl-6-morpholin-4-yl-9H-purine-8-carboxylic acid (215 mg, 0.53 mmol), 2-chloro-1-methylpyridinium iodide (324 mg, 1.27 mmol) and DIPEA (460 μL, 2.64 mmol) in DMF (2 mL) was stirred for 5 min before the addition of 1-azetidin-3-ylpiperidin-4-ol (140 mg, 0.90 mmol) in DMF (2 mL). The resulting mixture was allowed to stir for 2 h then loaded onto an Isolute® SCX-2 cartridge which was washed with MeOH and the product eluted with 2M NH$_3$/MeOH. The resulting residue was purified by column chromatography (Si-PCC, MeOH:DCM, 0-10%) affording 797 as a pale yellow solid (76 mg, 26%). LCMS (method G): $R_T$ 5.26 min, [M+H]$^+$ 546.4. $^1$H NMR (CDCl$_3$, 400 MHz): δ 8.06-8.06 (1 H, m), 7.76-7.75 (1 H, m), 7.31-7.24 (2 H, m), 4.72-4.71 (1 H, m), 4.50 (1 H, dd, J=10.65, 5.40 Hz), 4.30-4.20 (1 H, m), 4.14 (3 H, s), 4.14-4.07 (1 H, m), 3.88 (4 H, t, J=4.71 Hz), 3.81 (1 H, s), 3.37 (2 H, q, J=7.47 Hz), 3.28-3.27 (1 H, m), 2.72 (2 H, d, J=27.26 Hz), 2.25-2.10 (2 H, m), 2.01-1.91 (2 H, m), 1.68-1.60 (5 H, m), 1.46-1.43 (4 H, m)

Example 798

(2-(2-cyclopropyl-1H-benzo[d]imidazol-1-yl)-9-methyl-6-morpholino-9H-purin-8-yl)(4-(2-hydroxypropan-2-yl)piperidin-1-yl)methanone 798

A mixture of 2-(2-cyclopropylbenzoimidazol-1-yl)-9-methyl-6-morpholin-4-yl-9H-purine-8-carboxylic acid (200 mg, 0.48 mmol), 2-piperidin-4-ylpropan-2-ol (78 mg, 0.55 mmol), HATU (205 mg, 0.54 mmol) and DIPEA (96 μL, 0.55 mmol) in DCM (5 mL) was allowed to stir at r.t. for 19 h. The reaction mixture was loaded onto an Isolute® SCX-2 cartridge which was washed with MeOH and the product eluted with 2M NH$_3$/MeOH. The resulting residue was purified by column chromatography (Si-PCC, MeOH:DCM, 0-3%) then (Si-PCC, MeOH:EtOAc, 0-5%) affording 798 as a white solid (138 mg, 53%). LCMS (method G): $R_T$ 7.50 min,

[M+H]+ 545.4. ¹H NMR (CDCl₃, 400 MHz): δ 7.97-7.96 (1 H, m), 7.68-7.67 (1 H, m), 7.28-7.20 (2 H, s), 4.91-4.82 (1 H, m), 4.68-4.65 (1 H, m), 4.40 (4 H, brd s), 3.97 (3 H, s), 3.86 (4 H, t, J=4.70 Hz), 3.18-3.10 (1 H, m), 2.84-2.83 (2 H, m), 1.94-1.92 (2 H, m), 1.64-1.62 (1 H, m), 1.44-1.43 (2 H, m), 1.35-1.34 (2 H, m), 1.24-1.22 (7 H, m), 1.06-1.05 (2 H, m)

Example 799

(2-(2-cyclopropyl-1H-benzo[d]imidazol-1-yl)-9-methyl-6-morpholino-9H-purin-8-yl)(3-morpholinoazetidin-1-yl)methanone 799

To a mixture of 2-(2-cyclopropylbenzoimidazol-1-yl)-9-methyl-6-morpholin-4-yl-9H-purine-8-carboxylic acid (500 mg, 1.19 mmol), 2-chloro-1-methylpyridinium iodide (729 mg, 2.86 mmol) and DIPEA (500 µL, 2.87 mmol) in DMF (10 mL) was added 4-azetidin-3-ylmorpholine (288 mg, 2.0 mmol) and the resulting mixture allowed to stir at r.t for 18 h. The reaction mixture was concentrated in vacuo and the resulting residue dissolved in EtOAc which was washed with H₂O and brine, then dried (MgSO₄) and concentrated in vacuo. The resulting residue was purified by column chromatography (Si-PCC, MeOH:EtOAc, 0-5%) affording 799 as a cream solid (290 mg, 45%). LCMS (method G): R_T 5.90 min, [M+H]+ 544.5. ¹H NMR (CDCl₃, 400 MHz): δ 7.99-7.99 (1 H, m), 7.67-7.67 (1 H, m), 7.28-7.20 (2 H, m), 4.73-4.72 (1 H, m), 4.70-4.00 (4 H, brd s), 4.53-4.51 (1 H, m), 4.29-4.21 (1 H, m), 4.18-4.08 (4 H, m), 3.87 (4 H, t, J=4.67 Hz), 3.78 (4 H, t, J=4.60 Hz), 3.30-3.30 (1 H, m), 2.88-2.88 (1 H, m), 2.47-2.45 (4 H, m), 1.35-1.34 (2 H, m), 1.06-1.05 (2 H, m)

Example 800

1-(4-(2-(2-ethyl-1H-benzo[d]imidazol-1-yl)-9-methyl-6-morpholino-9H-purin-8-yl)-4-methoxypiperidin-1-yl)-2-hydroxy-2-methylpropan-1-one 800

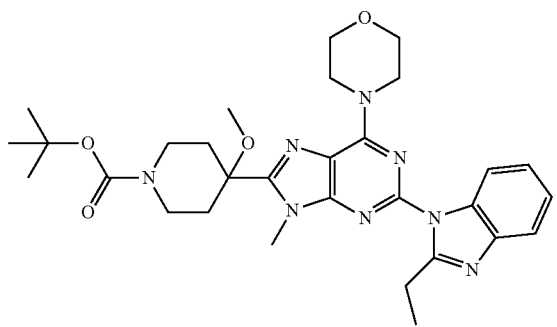

To a solution of 4-[2-(2-ethylbenzoimidazol-1-yl)-9-methyl-6-morpholin-4-yl-9H-purin-8-yl]-4-hydroxypiperidine-1-carboxylic acid tert-butyl ester (1.3 g, 2.31 mmol) in THF (50 mL) was added NaH (112 mg, 2.80 mmol, 60% dispersion in mineral oil) and the resulting mixture allowed to stir for 5 min before the addition of iodomethane (175 µL, 2.80 mmol) and 15-Crown-5 (5 drops). The resulting mixture was stirred for 20 h quenched with H₂O and extracted with 2-methyl THF. The organic phase was washed with brine, then dried (Na₂SO₄) and concentrated in vacuo. The resulting residue was purified by column chromatography (Si-PCC, EtOAc:cyclohexane, 40-80%) affording 4-[2-(2-Ethylbenzoimidazol-1-yl)-9-methyl-6-morpholin-4-yl-9H-purin-8-yl]-4-methoxypiperidine-1-carboxylic acid tert-butyl ester (915 mg, 69%). LCMS (method H): R_T 3.40 min [M+H]+ 577.5

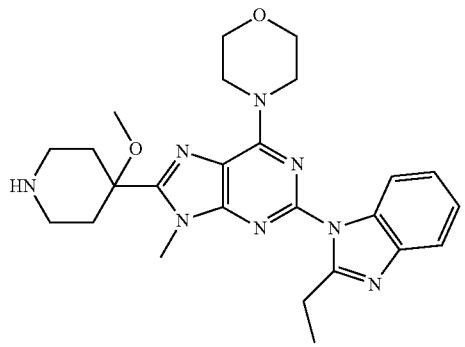

To a solution of 4-[2-(2-ethylbenzoimidazol-1-yl)-9-methyl-6-morpholin-4-yl-9H-purin-8-yl]-4-methoxypiperidine-1-carboxylic acid tert-butyl ester (915 mg, 1.59 mmol) in DCM (15 mL) was added TFA (3 mL) and the resulting mixture allowed to stir at r.t. for 2 h. The reaction mixture was concentrated in vacuo and the resulting residue loaded onto an Isolute® SCX-2 cartridge which was washed with MeOH and the product eluted with 2M NH₃/MeOH affording 2-(2-Ethylbenzoimidazol-1-yl)-8-(4-methoxypiperidin-4-yl)-9-methyl-6-morpholin-4-yl-9H-purine (775 mg, quant.). LCMS (method H): R_T 1.95 min, [M+H]+ 477.3

To a solution of 2-hydroxyisobutyric acid (49 mg, 0.47 mmol) in THF (3 mL) was added 2-(2-ethylbenzoimidazol-1-yl)-8-(4-methoxypiperidin-4-yl)-9-methyl-6-morpholin-4-yl-9H-purine (150 mg, 0.32 mmol), HOBt (47 mg, 0.35 mmol), NMM (77 µL, 0.69 mmol) and EDCI (91 mg, 0.47 mmol). The resulting mixture was allowed to stir at r.t. for 4 h then quenched with sat. aq. NH₄Cl and extracted with DCM. The organic phase was washed with brine, then dried (Na₂SO₄) and concentrated in vacuo. The resulting residue was purified by column chromatography (Si-PCC, MeOH:EtOAc, 0-20%) then triturated with MeOH/H₂O. The resulting solid was collected by filtration and dried in vacuo affording 800 (111 mg, 63%). LCMS (method G): R_T 7.36 min, [M+H]+ 563.4. ¹H NMR (DMSO, 400 MHz): δ 8.05-8.04 (1 H, m), 7.66-7.62 (1 H, m), 7.25-7.24 (2 H, m), 5.44 (1 H, s), 4.26 (6 H, brd s), 3.92 (3 H, s), 3.78 (4 H, t, J=4.52 Hz), 3.30-3.23 (4 H, m), 3.09 (3 H, s), 2.26-2.16 (2 H, m), 2.19-2.02 (2 H, m), 1.35-1.33 (9 H, m)

Example 811

1-(3-(2-(2-ethyl-1H-benzo[d]imidazol-1-yl)-9-methyl-6-morpholino-9H-purin-8-yl)-3-methoxyazetidin-1-yl)-2-hydroxy-2-methylpropan-1-one 811

A mixture of 2-(2-ethylbenzoimidazol-1-yl)-8-(3-methoxyazetidin-3-yl)-9-methyl-6-morpholin-4-yl-9H-purine (150 mg, 0.33 mmol), 2-hydroxy-2-methylpropionic acid (52 mg, 0.50 mmol), HOBt (50 mg, 0.37 mmol), NMM (81 µL, 0.74 mmol) and EDCI (96 mg, 0.50 mmol) in THF (3 mL) was allowed to stir at r.t. for 4 h. The resulting mixture was diluted with DCM and washed with sat. aq. NaHCO₃, dried (phase separator) and concentrated in vacuo. The resulting residue was purified by column chromatography (Si-PCC, THF:EtOAc, 0-50%) then triturated with Et₂O/cyclohexane. The resulting solid was collected by filtration and dried in vacuo affording 811 (108 mg, 60%). LCMS (method I): $R_T$ 3.21 min, [M+H]$^+$ 535.3. $^1$H NMR (DMSO, 400 MHz): δ 8.06-8.05 (1 H, m), 7.64-7.63 (1 H, m), 7.26-7.25 (2 H, m), 5.23 (1 H, s), 5.05 (1 H, d, J=10.74 Hz), 4.67 (1 H, d, J=10.76 Hz), 4.55 (1 H, d, J=10.69 Hz), 4.29 (4 H, brd s), 4.16 (1 H, d, J=10.75 Hz), 3.79 (4 H, t, J=4.62 Hz), 3.73 (3 H, s), 3.29-3.27 (2 H, m), 3.09 (3 H, s), 1.35 (3 H, t, J=7.43 Hz), 1.30 (3 H, s), 1.25 (3 H, s)

Example 812

4-(1-((2-(2-ethyl-1H-benzo[d]imidazol-1-yl)-6-morpholino-9H-purin-8-yl)methyl)azetidin-3-yl)piperazin-2-one 812

To a solution of 4-{1-[2-(2-ethylbenzoimidazol-1-yl)-6-morpholin-4-yl-9-(tetrahydropyran-2-yl)-9H-purin-8-ylmethyl]azetidin-3-yl}piperazin-2-one (470 mg, 0.78 mmol) in dioxane (20 mL) was added 4M HCl in dioxane (1 mL). The resulting suspension was stirred at r.t for 24 h then the precipitate collected by filtration, washing with dioxane. The resulting solid was partitioned between EtOAc and H$_2$O and the aqueous layer basified to pH 11 with NH$_4$OH. The aqueous phase was neutralised to pH 7 with HCl then loaded onto an Isolute® SCX-2 cartridge which was washed with H$_2$O and MeOH and the product eluted with 2M NH$_3$/MeOH. The resulting residue was purified by coulmn chromatography (C18, MeOH:H$_2$O, 30-95%) then loaded onto an Isolute® SCX-2 cartridge which was washed with H$_2$O and MeOH and the product eluted with 2M NH$_3$/MeOH affording 812 (69 mg, 17%). LCMS (method I): $R_T$ 2.16 min, [M+H]$^+$ 517.3. $^1$H NMR (DMSO, 400 MHz): δ 7.95-7.94 (1 H, m), 7.73 (1 H, s), 7.63-7.62 (1 H, m), 7.25-7.22 (2 H, m), 4.24 (4 H, brd s), 3.79-3.74 (6 H, m), 3.46 (2 H, s), 3.23 (3 H, q, J=7.46 Hz), 3.16-3.04 (5 H, m), 2.84 (2 H, s), 2.45-2.44 (2 H, m), 1.31 (3 H, t, J=7.45 Hz)

Example 813

4-(2-((2,2-dimethyl-4-(oxetan-3-yl)piperazin-1-yl)methyl)-5-(2-ethyl-1H-benzo[d]imidazol-1-yl)thiazolo[5,4-d]pyrimidin-7-yl)morpholine 813

A mixture of 5-(2-ethylbenzoimidazol-1-yl)-7-morpholin-4-ylthiazolo[5,4-d]pyrimidine-2-carbaldehyde (200 mg, 0.51 mmol), 3,3-dimethyl-1-oxetan-3-ylpiperazine (100 mg, 0.65 mmol) and 4 Å powdered molecular sieves (200 mg) in DCE (10 mL) was allowed to stir at r.t. for 1 h before the addition of sodium triacetoxyborohydride (150 mg, 0.71 mmol). The resulting mixture was allowed to stir for 5 h then loaded onto an Isolute® SCX-2 cartridge which was washed with MeOH and the product eluted with 2M NH$_3$/MeOH. The resulting residue was purified by column chromatography (Si-PCC, MeOH:EtOAc, 0-1%) followed by reverse phase HPLC (Phenomenex Gemini 5 μm C18, 20 mM triethylamine in water on a gradient of acetonitrile 5-98%) affording 813 (111 mg, 40%). LCMS (method G): $R_T$ 6.17 min [M+H]$^+$ 549.3. $^1$H NMR (CDCl$_3$, 400 MHz): δ 8.01-8.00 (1 H, m), 7.75-7.74 (1 H, m), 7.32-7.22 (2 H, m), 4.67 (2 H, t, J=6.47 Hz), 4.59 (2 H, t, J=6.08 Hz), 4.40 (4 H, brd s), 3.87 (6 H, t, J=4.72 Hz), 3.47-3.46 (1 H, m), 3.34 (2 H, q, J=7.47 Hz), 2.75 (2 H, t, J=4.94 Hz), 2.37 (2 H, brd s), 2.15 (2 H, brd s), 1.43 (3 H, t, J=7.47 Hz), 1.20 (6 H, s)

Example 814

1-(3-((5-(2-ethyl-1H-benzo[d]imidazol-1-yl)-7-morpholinothiazolo[5,4-d]pyrimidin-2-yl)methyl)azetidin-1-yl)-2-hydroxy-2-methylpropan-1-one 814

A mixture of 2-azetidin-3-ylmethyl-5-(2-ethylbenzoimidazol-1-yl)-7-morpholin-4-ylthiazolo[5,4-d]pyrimidine (209 mg, 0.48 mmol), 2-hydroxyisobutyric acid (56 mg, 0.54 mmol), HATU (200 mg, 0.53 mmol) and DIPEA (94 μL, 0.54 mmol) in DCM (5 mL) was allowed to stir at r.t. for 2 h. The reaction mixture was loaded onto an Isolute® SCX-2 cartridge which was washed with MeOH and the product eluted with 2M NH$_3$/MeOH. The resulting residue was purified by column chromatography (Si-PCC, MeOH:EtOAc, 0-2%) followed by reverse phase HPLC (Phenomenex Gemini 5 μm C18, 20 mM triethylamine in water on a gradient of acetonitrile 5-98%) affording 814 as a white solid (89 mg, 35%). LCMS (method I): $R_T$ 3.39 min, [M+H]$^+$ 522.2. $^1$H NMR (CDCl$_3$, 400 MHz): δ 8.00-7.99 (1 H, m), 7.75-7.74 (1 H, m), 7.28-7.28 (2 H, m), 4.62-4.12 (7 H, m), 4.05-3.92 (1 H, m), 3.88 (4 H, t, J=4.76 Hz), 3.45 (1 H, s), 3.43-3.38 (2 H, m), 3.33 (2 H, q, J=7.47 Hz), 3.27-3.21 (1 H, m), 1.43-1.42 (9 H, m)

Example 823

1-(4-(2-(2-ethyl-1H-benzo[d]imidazol-1-yl)-9-methyl-6-morpholino-9H-purin-8-yl)-4-methoxypiperidin-1-yl)-2-hydroxyethanone 823

A mixture of 2-(2-ethylbenzoimidazol-1-yl)-8-(4-methoxypiperidin-4-yl)-9-methyl-6-morpholin-4-yl-9H-purine (150 mg, 0.32 mmol), hydroxyacetic acid (36 mg, 0.47 mmol), HOBt (47 mg, 0.35 mmol), NMM (77 μL, 0.69 mmol) and EDCI (91 mg, 0.47 mmol) in THF (3 mL) was allowed to stir at r.t. for 4 h. The resulting mixture was diluted with DCM and washed with sat. aq. NaHCO$_3$, dried (phase separator) and concentrated in vacuo. The resulting residue was purified by column chromatography (Si-PCC, THF:EtOAc, 0-50%) then loaded onto an Isolute® SCX-2 cartridge which was washed with MeOH and the product eluted with 2M NH$_3$/MeOH affording 823 (88 mg, 52%). LCMS (method I): $R_T$ 3.25 min, [M+H]$^+$ 535.3. $^1$H NMR (DMSO, 400 MHz): δ 8.05-8.04 (1 H, m), 7.64-7.63 (1 H, m), 7.26-7.25 (2 H, m), 4.54 (1 H, t, J=5.40 Hz), 4.17-4.06 (6 H, m), 3.92 (3 H, s), 3.78 (4 H, t, J=4.51 Hz), 3.65-3.55 (1 H, m), 3.40-3.25 (3 H, m), 3.18 (1 H, m), 3.09 (3 H, s), 2.17-2.14 (4 H, m), 1.35 (3 H, t, J=7.43 Hz)

Example 824

1-(3-((2-(2-ethyl-1H-benzo[d]imidazol-1-yl)-9-methyl-6-morpholino-9H-purin-8-yl)methyl)azetidin-1-yl)-2-methylpropan-1-one 824

A mixture of 8-azetidin-3-ylmethyl-2-(2-ethylbenzoimidazol-1-yl)-9-methyl-6-morpholin-4-yl-9H-purine (121 mg, 0.28 mmol), isobutyryl chloride (30 mg, 0.29 mmol) and NEt$_3$ (50 μL, 0.36 mmol) in DCM (1 mL) was allowed to stir at r.t. for 2 h then concentrated in vacuo. The resulting residue purified by column chromatography (Si-PCC, MeOH:DCM, 0-6%) followed by triturating with Et$_2$O affording 824 as a white solid (86 mg, 61%). LCMS (method I): $R_T$ 3.42 min, [M+H]$^+$ 503.2. $^1$H NMR (CDCl$_3$, 400 MHz): δ 7.99-7.99 (1 H, m), 7.75-7.74 (1 H, m), 7.30-7.22 (2 H, m), 4.50-4.20 (4 H, brd s), 4.41 (1 H, t, J=8.45 Hz), 4.32-4.21 (1 H, m), 3.98 (1 H, dd, J=8.63, 5.41 Hz), 3.90-3.80 (5 H, m), 3.76 (3 H, s), 3.34 (2 H, q, J=7.49 Hz), 3.28-3.25 (1 H, m), 3.16-3.11 (2 H, m), 2.47-2.46 (1 H, m), 1.44 (3 H, t, J=7.48 Hz), 1.12 (6 H, dd, J=6.82, 2.82 Hz)

Example 825 cyclopropyl(3-((2-(2-ethyl-1H-benzo[d]imidazol-1-yl)-9-methyl-6-morpholino-9H-purin-8-yl)methyl)azetidin-1-yl)methanone 825

A mixture of 8-azetidin-3-ylmethyl-2-(2-ethylbenzoimidazol-1-yl)-9-methyl-6-morpholin-4-yl-9H-purine (108 mg, 0.25 mmol), cyclopropane carbonyl chloride (27 mg, 0.25 mmol) and NEt$_3$ (50 μL, 0.36 mmol) in DCM (1 mL) was allowed to stir at r.t. for 2 h then concentrated in vacuo. The resulting residue purified by column chromatography (Si-PCC, MeOH:DCM, 0-10%) followed by triturating with Et$_2$O affording 825 as a white solid (107 mg, 85%). LCMS (method I): R$_T$ 3.33 min, [M+H]$^+$ 501.2. $^1$H NMR (CDCl$_3$, 400 MHz): δ 7.99-7.98 (1 H, m), 7.76-7.73 (1 H, m), 7.32-7.22 (2 H, m), 4.53 (1 H, t, J=8.31 Hz), 4.45-4.20 (4 H, brd s), 4.28 (1 H, t, J=9.30 Hz), 4.09 (1 H, dd, J=8.45, 5.41 Hz), 3.86 (5 H, t, J=4.77 Hz), 3.77 (3 H, s), 3.34-3.33 (3 H, m), 3.18-3.15 (2 H, m), 1.45-1.43 (4 H, m), 0.99-0.98 (2 H, m), 0.77-0.76 (2 H, m)

Example 826

4-(2-(2-ethyl-1H-benzo[d]imidazol-1-yl)-8-(3-methoxy-1-(2-(methylsulfonyl)ethyl)azetidin-3-yl)-9-methyl-9H-purin-6-yl)morpholine 826

To a solution of 2-(2-ethylbenzoimidazol-1-yl)-8-(3-methoxyazetidin-3-yl)-9-methyl-6-morpholin-4-yl-9H-purine (100 mg, 0.22 mmol) in IMS (2 mL) was added methanesulfonylethene (21 μL, 0.25 mmol) and the resulting mixture allowed to stir at r.t. for 18 h. The reaction mixture was concentrated in vacuo and the resulting residue purified by column chromatography (Si-PCC, MeOH:EtOAc, 0-10%). The resulting residue was triturated with EtOAc and cyclohexane and the resulting solid dried in vacuo affording 826 (83 mg, 67%). LCMS (method I): R$_T$ 2.65 min, [M+H]$^+$ 555.3. $^1$H NMR (DMSO, 400 MHz): δ 8.05-8.05 (1 H, m), 7.64-7.63 (1 H, m), 7.26-7.25 (2 H, m), 4.27 (4 H, brd s), 4.02 (2 H, d, J=7.94 Hz), 3.79 (4 H, t, J=4.57 Hz), 3.72 (3 H, s), 3.42 (2 H, d, J=7.99 Hz), 3.28-3.25 (2 H, m), 3.17 (2 H, t, J=6.52 Hz), 3.05 (3 H, s), 2.89 (2 H, t, J=6.53 Hz), 1.40 (3 H, s), 1.35 (3 H, t, J=7.43 Hz)

Example 827

4-(2-(2-ethyl-1H-benzo[d]imidazol-1-yl)-8-(3-methoxy-1-(tetrahydro-2H-pyran-4-yl)azetidin-3-yl)-9-methyl-9H-purin-6-yl)morpholine 827

A mixture of 2-(2-ethylbenzoimidazol-1-yl)-8-(3-methoxyazetidin-3-yl)-9-methyl-6-morpholin-4-yl-9H-purine (100 mg, 0.22 mmol), tetrahydropyran-4-one (27 mg, 0.27 mmol) and AcOH (50 μL) in DCE (2 mL) was allowed to stir at r.t. for 20 min before the addition of sodium triacetoxyborohydride (104 mg, 0.49 mmol). The resulting mixture was allowed to stir for 18 h then partitioned between DCM and H$_2$O. The organic phase was dried (phase separator) and concentrated in vacuo. The resulting residue was purified by column chromatography (Si-PCC, MeOH:EtOAc, 0-20%) then triturated with MeCN and H$_2$O and the resulting solid dried in vacuo affording 827 (92 mg, 82%). LCMS (method I): R$_T$ 2.65 min, [M+H]$^+$ 555.3. $^1$H NMR (DMSO, 400 MHz): δ 8.04-8.04 (1 H, m), 7.65-7.62 (1 H, m), 7.25-7.24 (2 H, m), 4.40-4.10 (4 H, brd s), 3.91 (2 H, d, J=8.05 Hz), 3.80-3.79 (6 H, m), 3.71 (3 H, s), 3.41 (2 H, d, J=8.07 Hz), 3.28-3.26 (4 H, m), 3.02 (3 H, s), 2.37-2.28 (1 H, m), 1.67-1.63 (2 H, m), 1.34 (3 H, t, J=7.43 Hz), 1.23-1.10 (2 H, m)

Example 828 tert-butyl 3-(2-(2-ethyl-1H-benzo[d]imidazol-1-yl)-9-methyl-6-morpholino-9H-purin-8-yl)-3-fluoroazetidine-1-carboxylate 828

To a solution of 3-[2-(2-ethylbenzoimidazol-1-yl)-9-methyl-6-morpholin-4-yl-9H-purin-8-yl]-3-hydroxy-azetidine-1-carboxylic acid tert-butyl ester (300 mg, 0.56 mmol) in THF (2 mL) at 5° C. was added a solution of bis-(2-methoxyethyl)aminosulfur trifluoride (275 μL, 0.62 mmol, 50% solution in THF) in THF (3 mL). The resulting mixture was allowed to stir at 5° C. for 15 min then warmed to r.t. and stirred for a further 15 min. The reaction mixture was partitioned between sat. aq. NaHCO$_3$ and DCM, the organic phase dried (phase separator) and concentrated in vacuo. The resulting residue was purified by column chromatography (Si-PCC, EtOAc:cyclohexane, 35-85%) affording 828 as a pale yellow solid (238 mg, 79%). LCMS (method I): R$_T$ 4.65 min, [M+H]$^+$ 537.4. $^1$H NMR (DMSO, 400 MHz): δ 8.05-8.04 (1 H, m), 7.64-7.64 (1 H, m), 7.26-7.25 (2 H, m), 4.77 (2 H, dd, J=20.08, 10.62 Hz), 4.60-4.10 (4 H, brd s), 4.48 (2 H, dd, J=21.54, 10.50 Hz), 3.79 (4 H, t, J=4.55 Hz), 3.76 (3 H, d, J=1.32 Hz), 3.28-3.27 (2 H, m), 1.42 (9 H, s), 1.34 (3 H, t, J=7.46 Hz)

Example 829

(S)-1-(4-((5-(2-ethyl-1H-benzo[d]imidazol-1-yl)-7-morpholinothiazolo[5,4-d]pyrimidin-2-yl)methyl)-3,3-dimethylpiperazin-1-yl)-2-hydroxypropan-1-one 829

A mixture of 2-(2,2-dimethylpiperazin-1-ylmethyl)-5-(2-ethylbenzoimidazol-1-yl)-7-morpholin-4-ylthiazolo[5,4-d]pyrimidine (200 mg, 0.41 mmol), L-lactic acid (34 μL, 85% solution in H$_2$O), HATU (170 mg, 0.45 mmol) and DIPEA (80 μL, 0.46 mmol) in DCM (4 mL) was allowed to stir at r.t. for 3 h. The reaction mixture was loaded onto an Isolute® SCX-2 cartridge which was washed with MeOH and the product eluted with 2M NH$_3$/MeOH. The resulting residue was purified by column chromatography (Si-PCC, MeOH:EtOAc, 0-2%) then (C18, MeOH:H$_2$O, 10-20%). The resulting residue was loaded onto an Isolute® SCX-2 cartridge which was washed with MeOH and the product eluted with 2M NH$_3$/MeOH affording 829 (41 mg, 18%). LCMS (method I): R$_T$ 3.79 min, [M+H]$^+$ 565.3. $^1$H NMR (CDCl$_3$, 400 MHz): δ 8.03-7.98 (1 H, m), 7.76-7.75 (1 H, m), 7.32-7.22 (2 H,m), 4.41-4.38 (5 H, m), 4.08-4.01 (1 H, m), 3.89-3.88 (5 H, m), 3.79-3.77 (1 H, m), 3.59-3.44 (2 H, m), 3.34 (2 H, q, J=7.47 Hz), 3.27-3.25 (1 H, m), 2.75 (2 H, s), 1.44 (3 H, t, J=7.47 Hz), 1.37-1.35 (3 H, m), 1.27-1.11 (6 H, m)

Example 833

1-(3-(2-(2-ethyl-1H-benzo[d]imidazol-1-yl)-9-methyl-6-morpholino-9H-purin-8-yl)-3-methoxyazetidin-1-yl)-2-methylpropan-2-ol 833

To a solution of 2-(2-ethylbenzoimidazol-1-yl)-8-(3-methoxyazetidin-3-yl)-9-methyl-6-morpholin-4-yl-9H-purine (100 mg, 0.22 mmol) in MeCN (2 mL) was added 2,2-dimethyloxirane (198 μL, 2.23 mmol) and the resulting mixture stirred at 80° C. for 3 h before the addition of further 2,2-dimethyloxirane (1.0 mL, 11.15 mmol). The reaction mixture was stirred at 80° C. for a further 20 h then concentrated in vacuo. The resulting residue was purified by column chromatography (Si-PCC, MeOH:EtOAc, 0-20%) then triturated with Et$_2$O and the resulting solid dried in vacuo affording 833 (31 mg, 27%). LCMS (method I): R$_T$ 2.59 min, [M+H]$^+$ 521.3. $^1$H NMR (DMSO, 400 MHz): δ 8.04-8.04 (1 H, m), 7.66-7.62 (1 H, m), 7.25-7.24 (2 H, m), 4.29 (4 H, brd s), 4.07 (1 H, s), 3.99 (2 H, d, J=8.32 Hz), 3.80 (4 H, t, J=4.57 Hz), 3.70 (3 H, s), 3.52 (2 H, d, J=8.34 Hz), 3.34-3.19 (2 H, m), 3.02 (3 H, s), 2.43 (2 H, s), 1.34 (3 H, t, J=7.43 Hz), 1.05 (6 H, s)

Example 834

4-(2-(2-ethyl-1H-benzo[d]imidazol-1-yl)-8-(3-fluoroazetidin-3-yl)-9-methyl-9H-purin-6-yl)morpholine 834

To a solution of 3-[2-(2-ethylbenzoimidazol-1-yl)-9-methyl-6-morpholin-4-yl-9H-purin-8-yl]-3-fluoroazetidine-1-carboxylic acid tert-butyl ester (235 mg, 0.44 mmol) in DCM (10 mL) was added TFA (2 mL) and the resulting mixture was allowed to stir at r.t. for 3.5 h. The reaction mixture was concentrated in vacuo and the resulting residue was loaded onto an Isolute® SCX-2 cartridge which was washed with MeOH/DCM and the product eluted with 2M $NH_3$/MeOH. The resulting residue was triturated with $Et_2O$ and the resulting solid dried in vacuo affording 834 (185 mg, 97%). LCMS (method I): $R_T$ 2.50 min, $[M+H]^+$ 437.3. $^1$H NMR (DMSO, 400 MHz): δ 8.06-8.05 (1 H, m), 7.64-7.63 (1 H, m), 7.28-7.24 (2 H, m), 4.60-4.10 (4 H, brd s), 4.26 (2 H, dd, J=19.18, 10.17 Hz), 4.01 (2 H, dd, J=22.47, 10.23 Hz), 3.80 (4 H, t, J=4.63 Hz), 3.74-3.73 (3 H, m), 3.28-3.27 (2 H, m), 1.34 (3 H, t, J=7.43 Hz)

Example 839

1-(3-(2-(2-ethyl-1H-benzo[d]imidazol-1-yl)-9-methyl-6-morpholino-9H-purin-8-yl)-3-fluoroazetidin-1-yl)-2-methylpropan-2-ol 839

A mixture of 2-(2-ethylbenzoimidazol-1-yl)-8-3-fluoroazetidin-3-yl)-9-methyl-6-morpholin-4-yl-9H-purine (90 mg, 0.21 mmol) and 2,2-dimethyloxirane (1 mL) in IMS (2 mL) was heated to 80° C. for 24 h then concentrated in vacuo. The resulting residue was purified by column chromatography (Si-PCC, MeOH:EtOAc, 0-5%) then triturated with $Et_2O$. The resulting residue was further purified by reverse phase HPLC (Phenomenex Gemini 5 μm C18, 0.1% $HCO_2H$ in water on a gradient acetonitrile 5-95%) affording 839 (22 mg, 21%). LCMS (method I): $R_T$ 2.63 min, $[M+H]^+$ 509.3. $^1$H NMR (DMSO, 400 MHz): δ 8.04-8.03 (1 H, m), 7.65-7.62 (1 H, m), 7.26-7.25 (2 H, m), 4.28 (4 H, brd s), 4.14 (2 H, dd, J=18.78, 9.71 Hz), 3.82-3.74 (9 H, m), 3.31-3.29 (4 H, m), 1.34 (3 H, t, J=7.43 Hz), 1.07 (6 H, s)

Example 840

(S)-1-(3-(2-(2-ethyl-1H-benzo[d]imidazol-1-yl)-9-methyl-6-morpholino-9H-purin-8-yl)-3-methoxyazetidin-1-yl)-2-hydroxypropan-1-one 840

To a mixture of 2-(2-ethylbenzoimidazol-1-yl)-8-(3-methoxyazetidin-3-yl)-9-methyl-6-morpholin-4-yl-9H-purine (100 mg, 0.22 mmol) and sodium L-lactate (38 mg, 0.34 mmol) in DCM (2 mL) was added HOBt (33 mg, 0.25 mmol) and EDCI (64 mg, 0.34 mmol). The resulting mixture was allowed to stir at r.t. for 18 h then partitioned between DCM and sat. aq. $NH_4Cl$. The organic phase was dried (phase separator), concentrated in vacuo and the resulting residue purified by column chromatography (Si-PCC, MeOH:EtOAc, 0-25%). The resulting residue was triturated with $Et_2O$ and further purified by reverse phase HPLC (Phenomenex Gemini 5 μm C18, 0.1% $HCO_2H$ in water on a gradient MeOH 45-60%) affording 840 (29 mg, 23%). LCMS (method I): $R_T$ 3.10 min, $[M+H]^+$ 521.3. $^1$H NMR (DMSO, 400 MHz): δ 8.44 (1 H, brd s), 8.07-8.03 (1 H, m), 7.64-7.63 (1 H, m), 7.25-7.24 (2 H, m), 5.24 (1 H, brd s), 4.94 (1 H, dd, J=21.10, 10.14 Hz), 4.59-4.58 (2 H, m), 4.46-4.12 (4 H, brd s), 4.18-4.17 (2 H, m), 3.79 (4 H, t, J=4.51 Hz), 3.72 (3 H, s), 3.34-3.32 (2 H, m), 3.09 (3 H, s), 1.34 (3 H, t, J=7.43 Hz), 1.20 (3 H, d, J=6.71 Hz)

Example 846

(5-(2-ethyl-1H-benzo[d]imidazol-1-yl)-7-morpholinothiazolo[5,4-d]pyrimidin-2-yl)(3-morpholinoazetidin-1-yl)methanone 846

A mixture of (5-chloro-7-morpholin-4-ylthiazolo[5,4-d]pyrimidin-2-yl)-(3-morpholin-4-ylazetidin-1-yl)methanone (98 mg, 0.23 mmol), 2-ethylbenzimidazole (36 mg, 0.25 mmol), tris(dibenzylideneacetone)dipalladium (6 mg, 2.5 mol %), XPhos (10 mg, 9 mol %) and $Cs_2CO_3$ (107 mg, 0.33 mmol) in DMF (3 mL) was purged with argon then heated at 150° C. for 30 min in a microwave reactor. The reaction mixture was loaded onto an Isolute® SCX-2 cartridge which was washed with MeOH and the product eluted with 2M $NH_3$/MeOH. The resulting residue was purified by column chromatography (Si-PCC, MeOH:EtOAc, 0-4%) then triturated with EtOAc affording 846 as a white solid (61 mg, 50%). LCMS (method I): $R_T$ 2.96 min, $[M+H]^+$ 535.3. $^1$H NMR ($CDCl_3$, 400 MHz): δ 8.09-8.05 (1 H, m), 7.80-7.75 (1 H, m), 7.31-7.30 (2 H, m), 4.68-4.67 (1 H, m), 4.60-4.20 (4 H, brd s), 4.52 (1 H, dd, J=10.01, 5.05 Hz), 4.33-4.27 (1 H, m), 4.17 (1 H, dd, J=10.73, 5.02 Hz), 3.89 (4 H, t, J=4.65 Hz), 3.78 (4 H, t, J=4.57 Hz), 3.42-3.33 (3 H, m), 2.52-2.35 (4 H, m), 1.46 (3 H, t, J=7.44 Hz)

Example 849

2-(3-(2-(2-ethyl-1H-benzo[d]imidazol-1-yl)-9-methyl-6-morpholino-9H-purin-8-yl)-3-methoxyazetidin-1-yl)ethanol 849

To a solution of 1-{3-[2-(2-ethylbenzoimidazol-1-yl)-9-methyl-6-morpholin-4-yl-9H-purin-8-yl]-3-methoxyazetidin-1-yl}-2-hydroxyethanone (88 mg, 0.17 mmol) in THF (2 mL) at 0° C. was added $BH_3$.THF complex (350 μL, 0.35 mmol, 1M solution) and the resulting mixture allowed to stir for 1 h. Further $BH_3$.THF complex (800 μL, 0.80 mmol) was added and the mixture stirred at r.t. for 17 h. The reaction mixture was quenched with $H_2O$, acidified with 2M HCl then loaded onto an Isolute® SCX-2 cartridge which was washed with MeOH and the product eluted with 2M $NH_3$/MeOH. The resulting residue was dissolved in a mixture of MeCN and $H_2O$ and allowed to freeze-dry affording 849 as a white solid (74 mg, 86%). LCMS (method I): $R_T$ 2.48 min, $[M+H]^+$ 493.4. $^1$H NMR (DMSO, 400 MHz): δ 8.04-8.04 (1 H, m), 7.64-7.63 (1 H, m), 7.27-7.23 (2 H, m), 4.50-4.42 (1 H, m), 4.39-4.14 (4 H, brd m), 4.05-3.98 (2 H, m), 3.80 (4 H, t, J=4.56 Hz), 3.70 (3 H, s), 3.52-3.45 (2 H, m), 3.40 (2 H, q, J=5.63 Hz), 3.34-3.24 (2 H, m), 3.01 (3 H, s), 2.65-2.57 (2 H, m), 1.34 (3 H, t, J=7.43 Hz)

Example 850

2-(3-(2-(2-ethyl-1H-benzo[d]imidazol-1-yl)-9-methyl-6-morpholino-9H-purin-8-yl)-3-fluoroazetidin-1-yl)-2-methylpropan-1-ol 850

To a solution of 2-{3-[2-(2-ethylbenzoimidazol-1-yl)-9-methyl-6-morpholin-4-yl-9H-purin-8-yl]-3-fluoroazetidin- 1-yl}-2-methylpropionic acid ethyl ester (40 mg, 0.07 mmol) in IMS (4 mL) was added NaBH₄ (28 mg, 0.73 mmol) and the resulting mixture stirred at r.t for 3 h. Further NaBH₄ (28 mg, 0.73 mmol) was added and the mixture stirred for a further 18 h. The reaction mixture was quenched with H₂O, extracted with EtOAc and the organic phase dried (Na₂SO₄) and concentrated in vacuo. The resulting residue was purified by column chromatography (Si-PCC, MeOH:EtOAc, 0-10%) then dissolved in a mixture of MeCN and H₂O and allowed to freeze-dry affording 850 as a white solid (20 mg, 54%). LCMS (method I): $R_T$ 2.64 min, [M+H]⁺ 509.4. ¹H NMR (DMSO, 400 MHz): δ 8.05-8.04 (1 H, m), 7.64-7.63 (1 H, m), 7.26-7.25 (2 H, m), 4.58-4.49 (1 H, m), 4.44-4.14 (4 H, brd m), 4.08 (2 H, dd, J=18.70, 9.19 Hz), 3.81-3.74 (9 H, m), 3.28-3.26 (2 H, m), 3.19 (2 H, d, J=5.40 Hz), 1.34 (3 H, t, J=7.43 Hz), 0.91 (6 H, s)

Example 851

1-(4-((2(2-ethyl-1H-benzo[d]imidazol-1-yl)-9-methyl-6-morpholino-9H-purin-8-yl)methyl)piperidin-1-yl)-2-methylpropan-1-one 851

A mixture of 2-(2-ethylbenzoimidazol-1-yl)-9-methyl-6-morpholin-4-yl-8-piperidin-4-ylmethyl-9H-purine (230 mg, 0.50 mmol), isobutyryl chloride (59 mg, 0.55 mmol) and NEt₃ (140 μL, 1.00 mmol) in DCM (10 mL) was allowed to stir at r.t. for 5 h then concentrated in vacuo. The resulting residue was purified by column chromatography (Si-PCC, MeOH:DCM, 0-5%) then further purified by reverse phase HPLC (Phenomenex Gemini 5 μm C18, 20 mM triethylamine in water on a gradient of acetonitrile 40-98%) affording 851 as a white solid (57 mg, 21%). LCMS (method I): $R_T$ 3.69 min, [M+H]⁺ 531.4. ¹H NMR (DMSO, 400 MHz): δ 8.01-8.00 (1 H, m), 7.63-7.62 (1 H, m), 7.27-7.23 (2 H, m), 4.40 (1 H, d, J=13.34 Hz), 4.25 (4 H, brd s), 3.94 (1 H, d, J=13.78 Hz), 3.77-3.74 (7 H, m), 3.26 (2 H, q, J=7.45 Hz), 3.01 (1 H, t, J=13.02 Hz), 2.87-2.85 (3 H, m), 2.50-2.50 (1 H, m), 2.12-2.08 (1 H, m), 1.77-1.73 (2 H, m), 1.33 (3 H, t, J=7.44 Hz), 1.29-1.07 (2 H, m), 1.00-0.98 (6 H, m)

Example 852 cyclopropyl(4-((2-(2-ethyl-1H-benzo[d]imidazol-1-yl)-9-methyl-6-morpholino-9H-purin-8-yl)methyl)piperidin-1-yl)methanone 852

A mixture of 2-(2-ethylbenzoimidazol-1-yl)-9-methyl-6-morpholin-4-yl-8-piperidin-4-ylmethyl-9H-purine (230 mg, 0.50 mmol), cyclopropyl carbonyl chloride (50 μL, 0.55 mmol) and NEt₃ (140 μL, 1.00 mmol) in DCM (10 mL) was allowed to stir at r.t. for 5 h then concentrated in vacuo. The resulting residue was purified by column chromatography (Si-PCC, MeOH:DCM, 0-5%) then further purified by reverse phase HPLC (Phenomenex Gemini 5 μm C18, 20 mM triethylamine in water on a gradient of acetonitrile 40-98%) affording 852 as a white solid (46 mg, 17%). LCMS (method I): $R_T$ 3.59 min, [M+H]⁺ 529.4. ¹H NMR (DMSO, 400 MHz): δ 8.03-7.99 (1 H, m), 7.64-7.63 (1 H, m), 7.25-7.24 (2 H, m), 4.45-4.10 (6 H, m), 3.77-3.75 (6 H, m), 3.27-3.24 (3 H, m), 3.16-3.00 (1 H, m), 2.86 (1 H, d, J=7.07 Hz), 2.64-2.47 (1 H, m), 2.20-2.08 (1 H, m), 2.01-1.93 (1 H, m), 1.79-1.71 (2 H, m), 1.33 (3 H, t, J=7.43 Hz), 1.30-1.07 (2 H, m), 0.74-0.66 (4 H, m)

Example 854

2-hydroxy-1-(3-((2-(2-isopropyl-1H-benzo[d]imidazol-1-yl)-9-methyl-6-morpholino-9H-purin-8-yl)methyl)azetidin-1-yl)-2-methylpropan-1-one 854

A mixture of acetic acid 1,1-dimethyl-2-{3-[9-methyl-2-(2-isopropylbenzoimidazol-1-yl)-6-morpholin-4-yl-9H-purin-8-ylmethyl]azetidin-1-yl}-2-oxoethyl ester (56 mg, 0.17 mmol) and LiOH (84 μL, 0.33 mmol, 4M solution) in THF (3 mL) and MeOH (1 mL) was allowed to stir at r.t. for 18 h. Further LiOH (495 μL, 1.98 mmol, 4M solution) and the mixture stirred at 50° C. for 5 days. The reaction mixture was concentrated in vacuo and the resulting residue loaded onto an Isolute® SCX-2 cartridge which was washed with MeOH and the product eluted with 2M NH₃/MeOH. The resulting residue was purified by column chromatography (Si-PCC, MeOH:EtOAc, 0-5%) then partitioned between DCM and H₂O, the organic phase dried (Na₂SO₄) and concentrated in vacuo. The resulting residue was dissolved in a mixture of MeCN and H₂O and allowed to freeze-dry affording 854 as a white solid (62 mg, 70%). LCMS (method I): $R_T$ 3.15 min, [M+H]⁺ 533.4. ¹H NMR (DMSO, 400 MHz): δ 7.87-7.86 (1 H, m), 7.65-7.64 (1 H, m), 7.25-7.24 (2 H, m), 5.02 (1 H, brd s), 4.57 (1 H, t, J=8.92 Hz), 4.25 (4 H, brd s), 4.18 (1 H, dd, J=10.40, 5.66 Hz), 4.03 (1 H, t, J=9.00 Hz), 3.91-3.90 (1 H, m), 3.76 (4 H, t, J=4.59 Hz), 3.72 (3 H, s), 3.68 (1 H, dd, J=9.99, 5.41 Hz), 3.22-3.21 (3 H, m), 1.36 (3 H, s), 1.34 (3 H, s), 1.25 (6 H, d, J=2.06 Hz)

Example 855

2-hydroxy-2-methyl-1-(3-((9-methyl-2-(2-methyl-1H-benzo[d]imidazol-1-yl)-6-morpholino-9H-purin-8-yl)methyl)azetidin-1-yl)propan-1-one 855

A mixture of acetic acid 1,1-dimethyl-2-{3-[9-methyl-2-(2-methylbenzoimidazol-1-yl)-6-morpholin-4-yl-9H-purin-8-ylmethyl]azetidin-1-yl}-2-oxoethyl ester (125 mg, 0.23 mmol) and LiOH (114 μL, 0.46 mmol, 4M solution) in THF (3 mL) and MeOH (1 mL) was allowed to stir at r.t. for 18 h. Further LiOH (343 μL, 1.37 mmol, 4M solution) and the mixture stirred at 50° C. for 5 days. The reaction mixture was concentrated in vacuo and the resulting residue loaded onto an Isolute® SCX-2 cartridge which was washed with MeOH and the product eluted with 2M NH₃/MeOH. The resulting residue was purified by column chromatography (Si-PCC, MeOH:EtOAc, 0-10%) then dissolved in a mixture of MeCN and H₂O and allowed to freeze-dry affording 855 as a white solid (88 mg, 77%). LCMS (method I): $R_T$ 2.88 min, [M+H]⁺ 505.3. ¹H NMR (DMSO, 400 MHz): δ 8.09-8.08 (1 H, m), 7.64-7.61 (1 H, m), 7.28-7.27 (2 H, m), 5.02 (1 H, brd s), 4.57 (1 H, t, J=8.94 Hz), 4.26 (4 H, brd s), 4.17 (1 H, dd, J=10.24, 5.60 Hz), 4.03 (1 H, t, J=8.97 Hz), 3.77 (4 H, t, J=4.64 Hz), 3.74 (3 H, s), 3.67 (1 H, dd, J=9.96, 5.41 Hz), 3.21-3.20 (3 H, m), 2.85 (3 H, s), 1.28-1.21 (6 H, m)

Example 859

(S)-1-(3-((2-(2-(1-hydroxyethyl)-1H-benzo[d]imidazol-1-yl)-9-methyl-6-morpholino-9H-purin-8-yl)methyl)azetidin-1-yl)-2-methylpropan-1-one 859

To a solution of (S)-1-[1-(8-azetidin-3-ylmethyl-9-methyl-6-morpholin-4-yl-9H-purin-2-yl)-1H-benzoimidazol-2-yl]ethanol (70 mg, 0.16 mmol) in THF (2 mL) was added DIPEA (30 μL, 0.17 mmol) and isobutyryl chloride (17 μL, 0.16 mmol) and the resulting mixture stirred at r.t. for 1 h. The reaction mixture was partitioned between DCM and sat. aq. NaHCO$_3$, the organic phase dried (phase separator) and concentrated in vacuo. The resulting residue was purified by column chromatography (Si-PCC, MeOH:EtOAc, 0-30%) then (Si-PCC, MeOH:DCM, 0-8%) affording 859 (22 mg, 27%). LCMS (method I): R$_T$ 3.46 min, [M+H]$^+$ 519.3. $^1$H NMR (DMSO, 400 MHz): δ 7.95-7.95 (1 H, m), 7.70-7.69 (1 H, m), 7.30-7.26 (2 H, m), 5.59-5.57 (1 H, m), 5.39 (1 H, d, J=6.33 Hz), 4.39-4.10 (4 H, brd s), 4.34 (1 H, t, J=8.25 Hz), 4.02 (1 H, t, J=8.79 Hz), 3.95 (1 H, dd, J=8.47, 5.27 Hz), 3.80-3.75 (4 H, m), 3.72 (3 H, s), 3.67-3.65 (1 H, m), 3.27-3.21 (3 H, m), 2.48-2.39 (1 H, m), 1.60 (3 H, d, J=6.48 Hz), 0.98 (3 H, d, J=1.76 Hz), 0.96 (3 H, d, J=1.78 Hz)

Example 860

(R)-1-(3-((2-(2-(1-hydroxyethyl)-1H-benzo[d]imidazol-1-yl)-9-methyl-6-morpholino-9H-purin-8-yl)methyl)azetidin-1-yl)-2-methylpropan-1-one 860

To a solution of (R)-1-[1-(8-azetidin-3-ylmethyl-9-methyl-6-morpholin-4-yl-9H-purin-2-yl)-1H-benzoimidazol-2-yl]ethanol (57 mg, 0.13 mmol) in DCM (2 mL) was added DIPEA (24 μL, 0.14 mmol) and isobutyryl chloride (14 μL, 0.13 mmol) and the resulting mixture stirred at r.t. for 1 h. The reaction mixture was partitioned between DCM and H$_2$O, the organic phase dried (phase separator) and concentrated in vacuo. The resulting residue was purified by column chromatography (Si-PCC, MeOH:DCM, 0-8%) affording 860 (16 mg, 24%). LCMS (method I): R$_T$ 3.46 min, [M+H]$^+$ 519.3. $^1$H NMR (DMSO, 400 MHz): δ 7.96-7.95 (1 H, m), 7.70-7.69 (1 H, m), 7.30-7.25 (2 H, m), 5.58-5.57 (1 H, m), 5.39 (1 H, d, J=6.34 Hz), 4.36-4.09 (4 H, brd s), 4.35 (1 H, t, J=8.22 Hz), 4.02 (1 H, t, J=8.79 Hz), 3.95-3.94 (1 H, m), 3.80-3.75 (4 H, m), 3.72 (3 H, s), 3.67 (1 H, dd, J=9.77, 5.28 Hz), 3.24-3.23 (3 H, m), 2.45-2.44 (1 H, m), 1.60 (3 H, d, J=6.49 Hz), 0.98 (3 H, d, J=1.77 Hz), 0.97 (3 H, d, J=1.79 Hz)

Example 861

(R)-2-hydroxy-1-(3-((2-(2-(1-hydroxyethyl)-1H-benzo[d]imidazol-1-yl)-9-methyl-6-morpholino-9H-purin-8-yl)methyl)azetidin-1-yl)-2-methylpropan-1-one 861

To a solution of (R)-1-[1-(8-azetidin-3-ylmethyl-9-methyl-6-morpholin-4-yl-9H-purin-2-yl)-1H-benzoimidazol-2-yl]ethanol (57 mg, 0.13 mmol) in DCM (2 mL) was added 2-hydroxy-2-methyl-propionic acid (15 mg, 0.14 mmol), HOBt (19 mg, 0.14 mmol), NMM (31 μL, 0.28 mmol) and EDCI (27 mg, 0.14 mmol) and the resulting mixture stirred at r.t. for 1 h. The reaction mixture was partitioned between DCM and H$_2$O, the organic phase dried (phase separator) and concentrated in vacuo. The resulting residue was purified by column chromatography (Si-PCC, MeOH:DCM, 0-10%) affording 861 (14 mg, 21%). LCMS (method I): R$_T$3.05 min, [M+H]$^+$ 535.3. $^1$H NMR (DMSO, 400 MHz): δ 7.97-7.94 (1H, m), 7.71-7.68 (1 H, m), 7.30-7.26 (2 H, m), 5.58-5.57 (1 H, m), 5.39 (1 H, d, J=6.33 Hz), 5.02 (1H, s), 4.57-4.56 (1 H, m), 4.39-4.14 (4 H, brd s), 4.18 (1 H, dd, J=10.39, 5.70 Hz), 4.04-4.02 (1 H, m), 3.80-3.75 (4 H, m), 3.72 (3 H, s), 3.68 (1 H, dd, J=9.67, 5.21 Hz), 3.23-3.20 (2 H, m), 1.60 (3 H, d, J=6.48 Hz), 1.25 (6 H, s)

Example 862

(S)-1-(4-((2-(2-ethyl-1H-benzo[d]imidazol-1-yl)-9-methyl-6-morpholino-9H-purin-8-yl)methyl)piperidin-1-yl)-2-hydroxypropan-1-one 862

To a mixture of 2-(2-ethylbenzoimidazol-1-yl)-9-methyl-6-morpholin-4-yl-8-piperidin-4-ylmethyl-9H-purine hydrochloride (13 mg, 0.02 mmol), sodium L-lactate (5 mg, 0.04 mmol) and HOBt (4 mg, 0.03 mmol) in THF (1 mL) was added NMM (5 μL, 0.05 mmol) and EDCI (8 mg, 0.04 mmol) and the resulting mixture was stirred at r.t. for 1 h. The reaction mixture was partitioned between EtOAc and H$_2$O, the organic layer washed with brine, dried (Na$_2$SO$_4$) and concentrated in vacuo. The resulting residue was purified by column chromatography (Si-PCC, 2M NH$_3$/MeOH:DCM, 0-10%) affording 862 (12 mg, 92%). LCMS (method I): R$_T$ 3.18 min, [M+H]$^+$ 533.3. $^1$H NMR (MeOD, 400 MHz): δ 8.00-7.96 (1 H, m), 7.65-7.61 (1 H, m), 7.28-7.27 (2 H, m), 4.56-4.54 (2 H, m), 4.33 (4 H, brd s), 4.04-4.04 (1 H, m), 3.84 (4 H, t, J=4.75 Hz), 3.79 (3 H, s), 3.17-3.04 (2 H, m), 2.92-2.86 (2H, m), 2.76-2.64 (1 H, m), 2.28-2.25 (1 H, m), 1.92-1.82 (2 H, m), 1.38 (3 H, t, J=7.51 Hz), 1.36-1.26 (6 H, m)

Example 863

1-(4-(2-(2-ethyl-1H-benzo[d]imidazol-1-yl)-9-methyl-6-morpholino-9H-purine-8-carbonyl)piperidin-1-yl)-2-methylpropan-1-one 863

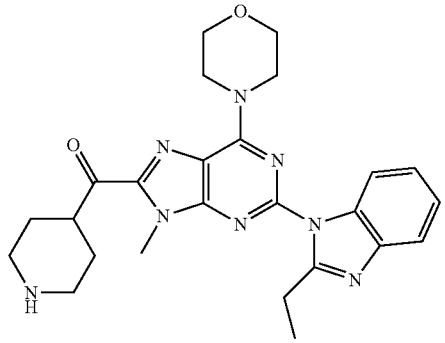

To a solution of 4-[2-(2-ethylbenzoimidazol-1-yl)-9-methyl-6-morpholin-4-yl-9H-purine-8-carbonyl]piperidine-1-carboxylic acid tert-butyl ester (58 mg, 0.10 mmol) in DCM (1 mL) was added TFA (1 mL) and the resulting mixture stirred at r.t. for 1 h. The reaction mixture was concentrated in vacuo and azeotroped with DCM affording [2-(2-Ethylbenzoimidazol-1-yl)-9-methyl-6-morpholin-4-yl-9H-purin-8-yl]piperidin-4-ylmethanone. LCMS (method A): R$_T$ 2.03 min, [M+H]$^+$ 475.3

To a solution of [2-(2-ethylbenzoimidazol-1-yl)-9-methyl-6-morpholin-4-yl-9H-purin-8-yl]piperidin-4-ylmethanone and NEt$_3$ (27 μL, 0.20 mmol) in DCM (5 mL) was added isobutyryl chloride (10 μL, 0.12 mmol) and the resulting mixture stirred at r.t. for 3 h. The reaction mixture was quenched with H$_2$O and extracted with DCM. The combined organic phases were dried (MgSO$_4$) and concentrated in vacuo and the resulting residue loaded onto an Isolute® SCX-2 cartridge which was washed with MeOH and the product eluted with 2M NH$_3$/MeOH. The resulting residue was purified by reverse phase HPLC (Phenomenex Gemini 5

μm C18, 0.1% NH₄OH in water on a gradient acetonitrile 40-70%) affording 863 (7 mg, 13%). LCMS (method I): $R_T$ 4.19 min, [M+H]⁺ 545.3. ¹H NMR (CDCl₃, 400 MHz): δ 8.06-8.05 (1 H, m), 7.88-7.81 (1 H, m), 7.39-7.31 (2 H, m), 4.75-4.63 (2 H, m), 4.14-4.02 (5 H, m), 3.93-3.91 (5 H, m), 3.51-3.40 (2 H, m), 3.31-3.40 (1 H, m), 2.84-2.82 (2 H, m), 2.08-1.96 (2 H, m), 1.89-1.62 (4 H, m), 1.49 (3 H, t, J=7.43 Hz), 1.20-1.12 (6 H, m)

Example 864

(1-(cyclopropanecarbonyl)piperidin-4-yl)(2-(2-ethyl-1H-benzo[d]imidazol-1-yl)-9-methyl-6-morpholino-9H-purin-8-yl)methanone 864

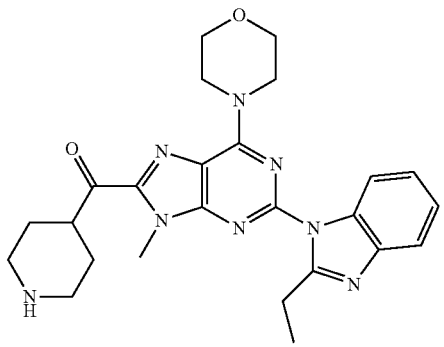

To a solution of 4-[2-(2-ethylbenzoimidazol-1-yl)-9-methyl-6-morpholin-4-yl-9H-purine-8-carbonyl]piperidine-1-carboxylic acid tert-butyl ester (58 mg, 0.10 mmol) in DCM (1 mL) was added TFA (1 mL) and the resulting mixture stirred at r.t. for 1 h. The reaction mixture was concentrated in vacuo and azeotroped with DCM affording [2-(2-Ethylbenzoimidazol-1-yl)-9-methyl-6-morpholin-4-yl-9H-purin-8-yl]piperidin-4-ylmethanone. LCMS (method A): $R_T$ 2.03 min, [M+H]⁺ 475.3

To a solution of [2-(2-ethylbenzoimidazol-1-yl)-9-methyl-6-morpholin-4-yl-9H-purin-8-yl]piperidin-4-ylmethanone (47 mg, 0.10 mmol) and NEt₃ (27 μL, 0.20 mmol) in DCM (5 mL) was added cyclopropane carbonyl chloride (10 μL, 0.12 mmol) and the resulting mixture stirred at r.t. for 3 h. The reaction mixture was quenched with H₂O and extracted with DCM. The combined organic phases were dried (MgSO₄) and concentrated in vacuo and the resulting residue loaded onto an Isolute® SCX-2 cartridge which was washed with MeOH and the product eluted with 2M NH₃/MeOH. The resulting residue was purified by reverse phase HPLC (Phenomenex Gemini 5 μm C18, 0.1% NH₄OH in water on a gradient acetonitrile 30-70%) affording 864 (13 mg, 25%). LCMS (method I): $R_T$ 4.06 min, [M+H]⁺ 543.3. ¹H NMR (CDCl₃, 400 MHz): δ 8.07-8.06 (1 H, m), 7.89-7.82 (1 H, m), 7.40-7.30 (2 H, m), 4.70-4.56 (3 H, m), 4.39-4.28 (1 H, m), 4.13 (3 H, s), 3.93-3.90 (6 H, m), 3.52-3.27 (3 H, m), 2.94-2.80 (1 H, m), 2.08-1.97 (2 H, m), 1.97-1.57 (4 H, m), 1.50 (3 H, t, J=7.40 Hz), 1.04-0.98 (2 H, m), 0.79-0.78 (2 H, m)

Example 865 cyclopropyl(4-(1-(2-(2-ethyl-1H-benzo[d]imidazol-1-yl)-9-methyl-6-morpholino-9H-purin-8-yl)-1-hydroxyethyl)piperidin-1-yl)methanone 865

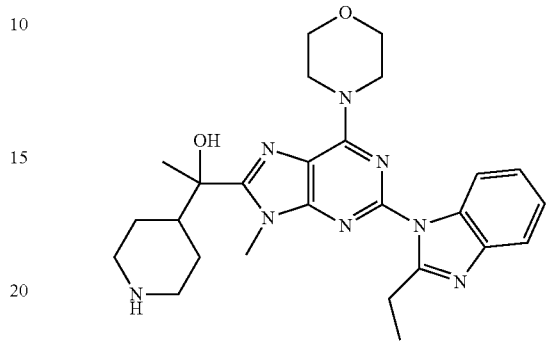

To a solution of 4-{1-[2-(2-ethylbenzoimidazol-1-yl)-9-methyl-6-morpholin-4-yl-9H-purin-8-yl]-1-hydroxyethyl}piperidine-1-carboxylic acid tert-butyl ester (104 mg, 0.18 mmol) in DCM (1 mL) was added TFA (1 mL) and the resulting mixture stirred for 1 h. The reaction mixture was concentrated in vacuo and azeotroped with DCM affording 1-[2-(2-Ethylbenzoimidazol-1-yl)-9-methyl-6-morpholin-4-yl-9H-purin-8-yl]-1-piperidin-4-ylethanol. LCMS (method A): $R_T$ 1.88 min, [M+H]⁺ 491.2

A solution of 1-[2-(2-ethylbenzoimidazol-1-yl)-9-methyl-6-morpholin-4-yl-9H-purin-8-yl]-1-piperidin-4-ylethanol and NEt₃ (74 μL, 0.53 mmol) in DCM (5 mL) was cooled to −78° before the addition of cyclopropane carbonyl chloride (18 μL, 0.20 mmol). The resulting mixture was stirred for 15 min then quenched with H₂O and extracted with DCM. The combined organics were dried (phase separator) and concentrated in vacuo. The resulting residue was purified by reverse phase HPLC (Phenomenex Gemini 5 μm C18, 0.1% NH₄OH in water on a gradient acetonitrile 10-70%) affording 865 as a white solid (44 mg, 44%). LCMS (method I): $R_T$ 3.51 min, [M+H]⁺ 559.4. ¹H NMR (CDCl₃, 400 MHz): δ 8.01-8.00 (1 H, m), 7.80 (1 H, d, J=7.13 Hz), 7.33-7.28 (2 H, m), 4.71 (1 H, brd s), 4.32 (4 H, brd s), 3.98 (3 H, s), 3.87 (4 H, t, J=4.69 Hz), 3.40 (2 H, q, J=7.47 Hz), 3.14-2.98 (1 H, m), 2.60-2.43 (1 H, m), 2.20-2.09 (1 H, m), 1.86-1.65 (6 H, m), 1.62-1.36 (3H, m), 1.47 (3 H, t, J=7.47 Hz), 1.00-0.93 (2 H, m), 0.75-0.74 (2 H, m)

Example 866

(9-methyl-2-(2-(methylamino)-1H-benzo[d]imidazol-1-yl)-6-morpholino-9H-purin-8-yl)(3-morpholinoazetidin-1-yl)methanone 866

A mixture of (2-chloro-9-methyl-6-morpholin-4-yl-9H-purin-8-yl)-(3-morpholin-4-ylazetidin-1-yl)methanone (211 mg, 0.50 mmol), (1H-benzoimidazol-2-yl)methylamine (81 mg, 0.55 mmol), tris(dibenzylideneacetone)dipalladium (12 mg, 0.01 mmol), XPhos (24 mg, 0.05 mmol) and Cs₂CO₃ (245 mg, 0.75 mmol) in dioxane (10 mL) was purged with argon then heated at 105° C. for 65 h. The reaction mixture was filtered through Celite®, washing with dioxane and the filtrate concentrated in vacuo. The resulting residue was purified by column chromatography (Si-PCC, MeOH:DCM, 0-10%) followed by reverse phase HPLC (Phenomenex Gemini 5 μm C18, 0.1% NH$_4$OH in water on a gradient acetonitrile 10-90%) affording 866 as a white solid (54 mg, 20%). LCMS (method I): R$_T$ 2.57 min, [M+H]$^+$ 533.3. $^1$H NMR (CDCl$_3$, 400 MHz): δ 8.48 (1 H, brd s), 8.27 (1 H, d, J=8.02 Hz), 7.51 (1 H, d, J=7.84 Hz), 7.20-7.19 (1 H, m), 7.09-7.07 (1 H, m), 4.73-4.66 (1 H, m), 4.68-4.16 (4 H, brd s), 4.50 (1 H, dd, J=10.48, 5.14 Hz), 4.24-4.23 (1 H, m), 4.16-4.08 (4 H, m), 3.90 (4 H, t, J=4.66 Hz), 3.77 (4 H, t, J=4.58 Hz), 3.30-3.26 (4 H, m), 2.45-2.42 (4 H, m)

Example 867

(R)-(2-(2-(1-hydroxyethyl)-1H-benzo[d]imidazol-1-yl)-9-methyl-6-morpholino-9H-purin-8-yl)(3-morpholinoazetidin-1-yl)methanone A mixture of (2-chloro-9-methyl-6-morpholin-4-yl-9H-purin-8-yl)-(3-morpholin-4-ylazetidin-1-yl)methanone (164 mg, 0.39 mmol), (R)-1-(1H-benzoimidazol-2-yl)ethanol (70 mg, 0.43 mmol), tris(dibenzylideneacetone)dipalladium (36 mg, 0.04 mmol), XPhos (75 mg, 0.16 mmol) and Cs$_2$CO$_3$ (255 mg, 0.78 mmol) in toluene (4 mL) was purged with argon then heated at 140° C. for 1 h in a microwave reactor. The reaction mixture was filtered through Celite®, washing with toluene and the filtrate concentrated in vacuo. The resulting residue was purified by column chromatography (Si-PCC, MeOH:DCM, 0-10%) affording 867 (40 mg, 18%). LCMS (method I): R$_T$ 2.73 min, [M+H]$^+$ 548.3. $^1$H NMR (CDCl$_3$, 400 MHz): δ 8.13-8.12 (1 H, m), 7.85-7.81 (1 H, m), 7.35-7.34 (2 H, m), 5.64 (1 H, s), 5.41-5.40 (1 H, m), 4.78-4.20 (4 H, brd s), 4.76-4.68 (1 H, m), 4.60-4.50 (1 H, m), 4.26-4.25 (1 H, m), 4.20-4.10 (4 H, m), 3.89 (4 H, t, J=4.72 Hz), 3.85-3.75 (4 H, m), 3.37-3.29 (1H, m), 2.58-2.41 (4 H, m), 1.80 (3 H, d, J=6.53 Hz)

Example 868

(S)-(2-(2-(1-hydroxyethyl)-1H-benzo[d]imidazol-1-yl)-9-methyl-6-morpholino-9H-purin-8-yl)(3-morpholinoazetidin-1-yl)methanone A mixture of (2-chloro-9-methyl-6-morpholin-4-yl-9H-purin-8-yl)-(3-morpholin-4-ylazetidin-1-yl)methanone (164 mg, 0.39 mmol), (S)-1-(1H-benzoimidazol-2-yl)ethanol (70 mg, 0.43 mmol), tris(dibenzylideneacetone)dipalladium (36 mg, 0.04 mmol), XPhos (75 mg, 0.16 mmol) and Cs$_2$CO$_3$ (255 mg, 0.78 mmol) in toluene (4 mL) was purged with argon then heated at 140° C. for 1 h in a microwave reactor. The reaction mixture was filtered through Celite®, washing with toluene and DCM and the filtrate concentrated in vacuo. The resulting residue was purified by column chromatography (Si-PCC, MeOH:DCM, 0-10%) affording 868 (121 mg, 55%). LCMS (method I): R$_T$ 2.74 min, [M+H]$^+$ 548.3. $^1$H NMR (CDCl$_3$, 400 MHz): δ 8.14-8.09 (1 H, m), 7.83-7.82 (1 H, m), 7.37-7.33 (2H, m), 5.64 (1 H, s), 5.42-5.40 (1 H, m), 4.76-4.20 (4 H, brd s), 4.73-4.71 (1 H, m), 4.59-4.51 (1 H, m), 4.26-4.25 (1 H, m), 4.20-4.12 (4 H, m), 3.88 (4 H, t, J=4.71 Hz), 3.83-3.76 (4 H, m), 3.37-3.29 (1 H, m), 2.58-2.42 (4 H, m), 1.80 (3 H, d, J=6.54 Hz)

Example 869

(2-(2-isopropyl-1H-benzo[d]imidazol-1-yl)-9-methyl-6-morpholino-9H-purin-8-yl)(3-morpholinoazetidin-1-yl)methanone A mixture of (2-chloro-9-methyl-6-morpholin-4-yl-9H-purin-8-yl)-(3-morpholin-4-ylazetidin-1-yl)methanone (211 mg, 0.50 mmol), 2-iso-propylbenzimidazole (88 mg, 0.55 mmol), tris(dibenzylideneacetone)dipalladium (12 mg, 0.01 mmol), XPhos (24 mg, 0.05 mmol) and Cs$_2$CO$_3$ (245 mg, 0.75 mmol) in dioxane (10 mL) was purged with argon then heated at 105° C. for 22 h. The reaction mixture was filtered through Celite®, washing with dioxane and the filtrate concentrated in vacuo. The resulting residue was purified by column chromatography (Si-PCC, MeOH:DCM, 0-10%) followed by reverse phase HPLC (Phenomenex Gemini 5 μm C18, 0.1% NH$_4$OH in water on a gradient acetonitrile 10-90%) affording 869 as a white solid (167 mg, 61%). LCMS (method I): R$_T$ 2.86 min, [M+H]$^+$ 546.3. $^1$H NMR (CDCl$_3$, 400 MHz): δ 7.93-7.92 (1 H, m), 7.81 (1 H, d, J=7.28 Hz), 7.33-7.23 (2 H, m), 4.77-4.36 (4 H, brd s), 4.73 (1 H, dd, J=10.47, 7.11 Hz), 4.52 (1 H, dd, J=10.63, 5.21 Hz), 4.27-4.24 (1 H, m), 4.17-4.08 (5 H, m), 4.02-3.99 (1 H, m), 3.87 (4 H, t, J=4.64 Hz), 3.78 (4 H, t, J=4.60 Hz), 3.34-3.28 (1 H, m), 2.50-2.43 (3 H, m), 1.49 (6 H, d, J=6.83 Hz)

Example 875

(4-(2-hydroxypropan-2-yl)piperidin-1-yl)(2-(imidazo[1,2-a]pyridin-5-yl)-9-methyl-6-morpholino-9H-purin-8-yl)methanone A mixture of [4-(1-hydroxy-1-methylethyl)piperidin-1-yl]-(9-methyl-6-morpholin-4-yl-2-tributylstannanyl-9H-purin-8-yl)methanone (101 mg, 0.15 mmol), 5-bromoimidazo[1,2-a]pyridine (32 mg, 0.16 mmol), Pd(PPh$_3$)$_4$ (17 mg, 10 mol %) and Cu(TC) (6 mg, 20 mol %) in dioxane (1.5 mL) was purged with argon then heated at 150° C. for 20 min in a microwave reactor. The reaction mixture was loaded onto an Isolute® SCX-2 cartridge which was washed with MeOH and the product eluted with 2 M NH$_3$/MeOH. The resulting residue was further purified by reverse phase HPLC (Phenomenex Gemini 5 μm C18, 0.1% NH$_4$OH in water on a gradient acetonitrile 10-90%) affording 875 as a white solid (22 mg, 29%). LCMS (method I): R$_T$ 2.84 min, [M+H]$^+$ 505.3. $^1$H NMR (CDCl$_3$, 400 MHz): δ 9.30 (1 H, s), 8.07-8.05 (1 H, m), 7.87 (1 H, d, J=8.89 Hz), 7.78 (1 H, d, J=1.39 Hz), 7.38 (1 H, dd, J=8.90, 7.23 Hz), 4.89-4.86 (1 H, m), 4.64-4.61 (1 H, m), 4.39 (4 H, brd s), 4.03 (3H, s), 3.89 (4 H, t, J=4.76 Hz), 3.22-3.05 (1 H, m), 2.81 (1 H, td, J=12.92, 2.90 Hz), 1.98-1.95 (1 H, m), 1.90-1.87 (1 H, m), 1.66-1.59 (1 H, m), 1.44 (2 H, qd, J=12.58, 4.23 Hz), 1.24 (6 H, d, J=5.99 Hz)

Example 876

1-(4-((5-(2-ethyl-1H-benzo[d]imidazol-1-yl)-7-morpholinothiazolo[5,4-d]pyrimidin-2-yl)methyl)piperidin-1-yl)-2-hydroxy-2-methylpropan-1-one A mixture of acetic acid 2-{4-[5-(2-ethylbenzoimidazol-1-yl)-7-morpholin-4-ylthiazolo[5,4-c]pyrimidin-2-ylmethyl]piperidin-1-yl}-1,1-dimethyl-2-oxoethyl ester (122 mg, 0.21 mmol) and LiOH (500 μL, 1.96 mmol, 4M solution) in THF (3 mL) and MeOH (3 mL) was allowed to stir at r.t. for 2 h. The reaction mixture was loaded onto an Isolute® SCX-2 cartridge which was washed with MeOH and the product eluted with 2M NH$_3$/MeOH. The resulting residue was purified by column chromatography (Si-PCC, MeOH:DCM, 0-5%) followed by reverse phase HPLC (Phenomenex Gemini 5 μm C18, 0.1% NH$_4$OH in water on a gradient acetonitrile 40-80%) affording 876 as a white solid (45 mg, 39%). LCMS (method I): R$_T$ 3.94 min, [M+H]$^+$ 550.4. $^1$H NMR (DMSO, 400 MHz): δ 8.00-7.99 (1 H, m), 7.84-7.80 (1 H, m), 7.35-7.30 (2 H, m), 4.43 (4 H, brd s), 3.89 (4 H, t, J=4.72 Hz), 3.39 (2 H, q, J=7.46 Hz), 3.05 (2 H, d, J=7.14 Hz), 2.91 (2 H, brd s), 2.17-2.15 (1 H, m), 1.90 (3 H, d, J=13.40 Hz), 1.50 (6 H, s), 1.46 (3 H, t, J=7.49 Hz), 1.39-1.28 (3 H, m)

Example 901

PI3K Isoform Inhibition Assay (p110 alpha, beta, gamma, delta: α, β, γ, δ)

PI3K enzymatic activity was assayed by measuring the amount of product phosphatidylinositol 3,4,5-phosphate (PIP3) formed from substrate 4,5 phosphatidylinositol 4,5-phosphate (PIP2) using a fluorescence polarization displacement assay. The decrease in fluorescence polarization of a fluorescent $PIP_3$ probe is measured as it is displaced from a $PIP_3$-binding protein GRP-1 detector by PI3K-catalyzed product. Assays were conducted in 384-well black Proxiplates in the presence of 10 mM Tris (pH 7.5), 50 mM NaCl, 4 mM $MgCl_2$, 5% glycerol, 25 μM ATP, 10 μM $PIP_2$ (Echelon Biosciences), 0.05% 3-[(3-cholamidopropyl) dimethylammonio]-1-propanesulfonate, 1 mM dithiothreitol, and 2% DMSO. The kinase reactions were initiated by the addition of 40 ng/mL p110α/p85α, 300 ng/mL p110β/p85α, 40 ng/mL p110γ, or 40 ng/mL p110δ/p85α (Upstate Group, Millipore; Dundee, UK), and 10 μM $PIP_2$ (Echelon Biosciences) to the wells. The reactions were stopped at timepoints that yielded a fixed change in fluorescence polarization consistent with initial rate conditions (typically 30 minutes), by the addition of 12.5 mM EDTA, 100 nM GRP-1 detector, and 5 nM tetramethylrhodamine-labeled $PIP_3$ (TAMRA-$PIP_3$; Echelon Biosciences). After 60 minutes of incubation at room temperature to allow equilibration of labeled and unlabeled PIP3 binding, the parallel and perpendicular components of the fluorescence emissions from each sample were measured at an excitation wavelength of 530 nm and an emission wavelength of 590 nm using an Envision fluorescent plate reader with a rhodamine filter (PerkinElmer Life and Analytical Sciences; Wellesley, Mass.). The assay is capable of detecting 0.1-2.0 μM $PIP_3$ product. The $IC_{50}$ values were obtained by fitting the dose-dependent inhibition data to a 4-parameter equation using Assay Explorer software (MDL, San Ramon, Calif.).

Alternatively, inhibition of PI3K was determined in a radiometric assay using purified, recombinant enzyme and ATP at a concentration of 1 uM. The Formula I compound was serially diluted in 100% DMSO. The kinase reaction was incubated for 1 h at room temperature, and the reaction was terminated by the addition of PBS. $IC_{50}$ values were subsequently determined using sigmoidal dose-response curve fit (variable slope).

The same protocol may be used to establish $IC_{50}$ values for p110α (alpha) PI3K binding.

Recombinant PI3K p110 isoforms alpha, beta, and delta may be prepared and purified according to US 2008/0275067 from recombinant PI3K heterodimeric complexes consisting of a p110 catalytic subunit and a p85 regulatory subunit overexpressed using the BAC-TO-BAC.™. HT baculovirus expression system (GIBCO/BRL), and then purified for use in biochemical assays. The four Class I PI 3-kinases are cloned into baculovirus vectors as follows:

p110 delta: A FLAG™-tagged (Eastman Kodak Co., U.S. Pat. Nos. 4,703,004; 4,782,137; 4,851,341) version of human p110.delta (Chantry et al., J. Biol. Chem. (1997) 272:19236-41) is subcloned using standard recombinant DNA techniques into the BamH1-Xba1 site of the insect cell expression vector pFastbac HTb (Life Technologies, Gaithersburg, Md.), such that the clone is in frame with the His tag of the vector.

p110 alpha: Similar to the method used for p110 delta, described above, a FLAG™-tagged version of p110 alpha (Volinia et al (1994) Genomics, 24(3):427-77) was subcloned in BamH1-HindIII sites of pFastbac HTb (Life Technologies) such that the clone was in frame with the His tag of the vector.

p110 beta: A p110 beta (see Hu et al (1993) Mol. Cell. Biol., 13:7677-88) clone was amplified from the human MARATHON™ Ready spleen cDNA library (Clontech, Palo Alto Calif.) according to the manufacturer's protocol using the specified primers.

The p110 delta binding IC50 values and delta/alpha selectivity of selected compounds from Tables 1 and 2 include:

| Compound No. | p110 delta IC50 (micromolar) | IC50 p110 alpha/IC50 p110 delta |
|---|---|---|
| 101 | 0.101 | 53 |
| 112 | 0.0018 | 29 |
| 115 | 0.0072 | 34 |
| 131 | 0.0013 | 32 |
| 149 | 0.0069 | 30 |
| 158 | 0.0016 | 84 |
| 162 | 0.0146 | 191 |
| 200 | 0.0222 | 54 |
| 211 | 0.0097 | >300 |
| 240 | 0.00274 | 64 |
| 248 | 0.0429 | 35 |
| 489 | 0.00137 | 157 |
| 490 | 0.00238 | 111 |
| 499 | 0.0063 | 75 |
| 501 | 0.000589 | 140 |
| 521 | 0.00145 | 150 |
| 528 | 0.00061 | 136 |
| 531 | 0.00108 | 96 |
| 535 | 0.0099 | 49 |
| 549 | 0.0094 | 14 |
| 676 | 0.0136 | 14 |
| 683 | 0.0317 | 23 |
| 689 | 0.0258 | 23 |
| 701 | 0.000658 | 50 |

Example 902

Collagen Induced Arthritis Efficacy Test

The efficacy of Formula I compound inhibitors of PI3K delta to inhibit the induction and/or progression of collagen induced arthritis was tested in mice. DBA1/J male mice (Jackson Labs; 5-6 weeks of age) are acclimatized for one week and are then injected intra-dermally at the base of the tail with 0.1 ml of an emulsion of Bovine Type II Collagen (100 mg) and an equal volume of Complete Freunds Adjuvant (200 mg *Mycobacterium tuberculosis*). Three weeks later, mice are injected intra-dermally at the base of the tail with 0.1 ml of an emulsion of Bovine Type II Collagen (100 mg) and an equal volume of Incomplete Freunds Adjuvant for boost. Dosing generally starts as soon as animals display signs of joint inflammation or clinical score 1-2.

All mice are evaluated 2-3 times a week for arthritis using a macroscopic scoring system for each paw. At the end of the experiment clinical scores are obtained to evaluate the intensity of edema in the four paws. A score of 0 to 4 is assigned to each paw Animals are scored 0 when no inflammatory signs (swelling and redness) are observed in any of the small joints (intraphalangeal, metacarpophalangeal, metatarsophalangeal) or large joints (wrist/carpus, ankle/tarsus) Animals are scored 1 when very slight to slight inflammation was observed (swelling and/or redness of paw or one digit), 2 moderate edema(swelling in two or more joint), 3 severe edema(gross swelling of the paw with more than two joints involved), and 4 when very severe edema(severe arthritis of the entire paw and digits) is present. The arthritic index for each mouse is evaluated by adding the four scores of the individual paws, giving a maximum score of 16. Plasma and serum samples are taken at 1 hour (orbital bleed) post dose and 24 hrs (cardiac puncture) post dose. Samples are stored at −20° C. until analysis. At termination, the hind paws are transected at the distal tibia, just proximal to the tarsal joint. The left and right hind paws are placed in the histology cassettes individually and fixed in 10% formalin. These paws are sent to histology dept for further process.

Materials: Bovine Type II collagen, immunization grade, 2 mg/ml (5 ml/vial) in 0.05 M acetic acid (solution), store at −20° C., from Chondrex, LLC, Seattle, Wash. Adjuvant complete H37 Ra, 6×10 ml/box, contains 1 mg/ml *Mycobacterium tuberculosis*. For use in animal immunological studies, for laboratory use, store at +4° C., from Difco Laboratories, Detroit, Mich. 48232-7058 USA. Adjuvant Incomplete H37 Ra, 6×10 ml/box: For use in animal immunological studies, for laboratory use, store at +4° C., from Difco Laboratories.

Example 903

CD69 Whole Blood Assay

Human blood is obtained from healthy volunteers, with the following restrictions: 1 week drug-free, non-smokers. Blood (approximately 20 mls to test 8 compounds) is collected by venipuncture into Vacutainer tubes with sodium heparin.

Cynomolgus monkey blood is obtained courtesy of the LAT group from monkeys not previously exposed to, or after a washout period from, chemical dosing. Additional cyno blood draws may be collected during the course of pharmacokinetic or toxicology studies. Blood (25-30 mls for naïve monkeys or 3-4 mls from monkeys on studies requiring repeated draws) is collected by venipuncture into Vacutainer tubes with sodium heparin.

Solutions of Formula I compounds at 1000 or 2000 μM in PBS (20×), are diluted by three-fold serial dilutions in 10% DMSO in PBS for a nine point dose-response curve. An aliquot of 5.5 μl of each compound is added in duplicate to a 2 ml 96-well plate; 5.5 μl of 10% DMSO in PBS is added as control and no-stimulus wells. Human whole blood—HWB (100 μl) is added to each well. After mixing the plates are incubated at 37° C., 5% $CO_2$, 100% humidity for 30 minutes. Goat F(ab')2 anti-human IgM (10 μl of a 500 μg/ml solution, 50 μg/ml final) is added to each well (except the no-stimulus wells) with mixing and the plates are incubated for an additional 20 hours. At the end of the 20 hour incubation, samples are incubated with florescent labeled antibodies for 30 minutes, at 37° C., 5% $CO_2$, 100% humidity. Include induced control, unstained and single stains for compensation adjustments and initial voltage settings. Samples are then lysed with Pharmingen Lyse according to the manufacturer's instructions. Samples are then transferred to a 96 well plate suitable to be run on the AMS 96 well system on the BD Calibur FACs machine. Data acquired and Mean Fluorescence Intensity values were obtained using Cell Quest Software. Results are initially analyzed by FACS analysis software (Flow Jo). The IC50 for test compounds is defined as the concentration which decreases by 50% the percent positive of CD69 cells that are also CD20 positive stimulated by anti-IgM (average of 8 control wells, after subtraction of the average of 8 wells for the no-stimulus background). The IC50 values are calculated by ActivityBase using Xlfit version 3, equation 201.

The IC50 values of selected compounds from Tables 1 and 2 in the CD69 Whole Blood Assay include:

| Compound No. | IC50 (nanomolar) |
|---|---|
| 240 | 17.8 |
| 314 | 44.1 |
| 388 | 51.1 |
| 403 | 22.0 |
| 406 | 20.6 |
| 427 | 56.7 |
| 428 | 34.2 |
| 438 | 65.9 |
| 490 | 38.3 |
| 689 | 29.0 |
| 702 | 28.6 |

The foregoing description is considered as illustrative only of the principles of the invention. Further, since numerous modifications and changes will be readily apparent to those skilled in the art, it is not desired to limit the invention to the exact construction and process shown as described above. Accordingly, all suitable modifications and equivalents may be considered to fall within the scope of the invention as defined by the claims that follow.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

The invention claimed is:

1. A compound selected from Formulas Ia and Ib:

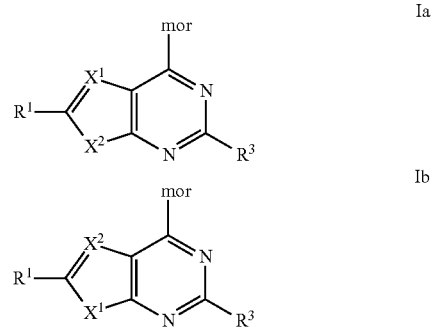

and stereoisomers, tautomers, or pharmaceutically acceptable salts thereof,
wherein (i) $X^1$ is N and $X^2$ is S, (iii) $X^1$ is N and $X^2$ is $NR^2$, or (iv) $X^1$ is $CR^7$ and $X^2$ is O;
$R^1$ is selected from
$C_6$-$C_{20}$ aryl,
$C_2$-$C_{20}$ heterocyclyl,
$C_3$-$C_{12}$ carbocyclyl,
$C_1$-$C_{20}$ heteroaryl,
—($C_1$-$C_{12}$ alkylene)-($C_3$-$C_{12}$ carbocyclyl),
—($C_1$-$C_{12}$ alkylene)-($C_2$-$C_{20}$ heterocyclyl),
—($C_1$-$C_{12}$ alkylene)-($C_2$-$C_{20}$ heterocyclyl)-($C_2$-$C_{20}$ heterocyclyl),
—($C_1$-$C_{12}$ alkylene)-($C_2$-$C_{20}$ heterocyclyl)-($C_3$-$C_{12}$ carbocyclyl),
—($C_1$-$C_{12}$ alkylene)-($C_2$-$C_{20}$ heterocyclyl)-C(=O)—($C_2$-$C_{20}$ heterocyclyl),
—($C_1$-$C_{12}$ alkylene)-($C_1$-$C_{20}$ heteroaryl), —($C_1$-$C_{12}$ alkylene)-($C_2$-$C_{20}$ heterocyclyl)-($C_1$-$C_{12}$ alkyl),
—($C_1$-$C_{12}$ alkylene)-($C_6$-$C_{20}$ aryl)-($C_1$-$C_{12}$ alkyl),
—($C_1$-$C_{12}$ alkylene)-($C_1$-$C_{20}$ heteroaryl)-($C_1$-$C_{12}$ alkyl),
—($C_1$-$C_{12}$ alkylene)-C(=O)—($C_2$-$C_{20}$ heterocyclyl),
—($C_1$-$C_{12}$ alkylene)-NHR$^{2'}$,
—($C_1$-$C_{12}$ alkylene)-NR$^{2'}$—($C_1$-$C_{12}$ alkyl),
—($C_1$-$C_{12}$ alkylene)-NR$^{2'}$—($C_3$-$C_{12}$ carbocyclyl),
—($C_1$-$C_{12}$ alkylene)-NR$^{2'}$—($C_2$-$C_{20}$ heterocyclyl),
—($C_1$-$C_{12}$ alkylene)-NR$^{2'}$—($C_1$-$C_{20}$ heteroaryl),
—($C_1$-$C_{12}$ alkylene)-NR$^{2'}$—($C_6$-$C_{20}$ aryl),
—($C_1$-$C_{12}$ alkylene)-NR$^{2'}$—($C_1$-$C_{12}$ alkylene)-($C_3$-$C_{12}$ carbocyclyl),
—($C_1$-$C_{12}$ alkylene)-NR$^{2'}$—($C_1$-$C_{12}$ alkylene)-($C_1$-$C_{20}$ heteroaryl),
—($C_1$-$C_{12}$ alkylene)-NR$^{2'}$—($C_1$-$C_{12}$ alkylene)-($C_1$-$C_{20}$ heterocyclyl),
—($C_1$-$C_{12}$ alkylene)-NR$^{2'}$—($C_1$-$C_{12}$ alkylene)-($C_6$-$C_{20}$ aryl),
—($C_1$-$C_{12}$ alkylene)-NR$^{2'}$—($C_1$-$C_{12}$ alkylene)-NHC(=O)—($C_1$-$C_{20}$ heteroaryl),
—($C_1$-$C_{12}$ alkylene)-($C_2$-$C_{20}$ heterocyclyl)-N($C_1$-$C_{12}$ alkyl)R$^{2'}$,
—($C_1$-$C_{12}$ alkylene)-($C_2$-$C_{20}$ heterocyclyl)-($C_1$-$C_{12}$ alkyl)-N($C_1$-$C_{12}$ alkyl)R$^{2'}$,
—($C_2$-$C_{12}$ alkenylene)-($C_2$-$C_{20}$ heterocyclyl),
—($C_1$-$C_{20}$ heteroaryl)-($C_2$-$C_{20}$ heterocyclyl),
—($C_1$-$C_{20}$ heteroaryl)-($C_3$-$C_{12}$ carbocyclyl),
—C(=O)—($C_2$-$C_{20}$ heterocyclyl),
—C(=O)—($C_1$-$C_{20}$ heteroaryl),
—C(=O)—($C_2$-$C_{20}$ heterocyclyl)-($C_2$-$C_{20}$ heterocyclyl),
—C(=O)—($C_2$-$C_{20}$ heterocyclyl)-($C_1$-$C_{20}$ heteroaryl),
—C(=O)—($C_1$-$C_{12}$ alkyl),
—C(=O)—NR$^{2'}$—($C_1$-$C_{12}$ alkyl), and
—CR$^4$=CR$^5$R$^6$ where R$^4$ is selected from H, F, Cl, Br, I and $C_1$-$C_{12}$ alkyl, and R$^5$ and R$^6$ form $C_2$-$C_{20}$ heterocyclyl, $C_1$-$C_{20}$ heteroaryl, or $C_3$-$C_{12}$ carbocyclyl,
where alkyl, alkenyl, alkynyl, alkylene, carbocyclyl, heterocyclyl, aryl, and heteroaryl are optionally substituted with one or more groups independently selected from F, Cl, Br, I, —CH$_3$, —CH$_2$CH$_3$, —CH$_2$CH(CH$_3$)$_2$, —CH$_2$NH$_2$, —CH$_2$N(CH$_3$)$_2$, —CH$_2$CH$_2$NH$_2$, —CH$_2$CH$_2$N(CH$_3$)$_2$, —CH$_2$OH, —CH$_2$OH, —CH$_2$OCH$_3$, —CH$_2$CH$_2$OH, —C(CH$_3$)$_2$OH, —CH$_2$C(CH$_3$)$_2$OH, —CH(OH)CH(CH$_3$)$_2$, —C(CH$_3$)$_2$CH$_2$OH, —CH$_2$CH$_2$SO$_2$CH$_3$, —CN, —CF$_3$, —CO$_2$H, —CHO, —COCH$_3$, —CO$_2$CH$_3$, —CO$_2$C(CH$_3$)$_3$, —COCH$_2$OH, —COC(OH)(CH$_3$)$_2$, —COCH(OH)CH$_3$, —CONH$_2$, —CONHCH$_3$, —CON(CH$_3$)$_2$, —CH$_2$CONH$_2$, —CH$_2$CON(CH$_3$)$_2$, —C(CH$_3$)$_2$CONH$_2$, —NO$_2$, —NH$_2$, —NHCH$_3$, —N(CH$_3$)$_2$, —NHCOCH$_3$, —N(CH$_3$)COCH$_3$, —NHS(O)$_2$CH$_3$, —N(CH$_3$)C(CH$_3$)$_2$CONH$_2$, —N(CH$_3$)CH$_2$CH$_2$S(O)$_2$CH$_3$, =O, —OH, —OCH$_3$, —S(O)$_2$N(CH$_3$)$_2$, —SCH$_3$, —CH$_2$OCH$_3$, —S(O)$_2$CH$_3$, —C(O)-cyclopropyl, cyclopropyl, cyclobutyl, oxetanyl, and morpholino;
R$^2$ and R$^{2'}$ are independently selected from H, $C_1$-$C_{12}$ alkyl, $C_2$-$C_8$ alkenyl, $C_2$-$C_8$ alkynyl, —($C_1$-$C_{12}$ alkylene)-($C_3$-$C_{12}$ carbocyclyl), —($C_1$-$C_{12}$ alkylene)-($C_2$-$C_{20}$ heterocyclyl), —($C_1$-$C_{12}$ alkylene)-C(=O)-($C_2$-$C_{20}$ heterocyclyl), —($C_1$-$C_{12}$ alkylene)-($C_6$-$C_{20}$ aryl), and —($C_1$-$C_{12}$ alkylene)-($C_1$-$C_{20}$ heteroaryl), where alkyl, alkenyl, alkynyl, alkylene, carbocyclyl, heterocyclyl, aryl, and heteroaryl are optionally substituted with one or more groups independently selected from F, Cl, Br, I, —CH$_3$, —CH$_2$OH, —CN, —CF$_3$, —CO$_2$H, —COCH$_3$, —COC(CH$_3$)$_3$, —COCF$_3$, —CO$_2$CH$_3$, —CONH$_2$, —CONHCH$_3$, —CON(CH$_3$)$_2$, —NO$_2$, —NH$_2$, —NHCH$_3$, —NHCOCH$_3$, —NHS(O)$_2$CH$_3$, —OH, —OCH$_3$, —S(O)$_2$N(CH$_3$)$_2$, —SCH$_3$, —CH$_2$OCH$_3$, and —S(O)$_2$CH$_3$;

R$^3$ is:

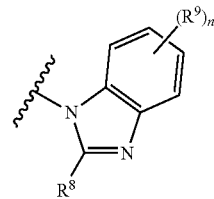

where R$^8$ is selected from H, F, Cl, Br, I, —CH$_3$, —CH$_2$CH$_3$, —CH$_2$CH$_2$CH$_3$, —CH(CH$_3$)$_2$, —C(CH$_3$)$_3$, —CH$_2$OCH$_3$, —CHF$_2$, —CH$_2$CN, —CN, —CF$_3$, —CH$_2$OH, —CH$_2$OCH$_3$, —CH$_2$CH$_2$OH, —CH$_2$C(CH$_3$)$_2$OH, —CH(CH$_3$)OH, —CH(CH$_2$CH$_3$)OH, —CH$_2$CH(OH)CH$_3$, —CH$_2$CH(OCH$_3$)CH$_3$, —C(CH$_3$)$_2$OH, —C(CH$_3$)$_2$OCH$_3$, —CH(CH$_3$)F, —C(CH$_3$)F$_2$, —CH(CH$_2$CH$_3$)F, —C(CH$_2$CH$_3$)$_2$F, —CO$_2$H, —CONH$_2$, —CON(CH$_2$CH$_3$)$_2$, —COCH$_3$, —CON(CH$_3$)$_2$, —NO$_2$, —NH$_2$, —NHCH$_3$, —N(CH$_3$)$_2$, —NHCH$_2$CH$_3$, —NHCH(CH$_3$)$_2$, —NHCH$_2$CH$_2$OH, —NHCH$_2$CH$_2$OCH$_3$, —NHCOCH$_3$, —NHCOCH$_2$CH$_3$, —NHCOCH$_2$OH, —NHS(O)$_2$CH$_3$, —N(CH$_3$)S(O)$_2$CH$_3$, —OH, —OCH$_3$, —OCH$_2$CH$_3$, —OCH(CH$_3$)$_2$, —SH, —NHC(=)NHCH$_3$, —NHC(=O)NHCH$_2$CH$_3$, —S(O)CH$_3$, —S(O)CH$_2$CH$_3$, —S(O)$_2$CH$_3$, —S(O)$_2$NH$_2$, —S(O)$_2$NHCH$_3$, —S(O)$_2$N(CH$_3$)$_2$, —CH$_2$S(O)$_2$CH$_3$, and a group selected from

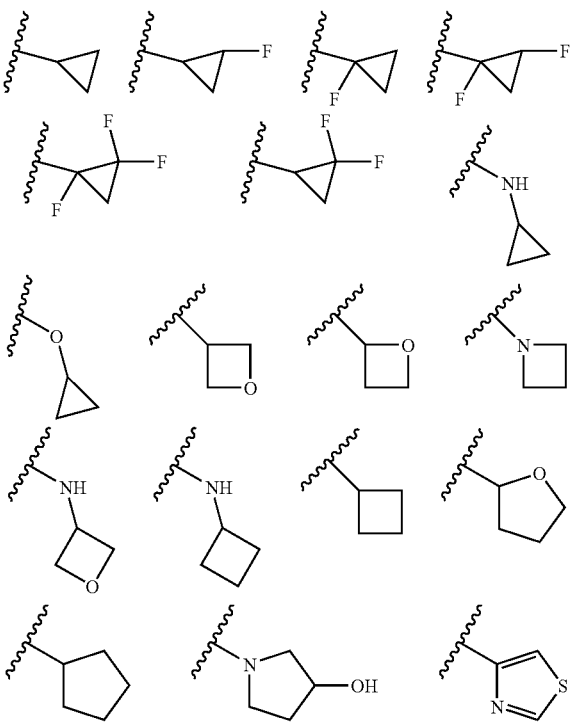

-continued

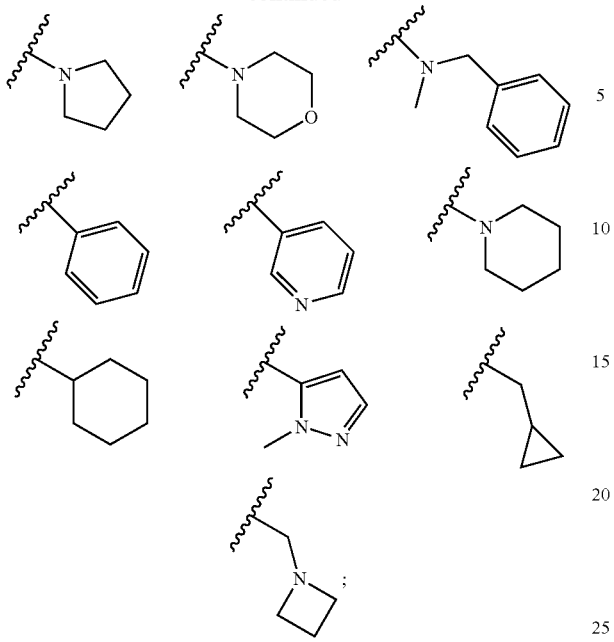

R⁹ is independently selected from F, Cl, Br, I, —CH₃, —CH₂CH₃, —CH₂CH₂CH₃, —CH(CH₃)₂, —CH₂CH(CH₃)₂, —CH₂OH, —CH₂CH₂OH, —CN, —CF₃, —CO₂H, —COCH₃, —CO₂CH₃, —CONH₂, —CONHCH₃, —CON(CH₃)₂, —NO₂, —NH₂, —NHCH₃, —NHCOCH₃, —NHS(O)₂CH₃, —OH, —OCH₃, —S(O)₂N(CH₃)₂, —SCH₃, —CH₂OCH₃, and —S(O)₂CH₃; and n is 0, 1, 2, 3, or 4;

R⁷ is selected from H, C₁-C₁₂ alkyl, C₂-C₈ alkenyl, C₂-C₈ alkynyl, —(C₁-C₁₂ alkylene)-(C₃-C₁₂ carbocyclyl), —(C₁-C₁₂ alkylene)-(C₂-C₂₀ heterocyclyl), —(C₁-C₁₂ alkylene)-C(=O)—(C₂-C₂₀ heterocyclyl), —(C₁-C₁₂ alkylene)-(C₆-C₂₀ aryl), and —(C₁-C₁₂ alkylene)—(C₁—C₂₀ heteroaryl), where alkyl, alkenyl, alkynyl, alkylene, carbocyclyl, heterocyclyl, aryl, and heteroaryl are optionally substituted with one or more groups independently selected from F, Cl, Br, I, —CH₃, —CH₂CH₃, —CH₂OH, —CN, —CF₃, —CO₂H, —COCH₃, —CO₂CH₃, —CONH₂, —CONHCH₃, —CON(CH₃)₂, —NO₂, —NH₂, —NHCH₃, —NHCOCH₃, —NHS(O)₂CH₃, =O, —OH, —OCH₃, —S(O)₂N(CH₃)₂, —SCH₃, —CH₂OCH₃, and —S(O)₂CH₃;

mor is a morpholine group or a bicyclic structure selected from:

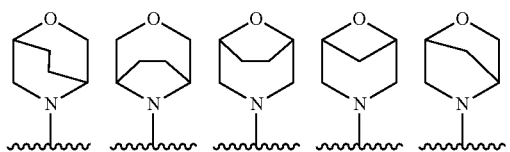

optionally substituted with one or more groups selected from F, Cl, Br, I, —CH₃, —CH₂CH₃, —CH₂CH₂CH₃, —CH(CH₃)₂, —C(CH₃)₃, —CH₂OCH₃, —CHF₂, —CN, —CF₃, —CH₂OH, —CH₂OCH₃, —CH₂CH₂OH, —CH₂C(CH₃)₂OH, —CH(CH₃)OH, —CH(CH₂CH₃)OH, —CH₂CH(OH)CH₃, —C(CH₃)₂OH, —C(CH₃)₂OCH₃, —CH(CH₃)F, —C(CH₃)F₂, —CH(CH₂CH₃)F, —C(CH₂CH₃)₂F, —CO₂H, —CONH₂, —CON(CH₂CH₃)₂, —COCH₃, —CON(CH₃)₂, —NO₂, —NH₂, —NHCH₃, —N(CH₃)₂, —NHCH₂CH₃, —NHCH(CH₃)₂, —NHCH₂CH₂OH, —NHCH₂CH₂OCH₃, —NHCOCH₃, —NHCOCH₂CH₃, —NHCOCH₂OH, —NHS(O)₂CH₃, —N(CH₃)S(O)₂CH₃, =O, —OH, —OCH₃, —OCH₂CH₃, —OCH(CH₃)₂, —SH, —NHC(=O)NHCH₃, —NHC(=O)NHCH₂CH₃, —S(O)CH₃, —S(O)CH₂CH₃, —S(O)₂CH₃, —S(O)₂NH₂, —S(O)₂NHCH₃, —S(O)₂N(CH₃)₂, —CH₂S(O)₂CH₃;

and wherein the IC50 binding activity to p110 delta is ten or more times lower than the binding activity to p110 alpha.

2. The compound of claim 1 selected from the structures:

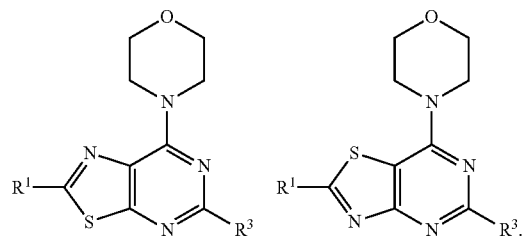

3. The compound of claim 1 selected from the structures:

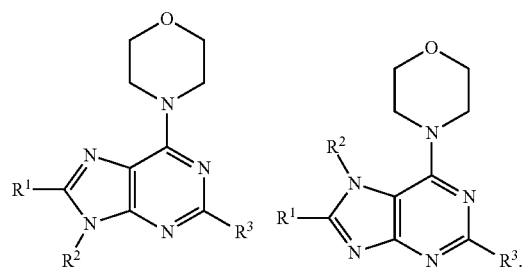

4. The compound of claim 1 selected from the structures:

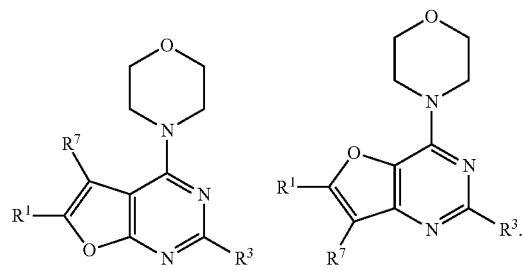

5. The compound of claim 1 wherein R¹ is selected from the structures

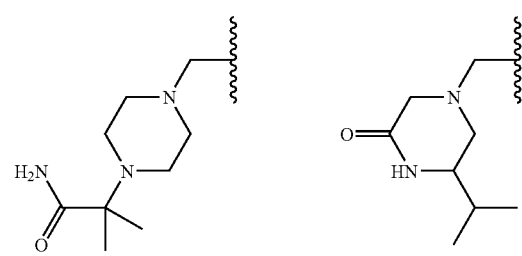

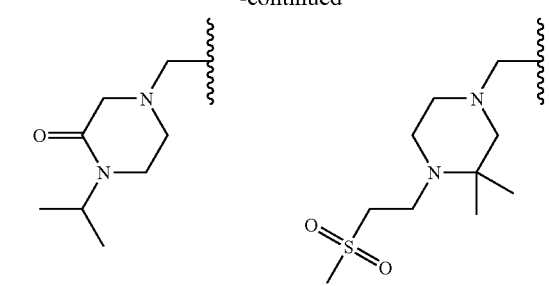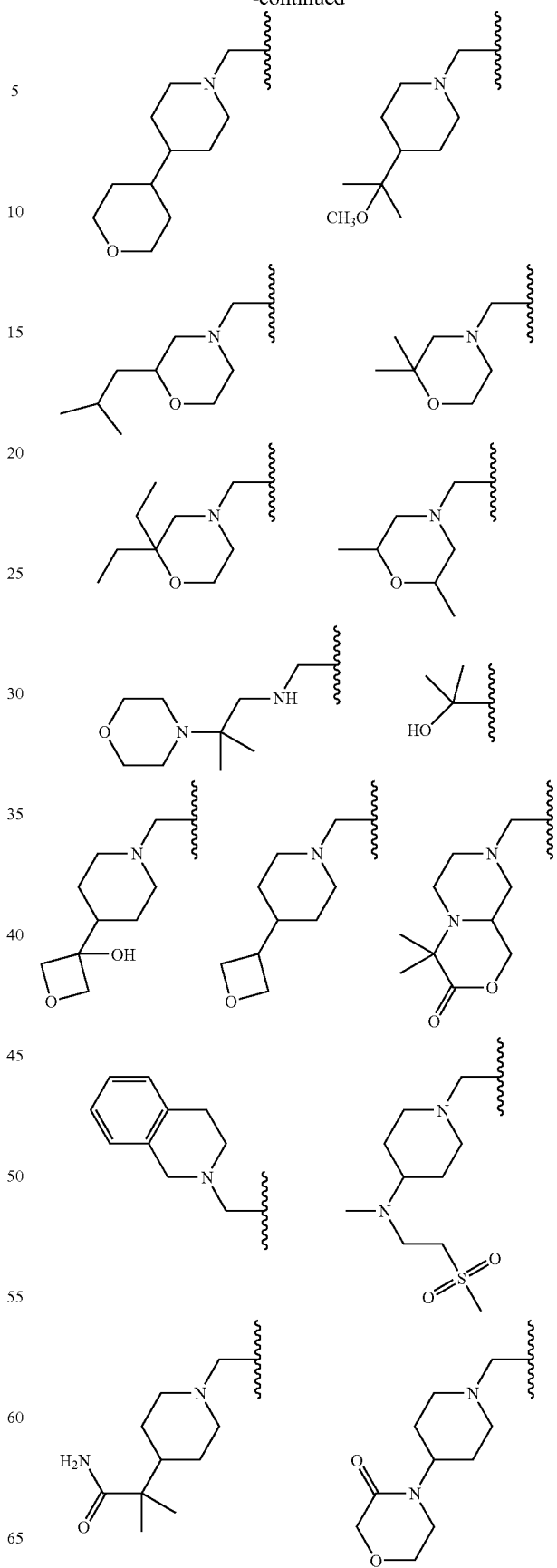

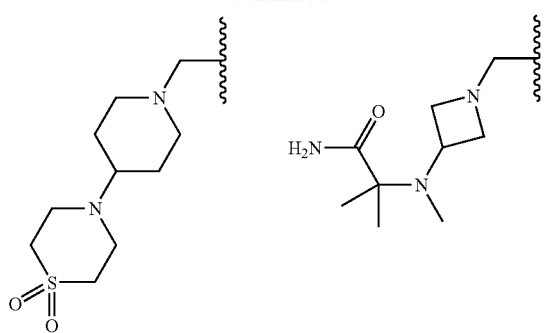
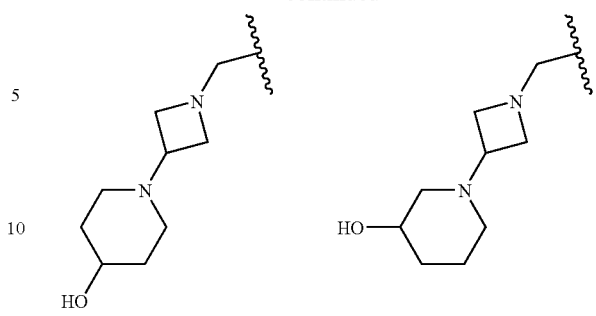
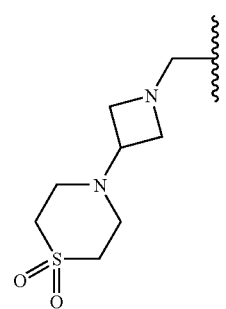
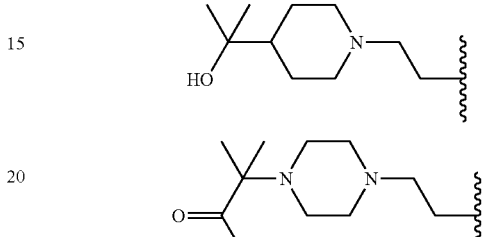
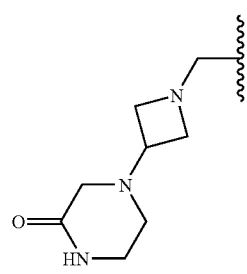
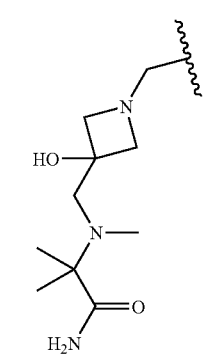
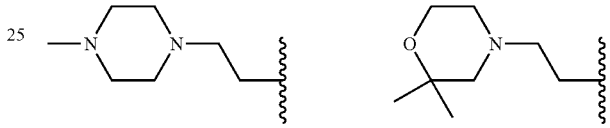
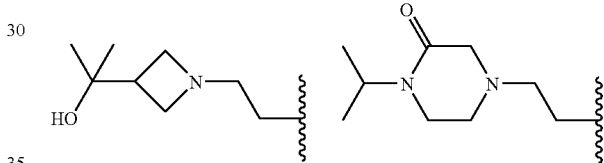
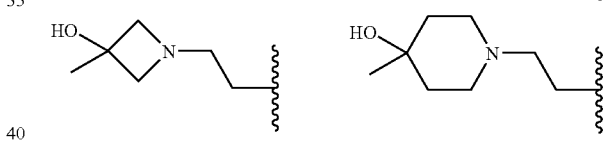
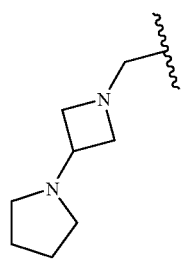
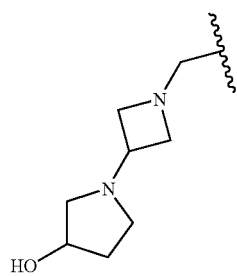
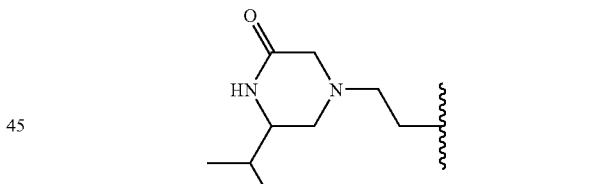
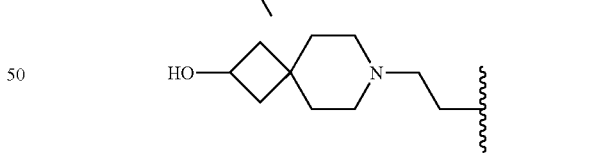
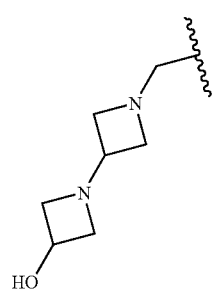
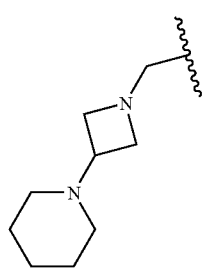
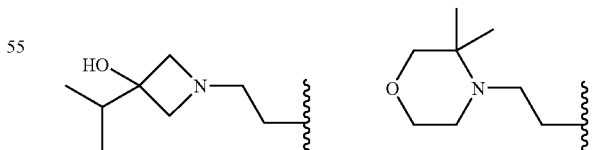
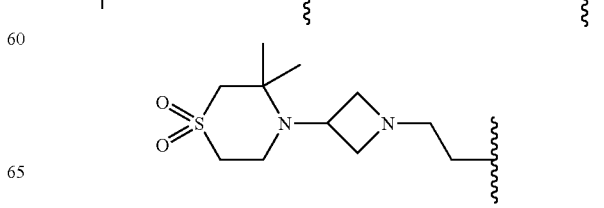

US 8,173,650 B2
831
-continued
832
-continued
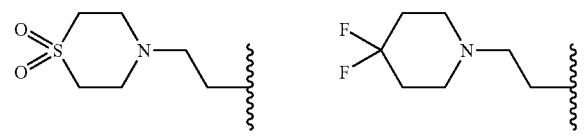
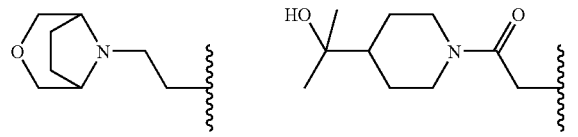
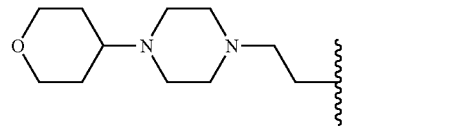
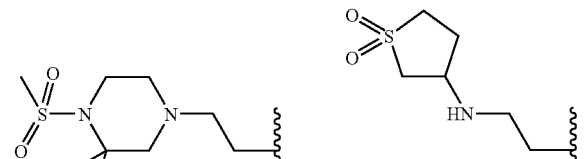
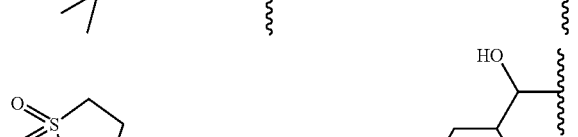
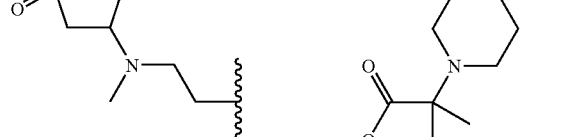
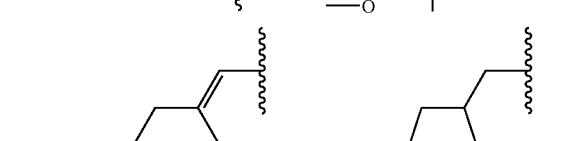
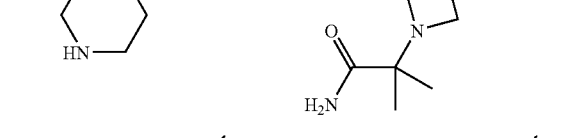
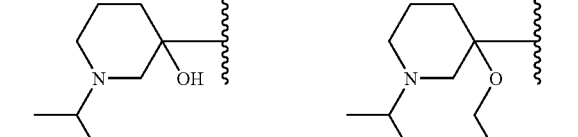
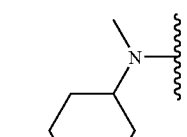
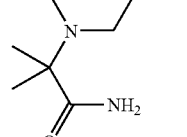
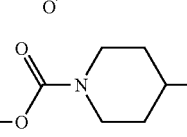
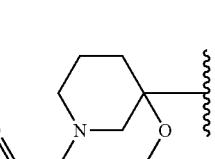
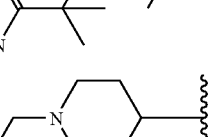
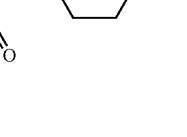
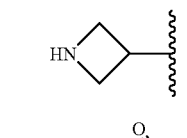
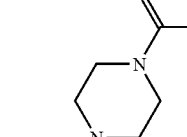
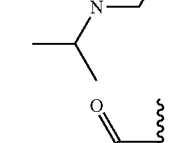
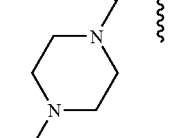
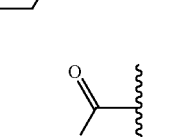
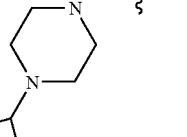

833
-continued
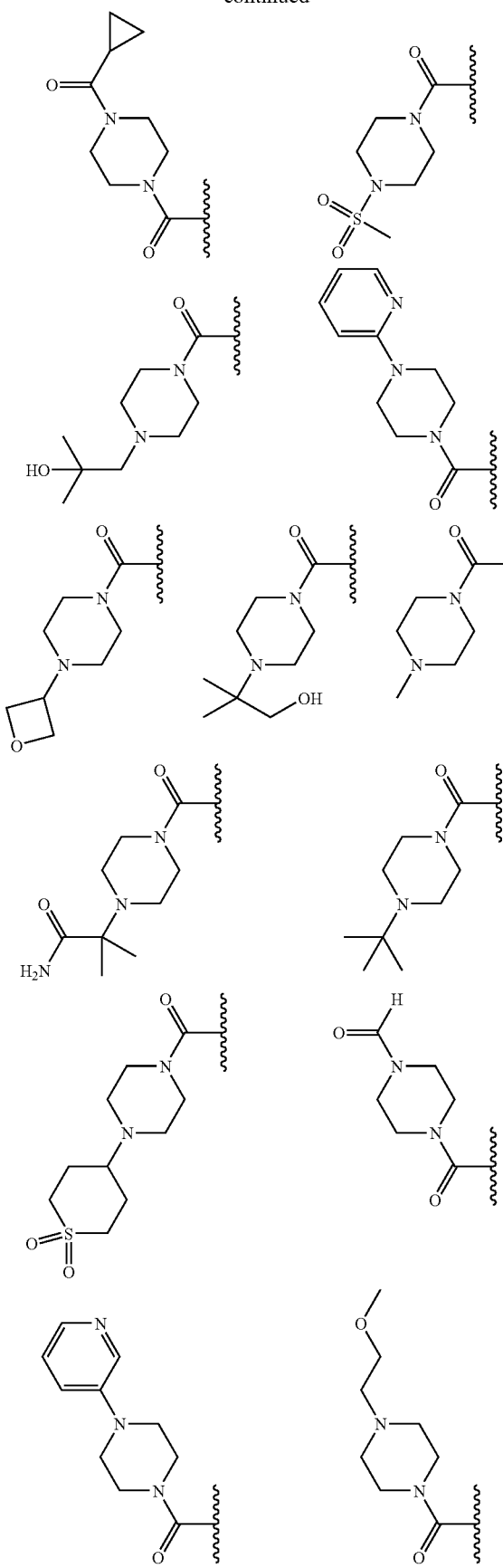
834
-continued
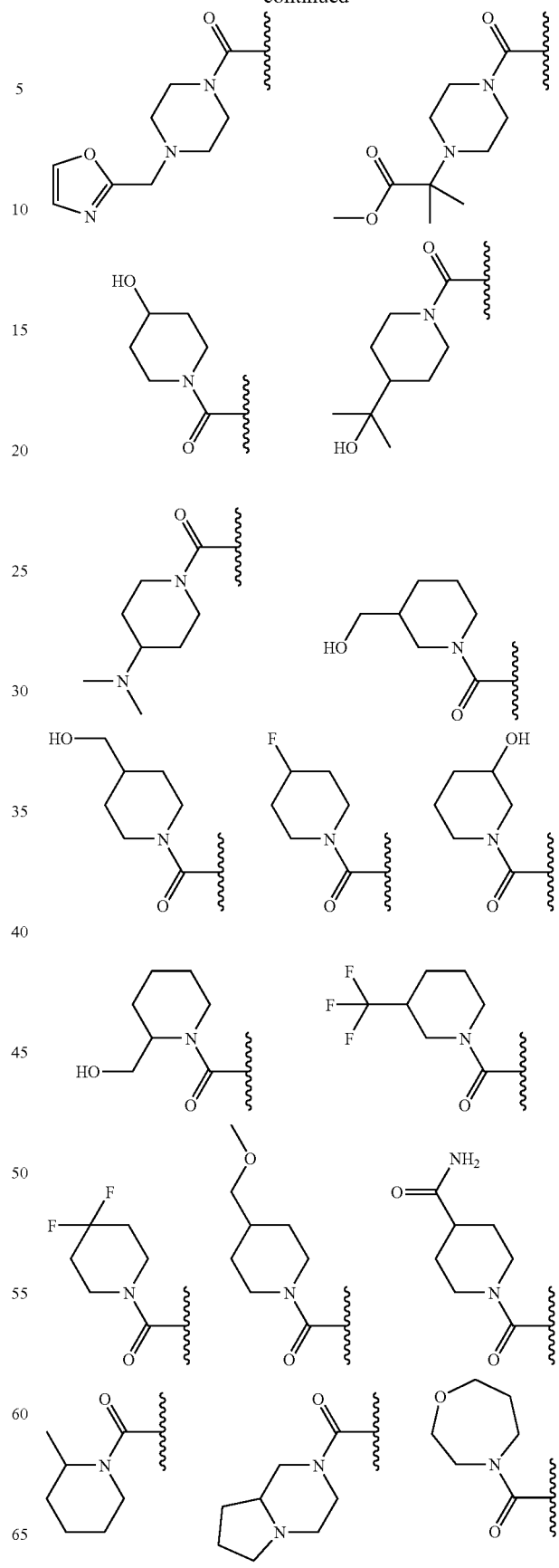

835
-continued
836
-continued
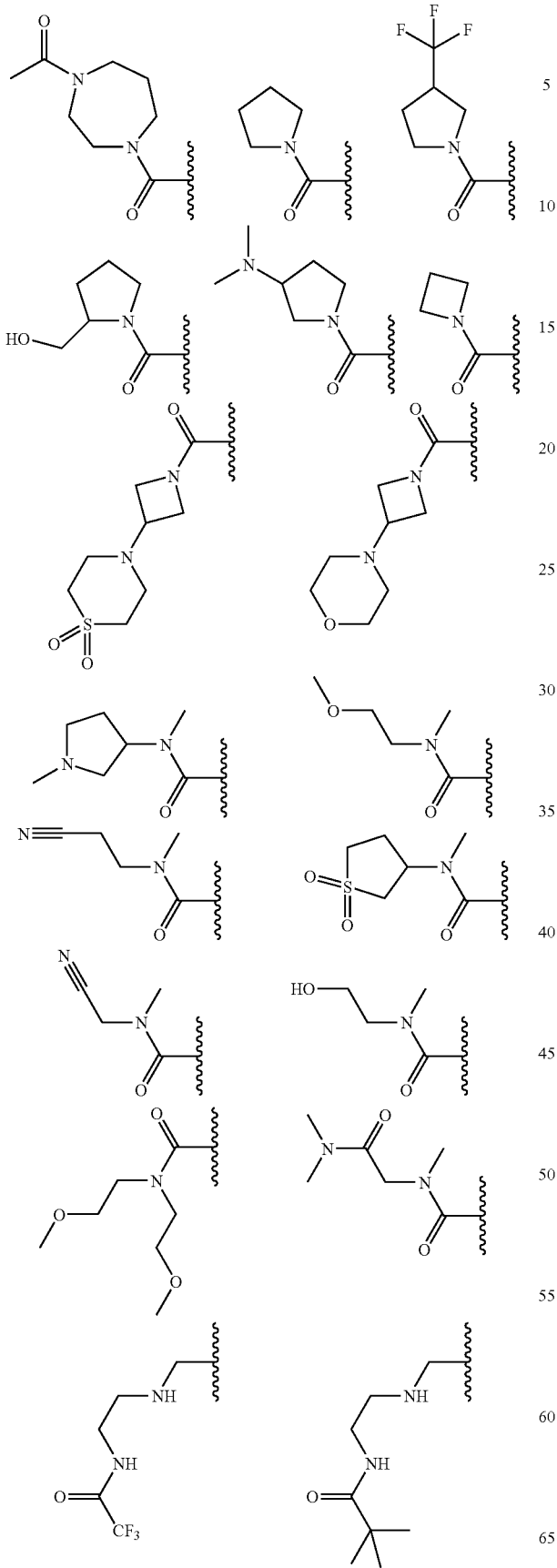
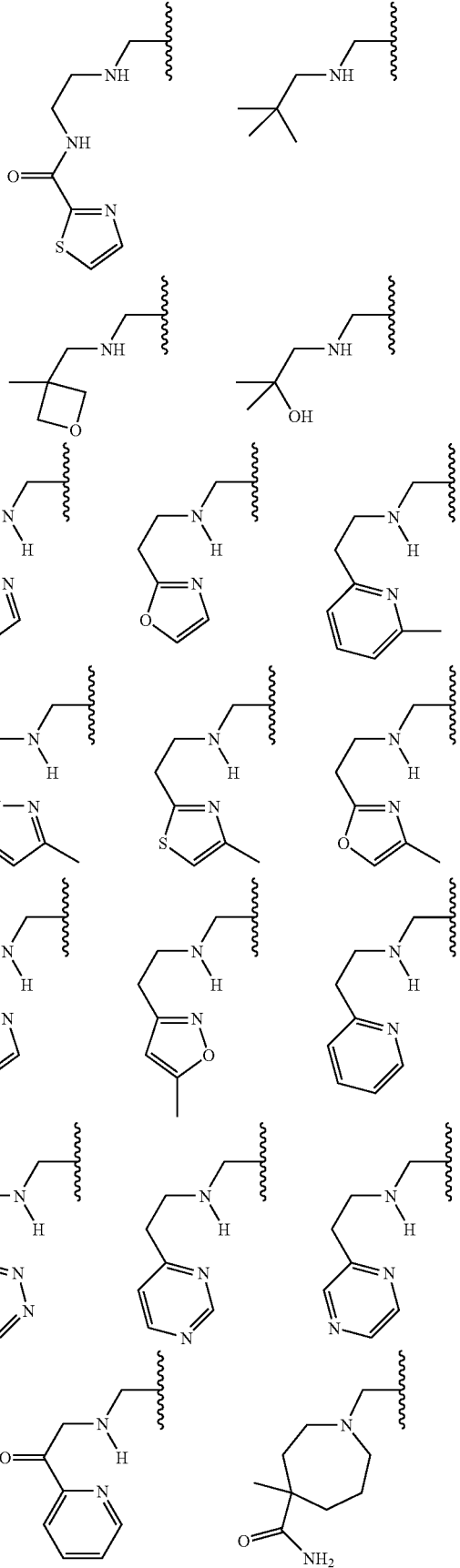

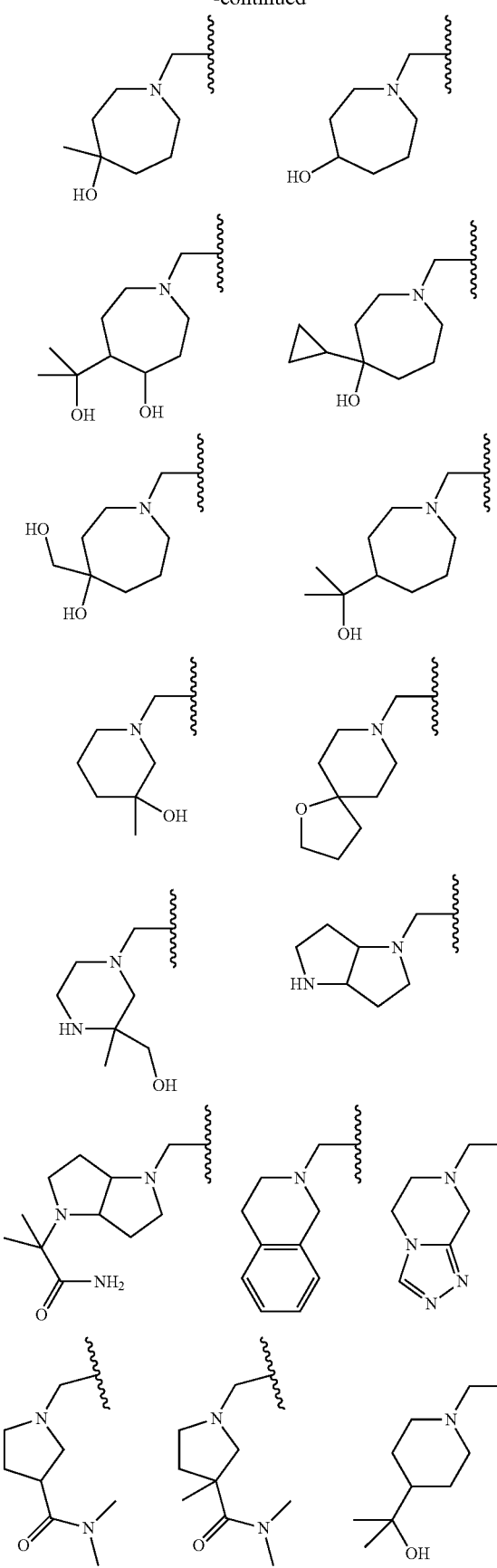
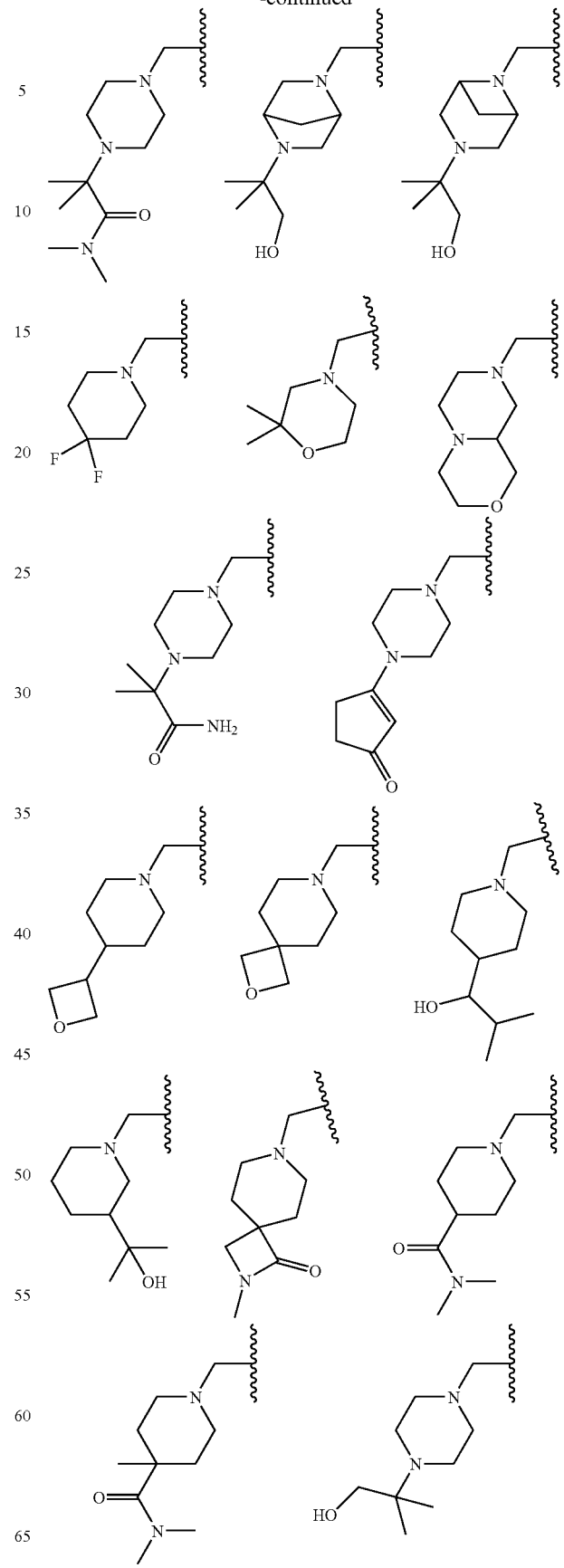

839
-continued
840
-continued
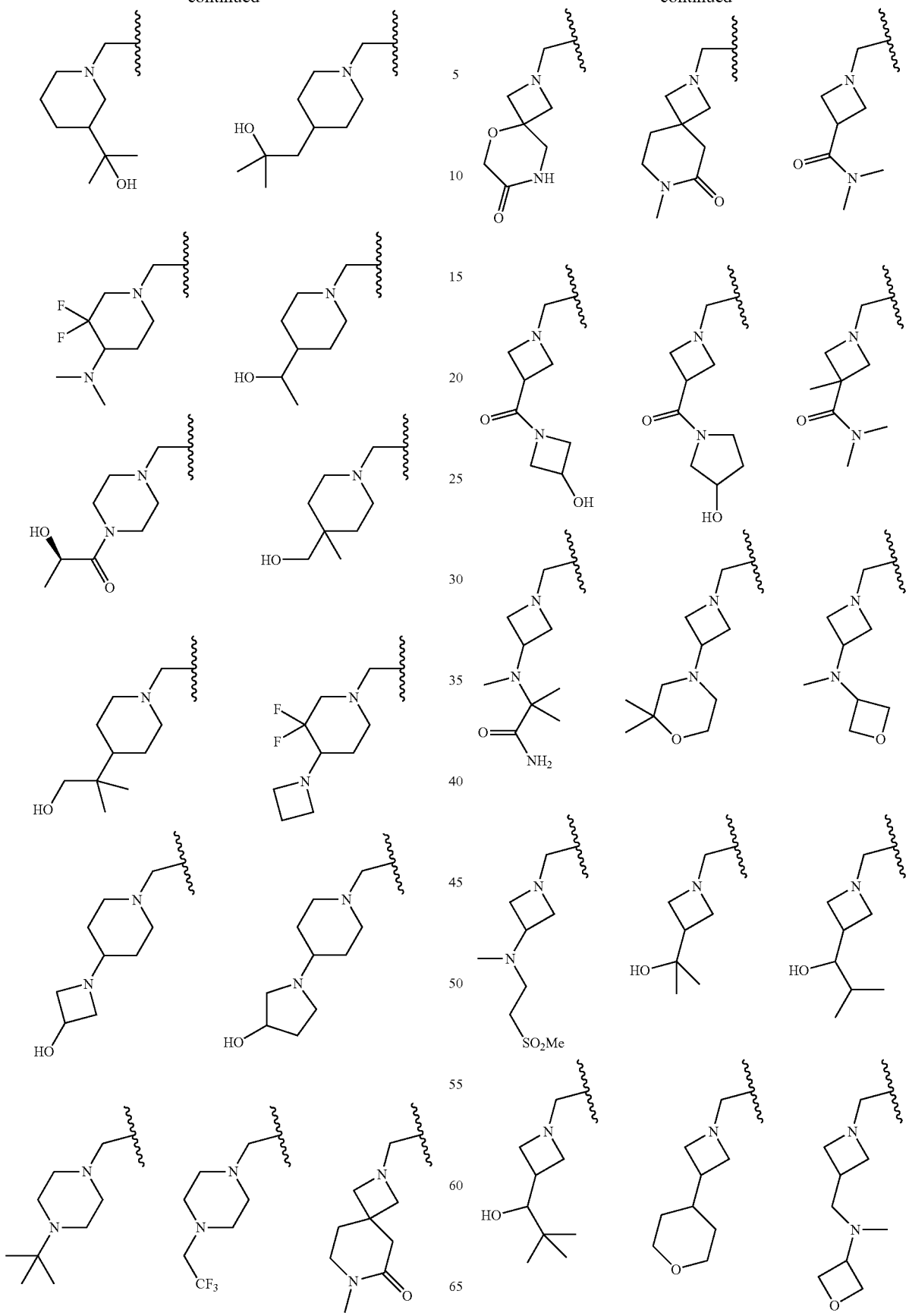

841
-continued

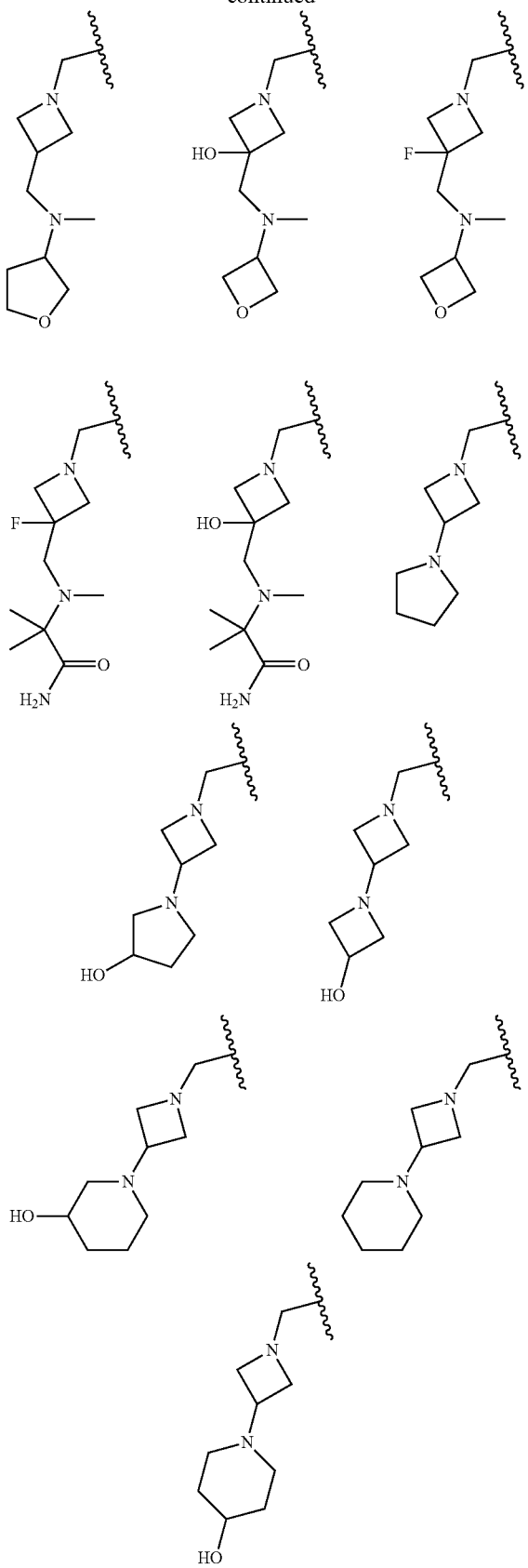

where the wavy line indicates the site of attachment.

6. The compound of claim 1 wherein $R^2$ is $C_1$-$C_{12}$ alkyl optionally substituted with one or more groups independently selected from F, Cl, Br, I, —$CH_3$, —$CH_2OH$, —CN, —$CF_3$, —$CO_2H$, —$COCH_3$, —$CO_2CH_3$, —$CONH_2$, —$CONHCH_3$, —$CON(CH_3)_2$, —$NO_2$, $NH_2$, —$NHCH_3$, —$NHCOCH_3$, —$NHS(O)_2CH_3$, —OH, —$OCH_3$, —$S(O)_2N(CH_3)_2$, —$SCH_3$, —$CH_2OCH_3$, and —$S(O)_2CH_3$.

7. The compound of claim 6 wherein $R^2$ is $CH_3$.

8. The compound of claim 1 having the structures:

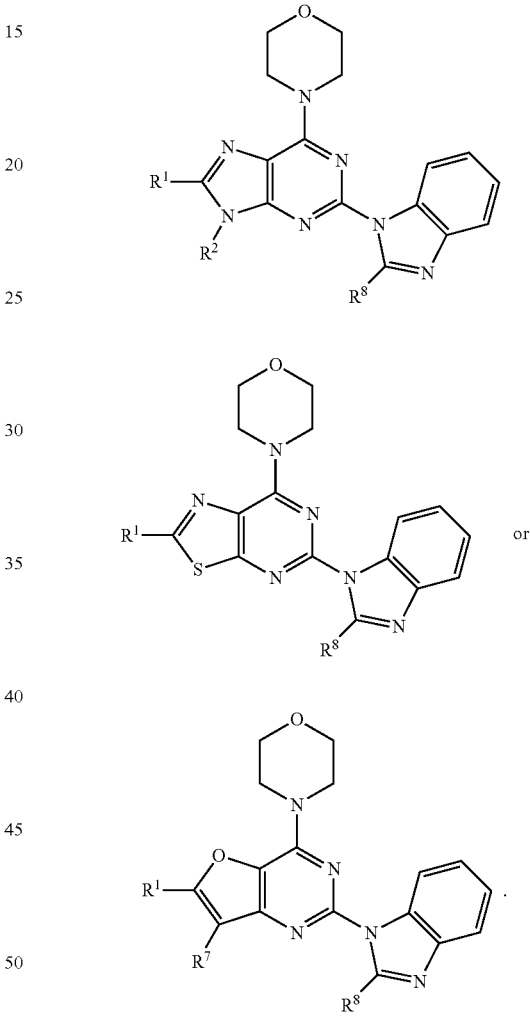

9. The compound of claim 1 wherein $R^7$ is H.

10. The compound of claim 1 wherein $R^7$ is $C_1$-$C_{12}$ alkyl optionally substituted with one or more groups independently selected from F, Cl, Br, I, —$CH_3$, —$CH_2OH$, —CN, —$CF_3$, —$CO_2H$, —$COCH_3$, —$CO_2CH_3$, —$CONH_2$, —$CONHCH_3$, —$CON(CH_3)_2$, —$NO_2$, —$NH_2$, —$NHCH_3$, —$NHCOCH_3$, —$NHS(O)_2CH_3$, —OH, —$OCH_3$, —$S(O)_2N(CH_3)_2$, —$SCH_3$, —$CH_2OCH_3$, and —$S(O)_2CH_3$.

11. The compound of claim 10 wherein $R^7$ is $CH_3$.

12. A compound having the structure:

and stereoisomers, tautomers, or pharmaceutically acceptable salts thereof, wherein:

$R^1$ is selected from
$C_6$-$C_{20}$ aryl,
$C_2$-$C_{20}$ heterocyclyl,
$C_3$-$C_{12}$ carbocyclyl,
$C_1$-$C_{20}$ heteroaryl,
—($C_1$-$C_{12}$ alkylene)-($C_3$-$C_{12}$ carbocyclyl),
—($C_1$-$C_{12}$ alkylene)-($C_2$-$C_{20}$ heterocyclyl),
—($C_1$-$C_{12}$ alkylene)-($C_2$-$C_{20}$ heterocyclyl)-($C_2$-$C_{20}$ heterocyclyl),
—($C_1$-$C_{12}$ alkylene)-($C_2$-$C_{20}$ heterocyclyl)-($C_3$-$C_{12}$ carbocyclyl),
—($C_1$-$C_{12}$ alkylene)-($C_2$-$C_{20}$ heterocyclyl)-C(=O)—($C_2$-$C_{20}$ heterocyclyl),
—($C_1$-$C_{12}$ alkylene)-($C_1$-$C_{20}$ heteroaryl),
—($C_1$-$C_{12}$ alkylene)-($C_2$-$C_{20}$ heterocyclyl)-($C_1$-$C_{12}$ alkyl),
—($C_1$-$C_{12}$ alkylene)-($C_6$-$C_{20}$ aryl)-($C_1$-$C_{12}$ alkyl),
—($C_1$-$C_{12}$ alkylene)-($C_1$-$C_{20}$ heteroaryl)-($C_1$-$C_{12}$ alkyl),
—($C_1$-$C_{12}$ alkylene)-C(=O)—($C_2$-$C_{20}$ heterocyclyl),
—($C_1$-$C_{12}$ alkylene)-NHR$^{2'}$,
—($C_1$-$C_{12}$ alkylene)-NR$^{2'}$—($C_1$-$C_{12}$ alkyl),
—($C_1$-$C_{12}$ alkylene)-NR$^{2'}$—($C_3$-$C_{12}$ carbocyclyl),
—($C_1$-$C_{12}$ alkylene)-NR$^{2'}$—($C_2$-$C_{20}$ heterocyclyl),
—($C_1$-$C_{12}$ alkylene)-NR$^{2'}$—($C_1$-$C_{20}$ heteroaryl),
—($C_1$-$C_{12}$ alkylene)-NR$^{2'}$—($C_6$-$C_{20}$ aryl),
—($C_1$-$C_{12}$ alkylene)-NR$^{2'}$—($C_1$-$C_{12}$ alkylene)-($C_3$-$C_{12}$ carbocyclyl),
—($C_1$-$C_{12}$ alkylene)-NR$^{2'}$—($C_1$-$C_{12}$ alkylene)-($C_1$-$C_{20}$ heteroaryl),
—($C_1$-$C_{12}$ alkylene)-NR$^{2'}$—($C_1$-$C_{12}$ alkylene)-($C_1$-$C_{20}$ heterocyclyl),
—($C_1$-$C_{12}$ alkylene)-NR$^{2'}$—($C_1$-$C_{12}$ alkylene)-($C_6$-$C_{20}$ aryl),
—($C_1$-$C_{12}$ alkylene)-NR$^{2'}$—($C_1$-$C_{12}$ alkylene)-NHC(=O)—($C_1$-$C_{20}$ heteroaryl),
—($C_1$-$C_{12}$ alkylene)-($C_2$-$C_{20}$ heterocyclyl)-N($C_1$-$C_{12}$ alkyl)R$^{2'}$,
—($C_1$-$C_{12}$ alkylene)-($C_2$-$C_{20}$ heterocyclyl)-($C_1$-$C_{12}$ alkyl)-N($C_1$-$C_{12}$ alkyl)R$^{2'}$,
—($C_2$-$C_{12}$ alkenylene)-($C_2$-$C_{20}$ heterocyclyl),
—($C_1$-$C_{20}$ heteroaryl)-($C_2$-$C_{20}$ heterocyclyl),
—($C_1$-$C_{20}$ heteroaryl)-($C_3$-$C_{12}$ carbocyclyl),
—C(=O)—($C_2$-$C_{20}$ heterocyclyl),
—C(=O)—($C_1$-$C_{20}$ heteroaryl),
—C(=O)—($C_2$-$C_{20}$ heterocyclyl)-($C_2$-$C_{20}$ heterocyclyl),
—C(=O)—($C_2$-$C_{20}$ heterocyclyl)-($C_1$-$C_{20}$ heteroaryl),
—C(=O)—C($C_1$-$C_{12}$ alkyl),
—C(=O)—NR$^{2'}$—($C_1$-$C_{12}$ alkyl), and
—CR$^4$=CR$^5$R$^6$ where R$^4$ is selected from H, F, Cl, Br, I and $C_1$-$C_{12}$ alkyl, and R$^5$ and R$^6$ form $C_2$-$C_{20}$ heterocyclyl, $C_1$-$C_{20}$ heteroaryl, or $C_3$-$C_{12}$ carbocyclyl, where alkyl, alkenyl, alkynyl, alkylene, carbocyclyl, heterocyclyl, aryl, and heteroaryl are optionally substituted with one or more groups independently selected from F, Cl, Br, I, —CH$_3$, —CH$_2$CH$_3$, —CH$_2$CH(CH$_3$)$_2$, —CH$_2$NH$_2$, —CH$_2$N(CH$_3$)$_2$, —CH$_2$CH$_2$NH$_2$, —CH$_2$CH$_2$N(CH$_3$)$_2$, —CH$_2$OH, —CH$_2$OH, —CH$_2$OCH$_3$, —CH$_2$CH$_2$OH, —C(CH$_3$)$_2$OH, —CH$_2$C(CH$_3$)$_2$OH, —CH(OH)CH(CH$_3$)$_2$, —C(CH$_3$)$_2$CH$_2$OH, —CH$_2$CH$_2$SO$_2$CH$_3$, —CN, —CF$_3$, —CO$_2$H, —CHO, —COCH$_3$, —CO$_2$CH$_3$, —CO$_2$C(CH$_3$)$_3$, —COCH$_2$OH, —COC(OH)(CH$_3$)$_2$, —COCH(OH)CH$_3$, —CONH$_2$, —CONHCH$_3$, —CON(CH$_3$)$_2$, —CH$_2$CONH$_2$, —CH$_2$CON(CH$_3$)$_2$, —C(CH$_3$)$_2$CONH$_2$, —NO$_2$, —NH$_2$, —NHCH$_3$, —N(CH$_3$)$_2$, —NHCOCH$_3$, —N(CH$_3$)COCH$_3$, —NHS(O)$_2$CH$_3$, —N(CH$_3$)C(CH$_3$)$_2$CONH$_2$, —N(CH$_3$)CH$_2$CH$_2$S(O)$_2$CH$_3$, =O, —OH, —OCH$_3$, —S(O)$_2$N(CH$_3$)$_2$, —CH$_3$, —CH$_2$OCH$_3$, —S(O)$_2$CH$_3$, —C(O)-cyclopropyl, cyclopropyl, cyclobutyl, oxetanyl, and morpholino;

$R^2$ and $R^{2'}$ are independently selected from H, $C_1$-$C_{12}$ alkyl, $C_2$-$C_8$ alkenyl, $C_2$-$C_8$ alkynyl, —($C_1$-$C_{12}$ alkylene)-($C_3$-$C_{12}$ carbocyclyl), —($C_1$-$C_{12}$ alkylene)-($C_2$-$C_{20}$ heterocyclyl), —($C_1$-$C_{12}$ alkylene)-C(=O)—($C_2$-$C_{20}$ heterocyclyl), —($C_1$-$C_{12}$ alkylene)-($C_6$-$C_{20}$ aryl), and —($C_1$-$C_{12}$ alkylene)-($C_1$-$C_{20}$ heteroaryl), where alkyl, alkenyl, alkynyl, alkylene, carbocyclyl, heterocyclyl, aryl, and heteroaryl are optionally substituted with one or more groups independently selected from F, Cl, Br, I, —CH$_3$, —CH$_2$OH, —CN, —CF$_3$, —CO$_2$H, —COCH$_3$, —COC(CH$_3$)$_3$, —COCF$_3$, —CO$_2$CH$_3$, —CONH$_2$, —CONHCH$_3$, —CON(CH$_3$)$_2$, —NO$_2$, —NH$_2$, —NHCH$_3$, —NHCOCH$_3$, —NHS(O)$_2$CH$_3$, —OH, —OCH$_3$, —S(O)$_2$N(CH$_3$)$_2$, —SCH$_3$, —CH$_2$OCH$_3$, and —S(O)$_2$CH$_3$;

$R^8$ is selected from H, F, Cl, Br, I, —CH$_3$, —CH$_2$CH$_3$, —CH$_2$CH$_2$CH$_3$, —CH(CH$_3$)$_2$, —C(CH$_3$)$_3$, —CH$_2$OCH$_3$, —CHF$_2$, —CN, —CF$_3$, —CH$_2$OH, —CH$_2$OCH$_3$, —CH$_2$CH$_2$OH, —CH$_2$C(CH$_3$)$_2$OH, —CH(CH$_3$)OH, —CH(CH$_2$CH$_3$)OH, —CH$_2$CH(OH)CH$_3$, —CH$_2$CH(OCH$_3$)CH$_3$, —C(CH$_3$)$_2$OH, —C(CH$_3$)$_2$OCH$_3$, —CH(CH$_3$)F, —C(CH$_3$)F$_2$, —CH(CH$_2$CH$_3$)F, —C(CH$_2$CH$_3$)$_2$F, —CO$_2$H, —CONH$_2$, —CON(CH$_2$CH$_3$)$_2$, —COCH$_3$, —CON(CH$_3$)$_2$, —NO$_2$, —NH$_2$, —NHCH$_3$, —N(CH$_3$)$_2$, —NHCH$_2$CH$_3$, —NHCH(CH$_3$)$_2$, —NHCH$_2$CH$_2$OH, —NHCH$_2$CH$_2$OCH$_3$, —NHCOCH$_3$, —NHCOCH$_2$CH$_3$, —NHCOCH$_2$OH, —NHS(O)$_2$CH$_3$, —N(CH$_3$)S(O)$_2$CH$_3$, =O, —OH, —OCH$_3$, —OCH$_2$CH$_3$, —OCH(CH$_3$)$_2$, —SH, —NHC(=O)NHCH$_3$, —NHC(=O)NHCH$_2$CH$_3$, —S(O)CH$_3$, —S(O)CH$_2$CH$_3$, —S(O)$_2$CH$_3$, —S(O)$_2$NH$_2$, —S(O)$_2$NHCH$_3$, —S(O)$_2$N(CH$_3$)$_2$, —CH$_2$S(O)$_2$CH$_3$, and a group selected from -continued
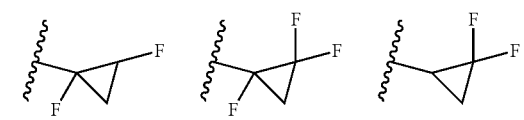
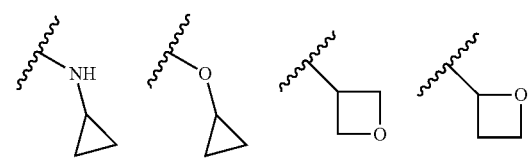
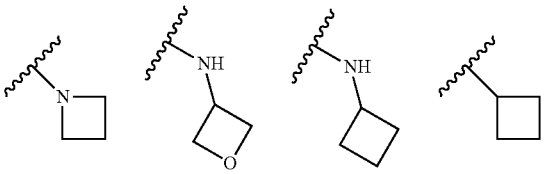
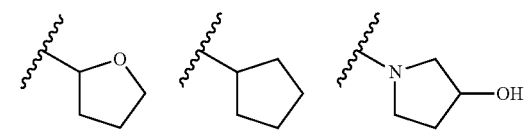
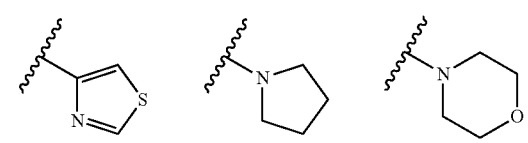
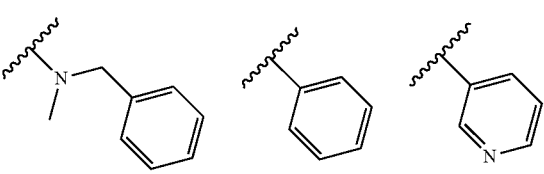
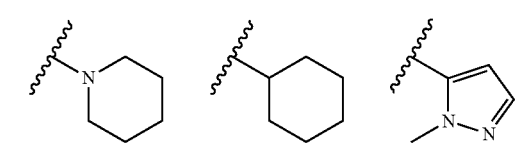
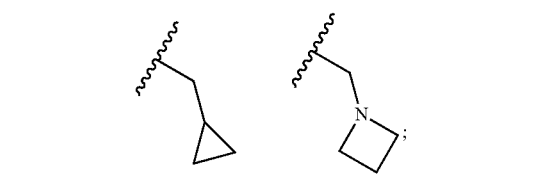
R$^9$ is independently selected from F, Cl, Br, I, —CH$_3$, —CH$_2$CH$_3$, —CH$_2$CH$_2$CH$_3$, —CH(CH$_3$)$_2$, —CH$_2$CH(CH$_3$)$_2$, —CH$_2$OH, —CH$_2$CH$_2$OH, —CN, —CF$_3$, —CO$_2$H, —COCH$_3$, —CO$_2$CH$_3$, —CONH$_2$, —CONHCH$_3$, —CON(CH$_3$)$_2$, —NO$_2$, —NH$_2$, —NHCH$_3$, —NHCOCH$_3$, —NHS(O)$_2$CH$_3$, —OH, —OCH$_3$, —S(O)$_2$N(CH$_3$)$_2$, —SCH$_3$, —CH$_2$OCH$_3$, and —S(O)$_2$CH$_3$; and
n is 0, 1, 2, 3, or 4.
13. The compound of claim 1 wherein R$^1$ is selected from the structures
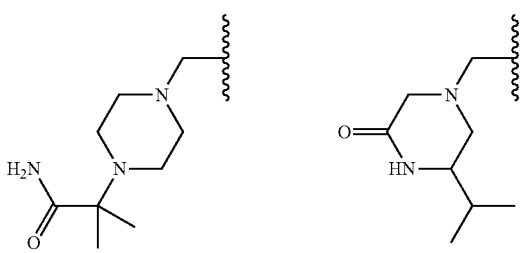
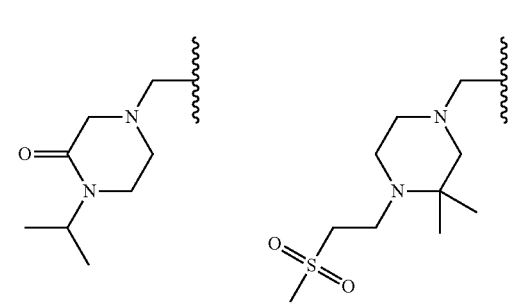
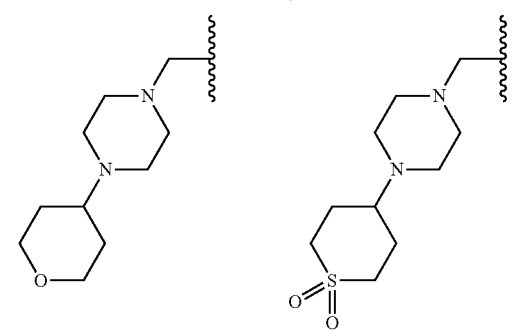
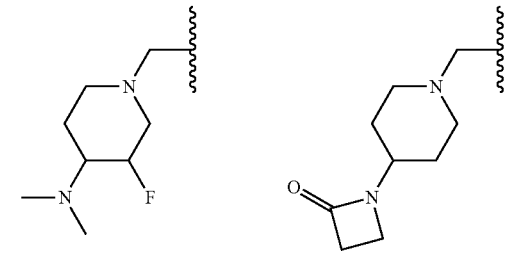
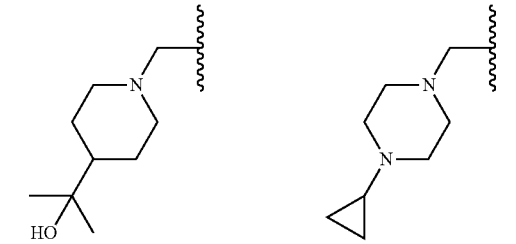
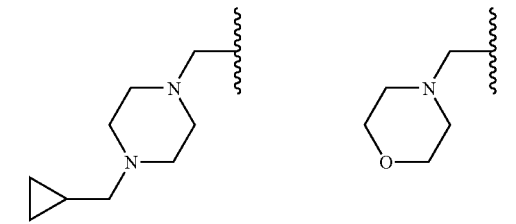

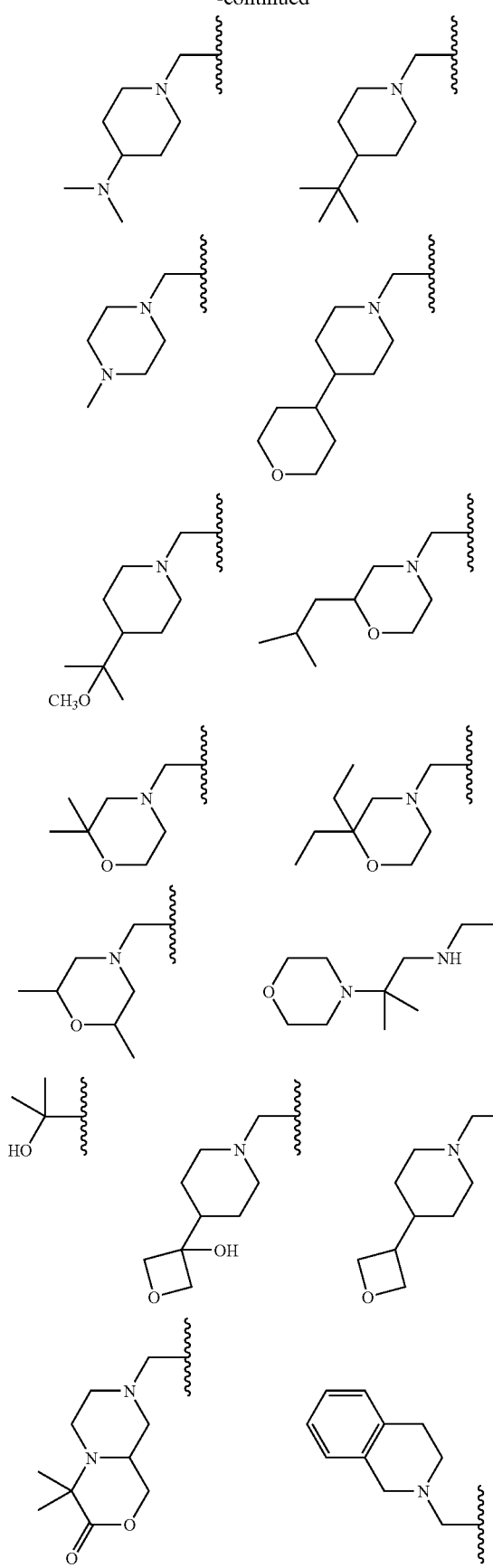
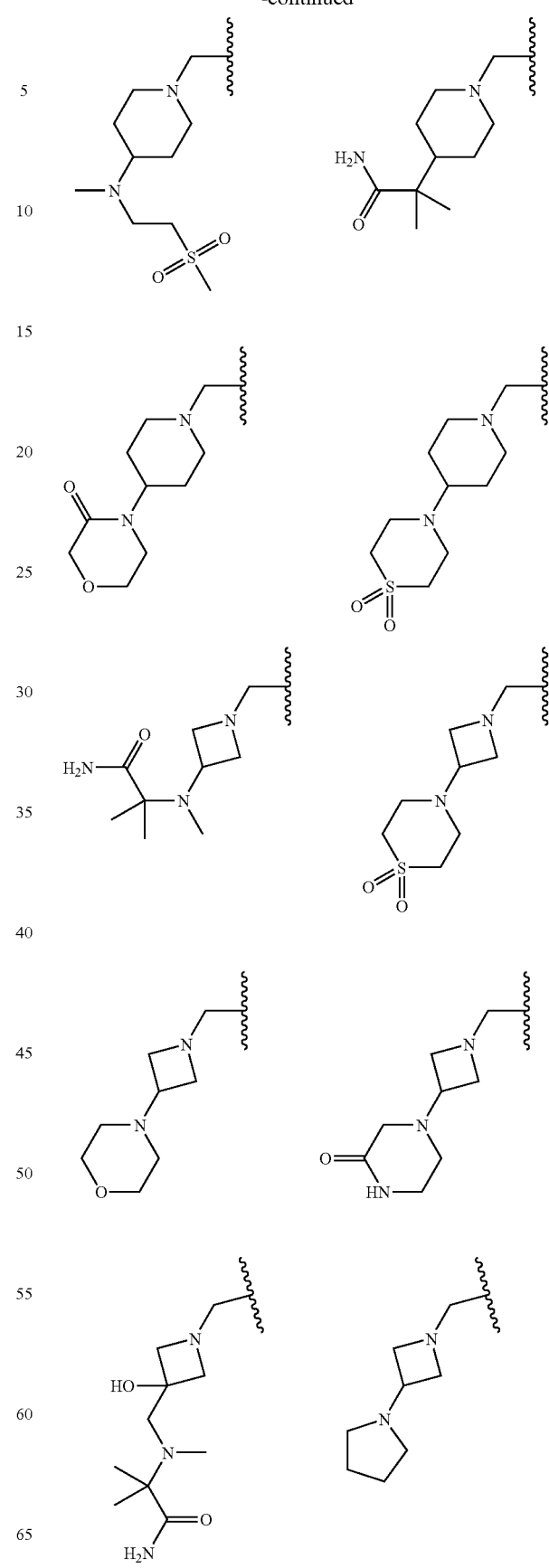

849
-continued
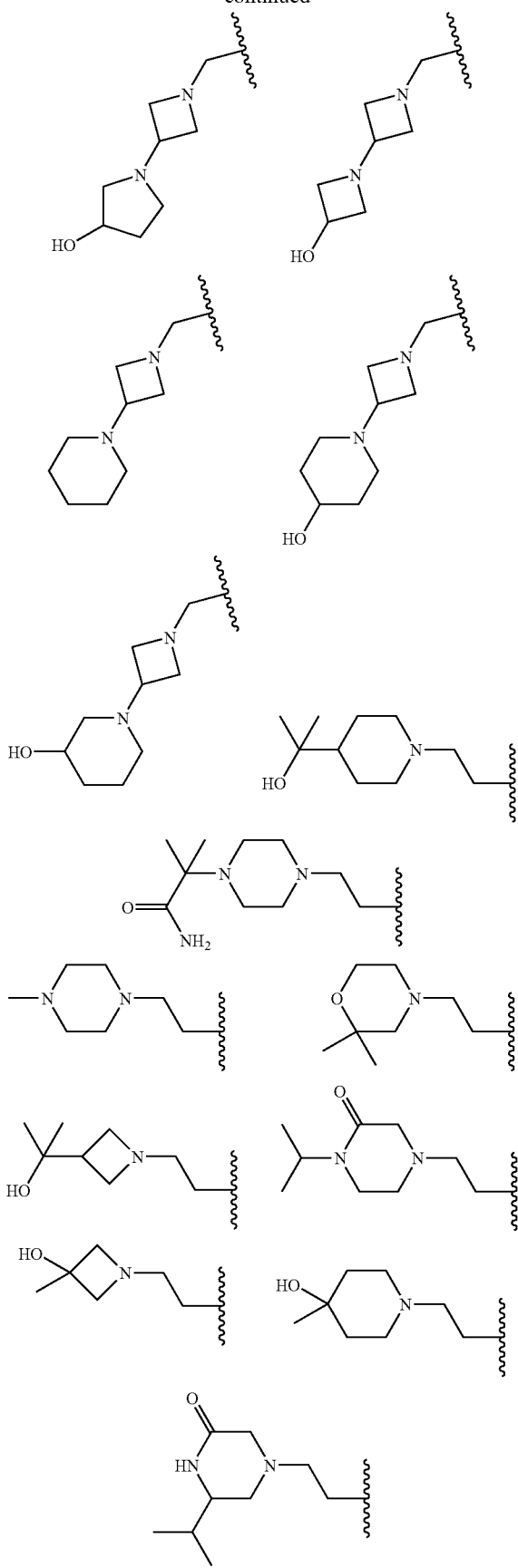
850
-continued
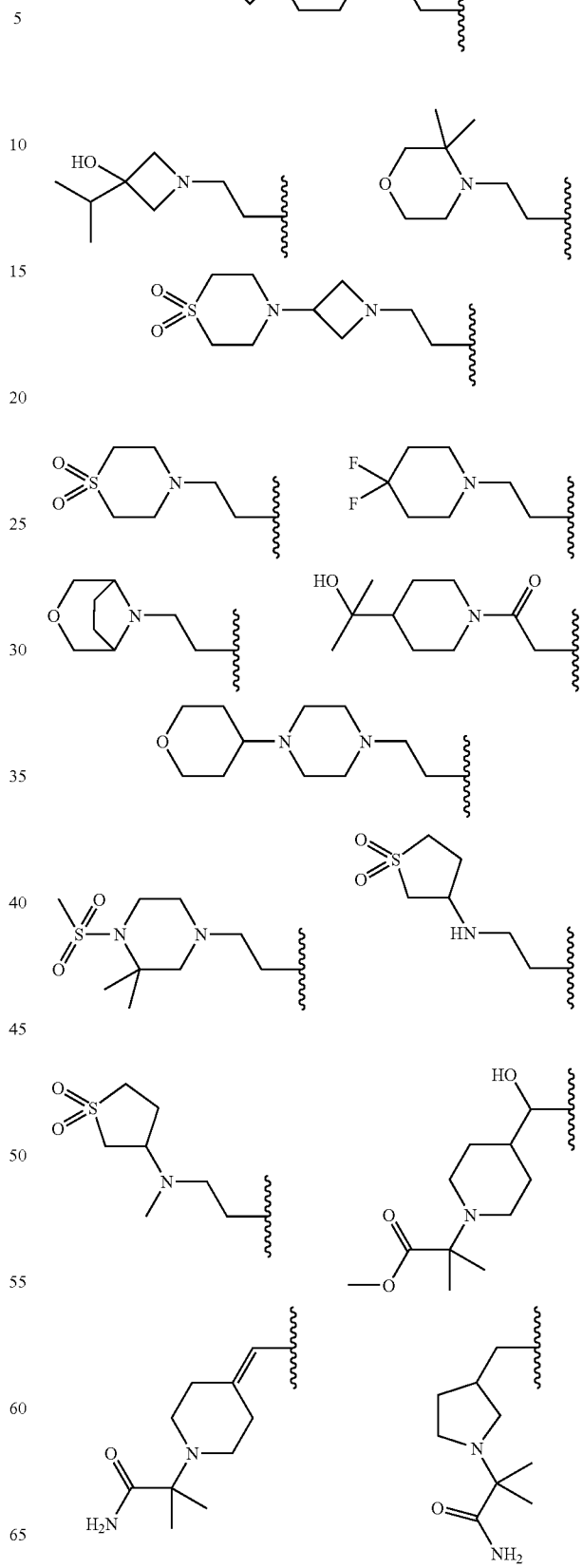

851
-continued
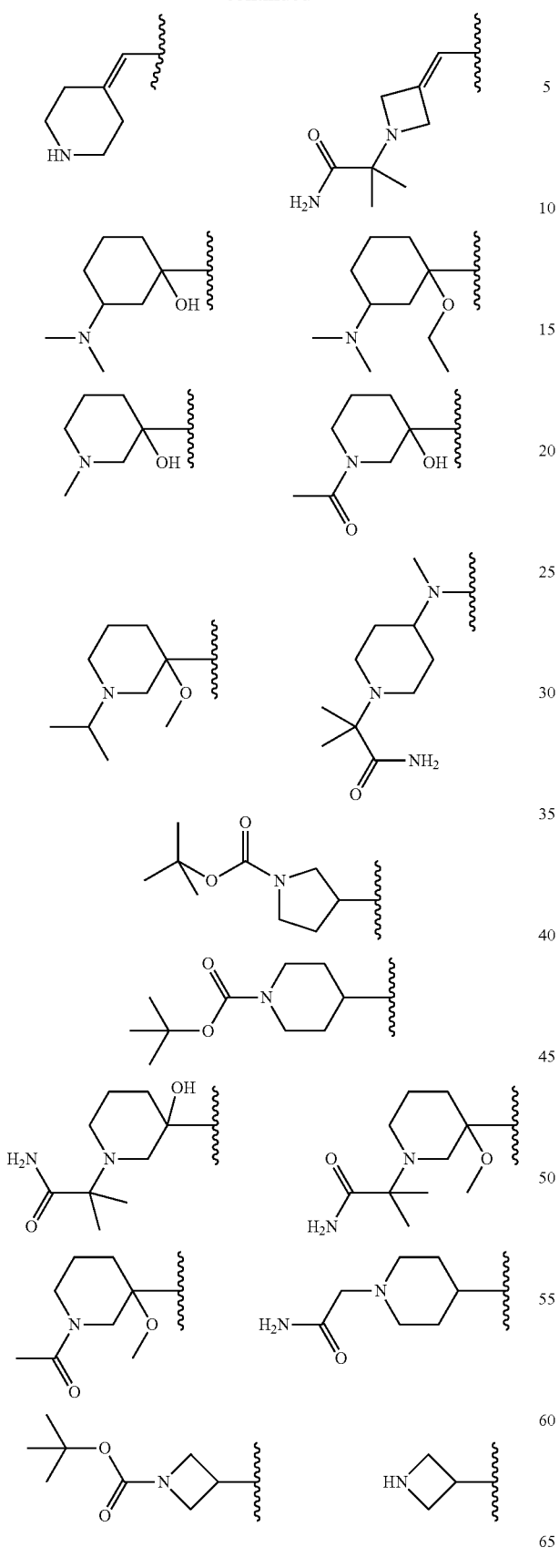
852
-continued
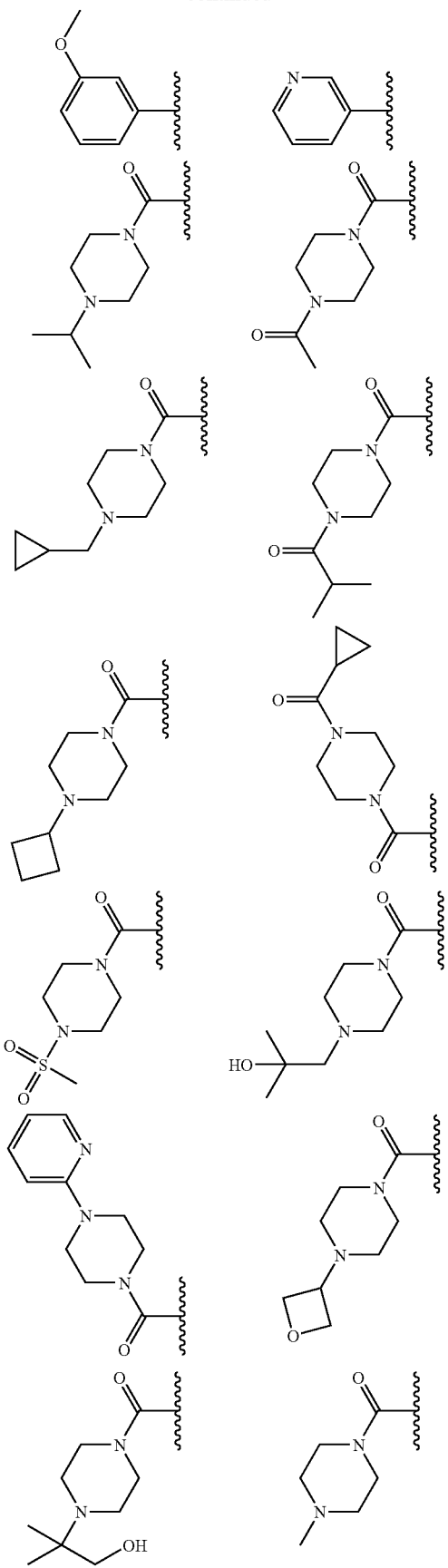

853
-continued
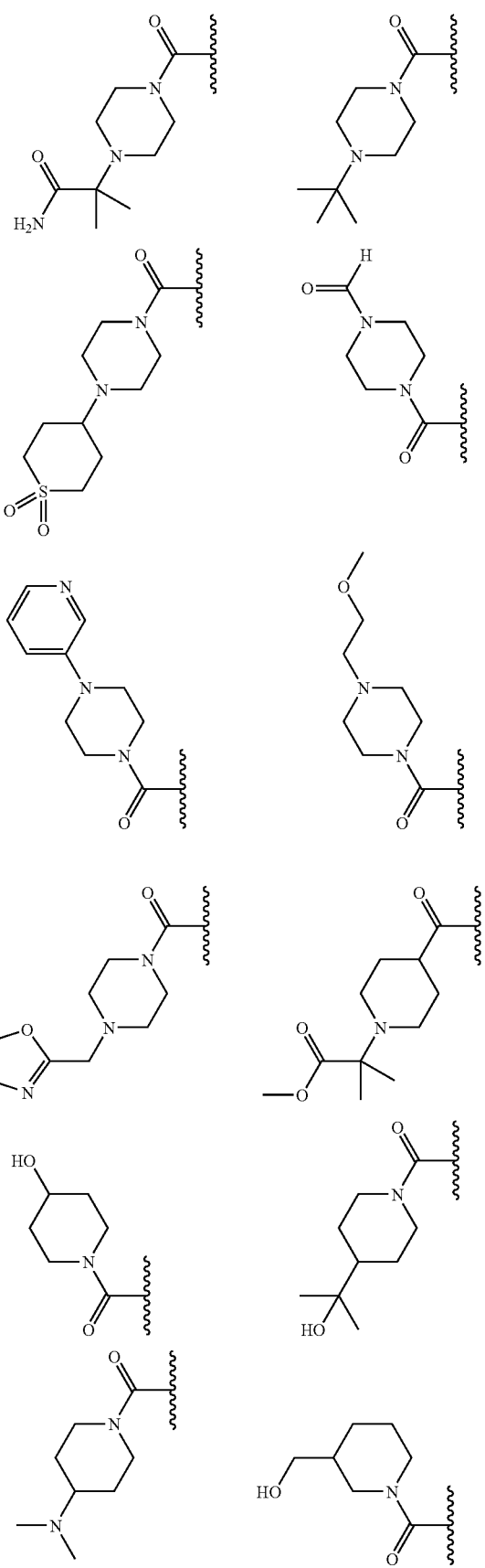
854
-continued
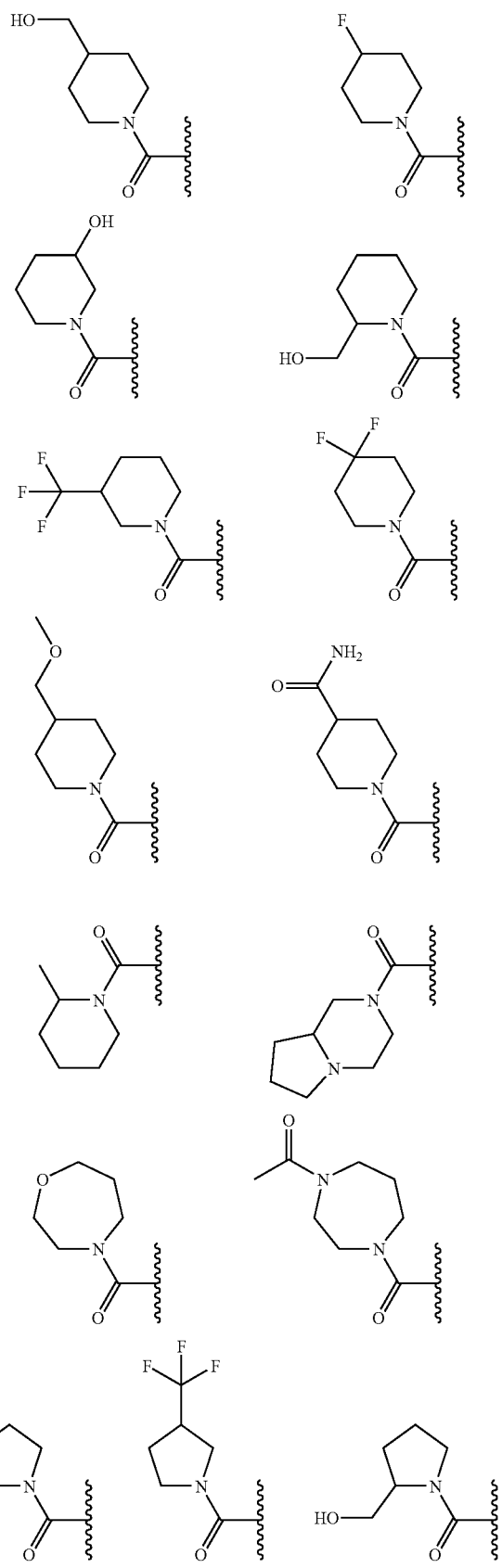

855
-continued
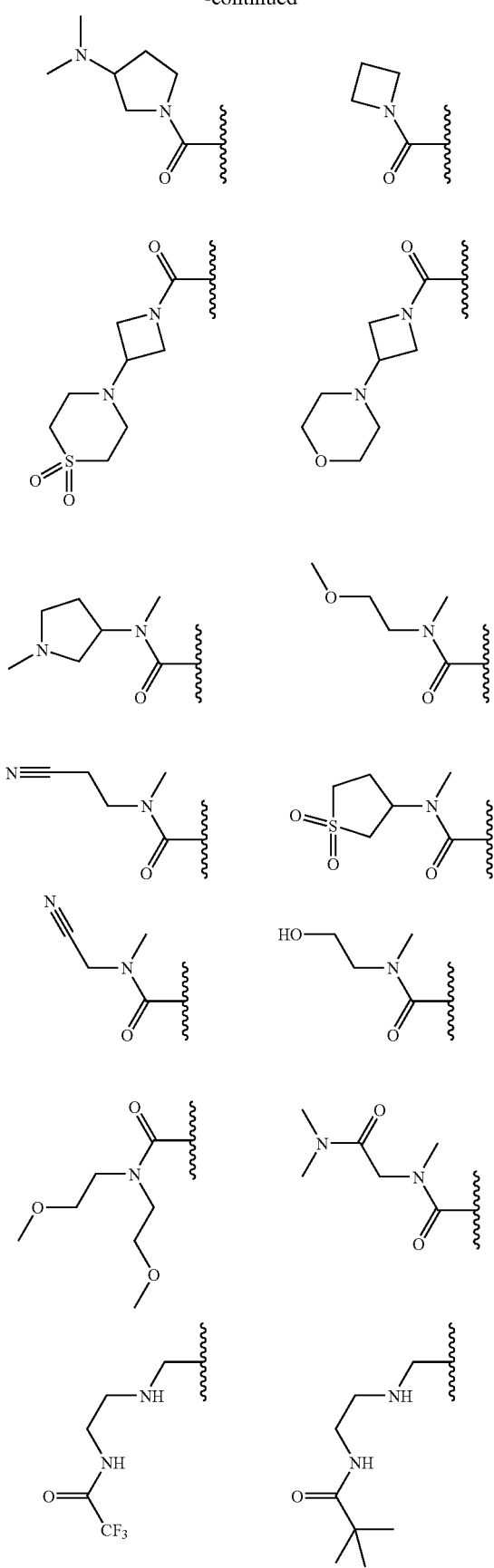
856
-continued
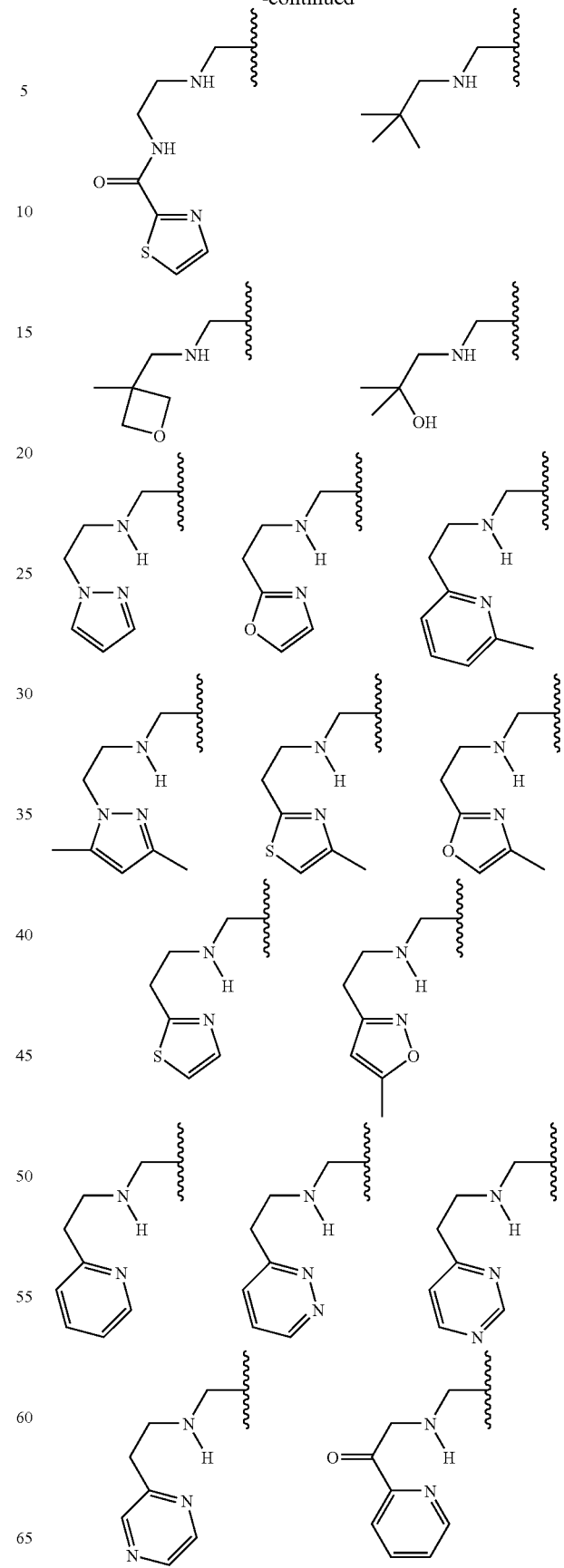

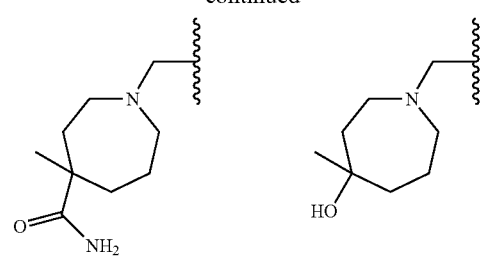
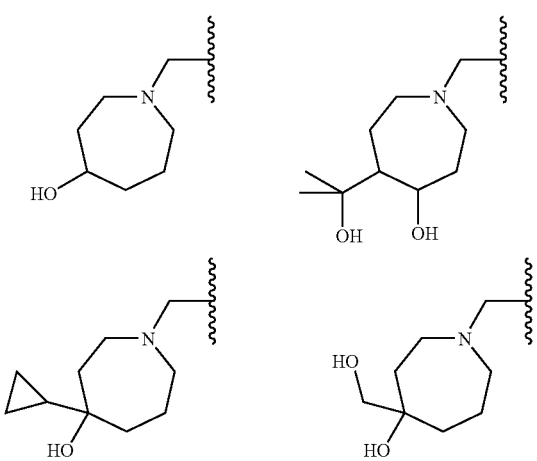
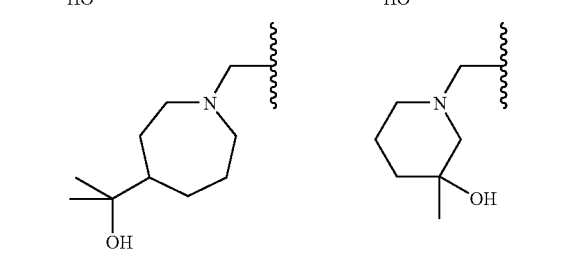
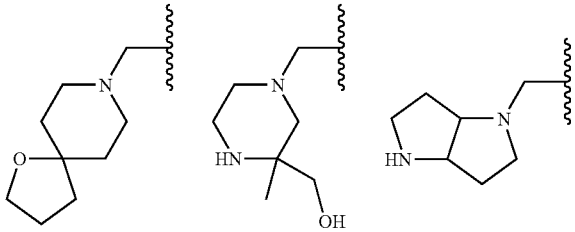
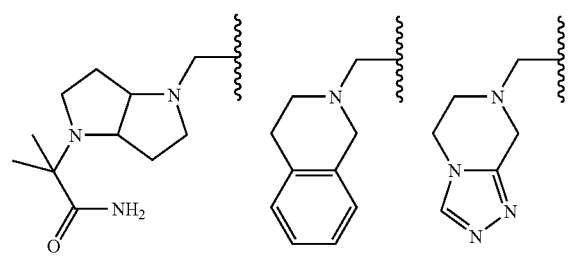
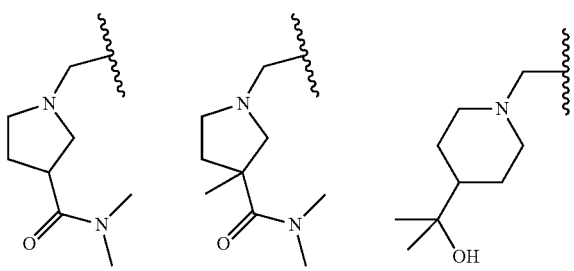
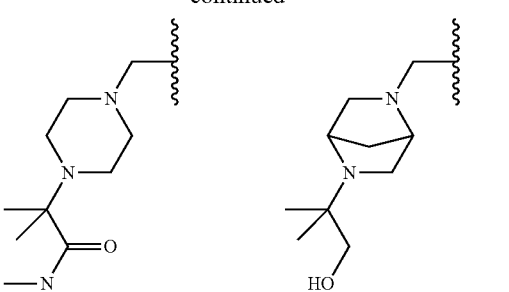
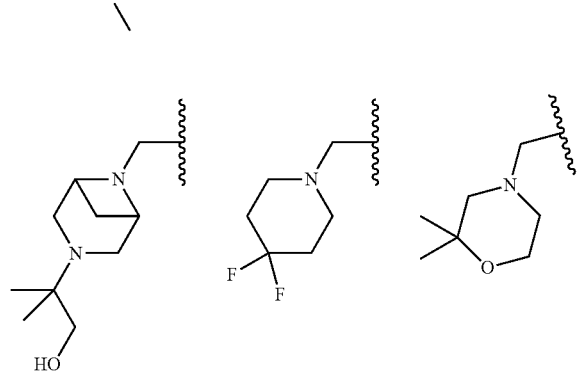
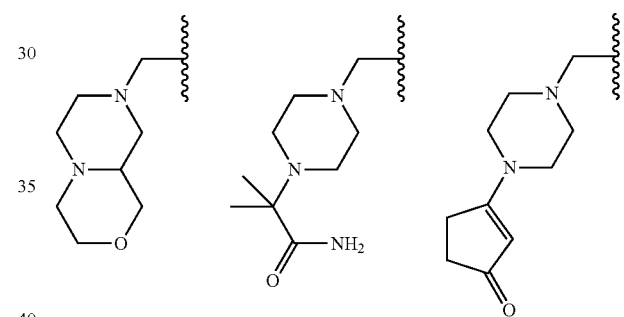
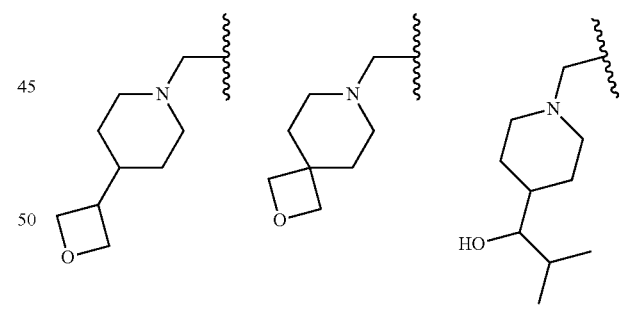
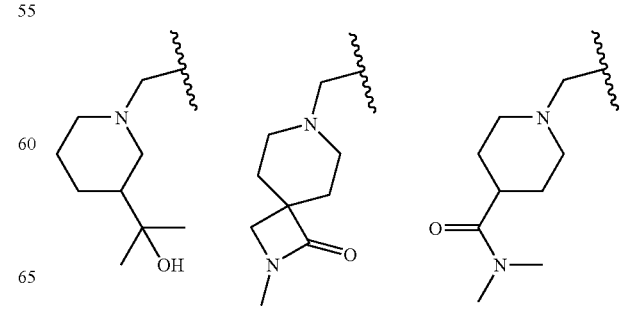

859
-continued
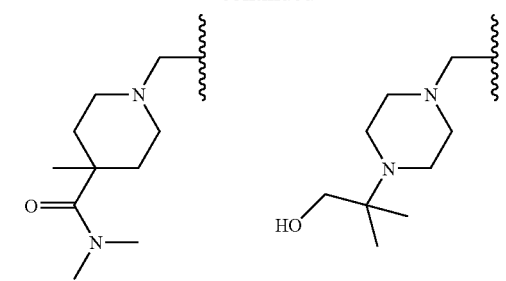
860
-continued
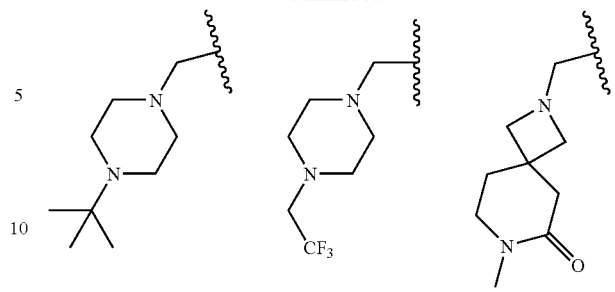
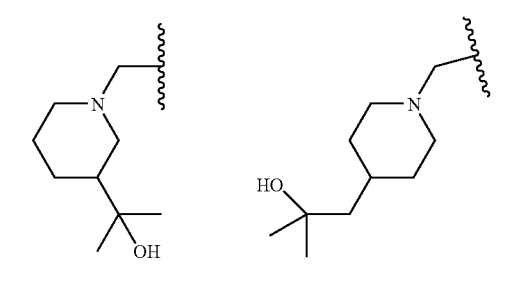
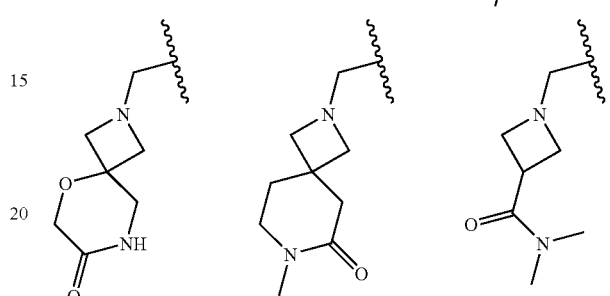
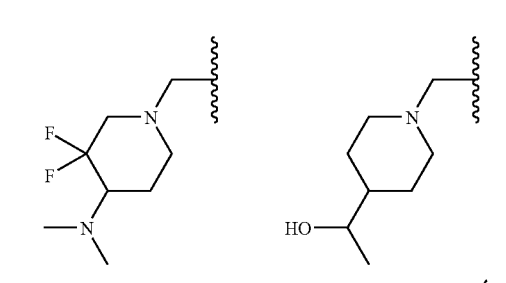
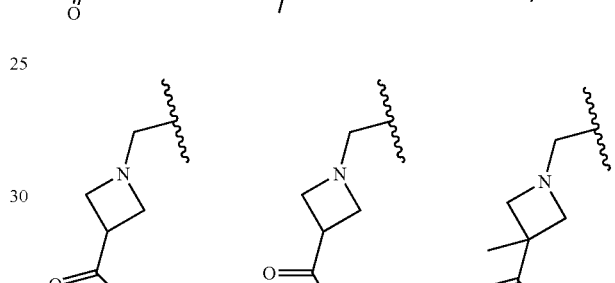
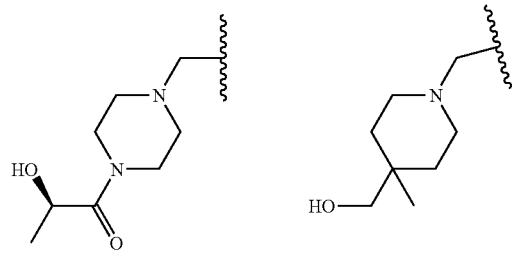
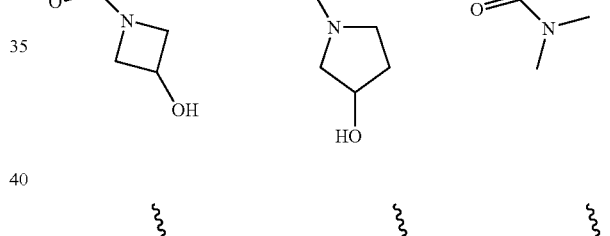
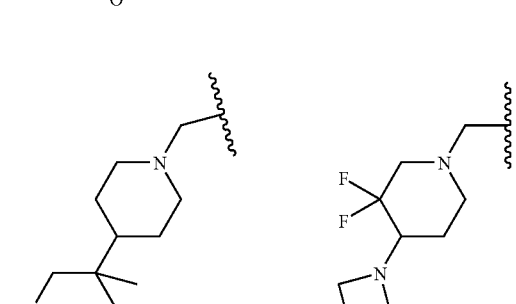
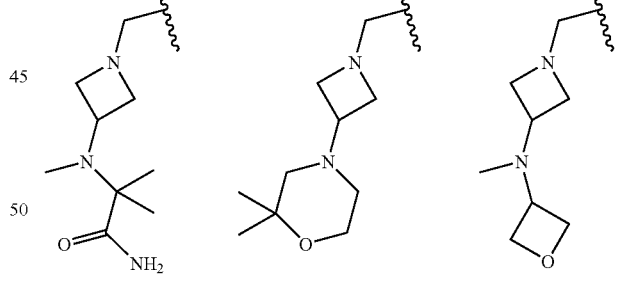
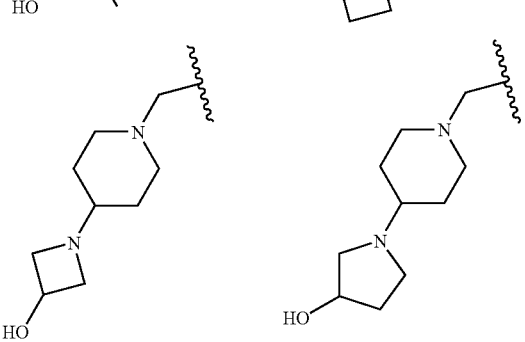
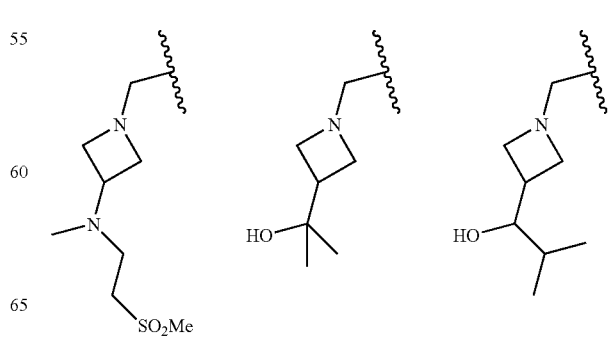

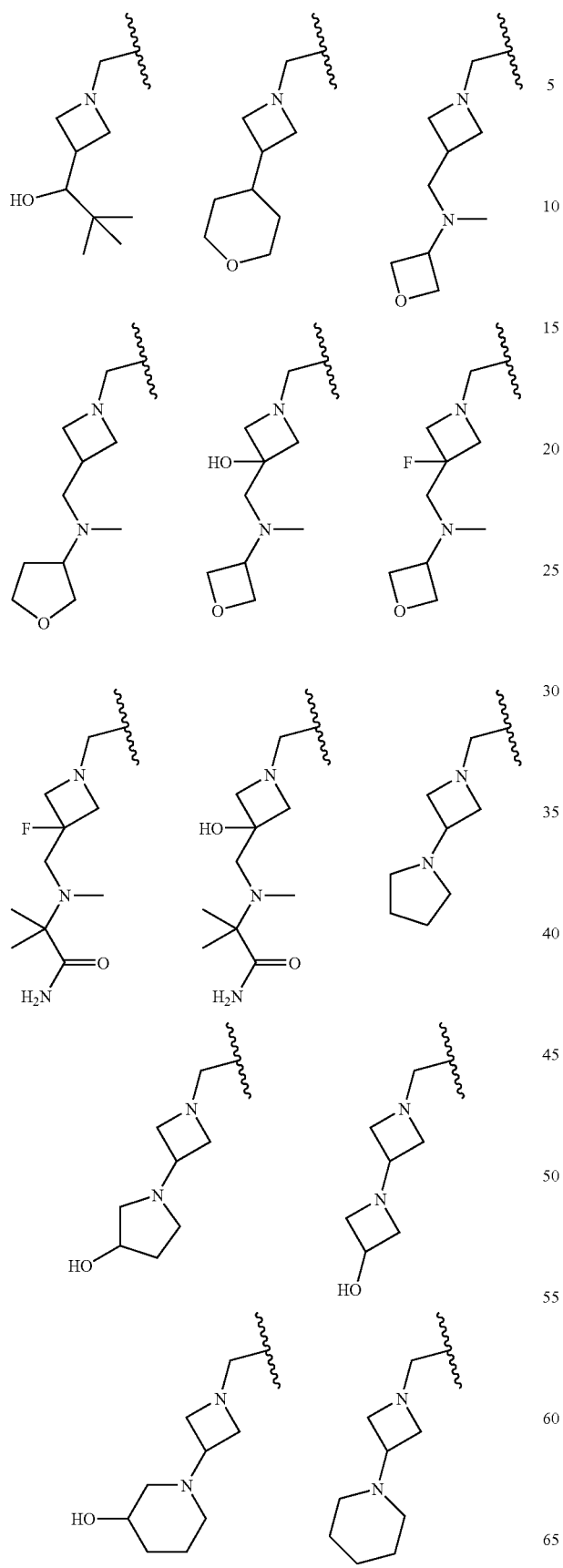
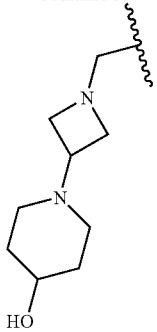

where the wavy line indicates the site of attachment.

14. The compound of claim 12 wherein $R^2$ is $C_1$-$C_{12}$ alkyl optionally substituted with one or more groups independently selected from F, Cl, Br, I, —$CH_3$, —$CH_2OH$, —CN, —$CF_3$, —$CO_2H$, —$COCH_3$, —$CO_2CH_3$, —$CONH_2$, —$CONHCH_3$, —$CON(CH_3)_2$, —$NO_2$, —$NH_2$, —$NHCH_3$, —$NHCOCH_3$, —$NHS(O)_2CH_3$, =O, —OH, —$OCH_3$, —$S(O)_2N(CH_3)_2$, —$SCH_3$, —$CH_2OCH_3$, and —$S(O)_2CH_3$.

15. The compound of claim 14 wherein $R^2$ is $CH_3$.

16. The compound of claim 1 selected from
4-(1-((9-methyl-2-(2-methyl-1H-benzo[d]imidazol-1-yl)-6-morpholino-9H-purin-8-yl)methyl)piperidin-4-yl)morpholine;
1-(8-((4-(2-hydroxypropan-2-yl)piperidin-1yl)methyl)-9-methyl-6-morpholino-9H-purin-2-yl)-1H-benzo[d]imidazol-2(3H)-one;
2-(1-((9-methyl-2-(2-methyl-1H-benzo[d]imidazol-1-yl)-6-morpholino-9H-purin-8 yl)methyl)piperidin-4-yl)propan-2-ol;
2-(1-((2-(2-ethyl-1H-benzo[d]imidazol-1-yl)-9-methyl-6-morpholino-9H-purin-8-yl)methyl)piperidin-4-yl)propan-2-ol;
2-(1-((2-(2-cyclopropyl-1H-benzo[d]imidazol-1-yl)-9-methyl-6-morpholino-9H-purin-8-yl)methyl)piperidin-4-yl)propan-2-ol;
2-(1-((2-(2-(methoxymethyl)-1H-benzo[d]imidazol-1-yl)-9-methyl-6-morpholino-9H-purin-8-yl)methyl)piperidin-4-yl)propan-2-ol;
2-(1-((2-(2-methoxy-1H-benzo[d]imidazol-1-yl)-9-methyl-6-morpholino-9H-purin-8-yl)methyl)piperidin-4-yl)propan-2-ol;
2-(1-((2-(2-amino-1H-benzo[d]imidazol-1-yl)-9-methyl-6-morpholino-9H-purin-8-yl)methyl)piperidin-4-yl)propan-2-ol;
2-(1-((2-(2-(hydroxymethyl)-1H-benzo[d]imidazol-1-yl)-9-methyl-6-morpholino-9H-purin-8-yl)methyl)piperidin-4-yl)propan-2-ol;
4-(8-((4-(2-methoxypropan-2-yl)piperidin-1-yl)methyl-9-methyl-2-(2-methyl-1H-benzo[d]imidazol-1-yl)-9H-purin-6-yl)morpholine;
(3S,4R)-3-fluoro-N,N-dimethyl-1-((9-methyl-2-(2-methyl-1H-benzo[d]imidazol-1-yl)-6-morpholino-9H-purin-8-yl)methyl)piperidin-4-amine;
1-(7-morpholino-2-((3-morpholinoazetidin-1-yl)methyl)thiazolo[5,4-d]pyrimidin-5-yl)-1H-benzo[d]imidazol-2(3H)-one;
4-(5-(2-(difluoromethyl)-1H-benzo[d]imidazol-1-yl)-2-((3-morpholinoazetidin-1-yl)methyl)thiazolo[5,4-d]pyrimidin-7-yl)morpholine;
2-(1-((9-methyl-6-morpholino-2-(2-(trifluoromethyl)-1H-benzo[d]imidazol-1-yl)-9H-purin-8-yl)methyl)piperidin-4-yl)propan-2-ol;

2-isobutyl-4-((9-methyl-2-(2-methyl-1H-benzo[d]imidazol-1-yl)-6-morpholino-9H-purin-8-yl)methyl)morpholine;
2-(1-((2-(2-(dimethylamino)-1H-benzo[d]imidazol-1-yl)-9-methyl-6-morpholino-9H-purin-8-yl)methyl)piperidin-4-yl)propan-2-ol;
2,2-diethyl-4-((9-methyl-2-(2-methyl-1H-benzo[d]imidazol-1-yl)-6-morpholino-9H-purin-8-yl)methyl)morpholine;
4-(5-(2-methyl-1H-benzo[d]imidazol-1-yl)-2-((3-morpholinoazetidin-1-yl)methyl)thiazolo[5,4-d]pyrimidin-7-yl)morpholine;
2,6-dimethyl-4-((9-methyl-2-(2-methyl-1H-benzo[d]imidazol-1-yl)-6-morpholino-9H-purin-8-yl)methyl)morpholine;
2-(1-((2-(2-isopropyl-1H-benzo[d]imidazol-1-yl)-9-methyl-6-morpholino-9H-purin-8-yl)methyl)piperidin-4-yl)propan-2-ol;
2,2-dimethyl-4-((9-methyl-2-(2-methyl-1H-benzo[d]imidazol-1-yl)-6-morpholino-9H-purin-8-yl)methyl)morpholine;
2-(1-((2-(2-(1,1-difluoroethyl)-1H-benzo[d]imidazol-1-yl)-9-methyl-6-morpholino-9H-purin-8-yl)methyl)piperidin-4-yl)propan-2-ol;
(R)-2-(1-((2-(2-(1-hydroxyethyl)-1H-benzo[d]imidazol-1-yl)-9-methyl-6-morpholino-9H-purin-8-yl)methyl)piperidin-4-yl)propan-2-ol;
(S)-2-(1-((2-(2-(1-hydroxyethyl)-1H-benzo[d]imidazol-1-yl)-9-methyl-6-morpholino-9H-purin-8-yl)methyl)piperidin-4-yl)propan-2-ol;
2-(1-((2-(2-(benzyl(methyl)amino)-1H-benzo[d]imidazol-1-yl)-9-methyl-6-morpholino-9H-purin-8-yl)methyl)piperidin-4-yl)propan-2-ol;
2-(1-((9-methyl-2-(2-(methylamino)-1H-benzo[d]imidazol-1-yl)-6-morpholino-9H-purin-8-yl)methyl)piperidin-4-yl)propan-2-ol;
2-(1-((9-methyl-6-morpholino-2-(2-phenyl-1H-benzo[d]imidazol-1-yl)-9H-purin-8-yl)methyl)piperidin-4-yl)propan-2-ol;
2-(1-((2-(2-(2-hydroxyethyl)-1H-benzo[d]imidazol-1-yl)-9-methyl-6-morpholino-9H-purin-8-yl)methyl)piperidin-4-yl)propan-2-ol;
2-(1-((9-methyl-6-morpholino-2-(2-(pyridin-3-yl)-1H-benzo[d]imidazol-1-yl)-9H-purin-8-yl)methyl)piperidin-4-yl)propan-2-ol;
2-(1-((5-(2-methyl-1H-benzo[d]imidazol-1-yl)-7-morpholinothiazolo[5,4-d]pyrimidin-2-yl)methyl)piperidin-4-yl)propan-2-ol;
2-(1-((9-methyl-6-morpholino-2-(2-(tetrahydrofuran-2-yl)-1H-benzo[d]imidazol-1-yl)-9H-purin-8-yl)methyl)piperidin-4-yl)propan-2-ol;
(3R,4S)-1-((2-(2-ethyl-1H-benzo[d]imidazol-1-yl)-9-methyl-6-morpholino-9H-purin-8-yl)methyl)-3-fluoro-N,N-dimethylpiperidin-4-amine;
(3S,4R)-1-((2-(2-ethyl-1H-benzo[d]imidazol-1-yl)-9-methyl-6-morpholino-9H-purin-8-yl)methyl)-3-fluoro-N,N-dimethylpiperidin-4-amine;
2-(1-((9-methyl-6-morpholino-2-(2-propyl-1H-benzo[d]imidazol-1-yl)-9H-purin-8-yl)methyl)piperidin-4-yl)propan-2-ol;
2-(1-((9-ethyl-2-(2-methyl-1H-benzo[d]imidazol-1-yl)-6-morpholino-9H-purin-8-yl)methyl)piperidin-4-yl)propan-2-ol;
2-(1-((2-(2-cyclobutyl-1H-benzo[d]imidazol-1-yl)-9-methyl-6-morpholino-9H-purin-8-yl)methyl)piperidin-4-yl)propan-2-ol;
2-(1-((9-methyl-6-morpholino-2-(2-morpholino-1H-benzo[d]imidazol-1-yl)-9H-purin-8-yl)methyl)piperidin-4-yl)propan-2-ol;
2-methyl-2-(4-((2-(2-methyl-1H-benzo[d]imidazol-1-yl)-4-morpholinofuro[3,2-d]pyrimidin-6-yl)methyl)piperazin-1-yl)propanamide;
2-(1-((2-(2-methyl-1H-benzo[d]imidazol-1-yl)-4-morpholinofuro[3,2-d]pyrimidin-6-yl)methyl)piperidin-4-yl)propan-2-ol;
2-(2-methyl-1H-benzo[d]imidazol-1-yl)-4-morpholino-6-((3-morpholinoazetidin-1-yl)methyl)furo[3,2-d]pyrimidine;
(S)-2-(1-((9-methyl-6-morpholino-2-(2-(tetrahydrofuran-2-yl)-1H-benzo[d]imidazol-1-yl)-9H-purin-8-yl)methyl)piperidin-4-yl)propan-2-ol;
(R)-2-(1-((9-methyl-6-morpholino-2-(2-(tetrahydrofuran-2-yl)-1H-benzo[d]imidazol-1-yl)-9H-purin-8-yl)methyl)piperidin-4-yl)propan-2-ol;
2-(1-((2-(2-(ethylamino)-1H-benzo[d]imidazol-1-yl)-9-methyl-6-morpholino-9H-purin-8-yl)methyl)piperidin-4-yl)propan-2-ol;
4-(5-(2-methyl-1H-benzo[d]imidazol-1-yl)-2-((3-morpholinoazetidin-1-yl)methyl)thiazolo[4,5-d]pyrimidin-7-yl)morpholine; and
3-(1-((9-methyl-2-(2-methyl-1H-benzo[d]imidazol-1-yl)-6-morpholino-9H-purin-8-yl)methyl)piperidin-4-yl)oxetan-3-ol.

17. The compound of claim 1 selected from
2,2-dimethyl-N((9-methyl-2-(2-methyl-1H-benzo[d]imidazol-1-yl)-6-morpholino-9H-purin-8-yl)methyl)propan-1-amine;
1-(9-methyl-2-(2-methyl-1H-benzo[d]imidazol-1-yl)-6-morpholino-9H-purin-8-yl)-N-((3-methyloxetan-3-yl)methyl)methanamine;
1-(1-((9-methyl-2-(2-methyl-1H-benzo[d]imidazol-1-yl)-6-morpholino-9H-purin-8-yl)methyl)piperidin-4-yl)cyclobutanol;
2-(1-((9-methyl-6-morpholino-2-(2-(pyrrolidin-1-yl)-1H-benzo[d]imidazol-1-yl)-9H-purin-8-yl)methyl)piperidin-4-yl)propan-2-ol;
2-(1-((2-(2-(3-fluorooxetan-3-yl)-1H-benzo[d]imidazol-1-yl)-9-methyl-6-morpholino-9H-purin-8-yl)methyl)piperidin-4-yl)propan-2-ol;
3-(1-((2-(2-ethyl-1H-benzo[d]imidazol-1-yl)-9-methyl-6-morpholino-9H-purin-8-yl)methyl)piperidin-4-yl)oxetan-3-ol;
2-methyl-2-(4-((9-methyl-2-(2-methyl-1H-benzo[d]imidazol-1-yl)-6-morpholino-9H-purin-8-yl)methyl)piperazin-1-yl)propan-1-ol;
2-(1-((9-methyl-2-(2-methyl-1H-benzo[d]imidazol-1-yl)-6-morpholino-9H-purin-8-yl)methyl)piperidin-3-yl)propan-2-ol;
2-methyl-1-(1-((9-methyl-2-(2-methyl-1H-benzo[d]imidazol-1-yl)-6-morpholino-9H-purin-8-yl)methyl)piperidin-4-yl)propan-2-ol;
4-(9-methyl-2-(2-methyl-1H-benzo[d]imidazol-1-yl)-8-((4-(2,2,2-trifluoroethyl)piperazin-1-yl)methyl)-9H-purin-6-yl)morpholine;
(4-methyl-1-((9-methyl-2-(2-methyl-1H-benzo[d]imidazol-1-yl)-6-morpholino-9H-purin-8-yl)methyl)piperidin-4-yl)methanol;
(R)-2-hydroxy-1-(4-((9-methyl-2-(2-methyl-1H-benzo[d]imidazol-1-yl)-6-morpholino-9H-purin-8-yl)methyl)piperazin-1-yl)propan-1-one;
adamantan-1-yl-[9-methyl-2-(2-methyl-benzoimidazol-1-yl)-6-morpholin-4-yl-9H-purin-8-ylmethyl]-amine;

N-((9-methyl-2-(2-methyl-1H-benzo[d]imidazol-1-yl)-6-morpholino-9H-purin-8-yl)methyl)-2,3-dihydro-1H-inden-1-amine;

(4R)-N-((9-methyl-2-(2-methyl-1H-benzo[d]imidazol-1-yl)-6-morpholino-9H-purin-8-yl)methyl)bicyclo[2.2.1]heptan-2-amine;

1-(((9-methyl-2-(2-methyl-1H-benzo[d]imidazol-1-yl)-6-morpholino-9H-purin-8-yl)methylamino)methyl)cyclohexanol;

(1-((9-methyl-2-(2-methyl-1H-benzo[d]imidazol-1-yl)-6-morpholino-9H-purin-8-yl)methylamino)cyclopentyl)methanol;

N,1-dimethyl-N-((9-methyl-2-(2-methyl-1H-benzo[d]imidazol-1-yl)-6-morpholino-9H-purin-8-yl)methyl)piperidin-4-amine;

4-(8-(isoindolin-2-ylmethyl)-9-methyl-2-(2-methyl-1H-benzo[d]imidazol-1-yl)-9H-purin-6-yl)morpholine;

4-(8-((4-(cyclopropylmethyl)piperazin-1-yl)methyl)-9-methyl-2-(2-methyl-1H-benzo[d]imidazol-1-yl)-9H-purin-6-yl)morpholine;

4-(8-((4,4-difluoropiperidin-1-yl)methyl)-9-methyl-2-(2-methyl-1H-benzo[d]imidazol-1-yl)-9H-purin-6-yl)morpholine;

N-((9-methyl-2-(2-methyl-1H-benzo[d]imidazol-1-yl)-6-morpholino-9H-purin-8-yl)methyl)-1-phenylethanamine;

4-(8-((4-(methoxymethyl)piperidin-1-yl)methyl)-9-methyl-2-(2-methyl-1H-benzo[d]imidazol-1-yl)-9H-purin-6-yl)morpholine;

4-((9-methyl-2-(2-methyl-1H-benzo[d]imidazol-1-yl)-6-morpholino-9H-purin-8-yl)methylamino)cyclohexanol;

1-(9-methyl-2-(2-methyl-1H-benzo[d]imidazol-1-yl)-6-morpholino-9H-purin-8-yl)-N-1-methylpiperidne-2-yl)methyl)methanamine;

4-(8-((dihydro-1H-pyrido[1,2-a]pyrazin-2(6H,7H,8H,9aH)-yl)methyl)-9methyl-2-(2-methyl-1H-benzo[d]imidazol-1-yl)-9H-purin-6-yl)morpholine;

1-methyl-N-((9-methyl-2-(2-methyl-1H-benzo[d]imidazol-1-yl)-6-morpholino-9H-purin-8-yl)methyl)piperidin-4-amine;

N,2-dimethyl-N-((9-methyl-2-(2-methyl-1H-benzo[d]imidazol-1-yl)-6-morpholino-9H-purin-8-yl)methyl)propan-1-amine;

1-(4-((9-methyl-2-(2-methyl-1H-benzo[d]imidazol-1-yl)-6-morpholino-9H-purin-8-yl)methylamino)piperidin-1-yl)ethanone;

4-(1-((9-methyl-2-(2-methyl-1H-benzo[d]imidazol-1-yl)-6-morpholino-9H-purin-8-yl)methyl)pyrrolidin-3-yl)morpholine;

N-((9-methyl-2-(2-methyl-1H-benzo[d]imidazol-1-yl)-6-morpholino-9H-purin-8-yl)methyl)tetrahydro-2H-pyran-4-amine;

4-(9-methyl-2-(2-methyl-1H-benzo[d]imidazol-1-yl)-8-((3-(trifluoromethyl)pyrrolidin-1-yl)methyl)-9H-purin-6-yl)morpholine;

N-methyl-1-(9-methyl-2-(2-methyl-1H-benzo[d]imidazol-1-yl)-6-morpholino-9H-purin-8-yl)-N-((tetrahydrofuran-2-yl)methyl)methanamine;

1-((9-methyl-2-(2-methyl-1H-benzo[d]imidazol-1-yl)-6-morpholino-9H-purin-8-yl)methyl)piperidine-4-carbonitrile;

2-methyl-1-((9-methyl-2-(2-methyl-1H-benzo[d]imidazol-1-yl)-6-morpholino-9H-purin-8-yl)methylamino)propan-2-ol;

3,3,3-trifluoro-N-((9-methyl-2-(2-methyl-1H-benzo[d]imidazol-1-yl)-6-morpholino-9H-purin-8-yl)methyl)propan-1-amine;

4,4-difluoro-N-((9-methyl-2-(2-methyl-1H-benzo[d]imidazol-1-yl)-6-morpholino-9H-purin-8-yl)methyl)cyclohexanamine;

1-isopropyl-N-methyl-N-((9-methyl-2-(2-methyl-1H-benzo[d]imidazol-1-yl)-6-morpholino-9H-purin-8-yl)methyl)piperidin-4-amine;

N,N-diethyl-1-((9-methyl-2-(2-methyl-1H-benzo[d]imidazol-1-yl)-6-morpholino-9H-purin-8-yl)methyl)pyrrolidin-3-amine;

1-(9-methyl-2-(2-methyl-1H-benzo[d]imidazol-1-yl)-6-morpholino-9H-purin-8-yl)-N-((tetrahydrofuran-3-yl)methyl)methanamine;

N-methyl-N-(1-((9-methyl-2-(2-methyl-1H-benzo[d]imidazol-1-yl)-6-morpholino-9H-purin-8-yl)methyl)pyrrolidin-3-yl)acetamide;

(R)-(1-((9-methyl-2-(2-methyl-1H-benzo[d]imidazol-1-yl)-6-morpholino-9H-purin-8-yl)methyl)pyrrolidin-3-yl)methanol;

4-(8-((3,3-dimethylpyrrolidin-1-yl)methyl)-9-methyl-2-(2-methyl-1H-benzo[d]imiadazol-1-yl)-9H-purin-6-yl)morpholine;

4-(8-((3,3-diethylpyrrolidin-1-yl)methyl)-9-methyl-2-(2-methyl-1H-benzo[d]imidazol-1-yl)-9H-purin-6-yl)morpholine;

4-(8-((3-isobutylpyrrolidin-1-yl)methyl)-9-methyl-2-(2-methyl-1H-benzo[d]imidazol-1-yl)-9H-purin-6-yl)morpholine;

N-((9-methyl-2-(2-methyl-1H-benzo[d]imidazol-1-yl)-6-morpholino-9H-purin-8-yl)methyl)-2-phenylpropan-2-amine;

4-(9-methyl-2-(2-methyl-1H-benzo[d]imidazol-1-yl)-8-((1,1-dioxo-4-(tetrahydro-2H-thiopyran-4-yl)piperazin-1-yl)methyl)-9H-purin-6-yl)morpholine;

(S)-(1-((9-methyl-2-(2-methyl-1H-benzo[d]imidazol-1-yl)-6-morpholino-9H-purin-8-yl)methyl)pyrrolidin-3-yl)methanol;

1-((2-(2-ethyl-1H-benzo[d]imidazol-1-yl)-9-methyl-6-morpholino-9H-purin-8-yl)methyl)-N,N-dimethylpiperidin-4-amine;

2-(1-((2-(2-(1-fluorocyclopropyl)-1H-benzo[d]imidazol-1-yl)-9-methyl-6-morpholino-9H-purin-8-yl)methyl)piperidin-4-yl)propan-2-ol;

2-(1-((2-(2-(cyclopropylmethyl)-1H-benzo[d]imidazol-1-yl)-9-methyl-6-morpholino-9H-purin-8-yl)methyl)piperidin-4-yl)propan-2-ol;

4-(1-((2-(2-ethyl-1H-benzo[d]imidazol-1-yl)-9-methyl-6-morpholino-9H-purin-8-yl)methyl)azetidin-3-yl)morpholine;

4-(8-((3,3-dimethyl-4-(2-(methylsulfonyl)ethyl)piperazin-1-yl)methyl)-2-(2-ethyl-1H-benzo[d]imidazol-1-yl)-9-methyl-9H-purin-6-yl)morpholine;

2-((1-((2-(2-ethyl-1H-benzo[d]imidazol-1-yl)-9-methyl-6-morpholino-9H-purin-8-yl)methyl)azetidin-3-yl)(methyl)amino)-2-methylpropanamide;

4-(2-(2-ethyl-1H-benzo[d]imidazol-1-yl)-9-methyl-8-((4-(2-(methylsulfonyl)ethyl)piperazin-1-yl)methyl)-9H-purin-6-yl)morpholine;

1-(1-((2-(2-ethyl-1H-benzo[d]imidazol-1-yl)-9-methyl-6-morpholino-9H-purin-8-yl)methyl)azetidin-3-yl)-2-methylpropan-1-ol;

4-(2-(2-ethyl-1H-benzo[d]imidazol-1-yl)-9-methyl-8-((4-(oxetan-3-yl)piperidin-1-yl)methyl)-9H-purin-6-yl)morpholine;

2-(1-((9-methyl-2-(2-methyl-1H-benzo[d]imidazol-1-yl)-6-morpholino-9H-purin-8-yl)methyl)azetidin-3-yl)propan-2-ol;

3-(1-((9-methyl-2-(2-methyl-1H-benzo[d]imidazol-1-yl)-6-morpholino-9H-purin-8-yl)methyl)piperidin-4-yl)pentan-3-ol;

4-(1-((9-methyl-2-(2-methyl-1H-benzo[d]imidazol-1-yl)-6-morpholino-9H-purin-8-yl)methyl)piperidin-4-yl)tetrahydro-2H-pyran-4-ol;

(S)-4-(8-((3-(1,1-dioxo-isothiazolidin-2-yl)pyrrolidin-1-yl)methyl)-9-methyl-2-(2-methyl-1H-benzo[d]imidazol-1-yl)-9H-purin-6-yl)morpholine;

2-(1-((9-methyl-2-(2-(1-methyl-1H-pyrazol-5-yl)-1H-benzo[d]imidazol-1-yl)-6-morpholino-9H-purin-8-yl)methyl)piperidin-4-yl)propan-2-ol;

(R)-4-(8-((3-(1,1-dioxo-isothiazolidin-2-yl)pyrrolidin-1-yl)methyl)-9-methyl-2-(2-methyl-1H-benzo[d]imidazol-1-yl)-9H-purin-6-yl)morpholine;

N-((9-methyl-2-(2-methyl-1H-benzo[d]imidazol-1-yl)-6-morpholino-9H-purin-8-yl)methyl)-2-(4-methylthiazol-2-yl)ethanamine;

N-((9-methyl-2-(2-methyl-1H-benzo[d]imidazol-1-yl)-6-morpholino-9H-purin-8-yl)methyl)-2-(pyridin-2-yl)ethanamine;

1-(1-((9-methyl-2-(2-methyl-1H-benzo[d]imidazol-1-yl)-6-morpholino-9H-purin-8-yl)methyl)piperidin-4-yl)cyclopentanol;

7-((2-(2-ethyl-1H-benzo[d]imidazol-1-yl)-9-methyl-6-morpholino-9H-purin-8-yl)methyl)-2-oxa-7-azaspiro[3.5]nonane;

4-(2-(2-ethyl-1H-benzo[d]imidazol-1-yl)-9-methyl-8-((3-(tetrahydro-2H-pyran-4-yl)azetidin-1-yl)methyl)-9H-purin-6-yl)morpholine;

N,N-dimethyl-1-((9-methyl-2-(2-methyl-1H-benzo[d]imidazol-1-yl)-6-morpholino-9H-purin-8-yl)methyl)piperidine-4-carboxamide;

8-((9-methyl-2-(2-methyl-1H-benzo[d]imidazol-1-yl)-6-morpholino-9H-purin-8-yl)methyl)-1-oxa-3,8-diazaspiro[4.5]decan-2-one;

4-(1-((9-methyl-2-(2-methyl-1H-benzo[d]imidazol-1-yl)-6-morpholino-9H-purin-8-yl)methyl)azetidin-3-yl)morpholine;

4-(9-methyl-2-(2-methyl-1H-benzo[d]imidazol-1-yl)-8-((4-(2-(methylsulfonyl)ethyl)piperazin-1-yl)methyl)-9H-purin-6-yl)morpholine;

4-(8-((3,3-dimethyl-4-(2-(methylsulfonyl)ethyl)piperazin-1-yl)methyl)-9-methyl-2-(2-methyl-1H-benzo[d]imidazol-1-yl)-9H-purin-6-yl)morpholine;

4-(1-((2-(2-ethyl-1H-benzo[d]imidazol-1-yl)-9-methyl-6-morpholino-9H-purin-8-yl)methyl)azetidin-3-yl)-2,2-dimethylmorpholine;

2-(1-((5-ethyl-1H-benzo[d]imidazol-1-yl)-7-morpholinothiazolo[5,4-d]pyrimidin-2-yl)methyl)piperidin-4-yl)propan-2-ol;

(R)-N-methyl-N-(1-((9-methyl-2-(2-methyl-1H-benzo[d]imidazol-1-yl)-6-morpholino-9H-purin-8-yl)methyl)pyrrolidin-3-yl)acetamide;

(R)-4-(1-((9-methyl-2-(2-methyl-1H-benzo[d]imidazol-1-yl)-6-morpholino-9H-purin-8-yl)methyl)pyrrolidin-3-yl)morpholine;

(S)-N-methyl-N-(1-((9-methyl-2-(2-methyl-1H-benzo[d]imidazol-1-yl)-6-morpholino-9H-purin-8-yl)methyl)pyrrolidin-3-yl)acetamide;

(S)-4-(1-((9-methyl-2-(2-methyl-1H-benzo[d]imidazol-1-yl)-6-morpholino-9H-purin-8-yl)methyl)pyrrolidin-3-yl)morpholine;

2-(1-((2-(2-ethoxy-1H-benzo[d]imidazol-1-yl)-9-methyl-6-morpholino-9H-purin-8-yl)methyl)piperidin-4-yl)propan-2-ol;

2-(1-((2-(2-isopropoxy-1H-benzo[d]imidazol-1-yl)-9-methyl-6-morpholino-9H-purin-8-yl)methyl)piperidin-4-yl)propan-2-ol;

2-methyl-2-(1-((9-methyl-2-(2-methyl-1H-benzo[d]imidazol-1-yl)-6-morpholino-9H-purin-8-yl)methyl)piperidin-4-yl)propan-1-ol;

4-(8-((4-tert-butylpiperazin-1-yl)methyl)-9-methyl-2-(2-methyl-1H-benzo[d]imidazol-1-yl)-9H-purin-6-yl)morpholine;

2-(1-((2-(2-ethyl-1H-benzo[d]imidazol-1-yl)-9-methyl-6-morpholino-9H-purin-8-yl)methyl)piperidin-4-yl)-2-methylpropan-1-ol;

N-((9-methyl-2-(2-methyl-1H-benzo[d]imidazol-1-yl)-6-morpholino-9H-purin-8-yl)methyl)-2-(pyrazin-2-yl)ethanamine;

7-((9-methyl-2-(2-methyl-1H-benzo[d]imidazol-1-yl)-6-morpholino-9H-purin-8-yl)methyl)-7-azaspiro[3.5]nonan-2-ol;

2-(1-(2-(9-methyl-2-(2-methyl-1H-benzo[d]imidazol-1-yl)-6-morpholino-9H-purin-8-yl)ethyl)piperidin-4-yl)propan-2-ol;

4-(2-(2-ethyl-1H-benzo[d]imidazol-1-yl)-8-((3-fluoro-1,3'-biazetidin-1'-yl)methyl)-9-methyl-9H-purin-6-yl)morpholine;

2-methyl-1-(1-((9-methyl-2-(2-methyl-1H-benzo[d]imidazol-1-yl)-6-morpholino-9H-purin-8-yl)methyl)piperidin-4-yl)propan-1-ol;

azetidin-1-yl(1-((9-methyl-2-(2-methyl-1H-benzo[d]imidazol-1-yl)-6-morpholino-9H-purin-8-yl)methyl)azetidin-3-yl)methanone;

(1-((9-methyl-2-(2-methyl-1H-benzo[d]imidazol-1-yl)-6-morpholino-9H-purin-8-yl)methyl)azetidin-3-yl)(pyrrolidin-1-yl)methanone;

(R)-azetidin-1-yl(1-((9-methyl-2-(2-methyl-1H-benzo[d]imidazol-1-yl)-6-morpholino-9H-purin-8-yl)methyl)pyrrolidin-3-yl)methanone;

(R)-(1-((2-(2-ethyl-1H-benzo[d]imidazol-1-yl)-9-methyl-6-morpholino-9H-purin-8-yl)methyl)pyrrolidin-3-yl)(pyrrolidin-1-yl)methanone;

(R)-N,N-dimethyl-1-((9-methyl-2-(2-methyl-1H-benzo[d]imidazol-1-yl)-6-morpholino-9H-purin-8-yl)methyl)pyrrolidine-3-carboxamide;

(R)-1-((2-(2-ethyl-1H-benzo[d]imidazol-1-yl)-9-methyl-6-morpholino-9H-purin-8-yl)methyl)-N,N-dimethylpyrrolidine-3-carboxamide;

2,2-dimethyl-4-(1-((9-methyl-2-(2-methyl-1H-benzo[d]imidazol-1-yl)-6-morpholino-9H-purin-8-yl)methyl)azetidin-3-yl)morpholine;

4-(2-(2-ethyl-1H-benzo[d]imidazol-1-yl)-9-methyl-8-((3-(1,1-dioxo-thiomorpholino)azetidin-1-yl)methyl)-9H-purin-6-yl)morpholine;

4-(2-(2-methyl-1H-benzo[d]imidazol-1-yl)-9-methyl-8-((3-(1,1-dioxo-thiomorpholino)azetidin-1-yl)methyl)-9H-purin-6-yl)morpholine;

2-methyl-2-(4-((9-methyl-2-(2-methyl-1H-benzo[d]imidazol-1-yl)-6-morpholino-9H-purin-8-yl)methyl)piperazin-1-yl)propane-1,3-diol;

(R)-3-methyl-2-(4-((9-methyl-2-(2-methyl-1H-benzo[d]imidazol-1-yl)-6-morpholino-9H-purin-8-yl)methyl)piperazin-1-yl)butan-1-ol;

2-(1-((2-(2-(2-methoxyethylamino)-1H-benzo[d]imidazol-1-yl)-9-methyl-6-morpholino-9H-purin-8-yl)methyl)piperidin-4-yl)propan-2-ol;

(R)-1-(1-((9-methyl-2-(2-methyl-1H-benzo[d]imidazol-1-yl)-6-morpholino-9H-purin-8-yl)methyl)piperidin-4-yl)propan-1-ol;

(S)-1-(1-((9-methyl-2-(2-methyl-1H-benzo[d]imidazol-1-yl)-6-morpholino-9H-purin-8-yl)methyl)piperidin-4-yl)propan-1-ol;

(S)-3-methyl-2-(4-((9-methyl-2-(2-methyl-1H-benzo[d]imidazol-1-yl)-6-morpholino-9H-purin-8-yl)methyl)piperazin-1-yl)butan-1-ol;

2-(1-((5-(2-methyl-1H-benzo[d]imidazol-1-yl)-7-morpholinothiazolo[5,4-d]pyrimidin-2-yl)methyl)piperidin-3-yl)propan-2-ol;

N,N-dimethyl-1-((9-methyl-2-(2-methyl-1H-benzo[d]imidazol-1-yl)-6-morpholino-9H-purin-8-yl)methyl)azetidine-3-carboxamide;

(R)-(1-((9-methyl-2-(2-methyl-1H-benzo[d]imidazol-1-yl)-6-morpholino-9H-purin-8-yl)methyl)pyrrolidin-3-yl)(pyrrolidin-1-yl)methanone;

(1-((2-(2-ethyl-1H-benzo[d]imidazol-1-yl)-9-methyl-6-morpholino-9H-purin-8-yl)methyl)azetidin-3-yl)(pyrrolidin-1-yl)methanone; 1-((2-(2-ethyl-1H-benzo[d]imidazol-1-yl)-9-methyl-6-morpholino-9H-purin-8-yl)methyl)-N,N-dimethylazetidine-3-carboxamide;

2-(1-(2-(2-(2-ethyl-1H-benzo[d]imidazol-1-yl)-9-methyl-6-morpholino-9H-purin-8-yl)ethyl)piperidin-4-yl)propan-2-ol;

2-methyl-2-(4-(2-(9-methyl-2-(2-methyl-1H-benzo[d]imidazol-1-yl)-6-morpholino-9H-purin-8-yl)ethyl)piperazin-1-yl)propanamide;

8-((9-methyl-2-(2-methyl-1H-benzo[d]imidazol-1-yl)-6-morpholino-9H-purin-8-yl)methyl)-1,4-dioxa-8-azaspiro[4.5]decane;

8-((9-methyl-2-(2-methyl-1H-benzo[d]imidazol-1-yl)-6-morpholino-9H-purin-8-yl)methyl)-1-oxa-8-azaspiro[4.5]decane;

N-(2-((9-methyl-2-(2-methyl-1H-benzo[d]imidazol-1-yl)-6-morpholino-9H-purin-8-yl)methyl)piperidin-4-yl)propan-2-yl)acetamide;

(S)-2-(1-((9-methyl-2-(2-methyl-1H-benzo[d]imidazol-1-yl)-6-morpholino-9H-purin-8-yl)methyl)piperidin-4-yl)butan-2-ol;

(S)-1-(1-((9-methyl-2-(2-methyl-1H-benzo[d]imidazol-1-yl)-6-morpholino-9H-purin-8-yl)methyl)piperidin-4-yl)ethanol;

(R)-1-(1-((9-methyl-2-(2-methyl-1H-benzo[d]imidazol-1-yl)-6-morpholino-9H-purin-8-yl)methyl)piperidin-4-yl)ethanol;

4-(8-((dihydro-1H-pyrido[1,2-a]pyrazin-2(6H,7H,8H,9H,9aH)-yl)methyl)-9-methyl-2-(2-methyl-1H-benzo[d]imidazol-1-yl)-9H-purin-6-yl)morpholine;

N,N-diethyl-1-((9-methyl-2-(2-methyl-1H-benzo[d]imidazol-1-yl)-6-morpholino-9H-purin-8-yl)methyl)pyrrolidin-3-amine;

4-(8-((dihydro-1H-pyrido[1,2-a]pyrazin-2(6H,7H,8H,9H,9aH)-yl)methyl)-9-methyl-2-(2-methyl-1H-benzo[d]imidazol-1-yl)-9H-purin-6-yl)morpholine;

N,N-diethyl-1-((9-methyl-2-(2-methyl-1H-benzo[d]imidazol-1-yl)-6-morpholino-9H-purin-8-yl)methyl)pyrrolidin-3-amine;

8-((9-methyl-2-(2-methyl-1H-benzo[d]imidazol-1-yl)-6-morpholino-9H-purin-8-yl)methyl)-2,8-diazaspiro[4.5]decan-1-one;

8-((9-methyl-2-(2-methyl-1H-benzo[d]imidazol-1-yl)-6-morpholino-9H-purin-8-yl)methyl)-3-oxa-8-azabicyclo[3.2.1]octane;

(R)-2-(4-((9-methyl-2-(2-methyl-1H-benzo[d]imidazol-1-yl)-6-morpholino-9H-purin-8-yl)methyl)piperazin-1-yl)butan-1-ol;

(S)-2-(4-((9-methyl-2-(2-methyl-1H-benzo[d]imidazol-1-yl)-6-morpholino-9H-purin-8-yl)methyl)piperazin-1-yl)butan-1-ol;

2-(1-((9-methyl-2-(2-methyl-1H-benzo[d]imidazol-1-yl)-6-morpholino-9H-purin-8-yl)methyl)piperidin-4-yl)propan-2-amine;

5-((9-methyl-2-(2-methyl-1H-benzo[d]imidazol-1-yl)-6-morpholino-9H-purin-8-yl)methyl)-2-oxa-5-azabicyclo[2.2.1]heptane;

(1-((2-(2-ethyl-1H-benzo[d]imidazol-1-yl)-9-methyl-6-morpholino-9H-purin-8-yl)methyl)-4-methylpiperidin-4-yl)methanol;

4-(9-methyl-2-(2-methyl-1H-benzo[d]imidazol-1-yl)-8-((3-(piperidin-1-yl)azetidin-1-yl)methyl)-9H-purin-6-yl)morpholine;

4-(8-((4-tert-butylpiperazin-1-yl)methyl)-2-(ethyl-1H-benzo[d]imidazol-1-yl)-9-9H-purin-6-yl)morpholine;

(S)-1-(1-((2-(2-ethyl-1H-benzo[d]imidazol-1-yl)-9-methyl-6-morpholino-9H-purin-8-yl)methyl)azetidin-3-yl)-2-methylpropan-1-ol;

N-methyl-1-((9-methyl-2-(2-methyl-1H-benzo[d]imidazol-1-yl)-6-morpholino-9H-purin-8-yl)methyl)-N-(tetrahydrofuran-3-yl)piperidin-4-amine;

1-((2-(2-ethyl-1H-benzo[d]imidazol-1-yl)-9-methyl-6-morpholino-9H-purin-8-yl)methyl)-N-methyl-N-(tetrahydrofuran-3-yl)piperidin-4-amine;

7-((2-(2-ethyl-1H-benzo[d]imidazol-1-yl)-9-methyl-6-morpholino-9H-purin-8-yl)methyl)-2-methyl-7-azaspiro[3.5]nonan-2-ol;

4-(2-(2-(2-ethyl-1H-benzo[d]imidazol-1-yl)-9-methyl-6-morpholino-9H-purin-8-yl)ethyl)-2,2-dimethylmorpholine;

(S)-azetidin-1-yl(1-((2-(2-ethyl-1H-benzo[d]imidazol-1-yl)-9-methyl-6-morpholino-9H-purin-8-yl)methyl)pyrrolidin-3-yl)methanone;

9-((2-(2-ethyl-1H-benzo[d]imidazol-1-yl)-9-methyl-6-morpholino-9H-purin-8-yl)methyl)-1-oxa-4,9-diazaspiro[5.5]undecan-3-one;

4-(8-((1S,4S)-2,5-diazabicyclo[2.2.1]heptan-2-ylmethyl)-2-(2-ethyl-1H-benzo[d]imidazol-1-yl)-9-methyl-9H-purin-6-yl)morpholine;

(3-methyl-1-((9-methyl-2-(2-methyl-1H-benzo[d]imidazol-1-yl)-6-morpholino-9H-purin-8-yl)methyl)pyrrolidin-3-yl)(pyrrolidin-1-yl)methanone;

2,2-dimethyl-4-(2-(9-methyl-2-(2-methyl-1H-benzo[d]imidazol-1-yl)-6-morpholino-9H-purin-8-yl)ethyl)morpholine;

(S)-1-((2-(2-ethyl-1H-benzo[d]imidazol-1-yl)-9-methyl-6-morpholino-9H-purin-8-yl)methyl)-N,N-dimethylpyrrolidine-3-carboxamide;

(S)-(1-((2-(2-ethyl-1H-benzo[d]imidazol-1-yl)-9-methyl-6-morpholino-9H-purin-8-yl)methyl)pyrrolidin-3-yl)(pyrrolidin-1-yl)methanone;

9-((9-methyl-2-(2-methyl-1H-benzo[d]imidazol-1-yl)-6-morpholino-9H-purin-8-yl)methyl)-1,5-dioxa-9-azaspiro[5.5]undecane;

4-(8-((4-tert-butylpiperazin-1-yl)methyl)-2-(2-ethyl-1H-benzo[d]imidazol-1-yl)-9H-purin-6-yl)morpholine;

2-(4-((2-(2-ethyl-1H-benzo[d]imidazol-1-yl)-9-methyl-6-morpholino-9H-purin-8-yl)methyl)piperazin-1-yl)-2-methylpropan-1-ol;

4-(8-((4-tert-butylpiperazin-1-yl)methyl)-2-(2-cyclopropyl-1H-benzo[d]imidazol-1-yl)-9-methyl-9H-purin-6-yl)morpholine;

2-((1R,5S,6r)-3-((9-methyl-2-(2-methyl-1H-benzo[d]imidazol-1-yl)-6-morpholino-9H-purin-8-yl)methyl)-3-azabicyclo[3.1.0]hexan-6-yl)propan-2-ol;

(R)-1-(1-((2-(2-ethyl-1H-benzo[d]imidazol-1-yl)-9-methyl-6-morpholino-9H-purin-8-yl)methyl)azetidin-3-yl)-2-methylpropan-1-ol;

2-methyl-2-(4-((9-methyl-2-(2-methyl-1H-benzo[d]imidazol-1-yl)-6-morpholino-9H-purin-8-yl)methyl)piperazin-1-yl)propanamide;

(R)-1-(1-(8-((4-(2-hydroxypropan-2-yl)piperidin-1-yl)methyl)-9-methyl-6-morpholino-9H-purin-2-yl)-1H-benzo[d]imidazol-2-yl)propan-2-ol;

(S)-1-(1-(8-((4-(2-hydroxypropan-2-yl)piperidin-1-yl)methyl)-9-methyl-6-morpholino-9H-purin-2-yl)-1H-benzo[d]imidazol-2-yl)propan-2-ol;

(R)-8-((2-(2-ethyl-1H-benzo[d]imidazol-1-yl)-9-methyl-6-morpholino-9H-purin-8-yl)methyl)octahydropyrazino[2,1-c][1,4]oxazine;

4-methyl-5-((9-methyl-2-(2-methyl-1H-benzo[d]imidazol-1-yl)-6-morpholino-9H-purin-8-yl)methylamino)pentane-1,4-diol;

2-(1-(8-((4-tert-butylpiperazin-1-yl)methyl)-6-morpholino-9H-purin-2-yl)-1H-benzo[d]imidazol-2-yl)ethanol;

(1S,2R)-2-(4-((9-methyl-2-(2-methyl-1H-benzo[d]imidazol-1-yl)-6-morpholino-9H-purin-8-yl)methyl)piperazin-1-yl)cyclopentanol;

2-(4-((2-(2-cyclopropyl-1H-benzo[d]imidazol-1-yl)-9-methyl-6-morpholino-9H-purin-8-yl)methyl)piperazin-1-yl)-2-methylprop an-1-ol;

4-(2-(2-ethyl-1H-benzo[d]imidazol-1-yl)-9-methyl-8-((4-(3-methyloxetan-3-yl)piperazin-1-yl)methyl)-9H-purin-6-yl)morpholine;

(S)-4-(8-((hexahydropyrrolo[1,2-a]pyrazin-2(1H)-yl)methyl)-9-methyl-2-2-methyl-1H-benzo[d]imidazol-1-yl)-9H-purin-6-yl)morpholine;

(R)-4-(8-((hexahydropyrrolo[1,2-a]pyrazin-2(1H)-yl)methyl)-9-methyl-2-(2-methyl-1H-benzo[d]imidazol-1-yl)-9H-purin-6-yl)morpholine;

ethyl 2-((1S,4S)-5-((2-(2-ethyl-1H-benzo[d]imidazol-1-yl)-9-methyl-6-morpholino-9H-purin-8-yl)methyl)-2,5-diazabicyclo[2.2.1]heptan-2-yl)-2methylpropanoate;

1-((2-(2-ethyl-1H-benzo[d]imidazol-1-yl)-9-methyl-6-morpholino-9H-purin-8-yl)methyl)-N-methyl-N-(oxetan-3-yl)piperidin-4-amine;

N-((1-((2-(2-ethyl-1H-benzo[d]imidazol-1-yl)-9-methyl-6-morpholino-9H-purin-8-yl)methyl)azetidin-3-yl)methyl)-N-methyltetrahydrofuran-3-amine;

2-(1-((5-(2-ethyl-1H-benzo[d]imidazol-1-yl)-7-morpholinothiazolo[4,5-d]pyrimidin-2-yl)methyl)piperidin-4-yl)propan-2-ol;

N-((1-((2-(2-ethyl-1H-benzo[d]imidazol-1-yl)-9-methyl-6-morpholino-9H-purin-8-yl)methyl)azetidin-3-yl)methyl)-N-methyloxetan-3-amine;

4-(2-(2-ethyl-1H-benzo[d]imidazol-1-yl)-8-((3-(tetrahydro-2H-pyran-4-yl)azetidin-1-yl)methyl)-9H-purin-6-yl)morpholine;

2-methyl-2-(4-((2-(2-methyl-1H-benzo[d]imidazol-1-yl)-6-morpholino-9H-purin-8-yl)methyl)piperazin-1-yl)propanamide;

2-(4-((2-(2-ethyl-1H-benzo[d]imidazol-1-yl)-6-morpholino-9H-purin-8-yl)methyl)piperazin-1-yl)-2-methylpropanamide;

2-(1-((2-(2-(2-hydroxyethyl)-1H-benzo[d]imidazol-1-yl)-6-morpholino-9H-purin-8-yl)methyl)piperidin-4-yl)propan-2-ol;

2-(4-((2-(2-(2-hydroxyethyl)-1H-benzo[d]imidazol-1-yl)-9-methyl-6-morpholino-9H-purin-8-yl)methyl)piperazin-1-yl)-2-methylpropan-1-ol;

1-(8-((4-tert-butylpiperazin-1-yl)methyl)-9-methyl-6-morpholino-9H-purin-2-yl)-N-methyl-1H-benzo[d]imidazol-2-amine;

4-methyl-1-((9-methyl-2-(2-methyl-1-benzo[d]imidazol-1-yl)-6-morpholino-9H-purin-8-yl)methyl)azepan-4-ol;

N-((9-methyl-2-(2-methyl-1H-benzo[d]imidazol-1-yl)-6-morpholino-9H-purin-8-yl)methyl)-2-(1H-pyrazol-1-yl)ethanamine;

(1-aminocyclopropyl)(4-((2-(2-ethyl-1H-benzo[d]imidazol-1-yl)-9-methyl-6-morpholino-9H-purin-8-yl)methyl)piperazin-1-yl)methanone;

2-(1-(2-(5-(2-ethyl-1H-benzo[d]imidazol-1-yl)-7-morpholinothiazolo[5,4-d]pyrimidin-2-yl)ethyl)piperidin-4-yl)propan-2-ol;

2-(1-(8-((4-tert-butylpiperazin-1-yl)methyl)-9-methyl-6-morpholino-9H-purin-2-yl)-1H-benzo[d]imidazol-2-yl)ethanol;

N-methyl-1-(9-methyl-6-morpholino-8-((3-(tetrahydro-2H-pyran-4-yl)azetidin-1-yl)methyl)-9H-purin-2-yl)-1H-benzo[d]imidazol-2-amine;

4-(5-(2-ethyl-1H-benzo[d]imidazol-1-yl)-2-((3-(1,1-dioxo-thiomorpholino)azetidin-1-yl)methyl)thiazolo[5,4-d]pyrimidin-7-yl)morpholine;

2-(4-((2-(2-ethyl-1H-benzo[d]imidazol-1-yl)-9-methyl-6-morpholino-9H-purin-8-yl)methyl)piperazin-1-yl)-2-methylpropanamide;

2-(4-((2-(2-cyclopropyl-1H-benzo[d]imidazol-1-yl)-9-methyl-6-morpholino-9H-purin-8-yl)methyl)piperazin-1-yl)-2-methylpropanamide;

2-(4-((2-(2-isopropyl-1H-benzo[d]imidazol-1-yl)-9-methyl-6-morpholino-9H-purin-8-yl)methyl)piperazin-1-yl)-2-methylpropanamide;

2-(4-((2-(2-ethyl-1H-benzo[d]imidazol-1-yl)-9-methyl-6-morpholino-9H-purin-8

4-(8-((4-isopropylpiperazin-1-yl)methyl)-9-methyl-2-(2-methyl-1H-benzo[d]imidazol-1yl)-9H-purin-6-yl)morpholine;

4-(2-(2-ethyl-1H-benzo[d]imidazol-1-yl)-8-((4-isopropylpiperazin-1-yl)methyl)-9-methyl-9H-purin-6-yl)morpholine;

4-(8-((4-cyclobutylpiperazin-1-yl)methyl)-2-(2-methyl-1H-benzo[d]imidazol-1-yl)-9-methyl-9H-purin-6-yl)morpholine;

4-(9-methyl-2-(2-methyl-1H-benzo[d]imidazol-1-yl)-8-((4-(oxetan-3-yl)piperidin-1-yl)methyl)-9H-purin-6-yl)morpholine;

N-methyl-1-(9-methyl-6-morpholino-8-((4-(oxetan-3-yl)piperidin-1-yl)methyl)-9H-purin-2-yl)-1H-benzo[d]imidazol-2-amine;

4-(5-(2-methyl-1H-benzo[d]imidazol-1-yl)-2-((3-(1,1-dioxo-thiomorpholino)azetidin-1-yl)methyl)thiazolo[5,4-d]pyrimidin-7-yl)morpholine;

4-(2-(2-isopropyl-1H-benzo[d]imidazol-1-yl)-9-methyl-8-((3-(1,1-dioxo-thiomorpholino)azetidin-1-yl)methyl)-9H-purin-6-yl)morpholine;

4-(2-(2-cyclopropyl-1H-benzo[d]imidazol-1-yl)-9-methyl-8-((4-(oxetan-3-yl)piperidin-1-yl)methyl)-9H-purin-6-yl)morpholine;

2-(1-(2-(2-(2-ethyl-1H-benzo[d]imidazol-1-yl)-9-methyl-6-morpholino-9H-purin-8-yl)ethyl)azetidin-3-yl)propan-2-ol;

1-(2-(2-(2-ethyl-1H-benzo[d]imidazol-1-yl)-9-methyl-6-morpholino-9H-purin-8-yl)ethyl)-4-methylpiperidin-4-ol;
2-methyl-2-(4-((9-methyl-2-(2-(methylamino)-1H-benzo[d]imidazol-1-yl)-6-morpholino-9H-purin-8-yl)methyl)piperazin-1-yl)propan-1-ol;
4-(2-(2-(azetidin-1-yl)-1H-benzo[d]imidazol-1-yl)-8-((4-tert-butylpiperazin-1-yl)methyl)-9-methyl-9H-purin-6-yl)morpholine;
2-(1-((2-(2-(azetidin-1-yl)-1H-benzo[d]imidazol-1-yl)-9-methyl-6-morpholino-9H-purin-8-yl)methyl)piperidin-4-yl)propan-2-ol;
ethyl 2-methyl-2-(4-((9-methyl-2-(2-methyl-1H-benzo[d]imidazol-1-yl)-6-morpholino-9H-purin-8-yl)methyl)piperidin-1-yl)propanoate;
4-(8-((4-tert-butylpiperazin-1-yl)methyl)-2-(2(1,1-difluoroethyl)-1H-benzo[d]imidazol-1-yl)-9H-purin-6-yl)morpholine;
1-(2-(2-(2-ethyl-1H-benzo[d]imidazol-1-yl)-9-methyl-6-morpholino-9H-purin-8-yl)ethyl)-3-methylazetidin-3-ol;
4-(2-(2-(1,1-difluoroethyl)-1H-benzo[d]imidazol-1-yl)-9-methyl-8-((4-(oxetan-3-yl)piperidin-1-yl)methyl)-9H-purin-6-yl)morpholine;
(S)-(1-((2-(2-ethyl-1H-benzo[d]imidazol-1-yl)-9-methyl-6-morpholino-9H-purin-8-yl)methyl)azetidin-3-yl)(3-hydroxypyrrolidin-1-yl)methanone;
(R)-(1-((2-(2-ethyl-1H-benzo[d]imidazol-1-yl)-9-methyl-6-morpholino-9H-purin-8-yl)methyl)azetidin-3-yl)(3-hydroxypyrrolidin-1-yl)methanone;
2-(1-((2-(2-tert-butyl-1H-benzo[d]imidazol-1-yl)-9-methyl-6-morpholino-9H-purin-8-yl)methyl)piperidin-4-yl)propan-2-ol;
4-(8-((4-tert-butylpiperazin-1-yl)methyl)-2-(2-(1,1-difluoroethyl)-1H-benzo[d]imidazol-1-yl)-9-methyl-9H-purin-6-yl)morpholine;
4-(8-((4-tert-butylpiperazin-1-yl)methyl)-9-methyl-2-(2-(trifluoromethyl)-1H-benzo[d]imidazol-1-yl)-9H-purin-6-yl)morpholine;
7-(2-(2-(2-ethyl-1H-benzo[d]imidazol-1-yl)-9-methyl-6-morpholino-9H-purin-8-yl)ethyl)-7-azaspiro[3.5]nonan-2-ol;
1-(2-(2-(2-ethyl-1H-benzo[d]imidazol-1-yl)-9-methyl-6-morpholino-9H-purin-8-yl)ethyl)-3-isopropylazetidin-3-ol;
4-(9-methyl-2-(2-methyl-1H-benzo[d]imidazol-1-yl)-8-((3-(tetrahydro-2H-pyran-4-yl)azetidin-1-yl)methyl)-9H-purin-6-yl)morpholine;
4-(2-(2-(1,1-difluoroethyl)-1H-benzo[d]imidazol-1-yl)-9-methyl-8-((3-(tetrahydro-2H-pyran-4-yl)azetidin-1-yl)methyl)-9H-purin-6-yl)morpholine;
4-((2-(2-ethyl-1H-benzo[d]imidazol-1-yl)-9-methyl-6-morpholino-9H-purin-8-yl)methyl)-1-isopropylpiperazin-2-one;
4-(5-(2-isopropyl-1H-benzo[d]imidazol-1-yl)-2-((3-(tetrahydro-2H-pyran-4-yl)azetidin-1-yl)methyl)thiazolo[5,4-d]pyrimidin-7-yl)morpholine;
4-(8-((4-tert-butylpiperazin-1-yl)methyl)-2-(2-isopropyl-1H-benzo[d]imidazol-1-yl)-9-methyl-9H-purin-6-yl)morpholine;
2-(4-((2-(2-(1,1-difluoroethyl)-1H-benzo[d]imidazol-1-yl)-9-methyl-6-morpholino-9H-purin-8-yl)methyl)piperazin-1-yl)-2-methylpropan-1-ol;
2-methyl-2-(4-((9-methyl-6-morpholino-2-(2-(trifluoromethyl)-1H-benzo[d]imidazol-1-yl)-9H-purin-8-yl)methyl)piperazin-1-yl)propan-1-ol;
2-(4-((2-(2-isopropyl-1H-benzo[d]imidazol-1-yl)-9-methyl-6-morpholino-9H-purin-8-yl)methyl)piperazin-1-yl)-2-methylpropan-1-ol;
2-(1-((2-(2-((1R,2S)-2-fluorocyclopropyl)-1H-benzo[d]imidazol-1-yl)-9-methyl-6-morpholino-9H-purin-8-yl)methyl)piperidin-4-yl)propan-2-ol;
(R)-2-(1-((2-(2-(2,2-difluorocyclopropyl)-1H-benzo[d]imidazol-1-yl)-9-methyl-6-morpholino-9H-purin-8-yl)methyl)piperidin-4-yl)propan-2-ol;
2-(1-((2-(2-((1S,2R)-2-fluorocyclopropyl)-1H-benzo[d]imidazol-1-yl)-9-methyl-6-morpholino-9H-purin-8-yl)methyl)piperidin-4-yl)propan-2-ol;
2-(1-((2-(2-((1R,2R)-2-fluorocyclopropyl)-1H-benzo[d]imidazol-1-yl)-9-methyl-6-morpholino-9H-purin-8-yl)methyl)piperidin-4-yl)propan-2-ol;
(S)-2-(1-((2-(2-(2,2-difluorocyclopropyl)-1H-benzo[d]imidazol-1-yl)-9-methyl-6-morpholino-9H-purin-8-yl)methyl)piperidin-4-yl)propan-2-ol;
4-(5-(2-methyl-1H-benzo[d]imidazol-1-yl)-2-((3-(tetrahydro-2H-pyran-4-yl)azetidin-1-yl)methyl)thiazolo[5,4-d]pyrimidin-7-yl)morpholine;
4-(5-(2-ethyl-1H-benzo[d]imidazol-1-yl)-2-((3-(tetrahydro-2H-pyran-4-yl)azetidin-1-yl)methyl)thiazolo[5,4-d]pyrimidin-7-yl)morpholine;
4-(5-(2-cyclopropyl-1H-benzo[d]imidazol-1-yl)-2-((3-(tetrahydro-2H-pyran-4-yl)azetidin-1-yl)methyl)thiazolo[5,4-d]pyrimidin-7-yl)morpholine;
2-(1-((2-(2-ethyl-4-fluoro-1H-benzo[d]imidazol-1-yl)-9-methyl-6-morpholino-9H-purin-8-yl)methyl)piperidin-4-yl)propan-2-ol;
1-(1-((2-(2-ethyl-1H-benzo[d]imidazol-1-yl)-9-methyl-6-morpholino-9H-purin-8-yl)methyl)azetidin-3-yl)piperidin-4-ol;
2-(1-((2-(2-(azetidin-1-ylmethyl)-1H-benzo[d]imidazol-1-yl)-9-methyl-6-morpholino-9H-purin-8-yl)methyl)piperidin-4-yl)propan-2-ol;
2-(4-((2-(2-cyclopropyl-1H-benzo[d]imidazol-1-yl)-6-morpholino-9H-purin-8-yl)methyl)piperazin-1-yl)-2-methylpropan-1-ol;
2-(4-((2-(2-ethyl-1H-benzo[d]imidazol-1-yl)-6-morpholino-9H-purin-8-yl)methyl)piperazin-1-yl)-2-methylpropan-1-ol;
2-(4-((2-(2-isopropyl-1H-benzo[d]imidazol-1-yl)-6-morpholino-9H-purin-8-yl)methyl)piperazin-1-yl)-2-methylpropan-1-ol;
4-(2-(2-ethyl-1H-benzo[d]imidazol-1-yl)-8-((3-(4-fluoropiperidin-1-yl)azetidin-1-yl)methyl)-9-methyl-9H-purin-6-yl)morpholine;
4-(8-((3-(4,4-difluoropiperidin-1-yl)azetidin-1-yl)methyl)-2-(2-ethyl-1H-benzo[d]imidazol-1-yl)-9-methyl-9H-purin-6-yl)morpholine;
4-(2-(2-(2-ethyl-1H-benzo[d]imidazol-1-yl)-9-methyl-6-morpholino-9H-purin-8-yl)ethyl)-1-isopropylpiperazin-2-one;
1'-((2-(2-ethyl-1H-benzo[d]imidazol-1-yl)-9-methyl-6-morpholino-9H-purin-8-yl)methyl)-1,3'-biazetidin-3-ol;
4-(2-(2-ethyl-1H-benzo[d]imidazol-1-yl)-9-methyl-8-((4-(tetrahydro-2H-pyran-4-yl)piperazin-1-yl)methyl)-9H-purin-6-yl)morpholine;
4-(5-(2-ethyl-1H-benzo[d]imidazol-1-yl)-2-((4-(oxetan-3-yl)piperidin-1-yl)methyl)thiazolo[5,4-d]pyrimidin-7-yl)morpholine;
4-(5-(2-cyclopropyl-1H-benzo[d]imidazol-1-yl)-2-((4-(oxetan-3-yl)piperidin-1-yl)methyl)thiazolo[5,4-d]pyrimidin-7-yl)morpholine;

N-methyl-1-(7-morpholino-2-((3-(tetrahydro-2H-pyran-4-yl)azetidin-1-yl)methyl)thiazolo[5,4-d]pyrimidin-5-yl)-1H-benzo[d]imidazol-2-amine;

4-(2-(2-cyclopropyl-1H-benzo[d]imidazol-1-yl)-9-methyl-8-((3-(tetrahydro-2H-pyran-4-yl)azetidin-1-yl)methyl)-9H-purin-6-yl)morpholine;

ethyl 2-(4-((2-(2-cyclopropyl-1H-benzo[d]imidazol-1-yl)-9-methyl-6-morpholino-9H-purin-8-yl)methyl)piperazin-1-yl)-2-methylpropanoate;

4-(2-(2-ethyl-1H-benzo[d]imidazol-1-yl)-9-methyl-8-((1-(tetrahydro-2H-(1,1-dioxo)-thiopyran-4-yl)azetidin-3-yl)methyl)-9H-purin-6-yl)morpholine;

ethyl 2-methyl-2-(4-((9-methyl-2-(2-methyl-1H-benzo[d]imidazol-1-yl)-6-morpholino-9H-purin-8-yl)methyl)piperazin-1-yl)propanoate;

4-(2-(2-ethyl-1H-benzo[d]imidazol-1-yl)-9-methyl-8-((1-(tetrahydro-2H-pyran-4-yl)azetidin-3-yl)methyl)-9H-purin-6-yl)morpholine;

4-(2-(2-ethyl-1H-benzo[d]imidazol-1-yl)-8-((4-(1-fluoro-2-methylpropan-2-yl)piperazin-1-yl)methyl)-9-methyl-9H-purin-6-yl)morpholine;

tert-butyl 4-((9-methyl-2-(2-methyl-1H-benzo[d]imidazol-1-yl)-6-morpholino-9H-purin-8-yl)methyl)piperidine-1-carboxylate;

2-methyl-2-(4-((9-methyl-2-(2-methyl-1H-benzo[d]imidazol-1-yl)-6-morpholino-9H-purin-8-yl)methyl)piperazin-1-yl)propanoic acid;

methyl 2-methyl-2-(4-((9-methyl-2-(2-methyl-1H-benzo[d]imidazol-1-yl)-6-morpholino-9H-purin-8-yl)methyl)piperidin-1yl)propanoate;

2-methyl-2-(4-((9-methyl-2-(2-methyl-1H-benzo[d]imidazol-1-yl)-6-morpholino-9H-purin-8-yl)methyl)piperidin-1-yl)propanamide;

2-methyl-2-(4-((9-methyl-2-(2-methyl-1H-benzo[d]imidazol-1-yl)-6-morpholino-9H-purin-8-yl)methyl)piperidin-1yl)propan-1-ol;

8-(2-(2-(2-ethyl-1H-benzo[d]imidazol-1-yl)-9-methyl-6-morpholino-9H-purin-8-yl)ethyl)-3-oxa-8-azabicyclo[3.2.1]octane;

2-(1-(9-methyl-6-morpholino-8-((4-(oxetan-3-yl)piperidin-1-yl)methyl)-9H-purin-2-yl)-1H-benzo[d]imidazol-2-yl)ethanol;

4-(2-(2-ethyl-1H-benzo[d]imidazol-1-yl)-9-methyl-8-((4-(oxetan-3-yl)piperazin-1-yl)methyl)-9H-purin-6-yl)morpholine;

4-(1-((2-(2-ethyl-1H-benzo[d]imidazol-1-yl)-9-methyl-6-morpholino-9H-purin-8-yl)methyl)azetidin-3-yl)piperazin-2-one;

(S)-3-(2-(2-ethyl-1H-benzo[d]imidazol-1-yl)-9-methyl-6-morpholino-9H-purin-8-yl)-1-isopropylpiperidin-3-ol;

(S)-2-(1-((2-(2-(1-methoxyethyl)-1H-benzo[d]imidazol-1-yl)-9-methyl-6-morpholino-9H-purin-8-yl)methyl)piperidin-4-yl)propan-2-ol;

N-(1-(8-((4-(2-hydroxypropan-2-yl)piperidin-1-yl)methyl)-9-methyl-6-morpholino-9H-purin-2-yl)-1H-benzo[d]imidazol-2-yl)acetamide;

(R)-3-(2-(2-ethyl-1H-benzo[d]imidazol-1-yl)-9-methyl-6-morpholino-9H-purin-8-yl)-1-isopropylpiperidin-3-ol;

(R)-2-(1-((2-(2-(1-methoxyethyl)-1H-benzo[d]imidazol-1-yl)-9-methyl-6-morpholino-9H-purin-8-yl)methyl)piperidin-4-yl)propan-2-ol;

4-(9-methyl-2-(2-methyl-1H-benzo[d]imidazol-1-yl)-8-(piperidin-4-ylmethyl)-9H-purin-6-yl)morpholine;

2-((1S,4S)-5-((2-(2-ethyl-1H-benzo[d]imidazol-1-yl)-9-methyl-6-morpholino-9H-purin-8-yl)methyl)-2,5-diazabicyclo[2.2.1]heptan-2-yl)-2-methylpropan-1-ol;

4-(2-(2-(2-ethyl-1H-benzo[d]imidazol-1-yl)-9-methyl-6-morpholino-9H-purin-8-yl)ethyl)-6-isopropylpiperazin-2-one;

1-(4-((2-(2-ethyl-1H-benzo[d]imidazol-1-yl)-9-methyl-6-morpholino-9H-purin-8-yl)methyl)piperazin-1-yl)-2-methylpropan-2-ol;

1-((2-(2-ethyl-1H-benzo[d]imidazol-1-yl)-9-methyl-6-morpholino-9H-purin-8-yl)methyl)azetidin-3-ol;

2-methyl-2-(4-((9-methyl-2-(2-methyl-1H-benzo[d]imidazol-1-yl)-6-morpholino-9H-purin-8-yl)methyl)piperidin-1yl)propanoic acid;

(R)-methyl 2-(4-((2-(2-ethyl-1H-benzo[d]imidazol-1-yl)-9-methyl-6-morpholino-9H-purin-8-yl)(hydroxy)methyl)piperidin-1-yl)-2-methylpropanoate;

(S)-methyl 2-(4-((2-(2-ethyl-1H-benzo[d]imidazol-1-yl)-9-methyl-6-morpholino-9H-purin-8-yl)(hydroxy)methyl)piperidin-1-yl)-2-methylpropanoate;

methyl 2-(4-(2-(2-ethyl-1H-benzo[d]imidazol-1-yl)-9-methyl-6-morpholino-9H-purine-8-carbonyl)piperidin-1-yl)-2-methylpropanoate;

4-(2-(2-ethyl-1H-benzo[d]imidazol-1-yl)-9-methyl-8-((1-(oxetan-3-yl)azetidin-3-yl)methyl)-9H-purin-6-yl)morpholine;

4-(8-(azetidin-3-ylmethyl)-2-(2-ethyl-1H-benzo[d]imidazol-1-yl)-9-methyl-9H-purin-6-yl)morpholine;

2-(3-((2-(2-ethyl-1H-benzo[d]imidazol-1-yl)-9-methyl-6-morpholino-9H-purin-8-yl)methyl)azetidin-1-yl)-2-methylpropanamide;

methyl 2-(3-((2-(2-ethyl-1H-benzo[d]imidazol-1-yl)-9-methyl-6-morpholino-9H-purin-8-yl)methyl)azetidin-1-yl)-2-methylpropanoate;

2-(3-((2-(2-ethyl-1H-benzo[d]imidazol-1-yl)-9-methyl-6-morpholino-9H-purin-8-yl)methyl)azetidin-1-yl)-2-methylpropan-1-ol;

1-(3-((2-(2-ethyl-1H-benzo[d]imidazol-1-yl)-9-methyl-6-morpholino-9H-purin-8-yl)methyl)azetidin-1-yl)-2-methylpropan-2-ol;

4-(2-(2-(2-ethyl-1H-benzo[d]imidazol-1-yl)-9-methyl-6-morpholino-9H-purin-8-yl)ethyl)-3,3-dimethylmorpholine;

(S)-1-(1-((2-(2-ethyl-1H-benzo[d]imidazol-1-yl)-9-methyl-6-morpholino-9H-purin-8-yl)methyl)azetidin-3-yl)pyrrolidin-3-ol;

4-(2-(2-ethyl-1H-benzo[d]imidazol-1-yl)-9-methyl-8-(2-((3-(1,-dioxo-thiomorpholino)azetidin-1-yl)ethyl)-9H-purin-6-yl)morpholine;

(R)-1-(1-((2-(2-ethyl-1H-benzo[d]imidazol-1-yl)-9-methyl-6-morpholino-9H-purin-8-yl)methyl)azetidin-3-yl)pyrrolidin-3-ol;

4-(2-(2-ethyl-1H-benzo[d]imidazol-1-yl)-9-methyl-8-(2-(1,1-dioxo-thiomorpholino)ethyl)-9H-purin-6-yl)morpholine;

4-(8-(2-(4,4-difluoropiperidin-1-yl)ethyl)-2-(2-ethyl-1H-benzo[d]imidazol-1-yl)-9-methyl-9H-purin-6-yl)morpholine;

2-(3-((2-(2-ethyl-1H-benzo[d]imidazol-1-yl)-9-methyl-6-morpholino-9H-purin-8-yl)methyl)azetidin-1-yl)acetamide;

2-methyl-1-(4-((9-methyl-2-(2-methyl-1H-benzo[d]imidazol-1-yl)-6-morpholino-9H-purin-8-yl)methyl)piperidin-1-yl)propan-2-ol;

4-(9-methyl-2-(2-methyl-1H-benzo[d]imidazol-1-yl)-8-((1-(2-(methylsulfonyl)ethyl)azetidin-3-yl)methyl)-9H-purin-6-yl)morpholine;

4-(9-methyl-2-(2-methyl-1H-benzo[d]imidazol-1-yl)-8-((1-(2-(methylsulfonyl)ethyl)piperidin-4-yl)methyl)-9H-purin-6-yl)morpholine;

(R)-2-(3-((2-(2-ethyl-1H-benzo[d]imidazol-1-yl)-9-methyl-6-morpholino-9H-purin-8-yl)methyl)azetidin-1-yl)propanamide;

(S)-2-(3-((2-(2-ethyl-1H-benzo[d]imidazol-1-yl)-9-methyl-6-morpholino-9H-purin-8-yl)methyl)azetidin-1-yl)propanamide;

4-(1-((2-(2-isopropyl-1H-benzo[d]imidazol-1-yl)-9-methyl-6-morpholino-9H-purin-8-yl)methyl)azetidin-3-yl)morpholine;

4-(1-((2-(2-cyclopropyl-1H-benzo[d]imidazol-1-yl)-9-methyl-6-morpholino-9H-purin-8-yl)methyl)azetidin-3-yl)morpholine;

2-(5-(2-ethyl-1H-benzo[d]imidazol-1-yl)-7-morpholinothiazolo[5,4-d]pyrimidin-2-yl)-1-(4-(2-hydroxypropan-2-yl)piperidin-1-yl)ethanone;

1-(1-((2-(2-isopropyl-1H-benzo[d]imidazol-1-yl)-9-methyl-6-morpholino-9H-purin-8-yl)methyl)azetidin-3-yl)piperidin-4-ol;

1-(1-((2-(2-ethyl-1H-benzo[d]imidazol-1-yl)-9-methyl-6-morpholino-9H-purin-8-yl)methyl)azetidin-3-yl)-4-methylpiperidin-4-ol;

4-(8-((3,3-diethylpiperazin-1-yl)methyl)-2-(2-ethyl-1H-benzo[d]imidazol-1-yl)-9-methyl-9H-purin-6-yl)morpholine;

4-(2-(2-ethyl-1H-benzo[d]imidazol-1-yl)-9-methyl-8-(((1S,4S)-5-(methylsulfonyl)-2,5-diazabicyclo[2.2.1]heptan-2-yl)methyl)-9H-purin-6-yl)morpholine;

1-(1-((2-(2-ethyl-1H-benzo[d]imidazol-1-yl)-9-methyl-6-morpholino-9H-purin-8-yl)methyl)piperidin-4-yl)azetidin-3-ol;

1-isopropyl-4-((2-(2-isopropyl-1H-benzo[d]imidazol-1-yl)-9-methyl-6-morpholino-9H-purin-8-yl)methyl)piperazin-2-one;

4-(1-((2-(2-ethyl-1H-benzo[d]imidazol-1-yl)-9-methyl-6-morpholino-9H-purin-8-yl)methyl)azetidin-3-yl)-1-methylpiperazin-2-one;

4-(2-(2-ethyl-1H-benzo[d]imidazol-1-yl)-9-methyl-8-(2-(4-(tetrahydro-2H-pyran-4-yl)piperazin-1-yl)ethyl)-9H-purin-6-yl)morpholine;

2-(4-((9-methyl-2-(2-methyl-1H-benzo[d]imidazol-1-yl)-6-morpholino-9H-purin-8-yl)methyl)piperidin-1-yl)acetamide;

(R)-2-(4-((9-methyl-2-(2-methyl-1-benzo[d]imidazol-1-yl)-6-morpholino-9H-purin-8-yl)methyl)piperidin-1-yl)propanamide;

(S)-2-(4-((9-methyl-2-(2-methyl-1-benzo[d]imidazol-1-yl)-6-morpholino-9H-purin-8-yl)methyl)piperidin-1-yl)propanamide;

(R)-4-(2-(2-ethyl-1H-benzo[d]imidazol-1-yl)-8-((4-(3-fluoropyrrolidin-1-yl)piperidin-1-yl)methyl)-9-methyl-9H-purin-6-yl)morpholine;

4-(8-((3,3-difluoro-1,3'-biazetidin-1'-yl)methyl)-2-(2-ethyl-1H-benzo[d]imidazol-1-yl)-9-methyl-9H-purin-6-yl)morpholine;

4-(2-(2-isopropyl-1H-benzo[d]imidazol-1-yl)-9-methyl-8-(((1S,4S)-5-(methylsulfonyl)-2,5-diazabicyclo[2.2.1]heptan-2-yl)methyl)-9H-purin-6-yl)morpholine;

4-(2-(2-isopropyl-1H-benzo[d]imidazol-1-yl)-9-methyl-8-((4-(tetrahydro-2H-pyran-4-yl)piperazin-1-yl)methyl)-9H-purin-6-yl)morpholine;

(S)-4-(2-(2-ethyl-1H-benzo[d]imidazol-1-yl)-8-((4-(3-fluoropyrrolidin-1-yl)piperidin-1-yl)methyl)-9-methyl-9H-purin-6-yl)morpholine;

2-(4-(2-(2-ethyl-1H-benzo[d]imidazol-1-yl)-9-methyl-6-morpholino-9H-purine-8-carbonyl)piperazin-1-yl)-2-methylpropanamide;

4-tert-butylpiperazin-1-yl)(2-(2-ethyl-1H-benzo[d]imidazol-1-yl)-9-methyl-6-morpholino-9H-purin-8-yl)methanone;

3-(4-((9-methyl-2-(2-methyl-1H-benzo[d]imidazol-1-yl)-6-morpholino-9H-purin-8-yl)methyl)piperidin-1-yl)propanenitrile;

(2-(2-ethyl-1H-benzo[d]imidazol-1-yl)-9-methyl-6-morpholino-9H-purin-8-yl)(4-(2-hydroxypropan-2-yl)piperidin-1-yl)methanone;

4-(8-((1-(isoxazol-5-ylmethyl)piperidin-4-yl)methyl)-9-methyl-2-(2-methyl-1H-benzo[d]imidazol-1-yl)-9H-purin-6-yl)morpholine;

4-(8-((1-(isoxazol-5-ylmethyl)azetidin-3-yl)methyl)-9-methyl-2-(2-methyl-1H-benzo[d]imidazol-1-yl)-9H-purin-6-yl)morpholine;

(S)-4-(9-methyl-2-(2-methyl-1-benzo[d]imidazol-1-yl)-8-((1-(tetrahydrofuran-3-yl)azetidin-3-yl)methyl)-9H-purin-6-yl)morpholine;

(R)-4-(9-methyl-2-(2-methyl-1H-benzo[d]imidazol-1-yl)-8-((1-(tetrahydrofuran-3-yl)azetidin-3-yl)methyl)-9H-purin-6-yl)morpholine;

4-(8-(2-(3,3-dimethyl-4-(methylsulfonyl)piperazin-1-yl)ethyl)-2-(2-ethyl-1H-benzo[d]imidazol-1-yl)-9-methyl-9H-purin-6-yl)morpholine;

4-(8-((4-(3,3-difluoroazetidin-1-yl)piperidin-1-yl)methyl)-2-(2-ethyl-1H-benzo[d]imidazol-1-yl)-9-methyl-9H-purin-6-yl)morpholine;

1-tert-butyl-4-((2-(2-ethyl-1H-benzo[d]imidazol-1-yl)-9-methyl-6-morpholino-9H-purin-8-yl)methyl)piperazin-2-one;

(S)-2-amino-1-(4-((9-methyl-2-(2-methyl-1H-benzo[d]imidazol-1-yl)-6-morpholino-9H-purin-8-yl)methyl)piperidin-1-yl)propan-1-one;

3-methyl-2-(3-((9-methyl-2-(2-methyl-1H-benzo[d]imidazol-1-yl)-6-morpholino-9H-purin-8-yl)methyl)azetidin-1-yl)butanamide;

N,2-dimethyl-2-(3-((9-methyl-2-(2-methyl-1H-benzo[d]imidazol-1-yl)-6-morpholino-9H-purin-8-yl)methyl)azetidin-1-yl)propanamide;

(S)-3-(2-(2-isopropyl-1H-benzo[d]imidazol-1-yl)-9-methyl-6-morpholino-9H-purin-8-yl)-1-methylpiperidin-3-ol;

(R)-3-(2-(2-isopropyl-1H-benzo[d]imidazol-1-yl)-9-methyl-6-morpholino-9H-purin-8-yl)-1-methylpiperidin-3-ol;

4-(2-(2-isopropyl-1H-benzo[d]imidazol-1-yl)-8-(1-isopropyl-3-methoxypiperidin-3-yl)-9-methyl-9H-purin-6-yl)morpholine;

4-(2-(2-isopropyl-1H-benzo[d]imidazol-1-yl)-8-(1-isopropyl-3-methoxypiperidin-3-yl)-9-methyl-9H-purin-6-yl)morpholine;

N,2-dimethyl-2-(4-((9-methyl-2-(2-methyl-1H-benzo[d]imidazol-1-yl)-6-morpholino-9H-purin-8-yl)methyl)piperidin-1-yl)propanamide;

(S)-4-(2-(2-ethyl-1H-benzo[d]imidazol-1-yl)-8-((3-(3-fluoropyrrolidin-1-yl)azetidin-1-yl)methyl)-9-methyl-9H-purin-6-yl)morpholine;

1'-((2-(2-ethyl-1H-benzo[d]imidazol-1-yl)-9-methyl-6-morpholino-9H-purin-8-yl)methyl)-3-methyl-1,3'-biazetidin-3-ol;

1-(1-((2-(2-ethyl-1H-benzo[d]imidazol-1-yl)-9-methyl-6-morpholino-9H-purin-8-yl)methyl)azetidin-3-yl)pyrrolidin-2-one;

4-(8-((3,3-difluoropyrrolidin-1-yl)azetidin-1-yl)methyl)-2-(2-ethyl-1H-benzo[d]imidazol-1-yl)-9-methyl-9H-purin-6-yl)morpholine;

(R)-4-(2-(2-ethyl-1H-benzo[d]imidazol-1-yl)-8-((3-(3-fluoropyrrolidin-1-yl)azetidin-1-yl)methyl)-9-methyl-9H-purin-6-yl)morpholine;

(R)-1-isopropyl-3-(2-(2-isopropyl-1H-benzo[d]imidazol-1-yl)-9-methyl-6-morpholino-9H-purin-8-yl)piperidin-3-ol;

(S)-1-isopropyl-3-(2-(2-isopropyl-1H-benzo[d]imidazol-1-yl)-9-methyl-6-morpholino-9H-purin-8-yl)piperidin-3-ol;

(2-(2-ethyl-1H-benzo[d]imidazol-1-yl)-9-methyl-6-morpholino-9H-purin-8-yl)(4-(tetrahydro-2H-(1,1-dioxo)-thiopyran-4-yl)piperazin-1-yl)methanone;

N-tert-butyl-1-((2-(2-ethyl-1H-benzo[d]imidazol-1-yl)-9-methyl-6-morpholino-9H-purin-8-yl)methyl)azetidin-3-amine;

N-(2-(2-(2-ethyl-1H-benzo[d]imidazol-1-yl)-9-methyl-6-morpholino-9H-purin-8-yl)ethyl)tetrahydro(1,1-dioxo)thiophen-3-amine;

4-(8-((2,2-dimethyl-4-(methylsulfonyl)piperazin-1-yl)methyl)-2-(2-ethyl-1H-benzo[d]imidazol-1-yl)-9-methyl-9H-purin-6-yl)morpholine;

2-(((1S,4S)-5-((2-(2-ethyl-1H-benzo[d]imidazol-1-yl)-9-methyl-6-morpholino-9H-purin-8-yl)methyl)-2,5-diazabicyclo[2.2.1]heptan-2-yl)acetamide;

4-(2-(2-ethyl-1H-benzo[d]imidazol-1-yl)-9-methyl-8-(((1S,4S)-5-(oxetan-3-yl)-2,5-diazabicyclo[2.2.1]heptan-2-yl)methyl)-9H-purin-6-yl)morpholine;

2-methyl-2-(4-(methyl(9-methyl-2-(2-methyl-1H-benzo[d]imidazol-1-yl)-6-morpholino-9H-purin-8-yl)amino)piperidin-1-yl)propanamide;

2-(2-ethyl-1H-benzo[d]imidazol-1-yl)-N,N-bis(2-methoxyethyl)-9-methyl-6-morpholino-9H-purine-8-carboxamide;

(4-(dimethylamino)piperidin-1-yl)(2-(2-ethyl-1H-benzo[d]imidazol-1-yl)-9-methyl-6-morpholino-9H-purin-8-yl)methanone;

2-methyl-2-(3-((9-methyl-2-(2-methyl-1H-benzo[d]imidazol-1-yl)-6-morpholino-9H-purin-8-yl)methyl)pyrrolidin-1-yl)propanamide;

2-methyl-2-(3-((9-methyl-2-(2-methyl-1H-benzo[d]imidazol-1-yl)-6-morpholino-9H-purin-8-yl)methyl)pyrrolidin-1-yl)propanamide;

1-(3-hydroxy-3-(2-(2-isopropyl-1H-benzo[d]imidazol-1-yl)-9-methyl-6-morpholino-9H-purin-8-yl)piperidin-1-yl)ethanone;

(S)-8-((2-(2-ethyl-1H-benzo[d]imidazol-1-yl)-9-methyl-6-morpholino-9H-purin-8-yl)methyl)-4,4-dimethylhexahydropyrazino[2,1-c][1,4]oxazin-3(1H)-one;

(R)-8-((2-(2-ethyl-1H-benzo[d]imidazol-1-yl)-9-methyl-6-morpholino-9H-purin-8-yl)methyl)-4,4-dimethylhexahydropyrazino[2,1-c][1,4]oxazin-3(1H)-one;

N-(2-(2-(2-ethyl-1H-benzo[d]imidazol-1-yl)-9-methyl-6-morpholino-9H-purin-8-yl)ethyl)-N-methyl-1,1-dioxotetrahydrothiophen-3-amine;

4-(2-(2-ethyl-1H-benzo[d]imidazol-1-yl)-8-((4-(3-fluoroazetidin-1-yl)piperidin-1-yl)methyl)-9-methyl-9H-purin-6-yl)morpholine;

2-methyl-2-(4-((9-methyl-2-(2-methyl-1H-benzo[d]imidazol-1-yl)-6-morpholino-9H-purin-8-yl)methylene)piperidin-1-yl)propanamide;

2-methyl-2-(4-((9-methyl-2-(2-methyl-1H-benzo[d]imidazol-1-yl)-6-morpholino-9H-purin-8-yl)methylene)piperidin-1-yl)propanamide;

(2-(2-ethyl-1H-benzo[d]imidazol-1-yl)-9-methyl-6-morpholino-9H-purin-8-yl)(hexahydropyrrolo[1,2-a]pyrazin-2(1H)-yl)methanone;

(2-(2-ethyl-1H-benzo[d]imidazol-1-yl)-9-methyl-6-morpholino-9H-purin-8-yl)(hexahydropyrrolo[1,2-a]pyrazin-2(1H)-yl)methanone;

4-(9-methyl-2-(2-methyl-1H-benzo[d]imidazol-1-yl)-8-(piperidin-4-ylidenemethyl)-9H-purin-6-yl)morpholine;

4-(8-(((3S,5R)-3,5-dimethylpiperazin-1-yl)methyl)-2-(2-ethyl-1H-benzo[d]imidazol-1-yl)-9-methyl-9H-purin-6-yl)morpholine;

4-(9-methyl-2-(2-methyl-1H-benzo[d]imidazol-1-yl)-8-(piperidin-4-ylidenemethyl)-9H-purin-6-yl)morpholine;

2-(3-((2-(2-ethyl-1H-benzo[d]imidazol-1-yl)-9-methyl-6-morpholino-9H-purin-8-yl)methylene)azetidin-1-yl)-2-methylpropanamide;

2-(3-((2-(2-ethyl-1H-benzo[d]imidazol-1-yl)-9-methyl-6-morpholino-9H-purin-8-yl)methylene)azetidin-1-yl)-2-methylpropanamide;

1-(4-(2-(2-ethyl-1H-benzo[d]imidazol-1-yl)-9-methyl-6-morpholino-9H-purine-8-carbonyl)-1,4-diazepan-1-yl)ethanone;

(2-(2-ethyl-1H-benzo[d]imidazol-1-yl)-9-methyl-6-morpholino-9H-purin-8-yl)(4-hydroxypiperidin-1yl)methanone;

(2-(2-ethyl-1H-benzo[d]imidazol-1-yl)-9-methyl-6-morpholino-9H-purin-8-yl)(pyrrolidin-1-yl)methanone;

azetidin-1-yl(2-(2-ethyl-1H-benzo[d]imidazol-1-yl)-9-methyl-6-morpholino-9H-purin-8-yl)methanone;

(2-(2-ethyl-1H-benzo[d]imidazol-1-yl)-9-methyl-6-morpholino-9H-purin-8-yl)(2-(hydroxymethyl)piperidin-1yl)methanone;

(2-(2-ethyl-1H-benzo[d]imidazol-1-yl)-9-methyl-6-morpholino-9H-purin-8-yl)(4-(hydroxymethyl)piperidin-1yl)methanone;

4-(2-(2-ethyl-1H-benzo[d]imidazol-1-yl)-9-methyl-6-morpholino-9H-purine-8-carbonyl)piperazine-1-carbaldehyde;

(2-(2-ethyl-1H-benzo[d]imidazol-1-yl)-9-methyl-6-morpholino-9H-purin-8-yl)(3-(hydroxymethyl)piperidin-1yl)methanone;

(2-(2-ethyl-1H-benzo[d]imidazol-1-yl)-9-methyl-6-morpholino-9H-purin-8-yl)(4-(pyridin-3-yl)piperazin-1-yl)methanone;

N-(2-(dimethylamino)-2-oxoethyl)-2-(2-ethyl-1H-benzo[d]imidazol-1-yl)-N,9-dimethyl-6-morpholino-9H-purine-8-carboxamide;

(2-(2-ethyl-1H-benzo[d]imidazol-1-yl)-9-methyl-6-morpholino-9H-purin-8-yl)(4-(2-methoxyethyl)piperazin-1-yl)methanone;

(2-(2-ethyl-1H-benzo[d]imidazol-1-yl)-9-methyl-6-morpholino-9H-purin-8-yl)(4-fluoropiperidin-1yl)methanone;

2-(2-ethyl-1H-benzo[d]imidazol-1-yl)-N-(2-methoxyethyl)-N,9-dimethyl-6-morpholino-9H-purine-8-carboxamide;

4-(2-(2-ethyl-1H-benzo[d]imidazol-1-yl)-9-methyl-6-morpholino-9H-purine-8-carbonyl)-N,N-dimethylpiperazine-1-carboxamide;

(S)-(3-(dimethylamini)pyrrolidin-1-yl)2-(2-ethyl-1H-benzo[d]imidazol-1-yl)-9-methyl-6-morpholino-9H-purin-8-yl)methanone;

(R)-(2-(2-ethyl-1H-benzo[d]imidazol-1-yl)-9-methyl-6-morpholino-9H-purin-8-yl)(3-hydroxypiperidin-1-yl)methanone;

(2-(2-ethyl-1H-benzo[d]imidazol-1-yl)-9-methyl-6-morpholino-9H-purin-8-yl)(1,4-oxazepan-4-yl)methanone;

2-(2-ethyl-1H-benzo[d]imidazol-1-yl)-N,9-dimethyl-N-(1-methylpyrrolidin-3-yl)-6-morpholino-9H-purine-8-carboxamide;

N-(2-cyanoethyl)-2-(2-ethyl-1H-benzo[d]imidazol-1-yl)-N,9-dimethyl-6-morpholino-9H-purine-8-carboxamide;

N-(cyanomethyl)-2-(2-ethyl-1H-benzo[d]imidazol-1-yl)-N,9-dimethyl-6-morpholino-9H-purine-8-carboxamide;

2-(2-ethyl-1H-benzo[d]imidazol-1-yl)-N-(2-hydroxyethyl)-N,9-dimethyl-6-morpholino-9H-purine-8-carboxamide;

(2-(2-ethyl-1H-benzo[d]imidazol-1-yl)-9-methyl-6-morpholino-9H-purin-8-yl)(3-(trifluoromethyl)piperidin-1-yl)methanone;

4,4-difluoropiperidin-1-yl)(2-(2-ethyl-1H-benzo[d]imidazol-1-yl)-9-methyl-6-morpholino-9H-purin-8-yl)methanone;

(2-(2-ethyl-1H-benzo[d]imidazol-1-yl)-9-methyl-6-morpholino-9H-purin-8-yl)(4-(methoxymethyl)piperidin-1-yl)methanone;

(2-(2-ethyl-1H-benzo[d]imidazol-1-yl)-9-methyl-6-morpholino-9H-purin-8-yl)(3-(trifluoromethyl)pyrrolidin-1-yl)methanone;

2-(2-ethyl-1H-benzo[d]imidazol-1-yl)-N,9-dimethyl-6-morpholino-N-(1,1-dioxo-tetrahydrothiophen-3-yl)-9H-purine-8-carboxamide;

(R)-(2-(2-ethyl-1H-benzo[d]imidazol-1-yl)-9-methyl-6-morpholino-9H-purin-8-yl)(2-(hydroxymethyl)pyrrolidin-1-yl)methanone;

1-(2-(2-ethyl-1H-benzo[d]imidazol-1-yl)-9-methyl-6-morpholino-9H-purine-8-carbonyl)piperidine-4-carboxamide;

tert-butyl 3-(2-(2-ethyl-1H-benzo[d]imidazol-1-yl)-9-methyl-6-morpholino-9H-purin-8-yl)pyrrolidine-1-carboxylate;

tert-butyl 4-(2-(2-ethyl-1H-benzo[d]imidazol-1-yl)-9-methyl-6-morpholino-9H-purin-8-yl)piperidine-1-carboxylate;

4-((2-(2-ethyl-1H-benzo[d]imidazol-1-yl)-9-methyl-6-morpholino-9H-purin-8-yl)methyl)-3-isopropylpiperazin-2-one;

4-((2-(2-ethyl-1H-benzo[d]imidazol-1-yl)-9-methyl-6-morpholino-9H-purin-8-yl)methyl)-3,3-dimethylpiperazin-2-one;

(2-(2-ethyl-1H-benzo[d]imidazol-1-yl)-9-methyl-6-morpholino-9H-purin-8-yl)(4-methylpiperazin-1-yl)methanone;

(2-(2-ethyl-1H-benzo[d]imidazol-1-yl)-9-methyl-6-morpholino-9H-purin-8-yl)(4-isopropylpiperazin-1-yl)methanone;

1-(4-(2-(2-ethyl-1H-benzo[d]imidazol-1-yl)-9-methyl-6-morpholino-9H-purine-8-carbonyl)piperazin-1-yl)ethanone;

(4-(cyclopropylmethyl)piperazin-1-yl)(2-(2-ethyl-1H-benzo[d]imidazol-1-yl)-9-methyl-6-morpholino-9H-purin-8-yl)methanone;

1-(4-(2-(2-ethyl-1H-benzo[d]imidazol-1-yl)-9-methyl-6-morpholino-9H-purine-8-carbonyl)piperazin-1-yl)-2-methylpropan-1-one;

(4-(cyclobutylpiperazin-1-yl)(2-(2-ethyl-1H-benzo[d]imidazol-1-yl)-9-methyl-6-morpholino-9H-purin-8-yl)methanone;

(4-(cyclopropanecarbonyl)piperazin-1-yl)(2-(2-ethyl-1H-benzo[d]imidazol-1-yl)-9-methyl-6-morpholino-9H-purin-8-yl)methanone;

(2-(2-ethyl-1H-benzo[d]imidazol-1-yl)-9-methyl-6-morpholino-9H-purin-8-yl)(4-(methylsulfonyl)piperazin-1-yl)methanone;

2-(3-hydroxy-3-(2-(2-isopropyl-1H-benzo[d]imidazol-1-yl)-9-methyl-6-morpholino-9H-purin-8-yl)piperidin-1yl)-2-methylpropanamide;

(2-(2-ethyl-1H-benzo[d]imidazol-1-yl)-9-methyl-6-morpholino-9H-purin-8-yl)(4-(2-hydroxy-2-methylpropyl)piperazin-1-yl)methanone;

(2-(2-ethyl-1H-benzo[d]imidazol-1-yl)-9-methyl-6-morpholino-9H-purin-8-yl)(4-(pyridin-2-yl)piperazin-1-yl)methanone;

2-(3-hydroxy-3-(2-(2-isopropyl-1H-benzo[d]imidazol-1-yl)-9-methyl-6-morpholino-9H-purin-8-yl)piperidin-1yl)-2-methylpropanamide;

(R)-2-(3-(2-(2-isopropyl-1H-benzo[d]imidazol-1-yl)-9-methyl-6-morpholino-9H-purin-8-yl)-3-methoxypiperidin-1yl)-2-methylpropanamide;

(S)-2-(3-(2-(2-isopropyl-1H-benzo[d]imidazol-1-yl)-9-methyl-6-morpholino-9H-purin-8-yl)-3-methoxypiperidin-1-yl)-2-methylpropanamide;

(R)-1-(3-(2-(2-isopropyl-1H-benzo[d]imidazol-1-yl)-9-methyl-6-morpholino-9H-purin-8-yl)-3-methoxypiperidin-1-yl)ethanone;

(S)-1-(3-(2-(2-isopropyl-1H-benzo[d]imidazol-1-yl)-9-methyl-6-morpholino-9H-purin-8-yl)-3-methoxypiperidin-1-yl)ethanone;

(2-(2-ethyl-1H-benzo[d]imidazol-1-yl)-9-methyl-6-morpholino-9H-purin-8-yl)(4-(oxetan-3-yl)piperazin-1-yl)methanone;

2-(4-(2-(2-isopropyl-1H-benzo[d]imidazol-1-yl)-4-morpholinofuro[3,2-d]pyrimidine-6-carbonyl)piperazin-1-yl)-2-methylpropanamide;

2-(4-(2-(2-ethyl-1H-benzo[d]imidazol-1-yl)-4-morpholinofuro[3,2-d]pyrimidine-6-carbonyl)piperazin-1-yl)-2-methylpropanamide;

(2-(2-ethyl-1H-benzo[d]imidazol-1-yl)-4-morpholinofuro[3,2-d]pyrimidin-6-yl)(4-(2-hydroxypropan-2-yl)piperidin-1-yl)methanone;

(4-(2-hydroxypropan-2-yl)piperidin-1-yl)(2-(2-isopropyl-1H-benzo[d]imidazol-1-yl)-4-morpholinofuro[3,2-d]pyrimidin-6-yl)methanone;

(2-(2-(1,1-difluoroethyl)-1H-benzo[d]imidazol-1-yl)-9-methyl-6-morpholino-9H-purin-8-yl)(4-(2-hydroxypropan-2-yl)piperidin-1-yl)methanone;

(2-(2-ethyl-1H-benzo[d]imidazol-1-yl)-9-methyl-6-morpholino-9H-purin-8-yl)(4-(1-hydroxy-2-methylpropan-2-yl)piperazin-1-yl)methanone;

(R)-(2-(2-ethyl-1H-benzo[d]imidazol-1-yl)-9-methyl-6-morpholino-9H-purin-8-yl)(2-methylpiperidin-1-yl)methanone;

(S)-(2-(2-ethyl-1H-benzo[d]imidazol-1-yl)-9-methyl-6-morpholino-9H-purin-8-yl)(2-methylpiperidin-1-yl)methanone;

(2-(2-ethyl-1H-benzo[d]imidazol-1-yl)-9-methyl-6-morpholino-9H-purin-8-yl)(3-(1,1-dioxo)thiomorpholinoazetidin-1-yl)methanone;

4-2-(2-isopropyl-1H-benzo[d]imidazol-1-yl)-9-methyl-8-(pyridin-3-yl)-9H-purin-6-yl)morpholine;

2-(4-(2-(2-ethyl-1H-benzo[d]imidazol-1-yl)-9-methyl-6-morpholino-9H-purin-8-yl)piperidin-1-yl)acetamide;

tert-butyl 3-(2-(2-ethyl-1H-benzo[d]imidazol-1-yl)-9-methyl-6-morpholino-9H-purin-8-yl)azetidine-1-carboxylate;

(R)-1-(3-((2-(2-ethyl-1H-benzo[d]imidazol-1-yl)-9-methyl-6-morpholino-9H-purin-8-yl)methyl)azetidin-1-yl)-2-hydroxypropan-1-one;
4-(8-(azetidin-3-yl)-2-(2-ethyl-1H-benzo[d]imidazol-1-yl)-9-methyl-9H-purin-6-yl)morpholine;
1-((2-(2-ethyl-1H-benzo[d]imidazol-1-yl)-9-methyl-6-morpholino-9H-purin-8-yl)methyl)-3-isopropylpiperazin-2-one;
4-(2-(2-isopropyl-1H-benzo[d]imidazol-1-yl)-8-(3-methoxyphenyl)-9-methyl-9H-purin-6-yl)morpholine;
4-(8-(3-ethoxy-1-isopropylpiperidin-3-yl)-2-(2-isopropyl-1H-benzo[d]imidazol-1-yl)-9-methyl-9H-purin-6-yl)morpholine;
(2-(2-ethyl-1H-benzo[d]imidazol-1-yl)-9-methyl-6-morpholino-9H-purin-8-yl)(3-morpholinoazetidin-1-yl)methanone;
(2-(2-ethyl-1H-benzo[d]imidazol-1-yl)-9-methyl-6-morpholino-9H-purin-8-yl)(4-(oxazol-2-ylmethyl)piperazin-1-yl)methanone;
2-(1-((2-(2-ethyl-1H-benzo[d]imidazol-1-yl)-6-morpholino-9H-purin-8-yl)methyl)piperidin-4-yl)propan-2-ol; and
2-(1-((2-(2-methyl-1H-benzo[d]imidazol-1-yl)-6-morpholino-9H-purin-8-yl)methyl)piperidin-4-yl)propan-2-ol.

18. The compound of claim 1 selected from
2-(4-(2-(2-ethyl-1H-benzo[d]imidazol-1-yl)-9-methyl-6-morpholino-9H-purin-8-yl)piperidin-1yl)-2-methyl-propanamide;
(R)-(2-(2-ethyl-1H-benzo[d]imidazol-1-yl)-9-methyl-6-morpholino-9H-purin-8-yl)(3-fluoropyrrolidin-1-yl)methanone;
(2-(2-ethyl-1H-benzo[d]imidazol-1-yl)-9-methyl-6-morpholino-9H-purin-8-yl)(3-(tetrahydro-2H-pyran-4-yl)azetidin-1-yl)methanone;
N-ethyl-4-(2-(2-ethyl-1H-benzo[d]imidazol-1-yl)-9-methyl-6-morpholino-9H-purine-8-carbonyl)piperazine-1-carboxamide;
(2-(2-ethyl-1H-benzo[d]imidazol-1-yl)-9-methyl-6-morpholino-9H-purin-8-yl)(pyridin-3-yl)methanone;
(S)-N-(2-(2-(2-ethyl-1H-benzo[d]imidazol-1-yl)-9-methyl-6-morpholino-9H-purin-8-yl)ethyl)-N-methyl-(1,1-dioxo)-tetrahydrothiophen-3-amine;
(R)-N-(2-(2-(2-ethyl-1H-benzo[d]imidazol-1-yl)-9-methyl-6-morpholino-9H-purin-8-yl)ethyl)-N-methyl-(1,1-dioxo)-tetrahydrothiophen-3-amine;
1-((2-(2-ethyl-1H-benzo[d]imidazol-1-yl)-9-methyl-6-morpholino-9H-purin-8-yl)methyl)-4-isopropylpiperazin-2-one;
2-(5-(2-ethyl-1H-benzo[d]imidazol-1-yl)-7-morpholinothiazolo[5,4-d]pyrimidin-2-yl)-1-(4-(1-hydroxy-2-methylpropan-2-yl)piperazin-1-yl)ethanone;
4-(2-(2-isopropyl-1H-benzo[d]imidazol-1-yl)-8-(3-methoxy-1-(2-(methylsulfonyl)ethyl)piperidin-3-yl)-9-methyl-9H-purin-6-yl)morpholine;
tert-butyl 3-(2-(2-ethyl-1H-benzo[d]imidazol-1-yl)-9-methyl-6-morpholino-9H-purin-8-yl)-3-methoxyazetidine-1-carboxylate;
(2,2-dimethyl-4-(methylsulfonyl)piperazin-1-yl)(2-(2-ethyl-1H-benzo[d]imidazol-1-yl)-9-methyl-6-morpholino-9H-purin-8-yl)methanone;
2-(3-(2-(2-isopropyl-1H-benzo[d]imidazol-1-yl)-9-methyl-6-morpholino-9H-purin-8-yl)-3-methoxypiperidin-1yl)acetamide;
2-(4-((2-(2-ethyl-1H-benzo[d]imidazol-1-yl)-9-methyl-6-morpholino-9H-purin-8-yl)methyl)-3,3-dimethylpiperazin-1-yl)acetamide;
(S)-1-(3-((2-(2-ethyl-1H-benzo[d]imidazol-1-yl)-9-methyl-6-morpholino-9H-purin-8-yl)methyl)azetidin-1-yl)-2-hydroxypropan-1-one;
3-(2-(2-ethyl-1H-benzo[d]imidazol-1-yl)-9-methyl-6-morpholino-9H-purin-8-yl)-1-(tetrahydro-2H-pyran-4-yl)azetidin-3-ol;
1-(3-((2-(2-ethyl-1H-benzo[d]imidazol-1-yl)-9-methyl-6-morpholino-9H-purin-8-yl)methyl)azetidin-1-yl)-2-hydroxy-2-methylpropan-1-one;
(R)-1-(4-((2-(2-ethyl-1H-benzo[d]imidazol-1-yl)-9-methyl-6-morpholino-9H-purin-8-yl)methyl)-3,3-dimethylpiperazin-1-yl)-2-hydroxypropan-1-one;
(S)-1-(4-((2-(2-ethyl-1H-benzo[d]imidazol-1-yl)-9-methyl-6-morpholino-9H-purin-8-yl)methyl)-3,3-dimethylpiperazin-1-yl)-2-hydroxypropan-1-one;
1-(4-(2-(2-ethyl-1H-benzo[d]imidazol-1-yl)-9-methyl-6-morpholino-9H-purine-8-carbonyl)piperazin-1-yl)propan-1-one;
methyl 4-(2-(2-ethyl-1H-benzo[d]imidazol-1-yl)-9-methyl-6-morpholino-9H-purine-8-carbonyl)piperazine-1-carboxylate;
(2-(2-ethyl-1H-benzo[d]imidazol-1-yl)-9-methyl-6-morpholino-9H-purin-8-yl)(4-(2,2,2-trifluoroethyl)piperazin-1-yl)methanone;
(R)-1-(4-(2-(2-ethyl-1H-benzo[d]imidazol-1-yl)-9-methyl-6-morpholino-9H-purine-8-carbonyl)piperazin-1-yl)-2-hydroxypropan-1-one;
(S)-1-(4-(2-(2-ethyl-1H-benzo[d]imidazol-1-yl)-9-methyl-6-morpholino-9H-purine-8-carbonyl)piperazin-1-yl)-2-hydroxypropan-1-one;
(2-(2-ethyl-1H-benzo[d]imidazol-1-yl)-9-methyl-6-morpholino-9H-purin-8-yl)(4-(1,1-dioxotetrahydrothiophen-3-yl)piperazin-1-yl)methanone;
4-(9-methyl-2-(2-methyl-1H-benzo[d]imidazol-1-yl)-8-((1-(1,1-dioxo-tetrahydrothiophen-3-yl)piperidin-4-yl)methyl)-9H-purin-6-yl)morpholine;
(2-(2-ethyl-1H-benzo[d]imidazol-1-yl)-9-methyl-6-morpholino-9H-purin-8-yl)(3-methylpyrrolidin-1-yl)methanone;
2-(1-((2-(2-isopropyl-1H-benzo[d]imidazol-1-yl)-6-morpholino-9H-purin-8-yl)methyl)piperidin-4-yl)propan-2-ol;
2-(1-(1-(2-(2-ethyl-1H-benzo[d]imidazol-1-yl)-9-methyl-6-morpholino-9H-purin-8-yl)ethyl)piperidin-4-yl)propan-2-ol;
2-(1-(1-(2-(2-ethyl-1H-benzo[d]imidazol-1-yl)-9-methyl-6-morpholino-9H-purin-8-yl)ethyl)piperidin-4-yl)propan-2-ol;
(4-(2-hydroxypropan-2-yl)piperidin-1yl)(2-(2-isopropyl-1H-benzo[d]imidazol-1-yl)-9-methyl-6-morpholino-9H-purin-8-yl)methanone;
4-(8-(((2R,6S)-2,6-dimethyl-4-(methylsulfonyl)piperazin-1-yl)methyl)-2-(2-ethyl-1H-benzo[d]imidazol-1-yl)-9-methyl-9H-purin-6-yl)morpholine;
3-(2-(2-ethyl-1H-benzo[d]imidazol-1-yl)-9-methyl-6-morpholino-9H-purin-8-yl)-1-isopropylazetidin-3-ol;
4-(2-(2-ethyl-1H-benzo[d]imidazol-1-yl)-8-(1-isopropyl-3-methoxyazetidin-3-yl)-9-methyl-9H-purin-6-yl)morpholine;
4-(8-((2,2-dimethyl-4-(oxetan-3-yl)piperazin-1-yl)methyl)-2-(2-ethyl-1H-benzo[d]imidazol-1-yl)-9-methyl-9H-purin-6-yl)morpholine;
1-(4-((2-(2-ethyl-1H-benzo[d]imidazol-1-yl)-9-methyl-6-morpholino-9H-purin-8-yl)methyl)-3,3-dimethylpiperazin-1-yl)-2-hydroxy-2-methylpropan-1-one;

2-(3-(2-(2-isopropyl-1H-benzo[d]imidazol-1-yl)-9-methyl-6-morpholino-9H-purin-8-yl)-3-methoxypiperidin-1-yl)acetamide;
2-(3-(2-(2-isopropyl-1H-benzo[d]imidazol-1-yl)-9-methyl-6-morpholino-9H-purin-8-yl)-3-methoxypiperidin-1-yl)acetamide;
4-(2-(2-ethyl-1H-benzo[d]imidazol-1-yl)-9-methyl-8-((7-(oxetan-3-yl)-4,7-diazaspiro[2.5]octan-4-yl)methyl)-9H-purin-6-yl)morpholine;
2-(3-(2-(2-ethyl-1H-benzo[d]imidazol-1-yl)-9-methyl-6-morpholino-9H-purin-8-yl)-3-hydroxypiperidin-1-yl)-N,N-dimethylacetamide;
3-(2-(2-ethyl-1H-benzo[d]imidazol-1-yl)-9-methyl-6-morpholino-9H-purin-8-yl)-1-(2-hydroxy-2-methylpropyl)piperidin-3-ol;
4-(2-(2-ethyl-1H-benzo[d]imidazol-1-yl)-9-methyl-8-(1-(tetrahydro-2H-pyran-4-yl)azetidin-3-yl)-9H-purin-6-yl)morpholine;
N-(2-(2-(2-ethyl-1H-benzo[d]imidazol-1-yl)-9-methyl-6-morpholino-9H-purin-8-yl)ethyl)-N,3-dimethyl-1,1-dioxotetrahydrothiophen-3-amine;
2-(4-(9-ethyl-2-(2-methyl-1H-benzo[d]imidazol-1-yl)-6-morpholino-9H-purine-8-carbonyl)piperazin-1-yl)-2-methylpropanamide;
4-(8-((2,2-dimethyl-4-(methylsulfonyl)piperazin-1-yl)methyl)-2-(2-isopropyl-1H-benzo[d]imidazol-1-yl)-9H-purin-6-yl)morpholine;
2-(1-((2-(2-(1,1-difluoroethyl)-1H-benzo[d]imidazol-1-yl)-6-morpholino-9H-purin-8-yl)methyl)piperidin-4-yl)propan-2-ol;
2-(1-((2-(2-cyclopropyl-1H-benzo[d]imidazol-1-yl)-6-morpholino-9H-purin-8-yl)methyl)piperidin-4-yl)propan-2-ol;
4-(1-((2-(2-(1,1-difluoroethyl)-1H-benzo[d]imidazol-1-yl)-6-morpholino-9H-purin-8-yl)methyl)azetidin-3-yl)morpholine;
(4-(2-hydroxypropan-2-yl)piperidin-1-yl)(2-(2-isopropyl-1H-benzo[d]imidazol-1-yl)-6-morpholino-9H-purin-8-yl)methanone;
4-(2-(2-(1,1-difluoroethyl)-1H-benzo[d]imidazol-1-yl)-8-((3-(tetrahydro-2H-pyran-4-yl)azetidin-1-yl)methyl)-9H-purin-6-yl)morpholine;
4-(2-(2-isopropyl-1H-benzo[d]imidazol-1-yl)-8-((3-(tetrahydro-2H-pyran-4-yl)azetidin-1-yl)methyl)-9H-purin-6-yl)morpholine;
(2-(2-ethyl-1H-benzo[d]imidazol-1-yl)-6-morpholino-9H-purin-8-yl)(4-(2-hydroxypropan-2-yl)piperidin-1-yl)methanone;
4-(1-((2-(2-ethyl-1H-benzo[d]imidazol-1-yl)-6-morpholino-9H-purin-8-yl)methyl)azetidin-3-yl)morpholine;
(9-ethyl-2-(2-methyl-1H-benzo[d]imidazol-1-yl)-6-morpholino-9H-purin-8-yl)(4-(2-hydroxypropan-2-yl)piperidin-1-yl)methanone;
(4)-2-hydroxypropan-2-yl)piperidin-1-yl)(9-methyl-2-(2-methyl-1H-benzo[d]imidazol-1-yl)-6-morpholino-9H-purin-8-yl)methanone;
2-(4-((2-(2-ethyl-1H-benzo[d]imidazol-1-yl)-6-morpholino-9H-purin-8-yl)methyl)piperidin-1-yl)-2-methylpropanamide;
4-(1-((2-(2-isopropyl-1H-benzo[d]imidazol-1-yl)-6-morpholino-9H-purin-8-yl)methyl)azetidin-3-yl)morpholine;
2-(4-((2-(2-ethyl-1H-benzo[d]imidazol-1-yl)-9-methyl-6-morpholino-9H-purin-8-yl)fluoromethylene)piperidin-1-yl)-2-methylpropanamide;
(2-(2-ethyl-1H-benzo[d]imidazol-1-yl)-9-methyl-6-morpholino-9H-purin-8-yl)(piperazin-1-yl)methanone;
3-(2-(2-ethyl-1H-benzo[d]imidazol-1-yl)-9-methyl-6-morpholino-9H-purin-8-yl)-1-(methylsulfonyl)piperidin-3-ol;
4-(2-(2-ethyl-1H-benzo[d]imidazol-1-yl)-8-(3-methoxy-1-(methylsulfonyl)piperidin-3-yl)-9-methyl-9H-purin-6-yl)morpholine;
1-(2-(2-ethyl-1H-benzo[d]imidazol-1-yl)-9-methyl-6-morpholino-9H-purine-8-carbonyl)piperidine-4-carbonitrile;
(2-(2-ethyl-1H-benzo[d]imidazol-1-yl)-9-methyl-6-morpholino-9H-purin-8-yl)(4-(2-hydroxyethyl)piperazin-1-yl)methanone;
(9-(2-hydroxyethyl)-2-(2-isopropyl-1H-benzo[d]imidazol-1-yl)-6-morpholino-9H-purin-8-yl)(4-(2-hydroxypropan-2-yl)piperidin-1-yl)methanone;
2-(1-((2-(2-ethyl-1H-benzo[d]imidazol-1-yl)-6-(octadeuterio)morpholino-9H-purin-8-yl)methyl)piperidin-4-yl)propan-2-ol;
(5-(2-ethyl-1H-benzo[d]imidazol-1-yl)-7-morpholinothiazolo[5,4-d]pyrimidin-2-yl)(4-(2-hydroxypropan-2-yl)piperidin-1-yl)methanone;
3-(2-(2-ethyl-1H-benzo[d]imidazol-1-yl)-9-methyl-6-morpholino-9H-purin-8-yl)-1-(tetrahydro-2H-pyran-4-yl)piperidin-3-ol;
2-amino-1-(4-(2-(2-ethyl-1H-benzo[d]imidazol-1-yl)-9-methyl-6-morpholino-9H-purine-8-carbonyl)piperazin-1-yl)ethanone;
(2-(2-ethyl-1H-benzo[d]imidazol-1-yl)-9-methyl-6-morpholino-9H-purin-8-yl)(4-(1-hydroxyethyl)piperidin-1-yl)methanone;
(S)-2-(1-((2-(2-ethyl-1H-benzo[d]imidazol-1-yl)-9-methyl-6-(3-methylmorpholino)-9H-purin-8-yl)methyl)piperidin-4-yl)propan-2-ol;
(4-(1,3-dihdroxypropan-2-yl)piperazin-1-yl)(2-(2-ethyl-1H-benzo[d]imidazol-1-yl)-9-methyl-6-morpholino-9H-purin-8-yl)methanone;
(4-(cyclopropanecarbonyl)piperazin-1-yl)(2-(2-(dimethylamino)-1H-benzo[d]imidazol-1-yl)-9-methyl-6-morpholino-9H-purin-8-yl)methanone;
(R)-1-(4-(2-(2-(dimethylamino)-1H-benzo[d]imidazol-1-yl)-9-methyl-6-morpholino-9H-purine-8-carbonyl)piperazin-1-yl)-2-hydroxypropan-1-one;
N-(1-(2-(2-ethyl-1H-benzo[d]imidazol-1-yl)-9-methyl-6-morpholino-9H-purine-8-carbonyl)piperidin-4-yl)acetamide;
(1-aminocyclopropyl)(4-((2-(2-ethyl-1H-benzo[d]imidazol-1-yl)-9-methyl-6-morpholino-9H-purin-8-yl)methyl)-3,3-dimethylpiperazin-1-yl)methanone;
(R)-2-(1-((2-(2-ethyl-1H-benzo[d]imidazol-1-yl)-9-methyl-6-(3-methylmorpholino)-9H-purin-8-yl)methyl)piperidin-4-yl)propan-2-ol;
N-(1-(2-(2-ethyl-1H-benzo[d]imidazol-1-yl)-9-methyl-6-morpholino-9H-purine-8-carbonyl)piperidin-4-yl)propionamide;
N-(1-(2-(2-ethyl-1H-benzo[d]imidazol-1-yl)-9-methyl-6-morpholino-9H-purine-8-carbonyl)piperidin-4-yl)-2-hydroxy-2-methylpropanamide;
4-(2-(2-ethyl-1H-benzo[d]imidazol-1-yl)-8-(1-isopropyl-1H-1,2,4-triazol-5-yl)-9-methyl-9H-purin-6-yl)morpholine;
(2-(2-ethyl-1H-benzo[d]imidazol-1-yl)-9-methyl-6-morpholino-9H-purin-8-yl)(3-(oxetan-3-ylamino)azetidin-1-yl)methanone;

N-(1-(2-(2-ethyl-1H-benzo[d]imidazol-1-yl)-9-methyl-6-morpholino-9H-purine-8-carbonyl)azetidin-3-yl)propionamide;

(2-(2-(dimethylamino)-1H-benzo[d]imidazol-1-yl)-6-morpholino-9H-purin-8-yl)(4-(2-hydroxypropan-2-yl)piperidin-1yl)methanone;

(S)-(4-(2-hydroxypropan-2-yl)piperidin-1-yl)2-(2-1-methoxethyl)-1H-benzo[d]imidazol-1-yl)-9-methyl-6-morpholino-9H-purin-8-yl)methanone;

1-(4-(2-(2-ethyl-1H-benzo[d]imidazol-1-yl)-9-methyl-6-morpholino-9H-purin-8-yl)-4-hydroxypiperidin-1yl)-2-hydroxy-2-methylpropan-1-one;

1-(3-(2-(2-ethyl-1H-benzo[d]imidazol-1-yl)-9-methyl-6-morpholino-9H-purin-8-yl)-3-methoxypiperidin-1yl)-2-methylpropan-2-ol;

(2,2-dimethyl-4-(oxetan-3-yl)piperazin-1-yl)(5-(2-ethyl-1H-benzo[d]idimidazol-1-yl)-7-morpholinothiazolo[5,4-d]pyrimidin-2-yl)methanone;

(R)-(4-(2-hydroxypropan-2-yl)piperidin-1-yl)(2-(2-(1-methoxethyl)-1H-benzo[d]imidazol-1-yl)-9-methyl-6-morpholino-9H-purin-8-yl)methanone;

1-(4-(2-(2-ethyl-1H-benzo[d]imidazol-1-yl)-9-methyl-6-morpholino-9H-purine-8-carbonyl)piperazin-1-yl)-2-hydroxy-2-methylpropan-1-one;

4-(1-((5-(2-ethyl-1H-benzo[d]imidazol-1-yl)-7-morpholinothiazolo[5,4-d]pyrimidin-2-yl)methyl)azetidin-3-yl)piperazin-2-one;

(2-(2-ethyl-1H-benzo[d]imidazol-1-yl)-9-methyl-6-morpholino-9H-purin-8-yl)(3-(4-hydroxypiperidin-1-yl)azetidin--1-yl)methanone;

(2-(2-cyclopropyl-1H-benzo[d]imidazol-1-yl)-9-methyl-6-morpholino-9H-purin-8-yl)(4-(2-hydroxypropan-2-yl)piperidin-1-yl)methanone;

(2-(2-cyclopropyl-1H-benzo[d]imidazol-1-yl)-9-methyl-6-morpholino-9H-purin-8-yl)(3-morpholinoazetidin-1-yl)methanone;

1-(4-(2-(2-ethyl-1H-benzo[d]imidazol-1-yl)-9-methyl-6-morpholino-9H-purin-8-yl)-4-methoxypiperidin-1-yl)-2-hydroxy-2-methylpropan-1-one;

(4-(2-hydroxypropan-2-yl)piperidin-1-yl)(2-(2-(methoxymethyl)-1H-benzo[]imidazol-1-yl)-9-methyl-6-morpholino-9H-purin-8-yl)methanone;

(2-(2-(2-hydroxypropan-2-yl)-1H-benzo[d]imidazol-1-yl)-9-methyl-6-morpholino-9H-purin-8-yl)(4-(2-hydroxypropan-2-yl)piperidin-1yl)methanone;

(R)-(2-(2-(1-methoxyethyl)-1H-benzo[d]imidazol-1-yl)-9-methyl-6-morpholino-9H-purin-8-yl)(3-morpholinoazetidin-1-yl)methanone;

N,N-diethyl-4-(2-(2-ethyl-1H-benzo[d]imidazol-1-yl)-9-methyl-6-morpholino-9H-purine-8-carbonyl)piperazine-1-carboxamide;

(S)-(4-tert-butylpiperazin-1-yl)(2-(2-(1-methoxyethyl)-1H-benzo[d]imidazol-1-yl)-9-methyl-6-morpholino-9H-purin-8-yl)methanone;

N-(1-(2-(2-ethyl-1H-benzo[d]imidazol-1-yl)-9-methyl-6-morpholino-9H-purine-8-carbonyl)piperidin-4-yl)-N-methylacetamide;

(4-(cyclopropanecarbonyl)piperazin-1-yl)(2-(2-ethyl-1H-benzo[d]imidazol-1-yl)-6-morpholino-9H-purin-8-yl)methanone;

1-(4-(2-(2-ethyl-1H-benzo[d]imidazol-1-yl)-6-morpholino-9H-purine-8-carbonyl)piperazin-1-yl)propan-1-one;

4-(2-(2-ethyl-1H-benzo[d]imidazol-1-yl)-9-methyl-8-(1-(1-methylpiperidin-4-yl)-1H-1,2,4-triazol-5-yl)-9H-purin-6-yl)morpholine;

(2-(2-(1,1-difluoroethyl)-1H-benzo[d]imidazol-1-yl)-9-methyl-6-morpholino-9H-purin-8-yl)(3-morpholinoazetidin-1-yl)methanone;

1-(3-(2-(2-ethyl-1H-benzo[d]imidazol-1-yl)-9-methyl-6-morpholino-9H-purin-8-yl)-3-methoxyazetidin-1-yl)-2-hydroxy-2-methylpropan-1-one 4-(1-((2-(2-ethyl-1H-benzo[d]imidazol-1-yl)-6-morpholino-9H-purin-8-yl)methyl)azetidin-3-yl)piperazin-2-one;

4-(2-((2,2-dimethyl-4-(oxetan-3-yl)piperazin-1-yl)methyl)-5-(2-ethyl-1H-benzo[d]imidazol-1-yl)thiazolo[5,4-d]pyrimidin-7-yl)morpholine;

1-(3-((5-(2-ethyl-1H-benzo[d]imidazol-1-yl)-7-morpholinothiazolo[5,4-d]pyrimidin-2-yl)methyl)azetidin-1-yl)-2-hydroxy-2-methylpropan-1-one;

4-(2-(2-ethyl-1H-benzo[d]imidazol-1-yl)-9-methyl-6-morpholino-9H-purine-8-carbonyl)-N-isopropylpiperazine-1-carboxamide;

4-(8-(1-cyclopentyl-1H-1,2,4-triazol-5-yl)-2-(2-ethyl-1H-benzo[d]imidazol-1-yl)-9-methyl-9H-purin-6-yl)morpholine;

4-(2-(2-ethyl-1H-benzo[d]imidazol-1-yl)-8-(1-isopropyl-1H-imidazol-2-yl)-9-methyl-9H-purin-6-yl)morpholine;

1-(4-(2-(2-ethyl-1H-benzo[d]imidazol-1-yl)-6-morpholino-9H-purine-8-carbonyl)piperazin-1-yl)-2-methylpropan-1-one;

1-(4-(2-(2-ethyl-1H-benzo[d]imidazol-1-yl)-6-morpholino-9H-purine-8-carbonyl)piperazin-1-yl)-2,2-dimethylpropan-1-one;

(2-(2-ethyl-1H-benzo[d]imidazol-1-yl)-6-morpholino-9H-purin-8-yl)(3-(1,1-dioxo)-thiomorpholinoazetidin-1-yl)methanone;

(2-(2-(hydroxymethyl)-1H-benzo[d]imidazol-1-yl)-9-methyl-6-morpholino-9H-purin-8-yl)(4-(2-hydroxypropan-2-yl)piperidin-1-yl)methanone;

4-(2-(2-ethyl-1H-benzo[d]imidazol-1-yl)-8-(1-isobutyl-1H-1,2,4-triazol-5-yl)-9-methyl-9H-purin-6-yl)morpholine;

1-(4-(2-(2-ethyl-1H-benzo[d]imidazol-1-yl)-9-methyl-6-morpholino-9H-purin-8-yl)-4-methoxypiperidin-1-yl)-2-hydroxyethanone;

1-(3-((2-(2-ethyl-1H-benzo[d]imidazol-1-yl)-9-methyl-6-morpholino-9H-purin-8-yl)methyl)azetidin-1-yl)-2-methylpropan-1-one;

cyclopropyl(3-((2-(2-ethyl-1H-benzo[d]imidazol-1-yl)-9-methyl-6-morpholino-9H-purin-8-yl)methyl)azetidin-1-yl)methanone;

4-(2-(2-ethyl-1H-benzo[d]imidazol-1-yl)-8-(3-methoxy-1-(2-(methylsulfonyl)ethyl)azetidin-3-yl)-9-methyl-9H-purin-6-yl)morpholine;

4-(2-(2-ethyl-1H-benzo[d]imidazol-1-yl)-8-(3-methoxy-1-(tetrahydro-2H-pyran-4-yl)azetidin-3-yl)-9-methyl-9H-purin-6-yl)morpholine;

tert-butyl 3-(2-(2-ethyl-1H-benzo[d]imidazol-1-yl)-9-methyl-6-morpholino-9H-purin-8-yl)-3-fluoroazetidine-1-carboxylate;

(S)-1-(4-((5-(2-ethyl-1H-benzo[d]imidazol-1-yl)-7-morpholinothiazolo[5,4-d]pyrimidin-2-yl)methyl)-3,3-dimethylpiperazin-1-yl)-2-hydroxypropan-1-one;

(S)-(2-(2-(1-methoxyethyl)-1H-benzo[d]imidazol-1-yl)-9-methyl-6-morpholino-9H-purin-8-yl)(3-morpholinoazetidin-1-yl)methanone;

2-(5-(2-(2-ethyl-1H-benzo[d]imidazol-1-yl)-9-methyl-6-morpholino-9H-purin-8-yl)-1H-1,2,4-triazol-1-yl)-N,N-dimethylethanamine;

1-(8-(1-isopropyl-1H-1,2,4-triazol-5-yl)-9-methyl-6-morpholino-9H-purin-2-yl)-N,N-dimethyl-1H-benzo[d]imidazol-2-amine;
1-(3-(2-(2-ethyl-1H-benzo[d]imidazol-1-yl)-9-methyl-6-morpholino-9H-purin-8-yl)-3-methoxyazetidin-1-yl)-2-methylpropan-2-ol;
4-(2-(2-ethyl-1H-benzo[d]imidazol-1-yl)-8-(3-fluoroazetidin-3-yl)-9-methyl-9H-purin-6-yl)morpholine;
(2-(2-ethyl-1H-benzo[d]imidazol-1-yl)-6-morpholino-9H-purin-8-yl)(3-morpholinoazetidin-1-yl)methanone;
4-(2-(2-ethyl-1H-benzo[d]imidazol-1-yl)-8-(1-isopropyl-4-methyl-1H-pyrazol-5-yl)-9-methyl-9H-purin-6-yl)morpholine;
1-(5-(2-(2-ethyl-1H-benzo[d]imidazol-1-yl)-9-methyl-6-morpholino-9H-purin-8-yl)-4-methyl-1H-pyrazol-1-yl)-2-methylpropan-2-ol;
1-(5-(2-(2-ethyl-1H-benzo[d]imidazol-1-yl)-9-methyl-6-morpholino-9H-purin-8-yl)-1H-1,2,4-triazol-1-yl)-2-methylpropan-2-ol;
1-(3-(2-(2-ethyl-1H-benzo[d]imidazol-1-yl)-9-methyl-6-morpholino-9H-purin-8-yl)-3-fluoroazetidin-1-yl)-2-methylpropan-2-ol;
(S)-1-(3-(2-(2-ethyl-1H-benzo[d]imidazol-1-yl)-9-methyl-6-morpholino-9H-purin-8-yl)-3-methoxyazetidin-1-yl)-2-hydroxypropan-1-one;
(4-(2-hydroxypropan-2-yl)piperidin-1-yl)(9-methyl-2-(2-(methylamino)-1H-benzo[d]imidazol-1-yl)-6-morpholino-9H-purin-8-yl)methanone;
1-(4-(2-(2-(dimethylamino)-1H-benzo[d]imidazol-1-yl)-9-methyl-6-morpholino-9H-purine-8-carbonyl)piperazin-1-yl)propan-1-one;
(2-(2-(dimethylamino)-1H-benzo[d]imidazol-1-yl)-9-methyl-6-morpholino-9H-purin-8-yl)(3-morpholinoazetidin-1-yl)methanone;
(2-(2-(dimethylamino)-1H-benzo[d]imidazol-1-yl)-9-methyl-6-morpholino-9H-purin-8-yl)(4-(2-hydroxypropan-2-yl)piperidin-1-yl)methanone;
1-(4-((2-(2-ethyl-1H-benzo[d]imidazol-1-yl)-9-methyl-6-morpholino-9H-purin-8-yl)methyl)piperidin-1-yl)-2-hydroxy-2-methylpropan-1-one;
(5-(2-ethyl-1H-benzo[d]imidazol-1-yl)-7-morpholinothiazolo[5,4-d]pyrimidin-2-yl)(3-morpholinoazetidin-1-yl)methanone;
(S)-1-(4-(2-(2-(1-methoxyethyl)-1H-benzo[d]imidazol-1-yl)-9-methyl-6-morpholino-9H-purine-8-carbonyl)piperazin-1-yl)propan-1-one;
1-(4-(9-methyl-2-(2-(methylamino)-1H-benzo[d]imidazol-1-yl)-6-morpholino-9H-purine-8-carbonyl)piperazin-1-yl)propan-1-one;
2-(3-(2-(2-ethyl-1H-benzo[d]imidazol-1-yl)-9-methyl-6-morpholino-9H-purin-8-yl)-3-methoxyazetidin-1-yl)ethanol;
2-(3-(2-(2-ethyl-1H-benzo[d]imidazol-1-yl)-9-methyl-6-morpholino-9H-purin-8-yl)-3-fluoroazetidin-1-yl)-2-methylpropan-1-ol;
1-(4-((2-(2-ethyl-1H-benzo[d]imidazol-1-yl)-9-methyl-6-morpholino-9H-purin-8-yl)methyl)piperidin-1-yl)-2-methylpropan-1-one;
cyclopropyl(4-((2-(2-ethyl-1H-benzo[d]imidazol-1-yl)-9-methyl-6-morpholino-9H-purin-8-yl)methyl)piperidin-1-yl)methanone;
4-(2-(2-ethyl-1H-benzo[d]imidazol-1-yl)-9-methyl-8-(pyridin-2-yl)-9H-purin-6-yl)morpholine;
2-hydroxy-1-(3-((2-(2-isopropyl-1H-benzo[d]imidazol-1-yl)-9-methyl-6-morpholino-9H-purin-8-yl)methyl)azetidin-1-yl)-2-methylpropan-1-one;
2-hydroxy-2-methyl-1-(3-((9-methyl-2-(2-methyl-1H-benzo[d]imidazol-1-yl)-6-morpholino-9H-purin-8-yl)methyl)azetidin-1-yl)prop an-1-one;
2-(1-(8-(4-(2-hydroxypropan-2-yl)piperidine-1-carbonyl)-9-methyl-6-morpholino-9H-purin-2-yl)-1H-benzo[d]imidazol-2-yl)acetonitrile;
(4-(2-hydroxypropan-2-yl)piperidin-1-yl)(9-methyl-6-morpholino-2-(2-(trifluoromethyl)-1H-benzo[d]imidazol-1-yl)-9H-purin-8-yl)methanone;
(2-(2-(difluoromethyl)-1H-benzo[d]imidazol-1-yl)-9-methyl-6-morpholino-9H-purin-8-yl)(4-(2-hydroxypropan-2-yl)piperidin-1-yl)methanone;
(S)-1-(3-((2-(2-(1-hydroxyethyl)-1H-benzo[d]imidazol-1-yl)-9-methyl-6-morpholino-9H-purin-8-yl)methyl)azetidin-1-yl)-2-methylpropan-1-one;
(R)-1-(3-((2-(2-(1-hydroxyethyl)-1H-benzo[d]imidazol-1-yl)-9-methyl-6-morpholino-9H-purin-8-yl)methyl)azetidin-1-yl)-2-methylpropan-1-one;
(R)-2-hydroxy-1-(3-((2-(2-(1-hydroxyethyl)-1H-benzo[d]imidazol-1-yl)-9-methyl-6-morpholino-9H-purin-8-yl)methyl)azetidin-1-yl)-2-methylpropan-1-one;
(S)-1-(4-((2-(2-ethyl-1H-benzo[d]imidazol-1-yl)-9-methyl-6-morpholino-9H-purin-8-yl)methyl)piperidin-1yl)-2-hydroxypropan-1-one;
1-(4-(2-(2-ethyl-1H-benzo[d]imidazol-1-yl)-9-methyl-6-morpholino-9H-purine-8-carbonyl)piperidin-1yl)-2-methylpropan-1-one;
(1-(cyclopropanecarbonyl)piperadin-4-yl)(2-(2-ethyl-1H-benzo[d]imidazol-1-yl)-9-methyl-6-morpholino-9H-purin-8-yl)methanone;
cyclopropyl(4-(1-(2-(2-ethyl-1H-benzo[d]imidazol-1-yl)-9-methyl-6-morpholino-9H-purin-8-yl)-1-hydroxyethyl)piperidin-1-yl)methanone;
(9-methyl-2-(2-(methylamino)-1H-benzo[d]imidazol-1-yl)-6-morpholino-9H-purin-8-yl)(3-morpholinoazetidin-1-yl)methanone;
(R)-(2-(2-(1-hydroxyethyl)-1H-benzo[d]imidazol-1-yl)-9-methyl-6-morpholino-9H-purin-8-yl)(3-morpholinoazetidin-1-yl)methanone;
(S)-(2-(2-(1-hydroxyethyl)-1H-benzo[d]imidazol-1-yl)-9-methyl-6-morpholino-9H-purin-8-yl)(3-morpholinoazetidin-1-yl)methanone;
(2-(2-isopropyl-1H-benzo[d]imidazol-1-yl)-9-methyl-6-morpholino-9H-purin-8-yl)(3-morpholinoazetidin-1-yl)methanone;
(2-(2-(2-hydroxyethyl)-1H-benzo[d]imidazol-1-yl)-9-methyl-6-morpholino-9H-purin-8-yl)(3-morpholinoazetidin-1-yl)methanone;
(4-(2-hydroxypropan-2-yl)piperidin-1-yl)(9methyl-2-(2-methyl-3H-imidazo[4,5-c]pyridin-3-yl)-6-morpholino-9H-purin-8-yl)methanone;
(9-methyl-2-(2-methyl-3H-imidazo[4,5-c]pyridin-3-yl)-6-morpholino-9H-purin-8-yl)(3-morpholinoazetidin-1-yl)methanone;
(4-(2-hydroxypropan-2-yl)piperidin-1-yl)(9methyl-2-(2-methyl-1H-imidazo[4,5-c]pyridin-1-yl)-6-morpholino-9H-purin-8-yl)methanone;
(9-methyl-2-(2-methyl-1H-imidazo[4,5-c]pyridin-1-yl)-6-morpholino-9H-purin-8-yl)(3-morpholinoazetidin-1-yl)methanone;
1-(4-((5-(2-ethyl-1H-benzo[d]imidazol-1-yl)-7-morpholinothiazolo[5,4-d]pyrimidin-2-yl)methyl)piperidin-1-yl)-2-hydroxy-2-methylpropan-1-one;
(2-(2-methoxy-1H-benzo[d]imidazol-1-yl)-9-methyl-6-morpholino-9H-purin-8-yl)(3-morpholinoazetidin-1-yl)methanone;

(2-(2-(difluoromethyl)-1H-benzo[d]imidazol-1-yl)-9-methyl-6-morpholino-9H-purin-8-yl)(3-morpholinoazetidin-1-yl)methanone;

(2-(2-(2-hydroxyethyl)-1H-benzo[d]imidazol-1-yl)-9-methyl-6-morpholino-9H-purin-8-yl)(4-(2-hydroxypropan-2-yl)piperidin-1-yl)methanone;

1-(4-(2-(2-(2-hydroxyethyl)-1H-benzo[d]imidazol-1-yl)-9-methyl-6-morpholino-9H-purine-8-carbonyl)piperazin-1-yl)propan-1-one;

1-(4-(9-methyl-2-(2-methyl-3H-imidazo[4,5-c]pyridin-3-yl)-6-morpholino-9H-purine-8-carbonyl)piperazin-1-yl)propan-1-one;

1-(4-(9-methyl-2-(2-methyl-1H-imidazo[4,5-c]pyridin-1-yl)-6-morpholino-9H-purine-8-carbonyl)piperazin-1-yl)propan-1-one;

1-(8-(4-(2-hydroxypropan-2-yl)piperidine-1-carbonyl)-9-methyl-6-morpholino-9H-purin-2-yl)-1H-benzo[d]imidazol-2(3H)-one;

(4-(2-hydroxypropan-2-yl)piperidine-1-yl)(2-(2-methoxy-1H-benzo[d]imidazol-1-yl)-9-methyl-6-morpholino-9H-purin-8-yl)methanone; and 1-(4-(2-(2-methoxy-1H-benzo[d]imidazol-1-yl)-9-methyl-6-morpholino-9H-purine-8-carbonyl)piperazin-1-yl)propan-1-one.

19. A pharmaceutical composition comprised of a compound of claim 1 or claim 12, and a pharmaceutically acceptable carrier, glidant, diluent, or excipient.

20. The pharmaceutical composition of claim 19 further comprising a therapeutic agent.

21. A kit comprising;
a) a pharmaceutical compsition comprising a compound of claim 1 or claim 12; and
b) instructions for use.

\* \* \* \* \*